US009677118B2

(12) United States Patent
Zimmermann et al.

(10) Patent No.: US 9,677,118 B2
(45) Date of Patent: Jun. 13, 2017

(54) METHODS FOR SIMULTANEOUS AMPLIFICATION OF TARGET LOCI

(71) Applicant: Natera, Inc., San Carlos, CA (US)

(72) Inventors: Bernhard Zimmermann, San Mateo, CA (US); Matthew Hill, Redwood City, CA (US); Philippe Lacroute, Sunnyvale, CA (US); Michael Dodd, San Francisco, CA (US); Alexander Wong, Mountain View, CA (US)

(73) Assignee: Natera, Inc., San Carlos, CA (US)

( * ) Notice: Subject to any disclaimer, the term of this patent is extended or adjusted under 35 U.S.C. 154(b) by 0 days.

(21) Appl. No.: 14/538,982

(22) Filed: Nov. 24, 2014

(65) Prior Publication Data

US 2015/0322507 A1    Nov. 12, 2015

Related U.S. Application Data

(60) Provisional application No. 61/982,245, filed on Apr. 21, 2014, provisional application No. 61/987,407, filed on May 1, 2014, provisional application No. 61/994,791, filed on May 16, 2014, provisional application No. 62/066,514, filed on Oct. 21, 2014.

(51) Int. Cl.
*C12Q 1/68* (2006.01)

(52) U.S. Cl.
CPC .......... *C12Q 1/68* (2013.01); *C12Q 1/6874* (2013.01); *C12Q 1/6883* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 5,635,366 A | 6/1997 | Cooke |
| 5,716,776 A | 2/1998 | Bogart |
| 5,753,467 A | 5/1998 | Jensen |
| 5,824,467 A | 10/1998 | Mascarenhas |
| 5,860,917 A | 1/1999 | Comanor |
| 5,972,602 A | 10/1999 | Hyland |
| 5,994,148 A | 11/1999 | Stewart |
| 6,001,611 A | 12/1999 | Will |
| 6,025,128 A | 2/2000 | Veltri |
| 6,108,635 A | 8/2000 | Herren |
| 6,143,496 A | 11/2000 | Brown |
| 6,180,349 B1 | 1/2001 | Ginzinger |
| 6,214,558 B1 | 4/2001 | Shuber |
| 6,258,540 B1 | 7/2001 | Lo |
| 6,300,077 B1 | 10/2001 | Shuber |
| 6,440,706 B1 | 8/2002 | Vogelstein |
| 6,479,235 B1 | 11/2002 | Schumm |
| 6,489,135 B1 | 12/2002 | Parrott |
| 6,720,140 B1 | 4/2004 | Hartley |
| 6,807,491 B2 | 10/2004 | Pavlovic |
| 6,852,487 B1 | 2/2005 | Barany |
| 6,958,211 B2 | 10/2005 | Vingerhoets |
| 7,035,739 B2 | 4/2006 | Schadt |
| 7,058,517 B1 | 6/2006 | Denton |
| 7,058,616 B1 | 6/2006 | Larder |
| 7,218,764 B2 | 5/2007 | Vaisberg |
| 7,297,485 B2 | 11/2007 | Bornarth |
| 7,332,277 B2 | 2/2008 | Dhallan |
| 7,414,118 B1 | 8/2008 | Mullah |
| 7,442,506 B2 | 10/2008 | Dhallan |
| 7,459,273 B2 | 12/2008 | Jones |
| 7,645,576 B2 | 1/2010 | Lo |
| 7,700,325 B2 | 4/2010 | Cantor |
| 7,718,367 B2 | 5/2010 | Lo |
| 7,718,370 B2 | 5/2010 | Dhallan |
| 7,727,720 B2 | 6/2010 | Dhallan |
| 7,805,282 B2 | 9/2010 | Casey |
| 7,838,647 B2 | 11/2010 | Hahn |
| 7,888,017 B2 | 2/2011 | Quake |
| 8,008,018 B2 | 8/2011 | Quake |
| 8,024,128 B2 | 9/2011 | Rabinowitz |
| 8,137,912 B2 | 3/2012 | Kapur |
| 8,168,389 B2 | 5/2012 | Shoemaker |
| 8,195,415 B2 | 6/2012 | Fan |
| 8,296,076 B2 | 10/2012 | Fan |
| 8,304,187 B2 | 11/2012 | Fernando |
| 8,318,430 B2 | 11/2012 | Chuu |
| 8,467,976 B2 | 6/2013 | Lo |
| 8,515,679 B2 | 8/2013 | Rabinowitz |
| 8,532,930 B2 | 9/2013 | Rabinowitz |
| 8,682,592 B2 | 3/2014 | Rabinowitz |

(Continued)

FOREIGN PATENT DOCUMENTS

| | | |
|---|---|---|
| EP | 1524321 | 7/2009 |
| EP | 1524321 B1 | 7/2009 |
| EP | 2902500 A1 | 8/2015 |
| GB | 2488358 | 8/2012 |
| JP | 2965699 | 8/1999 |
| JP | 2002-530121 A | 9/2002 |
| JP | 2004502466 A | 1/2004 |
| JP | 2004502466 A | 1/2004 |
| JP | 2004533243 A | 11/2004 |
| JP | 2004533243 A | 11/2004 |
| JP | 2005514956 A | 5/2005 |
| JP | 2005514956 A | 5/2005 |
| JP | 2005160470 A | 6/2005 |
| JP | 2005160470 A | 6/2005 |
| JP | 2006-254912 A | 9/2006 |

(Continued)

OTHER PUBLICATIONS

Podder et al. (BMC Med Genom, 2008, vol. 1, No. 5, p. 1 of 15).*
Donohoe et al. (Clinical Chemistry, 2000, 46:1540-1547).*
Pertl et al. (Hum Genet, 2000, 106:45-49).*
Ishii et al. (Appl Environ Micro, 2001, 67(8):3753-3755).*

(Continued)

Primary Examiner — Stephanie K Mummert

(57) ABSTRACT

The invention provides methods for simultaneously amplifying multiple nucleic acid regions of interest in one reaction volume as well as methods for selecting a library of primers for use in such amplification methods. The invention also provides library of primers with desirable characteristics, such as minimal formation of amplified primer dimers or other non-target amplicons.

24 Claims, 290 Drawing Sheets

(56) References Cited

U.S. PATENT DOCUMENTS

| | | |
|---|---|---|
| 8,825,412 B2 | 9/2014 | Rabinowitz |
| 8,949,036 B2 | 2/2015 | Rabinowitz |
| 9,163,282 B2 | 10/2015 | Rabinowitz |
| 2001/0053519 A1 | 12/2001 | Fodor |
| 2002/0006622 A1 | 1/2002 | Bradley |
| 2003/0009295 A1 | 1/2003 | Markowitz |
| 2003/0065535 A1 | 4/2003 | Karlov |
| 2003/0077586 A1 | 4/2003 | Pavlovic |
| 2003/0101000 A1 | 5/2003 | Bader |
| 2003/0228613 A1 | 12/2003 | Bornarth |
| 2004/0033596 A1 | 2/2004 | Threadgill |
| 2004/0137470 A1 | 7/2004 | Dhallan |
| 2004/0197797 A1 | 10/2004 | Inoko |
| 2004/0236518 A1 | 11/2004 | Pavlovic |
| 2004/0259100 A1 | 12/2004 | Gunderson |
| 2005/0009069 A1 | 1/2005 | Liu |
| 2005/0049793 A1 | 3/2005 | Paterlini-Brechot |
| 2005/0123914 A1 | 6/2005 | Katz |
| 2005/0142577 A1 | 6/2005 | Jones |
| 2005/0144664 A1 | 6/2005 | Smith |
| 2005/0164241 A1 | 7/2005 | Hahn |
| 2005/0221341 A1 | 10/2005 | Shimkets et al. |
| 2005/0227263 A1 | 10/2005 | Green |
| 2005/0250111 A1 | 11/2005 | Xie |
| 2005/0255508 A1 | 11/2005 | Casey |
| 2005/0272073 A1 | 12/2005 | Vaisberg |
| 2006/0019278 A1 | 1/2006 | Lo |
| 2006/0040300 A1 | 2/2006 | Dapprich |
| 2006/0052945 A1 | 3/2006 | Rabinowitz |
| 2006/0057618 A1 | 3/2006 | Piper |
| 2006/0068394 A1 | 3/2006 | Langmore |
| 2006/0088574 A1 | 4/2006 | Manning |
| 2006/0099614 A1 | 5/2006 | Gill |
| 2006/0121452 A1 | 6/2006 | Dhallan |
| 2006/0134662 A1 | 6/2006 | Pratt |
| 2006/0141499 A1 | 6/2006 | Sher |
| 2006/0210997 A1 | 9/2006 | Myerson |
| 2006/0216738 A1 | 9/2006 | Wada |
| 2006/0229823 A1 | 10/2006 | Liu |
| 2006/0281105 A1 | 12/2006 | Li et al. |
| 2007/0027636 A1 | 2/2007 | Rabinowitz |
| 2007/0059707 A1 | 3/2007 | Cantor |
| 2007/0122805 A1 | 5/2007 | Cantor |
| 2007/0178478 A1 | 8/2007 | Dhallan |
| 2007/0178501 A1 | 8/2007 | Rabinowitz |
| 2007/0184467 A1 | 8/2007 | Rabinowitz |
| 2007/0202525 A1 | 8/2007 | Quake |
| 2007/0202536 A1 | 8/2007 | Yamanishi |
| 2007/0207466 A1 | 9/2007 | Cantor |
| 2007/0212689 A1 | 9/2007 | Bianchi |
| 2007/0243549 A1 | 10/2007 | Bischoff |
| 2007/0259351 A1 | 11/2007 | Chinitz |
| 2008/0020390 A1 | 1/2008 | Mitchell |
| 2008/0026390 A1 | 1/2008 | Stoughton |
| 2008/0038733 A1 | 2/2008 | Bischoff |
| 2008/0070792 A1 | 3/2008 | Stoughton |
| 2008/0071076 A1 | 3/2008 | Hahn |
| 2008/0085836 A1 | 4/2008 | Kearns |
| 2008/0102455 A1 | 5/2008 | Poetter |
| 2008/0138809 A1 | 6/2008 | Kapur |
| 2008/0182244 A1 | 7/2008 | Tafas |
| 2008/0193927 A1 | 8/2008 | Mann |
| 2008/0234142 A1 | 9/2008 | Lietz |
| 2008/0243398 A1 | 10/2008 | Rabinowitz |
| 2009/0023190 A1 | 1/2009 | Lao |
| 2009/0029377 A1 | 1/2009 | Lo |
| 2009/0087847 A1 | 4/2009 | Lo |
| 2009/0098534 A1 | 4/2009 | Weier |
| 2009/0099041 A1 | 4/2009 | Church |
| 2009/0176662 A1 | 7/2009 | Rigatti |
| 2009/0221620 A1 | 9/2009 | Luke et al. |
| 2010/0035232 A1 | 2/2010 | Ecker |
| 2010/0112575 A1 | 5/2010 | Fan |
| 2010/0112590 A1 | 5/2010 | Lo |
| 2010/0120038 A1 | 5/2010 | Mir |
| 2010/0124751 A1 | 5/2010 | Quake |
| 2010/0138165 A1 | 6/2010 | Fan |
| 2010/0171954 A1 | 7/2010 | Quake |
| 2010/0184069 A1 | 7/2010 | Fernando |
| 2010/0184152 A1 | 7/2010 | Sandler |
| 2010/0196892 A1 | 8/2010 | Quake |
| 2010/0203538 A1 | 8/2010 | Dube |
| 2010/0216153 A1 | 8/2010 | Lapidus |
| 2010/0248231 A1 | 9/2010 | Wei |
| 2010/0255492 A1 | 10/2010 | Quake |
| 2010/0256013 A1 | 10/2010 | Quake |
| 2010/0285537 A1 | 11/2010 | Zimmermann |
| 2010/0291572 A1 | 11/2010 | Stoughton |
| 2010/0323352 A1 | 12/2010 | Lo |
| 2011/0033862 A1 | 2/2011 | Rabinowitz |
| 2011/0039724 A1 | 2/2011 | Lo |
| 2011/0086769 A1 | 4/2011 | Oliphant et al. |
| 2011/0092763 A1 | 4/2011 | Rabinowitz |
| 2011/0105353 A1 | 5/2011 | Lo |
| 2011/0151442 A1 | 6/2011 | Fan |
| 2011/0178719 A1 | 7/2011 | Rabinowitz |
| 2011/0201507 A1 | 8/2011 | Rava |
| 2011/0224087 A1 | 9/2011 | Quake |
| 2011/0246083 A1 | 10/2011 | Fan |
| 2011/0251149 A1 | 10/2011 | Perrine |
| 2011/0288780 A1 | 11/2011 | Rabinowitz |
| 2011/0300608 A1 | 12/2011 | Ryan |
| 2011/0318734 A1 | 12/2011 | Lo |
| 2012/0003635 A1 | 1/2012 | Lo |
| 2012/0034603 A1 | 2/2012 | Oliphant |
| 2012/0122701 A1 | 5/2012 | Ryan |
| 2012/0165203 A1 | 6/2012 | Quake |
| 2012/0185176 A1 | 7/2012 | Rabinowitz |
| 2012/0190020 A1 | 7/2012 | Oliphant |
| 2012/0190021 A1 | 7/2012 | Oliphant |
| 2012/0191358 A1 | 7/2012 | Oliphant et al. |
| 2012/0196754 A1 | 8/2012 | Quake |
| 2012/0214678 A1 | 8/2012 | Rava |
| 2012/0264121 A1 | 10/2012 | Rava et al. |
| 2012/0270212 A1 | 10/2012 | Rabinowitz |
| 2013/0017549 A1 | 1/2013 | Hong |
| 2013/0024127 A1 | 1/2013 | Stuelpnagel |
| 2013/0034546 A1 | 2/2013 | Rava |
| 2013/0060483 A1 | 3/2013 | Struble |
| 2013/0069869 A1 | 3/2013 | Akao |
| 2013/0090250 A1 | 4/2013 | Sparks |
| 2013/0123120 A1 | 5/2013 | Zimmermann |
| 2013/0178373 A1 | 7/2013 | Rabinowitz |
| 2013/0190653 A1 | 7/2013 | Alvarez Ramos |
| 2013/0196862 A1 | 8/2013 | Rabinowitz |
| 2013/0210644 A1 | 8/2013 | Stoughton |
| 2013/0225422 A1 | 8/2013 | Rabinowitz |
| 2013/0252824 A1 | 9/2013 | Rabinowitz |
| 2013/0253369 A1 | 9/2013 | Rabinowitz |
| 2013/0261004 A1 | 10/2013 | Ryan |
| 2013/0274116 A1 | 10/2013 | Rabinowitz |
| 2013/0303461 A1 | 11/2013 | Iafrate |
| 2013/0323731 A1 | 12/2013 | Lo |
| 2014/0032128 A1 | 1/2014 | Rabinowitz |
| 2014/0051585 A1 | 2/2014 | Prosen |
| 2014/0065621 A1 | 3/2014 | Mhatre et al. |
| 2014/0087385 A1 | 3/2014 | Rabinowitz |
| 2014/0094373 A1 | 4/2014 | Zimmermann |
| 2014/0100126 A1 | 4/2014 | Rabinowitz |
| 2014/0100134 A1 | 4/2014 | Rabinowitz |
| 2014/0141981 A1 | 5/2014 | Zimmermann |
| 2014/0154682 A1 | 6/2014 | Rabinowitz |
| 2014/0162269 A1 | 6/2014 | Rabinowitz |
| 2014/0193816 A1 | 7/2014 | Rabinowitz |
| 2014/0206552 A1 | 7/2014 | Rabinowitz |
| 2014/0256569 A1 | 9/2014 | Rabinowitz |
| 2014/0329245 A1* | 11/2014 | Spier ................. C12Q 1/686 435/6.12 |
| 2014/0336060 A1 | 11/2014 | Rabinowitz |
| 2015/0051087 A1 | 2/2015 | Rabinowitz |
| 2015/0064695 A1 | 3/2015 | Katz et al. |
| 2015/0072872 A1 | 3/2015 | Rabinowitz |

(56) References Cited

U.S. PATENT DOCUMENTS

| | | |
|---|---|---|
| 2015/0147815 A1 | 5/2015 | Babiarz |
| 2015/0232938 A1 | 8/2015 | Mhatre |
| 2015/0322507 A1 | 11/2015 | Zimmermann |

FOREIGN PATENT DOCUMENTS

| | | |
|---|---|---|
| WO | WO-0179851 | 10/2001 |
| WO | 0190419 A2 | 11/2001 |
| WO | WO-0190419 | 11/2001 |
| WO | 0204672 A2 | 1/2002 |
| WO | WO-0204672 A2 | 1/2002 |
| WO | WO-02055985 | 7/2002 |
| WO | WO02076377 | 10/2002 |
| WO | WO-03031646 | 4/2003 |
| WO | WO-03050532 | 6/2003 |
| WO | 03062441 A1 | 7/2003 |
| WO | WO-03062441 A1 | 7/2003 |
| WO | WO-03102595 | 12/2003 |
| WO | WO-03106623 | 12/2003 |
| WO | WO-2004087863 | 10/2004 |
| WO | WO-2005021793 | 3/2005 |
| WO | 2005035725 A2 | 4/2005 |
| WO | WO-2005035725 A2 | 4/2005 |
| WO | WO-2005100401 | 10/2005 |
| WO | WO-2005123779 | 12/2005 |
| WO | WO-2007057647 | 5/2007 |
| WO | WO-2007062164 | 5/2007 |
| WO | WO-2007070482 | 6/2007 |
| WO | WO-2007132167 | 11/2007 |
| WO | WO2007147074 A2 | 12/2007 |
| WO | WO-2008024473 | 2/2008 |
| WO | WO-2008048931 | 4/2008 |
| WO | WO-2008051928 | 5/2008 |
| WO | 2008081451 A2 | 7/2008 |
| WO | WO-2008081451 A2 | 7/2008 |
| WO | WO-2008115497 | 9/2008 |
| WO | WO-2008135837 | 11/2008 |
| WO | WO-2008157264 | 12/2008 |
| WO | WO-2009009769 | 1/2009 |
| WO | WO-2009013492 | 1/2009 |
| WO | WO-2009013496 | 1/2009 |
| WO | WO-2009019215 | 2/2009 |
| WO | WO-2009019455 | 2/2009 |
| WO | WO-2009030100 | 3/2009 |
| WO | WO-2009032779 | 3/2009 |
| WO | WO-2009032781 | 3/2009 |
| WO | WO-2009033178 | 3/2009 |
| WO | WO-2009091934 | 7/2009 |
| WO | WO-2009092035 | 7/2009 |
| WO | WO-2009105531 | 8/2009 |
| WO | WO-2009146335 | 12/2009 |
| WO | WO-2010017214 | 2/2010 |
| WO | WO2010075459 | 7/2010 |
| WO | WO-2011041485 | 4/2011 |
| WO | WO2011057094 | 5/2011 |
| WO | WO2011087760 | 7/2011 |
| WO | WO-2011146632 | 11/2011 |
| WO | 2012071621 | 6/2012 |
| WO | WO2012083250 | 6/2012 |
| WO | WO-2012088456 | 6/2012 |
| WO | WO-2012108920 | 8/2012 |
| WO | WO2013030577 | 3/2013 |
| WO | WO-2013052557 | 4/2013 |
| WO | 2013130848 | 9/2013 |
| WO | 2014018080 | 1/2014 |

OTHER PUBLICATIONS

U.S. Appl. No. 13/499,086, filed Mar. 29, 2012, Method for Determining the Number of Copies of a Chromosome in the Genome of a Target Individual Using Genetic Data From Genetically Related Individuals, Riggs II, Larry D.

U.S. Appl. No. 13/793,133, filed Mar. 11, 2013, System and Method for Cleaning Noisy Genetic Data From Target Individuals Using Genetic Data From Genetically Related Individuals, Riggs II, Larry D.

U.S. Appl. No. 13/793,186, filed Mar. 11, 2013, System and Method for Cleaning Noisy Genetic Data From Target Individuals Using Genetic Data From Genetically Related Individuals, Lin, Jerry.

U.S. Appl. No. 14/092,457, filed Nov. 27, 2013, System and Method for Cleaning Noisy Genetic Data From Target Individuals Using Genetic Data From Genetically Related Individuals, Riggs II, Larry D.

U.S. Appl. No. 14/156,433, filed Jan. 15, 2014, System and Method for Cleaning Noisy Genetic Data From Target Individuals Using Genetic Data From Genetically Related Individuals, Riggs II, Larry D.

U.S. Appl. No. 14/286,895, filed May 23, 2014, System and Method for Cleaning Noisy Genetic Data From Target Individuals Using Genetic Data From Genetically Related Individuals, Riggs II, Larry D.

U.S. Appl. No. 13/949,212, filed Jul. 23, 2013, System and Method for Cleaning Noisy Genetic Data and Determining Chromosome Copy Number, Riggs II, Larry D.

U.S. Appl. No. 12/918,445, filed Dec. 7, 2010, Methods for Cell Genotyping, Horlick Kenneth R.

U.S. Appl. No. 12/944,260, filed Dec. 20, 2010, Methods for Embryo Characterization and Comparison, Canty, Shannon Cantina.

U.S. Appl. No. 13/057,350, filed Mar. 29, 2011, Methods for Allele Calling and Ploidy Calling, Teixeira Moffat, Jonathan Charles.

U.S. Appl. No. 13/846,111, filed Mar. 18, 2013, Methods for Allele Calling and Ploidy Calling, Sims, Jason M.

U.S. Appl. No. 13/499,086, filed Mar. 29, 2012, Methods for Non-Invasive Prenatal Ploidy Calling, Riggs II, Larry D.

Chiu, Rossa W.K., "Effects of Blood-Processing Protocols on Fetal and Total DNA Quantification in Maternal Plasma", Clinical Chemistry, 47(9), (Jan. 1, 2001), 1607-1613.

Cole Neal, "Hyperglycemia-Induced Membrane Lipid Peroxidation and Elevated Homocysteine Levels Are Poorly Attenuated by Exogenous Folate in Embryonic Chick Brains", Comparative Biochemistry and Physiology, Part B, vol. 150, (2008), 338-343.

De Vries et al., "Diagnostic genome profiling in mental retardation", Am J Hum Genet, 77, p. 606-616, published online Aug. 30, 2005 (Aug. 30, 2005).

Forejt et al., "Segmental trisomy of mouse chromosome 17: introducing an alternative model of Down's syndrome", Genomics, 4(6), p. 647-652, 2003 (2003).

Frost, Mackenzie, "Differential Effects of Chronic Pulsatile Versus Chronic Constant Maternal Hyperglycemia on Fetal Pancreatic B-Cells", Journal of Pregnancy, vol. 2012, Article ID 812094, 8 pgs.

How Many Carbs in a Potato?, [Online]. Retrieved from the Internet:<http.//www.healthguide.org/How-Many-Carbs-In-A-Potato.html>, (Nov. 1, 2014), 3 pgs.

Ido, Yasuo, "Hyperglycemia-Induced Apoptosis in Human Umbilical Vein Endothelial Cells: Inhibition by the AMP-Activated Protein Kinase Activation", Diabetes, vol. 51, Jan. 2002, 159-167.

Liew et al., Clinical Chemistry, 2004, 50(7), 1156-1164.

Miller, Robert, "Homocysteine-Induced Changes in Brain Membrane Composition Correlate with Increased Brain Caspase-3 Activities and Reduced Chick Embryo Viability", Comparative Biochemistry and Physiology, Part B, vol. 136 (2003), 521-532.

Miller, Robert, "Hyperglycemia-Induced Changes in Hepatic Membrane Fatty Acid Composition Correlate with Increased Caspase-3 Activities and Reduced Chick Embryo Viability", Comparative Biochemistry and Physiology, Part B, vol. 141 (2005), 323-330.

Ricciotti Hope, "Eating by Trimester", [Online]. Retrieved from Internet :<http://www.youandyourfamily.com/article.php?story=Eating+by+Trimester>, (Oct. 7, 2014), 3 pgs.

Schoumans et al., "Detection of chromosomal imbalances in children with idiopathic mental retardation by array based comparative genomic hybridisation (array-CGH)", JMed Genet, 42, p. 699-705, Sep. 2005 (Sep. 2005).

(56) References Cited

OTHER PUBLICATIONS

Spiro Alexander, "A Bead-Based Method for Multiplexed Identification and Quantitation of DNA Sequences Using Flow Cytometry", Applied and Environmental Microbiology, Oct. 2000, vol. 66, No. 10, 4258-4265.
U.S. Appl. No. 13/683,604, Office Action mailed Nov. 22, 2013, 81 pages.
Wagner, Jasenka et al. "Non-invasive prenatal paternity testing from maternal blood", International Journal of Legal Medicine, Springer, Berlin, DE, vol. 123, No. 1, Oct. 24, 2008 (Oct. 24, 2008), pp. 75-79.
"Guideline related to genetic examination", Societies Related to Genetic Medicine, Japanese Society for Genetic Counseling, Japanese Society for Gene Diagnosis and Therapy, Japan Society of Obstetrics an, 2003, 2-15.
Ellison, Aaron M., "Bayesian Inference in Ecology", Ecology Letters, 2004, vol. 7, p. 509-520.
Fredriksson, et al., "Multiplex amplification of all coding sequences within 10 cancer genes by Gene-Collector", Nucleic Acids Research, 2007, vol. 35, No. 7 e47, 1-6.
Holleley, et al., "Multiplex Manager 1.0: a Cross-Platform Computer Program that Plans and Optimizes Multiplex PCR", BioTechniques46:511-517 (Jun. 2009), 511-517.
Sasabe, Yutaka, "Genetic Diagnosis of Gametes and Embryos Resulting from ART", Japanese Journal of Fertility and Sterility, 2001, vol. 46, No. 1, p. 43-46.
Shen, et al., "High-quality DNA sequence capture of 524 disease candidate genes", High-quality DNA sequence capture of 524 disease candidate genes, Proceedings of the National Academy of Sciences, vol. 108, No. 16, Apr. 5, 2011 (Apr. 5, 2011), pp. 6549-6554.
Aoki, Yasuhiro , "Statistical and Probabilistic Bases of Forensic DNA Testing", The Journal of the Iwate Medical Association, 2002, vol. 54, p. 81-94.
Muse, Spencer V. , "Examining rates and patterns of nucleotide substitution in plants", Plant Molecular Biology 42: 25-43, 2000.
Tamura, et al., "Sibling Incest and formulation of paternity probability: case report", Legal Medicine, 2000, vol. 2, p. 189-196.
"Blast of AAAAAAAAATTTAAAAAAAAATTT(http://blast.ncbi.nlm.nih.gov/Blast.cgi, downloaded May 4, 2015)", May 4, 2015.
"db SNP rs2056688 (http://www.ncbi.nlm.nih.gov/projects/SNP/snp_ref.cgi?rs=2056688, downloaded May 4, 2015", 2015.
"Declaration by Dr. Zimmerman of Oct. 30, 2014 filed in U.S. Appl. No. 14/044,434", Oct. 30, 2014.
"European Application No. 014198110, European Search Report Mailed Apr. 28, 2015, 3 pages."
"How ManyCarbs in a Potato?, [Online]", Retrieved from theInternet:<http://www.healthguide.org/How-Many-Carbs-ln-A-Potato.html>, Nov. 1, 2014, 3 pgs.
"Merriam-Webster.com (http://www.merriam-webster.com/dictionary/universal, downloaded Jul. 23, 2014)", Jul. 23, 2014.
"www.fatsecret.com (printed from internet Nov. 1, 2014)", Nov. 1, 2014.
Bentley, David R et al., "Accurate Whole Human Genome Sequencing Using Reversible Terminator Chemistry", Nature, 456, 6, 2008, 53-59.
Bianchi, D W. et al., "Fetal gender and aneuploidy detection using fetal cells maternal blood: analysis of NIFTY I data", Prenat Diagn 2002; 22, 2002, 609-615.
Chiu, Rossa W. et al., "Effects of Blood-Processing Protocols on Fetal and Total DNA Quantification in Maternal Plasma", Clinical Chemistry, 47(9), 2001, 1607-1613.
Cole, Neal W. et al., "Hyperglycemia-Induced Membrane Lipid Peroxidation and Elevated Homocysteine Levels Are Poorly Attenuated by Exogenous Folate in Embryonic Chick Brains", Comparative Biochemistry and Physiology, Part B, 150, 2008, 338-343.
Cross, Jillian et al., "Resolution of trisomic mosaicism in prenatal diagnosis: estimated performance of a 50K SNP microarray", Prenat Diagn 2007; 27, 2007, 1197-1204.

De Vries, et al., "Diagnostic genome profiling in mental retardation", Am J Hum Genet, 77, published online Aug. 30, 2005, 2005, 606-616.
Ding, C et al., "Direct molecular haplotyping of long-range genomic DNA with M1-PCR", PNAS 100(13), 2003, 7449-7453.
Fan, et al., "Whole-genome molecular haplotyping of single cells", Nature Biotechnology, vol. 29, No. 1, Jan. 1, 2011, 51-57.
Forejt, et al., "Segmental trisomy of mouse chromosome 17: introducing an alternative model of Down's syndrome", Genomics, 4(6), 2003, 647-652.
Frost, MacKenzie S et al., "Differential Effects of Chronic Pulsatile Versus Chronic Constant Maternal Hyperglycemia on Fetal Pancreatic B-Cells", Journal of Pregnancy, 2012,, Article ID 812094, 2012, 8.
Handyside, et al., "Isothermal whole genome amplification from single and small number of cells: a new era for preimplantation genetic diagnosis of inherited disease", Molecular Human Reproduction vol. IO, No. 10 pp. 767-772, 2004.
Harismendy, O et al., "Method for Improving Sequence Coverage Uniformity of Targeted Genomic Intervals Amplified by LR-PCR Using Illumina GA Sequencing-By-Synthesis Technology", Bio Techniques, 46(3), 2009, 229-231.
Howie, et al., "Fast and accurate genotype imputation in genome-wide association studies through pre-phasing", Nature Genetics, vol. 44, No. 8, Jul. 22, 2012, 955-959.
Ido, Yasuo et al., "Hyperglycemia-Induced Apoptosis in Human Umbilical Vein Endothelial Cells: Inhibition by the AMP-Activated Protein Kinase Activation", Diabetes, 51, 2002, 159-167.
Illumina Catalog, , "Paired-End Sample Preparation Guide, Illumina Catalog# PE-930-1 001, Part# 1005063 Rev. E", 2011, 1-40.
Liew, Michael et al., "Genotyping of Single-Nucleotide Polymorphisms", Clinical Chemistry, 50(7), 2004, 1156-1164.
Lo, "Non-Invasive Prenatal Diagnosis by Massively parallel Sequencing of Maternal Plasma DNA", Open Biol 2: 120086, 2012, 1-5.
Lo, et al., "Prenatal Sex Determination by DNA Amplification from Maternal Peripheral Blood", The Lancet,2, 8676, 1989, 363-1365.
Miller, Robert , "Hyperglycemia-Induced Changes in Hepatic Membrane Fatty Acid Composition Correlate with Increased Caspase-3 Activities and Reduced Chick Embryo Viability", Comparative Biochemistry and Physiology, Part B, 141, 2005, 323-330.
Miller, Robert R , "Homocysteine-Induced Changes in Brain Membrane Composition Correlate with Increased Brain Caspase-3 Activities and Reduced Chick Embryo Viability", Comparative Biochemistry and Physiology Part B, 136, 2003, 521-532.
PCT/US2014/051926, , "International Search Report mailed", Dec. 9, 2014, 3 pgs.
Price, T.S. et al., ""SW-ARRAY: a dynamic programming solution for the identification of copy-number changes in genomic DNA using array comparative genome hybridization data",", Nucleic Acids Research, vol. 33, No. 11, Jun. 16, 2005 (Jun. 16, 2005), pp. 3455-3464.
Ricciotti, Hope, "Eating by Trimester", Online]. Retrieved from Internet:<http://www.youandyourfamily.com/article.php?story=Eating+by+Trimester>, 2014, 3.
Roux, K , "Optimization and Troubleshooting in PCR", PCR Methods Appl. 4,, 1995, 185-194.
Ryan, et al., "The importance of phase information for human genomics", Nature Reviews Genetics, vol. 12, No. 3, Mar. 1, 2011.
Rychlik, et al., "Optimization of the annealing temperature for DNA amplification in vitro", Nucleic Acids Research, 18(21), 1990, 6409-6412.
Schoumans, J et al., "Detection of chromosomal imbalances in children with idiopathic mental retardation by array based comparative genomic hybridisation (array-CGH)", JMed Genet, 42, 2005, 699-705.
Sherlock, J et al., "Assessment of Diagnostic Quantitative Fluorescent Multiplex Polymerase Chain Reaction Assays Performed on Single Cells", Annals of Human Genetics,62, 1, 1998, 9-23.
Su, S.Y. et al., ""Inferring combined CNV/SNP haplotypes from genotype data"", Bioinformatics, vol. 26, No. 11,1, Jun. 6, 2010, 1437-1445.

(56) References Cited

OTHER PUBLICATIONS

Sun, Guihua et al., "SNPs in human miRNA genes affect biogenesis and function", RNA, 15(9), 2009, 1640-1651.
Varley, Katherine Elena et al., "Nested Patch PCR Enables Highly Multiplexed Mutation Discovery in Candidate Genes", Genome Res., 18(11), 2008, 1844-1850.
Wagner, Jasenka et al., "Non-Invasive Prenatal Paternity Testing from Maternal Blood", Int. J. Legal Med., 123, 2009, 75-79.
Merriam-Webster (attached, available at http://www.merriam-webster.com/medical/stimulant, accessed Mar. 14, 2016).
PRNewswire (Research Suggests Daily Consumption of Orange Juice Can Reduce Blood Pressure and May Provide Beneficial Effects to Blood Vessel Function: New Study Identified Health Benefits in Orange Juice, Dec. 8, 2010).
The Bump (Panorama Test, Jul. 1, 2013).
What to Expect (Weird Harmony results, May 1, 2015).
Wikipedia (attached, available at https://en.wikipedia.org/wiki/Stimulant, accessed Mar. 14, 2016).
Bevinetto, Gina, Bevinetto (5 Foods All Pregnant Women Need, American Baby, available at http://www.parents.com/pregnancy/mybody/nutrition/5greatpregnancyfoods/, Apr. 15, 2008).
Echeverri, et al., "Caffeine's Vascular Mechanisms of Action", International Journal of Vascular Medicine vol. 2010(2010), 10 pages, Aug. 25, 2010.
Liao, J. et al., "An Alternative Linker-Mediated Polymerase Chain Reaction Method Using a Dideoxynucleotide to Reduce Amplification Background", Analytical Biochemistry 253, 137-139 (1997).
Morand, et al., "Hesperidin contributes to the vascular protective effects of orange juice: a randomized crossover study in healthy volunteers", Am J Clin Nutr. Jan. 2011;93(1):73-80. Epub Nov. 10, 2010.
O'Malley, R et al., "An adapter ligation-mediated PCR method for high-throughput mapping of T-DNA inserts in the Arabidopsis genome", Nat. Protoc. 2, 2910-2917 (2007).
Hall, M., "Panorama Non-Invasive Prenatal Screening for Microdeletion Syndromes", Apr. 1, 2014 (Apr. 1, 2014), XP055157224, Retrieved from the Internet: URL:http://www.panoramatest.com/sites/default/files/files/PanoramaMicrodeletionsWhite Paper-2.pdf [retrieved on Dec. 8, 2014].
Forshew, et al., "Noninvasive Identification and Monitoring of Cancer Mutations by Targeted Deep Sequencing of Plasma DNA", Noninvasive identification and monitoring of cancer mutations by targeted deep sequencing of plasma DNA. Sci. Transl. Med. 4, 136 30 (2012)., 1-12.
Hayden, et al., "Multiplex-Ready PCR: A new method for multiplexed SSR and SNP genotyping", BMC Genomics 2008, 9(80), 1-12.
Nygren, et al., "Quantification of Fetal DNA by Use of Methylation-Based DNA Discrimination", Clinical Chemistry 56:10 1627-1635 (2010).
Srinivasan, et al., "Noninvasive Detection of Fetal Subchromosome Abnormalities via Deep Sequencing of Maternal Plasma", The American Journal of Human Genetics 92, 167-176, Feb. 7, 2013.
"Fixed Medium", dictionary definition, Academic Press Dictionary of Science and Technology [retrieved on Nov. 18, 2009]. Retrieved from the Internet: <URL: www.credoreference.com/entry/apdst/fixed_medium>, (1996),1 pg.
"Finishing the Euchromatic Sequence of the Human Genome", Nature vol. 431, (Oct. 21, 2004),931-945.
"Nucleic Acids, Linkers and Primers: Random Primers" New England BioLabs 1998/99 Catalog, (1998), 121 and 284.
"Competitive PCR Guide", TaKaRa Biomedicals, Lit. # L0126 Rev. Aug. 1999, 9 pgs.
"Genetics Home Reference", http://ghr.nlm.nih.gov/handbook/genomicresearch/snp, (Feb. 28, 2014),1-2.
"Ion AmpliSeq Comprehensive Cancer Panel", product brochure, Life Technologies Corporation. Retrieved from the Internet <URL: https://tools.lifetechnologies.com/content/sfs/brochures/Ion_CompCancerPanel_Flyer.pdf>, (2012),2 pgs.

"Ion AmpliSeq Designer Provides Full Flexibility to Sequence Genes of Your Choice", product brochure, Life Technologies Corporation. Retrieved from the Internet <URL: http://tools.lifetechnologies.com/content/sfs/brochures/IonAmpliSeq_CustomPanels_AppNote_CO111038_06042012.pdf>, (2012),4 pgs.
"Primer3", information sheet, Sourceforge.net. [retrieved on Nov. 12, 2012]. Retrieved from the Internet: <URL: http://primer3.sourceforge.net/>, (Oct. 26, 2009), 1 pg.
Abidi, et al., "Leveraging XML-based Electronic Medical Records to Extract Experimental Clinical Knowledge: An Automated approach to generate cases for medical case-based reasoning systems", International Journal of Medical Informatics, 68, (2002),187-203.
Agarwal, et al., "Commercial Landscape of Noninvasive Prenatal Testing in the United States", Prenatal Diagnosis, 33, (2013),521-531.
Alkan, et al., "Personalized Copy Number and Segmental Duplication Maps Using Next-Generation Sequencing", Nature Genetics, vol. 41, No. 10, (Oct. 2009),1061-1068.
Allaire, "Mate Selection by Selection Index Theory", Theor. Appl. Genet., 57, (1980),267-272.
Allawi, et al., "Thermodynamics of internal C•T Mismatches in DNA", Nucleic Acids Research, vol. 26, No. 11, (1998),2694-2701.
Ashoor, et al., "Chromosome-Selective Sequencing of Maternal Plasma Cell-Free DNA for First-Trimester Detection of Trisomy 21 and Trisomy 18", American Journal of Obstetrics & Gynecology, 206, (Apr. 2012),322.e1-322.e5.
Ashoor, et al., "Fetal Fraction in Maternal Plasma Cell-Free DNA at 11-13 Weeks' Gestation: Effect of Maternal and Fetal Factors", Fetal Diagnosis Therapy, (May 4, 2012),1-7.
Bada, et al., "Computational Modeling of Structural Experimental Data", Methods in Enzymology, vol. 317, (2000),470-491.
Beaumont, et al., "The Bayesian Revolution in Genetics", Nature Reviews Genetics, vol. 5, (Apr. 2004),251-261.
Beer, et al., "The Biological Basis of Passage of Fetal Cellular Material into the Maternal Circulation", Annals New York Academy of Sciences, 731, (1994),21-35.
Beerenwinkel, et al., "Geno2pheno: Estimating Phenotypic Drug Resistance from HIV-1 Genotypes", Nucleic Acids Research, vol. 31, No. 13, (2003),3850-3855.
Beerenwinkel, et al., "Methods for Optimizing Antiviral Combination Therapies", Bioinformatics, vol. 19, Suppl. 1, (2003),i16-i25.
Benn, et al., "Non-Invasive prenatal Diagnosis for Down Syndrome: the Paradigm Will Shift, but Slowly", Ultrasound Obstet. Gynecol., 39, (2012),127-130.
Benn, et al., "Non-Invasive Prenatal Testing for Aneuploidy: Current Status and Future Prospects", Ultrasound Obstet. Gynecol., 42, (2013),15-33.
Bermudez, et al., "Single-cell sequencing and mini-sequencing for preimplantation genetic diagnosis", Prenatal Diagnosis, vol. 23, (2003),669-677.
Birch, et al., "Accurate and Robust Quantification of Circulating Fetal and Total DNA in Maternal Plasma from 5 to 41 Weeks of Gestation", Clinical Chemistry, vol. 51, No. 2, (2005),312-320.
Bisignano, et al., "PGD and Aneuploidy Screening for 24 Chromosomes: Advantages and Disadvantages of Competing Platforms", Reproductive BioMedicine Online, 23, (2011),677-685.
Bodenreider, "The Unified Medical Language System (UMLS): Integrating Biomedical Terminology", Nucleic Acids Research, vol. 32 (Database issue), (2004),D267-D270.
Breithaupt, "The Future of Medicine", EMBO Reports, vol. 2, No. 61, (2001),465-467.
Brownie, et al., "The Elimination of Primer-Dimer Accumulation in PCR", Nucleic Acids Research, vol. 25, No. 16, (1997),3235-3241.
Cairns, et al., "Homozygous Deletions of 9p21 in Primary Human Bladder Tumors Detected by Comparative Multiplex Polymerase Chain Reaction", Cancer Research vol. 54, (1994), 1422-1424.
Caliendo, et al., "Multiplex PCR and Emerging Technologies for the Detection of Respiratory Pathogens", Clinical Infection Diseases vol. 52, Suppl. 4, (2011), S326-S330.

(56) References Cited

OTHER PUBLICATIONS

Carnevale, et al., "Attitudes of Mexican Geneticists Towards Prenatal Diagnosis and Selective Abortion", American Journal of Medical Genetics, 75, (1998),426-431.

Chen, et al., "Noninvasive Prenatal Diagnosis of Fetal Trisomy 18 and Trisomy 13 by Maternal Plasma DNA Sequencing", PLoS ONE, vol. 6, Issue 7, e21791, (Jul. 2011),7 pgs.

Chetty, et al., "Uptake of Noninvasive Prenatal Testing (NIPT) in Women Following Positive Aneuploidy Screening", Prenatal Diagnosis, 33, (2013),542-546.

Chiu, et al., "Maternal Plasma DNA Analysis with Massively Parallel Sequencing by Litigation for Noninvasive Prenatal Diagnosis of Trisomy 21", Clinical Chemistry, vol. 56, No. 3, (2010),459-463.

Chiu, et al., "Non-Invasive Prenatal Assessment of Trisomy 21 by Multiplexed Maternal Plasma DNA Sequencing: Large Scale Validity Study", BMJ, vol. 342, c7401, (2011),9 pgs.

Chiu, et al., "Non-Invasive Prenatal Diagnosis by Single Molecule Counting Technologies", Trends in Genetics, vol. 25, No. 7, (2009),324-331.

Chiu, et al., "Noninvasive Prenatal Diagnosis of Fetal Chromosomal Aneuploidy by Massively Parallel Genomic Sequencing of DNA in Maternal Plasma", PNAS, vol. 105, No. 51 (with Supporting Information), (Dec. 23, 2008),23 pgs.

Chu, et al., "A Novel Approach Toward the Challenge of Accurately Quantifying Fetal DNA in Maternal Plasma", Prenatal Diagnosis, 30, (2010),1226-1229.

Chu, et al., "Statistical Considerations for Digital Approaches to Non-Invasive Fetal Genotyping", Bioinformatics (Advance Access publication), vol. 26, No. 22, (2010),2863-2866.

Chu, et al., "Statistical Model for Whole Genome Sequencing and its Application to Minimally Invasive Diagnosis of Fetal Genetic Disease", Bioinformatics, vol. 25, No. 10, (2009),1244-1250.

Colella, et al., "QuantiSNP: an Objectives Bayes Hidden-Markov Model to Detect and Accurately Map Copy Number Variation Using SNP Genotyping Data", Nucleic Acids Research, vol. 35, No. 6, (2007),2013-2025.

Cossu, et al., "Rh D/d Genotyping by Quantitative Polymerase Chain Reaction and Capillary Zone Electrophoresis", Electrophoresis, 17, (1996),1911-1915.

Coyle, et al., "Standards for Detailed Clinical Models as the Basis for Medical Data Exchange and Decision Support", International Journal of Medical Informatics, 69, (2003),157-174.

D'Aquila, et al., "Maximizing Sensitivity and Specificity of PCR by Pre-Amplification Heating", Nucleic Acids Research, vol. 19, No. 13, (1991),3749.

Daruwala, et al., "A Versatile Statistical Analysis Algorithm to Detect Genome Copy Number Variation", PNAS, vol. 101, No. 46, (Nov. 16, 2004),16292-16297.

Deangelis, et al., "Solid-phase Reversible Immobilization for the Isolation of PCR Products", Nucleic Acids Research, vol. 23, No. 22, (Nov. 25, 1995),4742-4743.

Devaney, et al., "Noninvasive Fetal Sex Determination Using Cell-Free Fetal DNA: A Systematic Review and Meta-analysis", JAMA, vol. 306, No. 6, (Aug. 10, 2011),627-636.

Dhallan, et al., "A Non-Invasive Test for Prenatal Diagnosis Based on Fetal DNA Present in Maternal Blood: A Preliminary Study", Lancet, vol. 369, (Feb. 10, 2007),474-481.

Dhallan, et al., "Methods to Increase the Percentage of Free Fetal DNA Recovered from the Maternal Circulation", JAMA, vol. 291, No. 9, (Mar. 3, 2004),1114-1119.

Dieffenbach, et al., "General Concepts for PCR Primer Design", PCR Methods Appl. vol. 3, (1993), 30-37.

Dohm, et al., "Substantial Biases in Ultra-Short Read Data Sets From High-Throughput DNA Sequencing", Nucleic Acids Research, vol. 36, No. 16, e105, (2008),10 pgs.

Dolganov, et al., "A Novel Method of Gene Transcript Profiling in Airway Biopsy Homogenates Reveals Increased Expression of a Na +—K+-CL-Contransporter (NKCC1) in Asthmatic Subjects", Genome Res. 2001, vol. 11, (2001),1473-1483.

Donoso, et al., "Current Value of Preimplantation Genetic Aneuploidy Screening in IVF", Human Reproduction Update, vol. 13, No. 1, (2007),15-25.

Enrich, et al., "Noninvasive Detection of Fetal Trisomy 21 by Sequencing of DNA in Maternal Blood: A Study in a Clinical Setting", American Journal of Obstetrics & Gynecology, 204, (2011),205.e1-205.e11.

Eichler, et al., "Mild Course of Fetal Rh D Haemolytic Disease due to Maternal Alloimmunisation to Paternal HLA Class I and II Antigens", Vox Sang, 68, (1995),243-247.

Ellonen, et al., "Development of SNP Microarray for Supplementary Paternity Testing", International Congress Series, vol. 1261, (2004),12-14.

European Application No. 06838311.6, Communication and Extended European Search Report mailed Dec. 30, 2008, 8 pgs.

European Application No. 08742125.1, Communication pursuant to Article 94(3) EPC and Examination Report mailed Feb. 12, 2010, 5 pgs.

Fan, "Highly Parallel Genomic Assay", Nature Reviews, vol. 7, Aug. 2006, 632-644.

Fan, et al., "Noninvasive Diagnosis of Fetal Aneuploidy by Shotgun Sequencing DNA from Maternal Blood", PNAS, vol. 105, No. 42, (Oct. 21, 2008),16266-16271.

Fan, et al., "Non-Invasive Prenatal Measurement of the Fetal Genome", Nature, doi:10.1038/nature11251 (with Supplemental Information), (2012),26 pgs.

Fazio, et al., "Identification of RAPD Markers Linked to Fusarium Crown and Root Rot Resistance (Fri) in Tomato", Euphytica 105, (Mar. 1, 1999),205-210.

Fiorentino, et al., "Development and Clinical Application of a Strategy for Preimplantation Genetic Diagnosis of Single Gene Disorders Combined with HLA Matching", Molecular Human Reproduction (Advance Access publication), vol. 10, No. 6, (2004),445-460.

Fiorentino, et al., "Short Tandem Repeats Haplotyping of the HLA Region in Preimplantation HLA Matching", European Journal of Human Genetics, 13, (2005),953-958.

Fiorentino, et al., "Strategies and Clinical Outcome of 250 Cycles of Preimplantation Genetic Diagnosis for Single Gene Disorders", Human Reproduction, vol. 21, No. 3, (2006),670-684.

Freeman, et al., "Copy Number Variation: New Insights in Genome Diversity", Genome Research, 16, (2006),949-961.

Ganshirt-Ahlert, et al., "Fetal DNA in Uterine Vein Blood", Obstetrics & Gynecology, 80, (1992),601-603.

Ganshirt-Ahlert, et al., "Ratio of Fetal to Maternal DNA is Less Than 1 in 5000 at different Gestational Ages in Maternal Blood", Clinical Genetics, 38, (1990),38-43.

Ganshirt-Ahlert, et al., "Three Cases of 45,X/46,XYnf Mosaicism", Human Genetics, 76, (1987),153-156.

Gardina, et al., "Ploidy Status and Copy Number Aberrations in Primary Glioblastomas Defined by Integrated Analysis of Allelic Ratios, Signal Ratios and Loss of Heterozygosity Using 500K SNP Mapping Arrays", BMC Genomics, vol. 9, No. 489 (doi:10.1186/1471-2164-9-489), (2008),16 pgs.

Ghanta, et al., "Non-Invasive Prenatal Detection of Trisomy 21 Using Tandem Single Nucleotide Polymorphisms", PLoS ONE, vol. 5, Issue 10, e13184, (Oct. 2010), 10 pgs.

Gjertson, et al., "Assessing Probability of Paternity and the Product Rule in DNA Systems", Genetica, 96, (1995),89-98.

Greenwalt, et al., "The Quantification of Fetomaternal Hemorrhage by an Enzyme-Linked Antibody Test with Glutaraldehyde Fixation", Vox Sang, 63, (1992),268-271.

Guerra, et al., "Terminal Contributions for Duplex Oligonucleotide Thermodynamic Properties in the Context of Nearest Neighbor Models", Biopolymers, vol. 95, No. 3, (2011),194-201.

Guetta, et al., "Analysis of Fetal Blood Cells in the Maternal Circulation: Challenges, Ongoing Efforts, and Potential Solutions", Stem Cells and Development, 13, (2004),93-99.

Guichoux, et al., "Current Trends in Microsatellite Genotyping", Molecular Ecology Resources, vol. 11, (2011), 591-611.

(56) References Cited

OTHER PUBLICATIONS

Hara, et al., "Subtractive cDNA Cloning Using Oligo(dT)30-latex and PCR: Isolation of cDNA Clones Specific to Undifferentiated Human Embryonal Carcinoma Cells", Nucleic Acids Research, vol. 19, No. 25, (1991),7097-7104.
Hardenbol, et al., "Highly multiplexed molecular inversion probe genotyping: Over 10,000 targeted SNP's genotyped in a singled tube assay", Genome Research, 15, (Jan. 1, 2005), 269-275.
Hardenbol, et al., "Multiplexed Genotyping With Sequence-Tagged Molecular Inversion Probes", Nature Biotechnology vol. 21, No. 6, (Jun. 2003),673-678.
Harper, et al., "Recent Advances and Future Developments in PGD", Prenatal Diagnosis, 19, (1999), 1193-1199.
Harton, et al., "Preimplantation Genetic Testing for Marfan Syndrome", Molecular Human Reproduction, vol. 2, No. 9, (1996),713-715.
Hellani, et al., "Clinical Application of Multiple Displacement Amplification in Preimplantation Genetic Diagnosis", Reproductive BioMedicine Online, vol. 10, No. 3, (2005),376-380.
Hellani, et al., "Multiple displacement amplification on single cell and possible PGD applications", Molecular Human Reproduction (advance access publication), vol. 10, No. 11, (Oct. 1, 2004),847-852.
Hojsgaard, et al., "Bifrost—Block Recursive Models Induced from Relevant Knowledge, Observations, and Statistical Techniques", Computational Statistics & Data Analysis, 19, (1995),155-175.
Hollox, et al., "Extensive Normal Copy Number Variation of a β-Defensin Antimicrobial-Gene Cluster", Am. J. Hum. Genet., 73, (2003),591-600.
Homer, et al., "Resolving Individuals Contributing Trace Amounts of DNA to Highly Complex Mixtures Using High-Density SNP Genotyping Microarrays", PLOS Genetics, vol. 4, Issue 8, e1000167, (Aug. 2008),9 pgs.
Hoogendoorn, et al., "Genotyping Single Nucleotide Polymorphisms by Primer Extension and High Performance Liquid Chromatography", Hum Genet vol. 104, (1999), 89-93.
Hu, et al., "Aneuploidy Detection in Single Cells Using DNA Array-Based Comparative Genomic Hybridization", Molecular Human Reproduction, vol. 10, No. 4, (2004),283-289.
International Application No. PCT/US2006/045281, International Preliminary Report on Patentability mailed May 27, 2008, 1 pg.
International Application No. PCT/US2006/045281, International Search Report and Written Opinion mailed Sep. 28, 2007, 7 pgs.
International Application No. PCT/US2008/003547, International Search Report mailed Apr. 15, 2009, 5 pgs.
International Application No. PCT/US2009/034506, International Search Report mailed Jul. 8, 2009, 2 pgs.
International Application No. PCT/US2009/045335, International Search Report mailed Jul. 27, 2009, 1 pg.
International Application No. PCT/US2009/052730, International Search Report mailed Sep. 28, 2009, 1 pg.
International Application No. PCT/US2010/050824, International Search Report mailed Nov. 15, 2010, 2 pgs.
International Application No. PCT/US2011/037018, International Search Report mailed Sep. 27, 2011, 2 pgs.
International Application No. PCT/US2011/061506, International Search Report mailed Mar. 16, 2012, 1 pgs.
International Application No. PCT/US2011/066938, International Search Report mailed Jun. 20, 2012, 1 pg.
International Application No. PCT/US2012066339, International Search Report mailed Mar. 5, 2013, 1 pg.
International Application No. PCT/US2013/028378, International Search Report and Written Opinion mailed May 28, 2013, 11 pgs.
International Application No. PCT/US2013/57924, International Search Report and Written Opinion mailed Feb. 18, 2014, 8 pgs.
Johnson, et al., "Comprehensive Analysis of Karyotypic Mosaicism Between Trophectoderm and Inner Cell Mass", Molecular Human Reproduction, vol. 16, No. 12, (2010),944-949.

Johnson, et al., "Preclinical Validation of a Microarray Method for Full Molecular Karyotyping of Blastomeres in a 24-h Protocol", Human Reproduction, vol. 25, No. 4, (2010),1066-1075.
Kaplinski, et al., "MultiPLX: Automatic Grouping and Evaluation of PCR Primers", Bioinformatics (Advance Access publication), vol. 21, No. 8, (2005),1701-1702.
Kazakov, et al., "Extracellular DNA in the Blood of Pregnant Women", Tsitologia, vol. 37, No. 3, (1995),8 pgs.
Kijak, et al., "Discrepant Results in the Interpretation of HIV-1 Drug-Resistance Genotyic Data Among Widely Used Algorithms", HIV Medicine, 4, (2003),72-78.
Konfortov, et al., "An Efficient Method for Multi-Locus Molecular Haplotyping", Nucleic Acids Research, vol. 35, No. 1, e6, (2007),8 pgs.
Kuliev, et al., "Thirteen Years' Experience on Preimplantation Diagnosis: Report of the Fifth International Symposium on Preimplantation Genetics", Reproductive BioMedicine Online, vol. 8, No. 2, (2004),229-235.
Lambert-Messerlian, et al., "Adjustment of Serum Markers in First Trimester Screening", Journal of Medical Screening, vol. 16, No. 2, (2009),102-103.
Lathi, et al., "Informatics Enhanced SNP Microarray Analysis of 30 Miscarriage Samples Compared to Routine Cytogenetics", PLoS ONE, vol. 7, Issue 3, e31282, (Mar. 2012),5 pgs.
Leary, et al., "Detection of Chromosomal Alterations in the Circulation of Cancer Patients with Whole-Genome Sequencing", Science Translational Medicine, vol. 4, Issue 162, (Nov. 28, 2012),12 pgs.
Li, et al., "Highly Multiplexed Amplicon Preparation for Targeted Re-Sequencing of Sample Limited Specimens Using the Ion AmpliSeq Technology and Semiconductor Sequencing", Proceedings of the Annual Meeting of the American Society of Human Genetics [retrieved on Oct. 30, 2012]. Retrieved from the Internet: <URL: http://www.ashg.org/2012meeting/abstracts/fulltext/f120121811.htm>, (2012),1 pg.
Li, et al., "Non-Invasive Prenatal Diagnosis Using Cell-Free Fetal DNA in Maternal Plasma from PGD Pregnancies", Reproductive BioMedicine Online, vol. 19, No. 5, (2009), 714-720.
Li, et al., "Size Separation of Circulatory DNA in Maternal Plasma Permits Ready Detection of Fetal DNA Polymorphisms", Clinical Chemistry, vol. 50, No. 6, (2004),1002-1011.
Liao, et al., "Targeted Massively Parallel Sequencing of Maternal Plasma DNA Permits Efficient and Unbiased Detection of Fetal Alleles", Clinical Chemistry, vol. 57, No. 1, (2011),92-101.
Lindroos, et al., "Genotyping SNPs by Minisequencing Primer Extension Using Oligonucleotide Microarrays", Methods in Molecular Biology, vol. 212—Single Nucleotide Polymorphisms: Methods and Protocols, P-K Kwok (ed.), Humana Press, Inc., Totowa, NJ, (2003),149-165.
Lo, "Fetal Nucleic Acids in Maternal Plasma: Toward the Development of Noninvasive Prenatal Diagnosis of Fetal Chromosomal Aneuploidies", Ann. N.Y. Acad. Sci., 1137, (2008),140-143.
Lo, "Non-Invasive Prenatal Diagnosis by Massively parallel Sequencing of Maternal Plasma DNA", Open Biol 2: 120086, (2012),1-5.
Lo, et al., "Detection of Fetal RhD Sequence from Peripheral Blood of Sensitized RhD-Negative Pregnant Women", British Journal of Haematology, 87, (1994),658-660.
Lo, et al., "Detection of Single-Copy Fetal DNA Sequence from Maternal Blood", The Lancet, vol. 335, (Jun. 16, 1990), 1463-1464.
Lo, et al., "Digital PCR for the Molecular Detection of Fetal Chromosomal Aneuploidy", PNAS, vol. 104, No. 32, (Aug. 7, 2007), 13116-13121.
Lo, et al., "Fetal Nucleic Acids in Maternal Blood: the Promises", Clin. Chem. Lab. Med., vol. 50, No. 6, (2012),995-998.
Lo, et al., "Free Fetal DNA in Maternal Circulation", JAMA, vol. 292, No. 23 (Letters to the Editor), (Dec. 15, 2004),2835-2836.
Lo, et al., "Maternal Plasma DNA Sequencing Reveals the Genome-Wide Genetic and Mutational Profile of the Fetus", Science Translational Medicine, vol. 2, Issue 61, (Dec. 8, 2010), 13 pgs.
Lo, et al., "Plasma Placental RNA Allelic Ratio Permits Noninvasive Prenatal Chromosomal Aneuploidy Detection", Nature Medicine, vol. 13, No. 2, (Feb. 2007),218-223.

(56) References Cited

OTHER PUBLICATIONS

Lo, et al., "Prenatal Determination of Fetal RhD Status by Analysis of Peripheral Blood of Rhesus Negative Mothers", The Lancet, vol. 341, (Letters to the Editor), (May 1, 1993), 1147-1148.
Lo, et al., "Prenatal Determination of Fetal Rhesus D Status by DNA Amplification of Peripheral Blood of Rhesus-Negative Mothers", Annals New York Academy of Sciences, 731, (Sep. 7, 1994),229-236.
Lo, et al., "Prenatal Sex Determination by DNA Amplification from Maternal Peripheral Blood", The Lancet, vol. 2, No. 8676, (Dec. 9, 1989), 1363-1365.
Lo, et al., "Presence of Fetal DNA in Maternal Plasma and Serum", The Lancet, vol. 350, (Aug. 16, 1997),485-487.
Lo, et al., "Quantitative Analysis of Fetal DNA in Maternal Plasma and Serum: Implications for Noninvasive Prenatal Diagnosis", Am. J. Hum. Genet. 62, (1998),768-775.
Lo, et al., "Rapid Clearance of Fetal DNA from Maternal Plasma", Am. J. Hum. Genet., 64, (1999),218-224.
Lo, et al., "Strategies for the Detection of Autosomal Fetal DNA Sequence from Maternal Peripheral Blood", Annals New York Academy of Sciences, 731, (1994),204-213.
Lo, et al., "Two-way cell traffic between mother and fetus: biologic and clinical implications", Blood, vol. 88, No. 11, (Dec. 1, 1996),4390-4395.
Lun, et al., "Noninvasive Prenatal Diagnosis of Monogenic Diseases by Digital Size Selection and Relative Mutation Dosage on DNA in Maternal Plasma", PNAS, vol. 105, No. 50, (Dec. 16, 2008), 19920-19925.
Maniatis, et al., In: Molecular Cloning: A Laboratory Manual, Cold Spring Harbor Laboratory, New York, Thirteenth Printing, (Sep. 1986),458-459.
Mansfield, "Diagnosis of Down Syndrome and Other Aneuploidies Using Quantitative Polymerase Chain Reaction and Small Tandem Repeat Polymorphisms", Human Molecular Genetics, vol. 2, No. 1, (1993),43-50.
May, "How Many Species Are There on Earth?", Science vol. 241, (Sep. 16, 1988), 1441-1449.
McCray, et al., "Aggregating UMLS Semantic Types for Reducing Conceptual Complexity", MEDINFO 2001: Proceedings of the 10th World Congress on Medical Informatics (Studies in Health Technology and Informatics, 84), V. Patel et al. (eds.), IOS Press, Amsterdam, (2001),216-220.
Mennuti, et al., "Is It Time to Sound an Alarm About False-Positive Cell-Free DNA Testing for Fetal Aneuploidy?", American Journal of Obstetrics, (2013),5 pgs.
Mersy, et al., "Noninvasive Detection of Fetal Trisomy 21: Systematic Review and Report of Quality and Outcomes of Diagnostic Accuracy Studies Performed Between 1997 and 2012", Human Reproduction Update, vol. 19, No. 4, (2013),318-329.
Multiplexing with RainDrop Digital PCR, RainDance Technologies Application Note, (2013), 1-2.
Munne, et al., "Chromosome Abnormalities in Human Embryos", Textbook of Assisted Reproductive Techniques, (2004),355-377.
Murtaza, et al., "Non-Invasive Analysis of Acquired Resistance to Cancer Therapy by Sequencing of Plasma DNA", Nature (doi:10.1038/nature12065), (2013),6 pgs.
Myers, et al., "Accurate Detection of Aneuploidies in Array CGH and Gene Expression Microarray Data", Bioinformatics, vol. 20, No. 18, (2004),3533-3543.
Nannya, et al., "A Robust Algorithm for Copy Number Detection Using High-density Oligonucleotide Single Nucleotide Polymorphism Genotyping Arrays", Cancer Res., 65, (Jul. 15, 2005),6071-6079.
Nicolaides, et al., "Noninvasive Prenatal Testing for Fetal Trisomies in a Routinely Screened First-Trimester Population", American Journal of Obstetrics (article in press), 207, (2012),1.e1-1.e6.
Nicolaides, et al., "Prenatal Detection of Fetal Triploidy from Cell-Free DNA Testing in Maternal Blood", Fetal Diagnosis and Therapy, (Oct. 10, 2013), 1-6.
Nicolaides, et al., "Validation of Targeted Sequencing of Single-Nucleotide Polymorphisms for Non-Invasive Prenatal Detection of Aneuploidy of Chromosomes 13, 18, 21, X, and Y", Prenatal Diagnosis, 33, (Apr. 26, 2013),575-579.
Ogino, et al., "Bayesian Analysis and Risk Assessment in Genetic Counseling and Testing", Journal of Molecular Diagnostics, vol. 6, No. 1, (Feb. 2004),9 pgs.
Orozco, et al., "Placental Release of Distinct DNA-Associated Micro-Particles into Maternal Circulation: Reflective of Gestation Time and Preeclampsia", Placenta, 30, (2009),891-897.
Ozawa, et al., "Two Families with Fukuyama Congenital Muscular Dystrophy that Underwent In Utero Diagnosis Based on Polymorphism Analysis", Clinical Muscular Dystrophy: Research in Immunology and Genetic Counseling—FY 1994 Research Report (including text in Japanese), (1994),8 pgs.
Paez, et al., "Genome coverage and sequence fidelity of $\phi29$ polymerase-based multiple strand displacement whole genome amplification", Nucleic Acids Research, vol. 32, No. 9, (May 18, 2004),1-11.
Page, et al., "Chromosome Choreography: The Meiotic Ballet", Science, vol. 301, (Aug. 8, 2003),785-789.
Palomaki, et al., "DNA Sequencing of Maternal Plasma Reliably Identifies Trisomy 18 and Trisomy 13 as Well as Down Syndrome: an International Collaborative Study", Genetics in Medicine, (2012), 10 pgs.
Palomaki, et al., "DNA Sequencing of Maternal Plasma to Detect Down Syndrome: An International Clinical Validation Study", Genetics in Medicine (pre-print version), vol. 13, (2011),8 pgs.
Papageorgiou, et al., "Fetal-Specific DNA Methylation Ratio Permits Noninvasive Prenatal Diagnosis of Trisomy 21", Nature Medicine (advance online publication), 17, (Mar. 6, 2011),5 pgs.
Pena, et al., "Paternity Testing in the DNA Era", Trends in Genetics, vol. 10, No. 6, (Jun. 1994),204-209.
Perkel, et al., "Overcoming the Challenges of Multiplex PCR", Biocompare Editorial Article, Oct. 23, 2012, 1-5.
Perry, et al., "The Fine-Scale and Complex Architecture of Human Copy-Number Variation", The American Journal of Human Genetics, 82, (Mar. 2008),685-695.
Pertl, et al., "Detection of Male and Female Fetal DNA in Maternal Plasma by Multiplex Fluorescent Polymerase Chain Reaction Amplification of Short Tandem Repeats", Hum. Genet., 106, (2000),45-49.
Peters, et al., "Noninvasive Prenatal Diagnosis of a Fetal Microdeletion Syndrome", New England Journal of Medicine, vol. 365, No. 19, (Nov. 10, 2011), 1847-1848.
Pfaffl, "Relative Expression Software Tool (REST©) for Group-Wise Comparison and Statistical Analysis of Relative Expression Results in real-Time PCR", Nucleic Acids Research, vol. 30, No. 9, e36, (2002),10 pgs.
Phillips, et al., "Resolving Relationship Tests that Show Ambiguous STR Results Using Autosomal SNPs as Supplementary Markers", Forensic Science International: Genetics 2, (2008),198-204.
Porreca, et al., "Multiplex Amplification of Large Sets of Human Exons", Nature Methods (advance online publication), 4, (Oct. 14, 2007),6 pgs.
Rabinowitz, et al., "Accurate Prediction of HIV-1 Drug Response from the Reverse Transcriptase and Protease Amino Acid Sequences Using Sparse Models Created by Convex Optimization", Bioinformatics, vol. 22, No. 5, (2006),541-549.
Rabinowitz, et al., "Non-Invasive Prenatal Aneuploidy Testing of Chromosomes 13, 18, 21, X, and Y Using Targeted Sequencing of Polymorphic Loci", The American Society of Human Genetics, meeting poster, (2012).
Rabinowitz, et al., "Origins and Rates of Aneuploidy in Human Blastomeres", Fertility and Sterility, vol. 97, No. 2, (Feb. 2012),395-401.
Rahmann, et al., "Mean and Variance of the Gibbs Free Energy of Oligonucleotides in the Nearest neighbor Model Under Varying Conditions", Bioinformatics, vol. 20, No. 17, (2004),2928-2933.
Rava, et al., "Circulating Fetal Cell-Free DNA Fraction Differ in Autosomal Aneuploidies and Monosomy X", Clinical Chemistry (papers in press), vol. 60, No. 1, (Sep. 17, 2013),8 pgs.

(56) References Cited

OTHER PUBLICATIONS

Rechitsky, et al., "Preimplantation Genetic Diagnosis with HLA Matching", Reproductive BioMedicine Online, vol. 9, No. 2, (2004),210-221.
Renwick, et al., "Proof of Principle and First Cases Using Preimplantation Genetic Haplotyping—A Paradigm Shift for Embryo Diagnosis", Reproductive BioMedicine Online, vol. 13, No. 1, (2006),110-119.
Roper, et al., "Forensic Aspects of DNA-Based Human Identity Testing", Journal of Forensic Nursing, 4, (2008),150-156.
Roux, et al., "Optimization and Troubleshooting in PCR", PCR Methods Appl. vol. 4, (1995), 185-194.
Rozen, et al., "Primer3 on the WWW for General Users and for Biologist Programmers", Methods in Molecular Biology, vol. 132: Bioinformatics Methods and Protocols, (1999),365-386.
Russell, et al., "X Chromosome Loss and Ageing", Cytogenet Genome Res, vol. 116, (2007),181-185.
Ryan, et al., "Informatics-Based, Highly Accurate, Noninvasive Prenatal Paternity Testing", Genetics in Medicine (advance online publication), (Dec. 20, 2012),5 pgs.
Samango-Sprouse, et al., "SNP-Based Non-Invasive Prenatal Testing Detects Sex Chromosome Aneuploidies with High Accuracy", Prenatal Diagnosis, vol. 33, (2013),1-7.
Sander, et al., "Genetic Medicine and the Future of Health Care", Science, vol. 287, (Mar. 17, 200),1977-1978.
Santalucia, Jr., et al., "Improved Nearest-Neighbor Parameters for Predicting DNA Duplex Stability", Biochemistry, 35, (1996),3555-3562.
Santalucia, Jr., et al., "The Thermodynamics of DNA Structural Motifs", Annu. Rev. Biophys. Biomol. Struct., 33, (2004),415-440.
Sebat, et al., "Strong Association of De Novo Copy Number Mutations with Autism", Science, vol. 316, (Apr. 20, 2007),445-449.
Sehnert, et al., "Optimal Detection of Fetal Chromosomal Abnormalities by Massively Parallel DNA Sequencing of Cell-Free Fetal DNA from Maternal Blood", Clinical Chemistry (papers in press), vol. 57, No. 7, (2011),8 pgs.
Shaw-Smith, et al., "Microarray Based Comparative Genomic Hybridisation (array-CGH) Detects Submicroscopic Chromosomal Deletions and Duplications in Patients with Learning Disability/Mental Retardation and Dysmorphic Features", J. Med. Genet., 41, (2004),241-248.
Simpson, et al., "Fetal Cells in Maternal Blood: Overview and Historical Perspective", Annals New York Academy of Sciences, 731, (1994),1-8.
Sint, et al., "Advances in Multiplex PCR: Balancing Primer Efficiencies and Improving Detection Success", Methods in Ecology and Evolution vol. 3, (2012), 898-905.
Slater, et al., "High-Resolution Identification of Chromosomal Abnormalities Using Oligonucleotide Arrays Containing 116,204 SNPs", Am. J. Hum. Genet., vol. 77, No. 5, (2005),709-726.
Snijders, et al., "Assembly of Microarrays for Genome-Wide Measurement of DNA Copy Number", Nature Genetics vol. 29, (Nov. 2001),263-264.
Sparks, et al., "Non-Invasive Prenatal Detection and Selective Analysis of Cell-Free DNA Obtained from Maternal Blood: Evaluation for Trisomy 21 and Trisomy 18", American Journal of Obstetrics & Gynecology, 206, (Apr. 2012),319.e1-319.e9.
Sparks, et al., "Selective Analysis of Cell-Free DNA in Maternal Blood for Evaluation of Fetal Trisomy", Prenatal Diagnosis, 32, (2012),1-7.
Spiro, et al., "A Bead-Based Method for Multiplexed Identification and Quantitation of DNA Sequences Using Flow Cytometry", Applied and Environmental Microbiology, Oct. 2000, vol. 66, No. 10, 4258-4265.
Spits, et al., "Optimization and Evaluation of Single-Cell Whole Genome Multiple Displacement Amplification", Human Mutation, vol. 27, No. 5, (2006),496-503.

Stephens, et al., "A Comparison of Bayesian Methods for Haplotype Reconstruction from Population Genotype Data", Am. J. Hum. Genet., 73, (2003),1162-1169.
Stevens, et al., "Ontology-Based Knowledge Representation for Bioinformatics", Briefings in Bioinformatics, vol. 1, No. 4, (Nov. 2000),398-414.
Steyerberg, et al., "Application of Shrinkage Techniques in Logistic Regression Analysis: A Case Study", Statistica Neerlandica, vol. 55, No. 1, (2001),76-88.
Strom, et al., "Neonatal Outcome of Preimplantation Genetic Diagnosis by Polar Body Removal: The First 109 Infants", Pediatrics, vol. 106, No. 4, (Oct. 4, 2000),650-653.
Strom, et al., "Three births after preimplantation genetic diagnosis for cystic fibrosis with sequential first and second polar body analysis", American Journal of Obstetrics and Gynecology, vol. 178, No. 6, (1998),1298-1306.
Stroun, et al., "Prehistory of the Notion of Circulating Nucleic Acids in Plasma/Serum (CNAPS): Birth of a Hypothesis", Ann. N. Y. Acad. Sci., 1075, (2006),10-20.
Sweetkind-Singer, et al., "Log-Penalized Linear Regression", International Symposium on Information Theory, Yokahama, Japan, (Jun. 29, 2013-Jul. 4, 2003),p. 286.
Tang, et al., "Detection of Fetal-Derived Paternally Inherited X-Chromosome Polymorphisms in Maternal Plasma", Clinical Chemistry vol. 45, No. 11, (1999),2033-2035.
Thomas, et al., "The Time of Appearance and Disappearance of Fetal DNA from the Maternal Circulation", Prenatal Diagnosis, vol. 15, (1995),641-646.
Tong, "Noninvasive Prenatal Detection of Fetal Trisomy 18 by Epigenetic Allelic Ratio Analysis in Maternal Plasma: Theoretical and Empirical Considerations", Clinical Chemistry vol. 52, No. 12, (2006),2194-2202.
Tong, et al., "Noninvasive Prenatal Detection of Trisomy 21 by an Epigenetic-Genetic Chromosome-Dosage Approach", Clinical Chemistry, vol. 56, No. 1, (2010),90-98.
Troyanskaya, et al., "A Bayesian Framework for Combining Heterogeneous Data Sources for Gene Function Prediction (in *Saccharomyces cerevisiae*)", PNAS, vol. 100, No. 14, (Jul. 8, 2003),8348-8353.
Tsui, et al., "Non-Invasive Prenatal Detection of Fetal Trisomy 18 by RNA-SNP Allelic Ratio Analysis Using Maternal Plasma SERPINB2 mRNA: A Feasibility Study", Prenatal Diagnosis, 29, (2009),1031-1037.
Turner, et al., "Massively Parallel Exon Capture and Library-Free Resequencing Across 16 Genomes", Nature Methods, vol. 6, No. 5, (May 2009),315-316.
U.S. Appl. No. 11/004,274, Office Action mailed Nov. 24, 2009, 31 pgs.
U.S. Appl. No. 11/004,274, Office Action mailed Feb. 4, 2009, 26 pgs.
U.S. Appl. No. 11/004,274, Office Action mailed Mar. 2, 2011, 50 pgs.
U.S. Appl. No. 11/004,274, Office Action mailed May 13, 2008, 25 pgs.
U.S. Appl. No. 11/496,982, Office Action mailed Jan. 21, 2011, 25 pgs.
U.S. Appl. No. 11/496,982, Office Action mailed May 27, 2010, 8 pgs.
U.S. Appl. No. 11/603,406, Office Action mailed Feb. 18, 2011, 26 pgs.
U.S. Appl. No. 11/603,406, Office Action mailed Mar. 14, 2013, 15 pgs.
U.S. Appl. No. 11/603,406, Office Action mailed Aug. 19, 2010, 20 pgs.
U.S. Appl. No. 11/634,550, Office Action mailed Jan. 24, 2011, 13 pgs.
U.S. Appl. No. 11/634,550, Office Action mailed Aug. 4, 2010, 7 pgs.
U.S. Appl. No. 12/076,348, Office Action mailed Feb. 8, 2013, 9 pgs.
U.S. Appl. No. 12/076,348, Office Action mailed Mar. 4, 2011, 26 pgs.

(56) References Cited

OTHER PUBLICATIONS

U.S. Appl. No. 12/076,348, Office Action mailed Aug. 20, 2010, 22 pgs.
Vallone, et al., "AutoDimer: a Screening Tool for Primer-Dimer and Hairpin Structures", BioTechniques vol. 37, (Aug. 2004),226-231.
Verlinsky, et al., "Over a Decade of Experience with Preimplantation Genetic Diagnosis", Fertility and Sterility, vol. 82, No. 2, (Aug. 2004),302-303.
Wagner, et al., "Non-Invasive Prenatal Paternity Testing from Maternal Blood", Int. J. Legal Med., 123, (2009),75-79.
Wang, et al., Yuker, "Allele quantification using molecular inversion probes (MIP)", Nucleic Acids Research, vol. 33, No. 21, (Nov. 28, 2005), 14 pgs.
Wang, et al., "A Genotyping System Capable of Simultaneously Analyzing >1000 Single Nucleotide Polymorphisms in a Haploid Genome", Genome Res., vol. 15, (2005) 276-283.
Wang, et al., "Gestational Age and Maternal Weight Effects on Fetal Cell-Free DNA in Maternal Plasma", Prenatal Diagnosis, vol. 33, (2013),662-666.
Wapner, et al., "Chromosomal Microarray Versus Karyotyping for Prenatal Diagnosis", The New England Journal of Medicine, vol. 367, No. 23, (Dec. 6, 2012),2175-2184.
Watkins, Jr., et al., "Thermodynamic contributions of single internal rA •dA, rC • dC, rG • dG and rU • dT mismatches in RNA/DNA duplexes", Nucleic Acids Research, vol. 39, No. 5, (Nov. 10, 2010),1894-1902.
Wells, et al., "Detailed Chromosomal and Molecular Genetic Analysis of Single Cells by Whole Genome Amplification and Comparative Genomic Hybridisation", Nucleic Acids Research, 1999, vol. 27, No. 4, 1214-1218.
Wells, "Advances in Preimplantation Genetic Diagnosis", European Journal of Obstetrics and Gynecology and Reproductive Biology, 115S, (2004),S97-S101.
Wells, "Microarray for Analysis and Diagnosis of Human Embryos", 12th International Congress on Prenatal Diagnosis and Therapy, Budapest, Hungary, (Jun. 24-27, 2004),9-17.
Wen, "Universal Multiples PCR: A Novel Method of Simultaneous Amplification of Multiple DNA Fragments", Plant Methods vol. 8, No. 32, (2012), 1-9.
Wilton, "Preimplantation Genetic Diagnosis and Chromosome Analysis of Blastomeres Using Comparative Genomic Hybridization", Human Reproduction Update, vol. 11, No. 1, (2005),33-41.
Wilton, et al., "Birth of a Healthy Infant After Preimplantation Confirmation of Euploidy by Comparative Genomic Hybridization", N. Engl. J. Med., vol. 345, No. 21, (Nov. 22, 2001),1537-1541.
Xia, et al., "Thermodynamic Parameters for an Expanded Nearest-Neighbor Model for Formation of RNA Duplexes with Watson-Crick Base Pairs", Biochemistry, 37, (1998),14719-14735.
Yeh, et al., "Knowledge Acquisition, Consistency Checking and Concurrency Control for Gene Ontology (GO)", Bioinformatics, vol. 19, No. 2, (2003),241-248.
Zhang, et al., "Quantifying RNA Allelic Ratios by Microfluidic Multiplex PCR and Sequencing", Nature Methods, vol. 11, No. 1, Jan. 2014, 51-56.
Zhao, et al., "An Integrated View of Copy Number And Allelic Alterations in the Cancer Genome Using Single Nucleotide Polymorphism Arrays", Cancer Research, 64, (May 1, 2004),3060-3071.
Zhou, et al., "Counting Alleles Reveals a Connection Between Chromosome 18q Loss and Vascular Invasion", Nature Biotechnology, vol. 19, (Jan. 2001),78-81.
Zimmermann, et al., "Noninvasive Prenatal Aneuploidy Testing of Chromosomes 13, 18, 21 X, and Y, Using targeted Sequencing of Polymorphic Loci", Prenatal Diagnosis, 32, (2012),1-9.
Hospital, F et al., "A General Algorithm to Compute Mul Ti Locus Genotype Frequencies Under Various Mating Systems", Cabios Computer Applications in the Biosciences, vol. 12, No. 6, Jan. 1, 1996 (Jan. 1, 1996), pp. 455-462.
Krjutskov, K et al., "Development of a single tube 640-plex genotyping method for detection of nucleic acid variations on microarrays", Nucleic Acids Research, vol. 36, No. 12, May 23, 2008 (May 23, 2008), pp. e75-e75.
Markoulatos, P et al., "Multiplex Polymerase Chain Reaction: A Practical Approach", 2002 Wiley-Liss, Inc. DOI 10.1002/jcla.2058 Journal of Clinical Laboratory Analysis 16:47-51 (2002).
Servin, B et al., "MOM: A Program to Compute Fully Informative Genotype Frequencies in Complex Breeding Schemes", Journal of Heredity, vol. 93, No. 3, Jan. 1, 2002 (Jan. 1, 2002), pp. 227-228.
Shen, Zhiyong, "MPprimer: a program for reliable multiplex PCR primer design", BMC Bioinformatics 2010, 11:143, 1-7.
Tang, et al., Multiplex fluorescent PCR for noninvasive prenatal detection of fetal-derived paternally inherited diseases using circulatory fetal DNA in maternal plasma, Eur J Obstet Gynecol Reprod Biol, 2009, v.144, No. 1, p. 35-39.
You, Frank M. et al., "BatchPrimer3: A high throughput web application for PCR and sequencing primer design", BMC Bioinformatics, Biomed Central, London, GB, vol. 9, No. 1, May 29, 2008 (May 29, 2008), p. 253.
U.S. Appl. No. 14/866,223, filed Sep. 25, 2015, Rabinowitz, Methods for Non-Invasive Prenatal Ploidy Calling.
U.S. Appl. No. 14/877,925, filed Oct. 7, 2015, Zimmerman, Highly Multiplex Pcr Methods and Compositions.
U.S. Appl. No. 14/983,128, filed Dec. 29, 2015, Rabinowitz, Methods for Non-Invasive Prenatal Ploidy Calling.
U.S. Appl. No. 14/996,097, filed Jan. 14, 2016, Babiarz, Cell Free Dna Diagnostic Testing Standards.
U.S. Appl. No. 14/732,632, filed Nov. 12, 2014, Sigurjonsson, Systems and Methods for Detection of Aneuploidy.
U.S. Appl. No. 14/538,998, filed Nov. 24, 2014, Zimmerman, Methods for Simulatneous Amplification of Target Loci.
U.S. Appl. No. 14/692,703, filed Apr. 21, 2015, Babiarz, Detecting Mutations and Ploidy in Chromosomal Segments.
U.S. Appl. No. 14/882,763, filed Oct. 14, 2015, Babiarz, Detecting Cancer Mutations and Aneuploidy in Chromosomal Segments.
U.S. Appl. No. 14/918,544, filed Oct. 20, 2015, Babiarz, Methods for Simultaneous Amplification of Target Loci.
Chakraborty, R. et al., "Paternity Exclusion by DNA Markers: Effects of Paternal Mutations", Journal of Forensic Sciences, vol. 41, No. 4, Jul. 1996, 671-677.
Kinnings, S. L. et al., "Factors affecting levels of circulating cell-free fetal DNA in maternal plasma and their implications for noninvasive prenatal testing", Prenatal Diagnosis, vol. 35, 2015, 816-822.
PCT/US2015/026957, "International Preliminary Report in Patentability mailed on Nov. 3, 2016", Nov. 3, 2016, 3 pages.
Pearson, K., "On the criterion that a given system of deviations from the probable in the case of a correlated system of variables is such that it can be reasonably supposed to have arisen from random sampling", Philosophical Magazine Series 5, vol. 50, Issue 302, 1900, 157-175.
Rachlin, J. et al., "Computational tradeoffs in multiplex PCR assay design for SNP genotyping", BMC Genomics, vol. 6, No. 102, Jul. 25, 2005, 11 pages.
Wright, C. F. et al., "Cell-free fetal DNA and RNA in maternal blood: implications for safer antenal testing", BMJ, vol. 39, Jul. 18, 2009, 161-165.
Wu, Y. Y. et al., "Rapid and/or high-throughput genotyping for human red blood cell, platelet and leukocyte antigens, and forensic applications", Clinica Chimica Acta, vol. 363, 2006, 165-176.
Fan, H. Christina et al., "Sensitivity of Noninvasive Prenatal Detection of Fetal Aneuploidy from Maternal Plasma Using Shotgun Sequencing is Limited Only by Counting Statistics", PLos ONE, vol. 5, Issue 5 (e10439), May 3, 2010, 1-6.

* cited by examiner

| The sequencing-adaptor sequence is located inside the primer sequence and flanked by target specific sequence on both sides. 10 bases are target-specific at the 3'-end of each primer. Primers were tested successfully in real-time PCR. For sequencing this reduces the number of primer bases that need to be sequenced. | | |
|---|---|---|
| rs8130564 | int-tag 1.10 | AACTCACATAGCACACGAGCGCTCTTCCGATCTTGCAAGCACA |
| rs2832093 | int-tag 2.10 | TCCTCTGTGACACGAGCGCTCTTCCGATCTCCCTGCTCTT |
| rs12011281 | int-tag 3.10 | tcctctctctACACGAGCGCTCTTCCGATCTcGGGCTGTCA |
| rs6719561 | int-tag 4.10 | TACATCCTTGAGACACGAGCGCTCTTCCGATCTGCTGTGCAGT |
| rs10187018 | int-tag 5.10 | tttgcttgagctACACGAGCGCTCTTCCGATCTcgggagttc |
| rs10460481 | int-tag 6.10 | gtcttatggtggACACGAGCGCTCTTCCGATCTcaaagccagt |
| The sequencing-adaptor sequence is located inside the primer sequence and flanked by target specific sequence on both sides. The internal tag is formed into a hairpin structure by 10 complementary bases on either end. This brings the target-specific ends of the primer into close proximity and hinders unspecific binding to the "internal tag". 10 bases are target-specific at the 3'-end of each primer. Primers were tested successfully in real-time PCR. | | |
| rs8130564 | loop-int-tag 1.10 | AACTCACATAGCtgatcggtACACGAGCGCTCTTCCGATCTTGCAAGCACA |
| rs2832093 | loop-int-tag 2.10 | TCCTCTGTGtgatcggtACACGAGCGCTCTTCCGATCTCCCTGCTCTT |
| rs12011281 | loop-int-tag 3.10 | tcctctcttgatcggtACACGAGCGCTCTTCCGATCTcGGGCTGTCA |
| rs6719561 | loop-int-tag 4.10 | TACATCCTTGAGtgatcggtACACGAGCGCTCTTCCGATCTGCTGTGCAGT |
| rs10187018 | loop-int-tag 5.10 | tttgcttgagcttgatcggtACACGAGCGCTCTTCCGATCTcgggagttc |
| rs10460481 | loop-int-tag 6.10 | gtcttatggtggatcggtACACGAGCGCTCTTCCGATCTcaaagccagt |

FIG. 12

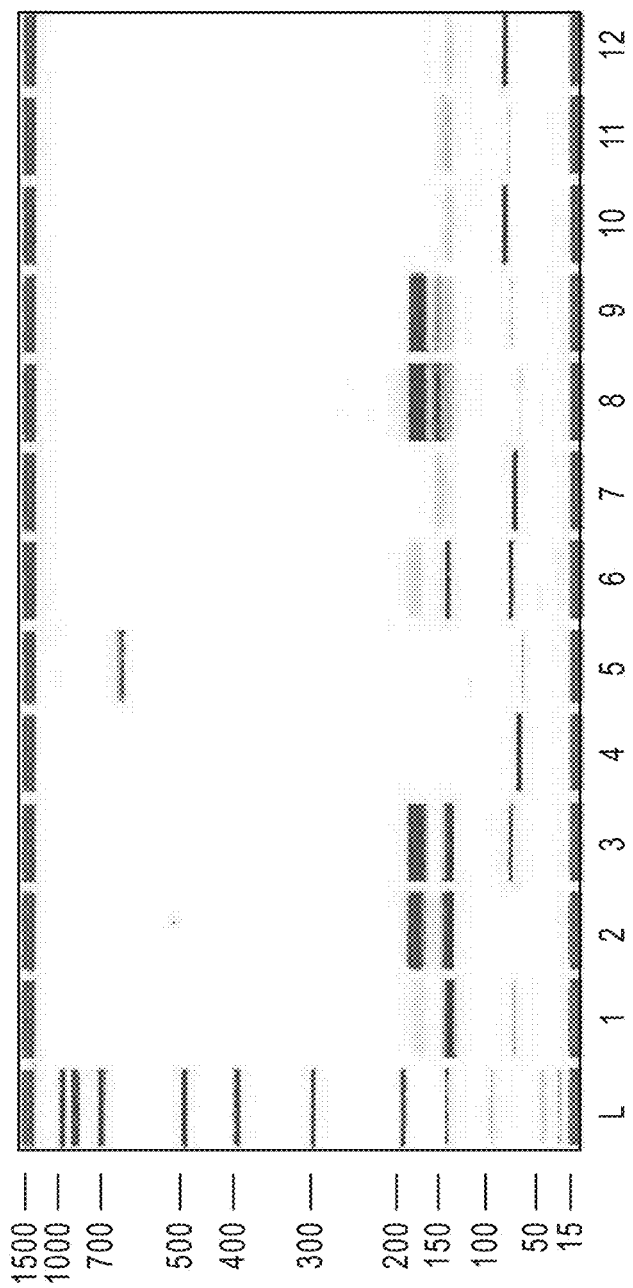

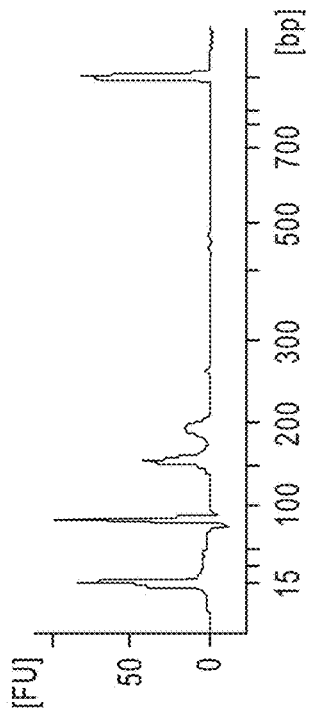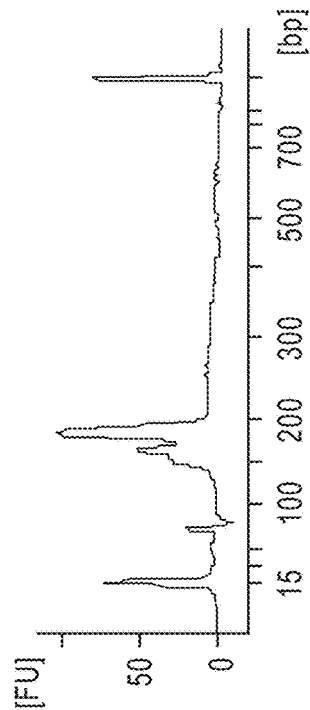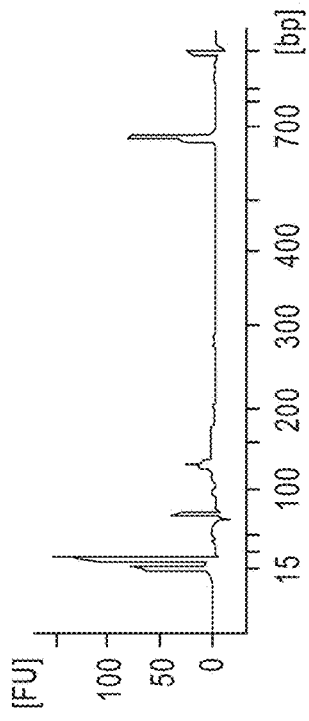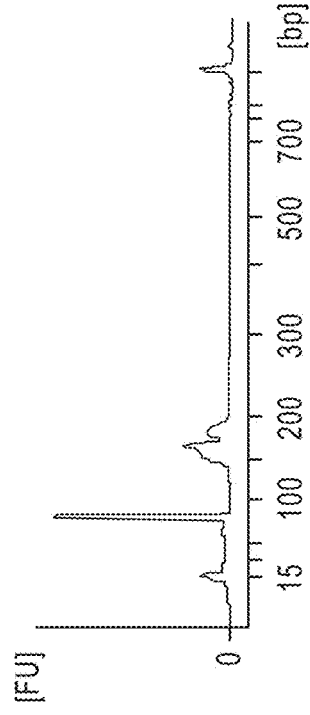

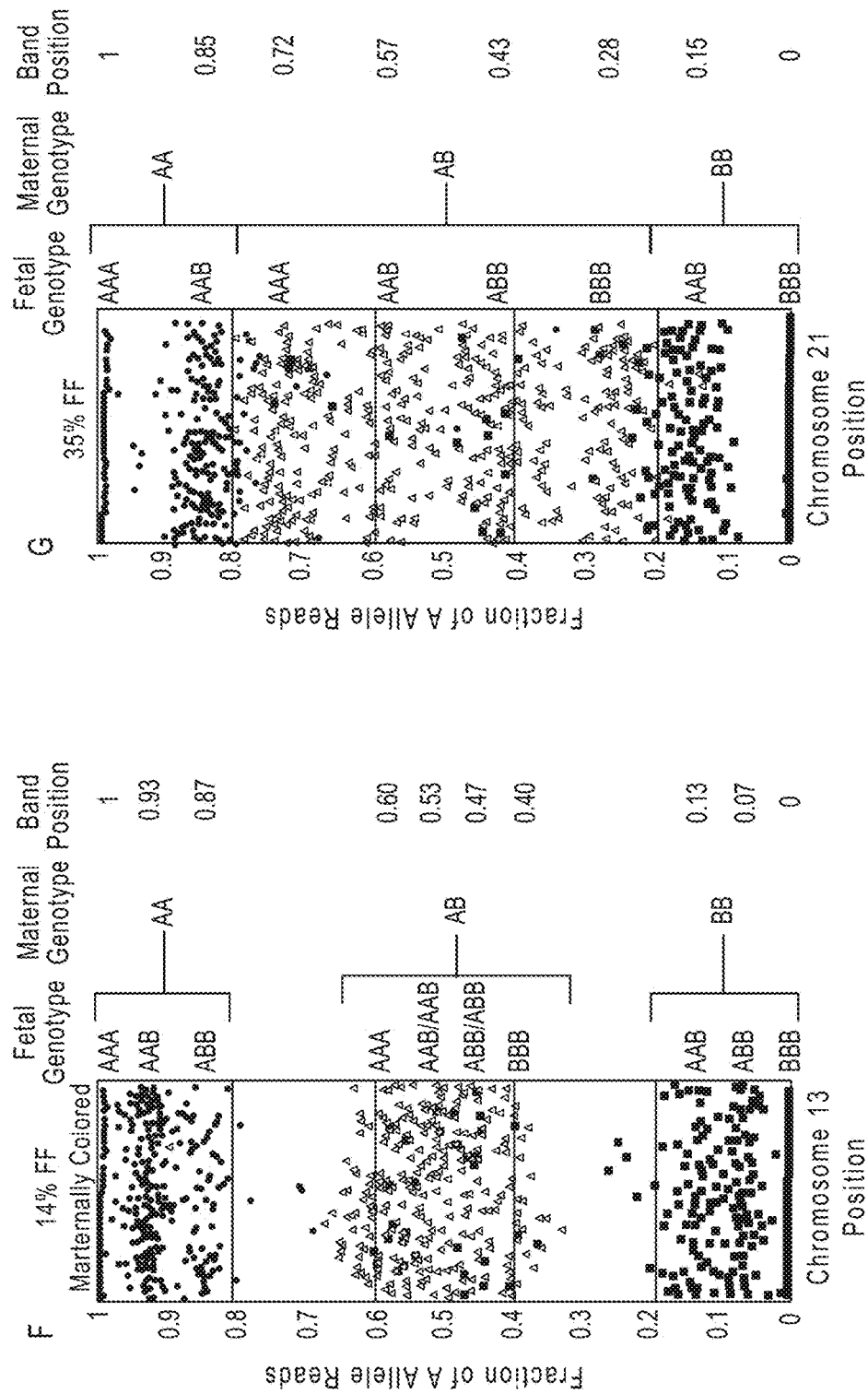

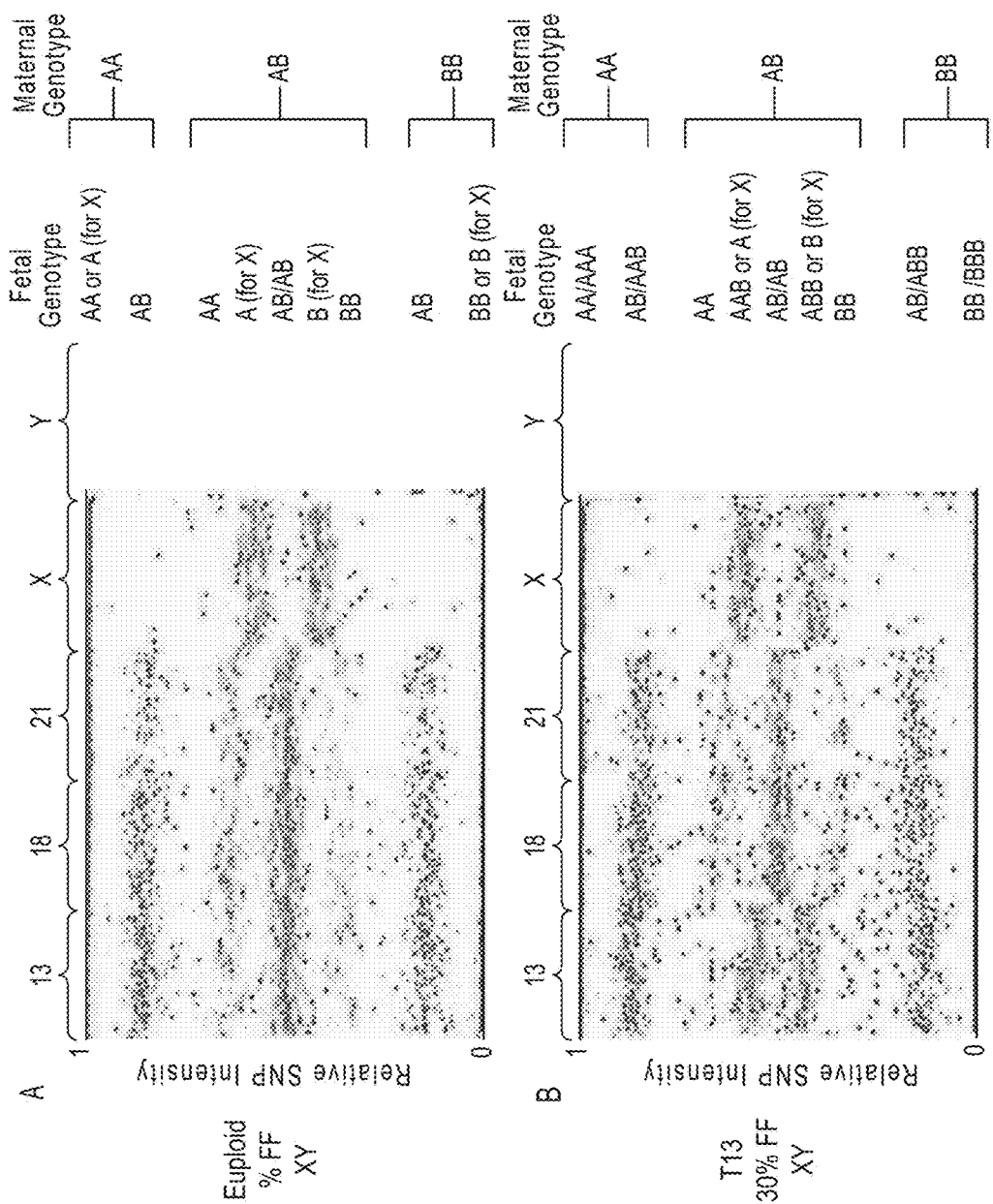

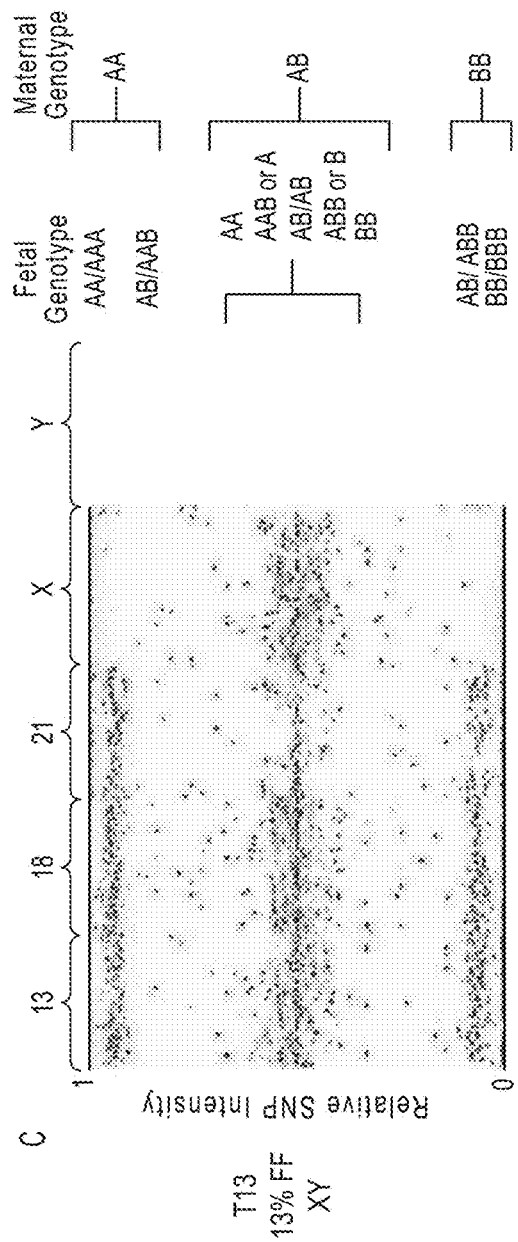
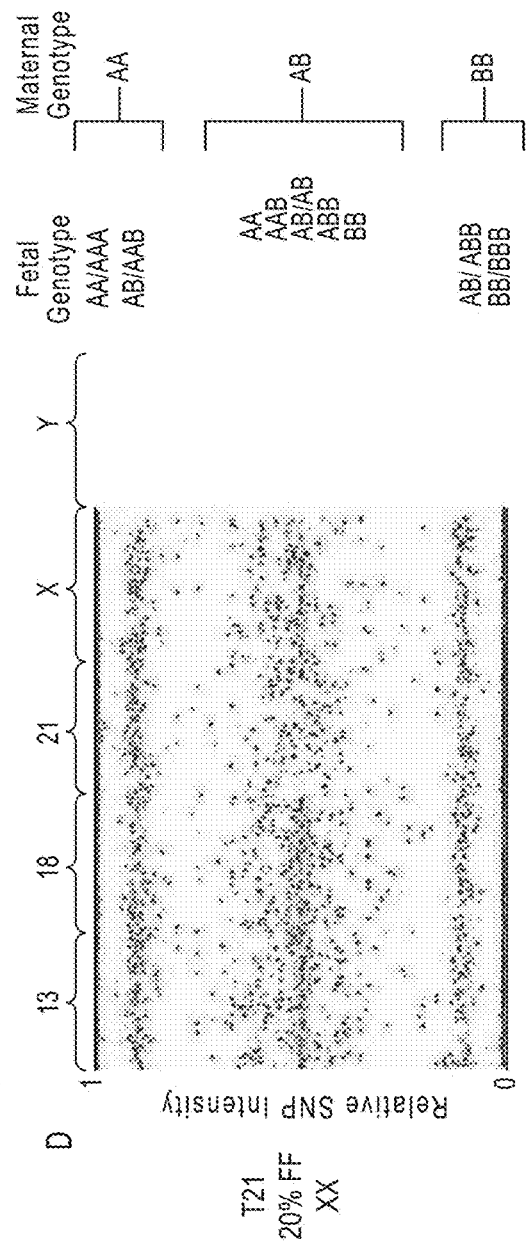
FIG. 31C
FIG. 31D

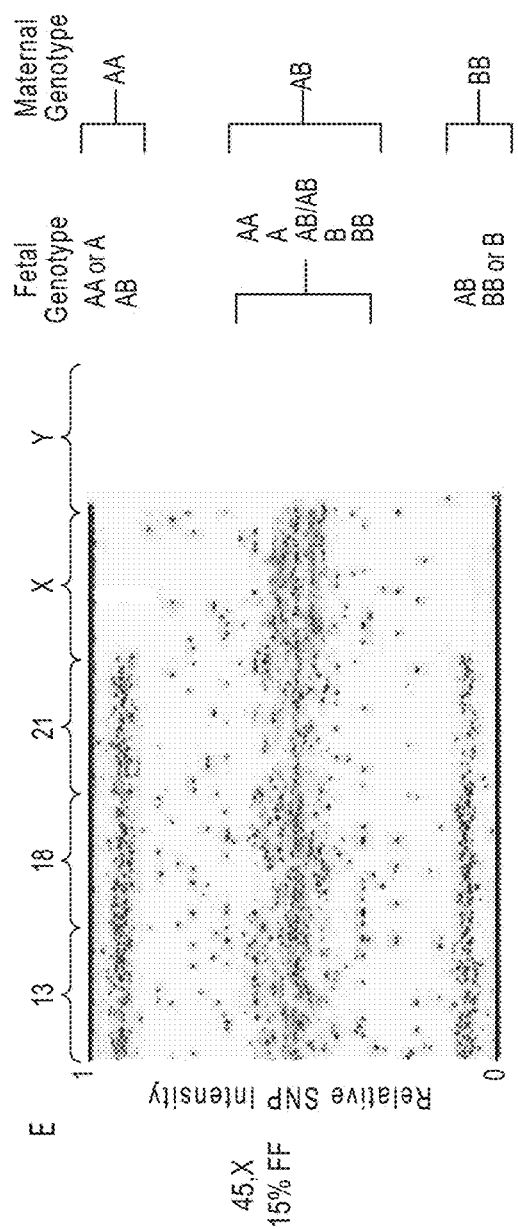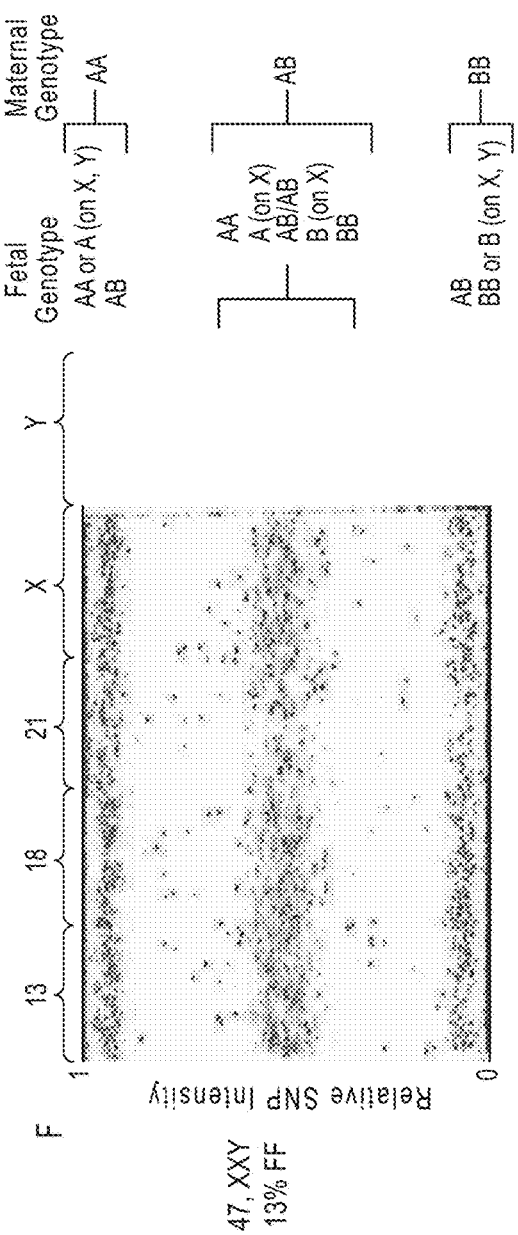

$\Delta G = \Delta G_1 + \Delta G_2 + ... + \Delta G_x$

To FIG. 33F

| Target No. | Pool A Sequence (5' to 3') | SEQ ID NO. | Pool B Sequence (5' to 3') | SEQ ID NO. | Pool C Sequence (5' to 3') | SEQ ID NO. |
|---|---|---|---|---|---|---|
| 1 | GGCACAACATTTGGGAGACAAA | 1 | CTCACTAAACTTTTCCCCAGAACTCA | 1201 | GCTTAAGCCACAGAAAGGCACAAC | 2401 |
| 2 | CCTGGAACCTGAAAGCTTGCAAAAG | 2 | CCTCTGAAGGGAGACTGAAACAAC | 1202 | CGAGTGCCCTGGAACCTGAAA | 2402 |
| 3 | ACAGGGTCCTCTCCCTTGA | 3 | GCAAGAATGCTTGGCTGCAA | 1203 | AGCCACCACTCCTGCTTCTGA | 2403 |
| 4 | GGAAGCAAACAGGTAGAGCCTGGTA | 4 | GTGGCATTTCACTGCCCTTTG | 1204 | TTGGGGACCCCTGGACTAAG | 2404 |
| 5 | CTACAACAACAGAGCTCCAGGAT | 5 | GCAGCTGTTCAATGTGGTTCA | 1205 | CCTCCCCAGTATCTTACCACTACAAC | 2405 |
| 6 | TGTCCTTGGTCGTATGTGAGAGA | 6 | GTGAGGATGAGTTTTCAGTGGCTATC | 1206 | CACCAAGCCCTCAACTCCTAAAA | 2406 |
| 7 | GCAGGAACTGGCTTGCCTTT | 7 | CCCTGGACAAAATGTAACAGCCAAAGT | 1207 | GAAGTGAAAGAAAATGGCAGGAACT | 2407 |
| 8 | AGGTTTCGGCTTTAGTTGTGTGA | 8 | ACCTAGCTATCCTTCCAGCCATTTC | 1208 | GCTGGTATTCTTTTGGGGATAGAGGTT | 2408 |
| 9 | TGTCTGCTTCTGCCCGCATTC | 9 | GCTGGACAAACTACTGCCTCTTC | 1209 | GTGGAGGAAATTAGATGTCTGCTTCT | 2409 |
| 10 | GTCCCTCACACCTTTCTACCAGAAG | 10 | GCCAATAGCTGCTTGATGCAAT | 1210 | GGGCAAGTCCCTGACACCTTT | 2410 |
| 11 | GGCTGCAGGAGTAGAGGTCTAAATG | 11 | TAGTTGCCCGGGATTCCCAAGA | 1211 | TGAGGTCTGGCTGCAGGAGTA | 2411 |
| 12 | GGCAAGAAGAAACTGGAGCCAAGA | 12 | GGGAGAGGCTGGTCCTGAGT | 1212 | CTGAAGCCCAACTGGCAAGAAG | 2412 |
| 13 | GAGCCTGAGTTCTTGATCACTACA | 13 | GTTTGTGAAAGGTCAATGTGAGGAA | 1213 | AAGTCCTGAGCCTGAGTTCTTG | 2413 |
| 14 | CCTGGAAAAAGCCCGGGTAGA | 14 | TCCTCGGGAGCTCAACCTTA | 1214 | TCTCAGGGTGCCCTGGAAAAAG | 2414 |
| 15 | GCAATGGTCCCAGTTGAGACTT | 15 | TCCTACTGATGCCAGACCAA | 1215 | GCACTGCAAAAGAAGAGGCTATTG | 2415 |
| 16 | GCCCTTTGGAACCTGACCAA | 16 | CCCAGCTTAAGCAAAATAGGGCAAGTA | 1216 | TGGGAACCAGCCCTTTGGAA | 2416 |
| 17 | GGCCCTGATTTGACCCTTCTTTTC | 17 | TGCCCAGTAGTAAGTTGAGATGACTA | 1217 | GGCTTCACTATCAAGAAGGGCCTTGATTT | 2417 |
| 18 | CCACCCCCTTCTGAAACACATC | 18 | CCGGAAGCTTCACGTTCTGT | 1218 | AAGAGGCCACCCGCTTCT | 2418 |
| 19 | TGGCGCTAAAGCCCAACA | 19 | GGAGGGAGAGCTCCATCTCTGA | 1219 | TGGGAGCAGGCTGGCGCTAA | 2419 |
| 20 | CCTTCCCCGCTTCTGGATATGAAA | 20 | CCCAGCAATAGGACTCAGCAA | 1220 | CCGAAAACCTTCCCCGCTTCT | 2420 |
| 21 | GTCAGCGTTTGACGGCTATTGAGT | 21 | TAGGGCAGGTGTCCTCTGCAT | 1221 | GGAAGGGGAATTGTCAGCGTTTA | 2421 |
| 22 | GCATCTCCAGTGCCCCTCTGT | 22 | GTGAACCAAGCTATACTACCTGCTTTTC | 1222 | GCAGTCTCAGCCTTTCCTTTGCAT | 2422 |
| 23 | CATCTTCCTAGACATGCACACAAC | 23 | GGCTTCTGTGCTCATAGTTCACACT | 1223 | GTTGGGAAGCATCTTCCTAGACAT | 2423 |
| 24 | GTCCCAAGTCAACTGCCATCT | 24 | GGGCACACGGAGGTGAAAAGT | 1224 | GGCTATTTTGGAGTCCCAAGTCAA | 2424 |
| 25 | GCGTCAGCACAGCTAACACA | 25 | CGGGAGCCGTTATACCAGCTTAG | 1225 | TGGGCCACGTTGCCTACT | 2425 |
| 26 | TCACAATGGGAGGGAACATTCAA | 26 | GCTCCTATGACCAAGTCCCTTT | 1226 | CACCTTATTACTACCTTCCTCTCACAATG | 2426 |
| 27 | GGTAAAGCCTGGTTGTAAAGTCCACAT | 27 | GTGTTGCCCAGACCCACTGT | 1227 | ACTGGGGTAAAGGCTGGTTGT | 2427 |
| 28 | CCGACTCAATGGGGAACTCCTACT | 28 | GGGCACTTTTGAGTTGGGCTTTG | 1228 | AAGCCTCGTGGCCGACTCAAT | 2428 |
| 29 | TCCTTACACCTTGGGGCGTCTA | 29 | GCTAGCTCGGTGCCTAATGGTT | 1229 | AACAGGGCGTGAGTTTTCCTT | 2429 |
| 30 | GGGCATTTCTAAGACACTTGGACAGT | 30 | CAGACCTGGCAGGATTCAGAATAGT | 1230 | GGAGAGGCCAGGGCATTTCTAAG | 2430 |
| 31 | CACTGTATCTCAAAGGGCAAAACAA | 31 | TGCAATGCAGAGGAGAAAGGTT | 1231 | CAGCCTGCTAGGACACACTGTA | 2431 |
| 32 | ACTTCTCTCTGCAGACAGTTCA | 32 | AGTCACAGGTATCCTGACTCTCATA | 1232 | GGTGATTCTGGCCGAACTGTCT | 2432 |
| 33 | GGCCTCTTGGTGCCTCTGTT | 33 | GGAGCAATCAGCCTTGCAGAGA | 1233 | TGGATCGGAAACACCAGACTCA | 2433 |
| 34 | CTAGAGAAACAAGACACATCCAAGTTC | 34 | TGCCGCCGGAAAACCAT | 1234 | CCTGAGACCGTTGCTAGAGAAACAAG | 2434 |
| 35 | GCGGGCATAGAGAGAAGGAAAT | 35 | TTCAAGAGCATCCTTGCGCTAT | 1235 | TGGGATGCGGGCATAGAGA | 2435 |
| 36 | GGCTTCAGTCCTTCACCTCTTTC | 36 | ACCTTGAGAAGGTGGTATTTGTGT | 1236 | TCTCCCAGGCTTCAGTCCTT | 2436 |
| 37 | TTCAGAGTCCTAGGCCAGCAT | 37 | AGAAAGACCCCAGGTAAGAACCAT | 1237 | CCAAGTTATGCCTGCTGCTGCAGA | 2437 |
| 38 | GGTTCCTCATGGAAGACTGGTTTG | 38 | CACTCACACATCCACAGGGAGACA | 1238 | GGGAACCTGGAAAGACCTTTACTT | 2438 |
| 39 | GTTGAGAAGGGGAGTAAGATCAGACAA | 39 | GACGCAGTATCCCACAGAGCATT | 1239 | GGTGGGATAGTTGAGAAGGGAGTAA | 2439 |
| 40 | CTCCCGCCTCTAAATGAATGGAT | 40 | ACCAGCTCTGAGTCAGGAAGT | 1240 | CCTCAGCTCCCGCCTCTAAA | 2440 |
| 41 | CATTCCCTCCCCTACCCTGGAA | 41 | CCCACAGTCCGACGAGTGTTTT | 1241 | GGATGGACATAAGCAGTGGTTCA | 2441 |
| 42 | GAGACTCAAACCTGGCACTTGT | 42 | TCACTCCACTTTACAGGCACATATT | 1242 | AGGAGTGAGAAGGGAGACTCAATC | 2442 |
| 43 | CCCGGCTGCCATTTAAGACCAT | 43 | ACGAGGATTAGACAAGTCATAGA | 1243 | TCAGTCCCGGCTGCCATT | 2443 |
| 44 | GGTTACGGCTGAGTATGGTCAAG | 44 | CCCATGACCCCAGGTTGGAATTG | 1244 | GACAGGAGAGATGAGGGCTGAGT | 2444 |
| 45 | CCCTTTCCTGAACCCCTTCATT | 45 | CACTCTGTGCAGTTGCTGGTT | 1245 | AATTGCCAGCTGATTCTCCTTCT | 2445 |
| 46 | GGGGCACCAAAGAAAAGACAAG | 46 | GTCGTGGAGCACACCTTGGAA | 1246 | ACAGAGGATGGGGCACCAAA | 2446 |
| 47 | CATCAGTACCCCACATAGGTTTAACT | 47 | GCCTTTCCATGGAGGCTTATGA | 1247 | GCATGAGGATGGAATGGACTCATCA | 2447 |
| 48 | GGAACTCAGTATGAGTAGAGGGGAAA | 48 | CAGCCTGGTTGGTTAGATTCGT | 1248 | GACCTTCAAGGGGAGCTCAGTAT | 2448 |
| 49 | TTGTGCACGACCCTGAATG | 49 | CTTATGTGTGGCTTTGGCTTCTTG | 1249 | TCTGATATGGAACCCAGGGATTGT | 2449 |
| 50 | TCGCTAGGCCATTCCTCCTGTT | 50 | GGGGCTGAATCAGACAAGGAA | 1250 | TGCACCATCGCTAGGCCATT | 2450 |
| 51 | CACGACACCCTTAGATAATGTTGGAT | 51 | CACAGCTTGGAAGGCCTGAA | 1251 | GTCAGTTCACACGACACCCTTAGA | 2451 |
| 52 | TGGCACAAGCCCAGGTCAT | 52 | CTCATGATGTCAAATGCTGCTCAA | 1252 | AGCCTGGAAAGCTGGCACAA | 2452 |
| 53 | GCCTCCTCTGCATCTCTGAACCAA | 53 | GTTGTGGTGACAGACAACCTTCT | 1253 | TTCCCAGCTCCTCTGCATCT | 2453 |
| 54 | TGCACAGCCCTTCACCTT | 54 | TGACAGCACAGTCCAATTCT | 1254 | CTCAAAAGGGAAGAACGTCAGT | 2454 |
| 55 | TGGTAGTCAGGCCTAGTGACTT | 55 | CCCCTGGGAAAGTTACTGTCGAT | 1255 | TCTGCGTGCTCACTTCCTGGTA | 2455 |
| 56 | GAGCTCTCCAAAGGCTATTCAGA | 56 | GTCACTGAGCTGCCAGTTTTC | 1256 | AAGGTGACAGGTCTTCCAAAG | 2456 |
| 57 | CCTGAGCCTGTCACACTATTTCT | 57 | TCCCAAATCCTGAGCCTGTCA | 1257 | TCCCAAATCCTGAGCCTGTCA | 2457 |

FIG. 34A1

| | | | |
|---|---|---|---|
| 58 GAGAGCAACAGGCGTTGAGA | 58 GCCAACCTATAGACACAACTTTGGTTAC | 1258 GGAGAAGAGTGGAGAGCAACA | 2458 |
| 59 AGCCCTACAGGTCAGTTTTCA | 59 GTTGACTTCCGGCAGTAAGTGATGA | 1259 GACTATACAATACCAAATAGCCCTACAAG | 2459 |
| 60 GGAGGCATTCACTCCTCCTA | 60 ACTGGGACATTTCTCACGTTATCA | 1260 GTCACAAGGGAGGCACTTCA | 2460 |
| 61 GTTGGGGTCAACTTTCCCTGAAG | 61 GGAATCCAGCCCATCCTCACATC | 1261 AGAGCTGCCCTGGAACTGAA | 2461 |
| 62 GAGGGTTGGCTCCATCATCAGA | 62 ACTGCATCACCACACGGAAA | 1262 GGAAAAGTACCCCAGAATGAGGGT | 2462 |
| 63 GAGGCTCATGTCTCTTCAGCCTTAG | 63 CCTTCAAGGGCTTTCTCTCACA | 1263 GGTGGTAGAGGGCTCATGTCTCTT | 2463 |
| 64 GTTGCTTCCGTTATCCTCACT | 64 ACTCCACATGGCTTAAACAGAGA | 1264 TCCCCAAATCCTTTGGCAATGT | 2464 |
| 65 GGGCCTGTCTTGTGATAGTGTT | 65 TCGTGAAGAACATGGAGAGGAGTTA | 1265 GTGTCAAAGGGCCTGTTCTTGT | 2465 |
| 66 GTTTGCTGTTACTGAATCCCGAATCT | 66 CTGGGACCAAACCCATTTCACA | 1266 CTCTCATCAGCTGTTGCTGTAAC | 2466 |
| 67 GCACATGTAAAAATCCTCCCTACTGT | 67 AAGGAAGTGGGGTATGGACTGA | 1267 GACTCTGTTTCTCCCCTGCACATGTAA | 2467 |
| 68 GCCTCTGGTAATAGTACCCAGGATAC | 68 TGTTGGCCACATACATTGTTCTCA | 1268 CCTTCCTTGAACTTGCCTCTGGTA | 2468 |
| 69 CTGAGGTCCAGAATCAGATGTTCT | 69 CTCTTGCCTTCGGGGATGT | 1269 GCTGTCACCAAGACTGAGACTGA | 2469 |
| 70 GGACAACACGATCGGGATGA | 70 CACAGGTCAGAGATTCACCAT | 1270 TGAAAGCTATTGGGACAACAGGAT | 2470 |
| 71 CCATGTCTAGGAACCCCTGTCA | 71 GGGAACCCTACCTTGACTCT | 1271 CAGGAAGATAAGTACTGACCCATGTCT | 2471 |
| 72 GCGACCTCACTTTTCCAGTCAT | 72 AAGCCCCTGAGAATCTAAAAGCAA | 1272 GCACATGTCTGCGACCTCACTTT | 2472 |
| 73 GTGCTATTGTGGCTCTGTAGGTTGA | 73 CGACAGGGCCTCCCAATTC | 1273 CAGCAGAGCAGAGTGCTATTGT | 2473 |
| 74 GTTTCAGCCTGAGAGGCAAGA | 74 AGGTAGACACCGGAAGTAATCACA | 1274 GCTGTTGCACTGTGAACTTGT | 2474 |
| 75 GAGATGAAGCGTGTGACCCAAGT | 75 TCAGGTAGAGGTCGCCAAGGTT | 1275 GCAGCAGACAGCTGGAGATGAA | 2475 |
| 76 TGCCTCATCTCTGCCCTCTTT | 76 GGAGGCTATGAGAAGTGAGGTTTG | 1276 CTCTGCTGTTCCCTCACCTGTAA | 2476 |
| 77 TCTCAGTGCGTTGGAAGGAAA | 77 GGGCGGTTAAAGAGCTTCAGAGA | 1277 TCTGGCTTCTCAGTGCGTTT | 2477 |
| 78 AGGTTTCCCTGGACACAGATTC | 78 TGGTCTTCTTTATGCCCAACAAAC | 1278 TGTCAAGGGACTAAGTTCTTAGGTTTC | 2478 |
| 79 AGGAGACAGGGACAGTTGAATG | 79 CTCACACGGGCTCACATTCT | 1279 GGCTCATGCTTGTGATAGGAGACA | 2479 |
| 80 TGGGGTGGAAACACGTCCTTTA | 80 CCTGCTCACCTGATCCCAA | 1280 GCCGAGGAGAATATGGGTTGGAAAC | 2480 |
| 81 GCCCTTAGCAACAGCTGCAT | 81 GGTCAGAAACAGAGCCTGTAAAAC | 1281 GCATCTTGTGGTTGCCCTTAGCAA | 2481 |
| 82 GCAGACACGCCTCTGGCAAAT | 82 CCTGAGACAAGCAGTAGCGTCTT | 1282 GTCCATTGGCAGCCTTCT | 2482 |
| 83 GCCAAAAGTGACAGCAACACA | 83 CGCAAATGGGCTCCTGCTT | 1283 CCTGATGCTCCCTCTGCCAAAA | 2483 |
| 84 GCACATCCAATCCTTCAGTAAATC | 84 GCGGCATTAGGCGTGGACTTTC | 1284 GGCTCATCCTTCGCACATCCAATC | 2484 |
| 85 TCCTCATCCAAGCTCCTCTCT | 85 GGAGGTATTCTGGCTTCCCTAAGA | 1285 GCCCCTTCCTCTTCCTGAACAGT | 2485 |
| 86 GGCACTTTCCACCCAGAACTTAAC | 86 GGAAGGGTGAGTTTAGCACAATGGTT | 1286 AGCTGAAGCCTACGGACTTTC | 2486 |
| 87 AAGCCCATCTGCTGCTCTCTG | 87 CCCACTTCCACAAATGCAAACA | 1287 TGGGAGAAAAAGCCCACGTT | 2487 |
| 88 CTCAGTAGGGTGAAAGGATGGAAGT | 88 AGCTGTGGTTTTCCTTCTGTCA | 1288 GCAAGGCTCAGTAGGGTGAAAAG | 2488 |
| 89 GTTGGATTTACAGAAACCTGCAAA | 89 TGTGTGTGTTTAGCAAGGGATTTC | 1289 GCCAAATCCTTTTGCTGGATCTT | 2489 |
| 90 TGGGTGCAGATCCTTGTCA | 90 CGTTTGGCAACGGAGATGTGT | 1290 GGAAAGGCGGTGGAATGTGGTT | 2490 |
| 91 GCTCTGCAGCCTCACGTTCTTA | 91 TGCCCATCCTTTTCTTTTGCTT | 1291 TCTGACTAAGTCCCCTCTCA | 2491 |
| 92 TCCCTTGACTCACGCCTTGA | 92 GGGCTATACATTTCTGGGCTCAA | 1292 CCTCACACTTTCCTGTCCTGACT | 2492 |
| 93 GGAGGACATGGTGTTTGAGGAT | 93 TACATTTCCCTCTCCGGAACA | 1293 CAGCTGATCTATGCATTGGAGGACAT | 2493 |
| 94 CTACAGTTAGAGTCACACGTCACA | 94 CCAGCCAATCAGGATCATGGACAGA | 1294 GCATCTACCCAATCACTACAGTTAGA | 2494 |
| 95 CATGCAGAGGGACTTAGCAA | 95 GGCCCATCACTCTGCTGGAT | 1295 CTCACACGACTCTGCTTA | 2495 |
| 96 GCTTTCAGAGTAGAGGCGTTC | 96 GGAGGCATCTCCGGCTACA | 1296 AGGGCAAAAGCTTCCAGAGTAG | 2496 |
| 97 TGATGGTGCAGAATTGCTACGATA | 97 AGTGCAAGGTTGGAGAATGAAAG | 1297 GCAAAGTTTCATGGCCAAGTGTCA | 2497 |
| 98 GCTGAAATGGACCCACAGAGA | 98 CCAGTTGGCCTCGTCTTACCAA | 1298 TGCTGCCAGGCTGCTGAAAT | 2498 |
| 99 TGCTCCAACGATGGCTGTTC | 99 CGTGGCAGCCGGCTTAAGAATC | 1299 TCCCCAGGCACCTGCTCCAA | 2499 |
| 100 AGGTGAAAGCGATCCTCGTCTTAG | 100 TGGTGCAGCCACCTCTCTTATC | 1300 TCACCTACCTAGGATTAAAGGTGAAAG | 2500 |
| 101 GCCCTGACCTCACCATTCCAAA | 101 CTCTGGCACATGCGTTAGTTG | 1301 GGACAGGTTGGTGCCAGATT | 2501 |
| 102 TGGGCAATTGCGGGTATT | 102 GGGGCTTTGGATAACACCAAGGTA | 1302 AAGGAGGTCCTGGGGCAAT | 2502 |
| 103 GCATTACAGGAGAGTGAAGATGGAT | 103 TTGCAACCCCTCCGACATTC | 1303 CTTGCCTAGGAAGGGCATTACA | 2503 |
| 104 GGAGGAGAAAGGTGGTACACCTG | 104 AGGAGAAGTTCAGGGGACCAA | 1304 GTTGCAGCCTGGAGGAGAAA | 2504 |
| 105 GGAGACAATACAGGTTGGGTGCTT | 105 AGAGCTGCTATCATGATGTGGAAA | 1305 GCTGGTCAATTCTGTAAATCAAGGAGACA | 2505 |
| 106 GCCGGATCTTCCTTACCTAGTCTGA | 106 AGGGTGAGTCTGAGGAGGTT | 1306 TGGGTGAGGGGGATCTTC | 2506 |
| 107 GGATACTGTGTAGGAAGGCAATACA | 107 CCCCACTCCCCTCAAGGTATGT | 1307 CCCAGAGAGGCTGGATACTGTGA | 2507 |
| 108 CAACTCCAACCCCAGCCTTTTG | 108 GTCACCCTCTGAGGTACACT | 1308 CCTGTGGCTCCTGAGAGAAATCAA | 2508 |
| 109 CAGGCCAAGAATGACATACGACTT | 109 ATGACAACATCACGGACAGAGAA | 1309 TGGGACACTTCAGGCCAAGA | 2509 |
| 110 GGCGAAAATGAGCACTGTGGAA | 110 TGCAAATGCCGAAGGGATTCT | 1310 GGCTACCATTCGGCGAAAATGA | 2510 |
| 111 GGAAGGACAGTACAAGAGCTTACT | 111 CTATGTTTCAGCCACACACATTC | 1311 GCTTGGAGTGTTTGGAAGGAGTACA | 2511 |
| 112 GGCGGATTCCTGCATTTGATTGCAT | 112 CAGGGTTGTTCGGGAAATAGAAG | 1312 TTCCGGTGGTGTTCTGGCGATT | 2512 |
| 113 GGGGTTTGTTTGGGTCAGAGA | 113 GCCGAGGTTCAAGGTCCAA | 1313 GGCATGTAAGGGTGACAAAGGAGTTG | 2513 |
| 114 CTGCAATATTGGCATTTCTCTTCA | 114 TGCTCAACTCAAACAGGACACT | 1314 CCCTGCCTAGGCTTCTCATCT | 2514 |
| 115 AGTGTCACGCCTGGTTGAA | 115 TGCGGCGATGCGGCTGTA | 1315 CCTGCCTAGGTCCTAAAGTGT | 2515 |
| 116 CCCCAGCTCCTTCACAAAGACT | 116 CACAGGGTGGATGGATACAGTTC | 1316 TCCCTCAAACCCAGCTCTT | 2516 |
| 117 TGGACGTGAGGAGGAAGAACA | 117 CGTGCCGTTTGCTCACTCAT | 1317 GGATGCGTTTTCATTGTGGCTGA | 2517 |
| 118 TGGGTCATAAAGTGACTCTGTAACATC | 118 GTGACGGCTCAAGTTGCTTCT | 1318 GGATCTTCCTTCTGGGTCATAAAGT | 2518 |
| 119 GCTGTCAATGTTACATGGCAGGAT | 119 GCTTGCTTGGAACCGATTTTGGAT | 1319 GCTTTTAAAAACCCAGCTGTGAATG | 2519 |

FIG. 34A2

| | | | |
|---|---|---|---|
| 120 CGTCCCTTACCGGAGCAACTTT | 120 GGCGGGACCAGTGCTTTA | 1320 TCTTCCCGCTCCGTCCTTA | 2520 |
| 121 AGTGAGCTAGAGGCTAGGACTTAC | 121 CCTCAATTACTCCCCAGATGTTCAGA | 1321 CTGTCCCGCAGAAGCCAAAAG | 2521 |
| 122 TCCTTTCCTCTCATCCCCTTTG | 122 TCAGCAGGAGGAAGGATGTTTG | 1322 CTGTACTGCTCCTTTCCTCTCA | 2522 |
| 123 GGGCACAGAAGGGTGTTCCAAA | 123 ACCTTCCGGCCATGTGTGAA | 1323 CCTGAGCAAGGGCACAGAAG | 2523 |
| 124 GGCCCTCATTCCAGTCAGCAT | 124 CAAATCTCCTCTGTCTATGCTAGGAA | 1324 AAGTTTCATGGGCCCTCATTG | 2524 |
| 125 TCCTGAGATGGGAAAGAGTGAAGA | 125 AGCTCCGACATTATGCCCAAA | 1325 GGGCTCCCACTTTCCTGAGAT | 2525 |
| 126 GAAACTGCACAAACTTCCTCTCCTA | 126 GGGAAAGCCAGACATCCTCCCTA | 1326 GCAGGCTCGATATCTAATTCCAGAGA | 2526 |
| 127 CGCCTCTGTTGTGATGAAAG | 127 GCCCAGGTAGAGGAACAAATCA | 1327 GCAGAATCGCCTGTGGTTGT | 2527 |
| 128 TCCCCAAGAGCACAGACTCAAC | 128 GGAGAATATCAAGCCTGTCATGGGATT | 1328 GAGAAGCTAAATGGTCCCCAAGA | 2528 |
| 129 CCTCTTCGCAGACCTTGAGGAT | 129 CCAAACTCAGGGCCCTCTCTCTCT | 1329 GGACTGAGGGGCTCTCTGGAA | 2529 |
| 130 TCCACACTCTACCATTTGCTGAAT | 130 GCCCAGAAGAGTGCTTCAGCA | 1330 GCCCCTGTAGTACATCCCACACT | 2530 |
| 131 TGAATTGTGCAGTGAGGCTATATCT | 131 GGCAGTCCTTAACTCCTGGTTTTC | 1331 CCTTTCGCATGAATTGTGCAGTGA | 2531 |
| 132 TGTGACTAGGATCTAGGCATGTTAGT | 132 CCAGCACATTCAGTCCAGAATCA | 1332 GAGCTCTAGCTGTGAGTAGGATCT | 2532 |
| 133 GGTCACACAGAGTTAATGGAGACA | 133 CAGCCAAGTGCAGACTGGAA | 1333 CCTCTTGCCAGGTCACACA | 2533 |
| 134 GGACCCAAGAGGCTGAGGAAG | 134 TCCTGGCAAATCTTGCACAAAG | 1334 ACTGGGTGAATAAGCACCCAAGA | 2534 |
| 135 CTCGTGGGTGTGATGGAACAGA | 135 GTGGGATTACATTCACAGATGCAGAA | 1335 AGAGGCTCCTGGGTGTGA | 2535 |
| 136 TGTTGAGCGTGGACCAGTGA | 136 AGACCTTCACCTCTGCCACAGT | 1336 TGGGCTCTGCTGCCTGTTG | 2536 |
| 137 GGCTGAGGCTGTAGCCTTGAT | 137 GGAACAGGAGGAAGAGCAAGGAA | 1337 GATGGTCCCCAGAGGGGATGA | 2537 |
| 138 GATGGGCTCAAGTCAGAGGTTAAG | 138 ACTGATGCTACCAAAGAGGCTAGA | 1338 ACCCCTGATGCCTCAAGTCA | 2538 |
| 139 GACAGCTGCTTCTCGGCTACAA | 139 CACAACCGCTTCCCTCTTGA | 1339 GTCAATACTGTGGACAGCTGCTTCT | 2539 |
| 140 ATCCACGTACTGCCATGT | 140 GGGAGACACTGCAGGACAAAGT | 1340 GGAAGCATCCCGCCAGCAT | 2540 |
| 141 CCAGACCATGCATCCATCCACAT | 141 GTCCCTGAGAGTTTCCTGGTT | 1341 ACTAGGATCTATTTCAACCCAGACCAT | 2541 |
| 142 GCAAAGAACCATCAGGGTAGACATC | 142 CACAGTGCTGTAGTTGCCTGTT | 1342 GCCTCTGCCTGCAAAGAACCAT | 2542 |
| 143 AAGGGGACGGCCTTCCACTGTCAT | 143 GCCACAAATCTAGGACCTGCAGAA | 1343 GCTCACCATCTTCCTCATCAAACAGA | 2543 |
| 144 AAGAGGGCCATTGCCATAGTTCA | 144 TTTCTGCCCTAGTTCAGGTCATC | 1344 GGGACAGACAGGTTAAGAGGCCATTG | 2544 |
| 145 TGGGGTTCAACCGGACAGT | 145 CCTGAAGATGCAACAGACATTCTTCTAC | 1345 CCAGCAAGCATGGGGTTCAA | 2545 |
| 146 CGTGCCTTAAGCCCAGTTATT | 146 GGATGCAGGCAGGCAAGT | 1346 CCCCAGGAATTCGTGCCTTA | 2546 |
| 147 GGTCTCAGGAATCCACCTCCAA | 147 GTGCTAGAGAGCGAAATACCCGTT | 1347 GGCTCTCAAAACCCTCAGGTCTCA | 2547 |
| 148 ACACAGGGAACGTCTCTGTAAATG | 148 CCCAGAACTCCCACTCGAATAAG | 1348 ATGCTTAGTGCTGACACACA | 2548 |
| 149 CCTGTCCCTCTTTGGTTGAAGGTT | 149 CCCCAGACCAATCCGAGGAGTT | 1349 ACCGACTCCTGTCCCTCTTTG | 2549 |
| 150 CAGGGCATTATCACATGTCTGCCTGTCT | 150 AAGCAACCCAGTTCCTTCCAA | 1350 CAGGAGGTGGTCTTTACCCAATTC | 2550 |
| 151 CGTCCAAGCCTCAGCTGTGTAA | 151 CAGCTGCTGCCTCATTTGCAT | 1351 CACCTTAGAAAAATGCCTACCCTGA | 2551 |
| 152 CTAGCCAAAAGCCATTCTGGTAGT | 152 AAPGTAGCCTTTGAGACGATGT | 1352 GGAAATAGATTTCAGGKACTAGCCAAAAG | 2552 |
| 153 TGTTACTGCCTTCTCCCAACAAA | 153 GCCCCTTCTTTTCTATGAGGATGT | 1353 GCCTTCTCACTGCTGAACCTT | 2553 |
| 154 CCTCACTGCCAAATCTGATACAGACA | 154 AGCATGGGAACCAGTGTTCATC | 1354 AGCCTCCTCACTGCCAAATC | 2554 |
| 155 CGAGAATTACACCCATCTGATCCCTTTC | 155 TGACAGGACGAGGAGACTCAA | 1355 CCCCACTACACGGAATTACACCCATCT | 2555 |
| 156 GGGCAAGGGCTAAGACTTTGAA | 156 TCTCGCCTTCAGAGTTACAGAAT | 1356 TTTAGCAGGGCAAGGGCTAAG | 2556 |
| 157 TCCTAACTCCTACCCATACCTCAAC | 157 AACCTTATCGCTACCCATGTACT | 1357 CAGGCAAAAAGACTGAATCCTAACTCCTA | 2557 |
| 158 CCGGGACTAGGGTGGAAGTCA | 158 CCGAGCTCGTCTGGGTTGAA | 1358 ATGAGGACGAGGCCGGGACTA | 2558 |
| 159 TGCTACACACTAGCTCCTCACA | 159 CTATCTGCCCGCATCACCTT | 1359 GAGTTAGATGACCCTTACTTTCTGCTA | 2559 |
| 160 GCACAGACATCCAGAACTGCTT | 160 CGACGGCTCGGAGAGAATC | 1360 CCATTAGTGCGCACAGACATC | 2560 |
| 161 GTGTGCCCACAGAGACTTGGAA | 161 CCCACGGGTTTGGGTAGCTT | 1361 TCCTGGCTGTCACTACTGTCT | 2561 |
| 162 AAGCCGCCTAATAAPGGAAACCTA | 162 CTTGACTTTGCCTAGCAGTTTTG | 1362 CTGGGAACAAAGCCGCCTAAT | 2562 |
| 163 ATGTTCTGTAGTCGTTAGGCTTGG | 163 CTCACGCTAGTCTCCACCGTCAT | 1363 CGTCTCCGCTGATGTTCGTAG | 2563 |
| 164 TGAAAGAGGCAGGAAAAGGTTGT | 164 AATCCCTTTCAACCCTCCACATT | 1364 GTGCCAACTGTGGCTGTGA | 2564 |
| 165 AGCCAGATACCCTGAGCCTAACA | 165 AGTTCTTCAGGCCGCCTTGTTC | 1365 TGGGTAGTGGGGAAGCCAGATA | 2565 |
| 166 CAGAAGTGGGATTCAAATCCACAGAGA | 166 CCCCGCAGGACTGAGCACAA | 1366 TTGGTACCAGAAGTGGGATTCAAA | 2566 |
| 167 GGCCCAAAGTGCTTTGAGAACA | 167 CATCCAGGCACACCGTTAAGA | 1367 CTGCGGTTTGTGCAGCCCAAAG | 2567 |
| 168 GTCACGGAAGAACTGGTGGATCA | 168 TCGGGAGCACGTTGCAGAT | 1368 GGGCCAACACATGAGGGATGT | 2568 |
| 169 GGTTAATAGGCGCCAACCATTT | 169 GGTTGCTCTCACGGGAATAAGA | 1369 CCACTGGATCACTGGGTGCTTA | 2569 |
| 170 CAGCTTCCCTGTGGAATTGTCTTC | 170 CCGGTAAACCCAATCCAAACAAA | 1370 TGGGACAGTGATTCCCAGCTT | 2570 |
| 171 TGAAGCTCACCACCAGAGA | 171 TCACACTGCGTCAGCTT | 1371 AGGGACAGGGCAGCCAGTCA | 2571 |
| 172 GCTGCCTCCTAGAGCCACTACA | 172 GCATGCCTCACAAACATTATCCCATTC | 1372 TTAAGCCGCTGCCTCCTAGA | 2572 |
| 173 TTTACGGGCCTTCCCAAGTCA | 173 GGGCATCCAAGGAGAGAAGAGA | 1373 GCTCATCCAGGACCCCATCTTT | 2573 |
| 174 CGTCAGCCGATAATACCTGTTGCTT | 174 TGTCAGCCTGGCTTCTGTAAG | 1374 CTCATTGGGGTCAGCCGATA | 2574 |
| 175 TCTTCCCTACCCTGACCGTGATG | 175 TGAGCTGGCCTGGTGAAATAG | 1375 CCTCCGTGATGGGTGGAAATA | 2575 |
| 176 GCCATGTTTCACCGCTGCTTAC | 176 ACCTCACCTTCTAATTCTGGACTGT | 1376 GCGAGTCACCTCTGCCATGTT | 2576 |
| 177 CAGGGCTTTGTGACCTAGACAGA | 177 CGTGACAGCTAATCACCCACAT | 1377 AGGCCACTCAGGGCTTGTGA | 2577 |
| 178 TCTTGCGCACAGGAGAGA | 178 GGAACACCTCTCCCCTCAATTCTTT | 1378 CTGGGGAGATGATATTAAAGCTGACTCT | 2578 |
| 179 CCTTCCCTCCTTCGTGTCTTCT | 179 CCTTGGCAGAGGGAGATTTGAGA | 1379 GCTGCCTCTGTGGTCAACATC | 2579 |
| 180 GCACTTGAGGTAGGATTGGAGGAA | 180 GTGAAGCGTCCTCCTCGTTGA | 1380 CCAAGGCAGCACTTGAGGTA | 2580 |
| 181 GTTGCTTGGTTGCCGTGTTC | 181 CCAGACTAGCCGAATTTCCAGGAT | 1381 GCCAACTGCTGTGTTGTCTTG | 2581 |

| | | | |
|---|---|---|---|
| 244 GGTAACCTTGGCACTGTGGAT | 244 CCCCAGTACTCAGGGGACTTTGT | 1444 TGAAATGAACAGACCAGCTAACCTT | 2644 |
| 245 GCTGTCATCATGGTCCAGACA | 245 GATGGGCATGTGGCTTCT | 1445 CCTGGGCTATGCTGTCATCCAT | 2645 |
| 246 CCATGGAAGAGGGAGATGGAAGT | 246 TCTCCCAGTGGAGCTATGT | 1446 GAGACTGCCTGAATACCATGGAAGA | 2646 |
| 247 CCACTTCTGGGCCLTTTG | 247 CACCAACAAGCTGGCTCTGA | 1447 TGGGACGGTGCCTACCTCTTG | 2647 |
| 248 CACAGAATATGGGCTGAGAATCAAGA | 248 CGGGTCCAAGTTCCCACAT | 1448 CTTTGGTTGCCAGGCCACAGA | 2648 |
| 249 GAGTCCCCACCAGCAAGAAG | 249 TGTCCAAGGTTGAGGGGTTGT | 1449 GGCTGCCTTGGGACACATCT | 2649 |
| 250 GTGAGTGGCTACTGCTTCACT | 250 CTGGAATGGCTGTTAGGCACCTT | 1450 GTCAGGAACACTGCTTGTGATG | 2650 |
| 251 GCTTCCCGCTTCCAGTGCTT | 251 GCACATAACTGTACCTCCTAAGCCAA | 1451 GAGAGGGGGTTGCTTCCCTCTT | 2651 |
| 252 CTGCACTGTGATTCTGGCATAGT | 252 GGGAAAGCAATGCTCTGTGTTATG | 1452 AGGGGCCTGCACTGTGATT | 2652 |
| 253 CCCCTCCACTAACGGTGCATTA | 253 TCCCACAGTCAGGCCTAACCAT | 1453 CCATCAGCAGATTCACACTCAGA | 2653 |
| 254 CAGGGGATGAAAGACAGAGAGCATTTG | 254 ACAGCTGGACCCAGGGGAAGTT | 1454 CAGGGGAAAACAGGGATGAAAGACA | 2654 |
| 255 CCCCTCGAGGCTGTTTTAGTGA | 255 CCTGGTGGCATAAGGGATGCTT | 1455 CTGCTGTGAAGCTGAGACTTTTTAC | 2655 |
| 256 CCAGTGTCAGGGCCGAGTAG | 256 GATGTTGGTACTCGCTTCTCAGT | 1456 TCCCCGGCGTTGACCAGTGT | 2656 |
| 257 TGCTGCTTTACGCCCAGTGA | 257 GGGTTACTAAAGGGCAGTTCTGTTC | 1457 GGACAGGTACTAGGTGCTGCTT | 2657 |
| 258 GACCAATGGGTGTCAGCTT | 258 TCCTAGGCTGACTAGGTGTCAT | 1458 GAAGCCGGTTTAACTGGTGTTG | 2658 |
| 259 AGGGTATGGGAGGTGGGAACA | 259 GCCTTCTCCCAGTCCATTTCT | 1459 CAGCAGGAGGGAAAAGGCTATG | 2659 |
| 260 CTGTGTATGTGGGTCTGAAGCTCAA | 260 TGTCTTTCACCAGCCCAGACT | 1460 CTCAAAAGGTAGGTGCTTGACA | 2660 |
| 261 GGGGCTCAGATCCCTTGGTT | 261 CGTGTGAGAAAACCTCTCCTACTAC | 1461 TGGTTCCCAAGGGCTCAGAT | 2661 |
| 262 AGCATCCTGGAGGCTTTTAAT | 262 TGTCCAACAGCTTTACATAGCACAT | 1462 GTGGTGAAAGTAATGGCATCAAGCAT | 2662 |
| 263 ACGATTCTGAAGCAGTCTTGGTA | 263 CAGAAGCAGTGAGCTGTGGTT | 1463 TGCCTGTGGTGTGGTCATTTGT | 2663 |
| 264 CAGGCATTAGCTGGCTTCACA | 264 CTGGGCCTGCAGAAATGCTA | 1464 TCCCAGTGCAAGGGCATTAG | 2664 |
| 265 TCCCACTTACAGGCCCGTTCT | 265 CACTGAGGCGATGCTCTGATCT | 1465 AGGCTGGCCTCCCACTTAC | 2665 |
| 266 TTTCAGAAGTGCTGGAACCAAGA | 266 TGGCCTCCTTCTCTAAAAGCATTC | 1466 AGAGTAAACTTGGAAGGATGGGTTC | 2666 |
| 267 CATGAAAGCACTGGGGTTCTCT | 267 CACTCACAACTCCTTTCCCAAGT | 1467 GCAATCCCTGCCGACCACAT | 2667 |
| 268 CGAGAGAGGAAGACACTGGAGTGAA | 268 GCTGGGCAAAGCCTCCAT | 1468 AGGCCAAAGTCCCTGTGAAC | 2668 |
| 269 CCTTCCCTCACACTAAGTGACTGAAA | 269 ATCCACTGCCCTGACCTTGT | 1469 GGATGCAGATTCCCTTCCTCCACACT | 2669 |
| 270 CAGCCCATCCTGGGCATCT | 270 ACTCCAAACCCACCTGCTA | 1470 CCTCGTTTCTCTGTCCCTCCTT | 2670 |
| 271 AGGCTGGCAAATGGGCTCAA | 271 GGGTCCTAACCCTCAGTCTTGT | 1471 GGGTGCTGGGAAACATGAGGAA | 2671 |
| 272 GCTGAGCCCAGCAGTGTGTT | 272 ACAGGGCTCCTGGTTCTAACT | 1472 CAGCCTTCTGTGTCCACTCCTTAG | 2672 |
| 273 CCTTGGCTGGGCTACATCTTACCTT | 273 CTCTAGGAGCATGGTCACCAAA | 1473 TGCTTCCAGAGCCCCACACT | 2673 |
| 274 GCATGGGGACCTGAGACTTTCT | 274 AAGCCGGCAGGCTGAGTT | 1474 CACTCCCGCATTGTTGTGCAT | 2674 |
| 275 GGGCCGATGAGCAAGTCAGTT | 275 GGAGCCACAAGGAATGCAGAGT | 1475 ACACCCTGTGGGGCGATGA | 2675 |
| 276 CCTCCCCGAAAGCAAACAGAGCAT | 276 CAAGACCTTGCCTGACCAACTAC | 1476 GTGGGTAGTTGAGACTTCCCCGAAAG | 2676 |
| 277 TGGATGGTGAGAAGAGCCAATG | 277 GGTTGCAGCCTTGCTCACT | 1477 GGGCAGAAGTGGGATGGTGAGA | 2677 |
| 278 GCCTGGTCACTATCGGCTTT | 278 GCTGGAAGGTGGAAGGACCTTT | 1478 GCCCCTACCCTGTTCCTCCAT | 2678 |
| 279 GACACTTACAGGCTCAGAGAAC | 279 GGGCACACTGAAGTCTAGAAGCAA | 1479 ACTTCCAGGAGCAACTTTGAATAG | 2679 |
| 280 TGATCACTCCTGGGTCAAGA | 280 TGGGCCCATCTCTTGACTTTC | 1480 CCATCAAAGAGTAACAAGCCAGTGA | 2680 |
| 281 CTTCCCTCGATTGGTCAACA | 281 GAAGGATGAGGGGATGGCTCTA | 1481 AACCCCGTCTTGGCTCGATT | 2681 |
| 282 CCAGCACCAGCCAGGGTCTTCA | 282 GCAGTACTTGGGGTCGTATATCTGT | 1482 GCTACACGCTGGGCACCAA | 2682 |
| 283 TCTCCTCCGCCAAGATCAGA | 283 TCCACCTACCCTGTGGGCAATC | 1483 GCCCTATGGCAAAGGGCTCACTA | 2683 |
| 284 CCTCAGCCCAGGACTCACTTTTAG | 284 CCCGGGTACAACAGTGACCTT | 1484 AAGCCTCTGGCTGGTGTTTC | 2684 |
| 285 TCCATGACGGGCAGCTGTA | 285 TCTCCCGGAAAGTCCGTTCTA | 1485 CCTGTGGTTTTGGGCAGGTT | 2685 |
| 286 CACCCTGGGATCAAGTCAAGT | 286 CACCCAAGCTCTCACTGTTACT | 1486 TGGTTACCACCCTGGGATCA | 2686 |
| 287 TGCATGCTGGGACACAGAGA | 287 GGGGCAGCTGACCAACTAC | 1487 TCTGGTACTCCCAGGGTGCAT | 2687 |
| 288 AGGGGCTGCTGGGGCTTGTA | 288 CTCCCTGAAGCAGCAGCAAA | 1488 TGGATACACGGGGCTTGTCT | 2688 |
| 289 GCGCTGCCTAGTGACATTGGTT | 289 GCTGTCACACTGACCCTGGATT | 1489 AAGACACCGCGCTGCCTAGT | 2689 |
| 290 TGGTGGTGGTCCCCAGTAATGT | 290 GCCATGCTGAGAGCCTCTGT | 1490 TCCAGAGGCAGGAGACAATCA | 2690 |
| 291 CCCTGGTGGGTTTTGAGTGAA | 291 GTCCACGTGTGAACATGTTATT | 1491 CTCGCAATTGGAGCTGAATTCTTAAATC | 2691 |
| 292 CCCACTTAGAGCCCCAGGAAA | 292 GCAAGGAGCTGATCTCATCTGTGT | 1492 CCTTGGGGTGGCCCACTTAG | 2692 |
| 293 CGATCGGCTTTGCAGGCTTT | 293 CAAAGGGTCTTTCCCCACAAA | 1493 TTTTCCCTGACGAFCGGCTTT | 2693 |
| 294 AACCAGATCGTGTCTCCTAGT | 294 GGGAAGCCTTTGAGGGTTCA | 1494 GTCAGGGAGAACCTATGCACCTA | 2694 |
| 295 CCAACAGCGTGAGGCTTCTGA | 295 TCTGCACCCTGCCCTGTGT | 1495 CCCCAGACAGATGTAAGTCCAACA | 2695 |
| 296 GCCTGGAACACACTGTACTCTGA | 296 TCCCCAGAGTGCAACCTCTT | 1496 CTGCATGCTTGGAACACACT | 2696 |
| 297 TCCTCCCCGTCTGCTCAA | 297 GTTTGGCTGCACGTAGAGAAAG | 1497 CTGGACTGCTCACTCTGGAACT | 2697 |
| 298 TGAAACCAGAAGCTTTCACCTCAT | 298 GTTGGCACTGGGGCCTTCT | 1498 TGCCCGAAGAGGCATGAAAC | 2698 |
| 299 AGTCAGGGTGTCTCCCATGA | 299 GACTCAGTCAGTAGAGAGGGAGAA | 1499 TCTTCTCCAAAATCAGGGTGTCT | 2699 |
| 300 GAGCAAAAGAGCTCTTCAGAGAA | 300 CGTGGGGAGGGACACCACTT | 1500 GCAGTGCAGGAGCAAAAGA | 2700 |
| 301 CCTTCTACACAGGATGGGATCAGT | 301 TCTTCTTTTGACAGATCGGGACAT | 1501 AGCCTTAAAACTGCCTCTACACA | 2701 |
| 302 TGAAGGGTTCCCCTTCAAAGT | 302 ACTTTCTGAGGTTTGGGGTAGA | 1502 GGCATTCACTAGTGTTGGATTGA | 2702 |
| 303 GCCTACATGTCTATCCCCTGAAG | 303 TGTAAGGCTAAGCCGATTTTG | 1503 CCAATCGTGGAAACAGCCTACA | 2703 |
| 304 GCTGGAAACCATGGGGAGTT | 304 TGACCAGATCCACTCGGACAGA | 1504 GCTAGATGCGGAGCTGGAATC | 2704 |
| 305 GGGCCAGTACCCAGGAGGAA | 305 ACAGGCCCACTGCCTGTCT | 1505 CCTGGATGTGGCTGGCAGTA | 2705 |

| | | | |
|---|---|---|---|
| 368 GGTHCTGCAGAGGGTGGAAA | 368 CGGGCTACPGGCTGCTATAC | 1568 GTGAGAGGATGPGTGCGTTCCAT | 2768 |
| 369 AACEACCCBCCCACCCAACA | 369 CTCTGCATGTGGAGCAAACCAA | 1569 CAPTACCCCAGTTGGCAGAAAAC | 2769 |
| 370 GPTGGGTGGACAGTCTTFTTCATCTTTG | 370 AGGTAAGGGGGAGGCTGCAGAA | 1570 GACAAGTTGGGTGGACAGTCTT | 2770 |
| 371 GTGCTCTCCCTTGAAATGAGGAT | 371 GCTAGATAATGCTGCCTGCTTTG | 1571 AAGGGGTGCTCTCCCTTGA | 2771 |
| 372 GATGGGGAAACCGACCAACT | 372 CTGAAAAGATCACTACCAGGATGCTA | 1572 CCCCGTGAAATGATGGGGGAAAC | 2772 |
| 373 TGCAGGGTGGCAGCATGA | 373 AGACAACAGCCTTGCTGAGTA | 1573 GGTAATCAACCCTCAGTCTCTCATC | 2773 |
| 374 GCCCTCTGACTTCACTGACCTACT | 374 AGGGAGAGCCTCTGATGAAAGAT | 1574 AGGCCAGCCCTCTGACTTC | 2774 |
| 375 TGGGGTTGAGCPCCCCTPATC | 375 CCAGTGTAGGCTCACATTCTGT | 1575 GCTTGGGACTCTGGGGTTGA | 2775 |
| 376 CCCCTTCATCTGCCCTGGTAGT | 376 GCCAGGAGTCTCTGTCCATTGT | 1576 CCTGGCTTTGCCCCTTCATCT | 2776 |
| 377 CCTCTGCATCCTTGGCCTACATT | 377 TCCTGGTGTGGACGTGTCTCAT | 1577 AGTCAGCCTCTGCACCTT | 2777 |
| 378 GGCGGAAACCAAACCCTCAGA | 378 CGTCAGGGGTCCCTTCTTTTG | 1578 CCPCTGAAAGGCCGAAACCAA | 2778 |
| 379 GGGCCCCTCCCACATACACA | 379 GCCAGAGCCTTCATTTGGGAGAAA | 1579 AGTGGCCACGCAGGAGCAA | 2779 |
| 380 GCCCATGCTGAGGACTAAACCTT | 380 TGGGCCTCCTCCAGCCTTT | 1580 CCAGGGCAGGACTCTAACCATTG | 2780 |
| 381 CCCTAAGGTTGGGTCGAGTTG | 381 GTTTCCCAGGCCTCTCTCTTC | 1581 GTTAGGAAAGGGTCCCCTAAGGTT | 2781 |
| 382 CAGGGTCCAACGGGTTTCTA | 382 GGGAKGTACCCAAAGGCTTCTCT | 1582 GGTGGCTGGATTGCCTACT | 2782 |
| 383 GCCCAGCCATTCACACTGCAT | 383 GGTGCTTCACAGGGTTCACAGT | 1583 TCCACCCTGGCCCCACCATT | 2783 |
| 384 GCAAGTAGCTGGGCTTGTCA | 384 AGCCAGCAGGTGCCATTCAT | 1584 CGTGGAGGGGAGGAAGTCTTG | 2784 |
| 385 GCACCATCAGGAGATGCAGACT | 385 GGGAAGTAAACATCCCAGCTTCA | 1585 ACCAATGGAGGCACCATCA | 2785 |
| 386 CTCTGCCAGTTCTGAGTGGGAGGA | 386 GCAGTTCTGCCTGCAGGCTTT | 1586 GAGTGCACTTGTACTCTGTCAGT | 2786 |
| 387 GAGGCCTCACTCTCCCCTTAT | 387 CTTCCCGTATGCTAAGGACTATTCT | 1587 GGCTTTTTGGCTTTCCCAGGTTGATG | 2787 |
| 388 TCATGCTGCTTGGGTAATGTTCT | 388 CTGTGCAGCAGAGGCAGTTATG | 1588 CCCGCAAGGGTTGGGGAAAT | 2788 |
| 389 CTGGGGCATCCTCCTGTCT | 389 GGGCCTCGAAAGGCAGAAATC | 1589 TCCAACACCATCCGCTCTC | 2789 |
| 390 TGGAGAGTGGGGAGGAGCCTT | 390 GCATCCATCCCGGCAGTTTTCA | 1590 GTGGGTGCCAGAGTTGAGATTC | 2790 |
| 391 GGAGCATGCCGCCTTGTTACT | 391 GAAGAGCAGGAGCTACTTCTATCCAT | 1591 GGCCGGGAAAAGGGAGCAT | 2791 |
| 392 GTCTCTTCCCTGAAGTAGGGTGT | 392 GACCCCAGACTCAGTCAGTAGATG | 1592 GTCTTCCCCATAGTTAAGTTGTCTCTTC | 2792 |
| 393 TCACTCACATCATCATGGTTGGAT | 393 CAAACTGGAAACCATACCCACTTC | 1593 GCAGCTACCCATACAAATCACTCACATC | 2793 |
| 394 GGAGTAGCATTGCCTTCGTT | 394 TGGGGCTCCACCAGCCAGAA | 1594 ACTGGACTCACGGAGCAGCAT | 2794 |
| 395 GCTTCGCATCACGGTAGTTTT | 395 CCGTCTAACAGCGTCCCCAAT | 1595 ACCGTCTAACAGCGTCCCCATCA | 2795 |
| 396 CCCGTTTGAAGAAATGATAGCTCGAA | 396 CTGGTGGGAGTGGGCCTTATTT | 1596 GGACTTTTGTTTTCCCCGTTTGAAG | 2796 |
| 397 GGGTGCTGTTCTGGCTTTGA | 397 GCAAGTGCTATCAGAAGTCCACCCTAGT | 1597 TCTAAATGTCTCTGGGTGCTGTTC | 2797 |
| 398 GGCTGTGGTTGTTGACACAGT | 398 TGAGCCAAAGACTTTCCCTGTATT | 1598 GGGGTCTAATGGCTGTGGTTGT | 2798 |
| 399 CCCTCTGGAACAAAGTGGGAACT | 399 GCCAGACGCAGGCCTAGTAA | 1599 GGCTGTTAGCCCTGGGAACAA | 2799 |
| 400 GCAAAGGCTTGTGTGGACAGTGA | 400 TGGCCACGTGCTCTCCACTA | 1600 ACGGCAGAGCAAAGGCTTGT | 2800 |
| 401 CAAGGGACCTTCGGAAACTTGA | 401 ATAGCAGGCTTAATCCTAGAGGTA | 1601 GGACAAGGGCCTTTAATTCATACCAAGA | 2801 |
| 402 AGGCACAGCAGGTCTCATC | 402 CCCAGAGTTTCAGTAGGACATAGT | 1602 AGCCCAHAGCAGCCTTCA | 2802 |
| 403 GTGTAGAGGGGCAACTTCCTATCTTG | 403 CTGCTTTCCCCGACCTCTT | 1603 TGGTAGTGTAGAGGGGCAACT | 2803 |
| 404 CAGACTACAAAGTGTTTGCTGTTTGT | 404 TGGTCCGCTCAGTTTGAAT | 1604 GGGCCAAGCGTTCAGACTAC | 2804 |
| 405 CTGCTTGTGCCTACTCTGT | 405 CTGCCCTTAGGGATCTGGGTGATG | 1605 ATGCTCAGGCTGCGTTGT | 2805 |
| 406 GGTCTCCCCGCACTTAGCAT | 406 CGGCTTTGGAAGCAGCCATCCTGT | 1606 TGGCTCCCTGAGGAGTGTTTG | 2806 |
| 407 GTGAGCCCAGACAGCAGTAATCA | 407 CCAGCTTCAGTGTGCACCAA | 1607 CAGAAAAGTTCTAGTGAAGCCAGACA | 2807 |
| 408 GGAGGGTGAACAAGGCAAAGATG | 408 CCTGAGACTCTACTGTTGCTCGAA | 1608 CACAGACTAACTGGAGGGTGAAC | 2808 |
| 409 ACCTCCAGGAGCTAGTTAGAGA | 409 TTTCCTCACTGGGTGGGATCT | 1609 ACATACCTGCTGTACCCCAAATG | 2809 |
| 410 GCTTCCAGTCCCCACTTGTGA | 410 GCGGGCAATTCCACATCTGA | 1610 GCAATGAACAACGACAGGCTTTCA | 2810 |
| 411 GTGAGGCAGGAAGGATGAGTTT | 411 CCAACTCAGGGCAAGTGGTTCT | 1611 GCTGAGCTTGGAGGCAGGAA | 2811 |
| 412 GAGCTTTGGAGCAGTGGGGTAAC | 412 GGTTGCAAGTACTGTGGGAATAAAG | 1612 GCATACTAAAGGAGCTTTGGAGACA | 2812 |
| 413 CTAGCCATCAGGTCACAATGAAC | 413 GAGGACTTGGGCCTTTCCPATC | 1613 GCCAACTAGGCCAGCATTA | 2813 |
| 414 ACTGAGGGCGGCATTGCTTA | 414 TCTGCGATGCGTTCCTGTT | 1614 ACGAGCGGTACAGCGGAATC | 2814 |
| 415 GCTGGCAAGGAGGGTTTCTAA | 415 GTGAAGCTTGGCCTGGTTTG | 1615 GAGAAAGTGAGCATTTGCCATGAAAG | 2815 |
| 416 TCAGAGTTCTGTCCTAATGGAGGAA | 416 CCATACAAAGCCAAGAGTGGGAAGT | 1616 GGTCTTACCTTCAGAGTCTGTCCTA | 2816 |
| 417 CACTAGTCTGCAAAACCAGCACCAA | 417 GGGAGGGTTTCCCCACTAAGA | 1617 GGGGAACATTCAGACCAGATAACACT | 2817 |
| 418 AATCCTGGAACACTCTTGCCTAAA | 418 CATCTTCCAATGTGAGCTGTCA | 1618 AGGGCAATCCTGGAACACT | 2818 |
| 419 GTGTGAGCTAGTTCCTTCTCCTCTTC | 419 CAGCCGCTGACTGCCTCAT | 1619 CCTTGCACCAAAAATAGAGTGTGAGCTA | 2819 |
| 420 CAACTGCAGCGTGCTGATTTTA | 420 CGAAAGGGGATGGCGCTTTC | 1620 ACTGCCAAGTGGCTGCAA | 2820 |
| 421 AAPCGGCCACAGCCCAGAGA | 421 CCCCTGCTGGTGGTCTGTTC | 1621 CACAGCTGAACCTCAGGCAATC | 2821 |
| 422 GGATCTCTGAACACCACTCCTT | 422 GGGCCTGGGTTCTCPCTTCT | 1622 CAACAGCCGGGGATCTTCTGAA | 2822 |
| 423 ATCCAGTTCCTGGGTCACTCT | 423 CAGTGCCTGTGGTTCTCACACT | 1623 GGCCCTAGGTGTGTGTATCCAGTT | 2823 |
| 424 GTTTTCTCACCAACACACCCTTTCT | 424 GCTTCACTTCACGCTGCAACTGA | 1624 CCTGTCCGAATCTTTTCTCACCAA | 2824 |
| 425 AAGGGGACTCCAGTAGCTCAAGA | 425 TGCCCCTCCACCCTCGATCT | 1625 GGGTCTAAGGACACCCGGTCTA | 2825 |
| 426 GGGCCAATGTGTCCTGGCTTTGT | 426 GGAGGCCACCACACCTCCTA | 1626 TTTCGGTGGGGCCAATGTGT | 2826 |
| 427 TGCCATGGCCTTTGGCTCTATAC | 427 TCTCAGCCGACTCAGACCT | 1627 GCATTGTCAGGCTTCTCTTTG | 2827 |
| 428 GCTCTCAGGTTGGAAATCATCCATTTG | 428 CATTCTGGAGTGTGGGTGGATT | 1628 CAGAAATCAGAAGCTCTCCAGGGAAA | 2828 |
| 429 CCTGGGATTACCATGTCCCATAA | 429 ACGGTGAAAAATGAGGCTGTGT | 1629 ACTCTTTTGCCTGGGATTACCAT | 2829 |

| | | | |
|---|---|---|---|
| 492 TGTGAGCTGTTCTGGCATGT | 492 GCAGAGTCCCTTGGTGGTGTAAG | 1692 GCAAGTTTGGCCATCTCTTGTGA | 2892 |
| 493 GTGTTACCTGGTGCCTGAATGT | 493 CAGGCCACATTCTCCACAGA | 1693 CGTCCATCAAGGAATAGCTGGTGTT | 2893 |
| 494 AGCTAAGTTTTCCAGGCGGATGT | 494 TGCAAACATGCACGGGTTGAT | 1694 ACCTGGCTATACGAGAACTCTTT | 2894 |
| 495 GTGAAAGAGCCATGATAGGTCTGA | 495 GTGTTGCAGCACTAAAACATCACA | 1695 GTTCATGAAAGTGAAAGAGCCATGA | 2895 |
| 496 GATGCCCGCACCTGCTAGA | 496 ACAAAGGGAAATCCAATGGTCACT | 1696 GGGACAAAATCGGCTCCTTCAGA | 2896 |
| 497 TCGCCCTTGTGGATCCAAGT | 497 GCTGGGAAGCTCTGCCTCAA | 1697 ATGCCCTGAATCGCCCTTGT | 2897 |
| 498 AGGGGACGTCTCCCAGGTT | 498 TGGGAAGTCCACCCACTCCAA | 1698 CCCACACTCTTGCCAAGGAA | 2898 |
| 499 ACCCTGCATCGGGTCTCA | 499 CCACGGAGGAAGAACCAGAGT | 1699 GCCATGGGTAAGGCAGGAA | 2899 |
| 500 GTCCTGTTCCCGCAAGGTTGA | 500 ATCACCCGGAGGACCCATGT | 1700 ACTGGCTGGTGGTCCTGTT | 2900 |
| 501 GTGTGTTCCTCCTTCCCAAGGAAT | 501 AGGGGCCTAAGTGGGCTCTTT | 1701 CGCTGTCCTGGAAGTGTTGTTC | 2901 |
| 502 GTCACAGAGATTCACACAGCCTACA | 502 GAAAAACGGGTTAGGGCAGAGA | 1702 TGGCCCACAGAAAGGGTCTCA | 2902 |
| 503 ACAGATGCAGATGCAGAAGAAA | 503 CGGAATGGGATGCCCTTGGAA | 1703 TCTCTGGTTAACAGATGCCAGATG | 2903 |
| 504 GGCTCTGAGGTCATCTCTGTATCA | 504 CACTGTCCCGCTGCAGAT | 1704 CCCAAAAGGCTCTGAGGTCATC | 2904 |
| 505 CAAGTCCCTCCCAGCAACAA | 505 TGTCATAGATCAGTTGGTGAATGT | 1705 GGACATGACTCCCTGGGTACAA | 2905 |
| 506 CGGCCTCGTCGTCCTGTCACTTT | 506 CCCAGGGACCCTGAGATGGCTGT | 1706 TGTCTTAGCTGCCCCTCTGT | 2906 |
| 507 GGAAACTAACCCCGCCAGAA | 507 AGAGACCAAGGCGCTCTCTCTAA | 1707 GCCAAGGGCAGGTGGGATA | 2907 |
| 508 CCATCATCTGGTTATGCTACAGTCT | 508 GAGGGAGGTGAATCCACGAGAGA | 1708 CCTTTCCAACTCCATCATCTGGTTA | 2908 |
| 509 CTTGATGACTCCACTTCTTCATCA | 509 AGGGGCCATCACGGTGAGAAA | 1709 CCTCCCTGATACCTTCTTCATGACT | 2909 |
| 510 GCCAAGGAGTGAACCAGGTTTG | 510 AGAGAGCCATCCTCCCTTCCAA | 1710 GGCCTAAAGGCCAAGGAGTGAA | 2910 |
| 511 CGAACTGTGTTAGGGTTCAGT | 511 ACTTCTGAGCAATGTGGTCATGA | 1711 CACTCGCCTACCGACCTGTGT | 2911 |
| 512 GTGGCCCAGAAGGCTGCTT | 512 GGGGACAGTTCTTCTGGACTTA | 1712 TGGCAGCGTGGAAGCTCTGT | 2912 |
| 513 CACAGGAGGTCATTAAGGTTCAACA | 513 CAGATTGGCGACCTCACCCTTAT | 1713 AGGTTCCACAGGAGGTCATT | 2913 |
| 514 GCAGCACATTGTATCTCGGTCAACA | 514 GGCCTTTCCTAAGCTGATGGTTGA | 1714 TGTGAAAGAAGGGCAGACATTGTA | 2914 |
| 515 TGGGTTCGCACGGCTGTT | 515 GCTGGCATCTAATGCTGCCATGT | 1715 CCAGTGTGGGATCTCAGGCATT | 2915 |
| 516 ACCACCACACCTAGCTGCAAAG | 516 GCTGCTCAGAGAGAAACTGCAT | 1716 GAATTTACTCTGACCACCACCTA | 2916 |
| 517 TGTCCCTGGGCTCACTGAA | 517 GATCGCCTGAGAGGACAAG | 1717 TGCTGTGTCAGGGACTGT | 2917 |
| 518 GTGGGGTAACAGCCACAGGTAT | 518 ATGCCCTGCGAGACCAGCTAGAA | 1718 TCAGGTGATAGGTGGGGTAACA | 2918 |
| 519 CTGCCGGAGACTATGCTCAGTA | 519 GAGCTTTGGGGTGCCGATGAT | 1719 GAAACCAACTGCCCAGAGT | 2919 |
| 520 GTCACCCAGGCCATGTGAACTT | 520 GCAGAAGTTGCTGGTTCTGTTT | 1720 AGGGAAGTGGCCGCAGTATG | 2920 |
| 521 GGGCCATGCATTCCTCTGTAG | 521 GGGCAGAGGCAGGACCATG | 1721 AGCCCTGGGCCATGTCATT | 2921 |
| 522 CCCCAAGATGCTGCATAGTCC | 522 GCTGGTATTTTCGTTTCTGCATGT | 1722 GGTTACTTCCCTTTATTGCCCAAGAT | 2922 |
| 523 GCAGTTGGTAAAGGCAAATCTTAACGAAA | 523 TTCCCCTCCTCCCCTCAA | 1723 GTGTGCAGTTGGTAAAGGCAAAG | 2923 |
| 524 AGACTAGGCAGGGTACACACA | 524 ACATGCCTACACCCAAAGTCATC | 1724 GTGATTTTCCAGCCACCTCCCCTA | 2924 |
| 525 GTGAGCACAAATTTGGATCGAGTGAGA | 525 TGCCTTGGAGGAAGGAAGTCA | 1725 GGGAAACCCTGTAATAACTCACTCTGT | 2925 |
| 526 GAGTGGCTAGCTCCAAGACACA | 526 CCCTCCCCCTGGATTTTGGGTTT | 1726 GTCAGTGCTTTCAGGCATCTT | 2926 |
| 527 GTGTGGGAAGGAGGATTCCAGCACT | 527 AGCTCCTCACCCAGCCTCAA | 1727 AAATTACTCCATGGTGGGAAGTGT | 2927 |
| 528 ATGGTAGGTCAGATCCAGAAGT | 528 ACACCTGTGGACCATGCTCGA | 1728 GCCTGATTGAACCCTACAACA | 2928 |
| 529 CGTCCAGGAGACAGTTAACCTCTTG | 529 GCCCAGGTATGCTTGACCATT | 1729 CGGCGTCCAGGAGACAGTT | 2929 |
| 530 TTCAAGAGCATTAGGTGTCTT | 530 ACTCAGACAACCCACCAAATC | 1730 CCAAGGTGCTTTCCAAGAGCATTC | 2930 |
| 531 AGCAGCTCAAATATGCCAAAGA | 531 GTAGACTAGAACATGACACTCCAAT | 1731 GTTTCTCAGGATAAGCAGCTCAAAG | 2931 |
| 532 AGTGCCAGACCCGCTAGAAA | 532 CTGGGCACCTTGCAGCTTTT | 1732 TGACCACCAAGGCTGGTGAT | 2932 |
| 533 ACCCCTGTGCCTAAGCTGAAGT | 533 AGGCCCTGTTCCCTGGAATG | 1733 TTGGCCACTCAGAGCAGTCAT | 2933 |
| 534 CTGCTGCTGGCTGCTGTTTCA | 534 ATCTGCCGAGCCAGGTCACTT | 1734 GCAGTGATGCGATGTGAGTCT | 2934 |
| 535 GATGGTTGTTGCAACGGCAAAG | 535 GGTTTTGCCCACCACCCTCGA | 1735 GAAACCTAAGCGATATCAAAGGCTGAT | 2935 |
| 536 GGGCCATTTACCCTTTCTATCATGT | 536 AAGGTTGTGCTTCTCTCGCTAT | 1736 CAGGCCCAATAGGCCCATTTAC | 2936 |
| 537 CAAGTGGATTGTGGGTGGCCACT | 537 CCTTAGCTCGGTCCCCAAACT | 1737 CTGGCCCGGTCCAAGTGGATTC | 2937 |
| 538 TGTGTGACATTCCGGTGCTAAA | 538 CCCACTAGGCAAAGATCCATCA | 1738 TGTGCCGCTGTGTTGACATCC | 2938 |
| 539 AGGCAGGCGATGAGCCAAAT | 539 TGGCACCCAGTCATCTGCTA | 1739 GCCCAGGCATCAATCCCTAAG | 2939 |
| 540 GTTCAATCACAGGACAGGGTAT | 540 CATCCCGTGTTCCAAGGAAAG | 1740 TGATGTGCCTCTCCTGTTCCAAT | 2940 |
| 541 GGAGATCCAATCGGCTATAA | 541 AAGGACGTACAATTCCGAGTCA | 1741 AGGAACTCTGGGCAGATCCAA | 2941 |
| 542 TGTTGGCTAGGGGTTAGGTT | 542 TGTTGCCTAGCTGGGCCTTT | 1742 CGTTGCTGCAATGAGGTGTTG | 2942 |
| 543 GTCATGGGAGCTGGATTGCTA | 543 GGGGCGATAGGCCACACACA | 1743 GACACCTCCTCTATCCTGGAATG | 2943 |
| 544 GCCACATGGACACCTCACACTT | 544 CTGACATAGGCGGCTGGAGTGA | 1744 AAAGGTAATGCCATTCGGCTAGAT | 2944 |
| 545 GGTTTTCCTATCGGTGTTGAGGCTAC | 545 CCGCAGACAGAGAAGCAGTCTA | 1745 CGGAGAAAATTGGTTTTCCTATCGGTGTT | 2945 |
| 546 CAGGGTGAAGTCACAGCATTC | 546 GACTGCCGCAGCTCTTGTAA | 1746 GCACTAAACGCCAGGGTGAT | 2946 |
| 547 CAGCACCAGAGAGCAGCTT | 547 GCTATGGTTAGGTCCTGGAT | 1747 AAACGGGACCTGCCACCTTCA | 2947 |
| 548 GCGCAGGCCAGCATTATT | 548 CTCCCCGTCAGCAGCGTGA | 1748 TGGCTCAGCCTCCGTTCCTTCT | 2948 |
| 549 CACGACACTACACGCATTCA | 549 CACTGGGGCTTCCCTTTACGAT | 1749 CACCACAGGTGCATCACA | 2949 |
| 550 TCCATCAGCACCAGTGGAAAC | 550 CCCGATGGCCAAAGGCTCTAAA | 1750 CCCATTGCCAAAAGCAAACTGT | 2950 |
| 551 GGGAGATCATACACAGAGGAGGTT | 551 ATACACTTCATCACGCCTTGT | 1751 AGGGGCCACAGCAGAGGAGAT | 2951 |
| 552 TCAGGCTAAAGACATTGCTCTAGAA | 552 TCCTTGATCTCCACTCCATTTGT | 1752 CTGCGTTTGTGTTCAGGCTAAAG | 2952 |
| 553 CCCTGCTCTTCCATGCTGCTAA | 553 ACCTGGCTGGCCACTTCTCA | 1753 ATGTTCCCAGGCCCTGCTCTT | 2953 |

FIG. 34A9

| | | | |
|---|---|---|---|
| 554 CCTAGGAGGGTAAAGGGGAGTT | 554 ACCTGTCTGGCTTCGTGTTC | 1754 CACGCCGAACTAGCAACCTA | 2954 |
| 555 TTGCCAGCTCTGCCCTGCTA | 555 AAGTCTCAGGGCCACTCCAT | 1755 ATGTGCTGCCTACCCCACTTG | 2955 |
| 556 GCACCAGGAGTGTGCTGAAGTT | 556 ATCAGGCCCAGAGAGACATGA | 1756 TGGGTGCACCAGGAGTGT | 2956 |
| 557 GTCTCTGACAATACATTCAGCCACTA | 557 GGATGAGGGGCTGGCTTCATAC | 1757 CTCAGGGACTAAGTGTCTCTGACAA | 2957 |
| 558 AAGGCTCGCCGAGGGGAA | 558 ACCCCAGGGAAGCAAGCAT | 1758 CCTAAATACAGGGAGTGGGATGTAGAAG | 2958 |
| 559 CGTGATTAAGTACGGCTGCCTGTT | 559 GCTTCCTCCACCCCGTGATTAAG | 1759 GCTTCCTCCACCCCGTGATTAAG | 2959 |
| 560 GACCACAGAAATTGGAAGGAGCTA | 560 AGTTCAAGGAAGATGTCTCCTA | 1760 GGAGAACCTCGACCACAGAAA | 2960 |
| 561 GGCAGCTTCCTTCGCTCTT | 561 GCCCTCCTCAAAGTTAGGACTGA | 1761 AGTCCCCAGGGAGGCAGCTT | 2961 |
| 562 GCCTCTGTTGGGTGAATTACTGT | 562 TGTCCCTAGCCCTGGAATTCA | 1762 ACCCCAGAGCCTGCTGTT | 2962 |
| 563 GTGATGCTGCTACGGAGGAA | 563 GGGCAGTGTCGCAAAGTTC | 1763 CTGGAGCTGAACACTTGTGTGAT | 2963 |
| 564 CCCGTAATGCTCAGTGACA | 564 AGACTCCGTCACCCTCCACAAT | 1764 TGGAAGGGACGCCCGCAAT | 2964 |
| 565 AGGCGGCTGAGTGCTTTTCTTC | 565 TTGTAGCCGTTCCAAGAGCAA | 1765 ATTTGCCCTGGAGGGGCTGAGT | 2965 |
| 566 GCATAGAGCACTGGCTTACA | 566 CCAGAAAACCTGTAGGCAAGATGT | 1766 GAAGTCAGTGGTTAGAGCATCA | 2966 |
| 567 TGTGAGGGAGGGAGTCGTTC | 567 CCACTCACCCGTCAGCAAA | 1767 CACCCGTGTCTCTAAGGGTCAGT | 2967 |
| 568 TGGGAGGGCCAGAGACTCATT | 568 CTGCCAGGCCTCTCTCACA | 1768 GGAGCCAGAATTAGCACAGTCA | 2968 |
| 569 GAAGAAAGCCAAGGCTCCAAAAC | 569 CCTGTCCCTGAGCCCTCTGT | 1769 CAGATTTGGCTGGCATTTCAGAAG | 2969 |
| 570 ACAGTTGGGGCAAGCACAT | 570 ACGGCTGGTCCTTCCAGTCA | 1770 CTCTGCCTCGTTTTGTGTCAACAGT | 2970 |
| 571 TGCAACGCGAGGGTGAGTT | 571 CTCGAGCCTTGTGGACATGT | 1771 AGAGAGGTGAGACGGTGCAA | 2971 |
| 572 GGAGAGATCGTCCATCACAGA | 572 CATGCACACTCTGCCTCGAA | 1772 CGACAGGGGAGCAGGAGAGAT | 2972 |
| 573 GGATGCTTCAGGCAGTTGA | 573 GCCAAATCACCTTCATCACTCAAG | 1773 GCTGGAAGGTCTAGGATGGCTTCA | 2973 |
| 574 CACTTCTGGGGCACTTGTGT | 574 CGGACACCAACTGTCTTGTTTTG | 1774 CCAACTTCAGCACATGCACTTC | 2974 |
| 575 CTCTTGCAAATCGAGGAACGAGAGA | 575 CCACCATGCCTGTTCTCACT | 1775 GCACGCACCTCTTGCAAATC | 2975 |
| 576 ACTTGCAGGTGCACCTAGPGTT | 576 GATTTAGTTGTACCTTCCCAACTT | 1776 CTCTGCCTCTTCCTCAGGTACACCTTCA | 2976 |
| 577 TGCATTCACTTAGGGCAGAAGT | 577 TGTGCTGCTTAGCCTGTGGTTA | 1777 TGCCGTTTGCACTCACTCA | 2977 |
| 578 GCAGTGCTGCTGTTCTTGCATCA | 578 CAGGCTCCTTCGTTTCTGTTCT | 1778 GCTATGAGCAGTGCCGTGTT | 2978 |
| 579 TCAGTCAGGGGTCAGAACTGT | 579 TTTCTCTTTCGCCCCAACACT | 1779 AGATGGGCCAGCACGCATTCA | 2979 |
| 580 TCCTCTGCCTTCCAGCACTGT | 580 CCCTCTGAGACCTGAATGGTGTGA | 1780 CTCATGACCTTTGCATTTGCTGAT | 2980 |
| 581 GGAGAAGACTGCCGAACACACA | 581 GGAAGAGCCCTCGCCCCTTGA | 1781 TGCCTCCCACTCTTGGTGTT | 2981 |
| 582 CACCCTAAGGTTGAGATCTGTTCGATTC | 582 ACGTGGCCCCAGTGTGGACT | 1782 GGCTTCTGCACCCCTAAGGTTG | 2982 |
| 583 TGCCCTTCCAATCCTGTGTGA | 583 GGCTGCAGCAGAGACTGCTTT | 1783 CTTGCTGTGCCCCTTCCAAT | 2983 |
| 584 GCCACAGGGGGATGAATAAAAGCAGTA | 584 CTCAATGAGACCGATGCAAGTTC | 1784 AGTACAGGCCCACAGGGGATGAA | 2984 |
| 585 CAAAGATGGGTCAAGTTCCTCTCA | 585 TGGACACAGAGGCAGAAGAGAT | 1785 AAAAGCCACAAAGATGGGTCAAG | 2985 |
| 586 GGTGGGCCCAGAACAAACT | 586 CCCGCTAGCCAACCTTCTGA | 1786 GCAGCCCTGAATTGGAAGTTCT | 2986 |
| 587 AAGGCTGCCCTGGTCAAACA | 587 AAGGCTCCCTGCATCCTAAAG | 1787 CCCATTCCCAACAGAGCAGGAA | 2987 |
| 588 GTTTAGGACAGCCAGTCGAGAA | 588 CCAGGCTAGAACACAGGGATGTTAC | 1788 CCCACACTAGCACCTGTTTTAG | 2988 |
| 589 ACAGTTGAAGTCCAGGCTTATTTGA | 589 AGAAGCTAGCATATGGTGGAAACT | 1789 CAGTAAATGGTGAGGCCACAGTTG | 2989 |
| 590 CAGTGGACCCGATGGTGACTTC | 590 GGCTGGTGCTGGTTGGAA | 1790 ACCAACCAGTGGACCCAGAT | 2990 |
| 591 TGCTTTTAGGAGCATGGAGTACA | 591 TCCTTTGCTGGGAGCTTTTCTT | 1791 CTCCAGTTCACTAAGGAACATGAAATGCTT | 2991 |
| 592 CCTCAGTCTTAGCCTGGGGCTT | 592 CCTGACCGGATGCCAACTTCA | 1792 GGTCCTTCCATGTCCCCAGTCT | 2992 |
| 593 ACAGACCCAGGACGCTGAAG | 593 CTCATGCCCAGTAGCCACAT | 1793 TCCTGTGGCTGAAGGACAGA | 2993 |
| 594 CGAGGGGCCTTTGTACCAGTGTT | 594 ACGCTGGCAGGCTCTCAATAG | 1794 AACTGAGTGCAGGGGCTTTGT | 2994 |
| 595 CCATCTGGAGCAGGGGAGAAG | 595 GCCTTGGCCCCTCAAACAAG | 1795 GGAGTCACAGGGGATGGAA | 2995 |
| 596 GGTTACCCCATTCCATCTCTCTGAA | 596 TGCTACCTTTGCCAGGGTGTA | 1796 TCCAGCAGGCTGAGGCATTG | 2996 |
| 597 GGGAGAGACTGCGGCTTCA | 597 AGAAGGAACTCCAGTGATG | 1797 TGCTGGTCCGGGAGAACGAT | 2997 |
| 598 GCTGCATGCTCTGTGGTCTCTTG | 598 GCCTAAGGTTTTCTTAGGTCTTGGGTA | 1798 AGGGAAGCCTGCATGTCTCT | 2998 |
| 599 CCGACAACTTACTATTGCTGTTG | 599 CCAGAGGAAGCTTGTTTGATGAGA | 1799 GTCTGGAACCCGCACAACTTAC | 2999 |
| 600 AGGAGTGAATCAACAAGGATGGAAGTAG | 600 TCTCCCACACCTTGCCCTTT | 1800 TGGGTTTTTCCACCATAGCAAGA | 3000 |
| 601 GTCTTCTGCAGGGGTGAAAACAGT | 601 GCAGGCACCTGCAGTCACA | 1801 GGACCGCACGGTGTCTCCT | 3001 |
| 602 AGGCCCTGAAGTTGCTGGAA | 602 CCAGCAAAGGCTCCTGCTTCT | 1802 GGTGGCTCCTTTGTGAGCAT | 3002 |
| 603 GTGAGTAAGTCAACAGTGATGAGGAA | 603 CCTCCAAAATCTACTCGGACTTT | 1803 CACCTGCTTCATATCCAGGTGAGT | 3003 |
| 604 CCAGCACAGAACCGACACGTT | 604 CCCCTCCACCACCTTCCTAGAACA | 1804 TGGAACTGCACCAGCACAGA | 3004 |
| 605 AGCCTGCCGATCTTGCTTTC | 605 CTCCTCACCACCCTTCCTAGAACA | 1805 GTACCCTCCAGCCTAGGAA | 3005 |
| 606 GATGGCCCAAGGAGCCAATGT | 606 AGGTTAGAGCCCCTGTGCAA | 1806 AGGAGCGGCTAGCATGGAT | 3006 |
| 607 CTGGCAGACCTCACATTACTCTTG | 607 GGAAAATGCACGGTGGAAAGAGA | 1807 TGGACGTGCAGACTTCACA | 3007 |
| 608 GCCTGAGTGTCACAGTCAACTTGT | 608 AGCAGACATGGGCTCAGAGAA | 1808 GGCAGGAAATGCAGTCAGGTAGTGT | 3008 |
| 609 TGGATAGCTACATGCTTGCTTCTT | 609 CAGGTGGGTTTCAGTGGTT | 1809 GGTCAGTGGGTAAGAAGAACCCATT | 3009 |
| 610 CGGAGCCACTCTACTCCCACAA | 610 TCCACCCTCTCCTAGCCTTTGT | 1810 TAGGCCACGGAGCCACTTTA | 3010 |
| 611 CTTAGCAAAGAGCCTTCTGACTGT | 611 GCAACATAGAAGCAAGGCAGTTTT | 1811 CGCTTCTGTTAATGCCTTAGCAA | 3011 |
| 612 ACAAGGGAAAGCTGAGGGTTCT | 612 CACAGGGCATGATTCCTGGCTTA | 1812 GGGCGAGTTTCAGAACAAGGGAAAG | 3012 |
| 613 CAAAGCACCAATCCTCTGTGTGA | 613 ATGGGCGGAGTTGTGTTCAA | 1813 CTGTATCTGTGGGCTTTTCCTTCA | 3013 |
| 614 GGGCAAAGGATACTCTGGTCAGT | 614 GCTACTTCCCAATTTGGTTTGACACA | 1814 TCTATCCCCATGGAAGGGCAAAAG | 3014 |
| 615 CACTTCTGCACCCTCCCTACA | 615 TGCTGGGGCAAGGCTCAAA | 1815 TCAAAACAGAGTCTCACTGTCACTT | 3015 |

FIG. 34A10

| | | | |
|---|---|---|---|
| 616 GCACTTTGCGTGGACTGTTTC | 616 ACATGTGACCCCAGGGATGT | 1816 GGCCCTCTCTGGGCACTTTG | 3016 |
| 617 CTCCGCCACAAACTGAAATCTCT | 617 TGGTCCCTGTCTTGCAGTCT | 1817 CCTCAGATTGCTCCGCCACAA | 3017 |
| 618 TGGGCAAGAGTGTGGAGTCA | 618 CCCAGACCCTGGAATAGGACTTG | 1818 CCTTGTTCTCCGGCGGATGTT | 3018 |
| 619 CCGAAATCATTGAACGAGCAGGCTAT | 619 AGGGCTGCCCCTTCACCTT | 1819 CTGATGTGTACCCCGAAATCATTGAAC | 3019 |
| 620 CCACCTAAGCCCTAGGATCATCT | 620 GGCTGAGGCAAGCGTTTTGCAT | 1820 GGCTCCTCCATTTCCTTCCACCTAA | 3020 |
| 621 CAGCAGGAAGGGGTGAGTTC | 621 CCTCCCCTTCTCTCTACTGAT | 1821 CACATCAGAAACGTTTGGGCTGATAC | 3021 |
| 622 CGCCTGGAGCCTCAAATTGGTT | 622 AGTGACCACAGGTGCAAGAAG | 1822 TGGGGCCAGCCCAGATTTACT | 3022 |
| 623 GTCTGGACCAACAGAATTGTCACT | 623 TGTCTATCCTTGGGATCTGGTACA | 1823 CAAGAATTTCCCTGTCTGGAACCAA | 3023 |
| 624 CAAGACCCTGGACGTCAAGAA | 624 GAGCTTTCCTGATGCCTTACACT | 1824 GGCTAGCCCAGAGTAGTAACAA | 3024 |
| 625 GTCAGCAAAGGAAGGAGTACCAT | 625 CGCAGGCTTTCTGCTGTTGA | 1825 CACAGACGGCTAAGGTCAGCAA | 3025 |
| 626 CAGAAGTCATTGCTGAGGAGGAA | 626 TGACCTGAAAGCTCTTGTTCCAT | 1826 CAGCCATCACCACGAAGTCA | 3026 |
| 627 CTGGAGAAAGATCAGTCGACCAT | 627 CCTCTGGAGGCCCCACTGTAAT | 1827 TGCCAGGCGCTGGAGAAAGA | 3027 |
| 628 AGCTCTACTTCACGAAAGGAGTTG | 628 TTGTAGTACATGCCTTTGGTGGAT | 1828 AGCATACCCTTAGCTCTACTTCACA | 3028 |
| 629 CCTGCTCCGTGGCCCTTA | 629 GCATGGAACCAGGGCATGACT | 1829 CCTTTGTTGTTGCTCTTCCAGTTC | 3029 |
| 630 CCAGCCTTGCTTCCCCTTCAAT | 630 CGCTTTGTCCCACTCTTACA | 1830 CAGTTTCCCAGCCTTGCTT | 3030 |
| 631 GGGGCAGGGAATACACGAATTT | 631 CACTCTGTGCAAACCAGTTGTAG | 1831 TTCACTGAGGGGCAGGGAAT | 3031 |
| 632 GAAATACTCACAATGCCCTCAGCAT | 632 TCAGCACCTATCTTCTCATC | 1832 GGGCAACTTGGTGTGTAAAAATCCCTTCAA | 3032 |
| 633 GTGAGGTGTGGAAACGAAGGTTTG | 633 GGAGACTCCTACCCCAGCTT | 1833 GAGTTACCACAGTGAGGTGTGGAAAAC | 3033 |
| 634 TTGATTGAGCGGGAGCAAAGA | 634 GGGGATTGTTAATGGCGCAGAGT | 1834 CGCCTCCACGGCTTGATTGA | 3034 |
| 635 CAAATCGAAGAATCTTTGTTCTTCAAG | 635 ACCCATCACTTGCACAGTTAC | 1835 GGCACCAACACTAAAAATCAACCCGAAGA | 3035 |
| 636 GGCATGGGAATAAATGCCAGGTGAA | 636 GGGTCCCTAAGCACTGTGAGAAG | 1836 TGCTTTCTTGGGCATGGGAATA | 3036 |
| 637 GGAGACTTGGAGGGTAAAGGCAACT | 637 AACCAGGCCTTGCGGTAAAG | 1837 AAGCCGAGGGGCAGGAGACTTG | 3037 |
| 638 GCAGTTTTGAAGGCCTAGTTATGTTC | 638 CCTAGGGAACAGTCCACTGAGAGA | 1838 GCAGAATAGCCAGCAGTTTTGAAG | 3038 |
| 639 GCAAGGTCTGAGTGGAGAGGAT | 639 GCCCGTGTTTTGAAGCTACTGCT | 1839 GCAGCTACTTGCAAGGTCTGAGT | 3039 |
| 640 ATTGCAGTCCAGGCTCCGAGAT | 640 GCCAACCAGTTCAGTTGGGAGTCA | 1840 CCTCCATTCTGGATGCCACTGTTG | 3040 |
| 641 CAGCCCTCTCCTGTTCAGTGTT | 641 GCCAGCTAGTGGCTTTAACCAAGT | 1841 GCACTTCACCAAGCTCTGTCTCA | 3041 |
| 642 CGAGGGTGTTGGCACTTCAAT | 642 GCTTCGCCCATGCGTGTCTT | 1842 GGCGTGGAAGGATGTCAACAAGT | 3042 |
| 643 TGGGAAAGAGCGAGATCCAAAA | 643 CGTGATCTACCCCACTGAGACA | 1843 CCAAATGGGCAGGTGGGAAA | 3043 |
| 644 CCTGCCCAGCCGATGGAGTA | 644 AGTTGGGCATGGAGGCCATGT | 1844 ACTCCTGGGCTCAAGCAATC | 3044 |
| 645 GTCAGTCCCTCTGTTCTCTGTCA | 645 AGGGCCTGCAGGAGAGAAATG | 1845 CTGCATTGCCAGTCCCTCTGT | 3045 |
| 646 TGACACAAGAATCAGCTTGGTTGA | 646 CACCCTCTGCTTTAGGTCTCAGGTTT | 1846 GCAGAAGCTTATAGCAGGGATGACA | 3046 |
| 647 TTTATTGGCTACCCCAGGTCCTA | 647 CGATGCTGAGACTAAGGAGCCTAAA | 1847 CCAGCAACCTTTTTGGAGTGTTT | 3047 |
| 648 GATGTCTTCCCTGAACAGTCAGAA | 648 GTCACTCATTCTGCCTACCCAAA | 1848 AACAGCTTGATGTCTTCCCTGAA | 3048 |
| 649 GCTGGGCTGGTTGAAGGAAACA | 649 GAGCATCCTCGAGAATTGCATTTGA | 1849 GGACAGAACAATATCCTGGTGGGAA | 3049 |
| 650 CAACACTGTGCTGTGGGGAAAT | 650 GACAAGTCAGCTGGTGAAGAGTGAA | 1850 CCACACAGCAGGCTTCTACAAC | 3050 |
| 651 CAACCCAGGAAGACACACCAA | 651 GCCTGTGGCAAAGTTGAACATGA | 1851 CCAAATGTGAGGATCAACCCAGGAA | 3051 |
| 652 AGAAGTAGTTCACCTGACAGCTTA | 652 TCCACTGTCTTTGAGTGGAAAG | 1852 GCAGCTAAGGCTAGAAGGTAGTTC | 3052 |
| 653 GGGGTGGCACATATGTAGTAGAAG | 653 AGACTTGCTCATTCACTCTCATTT | 1853 ACAGAGTGGGCTGGCACATA | 3053 |
| 654 GCCGATAACATTGCCAGGATCT | 654 GAATCCAGTTCAGCTTCCTCTA | 1854 GTGTGTTCAGGGTGACAACA | 3054 |
| 655 CTCAGCTCAGGTATTTGTGCTGTTA | 655 TCAAGCAGAACAGGACTGACAAT | 1855 GCCGCCCCTCTCTTTTCTCA | 3055 |
| 656 GCTCACTGCATACATACATGGAA | 656 TCTCAGCCTTCCCGCTTCAT | 1856 GAATGGGGCTGCACTGCATA | 3056 |
| 657 GGCAAAGTGATGGTGGCAGCTT | 657 AGGGCCCAGGTTCCTTCTT | 1857 TTCACCACACTAGTAAGGCAAAGT | 3057 |
| 658 GGAAATCTGAGCATGTGGAGTGA | 658 TCCCTTCCAGGATGACCATTGA | 1858 GTGAGAATCCATTGGAAATCTGAGCAT | 3058 |
| 659 CGATACCCAGGTACCATGTTGAGA | 659 AGTCAGGAAGCCTCAGAGT | 1859 GGGCCCTGAATAACCAATAGCGATAC | 3059 |
| 660 GGAAGGCCATTTGGCTAGAAATC | 660 TTGCTCTACCCTCTCCAGCCTT | 1860 GCCAGGAGACGAAGGCCATTT | 3060 |
| 661 CTTGGTCTGTGTCCCCAGGTTGTTAG | 661 CCTCTGCCCTATTTTAACCACAAAG | 1861 CAAACGTGCCCTTGGTCTGT | 3061 |
| 662 TCGAGAGAAAGATGGGGTAGAAAGT | 662 CCACTGCACCCAGCCAATCT | 1862 GGCCTTAAAGAGGACATGGAGAAAG | 3062 |
| 663 CCCTGCCTAACCCAACATCTGTGT | 663 AGGCAGGAAGCCTGTTCAGA | 1863 TATGGCTTCCACCCTGCCTAAC | 3063 |
| 664 GTGGAAAAGGCGCAGACTGT | 664 TGGCAAACTCTGTGATGGAATGTA | 1864 GGGGTGGTGACGGTTGGTGGAAA | 3064 |
| 665 CCTGCGAGTTCCTGAGACAAT | 665 AGGGGCCTTCTGGAGTGTTT | 1865 GGAGATAAACAGACCAAGGCGAACA | 3065 |
| 666 GGACTAGGTGGTTGGTGTGCAA | 666 TCGTTCCACCATGCCTTTCCTT | 1866 GCTCTTCTCACTGGGATGGACTA | 3066 |
| 667 AGGGCTTTTCATGTGAGTGTTGT | 667 TGCTTAAACGAACAGGGCTTTG | 1867 ACAACCTAGGAAGAATTAGGCCTTTTC | 3067 |
| 668 AGCACTTCGCTCCAAGTGCTA | 668 TCTCAGCGGTGTGCTATTTC | 1868 CCTACCCCAGGACAGAAGCAT | 3068 |
| 669 GGCAAGAGACAAGTCCAAGCATT | 669 CCAACCTATGCACCCAAGCTAT | 1869 GTCAAGGATACGCAAGAGACGAAGT | 3069 |
| 670 GCAAGTCTGGTGAAGTTATCTTGTTTC | 670 CCCTCCCTCGCAGAAGTATAAG | 1870 CTGAAGCAAGCTGGGTGAAGT | 3070 |
| 671 GCCAGTTGACCGGAAGCCATCT | 671 GCCTTCTAATGCCAATCCTAAAT | 1871 GGTCCCCAAAATTCTCTGCAGTTG | 3071 |
| 672 GCCTCCCTTAGTGGGCAGGTT | 672 GGCTCAGTCTCGGTTAGCTTCA | 1872 CCGGAAAAGAATCGGCCTCCTTAG | 3072 |
| 673 CGGGAACAAAACAACTCTTCCCAGAT | 673 TGCCCTGTGCCCTCAATTCT | 1873 GAAAAAGAGCTGAACAAACGGGAAC | 3073 |
| 674 TGAGCCTTGCTGGCTGTCA | 674 ACCCTGTACTCCTCTCATTCACA | 1874 TGCTGCTCCAGCCAGAGGTT | 3074 |
| 675 TGGGAGGGCATAGTCCCTGTGGAT | 675 CCCGTGTCTGGTCGCCTCTT | 1875 AACACCCTGGGAGGCATAGT | 3075 |
| 676 TTCCGTGGGGCACTTGTACTTTG | 676 CTGAAGGAGAGGCAGTCAT | 1876 CGGCCCTTCCAAACTCATGGAAGT | 3076 |
| 677 CAAAGGGAGGTTCAAAGACCAGTTGGT | 677 GGGATTACAAAGTTGCGCGTTTC | 1877 GCTCTCACAAAGGAGGTTCAAAGA | 3077 |

FIG. 34B1

| | | | |
|---|---|---|---|
| 678 CCTTAGTCCTACTTTTTCCCTTGCAG | 878 GGAGGGAGACGGCAGGAATG | 1878 CATGCCTATCTCCCTTAGTCCTACT | 3078 |
| 679 GACCCTTGCAAGAACGGAGTCA | 879 GGACAGAGAATCAGGTCACGGTAT | 1879 AGTCAGCTCAGGGGTGACCTT | 3079 |
| 680 GACTGCCATCTGGCATTGAGAAC | 880 ACCTCGGCCTCAGGACTTCT | 1880 CCACAGCACTGACTGCCATCT | 3080 |
| 681 AGCCGCTCCTGCTTTTGA | 881 TGCTCACAGGCTCGGAGATAGT | 1881 ACATGCTGAAAGCCAAAACCTCTA | 3081 |
| 682 GCCAAAAGTGCAGAGTTATTTCAGT | 882 AGCAGTCAGGTGCTCCTCCTT | 1882 CAGAATAGCACAGAGTGTCACAGA | 3082 |
| 683 TATTGGCGGCCAGCACTGT | 883 TGGTATGGGGCGGCAGTGA | 1883 CCACATCCTGCCATAGGAGCTA | 3083 |
| 684 GAGCGCCTAGTCAGTACTTTGT | 884 CCCAGCTGACACAGGCGCAT | 1884 TAGGGCAAAAGAGCGCCTAGT | 3084 |
| 685 GAAGCCAAGTTGGTGGAGGAT | 885 GTGTCCAGTCTCCTTGAGTCATTTG | 1885 GGAATTCTGTAAGCTAGAAGCCAAGT | 3085 |
| 686 GAGAAGGGAGAGATGCATGGGTTT | 886 GGAGGCATGCCCCATCTCA | 1886 GCTCCCAACCCCAGAACACT | 3086 |
| 687 GGCCACCCCTGTGCATCTTTA | 887 GTGGTGCTTGTTGCCACTGT | 1887 GGCATTCCAGCAGTGACCATAG | 3087 |
| 688 TGAATGGTGGCCGAATTGTGT | 888 GGGCAGTGATAGAACTGACATTTG | 1888 CCATGGGCACAATCCAAGCCTAT | 3088 |
| 689 GCCCTTTCTGGAGGTACTTGAGCTTAT | 889 GGAACGTCAGTGGTCAGCTT | 1889 GCGGGCCCTTTCTGGAGGTA | 3089 |
| 690 GCAGTCTCCAGTGCTGTCTTC | 890 TGTCACCCTCTCTGCTCATAAGC | 1890 AACGGCCAGGTGAGCAGTCT | 3090 |
| 691 CTTCACCCACAGCAGAAATGT | 891 GTTCCACCCCAAGGACACAGA | 1891 GTGGTTGCTTTCACCCTACTTCCTC | 3091 |
| 692 CTGGCTTGGAACAGAAACCATGACT | 892 GGGACTGGATCAAGAAGGGTATG | 1892 GACTCTTGGCTTGGAACAGAA | 3092 |
| 693 AAGGCTTGAGACGTGCCTTGT | 893 CCATGGCAGAAGCTCAGGAAAC | 1893 GCAAGATGACATAAGCAAAGGCTTGA | 3093 |
| 694 GCTGCAGTGAGCCACGAT | 894 GGTCTCGCTCTGTGACACCATT | 1894 GGAGTATCACTTTAGCACTGGAGTT | 3094 |
| 695 TGGCTGGAGCAGAGTGAACA | 895 GCTTCCCCGTGACTGTCCCTAT | 1895 AGGATGGGTCAGGCCAGTGT | 3095 |
| 696 CCGCCATCAGGGGTTGATGTAA | 896 GAGAGGGTACTGGTAGAAGCATTCC | 1896 TCCAAGCCACCGCCATCA | 3096 |
| 697 AGGGATCAGGGCCATCTTCA | 897 AAGTGTGGGGCCCTCCTAAG | 1897 CCTCCACTCTACCAAAGCTTATAACA | 3097 |
| 698 AGTCAGCAGGCTGGAAAAACT | 898 GCAGCTGCTGTCTCTGCAATGC | 1898 TACGCTGACCACCCTGACACT | 3098 |
| 699 CTGTGCAGGAAGCAAGGTAGAT | 899 CCTTGTCCTGTGCATCTCTGT | 1899 GTGGGTACTACTCTGTGCAGGAA | 3099 |
| 700 TGAGTCAAGGTGATACTTGCTTCTT | 900 CAAAGGCAAAAGTGGCATCTGT | 1900 TGAGGCATTTGTAGTCAAGGTGATAC | 3100 |
| 701 ACCCTATAACAAAGGGGAAGTCAGGAT | 901 CAGCCTACCTCTGTGGACTTCA | 1901 TGCCTGGGTTAAGGCGCATA | 3101 |
| 702 ACCTTCCCCACCATGTTCTACA | 902 GGAAAACCTCTGAGCCTCACATT | 1902 GGGAACCTACTGATCACTAGTACAAAC | 3102 |
| 703 CACATGCCCAGTAATGGAACAAA | 903 CGGACCCCTTAGCTTGAGTTAGT | 1903 CTCCTGACACATGCCCAGTAAA | 3103 |
| 704 CACTTGGAAGCTCAAGCCAAAG | 904 GAGCTCCCTAGAGAGACAGA | 1904 AGTGTGGGGCCACCTGGAA | 3104 |
| 705 AGTGGGCGAGCGCCCTTAT | 905 GGCCACACATGGGCATTTG | 1905 ATGTCCGGTCGGAGGTACAGT | 3105 |
| 706 AGCCCTGCTGCCTGACAA | 906 GGGGGCTCGGGTCTCTGTTT | 1906 AATACTCCCCTCCCGGCTACA | 3106 |
| 707 CTTGGGAAACTAAGTCAGGGCAAAG | 907 CTCTGGGATGTCCTGGAACTAC | 1907 CACTGCAGCAAAGGCTTTCAAC | 3107 |
| 708 GGAGTTTGCCTGGTGTCTTTC | 908 CTTGGAGAAAGGCTTGAGCATACT | 1908 CTGAGCTCTGTGCCTGGATAATG | 3108 |
| 709 GGGGTGGTTAAGTATGGGCTAGCAA | 909 TGGCCCTCAAGGAGCTGTA | 1909 CTGATGAATTGCTGGGTGGTTAAG | 3109 |
| 710 AGTGAGCATACAGCTTCTCAGAAAT | 910 GGCACCCAGCCAGCAATTGGATA | 1910 GGTTTAGGTGCTCCATAGTCAGCATA | 3110 |
| 711 GGATCTAAGCAGTCATCTCTGT | 911 CCCCGATTCTGCGTTGCTT | 1911 CAGGTTGCTTTGTTGCAGGGGATCT | 3111 |
| 712 GGTGACTGTGCACGCGTTAAT | 912 AGAACCGGTCCACATGCTAAC | 1912 AGGCTTCCCCTGCTGACTGT | 3112 |
| 713 GGCTCAAGTACTGCCTGCTTCT | 913 CCAAGGGCCTCCTCTCTCTAAGG | 1913 AGAGCTGGCAGGCTCAGTA | 3113 |
| 714 CAGGATGCTTCTTGTTTCAAGGAGCTT | 914 CACAGGCAGTTACGGTAGGTTCT | 1914 CTGGGGCCTGCAGTTTGATT | 3114 |
| 715 GGCAGACAAATCAGCCCAGTT | 915 TCCCCACGATGGCAGTGAGTT | 1915 GCAGCCTGAATCTTGGCAGACA | 3115 |
| 716 GTCATTGAACTCGCGCTTGCAT | 916 TGGAGCAATATGCTGTGCACTGTT | 1916 GAGCTGTCCACTAACCATTAATTAGGTCAT | 3116 |
| 717 GGGACTATCAGATAAGCACCACCTGT | 917 CACTCTGTCAAGTTTTGCCGTCTT | 1917 TCTCACCCTGCCCTGGATCCCAAGT | 3117 |
| 718 CAAAGAGGCCCTCATGCTCAGT | 918 GCAGGCATGACAGACTTTCCTT | 1918 TGGCTGCCCTCCTTCCATGAT | 3118 |
| 719 TTGGTCCCTACAACCTAAGCAAGT | 919 GCCGTTCCCCATGGCATGCTAAA | 1919 CCCAGGAGTGTATCTTGGTCCTACA | 3119 |
| 720 GCCAGAGATGAATGGTTTGCGAATG | 920 TTGGAGTGGACGTCTTCCTATTTC | 1920 GCGGATTTTTGAAGCCAGAGATGA | 3120 |
| 721 CCTGTGCTATAGAATCAGCACTGT | 921 CAGGGCTCCCTCCTTCCAGTT | 1921 CCATATGAGCTCTCCCCTGTGCTA | 3121 |
| 722 TGTGTCTTGTTGAGAGGAGAT | 922 CAGCACTGAGTTCATTGCCTCAAAAA | 1922 CCGTGGTGCAGATGGTGTTT | 3122 |
| 723 GAAGCTCCTTACATTAGTGCTAGGTT | 923 GCCATAGGAGAGATCCTGAATCT | 1923 TGGTCTCCTCGAAGCTCCTT | 3123 |
| 724 TGCACTCAGAGGAGAAGTTAAAACA | 924 CACTGCAACAGAGGCTGACCTA | 1924 TGTAAAACAGGGAGATGCACTCA | 3124 |
| 725 GGATCAAAGTTCAAGCAGTTAGTGTGA | 925 TGCCCTGGGTGGTCTTGT | 1925 CCTCCCTGTGAGGATCAAAGTTCAAG | 3125 |
| 726 CGGCTACCAGCATTTGAGTCTTG | 926 CAGCAGAGACCTGATAGCCCTATGT | 1926 GGAAAATCCGCTACCAGCAT | 3126 |
| 727 CCGGCCAAGAAGGTAGCAA | 927 GTAACAGGTTTTGTCCTCTGGTT | 1927 AGCAGTCAGTCAGTTCCAGCTA | 3127 |
| 728 GGGGCTTTCTGGTCGGAGATGAA | 928 CCTCGTCCTGCTCCCATCCAAAAA | 1928 CCTCAATGATTACCCGGGCTTTC | 3128 |
| 729 GCTACAGGTTGGAGGCAAGA | 929 CTGGAAACGGCCCACAGT | 1929 GGCTCTCTTGGGCACAGTT | 3129 |
| 730 AGTGCCCTGCTCAACCAATAC | 930 TGGTGGGGACATTTCCTGAAG | 1930 CACGCCCAGAATCAAAGCTAAAG | 3130 |
| 731 TCCCCCTTGTTCCAGGGTTTTGT | 931 CTGGGTGCAGTGTGGAGCAT | 1931 CCTCTTAGCTGTCCCCTCTTCGTTTC | 3131 |
| 732 GGAGGCTCCATCCACAGTCA | 932 TCAGATGTCAACCCGGCTAT | 1932 ACACACCCCACAGCTTCTTC | 3132 |
| 733 GGGGCAAATCTGTGTCCTCCGAGATA | 933 CGGCCGACTACTGGAGGCTTT | 1933 GGCTGGAGGGCAAATCTGTCT | 3133 |
| 734 GGGTTACAGGTTGACTCTGGAATT | 934 AGGTAGCCCAGCAGTTCTCCAT | 1934 CCATCACAGAGGGGTTACAGGTT | 3134 |
| 735 CCTAGCCTACAAGCGCACTCT | 935 TGGCCTGCCTCACTTCCTTA | 1935 TCATAAGTATAAGGCCTAGCCTACAA | 3135 |
| 736 GGAGTACTGAGGCAGGGAAGGTTT | 936 TCCCGAAGACACCGAGAGGAAA | 1936 GGGTCCAATGTGAAAAGCACAGAGT | 3136 |
| 737 CCAATGAGTTGTAGAGCTCAGATTGT | 937 ACAGGGTTTGAGTCAGCCATG | 1937 CAAGGCCATAAGGCCAATGAGT | 3137 |
| 738 GAGGGTGCTAGTCAACTGTGT | 938 GAACCTTGGCTCTTGCAAGTCATC | 1938 CCTGAGGGTGAGGGGCTAGT | 3138 |
| 739 AATGCCAAGCCACCCTGGAA | 939 TGACTGACTGGGCCTTCAGA | 1939 GGCAAGCTCTTCAGGGAGAAGTTAG | 3139 |

```
802 CCCGCGGTTACAATGCAACTT      802 GTGTGGATTGTTGCAGGAGGA        2002 AAGCCTAAACCCGCGTTAC           3202
803 CACTTCCAAAAGGCAGCTACAATC   803 CAGCAAAGACTGGCATTCCTACTCA    2003 AGCAGAAATCACACAATGGCAATAC     3203
804 TGCCTGTGATCCTCCATCA        804 GGCATCATTGCATTCAAAGACATTC    2004 TGCCTTCACCGCCTGGTGAT          3204
805 GCTTCAAACAGAACTAAAGCAT     805 CACCCATGGCCACCTTTCTT         2005 AGCCTCCCGGCCATCAAGTA          3205
806 GCCCTATGCACATTGGCTTGT      806 CCTCTCTGATCATTTGGCAGGAAGA    2006 CGTCTTTCTCCAGTTTCTGAGCCCTAT   3206
807 AAGGACTGAGCAATGGCTGTT      807 TCATTGTAACTAGGGACTCCACGTA    2007 GGTCAGCTGTGTCAATAAGGACTGA     3207
808 GGCCGCAGAGCCTCAACTTC       808 CATATTACCCTGGGAATCACAGCAA    2008 GGAAGCAGGTGTCAGTGTGA          3208
809 GGAGTCTGCAGTTGAGGTTATATG   809 TTGGCCTGCCACATCCCCTAT        2009 GGTCTGCTTCTGGAGTCTGCAGTT      3209
810 CCTGTTTCAGGATTAAGGGCTTCT   810 CCCAAATGGCAGAGGCTGTGT        2010 CACACTCGGTTCCTGTTTCAGGATT     3210
811 AGCTTAGGGGTTCCTCAGTAT      811 CCTGATTCCCTTCAGTTCTCTTCT     2011 ACACCCATCCCAAAGGGATTAAAAG     3211
812 AGATCAAATCACCCCAGCTTTGT    812 TCCACTAATGTCTTAGAGGAGCTTC    2012 CCTCTCCCTTGCCAGATCAA          3212
813 CACACATGTCCCTGCACGTTTG     813 CAAGCCCATACAGGATGTGTCT       2013 AGGCTTCCCTGAGCAGAGATATT       3213
814 GCTCTGACTCATGTCCTGTT       814 GGGTCAGGGTATAGGTGGAAGA       2014 TCTCTGGCTCCAGCGTCTGA          3214
815 CCGGCTTCTTACCCACATTAG      815 GGACCTCTGGAAAGGTGAGATT       2015 AGGGATATGCCGGCTTCT            3215
816 CACCCCAGACCCCAAGTTC        816 GGCCTGGTGTAAATTCTACCTACAA    2016 GTGGTGGTGGTTGTCTACT           3216
817 AGCCTGTCTGCCACCTGAAA       817 TGAGTCAAATGCAAAGGCTGCTA      2017 CCTTCCTTTCTCACTAAGCCTGCT      3217
818 GGAGCAGAGCGACCGTCAT        818 CACCTGGATGATTGCCATTGCTT      2018 GAGAGATTGGAAGGGGAGAGATTG      3218
819 GCACTGGACTAGTATTCGGGAGAT   819 GGTCAGTGACAGATCCAGGACTA      2019 GGTGGGAGTAAAAACAGCACTGGACTA   3219
820 GCACTTCTGGCACAAGGTGTGTCT   820 TTCAGGCCCTAGCTCCAGGAT        2020 CCTTCAGGGCAGTGAGTTCTCTCT      3220
821 CAGCCAGCAAAGAGGGAAGTTAGA   821 CAGCCTCTTTCCTAGGGTTGTGT      2021 TGCAGGAAAAGGAACTGCAAGA        3221
822 GATGTCAACGTACTGACTCCAACA   822 GGTAGTTATTCCAGCAAGGAAATCT    2022 CCCATCTGTACTTAATGATGTCAAC     3222
823 CCACTAGCTTCATTGGTGTCT      823 GTCACCCTAAGTGCTCATGT         2023 CCCTGAATGTTCCATCCAGCTT        3223
824 GGGATGGTTATCATGCCCTCTTC    824 CAGGACAAGGTGCTCAGAGTTTC      2024 GCCTGCCAGACCTAGGGATCGGTTA     3224
825 GGTTCTAGATCCGCTCTCTTCT     825 AAGATGGAGGCCGGCAGTTC         2025 TGGAGGGGACCGGGTTCTA           3225
826 CTCTGGTACCTGAACCTTCCCATT   826 GTTGAGGCTGAAGCCCATGA         2026 CCTGGATTGTCTCCTGTCACTTC       3226
827 TGCTTCCAGGGAGGTAGTGA       827 CCACTTAGCATTGCTTGTCATCAA     2027 GGGGACACGTCTTACTGTAGTCTT      3227
828 GCACTTGACTCACAGGGAGAA      828 TCCAGGAACAACCGCACAGT         2028 TCAGCAGGAAAAGCACTTGACT        3228
829 GGTATGCCAGCTGACACCAGTA     829 GGAGCCCCAAGAACCTTGATT        2029 CCTCTTCCTTGTTTGCAGAGTT        3229
830 GTCACAGATTCAGGGAGAAGCAA    830 GGCTATCGAAGCCTCATGTCTA       2030 CCATACCAGACACAAACTACAGTCACA   3230
831 CAGCCTTTTCCCTAGGCAATGT     831 GTGACAACTGTGTGGGTGAGTA       2031 CCTGACTTTCTAGTTCAACTCAGCCTTT  3231
832 GCCTGGCTACTGCTATTGGTGTGA   832 TGGACACCTGAGTCATGGAT         2032 GTTGATGCTCTGGCTACTGCTA        3232
833 ACACAAAGAGTTCCATGCCCTTT    833 AGTACTCATTTTGGTAGCACGTA      2033 CAAGGCTATTGAGGACTCACAAA       3233
834 TGTTTCCAGACAAGCCAACAGT     834 CAGGCTGTCAAGCCATTAGT         2034 CACTGCATACACAAATGAGTTGT       3234
835 GGCAGCAGCTTCTTTCCAGCT      835 GCTTGTTGTTCCCGGACTCTGAATA    2035 ACTGCATGGCAGAGCAGCTT          3235
836 GCCCAGCCTCGGAGCAAAA        836 GGATTGAGGAAGGTAGCGCTTT       2036 GCAGAGCCTCTTCAAAGGGAAA        3236
837 TCACTATGAACCCTACCACCACTA   837 GTGGTAGTAAAGCTGGTGATGACA     2037 CCACCACTACCATCATCACTATGAA     3237
838 CCCCTGCCTTCCGGTAGTAA       838 CCCAGCACCAATCCCATGAA         2038 GTGAGTGAATGGGTGGGAGGTA        3238
839 AAGGTGACCCTCCGGACA         839 CAAATTACAGGCAATGACGCACATAG   2039 CATGTGCTCTAGCAAGACAATCAAA     3239
840 AGGCGGAGCTCTAAGCACTA       840 TCTACGCACTTTAACACCTCATT      2040 CCACACGTCCCACAACCAGGTCTAC     3240
841 ATGAGCTCTCAGTCATTGAATTG    841 GGGTCATCGTTGCTTGATACTGT      2041 AGCTCTGTAGGAGGCAAGGAT         3241
842 CTGGCTGCTATGCACTCAGA       842 TCTTACCCTCACCCAGCAAAT        2042 TCCAGTGCTCTGGCTGCTAT          3242
843 GCTTCGTCGTTTACCTGACTGT     843 CACCAGAGCCCTCCATTTCTAAAC     2043 CCGTGACTAGTGCTTCGTCGTT        3243
844 CCAAGGACAGACCTTCCCAGAGA    844 GGAGGGCAAGGGCATCTCA          2044 GGACCAATGGCTGAAGACCAA         3244
845 GGGGTTACTTACCGGTCAGAGAATTC 845 CTCCCCTGTGCGCTCTTTCACT      2045 CAGAAGTGTGGTGGGGTTACTTAC      3245
846 GCAGAAGCATCACTGCGTAATATC   846 GGGTAGATAGACCCGGCTAGACT      2046 CCGTGTTCAGAAGGCATCACT         3246
847 ACCATCCTCCCCATCTCAGTAAA    847 GGTCCTGAGCAACTGGGTAAA        2047 CCAAACCTGCTCCTCACCAT          3247
848 CGTCTCCATTTCTGTATCCCTCTCAA 848 GAAGATGGGACAGGCGTTGT        2048 GGCCAGGTCTCCTCTCCATT          3248
849 GTGGGGTAACGGTTTAGGAGTTG    849 GGGTAAGGTGTGCCCTTGTTCT       2049 TGAGCCTTGCAGTGGGGTAAC         3249
850 CCTTAATTACTCCCGATTGCTCTT   850 CAAGCGGAGCACAGAACTGA         2050 GCATACGTCTTTGTAGAAACTTGACCCTTA 3250
851 AGCCTGGAGACAAAAGGTGAAA     851 GGAGACATCCTCGCCTGAACCTA      2051 CCACAGTGAAGCTGGAGGACA         3251
852 CGAGGCAATTTCCCCTGCAA       852 GGAGACATCCTCGCCTGAACCTA      2052 GGATATGGGAGGCAATTT            3252
853 GAGGTGACATGCTTGTTCAT       853 GGCCTGAGCTAAGCTTTTTCTTTGCTA  2053 ATCCCGCGGAGGAGGGTGACAT        3253
854 GCCCTTCTAGTGAATGTTGGGTTCA  854 CGCCAGCATTCTGCTGCTT          2054 CGCTGGCCCTTCTAGTGAATGT        3254
855 CCAACAATCTCTGTGCCTCTACT    855 ACAGTGGTGCCCAGTGTCA          2055 CTGCAATTCCCCAACAATCTCTGT      3255
856 CCCCTGCCTCAAAGGCTCCAAAAGT  856 GCAGAATAAACAGTTCCTTGGGCTA    2056 GGCTCTTCCTCCCCTGCCTCAAA       3256
857 TGAGGCTACCCTGACCTTT        857 GCCAATCAGCCCAGACATTTG        2057 GCTGTGGGGTTGAGGGCTAT          3257
858 GTGGTAGCTACTGAATCAGCCCTAT  858 TCGCTCTCTCTCCACCTCTGT        2058 CCCTGAGAGTGGTAGCTACTGAA       3258
859 TCCAGGTGAAAGCAGGCTCAAG     859 GTGTGTGGCAAGGTGTGCT          2059 GCCAGATCAAATCATTCCAGGTGAA     3259
860 GCAGATAAAGCAAAAGGGTGACTT   860 AGTTGGGATTGGAGCTTGGAA        2060 CACAGAAGGGCAGATAAAGCAAAA      3260
861 TCCAGGTGCACTGGCTCATAGAT    861 CAGGCAGAGGAGGAAGCCAAA        2061 GCATATGTGGATTTCAGGTGCACT      3261
862 TGTGGAGGAGGAGGCTCAACAT     862 CCTGCCCTCCCCAACAGTGA         2062 CGCTGTAGCCTGAAGCACTGTCCTA     3262
863 AGGGCCTAGTGGTCAACATT       863 TCCCTTAACAAGTCACCTACTTC      2063 CTGCTGATTCAGGACCACAGAA        3263
```

| | | | |
|---|---|---|---|
| 926 GAGGGAGGTGCTTGCTGTCAA | 926 PCCCTGAGCCTCCTCTGTTCT | 2126 GGAAAGGGAGGGAAGTGCTT | 3326 |
| 927 GGCTCTGTGAGGATGGAGAGAGT | 927 GGGGACAGTGGAGGATGCA | 2127 GCTCTCCTGGCTCTGTGAGGAT | 3327 |
| 928 GTCAGGGAAGTGGTGTTAAG | 928 ACTGGCTAGCCCCAGTGATG | 2128 ACAACCCAGTGCCAGGGAAGT | 3328 |
| 929 GTAGACTCCACACCTTCCTACCTT | 929 CGCCACCTGGACAGGAAACA | 2129 ACAAGCCTCACAGGGTAGACT | 3329 |
| 930 TCTCCTGGAAATGTGAACAGGATTG | 930 AGCAATCCTCAGGCCAGGAAAG | 2130 GAACCAGTTTCCTTTCTCCTGGAA | 3330 |
| 931 CTCGCTGCATCTGAGTGAGT | 931 GCCTCTGTTACCCTTCTCCCATT | 2131 GGAAGCCACTCGCTGGCAT | 3331 |
| 932 TCGGATGCTTCCTGGGCAAAG | 932 AGCTGCTGGGAGTGGGAAA | 2132 TGGGTGCCTCGGATGCTT | 3332 |
| 933 CAACCGCTCAGGCTGTGAA | 933 GCTCAGTGAAAGGGCAAAACT | 2133 GCTCATTAATGCACGCAGACACA | 3333 |
| 934 GATGATAAGCCTGTCCTGAGCATG | 934 GGTCCCTGCAGACACTGGACAAT | 2134 GGTGGTACAGAATACAATGGCTGTGATG | 3334 |
| 935 CAGGAGGGAGAAAGCTTTGGGAAGA | 935 TCCAGACATGCTGGCTGAAAAGT | 2135 TCTGGTAGCAGGAGGGAGAAAG | 3335 |
| 936 CATCCGCTCTTCACTAGCTGTTAAAT | 936 TCTATGCTCAGGGCCTAACACT | 2136 GGATGTGTTCATCCGTTCTTCACTA | 3336 |
| 937 GTCCCTCTGCTTCCTGCCATA | 937 CACCTTCCCACGTTGCCTAT | 2137 AGACAAGGGGTCCCTCTGCTT | 3337 |
| 938 GCTGTACTCCTGGGTGACATTC | 938 TGAGCTACCCATCAGGGTTATTCT | 2138 CCTGGTACCTGATATGATGTAGCCGTA | 3338 |
| 939 AGCCTCTGATTCCAGGTAAGA | 939 CCATTGAGTTTCAACTGGGGTACA | 2139 GGTCACCCATAGCCCTCTGA | 3339 |
| 940 TCGATGGCAGAGACAAATGACA | 940 GCCTCATCAACGACCCGATTCA | 2140 GGTAGGCATTTTTCGATGCAGAGA | 3340 |
| 941 CAGGGTCACACACTTGGGTATT | 941 ACCAGGACCCCACTGGTT | 2141 AGTAGAGGCAGGGTCACACA | 3341 |
| 942 CTCCAGCAGACGCATGCAAAC | 942 AGGTCTCAGCCCTGACTGTT | 2142 ACTAAGGAAGCCTTTGGGTTCT | 3342 |
| 943 GCACACCTGAAGGTCAAACGAACA | 943 TGCTTTACCCTGAATCCACTCTGA | 2143 CTCTTCCCCTGAAGACAACCAACTT | 3343 |
| 944 GTTGATGGCGCATTCCAGATGTA | 944 ACCATATGACCGTCAGGCTTCT | 2144 CCTTCCAGGTTGATGGCGCATT | 3344 |
| 945 TGTGGCCTGGCTCAGACATA | 945 CCAGGGGTTGGCGTGAAAG | 2145 CACTGCCCAGATGGCAGAAG | 3345 |
| 946 TTGCTGGCCACTGTCACTACT | 946 CAAACCAAGTGCCTGGTAGAATTCA | 2146 CGTGGCTGCATCTGATCCTTTC | 3346 |
| 947 CAAATCTTTGTGGGTGTTAAGTGT | 947 CCTCCACCTGCCCATCAGT | 2147 TGTGAGAGCCGTTGGGAAA | 3347 |
| 948 TGCCTGATGGATAGGTGGAT | 948 GTACCAGCCATGCATTTTTGA | 2148 GGAAATGTTTGACTCATCCCCTGATG | 3348 |
| 949 AGAGCTCCAGGCTCATCCCTAT | 949 CCCAGCTGTCCAAAGGACTTCA | 2149 AGTCAGCCAGATGCCAGAA | 3349 |
| 950 CAGAGTCCCTTGGATCTGTTCTCA | 950 CTGTCCGTGCCGTTCCAA | 2150 AGCTCAGGACTGCGTTCTTC | 3350 |
| 951 CTGGGGCAGGACCAGGAAA | 951 GCCACCTCCCTCCCAGCTAA | 2151 CCATGTACCCAGGAGAGGTGATGA | 3351 |
| 952 CAGTGGAGCTTGCTGGTTGACT | 952 GCTCTTTGCCTTTGATGCTGAAATA | 2152 TGTCTGCTGCAGTGCAGCTT | 3352 |
| 953 GGGTACCTTCCTCAAAGCAGCATCT | 953 CCGGCACAGTAGCACCTCTGTAAG | 2153 GGCGTACAGTGGACCTTCCTTCTCT | 3353 |
| 954 CATCCAGCACCATGGCATCT | 954 GGCCTCTCCTCTCCCCATT | 2154 GGCTCGGACAGAGGCATAACTTCA | 3354 |
| 955 TGGCAGAGACTGGCAGGAA | 955 TCCCACCCCTGGATCCCCATA | 2155 GTGGTAACTGCACGAGGACAAAG | 3355 |
| 956 TTCCTGAAGGGTTGTACCAGTTG | 956 GAAGGACATGGCCATCAGCAA | 2156 GGAGCCTCTTGGTTCCTGTGT | 3356 |
| 957 AGGGCCCTGCGAACACTGAA | 957 AGGCAGAGGGCGGTGTCTT | 2157 AAGACTTCTCGCAGGCCTGATT | 3357 |
| 958 CAGCTCAGACGTGGTGTTC | 958 CGTCTGCCTCCTGGGTT | 2158 AGTGAAGGCCCTCTCCTGAA | 3358 |
| 959 CTTGGCTTGGGACTGCTCTCT | 959 AGGTGACCATGTGACCACAGA | 2159 CCTCGATTCAGTCTGGGGACATTC | 3359 |
| 960 ACTGGCACAGCCCAGGATT | 960 GGGTAGCTTATTGGGGTTCAGTTCT | 2160 TCACTTTCCACCTCTCGAGGAA | 3360 |
| 961 CAGGGACTTCTGGAAACCCACTGT | 961 GCCGTTATTGCAGGCACAATCT | 2161 AGGTGAAGCAGAGCAGGACTTC | 3361 |
| 962 CATCCCTGCCCTAACTCTAAG | 962 AAGCAGGCAGGAAGGAGACA | 2162 GCCTCCTCATCTCATGCGTTCA | 3362 |
| 963 TGCACATGGCGGCCTAAACA | 963 TGACCACTCTCACAGCAGAT | 2163 AACCCCTTCACAGTGGATT | 3363 |
| 964 GGAGTCGCAGGTACCTCCCTTA | 964 CAGGCCAATGCACAGTGAAGCTA | 2164 GCTGCTAGGGTGGTATCAGGGAGTTC | 3364 |
| 965 AGCCATGCCGATTGCCTCCT | 965 GGTGGCGAAGGGGTAGTGAAA | 2165 GCAGGAGCAGGTTTAGCTGACA | 3365 |
| 966 TTGGCTTCAGGTCCGAGGTT | 966 ACTTCCGGGGCCTGGCTTCT | 2166 CTCACACCTTGGGCACTGCTT | 3366 |
| 967 GGCTTTTGTTGGAAGCACAGAA | 967 GCTAGGAACCTTCCAGGCATTTTA | 2167 GCTCCCCAGTGATGGGCTTTT | 3367 |
| 968 TTGAGTCGTGGCCCTCTCT | 968 GTTCTGACTTTCTAGTAACCACCGATT | 2168 CCTCTGTCTACATAGTGAACAGCATTG | 3368 |
| 969 TGTGGATGGCCACGTGCATCTGA | 969 TCCACAGCCCGTGCATCTGA | 2169 AGCACCCTGCACCATGTGGAT | 3369 |
| 970 CCATGACAGACACCCAGCATCT | 970 GTGATGCCAACTTGGGCTATGA | 2170 CGATGCAGGCCATGACAGACA | 3370 |
| 971 CCTCCCTCAAACAGAGGAACTCTA | 971 GCTGAAAGCTTGCTGGCTTCT | 2171 AGAATCAGCCTGCCTCAAACAGA | 3371 |
| 972 CACTGAGCAATCATGGCATTTGT | 972 CAATGGGTAACTAGGCAAGGGAATTAT | 2172 GCTGCCAAGAGAAATGGGACACT | 3372 |
| 973 TCCACCCCTGTCCCAGCTCCTA | 973 CCCGGCCTCCTTATAAGGAAAGA | 2173 GCCATCTCAAACTCGGCCAATG | 3373 |
| 974 GGACAGCAGCCTAAGTCATGT | 974 GCCAGTTCTGGCGATGGCTAA | 2174 GCCAGTTGCATGCTTTGGAACA | 3374 |
| 975 GTAAGAAGGAGGCGTCGGAATC | 975 TTCCCTACCCCTTCCCCAGAAC | 2175 GTGAATGGAAGGTGCATGTAAGAAG | 3375 |
| 976 TGCTGGCTCTGCTCAACAT | 976 GGAAGAAGCCCTCTCGAGCAA | 2176 GGGAGACAAGATAATGCTGGGTCTT | 3376 |
| 977 GCCCTGGAGATCAAGCTGCAAA | 977 GAACTAGCCACCTTGATGTCATCTGT | 2177 GACAGACCAAGCCTGGAGATCA | 3377 |
| 978 GACCAGGGTAGGTATCCAATACTGT | 978 TGCCCACCAGTGAGACTAAAC | 2178 GCTTCACTAACACCAGGCTAGGTATC | 3378 |
| 979 GCAACTGAATGCACGTTGGTGA | 979 GCAAGTGCTTAAGTGTCCTGCTT | 2179 GCTGGAGTTGGGATTTCAGCAA | 3379 |
| 980 GGACCCTAGAGCAATGACCTTCA | 980 GAGTTCCTTTCCCTCCAGTTTCTTG | 2180 GCCCATAACAGGACCTTAGAGCAA | 3380 |
| 981 GGAGTAGGTGGAAACAAACTGCTTCT | 981 GCCAGCTGAGGCACTCCTT | 2181 GCTCTTGGGAGTAGGTGGAAAC | 3381 |
| 982 GAAGCAGTCAGCAGTGCTCAGA | 982 CAGTGCCCAGTGGAATCCAGAT | 2182 GGTTTGGAACTAGAAGCAGTCA | 3382 |
| 983 GCAGTCTCCTCCTCCAGCAA | 983 CTCAGCCTCCTGAGAACAAAC | 2183 GGGATAGCAGGTCTCTGTTCCAA | 3383 |
| 984 CAAGCGCTACCCAACTTGGTCTA | 984 GCCATGCCCTTTCAACTT | 2184 CTCTTCTGGAGGACGGACACT | 3384 |
| 985 CCCTGAAGAGCTGAATCACAGACA | 985 ACAGACTGCGTGCCTGCAA | 2185 CCCCTTTTCCCTGAAGAGCTGAA | 3385 |
| 986 AGGAAGGTGTAGGAACTCAGAATAC | 986 GATTAGAACGTAGGGCACAAAC | 2186 GGACTTGGTGAGGAAGGTGTAGGAA | 3386 |
| 987 CCTCAACATACGGGCTACCAAA | 987 CCCAGGGGTTCCTGAAGTGAAAA | 2187 GCAAAACTCGGGATCCTCAAC | 3387 |

| | | | |
|---|---|---|---|
| 1050 CTGGAAGPCAGGAAAGPACAGPTCPA | 1050 ATCPTTGPGCPTGCTGAATCC | 2250 GGCCPTGGAAGPCAGGAAAG | 3450 |
| 1051 GGPTGPCCPGGPTPCGCAGAGPT | 1051 GACTGGCTGGCACPAAGAPT | 2251 CCAGGCCPTGGPTGPTCCPGGPTT | 3451 |
| 1052 CCCPGAPGGGAGPAPAGAAACT | 1052 CCTPCPACAGACAPTGCAGGPCAPC | 2252 GGPAGGPAATACAGCPTGAPGGGAGAA | 3452 |
| 1053 GGCAAAPCAAGCCPTGCCPPPTC | 1053 GGACAAPCAPTPGAGCPACPGGPGPA | 2253 GCAAGCAGPTGPCPTGGCAAAPC | 3453 |
| 1054 AGPGPGGGCCPPACCPGPGAPT | 1054 ACCCCACAGPGPCCPCCPAACA | 2254 CCAACPGCPPCCPGCPGACPGP | 3454 |
| 1055 PPPPGCCGCPGPCCCPGAP | 1055 CACPCCCAGGGAAGAAACPAA | 2255 GGPACPAAPGCPGCPGAPGPP | 3455 |
| 1056 GGACPGPGPPPGGPGPAAPAAC | 1056 GPCPAPGCCAGPPGCPAGAPAAAC | 2256 GPGGPPPAAGPGCGGACPGPTGPPC | 3456 |
| 1057 ACCCGAPGCCCATGACT | 1057 GGGGACCATCAGPGCCATCT | 2257 PGAGGGAGPPCGGCACCPAAA | 3457 |
| 1058 CCPAGPGAAGCPCCACCPPPAG | 1058 CCGCCAGCPPCAGACPPT | 2258 GGAGCCAGPCPCCCAGPGAA | 3458 |
| 1059 GPGGCAGACAAGGACAGPGAGP | 1059 PGGCCPPCCCPGAACAA | 2259 AGPGCPGAGGGPGGGCAGACA | 3459 |
| 1060 CCAPGGCAACPCCAPGCPPCCAA | 1060 GAGGAGPCAAGGAAPCGAGGAPGA | 2260 GPPCPCAAATCAATCCAPGGCAACT | 3460 |
| 1061 GCPPCCCAGGAPACCCACCCAPPA | 1061 GGPAAPGPGPAGACCCPACAGPPCA | 2261 CCPPCPCCAGCPPCCCAGGAPAC | 3461 |
| 1062 CCCPCPCGPTCCPCCPPACP | 1062 PGAACCCACAGCCCCAGPCA | 2262 AGCCGAPCGGCACPCPCT | 3462 |
| 1063 GAGCCCAPPPAPAPCCAPGCCPGPAC | 1063 ACCPGCCGCAAGAPPCAGP | 2263 CAACAPCCAACAGAGCCAPPPT | 3463 |
| 1064 CCCAGAAACPCAGPCAPGGAAAPC | 1064 PGCPGGGPPCCPGGAPGGAP | 2264 ACACAAGGCGCCACCCAGAAA | 3464 |
| 1065 AGPTCGCPAGAPTGCPGPGA | 1065 ACPCPCCACCAPGCATGCAGAP | 2265 GGPTCAPGGGAGAPAACGAAAPCAAGA | 3465 |
| 1066 CCAAAPCCAAPTGCAGCPGPGPAAC | 1066 PCPGAGAGAGCPGGCPACCPT | 2266 GCAATCACPCAAGACCAAACCAAT | 3466 |
| 1067 GCPGCCPPCPGAGCCCPGAPCP | 1067 AGCCPGAGGACPPGGCAGPCA | 2267 CAAGGGGCPGCCPTCPPGA | 3467 |
| 1068 CAGCCPAGAGGPAGCAAAACPGP | 1068 PCGGCCAACPGPTCCPCPGP | 2268 PGCCCCAPPPCCCPCAGAGP | 3468 |
| 1069 GPAAGPGPCAGGPCCCPCPAGPCA | 1069 GGGAACPPPGGGPCPPGA | 2269 PPPGPGGAGAAGGCAAGPGPCA | 3469 |
| 1070 AGCCAACPGAGCCAGGAACA | 1070 GGCCAAGCPPPCAGCCPPPC | 2270 GCCPGPGCCAPCAGCCAACT | 3470 |
| 1071 CCPCCAPCCPPCGGPPAAPPCPTG | 1071 CPGCAPGAGAAPGGPPGGCCPAAP | 2271 AACCAGAPACACCPGCAPGCPPT | 3471 |
| 1072 AAGGGPAGCPGPGPPCCPT | 1072 ACCGAPCCPGCAGPCAAGA | 2272 APGCCGGGAAAGPCAGAA | 3472 |
| 1073 CCAAPCCPACGACCGGACPCAAA | 1073 CAGAGCAGGGCPTGPCATPGPCT | 2273 CCAPCPGPGCPGGCCAAPTCPA | 3473 |
| 1074 PGCPGAPTCCCPGPGPTGCPA | 1074 CAGGAAAPCCAPGGGACAGAAGAA | 2274 PPCCCAPCAPCCGAPACPPTG | 3474 |
| 1075 GGGACACPGAPCPGPAACAAAA | 1075 GGCCAAACACAPCGGGAGCPAA | 2275 PGPGCCCPGPCAACPGA | 3475 |
| 1076 GGACCCPPCPAAGCCACPGAPCPCP | 1076 PGGGGPCPGCPGGGAGAGGAA | 2276 GCPGGPGCPGACCGPPCPAA | 3476 |
| 1077 CPAACCCPCAGCPCAAPPCPTG | 1077 GGGPGGCAACCCPCAGAPCC | 2277 GGPGPGCPTGGACGAGAGPPCPAAC | 3477 |
| 1078 GPGACACAGGGPCGCPPCPCAPC | 1078 CPPGPPPGCCAGAPPACCPCPGPT | 2278 PGCACGGACPTTCCCPPAPG | 3478 |
| 1079 PPGGPGPAGGGCAGCAGGAGAP | 1079 GCPPGPGGPCPGGPGPCA | 2279 GGAAPGCPGCCACPPGGPGPAG | 3479 |
| 1080 CCPPCPPACACCCACPGPPCCACPAAG | 1080 AAGGCGAGGCAGCPGAGGAAG | 2280 ACACCCACCCCATCPCPCPT | 3480 |
| 1081 GAAGCAPPCPGGGCPGAGAGAGA | 1081 CCAGAAGAGGCPGPGGCCPGAAAG | 2281 PGCCCCAGGCCPAGAAGCAP | 3481 |
| 1082 GGAAACCPGGPCCAAAACPACAA | 1082 CAGPGCAGCPAGAGGGCGCPGPT | 2282 CCGACCGGCAGAACCGAAAC | 3482 |
| 1083 AGGCACCPGPPTGCCCPGAATG | 1083 GGGAPGGGAAGGGPAAGGCACACA | 2283 GGCCAPGGACCAGAGGGPGCA | 3483 |
| 1084 GCPGPCAGAACCAGCPPGAGPAT | 1084 GGACPPPPTGACPTGGGPPTCACT | 2284 PGCCAGPTGCPGCPGPCAGA | 3484 |
| 1085 GCGGPAGGAPGPPAAAGGCPAGCPT | 1085 CCAAGGPCCPTGGPCPGGAAGT | 2285 TGPTCCCPGCGGPAGGAPGP | 3485 |
| 1086 GGPTCAATCPCAGGCPCACACT | 1086 GGGCAGAGCAAPAGCCGAAA | 2286 GCCCPTGPCCPTGGGGGPTCAA | 3486 |
| 1087 GCATGGATCPGPCPGPGPGPGAGACA | 1087 GGCCPCACGPCPCAGAPTGPT | 2287 PCPTPACPGCPCAGCAPGGAPCT | 3487 |
| 1088 CPGAACPGGGPGGPTGCGPPTPG | 1088 CPAGAGCCPGAGCAPGPACAAAT | 2288 GGAAACCPCCPAPAGPACPGGCAGAA | 3488 |
| 1089 CAGAACPACPTCAGAGCCAGPGPT | 1089 GPPAPCPPCPCACPCPCCPGPPCPTPAG | 2289 CACCAGCCATGGACAAAAGP | 3489 |
| 1090 GCPACCAAGGGAGGPCPCPPCT | 1090 GGPPCCPGPCCAGPGCPCAAGAT | 2290 GCPPCCPGGPTAPPCCPGPGCPA | 3490 |
| 1091 GAGGPGGCPAACAGACCCAPCA | 1091 GGCPCPGPAGGGCPPCPAGAAPGPT | 2291 CCGGGAAAPCAGAGGPGGGGAAC | 3491 |
| 1092 GGAAPCAAGCACAPACPGPCCPT | 1092 GGGPGPAGAPCAGPGGGGPPA | 2292 GCCPCAGGAAPCAAGPACAT | 3492 |
| 1093 ACPCCGPAAGCGPGGCAPA | 1093 GPCPCCGAAACPCACAPPGPAPPC | 2293 CCACAAGAGPAAACPGCGPAA | 3493 |
| 1094 GGPAPCAGCAGPGPGGGPPAAGGAP | 1094 CCCAAAACPGAGGPGGAGCPP | 2294 GGGCAGPAGAAGGPAPCAGCAGPGP | 3494 |
| 1095 CPCGGAAGPPCCCAGCAGAPCPPPT | 1095 GPGACCAGPPCPAPGCPGACAA | 2295 GPGCCPPACPPCGGAGCPPPC | 3495 |
| 1096 GGPCAGGPPCAPACCCPCCPPPC | 1096 PPCCGGAGGCAGAPCPCAAGA | 2296 PGPPGCGGPGAGGPPCA | 3496 |
| 1097 CPGCAGPCAPGCPGCCCACGA | 1097 CAGPCCAPCCGCCCCACGA | 2297 CCCAAPCCGAGCPGCAGPCAP | 3497 |
| 1098 CPCCPCCCPGPGGACCPPAPAPP | 1098 AGGGAGCAGPCGACPGAA | 2298 PCCPPCAPCPAACPCCPGCPCAP | 3498 |
| 1099 GGPPAPPCCPACAAPGCPPPP | 1099 GGCAGPGGGGPCPAPPGAAACA | 2299 CPPGCPPGAPAACPCPGGGCAPG | 3499 |
| 1100 GPGGCAACAGGCAGGGAPT | 1100 PCPCCAGAAGCPPCGCPPPGA | 2300 CPGGGGPACCPAGGGAPGP | 3500 |
| 1101 PPPAPGGACCAGGAPCCATCAGA | 1101 GCCGCAPGPCPCPACPPCPPCPT | 2301 PGGPCCAGGCPPPAAPCPA | 3501 |
| 1102 GGAAGGGPCPPPGAGGCAAACPC | 1102 AGGCCGAGCAGCPPPAGPCP | 2302 ACCGGCCGAGGGGPCPPPGA | 3502 |
| 1103 PCCCCACPCPCPPPPCPPPAGAGPAT | 1103 PCAAGAPGCAGPCACAACPAA | 2303 PCCCPPCCCACCPCPCPPPC | 3503 |
| 1104 CCAGGAAAGPCACCAATGCAA | 1104 GPGPPGAGCAGCAACPPGPCA | 2304 CPGAAAGCPCPGCPAGGAAA | 3504 |
| 1105 GGGCPGAPAPAAPGGAGGCAGCPPAG | 1105 ACPCAPCACCPPGGCAPGCPP | 2305 GPGCCAAPTPPPGPGGGCPGAPA | 3505 |
| 1106 GGCPCPGGPPPGPACPGACAPPCP | 1106 PCAGCCAAGAAGPAPPPGPPGGAA | 2306 GCPCPPCACCPACCAAGCAGAPAP | 3506 |
| 1107 PCPPPGGCCACACAGAPPPACPCPAG | 1107 CAAPGCAGGAPGCPPCPCCCACAA | 2307 CPGCCACPGPTGCCAPCCAPAPCP | 3507 |
| 1108 CAGAGPAGGGPGCCCGPAGGAA | 1108 CCCACCCAAAGGGAGCCAAPTCT | 2308 PGCAAAGPGCAPGCACAGA | 3508 |
| 1109 CGCPGPCPCPCPAPCCAAGPGPP | 1109 CPPPGCCCPGGCAPCPGAAAC | 2309 GGPPGCGCPGPCPCPCAP | 3509 |
| 1110 CCGAGCCPPGGAGCPAGGPGAPPA | 1110 CPCPCGGCACCPGGAAACPT | 2310 TCCPGGGCAPCAAGACPGPGAAC | 3510 |
| 1111 CAGGGPPCCPAGCPCPPPCCPGPTC | 1111 TCATCCAPCCPGAGPCAAAPPTCT | 2311 GPCPPPGPPPACPTCCAGGGPPCCPA | 3511 |

FIG. 34B8

| | | | |
|---|---|---|---|
| 1112 CATTCCCAAATGGATGTGGCTAGA | 1112 AAATCCAGCTACAGGATGATACAA | 2312 CCATCTCTGCATTCCCAAATGGAT | 3512 |
| 1113 GCTCCACTTTCGCCCTCACTT | 1113 GCACCAAGGAAGCATCAGGTACT | 2313 CCCTCTGTTTTCAGCTCCACTTTC | 3513 |
| 1114 CTTTGCTCTTGTCTGCACTGAGTA | 1114 CTGCTCAGGGGCCAGACTTC | 2314 CAGAACTTCACCCACTTTGCTCTT | 3514 |
| 1115 TTGAGCTGTGCAGGCTTGT | 1115 GAAGAGCAGTTTCACTTATCTGTGTCA | 2315 TGGGCTGAGCGGCTTTCTTA | 3515 |
| 1116 TGTGGCTACTTTCCCACAGTTTG | 1116 GCCTCCGGATCTGTTGCTAGTGA | 2316 GGGATAGCCCTTGTGGCTACTTTC | 3516 |
| 1117 CAAAGGACAATCACAGAGCTGTTC | 1117 AGGGGAGCCTCAGCATCCTAAA | 2317 TGCCATTGGAAAGTATGGACTACAAAG | 3517 |
| 1118 GGAATGGACCAAGTTTGTCTTGATT | 1118 CGGCTGACTGCAGTTGTCT | 2318 GTTCAGGAGTAAGGAATGGACCAA | 3518 |
| 1119 TGGATGTGGCCGCATTTGT | 1119 TCGCTTCGGCTTTCAGCAA | 2319 ACTTGGCAGGAAGGCTCGAT | 3519 |
| 1120 CCCCTGCCCCAAATAGCATTTTA | 1120 GATCAGAACTCCTGGCATGATGA | 2320 TCCACCCCTGCCCCAAAT | 3520 |
| 1121 ACTAAGCACTGGGGAAACTAAA | 1121 GAGAGCCCCTCAGGCTCTTTG | 2321 GGCAGACGGGATTCAGTTGCTA | 3521 |
| 1122 GGCATGCTCCGCACCAAGA | 1122 CCCCAGGAGAGCTGGTGTATGA | 2322 ACCATGCTGGCCCACAGT | 3522 |
| 1123 CAGGCCATGTAAAGACGCTCA | 1123 ACTGTCCTGTTCCACCCTTCA | 2323 GGGACTTTCCCAGGCCATGTA | 3523 |
| 1124 TGCTGAATGGTTTGCTCAGTTTG | 1124 AGGGGCCCTACTACCACTTTAG | 2324 GTCTTGTGCTGAATGCTGAATGGTTT | 3524 |
| 1125 TCGAGTCACTTACCTGCTCAAATG | 1125 GACCAGGGAAGAAAGACCCTCTGAA | 2325 CCTGGCTCCATGGGCTACT | 3525 |
| 1126 AGCAAGCGACGGTCCTCCAT | 1126 TGGACACTGCCGTAAGGTGAAG | 2326 TCTGGGGTGCCACCAGCAA | 3526 |
| 1127 ACCTGCAGAACTGAGGCTCTCT | 1127 GCCTTTCCACTTGCGATGTCTTC | 2327 GCCTCTTCATACCCTCAGAACT | 3527 |
| 1128 AGTGTCAGGAGGGGAAACGAA | 1128 TTCCCATGCAGATGCTGTT | 2328 GCAGGTGGAGTCTGAAGTGTCA | 3528 |
| 1129 CCACTCCTTCCCTTATACCCTGTA | 1129 GGGGATAAATGTCACAAGCTGGAT | 2329 GTCCTCATTATCCACTCTTCCCTTA | 3529 |
| 1130 GCAAAGATTGCTGCCCGTTCA | 1130 GGCTACTATGCCTGCTAAACATTAC | 2330 AGGCTGCAGAACAGCAAAGAT | 3530 |
| 1131 TGGACAAGAATGGAGAAAGACGTT | 1131 TGGTACCTGATATGCAGCCATTG | 2331 CTGGTCGGCCTTATGGACAAGA | 3531 |
| 1132 GCCTTTCCCAGGACTCCACAGT | 1132 AGGGAGGGCAAATGGCTATC | 2332 CTGGGGCCAGAGTCTGATTCTTAG | 3532 |
| 1133 CTGCTTTGAGGCAGATAGGAGCTT | 1133 GCAGACCTACTGACCCCTTTGGTT | 2333 GCACTGGGAGATGAGGCTGCTTT | 3533 |
| 1134 CCTGCACAAAGTGGCTGTCAAC | 1134 CAGGACTGAGTCCCTGTGTTTTG | 2334 TTTCTGCCCCACCTGCACAA | 3534 |
| 1135 GCAGGGAACCACAAAACATCACCTA | 1135 CATCACTCCCCTCTGCTGCTA | 2335 CCAAAACTATCTCAGGTGCAGGAA | 3535 |
| 1136 GCTTTCTCTCCCCTAGGACATACAGT | 1136 AGGCCACTGCCTTCTACCTT | 2336 CCTCTGGCAAAGCACCCACTTCA | 3536 |
| 1137 AGCCTGGCTCCCTACACATT | 1137 ACGAGGGCTGGGACGAAA | 2337 AGAGCTAAGAGGCTGCAACA | 3537 |
| 1138 TGCTATTGGGGCATTGGTTGTT | 1138 GACAGCTTGGTGTCAAGACCTTCT | 2338 GCAGCCTGTAGTCAAGCCCTTTG | 3538 |
| 1139 TGCATCCCGTTGCTGTCAAG | 1139 CATGGGGAAPGGGTCAGTACAGT | 2339 GCTCCAAGGTACTAGTGCTGCAT | 3539 |
| 1140 GACCTGTGTCCCTTTGTCCTTAG | 1140 GCCAGTGGAGGTAGTAGCATTTAC | 2340 GGCTAACCTCTGTACTTCAGT | 3540 |
| 1141 CCTTGCCCTTCCAGAGTCTCCTT | 1141 GTTACAGCATCAAGTGCAACAGT | 2341 CACTTCTCAGTCTCCCCCTTTG | 3541 |
| 1142 GCCTGGTACTCTCCTAGTTTTAG | 1142 TGAGGATTTCTGGGACACAGA | 2342 CTCCTTGGTTTGCCTGTACTCT | 3542 |
| 1143 GGGACCAGTCAACTTTGCCAGATT | 1143 AGCGGCTGTGTGCAGAATCA | 2343 AGGGGAGTGGACCAGTCAACTT | 3543 |
| 1144 ATTCCCATTCCTAAAAGCCGTGTA | 1144 ACTGCCTCCAATGACCCAGGAT | 2344 GCCCTACAGGTTTACATGCAAAGATATTC | 3544 |
| 1145 TCCAGGCACGCACCTCTGAT | 1145 TCCCTGCGTTGCTTCTCACT | 2345 GCTGTCCATGCAGAGCTAAGG | 3545 |
| 1146 GGCAGGCAGCATCTGTGCAGTCATT | 1146 TTGGACTCCAGTGCTTTGCAT | 2346 GAATGAACTGGCAGGCATCTGT | 3546 |
| 1147 TGCCGACATAACCCCTTCTT | 1147 TCTTTTGGCACTACGAGCTATGAA | 2347 GGCTAAGGGAATGCCGACATAA | 3547 |
| 1148 CGCCAATCTCAGTGGTTGGAAT | 1148 CCAAAGCACATTAGCCTGTGATG | 2348 GCCAGAAGGGAATCGCCAAT | 3548 |
| 1149 CGGAGGCAACTTGGCATGCTGTTAATACA | 1149 TGGCCCAGGTCCATTCTCT | 2349 TTCCATCCCCGGAGCAACTT | 3549 |
| 1150 GTGGCAGCCTTTCTGTAGTTGA | 1150 GGAAAACAACTTGTCCCTCACTTTT | 2350 TTGAAGGAAGTGGCAGCCTTT | 3550 |
| 1151 GCTCGTTAAGAATTAGCCCACACC | 1151 AGGAGGGTAGCTCGGTCTCTA | 2351 GCCTTCCCTGGCAGCTCCTTA | 3551 |
| 1152 CACCCAGCTAGAACCTCCTCTAGT | 1152 GTAGGGCTTCCAATGCCAAGAAATG | 2352 CTGAAATGCCAGCCTTTATGTTCATC | 3552 |
| 1153 GCTGCTTTGCGGGACCTT | 1153 CTCAGGGCATGGACACTTATCTTC | 2353 TTTCTCGGAGTGCTTCTTTG | 3553 |
| 1154 GGGACCAGTGCAGTGACAAGTGGTA | 1154 AGCTGCCCATGCCAACTCAGA | 2354 TGGAGCTGGCAGGAGTCAGT | 3554 |
| 1155 TGTGTCAAGCAGATTTGAAGCTAAC | 1155 GCAGGGCAGACTCCCTAAAC | 2355 GGGCTGTGAGGGTTTGTGTCA | 3555 |
| 1156 TGCACATTCCTTCCTTGGTGAT | 1156 TGCACTCTTGCGGAGGAAA | 2356 GCTCAGGGCGTTTGCATTCCTT | 3556 |
| 1157 CCTGCATTCAAGCCGTTT | 1157 GCTTAGGCTGGCTTGAACA | 2357 TGCCCAACTTCTCCTCATTG | 3557 |
| 1158 ACCTGCCTGTGTCGTATGAA | 1158 GGCTGGACAGTTGGTGCTGAT | 2358 ACCAGGCCTCCTTCTAGTCA | 3558 |
| 1159 GAGCCGAATCTCACTTATGTGAGTT | 1159 AGATCAGCGACCCTGAGTT | 2359 AGATGGTGAGCCGAATCTCACT | 3559 |
| 1160 CTGAAGCCTAATGGGGATCCAGAA | 1160 AGGCACCCCTACTGTGAGA | 2360 CCCAGCTCAGAGGGATCAACT | 3560 |
| 1161 AAATAGCTGTCCCATTCTGGTTGT | 1161 CCAGGATGGAGAATGTAGACACA | 2361 GCTACTTTGCAGCTACCACTGAA | 3561 |
| 1162 TCCCCGGATTCCACAGTAGT | 1162 AGACCAGAATGGATGAGGTGTA | 2362 CTGAAGTATCATCTCTTCCCGGATT | 3562 |
| 1163 GGGTAGGATGCATGAGAAGAACTGGAT | 1163 CGCTACCTCCTCAAGCCAGAAA | 2363 CAGAGGGTAGGATGCATGAGA | 3563 |
| 1164 GCTAGCTGAGGAACTATTAGACACT | 1164 TGGCAGCCCTCCACCATTTT | 2364 CTGATGCTAGATCCTCCTTCTACTTG | 3564 |
| 1165 CTGCAGATCTAGCCAATGAGGTT | 1165 TGGCAGGTGACAAGGTGGCAGAT | 2365 GGCAGGTAGGAGGCTGCAGAT | 3565 |
| 1166 GGCCAAGATTTTGGTGTTCAAGTGG | 1166 AATTTCCCTACGGAGTGAAACACAA | 2366 GGGCTGTTGGGCCAAGATTT | 3566 |
| 1167 ACAGCTCCGAATGGCCTAAT | 1167 TGTGTAAGGCAGGATAAAACAACT | 2367 CCCAACTATTTTCGGTTAGGAAGAAC | 3567 |
| 1168 GATCTCATGGCTACGGAGATCAAG | 1168 ACTCAACCTCTGTCTGTGTTC | 2368 GGGTGACACTCGAGTTCTTTA | 3568 |
| 1169 CCTCCTGGGAAACTGGTCAAGTAAAG | 1169 CCACAGTGAGGGTGAACAATCAT | 2369 CCCAAAATGGCTCCTGGGAAAC | 3569 |
| 1170 GTACATGGTATGCTACCAGGAA | 1170 CCTCACTAGCTGGATAAAACCTAGAGA | 2370 GGACACTAGGGCTCAATTTCGGCAGT | 3570 |
| 1171 TGGTCAGTGCTCCCAGAGTT | 1171 ACAAGCTAGCTGGAGAAAACCTAGAGA | 2371 GGTCTAGGGCTCAATTTCGCAGT | 3571 |
| 1172 CGCACATGTCTCGTGTCACT | 1172 CATTCTCTGCTACATTGGAGGGAACT | 2372 CCCTTGGATGACTCTTCGCACAT | 3572 |
| 1173 ACCACTGACAAACCTGTGCAT | 1173 GGTGGGACGAGTCAATCACTAAG | 2373 CCACTGCCACCACTGACAAA | 3573 |

FIG. 34B9

| | | | |
|---|---|---|---|
| 1174 CAGGGAGAATAAGCTCATGAAAGA | 1174 CACCGTGCCCAGCCTGTAA | 2374 GAGTGCTTTCCCATCAGGGATGA | 3574 |
| 1175 ACTGCAACACTGTGATGTCTTCA | 1175 GGCATGTTAGCCAGCATTTTACA | 2375 GGCAAAACTGCAACACTGTGA | 3575 |
| 1176 TTGCTCCCCAGAGTGTTGT | 1176 GTTCTGGTTCAGACAGTGGTTCT | 2376 TGCAGGTTTCTCACATAACTCCTT | 3576 |
| 1177 CAGTCGAAGAGTGAAAGGATGC | 1177 CAGGACCTCATCCTGAGTTGATTT | 2377 TTCTCTCCAGCAGCACTCTTTATT | 3577 |
| 1178 TGAAGCATCTGGCCTGTCTGA | 1178 TCTTGCTGACCAGAGTGTGA | 2378 CTGTGGCCCATGAAGCATCT | 3578 |
| 1179 TTCGGGGTGCATCCTCACAT | 1179 AGGCCCGAGGGAGTTTGTTTG | 2379 TGTCTGCTTCCTAGCCTCTTC | 3579 |
| 1180 CATCCACAGCTGTCTCCGTGTA | 1180 GGCCCTCAAAGTGGTGAAGAGT | 2380 CACACATTTCAGGAGCTTGATCTCATC | 3580 |
| 1181 TTCCAGGTTGTTTTCTGCAAAGTAG | 1181 CCTTGCCTGAGCTGGTATTTCT | 2381 GGAACCATGTTCCTTTCCAGGTTGTT | 3581 |
| 1182 TCCCAGAGACACAGCTAGTAAAAAC | 1182 TGTGGCTACAACTCAGGCAAA | 2382 TCATCATCCCAGAGACACAGCTA | 3582 |
| 1183 TGCTGCTCGTACAGTGGAAAG | 1183 GACATTGCTTGACTTGGGTGTGT | 2383 CCTTGTGCTGCTAACCATGAGACT | 3583 |
| 1184 GGAGCAGTATCATTTGGTGCATTG | 1184 CTCACGGTTCCCATGAATGAATC | 2384 GGACCCTAGTGATTCTCCATCAT | 3584 |
| 1185 CGGTGGTGCCTTTGTTTTAACT | 1185 TGTGTGCTGACAGGTTTGTGA | 2385 CACACTTTTCGGTGGTGCCTTT | 3585 |
| 1186 GGACAAGGAATGTCAGGAAGCAAAC | 1186 GTAACAGGAGCTACTTGCCAAA | 2386 AGGGAGCCAAGGACAAGTGAGAAG | 3586 |
| 1187 AGTAGGTGTGATGGCCAGGAT | 1187 GCCCCTGTTGTTGTGCTGAT | 2387 TGGCCATAACAGAGTAGGTGTGA | 3587 |
| 1188 TGTCTTCCTAGCCTCATCTCTCA | 1188 GGCTGCAGCATAAGGAATGTGA | 2388 TAGCCCCACGTGTCTTCCTA | 3588 |
| 1189 GCTAGGGATACTGAGTCCTGCAT | 1189 GCAGACCATTGCTTGGAGGAGATA | 2389 ACTTGTTCACTTGCTAGGGGATAC | 3589 |
| 1190 CCCAAAGAGTCCCCACCTGGTT | 1190 CTGAGCTGGAAGACTCAAACT | 2390 CAGAGAGAAGGAGGCCCAAAGA | 3590 |
| 1191 AGACCTAGGCGGCAAACAAA | 1191 GCAACTTTAGGCCAGCTGAGTT | 2391 TGTCAGTAACGGTGGAGACCA | 3591 |
| 1192 AGTTTCCTGGAGCCAGCTATTAAA | 1192 AAGACAGGGTGGGAGATGTAGT | 2392 GCCTTTTAATTAGCCTTGCAGCTT | 3592 |
| 1193 CGTAAGCATAGGGGCTGCAGTA | 1193 CCTTGGATTTGGGCATACGTGAA | 2393 AGTGGGAGCCTCGTAAGCAT | 3593 |
| 1194 GCAGTTGAGGGAGTTCAACTAAAGA | 1194 TTCCCCTGAACTCTTGCTGGTTT | 2394 GGAATAGGTAGGTGCAAGCAGTTG | 3594 |
| 1195 CCTAGGCTAGAAGCCCAGAAAAC | 1195 GGGTTGAAACTGGAGGCTTGTTC | 2395 ATCCACAATTTCCCTAGGCTAGAAG | 3595 |
| 1196 CCTTCCCTGTCACACCACATC | 1196 ACTCTGTACCGGGTATTTCACACT | 2396 GCCTAGGGTTCTCTTCCTTCCCTTT | 3596 |
| 1197 CCTGTGTTCAGGAAGAATGAGGAT | 1197 GCCCATCCAGACCCTTCTAATTG | 2397 TGGTTCCCCGAGCCTCTTTTC | 3597 |
| 1198 GAAGGAAACTGACTTGCAGCTTAAC | 1198 CAGCCTGGTGCAGCAGTTG | 2398 TGGGTCTAGAAGGAAACTGACTTTG | 3598 |
| 1199 AGGGAGAAAATCACACTCTTGCAT | 1199 AGAACCCATACCTGCATTACAAA | 2399 GGGCTCAGGGAGAAAATCACA | 3599 |
| 1200 GGGACGAAGTCAAGGTGTAG | 1200 TCCCTGGAACCTCCAAAACT | 2400 TGACTCTTACGGGGACGAAGT | 3600 |

| Target No. | Pool A Sequence (5' to 3') | SEQ ID NO. | Pool B Sequence (5' to 3') | SEQ ID NO. | Pool C Sequence (5' to 3') | SEQ ID NO. |
|---|---|---|---|---|---|---|
| 1 | GGCACAACATTGGAGACAAA | 11659 | CTCACTAAACTTTTCCCAGAACTCA | 22643 | GCTTAGCCACAGAAAGGCACAAC | 33627 |
| 2 | CCTGGAACCTGAAACTTGCAAAAAG | 11660 | CCTCTGAAGGGAGACTCAAACAAC | 22644 | CGAGTTCCCTGGAACCTGAAA | 33628 |
| 3 | ACAGGGTGCTCTCCTCTGA | 11661 | GCAAGAAAGCTTGGCTGGCAA | 22645 | AGCCACCACTCCTCCTCTGA | 33629 |
| 4 | GGAAGCAAACAGGTTAGAGCCTGGTA | 11662 | GTGGCATTTCACTGCCCTTTG | 22646 | TGGGGACCCCTGGACTAAG | 33630 |
| 5 | CTACAACAACAGAGCTCCAGGAT | 11663 | GCAGCTTGTTCAATTGTGGTTCA | 22647 | CCTCCCAGTATCTTACCACTACAAC | 33631 |
| 6 | TGTCCTTGGTGCTATGTGAGGA | 11664 | GTGAGGATGAGTTTTCAGTGGCTATC | 22648 | CACTAAGCTCTAACTCCTAAA | 33632 |
| 7 | GCAGGAACTGGCTTGCCTTT | 11665 | TCCTGGACAAAATGTAACAGCCAAAGT | 22649 | GAAGTGAAAGAAAATGCCAGGGAACT | 33633 |
| 8 | AGGTTTCGGCTTTAGTTGTGTGA | 11666 | ACCTAGCTATCCTTCCAGCATTTC | 22650 | GCTGGTATTGTTTTGGGGATAGAGGTT | 33634 |
| 9 | TGTCTGCTTCTCCCGGCATTC | 11667 | GTTGGACAAACTACTGCCTCTTC | 22651 | GTGGAGGAAATTAGATGTCTGCCTTCT | 33635 |
| 10 | GTCCCTCACACCTTCTACCAGAAG | 11668 | GCCAATAGCTGCTTTGATGCAAT | 22652 | GGGGCAAGTCCCTCCACACCTTT | 33636 |
| 11 | GGCTGCAGGAGTAGAGCTCTAAATG | 11669 | TAGTTTCCCTGGATTCCTAAGA | 22653 | TGAGGCTCGGCTGCAGGAGTA | 33637 |
| 12 | GGCAAGAAGAAACTGGAGCCTAAGA | 11670 | GGAGAAGGCTGGTTCCTGAGT | 22654 | CTGAAGCCCAGTGGCAAGAAG | 33638 |
| 13 | GAGCTGAGTCTTGAGTACTACA | 11671 | GTTTGGAAAGGTCAAGTGCAAGAA | 22655 | AAGTGCTGAGCCTGAGTTCTTG | 33639 |
| 14 | CCTGGAAAAGCCCAGGCTAGA | 11672 | TGCTCGGGAGCTCACAACCTTA | 22656 | TCTCAGGGTGCCTGGAAAAG | 33640 |
| 15 | GCAATGGTCCCAGTGAGACGTT | 11673 | ICCCATTGATGCCAGACACAA | 22657 | TCACTGCAAAAGAGGGCTATTG | 33641 |
| 16 | GCCCTTTGGAACCTGACCAA | 11674 | CTCAGCTTAAGCAAAATAGGGCAAGTA | 22658 | TGGGAACCAGCCCTTGGAA | 33642 |
| 17 | GGCCTTGATTGACCTTCCTTTC | 11675 | TGGCCAGTAGTAAGTTGAGAAGACTA | 22659 | GGCTTCACTCATGAAGAAGGGCTTGATTC | 33643 |
| 18 | GCACCCGCTTCTGAAATACAGC | 11676 | CCGGAAGCTTCACGTTCTGT | 22660 | AAGAGGCTACTGGTTCTT | 33644 |
| 19 | TGGCCTTAAAGCCCAACA | 11677 | GGAGGGAGAGCTCCATCTCTGA | 22661 | GGGCAAGTCCCTCACACCTTT | 33645 |
| 20 | CCTTCCTCGGCTTCTTGCATATAAAA | 11678 | CCGCAATAGGACTCAGCAA | 22662 | CGGAAACCTTTCCTCCTTCT | 33646 |
| 21 | GTCAGCAGTTTAGGCTATTGAGT | 11679 | TAGGGCAGGTGTCCTCTTGCAT | 22663 | GGAAGGGGAATTTGCTCAGCGTTTA | 33647 |
| 22 | GCATTTCAGTGCCTTCGT | 11680 | GTGAACCAAGCTATACTGCTGCTTTTG | 22664 | GTAGTCTCAGCCTTCCTTTGTAT | 33648 |
| 23 | CATCTTCCTAGACATGCACACAAC | 11681 | GGCTTCTTGGCAGTTCACACT | 22665 | GTTGGAAGCATCTTCCTAGACAT | 33649 |
| 24 | GTCCCAAGTCAACTGCCATCT | 11682 | GGCACACACAAGGAGTGAAAAGT | 22666 | GCCTATTTTGGGGCTCCAAGTCAA | 33650 |
| 25 | GCGCAGTACAGACTAACACA | 11683 | CGGAGCCGGTATATCAGCTTAG | 22667 | TGGCCATGTTGCTACT | 33651 |
| 26 | TGACAATGGGAGGGAACATTCAA | 11684 | CGTTCCTATGACCAAGTCCCTTT | 22668 | CACGTTATTACTAGCTTCCTCTCACAAGG | 33652 |
| 27 | GGTAAAGCTGGTTGGAAAGTCCACAT | 11685 | GTGTTGGCCAGACCCACTGT | 22669 | ACTGGGCTAAAAGGCTCAGTTGT | 33653 |
| 28 | CCGACTCAATGGGAACTCGCACC | 11686 | GGGCACTTTTGAGTTGGGCTTTG | 22670 | AAGCCTCCGTGGCCGCTCAAG | 33654 |
| 29 | TCCTTACACCTTGGGGCTCTCTA | 11687 | GCAGCTCGGTGCTAATGTT | 22671 | AACATGGCTGAGTTTTCCTT | 33655 |
| 30 | GGGGCATTTCCTAAGACACTTGGACAGT | 11688 | CAGACCTGCCAGGATCAGAATAGT | 22672 | GGAGAGGCCAGGCATTCTAAG | 33656 |
| 31 | CACTGTACTCAAATGGTAAAACAA | 11689 | TGCAATGCAGAGGAGAAATGTT | 22673 | CAGCCTGCTAGGAACACACTGTA | 33657 |
| 32 | ACTGCTCTGCACACAGTTCA | 11690 | AGTCACAGGGTATCCTGACTCTCATA | 22674 | GGTGATTTGGCCGAACTTGCT | 33658 |
| 33 | GGCCTCTTGGTGCCTCTGTT | 11691 | GGAGCAATAGCTTGCAGGAGA | 22675 | GGAGCAATAGCCTTGCAGGAGA | 33659 |
| 34 | GCTAGAGAACAAGACAACATCCAAGTTC | 11692 | TGGCCCCTGGAAACCAT | 22676 | CCTCAGCCCTTGCTAGAGAACAAG | 33660 |
| 35 | GCGGTATGAGAAGGAAAGT | 11693 | TTCAAGACCATCCTTCGCTTAT | 22677 | TGGAATGCGGCATGAGAA | 33661 |
| 36 | GGCTTCAGCCTTTACCTCTTC | 11694 | ACCTGCAGAAGGCGGTATTTGCGT | 22678 | TCTCCCAGCCTTCACTTCCTT | 33662 |
| 37 | TGAGACTGCCTAGGCCAGCAT | 11695 | AGAAAGACCCCAGGTGTGCTGCTCAGA | 22679 | CCAAGTTATGCCTGCTGCTCAGA | 33663 |
| 38 | GGTTCCTCATGTGAAGACTGGTTTG | 11696 | CACTCACACATGCACAGGAGACA | 22680 | GGGAACCTGCAAAAGACCTTTACTT | 33664 |
| 39 | GTTCAGCAGGGGAGTAAGATCAGACAA | 11697 | GATCCAGTATCCCACAGAGCATT | 22681 | GGTGGGATAGTTGAGAAGGGAGTAA | 33665 |
| 40 | CTCCGGCCTCTAAATGAATGGAT | 11698 | ACCAGCTCTGAGTCAGGAAGT | 22682 | CCTCAGCCTCCGCTCTAAA | 33666 |
| 41 | CATTCCCTCCCTACCCTGGAAA | 11699 | CCCACAGTCGACGAGTGTTTT | 22683 | GGATGAGCATAAGCAGTGGTTCA | 33667 |
| 42 | GAGACTCAATCTCGCAGTTTCTT | 11700 | TCACTGCACTTTGACAGACACATATT | 22684 | AGGAGTCAGAAGGAGGGACTTCAATC | 33668 |
| 43 | CCCGGCTGCCAGTTAGCACCAT | 11701 | ACGAGGATCAGACAACTCACAGA | 22685 | TCAAGTCCCGGCTGCCAGT | 33669 |
| 44 | GATGGAGGGCTCAGTATGGTCAAG | 11702 | CCCATGCAGTCCCCAGGTTGCAATG | 22686 | GACACAGAGATGAGGCTTAGT | 33670 |
| 45 | CCCTTTCCTGAACCCCTTCATT | 11703 | CACTCAGTGCAGTTGCTGGTT | 22687 | AATTGCTAGCCGTATTCTCCTTCT | 33671 |
| 46 | GGGGCACCAAAGAAAGAAAGAACAAG | 11704 | GCTGTGGAGTACACCTTGGAA | 22688 | ACAGAGGATGGGGCACCAAA | 33672 |
| 47 | CATCAGTAGCCTCACATAGGTTTACT | 11705 | GCCTTTCCACTGAGTCATCA | 22689 | GCATTAGGAATGGAAAGGGACTCATCA | 33673 |
| 48 | GGAGCTCAGTATGAGTAGAGGGCAAA | 11706 | CAGCCCTGGTTGGTTAGATTCGT | 22690 | GACCTTCAAGGGGAGCTCAGTAT | 33674 |
| 49 | TTGTGACTACACTCAAGTG | 11707 | CTTATGTTGGCTTTGCCTTCTTG | 22691 | TCTCATATCAAGCCTAGGCATTGT | 33675 |
| 50 | CCGCTAGGCCATTCCTCCTGTT | 11708 | GGGGCTGAATCAGACAAGCAA | 22692 | TGCACCATGCTCAGGCCATT | 33675 |
| 51 | CACGACACCCTTAGATAATGTTGGAT | 11709 | CACAGTTGAAGGCTCTAA | 22693 | CCAGCTCAAAAGCTGGCACAA | 33677 |
| 52 | TGCTACAAGCCCAGGTCAT | 11710 | CTCATGATGTCAAATGCTGCTCAA | 22694 | AGCCTGCAAAAGCTGGCACAA | 33678 |
| 53 | GCCTCCCTCGCTCTCTGAACCAA | 11711 | GTCTGGTGACAGACAACTTTCT | 22695 | TTCCCAGCCTCCTCTCCATCT | 33679 |
| 54 | GCTAGCGAACCCTTCACCTT | 11712 | TCAGCAGCACAGTCCAATTCT | 22696 | CTCAAAGGGAAGAACGCCAGT | 33680 |
| 55 | TGGTAGTCAGGCCTAGTGACTT | 11713 | CCCTCGGAAAGTTACTGTGGAT | 22697 | TCTGCTGTCCACTTCCTGGTA | 33681 |
| 56 | GAGTTCTTCCAGGATGATTTCAGA | 11714 | GTCAGGAGCGGCACGAGGCTCTTTACAA | 22698 | GTCAGGGAGTCAAAAAGCTCTGT | 33682 |
| 57 | CCTGAGCCTGTCACACTATTCCT | 11715 | TCCCAAATCCTGAGCCTGCA | 22699 | TCCCAAATCCTGAGCCTCTCA | 33683 |
| 58 | GAGACCAAGAAGCTTCAGA | 11716 | GCAAGCTTAGTACACAACTTGCCTTAC | 22700 | GTAGAAGAAGTGAGAGCAGACA | 33684 |
| 59 | AGCCCTACAAGGTCAAGTTTCA | 11717 | GTTGACTTCCGCAGTAAGTGATGA | 22701 | GACTATACGACCAAATAGCCCTACAAG | 33685 |
| 60 | AAGGGCACTTCACTCCTCCTA | 11718 | ACTGGGACTTCACGTTATCA | 22702 | GTCACAAGCAGCCACTTCA | 33686 |
| 61 | GTTGGGGTCAACTTCCCCATCGA | 11719 | GGAAAGCCAGCCCATCCTCACATC | 22703 | AGAGCTGCCCTGGAACTCAA | 33687 |
| 62 | GAGGTTTGCCTCCATCACAGA | 11720 | ACTGCACCACCACACGGAAA | 22704 | GGAAAGGTACCCAGAATGCAGGTT | 33688 |

| | | | |
|---|---|---|---|
| 1233 AARHACTGCTTCTTCACTGAGA | 12891 AGGAAAGCTGGCCTTTTCATC | 23875 CCCACAAGTTTTAGCAAATGACTGCTT | 34859 |
| 1234 GTATCCCATGTCCCATTACTTCTGT | 12892 GCAGTGGGGACCCAATCATCC | 23876 GCTGTCTGCTGATCTCCTAAATGT | 34860 |
| 1235 TCGCAGGGTTGCTTCAGT | 12893 CATGCAAGGAAGGAGCTTGAA | 23877 GGGACCTAGGACCTCCAATC | 34861 |
| 1236 CAAGACAGAGTCTTGGTCAATCAA | 12894 GACCTGGTCTGTCCTGAGT | 23878 TGGCTTCTAGAGTAAGAGATCAAGC | 34862 |
| 1237 TGTCCATGCTCACCTTGGT | 12895 GCAACAGAACGCAATGCAAGACA | 23879 GGCTGGTTTCCTAAGGCCTCTGCCCAT | 34863 |
| 1238 TGCTCATCAAGCTAAAATCTACCAT | 12896 TGGGAACGGTTTGGGAAGAA | 23880 CCCACTGCTGATCAAGCCAAA | 34864 |
| 1239 CCTTATTCCTGGCACAGGGTTTG | 12897 CCAAACTGCTAAGCAGGGTGGGTAA | 23881 CTGACCCTTCCCTCTCCCATCA | 34865 |
| 1240 GCAACTCCACCTAAACACTTTTC | 12898 CAACGGCAATCCTGACACAAG | 23882 CCCACAAAGCAACTCCACCCAAA | 34866 |
| 1241 CAGTAGTATCAGCCTGCCATTTTCTA | 12899 ACAGGCCCACACCCTATCCA | 23883 CCCCATTAAGAAAAAGTCAGCAGTATC | 34867 |
| 1242 CCAGCTCACAATTGCCAGCGATT | 12900 GGATCACAGAGGAATGGGATGAA | 23884 TGTCAATGGATTCCAGCTCACAT | 34868 |
| 1243 AGGGGCCAGCACCTTACTTCA | 12901 CTCCCTGGGAACTCTGGCTTAGA | 23885 AGGGTTCAGGGCATCTGTCT | 34869 |
| 1244 CACAGCGCAGGCATGCTTATTG | 12902 AGAATGTGCAGTTTAGGGAATCCAA | 23886 TGGTGTCTCCCTGTGAACAGA | 34870 |
| 1245 TTTACCCAACCTTCACGCTTAGAT | 12903 AATAATAAGGCCACAGCTACTTCT | 23887 TCCAGCTAATTTATTCAACCTTCA | 34871 |
| 1246 GAGCCTAAGAGGCCATATGGCAATG | 12904 AGTACTGGCTGGCCTTGT | 23888 TGGCCTGTGGAGTAAAAACTTG | 34872 |
| 1247 CCCTAAAGGAGTCAGCTGCTT | 12905 CATCCTAGGGTGAGATAGGAT | 23889 TTCTTCATCATCACAGTGACAAAT | 34873 |
| 1248 GGAAGTGCTGGACACAGA | 12906 TTCCTGCTATCTGAGTGTCA | 23890 GGAGCCAGTGCTTAGGAACT | 34874 |
| 1249 GGAGACGCTGATGGTCCTTAG | 12907 CTGATCCCTCAACACCAGAAG | 23891 GACCTTGTGAAGGAGATGCTGATG | 34875 |
| 1250 GGTCCAATCTGGCACACTATCA | 12908 TTCTGTCCAGGGGATCTCA | 23892 TGAAGAAGTGCTCCTGGCTCAAATC | 34876 |
| 1251 GCATGAGGCTCTTTTCCATGT | 12909 TCTCCCTCTGTGGGAAGACTTG | 23893 CACTTTGGATGCATGAGCCTGTT | 34877 |
| 1252 CAGTACCATGCTTCCTCTGAAAC | 12910 AGGAGGAGGCAAGCGAAGAT | 23894 GATGGTGTCAGGACCATGCTT | 34878 |
| 1253 GATCCTCAGGACAGCAATCA | 12911 GGACATGCTGACTACAGAGAAG | 23895 CCCCTAGTCAGCAGAGATTGATG | 34879 |
| 1254 GCCCATAAGGACTGCTTCTCTCAT | 12912 TGAGTATCCCTGCAGTCCTGGAT | 23896 CAAGCAPGCCTCTTCCTCTCAAGCCCATA | 34880 |
| 1255 CCCGCTTGACCTTCGGAAAGT | 12913 ACGGGAATGAAGCTTAGAGAAGC | 23897 TGCTACTTACTACCCGCTTGATCT | 34881 |
| 1256 ACACCTCCAACACGCCGACTCT | 12914 TTCCCAAGCACGGGGTCAAGA | 23898 GGACCCTCAGACACCTCAACA | 34882 |
| 1257 GTTGCTGACAGAAGTCATCTAGGAA | 12915 CACGAAGCTGTTGCTTCCTAGA | 23899 CCACTTCCTTGTGTTGGGACA | 34883 |
| 1258 GCTACTGGGACTGCCTGTTT | 12916 GCACATGGAGCACTGTCT | 23900 TGTTAGAGAAGGAGTGCTTTC | 34884 |
| 1259 CTGAGCTGGGCATGCATTGT | 12917 GCCTATGCCTTTTGTGCAACT | 23901 GCCCCCACTCATGCAGAATGA | 34885 |
| 1260 GCAACAAAATCGTTGTCAGA | 12918 GCTAGGCTCACTCTGTGCAA | 23902 AGTACCCGTAATTCTTCACTTAACA | 34886 |
| 1261 CTGTCCTTCCCTCTCTGACATT | 12919 AGGAGTGACCCCTGGTGTGAT | 23903 GACACTTGGAAATACTAGAGCTGTCCTT | 34887 |
| 1262 GTGGCTCTGGGTGGTGAGT | 12920 GGGCTGCTGACTGCTGAA | 23904 GGGAATTGGCTGATGTGGAAAAACTGT | 34888 |
| 1263 AGGGCGGTGAGGGGTGTCA | 12921 GAGGGGGTTTCATGTTGCTACT | 23905 GCTTGTGCTGTGCATTTGGGAAT | 34889 |
| 1264 ACCCATGACTTCTGGTTCAAAT | 12922 GGCAGCTGAGGTAGAGCAGAA | 23906 GCTACAGAGTTCAGACCCAAA | 34890 |
| 1265 GAGTGAAAGTTGGCCTCATCA | 12923 GCCACCATGCCCAGCCATTTA | 23907 CCCTTGTGAAGAGGGAAAGTTG | 34891 |
| 1266 CCCTACTGTTTTTGCTTAACTCAGAA | 12924 GCTAGTGACATGGAGTGATGAA | 23908 CAAGCATGCCTACTCCTTTTGTCT | 34892 |
| 1267 GCTCAAGCAATACTGCAGTTAGGAA | 12925 CCCATTACTCTCTCCCCGTTC | 23909 CCCAGGTAACCAGCTCAGCAA | 34893 |
| 1268 GTGCTAGGGCTGTCTCACT | 12926 GCAGACAATTTCTGGAGAATGTAGTTG | 23910 AGGTGCGGGGACAGTGGTA | 34894 |
| 1269 CTGCTGGTTGCTCAAGCTA | 12927 CTCCAAGCCAAGACCAACTTA | 23911 GCCCAGTGTTGAGTGTTGA | 34895 |
| 1270 CAAGACATCACCATCAGCAGCTA | 12928 GTCTTCTGTCTTCCAGGAGTTG | 23912 CAATTCTGTTCTCAAGCATCCTCACCAT | 34896 |
| 1271 GGCAGACACGGAGCATCCACA | 12929 CACTTCTCAAACTCGAGGACTCCAA | 23913 AGCACTGGCAGGCAGACA | 34897 |
| 1272 CAAGGACCAGATGTAACTGCATGCA | 12930 TGTGAGCAGTGGAGAGGTATCA | 23914 CCAGACCCAAGGACCATATGTAAT | 34898 |
| 1273 CCGTTTTGCTCCTCACACATC | 12931 GGCTGGAGACCCCACTATACA | 23915 TGTGGCACCTCTCGCTTTTG | 34899 |
| 1274 GGAACAAAATGGCTCTTGGACAT | 12932 GAAATTGTTCCTGGACTCTAAA | 23916 GCTACTAATTCTTGTCATAGGAGGAA | 34900 |
| 1275 CCGTTGTTTTCTACCCAT | 12933 GGGTTCTTAGGAGTTAGAATGT | 23917 ATCCCACTTCCTGCTGTTTC | 34901 |
| 1276 TGGCCTTTCAAACTCCAGAA | 12934 GTTGTGGAAATAGGAAGACCTAATG | 23918 TCTACATGTAAGGATGTGCTTCAA | 34902 |
| 1277 CGTGTCCGTCCTCTAAGGTCATTAG | 12935 GGCGCGAGCCAAGTCTTT | 23919 TGTCCTGTGCCGTTCCTCTA | 34903 |
| 1278 TGTTTGGAACAACCTAAGGAGTCA | 12936 TTCACAGTGGACCCATTCATTCA | 23920 CCTAGTACAGTGTCTGGAACA | 34904 |
| 1279 TCCCTTTTCTAAGCAGAATGATGT | 12937 CTACAGGGAAGGTTTCGTCCAAGT | 23921 CCCTTCCACTGCTTCTGCTACATTG | 34905 |
| 1280 GGGTAACCTGGAAAACTCAGA | 12938 CCAGTCCTGCGGTAATAACA | 23922 GCATTGGCTTTGAAGACTGTAAC | 34906 |
| 1281 TCTGCTAACCACTGACTTCA | 12939 GTGCGCTCTTATTTCCCCATTAGAATCA | 23923 ACCAAGTGTTGATCCTCTGTA | 34907 |
| 1282 CACCTGGCAGGAATGATGTTTT | 12940 TGATTGGTCCTTCAACCCTTCTT | 23924 GTTATTTCAATAACACCTGGCAGGAA | 34908 |
| 1283 GGGCTTCATTCAATCACAGATGTCT | 12941 AGGGCCTCACTGCTGCTTTCA | 23925 TCAAGTCTGGGCTTCATTCATC | 34909 |
| 1284 GTAGAAATGTTCCAATTGGCTTCAAA | 12942 CCAGCAGGAGAAAAAGCCTTGCAC | 23926 GGGGCAAGGTGGCCTTAGAA | 34910 |
| 1285 CAGGCTCAAGGGAGACTTCAATC | 12943 CCTACTAGACTACAGTGCATTTCT | 23927 CCTAACATCTTGACAGGGTGAAG | 34911 |
| 1286 CAACGTGCCGCATTGTGTTG | 12944 GAGGGGAGTTCCATGGTCTAACA | 23928 CGCCGTGTCCTTCCCACAA | 34912 |
| 1287 GCAACAGTCTGCAGATGAT | 12945 CCTTCTTTCTGTCTTCAGAA | 23929 GTATCGCCTGCTGAGCAAC | 34913 |
| 1288 CTCTCCCACCTTTTGCTACAGT | 12946 GTGTCATCTTGACCAGAAGTCAAGT | 23930 CCATGCTACTCACTCCAGTTC | 34914 |
| 1289 GAGGGAAGCAGTACCTTGCACTTTA | 12947 CCAAGCAGGTCGACCCAGAA | 23931 CTACACCATGAAGATGGAACCAT | 34915 |
| 1290 CAAGTCTATCTGCAGTGTGTTTG | 12948 GGTCCAAACCTCAGACATAGT | 23932 TGTCATCCGTACCGAATTTCAAGTTCTA | 34916 |
| 1291 CATAGGCCATGCCAGTGAGATT | 12949 GGGGGCTGATTTCACAGCAGTAG | 23933 AGGAAGGGTTCCTCTGGTACTAG | 34917 |
| 1292 CCCATGCATCTGCTGCTGCTGT | 12950 AGAATGCTAACTAGTGACTAGATCC | 23934 ATAGCCAGCCAGGCCGATCA | 34918 |
| 1293 GTGCTTCAGACTGTCCGTTTCA | 12951 TGTGTTTGTATGTTCACCATACC | 23935 GCAAAGAGTGAGCTTTGTGCTTAGA | 34919 |
| 1294 AGTGTGTGGCTGGCGTTGA | 12952 GCCAACGGACTGCAGTGAAAA | 23936 TCCTCCACAGCAGTTCAGT | 34920 |
| 1295 CCATGGGCAGGTTCACATC | 12953 CCCTCCTTTGCTGCACGTAACT | 23937 TCCTTTGCTCTCCACCATTG | 34921 |
| 1296 CACACAGGAAGGACTGAGTCTATG | 12954 GACTGAGAGACCTGGGACATGA | 23938 GATCACCTGTAGATAACACACATAG | 34922 |
| 1297 TAGGGCATGCTGTAGTCTGA | 12955 TGTGCCTCAGATCTGAGAGT | 23939 TGCTGCAGCACAGTGAA | 34923 |

| | | | |
|---|---|---|---|
| 3118 CCCAAGCAATCTCCCATCTCA | 14776 CCAGTGCTACAGTCCCAGCTA | 25760 TCCTCCTAGGCCTAAGCAAT | 36744 |
| 3119 GAGGGAGAAGGCAACATGAACTCTA | 14777 TGGGGAACTAGCAGGAACTGA | 25761 CGACCAGTGAGGGAGAAGGGAACA | 36745 |
| 3120 GGTGCCTCCTACTGTGTGGT | 14778 CACTGTGAGGGAGGGTACA | 25762 GCTCTTGGCCTTCCGCTTCAAT | 36746 |
| 3121 CAGCTTACCTGCTCTGTACT | 14779 TCTTTGAGTGTGTGCTGGAAA | 25763 TGTACGCTCTCCTTCACAGT | 36747 |
| 3122 CAGTCAGTGAAGAAGTGGCCATGT | 14780 GGAGGACTCTAGCAGTCTGGGGTA | 25764 AGGCGTCACAGTCAGTGGAT | 36748 |
| 3123 TGGTCCACACCTCCATCA | 14781 TGAAGCCCTGGCCAAGAA | 25765 CTGTCAGCCAAGTTTTCTAGA | 36749 |
| 3124 GGGCAAGTGCTGTGTCTTCTGT | 14782 AACCCATCTCAGCTTCCTGGTTAAT | 25766 GGCAGCAGCTGGCGAAGT | 36750 |
| 3125 GCTACCGACAAGGCCAACAAC | 14783 GGGCACATCCCAAACAGTCAT | 25767 CATCCGGCTACAGTTACTATCGCTAT | 36751 |
| 3126 CGGATTGAGCTCCGCTTCT | 14784 AGTGCCTGCTTGCCGAAT | 25768 CCTAGGAACTCTGCCTGGAT | 36752 |
| 3127 CCTCGGCACTTAGGTGGTT | 14785 CAAAGGGTGTAGTAAAAGCCTAGTTG | 25769 TCGTGCCCTCCGTCTCTTG | 36753 |
| 3128 GCAAGGGTGAACAGACTGGAT | 14786 TGCACAGGAGTGGTCAAA | 25770 CCCATCCTTACCTGCTAAGGTT | 36754 |
| 3129 TTCCATCCGACCGGGACAAG | 14787 AGTGCTTCACATCGAGGAAGATG | 25771 GGCACGTTGGATTCAGGTTCAT | 36755 |
| 3130 AGGGTACTCGTGCTTTTGA | 14788 AGGGCAAGCTGCCAGAATTC | 25772 CCTTCTGGGCTCGGCTTTA | 36756 |
| 3131 TCATCCTGCAGGGTGACAGAGATG | 14789 CCAGGGAACCCAGAATCATCA | 25773 AGCCCTCCTCCCGAGTCTTA | 36757 |
| 3132 TGACCTCGCACCCTTCCT | 14790 TGCAAAGACAAAGGTAAGTGTGTG | 25774 AGGACGAGGAGGCAGGTTTG | 36758 |
| 3133 GCAACTTGTCGATCCTTCTTTGA | 14791 GGGTGTGTGCACTCTACGTTCT | 25775 ACTGGTGTGAGCAACTTCTGAT | 36759 |
| 3134 GCACCACGGGAACTGGTGAAT | 14792 TGGTGCGTGACCTGGCTTT | 25776 GGCATGTCTGGGAGTGTTTG | 36760 |
| 3135 ATAAGCGTAGGCAGGACTCA | 14793 TGCTTGGAGAGTTGCTGTCAT | 25777 TGTGCGAGAGTTCCTGTGGAA | 36761 |
| 3136 TGTCGCTACGCCCTCTGT | 14794 CAGGCTCTCTGCCTCTGTTG | 25778 RAGGCCACCCTGGGGTGTAG | 36762 |
| 3137 TCAGCCACGCGAACCGAGCA | 14795 TGTCGTCGTGTGGGGATCT | 25779 CCTAGGACGGTCCGAGGTAATCATC | 36763 |
| 3138 CATTTCCACCCGGCTTCTGTT | 14796 TTTCCCATCACACTCTCCTTCT | 25780 CACCGTCTCCTCGGCATTT | 36764 |
| 3139 GTTCTGTGACTATCGTGGAGT | 14797 GGCTGTGGGACTTGTTACAGTGA | 25781 TGTCAGCGTTGGAATGTGTGA | 36765 |
| 3140 CAGATTGTAACCCTACCCAGAA | 14798 GCTTGCCACCTCCACATTCAA | 25782 CTGGGCATATGCTTGAACAGATTG | 36746 |
| 3141 AAACTCCAGAGTGACCCTTAAACTT | 14799 CCCCTCCACAGGCCTCTTT | 25783 GGCTGACTTTCTTGAGCCCTAAG | 36767 |
| 3142 CCTATAGGGCAATGTAAAGT | 14800 GCTGGCCAGAGAGTAGAGCAT | 25784 CACCAGAGAAGAGCCTATGCAAATC | 36768 |
| 3143 GCTCAAGAATCGCCAGGTGTGA | 14801 GGGAGCTGCAGAGACCAGTTTG | 25785 GGGAGAGGGAAAGCCATCTTCA | 36769 |
| 3144 CAGGCAGTCAGCTTCCTTCATCAT | 14802 GGCATCGAAAGCTGCCTAGTAG | 25786 CATCAGAGTGAAGAACTT | 36770 |
| 3145 GCACCAATCCACGCTGAACA | 14803 ACTGGCACAGCTGGTAGCT | 25787 GCCTGTGCTAGGCTGTAAATAACT | 36771 |
| 3146 AACGCTCTTCCTCTGCTCTA | 14804 CCTCTAACCGTTTCCTTAAGTGT | 25788 CTGCCGGAACGCTTCCT | 36772 |
| 3147 CCAAGGTGCTGAAACTGACCTGAGCCT | 14805 TAGGAGCATGGACTCAGGAA | 25789 CTGCTGTGCACAGTTCTCACCAA | 36773 |
| 3148 CATACTGCTCACGCTCTTGA | 14806 GGCTGAAAGGGTCCCACAAA | 25790 CGGCTTGTCCTTCAGTCTCTCACACT | 36774 |
| 3149 ACTCAGGTCTTCAGCAGCATTC | 14807 TGCCACCATCTTGCCCTTGT | 25791 CGCTCAGAACCCAGGCTTCA | 36775 |
| 3150 AGAACAGAACCATCGAGAGGTAA | 14808 GTTGGCGAACTGCTACCCAT | 25792 TGAGCCCAGGAGAGAACCAT | 36776 |
| 3151 GCCAAGACTACGCTCTCTT | 14809 CTCCTACAACAGGGACAAGA | 25793 CAAACCAGCACCAAGACTCA | 36777 |
| 3152 TCCTATGACGTCCCCTTCA | 14810 AGTAAAACAGGCAGGAACAGA | 25794 CTGCTTGCCGACCTGGTGGT | 36778 |
| 3153 CTTCTGGCCTGCTTTTGGTTAAGG | 14811 GTTCAGTCCTTCGTTATGTGTGTACA | 25795 GTTCTACCTTGCCACCGGGT | 36779 |
| 3154 CCTGCGAGTCTGCTGTCCTT | 14812 AGGGTTAGGGAGAGGGTGGCTCA | 25796 ACTAGGCAGCCTCCCGAGTCT | 36780 |
| 3155 GCACTTACTAAGGGGCATGTGCTC | 14813 CGTGTGACCAGGCTGCAA | 25797 GGAGGAGCTGCACCTTACTAAG | 36781 |
| 3156 GCTTCTTCTTCAGAGTTGA | 14814 GGGATGATGTTGGTCACCAT | 25798 GGTTGACATTGTTCTTTTT | 36782 |
| 3157 CCTTGGCAGCTTAGAGTATGTCAGT | 14815 GCACTCATTGCCAGTGAACAT | 25799 GCTGGGTGGCTCTTCTGGAA | 36783 |
| 3158 TGAACCACACGTAAAGGCAATTAG | 14816 CCGTGGCACCCTGAAGAGA | 25800 TCAGGGCATCACGGAACAT | 36784 |
| 3159 ATGGCACTGTTCCACTCT | 14817 TGGGACTGCAGGCATCA | 25801 TCTGTTTGAACGCACTGTCATTG | 36785 |
| 3160 ATGGCCCCTGGACTCATGT | 14818 AGGGACTGAGCTCAGACA | 25802 GGCTTGGCTTTAAGGTGTTG | 36786 |
| 3161 AGATTGGATGTGAATACCGCTTT | 14819 CATCCAAGTGCTGCTGTGTTTAG | 25803 GCCTAGGTTAGCTTGAACATGA | 36787 |
| 3162 CAGAGCTTGTTCTCTGGGCAAA | 14820 CGCCATTCCTGCTCAGCTT | 25804 AACGCCTGCCAGAACA | 36788 |
| 3163 GCCTAGGGAAACTTCGCTTCTA | 14821 TCCGGCCTGACCTATCA | 25805 TGCACCTGCCAGAGGAAAC | 36789 |
| 3164 CCATCCCCTGGTGAAGAAAAATC | 14822 GGAGTCTGGCCCCAGCTTT | 25806 TCTGGGCCCCTCCTCTTT | 36790 |
| 3165 GGTTCCGTATCAGCAGATGTAGT | 14823 GACCTTGCCTTCACATTCTGT | 25807 GAACAGTGTTGTTCCCATCA | 36791 |
| 3166 GGCTTTAGCTCCCAGGAAGT | 14824 GTTGAGCAACATCCAGCCATA | 25808 CCATGTTCCTCTTGACCCTGAA | 36792 |
| 3167 GCACTAACCGACAGCACACT | 14825 TCCACCTGGCCAGAGACAA | 25809 GCACCTTTCCCAGCACTAA | 36793 |
| 3168 CAGACTCCAAGACTGGTGTGTA | 14826 TGGGCCCTGTGTCTTAGTGA | 25810 TGTGTGGCAGACTCCAAG | 36794 |
| 3169 GGAGCCCGTGGTGAAGTT | 14827 GGTCCCTTGCCTCTTAGGAT | 25811 GGAACGGAGTGGTGTTGA | 36795 |
| 3170 TGTCCCGCGACACATCTT | 14828 TAGATGCGCCACTCCACTCT | 25812 GAGGTTCTCACCCTCACTCTG | 36796 |
| 3171 CCTTCCAGGAGCTTCAGAACAAC | 14829 GGTTGGGCAGGAGCTCTGA | 25813 TGCATGGTGTCACCCGAATC | 36797 |
| 3172 GGGGTCTGACACTGTGTAAAT | 14830 AGGAACCCGTACTTCAT | 25814 TTCAGCCTGGCCTCCGATACT | 36798 |
| 3173 TGCCTGATCGCCTCAAGAA | 14831 AGCTCAGTGAGGGGCTGAA | 25815 AGACTCGCCTTCGTGAC | 36799 |
| 3174 GTTCAGTAATGTCAGGCAAACAGA | 14832 GCCAGAGAACTTCAGAGCTT | 25816 ACTTTGGCCTTGTTAGAGTTCAGT | 36800 |
| 3175 TGAGCACGTAGCGGTGCATT | 14833 CGTCCTGCCGGGGAAAACTA | 25817 ACTGCGCCTGAGCACGTA | 36801 |
| 3176 GCAAAGTACGTCAGTGTTGGTCA | 14834 TGTGGTTGAGGTGGCAGTCAA | 25818 GGGTGGGAATGACAAAGCATGT | 36802 |
| 3177 GACTAAAAATGCCGTGGGTCTCA | 14835 TGGACACACAACACCCAACA | 25819 CCCCTGGGCTACGAGTATATGAA | 36803 |
| 3178 CAGATCAGCTGAGGGAGCAAT | 14836 GGGTAGCATTGTTCCATACTCT | 25820 TGTGGAGAGCATAAAGCCAGATCA | 36804 |
| 3179 AGTCCAGCACCTGCACTCA | 14837 GGTGAAGTCATCAGTGGAGTCA | 25821 GGCTACGATAGGAGAGCCTATCT | 36805 |
| 3180 GTGCTGTTGCAAAGAGTCGAGAA | 14838 GGAAAAGCTATGACCTTCCAGAT | 25822 TCCGCAAGCAAGTGCTGTT | 36806 |
| 3181 GGTGAAAGAGCAGCCTCTGA | 14839 AGTAGGCTTTCACAAGGTAAGT | 25823 AGGCCAGGGAGTCGTGAAAGA | 36807 |
| 3182 GCTACTGGGAAGAATGCTTGA | 14840 CACGGCTACTTGTTGACTTTG | 25824 GCACCTGTGCCCAGCTACT | 36808 |

| | | | |
|---|---|---|---|
| 4418 GCCAGTGCCCACTGAGGBA | 16076 GGGCCTTGCTCCCAGAAAAT | 27060 GCCTCCACAATCTCCTAGGTA | 38044 |
| 4419 GTCTACACACACGCCTCAATAGT | 16077 TTTCTATTTCTCTCTGCCTATTCT | 27061 GCACTAAGAAGTTCCTTTGCTGCTAC | 38045 |
| 4420 GCCAGAAGCGCCCTCTATTTCTGA | 16078 AACTCTTCCTGCAGCCCTTT | 27062 CCCAGCCATTCCTCCAACAT | 38046 |
| 4421 TCCCTTAAAATCCGCTATTTGT | 16079 TCCTAGCACAATGCCTTTCT | 27063 GCATATCTCTTGACTTTCCTCAAA | 38047 |
| 4422 CACAGCCCTGCTTAGCAAGA | 16080 GCCTTCAGTATGCTTTGCGTCTTG | 27064 TGCCAGTAGGGAGTTACTGAGA | 38048 |
| 4423 TTTGAGTCCAGGAGTTCGATTCT | 16081 GGAGGCAGTGGTACAATCATA | 27065 CCAAGGCAGCAGGATCATTTG | 38049 |
| 4424 TCCCTACACTCCTATCAAGA | 16082 AAGGGTGGCACCGAAGTTAGA | 27066 CTTTCCGGTCTCCTACACACT | 38050 |
| 4425 ACCCAGAGCTGGCCTCCAATTC | 16083 GGCCAAGGTGGAAGGATTGCTTA | 27067 CATAGATGGGGCATCACTGTGT | 38051 |
| 4426 GTGGCCCTGCAGGAAGCATAA | 16084 AGTGCAAGCTGAGCCACTTG | 27068 CCAGTAGAGCTCACCATGTCTGT | 38052 |
| 4427 GTGCATGACGTTTCACATGTCTCTCTT | 16085 CTATCAAGTCTGCTCTTCCAAA | 27069 GCAGAGAGTTCATCAGTTCACA | 38053 |
| 4428 TGTGGGCTGTAGGACACAA | 16086 CCCACGCTGATTAATGCTCCTGA | 27070 GTGCGTGAGAATAGATGCTGACAT | 38054 |
| 4429 GGGGTCAACTCCTATCACCTTC | 16087 GAGAGGCTTTGAGGCATTCAGA | 27071 GGTGCTGGGCTCAACTCCTA | 38055 |
| 4430 GTGGCATGGCTTTTGTACTTC | 16088 GGCAGTTGGTGAGGAAGTGTAT | 27072 TAGTCTCATTGTGTGCAGTTT | 38056 |
| 4431 GCGAGAGAGGCTACAGTAACGAA | 16089 GCAAGGCTGGACCAGGAATGT | 27073 AGGCCCTGTTACTGGCAGAGA | 38057 |
| 4432 GAGACCCTTTCCTTCTGCTTGA | 16090 AGACAAAGTCCTCCCCACTCT | 27074 CCTGCCACAGCTGGTAGCTTAA | 38058 |
| 4433 GAGCAGCACAAGGTGGGAAAAC | 16091 ACACAAGGCAGCGTTTGCTT | 27075 TGCCTTCTACAGAGAGGAGAA | 38059 |
| 4434 CTGTTTGTAAGGTCTGTGGGTATGA | 16092 ATTAAGCCCATGCGTGGTATC | 27076 CCTGGGACTAAGGGAGTTTCTGT | 38060 |
| 4435 CACCATCAGAGCTGGGGTCTTT | 16093 CAAAGTCGGCTCGCTCTCACT | 27077 GCACCTAGGCCACCCATCAGA | 38061 |
| 4436 GGATGTGAAAGCTGGACCATTGT | 16094 CCTCATCTACAGAGATTGCAAGGTT | 27078 GGTCACATCAGAGGATGTGA | 38062 |
| 4437 GACATCTGTGTCTTGTTAAGGGAATGA | 16095 CTACCTGCCTGCACTGTAGATG | 27079 GGTTCCTTGGTGGGCAAGATGT | 38063 |
| 4438 TCCAAGTTCAGGTCCAGTTCTATC | 16096 AGCCTGCTGATGCAAGCTTG | 27080 GGGATCAAGTCCACATCTTTGATTC | 38064 |
| 4439 TGCCTTGCCCTTCCTTTT | 16097 GCGAGACTGATTACAGACTCACCTA | 27081 ACCAAGATGCACTCCAGCAAAA | 38065 |
| 4440 CAAAGGGAAGACACGAACTCCTT | 16098 GCGCTGAGTGTTCCATTCTGT | 27082 CACAGAGTCTAAGGGAAGACAA | 38066 |
| 4441 CCATGGGGGCGTATACAGTGCTG | 16099 TGGGCAGGCTGTGAAGGTA | 27083 TGCAGTCCAGTCTGCAAGGTAT | 38067 |
| 4442 CGCTTCACTGGCAGAACTTG | 16100 CCAGCTCCTCCTTGGGGTAAA | 27084 TCAGTTTGCTTACGCTTCACT | 38068 |
| 4443 GTATTTGTTCATGTGCTGTGT | 16101 GGCATGCCTTTTCACTTAGT | 27085 GCTTCTATGTGCTAGTGTGTGCAT | 38069 |
| 4444 AGGGATAGAATTGTGACCAGATACA | 16102 AGCCTCCTACTCCCCTCCTTCT | 27086 GCACAGTCAGTTGTCAGGGATAG | 38070 |
| 4445 CTCAGCCGACAGTAGTTCCTTA | 16103 GCTTCCCGGAGGCTTGAGTGA | 27087 GCAACAACAGCTGCCAGCACACA | 38071 |
| 4446 CGTAACTGCCCTCCTCAGA | 16104 GGGTCACAGTGTTCGTGTTT | 27088 AGAGGAGGCTCCAGCGTGAA | 38072 |
| 4447 GCAGCTGAAGAGTTCAGGGTTCAA | 16105 AGCCTCACCTCTCCCAGGT | 27089 TCTCTGGCAGTGAGGAGTT | 38073 |
| 4448 CAGGCTTGGAAACTTAGGGACTT | 16106 TCCATGCTTCTGTGCCCATCT | 27090 CAGTCACATGCTTGCAAACT | 38074 |
| 4449 CCCACATGGAGACCGCTAA | 16107 GGTGAAGGCAAAGTCCTTCTT | 27091 CGTTCCTTGGTGGCAGAGATGT | 38075 |
| 4450 GCTGTGCTTTATGCTCCCCTAAAC | 16108 ACAGCCCTGCTCCTGCTT | 27092 CACCCTCGACTTAGCTGTGGTT | 38076 |
| 4451 AGCCGCTTGCTTCCTGATTTT | 16109 CACACACAGTCTAGGCCATAT | 27093 TTGCTCATTACCCCTCTGGTT | 38077 |
| 4452 CAGGGAAGGCCTAGAGTTAAGTTC | 16110 ACTGGGTCGCGTAACTCCAT | 27094 TGCAGACAGGGGAGGCCTAGA | 38078 |
| 4453 GGGGCTCCCCTCTCAATGTG | 16111 GCTGGGGAGCAGTGCGTA | 27095 GCCTCCACGAAGCCCAGTA | 38079 |
| 4454 CGGGCCCACCTGCAGAAAGAAGAG | 16112 AGGCAGCCAGGCTTACA | 27096 TGGTCCCACACTTCCTGAAC | 38080 |
| 4455 ATGGGTGGCTCTCGCTCAA | 16113 AGGCTTTGGCAAGGCGATCA | 27097 GAGTGTGGCAGTCGTACTAAG | 38081 |
| 4456 GCCAAGTTTTCAGAGAGTAGCAGAT | 16114 AGTCCTGGCTGTGTGCAT | 27098 TCTGATGCCAAGTTTTTCAGAGA | 38082 |
| 4457 CCCTCTCCTCTACTTTCTTC | 16115 TGCCTGTTATGCACAACACTA | 27099 CTCAGGAAGATCTTTCACT | 38083 |
| 4458 TGACACTGACCGGTGCGAT | 16116 GGGGCAGCCTGGAGCTGAT | 27100 CAAGCAGCTCTTGCTGGAA | 38084 |
| 4459 CCTATCCCATTCCTCACAGCCATT | 16117 AGGGAATGGGAATATTGAATGCT | 27101 TCTGCATGACGAAGCCCTATC | 38085 |
| 4460 TTGCCTGGAAGCTAATTTTGTTTG | 16118 GGGTTGGGCTCAGTGTTGA | 27102 CAAGCAGCTCTTGCTGGAA | 38086 |
| 4461 GAGGCCACTTACGGTATTCAAAC | 16119 GCAGAGCAGGGTGAACAGT | 27103 CATGTTACCCAGAGGCCACCTA | 38087 |
| 4462 GACTCCAGAACAGGAAGGGTCTTG | 16120 TGCCCAGGCTTCTTCCTGCTTT | 27104 GGAGGGGACAATTGCTGCTGTGA | 38088 |
| 4463 AGAAGTCCTCCTCTCCTCTGT | 16121 AGGAGGATGGAGCAAGGAT | 27105 CCTTCCCTAAAGTCCAAGGAGACAAA | 38089 |
| 4464 GTGGCTAGAGCTTTGAGCCTATG | 16122 GTTGCTGACAGATCCAGTGCT | 27106 TGTGCCCAGTGCTAGAGCTT | 38090 |
| 4465 CCAGTGGCCCGACACTCAAA | 16123 CCCTACGCCATGCAGCAA | 27107 CGATGTGCAGGGGAATCT | 38091 |
| 4466 GTCCTCGTCCTGTTAAGCTTTGT | 16124 CATAAGCTGCTGGGAAACTGT | 27108 CCCACACACTGCTGCAGAA | 38092 |
| 4467 GGGCTTCCCAAACACACAATC | 16125 ACGCAGCACCCAGAGGTAAT | 27109 AGGTGACTAGGGCTTCCCAAA | 38093 |
| 4468 AGAACAGATTACAGGAGCACACGTTA | 16126 TGTGGGCCAGCTCTTTGAA | 27110 CAGCTTTGGACTTCAGTCAACAGA | 38094 |
| 4469 GGTGAGGAATGCCCTGTCAAC | 16127 GCCTTTTGTGCAGTGGTCAGAT | 27111 TGGCTGAGGAGGTGGTGAATG | 38095 |
| 4470 TGTGGCTCCTGTGACATGAGTGA | 16128 TTAGGCCCACTGCAGTCA | 27112 CCAAGGCCTCTCCTGCTTTA | 38096 |
| 4471 GCCTTCGGTCACTAATTTCTTG | 16129 GGGAAACCCAAGGGTCTT | 27113 ACATGTCGCCCTCCTGCACT | 38097 |
| 4472 TGCCCTTCCTGGAACCACATTC | 16130 AGTGCACTTCCACCTGTGA | 27114 TCCAGTTGTCCCTCCTGAA | 38098 |
| 4473 CATGCCTGGAATAGTCAAGTGCTA | 16131 AGACTCAGAACCAGTTGTTC | 27115 AGGGATATCATGCTGCAATGAGT | 38099 |
| 4474 TGACTCCTGGGAATCTAGACTTAAA | 16132 AGACAGCAGAAGTGACTGT | 27116 AGCCTGCACAGGATGACT | 38100 |
| 4475 TCTGATTATGAGAACTCAAGGCTGTT | 16133 CACAGTACCACAGCGTTA | 27117 GGGAGGCTGGGCAGTATTTGATTA | 38101 |
| 4476 CTCCCCTGCTCCATCCTTCCTAT | 16134 GGGCAAAGCTCTTTGAGACCAGAA | 27118 GTTGCATCTTCACTCCCTGTCT | 38102 |
| 4477 TTGAGTGACCATCACTGACAAG | 16135 AGTGAACACTGTGGGTTCTT | 27119 TGGTGGATTCAGCTGCTATG | 38103 |
| 4478 GAAGTCTCCCATTAGCCACTGAAT | 16136 CCAGAGCCTTGGGTAGTTTTTG | 27120 CCATAGAACACTTCTGCTGAA | 38104 |
| 4479 GCTCTCTGCCTTGGGAGACTGT | 16137 AGTGTTCCGCTTGACTGGTA | 27121 GATATTCTTGGCTGTGTCTTG | 38105 |
| 4480 GCCAGTAAGCATCTATCTACA | 16138 GAGAGAACGCACAACTTTTCCAACA | 27122 CACTCCATCTAGCCTAGCAGCAT | 38106 |
| 4481 GGCCATCTGGAAACCTGCATGAATGA | 16139 GCAACCTCTACAGAGAACGT | 27123 TGCCTGTGTCCACATGCAAA | 38107 |
| 4482 GCGAGGACTAGCTTGCCTCTTT | 16140 CCTTCAGCCAAGTGCTTACTCT | 27124 TCAGAGGAAAGGCGAGGACTA | 38108 |

| | | | |
|---|---|---|---|
| 5458 TCAACTTGAGAGHTCTGAGAT | 17116 AGTCTGAGCATCTCTTGTCTGA | 28100 GGGAGAGTAGTTTAACCTGAGA | 39084 |
| 5459 GGGCTGATCTCTGATTCCTTGA | 17117 TGCAAGTTCCAGTGCTGCTT | 28101 CCAACTTACTTTTAGGGCTGAACT | 39085 |
| 5460 GAGAGAAGGCAGCTCTGCACTA | 17118 TCCTGCCCAGTCCCTACATTTT | 28102 GGAGTGCGAGTTCAGGAATGTT | 39086 |
| 5461 TGGCCAGGGCTGTCACT | 17119 GTGGGAGAGGCAGGTACTTCAGA | 28103 ATGCGCTGCTTGGACCATCTGT | 39087 |
| 5462 AGGCCTTTGTGCACTCTTTG | 17120 GCTTCCAAGCCACTGGTAAAGT | 28104 ATGCTAAGGCAGGCTCTCTGT | 39088 |
| 5463 GTCTGCCTTGACACCTAAAGA | 17121 GGCTTGGAAAAGGCTGAGAA | 28105 GGAAGGGAAGTCTGCCTTGA | 39089 |
| 5464 GAAGGAGAAGTGGGGACTGGTT | 17122 ACTAGGCACAGAGAGACATT | 28106 GCACAGGCTGAGGAGGAGAA | 39090 |
| 5465 CACAGCCAGCACTAGAGACAATC | 17123 GCACTGGAAAAGGAGTGTGA | 28107 GGTCCCTGCAGCTTTCATCA | 39091 |
| 5466 TCCAGTCTTTGAGTCTTCTCAT | 17124 ACAGAGTTCCCATGGTCATCAA | 28108 GGAGCTCTTCTAGGCTTTGACT | 39092 |
| 5467 CAGGCACACTGAGATGCCCAAA | 17125 CCAGTGCCCTGCACAGTATT | 28109 TGTGCAGGCAACGCGTTTC | 39093 |
| 5468 CCACTTTCACATCCAATGAAAACTGT | 17126 CAGCACTGTGTACTGAAAGTA | 28110 AAGAACCTACCACTTTCACATCCAA | 39094 |
| 5469 GCTTCCAGTACACACTAAGA | 17127 GGTTCAGAACCTTCAACACCTA | 28111 TTGTTTTACCCTGCCCTTGCTT | 39095 |
| 5470 CATGTGGCCTTAAATGTCTGATAAG | 17128 CTTGGCAGGAGGCAGAAA | 28112 CCCAGGCACTGAATTCTCAT | 39096 |
| 5471 GGAAAGCTGTGCAATGGATAC | 17129 AGGGTGAGTTGAGGACTGAA | 28113 GGAGGGATGGCATATGTCAGTGAAG | 39097 |
| 5472 GCTTCCACAAGGACAGAGAA | 17130 CACGCTGCTAGGCACAAACT | 28114 GGCTGGCAAGTTTGGGTGA | 39098 |
| 5473 CGAGCAGGCTGAGGGAGTCT | 17131 AGGGGAAGGTGAAGCTAAGTAAG | 28115 GCTCCAGAGTTTCACTACACA | 39099 |
| 5474 GTGCGAGGGACTAAAACCAAGT | 17132 GCACTTAAGAGCTGAGCCTTGTGA | 28116 AGCGACAGTGCGAGGACATA | 39100 |
| 5475 CATTCACGTTGCTAGTCTCTCTTC | 17133 GGAGCAGCTACGTTCATCTCT | 28117 GTTTCCTATCGTTGATACTGCATTC | 39101 |
| 5476 CATTCCAACTGGACTTAAGACAT | 17134 TCCACATGCTCTTAAAAGACACA | 28118 CCTCCATCTCATAAGACCCTGACT | 39102 |
| 5477 CTCCAAAATCCTCAGATCCTTTGT | 17135 GGATGTCTTTGTGAGCCGAACAAG | 28119 AGGACCCCTTTCCTAGACTTC | 39103 |
| 5478 GCAGACCATGGGGCTCTACTTAC | 17136 ACCCCTCGGAGAGCGTCTCA | 28120 AGGACACCAGGAGCAGACAT | 39104 |
| 5479 CTCCCACCACAAAGCAAAGACT | 17137 CCCAACACTGTGCCCATCAT | 28121 TGTCGAACCTCCACCACAT | 39105 |
| 5480 CATTTCAGCGTGACTTTGGAA | 17138 GAGGACAAGGAATTGCACTGTA | 28122 CAGAACCTGACGTTAAAACAGA | 39106 |
| 5481 ACCTCCCTACTACTGAGCTTGTAG | 17139 TGAGCACATCCACTGAGTGACT | 28123 AGTTTGAGAACTCCCTATCTTAGT | 39107 |
| 5482 GCAAAGGCTTCATGGGCAAGTCT | 17140 GCTTGGCAGTAGGACAGACCAAA | 28124 CCCAGCCTCTAGCAAAGATCTTC | 39108 |
| 5483 GACCAGAGCTGCTAATTCTACA | 17141 AACTGGCCTTACTCTGGAAAA | 28125 GGTTACAACAGCTTGTAGGCCTTGA | 39109 |
| 5484 GCCTTGGCAATTGGATCCATCAATGTT | 17142 GTTTCCTTTCTTCCTCTGACCAT | 28126 AAAAAGAATGGCCTGAATGGGA | 39110 |
| 5485 GGGGAAGAGAGTTGAAGAAGTGTTT | 17143 GCTTCAGCTTCAACCCTCTACT | 28127 AGAGCCTGGGAGAGAGAGTA | 39111 |
| 5486 GGCTACTCCTGCCAGTCTGTTGT | 17144 AGGAAGGGGATGAAGCAGGAA | 28128 CCTCTTGTGCAGGAATAGAAGGCTACT | 39112 |
| 5487 CCACCTGTTGGATTTACTTTCTTCA | 17145 TGAGGACTTCCCTTACCACTGT | 28129 GCCTTCCACCCTGCTTGGAATT | 39113 |
| 5488 GGATTATGTGGCTTGGAATT | 17146 TCAGGTCCACCATTGTGAAAC | 28130 TCTGCAAACTTGCAACAGGAATC | 39114 |
| 5489 AGTAGGGCCTACAGAGTGA | 17147 GGGATGTTGAGGTGCTAGGT | 28131 CCTGGATCTGAGTAATGTGCAGGAGTGA | 39115 |
| 5490 GAGGAGAGACAGCAGTGCTTTGTAA | 17148 GGGACCAGCCTCACCTCTACATT | 28132 GGCAAGAGACCTAGAGCAGAGACA | 39116 |
| 5491 GCTGCTGCGAGTGAGGAGTTG | 17149 ACCCGGCCATCTTTGGTACA | 28133 GGGATTCACTGGCTGCTGTGAT | 39117 |
| 5492 CTCCCTGGTACTCTGGAATTGA | 17150 GTTAGAGAGCCCTTTGTATCCAA | 28134 GGCCTTACTCCTCTGGTACT | 39118 |
| 5493 GTGGCAGAAGAACTGATTTCTCA | 17151 CCATGGTGCCAGAAGGTCTGA | 28135 GCCAAATTTAGCCAGGAGTAGAAG | 39119 |
| 5494 CCGCTGTGTTGCTTGCTTCT | 17152 GGCTGGCACGTTCAAGCTTAC | 28136 TCACTTCCACCGCTGTGTTG | 39120 |
| 5495 ACTTTCAAACGCTGTCCTT | 17153 AGTTAGATGGCAAAATCTGTGGAA | 28137 CCATCAGTGTAGTCCCTTAACTCTCAAAC | 39121 |
| 5496 AGTTAAGTGGGAGCAATTGGAT | 17154 GATGGAGTCTGAGGCATTAAACA | 28138 GGCCAGAAGATTGCAAAGTCA | 39122 |
| 5497 GGACAAGAGCCCATTTTAAGCAT | 17155 GGCCATGGCAGCATTTCT | 28139 CACAGCTCCGCTGTGAAAGTTGA | 39123 |
| 5498 ACTCCACCAACCCAGACCAA | 17156 CAGAGCAGAACCCACTGCTTTG | 28140 ACAGCACCACACTCTGACCAA | 39124 |
| 5499 CTCCAATGCCATAGCTCAGAAC | 17157 GAAATCCTTGCTGTCCGAATCA | 28141 ATCTGCACTTCCATTGCTCAATG | 39125 |
| 5500 GCTATGTGCCTTTTGGGTTAC | 17158 ACAATCTAGGGAAGGCAATTGTCA | 28142 CTGGATTTTAGCCTATGTGCCTCTT | 39126 |
| 5501 AGACAGGTCTGACTCTGTGAGA | 17159 CCACTGTCTCCCTTCCTTCAATG | 28143 GAGACTTAAGCCAGCAATTACACA | 39127 |
| 5502 GCTCTGCTGACTCTCATCTCTTC | 17160 GAACTTGGCTGGAACCAGGAT | 28144 CCTCTGTGCCCTGCAATG | 39128 |
| 5503 ACTCGAAATCATGGCTGAGTTTGT | 17161 ATGGAGCCCCACTACCGAAGTA | 28145 GCTCCAGGCATCTTACCTTAACTCGAA | 39129 |
| 5504 CACCAGCAACTACAAGGGCAAA | 17162 CAACTAAAGTGGCAACGAACT | 28146 GACCCTCACACCAGCAACTAC | 39130 |
| 5505 GCCCTGACTCAACTTCCTTCTGT | 17163 GGGCATGTTGCCTGAAAAGTTCA | 28147 GGTTGCATGCCTGGAGCCAAC | 39131 |
| 5506 GACATGGGCTGTGATCTCATCTA | 17164 GTATGAAGCCAACAGTCAGT | 28148 CTAGAATGCCATGGGCTGTGA | 39132 |
| 5507 CAGTTCAGGTAGGATGTCATCT | 17165 GTCACCGCACCTGGACTATT | 28149 CAGCAATTCAAGCACATACAGT | 39133 |
| 5508 CTCTCCTCCTCATGAGCTTGT | 17166 CTTTATTGGGCACCATCTCACATC | 28150 GGCCCTGGGACATACTTAATC | 39134 |
| 5509 TCCTATGAGCACCTCTCAGAA | 17167 CGTTCTCTCTCTCTCAACTTTAG | 28151 TGGCTGCCGCCTTGCTATCA | 39135 |
| 5510 GGTTGAATAAAGCGCACACTT | 17168 TGTCGCGATCCCAAGAA | 28152 GCTGGAAGACTGGGTTGGAAT | 39136 |
| 5511 CCCTGTCACTTGGTGTGTATAGA | 17169 GCTCAATGCTCTACCTTTTCAGA | 28153 CGTAGGCTGCATAACCTCAAGA | 39137 |
| 5512 GGAGATTGGAACAGTTCATGCAAACA | 17170 TGGCTCCAGGTCACCATCA | 28154 CCTCCCATCCAGGAGATTTAACA | 39138 |
| 5513 GGGGCGTTAACATTTACTGAGCAT | 17171 TCCAGCAAGGCCTTCATCA | 28155 GCCAAAGGCCTTTCATCCAT | 39139 |
| 5514 GAAGTCCAGTGGATATTCCCTCATT | 17172 ACCTCCACACTGCCTGTCAGA | 28156 GAGGCAAAGCAAGTCCAGTGATA | 39140 |
| 5515 ACTGCGCAGTCCTTCCTAAT | 17173 GTGTGGCCTAAAGGTGTGAGA | 28157 GTGGGATATAGGGACACA | 39141 |
| 5516 ACCAATTTGACTCAGGGTGTT | 17174 CCAAGAAAATCACCTTGGGAAAGA | 28158 CCCACCGCTGGTGTTGGAAAA | 39142 |
| 5517 GGCCTCACGATTTCTTTGTA | 17175 CCACCAGCATGCAGAAGTGA | 28159 CTCCACAACCGCCAGTGATT | 39143 |
| 5518 GAAGTCCAATGCACATCTTC | 17176 GTGTCACGGCAGAAAGTGA | 28160 ACACCAATCAGGAAGCTCAA | 39144 |
| 5519 AGCGCCCTTCTGTTCTA | 17177 GTGCTGCCAGTGGTTGGAC | 28161 TGGAACAGTCCCTGAA | 39145 |
| 5520 CCACTCCCTGGGGTTGTTATG | 17178 GCACCTACAGTACCACAT | 28162 GCACGGCTGCTGGGTTATG | 39146 |
| 5521 AGGCTGATGGCTGAATATCCT | 17179 GCACTAACTAGCTGACCTGTGA | 28163 GCCATCAGCAGGCTGGATTGA | 39147 |
| 5522 GTGTTGCCTTTGCCCCCTGATC | 17180 GGGAGGGTTGGAAGGAAAAGACA | 28164 CCTTTTCTCCCAATTGCTACTGTGT | 39148 |

| | | | |
|---|---|---|---|
| 7148 CCTGTAGTGATTCCAAGACCTGCCCAT | 18806 TCCTCCAAGTAGGATAGAACT | 29790 GCAGCATACACTCTGTAGTGA | 40774 |
| 7149 GCATGGTATTCTCTCCAGGTCCAGAA | 18807 CCCGTGAACAGGTTCTTGAGC | 29791 GTAAGCTGAAACTCTGGGCAGGT | 40775 |
| 7150 GCAGTGTTAGCACACAATGTCA | 18808 CCATCTAACCATCCACCTCATTTTTCAAC | 29792 CATCCTCTGAATTAGCCAGGTCCT | 40776 |
| 7151 CTTCCACGTGTAGAATCTGAGGAT | 18809 CCAGAGCCACTCCTCTCCCAAAAAG | 29793 GAAGAGTCAGCTTCTTCACAGT | 40777 |
| 7152 CCAACCCTGATCATTCCAGTAATGTT | 18810 CTTCTCAGTCTGTATCCCTGACTCT | 29794 GCCCAGGTTCCAACCCTGATT | 40778 |
| 7153 CCCTTCTGTTTCTCAACCTGTGT | 18811 GTATTACCCAAAGTGAACCAAATC | 29795 GCTTCTAGTATACCCTTCCTCGTT | 40779 |
| 7154 GGCTTATGAACCAAACCACTTCTCT | 18812 CCAGTATCCACTCTAACAGTCAAGGTAA | 29796 GCTCTGGCTTAGAACCAAAC | 40780 |
| 7155 CACTGTTCTGTTACTGACAGGAAAAAG | 18813 CTGCAACACTGTTGGCAATGACTT | 29797 CCACCACCACTACTGTTCTGT | 40781 |
| 7156 GGGCCAGCTGTGAGAGT | 18814 AACCAAGGAGCCTTAGAGATGA | 29798 GCAAAAGGATTGGGCCAGCTT | 40782 |
| 7157 GCTGATGAGTCAAGTGCTATCTGT | 18815 CAGATCCACAAATCAGGTCTCACCTATC | 29799 GGCTGGGAAGCTGATGAGTCAA | 40783 |
| 7158 CTCTTGTTTACTGAGTCATTCTAGTT | 18816 GGAAAGAAAAGGGTGCTTTGGAT | 29800 GGACCAGCTCAAATGTTCTCTTTT | 40784 |
| 7159 AGGAAGCCATAGGAACCCATCT | 18817 GGACAGATCCTGCCTGTACCATTG | 29801 CTCTGGAAGAAGTGGTGGATAGGAA | 40785 |
| 7160 CACTTTGGCTCCTCTTCCTTT | 18818 CTGTAACTCCATCCTAGTCCTTCT | 29802 AGATTGTCATCCTGTGACACTTTG | 40786 |
| 7161 TGGGGATGACTACTTTGCTATGT | 18819 GGGGAGAAGAAAGGGAGGACAAA | 29803 GGGATGGTGATGGGGATGACTA | 40787 |
| 7162 GGGAAGGATTCCAGTGGTGCAT | 18820 GTGATCCATAAAAACAGGCACAA | 29804 GGGAGAGCAACAAGAGGCAAGGAT | 40788 |
| 7163 CTCTCGGGAAAGTGAGAGCGTTTG | 18821 CAGGGCCTCCTGACCTGTC | 29805 GCTACACAAACTGCATCTCTTGGAA | 40789 |
| 7164 CTTCGGTATAATGTTTCCCTTCTA | 18822 ACTTTATTCCTGCAGTTGTGTATC | 29806 GGTGACCTACCTCGGGCTACTGTGT | 40790 |
| 7165 GGTACCCGAAGAAGGCTATTCCAA | 18823 AACGTGGCCAGCCTTCA | 29807 CTCCTGCAGGTGGTTCAAGGTA | 40791 |
| 7166 GGGCAGAAGAGTGGAAACAGCTA | 18824 GCAGCGTGAAAACGTAATACAAAC | 29808 TTAGACGCAGGAACAATTCCAGGTCAG | 40792 |
| 7167 GGTGGTGCCTAATGCTGCAT | 18825 CTGCATGTGAGGACACGCATTC | 29809 CTCTACTTCCAAGGTGGTGCTTA | 40793 |
| 7168 TGGAGTGGCAGAATCTTCA | 18826 GGAATATCAGTTTGTTTCCTAGCTTTT | 29810 GAAATTCAGTGGGCTGAGAACCTT | 40794 |
| 7169 TCCTGCTAGGAAGGTGATCTCT | 18827 TCCTTCTCCCCTGTCTGTGAAG | 29811 TCAGCCCTTCTGCATCCTGCTA | 40795 |
| 7170 GGTGGGACTGGGCCCTGAACA | 18828 GCAGATGAGACTGAAATAGGTAGGTT | 29812 TTCCACACAGGGCTGTGACT | 40796 |
| 7171 GATTCCAGCCTACTCCAGCTTTC | 18829 GCCTAGAATTCTTCCAGCAGGGTA | 29813 GTGAAGCATGGCAGATGAAGATTC | 40797 |
| 7172 GATGAAGATCGGCACTGGATGTTC | 18830 TCGTAGCTGTGGGAGGTAGA | 29814 CGTCCCTCCTGCAAGAGGAAGA | 40798 |
| 7173 GTCCAGCATAGCCAGCACTT | 18831 CCTTGCCACCTCAAATACTCT | 29815 GGTGAAGGACTCCAGTGCCAGGCATAG | 40799 |
| 7174 CAGCAAGGTCGAATTTGCTATCT | 18832 GAAATGGAGCCATTACTTAGTGTT | 29816 GGTGACACTCCAGTAACAGCAA | 40800 |
| 7175 CCTTGTATCATTCTATACCTCCTCTTTC | 18833 GTTGGCATAGGTCCCAGGAAAC | 29817 GCCCCTCCCAAACATCTGTATTCCAT | 40801 |
| 7176 CTCAGACCCACCTTACAGTTCT | 18834 AGGGGACAGGTGAGTCAGAAT | 29818 TGAGCCCAGACCCACCTG | 40802 |
| 7177 TCTTGAATCAGACAAAGAGTACCAT | 18835 TTGCTGGCTGTGGGCACTTC | 29819 CTGGAACTGCTGGTAATCTTGAATCT | 40803 |
| 7178 CATGGACTCAAGACTCACACAA | 18836 GGGGATCCACATGTGAATGT | 29820 TCTCCAGGTCATGGACTCAAG | 40804 |
| 7179 GGTCAGGCACAGGCATTGTTGT | 18837 TCCACCAGTCAGCCAAGACTA | 29821 GGTAGAAGAAACAATTCCAGGTCAGA | 40805 |
| 7180 TGGGTTTGAGCACAGTTAGATG | 18838 TCCAACTGCTTGTTGACATT | 29822 GGGTTTTAGGGGTGGTTGA | 40806 |
| 7181 TGTGGACCAGAGCCTCATGTA | 18839 GGAGGCATGACTAGGCTACAGT | 29823 GCAGATGGAGGTTACCAACTTGT | 40807 |
| 7182 GGGGTGCCATTCAGCTACCAT | 18840 CGCAGGCAGTCTCCGTTATAG | 29824 TGCTCTTGGGGTGCCATTT | 40808 |
| 7183 TCTTACTCTTAGGTAGAAATCTTAT | 18841 CTAATGCAGGGACACTTCT | 29825 TCCTCTTACTCCATTCTCAGCTCTT | 40809 |
| 7184 TCTGCCCCTTACCTCCTTCTTCT | 18842 CTGGCTGTTCCTCCAAAGAGTAAGT | 29826 TCCCCTTCCTCTCTGCCTTA | 40810 |
| 7185 ACCGAGTTAGAGTCTTGACTTTC | 18843 GGTCATTGTATGGGAAGCGGAATC | 29827 AACATTGTCGACTGAGTTAG | 40811 |
| 7186 GTCCAGGTTAATGCTCTAGAGGAA | 18844 CACAATTGCTCTTGGCAGTTC | 29828 CCCCTTAAAGTCCAGGTTAATGAGT | 40812 |
| 7187 CCCCTGTCTGTCCACACCCATT | 18845 GTACTTGCCAGTGAAGAAGT | 29829 ACCTGGAGTCCCTGATGAT | 40813 |
| 7188 CCATTGAAGTGAACATGCCTGAGT | 18846 TGCAACCTGGGTAGCCCATTC | 29830 GCCTTCCAGTGTTTGCCCATTG | 40814 |
| 7189 GCAAGATTTCTGATGCTACATTG | 18847 GGTAGATCAGCCTTCACTGTGTGCT | 29831 AGTTTGCCAACACTTTGGAT | 40815 |
| 7190 AGGTTTCAGGCCATTCCTCTCT | 18848 GCACCATGCAGGTCCAGAA | 29832 GGAGCTTGAGAGCCAGGAGCTTTC | 40816 |
| 7191 GAGACTTTCCCAAGCTTTTCAGCAAT | 18849 GTGGTGCAAACTGTGCTA | 29833 CTGATCAAAGGCAAGCAGACT | 40817 |
| 7192 GGAAGGGCTGTTTACAGACAAGTACA | 18850 CCTGCCTTTGCCATGTCCAGAG | 29834 GCTAAGGTGGAAGGGCTGTTT | 40818 |
| 7193 GGTGCCATAGATTACTCCAAGGGTCTT | 18851 GTGTTTCTCACAGTTCGGTGTT | 29835 TGGGTAAACGTTCCATGCA | 40819 |
| 7194 GCAAGAGTTCCATGATAGGCATGT | 18852 CCCAGTGCAAGSAAAGGGTAATG | 29836 GCCTAGAATTCCAAGAGTCCATGA | 40820 |
| 7195 GCCTACACTATTCATCCATGGTAAAC | 18853 ATCTTGCACATAGTTGCATGTTG | 29837 GGGATGCAGCTTATCCTACA | 40821 |
| 7196 ACTTTCTGATGTGTTCCTACTCTT | 18854 GAGGAACCAGCCAGCTCTGCC | 29838 CCCCTAGCACACAACACAGTTGTCA | 40822 |
| 7197 GACAGAACCTGTTGAACTCATGGTA | 18855 GCTAGGTTACTTATGCTCCTTCAAC | 29839 GCACCACAGCAACAAGAGGAACTTCA | 40823 |
| 7198 GCTCTAGAACTATGACGGGACACA | 18856 GACCTTTTCACTAACACTGGTGAGACT | 29840 CCATGCAACCCAGGGGCTCA | 40824 |
| 7199 CAGTGCTCAAAAGCTATTCCCAGTT | 18857 GCTTTTCCAGTCTCTGTTCT | 29841 CCTTAGGCACTTGAGTCTCAAA | 40825 |
| 7200 CCTTGCCCGAATCCTCCTACA | 18858 TGTGCAGTTAGAAGGGAGACAAG | 29842 GATTTGCCTCCTTGGCCTGAA | 40826 |
| 7201 GCACTAGCCTGCCTTCAT | 18859 CATCCTGTTTTCTCCTCAGTCA | 29843 GCTCATGGCTGATTCACTCACT | 40827 |
| 7202 ATGTCAGTTACACCTTCCTTGAT | 18860 TGGTGAGGTATAGTGAAGTTCAGT | 29844 CCGTCCAGGCTGTCATGT | 40828 |
| 7203 GGCTGCTTAAGACTTTTGCAGTTC | 18861 GGTATCTGGAATGACTTGTTCCAA | 29845 GGCTCAAAGTGCCTGCTT | 40829 |
| 7204 AGGTGCAAAGGTAGAGGAACAAC | 18862 GCTTCGGTAATGCTTCAGCTGTGA | 29846 TTGGTAAGCAGCAAGGTGCAAGGTA | 40830 |
| 7205 CTAGGACTCTCTCGGTTGAGTT | 18863 GGGCCAGGGACAATTCAGA | 29847 GGACTGTAAGCCAGGATTCTCT | 40831 |
| 7206 CTTGGCTCTCTCAGGTCCTGAGG | 18864 GCCTGCCAGTCACAGCCTTCT | 29848 TCCGTCCCCCTAAAACCTGTCTTC | 40832 |
| 7207 GTGACTCTAGCATTCCCAGTTCTCT | 18865 GGACAATCATCCAGAAAACCCTGTA | 29849 GCTTCCACACACTGTGACTGTAG | 40833 |
| 7208 CCCTGATCAATCATACCTCGAGTCAA | 18866 GCCCAAATAACAGGAGTGCCATAAT | 29850 GCAGAGGAACCTGATCAAATCAT | 40834 |
| 7209 GGGACTTTGGAACACACAGCAT | 18867 TGGCTGCGGGTCTGCTTCT | 29851 ACGAACGCACACGGGACTTT | 40835 |
| 7210 CAAACACTAAAACAACCTTTGCAA | 18868 GGCTACTTGACAAGAGTGTCTATAATG | 29852 TGGTCGTTCTGTAACACTAAAAGCAA | 40836 |
| 7211 GGGGCTGTCAAAAGAATTGCTAGGTGCTACT | 18869 GAGGGTTCAAACTGACAGCAGGATT | 29853 AGAATAAAATCTGCAAGGGCCTGTA | 40837 |
| 7212 GGAATGCAAAGAATTGCTCTGGAAAGA | 18870 GGGCTCCAAAAGCAACACACT | 29854 CGAAACACACAAGGATGGAAAGAA | 40838 |

| | | | |
|---|---|---|---|
| 7538 TGCCTCTAGAATGGCACTGTTTAG | 19195 TGCTGGACACCACAGAACTTT | 30180 GTGCTGGTACCTGTGCCTCTA | 41164 |
| 7539 GTGTCAGGGGTAGTGAGTTTGGTTT | 19197 GTTAACATTCACACGTCAGCACTT | 30181 GCTCATGCTGTCAGGGGTAGTGA | 41165 |
| 7540 TCCTGTGGACATACCTAGTTGA | 19198 TGTCTTCCATTAGCTCCAGACTCA | 30182 GCCCCTTGAATATTCCTGTGGACAT | 41166 |
| 7541 GCCAGCAGATGAGTCATGGAGTAT | 19199 CCATCCTCTTCACGCCCATCAGATA | 30183 GGTCAATGCCAGCAGATGAGT | 41167 |
| 7542 GTGGGATGCCAAGAACTTGACTTTG | 19200 TGCTCCCTTGCTATTGAGACTTG | 30184 GGCTAAGTGTGGGATGCCAAGA | 41168 |
| 7543 GAGCAATGAGAGAGCAATGTGTTAT | 19201 CCCACATTCACTCCTCTAGTCTGT | 30185 GTGCAGTATCACAGAGCAATG | 41169 |
| 7544 GCCACAGGGGAATCTGTCTTTGAAG | 19202 GGAGAAAGGTTGAGTCTGGGGAATG | 30186 GAGGAAAAACAGCCACAGGGAATC | 41170 |
| 7545 CGTGCTGACTTAGGCAGATTTG | 19203 CCACATACCAAGGAGAGTTGACAGAT | 30187 CTTTCAAGACCTACGTGCTGACT | 41171 |
| 7546 GCCAACAAAGTTCTGGCTTTG | 19204 GACGTCATTTAGCTCGGGTGAA | 30188 CCAGGCAGGTGGCAACAAAA | 41172 |
| 7547 CCAGGAAAAGAGGTGACTGCAT | 19205 GCAAAGATCCTGCTCTGTAGGGAAA | 30189 GTCCAATTCAGATGGCCTCTTC | 41173 |
| 7548 CTCGGCATGTTCTGAGGGCAGAGA | 19206 CCCTCGATAAGGCAATGTATACTCACA | 30190 TGCAGAATCACTCAGCATGTTCTA | 41174 |
| 7549 GTCCTCTGCCCATGAGTGAAC | 19207 GCCTCAGAATATGAAATTGGAACAGAAG | 30191 GGGGCCTCGTTTTGGAGTTG | 41175 |
| 7550 CCCTGGAAATGCATCCACGAT | 19208 CAGAATGGATCGTCCGCTAA | 30192 GCCTGCGAACCCTGGAAATG | 41176 |
| 7551 GGCTTGAGTGAAATGTAGTACTCAA | 19209 GTTCAGGGTTCTTCTTCTCTCCAA | 30193 AGTCTTGGCTTGAGTGAAATGGTA | 41177 |
| 7552 GCCTAGTGTAGGCAAAGGAAGTCT | 19210 GATTTCTTAAAGCGGTTGTGTGGAT | 30194 AGGGGCAGAGAAGCCTAGTGTA | 41178 |
| 7553 TGGGCCCTGTAGAGTGCATTTC | 19211 CCCTATGGAAAGACAGCACCCAAA | 30195 TCTTTCAGGATGGGCCCTGTAG | 41179 |
| 7554 GTGTCCTGGGTGTGTGTTCA | 19212 CCTCCTAGTTCCTACTCAGCCTCCTAAC | 30196 TTGCAAGCTCGGGAGTGT | 41180 |
| 7555 CTCCTACTTGGGTGGAGGAAGTCT | 19213 CATGCCTGAGGTAACACCTACTCT | 30197 GACCATAGATCCCCCTCTCCCTACTTG | 41181 |
| 7556 GTAGCAGTACAGATGAGTGACATAGAT | 19214 GTCTTGTCATTCCTACCGTTCAAATG | 30198 GGACGAAGGTGGTAGCAGTACAGA | 41182 |
| 7557 GGGTTCCTGCAAAATGGAGAGCTTTT | 19215 GCTTCATGCCTGCCATCCTT | 30199 CCTTCACTCGGGTTCCTGCAA | 41183 |
| 7558 CAAACCAAGCACTTGTCCAAAACT | 19216 ACTGGAGCTTCATCCTTTCATACAA | 30200 TGTGAAGTACAACCAAGCACTTC | 41184 |
| 7559 GCCCCTCTTCTCTGCATCTGGTA | 19217 CAGAAAGTAACAGGTCAGCTCAGAACTA | 30201 TCACCCTGCCCCTCTTCTCT | 41185 |
| 7560 CCTTTCAGCCACACCTGTTCTTTG | 19218 CAGGCTCATGCAGCAGACTGT | 30202 GTACTGCTTCAGCTCCTTCA | 41186 |
| 7561 GGAGACTGTATCCAGGCAGTGTGT | 19219 CTCAAATAGGCCCTTGGCAGAAAAG | 30203 CATCTCCTAGAGCTGGAGACTGTAT | 41187 |
| 7562 GCCCCTCTCTTGCTGGCATT | 19220 GGTTTGCCATCTAGATCAATGCAGACTT | 30204 TGACACCAGATGCCCCTCTCTT | 41188 |
| 7563 GCAGCCCTTTTTGCGAGGAT | 19221 CAATCCCTGTTAAATTACCCCATCCAT | 30205 CATGTCTGTACAGCAGCCTTT | 41189 |
| 7564 GAGCTTTGGGAAAGGGAAAGAGA | 19222 CTGAGGATCCCTGTGGTTGAGTT | 30206 CCACATCCAAGAGCAGAGCTT | 41190 |
| 7565 TGGCCTCGGGTTTTAGATGAAC | 19223 GGCTGCTTGCTAATTCCAGAGA | 30207 CAAAATATAGCTTCCGGTCACA | 41191 |
| 7566 GCACCTTACAGTGCCAACTGTTC | 19224 GCCTCTGCTGAGAGCAGCATTC | 30208 TTGGGGAGCAAGCACCTTAC | 41192 |
| 7567 CCACTTCTCTGTGACCATTGTTTGGTA | 19225 GTCTTGGATTGTACTTAGAGGAAGAAC | 30209 CACACCCACTTCTCTGTGACCAT | 41193 |
| 7568 TGGGCAGGTCACACCCTGAAT | 19226 ACCTCGAGTCGGAACCTCTT | 30210 TAGGTCGGGAGCTGAGACA | 41194 |
| 7569 CACTTGTCCACGCTGCGTTT | 19227 ACCTTCGGGCCCTGCATT | 30211 AAACCAGCCCGTCACACTTG | 41195 |
| 7570 CCATCTTCAGCTCTTGCTTTCTT | 19228 GCAACAGGTCTGTGGCAAATG | 30212 CCTCAAACCATCTTCAGCTCTT | 41196 |
| 7571 GGGGTCTCCTTAGTATCATCCCTTT | 19229 GTTTAGGACCCCTTCTGTAACAT | 30213 TTTGGGTCAGGGGTGTCCTT | 41197 |
| 7572 CCTTCCTGGATGTGCCTGAAGT | 19230 ACCTTCTCTGGTTGACTCTT | 30214 CAGGTGACAAACTTCCTGGATGT | 41198 |
| 7573 CCGGGTCATACTAACCATCT | 19231 ACCATGCGTAACATTCGAAGGTGAA | 30215 CAATAAAACTTTTTCCGGGTCACA | 41199 |
| 7574 GGGGTCCCACTGTTACCAACTCTTG | 19232 GGCTTGTTCAGTAAGGTGTCAGAA | 30216 ACTGAATGGGTCCCACTGTAAC | 41200 |
| 7575 GTGTGGAGGCAAACACTCCTGGTT | 19233 CCCCAAATCACCACTTAAATGGAATCAGA | 30217 GCTCAGGGTGTGAGTCAAACA | 41201 |
| 7576 GGATGAAAGAAACCCAGACAGAGACTTT | 19234 CGAGGTTCCATCCTAGTCCCAAGT | 30218 CGTGTCCTTTAGAGGATGAAAGAAAC | 41202 |
| 7577 TGGGGTTGTCTCAGTGGTGCTA | 19235 TGCCCAGTGGATGACGGAAT | 30219 TCCAATGAATGTGAAAGGGGTTGT | 41203 |
| 7578 GGGGTCTGCTGTAGAATTCCTGTTG | 19236 CGAAGCACTGGGAACTGCAGTAAA | 30220 CTGGATTTCAGGGGTCTGCTGTA | 41204 |
| 7579 GTTCTGGAAGACAAATCGGCATTAC | 19237 TGTGTATGAACACACAGACAGGTT | 30221 GCTGTTCACAGTTTCTGGAAGACA | 41205 |
| 7580 CCCTGCATCATATTCTGTGAAACACTTTT | 19238 ACACACATGGTGTAAGCAAGAAACT | 30222 TCCAGCTATTCCCTGCATCA | 41206 |
| 7581 GGGCAGGCAATTTCCCCTAAGA | 19239 GCGAGAAGACAGAGTTCAGTTTTCATC | 30223 TGTCAGTGTGGCAGGCAATT | 41207 |
| 7582 CTCTCTGATAAGGCCCGGGTTT | 19240 CCATGCCTGGAAATGCGCTAA | 30224 GTGGGGGCCTTCTCTCTCTT | 41208 |
| 7583 CCACCAAGGACCCTATGAGCAGTT | 19241 CCCTAGGGTTGTTCCCTTCTCAGT | 30225 TGGTAAGGGCTAGGCCACCAA | 41209 |
| 7584 TCCCATCCACAGTCCGACCAT | 19242 GTCAACGACAACCAGCAGACA | 30226 GCAGCTGTTCCCGTGACTGT | 41210 |
| 7585 GAACCAGCGATTTGGGCTAT | 19243 GCAACACCTTTGGAATCAGCTACT | 30227 TGCCTGAAGCCCCATGAAC | 41211 |
| 7586 GGGCCCGGCTTTTTAACACTTTG | 19244 GGGGTAAGGAATGTCAGTGAGTTTCATTG | 30228 TTGCATAAGGCCCGCTTT | 41212 |
| 7587 GAGGGTAGTTGTGGATACCCGAGAAA | 19245 GGGGAAACTTGAGAACTGAGAA | 30229 GGAACAGAACAAGAGAGTAGTTGTGAT | 41213 |
| 7588 TGTCAAAACCAGTAGCACTTTCA | 19246 AAGCTCCCTAAAAGTCAGCAAAGA | 30230 GCAACGCAGCAATATATGCTCAA | 41214 |
| 7589 CCAACCTAGACTTCCAGCGTTAAG | 19247 CCTGGGCTTCGGAGAGAGA | 30231 CACCAACCCCAACCTAGACTTC | 41215 |
| 7590 GCAAAGGGCCCAGTTTTGCTT | 19248 CAGTCACCAGAGTGGAGTCA | 30232 TAGCCTTGGGGCATGCAAAG | 41216 |
| 7591 GCCTGCACAGAACACATTTTTGCAT | 19249 GCCATGGGGAATAAGCACTCA | 30233 GCCACGTTTGCAGAGAAACA | 41217 |
| 7592 GGGGAGTATCATTTTCCCAGCTCCAA | 19250 CACGCCACTCAAGCTGAAGGAA | 30234 CCACAGTCCCTAAATGGGGAGTATCA | 41218 |
| 7593 GTGTGTCCGTTGTGTGCAACT | 19251 CCTGTGGCCAAGGAGGAAAG | 30235 GGTGGGCTCTGTGCTGTGT | 41219 |
| 7594 AGTCGGTGTAGCCGTTCTGA | 19252 TGCCAGGCTGCTCCTGCAT | 30236 CCAGGTGCAGAGCGGTGTA | 41220 |
| 7595 CGCTGAAGGACCCTCCTCAAAG | 19253 CCTAGGGTTCCTCCCTTAAGCAT | 30237 AAGCCTGGCTGGCGCTGAA | 41221 |
| 7596 AGAGAGGGCCTGAGGGACTTG | 19254 GACACTGTCCTTGCCAACCATTTC | 30238 AGGAGCCGGGCATTCAGAGA | 41222 |
| 7597 TTTTACTAAAGTGTAGGCTCGGTAT | 19255 GACCTTGAAGCCAGGCCTATG | 30239 GAGGATCCCTTTCCTGTAACTAAAGTGT | 41223 |
| 7598 GACCAACGATGTGTTGTGCTCTT | 19256 GACTCCTATGGCAAAGATCTGAGA | 30240 GTGTATAAAGCCAGAGATGT | 41224 |
| 7599 GGTGTCCATGCGGGCTTTAGTA | 19257 CCACAACAGAAGCATGGTGCATAC | 30241 TGCCAGGACGTGGTGTCCA | 41225 |
| 7600 CTGGGCGGATTTGGGAAATCACTCT | 19258 CTGAGCTGAAGTTGATGGAGAT | 30242 CCGCAACCCTCTCGGGGATTT | 41226 |
| 7601 CACGATGGGAGAGGTCATCTTG | 19259 CGCTCCCGTTGGCAAAGCAA | 30243 GGAGGCACCATTCCACGAT | 41227 |
| 7602 GCCTTTGCGACATCGTCTTC | 19260 GATGGAAACCAACCTTTTCACCTTCT | 30244 GATGCCAACCGATGCCTTTG | 41228 |

FIG. 36L7

| | | | |
|---|---|---|---|
| 7603 GCAAGACCCCATGAAAATCAATGGAACA | 19261 AGAGTAGGGCTCCCCATTCTTTT | 30245 GTTATGAATTGCAAGACCCCATGAA | 41229 |
| 7604 GCAGCTGCAGCATTTACAGCCTAA | 19262 GTGAACTTTGGGCATCCTCTGA | 30246 CAGAGGCAGCTGCACCATTT | 41230 |
| 7605 TGGCCAGGCAGCTCTGTCA | 19263 GAACAGGCTGCTTCCGATCA | 30247 TCAGCTGACAGGGCCAAAAC | 41231 |
| 7606 CCAAACTCATTGTCTTCCTGGTTT | 19264 GGGCTTGAGCATGGATTAAAGGGAAG | 30248 CCTCCAGAGCCCAAACTCATTGT | 41232 |
| 7607 GCTGTGGAAAGGTCATCTGAGACATC | 19265 GATGAGTGCAGACATGGAAGCATC | 30249 TGGGCTGTGGAAAGGTCATC | 41233 |
| 7608 TCACATCCACTGGCCGCAGTTC | 19266 GCTGAAGAAACTGGGCTCTGT | 30250 AGCAACGGAAGGAACTCACATC | 41234 |
| 7609 TGGCCCTGCTGAAACTTTAGAAC | 19267 CTGTGTGAAGGAAGGAGGATGAAAGT | 30251 CCAGTTGGCCCTGCTGAAA | 41235 |
| 7610 CGTCCACTTCCAGGACCAGAA | 19268 GGCACATACAGAGTTCAGCCTGTT | 30252 TGGCCGTCAGCGTCCACTT | 41236 |
| 7611 AGTTAGTCGTGAGCAGGAA | 19269 ACGCCGGTGCTGTCGTACT | 30253 CCTTGTAGCGCACGTAGT | 41237 |
| 7612 GGAAGTTTCCCTTGTGTGAAAGTCAA | 19270 CTGACTGGTTCCTGTCTCCAAGAAG | 30254 CTCCAGGAAGTTTCCCTTGTGT | 41238 |
| 7613 GGTTGGCTTGTCACCCTAGAGA | 19271 GGAGCAGGGAAGGATGGAACTA | 30255 CCTCCTGCTCTTGTTGGCTGT | 41239 |
| 7614 GTGATGCTTTTGGGAATTCACTTCT | 19272 CAGGATCTAGCCCTATGAGCATGTTA | 30256 CCACCAGTGCACTTAGTGATGCTT | 41240 |
| 7615 CTGAATTTTCCGATGACCAAGT | 19273 GGAGCCGCCAGGTTTACA | 30257 GTTGGGACACACCTTCCGAAT | 41241 |
| 7616 GTTCTGCTAGATGTTGAGGATGA | 19274 GTGAGCTCTGTGAGGATGGAGAT | 30258 TGCCGGTGCTCTCCTAGAT | 41242 |
| 7617 CTGGGAAGAGGTTGGATAAATGTTCA | 19275 GTGATAACAGGAAGGGGATGTTCTCT | 30259 CAGTTATTTGTCTGGGAAGAGGTGGAT | 41243 |
| 7618 AGGGAGGGAATGTGAAGAGAAAGT | 19276 CACTCAGCTGGCACTAGTCTTT | 30260 GAGGGAGGGAGGGAATGTGA | 41244 |
| 7619 GCCTCCCAGTGCTTAGGACCACAT | 19277 TGGGTGGTTTGCTGTCTAAGTT | 30261 ACCCGGCTTCCCAGTGCTTA | 41245 |
| 7620 GAGGCTTTGACTGGATGATGTTCA | 19278 GGGGCAATGACACTTCTGTT | 30262 GTGAAAGAAATCTCAGAGGCTTTGACT | 41246 |
| 7621 GCTCATGTCAACCCATCCAAA | 19279 CTCTCTCCTTAGTTGCTCTGCTTGAT | 30263 TCTTCCTTGAGGCTCATGTCAAC | 41247 |
| 7622 GTTGGATCCTTCTAGCTCCAAGA | 19280 AGCTCCAGAGCCTAGCACTT | 30264 GCCAACTTCCTTTTGTTGGATCCTTC | 41248 |
| 7623 GCCTCAGACCCTATTTGACACAAG | 19281 GAGACCCATTTCCTGACTGGTT | 30265 ACCACCTTGGCTCAGACCCTA | 41249 |
| 7624 AGAGGGGTATTGCCCTGTCTAA | 19282 GGGAAGAATCTGGACCTCACCAT | 30266 GGTGAAGCAGCATCTAGAGGGGTAT | 41250 |
| 7625 CGAACTCTCCATCCCTGCTCT | 19283 CTTCCCTTTACTTTGTGGAGTCATTT | 30267 GGTGGCCCGAACTCTCCAT | 41251 |
| 7626 GTGGGCTAGTTATCCTTCCAAAATC | 19284 GGAAGTAACACCCTACAGAACTGGAA | 30268 CCGTGGATGTGGGCTAGTTT | 41252 |
| 7627 GTGGTGGAGTATGGTGGTGTGA | 19285 ACCTGAGCCTGGGAGTTTGA | 30269 TTCACCTGTGCTGGAGTATG | 41253 |
| 7628 GTGCCGACTGTTTTGCTCACA | 19286 CCACTCATGACTGAAAACCCATCTT | 30270 TGTACCCAGTGCCGACTGT | 41254 |
| 7629 CACTGGCAGTTGGTGCAAGCAA | 19287 GGACAAGCTTCAAGAGTTAGGTTAGGTA | 30271 CCATGGAACCATTGGAGGTT | 41255 |
| 7630 GCCACAGTTGCCTCTATCTCCTA | 19288 GGAAAATAGCCTTCCTTCACAGCCTAT | 30272 TCTAAAACTACCTGAGCCACAGTTG | 41256 |
| 7631 GACTCCCAATTAGCCTCTTTTCTA | 19289 GCTGCCAGGGGTCAGGATTTTA | 30273 GCCAGCCTCTTGACTCCCAAT | 41257 |
| 7632 GACTTTCACCCACACATGGGATT | 19290 CAGTTATGTCCTAAAGACCCGTATCAT | 30274 GTGCTGCTGCCTCGATGACTTTC | 41258 |
| 7633 GCATGCGCATCATTAGTCACACA | 19291 GTGAACCAGGGTGAGCAAATTC | 30275 GGTTGCTGGGCATGGGCATCATT | 41259 |
| 7634 CCCTGCAGAACCACTTCCGTTA | 19292 CAGCATCGGGGAGTAGTTAGGTTTC | 30276 ACCTCGTCCCTGCAGAA | 41260 |
| 7635 GCCAGCTGAGACCATCCTCA | 19293 GGAGGCTAGAGAAATCCAGTTTGT | 30277 TGTCTTCCTCCCACCTGACA | 41261 |
| 7636 GGCTTATCCTGGCACCGATTCT | 19294 GCACCTAAGCCTGCGAGTAA | 30278 AGCCTCTCCAGCTGGCCTTAT | 41262 |
| 7637 GGGAGACAAACTCATTGGAGTCA | 19295 CCGTCTGTCTAGGAAAGGAAGCTCTA | 30279 TGGTGAGGAATAAAGGGAGACAAAC | 41263 |
| 7638 GGAAAGCACATTGTCCAGATGGTT | 19296 CTCACAGAGCTATAAGCAGGCAAA | 30280 AAGAGTCACTGGAAAGCACATTG | 41264 |
| 7639 GGCCCACACATGCATGAAGA | 19297 CCTGGCAGGGCGCTCTTTC | 30281 TGGTCCCAGGCCCACAT | 41265 |
| 7640 GGCTTGATCTGCTGTACTGGAAGAG | 19298 GCGATCTCCATTGCACCAT | 30282 ACAGTAATGGCTTGATCTGCTGTT | 41266 |
| 7641 CCCAAAGCTTCCTCATTACCTTCTT | 19299 GCTCAGCAAATGCCTACTAACTTG | 30283 ACTTCACATGGATCATCCCAAAG | 41267 |
| 7642 CCAGTGGGGCATTACTGGGTTA | 19300 CATGTCTGGAAACTGCTTCCTGTT | 30284 TACGGTGTCCAGTGGGCATT | 41268 |
| 7643 GGAGGCCTTTCAGGGATCTTTGCTA | 19301 TGGGTGAGTTGGTGAGGCTAC | 30285 GCCTATCACTTGGAGGCCTTTC | 41269 |
| 7644 GGTGTGTGAGGCTAATCTTGA | 19302 GCCTGGCTCTGCTCCATTTCA | 30286 GGCAGGAGACTTGGTGTGTGA | 41270 |
| 7645 CCTCCAGAGAAGTCGCAAATTT | 19303 AATGAGGTATAAGGCAAGCCACTT | 30287 CTTTTGCACCCCTCAGAGAAG | 41271 |
| 7646 GAGCGAAAGTGCGAGGCATAG | 19304 GCATCATTACAGGCAGACTTTACAAAC | 30288 TGCCCACAGAGCGAAAGT | 41272 |
| 7647 ACAGTGAACCAGCCCATCTTC | 19305 GAAGATCATCTGAAATTTGCCGGATTG | 30289 AGCCCTGCCGGGCAGTGAAC | 41273 |
| 7648 GACCAGCTTCCTTATGACTTTTGGTT | 19306 GAGAAGCCAAGGTGGCTACAAG | 30290 GCCATCTCTTTACTGACCAGCTT | 41274 |
| 7649 CCCATACACGTCACTGTCTCTCACA | 19307 GGCAGGCTTATGTACCCACTGAAA | 30291 GCTGTCTCTTTCCCATACACGTCACT | 41275 |
| 7650 CAAGAACCCCAGGTCAGAGAAC | 19308 GGGGTCCTTGCTCATAGAGCTT | 30292 TGAATCCGTGAGGCCAAGA | 41276 |
| 7651 GTGGTAGCAGCAAAGACTGTTAATC | 19309 GTACTCTAGGTTGAATAGGTGCTAGA | 30293 CTGAAACTGTGTGGTAGCAGCAA | 41277 |
| 7652 GCACACACAAGGACTTGCTCACA | 19310 CTGCCAGGAAGTAGGATTCATTCAT | 30294 ACAGGGCTGCACACACAA | 41278 |
| 7653 GCCAACAGGCAGGAAAGACTCA | 19311 GTCCTCTGCCACTTGAAGTCTCTAT | 30295 GGGCTCTTAGCCTTGGAGGAT | 41279 |
| 7654 GTTACAGAGTAGAAGGGTTGGGTTA | 19312 GAGCTGTGTAGACAGAGGTGTTTC | 30296 CCTTGGAGCTGCTGGGAAAGTT | 41280 |
| 7655 GTACAGCCAGCAATTCTACCTT | 19313 CCTGCAAGGAGAAGGAATGCAAAAC | 30297 AGCCCCACCGTTGTCTGTA | 41281 |
| 7656 GGTGTCATCTCTGTGTGCAATATTGTGATG | 19314 GCAGTTAACTACTTCTCTTAGCAGTGA | 30298 CAGGGTGCATCTCTGTGTGCAAT | 41282 |
| 7657 GCTGCCGGGAAAACCATTGAGA | 19315 TGCCGTTCCTCTCTCTTCT | 30299 GAGACAATGCTGCCGGGAAA | 41283 |
| 7658 CGGCAGTGATCTCAATGACAGGAT | 19316 GAACATTGGGTTGCAGAAGTACTGA | 30300 GCTTTGCTCCGGCAGTGATCT | 41284 |
| 7659 GCCAAGGAAGCTCGAGGGATT | 19317 GGAAAAACCGAGGACCAGAATGCA | 30301 TCCAAGCGCCAGACTGTAT | 41285 |
| 7660 CTCTCCCTGCTATGTCCCTGAAC | 19318 CGTTGAAGTGGTATTACAGCATGAGA | 30302 CCCATTGAAAACTCTCCTGCTATG | 41286 |
| 7661 GACTTCAAACAATGAGAGTGGGACTA | 19319 CCTCTTAGGTGTTGGTTGGTAGAA | 30303 CACCTGCTGGTGATATATGACTTCAAAT | 41287 |
| 7662 GGTGTGTACGTGGGAAATTTGGGATA | 19320 CCTCCCTGGAAGGCTGTAAAATC | 30304 CCAGGAAGGAGTCTGGTGTTGT | 41288 |
| 7663 GGAGAGATGAGAAGGGACAGATGATTT | 19321 AAACCGTCTGTGAAACCTGC | 30305 AGCCCTGTCCACGGACACTTCT | 41289 |
| 7664 GCACATCGGTTCTGCGTCTTG | 19322 TGGGCCTTCCCCATGTCT | 30306 CTGACCAGGGCACATCGTTTC | 41290 |
| 7665 TCCCTCCTTGTTGGTCTCTTCCT | 19323 GTAACATTTGGAGTCAGGGAAGT | 30307 CCTTGGTTCTTTTCTCCTCCTGTCT | 41291 |
| 7666 GACAGCCCAAATTCCCAGAGAGT | 19324 TCCGTGCTGGAGAGCTAAG | 30308 AGCTCAAGGGCACAGCCCAAATC | 41292 |
| 7667 GTAAGCGGAAGAATGGGAAGA | 19325 GTGTGTGACGCTGAGAGATCCAA | 30309 GGCAAAGGCAGCCAGAAAGCAA | 41293 |

| | | | |
|---|---|---|---|
| 7863 GCCTGTTACTCTTGGAGACAGAGT | 19521 GTTCCATATAGGCCTTGTTCTTCTACAAAG | 30505 AGGGTGTGGAGCCTGTTACTCT | 41489 |
| 7864 CACCCAGGCTTTCTGGCAGATT | 19522 GCGTATTCCTAGGGCCTGAAGT | 30506 ACTCCTACTCACCCAGGCCTTT | 41490 |
| 7865 CGTGCCACAATAGTTTTTAGAGGGTTT | 19523 GACCAAATGGAATGCTCAGCTACA | 30507 CTTTCCATTCGTGCCACAATAGTT | 41491 |
| 7866 TTACCGCGTCCGGAACTTCA | 19524 GGAATGTGTAAGAGGGTAAGAICCCATTTC | 30508 ACACTTGCCCGTCTTCCTGTTAC | 41492 |
| 7867 GGCATGCAAGTCAAGAGTCAAG | 19525 AGGATGTTATGTGGCAAGGATGAT | 30509 CAAGACCTAAGGGCATGCAAGTCA | 41493 |
| 7868 AGTAAGAGAGGGAAGGGATATTGCAT | 19526 ACCACTTGAAAGCAGGGATAGTTG | 30510 CTCCTTACAACTCTATCAAGTAAGAGA | 41494 |
| 7869 GCCCCTCTACCCCTCTCTGCAA | 19527 GGCAGAACTCAAGGGGCAAAAC | 30511 CAGTCGGAAGGCGACAGAGA | 41495 |
| 7870 GGAATTNAGTCTNTACAAGGGATNA | 19528 CTTGNCAACCTTCATTTAACCNAAA | 30512 CGGTTGATCCATGAATTCAGTCTGT | 41496 |
| 7871 GCACGTCCAAATCTTGCTCAATC | 19529 GCTTTGTGAAGGGGTGTCCTA | 30513 CCACATCCTTGCACGTCCAAATC | 41497 |
| 7872 CCACACTGCATTGGAATTTGGTATTG | 19530 GGAAAAAGAAGTGGACTGACATCGGAAT | 30514 CTAACTTTTGCTCACACACTGCAT | 41498 |
| 7873 GACACCTGACTCCTAAAAGAAACTTGA | 19531 AATCCCAACCCCTCTGTGCTTTT | 30515 GGAGAGACACCTGACTCCCTAA | 41499 |
| 7874 GGCCTCCAGAATAAGTGTGAAGA | 19532 CTGCATCTGCTGTATCTCTAGTGTCT | 30516 ATCCACTTGGCCCTTCCAGAA | 41500 |
| 7875 CCACTTCTACCTGGCCGATTTC | 19533 GAAAAGGAAGGGAATGTACCTAGTA | 30517 GCCATGCTCCGTACCACTTCTAC | 41501 |
| 7876 AGAGGGCTAGAGGGCTAAAT | 19534 CCCCAGGCCTTGGCTGTTATAC | 30518 AATGAACTAGGAGGAAGAGGGCTAGA | 41502 |
| 7877 AGTGTCCATCCAGTCCACGTA | 19535 CCTAAGAATGCACAAGGCTATTGAAGATG | 30519 GCGTAGGCCACCAACAGT | 41503 |
| 7878 TCTTCCCACACGTTTATGGACAAT | 19536 GCCCTGCATCAGTGCTACTAAG | 30520 TGGTGTTTCTTCCCACACGTT | 41504 |
| 7879 GCAAAACAGACAGGCAGCCAATAG | 19537 GCCCCGGCCAAGATCATGACTTTTAT | 30521 GGCACATCTGGGGCAAAACA | 41505 |
| 7880 CCTGTGCTCGTAGACTCACCAGTAA | 19538 GGAAGGCCGCTATCATCCTTATTCA | 30522 CAAGCCTGTGCTGCTAGACT | 41506 |
| 7881 CCCTATACGGCTTCACCAAAAAGT | 19539 GTGGACATTGCCTTTCTGAGTA | 30523 GCATCTCCTTACCCTATACGGCTTCA | 41507 |
| 7882 GGCAGTTCTCAACTTGCAGTAATAG | 19540 GGCATTGCCAACCTTTACAGACCTATC | 30524 ACCCAATTGGCAGTTCTCAACTT | 41508 |
| 7883 GCATGAAAGGGGCTAAGGTCCTAGT | 19541 CCCTGGAGTCAACATGAGAGTTTTGT | 30525 CCTGGCATGAAAGGGCTAA | 41509 |
| 7884 GGTATTGCAGCATCCCATAAGA | 19542 GTGGAGTCACTAGGGTTGACCAA | 30526 AGTGCTGCAGATGGGGCATT | 41510 |
| 7885 CAGAGGCAGCTTGGAGTACTGA | 19543 CTCCTTTATTCCCCAGATTGGTGA | 30527 TACCTCCACAGAGGCAGCTT | 41511 |
| 7886 CTGGGTTCTGGGTTCCCTTTC | 19544 GTAGAGTCATCAAAAGCCACTTTC | 30528 TTTCCTGGTATTCTGGGTTCT | 41512 |
| 7887 GGGTTAGGGACAGAATTCAACTCTC | 19545 GGCCCTCCAAACATCATTAGTCCAAA | 30529 GTCGGTGGGTTTAGGGACAGAA | 41513 |
| 7888 GGGAGGCTAAGTGATACACACA | 19546 GGCTTCCCTTGAAGAATCGTTGT | 30530 GCTGGAGGGAGGCTAAGTGA | 41514 |
| 7889 CTCCACCAAAGCGATTAGGAGACT | 19547 GGCTCACCAAGAATCCTAGCAAGA | 30531 CCACTTCTGTACCTGTCCACCAA | 41515 |
| 7890 GGGTGACCAAAGACGGAAAGTAGA | 19548 TTGCTATAACCACTCAGTTCTTTGT | 30532 CCCTCAAAACTAGGGTGACCAAA | 41516 |
| 7891 CTCCAAGAGGTTTCCCTAGTTGTGA | 19549 GGGAATGCTTCCAGGGGATGTTT | 30533 CCCACTAGACTCCAAGAGGTTTC | 41517 |
| 7892 GTCCTGCTGGATTGGGCTTTT | 19550 GCATTACCATGCCCTGTGATTAAG | 30534 CCATTCGTAGTCCTGCCTGGAT | 41518 |
| 7893 GGTGGGCTTCATGCTAGGGTTTT | 19551 GGGGAACTACTACCAGTGGTAAGTGAGA | 30535 ACCTACTGATGGTGGGCTTCA | 41519 |
| 7894 TGATAGTGAGGAGCCAAGATCACT | 19552 TCCAGGCTGCTATCATCTCTTCT | 30536 ACAAAGGACCACATAAGGGAGTATG | 41520 |
| 7895 GCAAAAGATGCCTGTGGACAAAGA | 19553 CCCTTCAGTGTCAACCTTATGGATCTTC | 30537 GGCACGCAGGTCTCTGCAAAA | 41521 |
| 7896 TGCATTCTTCCCAGTGGAGAAAC | 19554 GCTCATCTTCCATCGGAGCAACT | 30538 CCCCACACCCCTTGCATTCTT | 41522 |
| 7897 CTCGTACAGTACTCTTGGGGTGTAAAAATT | 19555 ACCAAAACGCCTCCAGAAAGT | 30539 GGACACAGATAAGTTGCCATTCTCGTA | 41523 |
| 7898 TGGGTGTTTAGTTCCTGAGAGT | 19556 TCACAGGGTAGAGTGGGGGCATA | 30540 TCAGCAGAGTCTGGCACTCA | 41524 |
| 7899 GCTGGGAGAAGGGTTTGTGTCA | 19557 AGAGAGGACATCAGGGGAACAA | 30541 AGGCTCTGGCGTGGGAGAAG | 41525 |
| 7900 GGGCTAATCAGGAATGGCTTCTTC | 19558 GGGCATGGCTAATAGGAAAAGGTTTG | 30542 GTGGAAGACACATGGCCTAATCA | 41526 |
| 7901 GCCAGTCACTCACACTGGGCTAT | 19559 GCCCAGAAACCAGGAGATGATG | 30543 TGACAGAGCCAGTCACTCA | 41527 |
| 7902 AGGGGAAGGTCCTTGCCTTGA | 19560 CATGTACCCACGCCTGAATCT | 30544 CTCTTTGTTGAGAAACAGGGGAAGT | 41528 |
| 7903 GGTGAAAGGTGACTTGTGGTCTGA | 19561 GCAAAGATTCAGGCATCGGAATAA | 30545 ACCAACAGGTGAAAGGTGACTT | 41529 |
| 7904 CAGCATTTCTTAACCTTGTTCCCAATC | 19562 TGGAATTGCAGGGCTTCTCT | 30546 CATGCTAAGGGCAACAGCATTTC | 41530 |
| 7905 AGCCTGTGCAGCTGGGTTTTG | 19563 CAGACGCACCTAGAGTTGTCCTA | 30547 AGGAGCACCAAGCCTGTGA | 41531 |
| 7906 CTGCCATGACAGCCCATTTCTCA | 19564 CCAGAGTCGGTATTTCAATCACCAAA | 30548 AGGAGGGGTGGGCTGCCATGA | 41532 |
| 7907 GGACGCGAAGGCTGAGGTTTTC | 19565 GTGTGTCATATTCTCCCTAGGACTT | 30549 TTCGTTGAAGGACGCGCAA | 41533 |
| 7908 CGGCAGCCAAAATATAGCAGAGA | 19566 CCCAGACATGCCCTTGACCTTT | 30550 CAGAAGATAAGTTAAACGGCAGCCAAA | 41534 |
| 7909 GCCAGAAGATGCTGGCAAAAA | 19567 GGCTAGAACTGAAAACAGAGGCTGTA | 30551 GGAAAAGTACAATTGCCAGAAGA | 41535 |
| 7910 TGAGCTGGTACTGGTGTCTCT | 19568 TGACCAGGGTTCACACCTCAGA | 30552 AGGAGGTCCTGTTGAGCTGGTA | 41536 |
| 7911 ACAATTGCCCTGAAGTTGTGCA | 19569 GGGCTATCACCAGTTTGACTATTCTGT | 30553 GTCCCCTCACAATTGCCCTGAA | 41537 |
| 7912 CCCGCTGATTCAGGGACTCT | 19570 CCATGTTAGAGGGTTAAGTCATGGAGTTC | 30554 CACACTCAAGACCCGCTGATTC | 41538 |
| 7913 GCGTGTTGAACCAACATCTGA | 19571 GTAGGTAAATTGGTAACAGGCAGTTC | 30555 CCGTTAAAATGGCCTAATGCGTGTTTG | 41539 |
| 7914 GCCCTAACACCTACAACCCCTTTT | 19572 TCCAGTGGCGAAATGTTCTGT | 30556 TCTGTGGCCTAACACCTACA | 41540 |
| 7915 CCTGTGGTTAGCTTCTGTGTTCCAT | 19573 CCAGACTAAGATGTCAAGGAGACTTGGTT | 30557 TTTACTCTCCTGTGGTTTAGCTTCT | 41541 |
| 7916 GCAAACCAGAAACTAGACAAAAGGTATC | 19574 TGATTGCCACTCAGCAACAGCCATT | 30558 GGACTGGAAGCAAACCAGAAACTA | 41542 |
| 7917 GTCATTGCTCTTCTGTAATCCTCAGTTTTC | 19575 CCACGTTGTAGGCTGTGTTATTC | 30559 TGCCAAGTCATTGCTCTTCTGT | 41543 |
| 7918 CTACCATCAGGGAGAAGGGATA | 19576 GCCCAAAACCTCTCTCTCAGAA | 30560 TCAAAGCCTGGCACCATCA | 41544 |
| 7919 CGTCCCTAAAACCATCTTCCTTCTTCA | 19577 TCAGGATTTTGTGAGTGTTCGGTTA | 30561 GTCCTCTGTCCTAAAACCATCTT | 41545 |
| 7920 CCCTCTGATGCGTGTCTATC | 19578 AGGCATGGAGGCTCTTCTTGA | 30562 TGCCCAACGATCCCCTCTGAT | 41546 |
| 7921 GCAACAGTGTAGTGGACACAAGT | 19579 CCTTGTGTGAGATCCTTAGGCCAAAAC | 30563 GAAGGCAGCCAACAGTGTAGT | 41547 |
| 7922 CTTTGCTAATCAACCCTCAGCAACT | 19580 GCCCTAGATAGTCACCCCTTATCTGTCT | 30564 CCGTTGCACTTTCCCTTCTTT | 41548 |
| 7923 CCAGACTCCCTCCCAGCTAGA | 19581 CTGTCCTAGCTCCTGGTAAAAGTTC | 30565 ACCCTCCCTTCCCAGACT | 41549 |
| 7924 CTCAGTCCTGAACAGGTCACCATT | 19582 TTTCCTGAAATGATGGCACTACA | 30566 CCAGCTCTCAGTCCTGAACA | 41550 |
| 7925 GACCACCACACTGATGTCAAGAGA | 19583 AAGGCTGCCTTGGGGTAGAGA | 30567 GCTTGTGACCACCACACTGA | 41551 |
| 7926 CCTAATGGACCTAACTCAAGAGTCATAG | 19584 GGTACTGTTACCGTGCTGTT | 30568 GCCCATGGAGTTACCTAATGGACCTA | 41552 |
| 7927 TCAGCCATGACAGAAGCAAATCTA | 19585 AGCACACTTGGCATGAAAAGAAAG | 30569 GAGCGGGTCACTTCACCTTTT | 41553 |

| | | | |
|---|---|---|---|
| 8123 | GCCCTAACTGATCCCATGAGAGGTT | 19781 | CCTGAGGGTACATTTCTCACAGATAC | 30765 | GTAAATTAGCCCTGTGCCCTAACTGA | 41749 |
| 8124 | ACAGCCCCTGTAGCTAGTGGAA | 19782 | GCAGACATTTGGCATTAGAGGAAGT | 30766 | ACATCTGCACAGCCCCTGTA | 41750 |
| 8125 | CATTCCAGTCCTGACGTACCAATC | 19783 | CTTTCTGTGATTACTGTGGTGAGATG | 30767 | CACACCTTCACATTTCAGTCCTTGA | 41751 |
| 8126 | ATGGATCCTTCCGCTGACA | 19784 | GCGTGTTCAGGAGCAAGACA | 30768 | GTCATTCTCCCACTACTCCCTATG | 41752 |
| 8127 | TGCCCCTTGCGCCCCCAATTC | 19785 | TGCTTTTGGTGTGTCCCAGTGA | 30769 | TGGGTCCCAGTGCCCTGT | 41753 |
| 8128 | CCATCCTCCAGTATATCCCTCCTGTATG | 19786 | CAAAACTGCTCCTGGTGGGAGAAC | 30770 | GGTGGGACACCATCCTCCAGTATATC | 41754 |
| 8129 | GGCTTCCCTGCTTCAGAGATAGA | 19787 | CTGTACTGCCCAAGATGAGCTTTC | 30771 | CTGTCTCTTGGCTTCCCTGCTT | 41755 |
| 8130 | CTGACATAGGGATCACTTCTGTAGCAT | 19788 | GGTCCTGGGCTGATTTTCTGA | 30772 | GCCTAAGCATGGAACTGACATAGGGAT | 41756 |
| 8131 | CAGAGCTGAATTTCCTGGCTAAGGAT | 19789 | GGACAGGCAGAGACAAAGGAAGAAG | 30773 | TGGCTGACTTACAGAGCTGAATTT | 41757 |
| 8132 | GCAAATGTATGCCTTGTTGGGCATTG | 19790 | CTTTTGCACCCAGGACTCTGAA | 30774 | CCTTATCTCTGCAAATGTATGCCTTGT | 41758 |
| 8133 | GCCCAGACATATCCTCAGTCATTTG | 19791 | TGGGTGGCTCAGACTGTCAA | 30775 | CCCTCTTTGCTACATGCCCAGACA | 41759 |
| 8134 | GGGGCGTTCTCAGCCATTCAA | 19792 | TGCCACAGGGAGAAGGAAGT | 30776 | GTCCTGCCATGGGGCTTCT | 41760 |
| 8135 | CTGTGCCTGCACAAAGTAGTGACAGA | 19793 | CGAAAGTAAATGCTAAGCCTTGCTA | 30777 | GCAGCTGTGCCTGACAAGT | 41761 |
| 8136 | GAGGCAAGGAAAGACCGTATCA | 19794 | CCCTCTGCCACAGTGCCTTT | 30778 | GCCCACCAAAGAGGCAAGGAAA | 41762 |
| 8137 | AGGGGTGCAGTTAGTGCTATGA | 19795 | GTGGAGTAGAGTCCTTCTGAATAAC | 30779 | CCTACCTCAAAGGGTGCAGTT | 41763 |
| 8138 | GGCTGCTGTTACAAGACAGAGACAT | 19796 | GAGAGGGAAGAGTTGTGGGTGTT | 30780 | GCACAAAGGCTGCTGTTACAAG | 41764 |
| 8139 | CCAGTAAGCCTGGCAAGAGTTTTT | 19797 | GGCTGCAGGATTCAAACCTAAT | 30781 | ACCTGCTGCAGAGACCAGGAA | 41765 |
| 8140 | CACTTCCTGCCACTTGCCTTAAA | 19798 | GAGAGCAGGGAACATGGGTTCT | 30782 | GACCCATCTAAAGGCAGTCACTT | 41766 |
| 8141 | ACTTGTAGTTGTCGGTAA | 19799 | GGAACTTACCCGTTCTCCTTTC | 30783 | ACCGGACTGAGTGGTTACT | 41767 |
| 8142 | GGATTCTGAGCCCATTTGACTATAAAC | 19800 | AAGTGCTACAACGGAAAGGAAGT | 30784 | GCCACCTGCAATATAAGGATCTGA | 41768 |
| 8143 | GCTAGGTTCAAGTGAGGATAACACT | 19801 | GCTCCAAGAGACCCTGACTCACT | 30785 | CCTCAGGCTAATGCTAGGTTCAAG | 41769 |
| 8144 | GTCTCAGGAATAAAGCTACTGGTTCA | 19802 | CTGGGCAGAGCACTGAAAGT | 30786 | GTCATTGGAGCTGGTCTCAGGAA | 41770 |
| 8145 | CCCCAGTGTCCCATCTGGTAA | 19803 | GTCGAGGTTGATTCGAGTCACTA | 30787 | CAGCTGTTGTCCCCAGTGT | 41771 |
| 8146 | CAAGACAATGGGTGCTGAGCT | 19804 | GTGACAAGATGTCATTGCCAACCAA | 30788 | GTCACCTGCCCCTCAACAAGA | 41772 |
| 8147 | GGCAGATTCACCATGTATGTTTTGT | 19805 | ACAACCAGCCCTTGCATTAACT | 30789 | CATAGGGGCAGATTCACCATGT | 41773 |
| 8148 | GGAACAGATCACCTAAATCTAAGGAA | 19806 | GATTGAAGCCCAGCCTTGAATAAG | 30790 | AAGGGTAGGAGCAGATCACCTAA | 41774 |
| 8149 | TGGCTGACAGTTATGTCCCATT | 19807 | AGGGCCAAAGATGAAGAATGTAGTT | 30791 | CCGAGACATTTGGCTGACAGT | 41775 |
| 8150 | TCCTGAATTCCCAGGTCTTGTCT | 19808 | GCTTGGGTGGTGGTGGAACA | 30792 | ACTTCTCCTGACCAAGGAAAACTTC | 41776 |
| 8151 | GACTGCCATGTTCTAGATATGTGT | 19809 | CAGAGTTGCAAGGTACCCATTCT | 30793 | CCTTTTTGGACTGGCATTTGTCTA | 41777 |
| 8152 | GGGAGCAAGAATAGAAGAAGGTGACT | 19810 | CTGCTCACCTGGCGTACAGAAAT | 30794 | GGAGAAGAGACCATAGGGAGCAAGA | 41778 |
| 8153 | GGTAAGTGTCCATTCAGCCATT | 19811 | CCACTACCCTTACTTCACTTGA | 30795 | GGGTCAGCCTTGTTAAGCTGTCAT | 41779 |
| 8154 | AGCCCTGCCAAGACCTAGAGAT | 19812 | CCCCACGGAACACTGCAT | 30796 | CATGCTTATTGTAAAAGCCCTGCAA | 41780 |
| 8155 | TCAGAGAGAGGGAAGCCCAAA | 19813 | TTCCCTGGAGCCTTCACTGTT | 30797 | GGATGAGGGAAGGTGTTCAGAGA | 41781 |
| 8156 | CTCTCCCTCTATATTAAAACGGTGCAT | 19814 | ACAGCTTCCCTGTAGGAAGTTATAAAG | 30798 | TGGGGAATCACCTCTCCCTCTA | 41782 |
| 8157 | GACAGAAGAAATCCAAGACCCAGAGATT | 19815 | GTGAAGACCAGGTATGCTTTTCAAG | 30799 | GGAGACCAAGAGACAGAAGAAATCCA | 41783 |
| 8158 | GCACCCAACCACTTTTGTACTCTTG | 19816 | CCCCATCAGGCAGGGAAACA | 30800 | CCATGGCACCCAACCACTTT | 41784 |
| 8159 | GGGGAGTAGCCTAGAAGTGATATAGAA | 19817 | CGGACTGGACTATAAGGGCAACA | 30801 | CCTCAGGGAGTAGCCTAGAAGT | 41785 |
| 8160 | GGCCCATGCTGAATTCCACGA | 19818 | GGAAGACACTGTGCTTACTTAACTTGTTG | 30802 | CAAAATTAACTTGGCCATGCTGAGA | 41786 |
| 8161 | GTTATGCACTCCTCAGCCAGTATC | 19819 | TTTCTCCCTCCCCTAATTACAAGGAT | 30803 | GTGAATGCTTCCAGTGGAGTTATG | 41787 |
| 8162 | CCTGAAGTAGAGCCTCCAGCAT | 19820 | CCTGAGGGTGGAACAAAATGTA | 30804 | GAGAAGGTATTGGCAACCCTGAAGTAG | 41788 |
| 8163 | CCATGGGCATACCTTCAACTGTAA | 19821 | CTTATTGGTGCAAGCCATGTTTAGT | 30805 | GAATACTGAATCCAGGGGATACCTT | 41789 |
| 8164 | GGGGCAAGTTCTCAGCCTTGA | 19822 | CCCTCAACAGCACCGAGTCTAT | 30806 | TGGTGGTCTGGGGCAAGTT | 41790 |
| 8165 | ATGCCAGTGTCTAGCTCAGCTTTT | 19823 | ACACACACAGAGCCATCCAGAA | 30807 | CCTTGAAATCCACATATCCCAGTCTA | 41791 |
| 8166 | CCAAGATCTAAGCCACCACCAT | 19824 | ACCGTTTGGGAGGCTATTTGAA | 30808 | CCCTCTGTCTCGACTGCTACCAA | 41792 |
| 8167 | CCTCCCAAGTGGCATGAGGAAA | 19825 | GCTAGGAATTACCAATTTTTGCCCTAA | 30809 | AGGGTAGGCCCTCTCAAGT | 41793 |
| 8168 | GCCAGAGACGTTACTGACTGGTT | 19826 | TCTACTGTCTTGCCATGCACATAA | 30810 | GGCTGAAGAAGCCAGAGACGTT | 41794 |
| 8169 | CAGTCCTTGCTTGTGTCCATTGAAGGAT | 19827 | CTTTATTCCATCCATTGCCTTAAAG | 30811 | TGGGGTCCAGTCCTTGTGT | 41795 |
| 8170 | GGATGTGCACCTTGATGAGTAGAAA | 19828 | CCCACCAACCCAAGAGTCTTCT | 30812 | ACCCTACCCAAGCTGGATGT | 41796 |
| 8171 | GGCTCTGAAGCAGCTGGAAT | 19829 | TGCCCAAAGTCACATAGGAATGAT | 30813 | GTCTTTATGGGTGTGGCTCTGAA | 41797 |
| 8172 | TGGCATGACTCAATCCTATGCTTT | 19830 | ACGAGAGGGAAGGGAGAAGA | 30814 | CCTGATCTCTACATATTGGCATGACT | 41798 |
| 8173 | GCTCCCTTGCTACTATAAAGTGATGTGC | 19831 | CTGCTGTACAGGTCTGCGACAA | 30815 | GAGGGTAAAGGTAGCTCCCTGCCA | 41799 |
| 8174 | GTACAGAGACCTATGACAGTTGA | 19832 | TGCTCATAGCTTCAGAATCTGCATT | 30816 | GGAAAGGTTACAAGACTTGCACAGA | 41800 |
| 8175 | GGGTGTCGAAGGGATCAGAGATTA | 19833 | ACCACCAGGCTGGGGATCT | 30817 | GAGAACTGGGTGTCGAAAGGAT | 41801 |
| 8176 | GCCTCAATATTACGAACTTGCCTTGTA | 19834 | AGCCTACAGGGGTCTGCAATG | 30818 | GTCTGAAAGCCTCAATATTACGAA | 41802 |
| 8177 | GAAGGTACCAAACCCTGCTCAA | 19835 | GGCTAAATCACGGGGTCAAAAC | 30819 | GCAAGCAAGCAATTAAGAAGGTACCAAAC | 41803 |
| 8178 | GCCAGACCCCTATTCCTCTGGACAA | 19836 | TCAGAGATTCTGAGTAATCCCAGTTTG | 30820 | CCCCCTAGAAATTAGTCAGACCCCTATTC | 41804 |
| 8179 | CCCAAGGACGTCAAGTGTTCTA | 19837 | GCTCCCCAGTGTTTTGAGGAGA | 30821 | CCACATCCCAAGGACGTCAA | 41805 |
| 8180 | GAGACCCAAAAGGTCAGCCATGT | 19838 | CCTCAGTCTCCTGAGCCTTTGT | 30822 | TGCCTGCCACTGAGACCAAA | 41806 |
| 8181 | CGCTGAGACCCAGGGCTTCTA | 19839 | GGAGTTGACTCCAATTGTCCTACA | 30823 | CCAGGCCAATACCGCTGAGA | 41807 |
| 8182 | GCCACTGGGCTAATTCCATGT | 19840 | GCTGGATCACTAACCACCACTCCTT | 30824 | TTCCATGCCACTGGGCTAA | 41808 |
| 8183 | GCCAGAGTGCATGACAAGTGTA | 19841 | GACTGCAGTGTCAGAATTTCATAACCCAAA | 30825 | GCAGATGCATTGTGAAAGCACCAAGT | 41809 |
| 8184 | TGGATGCTTCACCTGTCTTAGTCT | 19842 | CAGATTGAATGCAGGTTGCTCTGT | 30826 | ATTTGAGATGGTGGGATGCTTCA | 41810 |
| 8185 | GTCACAAGTCCTGACCAGTTACA | 19843 | GGTTTTCCCCTGGATAGGGAGTCTA | 30827 | AAGACAAAGTCGCTAGTCACAAGT | 41811 |
| 8186 | GATCCATGTGTCTTTATATCATCT | 19844 | AGGTGGCAGGACGCACTTAG | 30828 | GTCCTGCACAGTGTTCTCT | 41812 |
| 8187 | GCTCAACAGGAGGATCAGAGCAT | 19845 | CTGTTGCGTACAAGGGAGCTCTA | 30829 | GCCATCTAACTCCCTAGCTCAAC | 41813 |

FIG. 36M6

| | | | |
|---|---|---|---|
| 8188 GGGAGATACACAACACTGCTCAGA | 19846 GAATAACCAACGGAGTGGTTTTCAT | 30830 GCCACGTGTATACCAAAGGGAGATA | 41814 |
| 8189 GAGTGGTGGTAGGACAGAGACA | 19847 GCTCCATAAGGGCAGGGACAAA | 30831 CAAGTCAAGGTTTTGAGTGGTGGTA | 41815 |
| 8190 AGAGGCAAGATGGTGGGATGA | 19848 GGGCCAGAATCCAGTCTTCTGACTT | 30832 AGATGCCTAAGCTAGAGGCAAGA | 41816 |
| 8191 GGGTAAGACATTCCCCACTAAATCCATA | 19849 GCACCTTCCCAGTTCACCTCTAT | 30833 CCACCCTGCAGAAGGTTGGGGTAAGA | 41817 |
| 8192 GGATTGGCATTGTTTGCCTGTATG | 19850 CACCCAGCTTTGGCTCTTATCA | 30834 CATGGTACTGGAGCATTGTTT | 41818 |
| 8193 GGGTTTTTGTGAGCCTGATAGGAA | 19851 CAACAAGCTGCAGTCAACTCAA | 30835 GACAAACAGTGGGGTTTTTGTGA | 41819 |
| 8194 CACTCAAAAACATGCTGCTTTCTCT | 19852 AATGCACATGGAGTCTGGGAAA | 30836 CCACTAGGGACAAAACTTCACTCA | 41820 |
| 8195 CACTAGGCACCATACTCACATACTT | 19853 GGAAAGCCCTTGTGCACATACA | 30837 CCCATGCTTTTCACTAGGCACCATA | 41821 |
| 8196 GCTAACTCCAGCCTTCACTTC | 19854 GGGGTTTGCAGCAGGGAGCTTA | 30838 GACTGAGTAAACATTGGGGGTAA | 41822 |
| 8197 CGAGGCCATTGTAGAACAAGAAATC | 19855 GCTAACCCAGACCTATGAGGAAAC | 30839 GACATGAGCGAGGCCATTGT | 41823 |
| 8198 GCATGCCCTCCTTCATGGTCTA | 19856 CTGAAAGCAGGAGGCTTCCAA | 30840 GCTAGCTCAGGGCTGCAT | 41824 |
| 8199 ACCCAGCATGCAAAGTCAGT | 19857 GGCAGGTTGCATCTCTGTGT | 30841 ACTGGAGCACAACCCAGCAT | 41825 |
| 8200 CCGGGGCAAAACTTGGTAAAC | 19858 AGGGAAGTAAGCATCCAGAACTTTG | 30842 TGTTTGTAAAACCGGGCAAAAC | 41826 |
| 8201 TCAGCATTGCTTCACCTGTGT | 19859 GGTTTTCCGCCTAGGAAAGAGAT | 30843 CCTCTCTCCAAGGAATCAGCATTG | 41827 |
| 8202 CCCATGGCCTAAAGGGATTAAGACAGTTTC | 19860 CCTCTTTTCTCTACACTGGAGTTTTCA | 30844 CAGCCCATGGCCTAAAGGATT | 41828 |
| 8203 CAAGAGCTCCACTTACGTCCAAAG | 19861 CAGCATGGACAGATCATTAAGGGAGAA | 30845 GCTCCATTCAGTCAAGAGCTCCACTT | 41829 |
| 8204 GTCCAGTTTTCCAGGTCCAAGACA | 19862 GCTTCACCCCTGGTGGCTATTA | 30846 GAGTCGCACACATGTCCAGTT | 41830 |
| 8205 CCCTCCACCTTAAATGCTCTTTCCTGTA | 19863 GTGAATGTTGGGTAGGCGTTCA | 30847 GGTGCTCCCTCCACCTTAAATG | 41831 |
| 8206 TTTGGGGTTGGTTTTCCTGTACTT | 19864 TGGCTGGGCAAAGATTTCTTGA | 30848 TTGTGCATTTPGGGGGTTGTTT | 41832 |
| 8207 TGCAGCACCACACTCAATAATGT | 19865 GGGCACACATTTCCTCATTTG | 30849 GTGGAAATGCAGCACCACACT | 41833 |
| 8208 AGGTCAGTTACTTGGTTGTCAAGAA | 19866 GCTTGAGTTTACACTCCTTTTCTCTTC | 30850 GGCCTCCATCTATAGGTCAGTTACTTG | 41834 |
| 8209 AGTGGCAGAACTGAAGACCTCAT | 19867 GCACATGCTGCCCTTTGCTGAA | 30851 GTGGCTGAAAGTGGGAGAACTGA | 41835 |
| 8210 TTCAGAGGGTGTTAGGTTCAGCAAA | 19868 GTCCTACAGGTGGGCTCGAA | 30852 GAGAGCCCAAATTCAGAGGGTGTTAG | 41836 |
| 8211 CCGGCGAAGAGCCCCTGAAA | 19869 GTTCTGTGGGTGCAGGAGATTC | 30853 AAGTCCAAGGGTCCGCGAGAA | 41837 |
| 8212 GCAGTGGGGTTTGTTCATGGTA | 19870 TGAAAGGAACCACTGTGAGCAAATA | 30854 TCCCTTACTGCAGTGGGGTTTG | 41838 |
| 8213 GCTTGGTTTTTGGAACCATTCTTGA | 19871 CAAAAGCAGCACCAGAGGTGATA | 30855 GTCCTCGAGCGTAAGCTTGGTTTTG | 41839 |
| 8214 GTGCTTTGCATACAGTAGGTCATCA | 19872 GCCCCAAACTTCCTCTCAGTCA | 30856 TCGGAGGAGTGCTTTGCATAC | 41840 |
| 8215 GGCGGGGTACCAAGTAAAGTGT | 19873 CACCTGAGTAGGATGTATTCCTT | 30857 AGTTACAGGCGGGGTACCAA | 41841 |
| 8216 CGGGTCAACATTTACACTGACTCCAA | 19874 GAGAACAGAATGCGTGTGTGCAAT | 30858 AGGGGACAGCGGGTCAACATT | 41842 |
| 8217 GACTGTGTTTGAGAGGGGCTTCTA | 19875 GGAGAAGGTGTGTAGGAGATGCTT | 30859 GCAACGAAATGACTGTGTTTGAGA | 41843 |
| 8218 ACCCCTTAAGAGGCATTTGTGTCA | 19876 CAAAGAGACTGCATTCATACCCTCATC | 30860 GTGTTGGGAGGTGGTACCCTTA | 41844 |
| 8219 GACTCCTAGTTGCTGAAGTCTCTGTAG | 19877 GGAGGCCTGACGTAGAAGAAGTT | 30861 GCCATTTATGACTCCTAGTTGCTGAAG | 41845 |
| 8220 GGAATGGTTCCTATAACCTAAGGTGTTTACT | 19878 CTCGCTCTGTCTTTTPGTGTAAGGAT | 30862 GGCTTCAGGAATGGTTCCTATAACCTA | 41846 |
| 8221 CAAGGGGAGAGACATTATTGGCATT | 19879 GTCCAAGGCAGTTTCTACAGGATGAA | 30863 GTGTTTCTCAAGGGGCAGAGACATT | 41847 |
| 8222 GGAGAAGCCAAAATAAGGGTGTTGTTG | 19880 CTTGTTATGCAGCGTTCAGGTTCA | 30864 CCGTGCCAAACAAAGGGAGAAG | 41848 |
| 8223 ACGTTGCCTCAGACCCTATCA | 19881 ATACCTCCTCACTTAGATATCAA | 30865 TCCCAGAACTCAGTCCCACGTT | 41849 |
| 8224 CTCTCAGCGCAAGAACCTAGAAG | 19882 GCAGGCAGTAGGAATGGTCTATCTCA | 30866 AGGCTGGCTGCTGAACTCTCA | 41850 |
| 8225 CAGAGAAGCTAATGTGGCAGTGA | 19883 AGAGGGCCTAAAAAGCAAGAACT | 30867 GAGGGTTTCTGCAGAGAAGCTAATG | 41851 |
| 8226 TGGAGTCAGGCCTAGGGTTTAG | 19884 ACATCTGGCCCCGGGAATTTT | 30868 TGTTTAAGGGGTGAGATGGAGTCA | 41852 |
| 8227 TCCACTCTTTCAGGCTGTGAGA | 19885 AATTGCAGTTCATGGAGCTTGCTATG | 30869 TGACCAATCAGTTCCACTCTTTGA | 41853 |
| 8228 GCAACCATTTTCATGCCCCTTAGTATCA | 19886 GGTGACCTACAGCTGTGTTGTT | 30870 CCACCCGGCAACCATTTTCA | 41854 |
| 8229 TGGGGAAGGCGAAGAGGACAT | 19887 CTCTGTCCCTCTACACCTGAA | 30871 GATGTGGGCTTGATTGGGGAAA | 41855 |
| 8230 CAGGAAGAAATAGGGCTACTGTCAA | 19888 GATGTCACAGTAGAGTTACTTGGGTTCT | 30872 GCACTTGACCCTGGTTATCAGGAA | 41856 |
| 8231 GGAACTTTTTGCCTTGGTGTTGTT | 19889 GTTGGTACCTCCTAGACAAAGACA | 30873 TGGTGGATGACGGAGCAACT | 41857 |
| 8232 AGAGCCAGGTACATGCCAGCTA | 19890 GTGTGTTCTCCTGTTGCAGTTG | 30874 TGGCCAGAGCCAGGTACA | 41858 |
| 8233 GGGTTTAGGAATGGCAGGTCATTTG | 19891 GCTTCTAACCCAGGCACTAATTCATC | 30875 AGGGCCTGGAGGGGTTAGGAAT | 41859 |
| 8234 TCCTACACCTGCCTCTCCAATC | 19892 GCCACACGTGGAACATGGTAAC | 30876 GCTCTTGACTTCCCCTTCCTACA | 41860 |
| 8235 ACTCTGGCTGCTGGAATAAACAAT | 19893 GAGCAGTGACTGAAGGTTCTGA | 30877 ACAGTCACACAGGCCACTGT | 41861 |
| 8236 GTGGCTGTTGTCAGACTTTGATTC | 19894 GGAGACTTAGGAAGCCTACGGATAG | 30878 GCCTGCTAGAATACCATGCTGCTGTGT | 41862 |
| 8237 GGCCTGCTTCAAAGTCCCAGAA | 19895 CTTCTTTCTTACCGGAGTATGGACTCT | 30879 CTGGTAGGAAGGCTGCTTCAAA | 41863 |
| 8238 CTCTCAGCTAGCAGAACCACAT | 19896 GCATGGCCACAATTCTTCTTTC | 30880 GCTGTTGTTCAATGCTCTCAGCTA | 41864 |
| 8239 CAGTTTGGTGAATGGAAGGTTCTGA | 19897 GGACACTGTTTGTCCCTCTCTATCT | 30881 GGGCACTTGCAGTTTGGTGAATG | 41865 |
| 8240 AGCTGCCATTTCCCACAAT | 19898 GCAAGTCATCCAGCTTCTGCTT | 30882 CTCTAGGGTTGTCTTATAGCTGCCATT | 41866 |
| 8241 GCCCCAGGTGCTTTTCAGGCATTTAG | 19899 ACCTTTGCCCCAGCCTGACA | 30883 GCTCTGCCCCCAGGTGCTTTTCA | 41867 |
| 8242 GCCCTTTAGAAAGCTTGAAGTCCTTAG | 19900 GGCTTTTTGGAGGGTAGGTAATCAAAG | 30884 GCTTCTGCCCTTTAGAAAGCTTGA | 41868 |
| 8243 AGGCCAGCCCCTGGAGAACT | 19901 GGGAGTTCTTGGGGACAAACT | 30885 CCTGCCCACTGCAAGCTCA | 41869 |
| 8244 CACGGCAGTCTTCAATGAGTCAGA | 19902 GCATGGGGCAAAGGGTTTGT | 30886 GTTAAACACACGGCAGTCTTCAA | 41870 |
| 8245 GGGTGGGTGCTGGGTAACAT | 19903 TTTCAGCCGCTGTGGGTTTG | 30887 TGTACGATGGGTGGGTGCTT | 41871 |
| 8246 GCAACTTGGTTGCATATCCATTTGTT | 19904 GCCATPGTGAGGCTACTCCGTAA | 30888 GCCAGTAGCTGGCAACTTGGT | 41872 |
| 8247 GGAAGTTTCTTAAAGTGAGGAACCCATA | 19905 GTTCAGTCCTGTGCTGGGTCTT | 30889 CTGTTCCCAGTGATACTGGAAGTT | 41873 |
| 8248 GGGGAATTGTGTTTGCACCTTAGAGT | 19906 ACTTGCTGGCTCGCCGCTACT | 30890 GCAGAGGCAAGAGTAAAGGGGAAT | 41874 |
| 8249 GGATGCAAGCCACTTTAGCACTCA | 19907 GCATCTCTGAGTCCCAGTAACCTT | 30891 GCTTCCTGGATGCAAGCCACTT | 41875 |
| 8250 GTGAAGGATTAAAACAGCCCAACTGT | 19908 CCTGCTACAATTACCTCAATGTCTGT | 30892 GGAATGAAGCTTTGTGTGAAGGAT | 41876 |
| 8251 GAGAAGGGAACTGGAAGGGCAAT | 19909 GGATCAGGGTAGTTGGACTCTTTC | 30893 CGTGTTAGCAGAGAAGGGAACT | 41877 |
| 8252 CAGTATGGATCATGCTTCTCTTGTCA | 19910 GCCCTTTGTGCTATAAATAAGGGAATC | 30894 CCCACGACCAATAACAGTATGGATCA | 41878 |

FIG. 36M7

| | | | |
|---|---|---|---|
| 8253 TCACAGCAACAAGCCATGTGA | 19911 GTGAATGCATGAACACCCTGATGTAT | 30895 GGGTGGTAGGTATCACAGCAACA | 41879 |
| 8254 CTGTTGTTCCAAACCTCCCTTTC | 19912 TTCAAGGATCACTGAGGACTGAAG | 30896 TCCCTCAAGTTTGACATCTGTTGTT | 41880 |
| 8255 CTGCCCATCTCCTTCTGTCTTC | 19913 GAGCATACCCAGGTTATGTGTCA | 30897 TGATCTGCCTCTGCCCATCT | 41881 |
| 8256 CTGCTGAAGTCCTCCTCTGTCT | 19914 GTCAAAACCCTAGGGCAAGATGTTG | 30898 GAGCCATCTGCTGCTGAAGT | 41882 |
| 8257 CCACCAACTACTGCAGTCTGAAC | 19915 TCCAGTGCCAAAGTACAGGTAGA | 30899 CTGCTGCACCACCAACTACT | 41883 |
| 8258 GTCCCAGTGTGTTCCTAGACT | 19916 GGGATTAACATACGTAAGGTTGCTTCT | 30900 ACAAGGTGTCCCCAGTGTGT | 41884 |
| 8259 GTTTGACTGTCTGGCTCTTTCT | 19917 CCTCTTCTCTTCCTGCTCTATCAAA | 30901 ACCCGGATCAGTTTGACTGCT | 41885 |
| 8260 GCAATGGCCTCCACCATACGAT | 19918 CAGGCTGTTGGGTTTTGGAAGATTG | 30902 ACTCTGGGCACATGGAGCAA | 41886 |
| 8261 GCCAGGGCATTTGCACTTTG | 19919 CCGGGTTCCATTGGGTACAGA | 30903 CATTCTGGAGCCAGGGCATT | 41887 |
| 8262 GCACCATTTGGTTTCTGCTCATTTAG | 19920 CCGAGAGCAAGAAGCCAAACATC | 30904 GCTGCCAAAAGCACCATTTGGTTTC | 41888 |
| 8263 GGAAGTGAAGGAGGCTTCCTCCTGAT | 19921 CTGTTTCCAGATGGTATGGCTGTT | 30905 GGGGTGGTGGTTAGGAAGTGAA | 41889 |
| 8264 GCCCAGGGAAATCCACTTATC | 19922 CCCTGGTAAAAACCTGAGTCACTAC | 30906 AGTCCAAGCCCAGGGAAATCT | 41890 |
| 8265 CCAAGATAAGAAGTACAGGCCAATTCGTT | 19923 GGAACCAGAAAGAGGGCCTATC | 30907 GGTCTCCAGATAAGTCCAAGATAAGAAGTA | 41891 |
| 8266 GTTACTGACTCACTGTAGGCACAA | 19924 CCAAACCACAAATCAATGGGATAGTA | 30908 CATCTTCACCTCTTGTTGTTACTGA | 41892 |
| 8267 ACATAAGCCACGCTGGACAAAGAA | 19925 GGGGTAACTTTAGGAAAAGGCTGTCTAC | 30909 GCCCTTCTTCTGGGTACATAAGTCA | 41893 |
| 8268 CACAAGATGTGTGTTCTTAGCCATTAC | 19926 CCCATCATTAGTGATTCCCAGTTTTG | 30910 AGTGGAGCATGGATTTTCACACA | 41894 |
| 8269 GGGCACTGATGCTATCTCTGGAAA | 19927 GCACAGCAGTTTCGATGATCCCAAT | 30911 TGCAGTGGGCACTGATGCTA | 41895 |
| 8270 GTCAGGATCACCTCCAGACTGTACT | 19928 CTGGGGTTTGTTCTGCCAGAGT | 30912 GGCAGTCCACATGTCAGGATCA | 41896 |
| 8271 GTGACTCTGTCGAAGTGTGGTT | 19929 CCAAGTTACCTTCTGCTAAAGCCATACA | 30913 GCCCAGACAAGCTGACTCTGT | 41897 |
| 8272 GTGATGGCGTTTCTGAGAGGGATTG | 19930 TCAAATACCACCTACCCACAGATG | 30914 GGGTCAGGTGATGGTGTTTTCT | 41898 |
| 8273 GCTCACCTCTCTTGGGTAGTTTCACT | 19931 GCATTCCTGGCAAGAGGAATAGT | 30915 TGAAACCAAGCTCACCTCTCTTG | 41899 |
| 8274 AGAGTCCCTTTGGAATTTCAGCTT | 19932 TGCCAAGGTGGGGAGTCTAA | 30916 GACTGAACGGTAGAGCCCTTTG | 41900 |
| 8275 GGTGGCTCTTTTAGCCGACTTTAG | 19933 CTCTCCTCCTCGGAAAACATTTCGAT | 30917 CCAAAACCAATCTGGTGGCTCTTT | 41901 |
| 8276 GTTACTGACCTAGTAATTCATGGAGAGA | 19934 GGAAGTCTGAAAGCAAAGCATCA | 30918 TGTGCCTGGCCAAGTTAGT | 41902 |
| 8277 TCTCAGGAAGAAAGGGTAGACTGT | 19935 GGCTGGCTTTGTGAGTCCTTGT | 30919 CTGTCAGCTCAAATCTCAGGAAGA | 41903 |
| 8278 ACGGAGGACAGGTCTCTGCTA | 19936 GCTGCCTGCAGTACCAAGTCT | 30920 TGGGAGGTAGAACCTGCAACA | 41904 |
| 8279 TGACTACTTTGGGAATGGGGACTA | 19937 GACTGGAATCTCTAACACTCTCATTCAAG | 30921 CTGGCTCCCATTGACTACTTTG | 41905 |
| 8280 GTAGCTTCATGCTAGTGAAGAA | 19938 CAGTGCTGGACAAGGGAGAAAC | 30922 GGCAAGCAGGCTTCATGCTA | 41906 |
| 8281 CCCACTACCCACTGAATGTGAATC | 19939 CCTGAAGAATATAGAGCACCTAACCTA | 30923 TGGATTCCCACTCAGCCACTGA | 41907 |
| 8282 CAGCTGGGTTTTGACCAGTTTTGTCT | 19940 TCTAAACCCCTTGTGGCTAGTAGA | 30924 GAGTCATGTCGTCAGCTGGTTTG | 41908 |
| 8283 CACAATAGGGCAATGGAAGGGAAAC | 19941 ATCCTACGCCCTCCCATTTT | 30925 CCTGCTGCACAATAGGGCAATC | 41909 |
| 8284 TGATCCTTAGTCTGGGCTCACA | 19942 GGCTGTGAGTTCAGTTTAGATGGTTTCT | 30926 CCCCAGGTTGCTTCTGATCCTT | 41910 |
| 8285 GCTCCAGTTCCACTTTGCGTTT | 19943 GGGATGGAATCTTGGGTGAGTGTTG | 30927 TCTGTGACGTGCTCCAGTTC | 41911 |
| 8286 CCCAGCCTATGCCCCAAGT | 19944 CACCATGGAGTGTTCAGAGACAT | 30928 CCTCCCCTGATGCCACCTATG | 41912 |
| 8287 GGCAGGGCAGATAGTTCCACTAA | 19945 ACCCCATTGACCAAAGAATGTGT | 30929 AAGCCAGGCAGGGCAGATA | 41913 |
| 8288 GGCAAATTCCTGAATATCTTGCCTTCAGT | 19946 GTACACATCCTTGTTTTCCACAT | 30930 CTGACACTGGCAAATTCCTGAATATCT | 41914 |
| 8289 CAAGCAGTGACCAGGAGACCTT | 19947 CCTCTCTGGCTCCCATGTTCT | 30931 TCCAGCAGGACAAGCAGTGA | 41915 |
| 8290 TGGTTGAAGCACTGTCACTGTAA | 19948 CTGAGATGCCGCTTGGTCTAAAA | 30932 AGAGGGAAAAATGAGGACTGGTTGAA | 41916 |
| 8291 GAAGTGGATATTTCTGGGACTCT | 19949 AGTCAGGCGCTACTCATACAGAAAAT | 30933 GGCAGTTGTGTGAAGCTGGATATT | 41917 |
| 8292 GCTCTCTCACTGATCCTTCTGGACTAA | 19950 GTGTAGTAACCCAGCATCAGAGTTCTT | 30934 CTATAACTGCTCTCTCACTGATCCTTT | 41918 |
| 8293 CACAAGCTATGAACACATCAGACTACA | 19951 CCTTCAAAGGTCACCGCCTAA | 30935 GAGCCCTAATAGTCACAAGCTATGAACACA | 41919 |
| 8294 GGGTGCATCACTTCTGCTCACAT | 19952 CCAACTAGATATGGCCATGTAACTCCATTC | 30936 TTGGACTTTGTGTGCATCACTTC | 41920 |
| 8295 GAGTTTTCCCCTCCAATGTGACT | 19953 CTGGTGAGTCTAATCACTTGGGACAT | 30937 CACCCACAGCCTCTTTATGAGT | 41921 |
| 8296 TGGACTGCTGCTGTGTCTACTGTCTA | 19954 TGAGTTATCAGCCTGCTGCTACTGA | 30938 GGTGCAGTCAGTTGGACTGCTGCTGTGT | 41922 |
| 8297 TGCTTGGAGTACCACATGAAACA | 19955 CTTTCAGGCTGCACTGGATGT | 30939 CACTGGATGGCTGCTTGGAGTA | 41923 |
| 8298 GCTTGCCTTTTCAAGAGACTCAGCTT | 19956 CAGCTTTCGCGAAGTACTAGGTAT | 30940 GGTGAGGGCTTGCCTTTTCA | 41924 |
| 8299 GCCACCACTTTAATCACCTTGCCTAA | 19957 GGTCTGTCTTTCAGCTCTGATCAAT | 30941 CTTCTATGTTCGCACCACTTTAATC | 41925 |
| 8300 ACACCTGGTTGAAACCAAGACA | 19958 GACTGATCCATTAAGAGAGATGCTGTA | 30942 CCTCCTGTCCAAAAGGATGCAAAC | 41926 |
| 8301 CCTGTGCTTGAGGAGCCAAGA | 19959 CTCCTTGGAAGGCATTTCTGAGTGT | 30943 TGTCAGTGGCCTGCGTTGA | 41927 |
| 8302 GTTGCATCCTCTGCTTTACTTTGAAC | 19960 CCCCTCCAGCCAGAGACAGA | 30944 GGGTTGGCCACATTTGTTGCAT | 41928 |
| 8303 CCCAGTTCCTTCTCTCAGGAATCA | 19961 TGACCTGTGTCGAGGCATCTC | 30945 TCCTCTTTCCCAGTTTCTTCTCT | 41929 |
| 8304 GTGAATGGCCTCAGAACATTACAGA | 19962 GCAGTGAGGGTTGGTAAATAGTGTTCA | 30946 GCTCAGTGAATGGCCTCAGAA | 41930 |
| 8305 CGGTTTTCGTCAGGGTGATG | 19963 GGAGGGTGTGCAAACTGTGT | 30947 CCTTGATGGAAAGGGTCCGGTTT | 41931 |
| 8306 AGGGGAAAGAGGGTGAATTTGATT | 19964 CCTGAGAATGCTTTTGTGGGAACTTTCGTT | 30948 AGGACAATCCATTAGGGGAAAG | 41932 |
| 8307 CCCACTTTGTGGTCTCCTGAGTGT | 19965 GTTTCAGCCAGGAGGATGAGCTT | 30949 GCAGGAAGGAGCTACCCACTTT | 41933 |
| 8308 GGCATAATGTCATGCCACTTTGT | 19966 GGGTTCAGTCACGTTGCTTGCTT | 30950 CGTTCAAGCTGGAATGGCATA | 41934 |
| 8309 GCCTCCAGTTTGTAATGCAAATAA | 19967 CCAACCGGTAACCACCACTTC | 30951 AGGGCGGCCTCCGGTTTGTA | 41935 |
| 8310 GGACCCTCAGCACTTTTTGTAGCATTA | 19968 GGGTAAGCCTTCTGAGGGAGCATT | 30952 GTCACTGGACCTCAGCACTTT | 41936 |
| 8311 CCTCTTTCTCCGTCTAGTGCTTCTA | 19969 GGAAGGGTTGTTCTTGGGACAA | 30953 AGTCTCCTTCCTTTTCTCCGTGTA | 41937 |
| 8312 AGGCAAAGGCTGTATTTAGCAGAAC | 19970 AGATATACCCATTCCTCCCCTTCA | 30954 TGCCTGAACAAGACAAGCAAA | 41938 |
| 8313 TCCTTTTAGTCCTCATTCTTCCCTAT | 19971 GGAACTTACAGTGCGTGCAATAGGGT | 30955 CCGAGAGACACAATTCCTTCCAGG | 41939 |
| 8314 TGGGGAGGACATGGCCTAAAA | 19972 GGCCAGGCAATAAGCTTTCCTT | 30956 GCAAGCAAATGGGAGGGACAT | 41940 |
| 8315 CTTGACCACCTCTCTAAATAAGCTGA | 19973 GAGAGTCTCTACTCTTAGCTCTTAGTGTT | 30957 TGTAACCAACTTGACCACCTCT | 41941 |
| 8316 GATGGGAGGTCATTTACCAAGT | 19974 CCAATGGAGAATTTCAAAGCCCTAGA | 30958 GAGGGAAGTTGATGGGAGGTCATT | 41942 |
| 8317 TGGTCTTGTCCCAGGTTGTAGT | 19975 GCCAACCAAGTTTTGTAGCAGTT | 30959 GAGGGGTATGTGACTTTGGTCTTG | 41943 |

| | | | |
|---|---|---|---|
| 8448 TGCCACTGTCTTGCCGGTAA | 20106 GGTTCTGTGAAPGCCAGCGCTAA | 31090 GCACCCATCTTATTGCCACTGT | 42074 |
| 8449 CTGTAPGTCACCCCAAGGGAGTAT | 20107 CTGGGCCCTCTAACAGTGAGAA | 31091 ATTGGGGTGAATCAGAACTGTATGT | 42075 |
| 8450 TCAGGTAGTCCCTTAGGATTAACT | 20108 CCATCCATAAAGTGTATACCCTCCTTGT | 31092 GCTACCCAGGGAGCCCCTTA | 42076 |
| 8451 GCCCAGCCAAAGCAGGGATATT | 20109 AGGCATAGTGGTCCCCGTGTA | 31093 CCTCTATTCCAAGCCCAGGCAAAAG | 42077 |
| 8452 CGAAAGTAAGGGCTAAAGTCTCTTCTGATG | 20110 TCACTCACCTGGGCCCTAAA | 31094 GGGTTTTAACGAAAGTAAGGGCTAAAGTCT | 42078 |
| 8453 GGAGGAGTGCCTCATGTTATGATAAGT | 20111 GGCTTGCCATAATACTGAGTGCAAAA | 31095 GAGTAAGGAGGAGTGCCTCATGT | 42079 |
| 8454 CCTCTCTGTACGATGCAACTGAAAA | 20112 TCAGGATGGCACTGGAACTTAATC | 31096 GCTTCATGGCCATCCTCTCTGCTA | 42080 |
| 8455 GGGACCTACCATTACCATTCCCATCT | 20113 GGATAATAAGGCGTATGGCAACAAA | 31097 CACAGAGGTGGGACCTACCATTAC | 42081 |
| 8456 AGCATGGTTGCAGGACAGA | 20114 GGGAGAGACAGACTGCAGCAATCA | 31098 ATTCAGTGCCCAGCATGGTT | 42082 |
| 8457 GCCAACACGAAGTCGCTTCACA | 20115 CAGTGTCTTCATCCCTCACGGAAT | 31099 GCAAGTTCAGGCCAACACGAA | 42083 |
| 8458 TGCCTGAATTCCAACGAGGGATTTT | 20116 ACCCTCTGGATGGGTAAGGTAAG | 31100 TGTGTTCCAATACCTGCCTGAAT | 42084 |
| 8459 GTGGTCTAGGCAATCCCTCAGT | 20117 GTCCCTCTGGGACAACATACT | 31101 GGTGCCAGTGGTGATAAAGTGGTCTA | 42085 |
| 8460 GGTTGTCTAGGAATAGGCTATAGATTGGAA | 20118 CCCCTGAACATTGCTGATCCTCTT | 31102 GGGGTAGTCAAGGTGTCTAGGAA | 42086 |
| 8461 GTGCAGTTTTGCTTTCCCTCTT | 20119 CTGCAGCTGTTTCTTTCCCATAGT | 31103 GGAAGCTTGAAACGAATTGTGCAGTTT | 42087 |
| 8462 CACGCAAGCTCCTTAAGCTAATGT | 20120 TCAGGCTCAGAGTGGAGAATACA | 31104 TGTGCACGCAAGCTCCTT | 42088 |
| 8463 TGTCCTTCCGTGTGCTGCTT | 20121 GCTTCAATTCCTTTCTGGGGAAGT | 31105 AGGCTTGGGGCTTCTGTCCTT | 42089 |
| 8464 GGCTTCTGGGAAAACCCAAGTAAA | 20122 TCCTCCTCCTGTCTTTTAGGCTAT | 31106 CCTCAGGGATTGGCTGCTGGGAAAA | 42090 |
| 8465 TTGCCACGGATTTGCAGTGA | 20123 GCCCCTACCCAGACCAGAAAA | 31107 GGTCCATACCCAATGCCAGGATT | 42091 |
| 8466 GGAGAATGGCCTTAGGAGTCTGACA | 20124 GAGACTAACAGGTAAGATCCAGGATTCAA | 31108 AGGGGAAGGAGAATGGCCTTAG | 42092 |
| 8467 GCTCCTGAAACTGAGCCACACA | 20125 AGGCAAGGCCTCACGAATATATC | 31109 CCCTAAATGCTTGCTCCTGAAACT | 42093 |
| 8468 GTGTCATTCACCACAGAACCATGT | 20126 GCAAAGGAAATGAATGGCATCAGTA | 31110 CCACGCGTCATCTTCCAGTGTCA | 42094 |
| 8469 CTCCGGCTTTAACACTTCAAAGACT | 20127 GCAAGAGACAGACTGCTGCAT | 31111 GTCACTCTCCGGCTTTAACACT | 42095 |
| 8470 ACTGACGCGAAAGGAAATAAGGAT | 20128 GGCTGTAGCTGCCATTTATAACTACTTTC | 31112 GGAAGTGCTCACTGACCGCAAAG | 42096 |
| 8471 GTGCAACTGGTGACTAAAGACCAA | 20129 CAGAGAGCAAGTAAGCTGTCCCTTT | 31113 CAGTGTCCAACTGGGTGACT | 42097 |
| 8472 GCTGTCTCAGTGCAACAACAAGTGA | 20130 GCTTGGGTTACATGCTTCCTGGTA | 31114 CTGTGTGCTGTCTCAGTGCAA | 42098 |
| 8473 CCCACTTCAGGCCCCTCTCTT | 20131 ATCGGGAGCTATCAGGGATGGAA | 31115 ACCCACTGCCCCACTTCA | 42099 |
| 8474 GGCACAGCCTTAGAATAGCCTCTAAAAT | 20132 GGATTTAAGTAGGGGAGCAATGTGA | 31116 CTGACTCTTGGCACAGCCTTAG | 42100 |
| 8475 GTCTGATGTAATGGAAAGAGACACA | 20133 GGAGATACTCAGCCTTTGGACATGAAG | 31117 CTCAAACTGTCTAAGTCCCATCTAATGAA | 42101 |
| 8476 GCAGAGAGAGGCTCACATCTTACCATT | 20134 GCCCTGGGGAGAGATGCTCTA | 31118 ACTCACCGATGTGCAGACAGA | 42102 |
| 8477 GGCATGTATTGACAAAGCGTCTT | 20135 GACTTGTCCCCTACCACCTATAATCAA | 31119 CACTCCAAAAGCAGTGGCATGT | 42103 |
| 8478 GTCACAGACTGCCTGACTT | 20136 TGTCCAAGGTCGTGCAGATA | 31120 ACAGCTTTGGCACGCAGACT | 42104 |
| 8479 CACGCTCAGAGAAGCAGGCATTTG | 20137 GGCTAGCCAGCAAGGATTCTGA | 31121 CCAAAAGAGGCACGCTGAGCAAG | 42105 |
| 8480 CCAGAEGCTGATCTGCACTACCAA | 20138 CTCATGTACCAGTACTAAGCCATTCT | 31122 ATACTGGACCAGAGCCTGATCT | 42106 |
| 8481 TGGGGTGAAGCCAGAAGTCA | 20139 TTCCCAGGTGGCCATGTAGC | 31123 GCTGTTGGTATTCCCTGGGGTGAAG | 42107 |
| 8482 GTCCACCAGAGGCTATGTTAAAAGGTA | 20140 CGCCAAGGCCTGTTCCTAAAAAC | 31124 GCATAGTCCACCAGAGGCATGT | 42108 |
| 8483 ACCAAGCCCAAGTCCTCCTT | 20141 TGGCTGAAAGCAGGTCGCTATG | 31125 CCGCTTTCTGACACCACCAA | 42109 |
| 8484 CACGTCGTAAACATGACTGGTTTTA | 20142 GACAGGCAGAGGAGTTCTGTGA | 31126 GGCAGGACACGTCGTAAACA | 42110 |
| 8485 GTCCCTATCTTATTTGCCACTGAT | 20143 CCTGTGGGTTGCTTCTCTCTCCT | 31127 CCCTCCTTCCCCATCTCTACTT | 42111 |
| 8486 CTTCTGTCAGACCTACCTGCATT | 20144 AGAGCCCTATCCCCACTGAAC | 31128 TCTCCGCTCAGCTTCTGTCA | 42112 |
| 8487 CTGTGTGGTTTGTCTGTGGGTTA | 20145 CATCTGTGGCCAGGTAAGGAATAG | 31129 GCACCTGTGATGCTGTGTGGTT | 42113 |
| 8488 GGCAACAGAGAACGTGATGAAG | 20146 GTGAATCTTCAACAGCAGATGAGTCT | 31130 TGTGGCATGAAGGCAACAGA | 42114 |
| 8489 TCCCTCCCAAACTGCTCTCA | 20147 GGGCTGAACAGTGGTCTGACA | 31131 CTGCTACAACCTCCCTCCCAA | 42115 |
| 8490 GGCAGAAGGCAGGAGCTTTGAA | 20148 ATGCCCTCTCCCCTGCAT | 31132 ACTAAAGCCTTTGGGGCAGAAG | 42116 |
| 8491 GGCACATGCCATATGATGATACTGAT | 20149 GTGAGAAATATGGAGACAGCCAGTT | 31133 GCTCTTGGCACATGCCATATGATT | 42117 |
| 8492 CGGCGAACATCTAAAACAT | 20150 CAGGAACTGTCTGAAGAGCTAAAAG | 31134 AACCTGAGACCTGTCCCTGTTG | 42118 |
| 8493 CTCCCAATGCAACCCTGTTCTTG | 20151 GCTGAAAGGCTCACTGCTAGGTA | 31135 GCCTAGTGTCTGTCTCCCAATG | 42119 |
| 8494 GGCAACCCATGTTATTAGTAGGGAAA | 20152 CCCACAGAGTATGGTGATGACTGT | 31136 GGTTGGATAGTTGGCAACCCATGTT | 42120 |
| 8495 GAGCTGGCAAAAGCACAACTT | 20153 CACTCCATCTTCCTAATGGCCTACT | 31137 CCTCAGTCAGTTAAGAGCTGGCAAA | 42121 |
| 8496 CGTCAAATGCCAGCTTGT | 20154 GGATCAAGGACTGTATTCGAACTGA | 31138 ATGTPGGGCTCGGCTTTGT | 42122 |
| 8497 CAGGGCCCCTTTTCACAACAAC | 20155 GGAGTTAGCCCTTAGACGTCTTGT | 31139 TTCCATCCAGGGCCCCTTTT | 42123 |
| 8498 TTCGTTGCTGCATTTCTAGTCT | 20156 GGTGTGCTGCAGGGTATGTT | 31140 AGACCTTATATCGCTGCTGCAT | 42124 |
| 8499 TCTCTAGATGCCCAGGAACTGT | 20157 ATGTGAGGAAATCATCCCATCTTGT | 31141 GGCAAGTTCTAGGAAGACAGTTATTCT | 42125 |
| 8500 GGGTGTGTGTTTCCACCTGTGT | 20158 AAGGCAGGTGCAGGGATGAA | 31142 AGCCTCACTGGTGTGTGTTTC | 42126 |
| 8501 GCAGCTTGTGACCATGACAAGAAA | 20159 CCTTATGTGACATCCAGGACTCAA | 31143 GTGTCTGCAGCTTGTGACCAT | 42127 |
| 8502 CGGGCAGTGAGTCAGGAGTA | 20160 AGGTTGAGCAAGACTACACCTAATG | 31144 ACTAGAACACGGGGCAGTGA | 42128 |
| 8503 AGGCACACAACAAACCAGAAGA | 20161 CCCCACCTGCGCTTGACTT | 31145 CTCAATTCAGCTAGAAGGCACAA | 42129 |
| 8504 CCACCTTATAGGGTAGCCCTCATATCT | 20162 TGTACCAAAGCTGGGGCTAGTAG | 31146 GCCTTACAGGGTAGCCCACCTTA | 42130 |
| 8505 CGTCAAATGCCAGCTTTAGT | 20163 CTCGGCGAGTGACGGATAAACA | 31147 GCCCGGGCCARTTTTCAAATG | 42131 |
| 8506 GCATAGACCTGCGCCTGA | 20164 CCTCTTCCCTTCATCCCTCTCTGT | 31148 GCTCTCTTGGAGGAGGTTGCATA | 42132 |
| 8507 CTCCAAGGAGGGTGTGGTCAAC | 20165 TAGGGCCATGCTCCCGCTACT | 31149 GCTGAGGGCCCTTTTCTCCAAAG | 42133 |
| 8508 GGGGTAGATCTAGTTGTTTGGACCAGT | 20166 GACGCAGAAGAGGCATGGTT | 31150 CCACTCCAGGGGTAGATCTAGTT | 42134 |
| 8509 CCTTCGCCAGGGTACCATTTC | 20167 GCACAGCCAGACGAGCTTAT | 31151 GCAATCAAGGCTGGGTCCTT | 42135 |
| 8510 CTCATCTTACCTGTTCTTACACGGCTACT | 20168 TGGGTGGCATCGGACCTT | 31152 CTCCCATCCTCCATCTACCTGTT | 42136 |
| 8511 GTACATACGCCAATTGGGTGTAG | 20169 GGGTATTCATTGGTACCCGATGT | 31153 GGTTTAPACCTGCACATGCCAATG | 42137 |
| 8512 CCAACATATACACTGCACCTTGAGT | 20170 CCAAAAGCATTTGAGAAGAAGCAGTGA | 31154 CCCTGAACAGGCATACCAACATATACA | 42138 |

FIG. 36N1

| | | | |
|---|---|---|---|
| 8513 CCATCTTTGAACCCCTACTGCCTAT | 20171 GTGTTTTGAAAGGCTAACTCTGGTT | 31155 CCCCATAGTTTCCTGCCTTCCATCTTTGAA | 42139 |
| 8514 ACTAAGGCAATGCTGAGTGGGAAA | 20172 GCCCTTGCTGGGGACTTTGTGTA | 31156 CCCTGTGCGAGCGACTCTACTAA | 42140 |
| 8515 TGGGAAGGTTCCAGGCAGTT | 20173 TTAGGGCCTGGAATGGGCTTTC | 31157 AGGCAAGGAGCTGGGAAGGTT | 42141 |
| 8516 TGGCAGCTACTGGAGACTCGTA | 20174 GGCTTGAACCACTTGGCTCTCT | 31158 GTGGTCAGTTCCTTATGCAGCTA | 42142 |
| 8517 CAGGAGATATACCTTTCACCAAAAC | 20175 GGGATTCTGGGACTTCCTGTAATC | 31159 GGATGGTCCAGGAGATGTACCTT | 42143 |
| 8518 GGGGTAGGATGGAGATAGGTTTCAGA | 20176 CCTCTTGAAGTGCCCCAAATATTCTTGA | 31160 GGGACAATGGGGTAGGATGGAGAT | 42144 |
| 8519 CTCAATTTGGAGGGTCTGAATTGGTTT | 20177 GGGCATATGAGATTATAAGGGCTAGTTTG | 31161 TCTGTGTGCCCGTCTCAAT | 42145 |
| 8520 GATCCAAGCCAATGGGGTATTTTC | 20178 TGCTCTGCTGATACTGTGACTTGTT | 31162 GAGTGCCAGATCCAAGCCAATG | 42146 |
| 8521 GCCATCTTAGATCACAGGAGGGAAA | 20179 GAGGGGAAATGGAGATAAAGTGTCTAAG | 31163 CGGTAAGAGCTGGAGAAGCCATCT | 42147 |
| 8522 CACCATATCCCCTAGGGTCTTGACA | 20180 CCAATCCTCCCTCTGCAGTTTC | 31164 CCAGCCATAGATCACCATATCCCCTTAG | 42148 |
| 8523 GGCAAACAGGGAGAATGGGAATAC | 20181 GTGAGGCATTTCCCCACCACTT | 31165 GGTGGAAGGACAGGGCAAA | 42149 |
| 8524 GTGCAAGGAGAGCTGAATCCATGT | 20182 TGAACCACAGCAAGGCAGATAC | 31166 GCTACAGGCTGACTGTGCAA | 42150 |
| 8525 GTGGTGGGGTTTGTTGGCATTTC | 20183 TGAGCCCTGCAGACACCAA | 31167 AGGTGGTGAGTGGTGGGGTTT | 42151 |
| 8526 CGCAACCCTGTTTGTTGCAAAGATTC | 20184 GCCTTCTTAGTTCCTAGTAGCTGATT | 31168 GGCTTATTCATTCGCAACCCTGTT | 42152 |
| 8527 GGGTAGAGGAGACTTCAGTAGTTGTCA | 20185 GCTGCTGCCCTGATTCTAGCTT | 31169 GGCAGTGGGTAGAGGAGACTTCA | 42153 |
| 8528 CTTTTTCTCATACCTGCCACTCT | 20186 CTTCCAAGTGCTGCCATTTAGTCA | 31170 CCTGCGGCCAGTTTCTACTTTTTC | 42154 |
| 8529 AACCACGGAATGCGGGACTT | 20187 CTCTACAATAAGTGCATCCCCAGAA | 31171 CCATCACAGCCTAACCACGGAAT | 42155 |
| 8530 TGAACCTGCCTATGCCTGTTTAAT | 20188 CCTGCTGGACAAGCTTCCTTT | 31172 AGTTCAAGTTCTGACCTGGCTAT | 42156 |
| 8531 GTCTGGGAGGAGGAACAGGAAA | 20189 ACCCCTCCTCCACTGGTTTCA | 31173 TGGAAGGGGAGGCAACTCTGT | 42157 |
| 8532 GTTTGATGCAAAGGAAGGAAACT | 20190 CCCCATTGATGCCAAGAGATCCTAAG | 31174 GGCCACTGCTTGATGCAAAG | 42158 |
| 8533 GCCCAATGCCGTTAAAGAACTGA | 20191 GCTGAGCATGAAGTCAGGAGAAAC | 31175 ACAACAAGCCCAAGGCCGTTA | 42159 |
| 8534 CTCTCCAATTTAGCACAGCATA | 20192 GAGAGGAAGAAACTGACAGGTACTCAAG | 31176 CACATGAGGTGTTTCTCTCCCAAT | 42160 |
| 8535 CCCTAACTAGGCCAGGGAGCAA | 20193 CTGCTCAGAATTTGCCTCAAGTTT | 31177 CCTCATGGCCTGAAACAAACCCTAAC | 42161 |
| 8536 GGGGCTTCCCATAGCTAGGATTGT | 20194 GAGAGAACCCTAGGACTCCACATTTC | 31178 CAAAGGTTTAGGGGCTTCCCATAG | 42162 |
| 8537 AGGGGAGTAGCAAAGCCACTATTG | 20195 GCTGAAGCATAGTGGTGCTAGAT | 31179 TGCTACATTCAAAGGGGAGTACAAAG | 42163 |
| 8538 CACTCTCAGTGGGAAGGGAATTAG | 20196 CCACAAAGTTTTTGACACTCCTCTCT | 31180 GTCATTACATCTGACCCACTCTCAGT | 42164 |
| 8539 TGTCTTGAAACAGCTCGTCACT | 20197 CACACAAGGCAGTGTGTTGGTCCTA | 31181 CAATGCTCAGTCTCCTGCTTGAAAC | 42165 |
| 8540 GAGACTCAATAATGGCTGTAGGGATTTTA | 20198 ATGGGTACAGAAGCTACTTT | 31182 GGCACAGAGTGTGAGACCCAAT | 42166 |
| 8541 CTCACCAAGGTCCACCAATTTTCAT | 20199 GTCAAGCTATAAACTACAGACCCATCCT | 31183 GCTCTCCCAAGAATTATCTCACCAA | 42167 |
| 8542 CTCCACCCAATCTGCTGACCTAAGAAC | 20200 CTCATGGAGTTGAAGGCTTGGTTTG | 31184 GGGCCTAAGCTCCATCCAATCT | 42168 |
| 8543 ACTGCTTTCTAGCATGTCACCAA | 20201 GAAGTTTGAAAGGCCACTAGGTGTT | 31185 CCATCACATTGCTCAAACTGCTTTC | 42169 |
| 8544 GGGAATATCCTTGCAATAACTCCTA | 20202 GGCTCAATATGGAACCTACATTGTT | 31186 AGGACGTGCATTGGGAACATC | 42170 |
| 8545 GGGGTCCAGGTTTAGTTAGCAGAT | 20203 CGAGGGAGGTAATGGGAGCTAGA | 31187 CCAAGCAAGGGCTCAGGGTTTA | 42171 |
| 8546 GGCTACGTGACTTCTGCTTAGT | 20204 TGCATCCCAACAGGGCTTTC | 31188 CTGGATGCATAAACGCTACGTGACT | 42172 |
| 8547 CATCAAGATGGCTAAGTGACCAA | 20205 TGTCCAGGTATCCACACTGA | 31189 GGCTTTTTCCATCTAATCACCAAGATG | 42173 |
| 8548 GCCTGGGTAAGTGATGGCATAG | 20206 GGTTCCAAGGGCACCACATTG | 31190 AGCTACACAAAAAGCCTGGGTAA | 42174 |
| 8549 GGTCAACTATAGCCTTGCACGTGAT | 20207 CTGATACACCAGTGTCCCTAATTCCAA | 31191 CCTGATCCACTGGTGGTCAACT | 42175 |
| 8550 CGCTGACTCCAAGTTCTCTATTTG | 20208 CTGATCTTTAAGGCCCAATACTGTAGA | 31192 GATTAAAATGCGCTGACTCCAAGT | 42176 |
| 8551 GGGTGTGCTGTTTACTGGAT | 20209 CACCAAGCCAGTCCTGTGAGATA | 31193 CCCTGGTGGGTGTTGCTGTT | 42177 |
| 8552 TGTTGGAGGTCAGTCAGGTTGT | 20210 GAATGATGGGAGCTAGGCTCTAAG | 31194 GGCTTAGAGAGGGGAAGCAACT | 42178 |
| 8553 GTAGGGCAGATCAAAGGAATGAGA | 20211 ACTCCCCTGCCTGGGTGAT | 31195 AGAAGGTTCTAGGCAGAACAGTAG | 42179 |
| 8554 CCTGAGCCAAACCATGCATCTTC | 20212 GCTTTCTGGACTTAGCTCTTGTTCA | 31196 CCTCCTGGCCTGAGCCAAA | 42180 |
| 8555 AGGTTAGGTGGTGCTCAGCTATG | 20213 CTTGCTAGCTTCTGGTCTCATTC | 31197 ACAATTACAGCAGCTACTAGGTAG | 42181 |
| 8556 AGAGCATCCTCCAACCAACTTC | 20214 CTGGGAAGCAGTCTTTCTGAGACCAA | 31198 CCCAAAGGCAGGACCCAAA | 42182 |
| 8557 CTGGCACACCTGTTGATGTTGAAG | 20215 GGCTAGCCTCCATGTCAGCAAA | 31199 TTACCCTGGCACACCTGTTG | 42183 |
| 8558 GGGTTTACAGAAGAGGTGGTATGA | 20216 CTCCACCTGCCAAAATCCTACT | 31200 GGGAAATCCAGGTAGGCTTCACAGA | 42184 |
| 8559 GCTAGGCGCTACCCCTAGAAG | 20217 GTGTGTGTTTGAGACCCTTGCATCT | 31201 ACAGGCACACACCACTGCTA | 42185 |
| 8560 CCCACTGGAAGGAAGCTTAAGATG | 20218 CTACCGAAAGCTGTTGACCAGA | 31202 GCTTGCTCCTGGATGTAGCAGAT | 42186 |
| 8561 CCCACTGGAAGGAAGCTTAAGATG | 20219 CCTTTGCCTGTTTCCTGCAGATT | 31203 CCTCAATCTCCACTGGAAGGAA | 42187 |
| 8562 CTAGCTCTCTCGTATCATTCAGACTAC | 20220 AGTTTTCCCTGAAAGGAGTGACAT | 31204 TGATGTGCTAGCTCTCTCGTA | 42188 |
| 8563 TTCACACAGCTGTCACAGACAA | 20221 TGTCTGCCTCCCACATCTCT | 31205 GCCTTCACGTACCATTCACACA | 42189 |
| 8564 CTTGAGGTCTGATTGGATGAAGTGA | 20222 ACAGGACCATCCAATCACCTTGAA | 31206 GTGGGCCAACTTGAGGTCTGAT | 42190 |
| 8565 CACGTCCACTAAATTCCTGCTCTTG | 20223 CCTAAACACTTGCTGCTCTTTACACATCT | 31207 CGCTTGAAAACACGTCCACTAAA | 42191 |
| 8566 CCAGAGGCAAAGTGAAGACTCA | 20224 GCACATACCCAGTTGGGAAAC | 31208 CTTACTACTAGTGTCCAGAGGCAAAG | 42192 |
| 8567 GGCATAGATAAGCTGATGAACACAAG | 20225 GGGATTGGGTGTTGACGATGA | 31209 GGCCTCTTGGCCATAGATAACCTGAT | 42193 |
| 8568 TGAACTTGATTCTACAGGCAGTGAT | 20226 GATGTGTGTCACCTTCTCTTCA | 31210 GGACACCCAAAGAATTTGAACTTG | 42194 |
| 8569 TGGCTGCTACACCAAATGGTT | 20227 CCCCTTGCATTGGGCACAGA | 31211 TCCCAGGATTGGCTGCTACA | 42195 |
| 8570 ACAGTGCAAAGAAGAGGCTTAAA | 20228 CTGGAGGGAGTGTTTTCAAACCCAAAC | 31212 CCCCTGGGAACAGTGCAAGAA | 42196 |
| 8571 GGCTTTGTTGACTGCTTTGACTAACAGA | 20229 GGGCCTGAAAACTGGCATGA | 31213 AACAGGCTTTGTGACTGCTTTG | 42197 |
| 8572 CCTGCCAATCTCTTCAACTTGT | 20230 TCGTCAACCTGTGCATGGTAAG | 31214 CACTTTATCTTCAGGTCCGCCAATC | 42198 |
| 8573 GGTCTGTTCCTAAAGGTCGGAGACT | 20231 GCAATCAGGACGATCAGACAAAAGAAG | 31215 CCTGAAGTCTGGTCTGTTCCTAAAG | 42199 |
| 8574 GGGGATTGAAATTCAGCACCACCAA | 20232 CTCTGCTTTTGCAGGGATTGT | 31216 TGCTGCTGAGTGGGGATTGA | 42200 |
| 8575 CGGAGTAAGTCTTGTCTCAAACAGCAT | 20233 ACCCAAGGAGACAAGAGCATCA | 31217 GGGGCGACGGATAAGTCTTTGT | 42201 |
| 8576 AAGGCAGGTGCTGCTCCTAT | 20234 GAGGACTGAAGTGGTAAGTCACA | 31218 AGCTGGCCCTGTGGAGGAA | 42202 |
| 8577 GGGGTGCAGTAGCCCTCTATGAA | 20235 GCCCAAGACTGGCATTCTCA | 31219 ACCTCCTCAGGGGTGCAGTA | 42203 |

FIG. 36N2

| | | | |
|---|---|---|---|
| 8578 CGTTCGGAAGCTAACGCTTTCT | 20236 ACCTTTTCCGACTGGGATGATT | 31220 GCAGGGAAGATGGCTTGTTTC | 42204 |
| 8579 ACATTGTACAGATGCTGCCTAAGAA | 20237 CAGTGCTGGATGGCTGTGATAC | 31221 GCGCCAGGTGCAACAACATT | 42205 |
| 8580 GGATGAAAAGTGGAAGACAGGGAAA | 20238 CGCTTTTGTTAGCATCAGTTCCTTGA | 31222 AGACCATGAGTGAGGATGAAAAG | 42206 |
| 8581 GTACCCACTTACCTCTCCATAG | 20239 CCTAGCTTGTTGCCAAGAGGTTCT | 31223 TGTCACCTGGCACCTACTTAC | 42207 |
| 8582 GAGCTGTTGTGTCATGGTGAAAAAT | 20240 CCAATTCACGGGGAAGAAGT | 31224 CCCATGTGAGCTGTTGTGCA | 42208 |
| 8583 TGCTAGAGACTCAGAATCCAAGA | 20241 GGCAGAGGATCCCTATGTTACCAGTTC | 31225 GCCTGGAGAAGCATGCTAGAGA | 42209 |
| 8584 CTGGTCCCCATGTTTGCTTTCT | 20242 TGTCCCCTGTGGAAGTCAGAT | 31226 TCACGGCCACAGTGCATCAAC | 42210 |
| 8585 AGCGGTGTGAGGTAGAGACACT | 20243 AAGAATTGCTTCACCTAGCCTGAT | 31227 TCCTGGACTTAGGAGCGGTGTGA | 42211 |
| 8586 GCAGCCTGACAACCTTGGTAAGT | 20244 GGCCTTATACCCAATAAAGCCTCTA | 31228 GCTATCATGCAGTCTGACAAC | 42212 |
| 8587 CCTTAACTAGAACATTGGCCTTAGGAC | 20245 GGGGAACTCATGAACTCTACCTGAA | 31229 GGTAGTCAAGAGATGATGGTGTCTCT | 42213 |
| 8588 CTGTGAACCAATAGACGGAATTGATG | 20246 GGGACATTACCCAACCACGTT | 31230 AGTCGTGGCTCGGAATCTGTGA | 42214 |
| 8589 CAGAGCTGTACTAAGAGCTTGCTT | 20247 CACTGACTTCTCTGACCCAAGA | 31231 GACCCATTATAAACAGAGCTGGACTA | 42215 |
| 8590 TCCACCTCTTCGCTGCCTTTG | 20248 TGGGAAAAGTTACGGAGTCAGATG | 31232 TTTTGCAATGAGAATCTACCTCTTC | 42216 |
| 8591 TCCCAAAGTGAATGCTGACATAGA | 20249 CGTGTCAACTTTCTCCTTACCTGAT | 31233 TTTGACAGAGGACACTCCCAAAG | 42217 |
| 8592 GTGTCGTTGCCTATACAACTGTTAC | 20250 GGTTCAGTGGAGCTTGTAGTCTCA | 31234 CCTGTGTTGTCGTTGCCTATAC | 42218 |
| 8593 GGAGCCTACTGGGAATCAGGAA | 20251 CACCCTATGAATTCAGGGCTCCTTC | 31235 CTGTGATAAACCATGGAGCCTACT | 42219 |
| 8594 GGAGAGCTGGGCTTGTTTCTGT | 20252 TGGGATGGGATAAGGAGTAAGGAAA | 31236 GCTGGAAGAGCTGGGCTTT | 42220 |
| 8595 GCCATATCAGGAAAGGAACAATG | 20253 CCCATCCAGTGAGGTAGATGTTG | 31237 TGGAGAGGTCAGATGCAGGAA | 42221 |
| 8596 CGATCAGGACACTGAGCCTATCA | 20254 TGCCTTGTCTGCCTTCCTTTCTA | 31238 CCAGGACATCATCAGGACACT | 42222 |
| 8597 TTGGAGGGTAGATGAAGAGGTAGAT | 20255 GGACTGTTTTCCAAGTCTTCACCTT | 31239 GGGAACCTTTGGGAGGGTAGATG | 42223 |
| 8598 CCCCAGTGCAACACAGAGCTT | 20256 AGTGTGTCCCTAGCCCAAGT | 31240 ATGGACAGCCCCAGTGCAA | 42224 |
| 8599 AGGAGCAACGGCGCCATAC | 20257 GGCATATATGTAGGCCGGTTGTAAG | 31241 ACGCTGGCTGGAGGAGCAA | 42225 |
| 8600 CGGCCCTCATCTTTCAGGAAGTA | 20258 CCCCGTAACCAGATGATGAGTTT | 31242 CTGTCCATACTTGGGCCTCATC | 42226 |
| 8601 CTGGCTGCTTCCTCTTCCTATC | 20259 AGGGTAGTAGACAGGCTTGAAGTT | 31243 CACACATGTTGTATTACTGGCTGCTT | 42227 |
| 8602 GGGATCTAGGCATATAAACAGTTCTCTC | 20260 CCCGGATGGGGTAGCATTTCAA | 31244 GGCTTAGGCAGGGATCTAGGCATAAA | 42228 |
| 8603 CTGGAGCTCATTGGCTGGAAG | 20261 GCAACAAGACTTTACCCAGAGACCAA | 31245 TCCCTACACAGTGGAGCTTCATTG | 42229 |
| 8604 GGTATTCTCTGCTGCATGGATCT | 20262 GGTCCAATGGCAGACTGTTGAA | 31246 TCTACCTACCACGCTGGTATTCT | 42230 |
| 8605 GAGCCTCTTAAACTTCTGGAGCTAAAC | 20263 ACTGGCTAAGGAGAAGGGTAGT | 31247 GGAGATGAGAAATAGACCCCTTAAAC | 42231 |
| 8606 CCTTCTCAGGGCTTGGTTTC | 20264 TCCCTGCCCAGGACCAAGAATA | 31248 AGGCAGGTTGAATCCCTCTCA | 42232 |
| 8607 GCTAAGGACACCATCAAGGATAGCAA | 20265 CTGCTTATTCTCCTGGTTAGCACCAT | 31249 TGGTGTTGTTAGCTAGGACACCAT | 42233 |
| 8608 AAGTCAGGCGCTGTCTGGAA | 20266 TATGTCTCATCCGGCCCTCTCT | 31250 GGTGTCGTCTGCAGCAAAGT | 42234 |
| 8609 TGGCAGTGAGGAGGGATTC | 20267 CCACCACCTCCGAGGATGAAAG | 31251 AGATGCTGCTCTGGCAGTGA | 42235 |
| 8610 TGGGAGGAGATTCGCCTGATCA | 20268 AGGCAGCCTTACACATGACATT | 31252 GCTGCCTGCACAGGGATAAA | 42236 |
| 8611 GTCTAGATTTAAGAATGAGAGGAGATT | 20269 ACATGCCCTTTCCACTTTCTTTTT | 31253 CCAAGGCTCTAAGATGCAGTCCAGAT | 42237 |
| 8612 CTGTGCCTCAAGCCTGTACAAAGT | 20270 CTGGCGTCTGTATGAGGCTTTG | 31254 GCATCTGCAAACAAATCTGTCCTTCAA | 42238 |
| 8613 ACCCCTCTACCTTCCAGTGAAC | 20271 GGCTGGGATAAATGACAGTCCTTGA | 31255 TCCTCCATCCACCCCTCTACCTT | 42239 |
| 8614 GCCAGTTTCTCAGCTCCAAGT | 20272 GTGTGCGCTTCTGTGGGTTT | 31256 GGTGTTTCCAGATGCCAGTTTCTTC | 42240 |
| 8615 CCCTGAAGCTGTTCGGCTTTG | 20273 TGGCACTGGTGGACTCAGA | 31257 GCCATCTGCCTGCCTGGA | 42241 |
| 8616 TGGGGAGGGATCAGAGACACA | 20274 CCCCAACTGGAATAACTGTTGCTT | 31258 AGGAGACAGAGCTGCAGGAT | 42242 |
| 8617 GCCTCTTGAGGAGGGACCTTTC | 20275 GAATGGGAGAAAGAGTGGTGGTAT | 31259 CTGATGAATTAAGACAAGGCCTCTTGA | 42243 |
| 8618 TCCCACTGCCCAAGTCTTTGA | 20276 GACCGAGAAGCAGTACACTGAGA | 31260 GGGAAAAGGCTGTAGGGACTTC | 42244 |
| 8619 CGCCAATGGCTTCCTTCACTT | 20277 CAGCTCCATTCCTCACAAGACAGT | 31261 TTTGTGGGGCACGGCAGTG | 42245 |
| 8620 CTTCCCAGCATATTGCAAAGACACA | 20278 AGTGCTGGGTGGCCTTCCTA | 31262 TCAGCAGCTCTTCCCAGCAT | 42246 |
| 8621 GAACTCTGTGTGGACCTGATCAAAC | 20279 CTTGGTCCACTAAGTGCTGTCT | 31263 GTCTGTTCCCCTGAACCTGTGT | 42247 |
| 8622 GCTGTGGTTGGGCTGAAGAATT | 20280 GGGAGCATGAGCCATCCATCAT | 31264 GTCTTAAGGCAGCTGTGGTTTG | 42248 |
| 8623 GCTCAAGGGTTGGACTCCATGT | 20281 CTCGAAACTCATTCATCTTCTGTGTAAG | 31265 GAAAATCTGGGGCTCTGCTCAA | 42249 |
| 8624 GGGATGTGGTGGGAATCACCAT | 20282 TCAGTGCTACCATCAGGGATGCA | 31266 GGCAAGGTGAATGGGGATGT | 42250 |
| 8625 CAGAAACTACCAGGTGCTTCATGGTT | 20283 CCTCGCTGGAAACGGGAAA | 31267 CCGGCCTTTCGTATCAGAAACT | 42251 |
| 8626 GGCCTCATCTCCCAGTGCTT | 20284 GCAGTGCCTCTGCTCCAA | 31268 AAGTGCCAGGCCTCATCTCT | 42252 |
| 8627 GTCAGGGCATCTTACTTTTCTGTA | 20285 GGCATAAAGAAGATCACGTTCACA | 31269 GGACAAGTCAGGGCATCTTA | 42253 |
| 8628 ACTCTCCTTTACTGGATCTTCCTACT | 20286 TGAGCCTAGTGGAGGTCACTT | 31270 GAGACAGAAAACTAAGACTCACTCTCCTT | 42254 |
| 8629 CCTTGGAGTCAGCCCTAGATTCTTC | 20287 CCACAATAATTGGTGACTGACTTGCTA | 31271 GCCCAAAACATACCTTGAGTCA | 42255 |
| 8630 AGCCCCTGATGTACCTTTCTGT | 20288 TGCCTAGTGTTCACGAGTTAGA | 31272 AGAGTGCCAGCCCTGATGTA | 42256 |
| 8631 CTAGTCCATGGATACTGCCTTTTG | 20289 GGGTTCCTGACCTGCAAATCTCT | 31273 GCCCAAGGAGGTTAACTAGTCCAT | 42257 |
| 8632 GCCAGCATGGTTGGCTTTG | 20290 GCAAGAAAGCATCATCCATTACA | 31274 GAAGACCTAAGGTGCCAGCAT | 42258 |
| 8633 GGCCACCTTAGAGTTTGTTGCT | 20291 CTGTAGCTTCTGTGACTGGTTTC | 31275 CTGGTCCTATGGCCACCTTAGA | 42259 |
| 8634 GGGGAGGGTCAACTGCCCTCA | 20292 GGGGCAGAGGGGACTAAGGTAA | 31276 AGTTCTCATGGGAGGGTCAAC | 42260 |
| 8635 CCACCCAFTCCAAGCCAGTCA | 20293 CTCCTCCAACCTTAACACCTAGATATG | 31277 ACAGCAGCCTCAGCCAGTCA | 42261 |
| 8636 TGAATCCTAGAGAGCTGGAACTTTG | 20294 CAGCTCCCCTCAAAGTTCAGATAG | 31278 CCGCGCGTGTAAGGACTGAAT | 42262 |
| 8637 GTGTTACCTGTCATTTCCTACCCTTAG | 20295 GCAAAGGGAGACCTTCATTCCAA | 31279 CCAGTCACTTCTGTGTTACCTGTCA | 42263 |
| 8638 ATTCCCTGTGCCGGGACTTC | 20296 CGCAAAGGCCCAGGAAAAGACA | 31280 GGGCCTGATGTCCATGATGATTC | 42264 |
| 8639 GCAATGCTAGCTCTTAGCTATTCTA | 20297 GGGCCGGCTTATTTACCCTTCTC | 31281 GTGTTTTAGATGGGCTACAGCAATG | 42265 |
| 8640 GCCATGTGCCTTTGGTCATGAGA | 20298 GTGTAGGACTCAGCCATGTTCA | 31282 GTGGAATGCCATGTGCCTTTG | 42266 |
| 8641 GACAAGCCTCTTCACGATGAAACA | 20299 GAAGCCCAGCAAGTGGATCA | 31283 GCTGGACGAAGACAAGCCTCTT | 42267 |
| 8642 GGATATTTGTACGGGGACCTCCTATAC | 20300 AGGAGGTGCTTGTATTGACACTTG | 31284 TGTCCGACTACACTTGGATATTGT | 42268 |

| | | | |
|---|---|---|---|
| 8708 CCCTTAGTTGTGAAGGATGGTTCT | 20366 TCCTCCTTGGCCCAATCAAAG | 31350 GTCCTCTTGTTTTCCCTTAGTGTGAAG | 42334 |
| 8709 GCTGGTATCTACTGGCACACA | 20367 ATTGGCTAAGCAGGCCAATCT | 31351 TGTTACTACTTCAGCTGGCATCTAC | 42335 |
| 8710 GGACTGTGTCGGTGGTTTGA | 20368 ACCTGGTGTTCTAGTCTACTGTGA | 31352 GAAAAGAGTGGGAAGGACTGCTGT | 42336 |
| 8711 CAGTGTAAGTTCTGAGGTCCTGTGTT | 20369 ACTTGGGGAACAGAAGATGTCAA | 31353 GGCAGTAATGGGCAGTAAGTTCT | 42337 |
| 8712 GAEGAAAGGGTGGCCATCATCA | 20370 CTACTAGGAGCTCAGTTGTGT | 31354 CGACTACCAAGTTCTGGAGGAAAG | 42338 |
| 8713 GCTGCACAGGATTTTCACAATG | 20371 GTGGTTACTGCATCGGACAGT | 31355 AGGGCTGCTGCACAGGATTT | 42339 |
| 8714 TTGCCTGGGCTTTTGAGGTATT | 20372 GGGAAATGCTTCGGGACCTT | 31356 GCTTTTGTTGCCTGGGCTTT | 42340 |
| 8715 CTGCTCTTTGCTCCGTGACA | 20373 CTTTCGGCTGGTTGGTCTGA | 31357 TTCCCCTGTCCTCCTGCTCTT | 42341 |
| 8716 TCAGACTGGCCTTCGAGACA | 20374 AGTGATGGCTCCTGCCCAAAC | 31358 ACAGGCCAAGCCTCCTCAGA | 42342 |
| 8717 GGACCCCAGTCACTGCATTTCA | 20375 GCCCTCCCAGGCTAAGAATAAT | 31359 CACATTTGGAAAGGACCCCAGTCA | 42343 |
| 8718 GCAGATCTTGGAGATGACCATAATTC | 20376 CCTAAGCCTTCTGCAGCTGAAAT | 31360 CCTCCCAGATCTTGGAGATGA | 42344 |
| 8719 GCAAGAGCCAACTTCTGATCTGT | 20377 GTGAAGCAGCTGGAAGTCTCT | 31361 GGGAAACCAATAGCAAAGAGCCAACT | 42345 |
| 8720 AGGTAAGCAGGGCAGTTCTATGA | 20378 ACTGCCTCCCATTTCCATTTCT | 31362 TGCAAACAACCCAGGAAGGTAAG | 42346 |
| 8721 CGTGGTAACACCCACTCAAG | 20379 CTTCACTACGTAGATGCCATCCTATT | 31363 TTGTGCGGCGCGACGTGGTA | 42347 |
| 8722 GGGTCCAAAGGACATTTCTAGACTA | 20380 GACCCCTCTGTGCTCTTTGTGCAT | 31364 TGACCTGCAGAGAGGTCCAAAG | 42348 |
| 8723 AGGGCTGTGTGAGGTTCAT | 20381 AGCTGCCTCCCAGAGAAGAT | 31365 GATGGCATTATATCAGGGTGTGT | 42349 |
| 8724 GCCTTGAAGTTGCCTTCAAAACACT | 20382 AGTGCTGTGGGCAAAGGAA | 31366 TGCCCCTAGCCTTGAAGTTG | 42350 |
| 8725 GCCTGACCAATTCTGTGGCTCTT | 20383 GGCTTCACGGCTGAAAGGAT | 31367 CCACCGTTGCTGACCAATTCT | 42351 |
| 8726 GGTCTCATCTCACTCTGTCTCAAC | 20384 TGGCAAGGCATCCCAGAA | 31368 CGCTTTCCCAATGTACCAGGTCTCA | 42352 |
| 8727 CGGGCAATGGATAACCAAGTTTCTTC | 20385 GTTTCTGCCATGTAGGAGCTAGT | 31369 GCTCTAATAGCTACGGGCAATGAT | 42353 |
| 8728 GTGTCATCCACATTGAGTGAAAACT | 20386 GGACTCCAGAAGCTTCAGACAAC | 31370 GGTTTGACCTCAACATGTGTCAT | 42354 |
| 8729 GCCKCGCCACCTTTTCCACTCT | 20387 GGCAAGAGAACAAGACCTGGTGAA | 31371 GTGGAATCTACCCTCGTCAGCTT | 42355 |
| 8730 CTTGGTCCTTCGTGCCTTATTTAGT | 20388 GCACAAGACCATTTAGGAAAACA | 31372 TCTCTCCAGGCTTGGTCTT | 42356 |
| 8731 CGTGGGCCTAAGTTTTCACTCATT | 20389 CTATAACTTCCAGTAACTGTGCTCCTT | 31373 TGTGTAGAAGTTTACGTGGCCTAA | 42357 |
| 8732 TGGAGACCCATGCTGTCAGGAA | 20390 CCCCACCTAGCCACTCTCTAC | 31374 GTGTCTGGGGTAGTCACAGATG | 42358 |
| 8733 CCAAGGAGGCTGAATGAAGTGAT | 20391 GGGGAGGGAAGAAGAAGCATAATGTCA | 31375 CATACCAACCAAGGAGGCTGAA | 42359 |
| 8734 TGAAGAACCATTGCTGTCCTGAT | 20392 GGACCTGCTCCTTTCTGTCCAA | 31376 GCAACTATCAGGGTGAAGAACCATTG | 42360 |
| 8735 TCCATCCACCTCCGTCTCCAAA | 20393 GCCACCTTTCAGGACTTGCTAA | 31377 CTCCTGGACTCAAGCAATCCAT | 42361 |
| 8736 AGGGTCATTTTCTGGCCTTCACA | 20394 CCGTTCAGGCGTAGCTCACA | 31378 TTCCTTCAAAGCAGAGGTCATT | 42362 |
| 8737 GTGTTCTGACACGGACGTAAG | 20395 CTGGTTCTCAGGTCCTGCCTTT | 31379 TGCCCCAAGGCTAGTGTTCT | 42363 |
| 8738 GTGGATCTTTGCTCTTGGTGAAGATGTA | 20396 TCCAGGGCAGTGCCTCCTT | 31380 GGCATTTTGACTCTGGATCTTTGCTCTTG | 42364 |
| 8739 TTGCGGCATGCCGTCACT | 20397 GCTTTCTTTTAGTTCGCCTTAAGATT | 31381 CTTGGCTGCTTTTGGCAAGT | 42365 |
| 8740 GACAAGGTGGTCCTCAGATAGATTACA | 20398 TTCTCTGGCCAGCCTTTAAGTTT | 31382 ATCTACCTGGCCTGCAAGACAAG | 42366 |
| 8741 AGTGTGCTAACTTGGCTGCAA | 20399 CTCAAGGTCAGTCAGCTCTGT | 31383 GCACGGCTGGGTGGAAATAAGT | 42367 |
| 8742 GGCAGTGGACTTAAATATGGGGAAGAT | 20400 CTGTTCATGGCATCCCTAATGT | 31384 GCATGAAGGTGGCAGTGGACTT | 42368 |
| 8743 GCCAAAGGTTGTCTAACTCGTAGT | 20401 CAGCCTAGTGTTTTGTGACCATCTGT | 31385 GGAAAGATTTCCCAAAGGTTGTCTA | 42369 |
| 8744 CCTGCACCGTGCCTTCTCATT | 20402 GCCAAACAAAGGGAGCACTGTT | 31386 GGCTTCTGTGCACCCTGAA | 42370 |
| 8745 CCTGGACTCAGCTGCTGTGGTATG | 20403 ACTGCAGCAACTATGCATCACA | 31387 GTGTTGGGAGGCGTCTGGAATCA | 42371 |
| 8746 GCAGCTACACATCCCCTCTCT | 20404 GGCTTCTCTCCCTACCCAGATT | 31388 GCAGCAAGCAGCTACACAT | 42372 |
| 8747 CCTCTCCATTCTGGGCCTCCTT | 20405 AATGGGGAAGGGCTGTGAGTAG | 31389 CACCCGCTATGTCCTCTCCATTTC | 42373 |
| 8748 GCAGGAGTCAGAAAAGTAACACAAA | 20406 CTTCCCTATCCAGCTGGTCACT | 31390 CCAGAGGAATGCAGGAGTCAGA | 42374 |
| 8749 GTGAAGGGGCTGAGTCAAAATGAAC | 20407 GCAGCAGGTGATAATGCAGAATG | 31391 ACTCTGTGAAGGGGCTGAGT | 42375 |
| 8750 CAGGGTTTTCAGCAGCCCTAATC | 20408 ATGTGTCCGCAGAGGGCTTT | 31392 GGGTAGATAAACTGTATCCAGTCGGTTTTC | 42376 |
| 8751 GTGTCATTTGCTCGTTTGCCTTT | 20409 GGAATCCCATGTAAGGTACTTCCTGTT | 31393 AAAAGCTCCTGGCTGTGTTCAT | 42377 |
| 8752 GGTGGGGCACAAATTCAGTTAC | 20410 GTGGGCTTAGATTTGGGATATTGGTA | 31394 GGAGGTAGGTGGGGCACAAA | 42378 |
| 8753 GCACTTTACACATCCTGATGTCTCTT | 20411 AGTGGGGTTTTCCACCCTATC | 31395 GGATCCCAAAGCACTTTACACATC | 42379 |
| 8754 CCACGCCACAGACACCAT | 20412 CCTGGAAAACACCACGCTCTT | 31396 GCTAAACAGGTCTGCATCCAGGCTTG | 42380 |
| 8755 GCCTGACATTTTCCTAGAGGGAGAT | 20413 GAGAAGACGACAGGTCATTTCCTTTG | 31397 CTGAACACAAACCTGCCTGACA | 42381 |
| 8756 AGAAGGGAACTCAGAGGTTACCAA | 20414 GCAGGGCATGACTGACTTCT | 31398 CCAATGTCAGAACTAGAAGGGAACT | 42382 |
| 8757 GGCTTCAGCAGGGTCAGACT | 20415 GTGTCCATGCTCTAGGACATCAT | 31399 TGTAGAGTCCTCTGGCTTCA | 42383 |
| 8758 CCCACTACACCATGAGCTCTCCT | 20416 CCAGTAGTGCAGTTCCAGTCTGAGT | 31400 CCTTCTCCTACCCTCCCACTACA | 42384 |
| 8759 CCATCTGAAAACTGCTTCCCCTTCT | 20417 GCACTAACCTCCTGCCAGAAAA | 31401 GGCATTAACCTCCTGCCTTCCACCAGT | 42385 |
| 8760 GCTCAGGGGTTTAGCCTCCTTG | 20418 CTCCACCATCAAGACCGTTCT | 31402 TTGGCAGCTCAGGGGTTTAG | 42386 |
| 8761 CAAGAAGGAAGCCAAGTTGGTTATG | 20419 GGGCAGGGATGGATAGGAGAAA | 31403 TTGAGGGGCCTTTGCTCAAGAA | 42387 |
| 8762 CACAGTTCCTGATGGTTGTCATGGTT | 20420 CCTGTTTCTCATGCATACTTAGCCATGTT | 31404 GGCGTCACAGTCCTGATGGTT | 42388 |
| 8763 CAGAAGACAAGATCTCTCCTCAGATG | 20421 CTCCTGACAAAATAACGGCTGGAA | 31405 CTGCTTGCCACAGAGGACA | 42389 |
| 8764 GCTCCCTTTGACACTGGCCAAAA | 20422 AGCTTGAAGTAAGCCCCTTCATC | 31406 GCCCAGGGCTGTCTTCCTTT | 42390 |
| 8765 TCAACACACATGGGGTTGCAT | 20423 CCTTAGTCAATGCAATGGGAAAGTA | 31407 CCTCTTGGAAGATACCTAATCAACACACA | 42391 |
| 8766 GGACCTAGTCTTATTGGACTGGGAAT | 20424 GGAGCTGGTAGAGCCAGAATTCAA | 31408 GACTTCCTAAGAGCAAGGACCTAGT | 42392 |
| 8767 CGTCCGGCCTTATAGTATTTCAT | 20425 AAGACTGCCAGGTGCAGGTT | 31409 CCCGCCCGGCCTTATAGT | 42393 |
| 8768 CTCTGCCTTTTAGTTGACAGTGC | 20426 GAAACACCCATCCCACACAGATGA | 31410 AAGACCCTCCCACTCCACACAGAGTT | 42394 |
| 8769 TGCTCATTCACTTGGATTTGGAA | 20427 GAGAAGCCTTTTGAATGCTGTTACTGT | 31411 GTGGGTTTCCCATGCTCATTC | 42395 |
| 8770 CCATCAGCTGCAATGCCCATTGT | 20428 GTGAGGAGTGTTCTGAGCTTTAG | 31412 CGGTCTTCCCATCACCTGCAAT | 42396 |
| 8771 GGCACTGGGATTACTAGAGGAATAA | 20429 CCAACAGGTAGTTTCCAGCTCTT | 31413 GGAACAGTAGGCACTGGGATT | 42397 |
| 8772 TCTCTCTTCAGCCGAGATGTAATG | 20430 GGCAGAGTAGCATTTCTGCAAAC | 31414 ACTCACCGTACTTGTTCTCTCT | 42398 |

| | | | |
|---|---|---|---|
| 8968 CCCTGCTTCATGGGCTCAAA | 20626 TGAAAGGCATGCAAACAGTCTTC | 31610 PGGGTACTGCCCCTGCTTCAT | 42594 |
| 8969 ACCACATCCAGCTCACAGA | 20627 GGTGGGAGCTTCTCTTTAACTTTTC | 31611 GACCACACACTCTACACCACAT | 42595 |
| 8970 GGGCATTAATGAGCACATTCCTTTC | 20628 GCTTCCAACGTCCTATCTTAGTGT | 31612 GGCTCCAGTAAAAACAGTGGGCATT | 42596 |
| 8971 GTTGTPTGGCTCACTGAATGAGAAG | 20629 GCCATTGACATGTCTGGCTGAAG | 31613 GCCTGGGCAGGTCATGTTGTT | 42597 |
| 8972 CGCCTCTGATTCTAATCCCACTATAC | 20630 GCCTTTGACTTTGGTGTGAACCTA | 31614 AGGGGATCGCCTCTGATTCT | 42598 |
| 8973 GGCTACTGGTCTCAGACAAGGATAC | 20631 CTGGTGAGCTATTTTCCACTGGATATG | 31615 ACAGGGTGGCTACTGGTCTCA | 42599 |
| 8974 GCCTGAAGGTGAGACAATCAGAAA | 20632 TGAAAAGTGGCCTCTAGTCTGT | 31616 GCTTAACTTTGCCTGAAGGTGAGA | 42600 |
| 8975 AGTGGGGTATCCCTGCAGTTG | 20633 GGGAGAGAGAGTTTTGTCTGTTC | 31617 AAAGCAGACTCAGTGGGGTATG | 42601 |
| 8976 GTGTGGACTCGAAGAGGATTGTGA | 20634 CCACTACCAGCAGGCAACCTT | 31618 CACCATGTGTGTGGACTCGAA | 42602 |
| 8977 GAGTACGATCCTGAAACAGGTTA | 20635 CCTGGAATAAACTTTGCCCAGACA | 31619 GCAGGTTGACATTTGAGCACGAT | 42603 |
| 8978 AGTCAGTCTGGCCCAGCAGTA | 20636 CTCAATCCTGGAGTACAATTTCTGTCT | 31620 CTCACCAAGGCATAAAGTCAGTCT | 42604 |
| 8979 CCACCTGCCAAATGCAGTTAAAGT | 20637 AATCTCCTCCTTCCTGGTCTTC | 31621 TGGACTCCACCTGCCAAATG | 42605 |
| 8980 GGGGTAATAGGGCTTAAGGCTAAGA | 20638 GACACTCAAAAGGCTAAGGGCTAAC | 31622 CCAGGAAGGGGTAATAGGGCTTA | 42606 |
| 8981 ACAGGGCTGAGACCAGCACAT | 20639 CACAGTCGACAGCATGACTCAGA | 31623 AAGGGGAACACAGGGCTGAGA | 42607 |
| 8982 CACTGCTAGTACAGGTTGTAAATTGGTATG | 20640 GAAATGCTGCTAACTTGCTCTCCAA | 31624 CTCATTCACTGCTAGTACAGGTTGT | 42608 |
| 8983 GGTGCTGACTCCAACTACTGAAAC | 20641 GGCTGCCCCTTCAATGATGA | 31625 CTTCTGTAGGTGCTGACTCCAA | 42609 |
| 8984 CTTGGCTGCTGATTGGAATTGTT | 20642 GGGTGCAGCTGCAGATTATGTCATT | 31626 GTCCCTACTTGGCTGCTGATT | 42610 |
| 8985 CCACCAGTAAAGCCTTGTATGA | 20643 CAAGGGAGAAGGTGGGAGACA | 31627 CCAAATGTTTCCACCAGTAAAG | 42611 |
| 8986 GCTCCTTCATTCCCTTGGCAAGTA | 20644 AGTCCAAAACCGTGACAAGACA | 31628 CAGCTGTCAATGAATGGCTCCTT | 42612 |
| 8987 GGAAGGCATCTGGGGCTCTAAG | 20645 ACTGGACTTTGCCAGTCATC | 31629 CCTGACGGGAAGGCATCT | 42613 |
| 8988 AGGGCATCCTCGAGCCAAAT | 20646 GACACTTCTGGTTGCCACATACA | 31630 AAGCACCTGTGACTTTGCTCTGA | 42614 |
| 8989 GGATGTATCCAGATGGTGTGAAAG | 20647 GTCTCACACAGCCCAAACGTA | 31631 GGTTGGAGGAGAGTGTGGATGT | 42615 |
| 8990 GGGACTAGTGTACCTTCTGGTCTA | 20648 GTGGTCATTTGCCAAGGCTCTA | 31632 TGGGGCTCTGGGACTAGTGT | 42616 |
| 8991 GGACCTGGTTTGCTAAGGTGTT | 20649 GTCACACCCTTCATTCTCCCATCT | 31633 GTGGTGACAGGACTGGTTT | 42617 |
| 8992 ACTGTGTCCCCTGGCACCTA | 20650 GTGGTCAATGTTAGGGGTTCAGTCT | 31634 ATCGGAACTAACCATTCACTGTGT | 42618 |
| 8993 GCCAGGATCTGCCACGGAAAA | 20651 TTTGCAGCGTAGCCCTCAGGTT | 31635 PCTCTCACAGTGGGGCAGGAT | 42619 |
| 8994 GTCCTTCCTGTCTGCTCTTGGTA | 20652 CCTGGTTAAAGGGAGAGTGAGTCTCAGAA | 31636 GCTGCAGTAGTGCCTTCCTGTCT | 42620 |
| 8995 CCCAGACATACAGTGAGGCTTGA | 20653 GGCTAGGAGAAACCCACATTCAACA | 31637 CCAGGCAACTTTCCCAGACA | 42621 |
| 8996 GTTGAAGGCAGATCATGGAAGACT | 20654 GCTTACCAAATAAAGTCTTCACCCCTAG | 31638 CCAAAACTGGGTTGAAGCCAGATCA | 42622 |
| 8997 TCTGAAAGGACTACACATCTTT | 20655 CGAATGTCCACTACTTATGGTGAA | 31639 TGCCTGCACATCAGTGGATTCT | 42623 |
| 8998 CAAGATCTCGTGCTATTCATGTTTTG | 20656 CCTTGAATGATGCTAATCCTGAGCGAAA | 31640 GTGGCTATTAAPCAAGATCCTGTGCTA | 42624 |
| 8999 CCATCTGCCATGATAGTATTGTGTCT | 20657 GGTTTTTGTACTGGAGGAACCAAAATG | 31641 CTGCCTCCCATCTGCCATGATA | 42625 |
| 9000 CCGTATTTGGGTCCTATGTAT | 20658 CCTAGCAGTAGCAATTACAACCATCT | 31642 AAAAGCCCCAGTCGGTGTTTG | 42626 |
| 9001 GGCTTTGTTAGGACAGACCCAGTTC | 20659 GAGGGAAAGGAGCACTAGACTTC | 31643 GCACAGCACTGGGCCTTGTT | 42627 |
| 9002 CCTGCCCTGTATTAGCTGTGGAT | 20660 CTGAAGAAGACGACTACATAGCAGAATTAGA | 31644 CAGACAGTATTCCTGGCCCTGTA | 42628 |
| 9003 CCTCCAGCCTGGCCTGATAC | 20661 TGCAGGCCTGGAGCCTGAT | 31645 CAGGCTGCTACCTACCGATTGA | 42629 |
| 9004 GGGGAGAAACATTCCACTCATAAGTA | 20662 GCCTTCTGTGTCACCAGTGT | 31646 CCTCTTTAGGTTTTCGGGAGAAAACA | 42630 |
| 9005 GTCAAAGGCAGGAGCCATGAGA | 20663 AGCAGTGCAAAACAGACTAAGGTAT | 31647 CCCAGCCAGGAACTTTGTCA | 42631 |
| 9006 TGTCATATGGAGGACACAGTGTTTGA | 20664 AGATGGTTCTTCTTGAATGCTGTT | 31648 PTTTGCCCTTCTGTCCCTTATCT | 42632 |
| 9007 GGACATTATATGTCAGGGAGTGCAA | 20665 GGTGTTGGGTGTGTGGGATCAA | 31649 GCTTGCTCACAGGGTGGACATT | 42633 |
| 9008 GAGAGGCAGGTGTGAGAAATCATTG | 20666 ACGGCGTCAAGGCATCTGT | 31650 TGATCAGAGAGGCAGGTGTGA | 42634 |
| 9009 CCCATCTTTGTGTGGGAAAGTTAGTGA | 20667 GCTTGTGGCCAGGGAAAGGTT | 31651 GCATCTCAGTCTCCCATCTTTGTGT | 42635 |
| 9010 GTCCAGCTGTTCATGGAGTCAAC | 20668 TCCCCTTAGGCCTGGTGAT | 31652 CAGGGGATTTGAGTCCAGCTGTTCA | 42636 |
| 9011 TCAGGTTAGTGGGTTCCCTTCT | 20669 GACCCTAGGTCTTCAGTGACATTT | 31653 GGCTTGGTTTTTCACTTCAGGTTAG | 42637 |
| 9012 CCCTAGCAACACCAAGGAACAAAG | 20670 CTGGCAGGCAACAGCAAATG | 31654 GGACATCCTCCTTATCCAACACCAA | 42638 |
| 9013 GGAAAGGATAGGTAGGAGGTGCTTCTCT | 20671 AGTGGTTGGCAGATTGTCTGAAG | 31655 GGAACTCAGAGCCCTATGGAAAG | 42639 |
| 9014 TGGCAGAGAAAGTCTGAGAGTAAATG | 20672 GGTTGGTGAGGGACAAAGTGTAG | 31656 CCTTCTATTGGCAGAGAAAGTCTGA | 42640 |
| 9015 ACCCCTCTCAATAACCTCACTTGACA | 20673 GGAAGCCATTTGGGGCTCT | 31657 GTGACTCGGTAGTAAATCCCTCA | 42641 |
| 9016 GGGCAGGTAGCATCTACAGCAA | 20674 TGTCCTGCCTGGGATGTGAA | 31658 GTGACTGATGGGCAGGTAGCAT | 42642 |
| 9017 GGCCAACAGACCAAGAAGTGCTTA | 20675 CACAGGGAGGTCTTGCACATCA | 31659 GGGGAGAGGCAACAGACCAA | 42643 |
| 9018 CCAGGGAGCTCTAGGATGAACTGAA | 20676 GGGCAACCAACATCCACTCAGA | 31660 GCTCCAGGGAGCTCTAGGAT | 42644 |
| 9019 GGAAGTGGGTCTTTGAAGAGATATCT | 20677 GCTCCATCATTCAGCGCTTGCT | 31661 GGGCAAGGAAGTGGGTCTTTGA | 42645 |
| 9020 GCTGCCAGGATGAAACCAGAGA | 20678 GCTCCCCTCTGGGTAAAACCTACT | 31662 TGCAGCAGCTGCTGCCAGGAT | 42646 |
| 9021 GTTTGGTGTTAATGGGCGATAC | 20679 GGTGTTATTGGGGAAAGTTAGT | 31663 GCTGTGCAGGGTTTGGTGTT | 42647 |
| 9022 GTTCAGTGGAAAACTGATGCAACC | 20680 GGATCTGAGTCCTTGCAGGTGAT | 31664 GCACTCCAAGTCCAGTTCTAAAG | 42648 |
| 9023 CCCAACTTTCTGGCTCATTCCATCT | 20681 GTCCGCCATGGTTGAAGTGATG | 31665 CTTTCCACCACTTCCTATCTTTCT | 42649 |
| 9024 GCTTTAGGACCAAGTTGCTGAATTG | 20682 GCTGCTGCTGGTTTTAATGGATGT | 31666 CTGGAGTAAAATGCTTTAGGACCAAGT | 42650 |
| 9025 GGGGCTCAAACAGTGAAGGTT | 20683 GTGTCTTCAGGCCAGACTACTCTAA | 31667 AGGTAAGAAAATTGGGGCTCAAACA | 42651 |
| 9026 CCCAGCAAAGCCATGCTACAGT | 20684 TCCGCTAGTGCTTCAGTAGTCT | 31668 AGCAACCCCTATCCCCAGCAA | 42652 |
| 9027 GCCTGAAACAACCAAATACCAGGAAA | 20685 CTGGTTCTAGTGTCTTGAAAACTGTTG | 31669 CCCTCCTGCCTGAAACAACCAA | 42653 |
| 9028 CACCCTGGAACCTATGGAAGAATG | 20686 TCAACGGGCTGCTTCTCTT | 31670 GGGTTGTTCACCCTGGAACCTA | 42654 |
| 9029 AACCTGCAGAAGCACATCAGT | 20687 GCACCATCGACTTTGCACATTG | 31671 GAGGGGACTTTAAACCTGCAGAA | 42655 |
| 9030 CAAGTTAAGTAGTGTAGAAATGGGAGTAG | 20688 GCACCCTCTAGCATGCTTTTGTCA | 31672 GGTGAAGTCTATGCTGACCAAGTT | 42656 |
| 9031 CCCAGACCCTATCCTGTAGCTGAATG | 20689 GCAGAAGAAAGCACAGGATTTGCATAG | 31673 GCTTTAACTTGCCTCCCAGACCCTT | 42657 |
| 9032 AGGTAGCCTCTTGGCATCTGT | 20690 CGGGCCTTTAAGGAAACCAGGAA | 31674 CCATCTACAGACACTAAGGTAGCCTCTT | 42658 |

| | | | |
|---|---|---|---|
| 9358 CAGAGAACTGTGGATCAAGACTGA | 21016 ACAGGAGGTGCTGATGTCTCA | 32000 GGCAGAGAACAGAGAACTGTGGAT | 42984 |
| 9359 GGATCAGTCTGGCTTCTGATTCT | 21017 GCTGCATTGTCTTCTGTTTTGAA | 32001 GGGCAGGTAGHTAAAAGGATCAGTCT | 42985 |
| 9360 GAAACCCAACTCTGACACACTGA | 21018 GTGCTGAAGAGGCTCTGAGTCAT | 32002 TGCTCTGAATGAAACCCAACTCT | 42986 |
| 9361 CCCATTGACACAGGAACTGAGCTTTGA | 21019 GAGAGCTGCAGGGTGTTTGAAGA | 32003 CAAGGTACACTTTCTGCCATAAGACA | 42987 |
| 9362 CCTGGGGTAACTCATGTCTCT | 21020 GTCAGGTATCGTGCTGAAGTT | 32004 TGAGTCTAATTTAGCGTGGGGTAAC | 42988 |
| 9363 GACCAAAGGCAATCCAGAGTGTA | 21021 AAAAGAAGGCCTTGGAGTTCTAA | 32005 AGGAAGCCGACCAAAGGCAATC | 42989 |
| 9364 GTTAATGTTGGTTCTCTGCCTAGACT | 21022 AGGTGCCTCTGTAGCTGAGT | 32006 CCCGAGAGGAGCAGAGTTA | 42990 |
| 9365 CCATAATTGCTAGCCACAGGTTTCAGGAAT | 21023 GGGAAGCCAAAGGTTTCAGGAAT | 32007 ACTCAACCACTGCATAATTGTTA | 42991 |
| 9366 GCACAATCATTGCTATTGCCGTAA | 21024 GCTGATGCATCCATGAAAGACTACA | 32008 GTGATCCAGAGTAGGTGCACAATC | 42992 |
| 9367 TCCACACATCAAACTTGGAGCAT | 21025 ACCTCTGGACAGGCAGATGA | 32009 AGGGTGGCCTGCTGTGTCTA | 42993 |
| 9368 CCTCATCTCAGACTGCGTAGAA | 21026 GCAGAATGGATAGAGCTTGGCTACT | 32010 GACAACAGGGAACCCTCATCTCA | 42994 |
| 9369 GGATGTGATAGCCTGATCCTGAAG | 21027 CCACCCTACTCCCATTGTTGA | 32011 GGCTTGCCAGAGAAGGAAGGAT | 42995 |
| 9370 GTTCCAAGGCCTATTTTAGCAGTTG | 21028 AGGACCAGTCGCTCCAAGTCA | 32012 CTGGTTTCCAAATGTTCCAAGGCCTATT | 42996 |
| 9371 GCCCTCTCTTCCTTTGAACTTTTGT | 21029 AGTCCAACACATTTGAGCATTACTA | 32013 ACCCGCCCCTCTCTTCCTTTG | 42997 |
| 9372 GGATGACAGCATAAAGTCCAGACCAA | 21030 CCCTTCTTCGCGTGTGTGTT | 32014 GGCTCTGTGGGATGACAGCATA | 42998 |
| 9373 GTCACCACCCATTGGATGTGTGT | 21031 TGCTGTCCTGGAGGTGTTGAAG | 32015 TTGGCTGTCACCACCCATTG | 42999 |
| 9374 CCACCCCATTCTCTGACCAATC | 21032 GGAAGGGCAGTTGTACCTATTCA | 32016 GCTCAGCATTCCACCCCATTCT | 43000 |
| 9375 CCAAACAAAGTGCCTCTCTTTTCA | 21033 GAGGGTTTCCCCACAACCTCTA | 32017 CCAAGACTCCTGCTTATTTCTCCAA | 43001 |
| 9376 CACCTAAGCCAGCTTGTGCTCTTC | 21034 GGACACCCTTCAAATGGTTTTCTTG | 32018 CACTAGTGACACCTAAGCTCAGCTT | 43002 |
| 9377 GTGTTGTTTGGCCATAAGGTATGT | 21035 GGAAGCTGTGATCCACATTTTTG | 32019 CCCGTTGCACATGTGTTGTTTG | 43003 |
| 9378 CATCACACATGCCAATGCTCATATTC | 21036 GCACTCATGTGCTATGAGGGAGTT | 32020 CGTTCACCACACATGCCAATG | 43004 |
| 9379 ACGGTGCATTCAGGCAAGGTT | 21037 GGCTTGTAGCCTGAGTCTCTGTTTG | 32021 CCAGTGGCTGAACGTGCAT | 43005 |
| 9380 GTGTTGTGTGGAGAAGGTTTGAGTGCTA | 21038 AGCCCACTGGTGGTCATTTAAG | 32022 GGGAGTTTATGTGCTTGTGTTTG | 43006 |
| 9381 CGATAACTGCACTTCTCTGAA | 21039 GTGATGAGGATCATGGAAGGGAATAAA | 32023 CTGCTCATCAAGCACTCGACAA | 43007 |
| 9382 CCATGCCCTGGGCTGATTGTT | 21040 GAGCTCAGCCTAGAGCAATGAAG | 32024 CACTGAAATGCAAACATCCACCACCAT | 43008 |
| 9383 GCTTGGCTGATGTTAAAGCTTACTCCTT | 21041 TGGAGAGGACACCCCTCAAA | 32025 TTCTGTCAGCTTGGCTGATGTTA | 43009 |
| 9384 GGTTAGTGTCCTGGATCTCACACTGA | 21042 GCCCTATTTTTAGTATAACCCTGGAGCAT | 32026 CTGGTTCTAGGTTTAGTTCCTGGAT | 43010 |
| 9385 GCATCTCAGGACTGAGTGACTCTAC | 21043 CCCGCAAATCAAGCATCAGCTTAC | 32027 CACGAAGCTAAAGACTAGCATCTCA | 43011 |
| 9386 GACTTGGGTTATGAATGAGGCTAAAT | 21044 TCAGAGCCTCATGCTGAAT | 32028 GCACHTTAAAACTAGAGAAGACATGGGTTA | 43012 |
| 9387 GCAGTTTCTCTGTTCTGTGGGAAGA | 21045 CCCCACCCATGATACGTTGTTC | 32029 GCTCCTGTCTTGCAGTTTCTCT | 43013 |
| 9388 CCTCCCATCAATTTTACCCATTTCTTC | 21046 CTCATAAAGTAAGACACACCGTACCAATG | 32030 CCTGGGCTTCCTCCCACAATTT | 43014 |
| 9389 CCCGTCACAAGTCTGAGTCTAAGT | 21047 CCTAGATTCTGGAACGCCTTGTTC | 32031 GGTGCTAAATTTTCCCGTCACAAG | 43015 |
| 9390 TCCCACATGAAGGCAAACTTTCT | 21048 GGCCATGCTGCATTTTTCCATAG | 32032 TGTTCCCCATCCCAGTCATGAG | 43016 |
| 9391 AGGGTGAGAAGGAGTTATCCAACTT | 21049 TGCTCACCTCCAGGAAGACT | 32033 CCAAAGTCAAAAGGGTGAGAAGGAGTT | 43017 |
| 9392 CCCACACTGGTTGTCCACAT | 21050 GGAGTTCTAGGTTTGTCAGAAAC | 32034 TGTCTGTCCACTTCCCATACT | 43018 |
| 9393 CACGTCCACCTACTCTCCCTTAC | 21051 GACACAATGACTGGAATTTGCTTCA | 32035 GATCTGCACGTCCACCTACAT | 43019 |
| 9394 GGTTTTCAGATGGTAAAGTGGTGCAA | 21052 CATTGTGCAACCAGAGTCTGAGATT | 32036 GCTGAACCAGAGAAGGGTTTCAGA | 43020 |
| 9395 CCAAAGTTGAGGCAAGCATGACA | 21053 CAGAGTAGGCACCACCATCTATC | 32037 CCTCAAGCATGACTCCAAAGTTGA | 43021 |
| 9396 TCTAGGTACAGCCTGAGCATTCA | 21054 TGGAGCCACCCGAATGAGAT | 32038 CTTCTAGAGTGTGGAGAATCTAGGTACA | 43022 |
| 9397 GGCCTGACTTTGTCATGGAAGGAT | 21055 CTTTGTGGTGCAAATCTGATCTCT | 32039 CTGGCCAGGCCTGACTTTGT | 43023 |
| 9398 CTGTGGCTTGAGCTGAGAGTTCA | 21056 CACTGGAGTGCTTACTGAATGAAAACA | 32040 CCTGGTTCTCAGTCTGTGGCTTAG | 43024 |
| 9399 GAGGAAGAGTGCAATACAGCCAAT | 21057 AAAGCTGAGGGGTGAGAGA | 32041 AGGAAGGGGATGAGGAAGAGTT | 43025 |
| 9400 GGGTAATCCCAGCATGAAATGAGGTAAA | 21058 GCAGGTGCTAAGGACTGTAAGAGT | 32042 CCTCAAAGGTAATCCCAGCATGA | 43026 |
| 9401 GGACAGCCACTCTTAGTGTTTGA | 21059 CACCCCTTTAGAGCTAAGGAAACAAG | 32043 TTAAAACTGGACAGCCACTCCTT | 43027 |
| 9402 GGGTCATGTCTCATCCAGTGA | 21060 GAGACAGAGGTCCAGAGGTGTT | 32044 CCCATGGGTGGGTCATGTCT | 43028 |
| 9403 CCAGGAGTGGTCAAATGAGCTCTE | 21061 TGTCAGTCATAACCTTGGATGCTAA | 32045 GGTTCCTTTCCAGGAGTGCAA | 43029 |
| 9404 CTGTCTCTGTCTCATTATCTCTAA | 21062 GGAACCAGAGCTGAGGCTGTTA | 32046 GCTCTGAAACTCCTCTTCCTCATT | 43030 |
| 9405 GCATGTCCCTAATCGTGGAT | 21063 ACTCTGGGTGTGTCGGCATT | 32047 GGCAGTGAACCATGTCCCTAA | 43031 |
| 9406 GCACAGCCAGCATTCCCATAGT | 21064 ACCCTCGTGGCATGAGATGA | 32048 ACCTCTCTGCACAGTCAGCAT | 43032 |
| 9407 CGTTGCCTACAGTCTCCTCTATC | 21065 AGTGGGCCCAGTGGATGGA | 32049 CACACTGAATTCCGTTGCCTACAGT | 43033 |
| 9408 CCGAGAATGTCATTCTGCTCTATC | 21066 GTGGGCTGGCTTAATGGTATG | 32050 TCATAGAACTCCGAGAATGTCACTT | 43034 |
| 9409 GCCAAGTCTGTGGCTAGAGGAAGT | 21067 CCCAGTACCTAGGCAGAAGA | 32051 CCCAAATAGCTCAGCCAAGTCTGT | 43035 |
| 9410 GGCTGCCCGATTCTTAAATCATTC | 21068 CTGCCAAGCTCACTAGAGGTAAC | 32052 CCATCTTGGCTGCCCGATTCTT | 43036 |
| 9411 ACGGAAGGCTTAACCAATTTTG | 21069 GCCAGGTCGACGGAGCCTTAAC | 32053 AGGCAGCGGAAGCCTTAAC | 43037 |
| 9412 CCCTGGGAACCCTACCTGTCTAT | 21070 GCACCCTCTTCTTCTCATCACAGTT | 32054 CCCATGAGCTTAACAGCCCTGGAA | 43038 |
| 9413 GCCCACCAACCCACTTGAGTAT | 21071 GGACATAAGACCCATTCACCAATG | 32055 GGTTTTAGCTGGAACCCTAAGAAC | 43039 |
| 9414 GTATTACCCAGATGGATGTTTCA | 21072 GGTCTGTAAAGTTGCCATGAATACTGA | 32056 GACCAGAAGCTGTATTTACCCAGAT | 43040 |
| 9415 CAGGCCTGGAGTTGTGATGAGT | 21073 TGTCCTTGGGAAGGAGGTAGTTTAG | 32057 ATGGAAGGGCAGGGCCTTAAC | 43041 |
| 9416 TCCCACTATCGAACATTACCTGGAT | 21074 CCCTGAAAATAATACCCAGCTTTCATC | 32058 CTTCTAGCATTCCTCACTATCAGAACA | 43042 |
| 9417 GTGGAGCTCCACGTGATCCTT | 21075 CATCTGAGCTGAGGTCATGTTCTTC | 32059 CTGTCGAGCTTGTGGAGCTT | 43043 |
| 9418 GTTCCTACCCCATAGGATCAAGATG | 21076 GGGCAGGTCTTTCAGGAAGT | 32060 GCCTAAGCAGGTTCCTACCCCATA | 43044 |
| 9419 CTGAATGGTGAACAGGACAGTCT | 21077 AGTAACTATCTCAAGTCACAGGAGTCT | 32061 GTCCTAGCCTTACTGAATGGTGAAC | 43045 |
| 9420 TCAGCCTTCGACATCTTTCATTGT | 21078 CATAGTTCCTAATAACGGGAGCTACT | 32062 GAGTCATAGTTCCTTTCAGCCCTGATC | 43046 |
| 9421 GGAAAGGGCCACAGAAAATTAAGAGA | 21079 GGTCATTCAGACCAGCTCCAATAA | 32063 TGCCTAGGAAAGGGCTCACAGA | 43047 |
| 9422 GGGCTATTTCCATTGTAAGCACTTT | 21080 GGCCAGTGGCACATTAGCAAAC | 32064 AACAGAAGAGGCTATTTCCATTGT | 43048 |

FIG. 3605

| | | | |
|---|---|---|---|
| 9423 CTTGGTATGGTCAAGAAAACGGAAAC | 21081 CAGTCACCCTGGGATGAGAGTA | 32065 GGAGCTTAACATCTTGGTAGGGTCAAG | 43049 |
| 9424 GGCTGAGACTCTAGGACAGGTAATG | 21082 TGGTGCTGCTTAGCATTTCGTA | 32066 GCATTGTTCAAGGCTGAGACTCTA | 43050 |
| 9425 GCATCGAAAGGGATGTAGTCACTTA | 21083 AGAACAGGCAAGCCCACTCA | 32067 GCAGTAATTTGCATCGAAAGGGATGT | 43051 |
| 9426 CCTCCCAGAGGTAATAACGATGTAG | 21084 ACAACCTGTGGTCTACCTGAGT | 32068 AGCAGCCTCCCCAGAGGTAATA | 43052 |
| 9427 CAAAACCACACACAACACACCAT | 21085 GATCTCTGGAGAATTTGGGACTATGT | 32069 CCCATATGCATCAAAACCACACACA | 43053 |
| 9428 GCCAAAGACCAAAACCACCTAGA | 21086 GGGCAGAGCACCTGTTCTCTAAA | 32070 GTCTGACATTGCCAAAGACCAAA | 43054 |
| 9429 CATCTCAAGCATTCACACCCAGAT | 21087 CAGGGAGTCTCGCCATCTGTAAC | 32071 CCGACCAGCTAAGCTCATTCAAG | 43055 |
| 9430 ACCACTCCTTTCACACAAATCCTATG | 21088 CAGGTTAGGGAGATTATCTTGCTTTTC | 32072 TTGGAACGACTCCTTTCACACA | 43056 |
| 9431 CCACGTTAGATACCTGACAACCTCAGA | 21089 GCCCTAAAACCCTGCTGAGATG | 32073 ACCTATTGCTTCATTCCACGTTAGA | 43057 |
| 9432 CCCTGCCAAATTTTCCCTGGTT | 21090 CCTGAATCAGTCAGCAGATAGAGTT | 32074 ATCAGTATGCACACACCCCTGCCAAAT | 43058 |
| 9433 GGAGTCAAGCCCAGCCAAGTTT | 21091 CTTTCTTCCATGGATCAGCTGAGAT | 32075 GACCTAACATGCAGTTTGGAGTCAAG | 43059 |
| 9434 TGAGAGGCATTGAGTAGATAGCAA | 21092 GTTGCACTGCTAGGTTTTGTTGGTT | 32076 CAGCAGTTGTTTTTGAGAGGCATTG | 43060 |
| 9435 GGAAGATCCTAGCAAGAGGGTGAAA | 21093 GGCTAGGGTAGGAGTAGAGCAGTATC | 32077 GCTAGAAAAGGAAGATCCTAGCAA | 43061 |
| 9436 CCTTGCCATAGCAGGTAGTAGAAG | 21094 CCGGAGGCCCAAACGTTAAA | 32078 GATCACAGTTTGTTCCTTGCCATAG | 43062 |
| 9437 CACAACCTGAGTATTCCCCTGTATTC | 21095 CCTTGGAGATTCATTCGATAGCTACTTGT | 32079 TGGCTATCCACCACAACCTGAGT | 43063 |
| 9438 CCCATGCTCATCACTGCTCAAT | 21096 TGACAGCCCATCTCTCACCTT | 32080 GCCTCTCTCCCATGCTCATC | 43064 |
| 9439 CTGAAGCAAGGCACCTATGAACTCT | 21097 ACCTGGTCAGCACTGGCTTCT | 32081 ACCCTCCTCAACGAAGTAACTGAA | 43065 |
| 9440 GCATGTCCCAAACACTTCCTGTGT | 21098 GGAGAGAACTGGGCTCTGAAAAC | 32082 CCACACAGGCAGTCCCAAA | 43066 |
| 9441 CTGCATTCATTCGCTTTTCCAAAT | 21099 GAGGCACAGAACATGCTACCAAGG | 32083 AGGAACTGTGCTGCATTCCAT | 43067 |
| 9442 AGGGGAGCAGAGATCTAGGGATTC | 21100 CCCATGCCATAAGTAGGATGTGACTTC | 32084 AGCCTACAGGGGAGCAGAGAT | 43068 |
| 9443 GGCTGCCGTTAGGATGTAGAAC | 21101 ATGAGGAAAATGAGGGTTCTGT | 32085 AGACAGTGGGCTGCCGTTA | 43069 |
| 9444 CACACAAACCTGAGTAGCCATT | 21102 AGCAGCCCACACAGTGCAAA | 32086 GCCTGAACCCAGACAGATCACA | 43070 |
| 9445 CACTTGCCTTACAACCACCTGATG | 21103 GGTAGGTTCAGGGAGCTGGAATGA | 32087 CTCTTTTCCTTGACACTTGCCTTACAAC | 43071 |
| 9446 CACTTCCACTTCCACCCCTGA | 21104 GGTACTGTTCTTCCTATAACCAGGAT | 32088 TGAGTGGTGCCACTTCCACTTC | 43072 |
| 9447 TGTTGCCAGTAATATACGCCATCT | 21105 TGGGTTTAGCAGTGCAGATAGGGA | 32089 CCATCTGACATGTTGCCAGTA | 43073 |
| 9448 GCCCATAGCTTCCTAAACCTCCAT | 21106 AGCAGAATGGGGTGAAAAAGGTT | 32090 GACTGTTTAAPTGGCCCATAGCTTCCTA | 43074 |
| 9449 CCAAACCTGTAATTGCTGAGGTACA | 21107 GAGGGCACCCTGAAAAATGT | 32091 CCCAATAGGACTTTCCAAACCTGTA | 43075 |
| 9450 GCCATTGTGTGGAAGACATAGTGTGA | 21108 ACTCAATAGCTGCCCTTCCTACT | 32092 ACTTTGAGCCATTGTGTGGAAGA | 43076 |
| 9451 GATTCAGACTCAGACTGTCAGATTT | 21109 GATGTCTGGAAGATTTTGGATGATG | 32093 GGATGCAAAGCCAGATATCCA | 43077 |
| 9452 CTCCCTGCCGTGTTTTGCTCTCT | 21110 GAGGGTGCCTGGGCATTAC | 32094 TGGGACTCCTGCGGTGTT | 43078 |
| 9453 CCTGTTTACATCACTCCCACTTTC | 21111 CAAATGCAATGGTAGGTGATGAGTT | 32095 CTCACACTGTACCCTTCCTGGTT | 43079 |
| 9454 GCTAAGGAGGATTCTAAAGGTGCTAA | 21112 AGCAGCAAGGAGTGCATTT | 32096 CCTGGACTCAAAAGCTAAGGAGGATTCTA | 43080 |
| 9455 CAGTCACTGCTTGAACACCATGT | 21113 GGACATTTGGGTTAACCAGCCTAATTC | 32097 ATGATGGCCTCGGTATTAAACAGT | 43081 |
| 9456 GCCAGGAGCTTTCAGAGCTTGTA | 21114 CCTGTTGCACCAAAATAATGTGTCT | 32098 GGCCAAATGCCTCAGGAGCTT | 43082 |
| 9457 TGACTTGGGAGACCATTCATTTCAA | 21115 CAAAATCCCAAAGTAGTGCCCTGAGT | 32099 GGAGAATTTATGACTTGGGAGACCAT | 43083 |
| 9458 GCATTTAAGGGGTATTCGTGGGACTA | 21116 GGGGTAGTCCTGATGGGTAACAGA | 32100 TCTGTTGCAAGCATTTAAGGGGTAT | 43084 |
| 9459 GGGCAGTTTGTGTCACAGTCTTT | 21117 ACCAACCAGCATCTCTCTCAGT | 32101 CCTTCCAAAGGGCAGTTTGTGT | 43085 |
| 9460 CTGCAAGCTGGGTTTCAGTTTC | 21118 TGGTTTGATCTTAGACCGGTGACA | 32102 GCCTTCTGCAAGCTGTGGTT | 43086 |
| 9461 CAGATTCCAGCCACAAATATCTCATC | 21119 GTCTTCACAGTAGGGCTTTTGCTATG | 32103 GGGAAAGTTCAGATTCCAGCCACAA | 43087 |
| 9462 TTGGAAACAAGGGTCCAGAGA | 21120 CCTGGATCCCAGCCTGTTTATAG | 32104 GGCCTCCATGCAGATATTGGGAAA | 43088 |
| 9463 GCAGGAGGTAACTGGGCCATA | 21121 GTTTTCAAAAGCTGTGGTTGCTGAA | 32105 TGCTCCATTGGCAGGAGGTAAC | 43089 |
| 9464 CCTCTGGTCATCCCACTGACCCTTTG | 21122 GGAAGCTGTACTGTAGAAAATGAGCT | 32106 GCTGTTAAGTGGTAGGGCTGAGCAT | 43090 |
| 9465 AGGGTAAGCTGAGCCAAGTTTAG | 21123 CTCAGATGTGGCTTATGAGTGTCT | 32107 GGATAGAGTATGGGAATGAAAGGGTAAG | 43091 |
| 9466 GGCTTGTTCTTATGGTAGGGTTCCAAA | 21124 CCTTAAGGGGCCTTGGGTACATC | 32108 GGCTAGCCCAGGCTTGTTCTTA | 43092 |
| 9467 GGTGGAAGAATGAGGCTGTACCCT | 21125 GCTCAGCTGTAGGAGATTGTTCT | 32109 AGAGAAATCAAGCGTTTGGTGGAAGA | 43093 |
| 9468 GGTAGGCAATGGCCTGGATT | 21126 TCCGTGTCCACCTGTCAAA | 32110 CAGTGGTGTTTGTAAGGTAGGCAAT | 43094 |
| 9469 CTGTCGACTCTTCATCTTGCAGT | 21127 GCCAAAGCCAGTGCATAATTAGTTG | 32111 TGTTTAAGAGCTGTGGACTCTTTCA | 43095 |
| 9470 CAAGCAGGGAAAATCCTCTTTAGACA | 21128 CTCTGCTTAGATATTTGCCACTAATAC | 32112 CAGTAATTCTGATTCAAGAGGGGAAA | 43096 |
| 9471 CCAGTGTAACACTGCAGCTTAAGAA | 21129 CACACGAAGTCCAGTGGCATGA | 32113 CCACCTTGAGGCTCCAAGTAAC | 43097 |
| 9472 GCTCTGTCATCCCAGCTGAAA | 21130 GGAGTCAAGAAAGTCGAGCCTGTAAA | 32114 AAAACAACTGCAGTCTGTCATC | 43098 |
| 9473 CTGCCAACAGCACTTGTCATAC | 21131 GAAGGTTCCAGCAGGTGTAGATG | 32115 TCCAGGCCTTCTCTGCCAACA | 43099 |
| 9474 CTGGGGTAAAAGGAGGTTATCAAGCAT | 21132 GAGTGGGAGCTCTAACTTGACACTA | 32116 AGGATTCTGGGGTAAAAGGAGGTT | 43100 |
| 9475 CTCTCTCCCTGCTTAGATGTTGT | 21133 CCCAGGCTTGACTCTTTTTACACATTG | 32117 GGATGCAGGCCTTCTCTCT | 43101 |
| 9476 CGGCTAAGCTAACGATATCCCATCTC | 21134 ACTAATATTCACTGGCCAACTGTGA | 32118 GCCAACGGCTAAGCTAACGAT | 43102 |
| 9477 GGCTCCCATTGTTGTCGGCTAA | 21135 GGACAGGCTGGGATGGAAAATG | 32119 ACAGTAAACGGCTCCCCATTTGT | 43103 |
| 9478 CCGCTTAGCTAATATGCTCTTTG | 21136 CATTCAGACAAGTCCTGAGTAAGAGA | 32120 TGCCTCTCCGCTTAGCCAAT | 43104 |
| 9479 GAACCAGGTCAGTTTCAGGTAGATG | 21137 AGCCTGCGACCTTCTTCAGAGA | 32121 GGTAGGATGAACACAGGTCAGTT | 43105 |
| 9480 CAGTGTTCTGTTAAGGTCACCTCTTCT | 21138 GTGGATGCAGCTGCCAATGA | 32122 GATCTTACATGTCCCAGTGTTCTGT | 43106 |
| 9481 GCTCAGAGCACGTGTTTTC | 21139 ATGCACCCAGTCCCCACTT | 32123 GATCCATTCCAACAGTCTAGA | 43107 |
| 9482 CCACAGCTCAGATTGACTCACA | 21140 CCAGAAACAACCTTAGTATGCGACCTTTC | 32124 TGTCCACCCACAGCTCAGAT | 43108 |
| 9483 CCCTCAGCAATGTCGCTAGTAGT | 21141 TTCTCGGTCACCTCCACATC | 32125 AGCCAGAGGTGCCTCAGCAAT | 43109 |
| 9484 GGAGTCACATAGTGACTCTGAA | 21142 GAAAATAGTGCTCTGAAGGAGCAAGTAG | 32126 AGTGGCCTCTGGAGCACAT | 43110 |
| 9485 CCGTGGGTCCTACACCTGAGATA | 21143 TGGTGATCGCAGCAGAGAACAA | 32127 GCTAATAGACGGTGGGTCCTACA | 43111 |
| 9486 CCCCAATCTGTGCCTTCATGTT | 21144 GTGGGCAGAGGTATGCATATAA | 32128 GGATGTGTTGCCCCAATCTGT | 43112 |
| 9487 CCTCAGGCATAAAGCCAGGTCAGT | 21145 GTGAGCCTCAAGAGACGGGAAA | 32129 GGGCAGAAAATGTCCCCAGGCATAA | 43113 |

| | | | |
|---|---|---|---|
| 9618 GATCCCAGTTGTGTGCCCTTAG | 21276 AGAGCTCTGCTGGCCACCTT | 32260 CCCAGTTTCAGATCCCAGTTGT | 43244 |
| 9619 GGGTGGTCAGGAGATCAGACTGTA | 21277 CTCATCTTCCTCCTGGCCCTTA | 32261 GGGTGGCTGGTCAGGAGAT | 43245 |
| 9620 CACACACAGAGAAAGGTCACTTC | 21278 AGGGCCACCCTCTCACTATG | 32262 CCAGGGCTTTACACACAGAGAA | 43246 |
| 9621 GTAAGCCTAATCGGGATTTTAGCTCTT | 21279 GATAAGGCCGCCATTTTCTGAAC | 32263 TCAGTGGTCTATGCAAGCCTAATC | 43247 |
| 9622 GGAGAACAGAGCCACATGCTAAC | 21280 AGCTGCTTGGGATGATTATCTTGA | 32264 CGATGTAAGGGTGCAGGAGAACAGA | 43248 |
| 9623 GCTCTTCTTGGAATCCTGAAATG | 21281 CATGAGGCAGGACTTGGAAAACA | 32265 TCCTCATGCTCCTCGTCGAAT | 43249 |
| 9624 GCCCTCTGAGAGTAGTCAGGAACTA | 21282 ACTTTGAGGCCCAATAACCATGT | 32266 CTGCAAATGACGCCCTCTGA | 43250 |
| 9625 GCTGGTATGGAGAACAATTCCTGACA | 21283 GCGTGCCATTTGCAGTCTGT | 32267 GCTTTGAGCTGGTATGGAGAACAA | 43251 |
| 9626 CCCTCTCTTGCCTGGTCTATTTT | 21284 ACAAACCTAGACAGCCCTTGTTC | 32268 GACCTTCCAGAAGACCTCTCTTG | 43252 |
| 9627 CCCTGCCATTCCTTCTTCTTGGAT | 21285 GGGTACAGAAGCTTCAATCACATCA | 32269 GCCGATCACCCTGCCATCCTT | 43253 |
| 9628 GCAAGGAATCTTGTGTCTCTATGATTG | 21286 ACCAGCCTCAGATTTGTCTTTTACT | 32270 GCCTGAAGAGGACGAACTGTTG | 43254 |
| 9629 CTGGAGGAATACCAATCAGACGACAA | 21287 TGGGGTGGTCTGTGTCAGTT | 32271 GGGTGCCTGGAGGAATACCAATC | 43255 |
| 9630 ATGCAAGGGTGATGAAGAAGGAA | 21288 CTGTAACAGTGTCTGGTAGCAAATG | 32272 GTGCAAGCTATGCAAGGGTGATG | 43256 |
| 9631 GGAGTTAAGAGGGAGTTGAAGTCAAAG | 21289 GATGGAGTTCCTGTGAAGATGGTAAC | 32273 ACAGAAAAGGAGTTAAGAGGGAGTTG | 43257 |
| 9632 ACTCTGCCTCTGAGATTCTAGATAGT | 21290 CACTAATTGGTGCCATTATGCATCT | 32274 GAGCTTAGAAAACTCTGCCTCTGA | 43258 |
| 9633 TCCTCATTCCTCAGAGCTGACA | 21291 TGAGTACACCTAATGGCAGGTTTT | 32275 AACAGACTCCTGCTTCCTCATTC | 43259 |
| 9634 GACGGTGTACTACGGGTCCAT | 21292 CACCATGCAGCACCAGTGA | 32276 AAGCCACGGACGGGTACTA | 43260 |
| 9635 GACTGCCTCTATGAAGCCATTTCCTA | 21293 CCCTGAGGAGGGGTTGATTGT | 32277 TGTCCACTCTTGACTGCCTCTA | 43261 |
| 9636 CAGCCACAAGGAACAATCTCAAAA | 21294 GTGTCTGCAGGTGTGGTTGT | 32278 GCATGCAGCCACAAGGAACA | 43262 |
| 9637 TGCCGCTCGCCTCTCTCTAA | 21295 ACGAGACTCATCCTTATCCTCTAGAA | 32279 TGATCCTCCCCAGCTTCGTTTG | 43263 |
| 9638 GAGTAGGACTTCTTACATGGCAGTTG | 21296 TCCAAATTGGCCTTCCACAACA | 32280 GTTGGTTCCAGAGGAGTAGGACTT | 43264 |
| 9639 ATAGTCACCTCTTGCCTGTCT | 21297 AGATCGGGCTCCAGCTTCTA | 32281 GCAAGGCTGGCTGATTTCCAACA | 43265 |
| 9640 GGGTCTGATCACCCCAACATTC | 21298 AGAGTGACTACCTCCCCAGCAA | 32282 GCCTGTTAATAAAGGTGTGGGTCTGA | 43266 |
| 9641 CCCAGGAACTTAAATGAAATGGGCATAC | 21299 TGCAATAGGCTGAGTCTACAATG | 32283 CTCCAAGGCTCTTATCCCAGGAA | 43267 |
| 9642 TCGGAGCTGCTGGAAGTT | 21300 GCAGTCGCTTCCTCCACCATGT | 32284 CCCCGATCTCCGAGTACAGAT | 43268 |
| 9643 CCACATGCCTCCTATATGCTTTGT | 21301 GCTCAGTCTAAAACAATAGCCTCCCATA | 32285 TCCAGTCCACATGCCTCCTA | 43269 |
| 9644 CAGCACCACTTTGCACTACTTC | 21302 GCTACAAGCCACTGTTACGTTTC | 32286 GACAGCACAGCACCACTTTG | 43270 |
| 9645 AGTTCTCTCCAGTCTCTTCCAGTT | 21303 ACTGAAGGAATCTGGTCATGAAAGA | 32287 CAGATCACTCTAGTTCTCTCCAGTCT | 43271 |
| 9646 GCCCTGAGTTCATTCCAAGTCT | 21304 AGGGTGGGAGTGCAACACTAAC | 32288 CCAAGGAAGCCCTGAGTTCCAT | 43272 |
| 9647 CCAAACTGGTATCCCCTGGGTCAAC | 21305 GCAGCCAAGCAGGCTATTCA | 32289 GCACATCCAGCCGCAAACTGGTA | 43273 |
| 9648 GACCAATGGAAGCAACTACAGAAACTTTG | 21306 GGGCCTTTTCCTCTGAGTCACTA | 32290 GGTGTGGGCGTGAATATAGACCAA | 43274 |
| 9649 AGCGCTCTTGGCCTTTGTT | 21307 GCACATGCTCTTTGCAGGACAA | 32291 CCTCACCGTCGTGTGCATTTGAA | 43275 |
| 9650 CCTCAACATTCCTCCTCTACAAC | 21308 CACTGAGGTAATAACCAGCAGACA | 32292 GGCAGTTACCTCCTCCAACATTC | 43276 |
| 9651 AGGGAAGTCCCTGGCTCCTAAAG | 21309 TCAGGAGGGGAGTGGTGGAGTAT | 32293 GGAACCACAGGTGAAATAGGGAAGT | 43277 |
| 9652 CAAATGGGCCAGCTATATCTGATTG | 21310 TTTTCTGCTGCTCATGGGGATAG | 32294 GCTTTGTCAAATGCCCAGCTA | 43278 |
| 9653 CACCCAAGGAGGGGCTGTAAPGA | 21311 AAGCCCTTCCCTCTCCAGCAA | 32295 GGAACATTCCTCAGCCAAACA | 43279 |
| 9654 CCAAAGAGATCTAGGACACAGACAAACT | 21312 CCATCCTTCTTTCAAAGTGGCAGATA | 32296 GCTTTCAAAGAGATCTAGGACACA | 43280 |
| 9655 TCCAGGTGCCATTCCCCATTG | 21313 GTCTTGCTCTTACTACCTTGTTGAACT | 32297 GGTTCTCCACGGGACCCTTTC | 43281 |
| 9656 CCAAATTCTCTTGTTCCAATAGCGAGAA | 21314 AGCCCTAGATTAGTGCTGAAAATGA | 32298 CTCCAAGGAGGACCAATTCTCTTGT | 43282 |
| 9657 GTGGCTCTTCCCATTCCTA | 21315 AGCAGCTGTGGACAGAGCTAGA | 32299 CAATGACTGGATGTGTGGCTCTT | 43283 |
| 9658 GCACCTGACCATACTTGCTACACT | 21316 CAGTGCTTAGCGTTCACACTGGATTAT | 32300 GAGAAGACTGCACTGACCATAC | 43284 |
| 9659 ACCCAGATCTCTGCTTCTAAAACTTG | 21317 GTCCCTGGAAGCAGCTAAGCTAATG | 32301 GCAGAGCCAACTTTAAACCCAGAT | 43285 |
| 9660 CAGAGCTCTATACTGAGCTTTCCCTCTAT | 21318 CTCAGCCATACAAAGTGACTGTCTT | 32302 TGCATGTCCCAGAGCTCTATACT | 43286 |
| 9661 CCATCCTGCTATTGCCACTAT | 21319 GCCCACTGCACCTCTGTTTG | 32303 CCCCACATTCCATGCCTGCTA | 43287 |
| 9662 ACATGCAGGAGCTTAGAGACTGA | 21320 GTGAGGATTTATTGGACGGATTGT | 32304 CCAGGACATCTACATGCAGGAGCTT | 43288 |
| 9663 ACTGGACCCTTAGTTCCATCCATAAG | 21321 GACCACGCCACACTTGGTATGA | 32305 AACAAGAGAACTGGACCCTTAGTTC | 43289 |
| 9664 GCATGGCAGAAAAACTACCTTTGTCA | 21322 GCTCCTGGAAGCAAACACACA | 32306 GTTAACTTCAGCATGGCAGAAAAAC | 43290 |
| 9665 GCATGTACACAGTGCATACTCTGA | 21323 GGAACAAAAATCTGCTGTCTCCATTTC | 32307 TTATGCAGTGGCATGTACACAGT | 43291 |
| 9666 GTGACTCACACCAATGACAGTTACA | 21324 GCCAAATAGAGAACTAACAGGCACACT | 32308 GCCCAGTGACTCACACCAAT | 43292 |
| 9667 CCGACGTGTCATCTCACATTATC | 21325 CTCCTGCCCTGTGTCTGAAAC | 32309 CCAGGACCGACGTGTCATCT | 43293 |
| 9668 GCTCTCTGCAAATGGAGGATGGTA | 21326 TGTGCCAGACTCAATGCTAAAGT | 32310 GCCTTGGTTTGCTCTCTGCAA | 43294 |
| 9669 CTCTTGGTTTTCAGGCAGACA | 21327 GCCCATCACGCCCTTCAGTA | 32311 CGGTCAGGCCTTCTCTTGGTTT | 43295 |
| 9670 CGTTGGTTGTGTGCGTCTGA | 21328 GAGGGAAGCCCCGTTGTTCTGATTG | 32312 CACTTTCAGTCAGGTGGTTTG | 43296 |
| 9671 CCTTTGTGAATGCCTGATGCAA | 21329 GCTGTCCCCTTGTGAATGAGT | 32313 GGAGCAGCCACAGATCCTTGT | 43297 |
| 9672 GGCAAAATCCACTTCAGGAGGAT | 21330 ACATGTACACTGGCTTCAGATTTGT | 32314 GTCTTCAAAGCCAAACTCCACTT | 43298 |
| 9673 TCCACTCTGGATTCCTGAACAAC | 21331 GCTCTCCATGTTGCTGCTGCTTGT | 32315 GGTCAGCTTATTCCACTCTGGATTC | 43299 |
| 9674 AGGGAACCAGCAAAACCAATGA | 21332 CTTGGTTCTTGGGCCTTCCAA | 32316 TGCAAACTAGGGAACCAGCAA | 43300 |
| 9675 GCGGCAGTGTTTCCTCTGTT | 21333 TTCGTGGGAGAGAGAAGTTGATAAG | 32317 CCCTGAGAAGCGGCAGTGTT | 43301 |
| 9676 GTCTAAGGAAGTCTGTAGGCTGAATAC | 21334 TGGAACAATAGCCACAGCAGTT | 32318 GGAGTCAGGTCTAAGGAAGTCTGTA | 43302 |
| 9677 AGCACTTCCCCTTTGATCCATT | 21335 CCAGGGCCAGAGTAGCAAGT | 32319 GGCCAGGAAGCACTTCCCCTTT | 43303 |
| 9678 GGGACATAGGCAACAGGACAA | 21336 GCCCACACGCCATTTAAAGA | 32320 AGGGCAGGGTAGGGGACATA | 43304 |
| 9679 GAGCTTCTCACTGTCCCCTGTA | 21337 GTGTCCCAGAAAGGGAAATAGAGACA | 32321 TCCCTTTCCCTGGTTGAGCTT | 43305 |
| 9680 TGTCCAAGGAATGGGAAGGGTAA | 21338 GGCACCTGTCAGATAGGGTTGGAT | 32322 TGGCAAGTGTGTCCAAGGAAT | 43306 |
| 9681 CGCCCAACAGAAGAGGAAGTT | 21339 CTGGAGTGACCCTTTGGTGACTTA | 32323 TCTCCACCCTCGCCCCAACA | 43307 |
| 9682 ATGCAATGCCTTTCAGAGCTA | 21340 GGTCATGATGCATGGGACTAACAGTTA | 32324 GTTGTTAGCCTCAGAAACGCAATG | 43308 |

| | | | |
|---|---|---|---|
| 9748 GCCCAGGGTTCAAGTTTAGTGTTG | 21406 GCATGGAAAGCAGGGCTTTAG | 32390 TCAGAGCCTAGGGTTCAAGTT | 43374 |
| 9749 CCACCCTCCAAAACAAGTCACTCT | 21407 AGACAAGTGACGGAGTCTCA | 32391 GGCTCCCACCCTCCAAAACA | 43375 |
| 9750 GCCAGAGCATGTACCTAGCAAAC | 21408 CAAATGTCTTCCCTCTATCCTGATGTTG | 32392 CAAGCAGTGCCAGAGCATGT | 43376 |
| 9751 GCACCTTGGAATAGGGATTGA | 21409 CCTAGGTAGTCACAGAGGTAGTTC | 32393 GGGGACATAAATGCATCCTTGGAA | 43377 |
| 9752 GACATTGGCTGTCAAGTTCCATT | 21410 CAGTGAGAGGGAAAGAGAGCTTA | 32394 CTTAGTACTTGAGACATTGGCTGTCA | 43378 |
| 9753 AGCCATACCTTAGGGCCAGAAC | 21411 TGTTTGAGCTGGAGGCTATGGTG | 32395 GGGTACCAGAGGCATGATTAGCCATA | 43379 |
| 9754 CACCCTTGCAGTTGATATGGAAA | 21412 ACCTCCTCTAGCTCATGAAGAACAA | 32396 GGGGAATTTACATCCTGCTAGTTGA | 43380 |
| 9755 GGAAACTCAGGGTTTAAGCCCATAAGGAAA | 21413 GGTGTACTCCAGCAATGGACAGA | 32397 AGGCTGGGAAACTCAGGGTTTAAG | 43381 |
| 9756 GGCTTGAGTTGGCCTTCTCAGAT | 21414 GGATGGGTCCATACTTGTCATTAGGTT | 32398 GCTTCTGCCAATAGGGCTTGAGT | 43382 |
| 9757 GCTTAATTGCCAGATTCCGTATTCAAG | 21415 CCCAGTGCTTCTGGCTTCT | 32399 CCTGGGAGTTGCTTAATTGCCAGAT | 43383 |
| 9758 GGCTGGGTATATCAAAGGAGCTAGA | 21416 GGTGATCACTGACGGGTAAAAC | 32400 TTCTCTTTCTGTTTTGGCTTGGATA | 43384 |
| 9759 CAGTTGGCTCACCACGTGGTTTT | 21417 GGAAGATGAACGAGGGAGCTGCTA | 32401 GCCCCATCAATCCTAGCCAGTTG | 43385 |
| 9760 TGCCAAGGTAGATCTGGTTCATTTC | 21418 CGTGGCCAGCGTTCCACAT | 32402 GGCATCCGTCATTGCTAAGGTA | 43386 |
| 9761 AGGCCAGGGGGCTGTGTCAT | 21419 ACCTCCCATCCATTCAGCAGTTTAG | 32403 TGGCTTGAGGCCAGGAGTTTG | 43387 |
| 9762 GCACACTTGCCTGAAATGAGACACA | 21420 GTCCTGAGAATAGGCCAATCCAATTA | 32404 CAAAGCCCATTTGTAGCACACTT | 43388 |
| 9763 GGGCTAGAACAACAAGCCAAGT | 21421 ACAATGTCCCACCTTCTGATTGT | 32405 CAGAAAACACAGGGGCTAGAACAAC | 43389 |
| 9764 GTGACGTGTGTCACCACTGGAA | 21422 GGGTAAACATGCCCTGGTCAA | 32406 TGCAGCCTGTGACGTGTGT | 43390 |
| 9765 GTCCAACCAAATACTGCACAGA | 21423 AAAAGAACAAAGTGGATGCCAGTAG | 32407 GCAGTTAGCATTGTCCCAACCAA | 43391 |
| 9766 GGCAGGACTGGTTGAGAACATC | 21424 AGGCAGAACCTCTGAGCACTT | 32408 TAGGGCAGGCAGGACTGGTT | 43392 |
| 9767 AGAGCCTGAGCAACGTGTATAAG | 21425 ACAGTGGTACTCGGAGAATTTGTTGT | 32409 TGTGCTTAAAGAGCCTGAGCAA | 43393 |
| 9768 TGATCGGCCCAGTTTTCTACTTTG | 21426 AGGATGGCTCAGGTTAATAGAGTAGT | 32410 CCCTGTGATGGGCCTAGTTTT | 43394 |
| 9769 AGGCTAAGGTTAAGGCACTGAAG | 21427 TCCTGGCCATTGCCTTTTGT | 32411 TGTTGGGCTAAGGCTAAGGTTAAG | 43395 |
| 9770 CCTGCTTCCCTGCCACTTTTG | 21428 CCCAACTGAGAAAGGCTTACCTTCTAC | 32412 CTGGAGGAAATTGCCCTGCTT | 43396 |
| 9771 CGTGCGGTGACTTCTTTCTGTGA | 21429 AAGGAAGGTGAGGAAAGGGAAAG | 32413 TGTGAGTCGTGCGGTGACTT | 43397 |
| 9772 TGCTGAAAGGCTGCCATATTTGT | 21430 AGATAACGAGGACAGAGCTTATCTTAC | 32414 GTCTGCATTTGCCTTTTGCTGAA | 43398 |
| 9773 CTCTCTCAATGTCCATTGTGTAGA | 21431 TCTATTGACTCTAGGTGCTGTCTTA | 32415 CACGAACGAGTCCCTCTCAATG | 43399 |
| 9774 GCAAAGAGAGCCCCTCGAAGTC | 21432 GTCTCCAGTCACGCCTCCAAATGT | 32416 GGACTCTTGCAATTCTAGGCAAAG | 43400 |
| 9775 GGAAGGAACAACCTCATTATGCTTTCA | 21433 GGGAATACAACCACTGCCTCA | 32417 TGACAAAAGGAAGGAACAACCTCAT | 43401 |
| 9776 CCCCACAATGAGTCTCTGCAACT | 21434 TGACCTCAGACAGTTTGCTTTTAAC | 32418 CTTCCCACAACCCCACAATGA | 43402 |
| 9777 CAACAGGACTTGATCACCAAGCAA | 21435 AGCGAGACCCTCTGCTCAGTA | 32419 TTTCCACTCTTCAACAGGACTTGA | 43403 |
| 9778 TCCACAGTGACACGGAGCTA | 21436 AGGATCCTACTGGAGATCAATCAGAAA | 32420 CACTGGAATCCTATTTCCACAGTCA | 43404 |
| 9779 CACAGAATCTCTGCCTGTATCA | 21437 CCTCCTTTTTGTGCTCTGTCCCATAG | 32421 GGAGCAGGAGTTCAGGGAAGACA | 43405 |
| 9780 GCTGGTGATAAATTGCCACGACTTC | 21438 GCTCCACACAGGTTGAGGAGAT | 32422 GCTGAACATCTGTGCTGGTGA | 43406 |
| 9781 GCTTGGGGCTACTCCCTTCCTA | 21439 GTGGCTCTGATCCCTGTCACTAAG | 32423 CTGTCCTGTCTCCCAAGTGCTTT | 43407 |
| 9782 GCCAGGATAAACCTGGCTTCAGA | 21440 CTCCTTGGCACCTTGAGGTACT | 32424 AGTAGGAAGCCCTGATAGACATA | 43408 |
| 9783 CTCCTCAGTGCAATTAGAGGACTTC | 21441 GAAATTCAGGCTAAGGGAAGATGTGT | 32425 GACAGGAAACTCCTCAGTGCAA | 43409 |
| 9784 GCTGCAACAAGGGATCAGACTCA | 21442 CAGGTCCTGGTGTCTTGGTTT | 32426 GAAGTAATGCCTAGCTGCAACA | 43410 |
| 9785 GCTTCTGAATGTCTCTGAATGACAA | 21443 GCCAGAGGTAGGGGTGGAAGT | 32427 TCGAGCCTATCCATTCTAGCTTCT | 43411 |
| 9786 TGCCAGGTAGTGGGTGAGTCAA | 21444 CGGATTGACAAAACACGCAGTGA | 32428 TGTGTGCCTGCCAGGTAGT | 43412 |
| 9787 CTCGTAGCCGCAAGTAGAAATGAAG | 21445 CCATAAACTTTCTTCAAGTACTACTTTG | 32429 TACCCTGGTGGTAGCCGCAAGTA | 43413 |
| 9788 AGATGGAGGCTCCTCCTTGACA | 21446 GGGGCATGTGGGACTTTAGTTCT | 32430 GAAGACTGCTTCAAAAGGCAGATG | 43414 |
| 9789 GATTGCCCAAGGACATATAGAGGAA | 21447 GGCTTCTTGACCTCCATGGGAATG | 32431 ACTGCAGGAGTGACTGAGGATTG | 43415 |
| 9790 CAGACATGTGTGGAGCGACTGT | 21448 AAAGATGTACCTACTGCACTCTGTT | 32432 GCAATCCTTGGTTCAGCAGACA | 43416 |
| 9791 CCTTGTGAAACAGTACCTACCCAAT | 21449 ACAGGAGCCCTGATAGCCATA | 32433 GACAGCAAGCCCTGGAACAGT | 43417 |
| 9792 GGCCAAATGCCTGCAAAGA | 21450 ACCCTGTAGCTAGTGCTTTATGTCA | 32434 AGTAAGGGAAGGAAAGGCCAAATG | 43418 |
| 9793 AGCCAAGCAGCTGGTTTTTAGAAGA | 21451 GTTTTGCAACAAGCTCCACTCT | 32435 CAGCAAGCCAAGAGCTGGTT | 43419 |
| 9794 TGTCTTCAAACACTCAGCACCTTT | 21452 TCAAGTTAAGGAGTGGCTTTGAGT | 32436 CACATGACCCACATACTGTCTTCAAAC | 43420 |
| 9795 CCTTTGTCGTCCCCTTCT | 21453 GAGGGAAAGCCCTAAGCCAAGAT | 32437 ATGGCTGCCCCTCCCTTTGTG | 43421 |
| 9796 GGTGGATCTTTTGTTAGGGTGACATTTCTA | 21454 CCCCTGAGGGTAAGTGGTACCTAA | 32438 CACTTTTAGGGGAACTTGGTGGATCT | 43422 |
| 9797 CCAGATCTGACTTCATGGAGCTGTG | 21455 TGTCTCAGCAGGGACTGAGTAT | 32439 CAGTACTCCATCCAGATCTGACTTCAT | 43423 |
| 9798 GTCCTGCTACATCTAACCTTCCTTT | 21456 AACACCCTTCAAGCTTCCAAT | 32440 CACTCTGTCCAAGTCCTGCTACATC | 43424 |
| 9799 GCTCAGAGAGTTCAGACCACTT | 21457 GGGGTACTGATGCTGCTCTGTT | 32441 GTGATAGAAATTCCTTGCCACAGAGG | 43425 |
| 9800 GCTCTGCTTCCATCTCAGTCACA | 21458 AAGCCGGTGCAGCTGTCTT | 32442 GGTCTTACAAGCTGCTTCCAT | 43426 |
| 9801 GTGGTGTGTAAAGGTTAGAAGCACAAA | 21459 CCAAGTGCTGGACCCAAATCT | 32443 TGATAGATCGTGTGGTGTAAAGGTTAG | 43427 |
| 9802 CAGTGCCCAGAAATTGCCAACA | 21460 TGGCTGGGCATAGGGTACA | 32444 CAGCTCACAGTGCCCAGAA | 43428 |
| 9803 CGTTCTAAGGAGTTTGTAGTACA | 21461 GTAGCTAGCAGGAGTAGAAAATTG | 32445 CAGGCACAGTCTGGAGAAC | 43429 |
| 9804 AGAGCAAGGCCACTCAGAGA | 21462 GGGTGCTGTCAATAAAAGCTGTGTA | 32446 AAACTTCCCATGGACAGAGCAA | 43430 |
| 9805 GGTGGAGAGTGAATCTGGCAAATG | 21463 GCTGTGATTCAAATTCAGTGGGTCTGT | 32447 GGCACTGAAGTTAGGTGGAGAGT | 43431 |
| 9806 GCCCCAATAAGTGGTGCTTGACT | 21464 CCAGGATGGAGAGGGGATGAAT | 32448 TGGCACTGCAGCCCCAATAA | 43432 |
| 9807 CAGTGTTGGCAGCCAGGATACA | 21465 CTTTAGATAGTACCTCCAAAGGCTAAT | 32449 TGGGCACAGATGCAGTGTTG | 43433 |
| 9808 ACTCTCAACCCCAGTAGTCT | 21466 CCCCATAGCTCCTGCTGTTCACT | 32450 CTAGAATACTCCCAGTCTACT | 43434 |
| 9809 CTCTGGGGACTCTTCCATCAGA | 21467 CTCAAAGCATGCAGCCTAGATGA | 32451 ACCTTTGCCTCTGGGGACTTC | 43435 |
| 9810 GCCTGGAACTGCACGGCTTAGA | 21468 CCCTGCTTCTCAGGTCCTA | 32452 GGAACACAGAAACCCTGGAACT | 43436 |
| 9811 CCCAACTGTCACCTCCTTCTATGG | 21469 GCTCTGCTAAGAAAGATGGAACGATGA | 32453 GTTGTAATTCTCCAATCCCAACTGTCA | 43437 |
| 9812 CGGGGTGGAAGAAGTAGGACAT | 21470 TCAGGCCCAGAGAGGCATTA | 32454 TCAAGTCGGGGTGGGAAGAA | 43438 |

FIG. 36P1

| | | | |
|---|---|---|---|
| 9813 GAAAGCAAGCCATTGCTCCAAA | 21471 GCATTTCTGGAGAGCAAGCTATTG | 32455 CAGAAAAGTGACTGGAAAGCAAGT | 43439 |
| 9814 GCACAGGATGAGGCTATTCTCTGAA | 21472 CTCTTTAGCAGGCCCAGTTCT | 32456 GTCTTTCCCAAAGCACAGGATGA | 43440 |
| 9815 GCTGCTTGGAATAGTTTGTTCTCATCTTAG | 21473 CTGAGATGTGTTAGCGTCATTGCTT | 32457 TCTGATGCTGCTTGGAATAGTTTGT | 43441 |
| 9816 CAGGGTGTAGCCATCTGATTTACA | 21474 CTGTCACTTGTCAGCGTGGAT | 32458 GCACGCTTTTAATCAGGGTGTAG | 43442 |
| 9817 CAAGGTGCGTCAAGGAAACTGA | 21475 CTCTTTCCTATCGAGGTGGGTTTCA | 32459 TGGGAGGAGGACAGCCACAA | 43443 |
| 9818 ACCCACTCCAATTTTGAAGCAAAC | 21476 ACACCTGGTCAGGTCGTAATAGT | 32460 CCCAGCACCCACTCCAATTT | 43444 |
| 9819 CAGGCTTGGAAAGAGAGTGATAG | 21477 CAGGGGATCTAGAAGGCAGCTTT | 32461 CACAGGTTACCTAATCAGGCTTGGAA | 43445 |
| 9820 GACAGCCAAAAGCCAGGTGTTAG | 21478 CCTTACAAGGTGTGTCTGTGCTTCT | 32462 GGTGGCAATGACAGCCAAAAG | 43446 |
| 9821 GGTTGTTGGTGTTAGAGCGTATTTC | 21479 GCTTTGTTAAGCACTTGTCTGTTGAGA | 32463 CACTCACATGGTTGTTGGCTGTTAG | 43447 |
| 9822 TGGGTGGTAGGGCACATTCA | 21480 GTCAGGATAAGGAGGTGGTGGTAT | 32464 CCTTTGGCCTGTATAATTGGTGGTA | 43448 |
| 9823 GGGTGTTATAGCCAGACCAGAAAACA | 21481 CCTGTCAATTATGAAAACTGGGCCTTTTGT | 32465 CTCCAAATGTCAGCAGGGTGTT | 43449 |
| 9824 CCAGGTAGCTAAGCAGTGAAGACA | 21482 GAGTGAATGATGGAGGATACAGAGAT | 32466 CTTGGCTTCAGAGTTTCAGGTA | 43450 |
| 9825 GGCAAGGCAATTTGGATTATGCTTCA | 21483 GAPGACAAGGGTACAGAAAGATCAACT | 32467 AGCTGGCAAGGCAATTTGGAT | 43451 |
| 9826 GCAATGTCTGCTTTCACTGCTTT | 21484 ACCTGACTGCACTAACTAGACTCTT | 32468 AGAACAACACAGGAATGTCTGCTT | 43452 |
| 9827 CCTGTACAGCATCTGTCGCTAT | 21485 GGGGCACTGTACAGCCAAAT | 32469 CCCTTCTGCTACCACCTCTA | 43453 |
| 9828 GAACAGGCCAGATCGCATGCAAG | 21486 GGCCAGGCTGAGTTCTTCT | 32470 CCAAGGAACCTGACAATTGTTGAA | 43454 |
| 9829 GTTTCTTTTCACCTCCAACATGGAA | 21487 GTGCAGCACACAGAAAATACATCACT | 32471 CACTGTGTGTCGTCATCTTGT | 43455 |
| 9830 CCCTACTTGGGTACCTTGTTGCTA | 21488 GGCTTTGCAACCTGCTAATTCCTA | 32472 CTACAGCCCATTTTAACCTCACTTG | 43456 |
| 9831 AGGGTGAGTCCATGAGTACAGACA | 21489 CACGATAATGCCACTTAGGTATGATG | 32473 GGAAGGGAAGGTTGAGTCCATGA | 43457 |
| 9832 CCGAACTTCAGGGAATAGCCAAGA | 21490 CCCCACAGCCTAGGGTAATGAA | 32474 ACCCATAGGGTGCCGAACTT | 43458 |
| 9833 GCTCAAACCCCACCCTACTTCTGTCT | 21491 GTGCCAAAGAAATGCCTAGGTTATGCTG | 32475 AGCAGCCCCAGCTCAAAC | 43459 |
| 9834 CCTCCCAAGAAGTAGCCTTCGAT | 21492 GACATGGTGAAGTGCCTCCTAACA | 32476 CTGTGTGAAAATCCTCCCCAAGAAG | 43460 |
| 9835 GCAATCTCCTCACCCTCTGGAGAA | 21493 ATTGATTCATGTGCCACTCATT | 32477 GAGTCCTGATGCTGTGTGCAATC | 43461 |
| 9836 AGCAACAAGCTTGGTATGTTCAAG | 21494 TGCTCTGCACATTTTTCACTCTGA | 32478 ACTGCTGAGGCAGCAACAA | 43462 |
| 9837 CCCCATGTGTTCAGTGAGTACTTTG | 21495 TGGGGTGTAGCTGGGAAAACTGAAG | 32479 GGATTTGCTCAAGTCTGTTGAGT | 43463 |
| 9838 CCCACTGGGAGAAAAGGGCAGTGA | 21496 TGGTCAGGCAGTGGGAACT | 32480 TCCCTTGCCCACTGGGAGAAA | 43464 |
| 9839 GGCTGAATAGACAACCAGCCTTGA | 21497 TCCTCAGGGAGTGGGCTTTTGA | 32481 GCAAGCTGTGGCTGAATAGACAAC | 43465 |
| 9840 CTCTGTCACCAACTCTGTGTCAT | 21498 GAGTAATCTGAGAGCTCAAGGAGTCAA | 32482 GTGCTCTTCACTCTGTCACCAACT | 43466 |
| 9841 CTCCTTCATGGAATGGGTGATCCTT | 21499 CTGAAGGGGTCTGTGCCTGGGTAAG | 32483 TCCACAGCTTCGAAACTCTTCAT | 43467 |
| 9842 CCCTTCTCACTCCCCTAGCTTTGTT | 21500 TCTCTCATCTCTTGAGTGTGGAATG | 32484 CGGATTTGCTACCCTCCTTCTCA | 43468 |
| 9843 GGCTGTGCTGAAGTTTGTCTCT | 21501 CTGTGCAACCTTCATGCTCACAAC | 32485 GCCTCCTAGGCTGTGCGAA | 43469 |
| 9844 CGTAACCTCTACATGGCCAATGACT | 21502 CGGCTCACCCTAGCTTCTTG | 32486 TGTGCTCCCGTAACCTCTACA | 43470 |
| 9845 GTCCTCTCCTTGCTGTGTCTCAAAG | 21503 GCTGACGGGCAGAGTTGTTCA | 32487 GGACTCAGCGTCCTCTCCTT | 43471 |
| 9846 GCTGCTTCGATGTAGAGAGGTCAA | 21504 AGGCTGGCTCTTGGTCTCAAC | 32488 GCAAGTCAGTCTGCTGGATGTAG | 43472 |
| 9847 CAGGGCTACCAAGGTTTCCATT | 21505 GCACAGTTAGATTTAAGGCGTGAAC | 32489 CTCTTGAAAATCTATCTACAGGGCTACCAA | 43473 |
| 9848 GGAGAGGATTCCAATGCTCAATGTT | 21506 ATGAGCCAAGGAGAGGATTAGCAA | 32490 CACATGGCTTTTGGAGACGATTC | 43474 |
| 9849 CAGTTACTTTACCCAGACATTGTCATC | 21507 CACTCAAGCAGTCAGGTTGGTT | 32491 GGATTGACCCTTCCCAGTTAC | 43475 |
| 9850 CCTTGGGTGGAATTTTTGAAGAGAAA | 21508 TGTGGACACTGGGACCTCTCT | 32492 GCATGTCCTTCGGTGGGAAT | 43476 |
| 9851 AGGTCCAGTGATGCACAGAT | 21509 GACCCATCTGTGAAGGATGCAA | 32493 APGTGGCAGGCCCAGTGA | 43477 |
| 9852 GGCGGATAAGCCCAGATAGTTTC | 21510 GGATGCTTGAGGGAAAACTGGAT | 32494 GCCTGAGTTGACAGGCGGATAA | 43478 |
| 9853 GGGCAGAAACCCATACTTTTGCATT | 21511 TTTCCTGTGCTTACTTCTGTGCTA | 32495 GCTCTGTTAGGGCAGAAACCAT | 43479 |
| 9854 GCACTTGGATGATTCTTGAGAAAA | 21512 TGTAACCTTCTGGGATTGGCTTT | 32496 CCCATTGATACAGCACCTTGGATGA | 43480 |
| 9855 CCTCGACCTACAAAACTACTGAA | 21513 GGAAACGCAGCTAGCCTTAGA | 32497 CTACTTTCAAAPCCTCGACCTACA | 43481 |
| 9856 GCAAGGATGGGTCAGTTGCATT | 21514 AGCCCAGGTCACCAAGAGACT | 32498 GGTGGTTGCAAGGATGGGTCA | 43482 |
| 9857 CCACTCATAGCATTGAGGGCAAAG | 21515 GGAAGCAAGGCCCACACATCA | 32499 GCTCCAGATCCCACTCATAGCATTG | 43483 |
| 9858 CCAGTAGAGTGGGGATGTGA | 21516 CCCTCCCCAGCTGACAATCAT | 32500 ATTCCCACACGCAGTAGAA | 43484 |
| 9859 ACAATTGTGATGCCATGGGGAAT | 21517 GCCCATTTATTCTCTGCCTAAAACAACAAG | 32501 GTCAACATACATAGGGCCAGAACA | 43485 |
| 9860 CAGGGCTTGATCTTTGGTAGAGTGA | 21518 ATTCCCCTAAACCATCCAGGATTC | 32502 AAAACTGACAGGCCTTGATCTTTG | 43486 |
| 9861 GGGGCTTTTGTTAAGGCTGGAGTATTTAG | 21519 GCAAATACCTGTGTAGCCAGCATCA | 32503 GGAAGGCACATGGGGCTTTGT | 43487 |
| 9862 GGAGACCTGTCAATCCCACAGAAG | 21520 AGCAGGCCAGTAGGCAGAGA | 32504 CCAGCCTTTGGAGACCTGTCAA | 43488 |
| 9863 CCAGGTGGGTCAGAAACATCACA | 21521 GGGAAAACTCTTCCTAAGCTTCAGTT | 32505 TCAAAGTCCAGGTGGGTCAGA | 43489 |
| 9864 GGGGGTCACTCAGGAAAATTAACCAT | 21522 TTCCCTTTCAGTGTAAACCTGTGT | 32506 AAGCCAGGCGCCTCTCA | 43490 |
| 9865 CGTGTTCTGAGGACCTACAGTTATT | 21523 GAAGTACCAGCGGTGCATTTC | 32507 CCTGGCCTTCCGTGTCTGA | 43491 |
| 9866 TGACAGTGCACACAGTGACTT | 21524 CTCACCCAGGGATTCATGACA | 32508 GGGGCATGGTGTGGAATGACA | 43492 |
| 9867 ACCAGATGGGCTTCCACACA | 21525 GCAGCTCGTCTGGATGAAAAC | 32509 CACGTAACCTCTGCCACCAGAT | 43493 |
| 9868 CCCAACCTCAGCATAGCTTTTGA | 21526 ACAGGTTGTTTGTGATACAGCTTCT | 32510 CCACCATACCAACCTCAGCAT | 43494 |
| 9869 GGGCTTTGCTCAGTCTTCCTGTTC | 21527 CCATGGCATAGGCATGCAGGAT | 32511 TGGAGTGCTGGAGGGGCTTT | 43495 |
| 9870 GCAGATCCAGTCAAGACAACCTGTCA | 21528 GCTTGGACAGCTTGATTCTGAAGTT | 32512 TGGTCCATATGCAGATCCAGTAAAG | 43496 |
| 9871 GCACCAGTTCCCCTTTTCTCCTT | 21529 AGCCCAGAGGCCCTAAAG | 32513 CCATGCATTTTAGGCACCAGTTC | 43497 |
| 9872 CTGGTTCCACAGAGCGTTGTCC | 21530 TGCTATGCTCCCTCTGGTAGT | 32514 CCAACAAAACTGGTTCCACAT | 43498 |
| 9873 CCAGATCAGTCCTCACCCTGT | 21531 GATGACTGTCTTTCCTCCGTAATAAAC | 32515 GGGGATAAAATAGGAGCAAACCAGAT | 43499 |
| 9874 CTGATAGCTCTGTGACCTAAGCCTAGTA | 21532 CAGATGAAGAACCCTAGACTCCAACT | 32516 CAGAAGTTCACTGATGCTGTGTA | 43500 |
| 9875 GCTCTCCTCCCTCCCAGTCT | 21533 GCAGAGCCCGTGCATTTG | 32517 TAGGCGGCCAGCCATCTCT | 43501 |
| 9876 GAGGAAGACAGCTTGGAAGTTTGA | 21534 GGGGCAGGAATGGGAATCAAGGTA | 32518 TGGTGGTGGGTGCAGAGA | 43502 |
| 9877 CACTAACCCTAAACCACCTCCTGAA | 21535 TTAGGGGCCCATGGCTCACA | 32519 TGGGGCTGCCGATCTCACTAA | 43503 |

| | | | |
|---|---|---|---|
| 10008 GGTCCTGCCCAGTTCCAATTT | 21666 ATGCAAGGGAGCAATTTGCAGAG | 32650 CCCCAATGCAGGCGATGA | 43634 |
| 10009 AGCAGGTGCGGCCAATGA | 21667 CCTGAAAACATTTAGAGGAGCTTTGATG | 32651 GCAGGAAGGGTGAAGTAGGCAGGTT | 43635 |
| 10010 AGCTGGAGTGGAGATGGAGTTC | 21668 CCGAGGCCAGACCTGCTACATATT | 32652 AGACCAGGGTAGCTGGAGTGA | 43636 |
| 10011 AGTGCGAGGAAGCCACCATCTA | 21669 GCAACGAGCTCCTTCTGATGA | 32653 CCTGAGTAGTTGACAGTGCGAGGAA | 43637 |
| 10012 GACCTGGTATTGGTGACCCTAAGA | 21670 CCTAGCTCAGCCACAGTGGAATA | 32654 AAGGGCCCAAGACCTGCTA | 43638 |
| 10013 GGCTGGGACATGAAATCCTTGACT | 21671 GGAGCAGGGCTCAGAAAAGTT | 32655 CAGTTGTCTGCTGGGACATGA | 43639 |
| 10014 CGCTGTTGGTAAATTTCAGTTG | 21672 TTCACATATTAGCCTACACTCCTCTTC | 32656 AGGCAATCCGCTGTTGTT | 43640 |
| 10015 GTAGCCACAGACAACACAGA | 21673 AGTTCTTGGACCCTAGACATTC | 32657 AGCACAAAATCAGCCCACAGA | 43641 |
| 10016 GGTGACATGCTGGGTAGGTGATGA | 21674 ACGTAGCTGAGTTCCACGTT | 32658 CCTCAGTACTTACACGGTGACA | 43642 |
| 10017 GGTTTTGAGAGGGTAGGTAGGTTTG | 21675 TGTCTTGGCCCTATCTCCTT | 32659 GGGAGGGATTACCCACCTAGGTTTTG | 43643 |
| 10018 GCAGTGTCTTGAAAGGAAAGGGATA | 21676 GTTCACCTTCAAGCAAACCCTATAC | 32660 CAGAGTCTGAGCAGTGTCTGGAA | 43644 |
| 10019 CTGGTGTTAGGCTCCTGGATATG | 21677 CCCCTTTTTGTTCTGTTTATCGCAAGT | 32661 TTCTGCTGGGGGCTTGTGTTA | 43645 |
| 10020 TGGCTGGTGCTTCACACTT | 21678 GCTCAGCCTATAGTAGCCAGGAAAA | 32662 ACACTCGCGTGCCACTGAT | 43646 |
| 10021 CAGCCTCTTAGTTTTCCACCCTTCT | 21679 TTGCAGTGTCACCTGGGATAAG | 32663 GCAAGTCTCCACCAGGCTCTT | 43647 |
| 10022 ATGTGTAGGGACTAGAGGTCCTT | 21680 GCAGAGAGAAGCAACTCAGCTTAC | 32664 CCCACTCCTAAATGTGTAGGGACTA | 43648 |
| 10023 CTCCAGAGAGTGACCTCTCCAT | 21681 GCAGACCATAGTGGCTGAGGTT | 32665 GAGTAGTTCCTCCCTACTCCAGAGA | 43649 |
| 10024 TCCCAGCTCCAGGCTCCAA | 21682 GGAGGTGGGGCATAAGGTGATTC | 32666 TTCCTGGCCACCCTCAGT | 43650 |
| 10025 GGGATCAGGCGAAACATTGAATGCCTTTT | 21683 GCCAGCTGCAACAACCATTAG | 32667 GCCTGAGGGGATCAGTGGAAACATTG | 43651 |
| 10026 GCAGAGGGTTATCCTATTCCAAAC | 21684 GCATCTGAGCCAAGTCTCCTTCTGT | 32668 CGTGCTCAAGGCAGAGGGTTTA | 43652 |
| 10027 GCTTGTTACACAGCTGCCTATTATTTC | 21685 GCAGAGGGAGCTCAGCTGTTT | 32669 GTTTTGGAGGGAGTGTGATGCTT | 43653 |
| 10028 GTGTACTGAAATTCCTCAGTGGTTAC | 21686 CGGTTTTCAGATTTCAAGACGGTGTGT | 32670 GAGTCTTGGTAGTCTGGTGTCGACTGA | 43654 |
| 10029 GTAAAGTCTGTCTTTTGTGAGGAAGA | 21687 GGTGCACCGATGCAGATTTCT | 32671 GCCAGTAAACAGAAGTTGTCCTGCAAA | 43655 |
| 10030 TCTACCTGCAAAGGTCCACTCA | 21688 AGGGACCTAGAAGGGACAACTAC | 32672 TGAATTCGAACCATCTACCCGCAA | 43656 |
| 10031 TGGTGGATGAAGGCGACGTT | 21689 CCACTTGGACCAGAGAGACGTT | 32673 GTGGGGTTAAAGAGGATGGTGGATGA | 43657 |
| 10032 GGCATATTTGCTGTTTCACAAGGCTAG | 21690 CCCTTGATCCCAAAGGCAACAA | 32674 GCAGGGTCCCATTGCTCTGTTTC | 43658 |
| 10033 GCACGGTTTCATCACTAAGTTGAGATT | 21691 TGCTCTTCTGCTGGAATTTACCAA | 32675 CAATAAAGAGCACGGTTTCATCACT | 43659 |
| 10034 GGCTCCATCAAACCCACTCT | 21692 GCAGGGAATTCAGAGGAATTGGACTT | 32676 GGCCTCTTAAGTTCTAGGCTGCAT | 43660 |
| 10035 GGCATCACCTAGGTCCAACTAC | 21693 TCTCTCTGAATCCACCTGCTCTTA | 32677 AAGGGCCTTAGCCATCACCTA | 43661 |
| 10036 GTCAAGTCTCAACTGTCATCTGCTT | 21694 TCGGACAATCACCTGAGATGAAAAC | 32678 GGACCTGACCTCAGTCAAGCTCAA | 43662 |
| 10037 GCCTTCATCGAGGTAGGATAATTTGT | 21695 GTCAGAATTAGGACCTCCTCAACCTA | 32679 AGCTTGCTAGCCTGCCTTCA | 43663 |
| 10038 GTGTGCTCATCCATCCCACCTT | 21696 GTGTGGGTGAGTACTGAAGGAA | 32680 AATCCTAGCGTGTTCTCATC | 43664 |
| 10039 CCCAAACTGCCTATTCTAGGACGAA | 21697 GGTGTTGAACGCCATTTTCACA | 32681 TCACAAGACCCAAACTGCCTATTC | 43665 |
| 10040 ACAGGCTCTTGACCCCTAAAGT | 21698 CCTTTTCTCCCATTAATCCATCTGCCTAT | 32682 TAGGGGCCACAGGCTCTTGA | 43666 |
| 10041 CCTTGCAGAATTTGTTTGGAGAAGA | 21699 CTTTGTCTGTCTGCATCTGACATTT | 32683 CCGGGAGAACGTGTAGGAATTT | 43667 |
| 10042 AACCTGTGAAGGAGAGATTG | 21700 GAGAAGAGCCTGGGCTATATTTCAA | 32684 GTTTGGACTGAGCCTGTGA | 43668 |
| 10043 AGCCTCTGGAAGAGCCAGGAA | 21701 CGCTTGGCCAAGGTTCAGGTTTG | 32685 AAGAGCCACCAGCCTCTGGAA | 43669 |
| 10044 GCCATACCACCAAGGGCTATTTG | 21702 ATCGCGGGCATCTGTGTAAC | 32686 GTCTCTGCAGCCATACCACCAA | 43670 |
| 10045 GGGACGGGTGTAGACCCTAAA | 21703 TCACAGGGTTGGCGGAACT | 32687 GTTTTTCAGGCAGCGGTTT | 43671 |
| 10046 CCTAGTGACCTTCCTCACCAT | 21704 GACCATTTCATGCTCACTCCTTCTTG | 32688 CGCTGGTTCCCAGTGACCTTT | 43672 |
| 10047 CTGCTGAAATTAGACGGTTAGGCTGAGA | 21705 AGCTGCTGCAGACCCATGT | 32689 ACACACCCATCTCTGCTGAA | 43673 |
| 10048 ACTGTTCCAGATTTCAGCAAAC | 21706 TCTGGCTCAGCATGGTCACT | 32690 GGCTTTGAGTTAACTGTTCCAGAT | 43674 |
| 10049 GGGGATTAGGGTGCTAATGCAGT | 21707 GGCCCTCTCTGTAAAGTGCAT | 32691 CACACATCGCGTGCTAATGGGGATT | 43675 |
| 10050 GCTGGAACACAGGGTGCATGTAAG | 21708 AGCTGCGGGCAAGGTATCA | 32692 TGCAGGGCGTGGGAACACA | 43676 |
| 10051 GACCCTGTCGTGAGGCTGTT | 21709 CCTATTGCACAGGGTCACAATTT | 32693 CCTAGAGACCATGACCCTGTTGT | 43677 |
| 10052 CCGTAAAACACCAATGACTACCTTTG | 21710 CCCTACTCCCAACTGCACTTGAAC | 32694 CGTGCATCCGTAAAACACCAATG | 43678 |
| 10053 GGGCTGCATGAAGACAGAACAGTGTA | 21711 CCCCAGACCTGTGATTCCACAA | 32695 CAGGTGGGCTGCATGAAAACA | 43679 |
| 10054 CTCAACCCAGTAGCCAGAGTGA | 21712 GCAAGAGTAATACGATCTGACATCT | 32696 CCTGGGGTCTATTCTCAACCCAGTAG | 43680 |
| 10055 TGGCATCTACAGGGTGTTG | 21713 CCTTGAGGGTGCACCTGCTTAG | 32697 TGAACCTCTGGGCATCTTACA | 43681 |
| 10056 CAGCTCTCATGCTTCTGAACTGG | 21714 GCAGGCAATAACGAATGAGAGTTTA | 32698 GTTGACCTCAGCCTTCCAGGCTT | 43682 |
| 10057 GGAAAGTCAGCATTAGCAGCAAGT | 21715 GGCAGTTCCCTCTGGGAGGTT | 32699 GGCCAGGTGGCCTCAGGCAGGAAAGT | 43683 |
| 10058 GGCTTGTTACTCACCCAGGAAGA | 21716 CCTCTTCCCTCACCGTGTTGA | 32700 GACTCCAGGGCTTGTTACTCA | 43684 |
| 10059 TGTCTGGGCTCTTGCATCTTTG | 21717 TTCTGAGTTCCAGATGACACTACAAG | 32701 GCTTCCTAAAATGTCTGGGCTCTT | 43685 |
| 10060 CAAACCTGCATGTGATACTTTAGA | 21718 ACGCCCAGCCCCAACTTTA | 32702 GGGTGGGACACACCACATAACA | 43686 |
| 10061 GTAACATACCCAAATGCTAATGCTAGT | 21719 GCTCTCCTCCCAGGAACCAT | 32703 GTTGGGAACACTGTGCAACATAC | 43687 |
| 10062 CCAGCAGTGGCTGTTCTCTGAA | 21720 CGCTGGAGACTGGTCTGAGTTCAA | 32704 GGATGGGACGCCTGACTC | 43688 |
| 10063 TCGCCTCTACGGACCAAACCTC | 21721 GGGTGCCAGGACTTCCTCTGA | 32705 TCTCGTGCAGTTCGCTCTAC | 43689 |
| 10064 GGGCTTGTTTGAGGGTCACT | 21722 ACACGGGACATGGAGATGAA | 32706 GCAGAGTGCTGGGCTTGTTTC | 43690 |
| 10065 CCCAGTTAGTAACAAAGAGTGGTTTC | 21723 GTGTGAGCATATTTAGGAGGCACTGT | 32707 CAGAGTGTTCAGAACCCAGTTAGT | 43691 |
| 10066 GGACCCGGTCAAGTCACTAAACAGTA | 21724 GACCCGGTCAAGTCACTAAACAGTA | 32708 ATGCTAGCCACCCTGTCCAA | 43692 |
| 10067 CGTTACAGGCTGGGCTTTC | 21725 TCTTGGGAACATCCACTCTTAAAC | 32709 CACCTATAAATAGGCTTCGTCACA | 43693 |
| 10068 AACGTGCTCACGGGAGAAAA | 21726 GCTTCATATCCAAGGGGTCTAGATG | 32710 TCCCTTGCACCGTGCTCACA | 43694 |
| 10069 GCCAGCTCCATGGCCTTTGT | 21727 GCACACACTTGTTTCCATAGCAGTC | 32711 ACACACGGCCAGCTCCAT | 43695 |
| 10070 GGAGTCAAAGACATTGATTTCCCTTCA | 21728 GGCCTCAACTGGATCGGAAGTC | 32712 GGAACCAACTGATGGACTCAAAGACA | 43696 |
| 10071 CAAGGTCTATATCCCTTCCCCTTGAAC | 21729 ACTCTTGGTCGAGGAGATCACA | 32713 GCCTCCTATTGAGAGTCAAGGTCTA | 43697 |
| 10072 GGAGGGCCTTGGTGTCTGAATC | 21730 CCTGCCCTCGCACAAACA | 32714 CGGTCCTTCAGGAGGGCTTTG | 43698 |

| | | | |
|---|---|---|---|
| 10138 CGGGGCTTCTGTGGGTCATT | 21796 CTCAAAACCGAAATGTGACCCTTTTC | 32780 GGCATAAAGGCGGGGCTTCT | 43764 |
| 10139 GACGTGATCTTTACCCCTAAT | 21797 CGGTACTCGGCCACACCAA | 32781 CTGCATGGAGACGCTGATCT | 43765 |
| 10140 GCAGTGGGATAAGTGGCTTCAA | 21798 CTCAGTGGCCTGATAATTACATTGAGT | 32782 GCAGAAATCTTGCAGTGGGATAAG | 43766 |
| 10141 GGGATCTGAACCTCTTTGGGATT | 21799 CAGCACCAGCTCTGTATAGTAGTTA | 32783 TGAGAGGACCAGTGGGATCTGA | 43767 |
| 10142 GAGGAACAGGCTCTCACTAGACATTG | 21800 GGCCAGGAAGTCCACAATCA | 32784 GCAGGAAGTCTCCATCTATGAGGAACA | 43768 |
| 10143 GCCCAGTTCATGGTCCTAGAGAA | 21801 GCTTCTCATACTGGTCTTGATGGAT | 32785 TGAAGAAGGATTCAGCCCAGTTTC | 43769 |
| 10144 CCGAGGACTATAGAAGAGTGAGGTTTC | 21802 ACGGAGCCGGAATCTCTGA | 32786 CTCAGAAGTTTTACCGAGGACTATAGAAG | 43770 |
| 10145 GAAGGGGAATGAACAAGAGGAGAGA | 21803 CCCCTAAAAATGGGTGCAGGAATC | 32787 GGCCAAGAAGGGGAATGAACA | 43771 |
| 10146 GCTCAGCTCACAGTCCCTTACAA | 21804 GACCCTTCCTAATCATGGAAGCTTT | 32788 ACCCCACCTCCATTCTCCTTAG | 43772 |
| 10147 GCTTTTGGTTGAGTTACAGTGGTTAC | 21805 GTCTTACAAAGTCGTTGATCCCACAA | 32789 TGGTGGCTTTTGTTGAGTTACA | 43773 |
| 10148 GGACTGTGTCCACATCTGGAGCTT | 21806 TCGGCCATGTCATCTGAGGAT | 32790 CGGTAGGTGAAGGGACTGTGT | 43774 |
| 10149 GCTCATCAGCTTAATCTACCCTACT | 21807 GGACTGGCTGCCTAAACTGTCA | 32791 GGTGAGGCTTTCTGCTCCAT | 43775 |
| 10150 CTGGGAGTGTCTCTCTCTTGAGT | 21808 GCAAAGTGAATCTCCACGGAAGT | 32792 CAAGCCCCTCTGGGAGTGT | 43776 |
| 10151 GAGAGGGGAGAAGCAGGAGGATA | 21809 AGAGGGTTGCTGGATGGGTTAC | 32793 ATGCGGGAGAGGGGAGAAG | 43777 |
| 10152 CTAGCCAAGATGTTCTGTGGAT | 21810 GCTCACCACTGCTCTTGTTCCTT | 32794 CTGAACTCTGCCAGCCCAAGAT | 43778 |
| 10153 CTAGCATTCCCCTCCCTCTCAAAATC | 21811 GCCCAGGAAATGTAGCCCTAT | 32795 TGCCACCACGCCAGCATT | 43779 |
| 10154 TGGAAAGACAAGCCCCAGACA | 21812 AGATGCTTTGTGCCGCATGTAGTTTG | 32796 CTGGGAGTGGGAGGAATGGAAA | 43780 |
| 10155 CCACATTCCAAAGCCAGGGAAAA | 21813 TCCATACGGGCCTTGACCTTTG | 32797 TGCCTATTGCCTTGAACCACATTC | 43781 |
| 10156 CTACTTTTGAGTGGAAAATGCATCAA | 21814 AGCCACCACGTGCTGTGAT | 32798 CCCCTGTAGCCACTTTTGAGTGGAAA | 43782 |
| 10157 CTGCTGATTGCCTGACAATTTGGATT | 21815 AGTGACAGCTCAATTCTGATGCTA | 32799 GGAGTTACTGCTGATTGCCTGACA | 43783 |
| 10158 ACGAGGACTGAGCATTACGAA | 21816 CTGCAGGTCCATGCTCTCTTC | 32800 ACACTGGGAACCAGGGACTGA | 43784 |
| 10159 GCATCTCAACACTCACCTCCATTG | 21817 GAACCCAACAGAACCCAAGACT | 32801 TGGGGCAGCATCTCAACACT | 43785 |
| 10160 GTGTGTGCAAAACTTGGCTCTCA | 21818 TGATGCTTGGAGTGAAGTGATGCTT | 32802 GCTTGGTTTCTGCTTGTGAA | 43786 |
| 10161 ACCTCAGCCTCCAGCACCTTA | 21819 ACACAGCAGCTCCCTCTTGT | 32803 AAGCGGCTGCAGGCTGGAA | 43787 |
| 10162 ACCAGTACAACCATCAAAACTCT | 21820 GCCAACTACCAGTCACTTATCA | 32804 CTCTTCCTACCAGCACAACCAT | 43788 |
| 10163 GCTGCAATGGAAGCCACTTGA | 21821 AGGACGTAAACATACAATGGTGACA | 32805 CCCACCCTCCTGCAATGAAA | 43789 |
| 10164 GCGGGACACACCCAAAGGAA | 21822 GGGTTTGGGCTGTTTTCACCTCTA | 32806 ACAGCAGAGGCGGGACACA | 43790 |
| 10165 GGGTCAGTGGGAGTTCCTGTCT | 21823 GCAGAAGAAGCATGGGTTTAAGT | 32807 TGATGTAGGAACCAAGGGTCAGT | 43791 |
| 10166 AGGCTTCTTCTTCCCAGTGA | 21824 CCCCAAGCCTATTGAGACATCTGTA | 32808 AGCGCTCTCCAGCCTTGAA | 43792 |
| 10167 GCCTGGGTTCTAGGTAACAAAGCAA | 21825 TCTGCCTGGGTCCCCGAAA | 32809 AGAGGCCCTGGGTTCTAGGTA | 43793 |
| 10168 GCCCAGACTCGATTTGGACTT | 21826 GAATGCATGTGGGATCCATTACTCA | 32810 AAGGCCAGTTAGCCCCAGACT | 43794 |
| 10169 GAGAAGCTGGGACCAGAGATCAGT | 21827 TGAGGAGGGAAGGAAGGAAACT | 32811 ACCAGTTGGCCATCCTAGAGAA | 43795 |
| 10170 GGAACTGTCCCTGCTGGCAAT | 21828 TGATGGAAGATGAACACTCCACTTG | 32812 CTCCATTTGCACTTTGGAACTGT | 43796 |
| 10171 AACCCATCACACTGTCTTAACTGA | 21829 GTTTCATGTGGGTTTTTGGCAGTT | 32813 CAGGCACAATTTAACCATCACACT | 43797 |
| 10172 TCTTGCTTGCCAGCATCAGTAG | 21830 AGAGCTGCCTAAAGCTATCCTTTA | 32814 GCTCGCCCTACGACTCTTGCTT | 43798 |
| 10173 CACCTCGCTTCAAATCCTCTTC | 21831 ACTTGGCTAGGGCCTTCAGA | 32815 TCTTCCTAAACACCTCGCTTCAA | 43799 |
| 10174 GCAAATACCGACCCCACTATGTCA | 21832 GTGTTCCCATCACATTTTCGGTATG | 32816 TGTAGTGCACAGGCTGCAAATAC | 43800 |
| 10175 CAGGGTGGAGTGAAGGGCTTTT | 21833 GGTGCAAATCTCATTCTCCTTGAA | 32817 AGACTGCCAGGCTGGAGTGA | 43801 |
| 10176 GCAGTGTTTCTTTCCACCTGTAG | 21834 TGAAGGTGGGGAGGGTAAAGT | 32818 TGAGTTTCTTCTCTGCCAGGTGTT | 43802 |
| 10177 GCTCACACAGCATGCCTCCTA | 21835 GGTGAGTTCCTCGAATGGTGCAT | 32819 TTTGCCCCAGAGGCTCACACA | 43803 |
| 10178 TCCACTTGCTATGTGCCTCATCC | 21836 AGCAGGCCCTGAGTTCTGT | 32820 CTTGCTCATCCTCCACTTGTCT | 43804 |
| 10179 TCTGTAGCCTAAAATCTCATCT | 21837 CAGGGCTCATGGGCAGAAAGT | 32821 CTGAAAAGTCTGCACCCCAAAA | 43805 |
| 10180 CCCAGCGATTGTGTATCTAGGGTGTT | 21838 TGCCCGGCCTGTGAACAT | 32822 CCTCTAATATGACCCAGCGATTGTGT | 43806 |
| 10181 CCTCCTAGAAGGAACTGTAGTTAATCA | 21839 ATGCACGGAATACCTCTGGAAAT | 32823 GGTTTCTCCCCTAGAAGGAACTGT | 43807 |
| 10182 GCCAGCAGCTGAAGGTAAACAA | 21840 CGTGGCCCATGAAGGGTGAA | 32824 CTCCATTGCCAGCAGCTGAA | 43808 |
| 10183 TCATGCGTGCTGGGCAAA | 21841 TCCTGCCACCCCTTCTCCAT | 32825 TCCTTGGGACCTGGGGTCAT | 43809 |
| 10184 GCTTGCTTACGCCCAGGAA | 21842 AGACTCCACCTTGCTTCTGATCT | 32826 TCCTCCATGGTTAGCTTGGTTAC | 43810 |
| 10185 GGCCACAAGCTCTGCTGTGAA | 21843 AGAACGCCTGATTGCAAGATGA | 32827 AGCCATGGCCACAGTCTCT | 43811 |
| 10186 CTCAGATATGGGTATGTGACCATCAA | 21844 AAATTGGTGGGATACCATGTCAA | 32828 ACACAAACAACAGTCCTTCTCAGAT | 43812 |
| 10187 CCCTTCATCTACTCGCTACT | 21845 TCCATGCCACCTAACATTCA | 32829 CAGGGTTCCAGCCTCCAT | 43813 |
| 10188 CCTTATAGCTGCTTCCTAACCAAAGT | 21846 GGATGGGCAAGTGGTTGTATCT | 32830 GGTCACTTCCCTTATAGCTGCTT | 43814 |
| 10189 GCTATCCTCCTCACCCAGTCA | 21847 TGAGTGTCCCTGACCTCAAGT | 32831 CCAAGTGTGCAAAAAGAAGGCTAT | 43815 |
| 10190 GGAACAGTCAGGTGAGAGGGTAAGA | 21848 AGGCCAAGTCACAGGATCT | 32832 GCACTATGAGAAGGGGAGCAGTCA | 43816 |
| 10191 GCCCTGGGAAAGAAAAGTCAGA | 21849 GGTGGGAGCACTGTTCTCAAG | 32833 AGGGAATTAGCCCTGGGGAAA | 43817 |
| 10192 CAGCAGTCATGGCAGGGAAA | 21850 TGCAGAGCAGGACAGGGATT | 32834 CCGGCGATTAAGCAACAGCAAGT | 43818 |
| 10193 GTCAGGATGCTATTCACGTCATC | 21851 CGGCTCTTCGTGGCTTCA | 32835 CCCTGATGAAAACAACCGTCAGGAT | 43819 |
| 10194 GTGAGCGTGCACCATGGATGTA | 21852 GTACTCCTGAAAAGTGGACCCAAT | 32836 TATCCCGTAGCGTCAGTGT | 43820 |
| 10195 CCAGCCATGACCCAGACA | 21853 GACCCACAAAGCTGAAGATGTTAC | 32837 ACCATGCCCAGCCATGAAC | 43821 |
| 10196 CTCTGTATGCCAGCTCCCTTTC | 21854 AGGGATTCAGGCTGTTTCCATTC | 32838 CCTCTCTTGCCACATGTCTCTATG | 43822 |
| 10197 GGTGGAAGGAACACATAGAGTTGCAT | 21855 CAGTCTTTACTAGTGCGGCCAAATC | 32839 GGGTATGGCGATAATGGTGGAAGGAACA | 43823 |
| 10198 GCATCCATTGCTATCCAGCATCAGT | 21856 GGAAATCAGGAAGGTGATGTGTCA | 32840 CATGGTCATGCAAAGCATCCAT | 43824 |
| 10199 GCTATGCCACTTCCTCTGAGACT | 21857 ACAGCAGGGACAAAAAGGATCA | 32841 CTCTCCTTTGGTTTTCGATCTCCTATG | 43825 |
| 10200 GCACAGCACTGAGGACAGCTT | 21858 TTTCCCAACGGCTCTCACA | 32842 CGTATTCTGTAGCACAGCACTGA | 43826 |
| 10201 AGAAACACCAAAGGGCAGACA | 21859 TGGTCCTCTGGCTAGAAACAGT | 32843 AGCTGGAAAGCTAGAAACACCAA | 43827 |
| 10202 GCACTGTGAGCACAGGTTCTTC | 21860 GCTGTGCAGTGAGATACAGGTAA | 32844 TGCCACCCAGCACTGTGA | 43828 |

| | | | |
|---|---|---|---|
| 10463 GGGTATGGAGATAGGGGTCACA | 22121 GGAACTCCACACAGCTTTCTCT | 33105 GGAAAGCCCCTGGGTATGGAGATA | 44089 |
| 10464 CCTGTCCATTCTGCATTGCACTTG | 22122 TTCTCCTGCCGACCTGTCTAC | 33106 TCCGGTCCTCCCTGTCCATT | 44090 |
| 10465 CCCTTATTGCCATTGGACTCAAAGA | 22123 GCTACTATATCATCCTGACCTTGCATTAG | 33107 GAGATGACTATTCGTCCCTTATTGCCATT | 44091 |
| 10466 TGGCAGTAGGCAGGAGTGT | 22124 CTCTCCTTAGGCAGTGATTCTTC | 33108 TGACCCTTGTGGGTGGCAGTA | 44092 |
| 10467 TCACCCTTGATAAGAGAGGGAAATG | 22125 GGGAGGGAGAAAGGAGGAGAAAC | 33109 GGCTTCTGAGAATGACTTTCACCCTTGAT | 44093 |
| 10468 AGGGAAGTGTCCTTGCAGGATTG | 22126 CTGTAAAGAGTACAGGGTTCTCTGA | 33110 GCCCATGTACCTTTAGGAAAGTGT | 44094 |
| 10469 TGATGCCTACAGGGAGACACT | 22127 CACCCTTACTCTTCCCTCTGCTT | 33111 ACATTCACAGCTTTGATGCCTACA | 44095 |
| 10470 GCTAAAGCCACTTTCTCCAGTGT | 22128 CTAGGAGAGATTTCTAGGGTGGTT | 33112 GGAGGTGTGCCAAAGCCACTT | 44096 |
| 10471 GCACGGGACTCAGAATAGCCAAA | 22129 GGGACATGTGACTCCTCCAACT | 33113 GAAAACGCACGGGACTCAGA | 44097 |
| 10472 CTGATTGCCGTGCTAGTTGTGT | 22130 GTGAACTCAGCCTCCTCTAAAGATCAA | 33114 CTGGGCAGTCATGACTGATTG | 44098 |
| 10473 GTCAGTCGCAGTTCCAGTCAAC | 22131 CCCTTCCTTCTCAGCTCCATTTG | 33115 GGTCCCAAGATGTCAGTCGCAGTT | 44099 |
| 10474 CGGGACTTGATTCAGGTTGTGA | 22132 GGTAAAGTCAGGATTTACACCCAAGTT | 33116 GAGACAGACATGACGGGACTTGA | 44100 |
| 10475 CTCAGGACTTCTGGACATTCACA | 22133 CTGCCAGAGGGATACCCATGTA | 33117 CAGACGCTAAAGCTCAGGACTTC | 44101 |
| 10476 GAACCAAGGAGTGACACAACTGA | 22134 TTGCAACCTAGTCAGTGAGAATGA | 33118 CCCTGGGAGGGTTTTGAACCAA | 44102 |
| 10477 GGCATGGATATGGCACAGAATAAGAAAC | 22135 TGACATGTTATGGCTCATGTCTCAA | 33119 GAAAGGCATGGATATGGCACAGA | 44103 |
| 10478 GAGGTTCACAGGGTTGGGTAT | 22136 PTCCAGCCCTCCCTTAGTAG | 33120 CAGACGTGAGCTTGAGGTTCACA | 44104 |
| 10479 CAATGAGGTTGTCTTAGCCCTGT | 22137 ACACCCACTCTGGGCATGT | 33121 GCTACAGGATACAATGAGGTTGTCT | 44105 |
| 10480 AGCAGATGTGCTGCCACATAG | 22138 TTGCCTCCACCATGCCAAA | 33122 CCCAGGAATGCCTTCCAGCTTAG | 44106 |
| 10481 GCCAGGAACGATGTGTTAAATGCTT | 22139 CTGAGCCTCCAAGTCCTCATTTC | 33123 ATGTGCCAGGAACGATGTGT | 44107 |
| 10482 ACTTTCCACCCAGTCACTCA | 22140 TTGAGAAAGAGGGAAGAGTCTAGGAT | 33124 TTGGTGACAGTGTCACCTT | 44108 |
| 10483 GCCTCAACCCAGTTAGGCAAT | 22141 AGAGGCACACTTGAAAAGACTGA | 33125 TGGATCTGTGCCTGCCTCAAC | 44109 |
| 10484 GGAGCTGCTTTTGCCTGTT | 22142 CACCCACACACATTCTACCTTGA | 33126 TCCAGACGTGAAGCTCAGGACTTC | 44110 |
| 10485 CCAGTGTGTAGTCTGTGAGTAGT | 22143 TACTGCTGGCCGTGAGGATGT | 33127 TCCCTGTGTGTCTCCCAGTGTAG | 44111 |
| 10486 ACTGGTCTTGTTCCAGCTTCTTC | 22144 GTGAGCAAGGTATAGGAGATGAAAGA | 33128 CCCAATTGCTGCACTGGTCTTG | 44112 |
| 10487 TGGTGTTTGACTGGGCCTTA | 22145 TGCACTCCTTTCCCTATCTCCTTATTA | 33129 ACTTCATGGAGAAGATGTGTGTTGA | 44113 |
| 10488 AGGCCAGATGTCCTGCCAATG | 22146 GGGCAATAGCCCCAAGGTATATTTTC | 33130 GCCAAAGCAAGGCCAGATGT | 44114 |
| 10489 GCCAAGGAACCAATACTGATAAACAGAAG | 22147 TCACTTCAGCAAACATGCTTAAG | 33131 GCCTCAAGGAACCCTATACTGA | 44115 |
| 10490 CTGGCAACTGACCCAACCTATTG | 22148 GACCAGCATATAAGAGGGTCATGAAT | 33132 AGGCTGTCTCTGGCAACTGA | 44116 |
| 10491 GTGACCTTGGCTCTACCACTAAC | 22149 CTGGAACATTAAGCAGCTCACCTA | 33133 GTCCCCAGGAATGTGACTTTTG | 44117 |
| 10492 CACAGTGCCTGTTCTATCTCTGAT | 22150 AGGGGTCTGGGAGGGAAGATAA | 33134 CCTCAGAATTTCACAGTGCCTGTTC | 44118 |
| 10493 CCAGAATTGTCCAGAAGCTCTCA | 22151 GGGTCAGGGGAGGTCACTAAT | 33135 TGGACCTGCTAAGCTCCAGAA | 44119 |
| 10494 CCACCCCAGATTCAGGTACTTC | 22152 TCTCTTTATCTCAGGCCATGTAGTCA | 33136 CGCTCCTTTCCACCCCAGATT | 44120 |
| 10495 CTGCAACTGCACCCAAATGCTT | 22153 GGTTACCAAGGGCAGTTGAGAGT | 33137 TTTCCCTTTGATGCGTCCAACT | 44121 |
| 10496 AGGGCAACTGGCGGAAAG | 22154 CCGATATTCCTTCCCTTTATTGGTT | 33138 GGAGGGAGGTAGAAGGGCAACT | 44122 |
| 10497 GGAGGCGCTTACAGTACTCTCT | 22155 AGGGCCATATGCTCTTCTGT | 33139 AGCACCGGAGGCCTTA | 44123 |
| 10498 GGCTCCTTCTCAACCCCTAGTTC | 22156 TGGCTGGCAATTCTGATGCAA | 33140 TGCCCTGGCTGCTTCTCAA | 44124 |
| 10499 GACTGGATACTTAGTGTGCTTCTT | 22157 TCAGGCGCAGAACTCTCAATG | 33141 GGTTACACTCTTTCAGACTGGATACT | 44125 |
| 10500 CCTTCCTGAACGTCCACCTGAA | 22158 GTGAAAGCTATGCCCTGGAGAACA | 33142 TGGCACCTACACCTTCCTGAAC | 44126 |
| 10501 GCCCTCCATAATTTGGTGCCCTTCA | 22159 CACAGAGTAGGTGCTCGTGAAGTT | 33143 GGCACCAAGGCCCTCCATAAT | 44127 |
| 10502 CCTACCCCAGACTATGATGATTGAAGT | 22160 GAGATGCATATTCAGGGAGCAGTAAAC | 33144 TCTTCCCACTTACAGCCCAGACT | 44128 |
| 10503 GAAGTTGCTTCATCTCAGAGTTTAGTGA | 22161 CTATGAACTTGACTTGGCCAGCTA | 33145 ATCATGGAAGGAAGTGCTTGATCT | 44129 |
| 10504 CAGACACCCTCAAGCTCAGTCA | 22162 GCAGTTTGACTCTGGCCAGCTA | 33146 ACTCCACCAAGGCACAGACA | 44130 |
| 10505 GTGGGGTATCACAGCAATCCTACT | 22163 AACAACACAGGGCTTTGTTTC | 33147 TCTCTGACACAGTGGGGTATCA | 44131 |
| 10506 TGACACTAGGAGTGACAGGACAA | 22164 GACTTCAGTCTGCCCATTGGTGAT | 33148 CCCACATTAGCAGAGACCACTGA | 44132 |
| 10507 AGTGACGTTACAGGGAGTCT | 22165 CATCACACTCTGGTACACTTTGATT | 33149 GGTGAGGAGGACCAAGTGACCTT | 44133 |
| 10508 TTCTGGGTTCAATCTGGGGTCTATG | 22166 AGCCTCAGCCGAGCCAAGT | 33150 AGGGAAACTTCATTCTGGGTTCAT | 44134 |
| 10509 CCCAACCTTTACTTGGAGGTCAGA | 22167 GACCCAGAAAGGGAAGGGACTTA | 33151 TGCCCCCCTTCCCACCCTTACTT | 44135 |
| 10510 AAGGGCTGTGGGCACCTAAG | 22168 CTTTTGCAGTACCCTAGGCACATA | 33152 GGTAGGTCAGGCAGCAATCAAG | 44136 |
| 10511 GTTCTCTATTCCAAAGGCTATCATC | 22169 GACACAGAGGTAGTCCTCAGTCTATG | 33153 CCTTCCACTTACAGCTTAGTTCCTGTA | 44137 |
| 10512 CCCTGCTAACCCACCCTGTCT | 22170 TGTCCTCACACTATGCCCAGTA | 33154 TCCCGTACACCTCCCTGCTAA | 44138 |
| 10513 ACTCAGGGTTCAGTCTAACA | 22171 GTATAGAAAGGGTAGACACTGTGGATAAC | 33155 TGGCCTGTACCCAGGCATGGAA | 44139 |
| 10514 TCCTCCATGGCAGCAGTGTT | 22172 GGTGGGGCCTCTTCCTAACAA | 33156 CAGTGTGTCCAGCCACTAACTTC | 44140 |
| 10515 CTCTCCTGAAATGAATCATGCAAAC | 22173 GCCCACTGAAGAGCATCGTA | 33157 GGCACTTGACCTCTCCTGAAA | 44141 |
| 10516 GTGAGCATGAAGTGAAGTGGGGAGATT | 22174 CCCCTCACTCCATCACACAGA | 33158 GGGGAAAGGTAAGAGTGAGCATGAA | 44142 |
| 10517 GCATTCAATCACCCTATCTGGAGAA | 22175 GCTGTACATAGGGATGTGAGTGAAAG | 33159 TGCTGGGCCACTGTTGCAT | 44143 |
| 10518 TGACCTTGGTACTTCCCTGTGT | 22176 CAGATCCCAAGAGGAGGGGAAAT | 33160 GAGCCTTCTGACTGACCTTGGTA | 44144 |
| 10519 GTTGGGAAAAGAGTTTGGAGTCAGA | 22177 AGGCCAACTCCTCAGCTCAT | 33161 GGGCAGTGCTGAGGTAAAGT | 44145 |
| 10520 GGGAAGTGAGGAAAGGGAGCTT | 22178 TGTTTCTCTCCACTGCTTCAA | 33162 GTGGTGGTTAGGGAAATGAGGAA | 44146 |
| 10521 GCAGGAGTGAGGAAATGGGGAAA | 22179 CCTTGCATTGGCCATTGGCTTT | 33163 CCCATGAAGCAGGAGTGAGGAA | 44147 |
| 10522 GTGAGCAAGTTGGAGGTTGATGA | 22180 TGTTTCTGACAGAGAAGAGTTGCTA | 33164 GGGGAAGTGAGTGAAGCAAGT | 44148 |
| 10523 AGGCCCTGACTCTCATCCTAAC | 22181 GAGAGAATCCAGGTAACAAACCAATG | 33165 AAGCTCACCAGGCCCTGACT | 44149 |
| 10524 CCCTCCACCTGTACCTAGTGTCA | 22182 TCACAAAGTTTGGCCATACAGAAGA | 33166 TCCCTCCACCCCTCTACCTGTA | 44150 |
| 10525 GCTACAAGCATGCCACGATCT | 22183 GGGTGAGTAGAAGCAACGAGGACA | 33167 AGCCCTTACAGTGGCTACAAG | 44151 |
| 10526 GTTCAAAAATATGGCCAAGGCTCT | 22184 GCAGGGAAGGGAATCCAACAGT | 33168 GTTTGGCAGTGTCTGTTGTTCA | 44152 |
| 10527 GGTCAGTGGCGTGGGCTTA | 22185 ACAGTCTGACCCCATTTGTCTT | 33169 TCAAGGGTGCCTGGTCAGT | 44153 |

| | | | |
|---|---|---|---|
| 10658 CCTGTTCCTTCCACTCTTTTCA | 22316 CCTGACCAGGTACAGTCACTAAG | 33390 GAGTTTCAAGGCTTAACCTGTTCCTT | 44284 |
| 10659 CCACAAAGCTCCCCTACCATGT | 22317 CAGCAACCAAGCCAATCCTGAA | 33391 GGGTGAGTTGAAATGCCACAAA | 44285 |
| 10660 CAAAGGCTGTTCAGAACTGATCCT | 22318 GGGTAAAGGTGGGAGAGAAGAGAGTTTC | 33392 TCCCATTACAAAGGCTGTTTCAGA | 44286 |
| 10661 GCCTACCCAGTGAGGAGTATTAG | 22319 TGTAAAAGTGGCCAGTCTGTTCT | 33393 AGAGGGCCCTACCCAGTGA | 44287 |
| 10662 ATCCAGAAGGCAGCAAGCAA | 22320 AGGCAGAGCAGCTCCACAA | 33394 TGCGGGTCAAGAATCCAGAA | 44288 |
| 10663 CCTGCTGTAGACATTCAACAACCAA | 22321 GGTGCTTGAAGTGGGCTTTTC | 33395 TGGACTCTACACAACATCCTGCTGTAGACAT | 44289 |
| 10664 CACGGGAAGTCAAATCAATTACGAT | 22322 GGCCAGTTCGCTACCAAGGAA | 33396 GGAGAAGAATTCACGGAAGTCAAA | 44290 |
| 10665 GGTTTTGACCTCCCGGAATATTAGGAA | 22323 CACCTCAGCCTCCTGCATAG | 33397 CTTTGGTTTTGACCTCCCGGAAT | 44291 |
| 10666 GGCTTCTGGGGTCAAGAACACACT | 22324 AGTAGTCCCCAACCAGCAGAGA | 33398 GAGTTGAGGCTTTTGGGGTGTCA | 44292 |
| 10667 TGCACGTAGTGCTAAGAGAGTTATG | 22325 CCTCTTCTTCATCCTGGTTAATTGGAAGT | 33399 GTGATTGGTTGCACGTAGTTGCTAAG | 44293 |
| 10668 GACTGATTATGAGGCAACGTGTGT | 22326 AGACAAGGCTCAATGTAGACAAG | 33310 AGCAATGTTCCCCTTCTGCACTGAT | 44294 |
| 10669 TGGCATCTTGGGCCTAGAA | 22327 CGTCTGTCACAGTTAACGGCAAA | 33311 GCTTCCGGCTGGGCATCTT | 44295 |
| 10670 CCGGAGCACAAAGCAAGTGAA | 22328 TCCACACCTGCGGCCAAAAT | 33312 CTGTTCACAAACCGGAGCACAA | 44296 |
| 10671 ACACACCAACAGGCACAGAAG | 22329 TGCTGGGTGCCATGTGCTT | 33313 CACACCATCGTACACACCAACAA | 44297 |
| 10672 CGCTTCATCAACCTCAATGGTAAG | 22330 AGCTGGGTGCCAGGACATC | 33314 GGAGAGCTGCATTCGCTTCATC | 44298 |
| 10673 GTGTTAGGAGGAAAGTGTCCAGGTTT | 22331 CTGCAGAAGAACCTACAGGTAACATC | 33315 GCCTTGTTCCCAGTCTTAGGAGGAA | 44299 |
| 10674 CCATCAGTGGAGCTTTCAGTTCTTC | 22332 GCCCTGTGCTATGGTCATTT | 33316 ACCCTCCATCAGTGGAGCTTT | 44300 |
| 10675 GCACAGCATGGAATGAGAGACA | 22333 GTGAGAGGAAAATCTTGGGCTATGA | 33317 CTTTGGTTAATGCACAGCATGGAA | 44301 |
| 10676 AGGCACTAAAAGCTGACCTAAAGT | 22334 GGAGCAAGGCACAGTTTTCAGA | 33318 TGCTGAGGTCAAGGCACTAAAAG | 44302 |
| 10677 AGTGGCTCCAGTGTGGATGA | 22335 GCCCTTTAAGCCAACCCTACA | 33319 GGGGAAGCCCACTGGAAAAA | 44303 |
| 10678 GCTTGCCTTGTAGCTTGGTGTT | 22336 GGCCAGCCACTGGTGAACT | 33320 CCTGCTGTATTTGCTTGCCTTGTAG | 44304 |
| 10679 AGGGTAAGGTGGAGAGAGAGTCT | 22337 TTGTCACCACCGGCGCACATT | 33321 TCACGGAGCTCAGAGGGTAAG | 44305 |
| 10680 AGAGTCTTGGTCCCGGAGTT | 22338 GCGTAGCAGATGTGATGCCTAT | 33322 GGCCAGTCACGCTAGAGTCTT | 44306 |
| 10681 TGGAAGACAGGGGTGGAAAAAG | 22339 CAATCTCACCCAAACCTGCTTCT | 33323 AGAGGGCTCACCCAGATTGGAA | 44307 |
| 10682 TGTGCCGCTACAGAAGGCTAAAG | 22340 CCCCGGTACCCAATGAGGAGCTAG | 33324 AACAAACACTGTGCTGCTAGA | 44308 |
| 10683 CACTTCGTTTTTGCAGGACACA | 22341 ACAGAAAAGTGTGTGTTCACTGATA | 33325 CACACCTCCTGCTACCTAACA | 44309 |
| 10684 TCCAGTCATTTGGAGTAGAGA | 22342 CAGTGCAAGAACACTGAAGACTCA | 33326 GTAGAGTGTGATTCAGCCATT | 44310 |
| 10685 CTCGTCTGTTGGCAGAGACAACT | 22343 ACTGATCTCCCAGTCAGGGTCAAG | 33327 GTCCTCAACGATCTCGTCTGTT | 44311 |
| 10686 GGGGAAGAGTAATCTATGGGAGCTAAC | 22344 CGAGCCTGTTGCTTCACATTA | 33328 GCTCAGGAAGGGGAAGAATAATCTATG | 44312 |
| 10687 CCTGACCATGTCCCCTTTGACA | 22345 CCCGAGGCTCCTCCGGTTATTA | 33329 ACAGCTGACCCTGACCATGT | 44313 |
| 10688 GCTGTAGGGTCAAAGAATGTGACT | 22346 CCCAGAAGGAACCTCACACCTCAG | 33330 TGGAGAGCATGGGACTCCTTCA | 44314 |
| 10689 GCAGCATGCAAGCCAATTGTCA | 22347 CACTCTGAATGTGAGGCTGTAGT | 33331 AGCCAGAAAGCAGCATGTAA | 44315 |
| 10690 TGGTAACTAAGATTAAGGGCACTATCT | 22348 GTTCAGCAAGGTGTGTTCTGT | 33332 CTGAGCTCACTTATGCTGACTAAGAT | 44316 |
| 10691 CAACTTGCCAGTCTTCACGTATC | 22349 TGGAGGGCCAGTGGGATGT | 33333 CCCAGCTCAACTAGCCAGTCTT | 44317 |
| 10692 CTGGTTCTCTGCATAGACCTAAC | 22350 GCATTACCAAGAGTCTCCCCTTGT | 33334 TTCTGCTGGTGCTCTGCAT | 44318 |
| 10693 GCCTGTGTTACATCCTGAGGAAG | 22351 GGACAGGGTGGATACTGTGTTTGTAG | 33335 CCACAGTGCCTTTGTCACATC | 44319 |
| 10694 TCCTCCTTCACTCCCTGTCATAG | 22352 CTTAGCACAGAGTAAACCCACACA | 33336 GTTTTCCCCAATTATCCTCTTCACT | 44320 |
| 10695 GGAGAAGGTCTCATTAAGGGAGTAGA | 22353 CCCTCCCAAACCTGGACTGTTCT | 33337 CCCAGGAGTTGGAGAAGGTCTCAAT | 44321 |
| 10696 GGAGGGAGTGATGGGATGTGGATT | 22354 CCCCTCCCTGCAGGACTTAAATA | 33338 TGCACGTCTGAAGGGATGAT | 44322 |
| 10697 CAAGCCTTATCAGTTCTTGGCATCA | 22355 CAGACCCAAACCATATCACCTTCCTTTC | 33339 CCAACCTCACTCAAGCCTTATTCAGT | 44323 |
| 10698 GTCAATAGCCAGGAAACATGGTAA | 22356 GGGTCAGTCTGTAGAGTCCGTTCG | 33340 GGGCAGTTTCTAATTGTCAATAGCCAGGAA | 44324 |
| 10699 GCAACTGCACCGGTCTTTTG | 22357 TAGCAGGGCCAGAGCAA | 33341 GGCTCCTCTGGCTTCACAGCAA | 44325 |
| 10700 CTCCCCTAGTTATTAAGGGTGAGGTATC | 22358 CTGCAGACATCTGTGTACTGTGAGA | 33342 CTGCTGGTAACCTCCCCTAGT | 44326 |
| 10701 GTGCTTGTATCCCACTCCAACTAC | 22359 AAGTGTGGTCTTCATGGTTCCAA | 33343 GGGAATAAAAGATCTGGGCTTGT | 44327 |
| 10702 TTGGGCTGAGAATACCTCTCT | 22360 GTTCCCACAGAGGGAGCATTTA | 33344 CCGGGGTTTGGATTTCTCTGGTT | 44328 |
| 10703 CCTTGTTACTGTTGCTTGGGATA | 22361 GCACAATTTCAGCAAGCAGAATC | 33345 CTGAGCCTTTGATCCTGCTGCTGT | 44329 |
| 10704 GGGCACTAAGAAGGGCTCAGAGAT | 22362 CTGTGAGCACTCAGGGTCACGAT | 33346 TCCCTGAGCTGGGCACTAA | 44330 |
| 10705 CCTAGATCAGCCTCTATCGAGTTC | 22363 CACAATGGTCCCAGACAGAGCAA | 33347 CAGGCTAACTCAGACACTTCCTAGA | 44331 |
| 10706 TGCCACCAGGATATTGATTGAGATT | 22364 GTGCCATACTACCCAAAGCAATAC | 33348 CTGTGAAGAATGCCACCGGATATT | 44332 |
| 10707 CAGCCCTAAGGGTGGGATTTGA | 22365 TGGCCAGGGTACCCAGTGA | 33349 CCCACCATGACACAGCCCTAA | 44333 |
| 10708 ACGCCAAGCCAGAAAAATATTACA | 22366 CAGTTTCCTTGGGCTACACACTC | 33350 CATCAACGCCAGGCCAGAAA | 44334 |
| 10709 GACCAAGCTGCGTCAATTCT | 22367 GGTGGTGATGAATGATGGACATACT | 33351 CTTTATATCCAACCCGACCCAAGT | 44335 |
| 10710 GGGAGAGCTGGTCTATAAGAGGAACTTG | 22368 TCTGAAGATTTCACGACAGGAAGAA | 33352 GGGTGGGAGAGCTGGTCTATAA | 44336 |
| 10711 TGCCTGTAGCATTTGCATAGGAAT | 22369 GAACCACAAACCTTTGGAATGGAA | 33353 CCCTGCCTTGCCTGTAGCATTT | 44337 |
| 10712 GTTGGGTAAATCTGCCTATTTCAGA | 22370 GCTCTGCTAGCAAACTGTGCTTGTT | 33354 GAGTATTGTGACTAGGTGGGTAAATCT | 44338 |
| 10713 CCACCCTAGTCAATGTCACTACCTTTC | 22371 ACCAGTAGGAGGCTCTTT | 33355 TGCTACCACCCTAGTCAATGTCA | 44339 |
| 10714 GCCTGTCTGCCAATTTGAACAT | 22372 GGGGAAGGATGGAGGTATTAAGTGA | 33356 CTGTGGGACTTTAGCCTGTCT | 44340 |
| 10715 CAGTAGGCCTGAAGAAAGGCTGTGT | 22373 TCGAGAGAAAGGCGTGT | 33357 TCCCAACAGTAGGCCTGAAG | 44341 |
| 10716 CCACTGACAGGTCTGCTGTT | 22374 AAGGCCAGGCACCCACAGA | 33358 GGCTTGAAGGGTTCCCACTGACA | 44342 |
| 10717 TGGGGACTCTGCAGGTCAAA | 22375 TGTGCCCACGCCTAAACTGT | 33359 CGCTGAAGCTTGGGGACTCT | 44343 |
| 10718 TGGGTGTCAGGTCACCAGGTA | 22376 AGCCTCCAGCTACCCGGAAT | 33360 AGGCCTCCTGGGTTGTCAGT | 44344 |
| 10719 GCTCAAGGTCTCATTGCATAGAGAAAT | 22377 GTGTGGTGAGGACCATGGATT | 33361 CTCGCAGCCTCAAGGTGTCAT | 44345 |
| 10720 GCTGCTGGTCATTCTGAGTTG | 22378 GGGAGGGCTTCCCACAAAG | 33362 TGTCACCTGCTGCTGGTCAT | 44346 |
| 10721 GTGCAGAATCAAAGACAGTGTAGAAAC | 22379 CCCCGTAGAGAACTGTCTCACATC | 33363 TGGGAACATGTGCAGAATCAAAGA | 44347 |
| 10722 GCCCTGAGACCAAGCAATCA | 22380 ACTCAAAATGCAGCCTAGATAGCAA | 33364 GCAGCAAGTTAGCCCTGAGA | 44348 |

FIG. 36Q5

| | | | |
|---|---|---|---|
| 10723 GTGGTATGCTTCCTGCCATACTARACA | 22381 GCAGCTACCAGATAGACTTAGCTGTAA | 33365 GTAGCAAGTGGTATGCCTTCCTT | 44349 |
| 10724 GTGCCCTTCCTCCCAGTTTCA | 22382 GACAGAACCCCTTGTATAACAATCAGACT | 33366 CCAAGTCCAAGTGCCCTTCCTT | 44350 |
| 10725 CACACTAGAATAGGTAGGGTGGTCTT | 22383 GTCCAGGCAGAGCCATACATC | 33367 GGAAGCCTCCCACACTAGAATAGGTA | 44351 |
| 10726 TGCTTCGGAGTAAGACCTCCAT | 22384 TAGGGCCAAGAGCTCCTTGCAA | 33368 GATGACAAATACTATGCTTCGGAGTAA | 44352 |
| 10727 GACAGTGGCCAGTGGGATCAGT | 22385 GAAGCCATGCAGAAACACATTCCTTAC | 33369 CCTCCCCAGCCTCTTTTGACAT | 44353 |
| 10728 TGTTTCCCACTCTCCAAGA | 22386 CCTGCCCCGCCTCCATATTTA | 33370 GGTTGCTGCTGCGCTTTGT | 44354 |
| 10729 GCCAGATGCTATGTAGTGGCAAA | 22387 GTGGAAATAGAAGCTCACTCTCAACT | 33371 GCACTGTGCCAGATGCTATGT | 44355 |
| 10730 TGATCAGGCACAATACTCAGTCTCA | 22388 CAACACACCAATGCAGCCAATC | 33372 CCCAGACAAAATGATCAGGCACAATACT | 44356 |
| 10731 CCAGGTACTATCAGTGCCGACTGT | 22389 CCTGCAGAGTTATTGGGAAGATGA | 33373 GGAGGTAGGCCAGGTACTATCA | 44357 |
| 10732 CTGTTGTTTGGAGCCAAAAGTGT | 22390 TGGGCACACGTCACAGAATC | 33374 GGGGTCAGTCGTATTTTCTGTTGT | 44358 |
| 10733 CCTTCCACAATGCAGAGCAGTGA | 22391 AGCAGGCTGGGCCAAAATCA | 33375 AGTATCAGGGGCCTTCCACAA | 44359 |
| 10734 CTCTGCCCTGTAAGTTTCTACTGACTA | 22392 CACTTGCGAAGGAATCACCATCA | 33376 TCTCCTCTGCCCTGTAAGTTTC | 44360 |
| 10735 GGAGAAGGTCTTCTACAGTGAAACT | 22393 TGGTGGAGCAGTCACCTCTCT | 33377 CCCCACCATAGGAGAAGGTCTTT | 44361 |
| 10736 CGGCAAGACTAGGAATACCAGGGAA | 22394 GCCTGCCTTTGCAGAGCTTTT | 33378 GCGCTCGGCAAGACTAGGAATA | 44362 |
| 10737 GTATCTTCACATACAGGAAGGAGCAAA | 22395 AGGGCCTTTACAAAAGAGTCTTGA | 33379 AATGGCACCTTTTTGCTGCAT | 44363 |
| 10738 GGTAAGCTGCTCAATGGGCAATAG | 22396 CAGCCCAGGACCCTCTTTTGAT | 33380 TTTCCCAGGTAAAGCTGCTCAAT | 44364 |
| 10739 GCATCCATGTTGCTCTCAGTGT | 22397 GCAGGATATGAGTGATGTTCCAT | 33381 CCAAAATCTCTCTTGGCACCCATGTT | 44365 |
| 10740 CCTGTTTCCTAGCTTGGCTCTCCTTT | 22398 GCCGCCATCTCTGAACTGT | 33382 GCCGATCCGTCTATCAACCTGTTTC | 44366 |
| 10741 TCACCAACACCTTCCTGGAATTAAG | 22399 GTCATAACTACATGGCTGGAACCTA | 33383 CAAGCAATTCTTCACCAACACCTT | 44367 |
| 10742 TGCATGGATCACAGTTCTTCTGTA | 22400 ACCATGCACTACTGAAATCTGGCTATG | 33384 CCCTGGTGCATGGATCACAGTT | 44368 |
| 10743 CCATGTTCTTCTCAATTCTCTGAAAG | 22401 ATCACACGCCAGCCATCAAG | 33385 CAGTTGCAACCATGTTCTTCTCA | 44369 |
| 10744 GGTGATGTGGCCAGACTTGT | 22402 GAGTGCTCACTCAGCACATATCGCTATC | 33386 GGGCTCGGCAAGACTAGGAAT | 44370 |
| 10745 CTTGTGTAGGGACAAAAGCATACCAA | 22403 TTCTGGGGACACCTGATAGACA | 33387 CCCAAGGTAAAAGCAATTCTTGTGT | 44371 |
| 10746 CCAAAGGCCAGGAGGAGGTTT | 22404 AGCAAAAATACCGAGGTAGCCAAT | 33388 ACTGGGCTTCAAAGACCCAAAG | 44372 |
| 10747 GAGAACTGACTCTCCCAGATATAAAGAGTT | 22405 GCCCAATAGGTGTGAAACTTTGAA | 33389 AAGGAGAACTGACTCTCCCAGAT | 44373 |
| 10748 TCTCTGGATTAGGTCCTGCTTTAG | 22406 GGATAGGCAAGTACTGGCTAAAAGT | 33390 GGCTACGAATCAATTCCAGCTGTCT | 44374 |
| 10749 GCCTGGCCTCAATTCTCATTTTT | 22407 CCCCTACCATGACTGATGAAGAAA | 33391 CCACTGTGCCTGGCCTCAAT | 44375 |
| 10750 CTTGGTATGGAATCCTAGTGTATTCTGACT | 22408 GGCTGAGGCCATGGAGTTAAGAT | 33392 GGTTCTTGTATGGAATCCTAGTGT | 44376 |
| 10751 TTCCTGTGAGGACATGTGTGTT | 22409 CAGCCTGCCAATTCCTATGGACTA | 33393 CCCATAAGTGGATTCCTGCGAGA | 44377 |
| 10752 GCTAGCTAGAGGCTACTCTGTCA | 22410 ACCTGTTGCTCTCCATCT | 33394 ACAAACAGCAATGCTCCAGCTA | 44378 |
| 10753 GGCAGAGTCAAAAGGAAGTCAAC | 22411 GAGTCTGATCATACCAGACCATCCTT | 33395 GCCCTTTGAAATAAGGCAGAGTCA | 44379 |
| 10754 TGTCTGGACTCAGGGTGGAATATG | 22412 GAGCTCGTGATAACAATATCCCTTTG | 33396 TCCATAAGGCTTGCTGGACTCA | 44380 |
| 10755 ACACCTGCGAAACACTTTATTGTAG | 22413 CACGCTCAATTTCTCCTGTTTTCA | 33397 GACACCACACACCTGCGAAA | 44381 |
| 10756 CCTGTCATTACCAGTGACTGCGT | 22414 GGAAAGTGGGAAACTTGAAACTGAGA | 33398 AGGTCACACTCTAGACCTGTCATT | 44382 |
| 10757 GGCATCCTTGACCCATGATGAGA | 22415 CCAGCAGGACCCTGACTGTACT | 33399 GGGTTGGCTTGGCATCCTTGA | 44383 |
| 10758 AGGACCAGGCCTCCCTGTTT | 22416 CAGGACCCTGACATTAACCTTGGTGTTTAG | 33400 AGCAGCTTGTGGCCTGGGTA | 44384 |
| 10759 CCACAATGACCTAGCAGACCTT | 22417 GCATCTATGGGGAATGGGAGCAA | 33401 GAAATACAGTGGAACCACAATGACCTA | 44385 |
| 10760 CCAGCTCACCATTGCCTTTC | 22418 CAGCAAGGCGTTTCCACTGA | 33402 GACACGAATCAATTCCAGCTGTCA | 44386 |
| 10761 GTGTCTACTAATAAGTACTAGGGCAAA | 22419 GGCTGCTTGGTATCCCCTGAAT | 33403 GGTAGCTCCACTACAAAGTGTCT | 44387 |
| 10762 TCTCAAAGTACCCCATTCAAGTCAAG | 22420 CAGGACTACAATTGGAGACACTGTTA | 33404 GAGTCTGTATCTGAAAGTACCCCATT | 44388 |
| 10763 GTGGGTCATTTCCTCAGTGCCAGAA | 22421 CTGCCAGCTACTAAGTATGCTCTAGCTA | 33405 GGACCCCATCCTGTGGTCATTTC | 44389 |
| 10764 GCTTTGCTTCAAGGGACTGT | 22422 GCCTAAGACAGCAGCATCCAA | 33406 CCTCCCTGTAGCTTCAGGGGCT | 44390 |
| 10765 GGCATATTCAGCACAATCTGCTTTAC | 22423 GGCAGCTGTGGTAGACCTTTGT | 33407 GCTAAGAGAAGCGTTTGCGCATA | 44391 |
| 10766 GCCATGCAGTTGATGATTGCCAGGAA | 22424 CCATTAGTGCCTCCATACCCTTCA | 33408 AGGGAGGTCCATGAGTGCA | 44392 |
| 10767 GCAGCAATGCCAGGTACTACA | 22425 CCTGGAAGCCATCAAGTTTCAGGTTTA | 33409 GCCCTGAATAACTGCAGCAATG | 44393 |
| 10768 CTGGTGGGGTCTGGAATTTGGAT | 22426 CTGGGGGACTGGTCGTATAGGTATC | 33410 GCTGAACTGCCGCCTTCCCTTGT | 44394 |
| 10769 TGTCCTGGGTGTAGTCTGGATTC | 22427 GGCCATGGACCCTTTGGCAAT | 33411 GGACTTCATTGGTCCTGGCTGTA | 44395 |
| 10770 GTAAGCACAAACATGCATTCAGA | 22428 GAAATGTGGATTTAGCTTCTCCCTAGA | 33412 ACTCTGCAGGAGGCACAAAT | 44396 |
| 10771 GTACTTGTCCTTGTATCGTTTTCCTA | 22429 CACCCATGAGTTGACTTTGTACTTGAT | 33413 ACTTACTGTGTACTTGCCTTGGAT | 44397 |
| 10772 TGGGAGTTAAGAGTGAGTGGAATG | 22430 TTCCTGACTCACCGTGTCTT | 33414 GGTGACCTCTCTGGAGTTAAGAGT | 44398 |
| 10773 CCAGAGCACACAGCTTCACAAC | 22431 GGAGAAATCTCTGTTTCTCACCATGACTCT | 33415 GTGGAAATACCCAGAGCACACA | 44399 |
| 10774 TCTCACCCATGTGTGGGCTCTA | 22432 TTCCCTCACCCTCAGGGATCTT | 33416 GCAGCACGTATATCTCACCGATGT | 44400 |
| 10775 GACACAATGCTGCGTGTTGCTT | 22433 AGGGGCCAGAGGTCGCAAA | 33417 GGCAGGGCTAATTTGACACAATG | 44401 |
| 10776 GAGTGAGTGAGGGTGGGGAAGTT | 22434 CAAGCTGCCCCTACTACAACA | 33418 GAGGAGAAAAGGTACAGGTGAGTGA | 44402 |
| 10777 TGCCCAAAGCTCCTGCTAGT | 22435 AGCCAGTGGGAGGAGCAGATA | 33419 ACACAACGTCCTGCCCAAAG | 44403 |
| 10778 CAGAGGCCTGAGTTGTTTAGTTG | 22436 TGTCACGGAAACTATCACCTTTGA | 33420 TTCCTCAGAGGCCTGAGTT | 44404 |
| 10779 AGGCCAGCCTCCACACATACT | 22437 GGGACTAAAGCCTGAGAGCATGAGA | 33421 CCTGTGGGCCCAGACTTCA | 44405 |
| 10780 GCCATTTTGAGAGCTGCCTAT | 22438 GTTGAGCCACCTGCCATTTCTTAC | 33422 AGCCAGCTGCCCATTGAGA | 44406 |
| 10781 CCCACACAATCACACCTTACCCTTC | 22439 AACCAGGGAGGACCAGGATATGGT | 33423 CCTGAAAGCCCACCCACACAAT | 44407 |
| 10782 GGGACTTCTGTTTCTCAAGAGTAGTTC | 22440 GGGTGAGTGTCTCGTGTCGT | 33424 GGGTAGTTCAAGGGACTTCTGTTTC | 44408 |
| 10783 TGAGAAGGCAGGAGCAGTGATA | 22441 CTCATTCCCTCTCTCCCACCTAAC | 33425 GCTTCAGCAGTGGCTAAGAATGA | 44409 |
| 10784 GGGTCTGTATAGCCCATTTCACA | 22442 GAGCCAAGCCATGACACACT | 33426 GGTCTGCTGTCATAGGGTCTGTA | 44410 |
| 10785 GGAGCACTTAATTCGCCAACAA | 22443 GGAGGAGCTTCCCTGATGGTAT | 33427 GGGAGCTATGCAGGATGCACTT | 44411 |
| 10786 CCAAGTTTTGGCTTGAGAGCTT | 22444 GCACATGAACTGCCACGTCCTA | 33428 AGCCCACCCACTCTCACTTA | 44412 |
| 10787 GCACTGTCTGCCTTCCTTCTAGACT | 22445 GGTGGTTGTAGCTGTGATTAACAAGA | 33429 CGCCTTGAAGTTAGATGCACTGT | 44413 |

| | | | |
|---|---|---|---|
| 10853 CCTCCTCTATCTCATCCCATTC | 22511 TGGGGAGGAGGGACTCTAGTTT | 33495 CCTTCTGCCTCCTGTATCTCA | 44479 |
| 10854 CACCATGCCATTTTGCTGTGA | 22512 AGGTGCCAGAGACTGCAGAAAC | 33496 CGACATCCTTCACCATGCCATT | 44480 |
| 10855 CAGACATGAAGCTCACTGAAGGTGTAA | 22513 CCACTTCACCTGGCCTATTA | 33497 TGAAGCAGACATGAAGCTCACT | 44481 |
| 10856 GTACAGTTAACATACTCAGTGGTGAA | 22514 TCTTTGTCATCTTCCTCCTCTTTT | 33498 ACACATATGCACAGCTAACATACT | 44482 |
| 10857 CAGAGCCTTTGCTCATCCCACTAC | 22515 CAGATATCCATGGAATCAACAGTTTC | 33499 GTACTGACCTTGCAGAGCCTTT | 44483 |
| 10858 GTGAATCCAGCGGGTTACAAG | 22516 TGTGCTTTCACTCCTGGAAACTT | 33500 GGTGGAGGTGTTGTGGTGAAPC | 44484 |
| 10859 GCACGTGCTGGTGCTCAGA | 22517 GCCCAGTTCAAAATCTCTTGTCA | 33501 CCCTGGCTTTGGGTTGGTGAT | 44485 |
| 10860 CCCTACTGCCAGCCAATTTCCAT | 22518 GGAAGACCAAAAGGGATAAAGGTTGA | 33502 CCAGCCTCTTCTTAGCACCCTACT | 44486 |
| 10861 GTCTACACACACAGCCTCACTATG | 22519 GCCTAGAGGGGTGGAAAGCAAAG | 33503 CACAGAGCTAGTCTACACACACA | 44487 |
| 10862 GGCACATACTGTACTCTTGCATGTTG | 22520 TGCGTTTGCATGGGTGGTTT | 33504 GGGTGCAAGGCACATACTGTACT | 44488 |
| 10863 CCTAATCCACGATCTCCTCATCTGT | 22521 GACAGCCCTGTGACGTAGGAAT | 33505 GGCACTGCTTCCTAATCCACGAT | 44489 |
| 10864 GCAATTCCCTGAAGATACCTGCTA | 22522 GAGAAACAGTAGGGTCAAAGGAACAGA | 33506 CCTTGACCTTTGCAAPTCCCTGAA | 44490 |
| 10865 CGGGTACACAATTGTCCCAGTT | 22523 GGAGCAAATTTGTGGATTAAGGATAG | 33507 TGTCCCCTCGGGTACACAAT | 44491 |
| 10866 ACTTGGGGAGGTGCTAAG | 22524 CGCTCCTGCCGCAAAACTCTA | 33508 GGCTACAGGCCTTGGCACTT | 44492 |
| 10867 TCACTGGTATGTCTGGGAAAGTTG | 22525 TGCCTCCACCTGCTGCTA | 33509 GGTTTCAAGCCTCACTGGTATGTCT | 44493 |
| 10868 GTACCCAAGTGTGAGAGGTAAATC | 22526 GAGCAAAGAGGTTAAGGTCACAGT | 33510 GAAGGACAGTGCACCCAAGT | 44494 |
| 10869 CCCAAGAAGCTCTCTGTGCTATG | 22527 GGCTACCTGCAGACCAGTTCTT | 33511 GGGCTAAGGCTCCCTACACAT | 44495 |
| 10870 GCTCCTGCACAAGACACAGATG | 22528 CGATCCCCTTGGTGTGAGAGTTG | 33512 CCTGGTAGCTTTGCTCCTGCACAA | 44496 |
| 10871 CTGAACACCTCCTTGGAGTACAGTTC | 22529 CCTAGGATAGCCCACTGGATGTAG | 33513 CCTTGGATCACTGAACACCTCCTT | 44497 |
| 10872 CCCAGTTTGCAAGAAGCATGAAAG | 22530 CCCTCCAAGGACGTCTTCCCTAA | 33514 GCCTGTAAGACTTTAACCCAGTTTG | 44498 |
| 10873 GGTTATTCCTGTGTTCTTGATCTTGCTT | 22531 CTTTGTGTCTCAGCCTCACCAT | 33515 GCAGCTCTCTGGTTATTCCGTGTTC | 44499 |
| 10874 GCAGTGGCAGAAGGGCATTTG | 22532 AGTCCTGCCTCCTCTATAGTCATC | 33516 CCTGATAGGCAGTGGCAGAA | 44500 |
| 10875 CTCCTCTAAGAAACTAAGGGCARCA | 22533 GCTAGGGATAGCTAACAATGACA | 33517 CTGCAAACTCTTTCTTCTCCTCTAAGAAAC | 44501 |
| 10876 CGCTAGGTTGCTGTACTGGGAACA | 22534 GTGGACTCCTCTAGGTCAAGCTATTTG | 33518 AGCCGTACGCTAGGTTGCTGTGT | 44502 |
| 10877 GCCCATAGCTCTGTCCCATTGACTGTT | 22535 ATACATCATGTGGATAGAATGGGGATTAG | 33519 GTATCCAGATTTGCCATAGCTTGT | 44503 |
| 10878 CCTAAGCTTTACCTTAGATGCAGAGAAAG | 22536 CTAGCCTGAGGTTCTTCAGAT | 33520 GAGGATCAGGAACCCTAAGCTTAC | 44504 |
| 10879 CACACTGGAACCAAAGACCTTTATC | 22537 GCGAGCTATCTTGCAGGCTAGTAA | 33521 GCCACATCAACTGTGGGAACCAAG | 44505 |
| 10880 GGGCTCACTAACAAGACTGGTTCT | 22538 AAGTAATGCAGGATCAGTGATGGAG | 33522 AGAATCTTCTGGGCTGAGTAACAA | 44506 |
| 10881 GTTTCCCTGCTAGCTTAAGACCAT | 22539 GGGGTGGCTCAGGAACCCTTT | 33523 CCCTCTGTATAGTTTCCCTGTAGCTT | 44507 |
| 10882 GGTGGAGAATGACAACATGCAGAA | 22540 CTCTACTGAGAGACAAGCAAAGTTCA | 33524 GCTAGGCTATGTAAGTAGGTGGAGAATG | 44508 |
| 10883 ACCAGTGGGATTGATGAGACAAAA | 22541 CGGCCTACTTCACTTGTTTCTTG | 33525 GCCCCTGATTCTAACCAGTGGGATTG | 44509 |
| 10884 CCACAGAGCCTAGCAAGGTGTT | 22542 GGGAGGCTATCCAACCAGTAAGT | 33526 AGAGCACAGGGGACCACAGA | 44510 |
| 10885 CCCTTCTGTGCAATGGGACTTG | 22543 CCCACCCCTGCCCATCTTAC | 33527 CAGCTTCCCCTTCTGTGCAA | 44511 |
| 10886 TGTTGGCTTCTGCAGTGTGA | 22544 TGGGCTCCCACACCTGTTTC | 33528 AGGACCTTTCTGGCATGTGTTG | 44512 |
| 10887 CTAACTGAGAATTCCTTCCCAAAAG | 22545 GGCTGTGAAGAGGCAGTGAGGAT | 33529 GCCACAACCCTACCAACTGAGA | 44513 |
| 10888 CTGCCCAGGCTTTTGACTTTG | 22546 CCTCAATGAATAGTTCCCACCTCAA | 33530 AAGGTTTCTGCCCAGGCTTT | 44514 |
| 10889 GTGAAAGCTAGCATCTGGGCTTTT | 22547 CTTTAAACTGGGATCGCTACAGAAAAG | 33531 GCAAAAGTACTCGGCAGTTGAAAGCTA | 44515 |
| 10890 CAAAATCTGGGGATACAGATCTT | 22548 TGCCCAGGCAGAGGGAGCAA | 33532 CCTCTGCCCCAGCATATCAAA | 44516 |
| 10891 GAACCCACTGGAATACGTCCTT | 22549 CCCAAAGTGCTTGTTTCTCTGATAC | 33533 CACACCCAAGAACCCACTGGAA | 44517 |
| 10892 GACATGAACTGACCCTTGACACA | 22550 GGCTGCAGCAGAGTGAATAAGA | 33534 GCCCAGAGGCCTGACATGATCT | 44518 |
| 10893 AGGGAGCTTGAGGGAAGGTCAA | 22551 CACTCTGACAGTGAGGTTCTTGGTA | 33535 GTCATTGCTCAAAGGGAGCTAAG | 44519 |
| 10894 CAGCCACATTCAGAGCCAATC | 22552 GCCATCTCCTGCTGGTTACT | 33536 CTAGCCTTCTCAGCCACATTC | 44520 |
| 10895 GTGTGTGTGGGCTTTATGAAGAAAA | 22553 TGGATACAGCATACTGCTGTGTGCAT | 33537 GCTCACAGTGTGTGTGGGCTTT | 44521 |
| 10896 GAAGTGAAGAAGAGTGGTCAGCTA | 22554 TCCTACAGGCCCCTGAACTT | 33538 CCTACTTTTGGGAGGGAAGTGAA | 44522 |
| 10897 ACCATGGTTTCCTTGTCAGCATAA | 22555 CCGTACAAGAGGTAGGCAGAGCTAAT | 33539 GCCCCTTGATTCCTCTAAACCAT | 44523 |
| 10898 GAAATCAGCTTCTCTCTCACTCAGTT | 22556 GTGATTGGGCACAGAACTCTCTA | 33540 GAGCCCTGAAATCAGCTTCTCTCT | 44524 |
| 10899 TGTGGTAGAAGAGTTGTCTCCATTG | 22557 CTGAAGCTAGGTCAGATCAAGCAA | 33541 GGTGGTTCAGTGTATTGTGGTAGAAG | 44525 |
| 10900 GCCTAGCTTCAAGCTTCCTTCT | 22558 ATTCCAGCCAGCCAGCAATG | 33542 GGCCTGTGCCTAGCTTCAAGA | 44526 |
| 10901 GTGGCTTACCACCAGCAAACT | 22559 ACTGTCATGTTCTCTCTGCCTTTT | 33543 AATGGGCAGCAGTTGCCTTA | 44527 |
| 10902 CTGAGTGTTCTGGGGCTAGTTT | 22560 GCCCTTGCACCACTACACAGAGA | 33544 GAGGCAAGCCTGAGTGTTCT | 44528 |
| 10903 CAGAGGGCTAGTGTATCTCAAGA | 22561 GGGGAGTATTACAAAGACCTAAGGAGGTA | 33545 TCACCCATCAGAGGGCTAGTGT | 44529 |
| 10904 GTCTCTGGCTTAATGTGCAAGT | 22562 GTAATGTGTACCGGTTCTGTACT | 33546 TTCCAGCTTGCTTCTGGGGCTTA | 44530 |
| 10905 CACAGTGGACTTGTTGTTCTTGAGT | 22563 GGGTCTGTTCATCACTCAATCATTC | 33547 CAGATTCTGACTCACAGTGGACTTGTT | 44531 |
| 10906 GCTCCATTATGTTTCCATTGTGCT | 22564 GACACTGCCTAGCCTTGTCATTG | 33548 CCTGCCACCTTCATTGCTCCAT | 44532 |
| 10907 GCTTATTTGGTAACGACTAGGCAGAT | 22565 TGCTGGGCTGTGGATTGGTA | 33549 CCACATACATTACGTCTGCTTATTTG | 44533 |
| 10908 TCTCCAGACCTTTGCTTCCTCTTA | 22566 AGCCAAGAGGAGTTGGGACTTG | 33550 CGAACCCAAGCAGCTTCTGTCT | 44534 |
| 10909 CCACCAGCATTCAAGTGCAATGTA | 22567 GCACTCACAGAAGGGCAGGTAA | 33551 GCTAGGACATCCACCAGCATTCA | 44535 |
| 10910 ACCTTCCAGGTCTCACCTCTCT | 22568 GTGTGGGGAGAGCAGTATAGAT | 33552 CTGTGTTTGCCATGGACACCTT | 44536 |
| 10911 CACCCTTGAGACAATGGTTGTAG | 22569 GACCCACTGCGGAAGGTATGGTA | 33553 GCCCTCAATCACCTTGAGACA | 44537 |
| 10912 GGACATGGAAAGATTGGGACAGGTT | 22570 TCCTATGGGGTCTCATCATTTCT | 33554 GCTGGCTGAATAGGCACATGGA | 44538 |
| 10913 CCAGTGTCAGCTGGGTTTTGT | 22571 CATTAAACTCAGTGCTGTCCTGTTAG | 33555 TCCTTCCAGGGCCAGTGTCA | 44539 |
| 10914 AGTAAAGCGGTGGAAAAAGACATT | 22572 GTGTTCTGGATATTCCTTCTCACTTTGT | 33556 CACAAACTTAAGGTAAAGGGTGGAA | 44540 |
| 10915 CCTTCTAACCCCTTCTCTGTGAGAT | 22573 CAGTCCCAACAGCATGCCTAGATA | 33557 AGAGTTCCTTCTAACACCCCTTCT | 44541 |
| 10916 GAGTGAAGACCAGCAGACAGAAG | 22574 GGTTAGCTTCAGTTCTTGGAAGTA | 33558 GGAAATGATCCACCCATGCAGTGAAGA | 44542 |
| 10917 GGTGGAACCAAAGAAGAAAGGGTTT | 22575 GCATCTCAGCCTTTGGGTTTTG | 33559 TTTGGACAGGTGGAACCAAAGA | 44543 |

FIG. 36Q8

| | | | |
|---|---|---|---|
| 10918 GCTGCCACCTAGGAAACAAAGT | 22576 CCTAGCCCTATGGCAGAGTTTC | 33560 CCAGACCAAAGCTGCCACCTA | 44544 |
| 10919 GGGACATGTGGTCTTGCAT | 22577 AACTGTTGCCCTATCCTCCATTAC | 33561 GGAGAGGCAAGAGTGGGACAT | 44545 |
| 10920 GCCACTTGCAAAGAACACTTTTGT | 22578 CTGGTTGTCTTCATGGGATTCCCTTA | 33562 GACGTCTAAATGTTCTTGCCACTTG | 44546 |
| 10921 GCCTTTCTGCTGGCTCTTG | 22579 CAGCCCTGGAGGAGTTCTGA | 33563 TCCTTTTTCCTGGTGCCTTTCT | 44547 |
| 10922 GGACCATTTAGACTCACTGCCATCA | 22580 CCAGGGTGCTGGAGACATT | 33564 CTATTTCACCTGGACCATTTAGACTCA | 44548 |
| 10923 ACCCGTGTATTATGACTTCCAGAGTTC | 22581 CCAGAGGATATCCCACAGTTCATCTCA | 33565 GCCCCACCCGTGTATTATGACT | 44549 |
| 10924 TGGGGAGGTAACCAAATCTTTTGA | 22582 CCACATCAACACTATTATCCCCAATTC | 33566 ACGAAGCCTTGGGAGGTAAC | 44550 |
| 10925 CCAAGGACTTGGGACGACTTT | 22583 CGGCCTGAAATTTCTTTACAACCAT | 33567 AGGGCTGGCACCCTACCA | 44551 |
| 10926 GACGTTGCTGTGTTCTTTTGCTT | 22584 CAGTCTGGTGGACACTTTGATT | 33568 TGGCTATGACGTTGCTGTGT | 44552 |
| 10927 GCCACTGGATAGCATGATTGGATCT | 22585 GTCTGAGCTGTTCTGTCTTTTG | 33569 GGCTATCTGCCGACTGGATAGCAT | 44553 |
| 10928 CCGCTTCCATAACCTGGAGATAACCTA | 22586 GGAGCCTCCTACATATATCATTCCAA | 33570 CCTGACCTACCGCCTTCATAAC | 44554 |
| 10929 CCCCTCTATTCAAGGCTATGTTGT | 22587 CCAGGAGTAAAATCAGGGAATCTGATT | 33571 TGACACTTTGTTGTCCCCTCTATTC | 44555 |
| 10930 CATGCCCAACAGCCCTTCTTTC | 22588 ACACACTGTGACATGACATGGGATT | 33572 GGACAAAGCTCATGCCCAACA | 44556 |
| 10931 CTTGAGGGGAGGTAGGAGGAAAAA | 22589 TCCACTCTGACTCAGTCTTCAGTA | 33573 CAGTTGCCTGAGGGGAGGTA | 44557 |
| 10932 TTAAGCCTCAGATCTAGAGTCA | 22590 AGTTGACCTTTTGGGTTCTTCTTG | 33574 TTTTCTTCATTTCCCATGCTTAAA | 44558 |
| 10933 GGGCATTTAACAACTACCCATGCATTT | 22591 CTGTCTCTGGATCCTTGAGTCT | 33575 GGGAACTTTGGGGCATCTAACAAC | 44559 |
| 10934 GAGAGCCATCACATTCTGGTCTTC | 22592 GCCCAGACAGTAAGAAAGGAAGT | 33576 ACCTGAGCTGAGCCATCACA | 44560 |
| 10935 GAATCCACCCATTCAAGGAAAGAAG | 22593 GAACCCGCTGGCCATTCTCTT | 33577 TGGTAGGCAGAATCCACCCATT | 44561 |
| 10936 GGCAGTAGTGCTCCAAATATGCTA | 22594 ACAGGAAGGGCGGGAGTAG | 33578 CGACATCCTCACGAATGCCAGTAG | 44562 |
| 10937 TGGCTACAGAACAAGTGAGGATGA | 22595 GACCTATTGAAGCTTGGGCAAAGT | 33579 CCCCACCTATTAACTACTTGGCTACAGA | 44563 |
| 10938 ACTCAAAGCAAAAGAGGGACAACT | 22596 ACCTACCTGTGGCCTGGAAGCAA | 33580 AGGTGGAGCAACTCAAAGCAA | 44564 |
| 10939 ACACAATCGGTGTCTCAGGAACT | 22597 GACAGAGCTGCAGCCACTAAT | 33581 GCCACCCACTGACGAACACAT | 44565 |
| 10940 CCTCACTAGACCCTTAACTGGGATGACT | 22598 AGGCAGAGCCAGGGCCTAAAT | 33582 GGCCAATGTCCTCACTAGACCTT | 44566 |
| 10941 GCCATCCTTGCTTGTATCCTTCTCTT | 22599 GAGCATGGCATGACTCGGAAT | 33583 GTGACAAAGCCAGTCCTTGCTTGTA | 44567 |
| 10942 CTGAGTCACACAGTCCATTGAAAC | 22600 AGCGCCACATGGCTGATG | 33584 TCTCCACCAGCTGAGTCACA | 44568 |
| 10943 TGCTGACAGCCCTCCTAAGCTA | 22601 GCAAAGCTTGATGGTGGAAGAAAG | 33585 GAAAAGTTGTTTAACCCTGCTGACA | 44569 |
| 10944 GCCTCCATTGTCTCTCCTGGATAA | 22602 GGGAAGCAAGGAGAGCAGCTAGTA | 33586 TCCAAGCCTCCATTGTCTCTCT | 44570 |
| 10945 GGCCGGAGAAAGGTTTGGCATT | 22603 GGCTCAGGGGCAAAGTTGT | 33587 GAACTACTCAAGGCCGGAGAA | 44571 |
| 10946 GCCACCAATTCCTTTGGAGATCCTTT | 22604 GTCACCAGGAAATGCACATCTTTT | 33588 CCTCATATGCCACCAATTCCTTTG | 44572 |
| 10947 TCCATTCCATGTTGGAGCAAAAC | 22605 GCCCTGAAAATTCGTGCTATCAAATG | 33589 CCACCTAATTTGCTCCATTCCATGT | 44573 |
| 10948 TGAGTAGGAATGGCAACAGCTAAT | 22606 TGACAGGGGCTCTAGAAGTAGTAAG | 33590 GTGGAGTAGACAGCAAATGAGTAGGAA | 44574 |
| 10949 CCCATTCAGTGGGGTTTCGTT | 22607 GGCCAACTTCCTGCTAAGGATTG | 33591 GTGCAGTAAGACCCCATTCAGT | 44575 |
| 10950 CGGCACAGAGTGTTAAGAATAAGA | 22608 GCTAGGCATTTTGCCAGAGGCTTT | 33592 CACCTATATAATCGGCACAGAGTGGTT | 44576 |
| 10951 GCATCAGAACTCATAGACACTTGATTG | 22609 AGAACCCGAGAGGCCTATCCAA | 33593 CATGTTTCCAAACACATGCATCAGA | 44577 |
| 10952 GTTGCATGGAAGATCATGTGCTTAG | 22610 GCTTTCCTGCTCTGGTTGCTGAA | 33594 CCAGCTCCCTGCTCAAGTGGTGGCAT | 44578 |
| 10953 ACTTCTCTATAGTCCAGTCTGT | 22611 AACTGATCTGGCCTGCTAAAACT | 33595 CAGGCTTCCTAACCCTCTCATAG | 44579 |
| 10954 GCTCTTAAATAGCTCCACACGCTAGT | 22612 TGTGCTTAACCTCCTAGCCTCAT | 33596 ACCCGTGGCACCTGTCCTTA | 44580 |
| 10955 CGTTTGTGCAATGGCTCAAGATT | 22613 GGTGATATAGTGAAGCCCTCTGTTG | 33597 CAGCAAAGCAGACGTTGTGGAATG | 44581 |
| 10956 TCCCCACCTTGAGTGCTCAGT | 22614 CCAAAGTAGCAAAAGTGTTTGCATTC | 33598 GCCTATAGTGAACACCACCCTT | 44582 |
| 10957 GCTCTATACACATTGTCGTGCCTGCAA | 22615 GGAPGATGCTGGCTAATGGGAGAA | 33599 ACCCCAGTGTGCTCCTATACATTG | 44583 |
| 10958 GAGTATGGGATCAGGTGCATGTCA | 22616 ACGTTGTCTGCCCACTCCAGAT | 33600 CTGGGTACCGAGTATGGGATCA | 44584 |
| 10959 GGCAAACCCTACATTCTTTTGTAAAAAC | 22617 CACATGCATAGGCTTAGCCAGGGA | 33601 CCAGAAAAGGCAAACCCTACATTC | 44585 |
| 10960 GCTGGTGACTGGTTCATCCTACA | 22618 GGAGAGATTGGCAGTCCCAGTT | 33602 AGCAGTGAGGCCAGAAACTTAG | 44586 |
| 10961 GGGTGCTAGCCAAACTGTTG | 22619 CCCCATTCAAAGGGCTCTCAGT | 33603 TGGATTCCAAACTTTTGCGTGCTA | 44587 |
| 10962 GGTTGGGAAGACTGTGGGACAA | 22620 AGCCTGAGTAACCAGGGACTCT | 33604 TGGTCTGTGGGTTGGGAAGACT | 44588 |
| 10963 CCAAGTGGTGGCAATTACAGGACTA | 22621 CACAGCCTGCTGCTAATTGTTG | 33605 GGCTTCCAAGTGGTGGCAAT | 44589 |
| 10964 TGGTCACTCAGGGTGGGTAAG | 22622 GCTGCAGGAGTAGAAACTAGGAACA | 33606 AGGCAGGGGTTGGTCACTCA | 44590 |
| 10965 ACACACTCCCCACCCCAAAC | 22623 TCTTCCAGAATTCCCTTCAAAGCAT | 33607 TCGCCACTGCCACACACT | 44591 |
| 10966 GCTTCCCACTCTGCCCATCAAT | 22624 GTGAAAGCAGGTGGTCATACCCT | 33608 AGTAGAAGATCAGCTCCCACCTCT | 44592 |
| 10967 CACCACCGGAGATCCAAAAGTGT | 22625 CTGCAGGTAGCAGAATTAACTGACA | 33609 GCTCATATGTGAACACCACCGTAGA | 44593 |
| 10968 GGTGCTATTGCTCTCTGTTCA | 22626 CTGTGCTCAGATCTGCATTGGAT | 33610 TCCATGTCCATTGCTAGTCCTATTG | 44594 |
| 10969 GAACCTTTCCTTTACGGTGCAA | 22627 CACTCATTTGACTTCCCGCTTTT | 33611 CGACGGAACAGAACCCTCCCTT | 44595 |
| 10970 CTCTCTGGTCAGGTGACATTGTAT | 22628 ACAGGGGATTCACTGTATGATAAAGA | 33612 GCTCACTGCAGCTTCTCTCT | 44596 |
| 10971 GTTCAAAACGGCATTGATGGTA | 22629 CTGAGCAGGCTATTCAGTCTGT | 33613 GCCAATAGCTAATGCTACAAGTAGCTCAAA | 44597 |
| 10972 TTAACCAACTCAGCCGTCAGA | 22630 TCGCCAAGGACCTAGGAACA | 33614 TTCTCCATGACGTGACCATCAAC | 44598 |
| 10973 GAGTTTCGTCACAACGTTCCTT | 22631 CGGTGGTGCGCAAGTAGT | 33615 GCACCTGGAGTTTCGTCACA | 44599 |
| 10974 AGGGAGGGAGTTATTGTGTTACT | 22632 GAGTTGTTGCAGATGGGTTGAAAA | 33616 CCTTCAGCCAAGGGAGGGAGTTAT | 44600 |
| 10975 GAAGCTGGGTTGAAGTGCTTTG | 22633 CCTTGCATTCACAGTGGCTACAA | 33617 GCAAAATCTTAGAGAAGCTGGGTTGA | 44601 |
| 10976 GGAGAGTTATCAATGAGCCTTCTT | 22634 AGTTCCCCACCTGGTGTTT | 33618 GGTTTTCCATGTACTAGAAGGAGAGTTATC | 44602 |
| 10977 TGGCAAAGTGAGAACCTGCAT | 22635 CCTTATAGTGGGTTCTGGGACTTAGTA | 33619 GCTTTTTTGAAGCTGGCAAAGT | 44603 |
| 10978 CGTGTCTCCTGGAGACATGGAT | 22636 GGGAGTAGCCCTGGGAATGCTT | 33620 TGCTCACGTGTCTCCTGGA | 44604 |
| 10979 GAGAGACAGCAATTCTGGTGGAACAT | 22637 GAACCTGGCCTCATTGTGATTTC | 33621 GCCCCATCTGAGAGACAGCAATTC | 44605 |
| 10980 AGGGTTGGACTAGGGGAAGTGA | 22638 AGCACCGGCAGGCGACTTT | 33622 TAGGCGCAGCAGGGTTGGACTA | 44606 |
| 10981 GGTTTCTCCCTGAAATGTGTGTGA | 22639 CTCCAAGAATTCTAGGAAGACTGGAAGT | 33623 CCAGGGTGGTTCTGCCTGAAA | 44607 |
| 10982 CTGCACCTTGGCAACACTTTGA | 22640 GCTCTGTACTGGCCACTTTGTTC | 33624 ATCACCTCTCCCTGCACCTT | 44608 |
| 10983 GGACCCCAGGATTGAGGGAGCAA | 22641 CCAGCCTAGACCTAAACCCTTGA | 33625 CAACTAAGACATGGACCCCAGGAATG | 44609 |
| 10984 TGCACATGCGCTCTTCTCA | 22642 GTGATGCCAGACAGAGCTGACA | 33626 CCTGTGCCTGCCTTCCGAAT | 44610 |

FIG. 36Q9

| Description | MAPPED_READS | TOTAL_READS | %Mapped Reads |
|---|---|---|---|
| gMother | 3,633,900 | 3,647,446 | 100% |
| gMother | 3,567,685 | 3,578,549 | 100% |
| gMother | 3,733,706 | 3,747,692 | 100% |
| gChild | 3,725,554 | 3,737,742 | 100% |
| gChild | 3,816,989 | 3,829,450 | 100% |
| gChild | 3,524,956 | 3,536,569 | 100% |
| 1 mother | 3,467,493 | 7,564,869 | 46% |
| 1 mother | 3,868,210 | 7,107,028 | 54% |
| 1 mother | 4,918,140 | 7,613,240 | 65% |
| 1 child | 361,390 | 6,507,434 | 6% |
| 1 child | 1,885,864 | 6,496,348 | 29% |
| 1 child | 2,789,647 | 6,259,288 | 45% |

FIG. 37

| Description | MAPPED_READS | TOTAL_READS | %Mapped Reads |
|---|---|---|---|
| case 1 blastoceol | 68,123 | 8,470,872 | 1% |
| case 1 cell 1 | 4,340,613 | 8,248,598 | 53% |
| case 1 cell 2 | 5,480,580 | 8,230,870 | 67% |
| case 1 cell 3 | 4,664,577 | 7,846,040 | 59% |
| case 2 blastoceol | 45,794 | 6,302,957 | 1% |
| case 2 cell 1 | 6,988,854 | 8,622,495 | 81% |
| case 2 cell 2 | 7,083,600 | 8,843,495 | 80% |
| case 2 cell 3 | 5,811,364 | 8,256,310 | 70% |

FIG. 39

|  | gDNA | Single Cell |
| --- | --- | --- |
| Count | 75 | 510 |
| Mean | 0.15 % | 0.51 % |
| Median | 0.09 % | 0.33 % |
| Max | 1.03 % | 10 % |
| Standard Deviation | 0.16% | 0.79 % |
| 95th percentile | 0.43 % | 1.22 % |
| 90th percentile | 0.37 % | 0.92 % |

FIG. 46

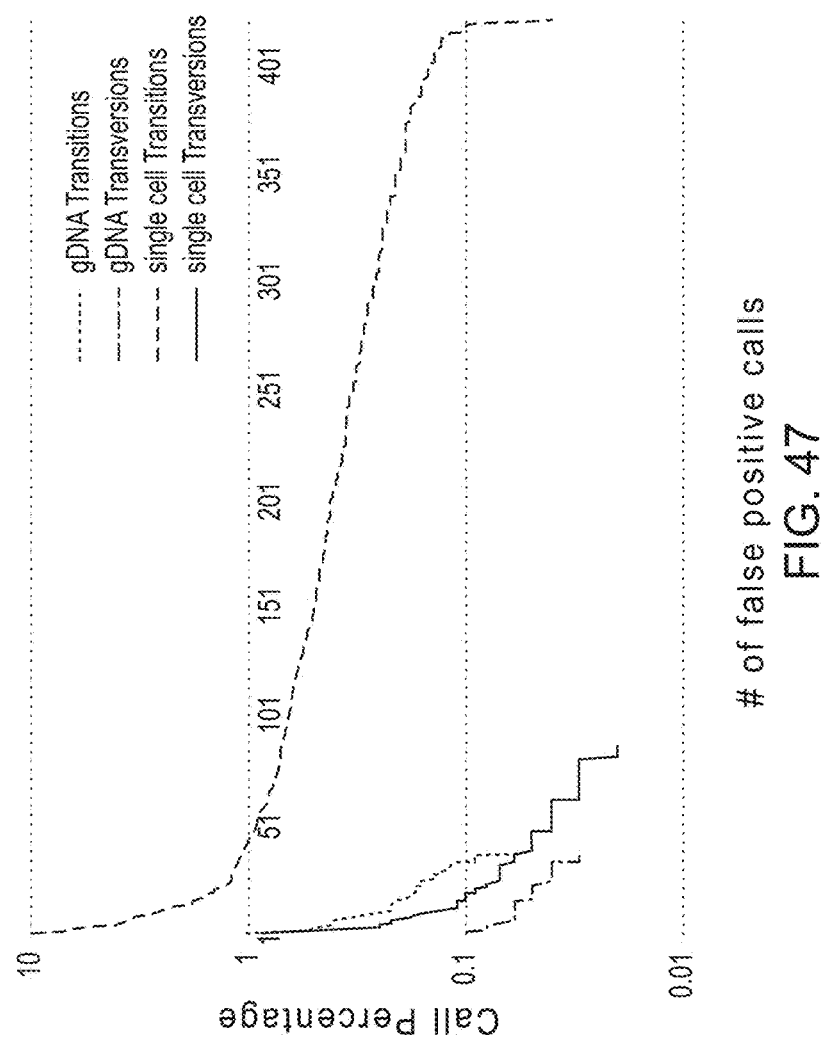

| DOE1 | Mapped READS | TOTAL READS | % Mapped | Dropout Count | Median DOR All | NOR | Error Rate (%) |
|---|---|---|---|---|---|---|---|
| 1xMM | 1,112,007 | 1,262,558 | 80.0% | 436 | 26.25 | 1,043,539 | 0.107% |
| 2xMM | 3,412,593 | 3,615,347 | 94.4% | 105 | 147.75 | 3,206,478 | 0.141% |
| F-A | 449,074 | 635,571 | 70.6% | 1379 | 9.625 | 421,228 | 0.077% |
| F-B | 3,293,944 | 3,519,378 | 93.7% | 105 | 142.5 | 3,106,520 | 0.072% |
| F-D | 4,028,128 | 4,109,448 | 98.0% | 122 | 142.5 | 3,796,213 | 0.064% |
| F-J | 3,676,617 | 3,922,330 | 93.7% | 102 | 159.25 | 3,461,304 | 0.079% |

F-A is : 25 mM Tris pH 7.8, 3 mM MgCl$_2$, 0 mM KCl, 10 mM (NH$_4$)$_2$SO$_4$, 50 U/mL Taq Gold    aka F-A Gold F-B is : 75 mM Tris pH 7.8, 6 mM MgCl$_2$, 0 mM KCl, 40 mM (NH$_4$)$_2$SO$_4$, 150 U/mL Taq Gold    aka F-B Gold F-D is : 25 mM Tris pH 8.2, 3 mM MgCl$_2$, 30 mM KCl, 40 mM (NH$_4$)$_2$SO$_4$, 150 U/mL Taq Gold F-J is : 75 mM Tris pH 7.8, 6 mM MgCl$_2$, 0 mM KCl, 40 mM (NH$_4$)$_2$SO$_4$, 150 U/mL Qiagen HS Taq    aka F-B Qiagen

FIG. 48

METHODS FOR SIMULTANEOUS AMPLIFICATION OF TARGET LOCI

CROSS-REFERENCE TO RELATED APPLICATIONS

This application claims the benefit of U.S. Provisional Application Ser. No. 61/982,245, filed Apr. 21, 2014; U.S. Provisional Application Ser. No. 61/987,407, filed; May 1, 2014, U.S. Provisional Application Ser. No. 61/994,791, filed May 16, 2014; and U.S. Provisional Application Ser. No. 62/066,514 filed Oct. 21, 2014. The entireties of all these applications are each hereby incorporated by reference for the teachings therein.

REFERENCE TO SEQUENCE LISTING AS TEXT FILE

This application refers to a "Sequence Listing" listed below, which is provided as a text file. The text file contains a document entitled "U21_Seq_Listing" (8,520 bytes, created Nov. 6, 2014), which is incorporated by reference in its entirety.

FIELD OF THE INVENTION

The present invention generally relates to methods and compositions for simultaneously amplifying multiple nucleic acid regions of interest in one reaction volume.

BACKGROUND OF THE INVENTION

To increase assay throughput and allow more efficient use of nucleic acid samples, simultaneous amplification of many target nucleic acids in a sample of interest can be carried out by combining many oligonucleotide primers with the sample and then subjecting the sample to polymerase chain reaction (PCR) conditions in a process known in the art as multiplex PCR. Use of multiplex PCR can significantly simplify experimental procedures and shorten the time required for nucleic acid analysis and detection. However, when multiple pairs are added to the same PCR reaction, non-target amplification products may be generated, such as amplified primer dimers. The risk of generating such products increases as the number of primers increases. These non-target amplicons significantly limit the use of the amplified products for further analysis and/or assays. Thus, improved methods are needed to reduce the formation of non-target amplicons during multiplex PCR.

Improved multiplex PCR methods would be useful for a variety of application, such as Non-Invasive Prenatal Genetic Diagnosis (NPD). In particular, current methods of prenatal diagnosis can alert physicians and parents to abnormalities in growing fetuses. Without prenatal diagnosis, one in 50 babies is born with serious physical or mental handicap, and as many as one in 30 will have some form of congenital malformation. Unfortunately, standard methods have either poor accuracy, or involve an invasive procedure that carries a risk of miscarriage. Methods based on maternal blood hormone levels or ultrasound measurements are non-invasive, however, they also have low accuracies. Methods such as amniocentesis, chorion villus biopsy and fetal blood sampling have high accuracy, but are invasive and carry significant risks. Amniocentesis was performed in approximately 3% of all pregnancies in the US, though its frequency of use has been decreasing over the past decade and a half.

Normal humans have two sets of 23 chromosomes in every healthy, diploid cell, with one copy coming from each parent. Aneuploidy, a condition in a nuclear cell where the cell contains too many and/or too few chromosomes is believed to be responsible for a large percentage of failed implantations, miscarriages, and genetic diseases. Detection of chromosomal abnormalities can identify individuals or embryos with conditions such as Down syndrome, Klinefelter's syndrome, and Turner syndrome, among others, in addition to increasing the chances of a successful pregnancy. Testing for chromosomal abnormalities is especially important as the mother's age: between the ages of 35 and 40 it is estimated that at least 40% of the embryos are abnormal, and above the age of 40, more than half of the embryos are abnormal.

It has recently been discovered that cell-free fetal DNA and intact fetal cells can enter maternal blood circulation. Consequently, analysis of this genetic material can allow early NPD. Improved methods are desired to improve the sensitivity and specificity and reduce the time and cost required for NPD.

SUMMARY OF THE INVENTION

In one aspect, the invention features methods of amplifying target loci in a nucleic acid sample. In some embodiments, the method involves (i) contacting the nucleic acid sample with a library of test primers (such as non-immobilized primers) that simultaneously hybridize to at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci to produce a reaction mixture; and (ii) subjecting the reaction mixture to primer extension reaction conditions to produce amplified products that include target amplicons. In some embodiments, the method also includes determining the presence or absence of at least one target amplicon (such as at least 50, 60, 70, 80, 90, 95, 96, 97, 98, 99, or 99.5% of the target amplicons). In some embodiments, the method also includes determining the sequence of at least one target amplicon (such as at least 50, 60, 70, 80, 90, 95, 96, 97, 98, 99, or 99.5% of the target amplicons). In some embodiments, the method involves multiplex PCR and sequencing (such as high throughput sequencing). In some embodiments, the method includes selecting the test primers from a library of candidate primers by removing one or more of the candidate primers based at least in part on the likelihood of dimer formation between candidate primers (such as $\Delta G$ values, undesirability scores, or interaction scores) prior to contacting the nucleic acid sample with the library of test primers.

In some embodiments, the method involves (i) contacting a sample comprising target human loci with a library of at least 50 (such as at least 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000) non-immobilized, non-identical primers that simultaneously hybridize to at least 50 (such as at least 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000) non-identical target human loci to produce a reaction mixture; wherein the primers do not include molecular inversion probes (MIPs); (ii) subjecting the reaction mixture to primer extension reaction conditions to produce amplified products comprising target amplicons; wherein the annealing temperature for the reaction conditions is greater than a melting temperature (such as the empirically measured or calculated $T_m$) of at least 50 (such as at least 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000) of the non-identical primers and/or the length of the annealing step of the reaction conditions is greater than 5 minutes (such as at least 8, 10, 15, 20, 30, 45, 60, 75, 90, 120, 150, or 180 minutes; and wherein at least 50 (such as at least 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000) non-identical target human loci are simultaneously amplified; and (iii) detecting the amplified products such as by sequencing the amplified products or hybridizing the amplified products to an array. In some embodiments, the method includes empirically measuring or calculating (such as calculating with a computer) the melting temperature of at least 25, 50, 80, 90, 92, 94, 96, 98, 99, or 100% of the primers in the library and selecting an annealing temperature that satisfies any of these embodiments for PCR amplification of target loci.

In some embodiments, the method involves (i) contacting a sample comprising target human loci with a library of at least 2 (such as at least 5, 10, 25 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000) non-immobilized, non-identical primers that simultaneously hybridize to at least 2 (such as at least 5, 10, 25 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000) non-identical target human loci to produce a reaction mixture; wherein the primers do not include molecular inversion probes (MIPs); (ii) subjecting the reaction mixture to primer extension reaction conditions to produce amplified products comprising target amplicons; wherein at least 2 (such as at least 5, 10, 25 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000) non-identical target human loci are simultaneously amplified; and (iii) detecting the amplified products such as by sequencing the amplified products or hybridizing the amplified products to an array. In various embodiments, (i) the annealing temperature is at least 1, 2, 3, 4, 5, 6, 7, 8, 9, 10, 11, 12, 13, or 15° C. greater than the melting temperature (such as the empirically measured or calculated $T_m$) of at least 2, 5, 10, 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers; (ii) the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the melting temperature (such as the empirically measured or calculated $T_m$) of at least 2, 5, 10, 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers; (iii) the annealing temperature is at least 1, 2, 3, 4, 5, 6, 7, 8, 9, 10, 11, 12, 13, or 15° C. greater than the highest melting temperature (such as the empirically measured or calculated $T_m$) of the primers; (iv) the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the highest melting temperature (such as the empirically measured or calculated $T_m$) of the primers; (v) the annealing temperature is at least 1, 2, 3, 4, 5, 6, 7, 8, 9, 10, 11, 12, 13, or 15° C. greater than the average melting temperature (such as the empirically measured or calculated $T_m$) of at least 2, 5, 10, 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers; or (vi) the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the average melting temperature (such as the empirically measured or calculated $T_m$) of at least 2, 5, 10, 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers. In various embodiments, (i) the length of the annealing step (per PCR cycle) is greater than 1, 3, 5, 8, 10, 15, 20, 30, 45, 60, 75, 90, 120, 150, or 180 minutes or (ii) the length of the annealing step (per PCR cycle) is between 5 and 180 minutes, such as 5 to 60, 10 to 60, 5 to 30, or 10 to 30 minutes, inclusive. In various embodiments, any of the embodiments for annealing temperature are combined with any of the embodiments for annealing time. In various embodiments, the annealing temperature is at least 3° C. greater than the melting temperature of at least 50 of the non-identical primers, the annealing temperature is at least 3° C. greater than the highest melting temperature of the primers, the annealing temperature is at least 8° C. greater than the highest melting temperature of the primers, the annealing temperature is at least 3° C. greater than the average melting temperature of the primers, the annealing temperature is at least 8° C. greater than the average melting temperature of the primers, the range of melting temperature of the primers is between 1 to 5° C., inclusive, the range of melting temperatures of the primers is less than 5° C., or any combination thereof. In some embodiments, the method includes empirically measuring or calculating (such as calculating with a computer) the melting temperature of at least 25, 50, 80, 90, 92, 94, 96, 98, 99, or 100% of the primers in the library and selecting an annealing temperature that satisfies any of these embodiments for PCR amplification of target loci. In some embodiments, a crowding agent, such as PEG or glycerol is included in the reaction mixture.

In various embodiments of any of the aspects of the invention, the method includes non-specifically amplifying nucleic acids in a sample comprising target human loci; contacting the amplified nucleic acids with a library of non-identical primers (such as non-immobilized primers) that simultaneously hybridize to at least 1,000 non-identical target human loci to produce a reaction mixture; wherein the primers do not include molecular inversion probes (MIPs); subjecting the reaction mixture to primer extension reaction conditions to produce amplified products comprising target amplicons; wherein at least 1,000 non-identical target human loci are simultaneously amplified; and sequencing the amplified products. In some embodiments, the non-specific amplification comprises universal polymerase chain reaction (PCR), whole genome application, ligation-mediated PCR, degenerate oligonucleotide primer PCR, or multiple displacement amplification. In some embodiments, the method includes contacting a sample comprising target human loci with a library of non-identical primers (such as non-immobilized primers) that simultaneously hybridize to at least 1,000 non-identical target human loci to produce a reaction mixture; wherein the primers do not include molecular inversion probes (MIPs); subjecting the reaction mixture to primer extension reaction conditions to produce amplified products comprising target amplicons; wherein the annealing temperature for the reaction conditions is greater than the melting temperature of at least 1,000 of the non-identical primers; and wherein at least 1,000 non-identical target human loci are simultaneously amplified; and sequencing the amplified products. In some embodiments, the method includes contacting a sample comprising target human loci with a library of non-identical primers (such as non-immobilized primers) that simultaneously hybridize to at least 1,000 non-identical target human loci to produce a reaction mixture in which the concentration of each primer is less than 20 nM; wherein the primers do not include molecular inversion probes (MIPs); subjecting the reaction mixture to primer extension reaction conditions to produce amplified products comprising target amplicons; wherein the length of the annealing step of the reaction conditions is greater than 10 minutes; and wherein at least 1,000 non-identical target human loci are simultaneously amplified; and sequencing the amplified products. In some embodiments, the method includes contacting a sample comprising target human loci with a library of non-identical primers (such as non-immobilized primers) that simultaneously hybridize to at least 1,000 non-identical target human loci to produce a reaction mixture; wherein the guanine-cytosine (GC) content of the primers is between 30% and 80%, inclusive; wherein the range of melting temperatures of the primers is less than 5° C.; wherein the length of the primers is between 15 to 75 nucleotides, inclusive; and wherein the primers do not include molecular inversion probes (MIPs); subjecting the reaction mixture to primer extension reaction conditions to produce amplified products comprising target amplicons; wherein at least 1,000 non-identical target human loci are simultaneously amplified; and sequencing the amplified products. In some embodiments, the method does not comprise using a microarray. In some embodiments, the library includes a least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different primers. In some embodiments, at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci are amplified.

In various embodiments of any of the aspects of the invention, the ΔG values for each possible combination of two primers in the library are all equal to or greater than −5 kcal/mol. In some embodiments, the method simultaneously PCR-amplifying at least 1,000 non-identical target human loci in the sample using at least 1,000 non-identical primer pairs (such as non-immobilized primer pairs) to produce a first set of amplified products; wherein each primer pair includes a forward primer and a reverse primer that hybridize to the same target human locus. In some embodiments, the method also includes simultaneously PCR-amplifying at least 1,000 non-identical target human loci in the first set of amplified products using at least 1,000 non-identical primer pairs (such as non-immobilized primer pairs) to produce a second set of amplified products; wherein each primer pair includes a forward primer and a reverse primer that hybridize to the same target human locus. In some embodiments, the primer pairs used in the first and second round of PCR are the same. In some embodiments, the primer pairs used in the first and second round of PCR are different. In some embodiments, the forward primers used in the first and second round of PCR are the same, and the reverse primers used in the first and second round of PCR are different. In some embodiments, the forward primers used in the first and second round of PCR are different, and the reverse primers used in the first and second round of PCR are the same. In some embodiments, the method simultaneously PCR-amplifying at least 1,000 non-identical target human loci in the sample using at least 1,000 non-identical primer pairs (such as non-immobilized primer pairs) to produce a first set of amplified products; wherein each primer pair includes an outer forward primer and an outer reverse primer that hybridize to the same target human locus; and simultaneously PCR-amplifying at least 1,000 non-identical target human loci in the first set of amplified products using a universal reverse primer and at least 1,000 non-identical inner forward primers to produce a second set of amplified products; wherein each inner forward primer hybridizes to a region downstream from the corresponding outer forward primer. In some embodiments, the method includes simultaneously PCR-amplifying at least 1,000 non-identical target human loci in the sample using at least 1,000 non-identical primer pairs to produce a first set of amplified products; wherein each primer pair includes an outer forward primer and an outer reverse primer that hybridize to the same target human locus; and simultaneously PCR-amplifying at least 1,000 non-identical target human loci in the first set of amplified products using a universal forward primer and at least 1,000 non-identical inner reverse primers to produce a second set of amplified products; wherein each inner reverse primer hybridizes to a region upstream from the corresponding outer reverse primer. In some embodiments, the method includes simultaneously PCR-amplifying at least 1,000 non-identical target human loci in the sample using at least 1,000 non-identical forward primers and a universal reverse primer to produce a first set of amplified products; and simultaneously PCR-amplifying at least 1,000 non-identical target human loci in the first set of amplified products using a universal forward primer and at least 1,000 non-identical reverse primers to produce a second set of amplified products. In some embodiments, the method includes simultaneously PCR-amplifying at least 1,000 non-identical target human loci in the sample using at least 1,000 non-identical reverse primers and a universal forward primer to produce a first set of amplified products; and simultaneously PCR-amplifying at least 1,000 non-identical target human loci in the first set of amplified products using a universal reverse primer and at least 1,000 non-identical forward primers to produce a second set of amplified products. In some embodiments, at least 96% of the primer molecules are extended to form amplified products. In some embodiments, the annealing temperature is at least 1, 2, 3, 4, 5, 6, 7, 8, 9, 10, 11, 12, 13, or 15° C. greater than the melting temperature of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers. In some embodiments, the annealing temperature is at least 1, 2, 3, 4, 5, 6, 7, 8, 9, 10, 11, 12, 13, or 15° C. greater than the highest melting temperature of the non-identical primers. In some embodiments, the annealing temperature is at least 1, 2, 3, 4, 5, 6, 7, 8, 9, 10, 11, 12, 13, or 15° C. greater than the average melting temperature of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers. In some embodiments, the range of melting temperature of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers is between 1 to 5° C., inclusive. In some embodiments, at least 25; 50; 75; 100; 300; 500; 750; 1,000; 2,000; 5,000; 7,500; 10,000; 15,000; 19,000; 20,000; 25,000; 27,000; 28,000;

30,000; 40,000; 50,000; 75,000; 100,000; or all of the non-identical primers have 2, 1, or 0 guanines or cytosines in the last 5 bases at the 3' end of the primers. In some embodiments, the sample comprises maternal DNA from the pregnant mother of a fetus and fetal DNA, and wherein the method comprises determining the presence or absence of a fetal chromosome abnormality from the sequencing data. In some embodiments, the sample is from an individual suspected of having cancer or an above normal risk for cancer; and wherein one or more of the target human loci comprises a polymorphism or other mutation associated with an above normal risk for cancer or associated with cancer.

In various embodiments of any of the aspects of the invention, at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci are amplified. In some embodiments, at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci are amplified at least 5, 10, 20, 40, 50, 60, 80, 100, 120, 150, 200, 300, or 400-fold. In some embodiments, at least 50, 60, 70, 80, 90, 95, 96, 97, 98, 99, or 99.5% of the amplified products are target amplicons. In some embodiments, at least 50, 60, 70, 80, 90, 95, 96, 97, 98, 99, or 99.5% of the target loci are amplified. In some embodiments, at least 50, 60, 70, 80, 90, 95, 96, 97, 98, 99, or 99.5% of the target loci are amplified at least 5, 10, 20, 40, 50, 60, 80, 100, 120, 150, 200, 300, or 400-fold. In various embodiments, less than 60, 50, 40, 30, 20, 10, 5, 4, 3, 2, 1, 0.5, 0.25, 0.1, or 0.05% of the amplified products are primer dimers. In some embodiments, the library of test primers includes at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 test primer pairs, wherein each pair of primers includes a forward test primer and a reverse test primer that hybridize to the same target locus. In some embodiments, the library of test primers includes at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 individual test primers that hybridize to different target loci, wherein the individual primers are not part of primer pairs.

In various embodiments of any of the aspects of the invention, the concentration of each test primer is less than 100, 75, 50, 25, 10, 5, 2, 1, 0.5, 0.1, or 0.05 nM. In various embodiments, the guanine-cytosine (GC) content of the test primers is between 30 to 80%, such as between 20 to 70%, 40 to 70%, or 50 to 60%, inclusive. In some embodiments, the range of GC content (e.g., the maximum GC content minus minimum GC content, such as 80%-60%=a range of 20%) of the test primers is less than 30, 20, 10, or 5%. In some embodiments, there are at least 2 (such as 3, 4, or 5) guanines or cytosines in the last 5 bases at the 3' end of the primers. In some embodiments, a maximum of 2 (such as 2, 1, or 0) of the bases in the last 5 bases at the 3' end of the primers are guanines or cytosines. In some embodiments, there are at least 1 (such as 2 or 3) guanines or cytosines in the last 3 bases at the 3' end of the primers. In some embodiments, the melting temperature ($T_m$) of the test primers is between 40 to 80° C., such as 50 to 70° C., 55 to 65° C., 54 to 60.5° C., or 57 to 60.5° C., inclusive. In some embodiments, the range of melting temperatures of the test primers is less than 20, 15, 10, 5, 3, or 1° C. In some embodiments, the length of the test primers is between 15 to 100 nucleotides, such as between 15 to 75 nucleotides, 15 to 40 nucleotides, 17 to 35 nucleotides, 18 to 30 nucleotides, or 20 to 65 nucleotides, inclusive. In some embodiments, the test primers include a tag that is not target specific, such as a tag that forms an internal loop structure. In some embodiments, the tag is between two DNA binding regions. In various embodiments, the test primers include a 5' region that is specific for a target locus, an internal region that is not specific for the target locus and forms a loop structure, and a 3' region that is specific for the target locus. In various embodiments, the length of the 3' region is at least 7 nucleotides. In some embodiments, the length of the 3' region is between 7 and 20 nucleotides, such as between 7 to 15 nucleotides, or 7 to 10 nucleotides, inclusive. In various embodiments, the test primers include a 5' region that is not specific for a target locus (such as a tag or a universal primer binding site) followed by a region that is specific for a target locus, an internal region that is not specific for the target locus and forms a loop structure, and a 3' region that is specific for the target locus. In some embodiments, the range of the length of the test primers is less than 50, 40, 30, 20, 10, or 5 nucleotides. In some embodiments, the length of the target amplicons is between 50 and 100 nucleotides, such as between 60 and 80 nucleotides, or 60 to 75 nucleotides, inclusive. In some embodiments, the length of the target amplicons is at least 100; 200; 300; 400; 500; 600; 700; 800; 900; 1,000; 1,200; 1,500; 2,000; or 3,000 nucleotides. In some embodiments, the length of the target amplicons is between 100 and 1,500 nucleotides, such as between 100 to 1,000; 100 to 500, 500 to 750, or 750 to 1,000 nucleotides, inclusive. In some embodiments, the range of the length of the target amplicons is less than 50, 25, 15, 10, or 5 nucleotides. In some embodiments, at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 or all of the target amplicons have a length that falls within the range of the average length of the amplicons ±5% of the average length, average length ±20%, average length ±20%, average length ±30%, or average length ±50%.

In various embodiments of any of the aspects of the invention, the primer extension reaction conditions are polymerase chain reaction conditions (PCR). In various embodiments, the length of the annealing step is greater than 3, 5, 8, 10, 15, 20, 30, 45, 60, 75, 90, 120, 150, or 180 minutes. In various embodiments, the length of the extension step is greater than 0.2, 0.5, 1, 3, 5, 8, 10, or 15 minutes.

In various embodiments of any of the aspects of the invention, the test primers are used to simultaneously amplify at least 300 different target loci in a sample that includes maternal DNA from the pregnant mother of a fetus and fetal DNA to determine the presence or absence of a fetal chromosome abnormality. In various embodiments, the method includes ligating a universal primer binding site to the DNA molecules in the sample; amplifying the ligated DNA molecules using at least 300 specific primers and a universal primer to produce a first set of amplified products; and amplifying the first set of amplified products using at least 300 pairs of specific primers to produce a second set of amplified products.

In various embodiments of any of the aspects of the invention, the test primers are used to simultaneously amplify e.g. at least 100 (e.g., at least 300 or 1,000) different target loci in sample includes DNA from an alleged father of a fetus and to simultaneously amplify the target loci in a sample that includes maternal DNA from the pregnant mother of the fetus and fetal DNA to establish whether the alleged father is the biological father of the fetus.

In various embodiments of any of the aspects of the invention, the test primers are used to simultaneously amplify e.g. at least 100 (e.g., at least 300 or 1,000) different target loci in one cell or multiple cells from an embryo to determine the presence or absence of a chromosome abnormality. In various embodiments, cells from a set of two or more embryos are analyzed, and one embryo is selected for in vitro fertilization.

In various embodiments of any of the aspects of the invention, the test primers are used to simultaneously amplify e.g. at least 100 (e.g., at least 300 or 1,000) different target loci in a forensic nucleic acid sample. In various embodiments, the length of the annealing step is greater than 3, 5, 8, 10, 15, 20, 30, 45, 60, 75, 90, 120, 150, or 180 minutes In various embodiments of any of the aspects of the invention, the method involves using the test primers to simultaneously amplify e.g. at least 100 (e.g., at least 300 or 1,000) different target loci in a control nucleic acid sample to produce a first set of target amplicons and to simultaneously amplify the target loci in a test nucleic acid sample to produce a second set of target amplicons; and comparing the first and second sets of target amplicons to determine whether a target locus is present in one sample but absent in the other, or whether a target locus is present at different levels in the control sample and the test sample. In various embodiments, the test sample is from an individual suspected of having a disease or phenotype of interest (such as cancer), or an increased risk (such as an above normal level of risk) for a disease or phenotype of interest; and wherein one or more of the target loci include a sequence (e.g., a polymorphism or other mutation) associated with an increased risk (such as an above normal level of risk) for the disease or phenotype of interest, or associated with the disease or phenotype of interest. In various embodiments, the method involves using the test primers to simultaneously amplify e.g. at least 100 (e.g., at least 300 or 1,000) different target loci in a control sample that includes RNA to produce a first set of target amplicons and to simultaneously amplify the target loci in a test sample that includes RNA to produce a second set of target amplicons; and comparing the first and second sets of target amplicons to determine the presence or absence of a difference in the RNA expression levels between the control sample and the test sample. In various embodiments, the RNA is mRNA. In various embodiments, the test sample is from an individual suspected of having a disease or phenotype of interest (such as cancer) or an increased risk for the disease or phenotype of interest (such as cancer); and wherein one or more of the target loci includes a sequence (e.g., a polymorphism or other mutation) associated with an increased risk for the disease or phenotype of interest or associated with the disease or phenotype of interest. In some embodiments, the test sample is from an individual diagnosed with a disease or phenotype of interest (such as cancer); and wherein a difference in the RNA expression level between the control sample and test sample indicates a target locus includes a sequence (e.g., a polymorphism or other mutation) associated with an increased or decreased risk for the disease or phenotype of interest.

In some embodiments of any of the aspects of the invention, the test primers are selected from a library of candidate primers based on one or more parameters, such as the selection of primers using any of the methods of the invention. In some embodiments, the test primers are selected from a library of candidate primers based at least in part on the ability of the candidate primers to form primer dimers.

In one aspect, the invention features methods of selecting test primers from a library of candidate primers. In various embodiments, the selection involves (i) calculating on a computer a score (such as an undesirability score) for most or all of the possible combinations of two candidate primers from the library, wherein each score (such as an undesirability score) is based at least in part on the likelihood of dimer formation between the two candidate primers; (ii) removing the candidate primer with the highest score (such as an undesirability score) from the library of candidate primers; and (iii) if the candidate primer removed in step (ii) is a member of a primer pair, then removing the other member of the primer pair from the library of candidate primers; and (iv) optionally repeating steps (ii) and (iii), thereby selecting a library of test primers. In some embodiments, the selection method is performed until the score (such as the undesirability score) for the candidate primer combinations remaining in the library are all equal to or below a minimum threshold. In some embodiments, the selection method is performed until the number of candidate primers remaining in the library is reduced to a desired number. In various embodiments, a score (such as an undesirability score) is calculated for at least 80, 90, 95, 98, 99, or 99.5% of the possible combinations of candidate primers in the library. In various embodiments, the candidate primers remaining in the library are capable of simultaneously amplifying at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci. In various embodiments, the method also includes (v) contacting a nucleic acid sample that includes target loci with the candidate primers remaining in the library to produce a reaction mixture; and (vi) subjecting the reaction mixture to primer extension reaction conditions to produce amplified products that includes target amplicons.

In one aspect, the invention features methods of selecting test primers from a library of candidate primers. In various embodiments, the selection of test primers are selected from a library of candidate primers involves (i) calculating on a computer a score (such as an undesirability score) for most or all of the possible combinations of two candidate primers from the library, wherein each score (such as an undesirability score) is based at least in part on the likelihood of dimer formation between the two candidate primers; (ii) removing from the library of candidate primers the candidate primer that is part of the greatest number of combinations of two candidate primers with a score (such as an undesirability score) above a first minimum threshold; (iii) if the candidate primer removed in step (ii) is a member of a primer pair, then removing the other member of the primer pair from the library of candidate primers; and (iv) optionally repeating steps (ii) and (iii), thereby selecting a library of test primers. In some embodiments, the selection method is performed until the score (such as the undesirability score) for the candidate primer combinations remaining in the library are all equal to or below the first minimum threshold. In some embodiments, the selection method is performed until the number of candidate primers remaining in the library is reduced to a desired number. In various embodiments, a score (such as an undesirability score) is calculated for at least 80, 90, 95, 98, 99, or 99.5% of the possible combinations of candidate primers in the library. In various embodiments, the candidate primers remaining in the library are capable of simultaneously amplifying at least 25; 50; 75; 100; 300; 500; 750; 1,000; 2,000; 5,000; 7,500; 10,000; 15,000; 19,000; 20,000; 25,000; 27,000; 28,000; 30,000;

40,000; 50,000; 75,000; or 100,000 different target loci. In various embodiments, the method also includes (v) contacting a nucleic acid sample that includes target loci with the candidate primers remaining in the library to produce a reaction mixture; and (vi) subjecting the reaction mixture to primer extension reaction conditions to produce amplified products that includes target amplicons.

In various embodiments of any of the aspects of the invention, the selection method involves further reducing the number of candidate primers remaining in the library by decreasing the first minimum threshold used in step (ii) to a lower second minimum threshold and optionally repeating steps (ii) and (iii). In some embodiments, the selection method involves increasing the first minimum threshold used in step (ii) to a higher second minimum threshold and optionally repeating steps (ii) and (iii). In some embodiments, the selection method is performed until the score (such as the undesirability score) for the candidate primer combinations remaining in the library are all equal to or below the second minimum threshold, or until the number of candidate primers remaining in the library is reduced to a desired number.

In various embodiments of any of the aspects of the invention, the method involves, prior to step (i), identifying or selecting primers that hybridize to the target loci. In some embodiments, multiple primers (or primer pairs) hybridize to the same target locus, and the selection method is used to select a one primer (or one primer pair) for this target locus based on one or more parameters. In various embodiments, the method involves, prior to step (ii), removing a primer pair from the library that produces a target amplicon that overlaps with a target amplicon produced by another primer pair. In various embodiments, a candidate primer is selected out of a group of two or more candidate primers with equal scores (such as undesirability scores) for removal from the library of candidate primers based on one or more other parameters. In some embodiments, the candidate primers remaining in the library are used as a library of test primers in any of the methods of the invention. In some embodiments, the resulting library of test primers includes any of the primer libraries of the invention.

In various embodiments of any of the aspects of the invention, the selection method selects candidate primers and divides them into different pools (e.g., 2, 3, 4, 5, 6, or more different pools). Each pool can be used to simultaneously amplify a large number of target loci (or a subset of target loci) in a single reaction volume. In some embodiments, a graph coloring algorithm is used to divide candidate primers into different pools. If desired, this method can be used to minimize the number of different pools needed to amplify most or all of the target loci.

In some embodiments, most or all of the target loci (such as at least 70, 80, 90, 92, 94, 96, 98, 99, or 100% of the target loci) are amplified by at least 2, 3, 4, 5, 6, or more different pools. In some embodiments, most or all of the bases in the target loci (such as at least 70, 80, 90, 92, 94, 96, 98, 99, or 100% of the bases in the target loci) are amplified by at least 2, 3, 4, 5, 6, or more different pools. In some embodiments, most or all of the bases in the target loci (such as at least 70, 80, 90, 92, 94, 96, 98, 99, or 100% of the bases in the target loci) are amplified by at least 2, 3, 4, 5, 6, or more different primers or primer pairs in different pools. For example, a particular base in a target locus may be amplified by at least 2, 3, 4, 5, 6, or more different primers or primer pairs; wherein each different primer or primer pair is in a different pool. Using different primers or primer pairs to amplify each base allows multiple independent measurements of the base to be made, thereby increasing the accuracy of the method. Dividing the different primers or primer pairs that amplify the same base into different pools prevents interference due to overlapping amplicons being formed by different primers or primer pairs.

In one aspect, the invention features methods of selecting test primers from a library of candidate primers to form 2 or more different primer pools. In various embodiments, the selection involves (i) calculating on a computer a score (such as an undesirability score) for most or all of the possible combinations of two candidate primers from the library, wherein each score (such as an undesirability score) is based at least in part on the likelihood of dimer formation between the two candidate primers; (ii) removing the candidate primer with the highest score (such as an undesirability score) from the library of candidate primers; and (iii) if the candidate primer removed in step (ii) is a member of a primer pair, then removing the other member of the primer pair from the library of candidate primers; and (iv) optionally repeating steps (ii) and (iii), thereby selecting a first pool. In some embodiments, the selection method is performed until the score (such as the undesirability score) for the candidate primer combinations remaining in the library are all equal to or below a minimum threshold for the first pool. In some embodiments, the selection method is performed until the number of candidate primers remaining in the library is reduced to a desired number for the first pool. In some embodiments, after the first pool is selected those primers are removed from further consideration and steps of the method (such as steps (ii) and (iii)) are repeated with the remaining primers to select a second pool. If desired, this method may be repeated to select the desired number of primer pools. In various embodiments, a score (such as an undesirability score) is calculated for at least 80, 90, 95, 98, 99, or 99.5% of the possible combinations of candidate primers in the library. In some embodiments, the score is based at least in part on the current coverage of the bases in the target locus (such as the number of other primer pools that have a primer or primer pair that amplifies a particular base in the target locus). In various embodiments, one or more of the pools are each capable of simultaneously amplifying at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci. In various embodiments, the method also includes separately contacting a nucleic acid sample that includes target loci with two or more of the pools to produce separate reaction mixtures; and (vi) subjecting the reaction mixtures to primer extension reaction conditions to produce amplified products that includes target amplicons.

In one aspect, the invention features methods of selecting test primers from a library of candidate primers to form 2 or more different primer pools. In various embodiments, the selection of test primers are selected from a library of candidate primers involves (i) calculating on a computer a score (such as an undesirability score) for most or all of the possible combinations of two candidate primers from the library, wherein each score (such as an undesirability score) is based at least in part on the likelihood of dimer formation between the two candidate primers; (ii) removing from the library of candidate primers the candidate primer that is part of the greatest number of combinations of two candidate primers with a score (such as an undesirability score) above a first minimum threshold; (iii) if the candidate primer removed in step (ii) is a member of a primer pair, then removing the other member of the primer pair from the library of candidate primers; and (iv) optionally repeating steps (ii) and (iii), thereby selecting a first pool. In some embodiments, the selection method is performed until the score (such as the undesirability score) for the candidate primer combinations remaining in the library are all equal to or below the first minimum threshold for the first pool. In some embodiments, the selection method is performed until the number of candidate primers remaining in the library is reduced to a desired number for the first pool. In various embodiments, the selection method involves further reducing the number of candidate primers remaining in the library by decreasing the first minimum threshold used in step (ii) to a lower second minimum threshold and optionally repeating steps (ii) and (iii). In some embodiments, the selection method involves increasing the first minimum threshold used in step (ii) to a higher second minimum threshold and optionally repeating steps (ii) and (iii). In some embodiments, the selection method is performed until the score (such as the undesirability score) for the candidate primer combinations remaining in the library are all equal to or below the second minimum threshold, or until the number of candidate primers remaining in the library is reduced to a desired number for the first pool. In some embodiments, after the first pool is selected those primers are removed from further consideration and steps of the method (such as steps (ii) and (iii)) are repeated with the remaining primers to select a second pool. If desired, this method may be repeated to select the desired number of primer pools. In various embodiments, a score (such as an undesirability score) is calculated for at least 80, 90, 95, 98, 99, or 99.5% of the possible combinations of candidate primers in the library. In some embodiments, the score is based at least in part on the current coverage of the bases in the target locus (such as the number of other primer pools that have a primer or primer pair that amplifies a particular base in the target locus). In various embodiments, one or more of the pools are each capable of simultaneously amplifying at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci. In various embodiments, the method also includes separately contacting a nucleic acid sample that includes target loci with two or more of the pools to produce separate reaction mixtures; and (vi) subjecting the reaction mixtures to primer extension reaction conditions to produce amplified products that includes target amplicons.

In some embodiments, at least 70, 80, 85, 90, 95, or 100% of the nucleotides in a region of interest (such as an exon) are included in at least 1, 2, 3, or 4 different amplicons (i.e., amplicons with non-identical sequences that are formed by different primers or primer pairs). In some embodiments, at least 70, 80, 85, 90, 95, or 100% of the nucleotides in at least 70, 80, 85, 90, 95, or 100% of the regions of interest are amplified by at least 1, 2, 3, or 4 different amplicons. In some embodiments in which 2-fold coverage is desired, the primers are divided into at least two different pools such the amplicons in each pool do not overlap with each other (which would cause interference during amplification).

In various embodiments of any of the aspects of the invention, the score (such as the undesirability score) are based at least in part on one or more parameters selected from the group consisting of heterozygosity rate of the target locus, disease prevalence associated with a sequence (e.g., a polymorphism) at the target locus, disease penetrance associated with a sequence (e.g., a polymorphism) at the target locus, specificity of the candidate primer for the target locus, size of the candidate primer, melting temperature of the candidate primer, melting temperature of the target amplicon, GC content of the target amplicon, GC content of the 3' end of the candidate primer, homopolymer length in the candidate primer, amplification efficiency of the target amplicon, and size of the target amplicon.

In various embodiments of any of the aspects of the invention, the score (such as the undesirability score) are based at least in part on one or more parameters selected from the group consisting of heterozygosity rate of the target locus, specificity of the candidate primer for the target locus; size of the candidate primer, melting temperature of the candidate primer, melting temperature of the target amplicon, GC content of the target amplicon, GC content of the 3' end of the candidate primer, homopolymer length in the candidate primer, amplification efficiency of the target amplicon, and size of the target amplicon; and the test primers are used to simultaneously amplify e.g. at least 100 (e.g., at least 300 or 1,000) different target loci in a sample that includes maternal DNA from the pregnant mother of a fetus and fetal DNA to determine the presence or absence of a fetal chromosome abnormality. In various embodiments, the method includes ligating a universal primer binding site to the DNA molecules in the sample; amplifying the ligated DNA molecules using e.g. at least 100 (e.g., at least 300 or 1,000) specific primers and a universal primer to produce a first set of amplified products; and amplifying the first set of amplified products using e.g. at least 100 (e.g., at least 300 or 1,000) pairs of specific primers to produce a second set of amplified products. In various embodiments, at least 500; 750; 1,000; 2,000; 5,000; 7,500; 10,000; 15,000; 19,000; 20,000; 25,000; 27,000; 28,000; 30,000; 40,000; 50,000; 75,000; or 100,000 different primer pairs are used. In various embodiments, at least 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci are amplified. In some embodiments, at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci are amplified at least 5, 10, 20, 40, 50, 60, 80, 100, 120, 150, 200, 300, or 400-fold. In some embodiments, at least 50, 60, 70, 80, 90, 95, 96, 97, 98, 99, 99.5, or 100% of the target loci are amplified at least 5, 10, 20, 40, 10 50, 60, 80, 100, 120, 150, 200, 300, or 400-fold.

In various embodiments of any of the aspects of the invention, the score (such as the undesirability score) are based at least in part on one or more parameters selected from the group consisting of heterozygosity rate of the target locus, specificity of the candidate primer for the target locus; size of the candidate primer, melting temperature of the candidate primer, melting temperature of the target amplicon, GC content of the target amplicon, GC content of the 3' end of the candidate primer, homopolymer length in the candidate primer, amplification efficiency of the target amplicon, and size of the target amplicon; and the test primers are used to simultaneously amplify e.g. at least 100 (e.g., at least 300 or 1,000) different target loci in sample includes DNA from an alleged father of a fetus and to simultaneously amplify the target loci in a sample that includes maternal DNA from the pregnant mother of a fetus and fetal DNA to establish whether the alleged father is the biological father of the fetus. In various embodiments, at least 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci are amplified. In some embodiments, at least 25; 50; 75; 100; 300; 500; 750; 1,000; 2,000; 5,000; 7,500; 10,000; 15,000;

19,000; 20,000; 25,000; 27,000; 28,000; 30,000; 40,000; 50,000; 75,000; or 100,000 different target loci are amplified at least 5, 10, 20, 40, 50, 60, 80, 100, 120, 150, 200, 300, or 400-fold. In some embodiments, at least 50, 60, 70, 80, 90, 95, 96, 97, 98, 99, 99.5, or 100% of the target loci are amplified at least 5, 10, 20, 40, 50, 60, 80, 100, 120, 150, 200, 300, or 400-fold.

In various embodiments of any of the aspects of the invention, the score (such as the undesirability score) are based at least in part on one or more parameters selected from the group consisting of heterozygosity rate of the target locus, specificity of the candidate primer for the target locus; size of the candidate primer, melting temperature of the candidate primer, melting temperature of the target amplicon, GC content of the target amplicon, GC content of the 3' end of the candidate primer, homopolymer length in the candidate primer, amplification efficiency of the target amplicon, and size of the target amplicon; and the test primers are used to simultaneously amplify e.g. at least 100 (e.g., at least 300 or 1,000) different target loci in one cell or multiple cells from an embryo to determine the presence or absence of a chromosome abnormality. In various embodiments, cells from a set of two or more embryos are analyzed, and one embryo is selected for in vitro fertilization. In various embodiments, at least 300, 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci are amplified. In some embodiments, at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci are amplified at least 5, 10, 20, 40, 50, 60, 80, 100, 120, 150, 200, 300, or 400-fold. In some embodiments, at least 50, 60, 70, 80, 90, 95, 96, 97, 98, 99, 99.5, or 100% of the target loci are amplified at least 5, 10, 20, 40, 50, 60, 80, 100, 120, 150, 200, 300, or 400-fold.

In various embodiments of any of the aspects of the invention, the scores (such as the undesirability scores) are based at least in part on one or more parameters selected from the group consisting of heterozygosity rate of the target locus, specificity of the candidate primer for the target locus; size of the candidate primer, melting temperature of the candidate primer, melting temperature of the target amplicon, GC content of the target amplicon, GC content of the 3' end of the candidate primer, homopolymer length in the candidate primer, amplification efficiency of the target amplicon, and size of the target amplicon; and the test primers are used to simultaneously amplify e.g. at least 100 (e.g., at least 300 or 1,000) different target loci in a forensic nucleic acid sample. In various embodiments, the length of the annealing step is greater than 3, 5, 8, 10, 15, 20, 30, 45, 60, 75, 90, 120, 150, or 180 minutes. In various embodiments, at least 300, 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci are amplified. In some embodiments, at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci are amplified at least 5, 10, 20, 40, 50, 60, 80, 100, 120, 150, 200, 300, or 400-fold. In some embodiments, at least 50, 60, 70, 80, 90, 95, 96, 97, 98, 99, 99.5, or 100% of the target loci are amplified at least 5, 10, 20, 40, 50, 60, 80, 100, 120, 150, 200, 300, or 400-fold.

In various embodiments of any of the aspects of the invention, the scores (such as the undesirability scores) are based at least in part on one or more parameters selected from the group consisting of heterozygosity rate of the target locus, disease prevalence associated with a sequence (e.g., a polymorphism) at the target locus, disease penetrance associated with a sequence (e.g., a polymorphism) at the target locus, specificity of the candidate primer for the target locus, size of the candidate primer, melting temperature of the candidate primer, melting temperature of the target amplicon, GC content of the target amplicon, GC content of the 3' end of the candidate primer, homopolymer length in the candidate primer, amplification efficiency of the target amplicon, and size of the target amplicon; and the method involves using the test primers to simultaneously amplify e.g. at least 100 (e.g., at least 300 or 1,000) different target loci in a control nucleic acid sample to produce a first set of target amplicons and to simultaneously amplify the target loci in a test nucleic acid sample to produce a second set of target amplicons; and comparing the first and second sets of target amplicons to determine whether a target locus is present in one sample but absent in the other, or whether a target locus is present at different levels in the control sample and the test sample. In various embodiments, the test sample is from an individual suspected of having a disease or phenotype of interest, or an increased risk for a disease or phenotype of interest; and wherein one or more of the target loci include a sequence (e.g., a polymorphism) at the target locus associated with an increased risk for the disease or phenotype of interest, or associated with the disease or phenotype of interest. In various embodiments, at least 300, 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci are amplified. In some embodiments, at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci are amplified at least 5, 10, 20, 40, 50, 60, 80, 100, 120, 150, 200, 300, or 400-fold. In some embodiments, at least 50, 60, 70, 80, 90, 95, 96, 97, 98, 99, 99.5, or 100% of the target loci are amplified at least 5, 10, 20, 40, 50, 60, 80, 100, 120, 150, 200, 300, or 400-fold.

In various embodiments of any of the aspects of the invention, the scores (such as the undesirability scores) are based at least in part on one or more parameters selected from the group consisting of heterozygosity rate of the target locus, disease prevalence associated with a sequence (e.g., a polymorphism) at the target locus, disease penetrance associated with a sequence (e.g., a polymorphism) at the target locus, specificity of the candidate primer for the target locus, size of the candidate primer, melting temperature of the candidate primer, melting temperature of the target amplicon, GC content of the target amplicon, GC content of the 3' end of the candidate primer, homopolymer length in the candidate primer, amplification efficiency of the target amplicon, and size of the target amplicon; and the method involves using the test primers to simultaneously amplify e.g. at least 100 (e.g., at least 300 or 1,000); different target loci in a control sample that includes RNA to produce a first set of target amplicons and to simultaneously amplify the target loci in a test sample that includes RNA to produce a second set of target amplicons; and comparing the first and second sets of target amplicons to determine the presence or absence of a difference in the RNA expression levels between the control sample and the test sample. In various embodiments, the RNA is mRNA. In various embodiments, the test sample is from an individual suspected of having a disease or phenotype of interest (such as cancer) or an increased risk for the disease or phenotype of interest (such as cancer); and wherein one or more of the target loci includes a sequence (e.g., a polymorphism or other mutation) associated with an increased risk for the disease or phenotype of interest or associated with the disease or phenotype of interest. In some embodiments, the test sample is from an individual diagnosed with a disease or phenotype of interest (such as cancer); and wherein a difference in the RNA expression level between the control sample and test sample indicates a target locus includes a sequence (e.g., a polymorphism or other mutation) associated with an increased or decreased risk for the disease or phenotype of interest. In various embodiments, at least 300; 500; 750; 1,000; 2000; 5,000; 7,500; 10,000; 15,000; 19,000; 20,000; 25,000; 27,000; 28,000; 30,000; 40,000; 50,000; 75,000; or 100,000 different target loci are amplified. In some embodiments, at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci are amplified at least 5, 10, 20, 40, 50, 60, 80, 100, 120, 150, 200, 300, or 400-fold. In some embodiments, at least 50, 60, 70, 80, 90, 95, 96, 97, 98, 99, 99.5, or 100% of the target loci are amplified at least 5, 10, 20, 40, 50, 60, 80, 100, 120, 150, 200, 300, or 400-fold.

In one aspect, the invention features libraries of primers (such as non-immobilized primers). In some embodiments, the primers are selected from a library of candidate primers using any of the methods of the invention. In some embodiments, the library includes primers that simultaneously hybridize to at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci. In some embodiments, the library includes primers that simultaneously amplify at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci. In some embodiments, the library includes primers that simultaneously amplify at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci such that less than 60, 40, 30, 20, 10, 5, 4, 3, 2, 1, 0.5, 0.25, 0.1, or 0.05% of the amplified products are primer dimers. In some embodiments, the library includes primers that simultaneously amplify at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci such that at least 50, 60, 70, 80, 90, 95, 96, 97, 98, 99, or 99.5% of the amplified products are target amplicons. In some embodiments, the library includes primers that simultaneously amplify target loci such that at least 50, 60, 70, 80, 90, 95, 96, 97, 98, 99, or 99.5% of the target loci out of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci are amplified. In some embodiments, at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci are amplified at least 5, 10, 20, 40, 50, 60, 80, 100, 120, 150, 200, 300, or 400-fold. In some embodiments, at least 50, 60, 70, 80, 90, 95, 96, 97, 98, 99, 99.5, or 100% of the target loci are amplified at least 5, 10, 20, 40, 50, 60, 80, 100, 120, 150, 200, 300, or 400-fold. In some embodiments, the library of primers includes at least 25; 50; 75; 100; 300; 500; 750; 25 1,000; 2,000; 5,000; 7,500; 10,000; 15,000; 19,000; 20,000; 25,000; 27,000; 28,000; 30,000; 40,000; 50,000; 75,000; or 100,000 non-identical primers or primer pairs. In some embodiments, the library of primers includes at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 primer pairs, wherein each pair of primers includes a forward test primer and a reverse test primer where each pair of test primers hybridize to a target locus. In some embodiments, the library of primers includes at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 individual primers that each hybridize to a different target locus, wherein the individual primers are not part of primer pairs. In some embodiments, the primers in the library are not immobilized (such as not immobilized to a solid support) or not part of a microarray. In some embodiments, the primers are dissolved in solution (such as dissolved in the liquid phase). In some embodiments, the library of primers consists essentially of, or consists of primers.

In some embodiments, ΔG values for each possible combination of two primers (each possible primer dimer) in a library are all equal to or greater than −20, −18, −16, −14, −12, −10, −9, −8, −7, −6, −5, −4, −3, −2, or −1 kcal/mol. In some embodiments, ΔG values for at least 80, 85, 90, 92, 94, 96, 98, 99, or 100% of the primers in the library for possible combinations of that primer with other primers in the library are all equal to or greater than −20, −18, −16, −14, −12, −10, −9, −8, −7, −6, −5, −4, −3, −2, or −1 kcal/mol.

In various embodiments of any of the aspects of the invention, the library of primers includes one or more primers (e.g., at least 10; 20; 50; 25; 50; 75; 100; 300; 500; 750; 1,000; 2,000; 5,000; 7,500; 10,000; 15,000; 20,000; 25,000; 30,000; 40,000; or 50,000 different primers) with at least 60, 70, 80, 90, 95, 96, 97, 98, 99, 99.5, or 100% identity to the corresponding region (e.g., a region of at least 10, 20, 30, 40, 50, or more contiguous nucleotides) of a primer in FIG. 34 (SEQ ID NOs. 1-3,600), FIG. 35 (SEQ ID NOs. 3,601-11,658), or FIG. 36 (SEQ ID NOs 11,659-44,610). In some embodiments, the library of primers includes one or more primers (e.g., at least 10; 20; 50; 25; 50; 75; 100; 300; 500; 750; 1,000; 2,000; 5,000; 7,500; 10,000; 15,000; 20,000; 25,000; 30,000; 40,000; or 50,000 different primers) with at least 60, 70, 80, 90, 95, 96, 97, 98, 99, 99.5, or 100% identity over the entire length of a primer in FIG. 34 (SEQ ID NOs. 1-3,600), FIG. 35 (SEQ ID NOs. 3,601-11-658), or FIG. 36 (SEQ ID NOs 11,659-44,610). In some embodiments, the library of primers includes at least 10; 20; 50; 75; 100; 300; 500; 750; 1,000; 2,000; 5,000; 7,500; 10,000; 15,000; 20,000; 25,000; 30,000; 40,000; or 50,000 different primers from the primers in FIG. 34 (SEQ ID NOs. 1-3,600), FIG. 35 (SEQ ID NOs. 3,601-11,658), or FIG. 36 (SEQ ID NOs 11,659-44,610. In some embodiments, the library of primers includes one or more primers (e.g., at least 10; 20; 50; 75; 100; 300; 500; 750; 1,000; 2,000; 5,000; 7,500; 10,000; 15,000; 20,000; 25,000; 30,000; 40,000; or 50,000 different primers) that hybridize to the complement of a primer in FIG. 34 (SEQ ID NOs. 1-3,600), FIG. 35 (SEQ ID NOs. 3,601-11,658), or FIG. 36 (SEQ ID NOs 11,659-44, 610) under very high stringency hybridization conditions or under high stringency hybridization conditions.

In various embodiments of any of the aspects of the invention, the concentration of each primer is less than 100, 75, 50, 25, 10, 5, 2, 1, 0.5, 0.1, or 0.05 nM. In various embodiments, the GC content of the primers is between 30 to 80%, such as between 40 to 70%, 20 to 70%, or 50 to 60%, inclusive. In some embodiments, the range of GC content of the primers is less than 30, 20, 10, or 5%. In some embodiments, there are at least 2 (such as 3, 4, or 5) guanines or cytosines in the last 5 bases at the 3' end of the primers. In some embodiments, there are at least 1 (such as 2 or 3) guanines or cytosines in the last 3 bases at the 3' end of the primers. In some embodiments, a maximum of 2 (such as 2, 1, or 0) bases in the last 5 bases at the 3' end of the primers are guanines or cytosines. In some embodiments, the melting temperature of the primers is between 40 to 80° C., such as 50 to 70° C., 55 to 65° C., 54 to 60.5° C., or 57 to 60.5° C., inclusive. In some embodiments, the range of melting temperature of the primers is less than 15, 10, 5, 3, or 1° C. In some embodiments, the length of the primers is between 15 to 100 nucleotides, such as between 15 to 75 nucleotides, 15 to 40 nucleotides, 17 to 35 nucleotides, 18 to 30 nucleotides, or 20 to 65 nucleotides, inclusive. In some embodiments, the primers include a tag that is not target specific, such as a tag that forms an internal loop structure. In some embodiments, the tag is between two DNA binding regions. In various embodiments, the primers include a 5' region that is specific for a target locus, an internal region that is not specific for the target locus and forms a loop structure, and a 3' region that is specific for the target locus. In various embodiments, the length of the 3' region is at least 7 nucleotides. In some embodiments, the length of the 3' region is between 7 and 20 nucleotides, such as between 7 to 15 nucleotides, or 7 to 10 nucleotides, inclusive. In various embodiments, the primers include a 5' region that is not specific for a target locus (such as another tag or a universal primer binding site) followed by a region that is specific for a target locus, an internal region that is not specific for the target locus and forms a loop structure, and a 3' region that is specific for the target locus. In some embodiments, the range of the length of the primers is less than 50, 40, 30, 20, 10, or 5 nucleotides. In some embodiments, the length of the target amplicons is between 50 and 100 nucleotides, such as between 60 and 80 nucleotides, or 60 to 75 nucleotides, inclusive. In some embodiments, the range of the length of the target amplicons is less than 50, 25, 15, 10, or 5 nucleotides. In some embodiments, the target loci are on two or more different chromosomes, such as two or more of chromosomes 13, 18, 21, X and Y. In some embodiments, the target loci are target human loci. In some embodiments, the target loci includes a sequence (e.g., a polymorphism or other mutation) associated with an increased risk for the disease or phenotype of interest (such as cancer), or associated with the disease or phenotype of interest (such as cancer). In some embodiments, the polymorphism or mutation is a driver mutation that has a causative role in the disease or phenotype of interest (such as cancer). In some embodiments, the polymorphism or mutation is not a causative mutation. For example, in some cancers, multiple mutations accumulate but some of them are not causative mutations. Polymorphisms or mutations (such as those that are present at a higher frequency in subjects with a disease or phenotype of interest such as cancer than subjects without the disease or phenotype of interest such as cancer) that are not causative can still be useful for diagnosing the disease or phenotype. In some embodiments, the polymorphisms or mutation is present at a higher frequency in subjects with a disease or disorder (such as cancer) than subjects (such as healthy or normal subjects) without the disease or disorder (such as cancer). In some embodiments, the polymorphisms or mutation is indicative of cancer, such as a causative mutation. In some embodiments, the polymorphism(s) or mutation(s) are directly detected. In some embodiments, the polymorphism(s) or mutation(s) are indirectly detected by detection of one or more sequences (e.g., a polymorphic locus such as a SNP) that are linked to the polymorphism or mutation).

In one aspect, the invention provides a composition that includes any of the primer libraries of the invention (such as non-immobilized primers). In some embodiments, the composition includes one or more free nucleotides (such as deoxynucleotides, ATP, CTP, GTP, TTP, UTP, dATP, dCTP, dGTP, dTTP, dUTP an activated nucleotide or deoxynucleotide, or a non-naturally occurring nucleotide or deoxynucleotide). In some embodiments, the composition includes at least one primer (e.g., at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical primers) with a polynucleotide sequence of a human nucleic acid and at least one primer (e.g., at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical primers) with a polynucleotide sequence that is not found in a human (such as a universal primer, a primer that comprises a region or consists entirely of random nucleotides, or a primer with a region such as a tag or barcode of one or more nucleotides that are not found in a human or are not found in nature as part of the polynucleotide sequence of the primer). In some embodiments, the composition includes at least one primer (e.g., at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical primers) with the polynucleotide sequence of a human nucleic acid and one or more non-human or non-naturally occurring enzymes (e.g., ligase or polymerase from a species other than a human, such as a bacterial or non-naturally-occurring ligase or polymerase). In some embodiments, the composition includes at least one primer (e.g., at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical primers) with the polynucleotide sequence of a human nucleic acid and a buffer or additive that is non-naturally-occurring or is not found in a human. In some embodiments, the composition comprises, consists essentially of, or consists of one or more of the following: primer(s), amplicon(s) free nucleotide(s), non-human or non-naturally occurring enzyme(s), buffer(s), additive(s), or any combination thereof. In some embodiments, the composition comprises, consists essentially of, or consists of primers and one or more non-human or non-naturally occurring enzymes. Exemplary non-naturally occurring enzymes contain at least one sequence difference compared to naturally occurring (wild-type) enzymes.

In one aspect, the invention provides a composition comprising at least 100 different amplicons (e.g., at least 300, 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical amplicons) in solution in one reaction volume. In some embodiments, the amplicons are produced from the simultaneous PCR amplification of at least 100 different target loci (e.g., at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical target loci) using at least 100 different primers or primer pairs (e.g., at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical primers or primer pairs) in one reaction volume. In some embodiments, (i) less than 60% of the amplified products are primer dimers and at least 40% of the amplified products are target amplicons, (ii) less than 40% of the amplified products are primer dimers and at least 60% of the amplified products are target amplicons, (iii) less than 20% of the amplified products are primer dimers and at least 80% of the amplified products are target amplicons, (iv) less than 10% of the amplified products are primer dimers and at least 90% of the amplified products are target amplicons, or (v) less than 5% of the amplified products are primer dimers and at least 95% of the amplified products are target amplicons. In some embodiments, the length of the target amplicons is between 50 and 100 nucleotides, such as between 60 and 80 nucleotides, or 60 and 75 nucleotides, inclusive. In some embodiments, the range of the length of the target amplicons is less than 50, 25, 15, 10, or 5 nucleotides. In some embodiments, the range of the length of the target amplicons is between 5 to 50 nucleotides, such as 5 to 25 nucleotides, 5 to 15 nucleotides, or 5 to 10 nucleotides, inclusive. In some embodiments, the composition includes at least 1,000 different amplicons in solution in one reaction volume. In some embodiments, the amplicons are produced from the simultaneous PCR amplification of at least 1,000 different target human loci using at least 1,000 different primers in one reaction volume; wherein (i) less than 20% of the amplicons are primer dimers, and (ii) at least 80% of the amplicons comprise one of the target human loci and are between 50 and 100 nucleotides in length, inclusive. In some embodiments, the composition consists essentially of, or consists of one or more of the following: amplicons, primers (such as any of the primers disclosed herein), free nucleotide(s), non-human or non-naturally occurring enzyme(s), buffer(s), or any combination thereof. In some embodiments, at least one amplicon or primer has a non-human or non-naturally occurring sequence, nucleotide, or linkage between nucleotides.

In one aspect, the invention provides a composition comprising at least 100 different primers or primer pairs (e.g., at least 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical primers or primer pairs) and at least 100 different amplicons (e.g., at least 300, 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical amplicons) in solution in one reaction volume. In some embodiments, the amplicons are produced from the simultaneous PCR amplification of at least 100 different target loci (e.g., at least 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical target loci) using the primers or primer pairs in one reaction volume. In some embodiments, (i) less than 60% of the amplified products are primer dimers and at least 40% of the amplified products are target amplicons, (ii) less than 40% of the amplified products are primer dimers and at least 60% of the amplified products are target amplicons, (iii) less than 20% of the amplified products are primer dimers and at least 80% of the amplified products are target amplicons, (iv) less than 10% of the amplified products are primer dimers and at least 90% of the amplified products are target amplicons, or (v) less than 5% of the amplified products are primer dimers and at least 95% of the amplified products are target amplicons. In some embodiments, the length of the target amplicons is between 50 and 100 nucleotides, such as between 60 and 80 nucleotides, or 60 and 75 nucleotides, inclusive. In some embodiments, the range of the length of the target amplicons is less than 50, 25, 15, 10, or 5 nucleotides. In some embodiments, the range of the length of the target amplicons is between 5 to 50 nucleotides, such as 5 to 25 nucleotides, 5 to 15 nucleotides, or 5 to 10 nucleotides, inclusive. In some embodiments, the composition comprising at least 1,000 different primers and at least 1,000 different amplicons in solution in one reaction volume. In some embodiments, the amplicons are produced from the simultaneous PCR amplification of at least 1,000 different target human loci with the primers in one reaction volume; wherein (i) less than 20% of the amplicons are primer dimers, and (ii) at least 80% of the amplicons comprise one of the target loci and are between 50 and 100 nucleotides in length, inclusive. In some embodiments, the composition consists essentially of, or consists of one or more of the following: amplicons, primers (such as any of the primers disclosed herein), free nucleotide(s), non-human or non-naturally occurring enzyme(s), buffer(s), or any combination thereof. In some embodiments, at least one amplicon or primer has a non-human or non-naturally occurring sequence, nucleotide, or linkage between nucleotides.

In one aspect, the invention provides kits that include any of the primer libraries or compositions of the invention for amplifying target loci in a nucleic acid sample. In some embodiments, the kits consists essentially of, or consists of primers, primers and instructions for using the primers, a composition of the invention, or a composition of the invention and instructions for using the composition. In some embodiments, the kit includes instructions for using the library to amplify the target loci.

In one aspect, the invention provides an apparatus, device, or composition that includes any of the primer libraries or compositions of the invention. In some embodiments, the apparatus, device, or composition includes a physical structure (such as one or more 30 reaction vessels, reaction chambers, or wells) that contains the primer library or composition of the invention (for example, the primers may be dissolved in a solution that is in the physical structure). In some embodiments, the physical structure is a non-naturally occurring physical structure or a physical structure that does not naturally contain a primer library or composition of the invention (such as a physical structure that is not found in nature with nucleic acids in it).

In one aspect, the invention features methods for determining a ploidy status of chromosome in a gestating fetus. In some embodiments, the method involves contacting a nucleic acid sample with a library of primers that simultaneously hybridize to at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different polymorphic loci to produce a reaction mixture; wherein the nucleic acid sample includes maternal DNA from the mother of the fetus and fetal DNA from the fetus. In some embodiments, the reaction mixture is subjected to primer extension reaction conditions to produce amplified products; the amplified products are measured with a high throughput sequencer to produce sequencing data; allele counts at the polymorphic loci are calculated on a computer based on the sequencing data; a plurality of ploidy hypotheses each pertaining to a different possible ploidy state of the chromosome are created on a computer; a joint distribution model for the expected allele counts at the polymorphic loci on the chromosome is built on a computer for each ploidy hypothesis; a relative probability of each of the ploidy hypotheses is determined on a computer using the joint distribution model and the allele counts;

and the ploidy state of the fetus is called by selecting the ploidy state corresponding to the hypothesis with the greatest probability.

In one aspect, the invention features methods for determining a ploidy status of a chromosome in a gestating fetus. In an embodiment a method for determining a ploidy status of a chromosome in a gestating fetus includes obtaining a first sample of DNA that comprises maternal DNA from the mother of the fetus and fetal DNA from the fetus, preparing the first sample by isolating the DNA so as to obtain a prepared sample, measuring the DNA in the prepared sample at a plurality of polymorphic loci on the chromosome, calculating, on a computer, allele counts at the plurality of polymorphic loci from the DNA measurements made on the prepared sample, creating, on a computer, a plurality of ploidy hypotheses each pertaining to a different possible ploidy state of the chromosome, building, on a computer, a joint distribution model for the expected allele counts at the plurality of polymorphic loci on the chromosome for each ploidy hypothesis, determining, on a computer, a relative probability of each of the ploidy hypotheses using the joint distribution model and the allele counts measured on the prepared sample, and calling the ploidy state of the fetus by selecting the ploidy state corresponding to the hypothesis with the greatest probability.

In one aspect, the invention features methods of testing for an abnormal distribution of a chromosome in a sample that includes a mixture of maternal and fetal DNA. In some embodiments, the method involves (i) contacting the sample with a library of primers that simultaneously hybridize to at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci to produce a reaction mixture; wherein the target loci are from a plurality of different chromosomes; and wherein the plurality of different chromosomes include at least one first chromosome suspected of having an abnormal distribution in the sample and at least one second chromosome presumed to be normally distributed in the sample; (ii) subjecting the reaction mixture to primer extension reaction conditions to produce amplified products; (iii) sequencing the amplified products to obtain a plurality of sequence tags aligning to the target loci; wherein the sequence tags are of sufficient length to be assigned to a specific target locus; (iv) assigning on a computer the plurality of sequence tags to their corresponding target loci; (v) determining on a computer a number of sequence tags aligning to the target loci of the first chromosome and a number of sequence tags aligning to the target loci of the second chromosome; and (vi) comparing on a computer the numbers from step (v) to determine the presence or absence of an abnormal distribution of the first chromosome.

In one aspect, the invention provides methods for detecting the presence or absence of a fetal aneuploidy. In some embodiments, the method involves (i) contacting a sample that includes a mixture of maternal and fetal DNA with a library of primers that simultaneously hybridize to at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different non-polymorphic target loci to produce a reaction mixture; wherein the target loci are from a plurality of different chromosomes; (ii) subjecting the reaction mixture to primer extension reaction conditions to produce amplified products that includes target amplicons; (iii) quantifying on a computer a relative frequency of the target amplicons from the first and second chromosomes of interest; (iv) comparing on a computer the relative frequency of the target amplicons from the first and second chromosomes of interest; and (v) identifying the presence or absence of an aneuploidy based on the compared relative frequencies of the first and second chromosome of interest. In some embodiments, the first chromosome is a chromosome suspected of being euploid. In some embodiments, the second chromosome is a chromosome suspected of being aneuploidy.

In one aspect, a method is disclosed for determining presence or absence of fetal aneuploidy in a maternal tissue sample comprising fetal and maternal genomic DNA, the method including (a) obtaining a mixture of fetal and maternal genomic DNA from said maternal tissue sample, (b) conducting massively parallel DNA sequencing of DNA fragments randomly selected from the mixture of fetal and maternal genomic DNA of step (a) to determine the sequence of said DNA fragments, (c) identifying chromosomes to which the sequences obtained in step (b) belong, (d) using the data of step (c) to determine an amount of at least one first chromosome in said mixture of maternal and fetal genomic DNA, wherein said at least one first chromosome is presumed to be euploid in the fetus, (e) using the data of step (c) to determine an amount of a second chromosome in said mixture of maternal and fetal genomic DNA, wherein said second chromosome is suspected to be aneuploid in the fetus, (f) calculating the fraction of fetal DNA in the mixture of fetal and maternal DNA, (g) calculating an expected distribution of the amount of the second target chromosome if the second target chromosome is euploid, using the number in step (d), (h) calculating an expected distribution of the amount of the second target chromosome if the second target chromosome is aneuploid, using the first number is step (d) and the calculated fraction of fetal DNA in the mixture of fetal and maternal DNA in step (f), and (i) using a maximum likelihood or maximum a posteriori approach to determine whether the amount of the second chromosome as determined in step (e) is more likely to be part of the distribution calculated in step (g) or the distribution calculated in step (h); thereby indicating the presence or absence of a fetal aneuploidy.

In various embodiments of any of the aspects of the invention, the target loci include one or more SNPs in the homologous non-recombining region of chromosome X and/or chromosome Y. In some embodiments, the method includes determining the relative amount of chromosome X and chromosome Y. In some embodiments, the method includes determining the number of copies of chromosome X and/or chromosome Y.

In some embodiments, the method also includes obtaining genotypic data from one or both parents of the fetus. In some embodiments, obtaining genotypic data from one or both parents of the fetus includes preparing the DNA from the parents where the preparing comprises preferentially enriching the DNA at the plurality of polymorphic loci to give prepared parental DNA, optionally amplifying the prepared parental DNA, and measuring the parental DNA in the prepared sample at the plurality of polymorphic loci.

In various embodiments of any of the aspects of the invention, building a joint distribution model for the expected allele count probabilities of the plurality of polymorphic loci on the chromosome is done using the obtained genetic data from the one or both parents. In some embodiments, the sample (e.g., the first sample) has been isolated from maternal plasma and where the obtaining genotypic data from the mother is done by estimating the maternal genotypic data from the DNA measurements made on the prepared sample.

In one aspect, a diagnostic box is disclosed for helping to determine a ploidy status of a chromosome in a gestating fetus where the diagnostic box is capable of executing the preparing and measuring steps of any of the methods of the invention.

In various embodiments of any of the aspects of the invention, the allele counts are probabilistic rather than binary. In some embodiments, measurements of the DNA in the prepared sample at the plurality of polymorphic loci are also used to determine whether or not the fetus has inherited one or a plurality of disease linked haplotypes.

In various embodiments of any of the aspects of the invention, building a joint distribution model for allele count probabilities is done by using data about the probability of chromosomes crossing over at different locations in a chromosome to model dependence between polymorphic alleles on the chromosome. In some embodiments, building a joint distribution model for allele counts and the step of determining the relative probability of each hypothesis are done using a method that does not require the use of a reference chromosome.

In various embodiments of any of the aspects of the invention, determining the relative probability of each hypothesis makes use of an estimated fraction of fetal DNA in the prepared sample. In some embodiments, the DNA measurements from the prepared sample used in calculating allele count probabilities and determining the relative probability of each hypothesis comprise primary genetic data. In some embodiments, selecting the ploidy state corresponding to the hypothesis with the greatest probability is carried out using maximum likelihood estimates or maximum a posteriori estimates.

In various embodiments of any of the aspects of the invention, calling the ploidy state of the fetus also includes combining the relative probabilities of each of the ploidy hypotheses determined using the joint distribution model and the allele count probabilities with relative probabilities of each of the ploidy hypotheses that are calculated using statistical techniques taken from a group consisting of a read count analysis, comparing heterozygosity rates, a statistic that is only available when parental genetic information is used, the probability of normalized genotype signals for certain parent contexts, a statistic that is calculated using an estimated fetal fraction of the sample (e.g., the first sample) or the prepared sample, and combinations thereof.

In various embodiments of any of the aspects of the invention, a confidence estimate is calculated for the called ploidy state. In some embodiments, the method also includes taking a clinical action based on the called ploidy state of the fetus, wherein the clinical action is selected from one of terminating the pregnancy or maintaining the pregnancy.

In various embodiments of any of the aspects of the invention, the method may be performed for fetuses at between 4 and 5 weeks gestation; between 5 and 6 weeks gestation; between 6 and 7 weeks gestation; between 7 and 8 weeks gestation; between 8 and 9 weeks gestation; between 9 and 10 weeks gestation; between 10 and 12 weeks gestation; between 12 and 14 weeks gestation; between 14 and 20 weeks gestation; between 20 and 40 weeks gestation; in the first trimester; in the second trimester; in the third trimester; or combinations thereof.

In various embodiments of any of the aspects of the invention, a report displaying a determined ploidy status of a chromosome in a gestating fetus generated using the method. In some embodiments, a kit is disclosed for determining a ploidy status of a target chromosome in a gestating fetus designed to be used with any of the methods of the invention, the kit including a plurality of inner forward primers and optionally the plurality of inner reverse primers, where each of the primers is designed to hybridize to the region of DNA immediately upstream and/or downstream from one of the polymorphic sites on the target chromosome, and optionally additional chromosomes, where the region of hybridization is separated from the polymorphic site by a small number of bases, where the small number is selected from the group consisting of 1, 2, 3, 4, 5, 6 to 10, 11 to 15, 16 to 20, 21 to 25, 26 to 30, 31 to 60, and combinations thereof.

In one aspect, the invention features methods for establishing whether an alleged father is the biological father of a fetus that is gestating in a pregnant mother. In some embodiments the method involves, (i) simultaneously amplifying a plurality of polymorphic loci that includes at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different polymorphic loci on genetic material from the alleged father to produce a first set of amplified products; (ii) simultaneously amplifying the corresponding plurality of polymorphic loci on a mixed sample of DNA originating from a blood sample from the pregnant mother to produce a second set of amplified products; wherein the mixed sample of DNA includes fetal DNA and maternal DNA; (iii) determining on a computer the probability that the alleged father is the biological father of the fetus using genotypic measurements based on the first and second sets of amplified products; and (iv) establishing whether the alleged father is the biological father of the fetus using the determined probability that the alleged father is the biological father of the fetus. In various embodiments, the method further includes simultaneously amplifying the corresponding plurality of polymorphic loci on genetic material from the mother to produce a third set of amplified products; wherein the probability that the alleged father is the biological father of the fetus is determined using genotypic measurements based on the first, second, and third sets of amplified products.

In one aspect, the invention provides methods of estimating relative likelihoods that each embryo from a set of embryos will develop as desired. In some embodiments, the method involves contacting a sample from each embryo with a library of primers that simultaneously hybridize to at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci to produce a reaction mixture for each embryo, wherein the samples are each derived from one or more cells from an embryo. In some embodiments, each reaction mixture is subjected to primer extension reaction conditions to produce amplified products. In some embodiments, the method includes determining on a computer one or more characteristics of at least one cell from each embryo based on the amplified products; and estimating on a computer the relative likelihoods that each embryo will develop as desired, based on the one or more characteristics of the at least one cell for each embryo.

In one aspect, the invention features methods of measuring the amount of two or more target loci in a nucleic acid sample. In some embodiments, the method involves (i) using PCR to amplify a nucleic acid sample that includes a first standard locus, a second standard locus, a first target locus, and a second target locus to form amplified products; wherein the first standard locus and the first target locus have the same number of nucleotides but have a sequence that differs at one or more nucleotides; and wherein the second standard locus and the second target locus have the same number of nucleotides but have a sequence that differs at one or more nucleotides; (ii) sequencing the amplified products to determine a standard ratio that compares the relative amount of the amplified first standard locus compared to the amplified second standard locus; wherein the standard ratio indicates the difference in PCR efficiency for the amplification of the first standard locus and the second standard locus; (iii) determining a target ratio that compares the relative amount of the amplified first target locus compared to the amplified second target locus; and (iv) adjusting the target ratio from step (iii) based on the standard ratio from step (ii) to determine the relative amount of the first target locus and the second target locus in the sample. In various embodiments, the method involves determining the absolute amount of the first target locus and the second target locus in the sample. In various embodiments, the method further includes determining the presence or absence of a target locus (e.g, at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci) in the sample. In various embodiments, the method involves using any of the primer libraries of the invention. In various embodiments, the method involves simultaneously amplifying at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci.

In one aspect, the invention features methods of quantitatively measuring a plurality of genetic targets in a sample for analysis. In some embodiments, the method includes (i) mixing genetic material derived from the sample for analysis with a plurality of target specific amplification reagents, and a plurality of standard sequences corresponding to the target specific amplification reagent targets; (ii) amplifying target regions of the genetic material and the standard sequences to produce target amplicons and standard sequence amplicons; and (iii) measuring the quantity of target amplicons and standard sequence amplicons produced. In some embodiments, the genetic material is present in a genetic library. In some embodiments, the genetic targets are polymorphic loci (such as SNPs). In some embodiments, the measuring of quantity is achieved by counting sequences. In some embodiments, the method further includes determining the estimated copy number of at least one chromosome in a sample from which the genetic library was derived, wherein the determination involves comparing the number of sequence reads of a target amplicon with the number of sequence reads of a standard amplicon. In some embodiments, the standard sequences and the genetic library include universal priming sites cable of being primed by the same primer. In some embodiments, the mixing step includes at least 10; 100; 500; 1,000; 2,000; 5,000; 7,500; 10,000; 15,000; 19,000; 20,000; 25,000; 27,000; 28,000; 30,000; 40,000; 50,000; 75,000; or 100,000 different target specific amplification reagents and at least 10; 100; 500; 1,000; 2,000; 5,000; 7,500; 10,000; 15,000; 19,000; 20,000; 25,000; 27,000; 28,000; 30,000; 40,000; 50,000; 75,000; or 100,000 standard sequences. In various embodiments, the method involves using any of the primer libraries of the invention. In various embodiments, the method involves simultaneously amplifying at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target regions. In some embodiments, the relative amounts of each of the standard sequences are known. In some embodiments, the relative amounts of each of the sequences is has been calibrated with respect to a reference genome. In some embodiments, the sample for analysis includes a mixture of fetal and maternal genomes. In some embodiments, the sample for analysis is derived from the blood of a pregnant woman or derived from blood plasma. In some embodiments, the reference genome has at least one aneuploidy, such as an aneuploidy at chromosome 13, 18, 21, X, or Y. In some embodiments, the reference genome is diploid.

In one aspect, the invention features a mixture that includes a plurality of genetic standard sequences, wherein the relative amount of each genetic standard sequence in the mixture has been determined by calibration to a reference genome. In various embodiments, the mixture includes at least 10; 100; 500; 1,000; 2,000; 5,000; 7,500; 10,000; 15,000; 19,000; 20,000; 25,000; 27,000; 28,000; 30,000; 40,000; 50,000; 75,000; or 100,000 genetic standard sequences. In various embodiments, the genetic standard sequences include a first universal priming site, a second universal priming site, a first target specific priming site, a second target specific priming site, and a marker sequence located between the first and second target specific priming sites, wherein the first target specific site and the second target specific priming site are located between the first and second universal priming sites. In various embodiments, the calibration involves using any of the primer libraries of the invention. In various embodiments, the calibration involves simultaneously amplifying at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target regions. In some embodiments, the reference genome has at least one aneuploidy, such as an aneuploidy at chromosome 13, 18, 21, X, or Y. In some embodiments, the reference genome is diploid.

In one aspect, the invention features methods of producing a set of calibrated genetic standard sequences. In some embodiments, the method includes (i) forming an amplification reaction mixture that includes a genetic library prepared from a reference genome, a plurality of target-specific amplification primer reagent sets, and a plurality of genetic standard sequences corresponding to the target specific amplification reagent sets, (ii) amplifying the genetic library and the genetic standard sequences to produce amplicons from the target sequences and amplicons from the genetic standard sequences, (iii) measuring the quantity of the amplicons from the target sequences and amplicons from the genetic standard sequences, and (iv) determining the relative amount of each of genetic standard sequences with respect to each other, whereby the plurality of genetic standard sequences is calibrated. In various embodiments, at least 10; 100, 500; 1,000; 2,000; 5,000; 7,500; 10,000; 15,000; 19,000; 20,000; 25,000; 27,000; 28,000; 30,000; 40,000; 50,000; 75,000; or 100,000 genetic standard sequences are used. In various embodiments, the method involves using any of the primer libraries of the invention. In various embodiments, the method involves simultaneously amplifying at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different sequences. In some embodiments, the reference genome has at least one aneuploidy, such as an aneuploidy at chromosome 13, 18, 21, X, or Y. In some embodiments, the reference genome is diploid.

In one aspect, the invention provides a set of genetic standard sequences that have been calibrated according to any of the methods of the invention. In one aspect, the invention provides a set of genetic standard sequences that may be calibrated either before, during or after the method is performed.

In one aspect, the invention features methods of measuring the number of copies of a gene of interest having at least one allele that has a deletion. In some embodiments, the method includes (i) mixing genetic material derived from a sample for analysis with an amplification reagent specific for the gene of interest and not capable of significantly amplifying the deletion comprising allele of the gene of interest, a standard sequence corresponding to gene of interest, an amplification reagent specific for a reference sequence, and a standard sequence corresponding to the reference sequence; (ii) amplifying the gene sequence of interest, the standard sequence corresponding to the gene of interest, the reference sequence, and the standard sequence corresponding to the reference sequence to produce gene of interest amplicons, reference sequence amplicons, and standard sequence amplicons; and (iii) measuring the quantity of target amplicons and standard sequence amplicons produced. In some embodiments, the measuring of quantity is achieved by counting sequence reads. In some embodiments, the method further includes determining the estimated copy number of at least one chromosome in the sample from which the genetic library was derived, wherein the determination involves comparing the number of sequences of target amplicons with the number of sequences of a standard amplicons. In some embodiments, the standard sequences and the genetic library include universal priming sites capable of being primed by the same primer. In some embodiments, the relative amounts of each of the sequences have been calibrated with respect to reference genome. In various embodiments, at least 10; 100, 500; 1,000; 2,000; 5,000; 7,500; 10,000; 15,000; 19,000; 20,000; 25,000; 27,000; 28,000; 30,000; 40,000; 50,000; 75,000; or 100,000 genetic standard sequences are used. In various embodiments, the method involves using any of the primer libraries of the invention. In various embodiments, the method involves simultaneously amplifying at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target regions. In some embodiments, the reference genome is diploid. In some embodiments, the sample for analysis is derived from blood.

In some embodiments of any of the aspects of the invention, preferentially enriching the DNA in the sample (e.g., the first sample) at the target loci (e.g., the plurality of polymorphic loci) includes obtaining a plurality of pre-circularized probes where each probe targets one of the loci (e.g., polymorphic loci), where the 3' and 5' end of the probes are preferably designed to hybridize to a region of DNA that is separated from the polymorphic site of the locus by a small number of bases, where the small number is 1, 2, 3, 4, 5, 6, 7, 8, 9, 10, 11, 12, 13, 14, 15, 16, 17, 18, 19, 20, 21 to 25, 26 to 30, 31 to 60, or a combination thereof, hybridizing the pre-circularized probes to DNA from the sample (e.g., the first sample), filling the gap between the hybridized probe ends using DNA polymerase, circularizing the pre-circularized probe, and amplifying the circularized probe.

In some embodiments of any of the aspects of the invention, the preferentially enriching the DNA at the target loci (e.g., the plurality of polymorphic loci) includes obtaining a plurality of ligation-mediated PCR probes where each PCR probe targets one of the target loci (e.g., the polymorphic loci), and where the upstream and downstream PCR probes are designed to hybridize to a region of DNA on one strand of DNA that is preferably separated from the polymorphic site of the locus by a small number of bases, where the small number is 1, 2, 3, 4, 5, 6, 7, 8, 9, 10, 11, 12, 13, 14, 15, 16, 17, 18, 19, 20, 21 to 25, 26 to 30, 31 to 60, or a combination thereof, hybridizing the ligation-mediated PCR probes to the DNA from the sample (e.g., the first sample), filling the gap between the ligation-mediated PCR probe ends using DNA polymerase, ligating the ligation-mediated PCR probes, and amplifying the ligated ligation-mediated PCR probes.

In some embodiments of various aspects of the invention, preferentially enriching the DNA at the target loci (e.g., plurality of polymorphic loci) includes obtaining a plurality of hybrid capture probes that target the loci (e.g., the polymorphic loci), hybridizing the hybrid capture probes to the DNA in the sample (e.g., the first sample) and physically removing some or all of the unhybridized DNA from the sample (e.g., the first sample) of DNA.

In some embodiments of any of the aspects of the invention, the hybrid capture probes are designed to hybridize to a region that is flanking but not overlapping the polymorphic site. In some embodiments, the hybrid capture probes are designed to hybridize to a region that is flanking but not overlapping the polymorphic site, and where the length of the flanking capture probe may be selected from the group consisting of less than about 120 bases, less than about 110 bases, less than about 100 bases, less than about 90 bases, less than about 80 bases, less than about 70 bases, less than about 60 bases, less than about 50 bases, less than about 40 bases, less than about 30 bases, and less than about 25 bases. In some embodiments, the hybrid capture probes are designed to hybridize to a region that overlaps the polymorphic site, and where the plurality of hybrid capture probes comprise at least two hybrid capture probes for each polymorphic loci, and where each hybrid capture probe is designed to be complementary to a different allele at that polymorphic locus.

In some embodiments of any of the aspects of the invention, preferentially enriching the DNA a plurality of polymorphic loci includes obtaining a plurality of inner forward primers where each primer targets one of the polymorphic loci, and where the 3' end of the inner forward primers are designed to hybridize to a region of DNA upstream from the polymorphic site, and separated from the polymorphic site by a small number of bases, where the small number is selected from the group consisting of 1, 2, 3, 4, 5, 6 to 10, 11 to 15, 16 to 20, 21 to 25, 26 to 30, or 31 to 60 base pairs, optionally obtaining a plurality of inner reverse primers where each primer targets one of the polymorphic loci, and where the 3' end of the inner reverse primers are designed to hybridize to a region of DNA upstream from the polymorphic site, and separated from the polymorphic site by a small number of bases, where the small number is selected from the group consisting of 1, 2, 3, 4, 5, 6 to 10, 11 to 15, 16 to 20, 21 to 25, 26 to 30, or 31 to 60 base pairs, hybridizing the inner primers to the DNA, and amplifying the DNA using the polymerase chain reaction to form amplicons.

In some embodiments of any of the aspects of the invention, the method also includes obtaining a plurality of outer forward primers where each primer targets one of the target (e.g., polymorphic loci), and where the outer forward primers are designed to hybridize to the region of DNA upstream from the inner forward primer, optionally obtaining a plurality of outer reverse primers where each primer targets one of the target loci (e.g., polymorphic loci), and where the outer reverse primers are designed to hybridize to the region of DNA immediately downstream from the inner reverse primer, hybridizing the first primers to the DNA, and amplifying the DNA using the polymerase chain reaction.

In some embodiments of any of the aspects of the invention, the method also includes obtaining a plurality of outer reverse primers where each primer targets one of the polymorphic loci, and where the outer reverse primers are designed to hybridize to the region of DNA immediately downstream from the inner reverse primer, optionally obtaining a plurality of outer forward primers where each primer targets one of the target loci (e.g., the polymorphic loci), and where the outer forward primers are designed to hybridize to the region of DNA upstream from the inner forward primer, hybridizing the first primers to the DNA, and amplifying the DNA using the polymerase chain reaction.

In some embodiments of any of the aspects of the invention, preparing the sample (e.g., the first sample) further includes appending universal adapters to the DNA in the sample (e.g., the first sample) and amplifying the DNA in the sample (e.g., the first sample) using the polymerase chain reaction. In some embodiments, at least a fraction of the amplicons that are amplified are less than 100 bp, less than 90 bp, less than 80 bp, less than 70 bp, less than 65 bp, less than 60 bp, less than 55 bp, less than 50 bp, or less than 45 bp, and where the fraction is 10%, 20%, 30%, 40%, 50%, 60%, 70%, 80%, 90%, or 99%.

In some embodiments of any of the aspects of the invention, amplifying the DNA is done in one or a plurality of individual reaction volumes, and where each individual reaction volume contains more than 100 different forward and reverse primer pairs, more than 200 different forward and reverse primer pairs, more than 500 different forward and reverse primer pairs, more than 1,000 different forward and reverse primer pairs, more than 2,000 different forward and reverse primer pairs, more than 5,000 different forward and reverse primer pairs, more than 10,000 different forward and reverse primer pairs, more than 20,000 different forward and reverse primer pairs, more than 50,000 different forward and reverse primer pairs, or more than 100,000 different forward and reverse primer pairs. In various embodiments of any of the aspects of the invention, at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different primer pairs are used.

In some embodiments of any of the aspects of the invention, preparing the sample (e.g., the first sample) further comprises dividing the sample (e.g., the first sample) into a plurality of portions, and where the DNA in each portion is preferentially enriched at a subset of the target loci (e.g., plurality of polymorphic loci). In some embodiments, the inner primers are selected by identifying primer pairs likely to form undesired primer duplexes and removing from the plurality of primers at least one of the pair of primers identified as being likely to form 15 undesired primer duplexes. In some embodiments, the inner primers contain a region that is designed to hybridize either upstream or downstream of the targeted locus (e.g., the polymorphic locus), and optionally contain a universal priming sequence designed to allow PCR amplification. In some embodiments, at least some of the primers additionally contain a random region that differs for each individual primer molecule. In some embodiments, at least some of the primers additionally contain a molecular barcode.

In some embodiments of any of the aspects of the invention, preferential enrichment results in average degree of allelic bias between the prepared sample and the sample (e.g., the first sample) of a factor selected from the group consisting of no more than a factor of 2, no more than a factor of 1.5, no more than a factor of 1.2, no more than a factor of 1.1, no more than a factor of 1.05, no more than a factor of 1.02, no more than a factor of 1.01, no more than a factor of 1.005, no more than a factor of 1.002, no more than a factor of 1.001 and no more than a factor of 1.0001. In some embodiments, the plurality of polymorphic loci are SNPs. In some embodiments, measuring the DNA in the prepared sample is done by sequencing.

In some embodiments, the nucleic acids in the sample are non-specifically amplified prior to amplification of the target loci (such as specific amplification of the target loci with a primer library of the invention). In some embodiments, the non-specific amplification includes whole genome application (WGA), such as ligation-mediated PCR (LM-PCR), degenerate oligonucleotide primer PCR (DOP-PCR), or multiple displacement amplification (MDA). In some embodiments, the non-specific amplification includes universal PCR, such as adaptor-mediated universal PCR.

In some embodiments of any of the aspects of the invention, the target loci are present on the same nucleic acid of interest (e.g, the same chromosome or the same region of a chromosome). In some embodiments, at least some of the target loci are present on different nucleic acids of interest (e.g, different chromosomes). In some embodiments, the nucleic acid sample includes fragmented or digested nucleic acids. In some embodiments, the nucleic acid sample includes DNA, such as genomic DNA, cDNA, cell-free DNA (cfDNA), cell-free mitochondrial DNA (cf mDNA), cell-free DNA that originated from nuclear DNA (cf nDNA), cellular DNA, or mitochondrial DNA. In some embodiments, nucleic acid sample includes RNA, such as cfRNA, cellular RNA, cytoplasmic RNA, coding cytoplasmic RNA, non-coding cytoplasmic RNA, mRNA, miRNA, mitochondrial RNA, rRNA, or tRNA. In some embodiments, the nucleic acid sample includes DNA from a single cell, 2 cells, 3 cells, 4 cells, 5 cells, 6 cells, 7 cells, 8 cells, 9 cell, 10 cells, or more than 10 cells. In some embodiments, the nucleic acid sample is a blood or plasma sample that is substantially free of cells. In some embodiments, the nucleic acid sample includes or is derived from blood, plasma, saliva, semen, sperm, cell culture supernatant, mucus secretion, dental plaque, gastrointestinal tract tissue, stool, urine, hair, bone, body fluids, tears, tissue, skin, fingernails, blastomeres, embryos, amniotic fluid, chorionic villus samples, bile, lymph, cervical mucus, or a forensic sample. In some embodiments, the target loci are segments of human nucleic acids. In some embodiments, the target loci are segments of human nucleic acids found in the human genome. In some embodiments, the target loci comprise or consist of single nucleotide polymorphisms (SNPs). In some embodiments, the primers are DNA molecules.

In some embodiments of any of the aspects of the invention, the DNA in the sample (e.g., the first sample) originates from maternal plasma. In some embodiments, preparing the sample (e.g., the first sample) further comprises amplifying the DNA. In some embodiments, preparing the sample (e.g., the first sample) further comprises preferentially enriching the DNA in the sample (e.g., the first sample) at the target loci (e.g., a plurality of polymorphic loci).

In various embodiments, the primer extension reaction or the polymerase chain reaction includes the addition of one or more nucleotides by a polymerase. In some embodiments, greater than or equal to 5, 10, 20, 30, 40, 50, or 60 cycles of PCR are performed. In some embodiments, the amplification of loci is performed using a polymerase (e.g., a DNA polymerase, RNA polymerase, or reverse transcriptase) with low 5'→3' exonuclease and/or low strand displacement activity. In some embodiments, a DNA polymerase is used produce DNA amplicons using DNA as a template. In some embodiments, a RNA polymerase is used produce RNA amplicons using DNA as a template. In some embodiments, a reverse transcriptase is used produce cDNA amplicons using RNA as a template.

In various embodiments, the primer extension reaction or the polymerase chain reaction does not include ligation-mediated PCR. In various embodiments, the primer extension reaction or the polymerase chain reaction does not include the joining of two primers by a ligase. In various embodiments, the primers do not include Linked Inverted Probes (LIPs), which can also be called pre-circularized probes, pre-circularizing probes, circularizing probes, Padlock Probes, or Molecular Inversion Probes (MIPs). In some embodiments, the primers are not loopable primers. In some embodiments, the primers do not form a loop structure, for example, the primers do not comprise a 3' target specific portion, a stem (comprising a first loop forming region and a second loop forming region), and a loop portion. In various embodiments, the primer library, composition, kit, or method does not include an array (such as a microarray) or do no use an array (such as a microarray). In some embodiments, multiplex PCR and/or sequencing is performed without use of an array (such as a microarray). In some embodiments, the primer library, composition, kit, or method comprises a microarray. In some embodiments, the primers or the target loci do not comprise an STR allele (for example, the target loci may be non-polymorphic loci or the loci may comprise a polymorphism other than an STR allele). In some embodiments, some or all of the target loci comprise an STR allele.

It is understood that all of the aspects and embodiments of the invention described herein include "comprising," "consisting," and "consisting essentially of" aspects and embodiments. It is understood that aspects and embodiments of the invention described herein include combinations of any two or more of the aspects or embodiments of the invention.

Definitions

Single Nucleotide Polymorphism (SNP) refers to a single nucleotide that may differ between the genomes of two members of the same species. The usage of the term should not imply any limit on the frequency with which each variant occurs.

Sequence refers to a DNA sequence or a genetic sequence. It may refer to the primary, physical structure of the DNA molecule or strand in an individual. It may refer to the sequence of nucleotides found in that DNA molecule, or the complementary strand to the DNA molecule. It may refer to the information contained in the DNA molecule as its representation in silico.

Locus refers to a particular region of interest on the DNA (or corresponding RNA) of an individual, which may refer to a SNP, the site of a possible insertion or deletion, or the site of some other relevant genetic variation. Disease-linked SNPs may also refer to disease-linked loci.

Polymorphic Allele, also "Polymorphic Locus," refers to an allele or locus where the genotype varies between individuals within a given species. Some examples of polymorphic alleles include single nucleotide polymorphisms, short tandem repeats, deletions, duplications, and inversions.

Polymorphic Site refers to the specific nucleotides found in a polymorphic region that vary between individuals.

Allele refers to the genes that occupy a particular locus.

Genetic Data also "Genotypic Data" refers to the data describing aspects of the genome of one or more individuals. It may refer to one or a set of loci, partial or entire sequences, partial or entire chromosomes, or the entire genome. It may refer to the identity of one or a plurality of nucleotides; it may refer to a set of sequential nucleotides, or nucleotides from different locations in the genome, or a combination thereof. Genotypic data is typically in silico, however, it is also possible to consider physical nucleotides in a sequence as chemically encoded genetic data. Genotypic Data may be said to be "on," "of," "at," "from" or "on" the individual(s). Genotypic Data may refer to output measurements from a genotyping platform where those measurements are made on genetic material.

Genetic Material also "Genetic Sample" refers to physical matter, such as tissue or blood, from one or more individuals comprising DNA or RNA Noisy Genetic Data refers to genetic data with any of the following: allele dropouts, uncertain base pair measurements, incorrect base pair measurements, missing base pair measurements, uncertain measurements of insertions or deletions, uncertain measurements of chromosome segment copy numbers, spurious signals, missing measurements, other errors, or combinations thereof.

Confidence refers to the statistical likelihood that the called SNP, allele, set of alleles, ploidy call, or determined number of chromosome segment copies correctly represents the real genetic state of the individual.

Ploidy Calling, also "Chromosome Copy Number Calling," or "Copy Number Calling" (CNC), may refer to the act of determining the quantity and/or chromosomal identity of one or more chromosomes present in a cell.

Aneuploidy refers to the state where the wrong number of chromosomes (e.g., the wrong number of full chromosomes or the wrong number of chromosome segments, such as the presence of deletions or duplications of a chromosome segment) is present in a cell. In the case of a somatic human cell it may refer to the case where a cell does not contain 22 pairs of autosomal chromosomes and one pair of sex chromosomes. In the case of a human gamete, it may refer to the case where a cell does not contain one of each of the 23 chromosomes. In the case of a single chromosome type, it may refer to the case where more or less than two homologous but non-identical chromosome copies are present, or where there are two chromosome copies present that originate from the same parent. In some embodiments, the deletion of a chromosome segment is a microdeletion.

Ploidy State refers to the quantity and/or chromosomal identity of one or more chromosomes types in a cell.

Chromosome may refer to a single chromosome copy, meaning a single molecule of DNA of which there are 46 in a normal somatic cell; an example is 'the maternally derived chromosome 18'. Chromosome may also refer to a chromosome type, of which there are 23 in a normal human somatic cell; an example is 'chromosome 18'.

Chromosomal Identity may refer to the referent chromosome number, i.e. the chromosome type. Normal humans have 22 types of numbered autosomal chromosome types, and two types of sex chromosomes. It may also refer to the parental origin of the chromosome. It may also refer to a specific chromosome inherited from the parent. It may also refer to other identifying features of a chromosome.

The State of the Genetic Material or simply "Genetic State" may refer to the identity of a set of SNPs on the DNA, to the phased haplotypes of the genetic material, and to the sequence of the DNA, including insertions, deletions, repeats and mutations. It may also refer to the ploidy state of one or more chromosomes, chromosomal segments, or set of chromosomal segments.

Allelic Data refers to a set of genotypic data concerning a set of one or more alleles. It may refer to the phased, haplotypic data. It may refer to SNP identities, and it may refer to the sequence data of the DNA, including insertions, deletions, repeats and mutations. It may include the parental origin of each allele.

Allelic State refers to the actual state of the genes in a set of one or more alleles. It may refer to the actual state of the genes described by the allelic data.

Allelic Ratio or allele ratio, refers to the ratio between the amount of each allele at a locus that is present in a sample or in an individual. When the sample was measured by sequencing, the allelic ratio may refer to the ratio of sequence reads that map to each allele at the locus. When the sample was measured by an intensity based measurement method, the allele ratio may refer to the ratio of the amounts of each allele present at that locus as estimated by the measurement method.

Allele Count refers to the number of sequences that map to a particular locus, and if that locus is polymorphic, it refers to the number of sequences that map to each of the alleles. If each allele is counted in a binary fashion, then the allele count will be whole number. If the alleles are counted probabilistically, then the allele count can be a fractional number.

Allele Count Probability refers to the number of sequences that are likely to map to a particular locus or a set of alleles at a polymorphic locus, combined with the probability of the mapping. Note that allele counts are equivalent to allele count probabilities where the probability of the mapping for each counted sequence is binary (zero or one). In some embodiments, the allele count probabilities may be binary. In some embodiments, the allele count probabilities may be set to be equal to the DNA measurements.

Allelic Distribution, or 'allele count distribution' refers to the relative amount of each allele that is present for each locus in a set of loci. An allelic distribution can refer to an individual, to a sample, or to a set of measurements made on a sample. In the context of sequencing, the allelic distribution refers to the number or probable number of reads that map to a particular allele for each allele in a set of polymorphic loci. The allele measurements may be treated probabilistically, that is, the likelihood that a given allele is present for a give sequence read is a fraction between 0 and 1, or they may be treated in a binary fashion, that is, any given read is considered to be exactly zero or one copies of a particular allele.

Allelic Distribution Pattern refers to a set of different allele distributions for different parental contexts. Certain allelic distribution patterns may be indicative of certain ploidy states. Allelic Bias refers to the degree to which the measured ratio of alleles at a heterozygous locus is different to the ratio that was present in the original sample, such as a sample of DNA. The degree of allelic bias at a particular locus is equal to the observed allelic ratio at that locus, as measured, divided by the ratio of alleles in the original DNA or RNA sample at that locus. Allelic bias may be defined to be greater than one, such that if the calculation of the degree of allelic bias returns a value, x, that is less than 1, then the degree of allelic bias may be restated as 1/x. Allelic bias may be due to amplification bias, purification bias, or some other phenomenon that affects different alleles differently.

Primer, also "PCR probe" refers to a single DNA molecule (a DNA oligomer) or a collection of DNA molecules (DNA oligomers) where the DNA molecules are identical, or nearly so, and where the primer contains a region that is designed to hybridize to a targeted locus (e.g, a targeted polymorphic locus or a nonpolymorphic locus), and may contain a priming sequence designed to allow PCR amplification. A primer may also contain a molecular barcode. A primer may contain a random region that differs for each individual molecule. The terms "test primer" and "candidate primer" are not meant to be limiting and may refer to any of the primers disclosed herein.

Library of primers refers to a population of two or more primers. In various embodiments, the 75,000; or 100,000 different primers. In various embodiments, the library includes at least 25; 50; 75; 100; 300; 500; 750; 1,000; 2,000; 5,000; 7,500; 10,000; 15,000; different primer pairs, wherein each pair of primers includes a forward test primer and a reverse test primer where each pair of test primers hybridize to a target locus. In some embodiments, the library of primers includes at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different individual primers that each hybridize to a different target locus, wherein the individual primers are not part of primer pairs. In some embodiments, the library has both (i) primer pairs and (ii) individual primers (such as universal primers) that are not part of primer pairs.

Different primers refers to non-identical primers.

Different pools refers to non-identical pools.

Different target loci refers to non-identical target loci.

Different amplicons refers to non-identical amplicons.

Hybrid Capture Probe refers to any nucleic acid sequence, possibly modified, that is generated by various methods such as PCR or direct synthesis and intended to be complementary to one strand of a specific target DNA sequence in a sample. The exogenous hybrid capture probes may be added to a prepared sample and hybridized through a deanture-reannealing process to form duplexes of exogenous-endogenous fragments. These duplexes may then be physically separated from the sample by various means.

Sequence Read refers to data representing a sequence of nucleotide bases that were measured using a clonal sequencing method. Clonal sequencing may produce sequence data representing single, or clones, or clusters of one original DNA molecule. A sequence read may also have associated quality score at each base position of the sequence indicating the probability that nucleotide has been called correctly.

Mapping a sequence read is the process of determining a sequence read's location of origin in the genome sequence of a particular organism. The location of origin of sequence reads is based on similarity of nucleotide sequence of the read and the genome sequence.

Matched Copy Error, also "Matching Chromosome Aneuploidy" (MCA), refers to a state of aneuploidy where one cell contains two identical or nearly identical chromosomes. This type of aneuploidy may arise during the formation of the gametes in meiosis, and may be referred to as a meiotic non-disjunction error. This type of error may arise in mitosis. Matching trisomy may refer to the case where three copies of a given chromosome are present in an individual and two of the copies are identical.

Unmatched Copy Error, also "Unique Chromosome Aneuploidy" (UCA), refers to a state of aneuploidy where one cell contains two chromosomes that are from the same parent, and that may be homologous but not identical. This type of aneuploidy may arise during meiosis, and may be referred to as a meiotic error. Unmatching trisomy may refer to the case where three copies of a given chromosome are present in an individual and two of the copies are from the same parent, and are homologous, but are not identical. Note that unmatching trisomy may refer to the case where two homologous chromosomes from one parent are present, and where some segments of the chromosomes are identical while other segments are merely homologous.

Homologous Chromosomes refers to chromosome copies that contain the same set of genes that normally pair up during meiosis.

Identical Chromosomes refers to chromosome copies that contain the same set of genes, and for each gene they have the same set of alleles that are identical, or nearly identical.

Allele Drop Out (ADO) refers to the situation where at least one of the base pairs in a set of base pairs from homologous chromosomes at a given allele is not detected.

Locus Drop Out (LDO) refers to the situation where both base pairs in a set of base pairs from homologous chromosomes at a given allele are not detected.

Homozygous refers to having similar alleles as corresponding chromosomal loci.

Heterozygous refers to having dissimilar alleles as corresponding chromosomal loci.

Heterozygosity Rate refers to the rate of individuals in the population having heterozygous alleles at a given locus. The heterozygosity rate may also refer to the expected or measured ratio of alleles, at a given locus in an individual, or a sample of DNA.

Highly Informative Single Nucleotide Polymorphism (HISNP) refers to a SNP where the fetus has an allele that is not present in the mother's genotype.

Chromosomal Region refers to a segment of a chromosome, or a full chromosome.

Segment of a Chromosome refers to a section of a chromosome that can range in size from one base pair to the entire chromosome.

Chromosome refers to either a full chromosome, or a segment or section of a chromosome.

Copies refers to the number of copies of a chromosome segment. It may refer to identical copies, or to non-identical, homologous copies of a chromosome segment wherein the different copies of the chromosome segment contain a substantially similar set of loci, and where one or more of the alleles are different. Note that in some cases of aneuploidy, such as the M2 copy error, it is possible to have some copies of the given chromosome segment that are identical as well as some copies of the same chromosome segment that are not identical.

Haplotype refers to a combination of alleles at multiple loci that are typically inherited together on the same chromosome. Haplotype may refer to as few as two loci or to an entire chromosome depending on the number of recombination events that have occurred between a given set of loci. Haplotype can also refer to a set of single nucleotide polymorphisms (SNPs) on a single chromatid that are statistically associated.

Haplotypic Data, also "Phased Data" or "Ordered Genetic Data," refers to data from a single chromosome in a diploid or polyploid genome, i.e., either the segregated maternal or paternal copy of a chromosome in a diploid genome.

Phasing refers to the act of determining the haplotypic genetic data of an individual given unordered, diploid (or polyploidy) genetic data. It may refer to the act of determining which of two genes at an allele, for a set of alleles found on one chromosome, are associated with each of the two homologous chromosomes in an individual.

Phased Data refers to genetic data where one or more haplotypes have been determined.

Hypothesis refers to a possible ploidy state at a given set of chromosomes, or a set of possible allelic states at a given set of loci. The set of possibilities may comprise one or more elements.

Copy Number Hypothesis, also "Ploidy State Hypothesis," refers to a hypothesis concerning the number of copies of a chromosome in an individual. It may also refer to a hypothesis concerning the identity of each of the chromosomes, including the parent of origin of each chromosome, and which of the parent's two chromosomes are present in the individual. It may also refer to a hypothesis concerning which chromosomes, or chromosome segments, if any, from a related individual correspond genetically to a given chromosome from an individual.

Target Individual refers to the individual whose genetic state is being determined. In some embodiments, only a limited amount of DNA is available from the target individual. In some embodiments, the target individual is a fetus. In some embodiments, there may be more than one target individual. In some embodiments, each fetus that originated from a pair of parents may be considered to be target individuals. In some embodiments, the genetic data that is being determined is one or a set of allele calls. In some embodiments, the genetic data that is being determined is a ploidy call.

Related Individual refers to any individual who is genetically related to, and thus shares haplotype blocks with, the target individual. In one context, the related individual may be a genetic parent of the target individual, or any genetic material derived from a parent, such as a sperm, a polar body, an embryo, a fetus, or a child. It may also refer to a sibling, parent or a grandparent.

Sibling refers to any individual whose genetic parents are the same as the individual in question. In some embodiments, it may refer to a born child, an embryo, or a fetus, or one or more cells originating from a born child, an embryo, or a fetus. A sibling may also refer to a haploid individual that originates from one of the parents, such as a sperm, a polar body, or any other set of haplotypic genetic matter. An individual may be considered to be a sibling of itself.

Fetal refers to "of the fetus," or "of the region of the placenta that is genetically similar to the fetus". In a pregnant woman, some portion of the placenta is genetically similar to the fetus, and the free floating fetal DNA found in maternal blood may have originated from the portion of the placenta with a genotype that matches the fetus. Note that the genetic information in half of the chromosomes in a fetus is inherited from the mother of the fetus. In some embodiments, the DNA from these maternally inherited chromosomes that came from a fetal cell is considered to be "of fetal origin," not "of maternal origin."

DNA of Fetal Origin refers to DNA that was originally part of a cell whose genotype was essentially equivalent to that of the fetus.

DNA of Maternal Origin refers to DNA that was originally part of a cell whose genotype was essentially equivalent to that of the mother.

Child may refer to an embryo, a blastomere, or a fetus. Note that in the presently disclosed embodiments, the concepts described apply equally well to individuals who are a born child, a fetus, an embryo or a set of cells therefrom. The use of the term child may simply be meant to connote that the individual referred to as the child is the genetic offspring of the parents.

Parent refers to the genetic mother or father of an individual. An individual typically has two parents, a mother and a father, though this may not necessarily be the case such as in genetic or chromosomal chimerism. A parent may be considered to be an individual.

Parental Context refers to the genetic state of a given SNP, on each of the two relevant chromosomes for one or both of the two parents of the target.

Develop As Desired, also "Develop Normally," refers to a viable embryo implanting in a uterus and resulting in a pregnancy, and/or to a pregnancy continuing and resulting in a live birth, and/or to a born child being free of chromosomal abnormalities, and/or to a born child being free of other undesired genetic conditions such as disease-linked genes. The term "develop as desired" is meant to encompass anything that may be desired by parents or healthcare facilitators. In some cases, "develop as desired" may refer to an unviable or viable embryo that is useful for medical research or other purposes.

Insertion into a Uterus refers to the process of transferring an embryo into the uterine cavity in the context of in vitro fertilization.

Maternal Plasma refers to the plasma portion of the blood from a female who is pregnant.

Clinical Decision refers to any decision to take or not take an action that has an outcome that affects the health or survival of an individual. In the context of prenatal diagnosis, a clinical decision may refer to a decision to abort or not abort a fetus. A clinical decision may also refer to a decision to conduct further testing, to take actions to mitigate an undesirable phenotype, or to take actions to prepare for the birth of a child with abnormalities.

Diagnostic Box refers to one or a combination of machines designed to perform one or a plurality of aspects of the methods disclosed herein. In an embodiment, the diagnostic box may be placed at a point of patient care. In an embodiment, the diagnostic box may perform targeted amplification followed by sequencing. In an embodiment the diagnostic box may function alone or with the help of a technician.

Informatics Based Method refers to a method that relies heavily on statistics to make sense of a large amount of data. In the context of prenatal diagnosis, it refers to a method designed to determine the ploidy state at one or more chromosomes or the allelic state at one or more alleles by statistically inferring the most likely state, rather than by directly physically measuring the state, given a large amount of genetic data, for example from a molecular array or sequencing. In an embodiment of the present disclosure, the informatics based technique may be one disclosed in this patent. In an embodiment of the present disclosure it may be PARENTAL SUPPORT™.

Primary Genetic Data refers to the analog intensity signals that are output by a genotyping platform. In the context of SNP arrays, primary genetic data refers to the intensity signals before any genotype calling has been done. In the context of sequencing, primary genetic data refers to the analog measurements, analogous to the chromatogram, that comes off the sequencer before the identity of any base pairs have been determined, and before the sequence has been mapped to the genome.

Secondary Genetic Data refers to processed genetic data that are output by a genotyping platform. In the context of a SNP array, the secondary genetic data refers to the allele calls made by software associated with the SNP array reader, wherein the software has made a call whether a given allele is present or not present in the sample. In the context of sequencing, the secondary genetic data refers to the base pair identities of the sequences have been determined, and possibly also where the sequences have been mapped to the genome.

Non-Invasive Prenatal Diagnosis (NPD), or also "Non-Invasive Prenatal Screening" (NPS), refers to a method of determining the genetic state of a fetus that is gestating in a mother using genetic material found in the mother's blood, where the genetic material is obtained by drawing the mother's intravenous blood.

Preferential Enrichment of DNA that corresponds to a locus, or preferential enrichment of DNA at a locus, refers to any method that results in the percentage of molecules of DNA in a post-enrichment DNA mixture that correspond to the locus being higher than the percentage of molecules of DNA in the pre-enrichment DNA mixture that correspond to the locus. The method may involve selective amplification of DNA molecules that correspond to a locus. The method may involve removing DNA molecules that do not correspond to the locus. The method may involve a combination of methods. The degree of enrichment is defined as the percentage of molecules of DNA in the post-enrichment mixture that correspond to the locus divided by the percentage of molecules of DNA in the pre-enrichment mixture that correspond to the locus. Preferential enrichment may be carried out at a plurality of loci. In some embodiments of the present disclosure, the degree of enrichment is greater than 20. In some embodiments of the present disclosure, the degree of enrichment is greater than 200. In some embodiments of the present disclosure, the degree of enrichment is greater than 2,000. When preferential enrichment is carried out at a plurality of loci, the degree of enrichment may refer to the average degree of enrichment of all of the loci in the set of loci.

Amplification refers to a method that increases the number of copies of a molecule, such as a molecule of DNA.

Selective Amplification may refer to a method that increases the number of copies of a particular molecule of DNA, or molecules of DNA that correspond to a particular region of DNA. It may also refer to a method that increases the number of copies of a particular targeted molecule of DNA, or targeted region of DNA more than it increases non-targeted molecules or regions of DNA. Selective amplification may be a method of preferential enrichment.

Universal Priming Sequence refers to a DNA sequence that may be appended to a population of target DNA molecules, for example by ligation, PCR, or ligation mediated PCR.

Once added to the population of target molecules, primers specific to the universal priming sequences can be used to amplify the target population using a single pair of amplification primers. Universal priming sequences are typically not related to the target sequences.

Universal Adapters, or 'ligation adaptors' or 'library tags' are DNA molecules containing a universal priming sequence that can be covalently linked to the 5-prime and 3-prime end of a population of target double stranded DNA molecules. The addition of the adapters provides universal priming sequences to the 5-prime and 3-prime end of the target population from which PCR amplification can take place, amplifying all molecules from the target population, using a single pair of amplification primers.

Targeting refers to a method used to selectively amplify or otherwise preferentially enrich those molecules of DNA that correspond to a set of loci, in a mixture of DNA.

Joint Distribution Model refers to a model that defines the probability of events defined in terms of multiple random variables, given a plurality of random variables defined on the same probability space, where the probabilities of the variable are linked. In some embodiments, the degenerate case where the probabilities of the variables are not linked may be used.

Percent identity in reference to nucleic acid sequences refers to the degree of sequence identity between nucleic acid sequences.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 12: An example of some primers with internal tags (SEQ ID NOs: 44,610-44,622).

FIG. 17A) The fetal fraction for POOL1_BC1_ref_rate is about 25%. FIG. 17B) If there is not fetal DNA detected, we do not expect to see (2), (3), (5), or (6); alternately we could say that the separation is zero, and therefore (1) and (2) are on top of each other, as are (3), (4) and (5), and also (6) and (7). FIG. 17C) If the DNA is 8% fetal, and 92% maternal, we expect (1) through (7) to be centered at 1.00, 0.96, 0.54, 0.50, 0.46, 0.04 and 0.00 respectively. FIG. 17D) If the DNA is 20% fetal, and 80% maternal, we expect (1) through (7) to be centered at 1.0, 0.9, 0.6, 0.5, 0.4, 0.1 and 0.0 respectively.

FIG. 24 shows normalized depth of read ratios (vertical axis) for six samples at three chromosomes (1=chrom 1; 2=chrom 21; 3=chrom X). The ratios were set to be equal to the number of reads mapping to that chromosome, normalized, and divided by the number of reads mapping to that chromosome averaged over three wells each comprising three 46XY cells. The three sets of data points corresponding to the 46XY reactions are expected to have ratios of 1:1. The three sets of data points corresponding to the 47XX+21 cells are expected to have ratios of 1:1 for chromosome 1, 1.5:1 for chromosome 21, and 2:1 for chromosome X.

FIGS. 25A-C show allele ratios plotted for three chromosomes (1, 21, X) for three reaction. FIG. 25A) The plot was made on a reaction comprising 1 ng of genomic DNA from the 47XX+21 cell line. FIG. 25B) The reaction shows a reaction on three 46XY cells. FIG. 25C) The reaction shows a reaction on three 47XX+21 cells (FIG. 25C).

FIGS. 26A and 26B: Allele ratios for two single-cell reactions (FIGS. 26A and 26B) at three chromosomes. The left graph was a reaction that contained a 47XX+21 cell (FIG. 26A), and the right graph was for a reaction that contained a 46XX cell (FIG. 26B).

FIG. 28A: Graph of the electrophoresis of PCR products.

FIGS. 28B-28M are electropherograms of lanes 1-12, respectively, in FIG. 28A.

FIGS. 30A-30H: Typical graphical representations of euploidy (FIGS. 30A-30C), monosomy (FIG. 30D), and trisomy (FIGS. 30E-30H). For all plots, the x-axis represents the linear position of the individual polymorphic loci along each chromosome (as indicated below the plots), and the y-axis represents the number of A allele reads as a fraction of the total (A+B) allele reads. Maternal and fetal genotypes, as well as the position on the y-axis around which the bands are centered, are indicated to the right of the plots. If desired to facilitate visualization, the plots may be color-coded according to maternal genotype, such that red indicates a maternal genotype of AA, blue indicates a maternal genotype of BB, and green indicates a maternal genotype of AB. If desired, maternal allele contributions may be indicated in color in the "Fetal Genotype" column. Allele contributions are indicated as maternal|fetal, such that alleles for which the mother is AA and the fetus is AB are indicated as AA|AB. FIG. 30A: Generated plots when two chromosomes are present and the fetal cfDNA fraction is 0%. This plot is from a non-pregnant woman, and thus represents the pattern when the genotype is entirely maternal. Allele clusters are thus centered around 1 (AA alleles), 0.5 (AB alleles), and 0 (BB alleles). FIG. 30B: Generated plot when two chromosomes are present and the fetal fraction is 12%. The contribution of fetal alleles to the fraction of A allele reads shifts the position of some allele spots up or down along the y-axis, such that the bands are centered around 1 (AA|AA alleles), 0.94 (AA|AB alleles), 0.56 (AB|AA alleles), 0.50 (AB|AB alleles), 0.44 (AB|BB alleles), 0.06 (BB|AB alleles), and 0 (BB|BB alleles). FIG. 30C. Generated plot when two chromosomes are present and the fetal fraction is 26%. The pattern, including two red and two blue peripheral bands and a trio of central green bands, is readily apparent. Bands are centered around 1 (AA|AA alleles), 0.87 (AA|AB alleles), 0.63 (AB|AA [[25]] alleles), 0.50 (AB|AB alleles), 0.37 (AB|BB alleles), 0.13 (BB|AB alleles), and 0 (BB|BB alleles). FIG. 30D: Generated plot when one chromosome is present and the fetal fraction is 26%. The hallmark pattern of one external red and one external blue peripheral band as well as two central green bands indicated maternally-inherited monosomy. Because the fetus only contributes a single allele (A or B) to the allele reads, the internal peripheral red and blue bands are not present, and the center trio of bands condenses into two bands. Bands that are centered around 1 (AA|A alleles), 0.57 (AB|A alleles), 0.43 (AB|B alleles), and 0 (BB|B alleles). FIG. 30E: Generated plot when three chromosomes are present and the fetal fraction is 27%. This pattern of two red and two blue peripheral bands as well as two central green bands indicates maternally-inherited meiotic trisomy. Bands are centered around 1 (AA|AAA alleles), 0.88 (AA|AAB alleles), 0.56 (AB|AAB alleles), 0.44 (AB|ABB alleles), 0.12 (BB|ABB alleles), and 0 (BB|BBB alleles). FIG. 30F: Generated plot when three chromosomes are present and the fetal fraction is 14%. This pattern of three red and three blue peripheral bands, as well as two central green bands, indicates paternally-inherited meiotic trisomy. Bands are centered around 1 (AA|AAA alleles), 0.93 (AA|AAB alleles), 0.87 (AA|ABB alleles), 0.60 (AB|AAA alleles), 0.53 (AB|AAB alleles), 0.47 (AB|ABB alleles), 0.40 (AB|BBB alleles), 0.13 (BB|AAB alleles), 0.07 (BB|ABB alleles), and 0 (BB|BBB alleles). FIG. 30G: Generated plot when three chromosomes are present and the fetal fraction is 35%. This pattern of two red and two blue peripheral bands and four central green bands indicates maternally-inherited mitotic trisomy. Bands are centered around 1 (AA|AAA alleles), 0.85 (AA|AAB alleles), 0.72 (AB|AAA alleles), 0.57 (AB|AAB alleles), 0.43 (AB|ABB alleles), 0.28 (AB|BBB alleles), 0.15 (BB|ABB alleles), and 0 (BB|BBB alleles). FIG. 30H: Generated plot when three chromosomes are present and the fetal fraction is 25%. This pattern of two red and two blue peripheral bands as well as four central green bands indicates paternally-inherited mitotic trisomy. This pattern can be distinguished from that of maternally-inherited mitotic trisomy (as in FIG. 30G) by the position of the internal peripheral bands. Specifically, bands are centered around 1 (AA|AAA alleles), 0.78 (AA|ABB alleles), 0.67 (AB|AAA alleles), 0.56 (AB|AAB alleles), 0.44 (AB|ABB alleles), 0.33 (AB|BBB alleles), 0.22 (BB|AAB alleles), and 0 (BB|BBB alleles).

FIG. 33A shows the first two bases (dinucleotide) of a primer that align to the other primer for calculation of ΔG. Iterate over the remainder of the primer that aligns with the other primer by sliding the bases being observing one base to the right. Continue until ΔG has been calculated for all pairs of bases that align (FIG. 33B). Shift the alignment of the two primers (FIGS. 33C and 33D). Determine ΔG for the new alignment (FIGS. 33E and 33F).

Figure 34A4:
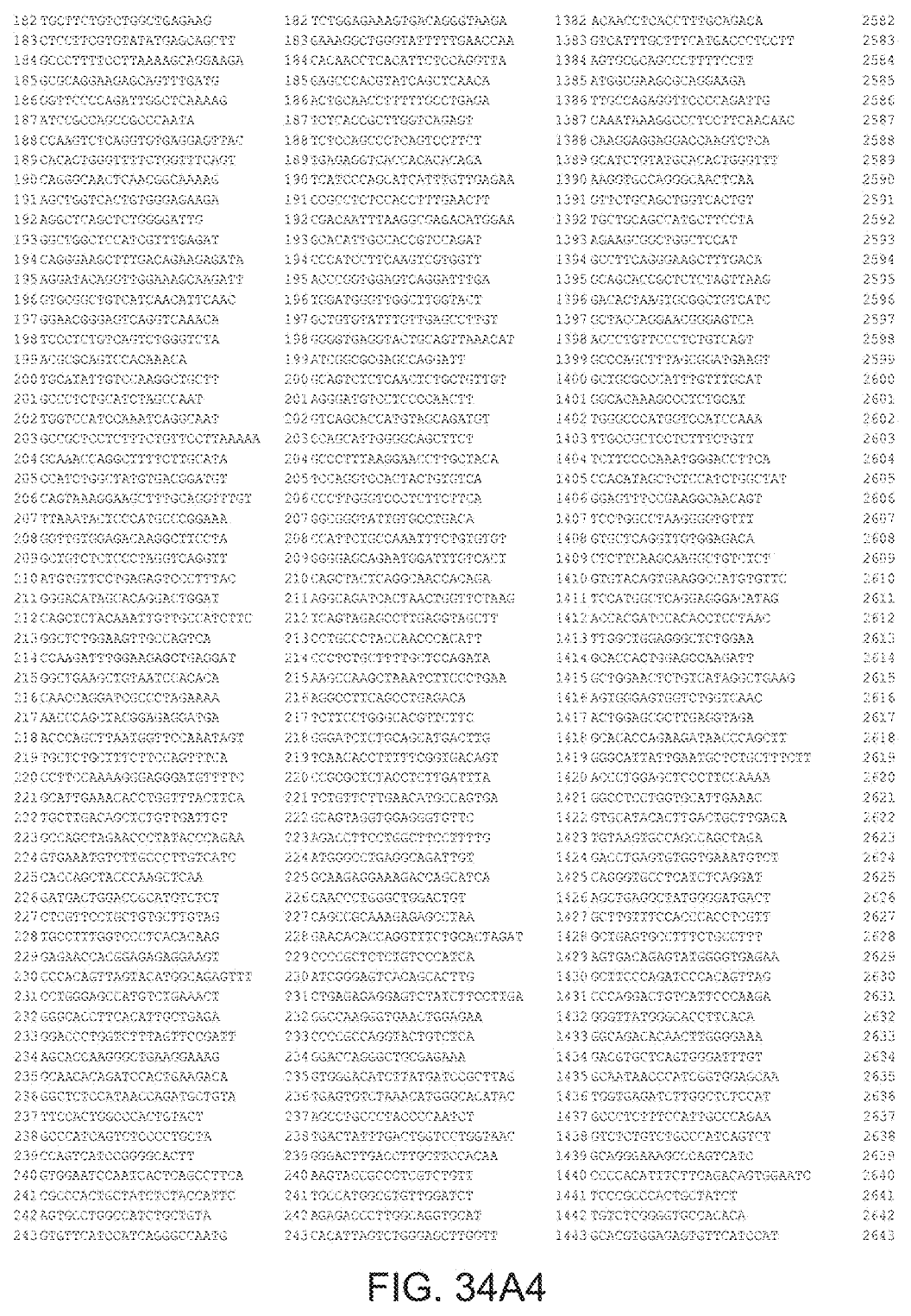
Figure 34A6:
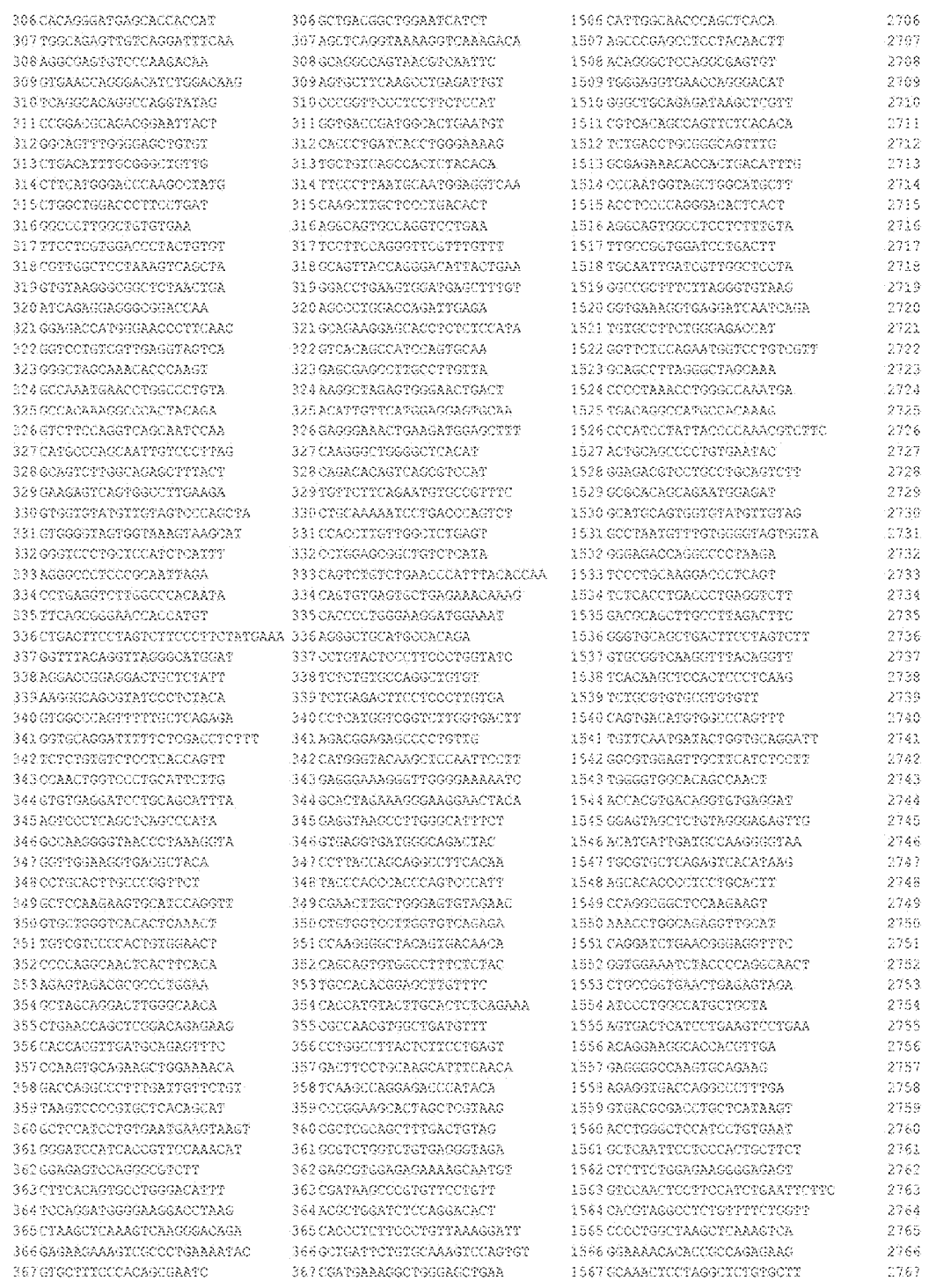
Figure 34A8:
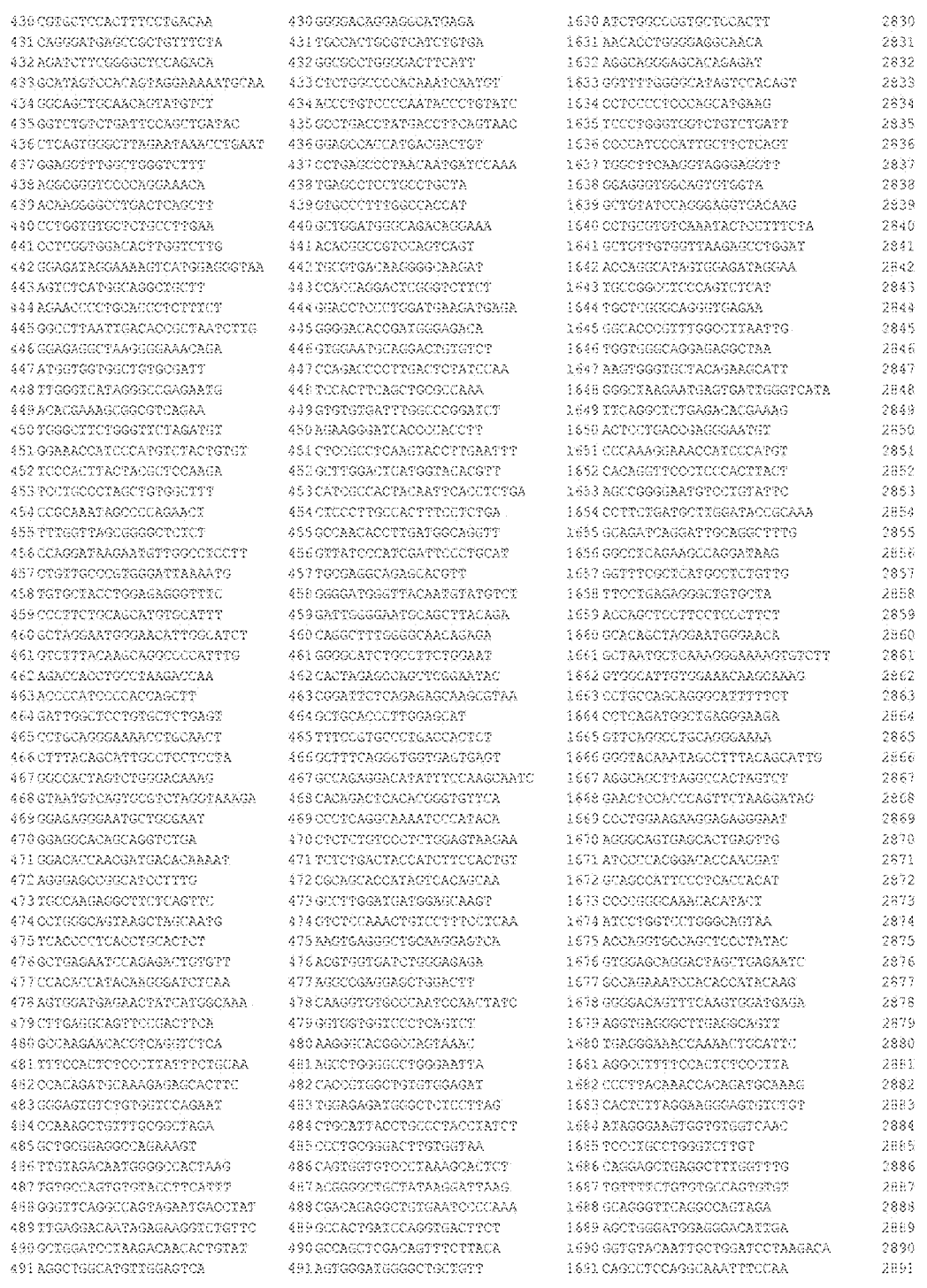
Figure 34B3:
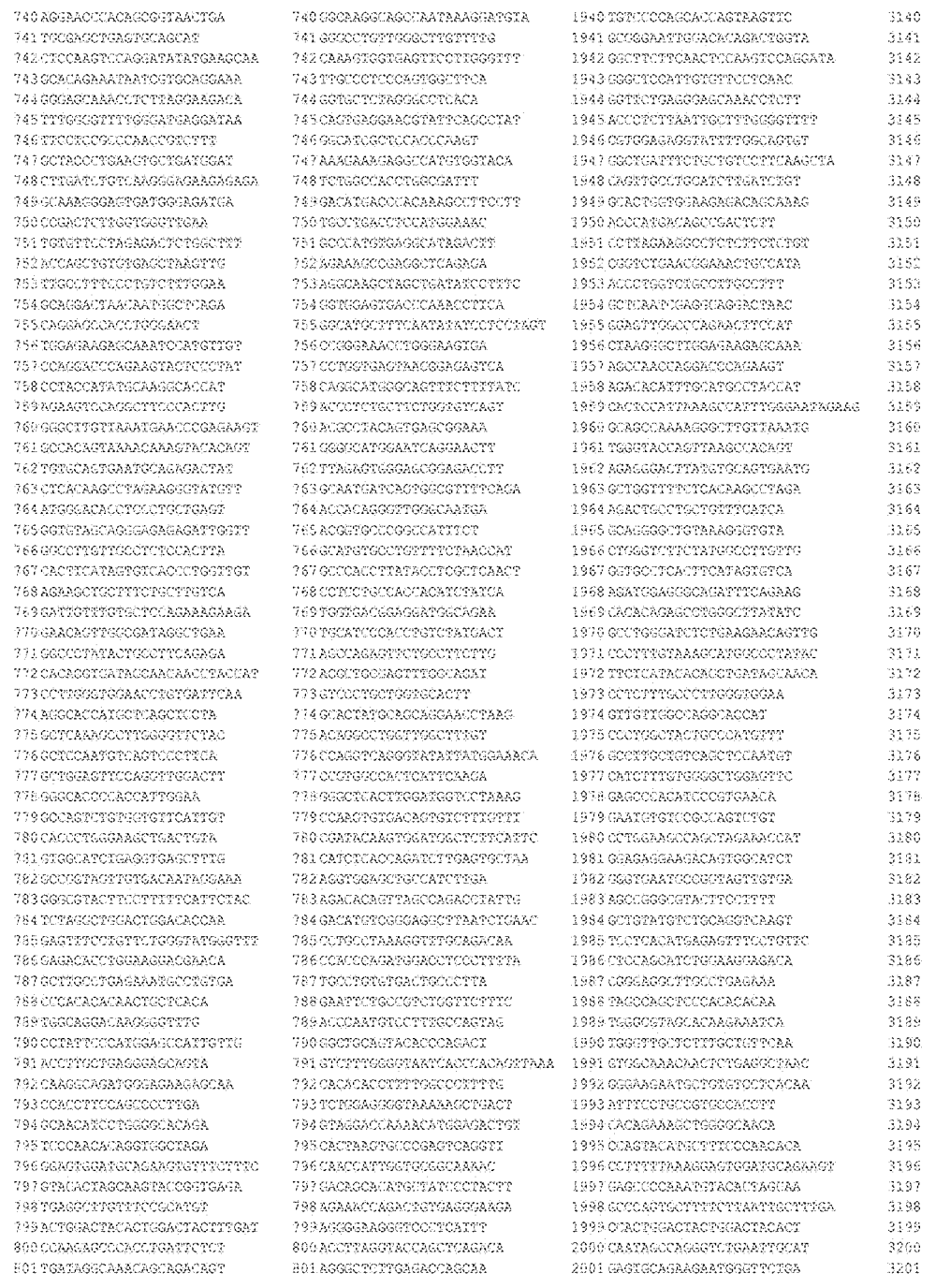
Figure 34B5:
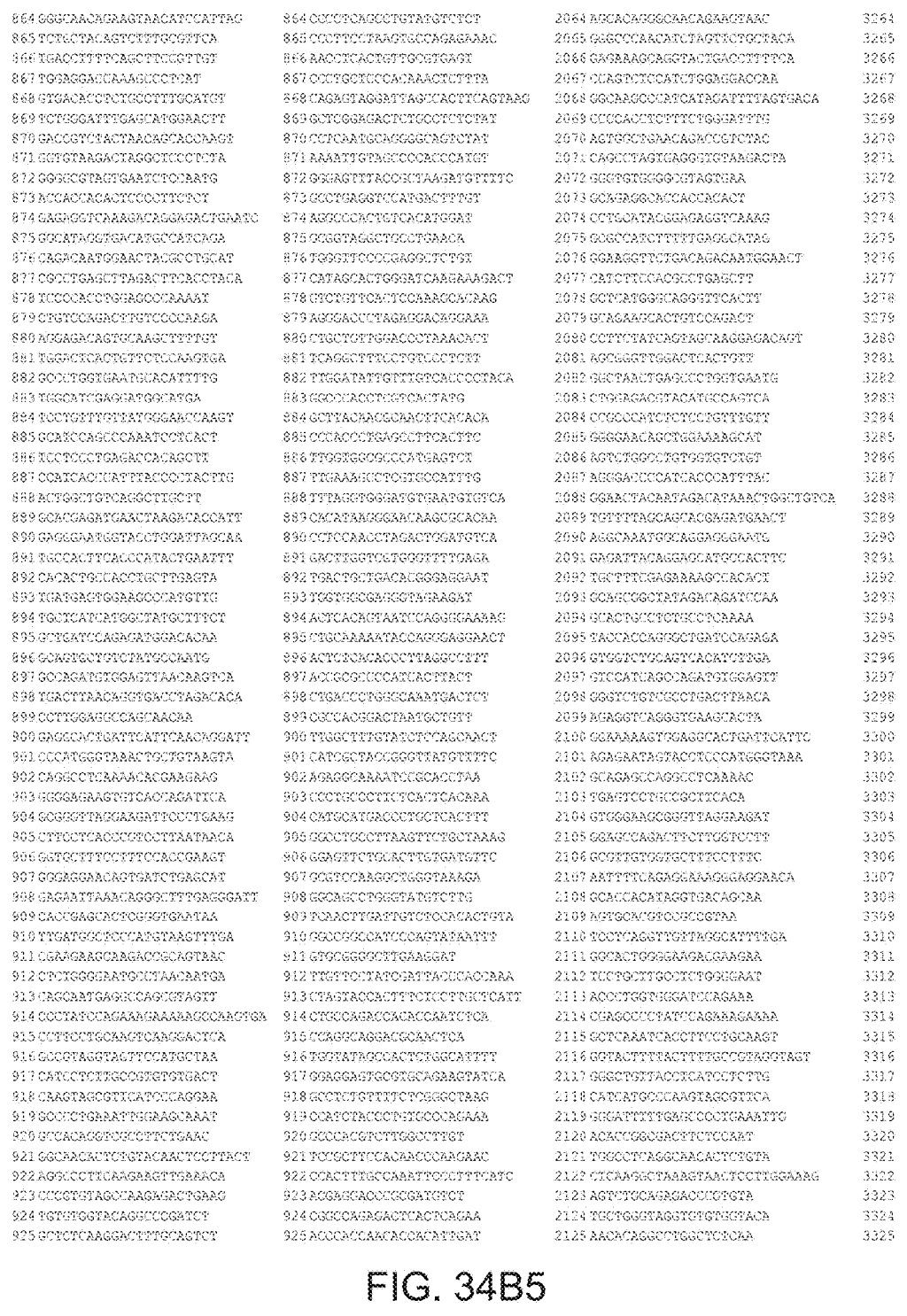
Figure 34B7:
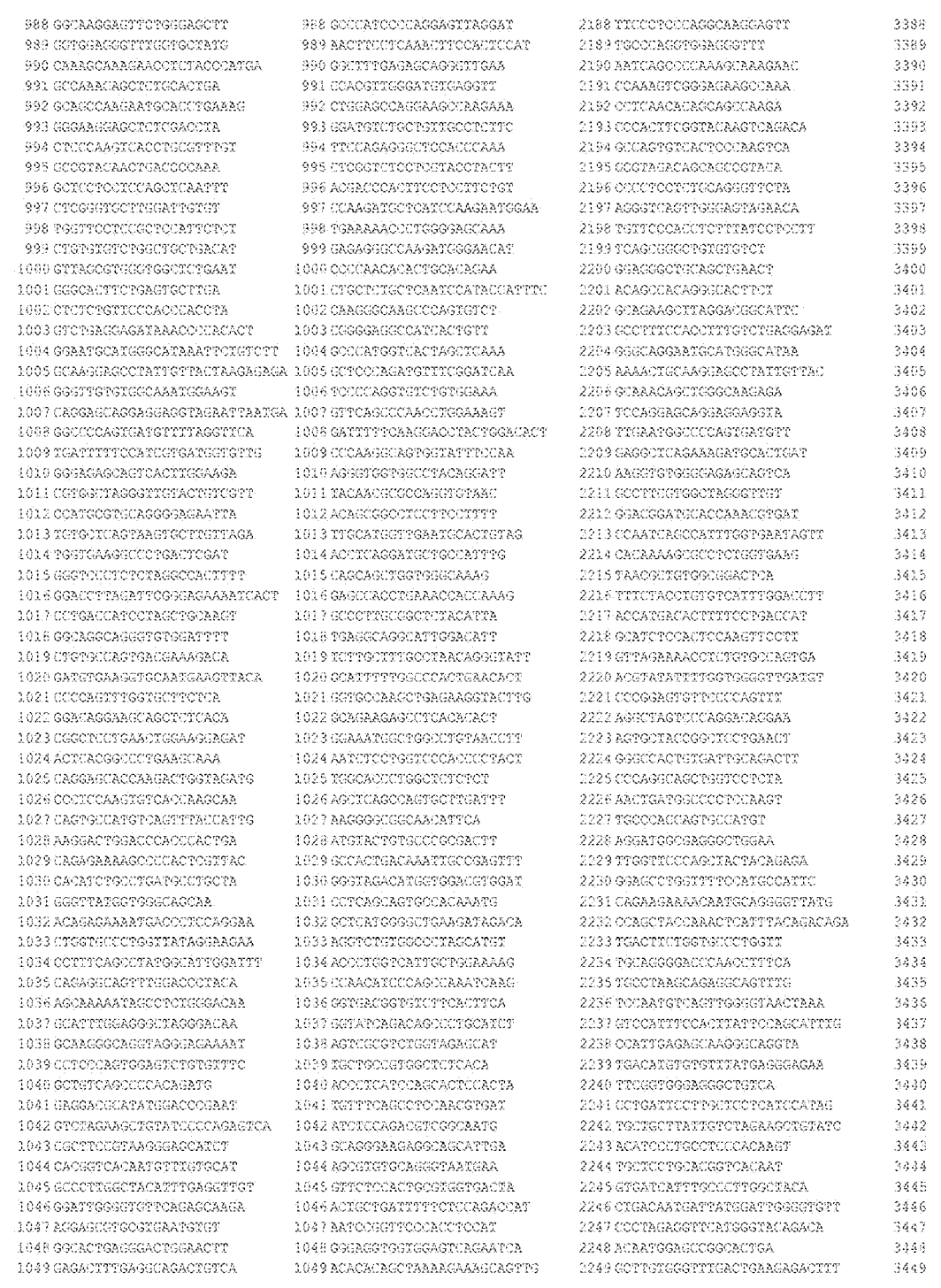

FIG. 34A1-A10, FIG. 34B1-B10: Sequences of an exemplary 1,200-plex primer library (SEQ ID NOs. 1-3,600). The three primers (one from pool A, one from pool B, and one from pool C) in each row all hybridize to the same target locus.

Figure 35A1:
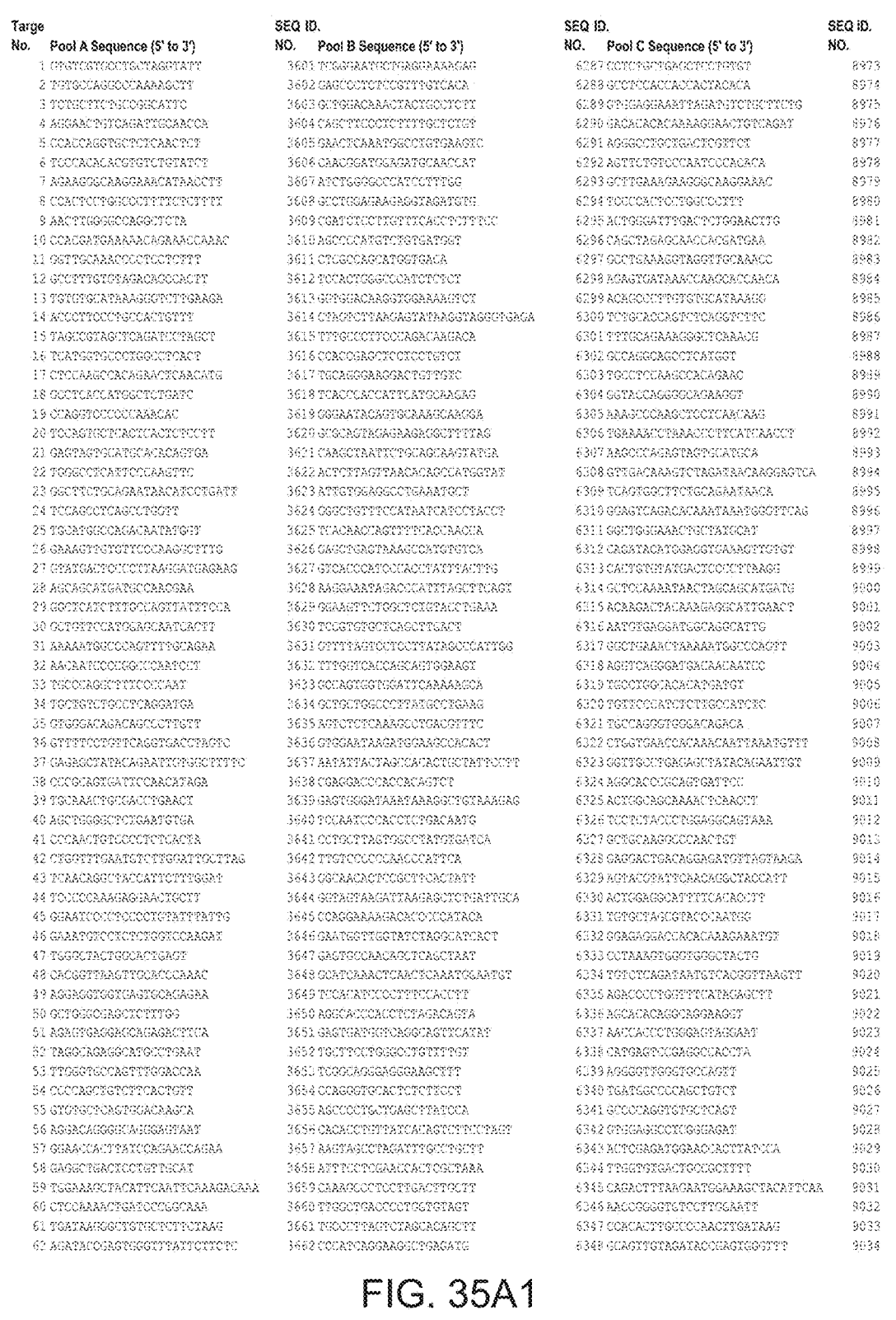
Figure 35A2:
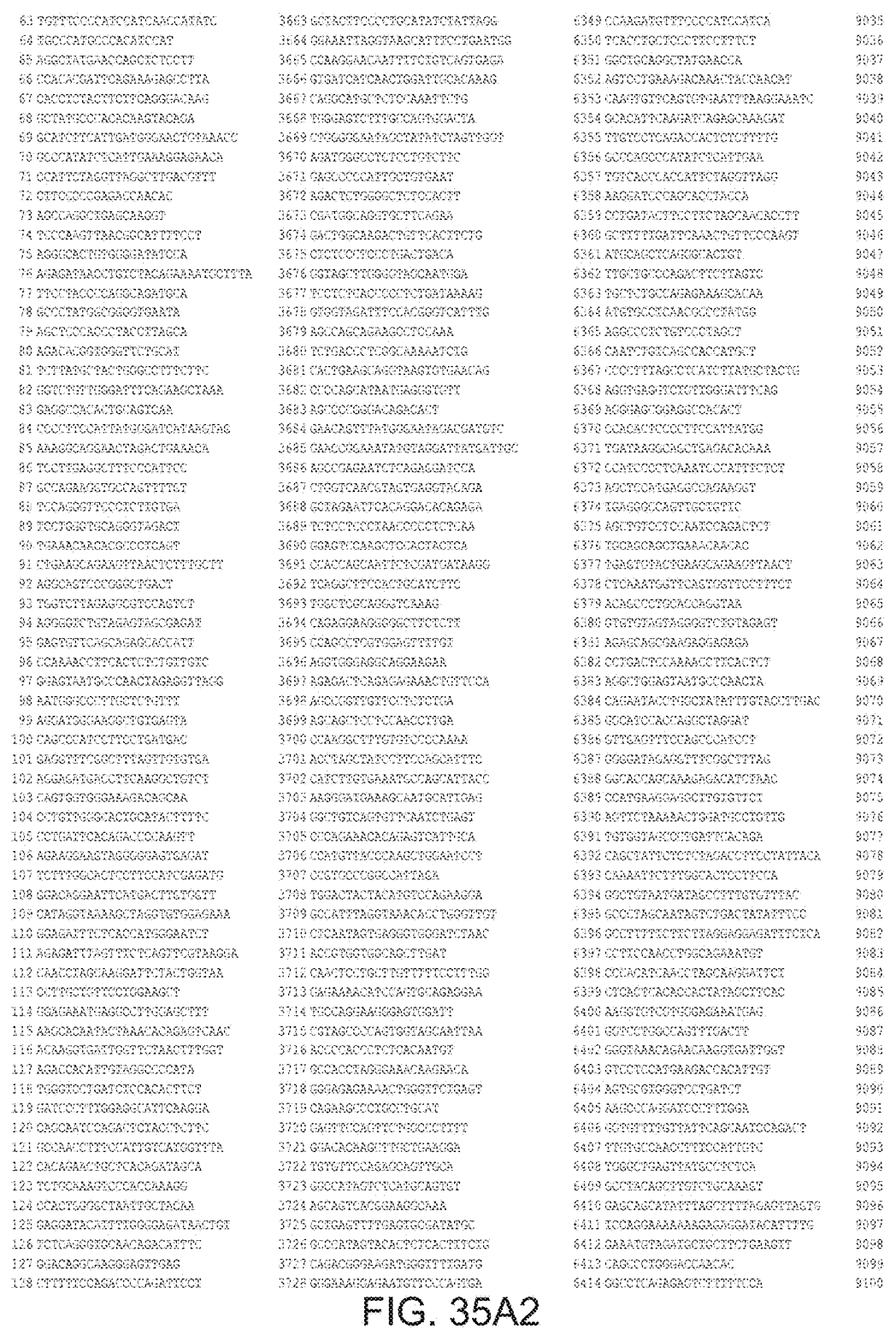
Figure 35A3:
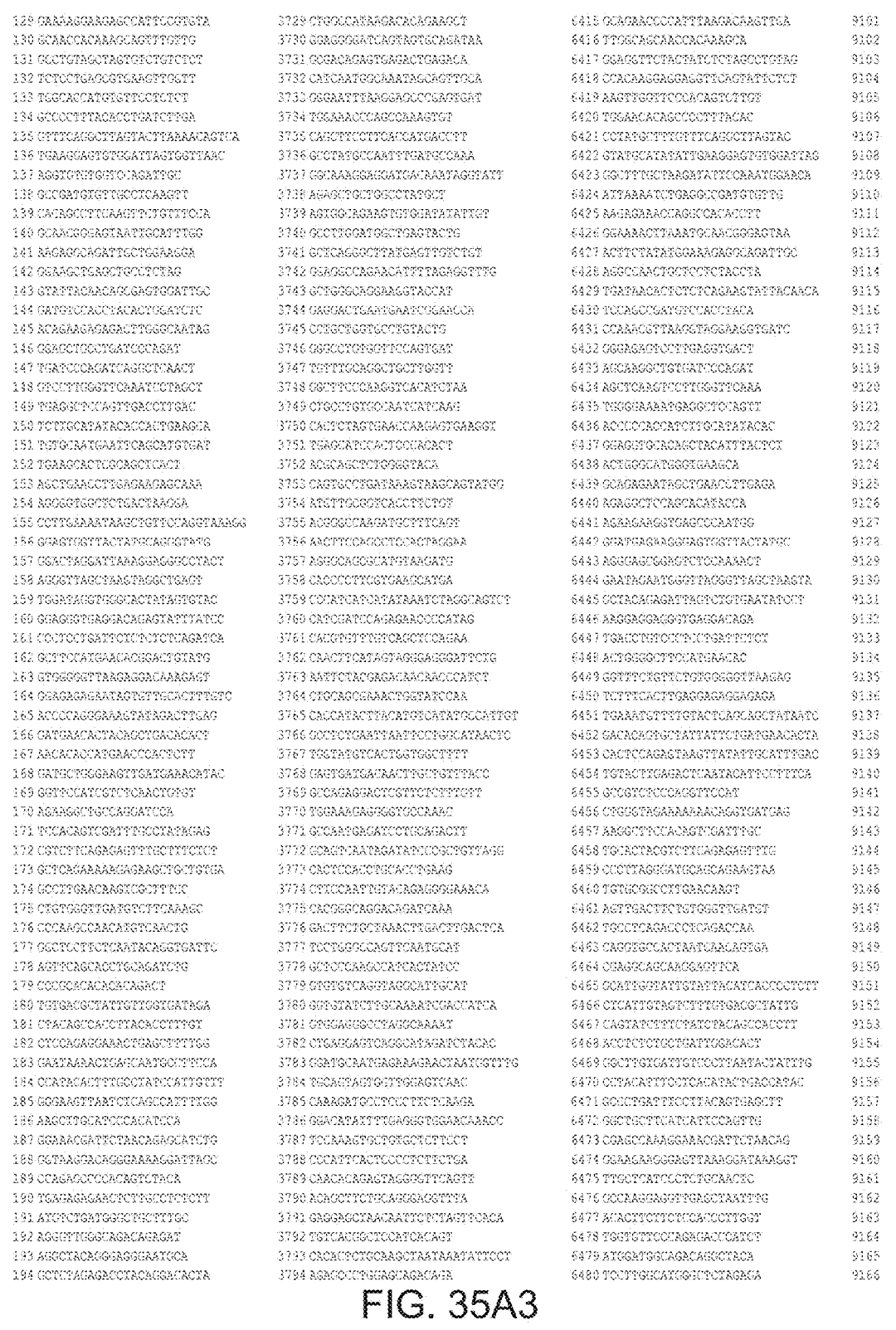
Figure 35A4:
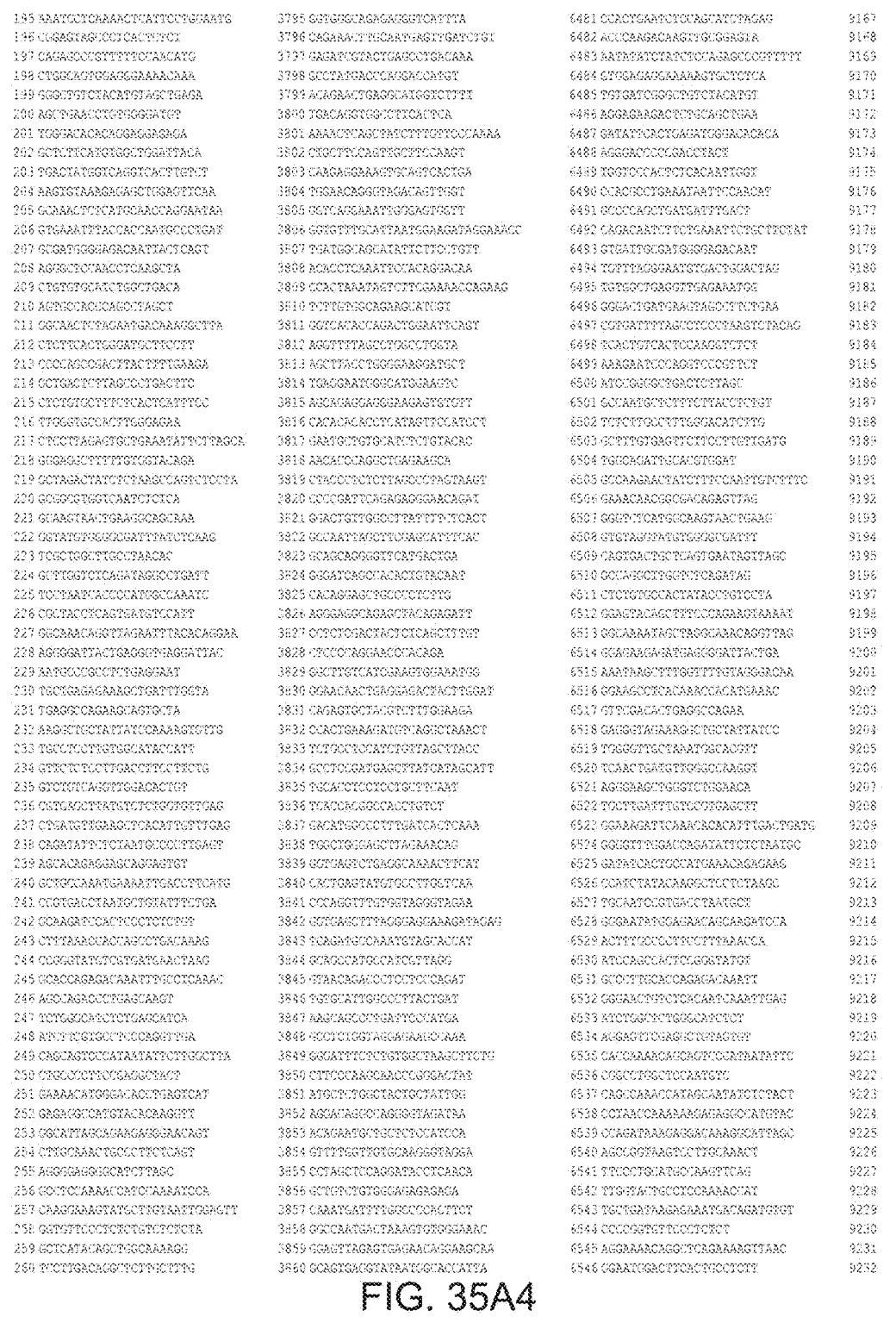
Figure 35A5:
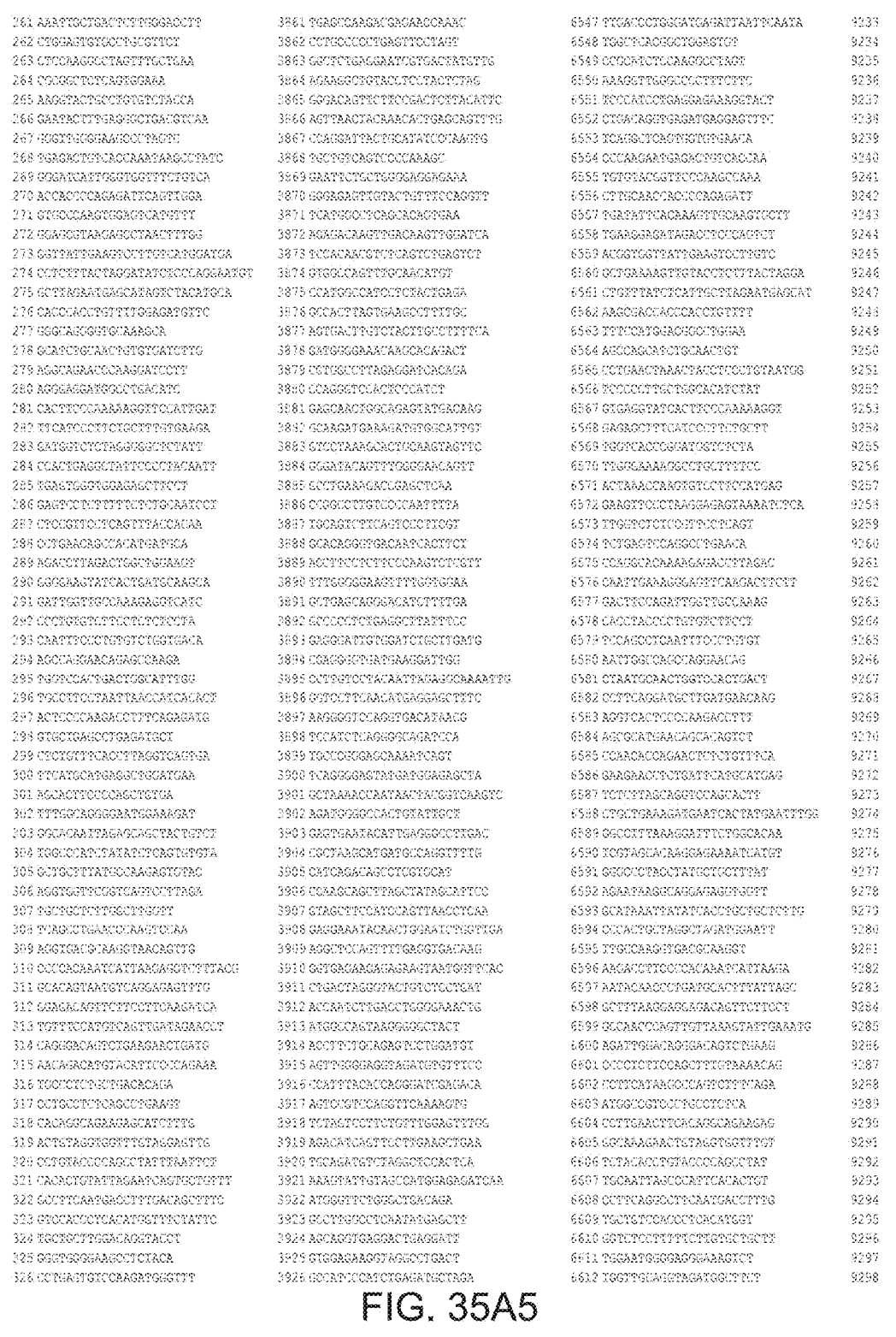
Figure 35A6:
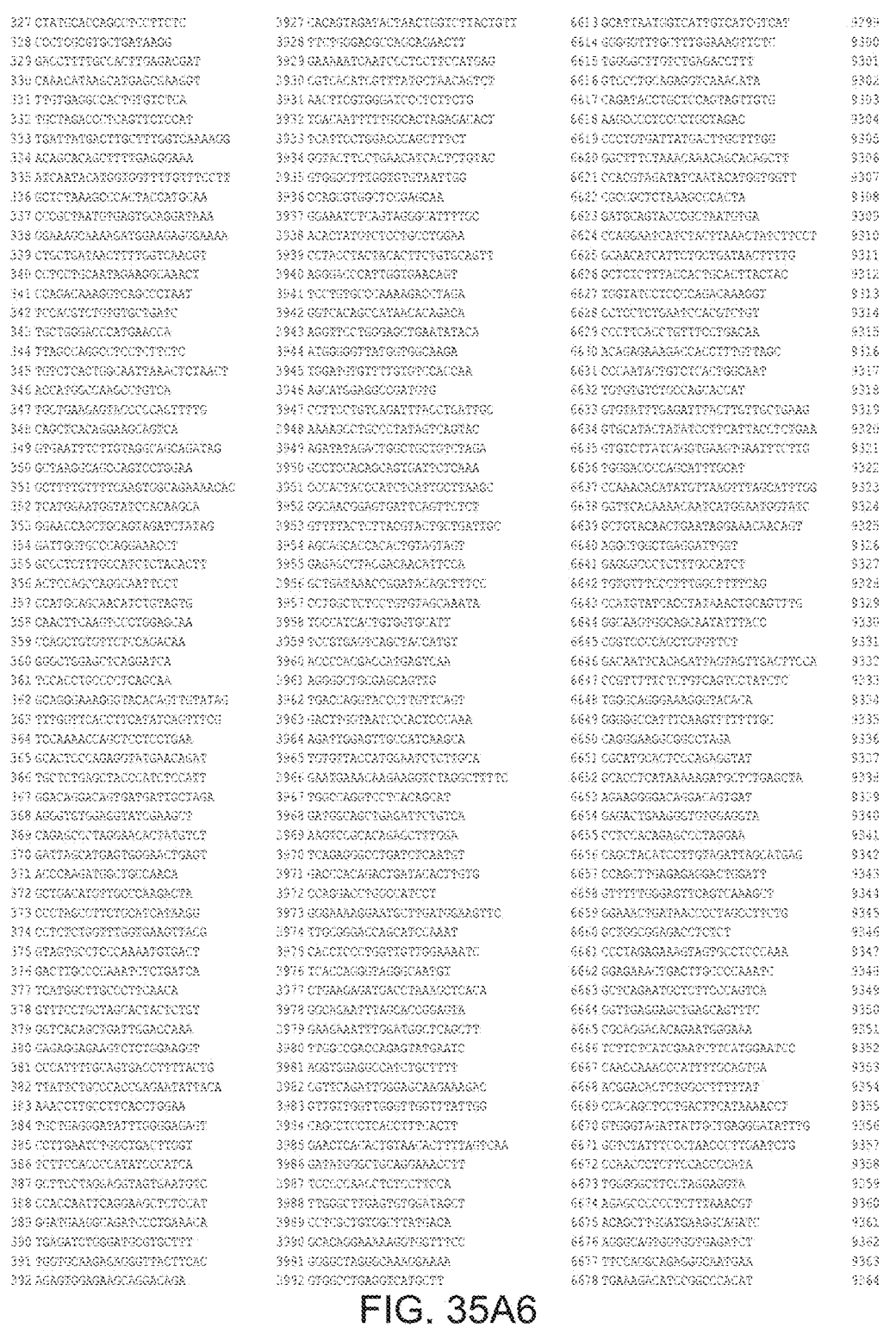
Figure 35A7:
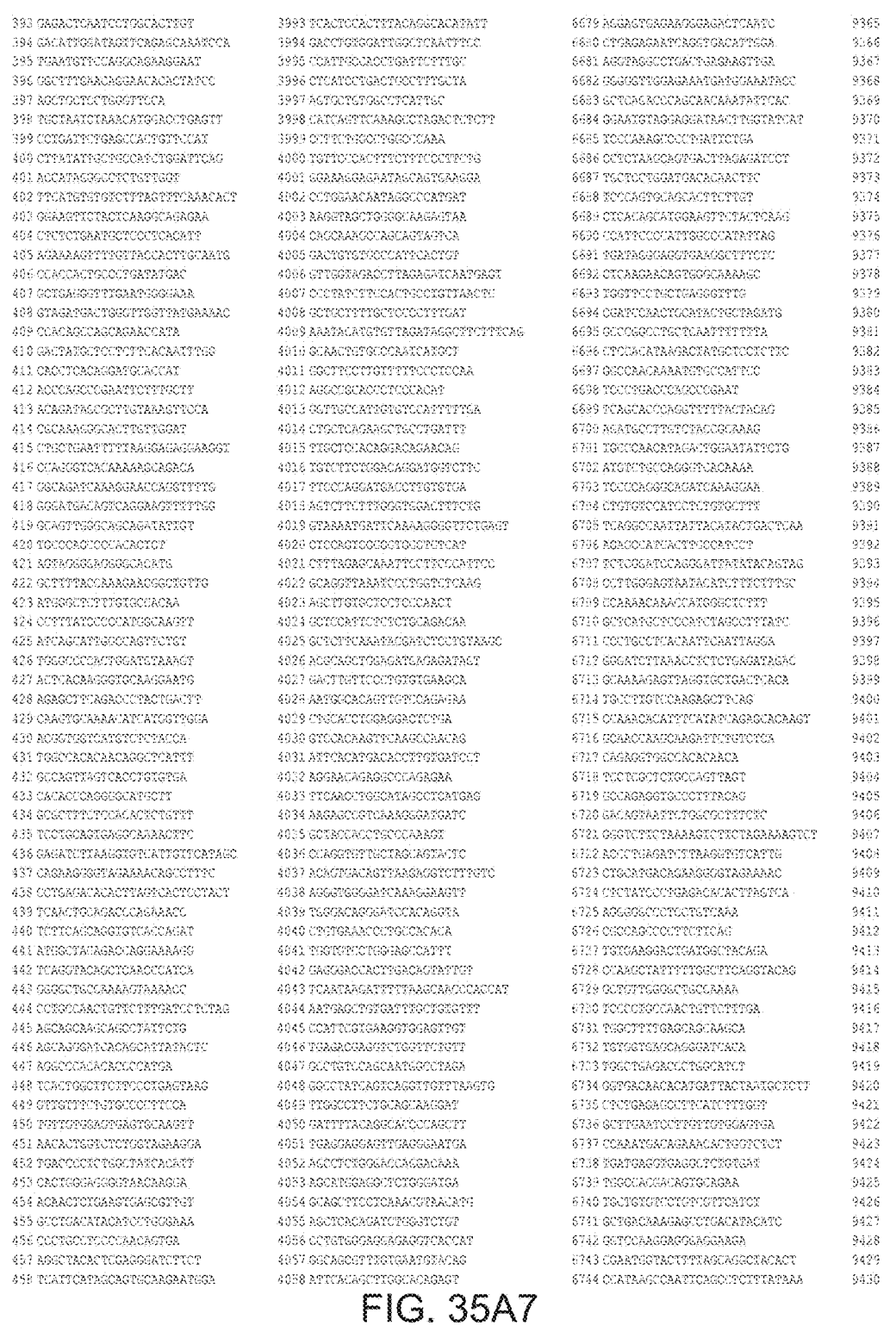
Figure 35A9:
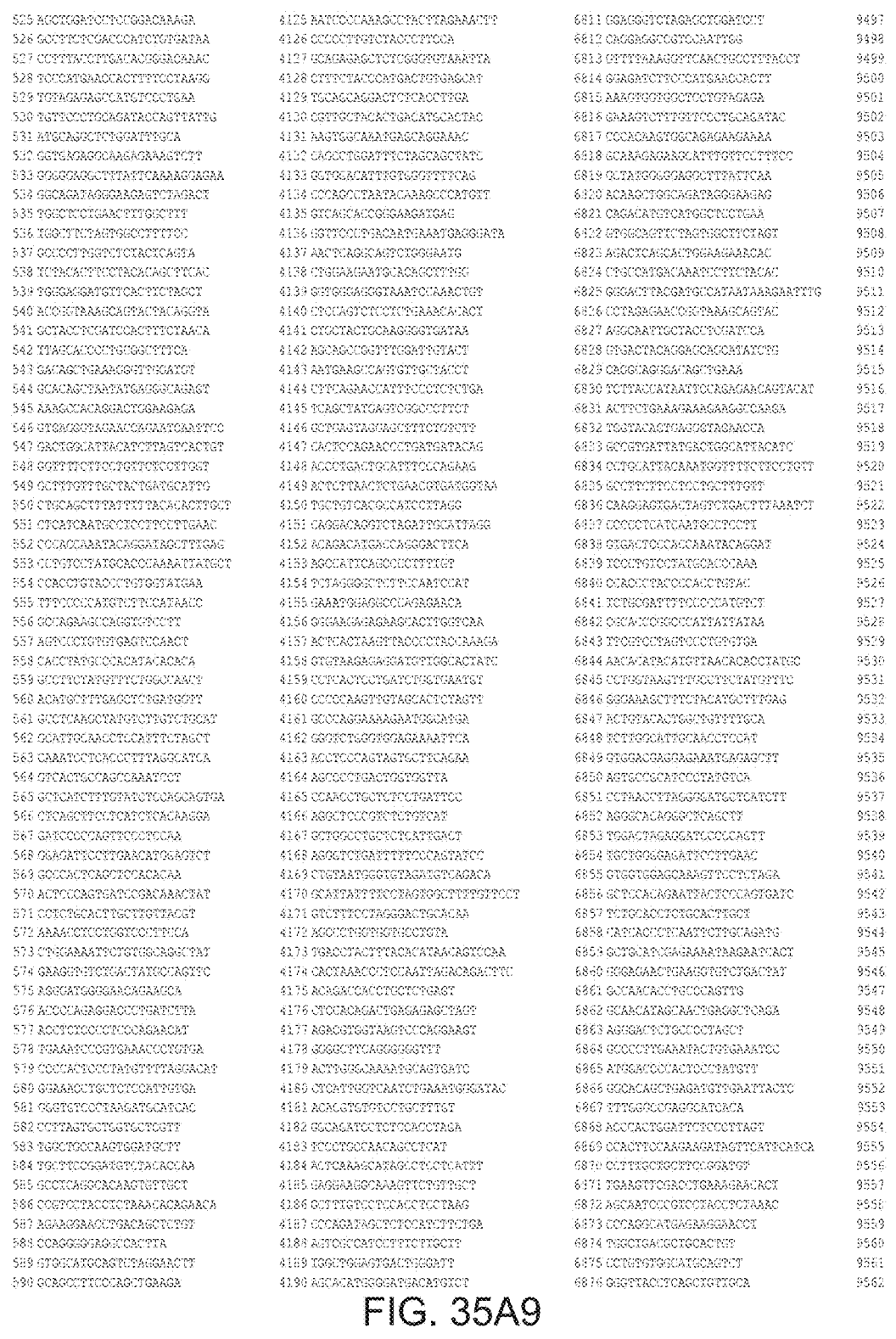
Figure 35A10:
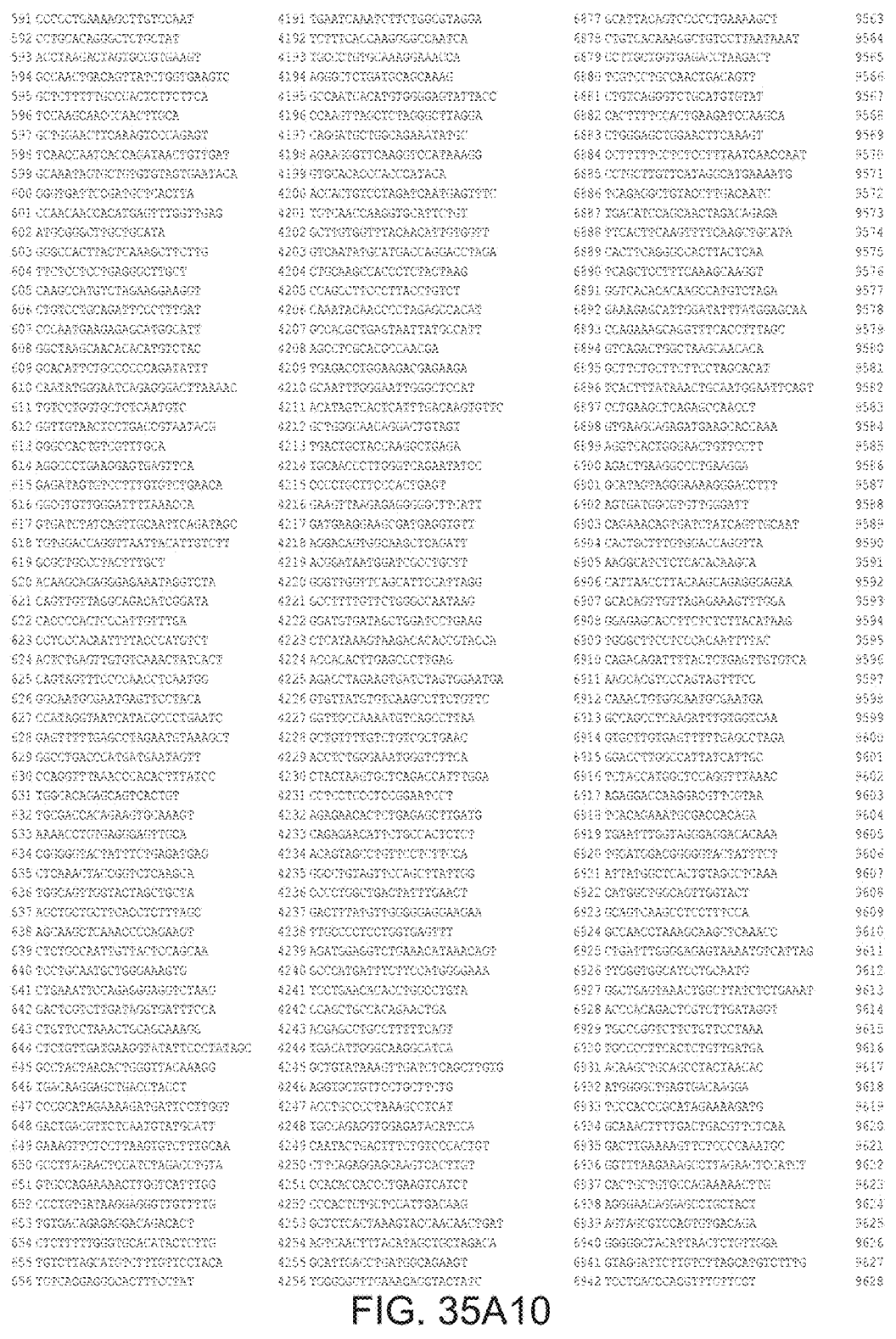
Figure 35B3:
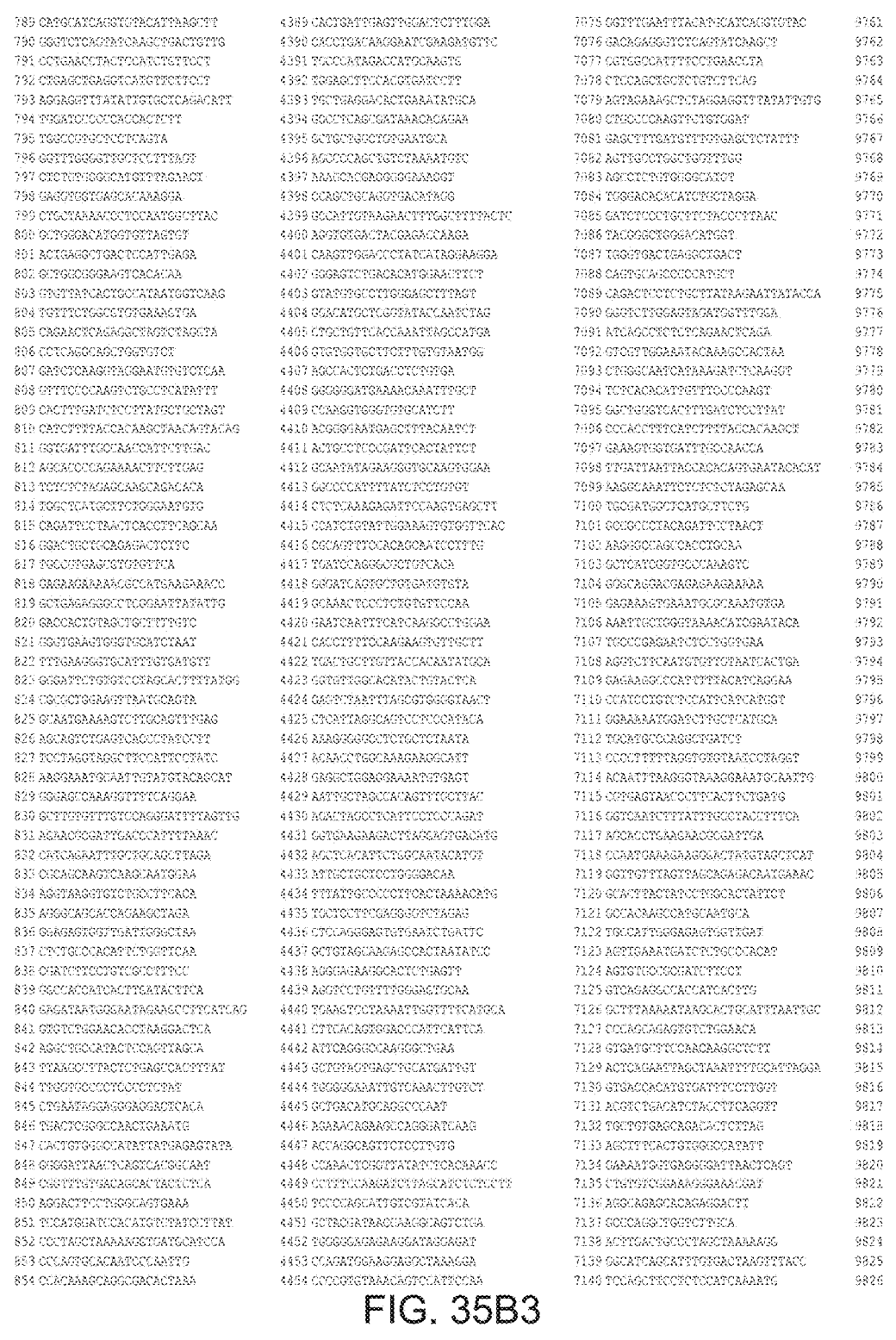
Figure 35B4:
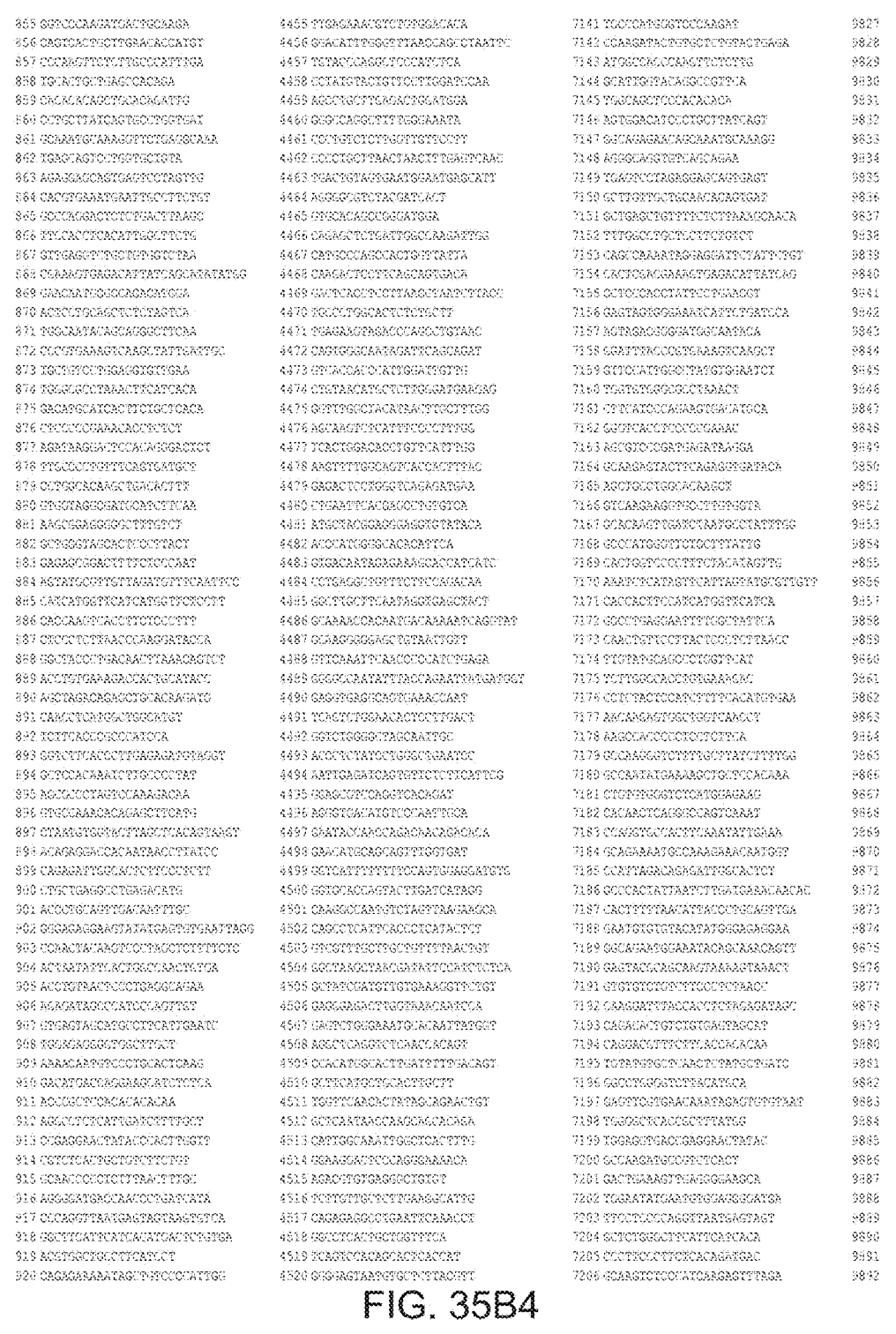
Figure 35B5:
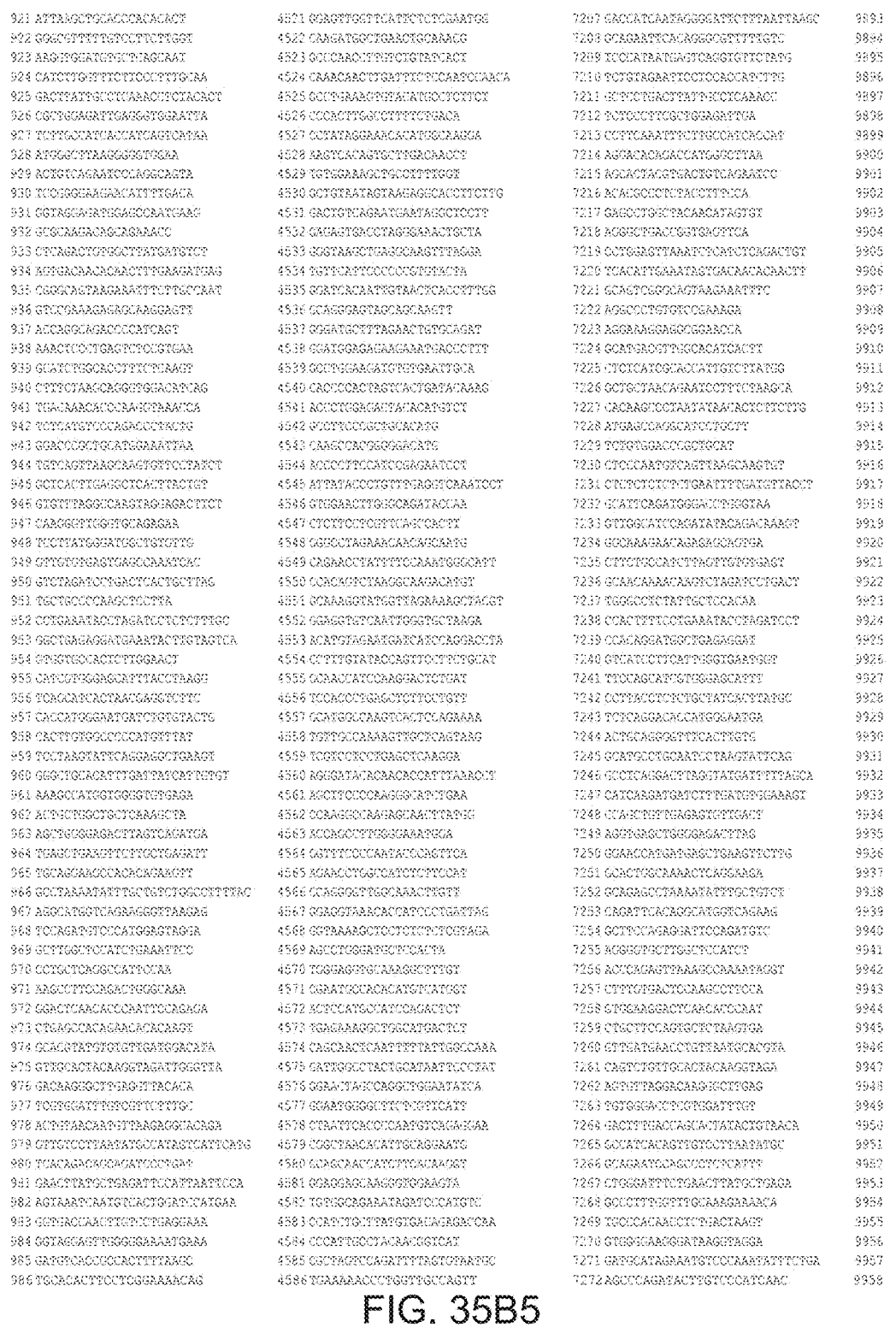
Figure 35B9:
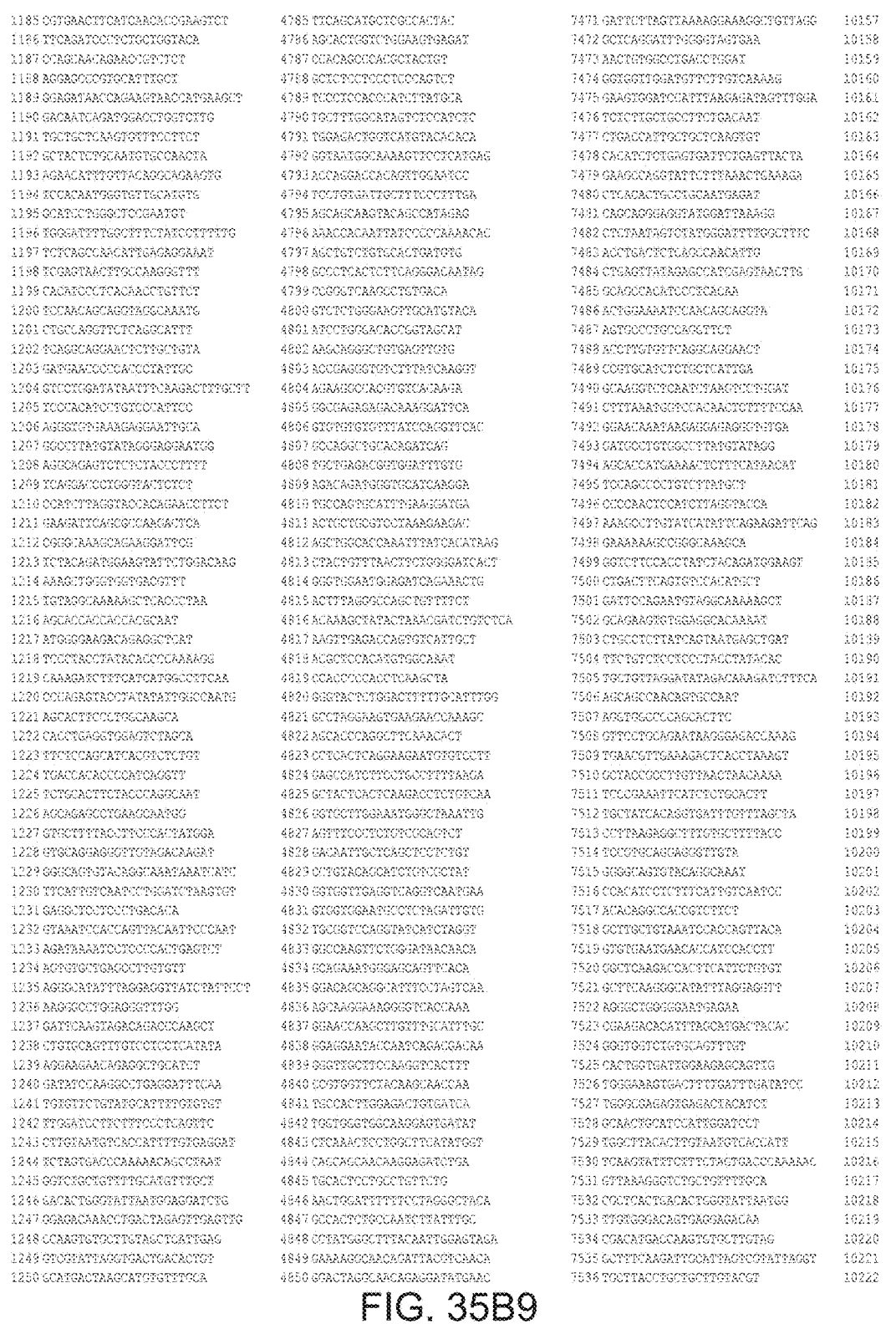
Figure 35C1:
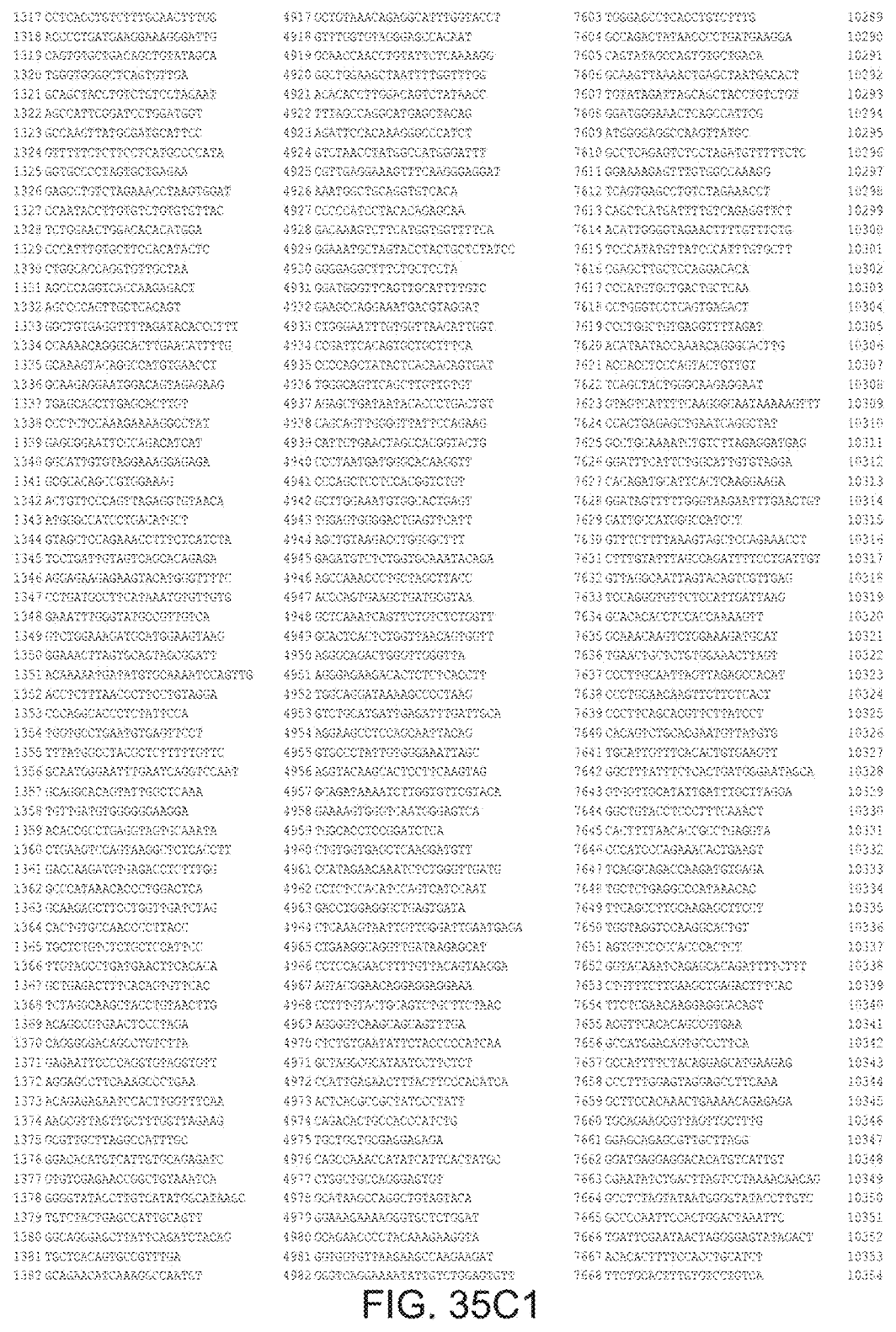
Figure 35C2:
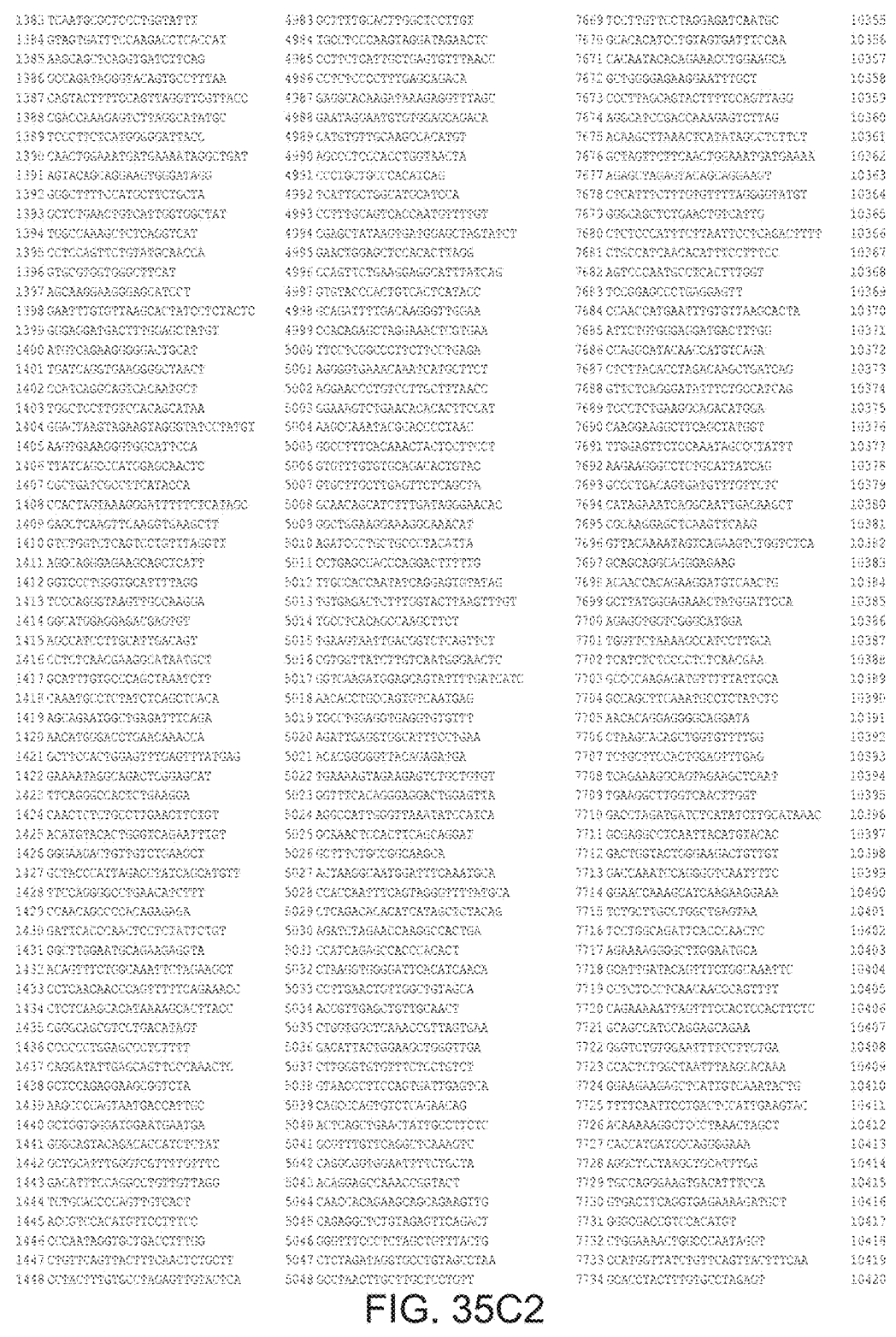
Figure 35C3:
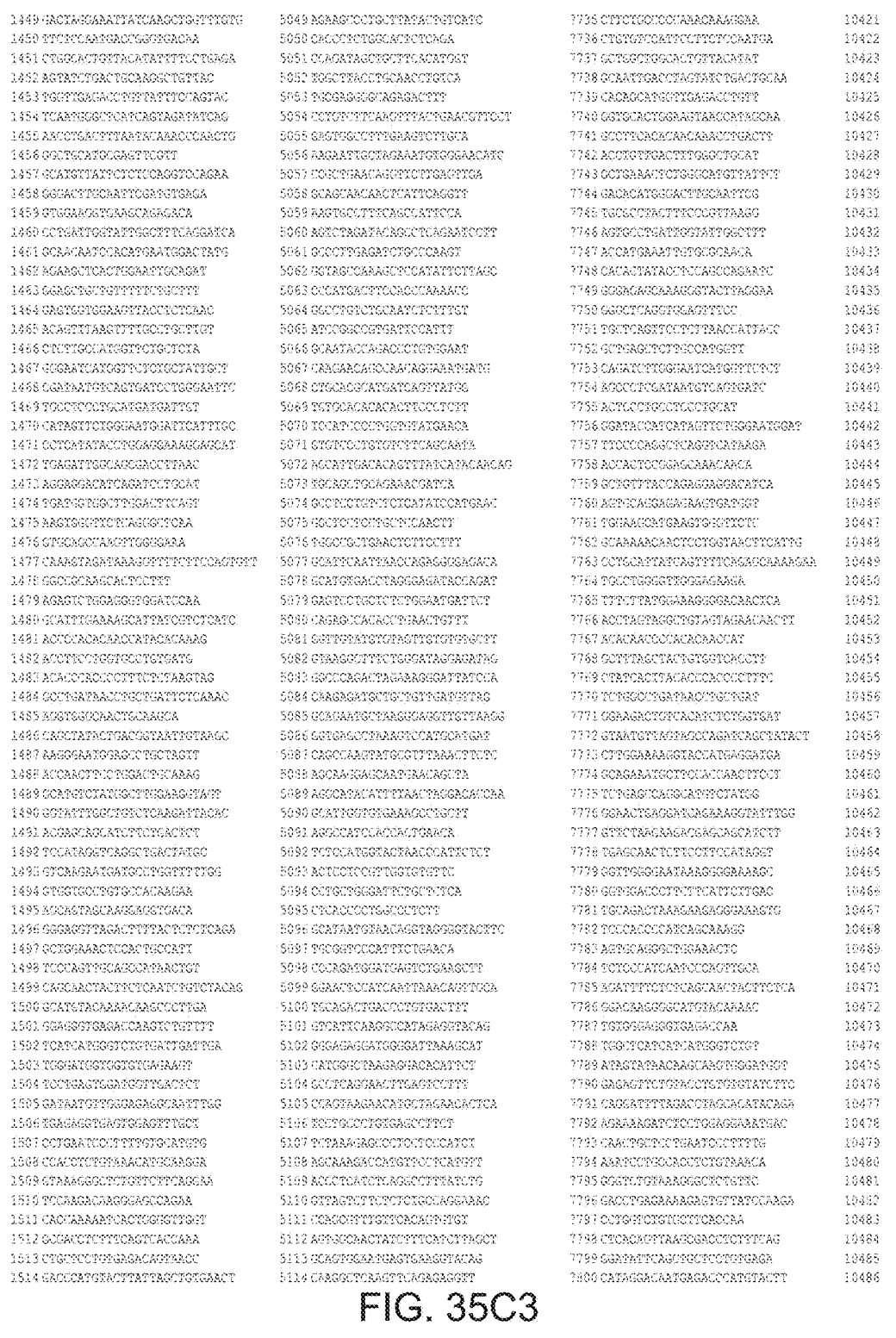
Figure 35C7:
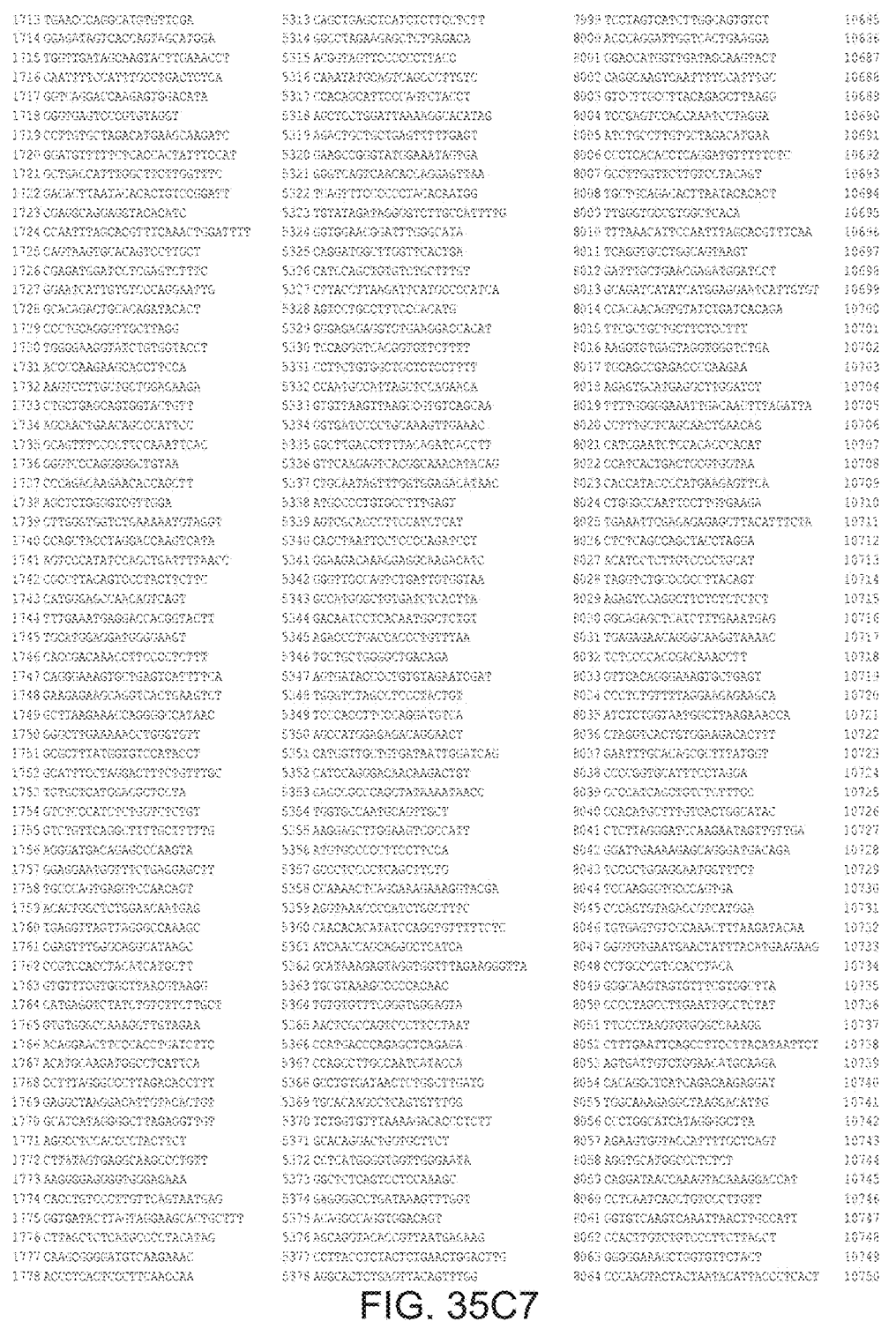
Figure 35C8:
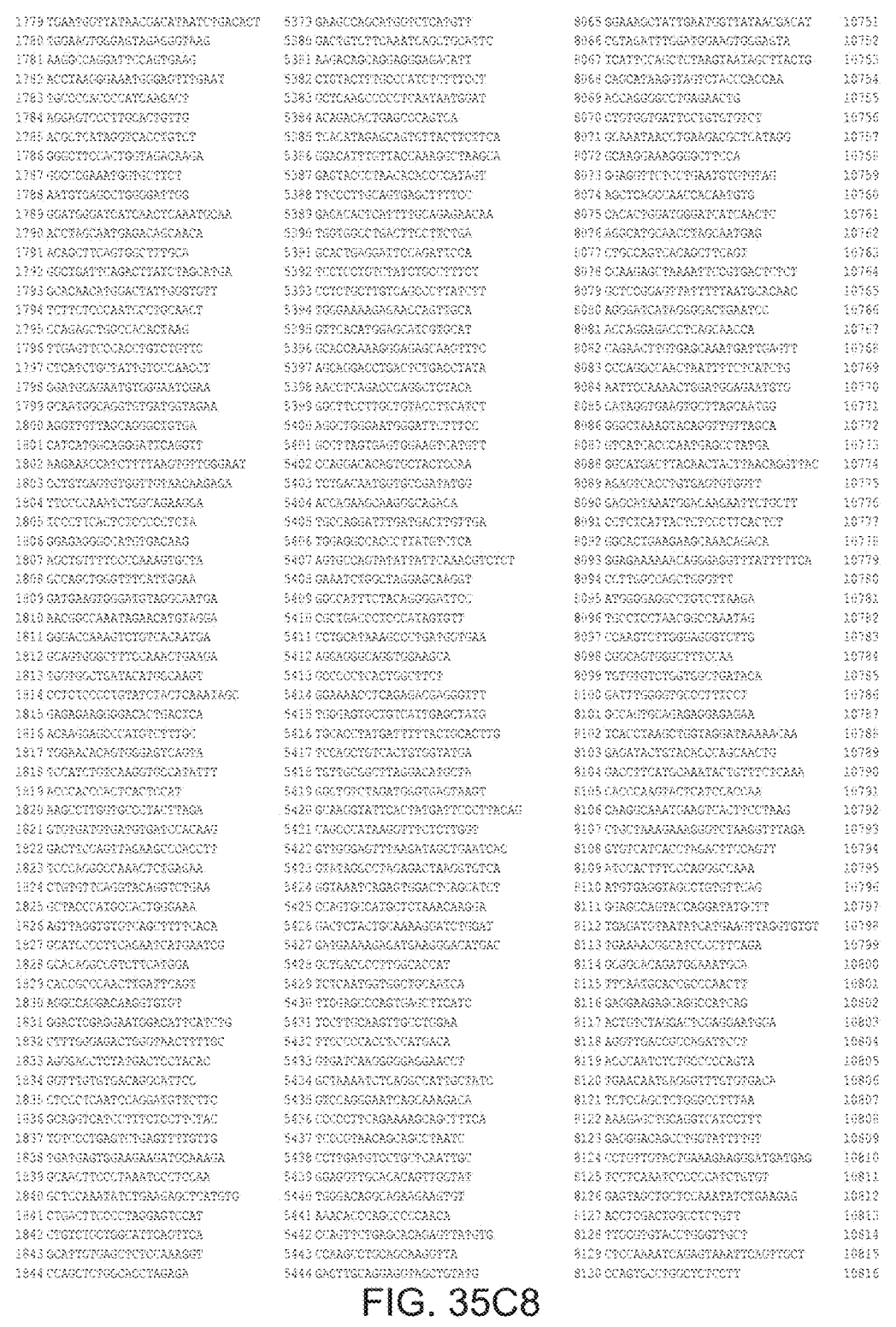
Figure 35C9:
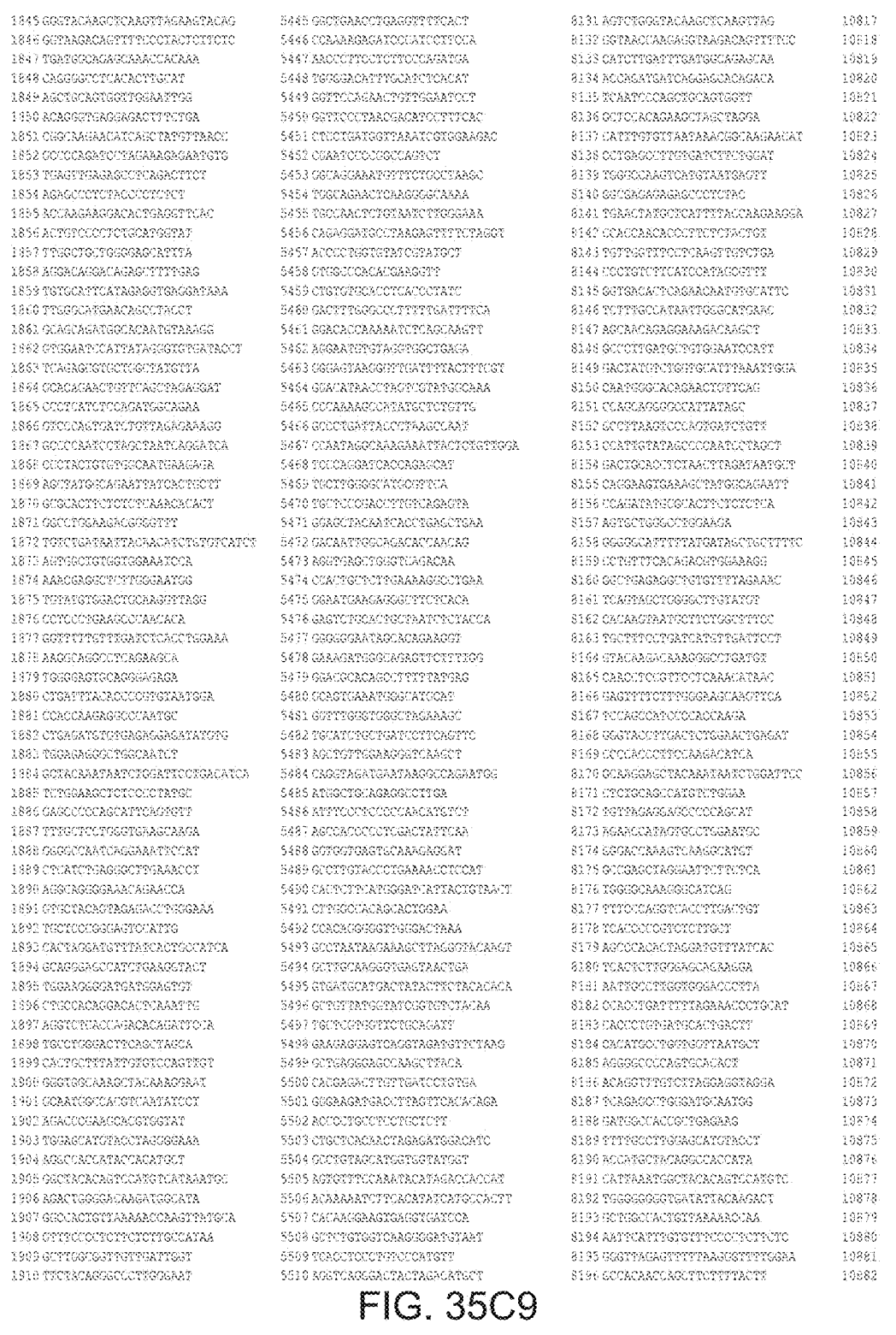
Figure 35D1:
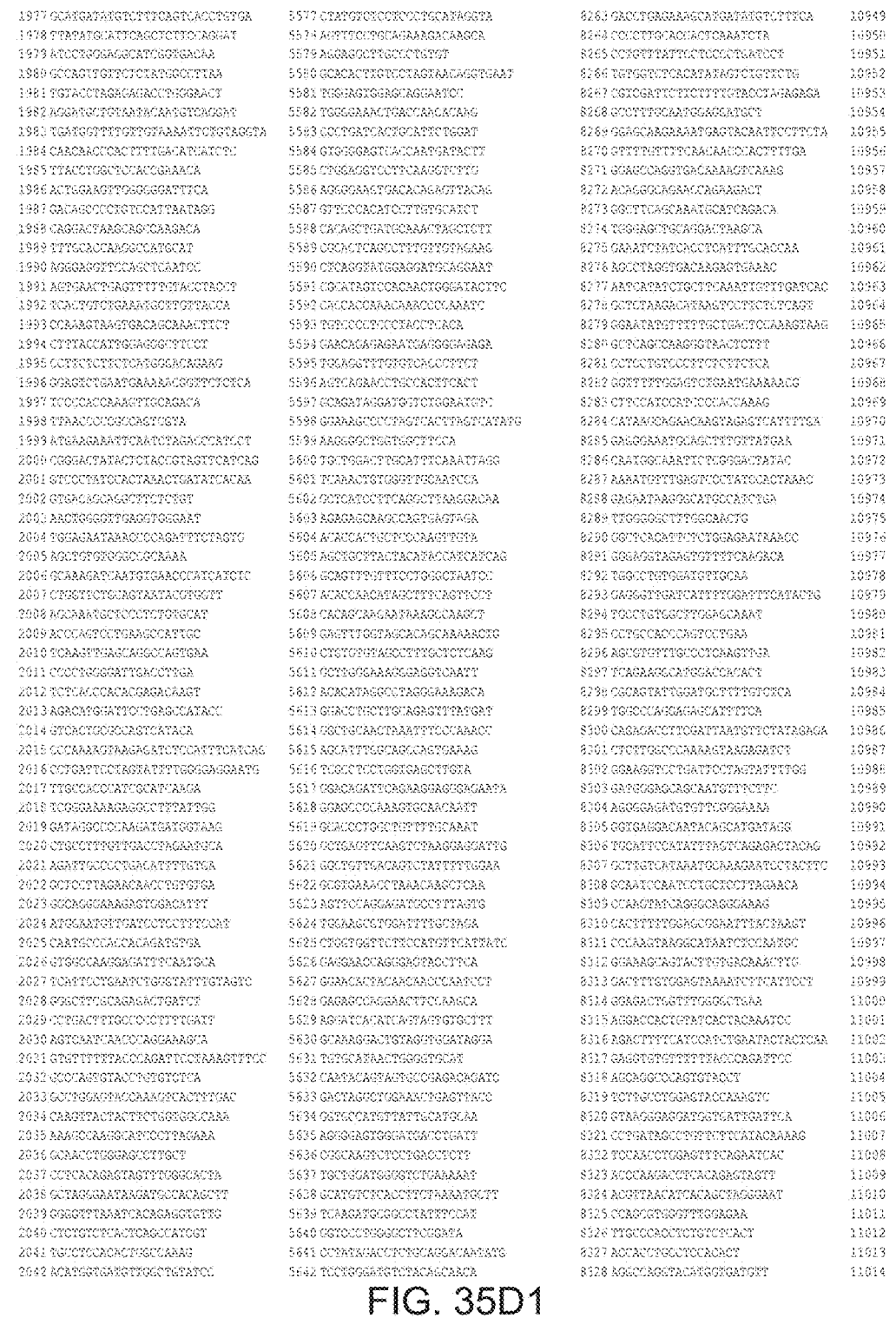
Figure 35D4:
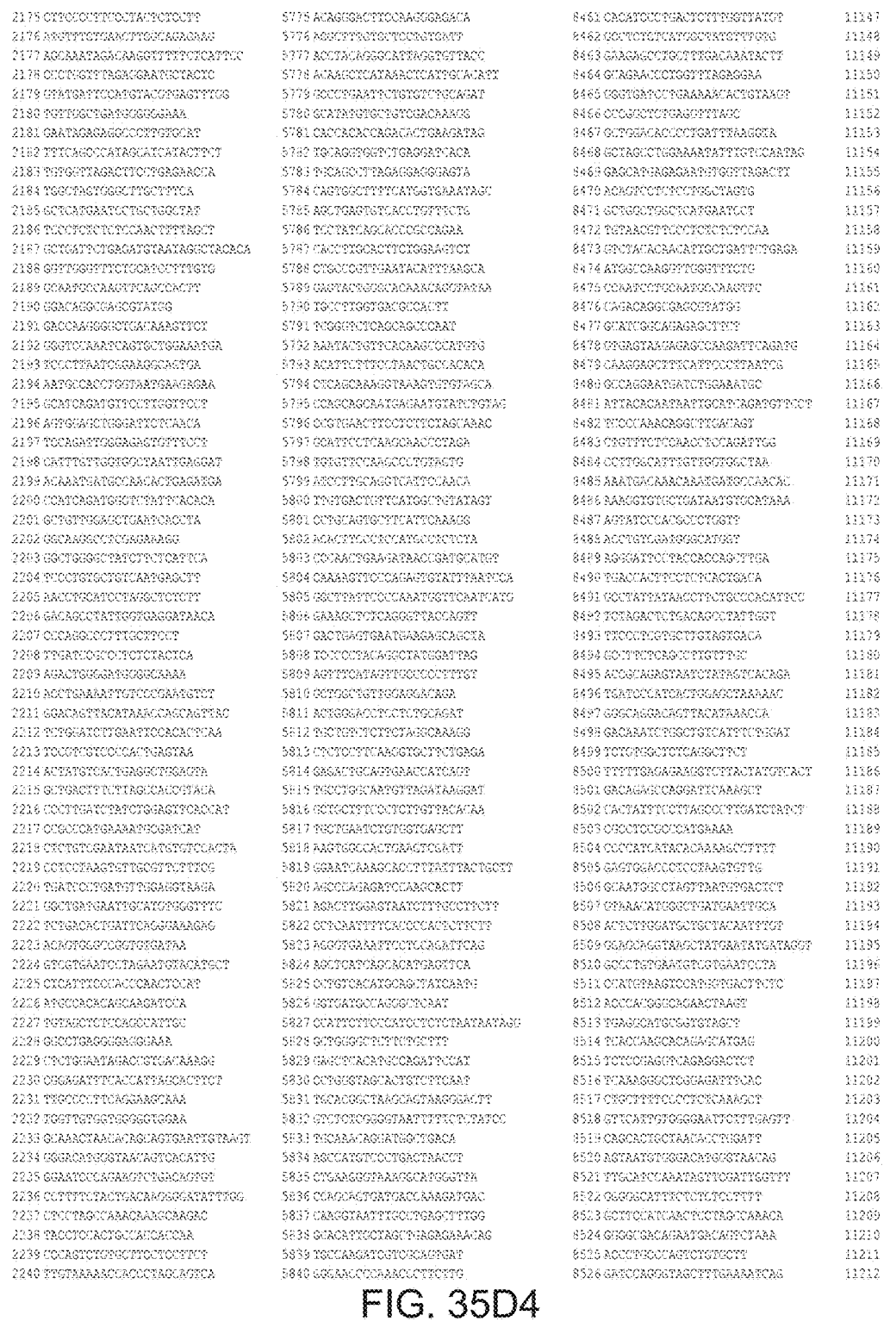
Figure 35D5:
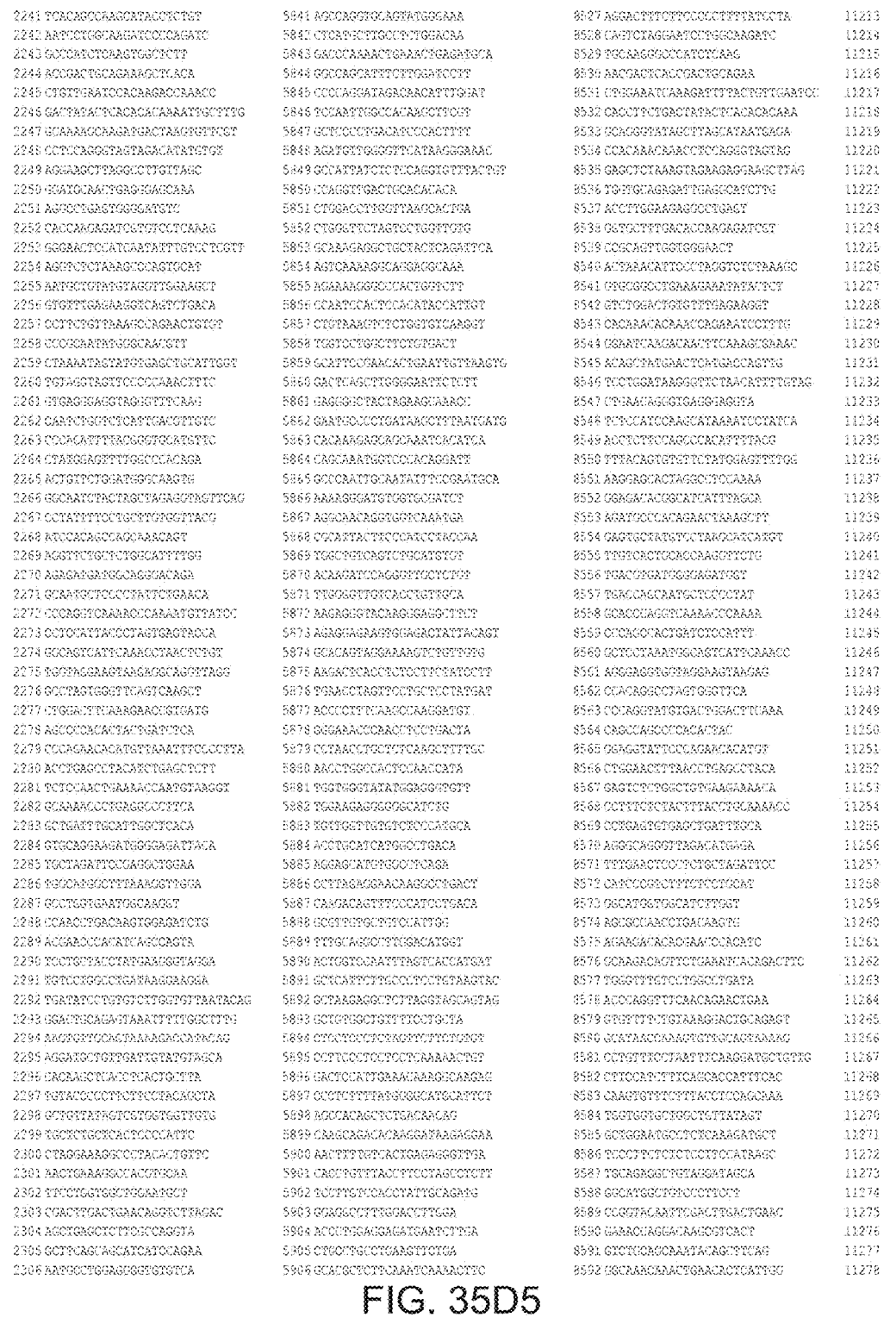
Figure 35D6:
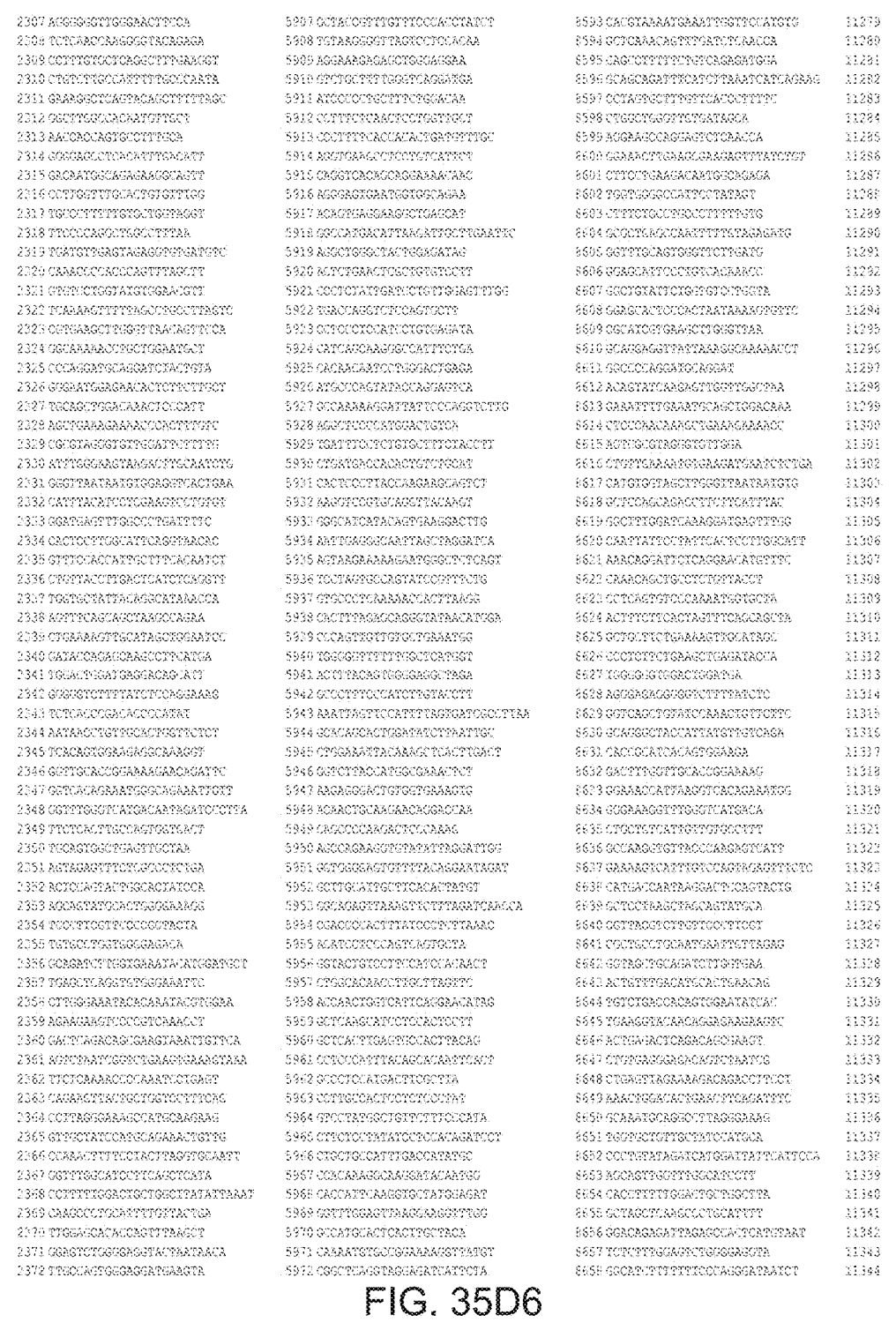
Figure 35D7:
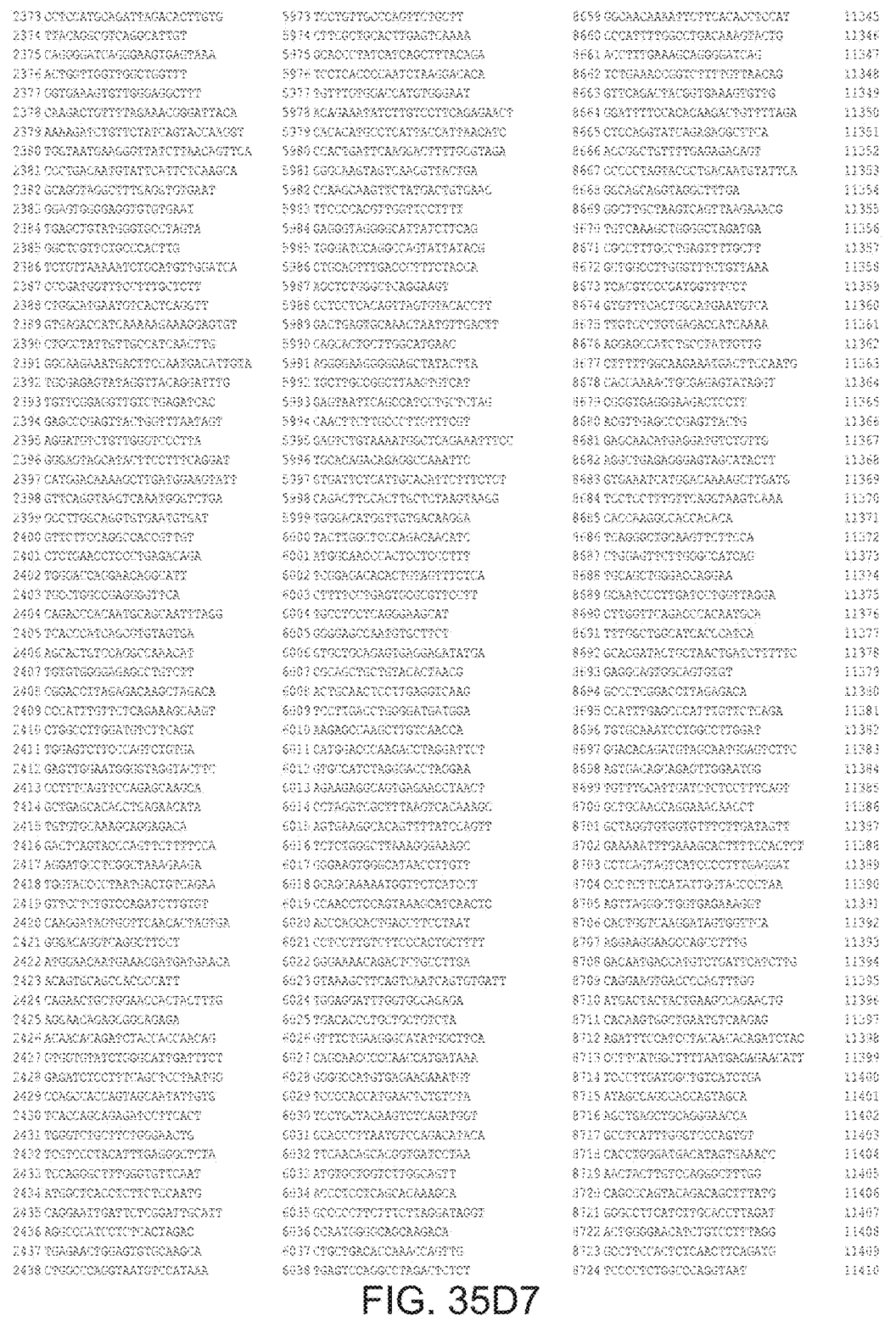
Figure 35D8:
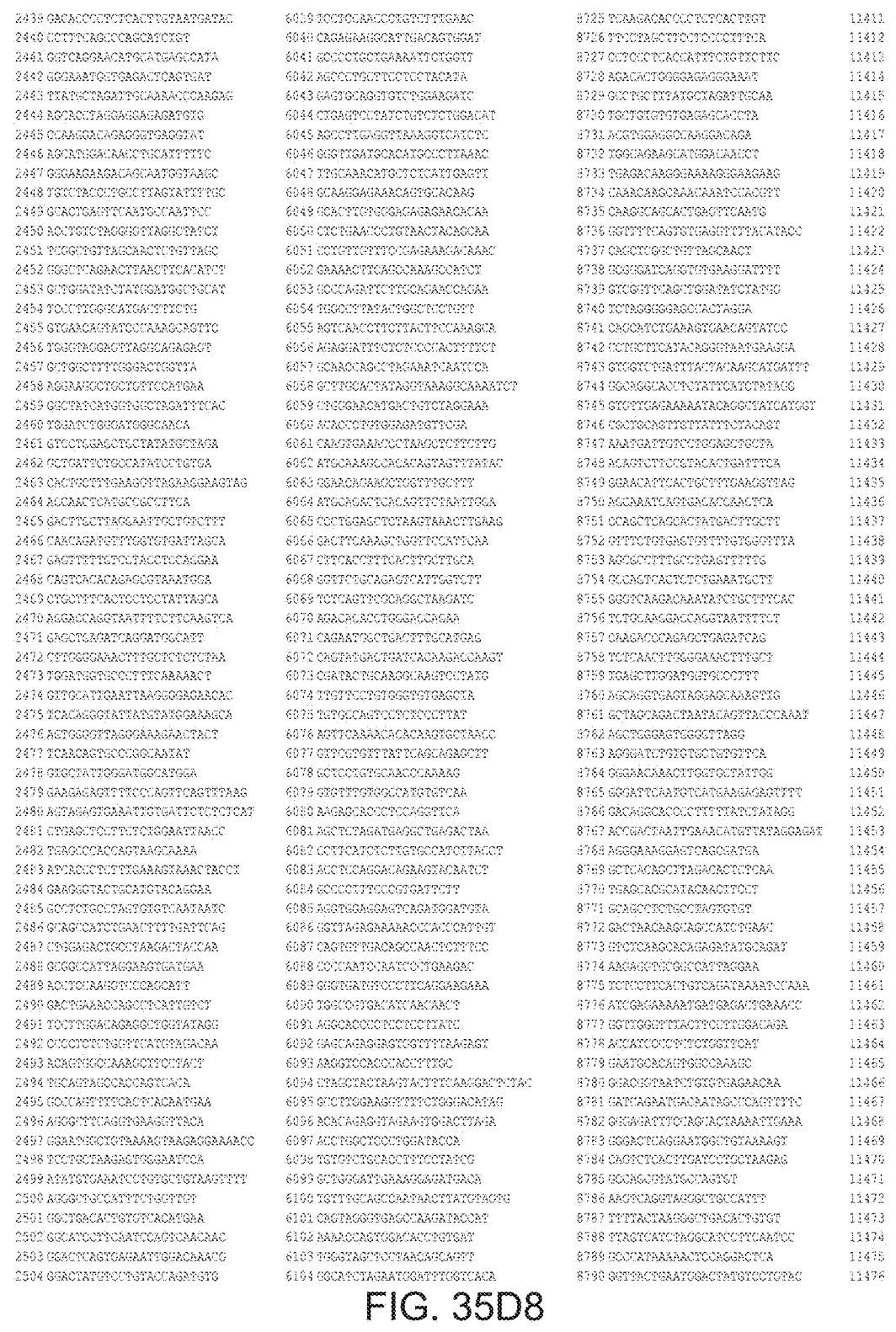
Figure 35D9:
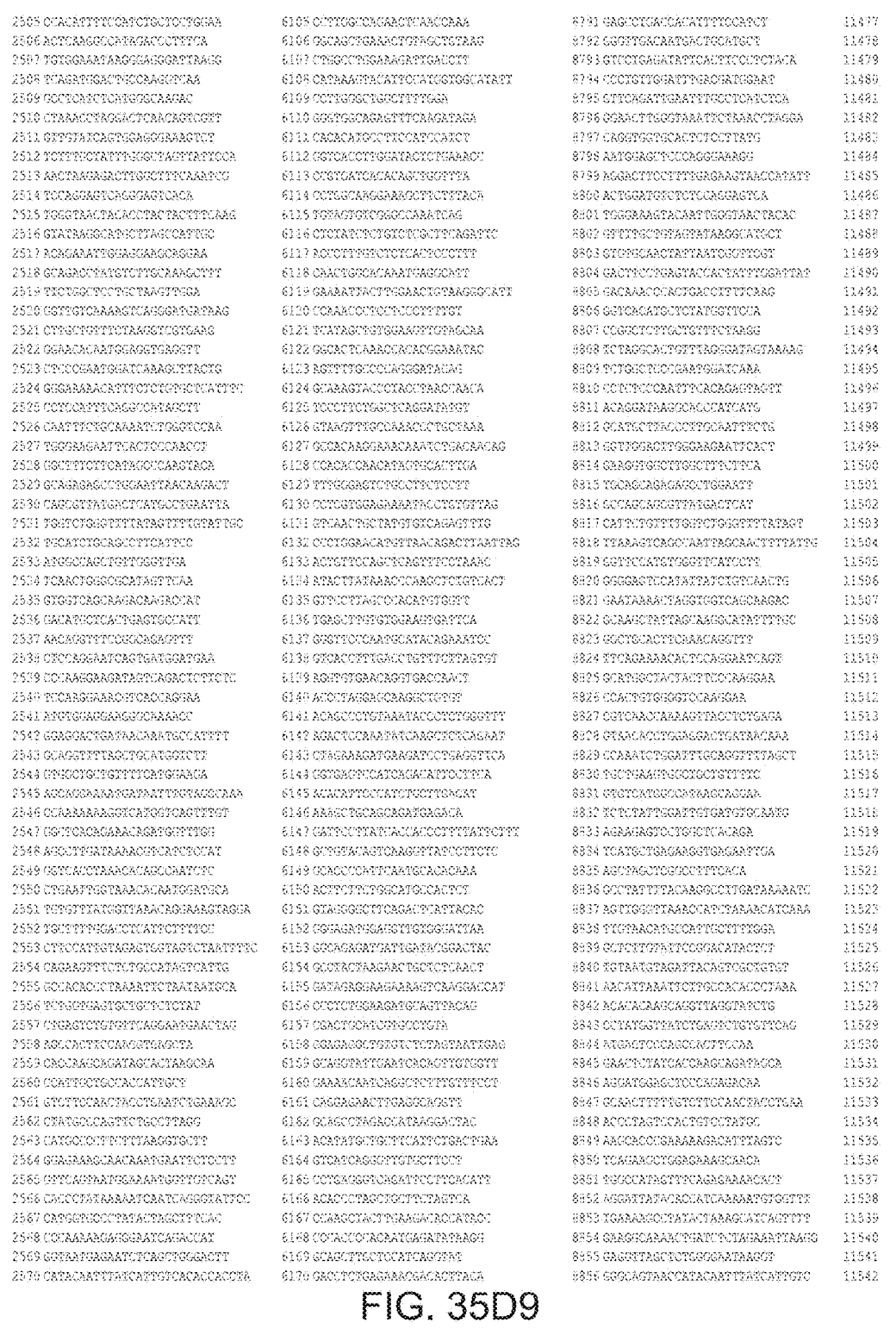
Figure 35D10:
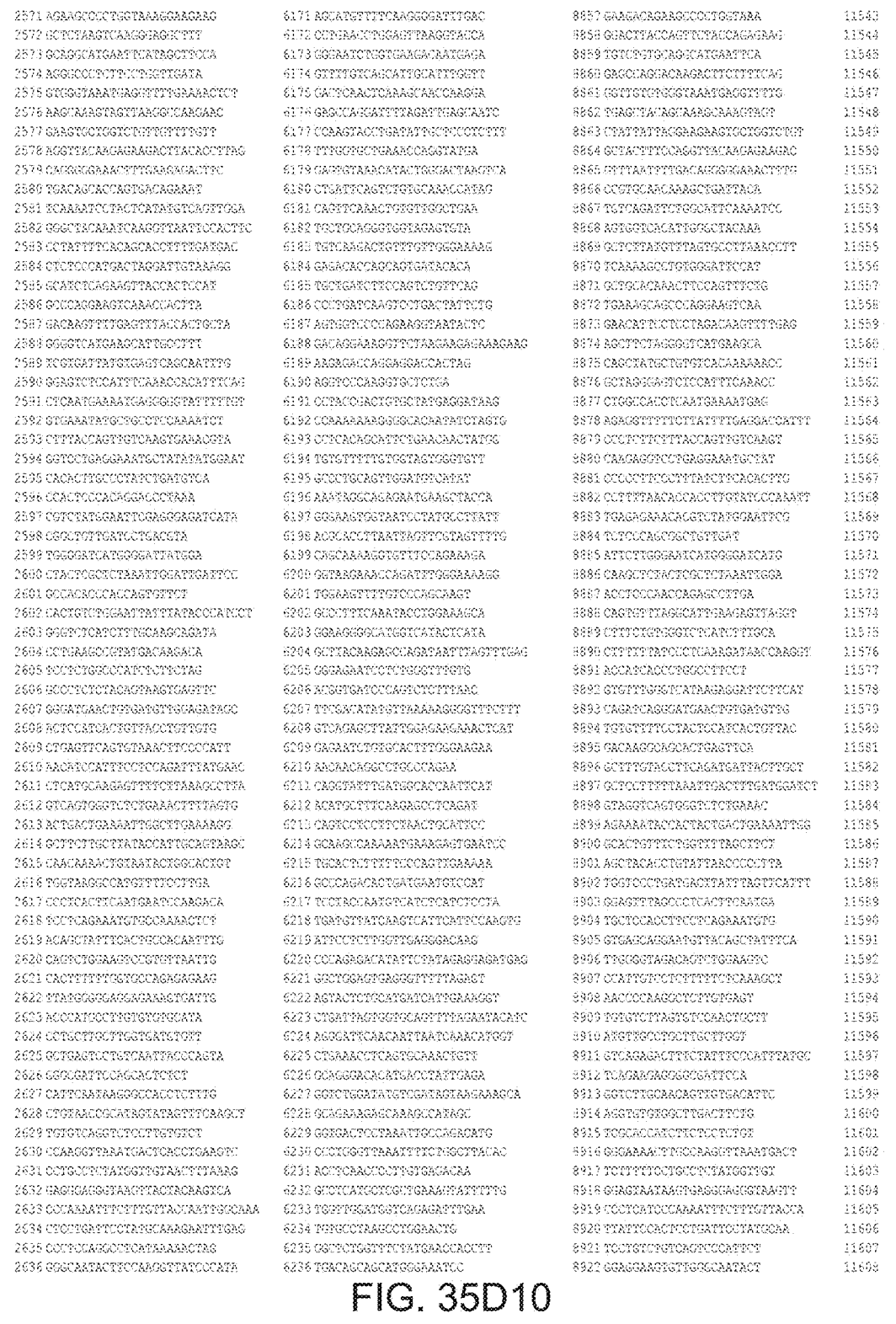

FIG. 35A1-E1: Sequences of an exemplary 2,686-plex primer library (SEQ ID NOs. 3,601-11,658). The three primers (one from pool A, one from pool B, and one from pool C) in each row all hybridize to the same target locus.

Figure 36A2:
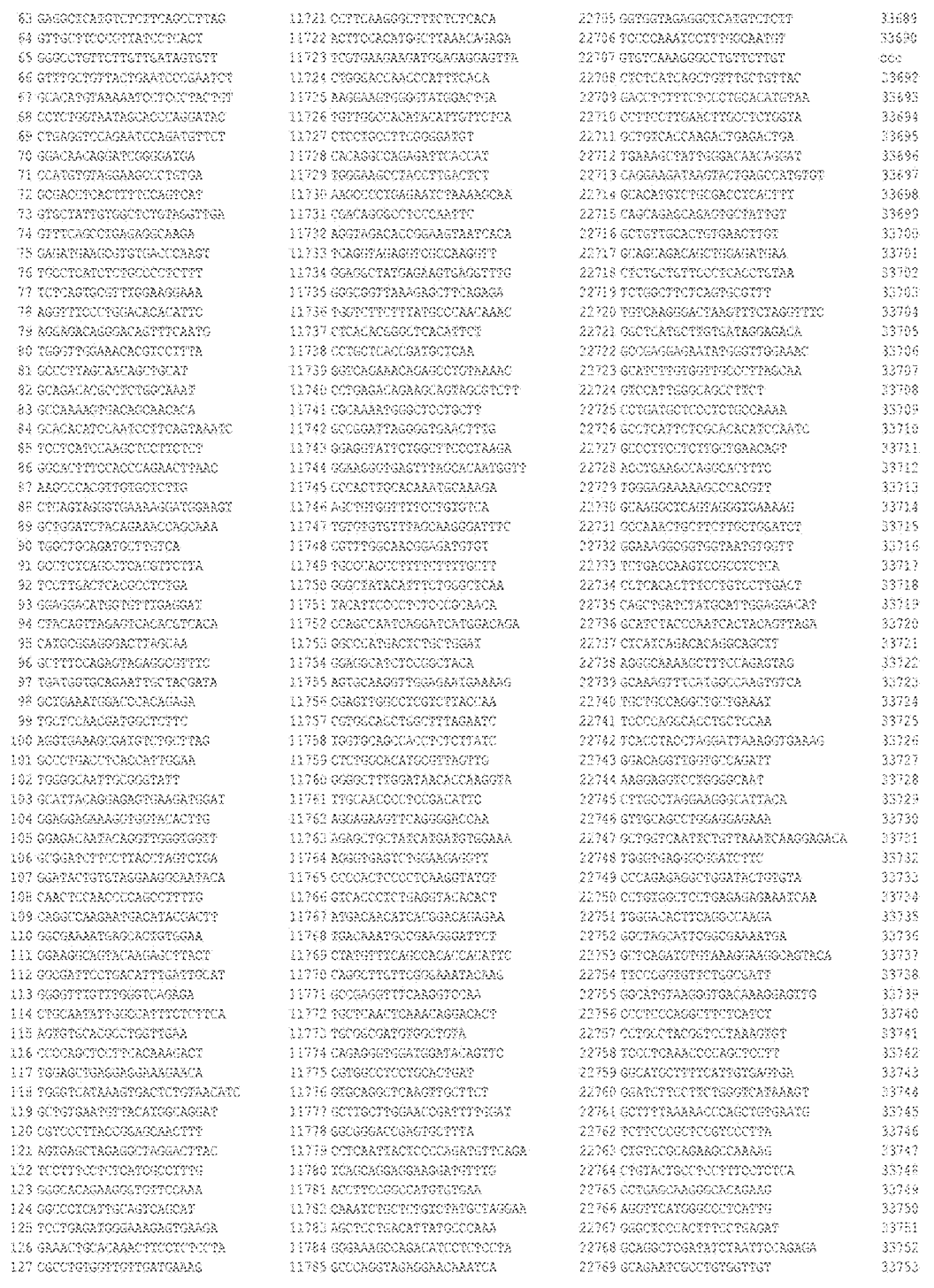
Figure 36A3:
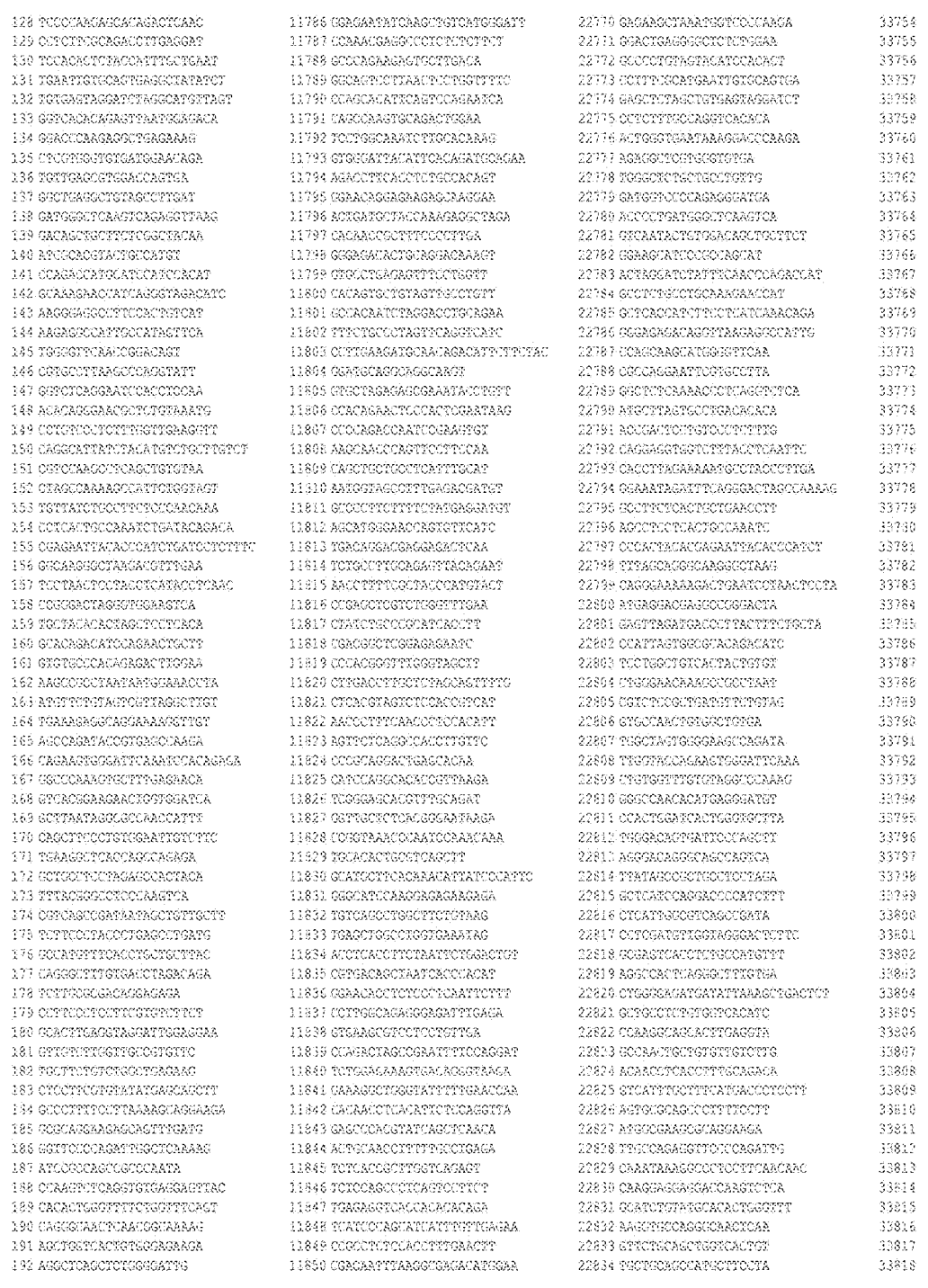
Figure 36A4:
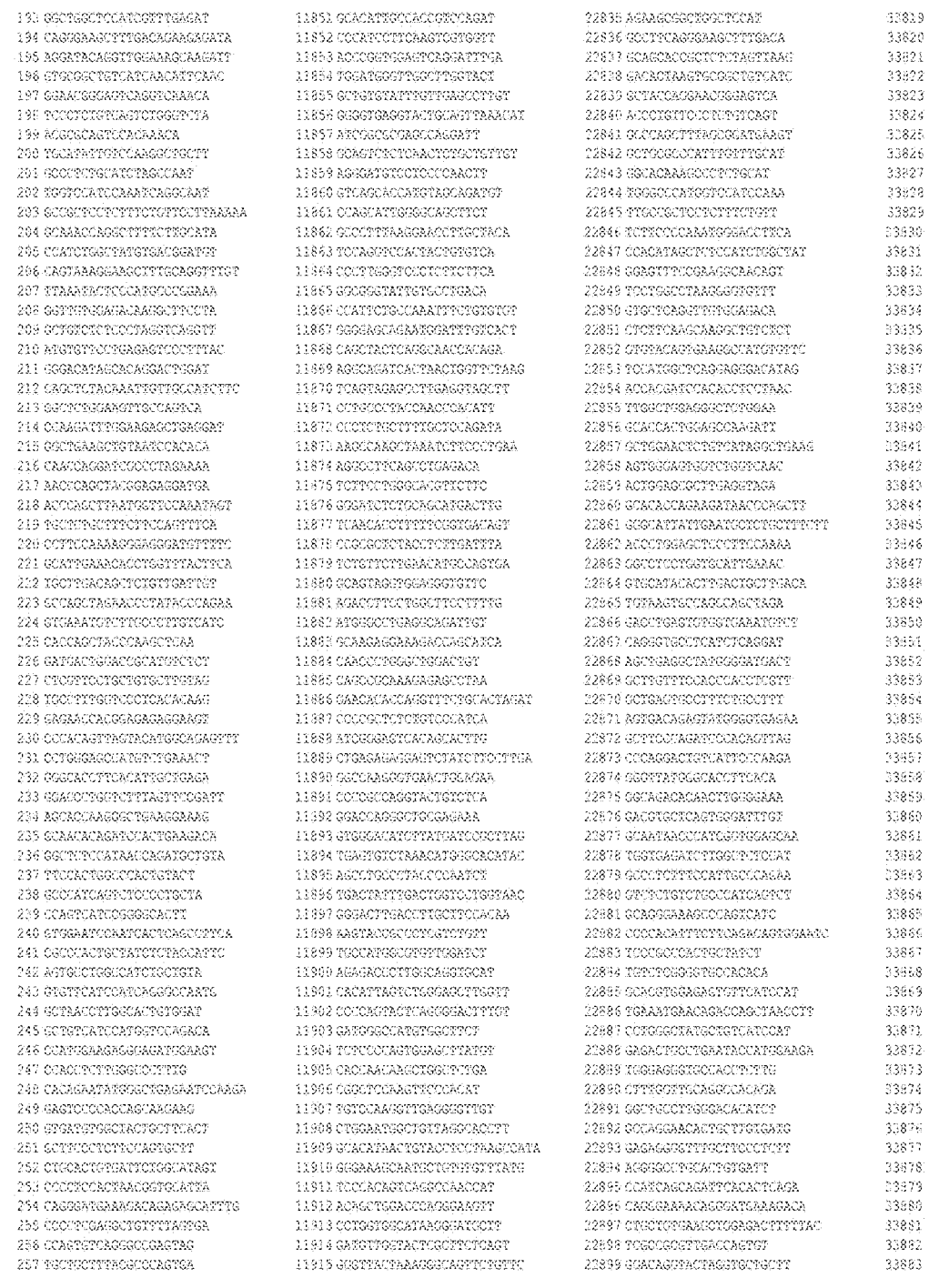
Figure 36A5:
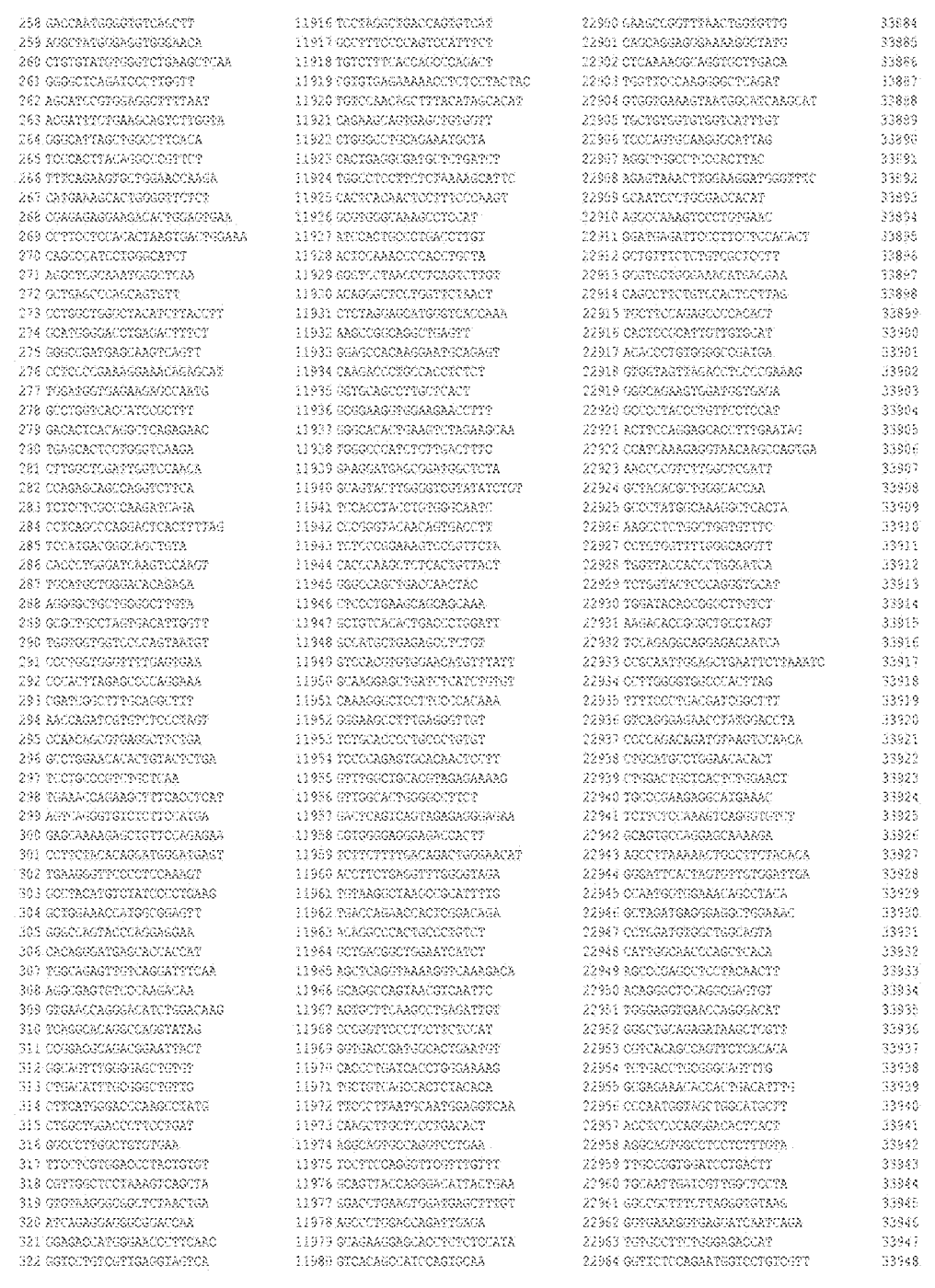
Figure 36A6:
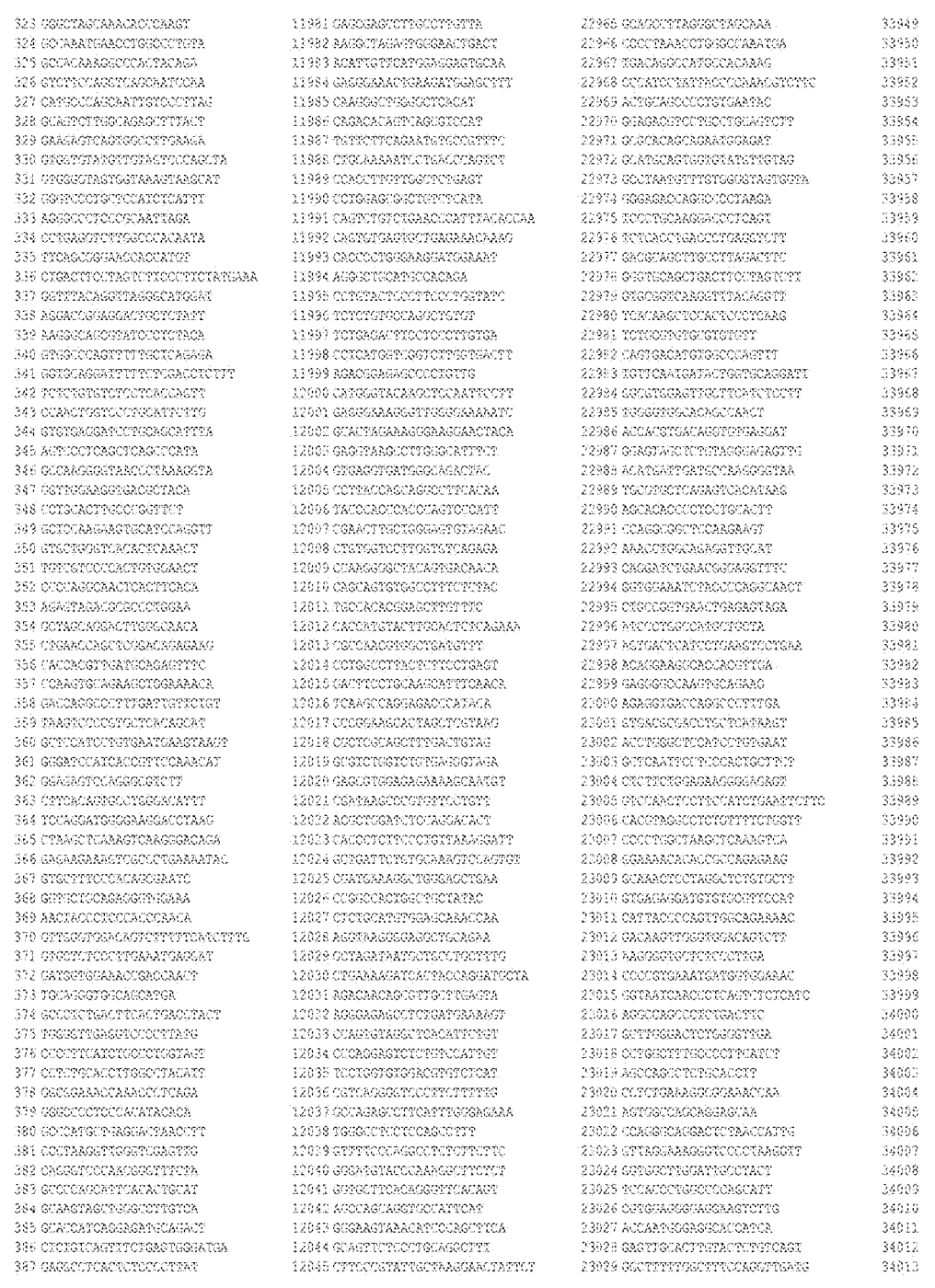
Figure 36A7:
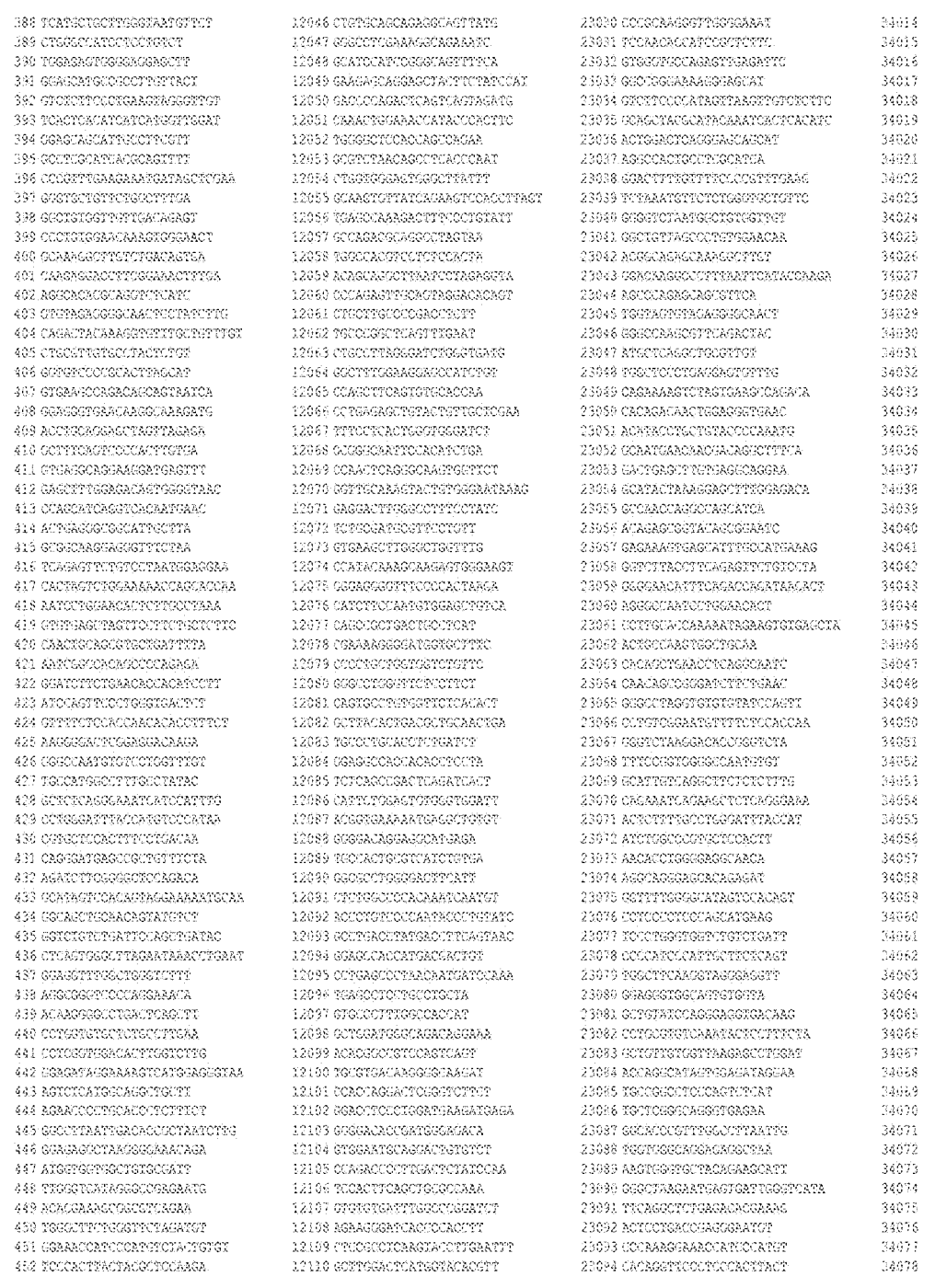
Figure 36A8:
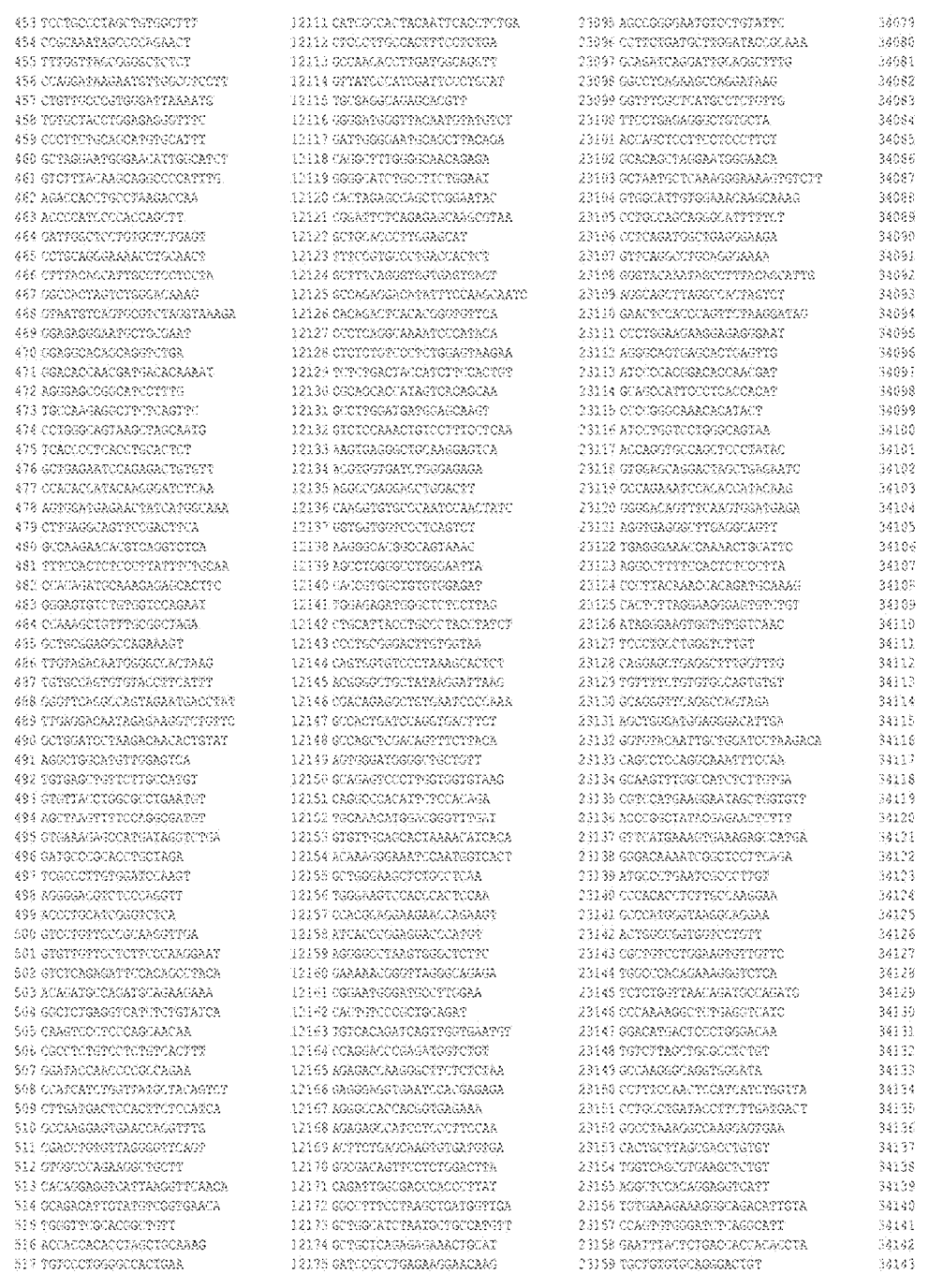
Figure 36A9:
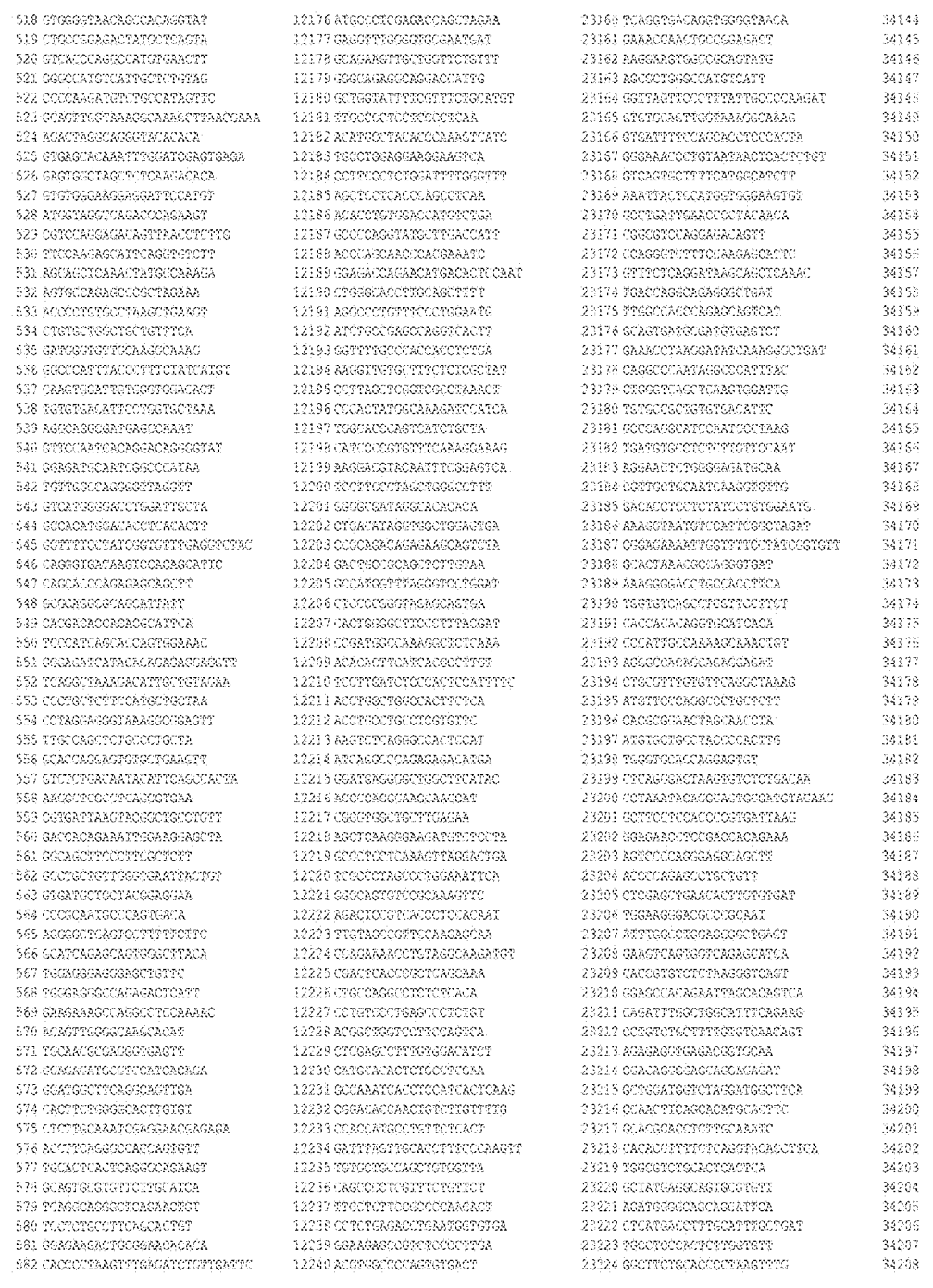
Figure 36A10:
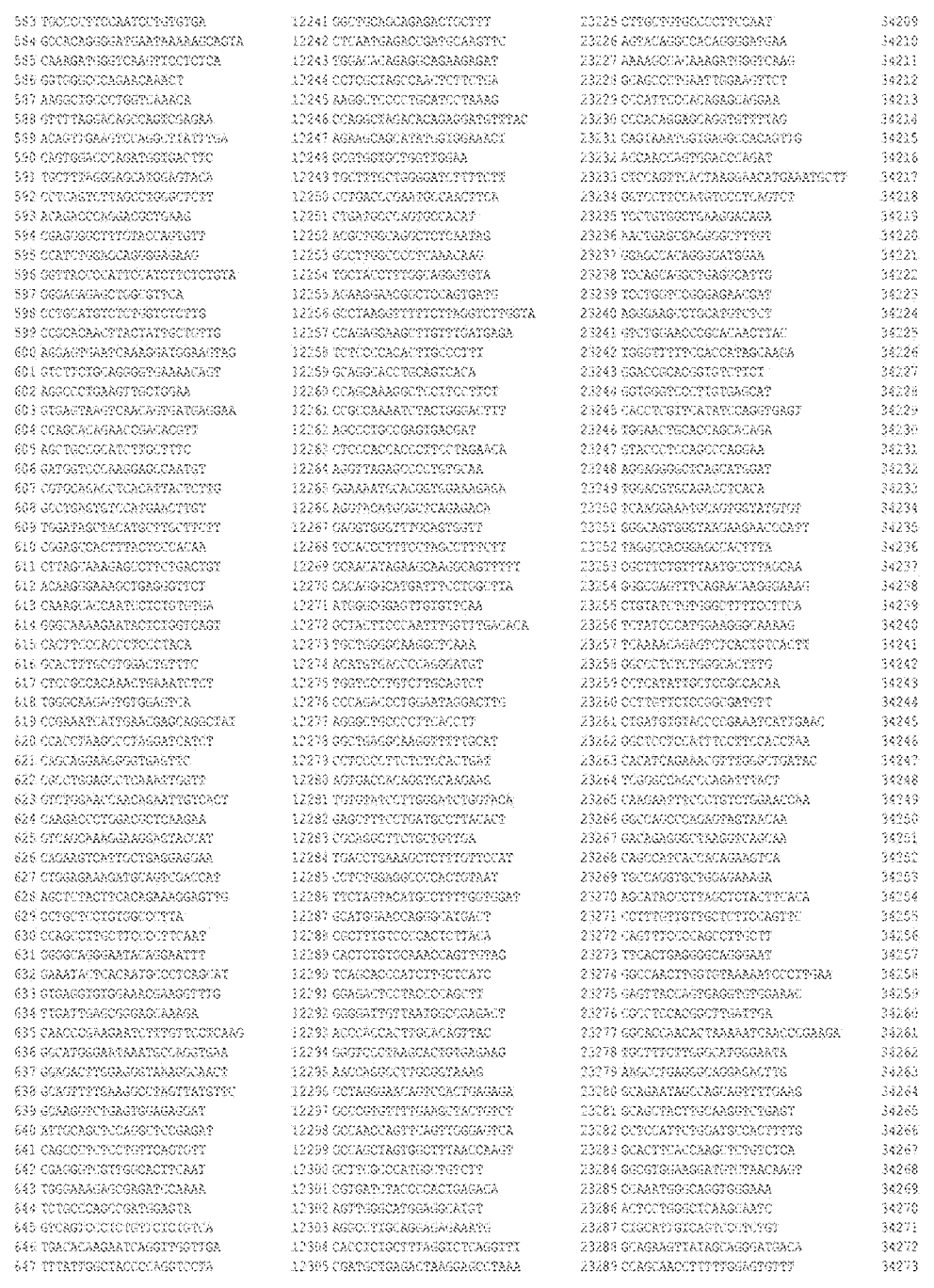
Figure 36B1:
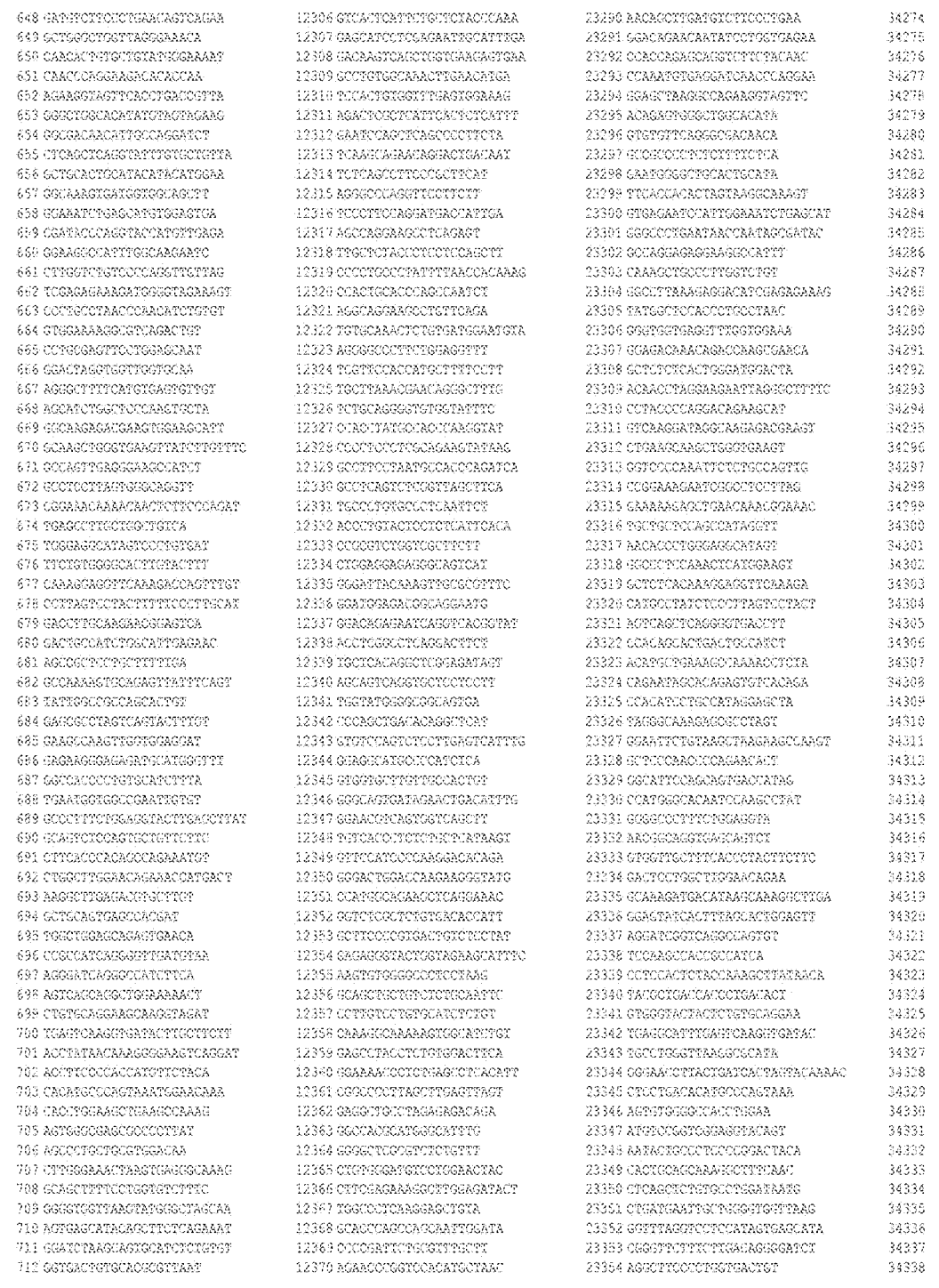
Figure 36B2:
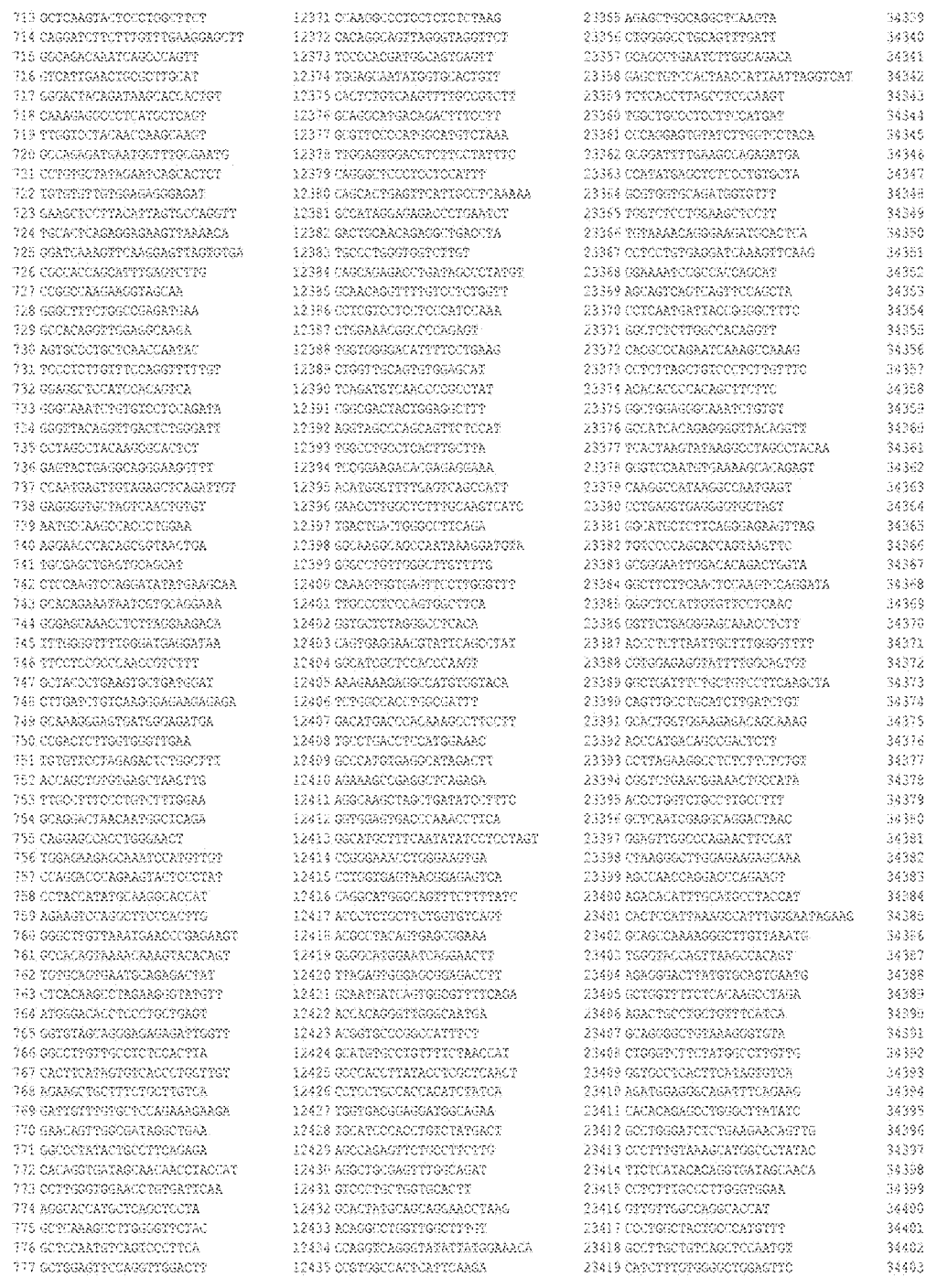
Figure 36B3:
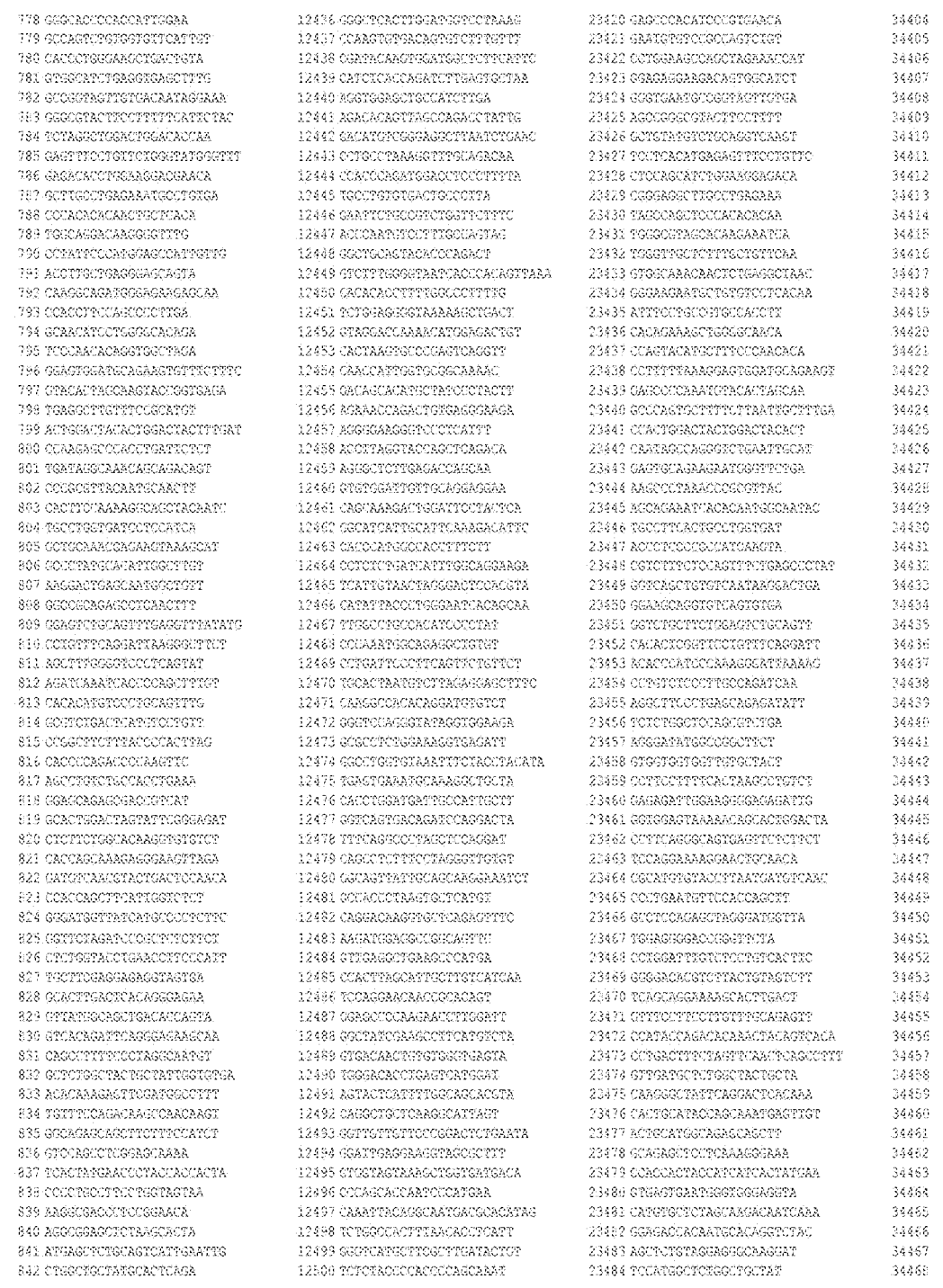
Figure 36B4:
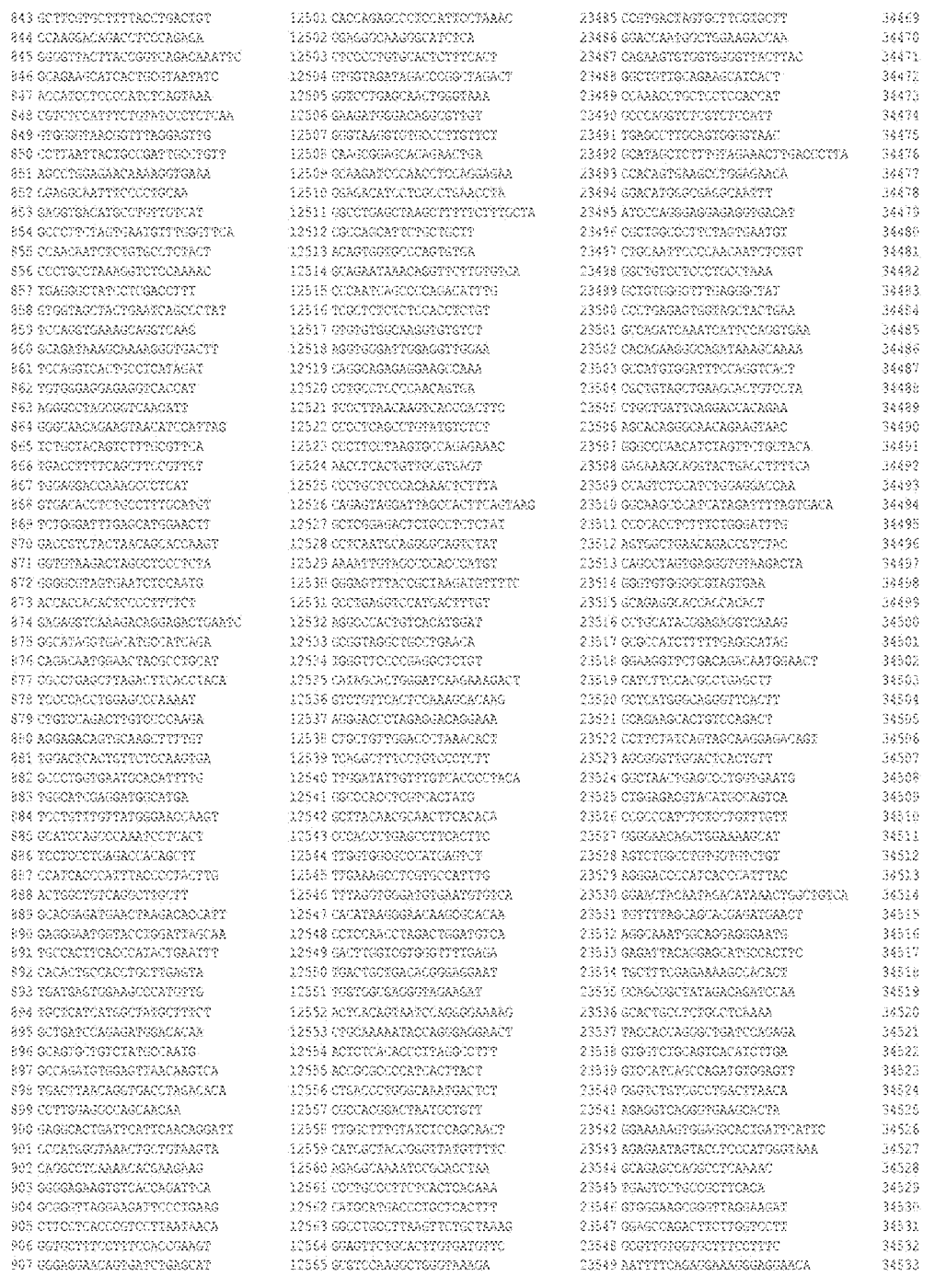
Figure 36B5:
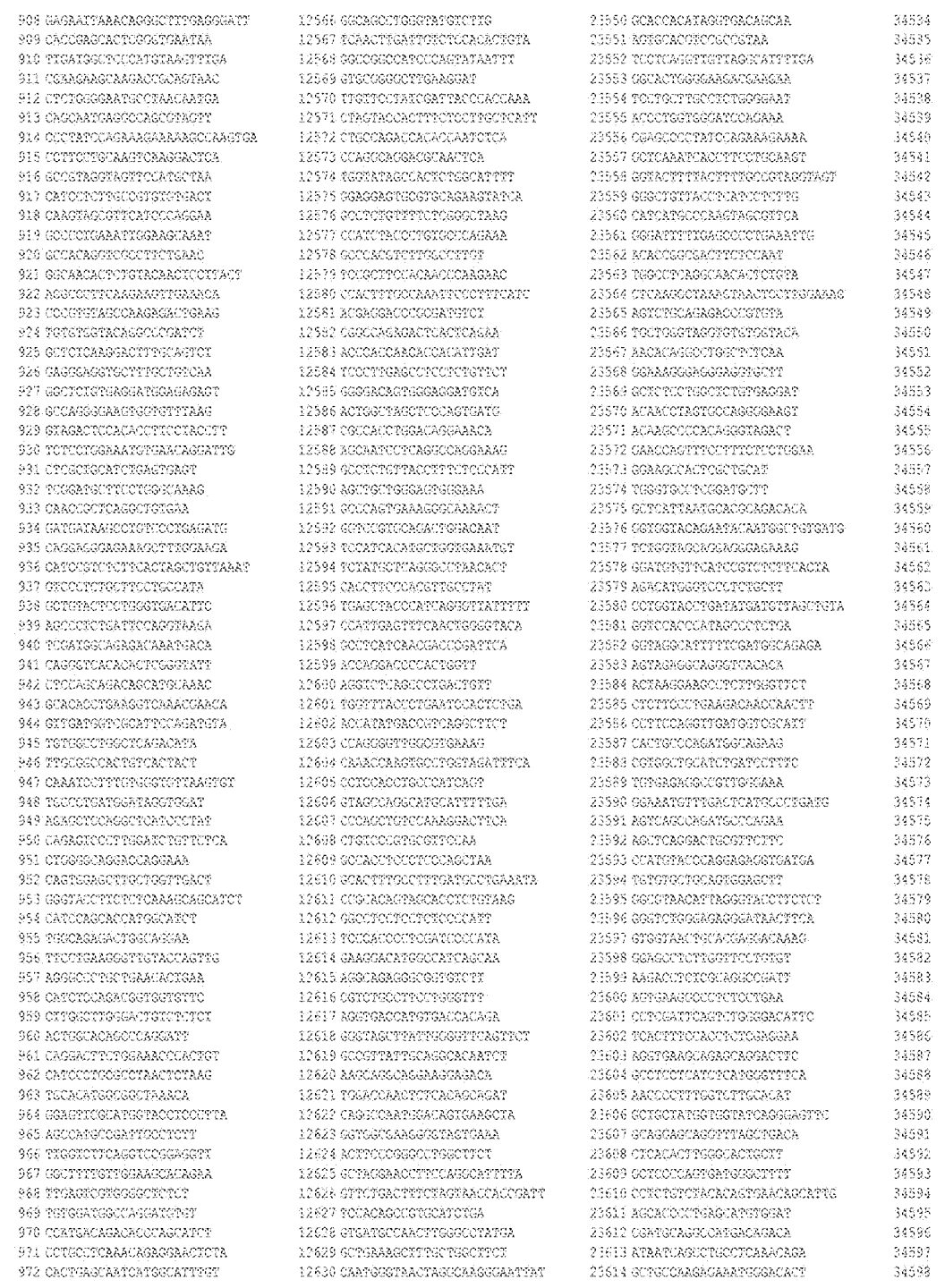
Figure 36B6:
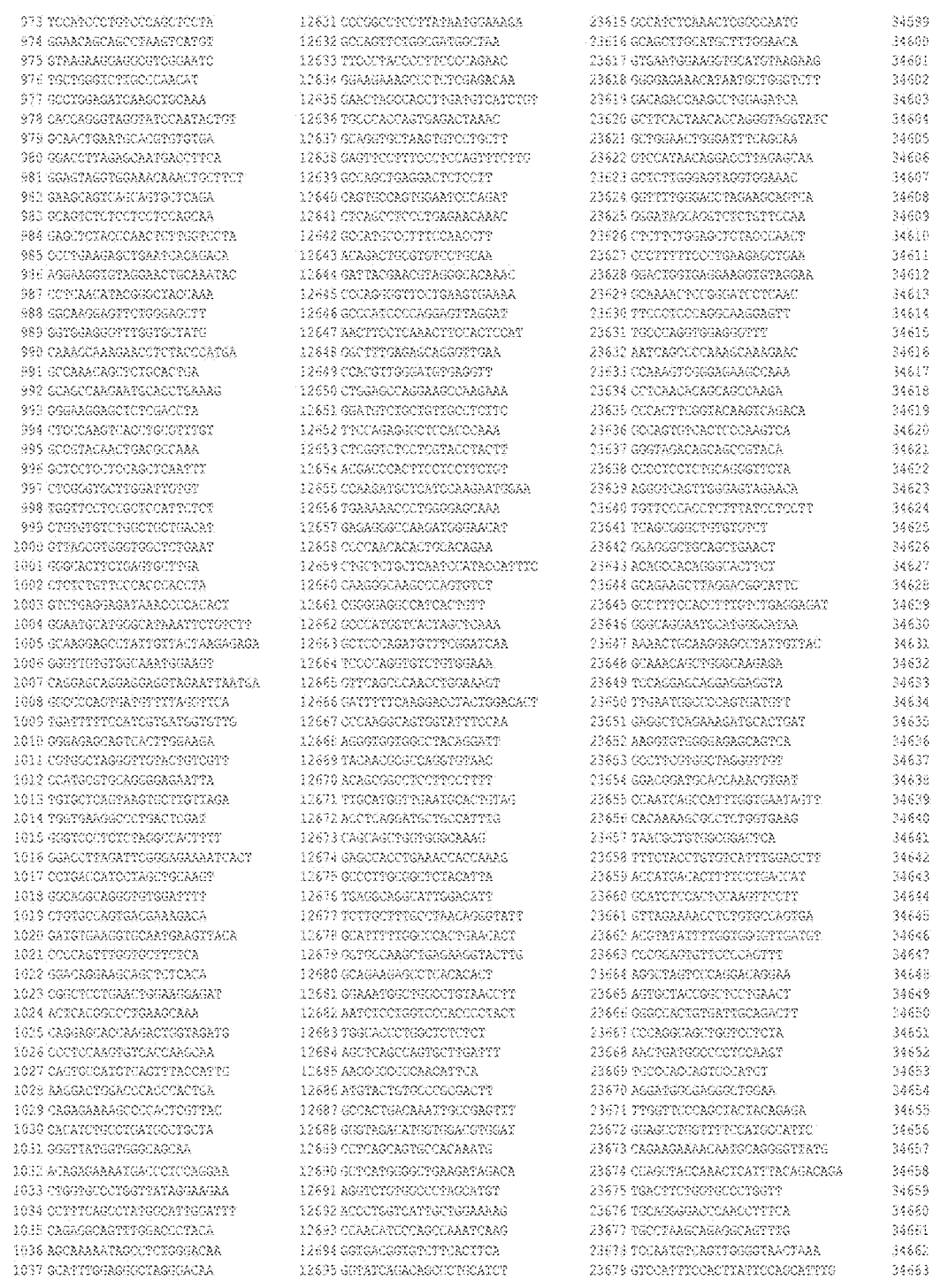
Figure 36B7:
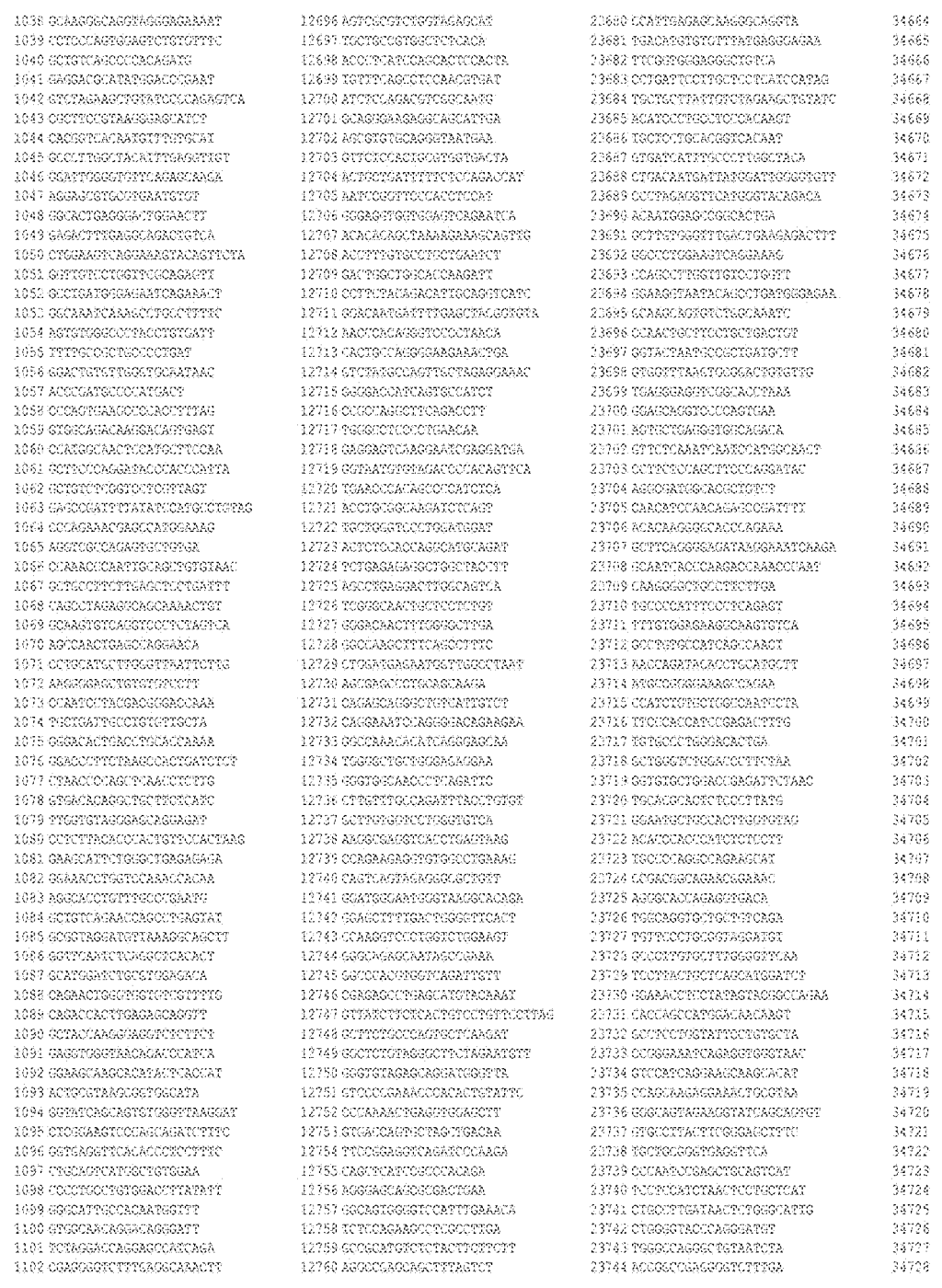
Figure 36B8:
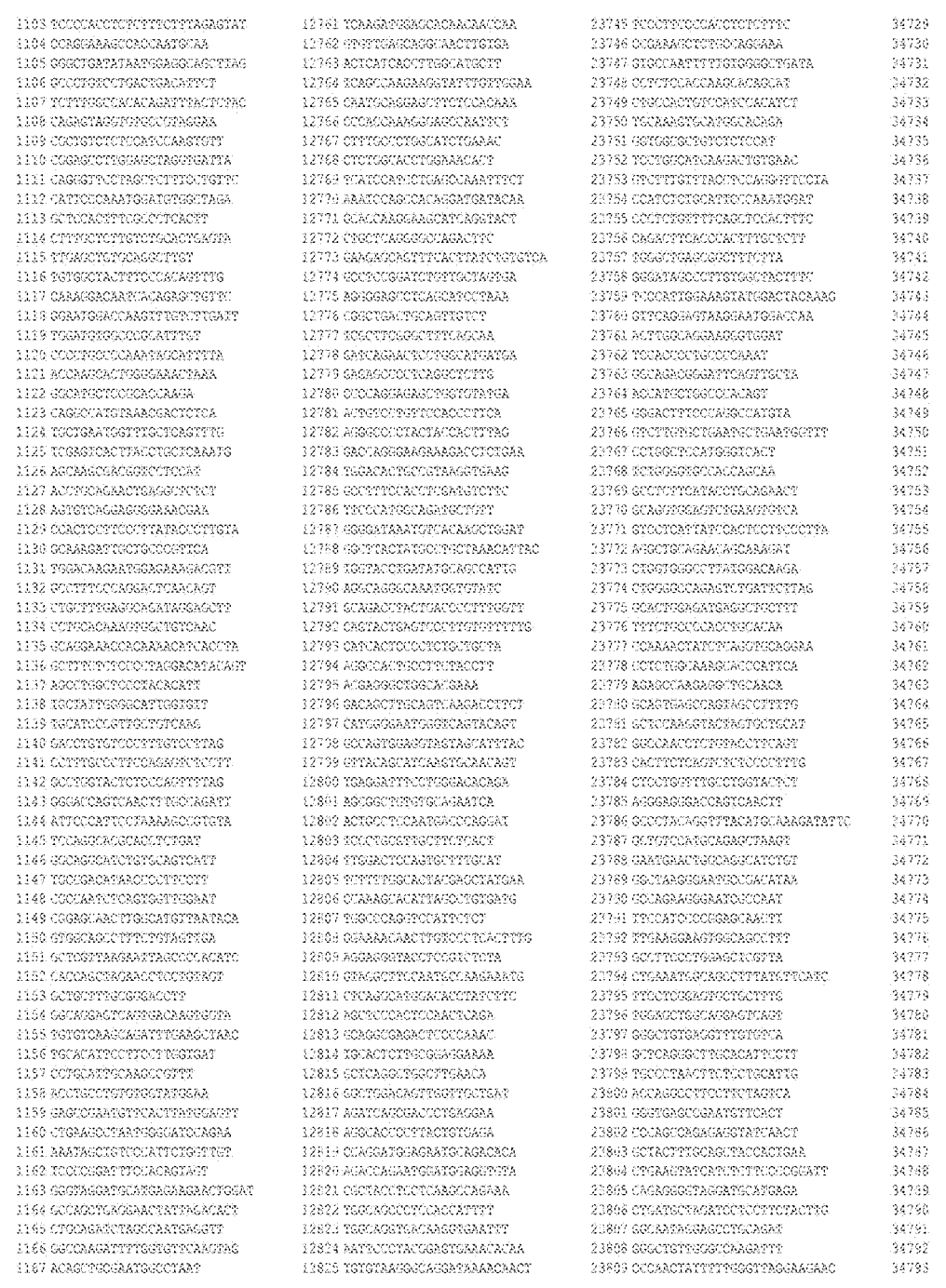
Figure 36B9:
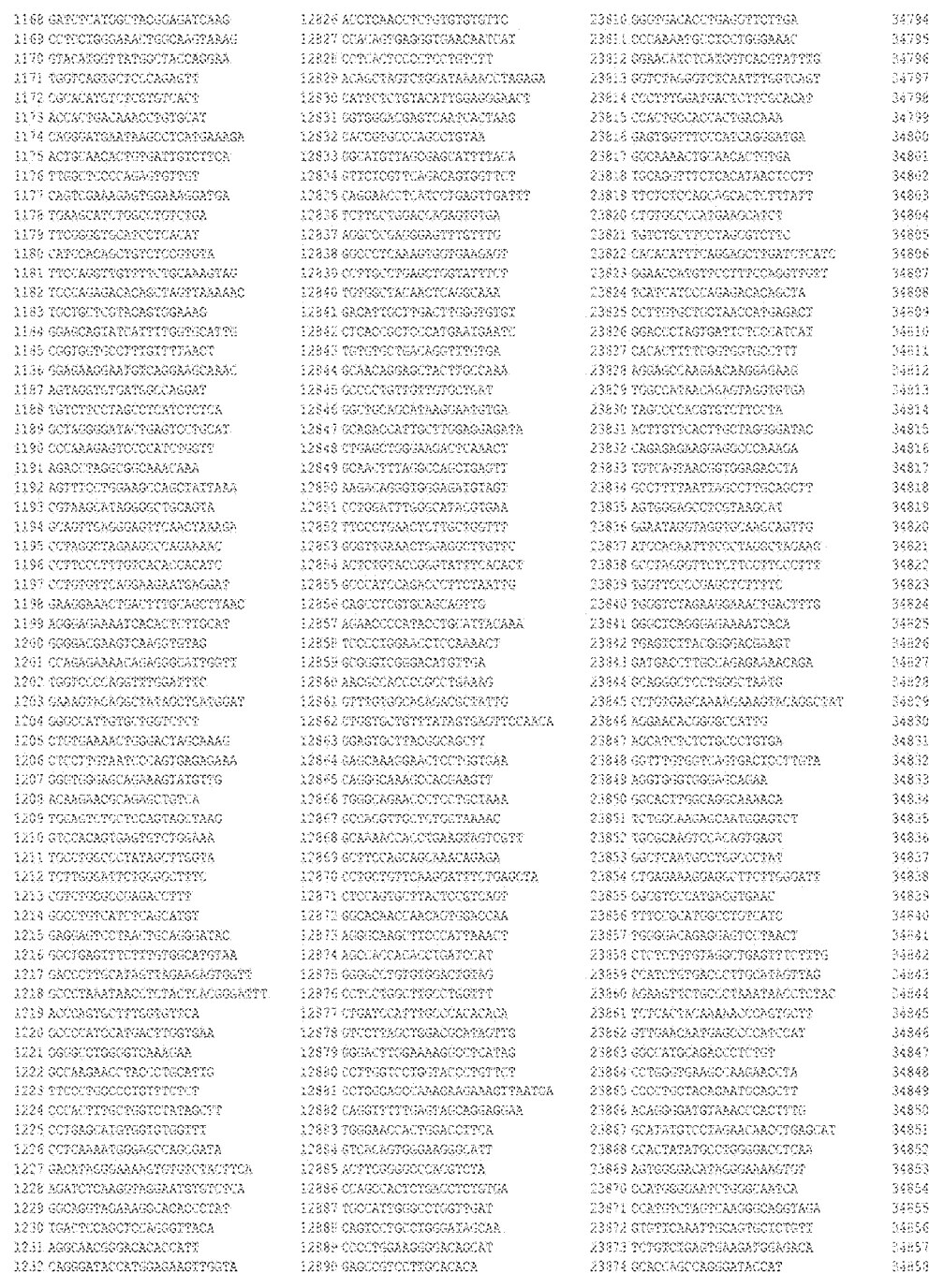
Figure 36C1:
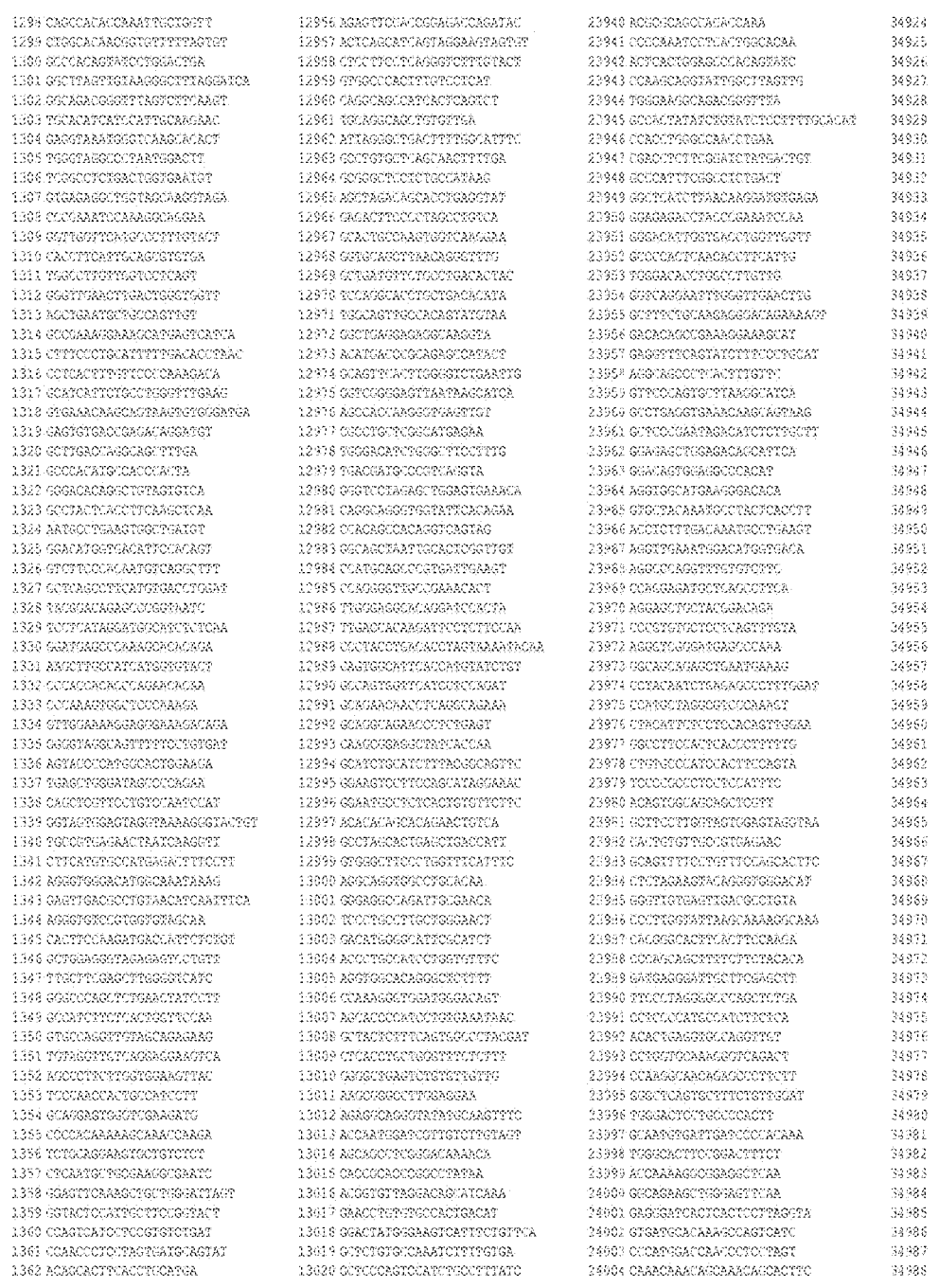
Figure 36C3:
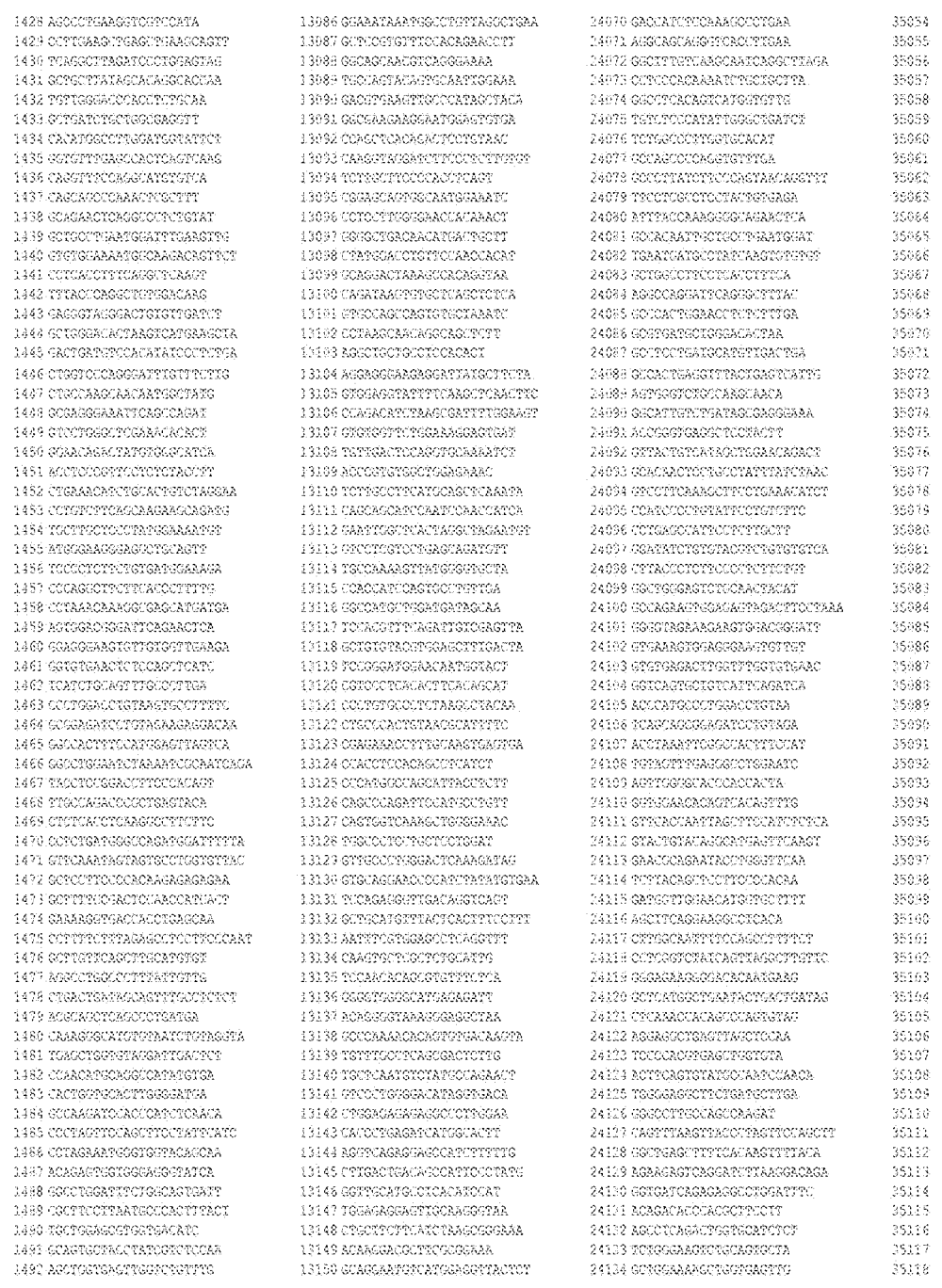
Figure 36C4:
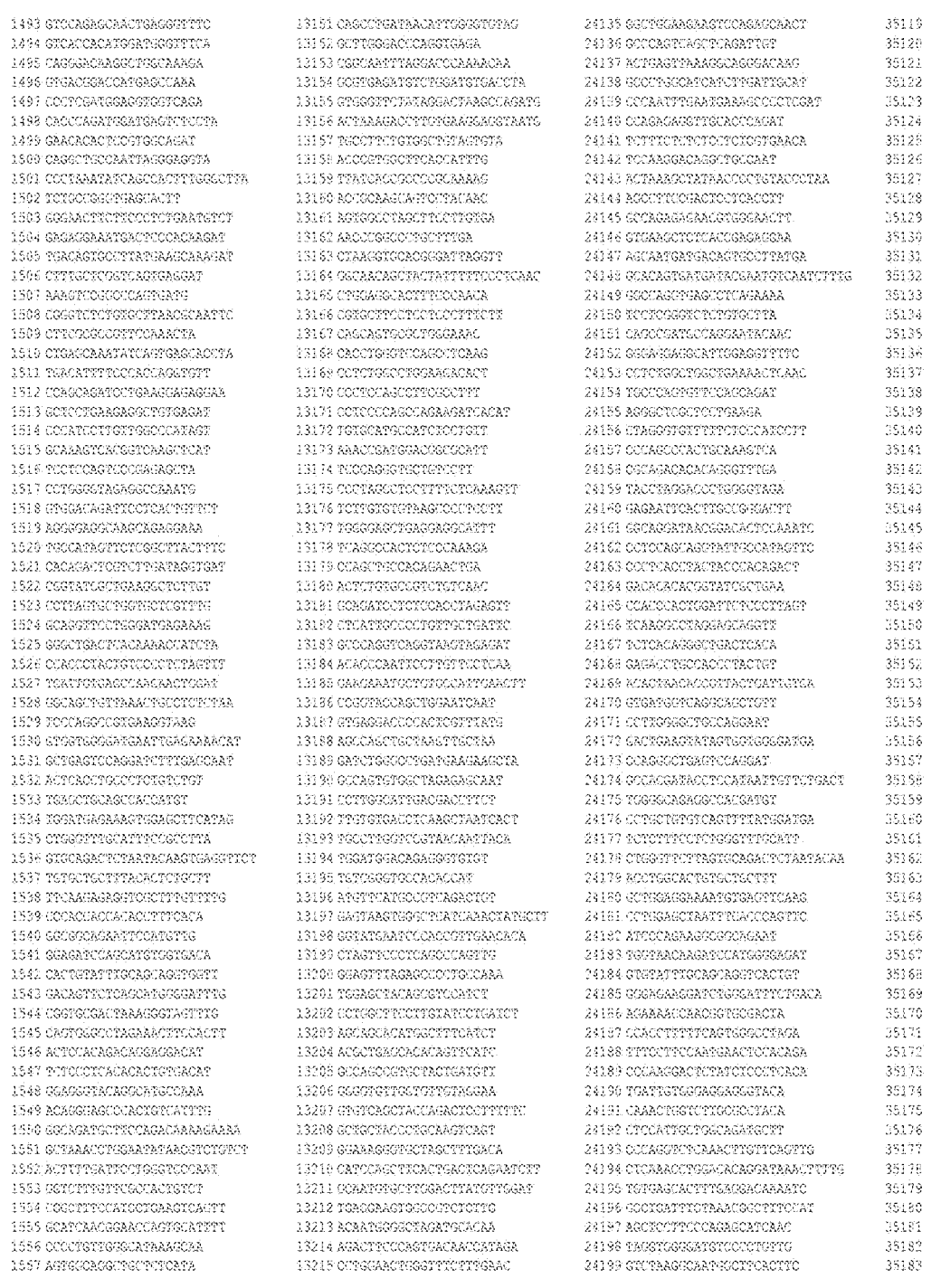
Figure 36C5:
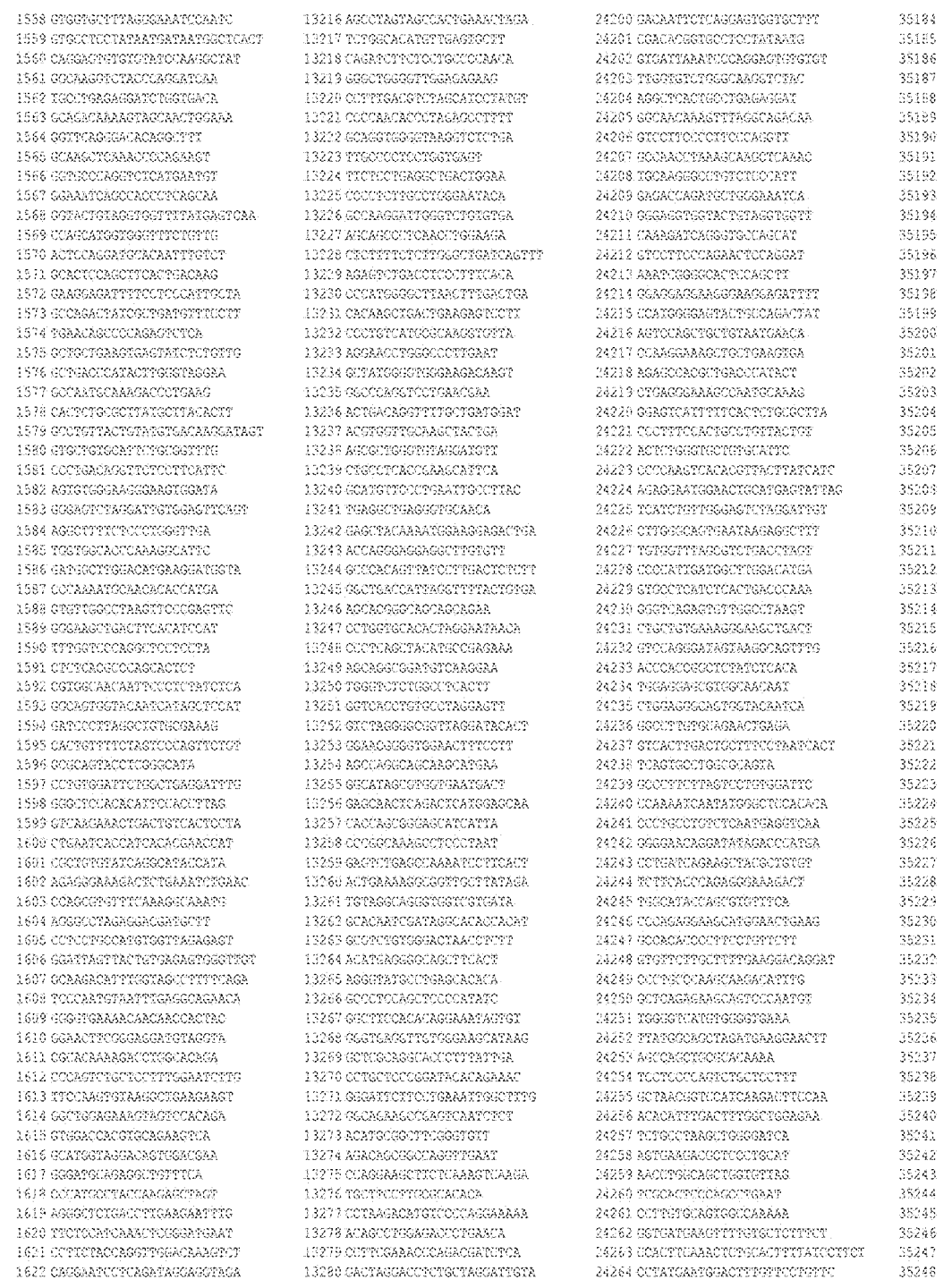
Figure 36C6:
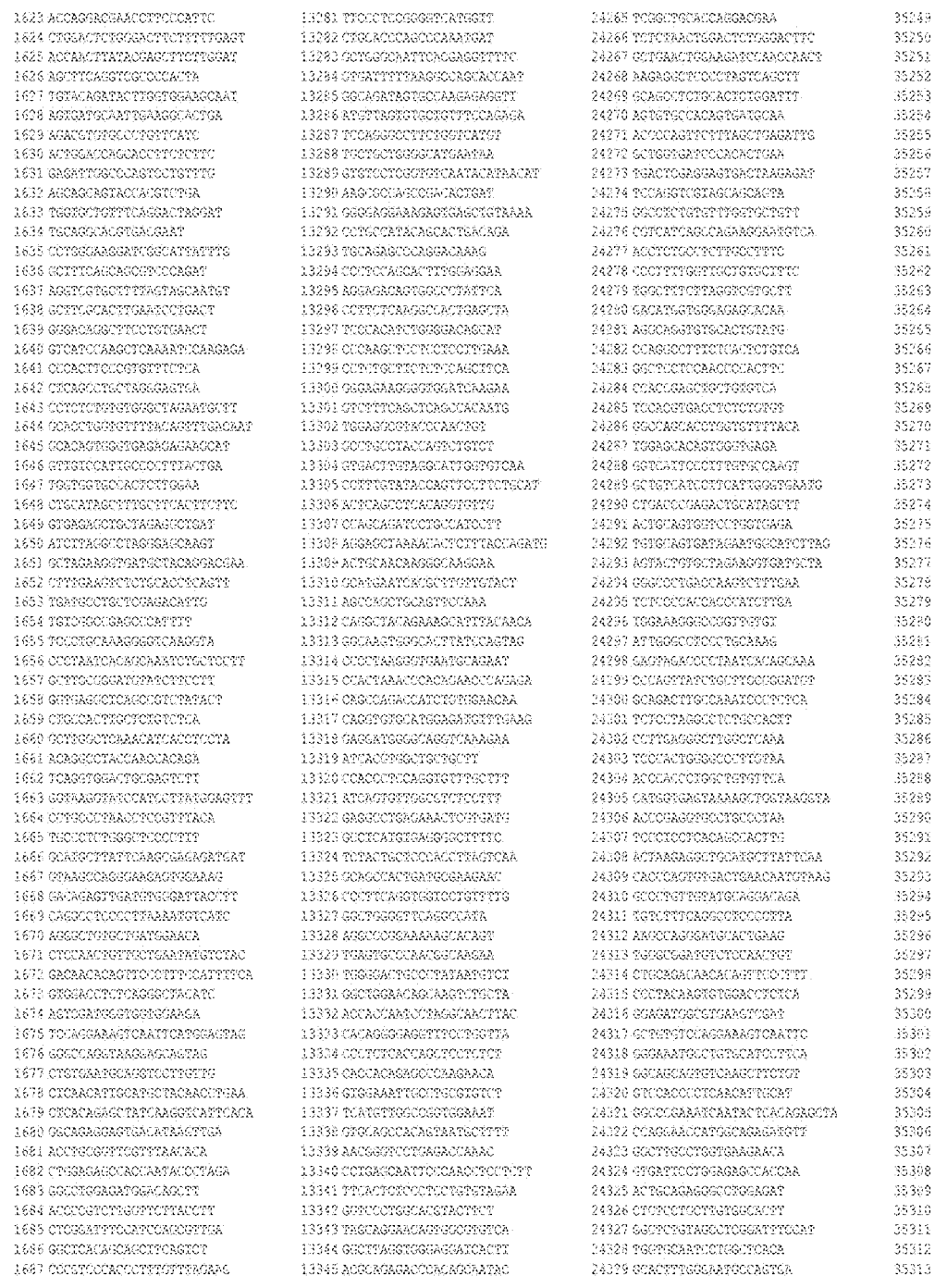
Figure 36C7:
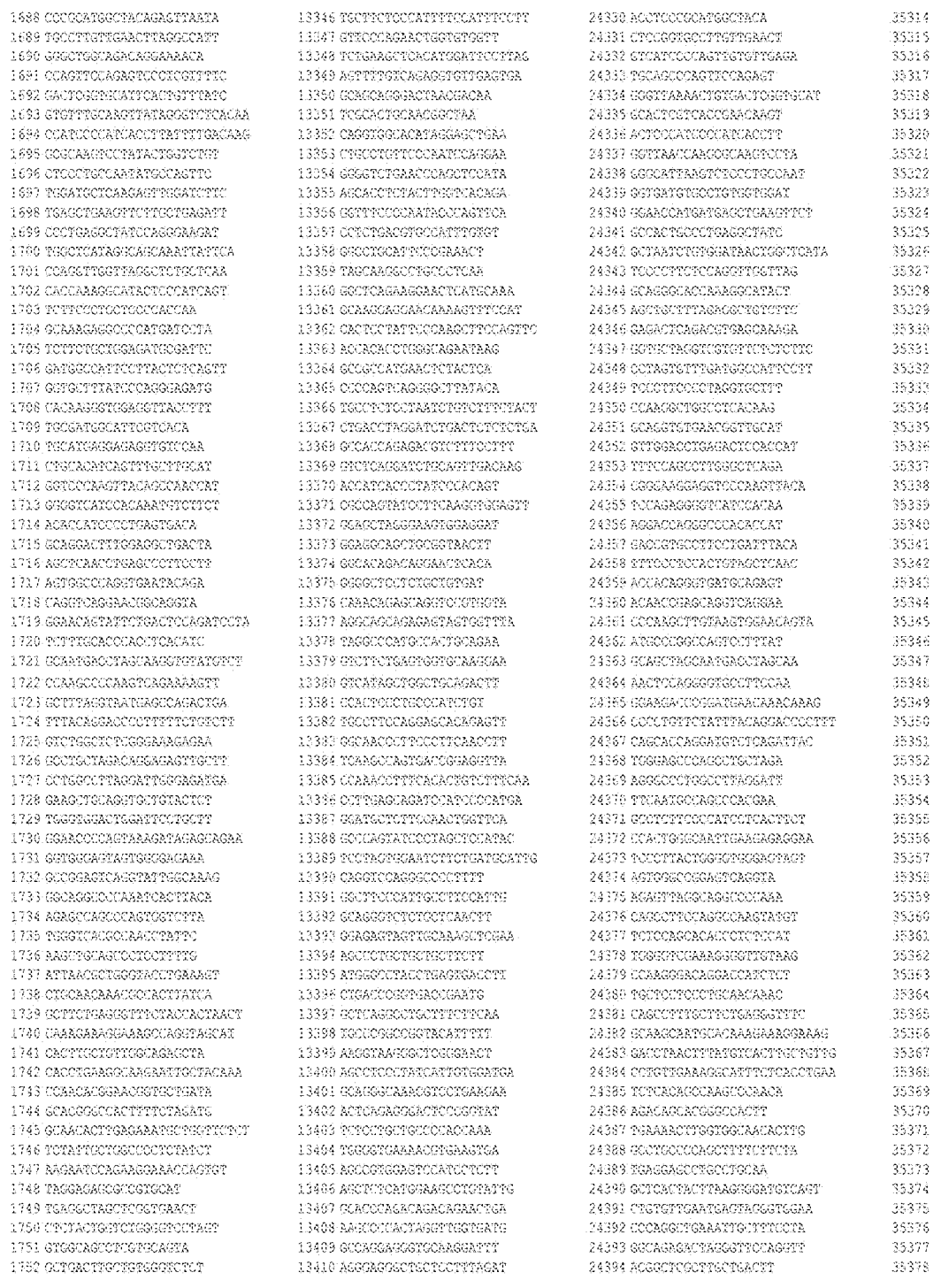
Figure 36C8:
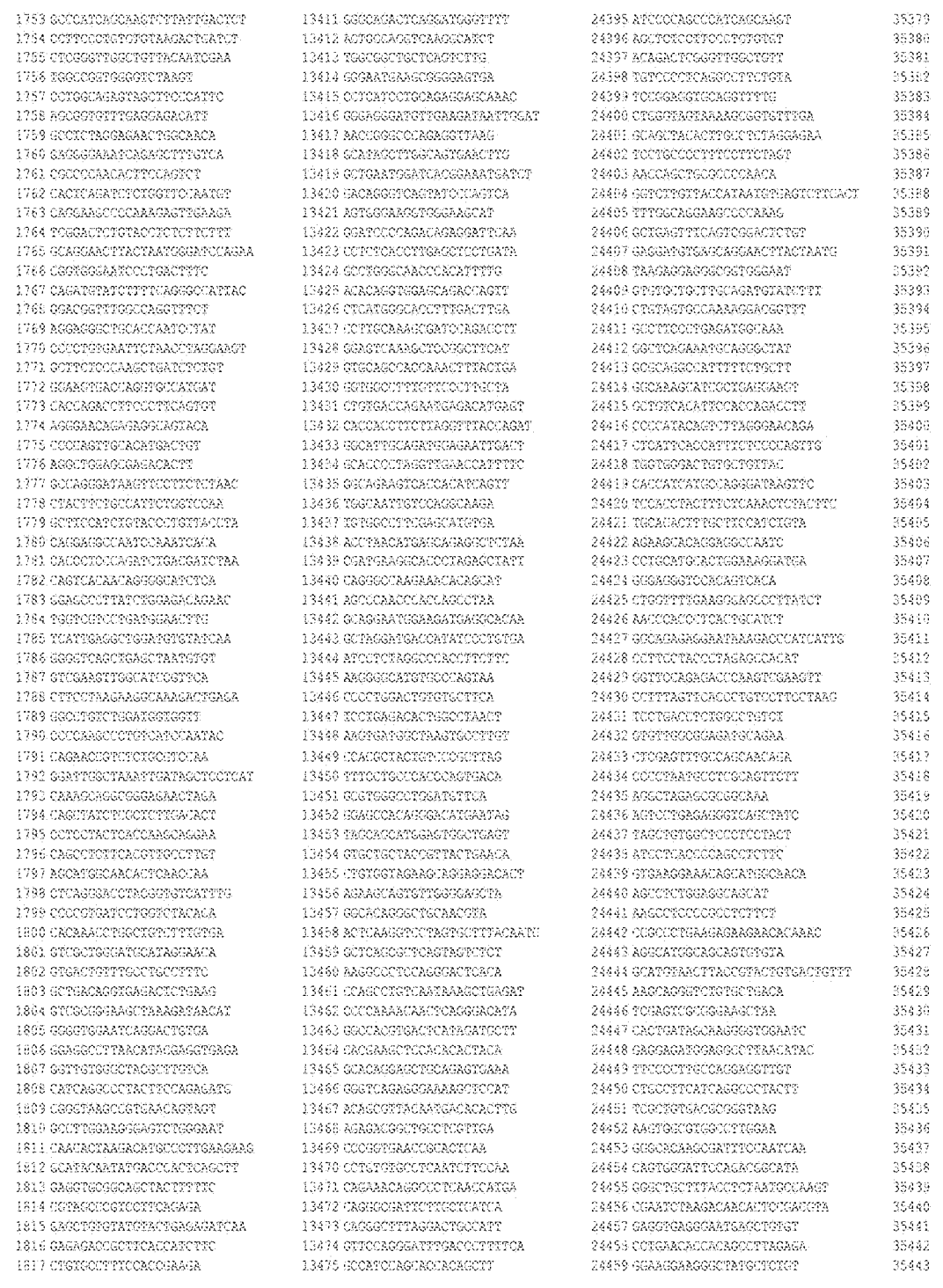
Figure 36C10:
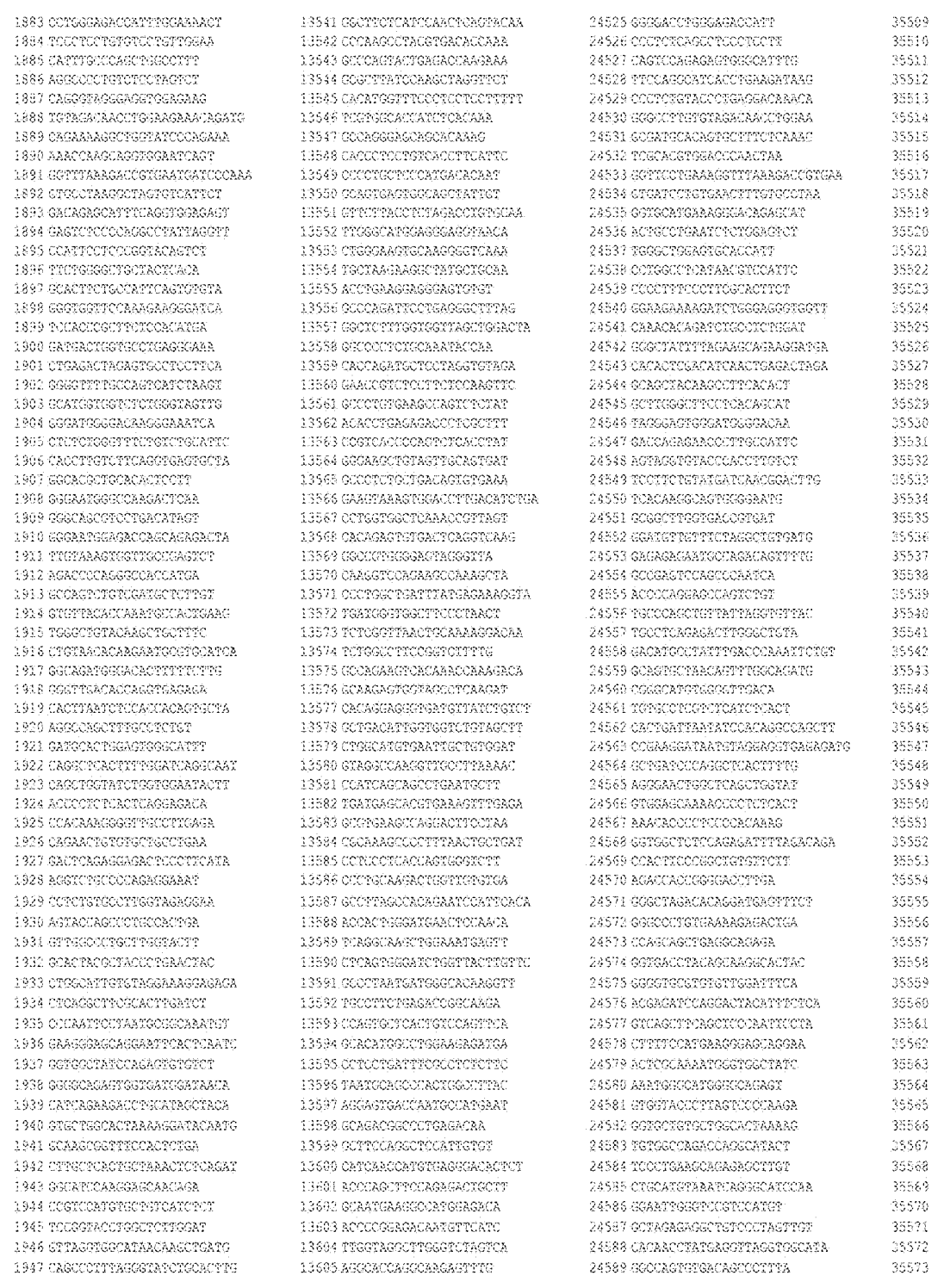
Figure 36D1:
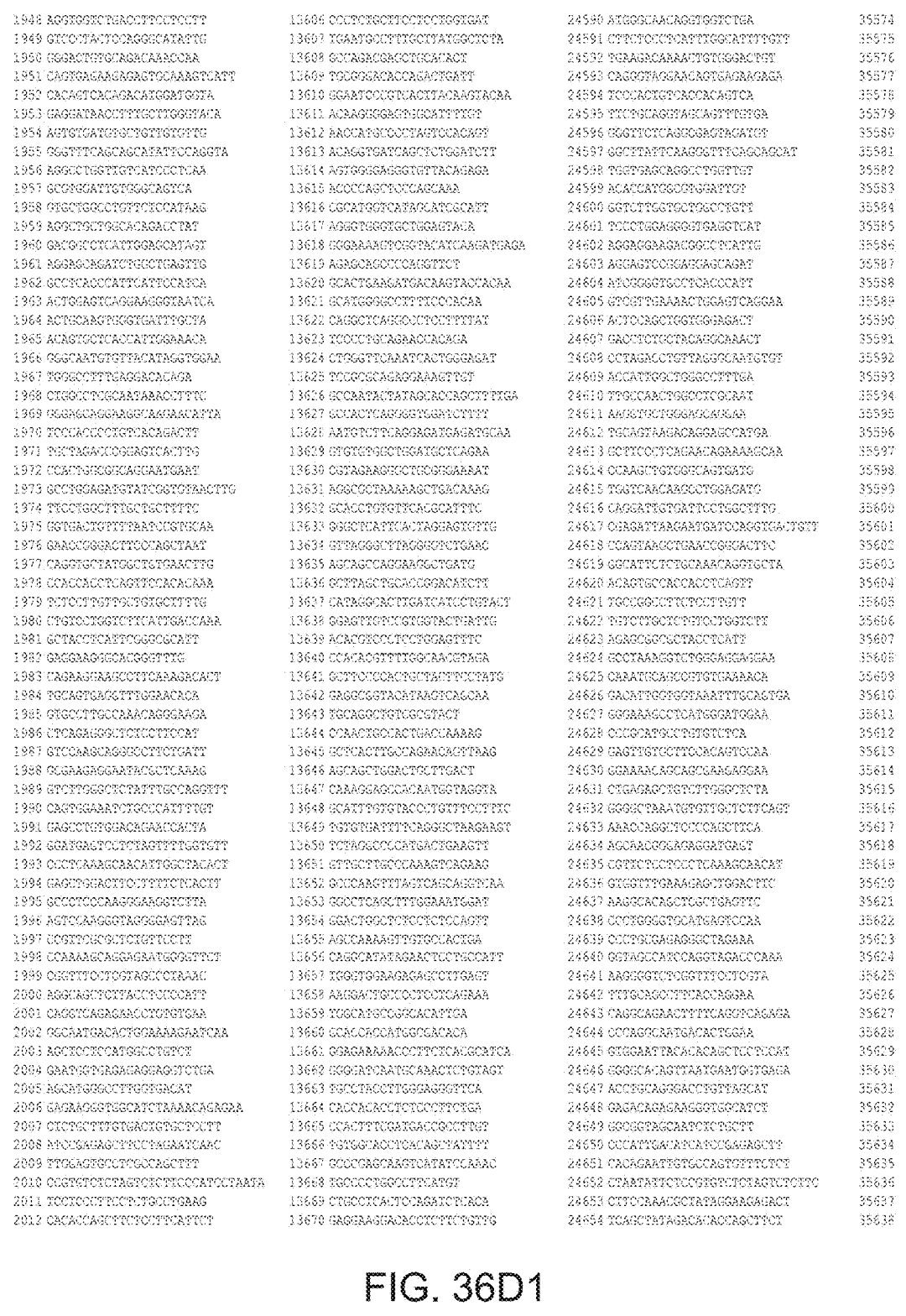
Figure 36D2:
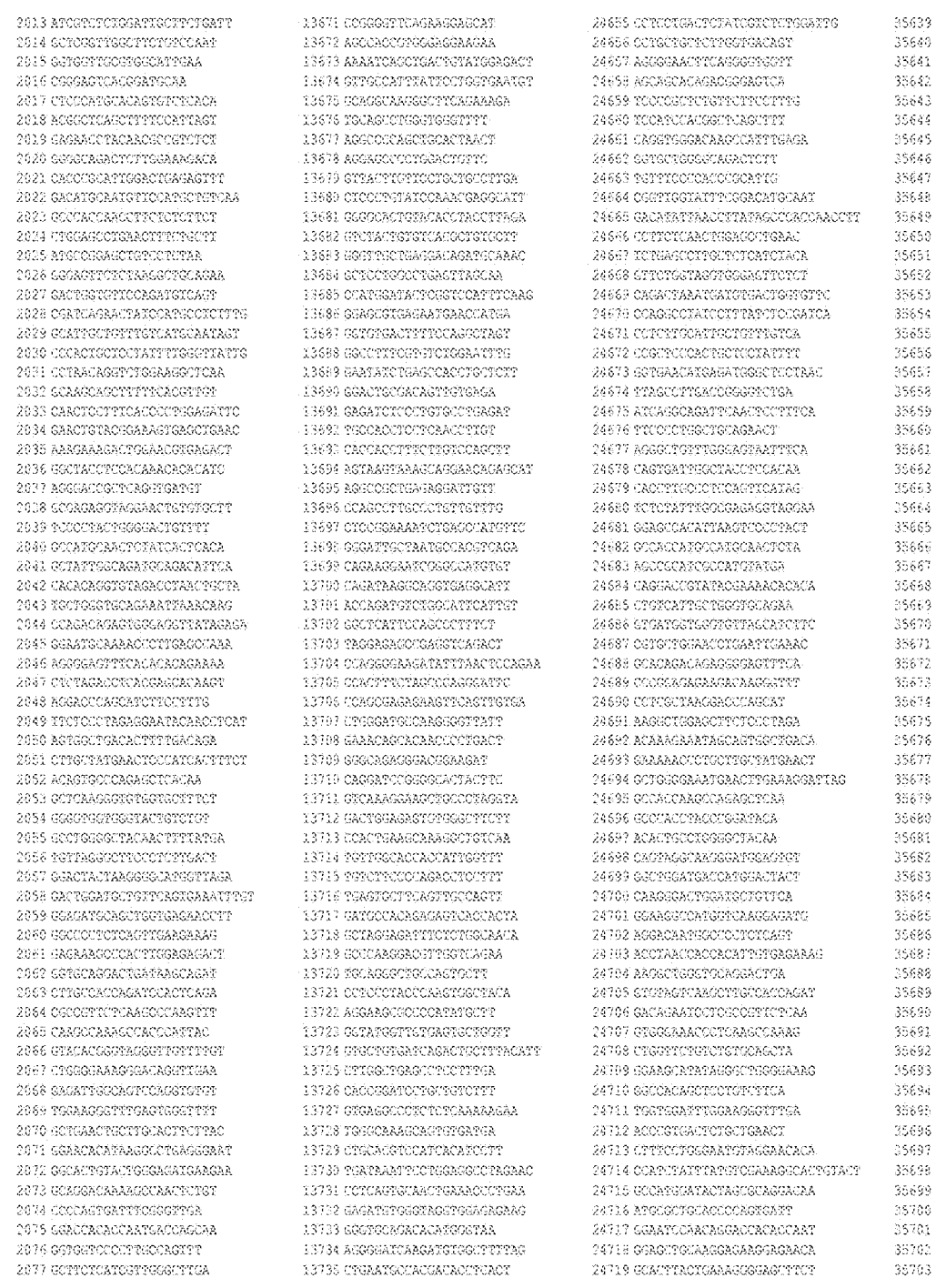
Figure 36D3:
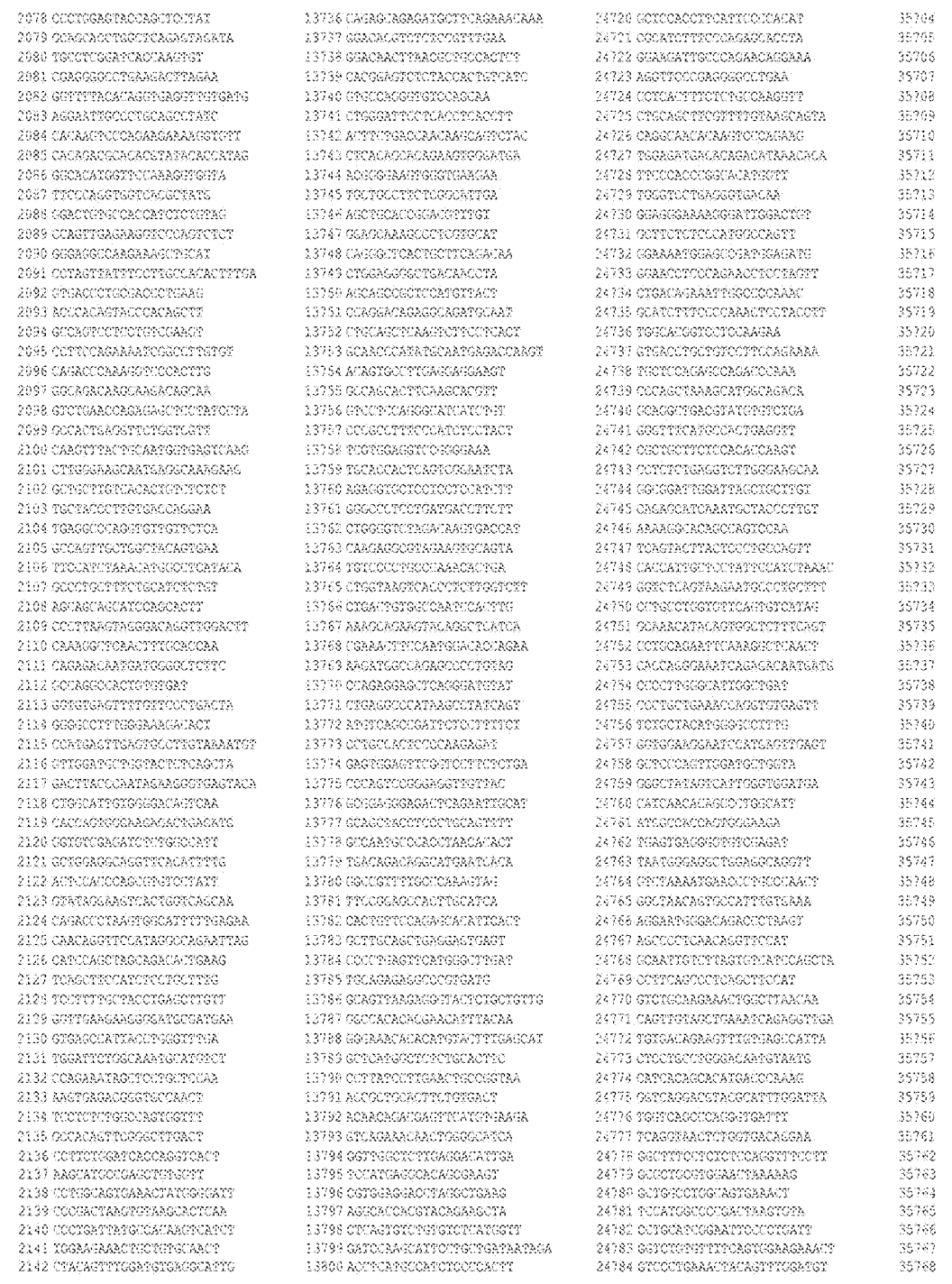
Figure 36D4:
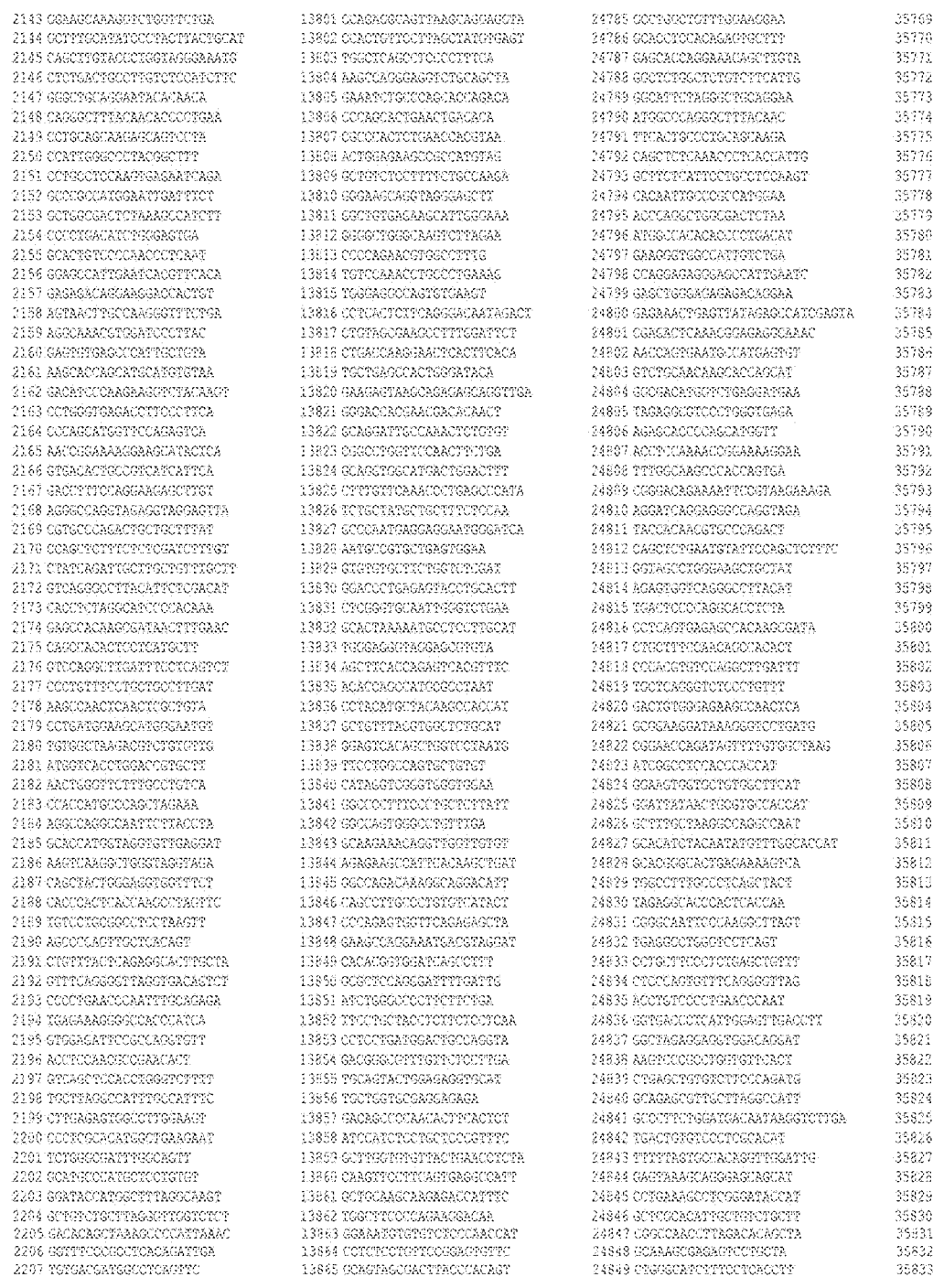
Figure 36D5:
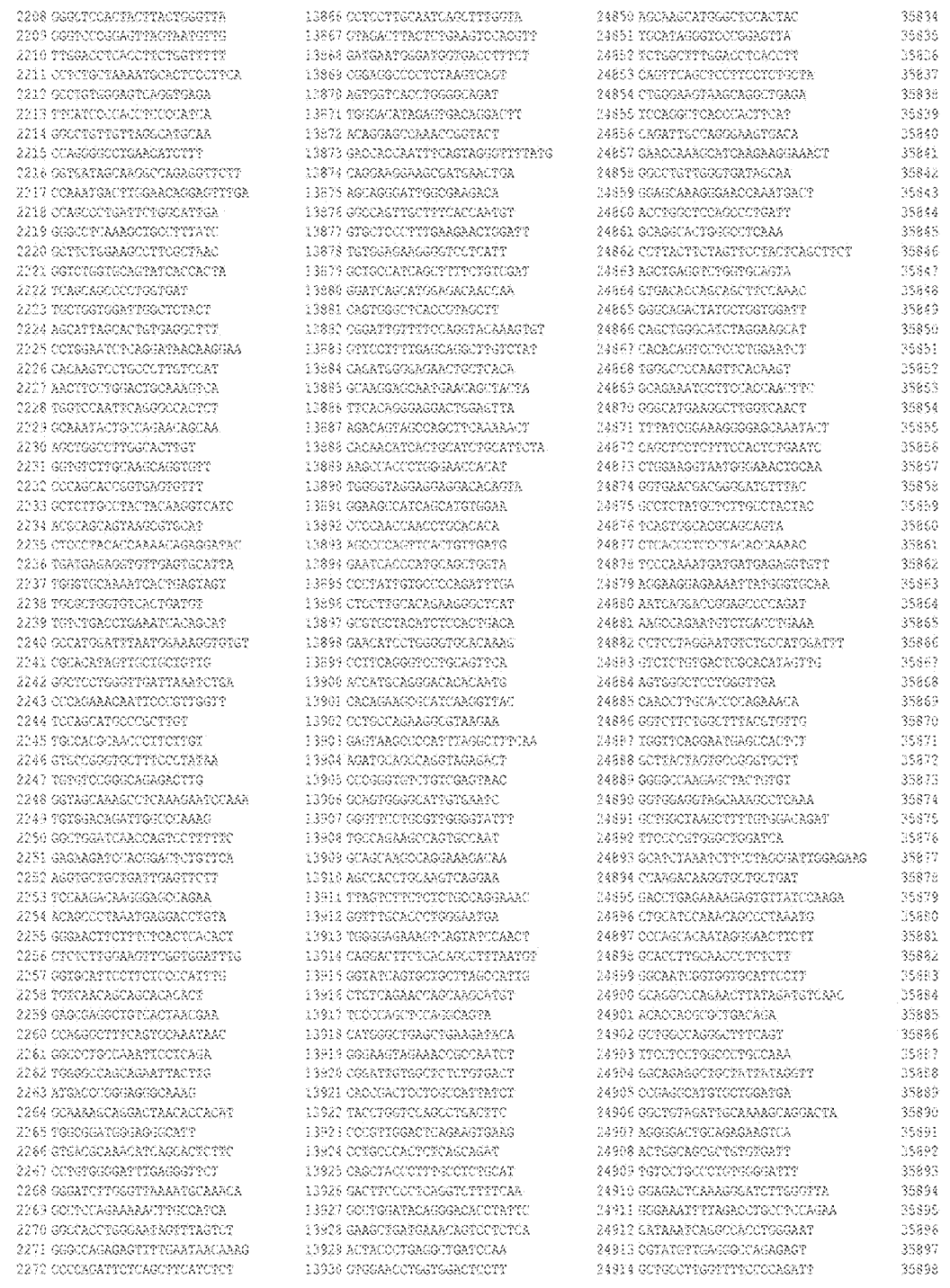
Figure 36D6:
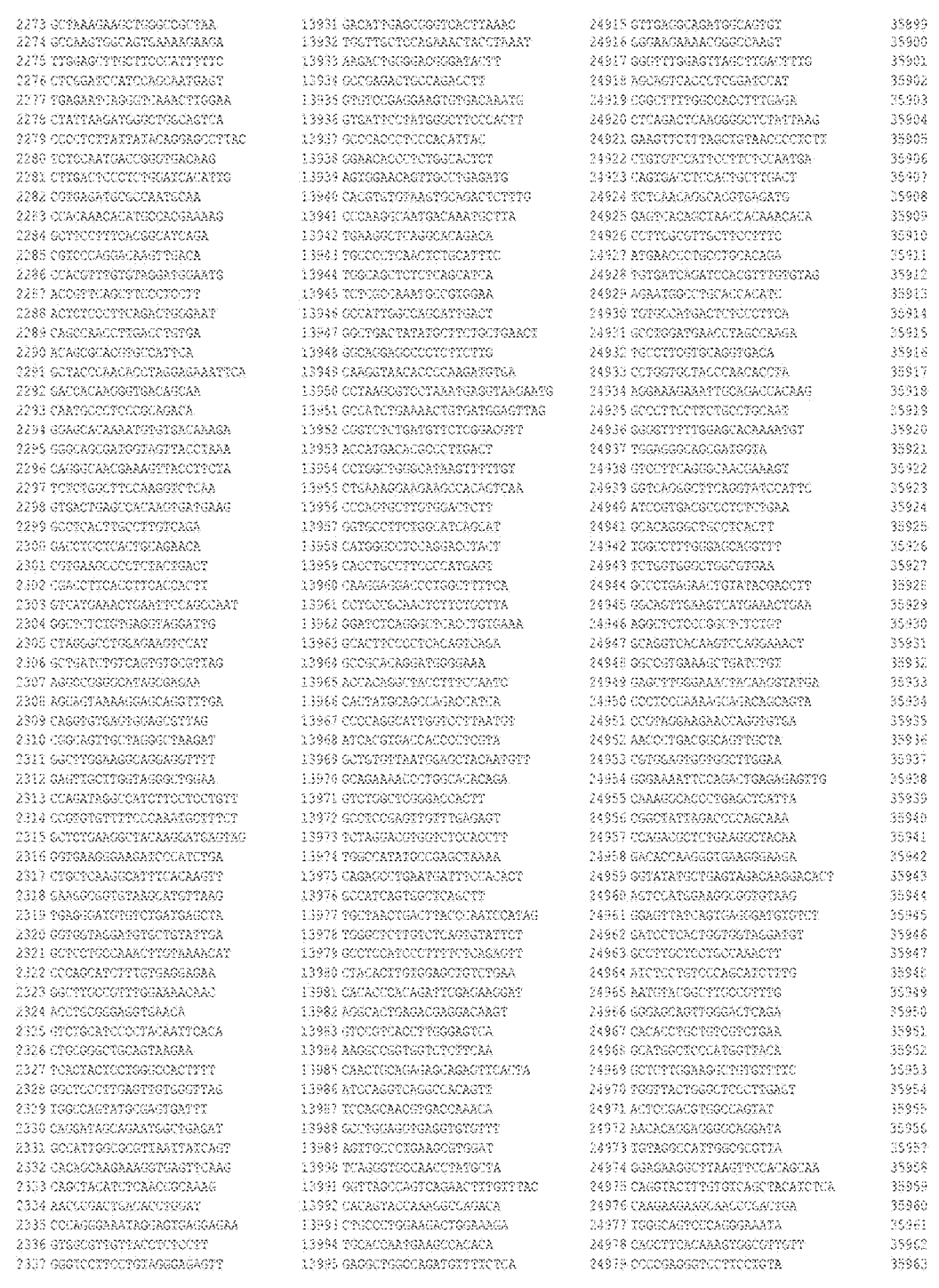
Figure 36D7:
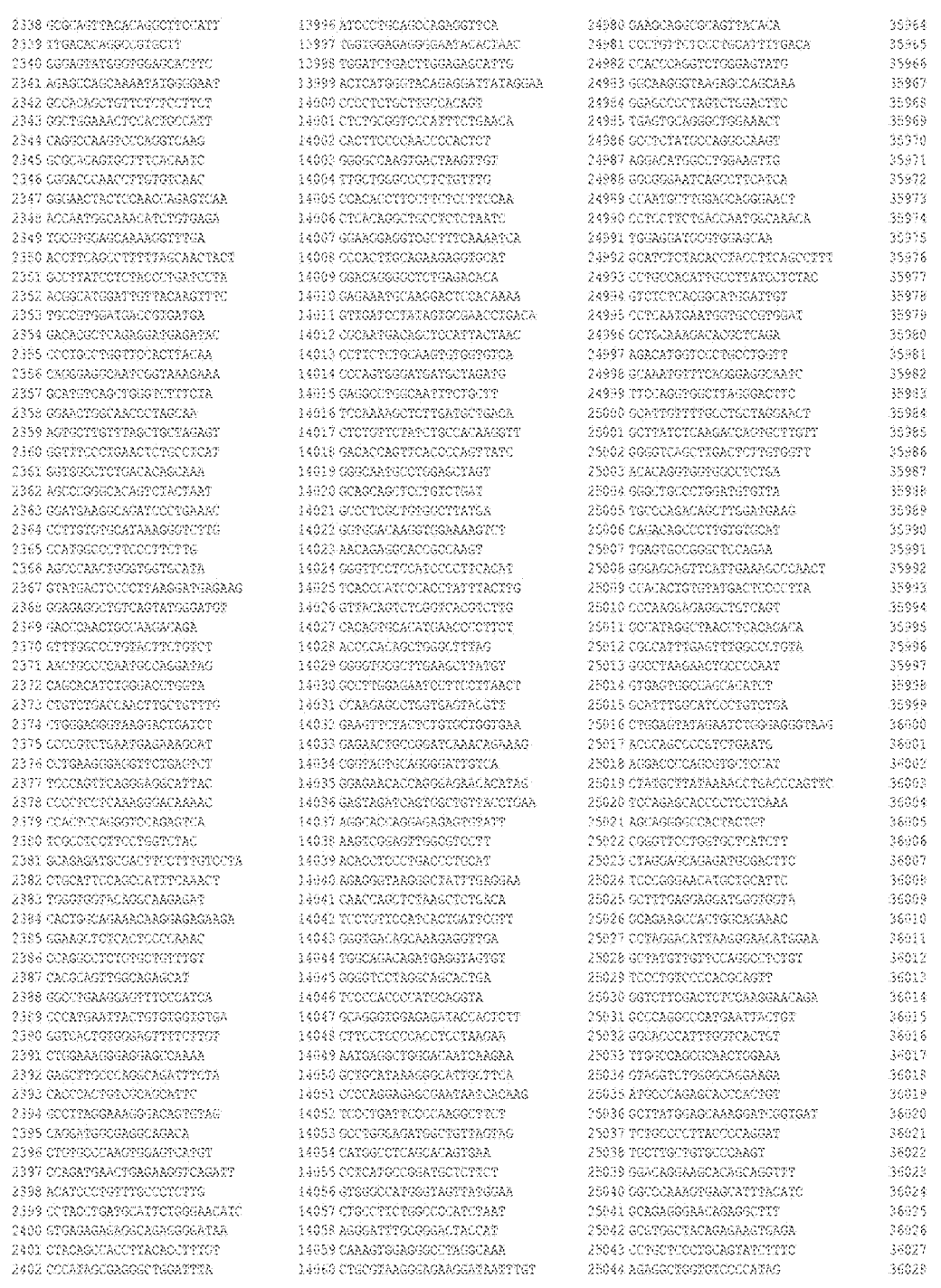
Figure 36D8:
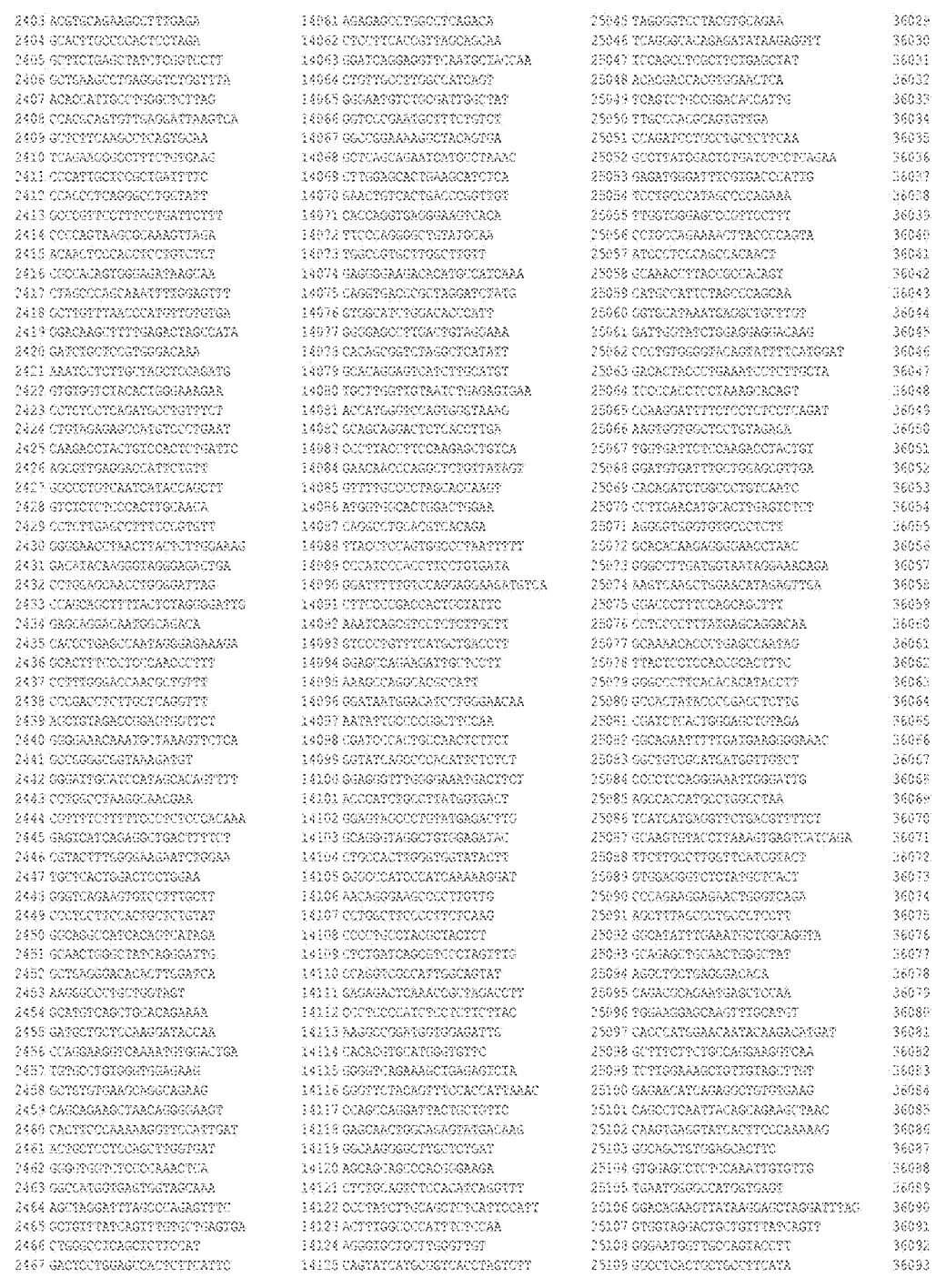
Figure 36D9:
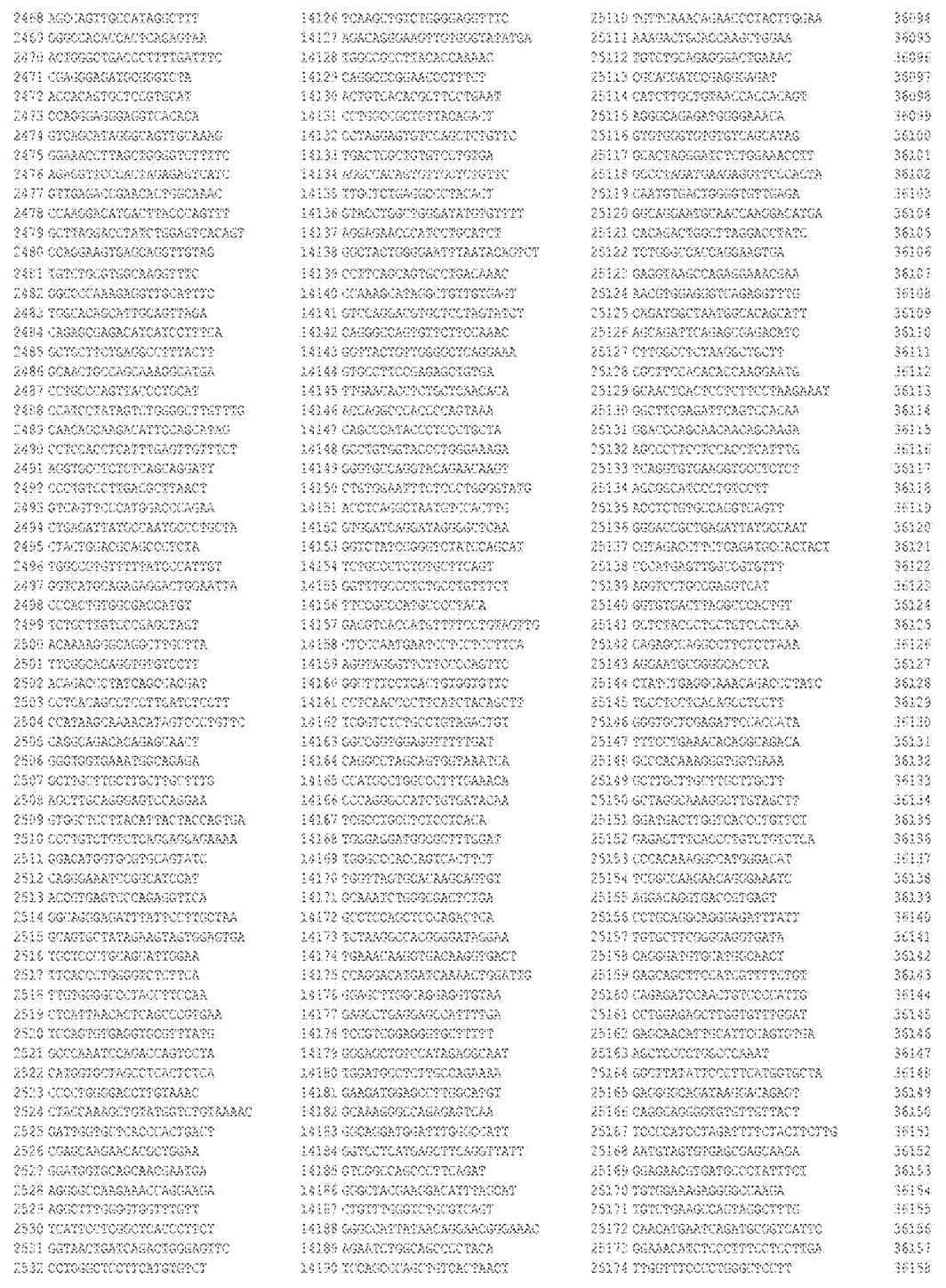
Figure 36D10:
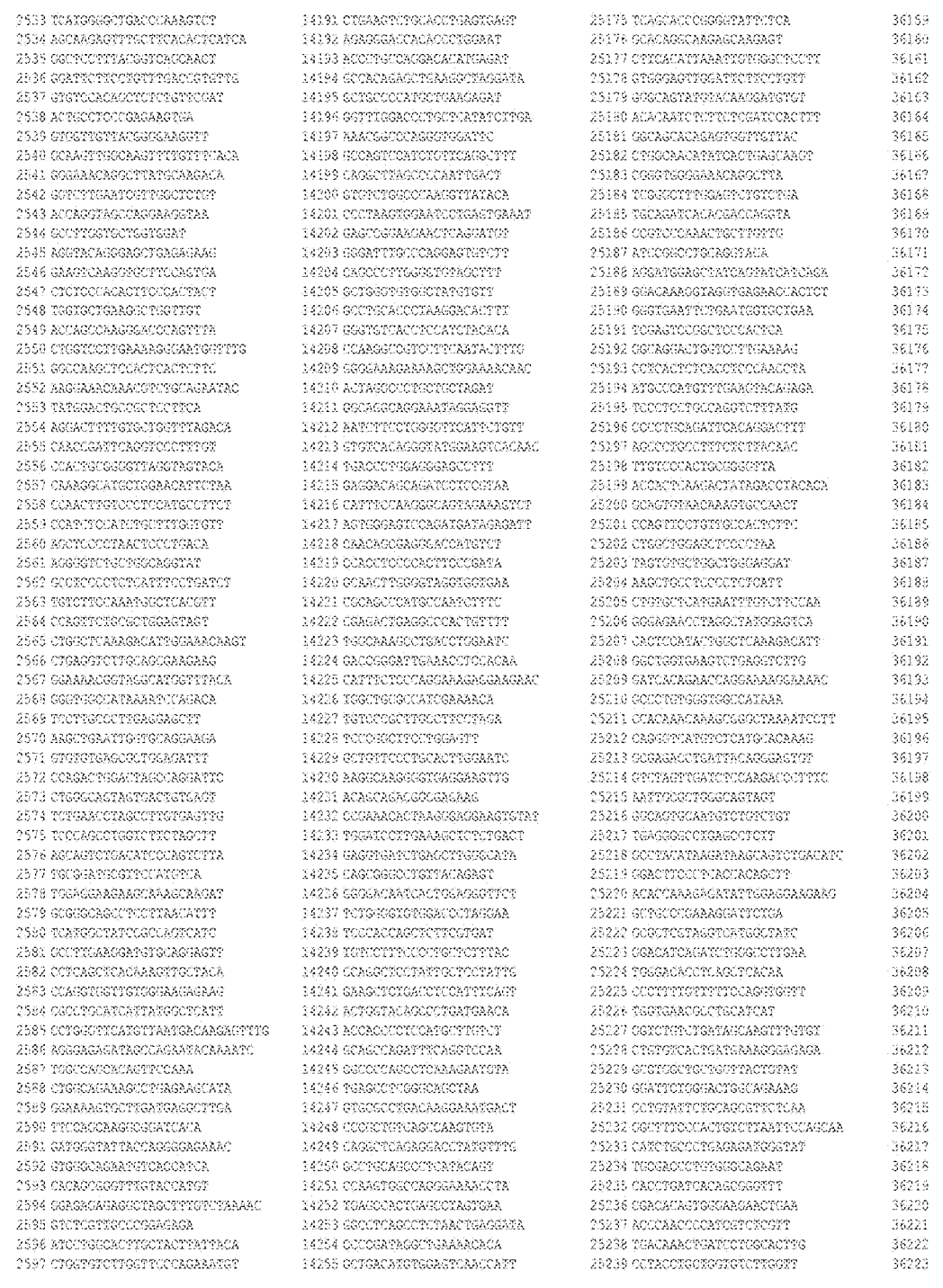
Figure 36E1:
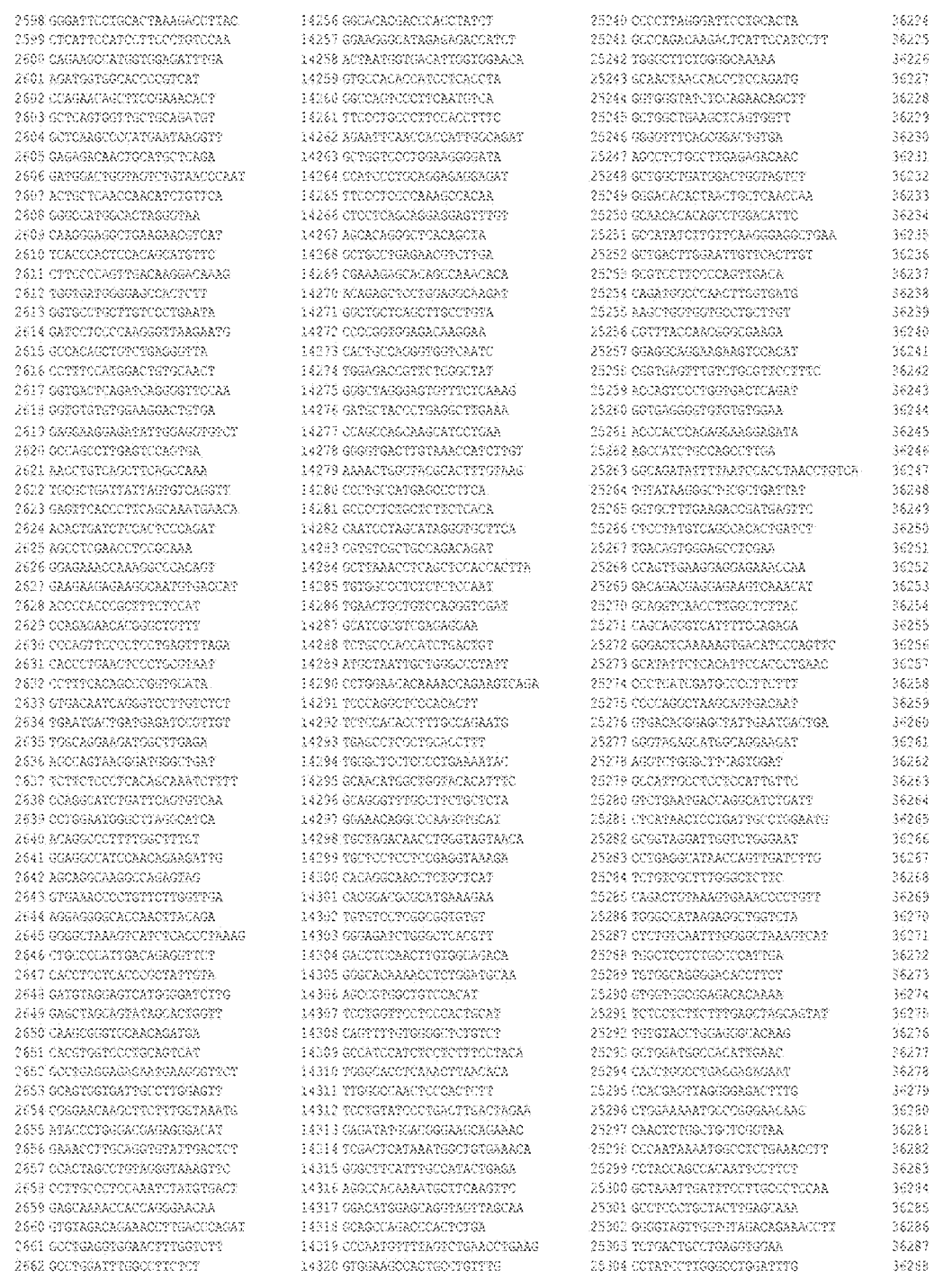
Figure 36E2:
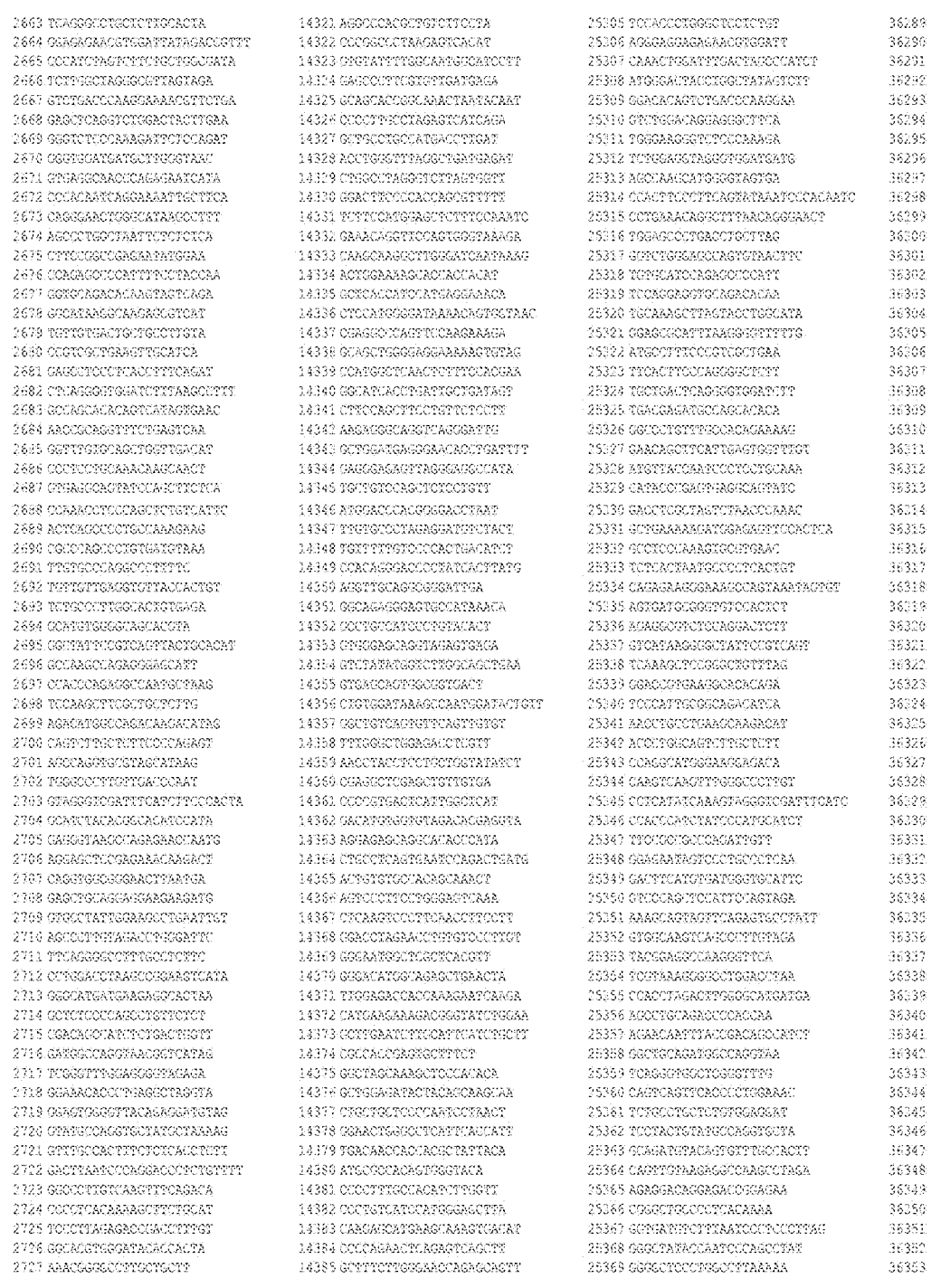
Figure 36E3:
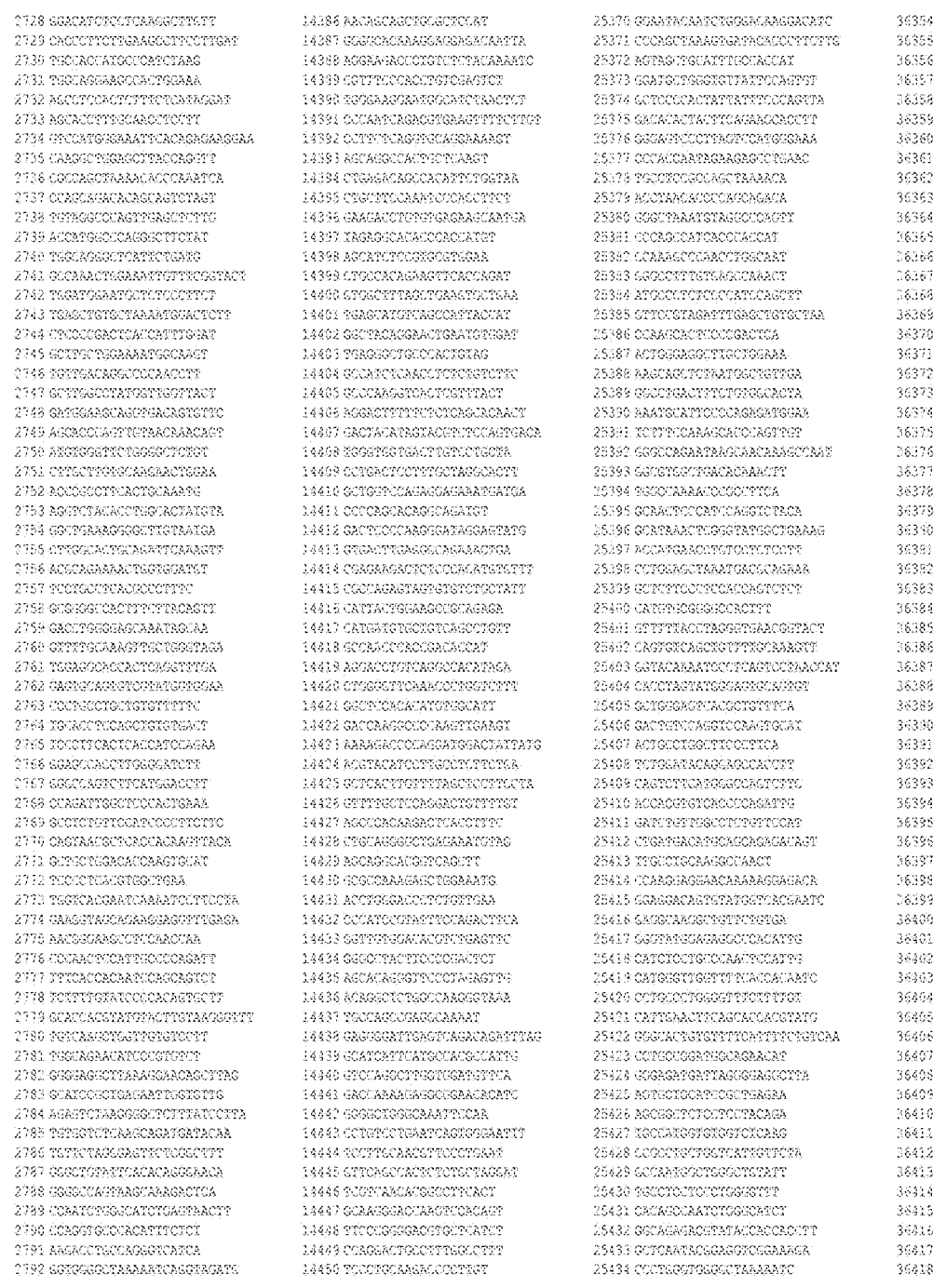
Figure 36E4:
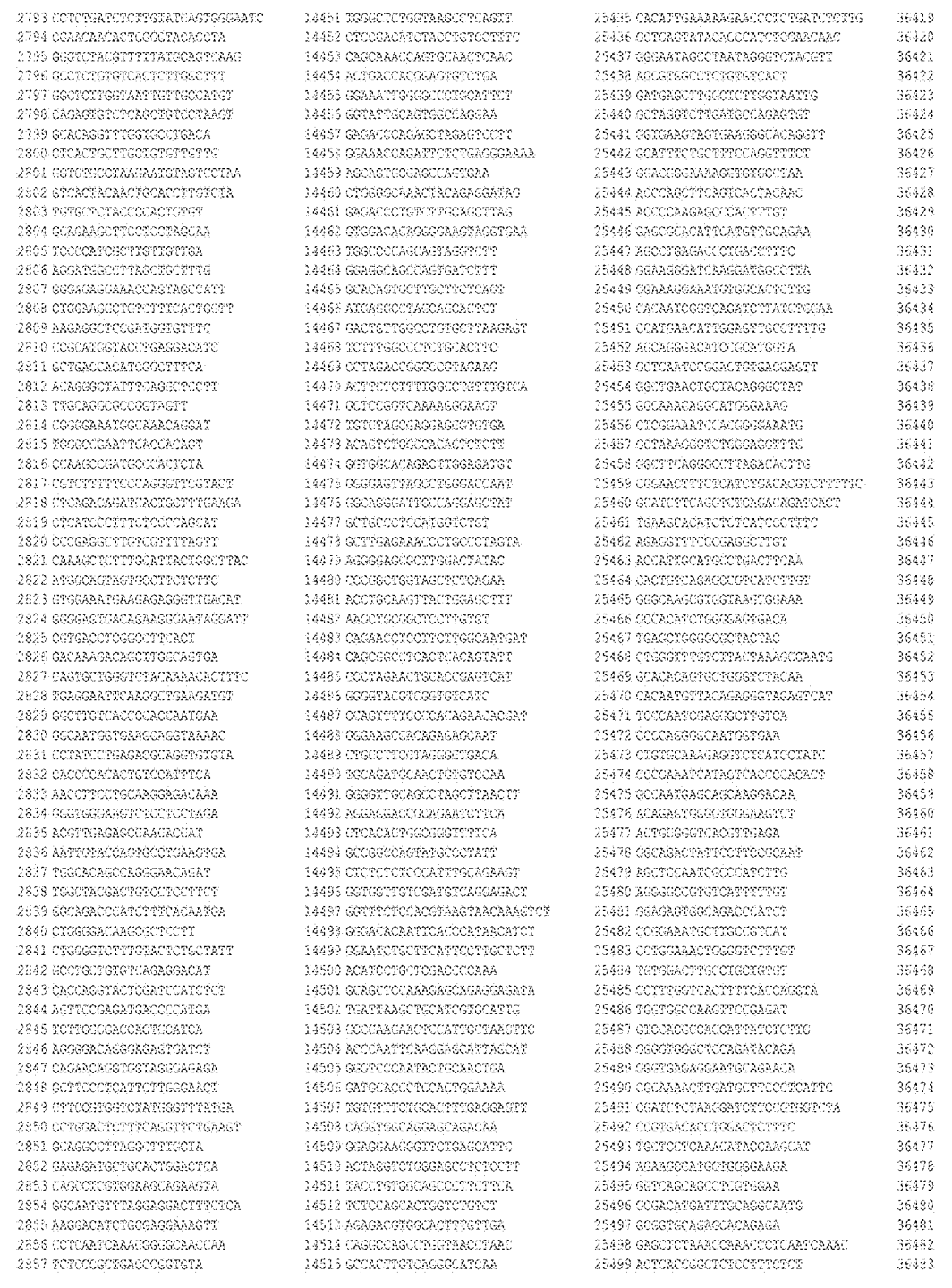
Figure 36E5:
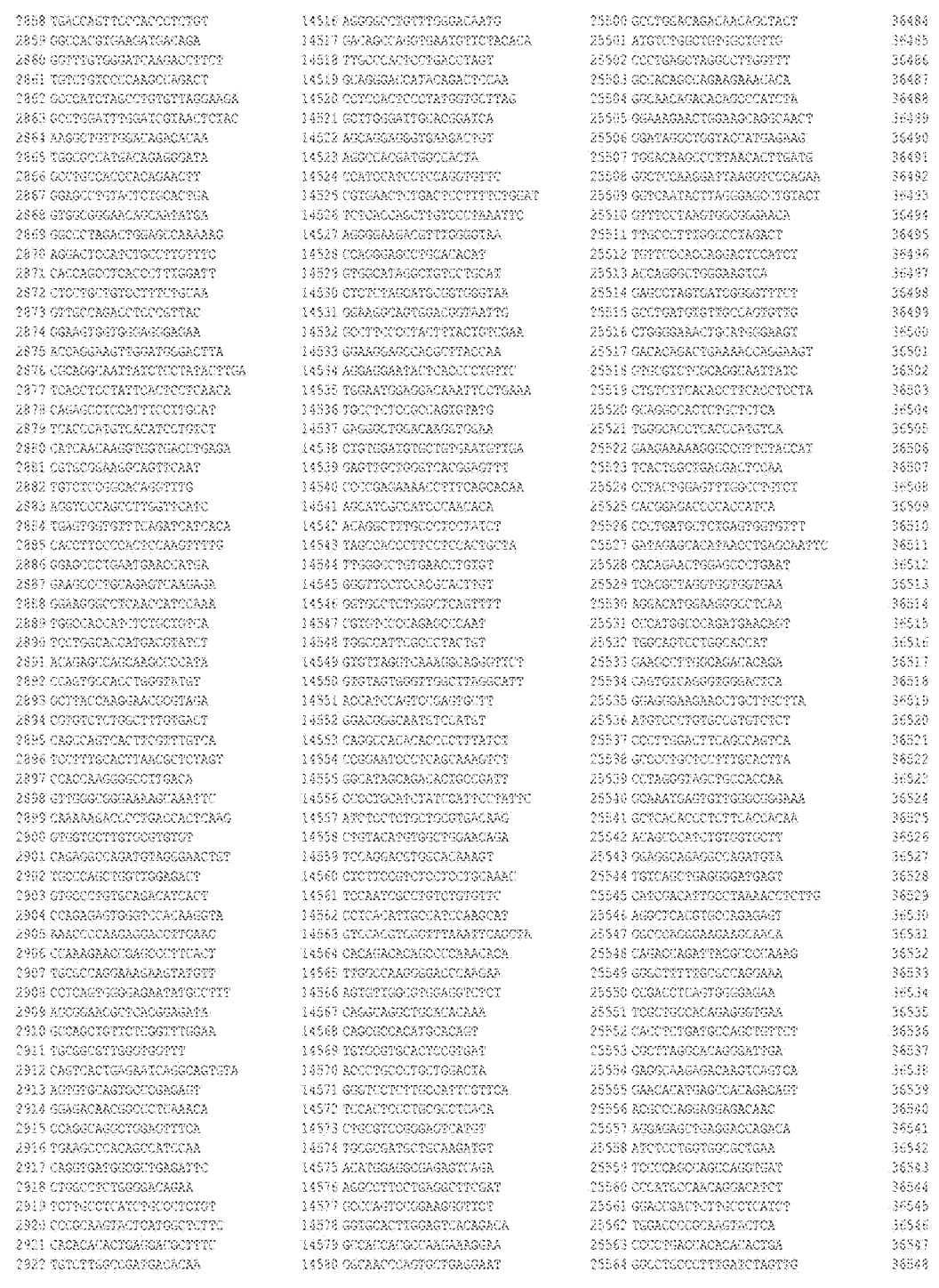
Figure 36E6:
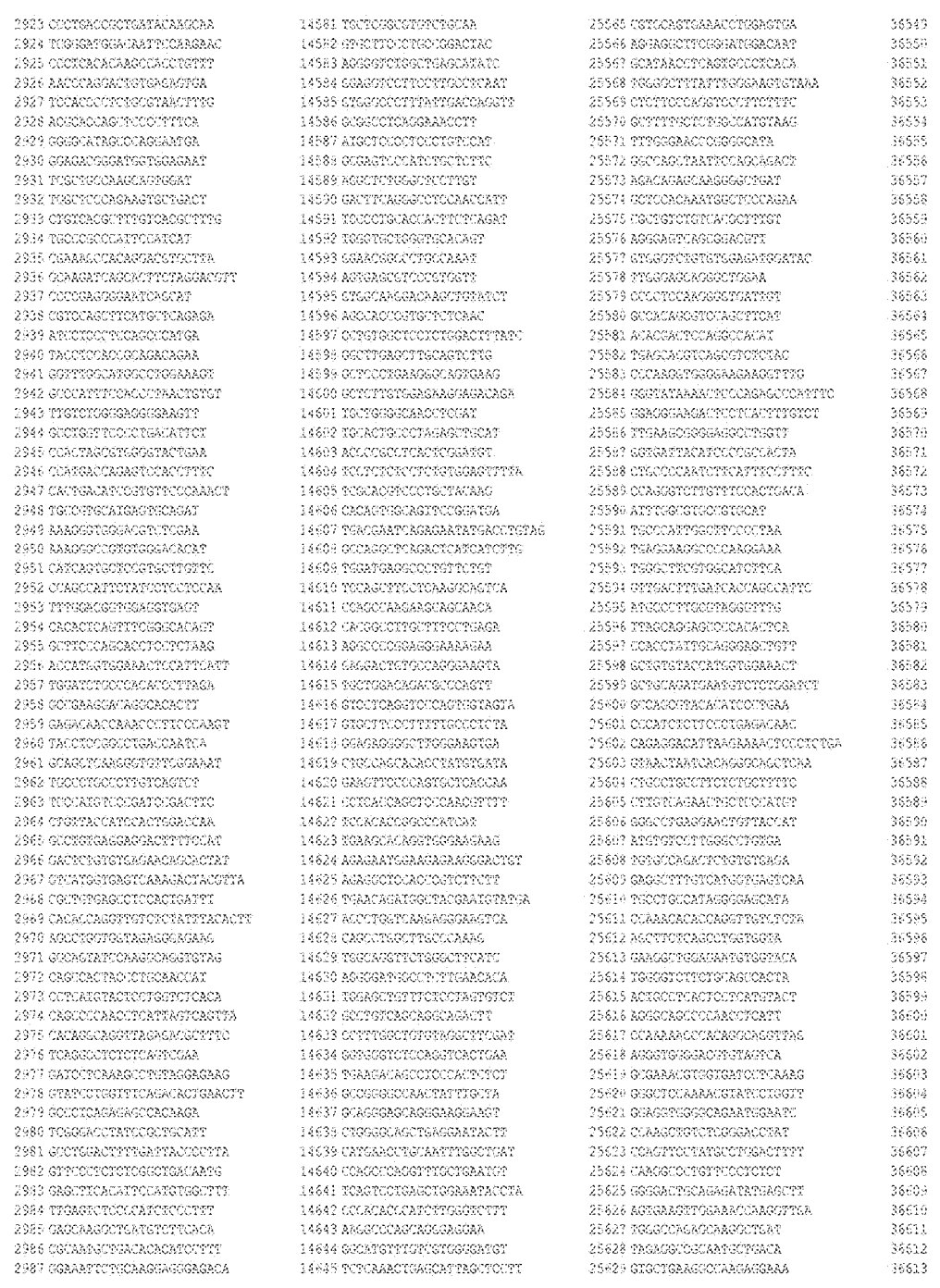
Figure 36E7:
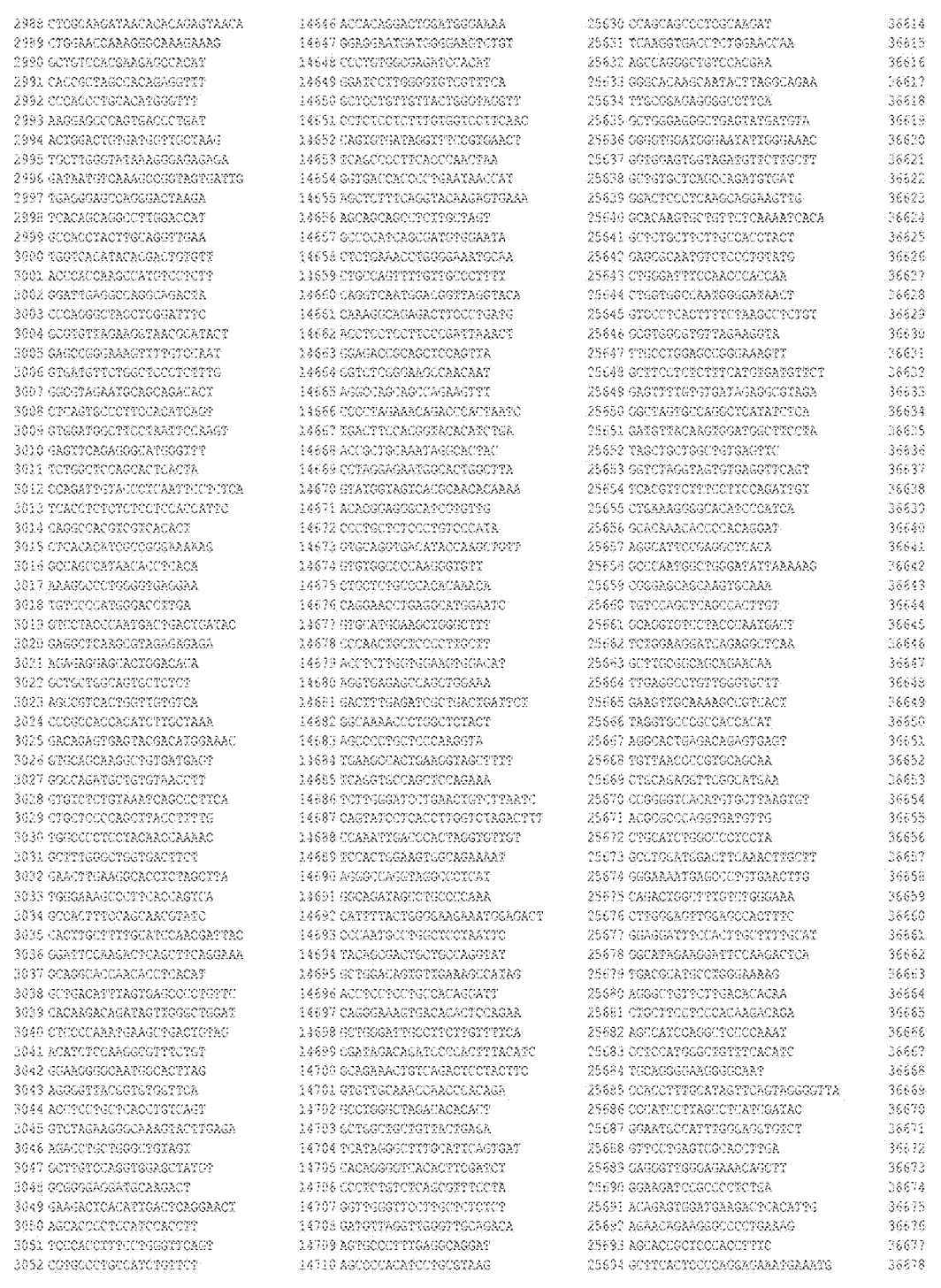
Figure 36E8:
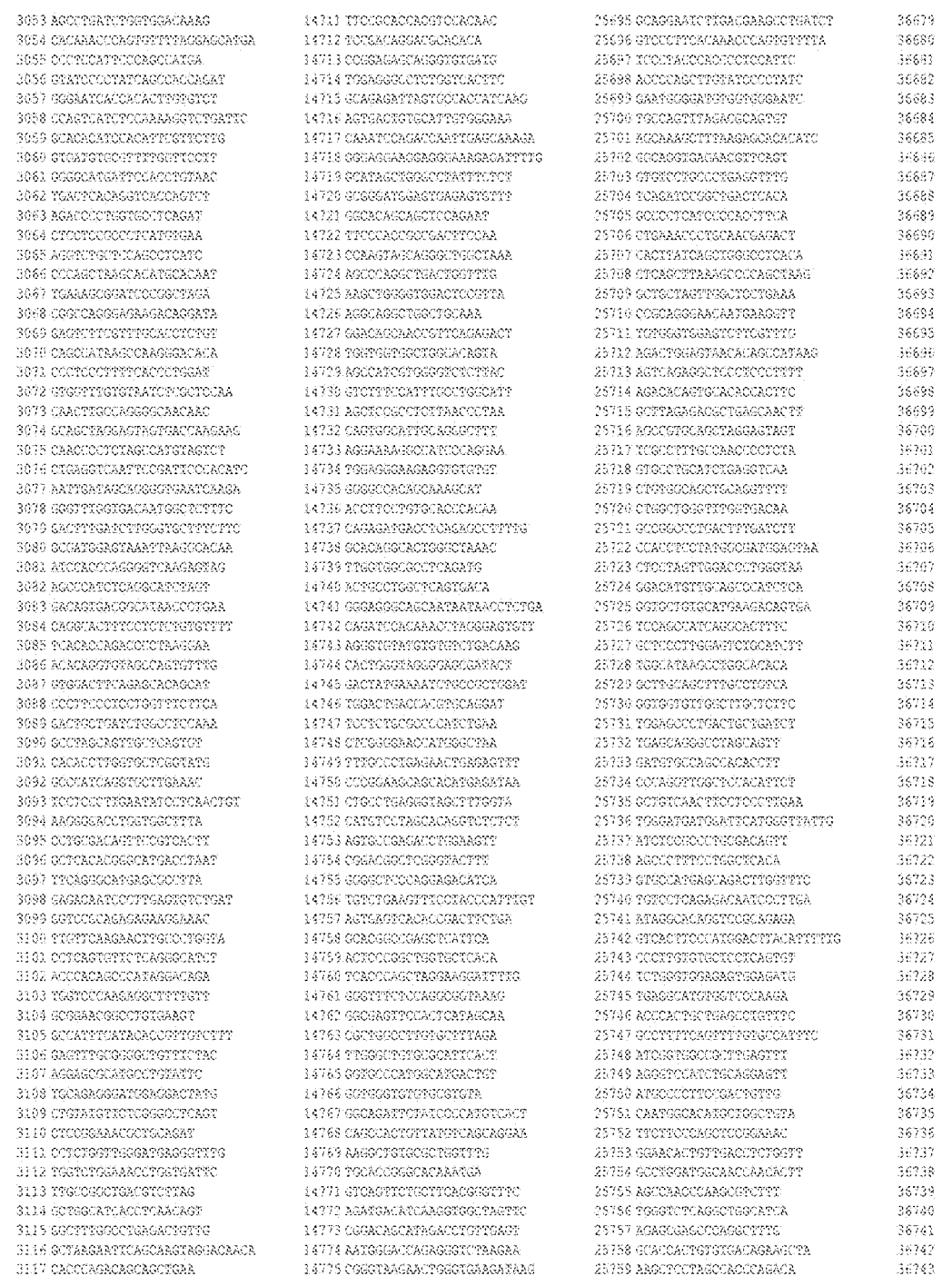
Figure 36E10:
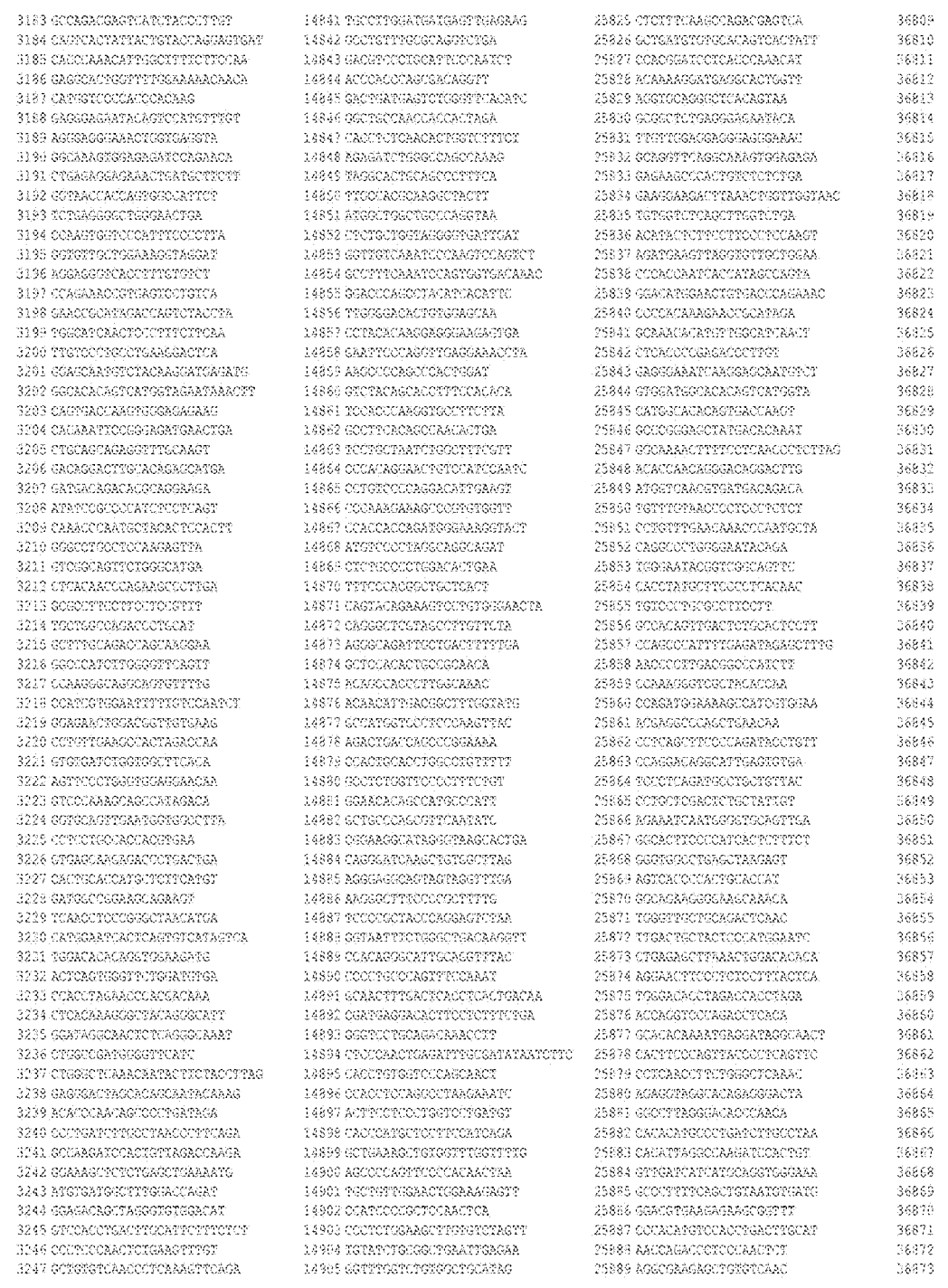
Figure 36F1:
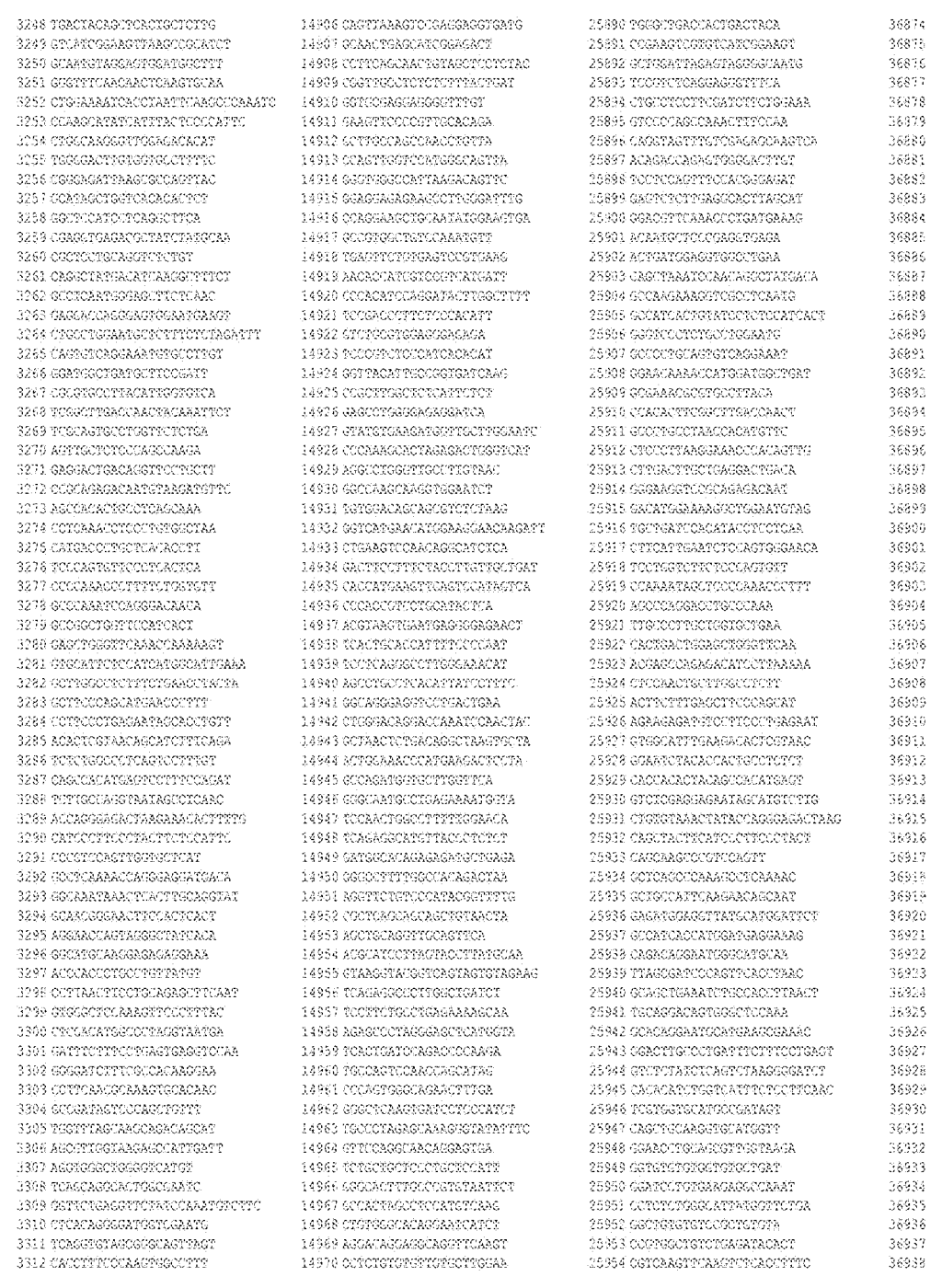
Figure 36F2:
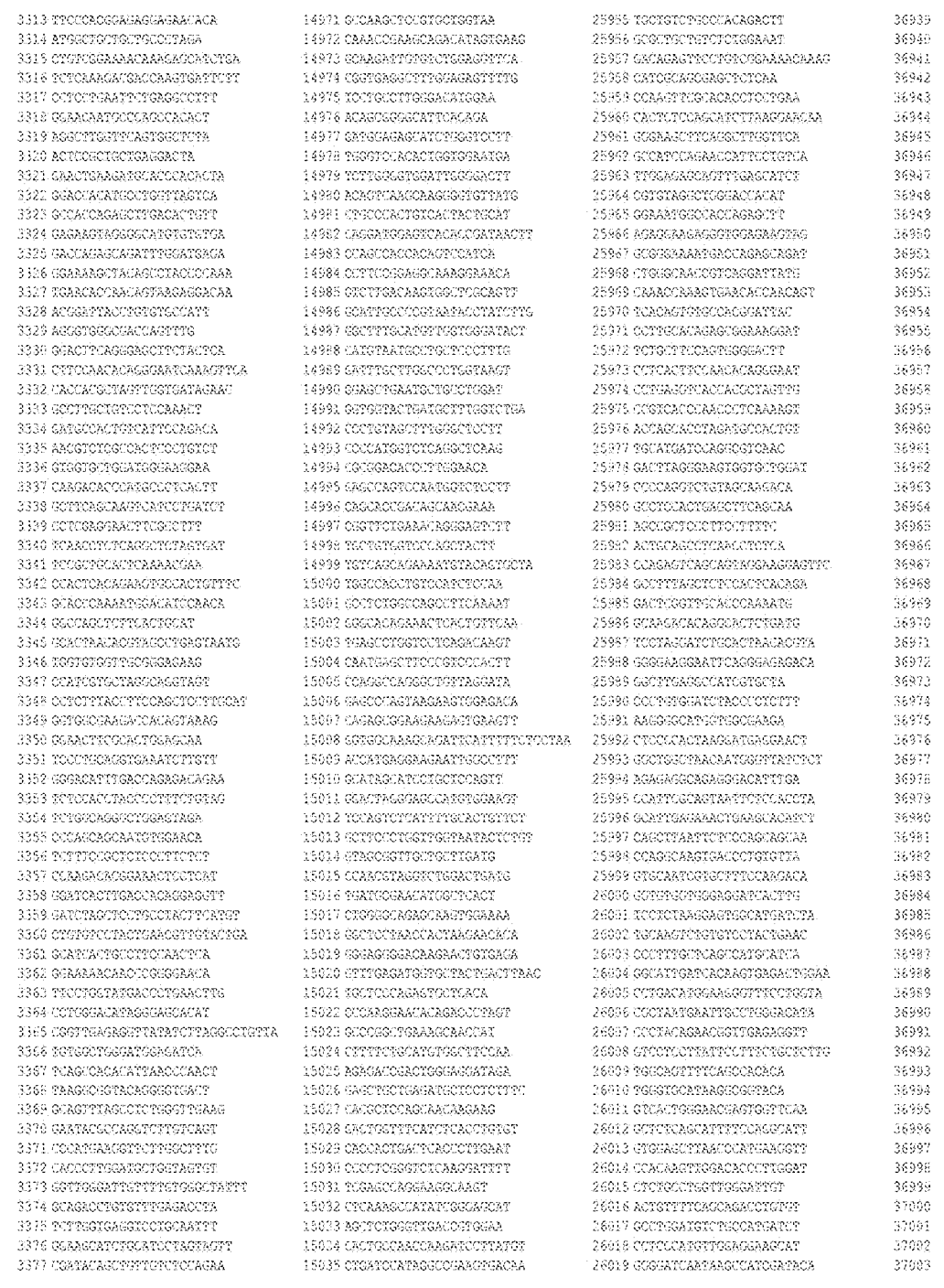
Figure 36F3:
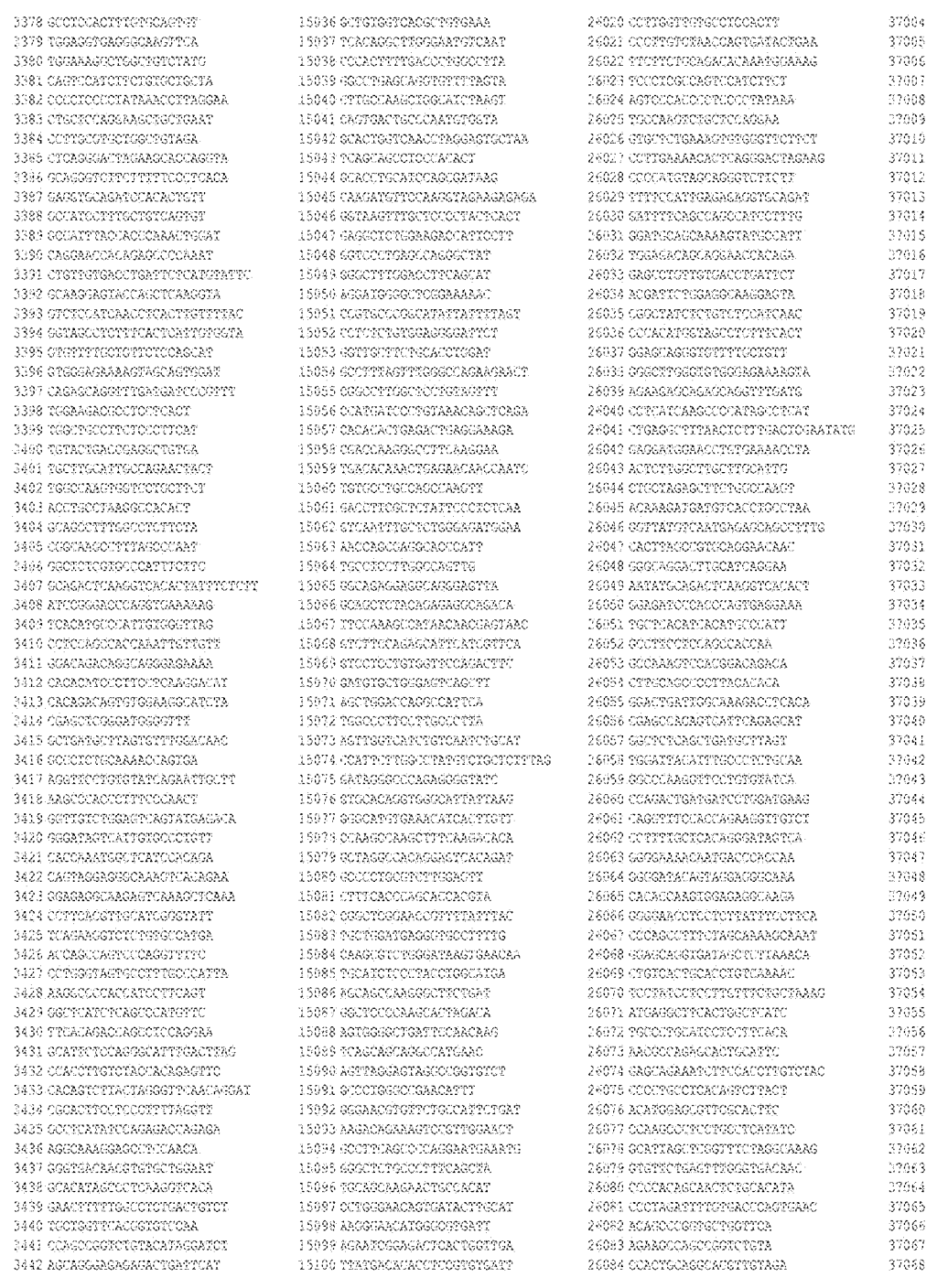
Figure 36F4:
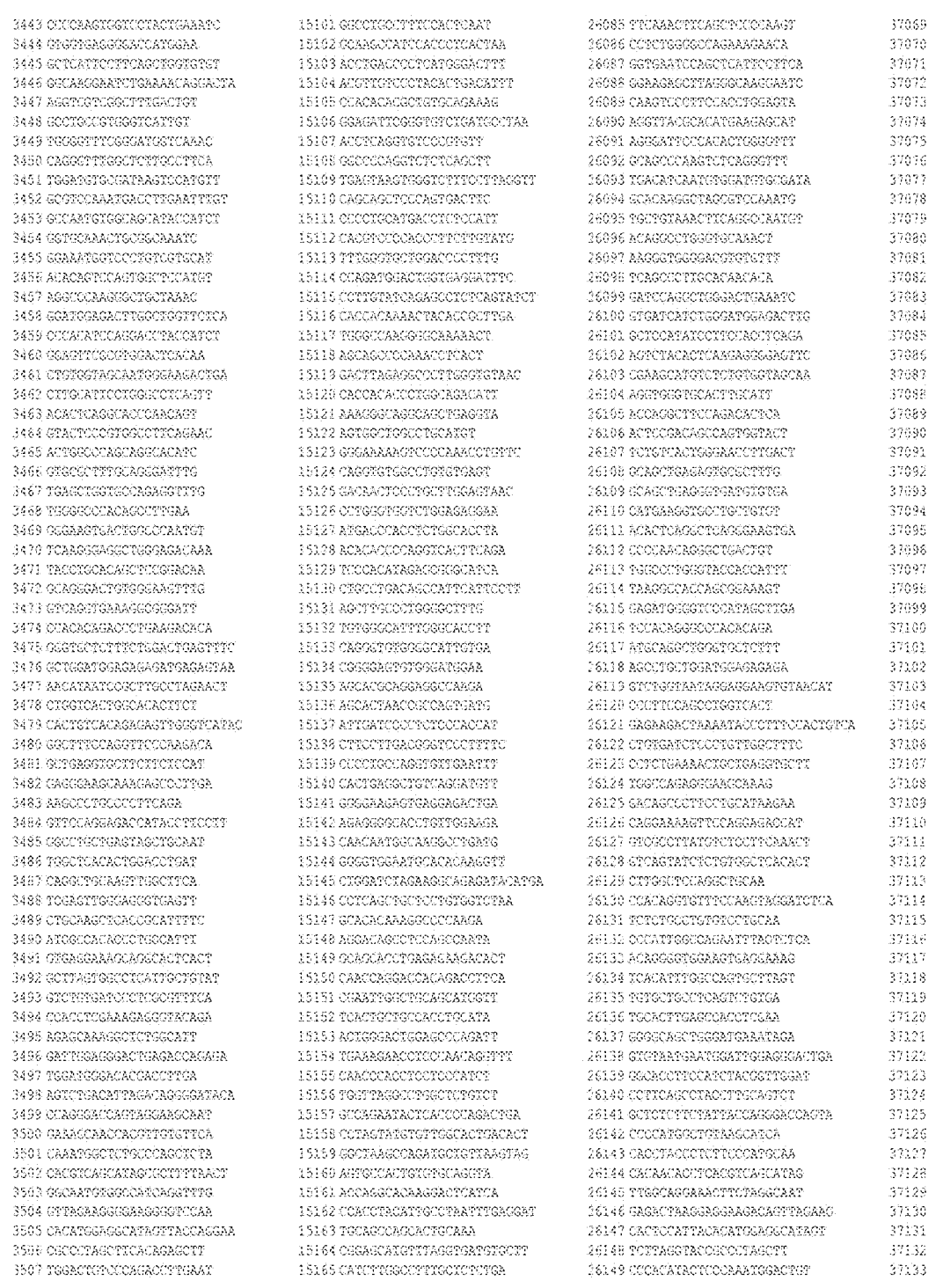
Figure 36F5:
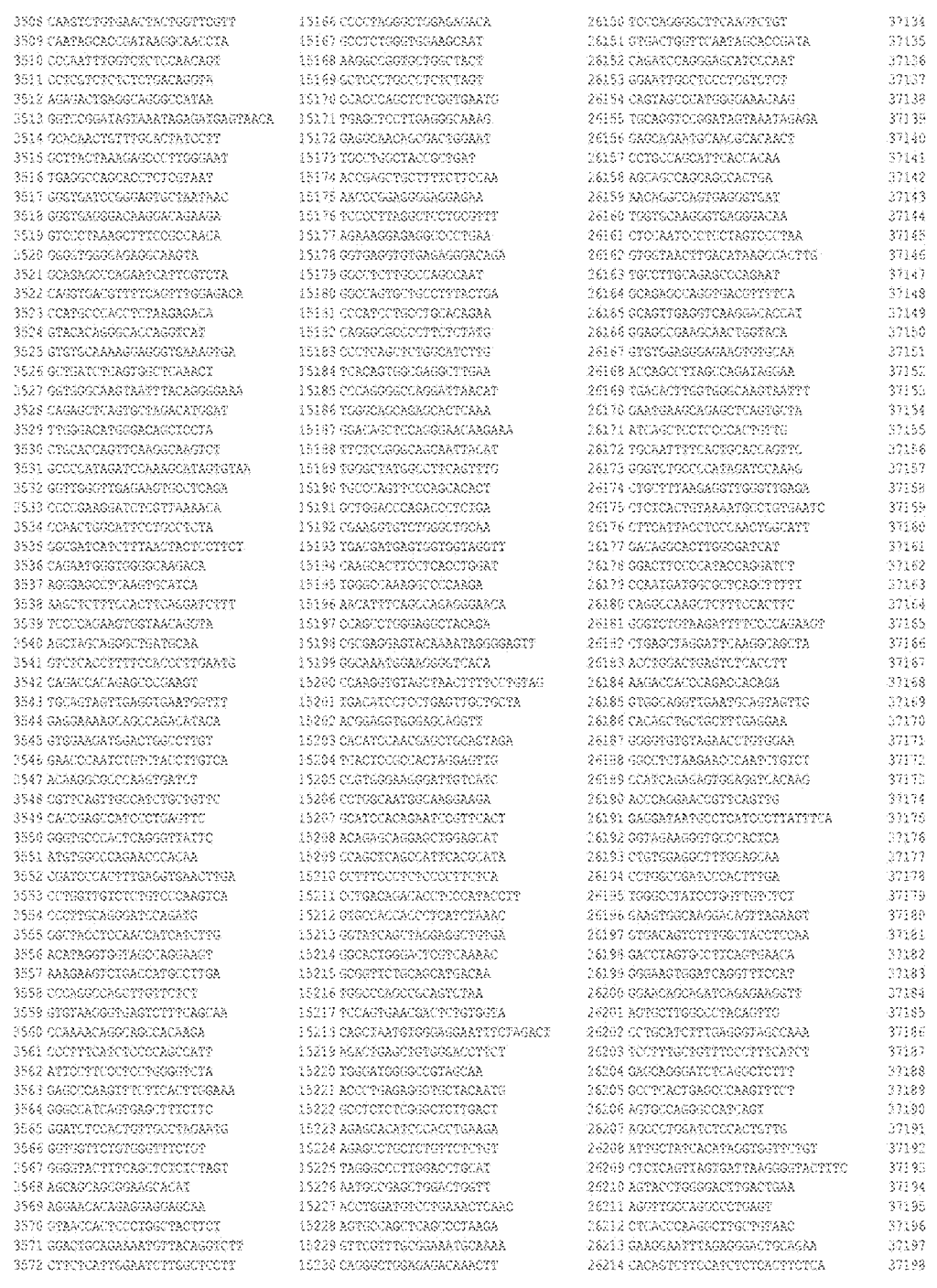
Figure 36F6:
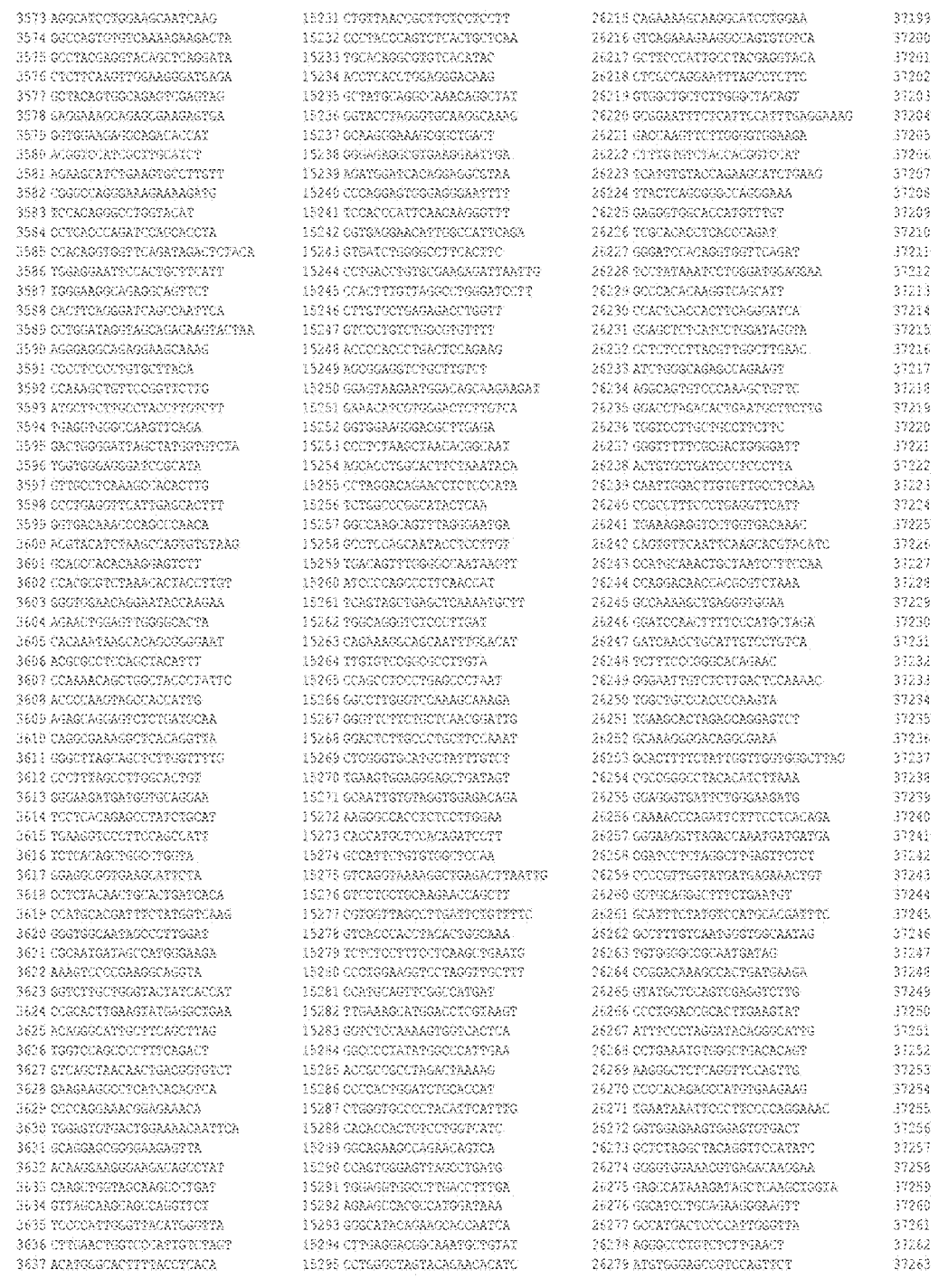
Figure 36F7:
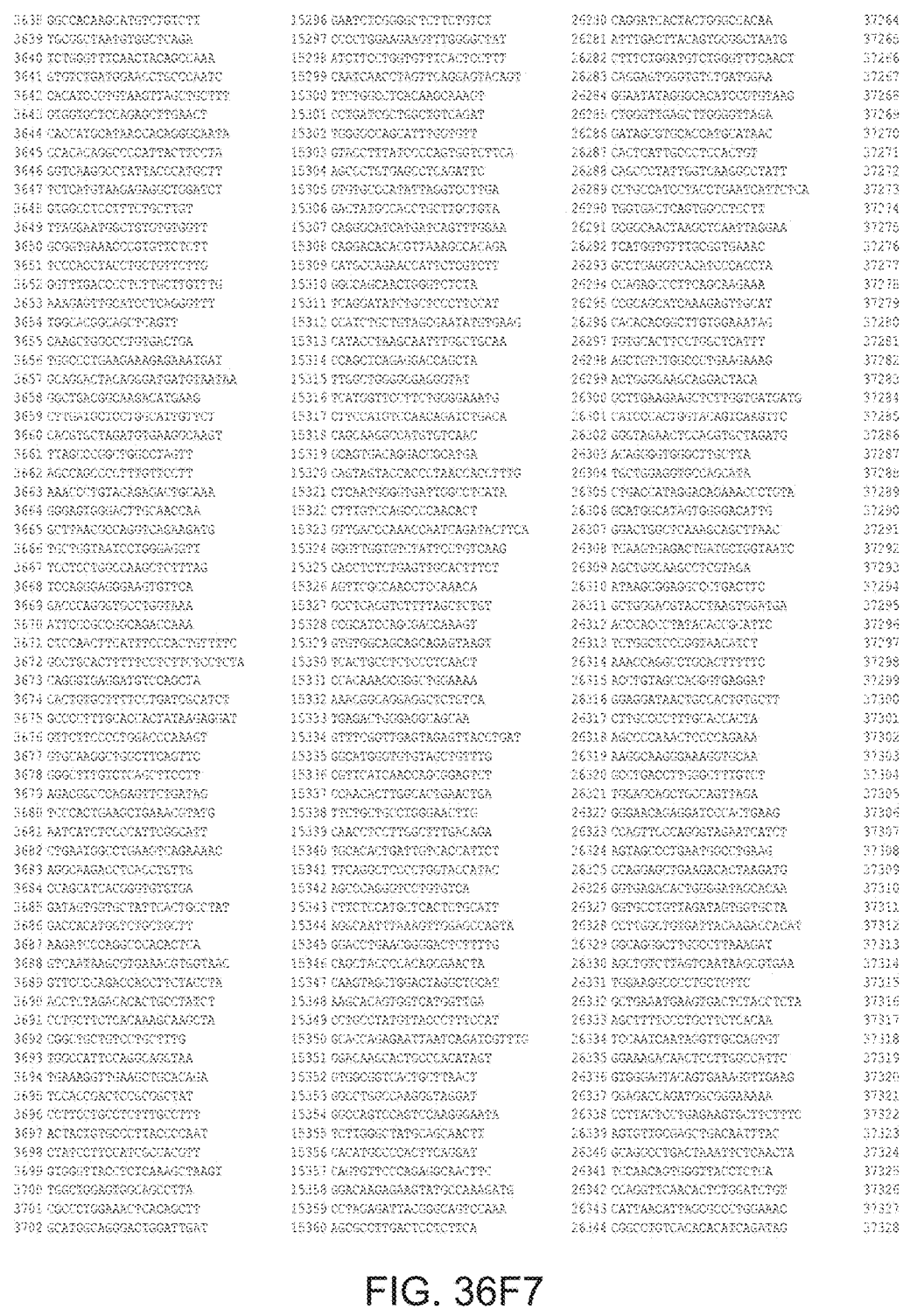
Figure 36F8:
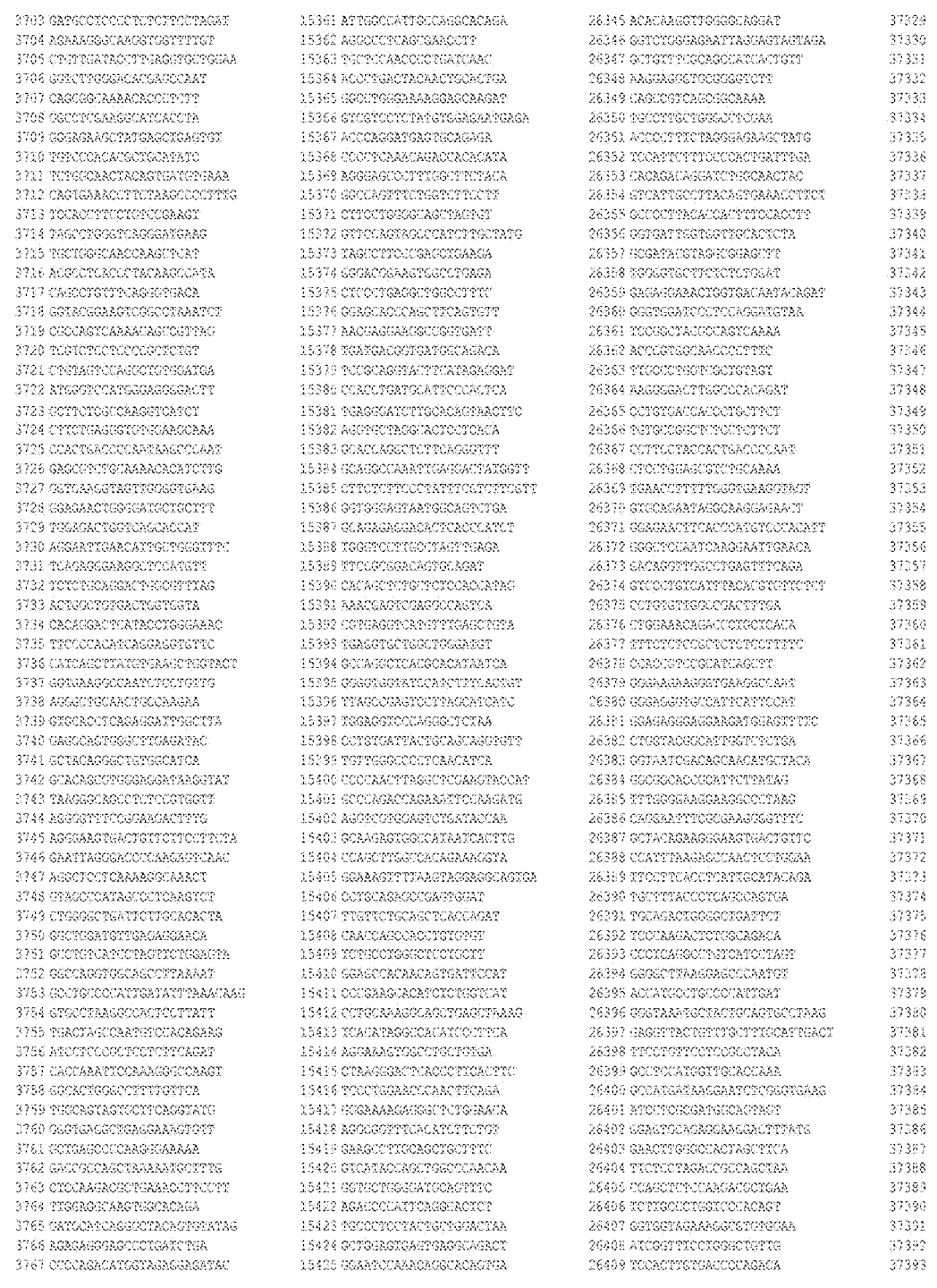
Figure 36F9:
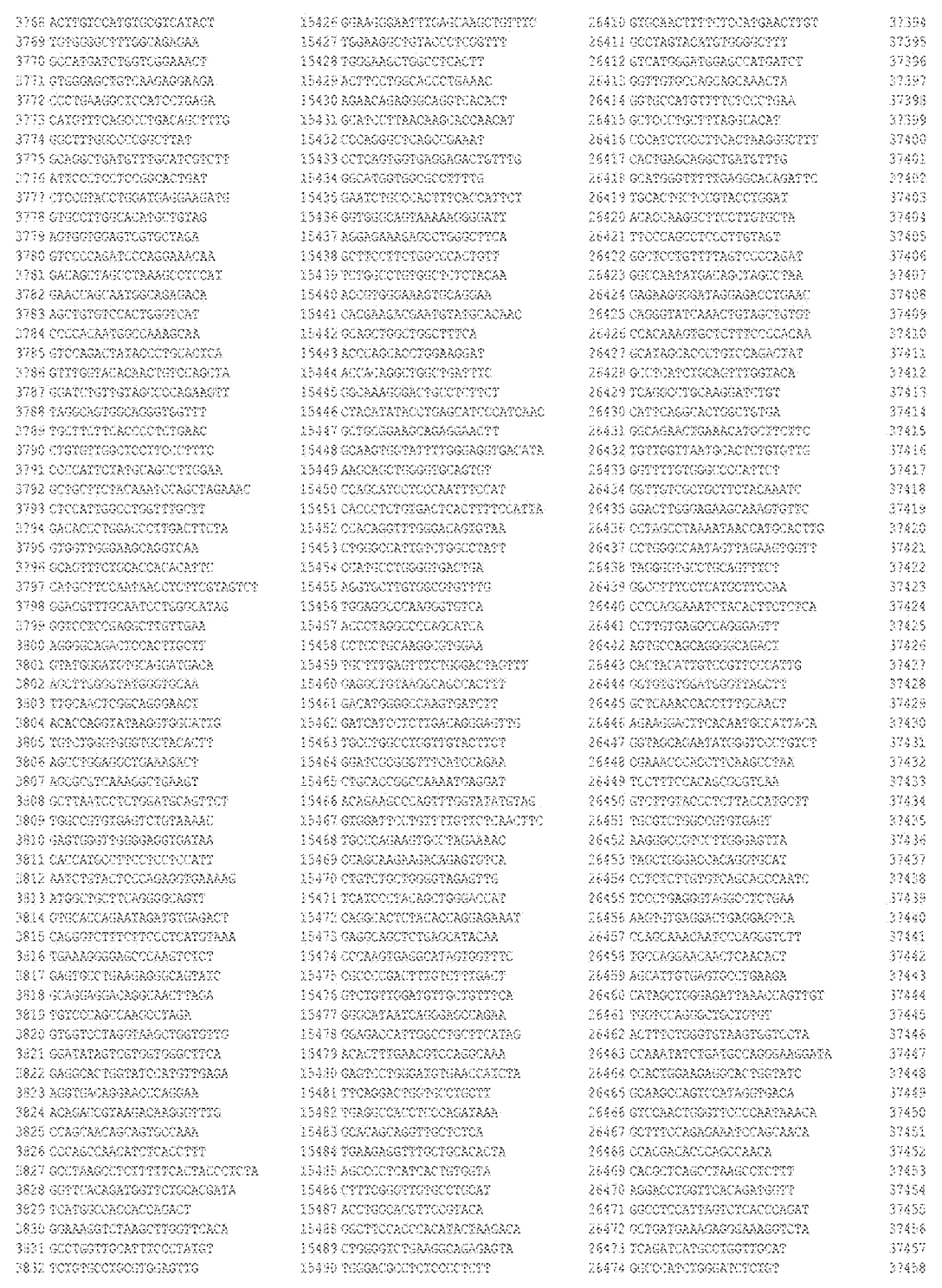
Figure 36F10:
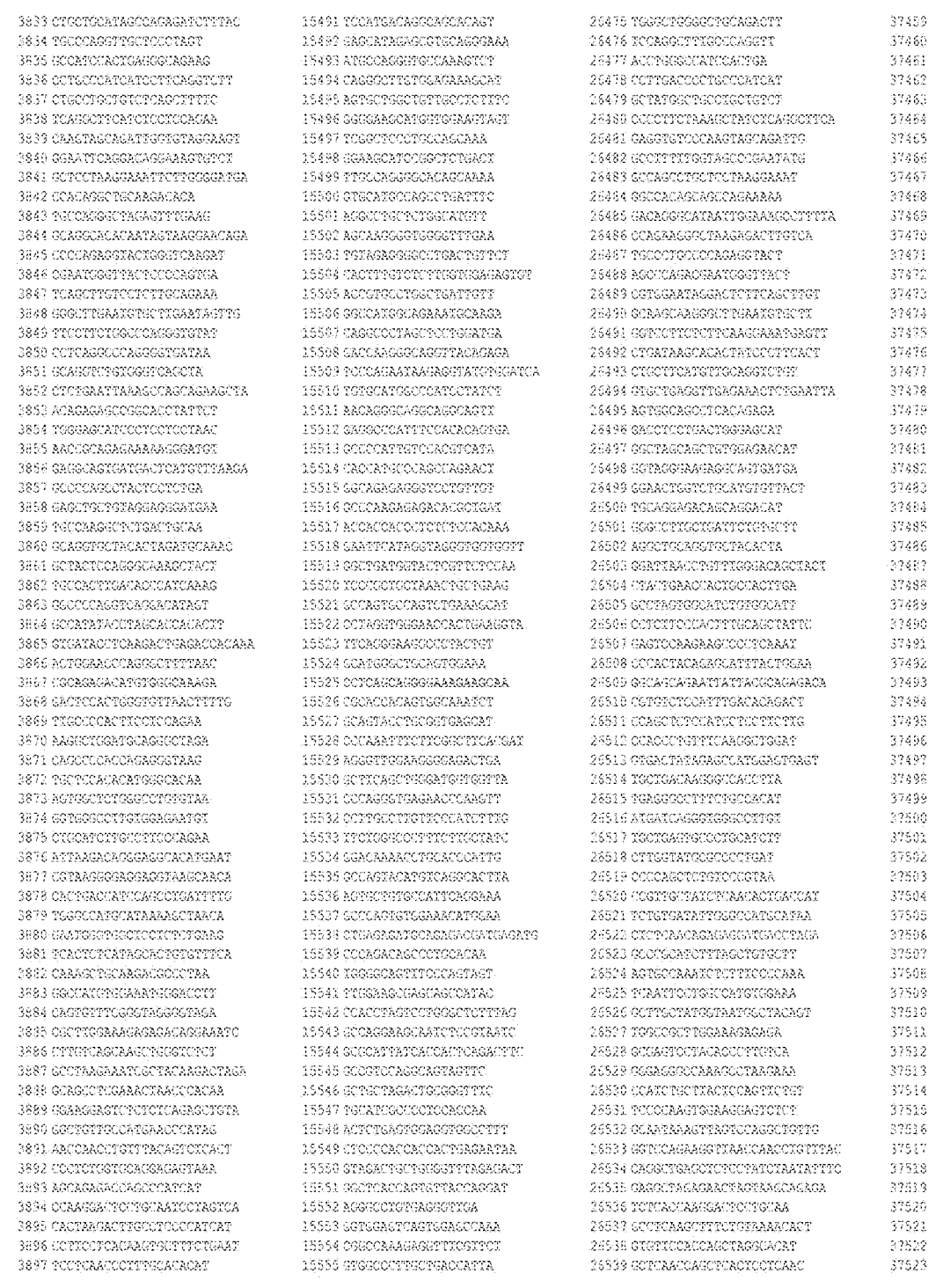
Figure 36G1:
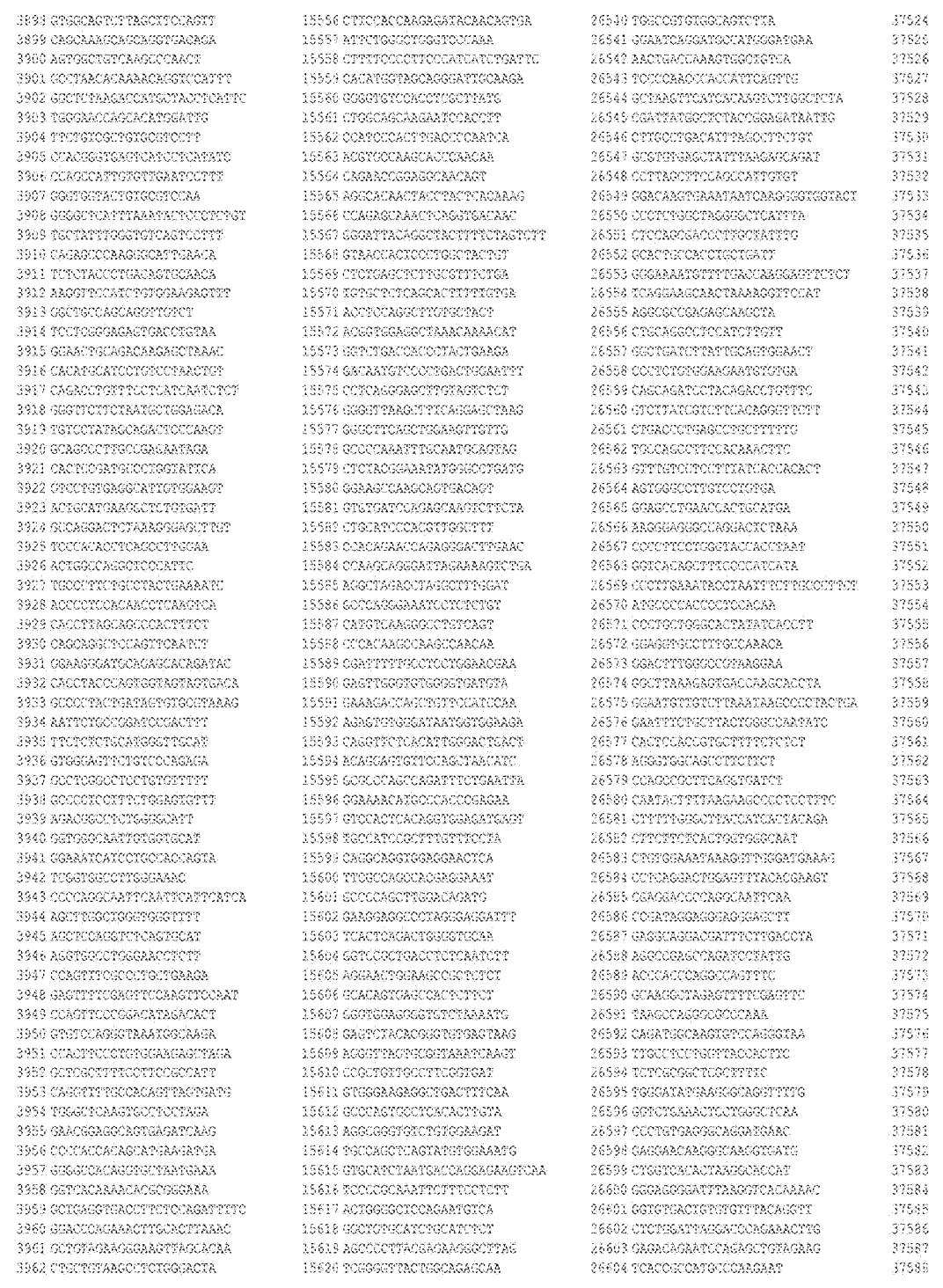
Figure 36G2:
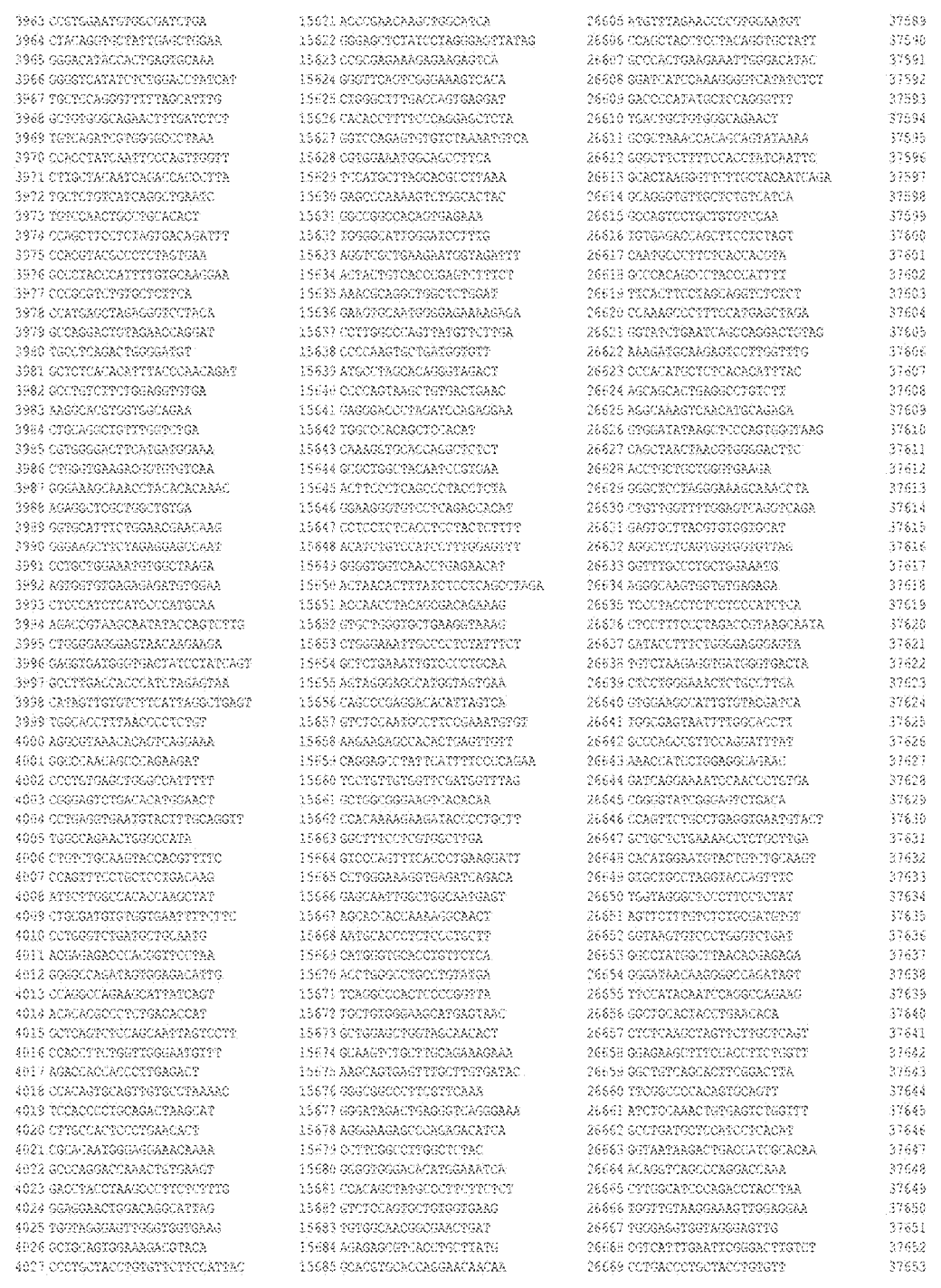
Figure 36G3:
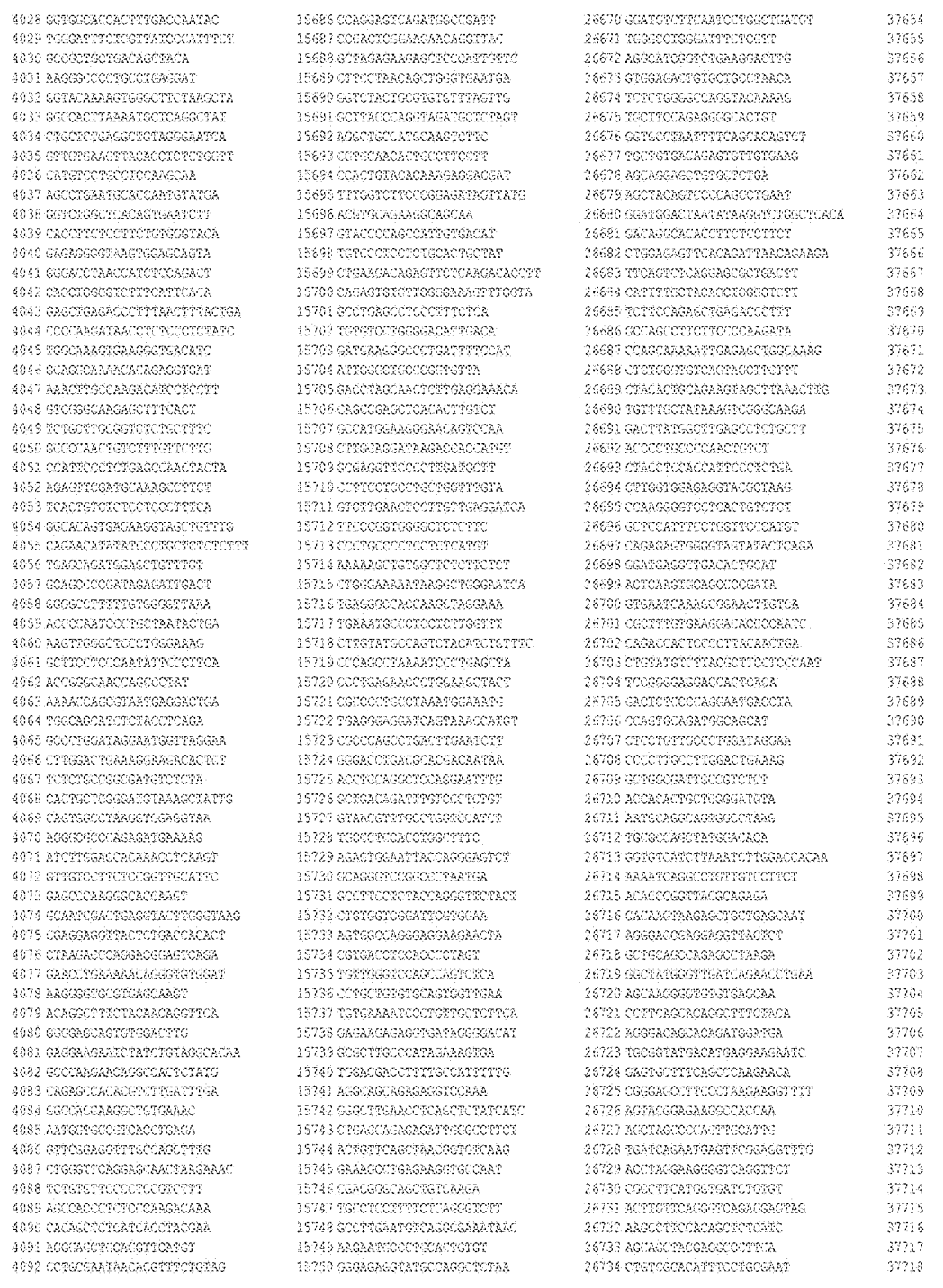
Figure 36G4:
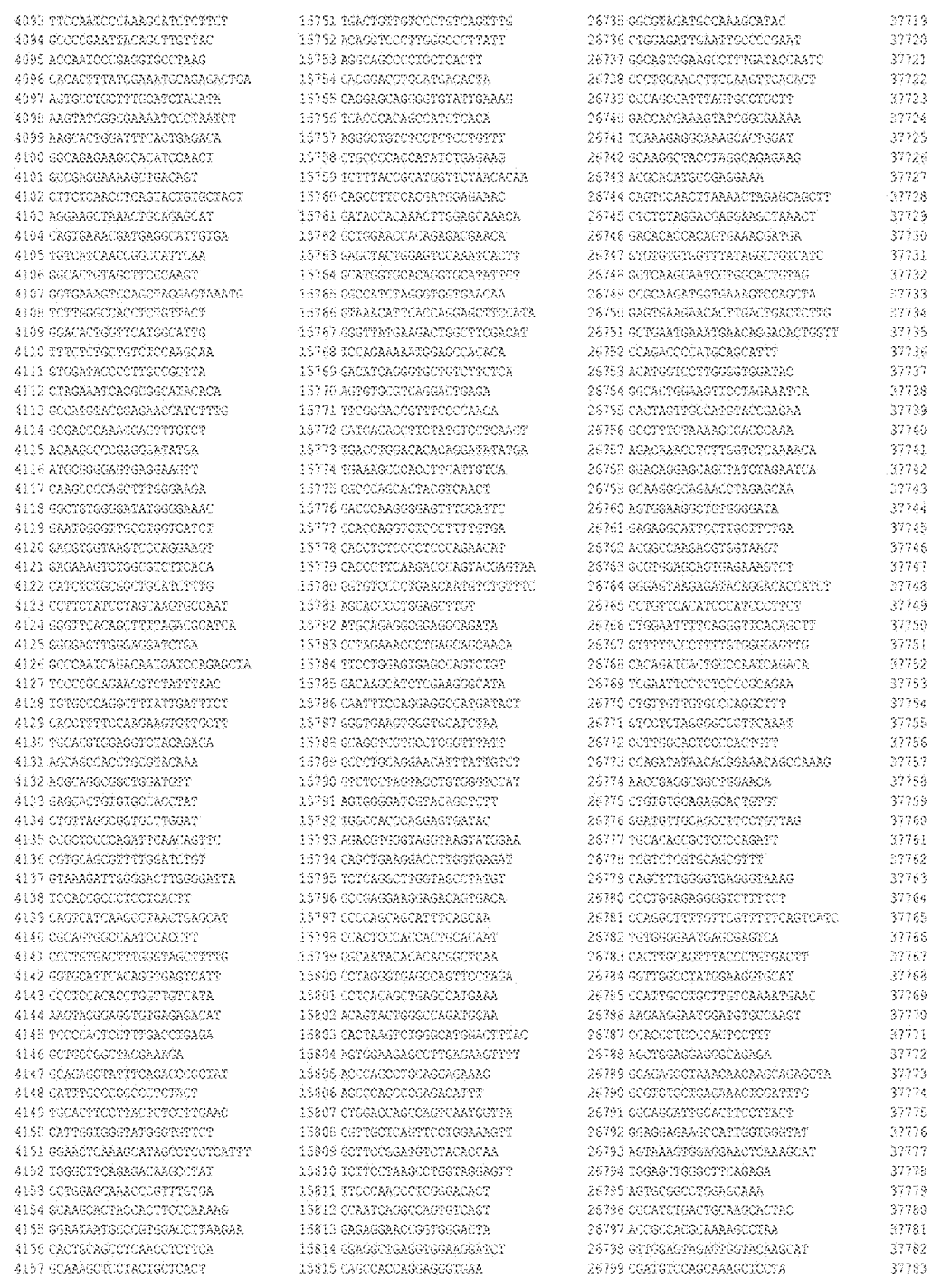
Figure 36G5:
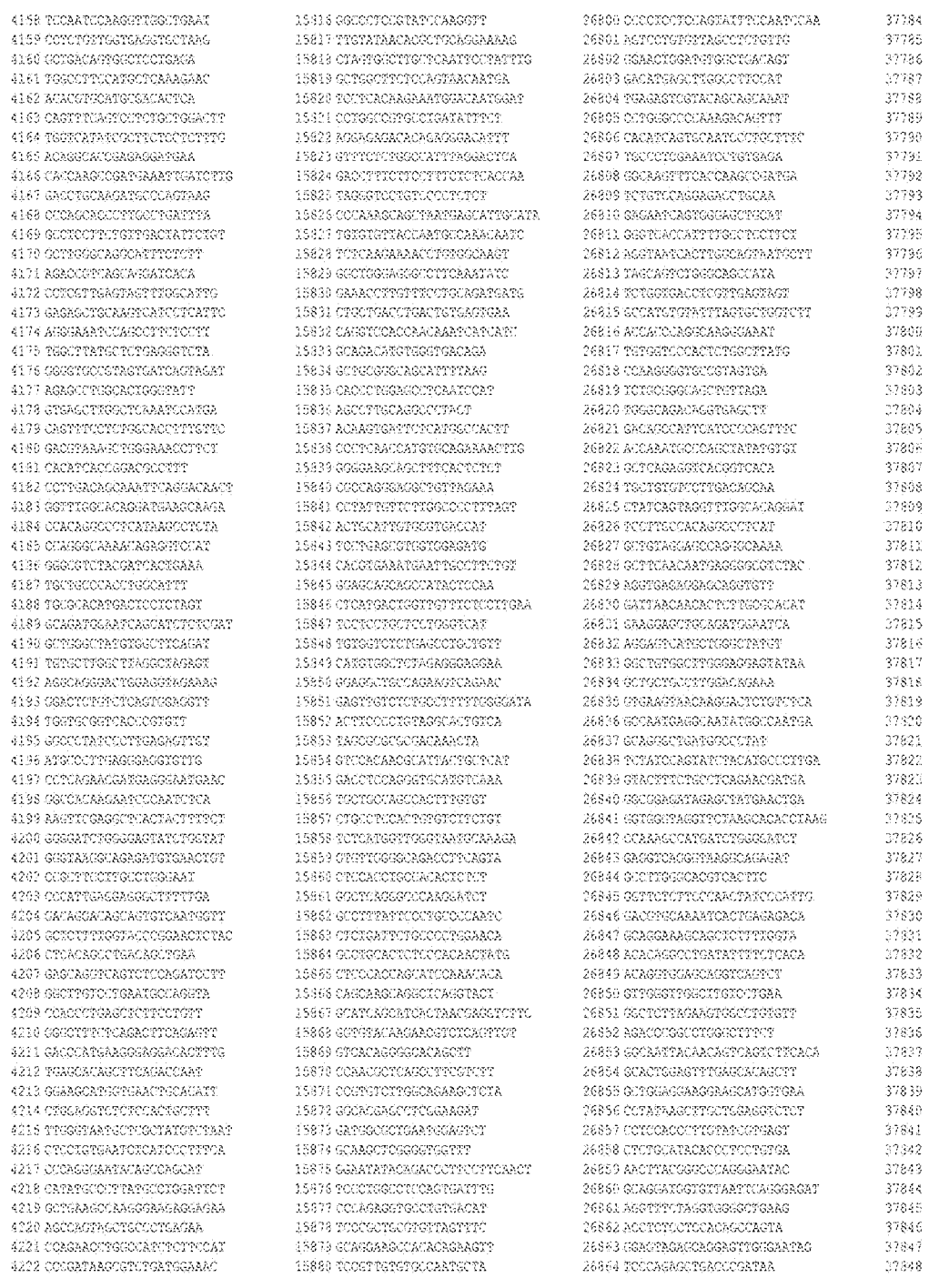
Figure 36G6:
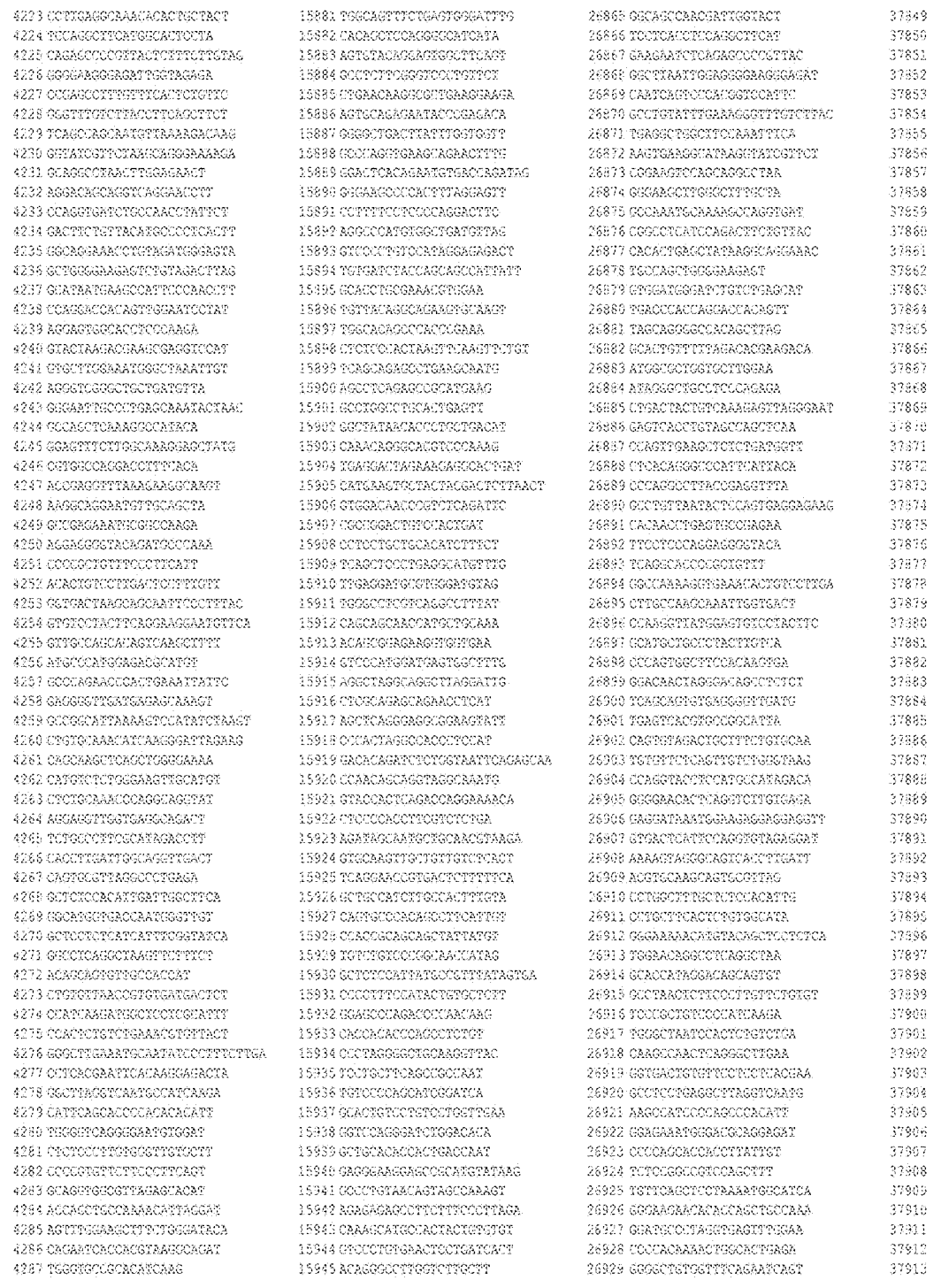
Figure 36G7:
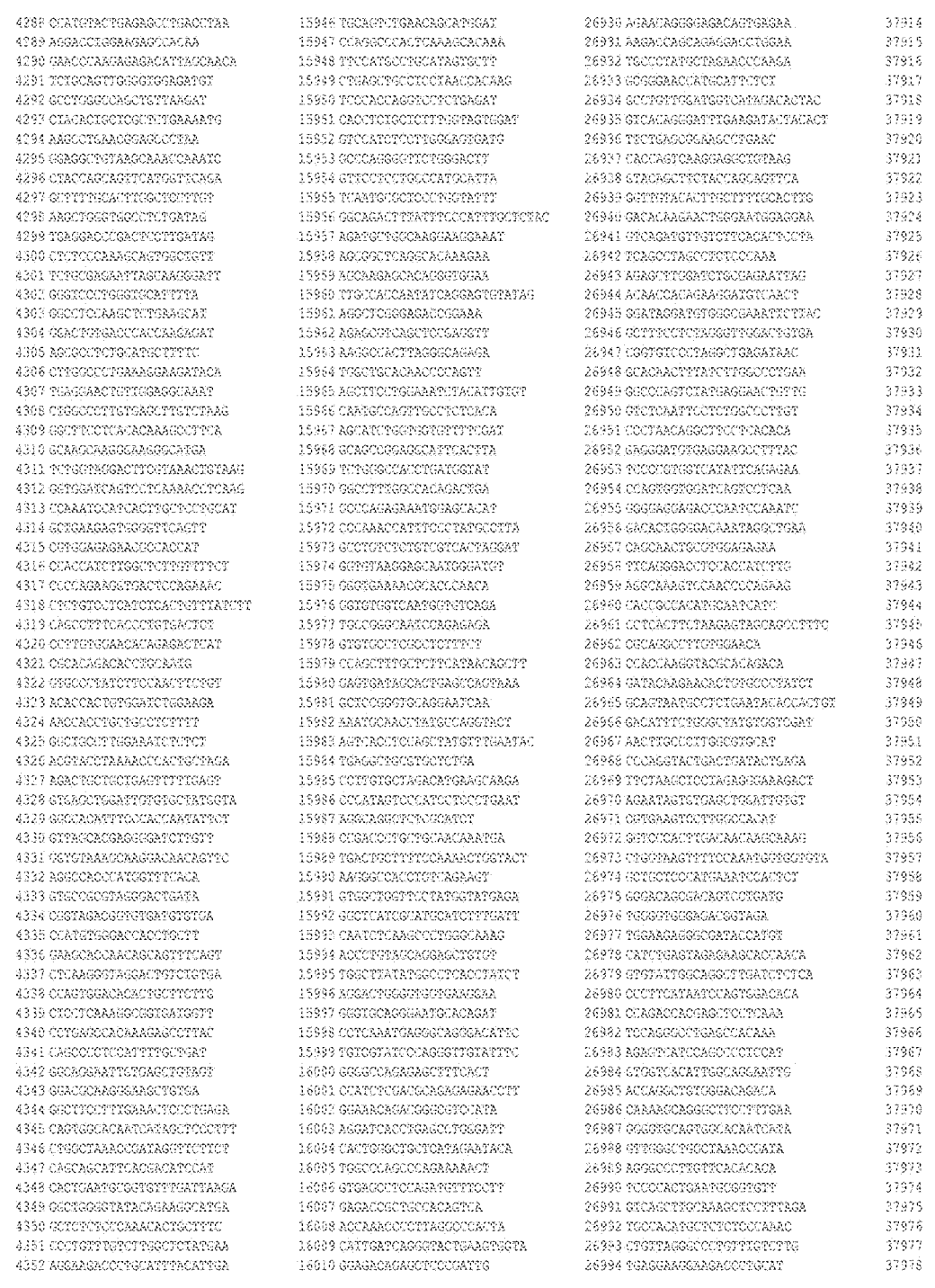
Figure 36G8:
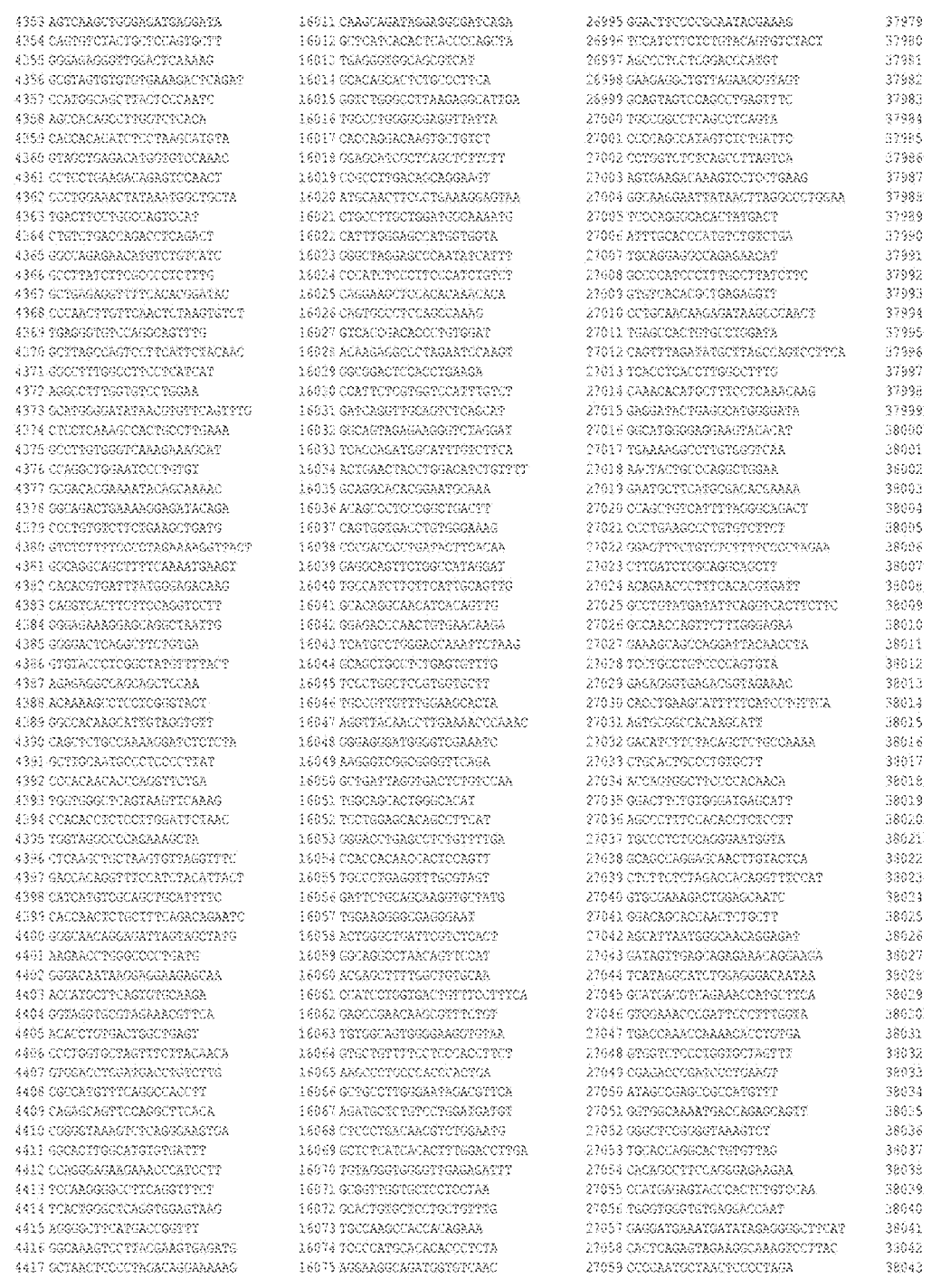
Figure 36G10:
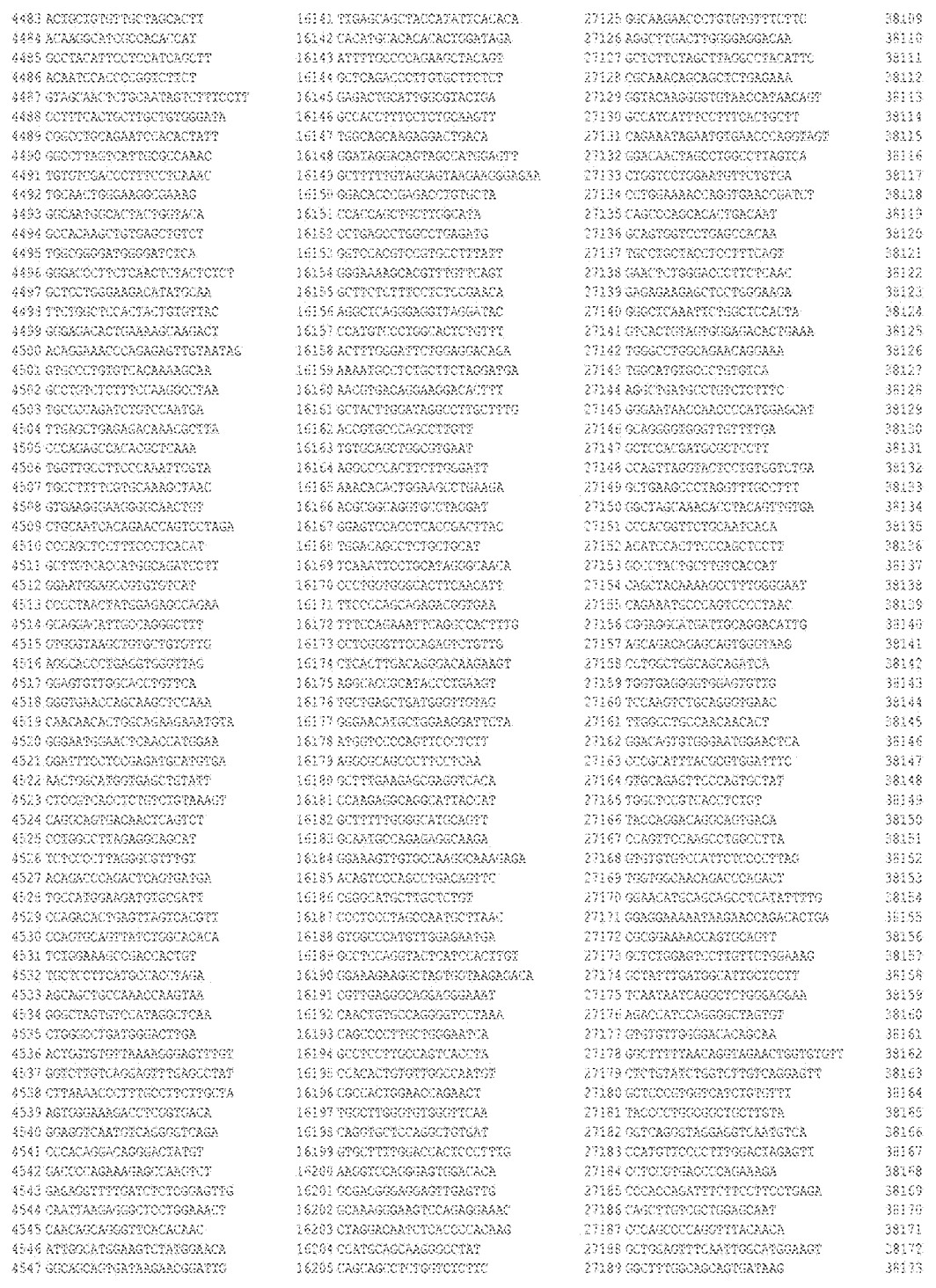
Figure 36H1:
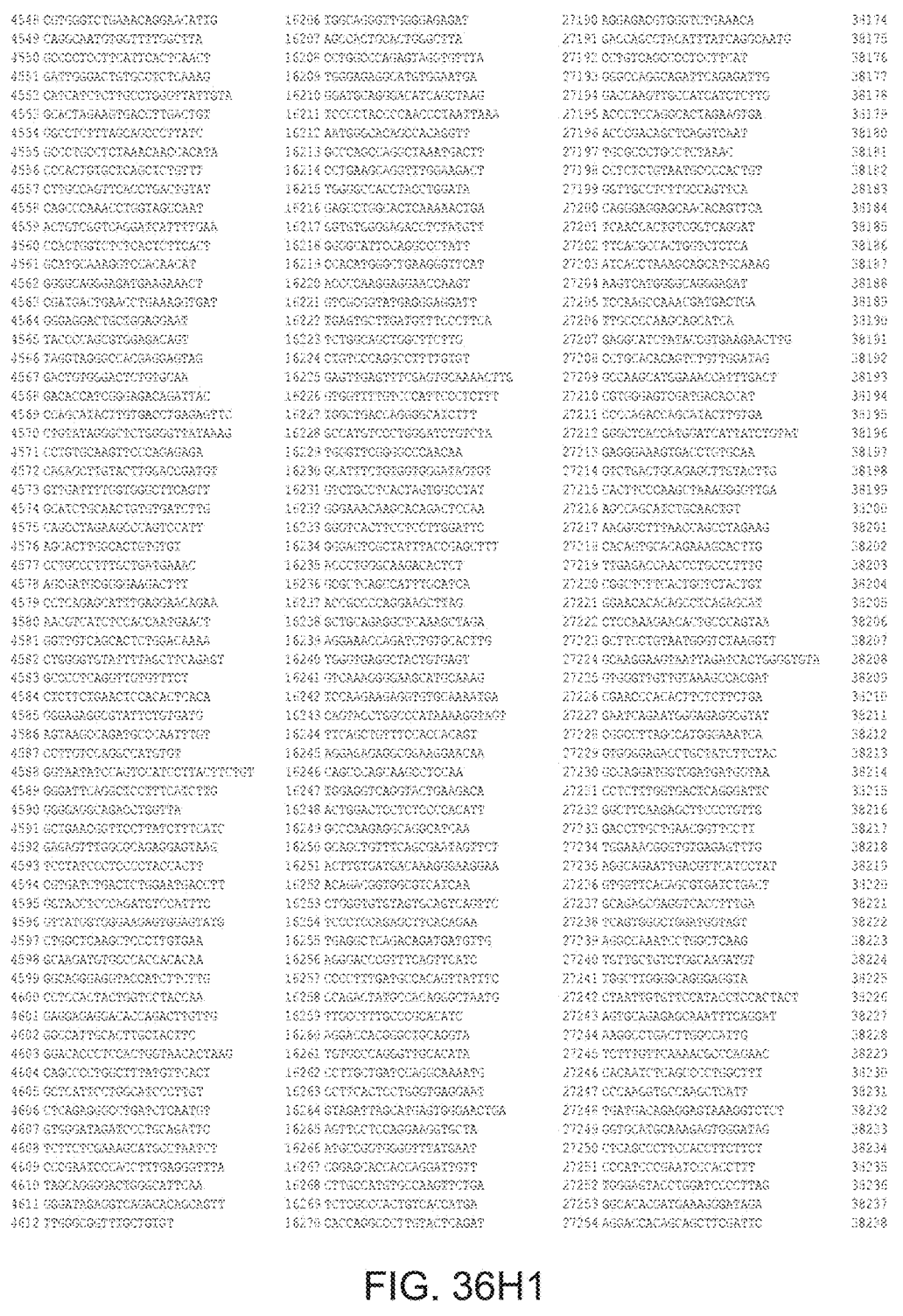
Figure 36H2:
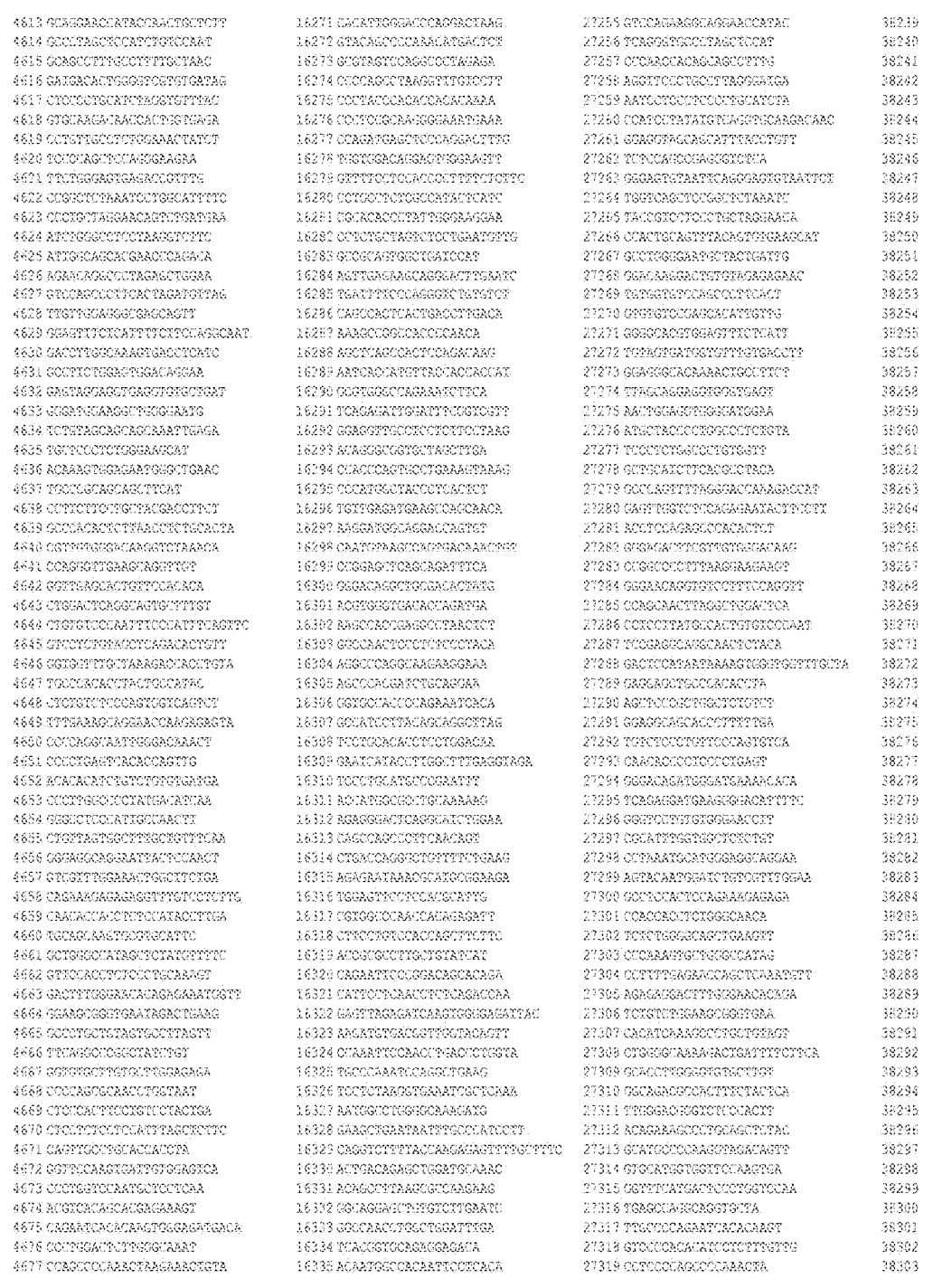
Figure 36H3:
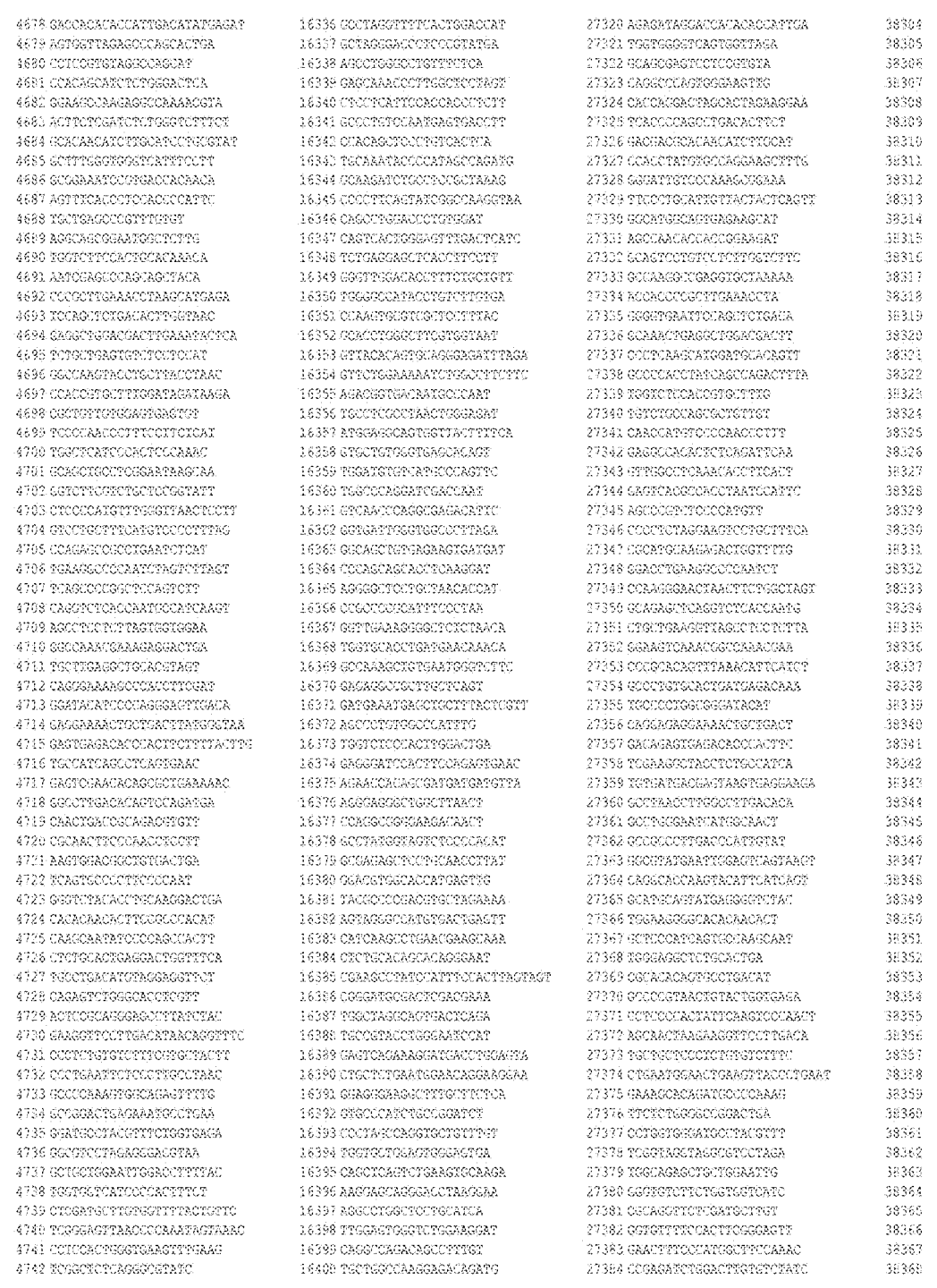
Figure 36H4:
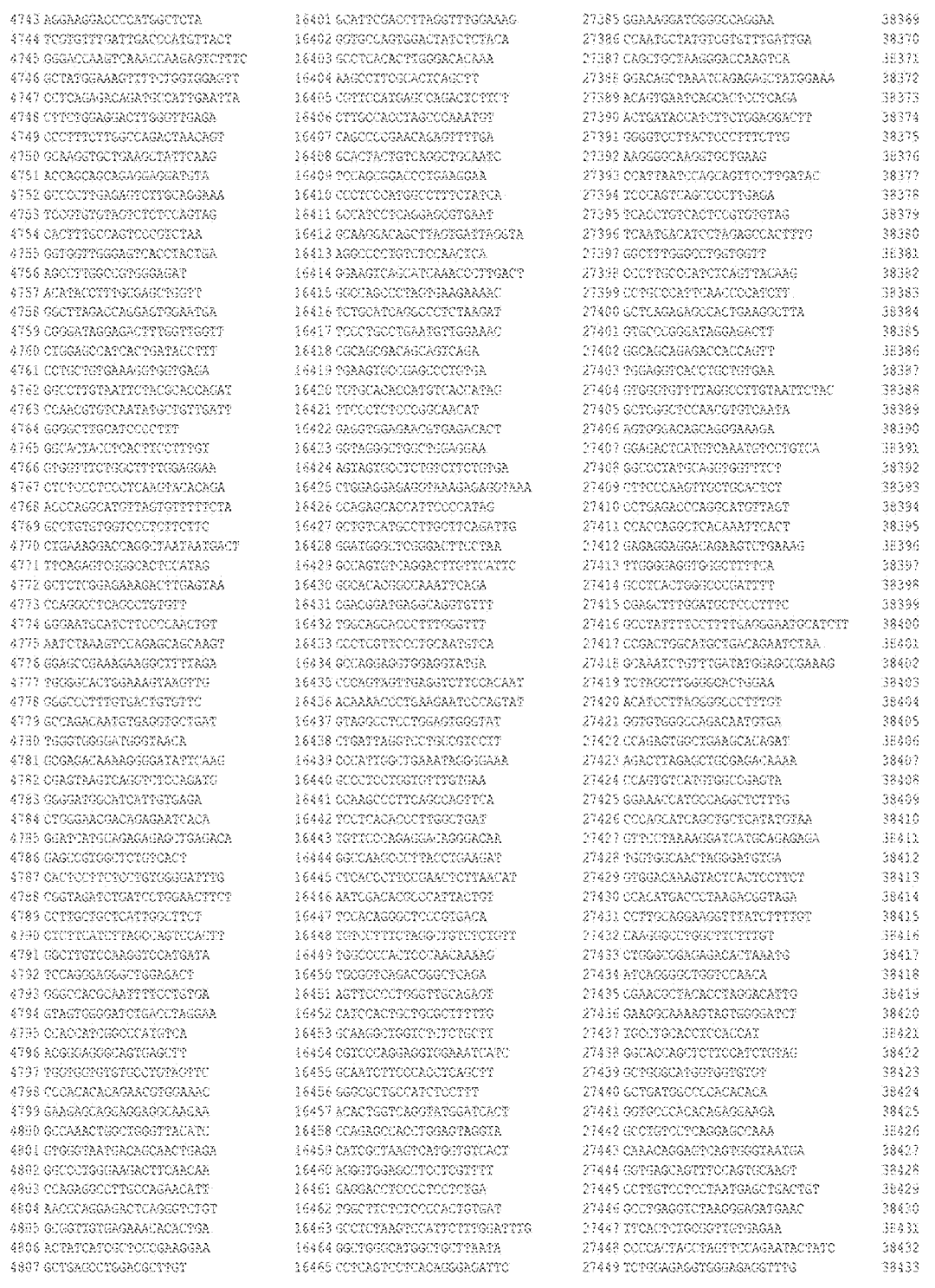
Figure 36H5:
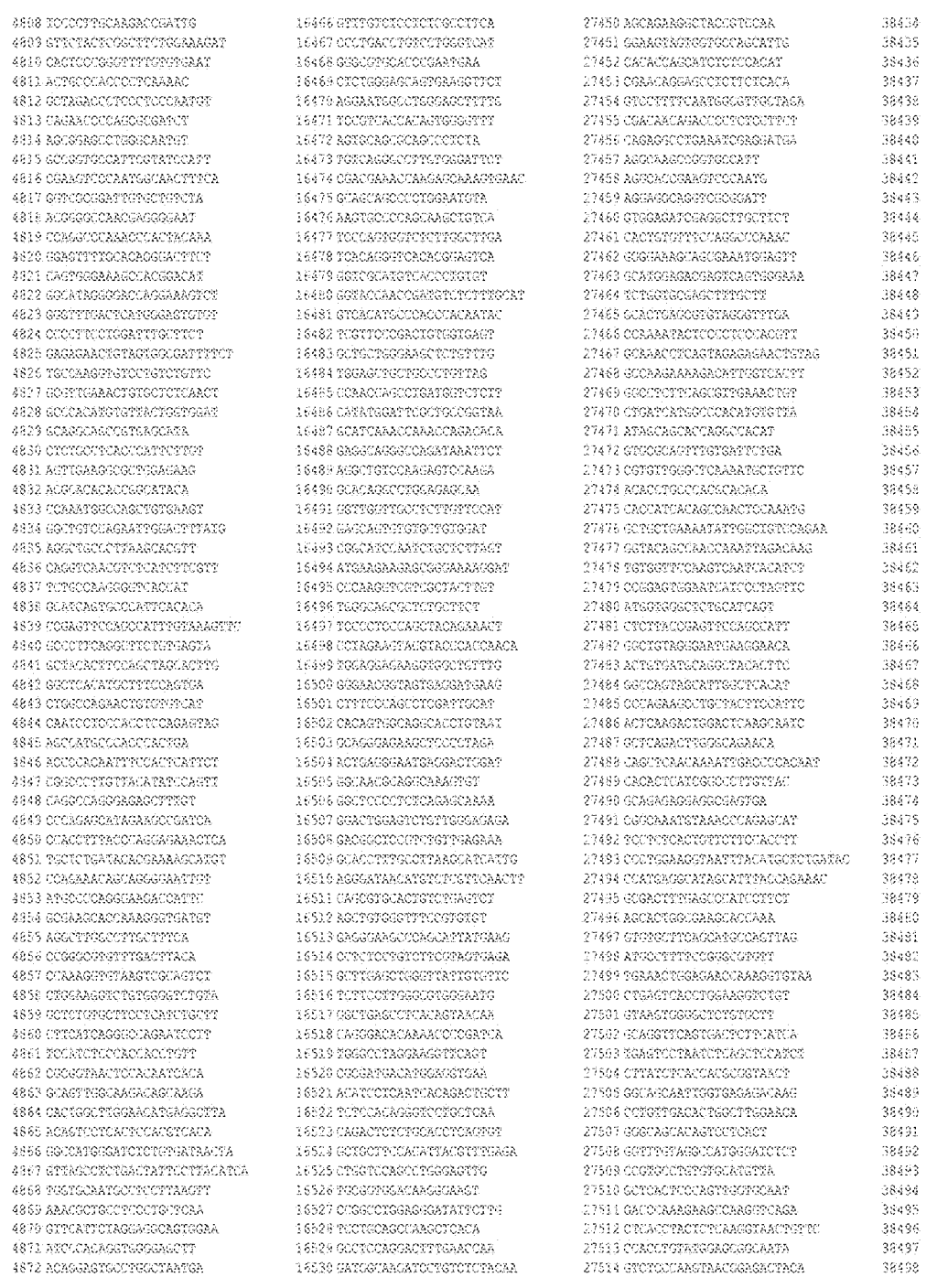
Figure 36H6:
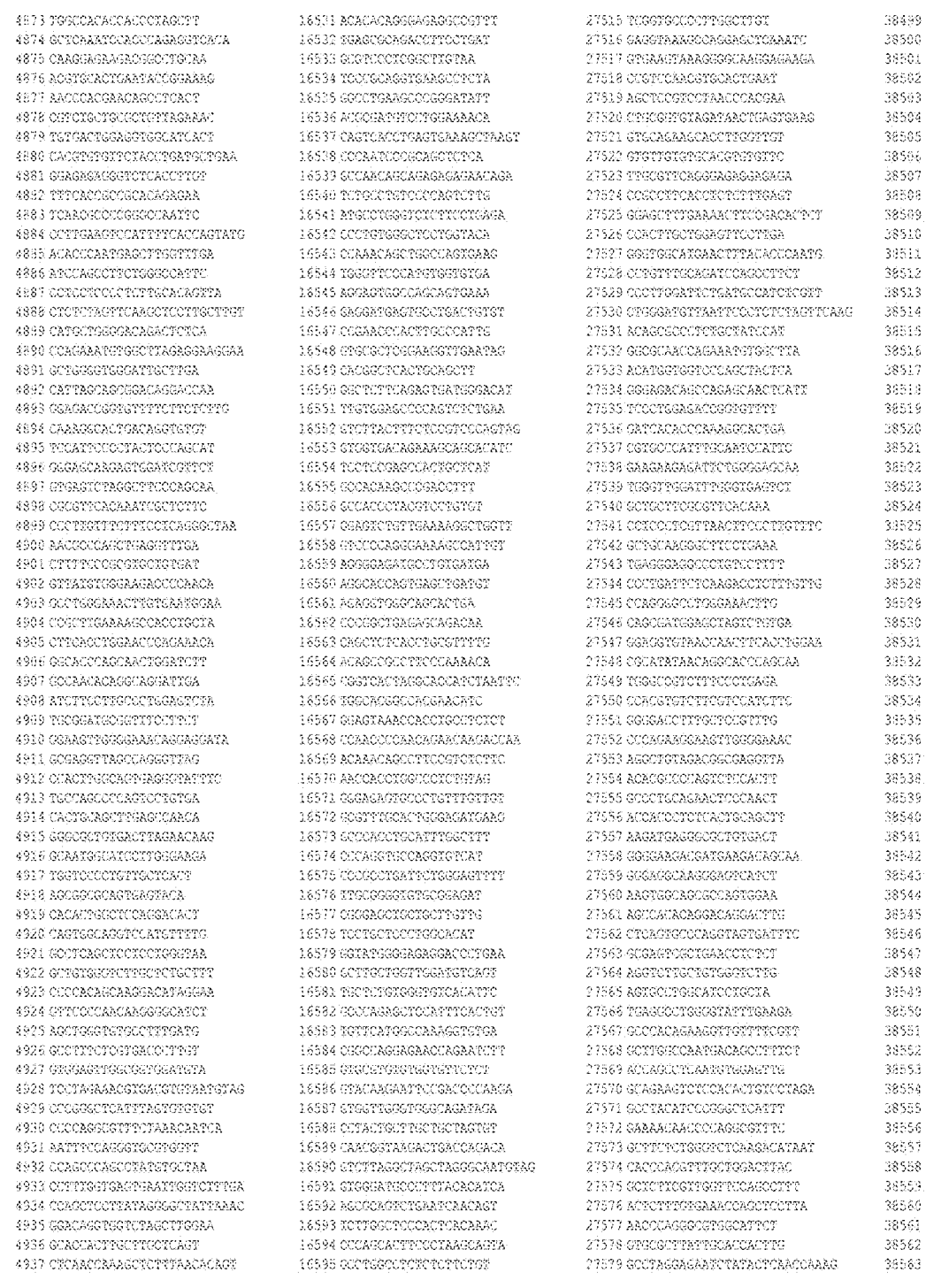
Figure 36H7:
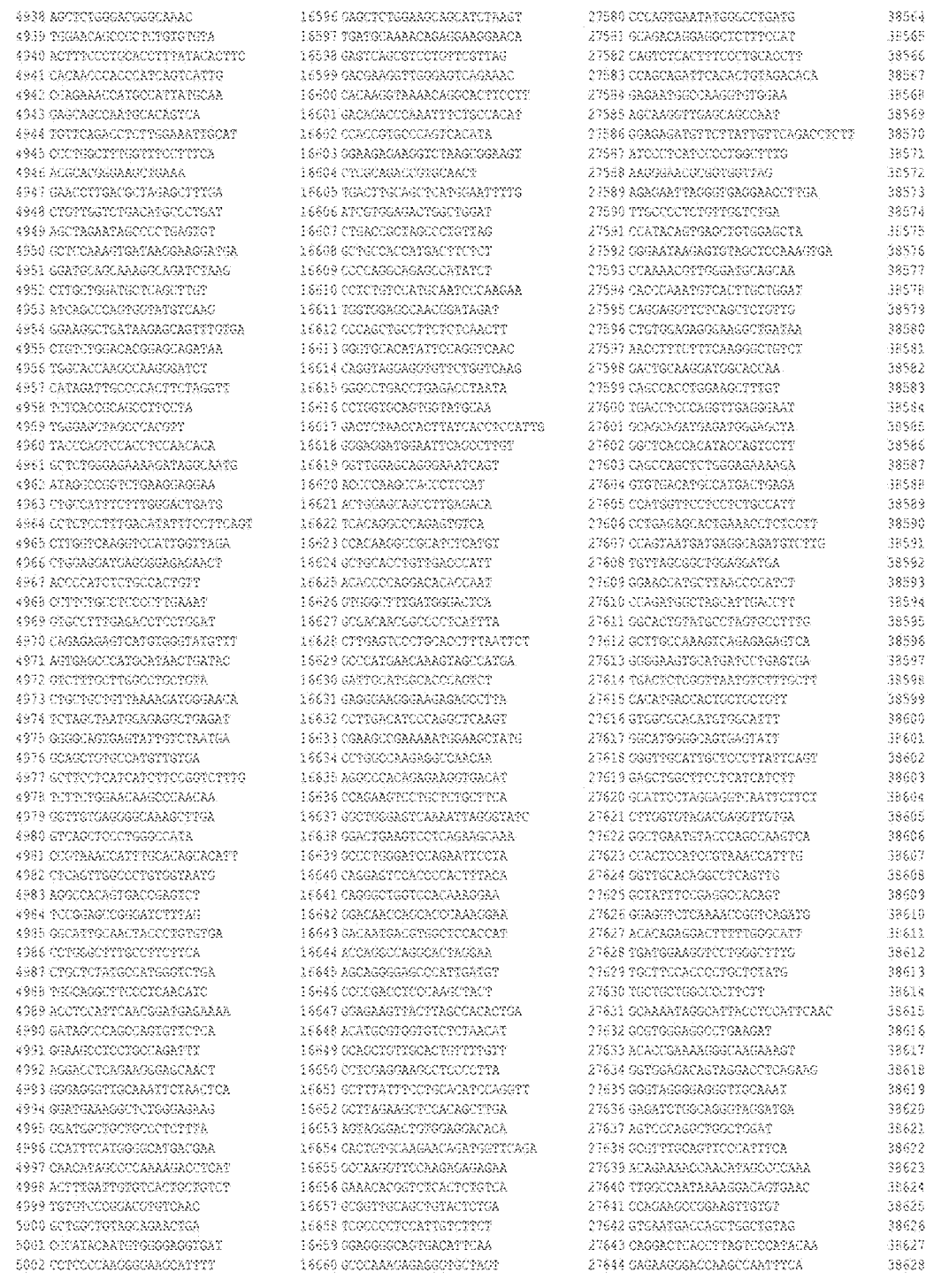
Figure 36H8:
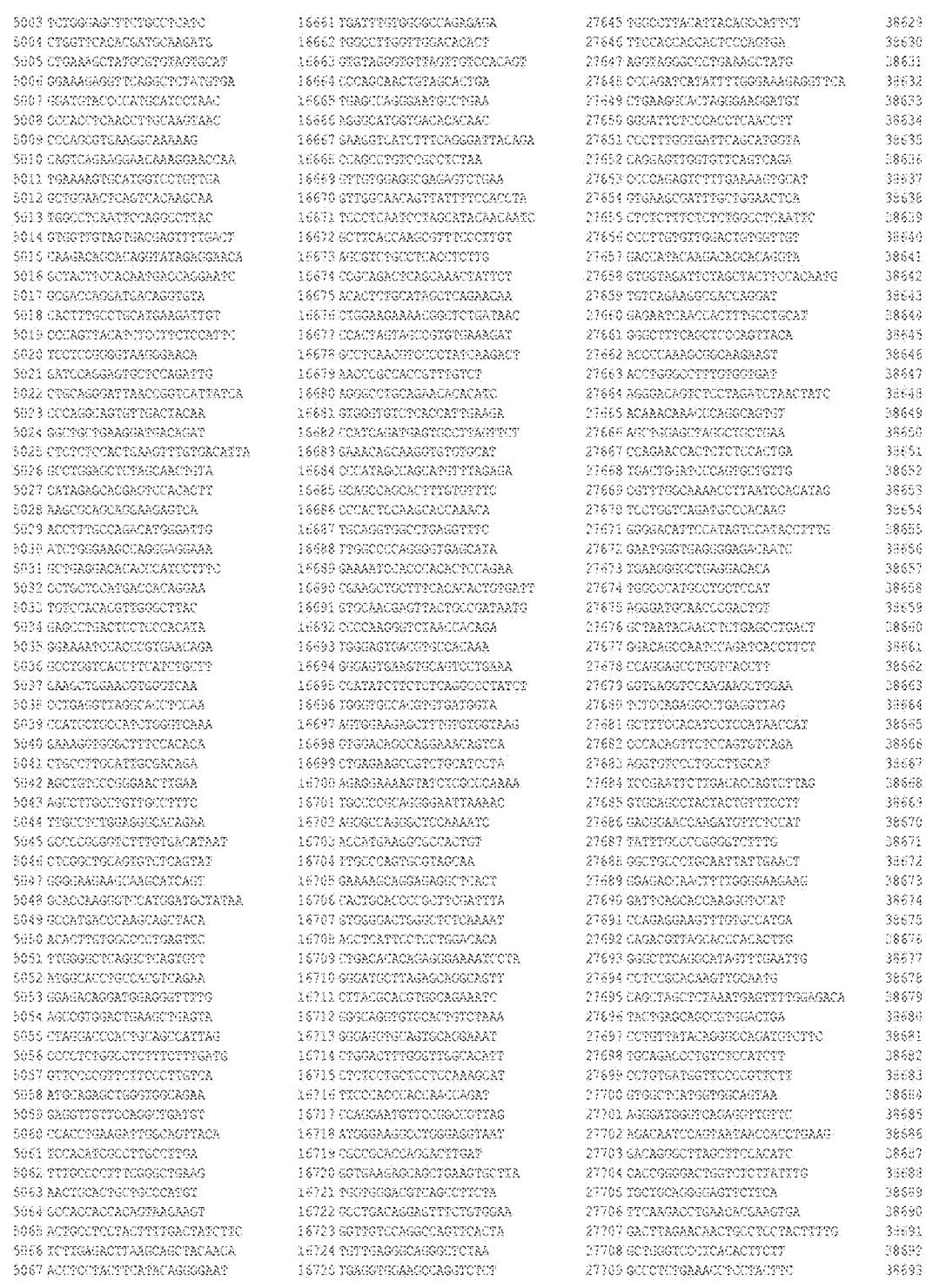
Figure 36H9:
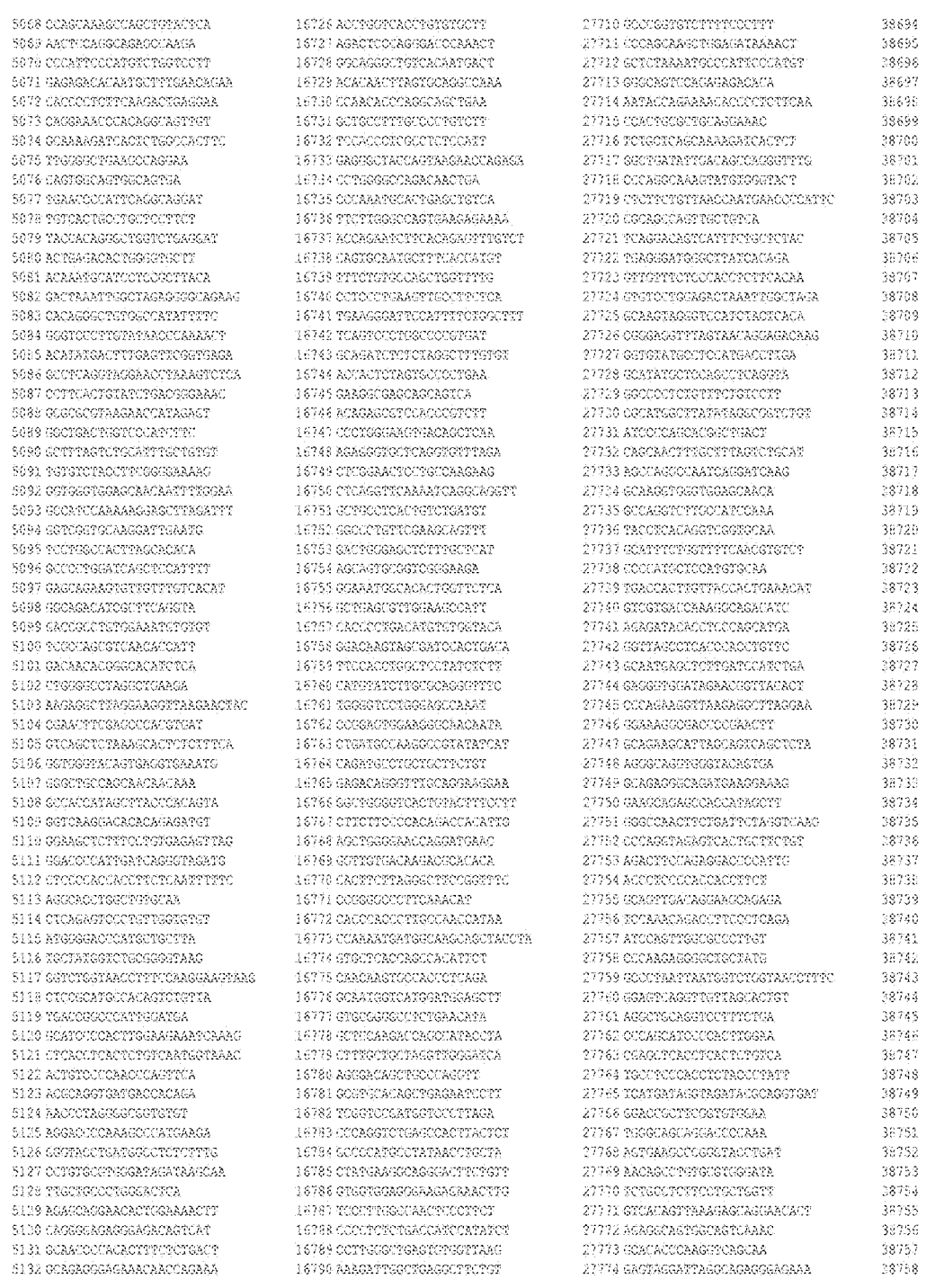
Figure 36H10:
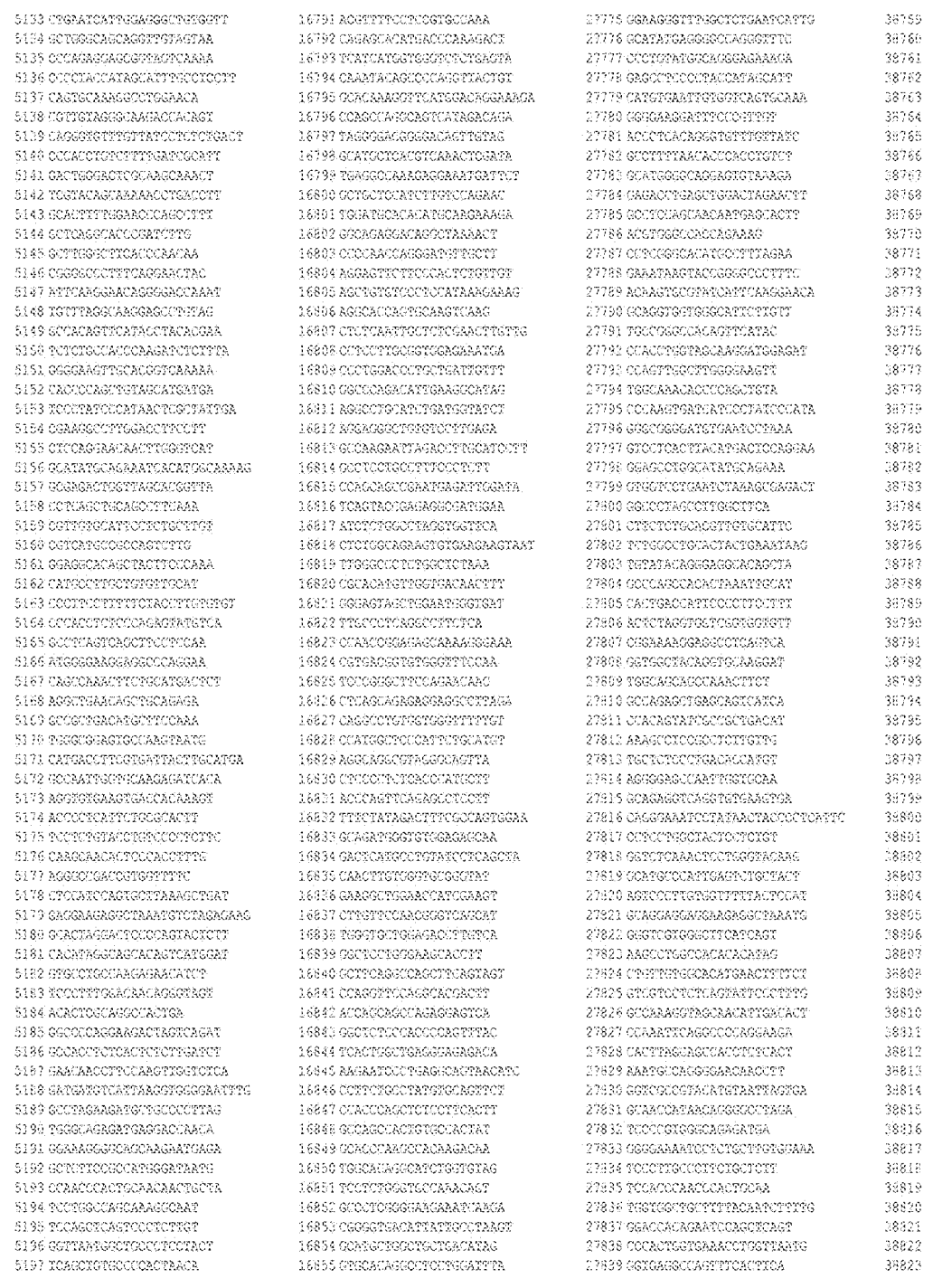
Figure 36I1:
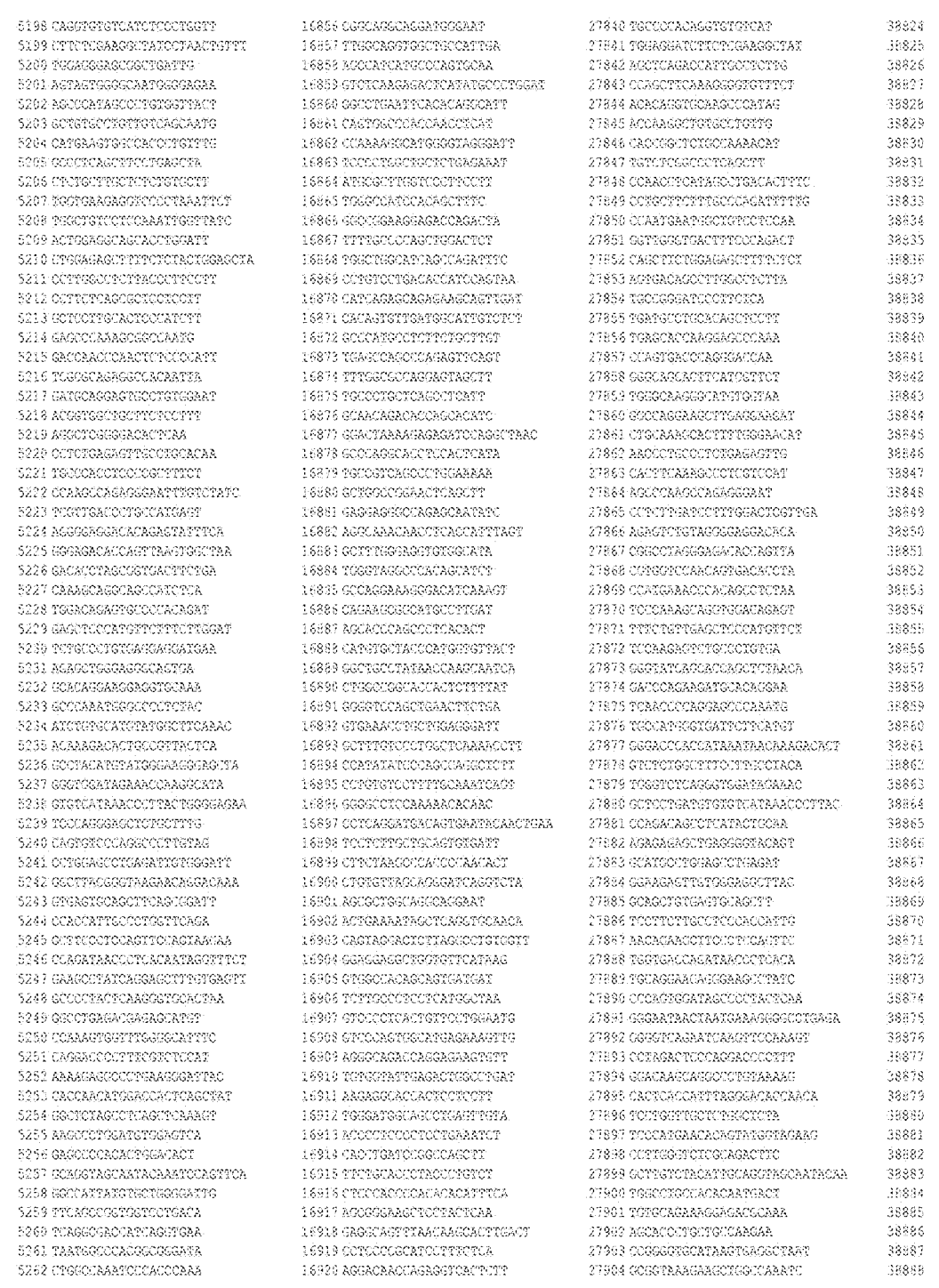
Figure 36I2:
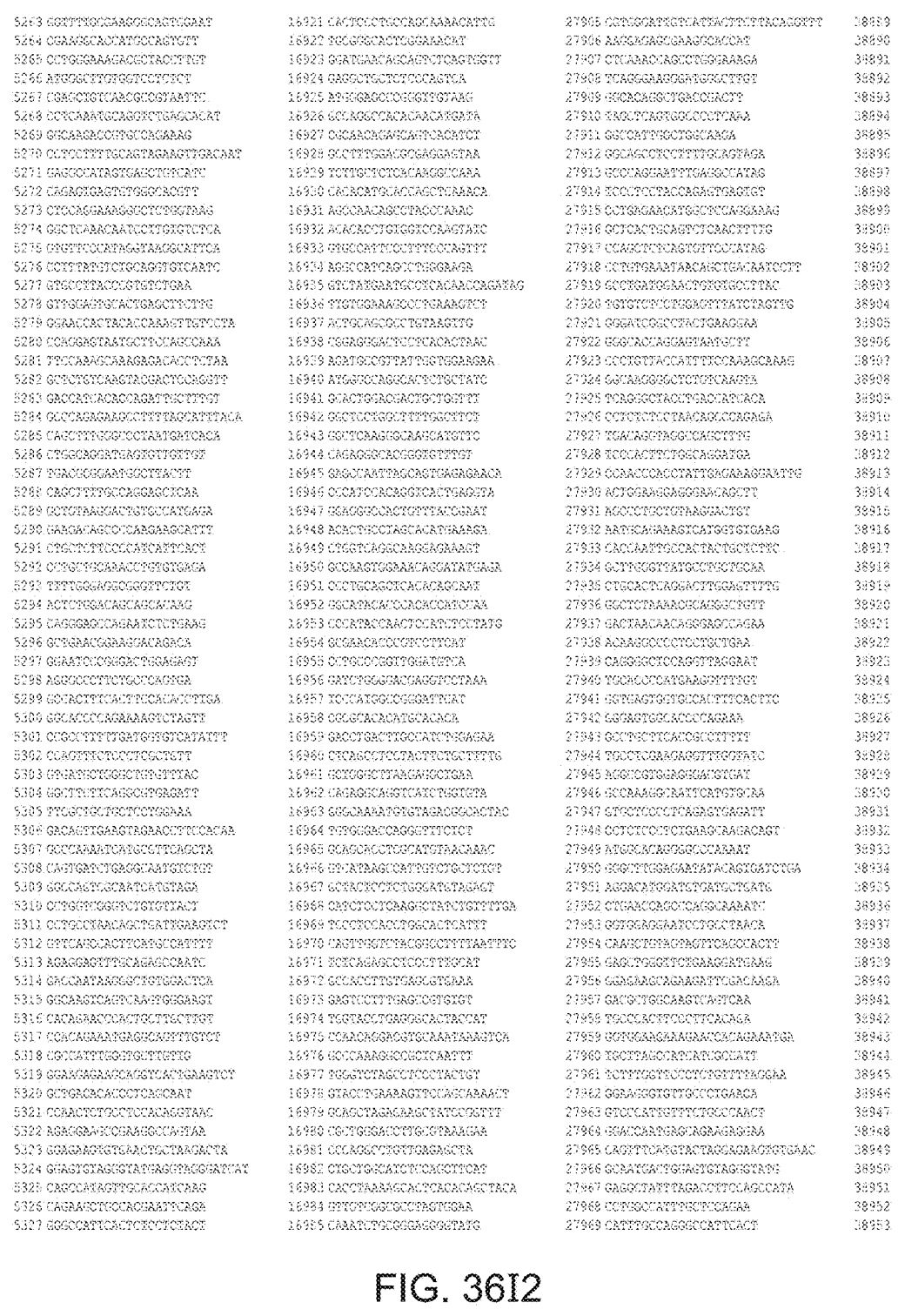
Figure 36I3:
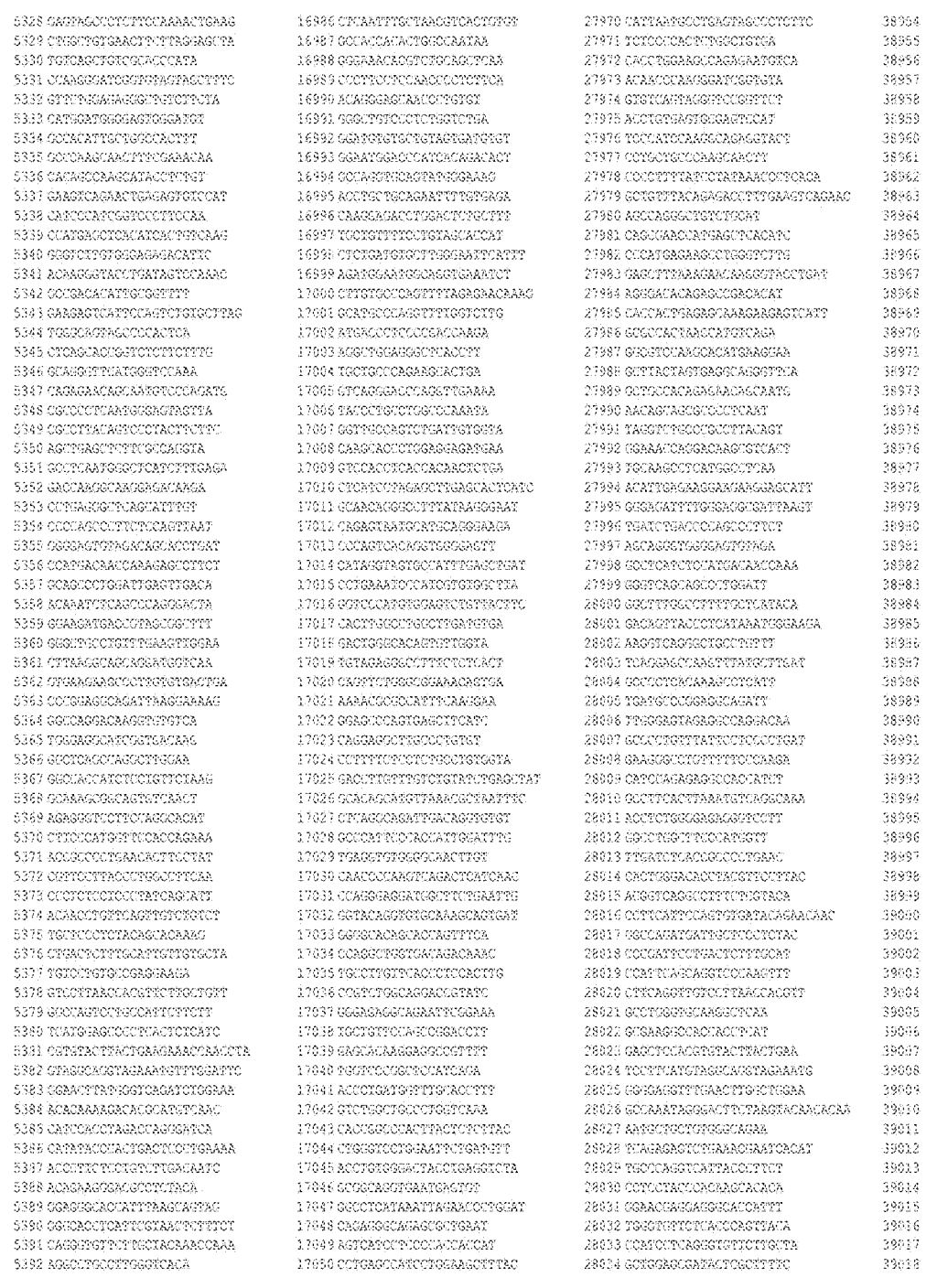
Figure 36I4:
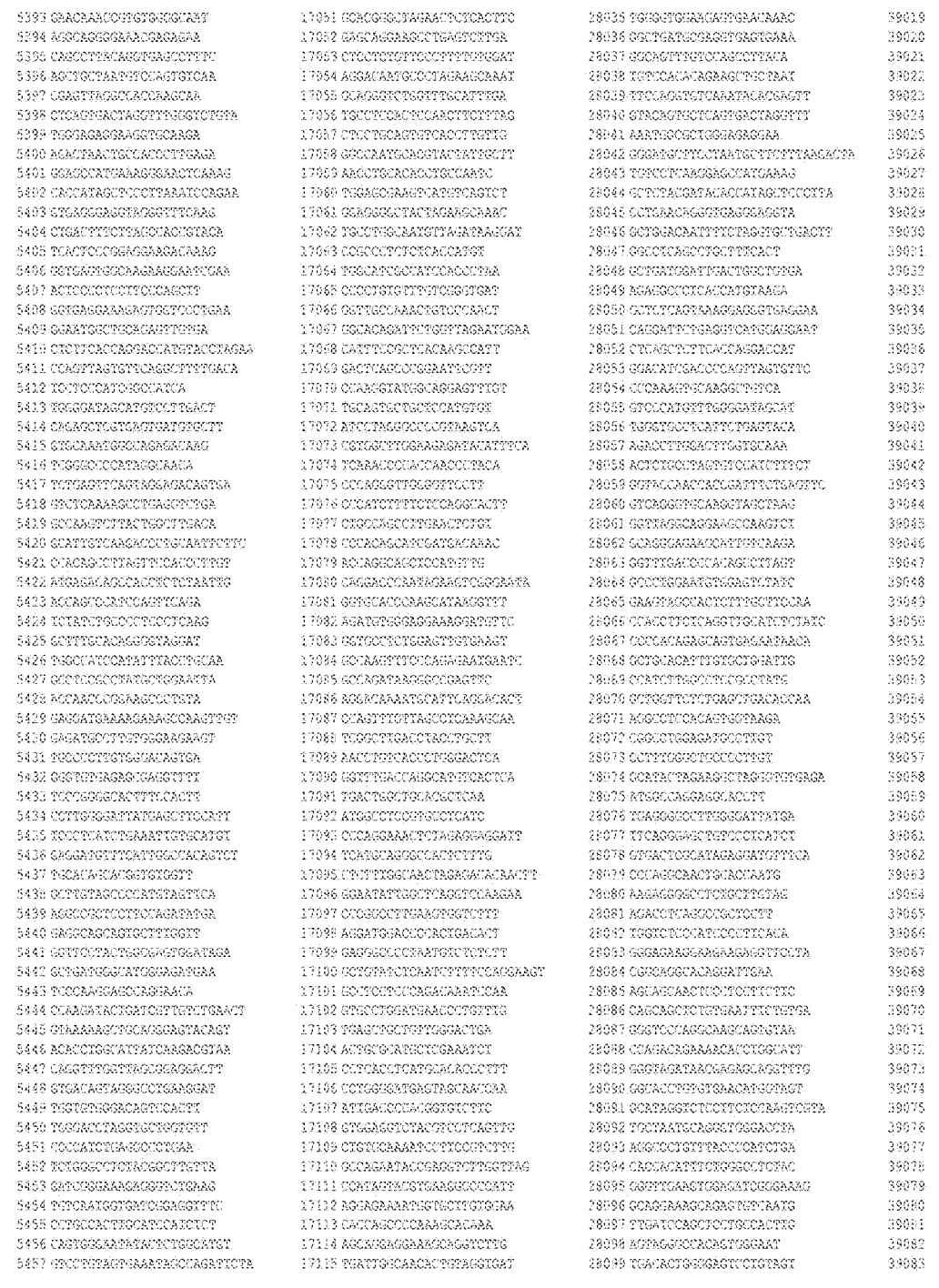
Figure 36I6:
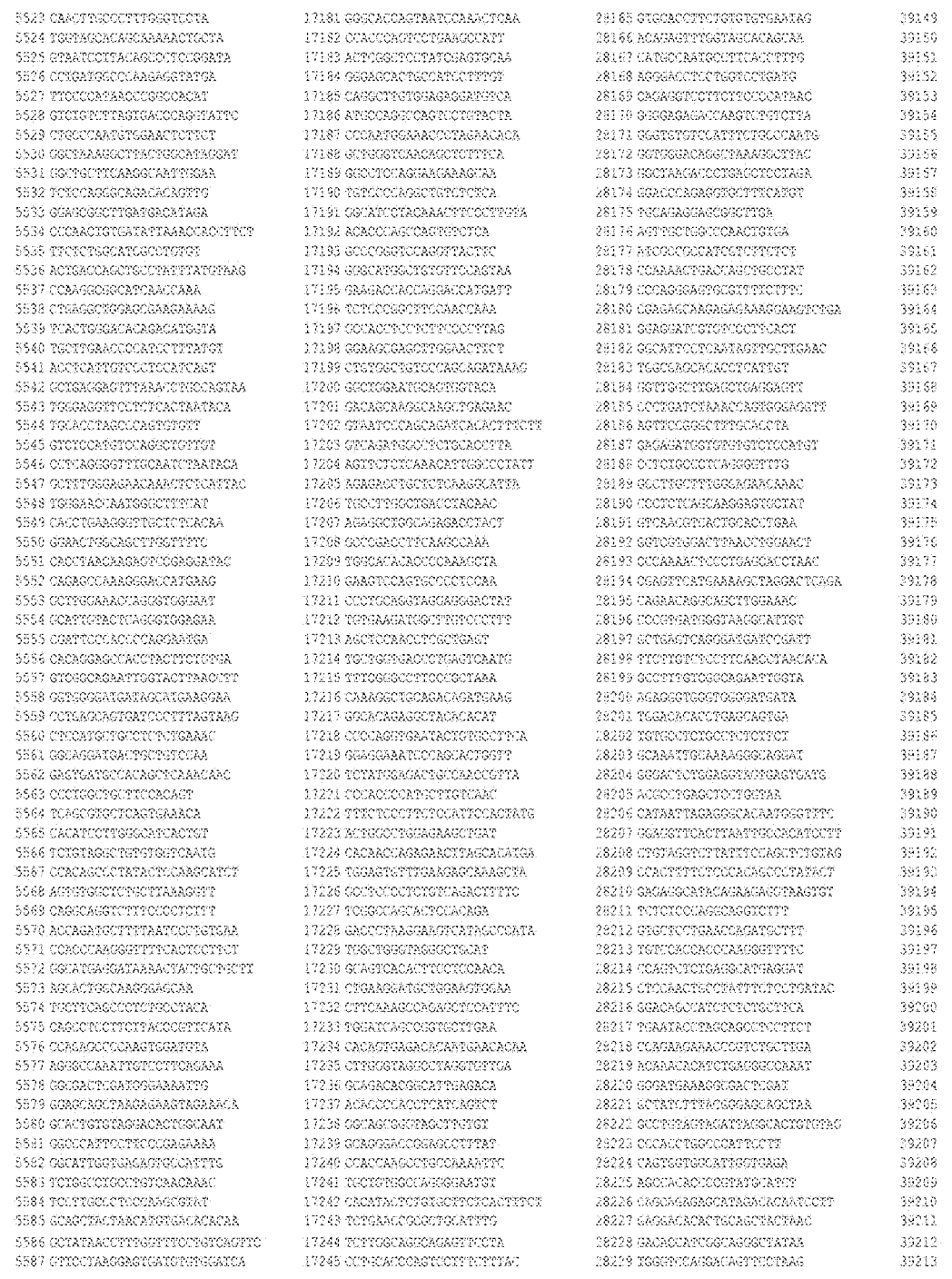
Figure 36I7:
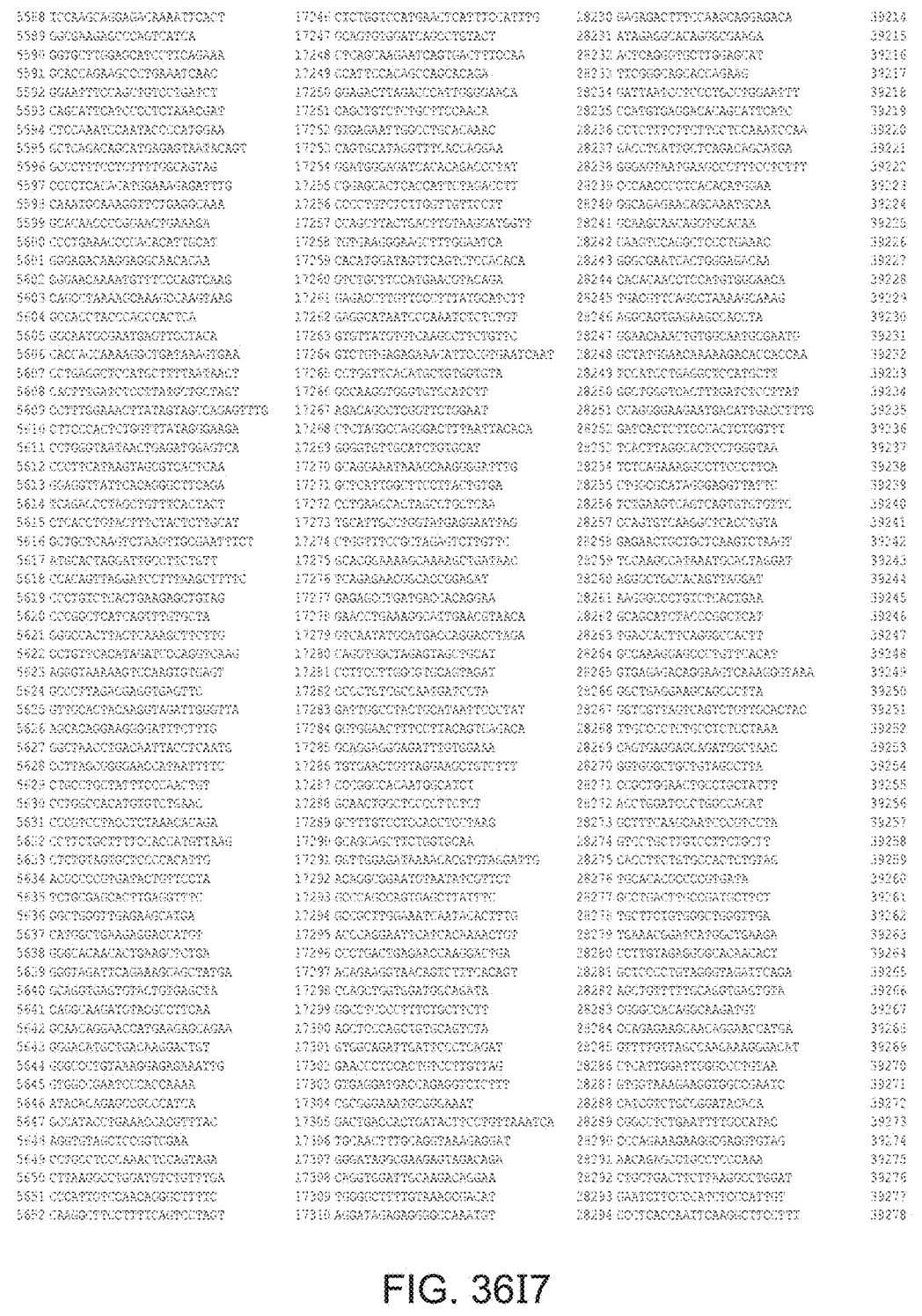
Figure 36I8:
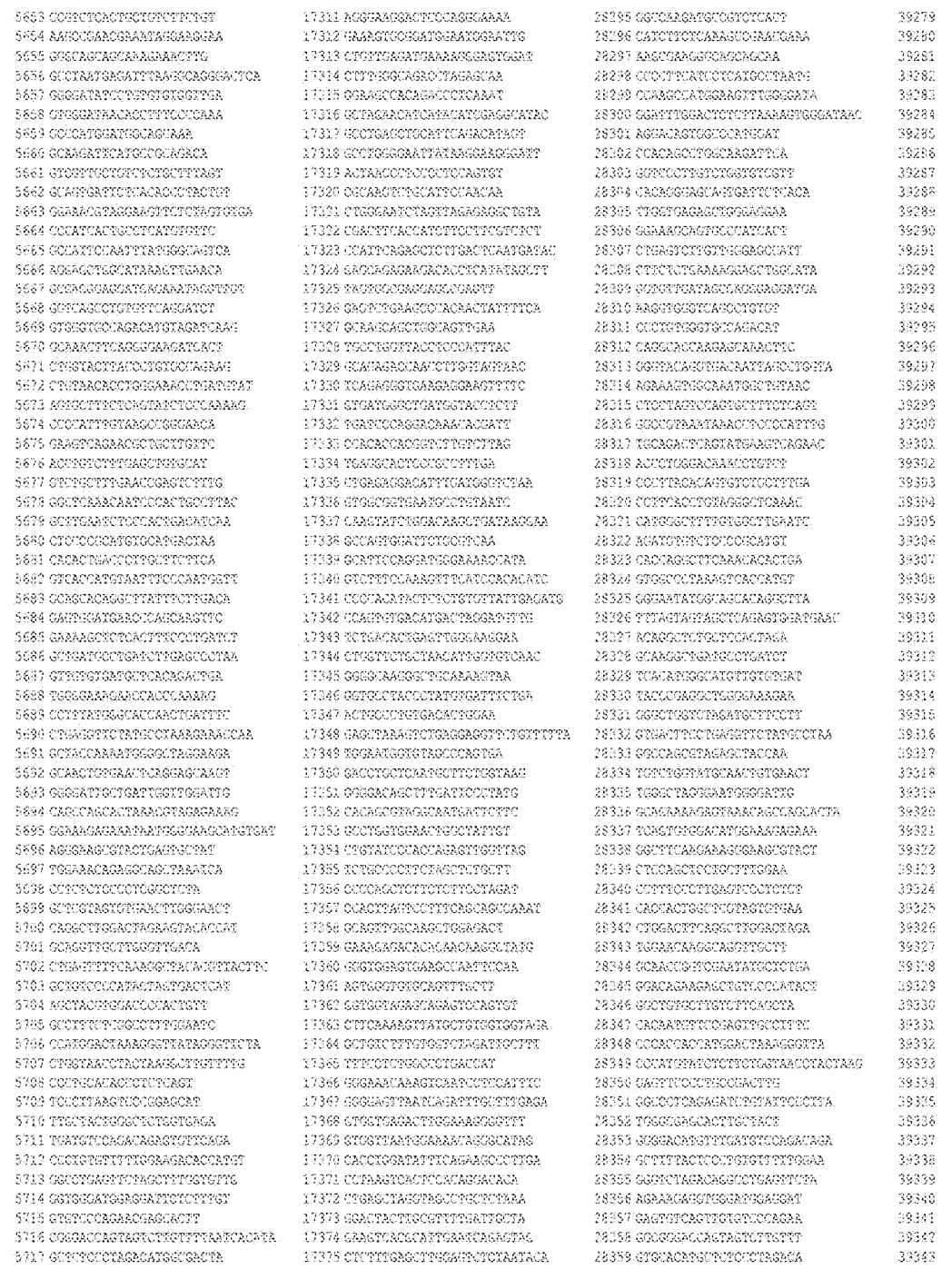
Figure 36I9:
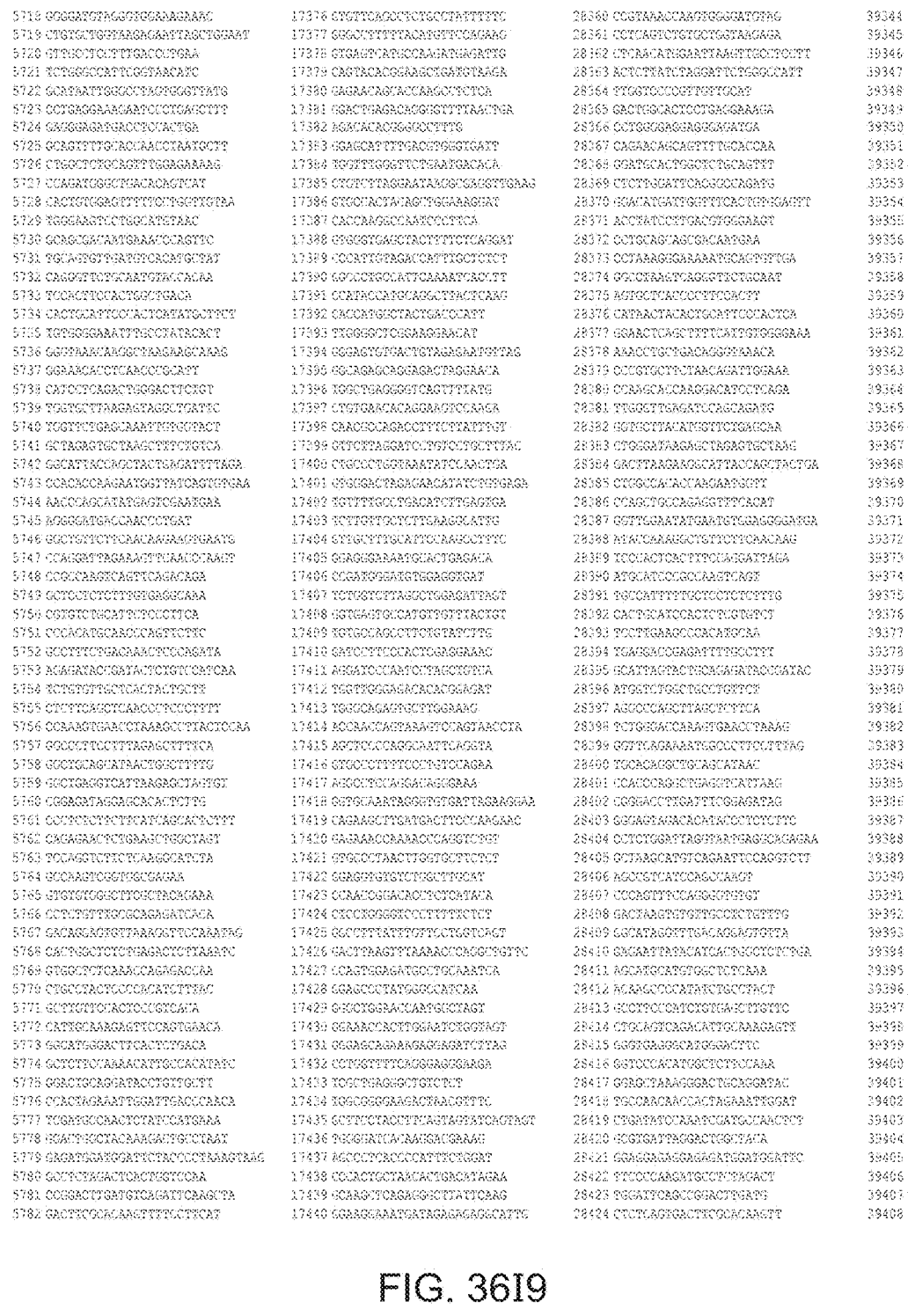
Figure 36I10:
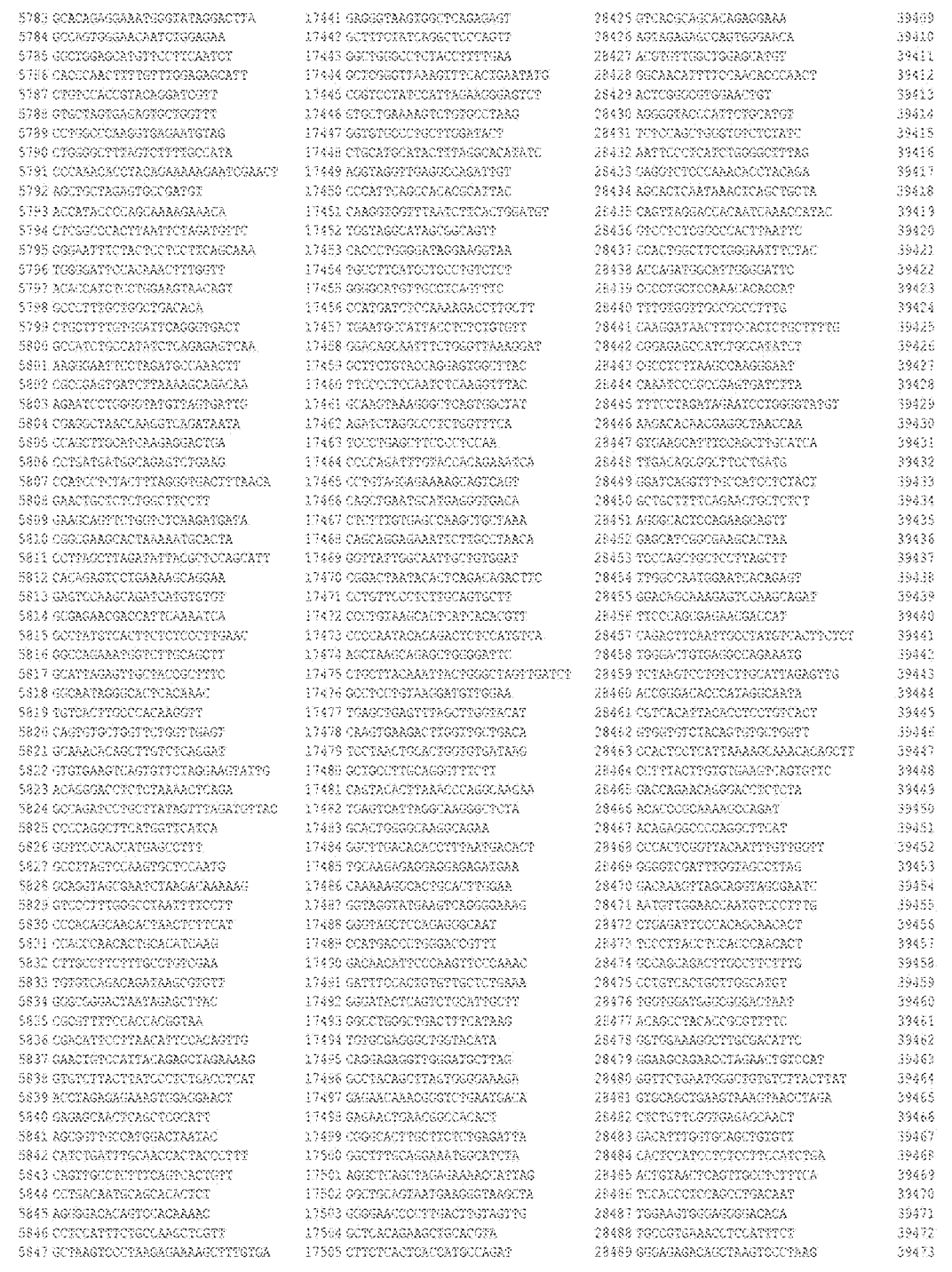
Figure 36J2:
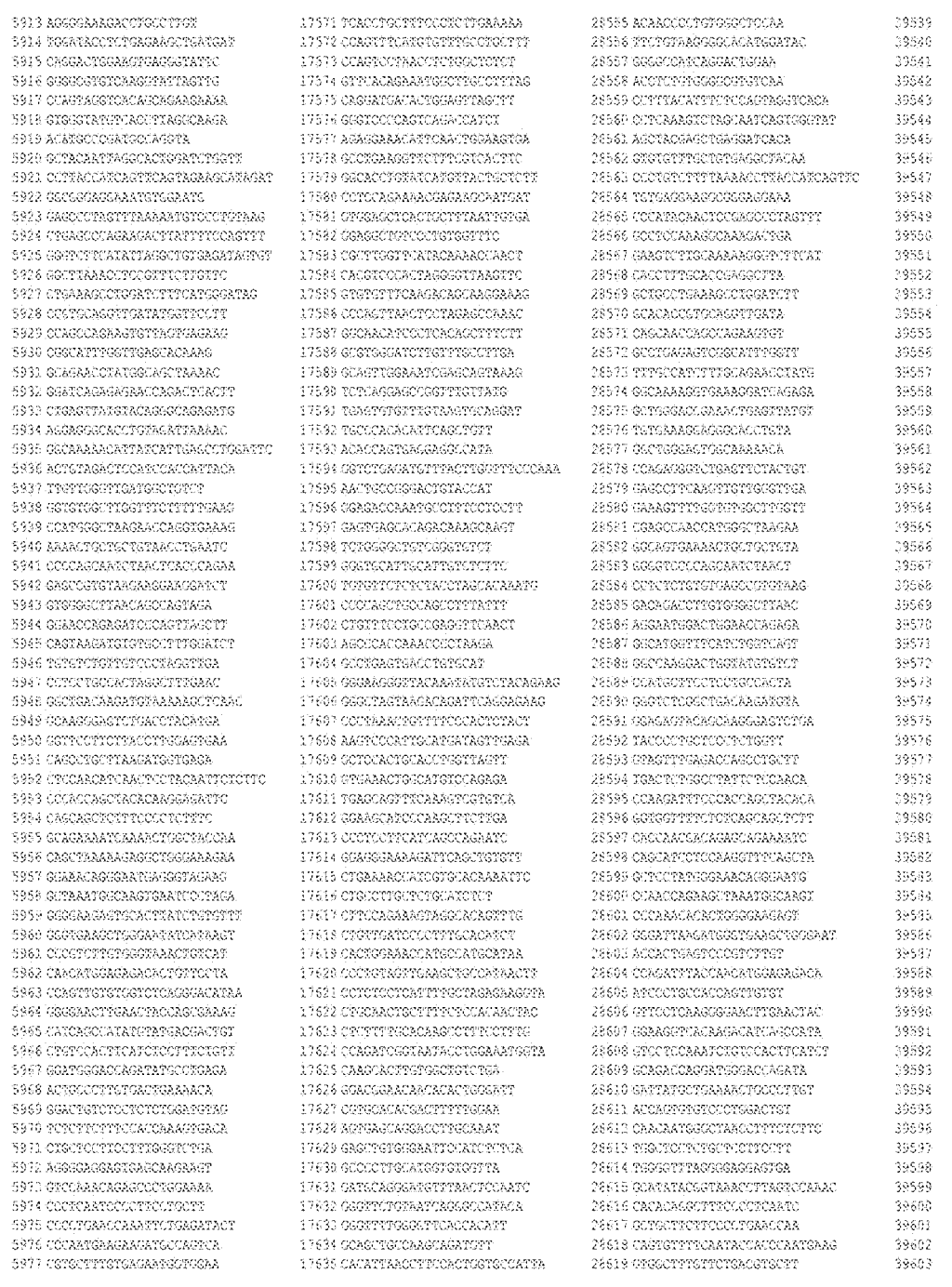
Figure 36J3:
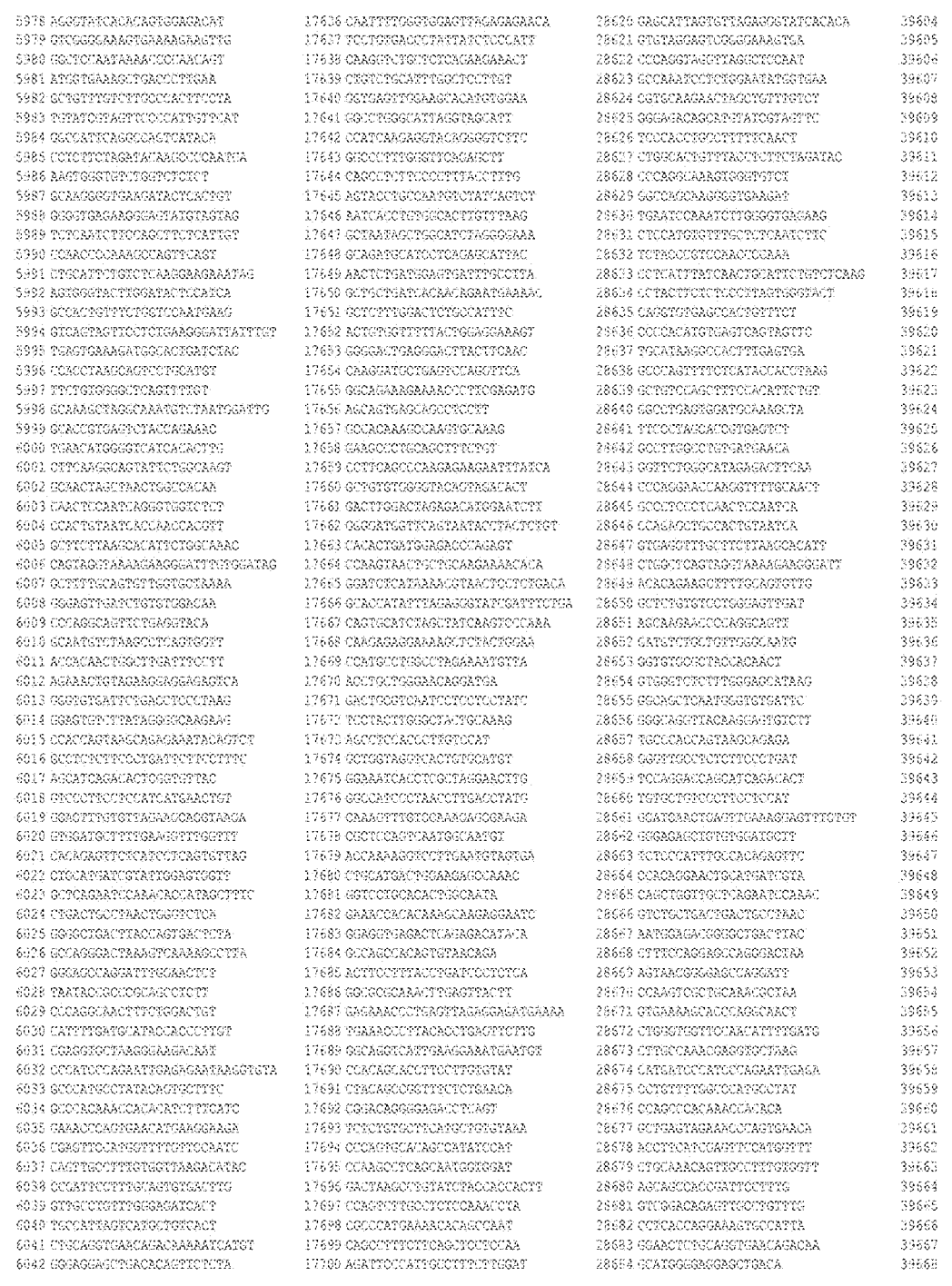
Figure 36J5:
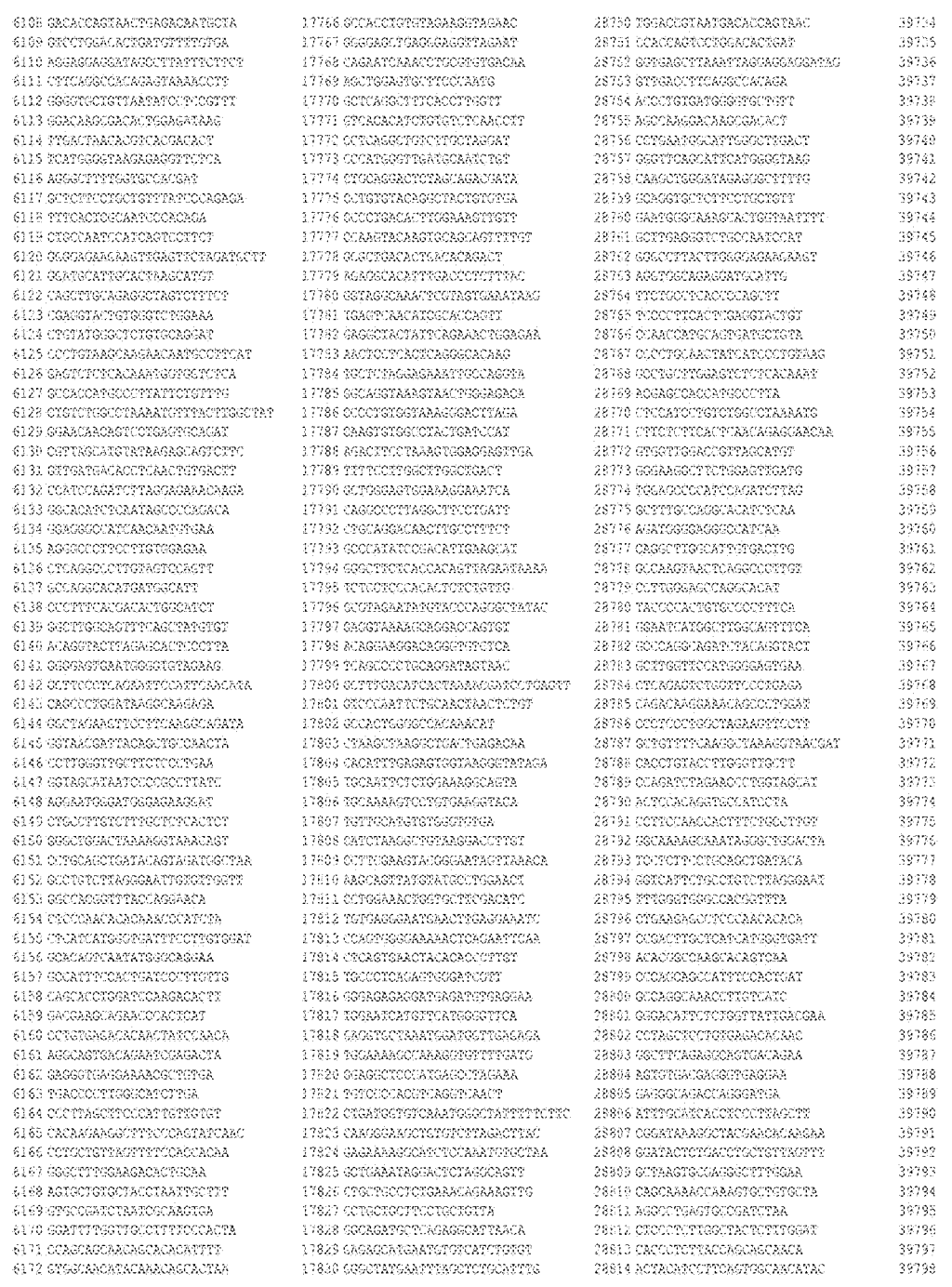
Figure 36J6:
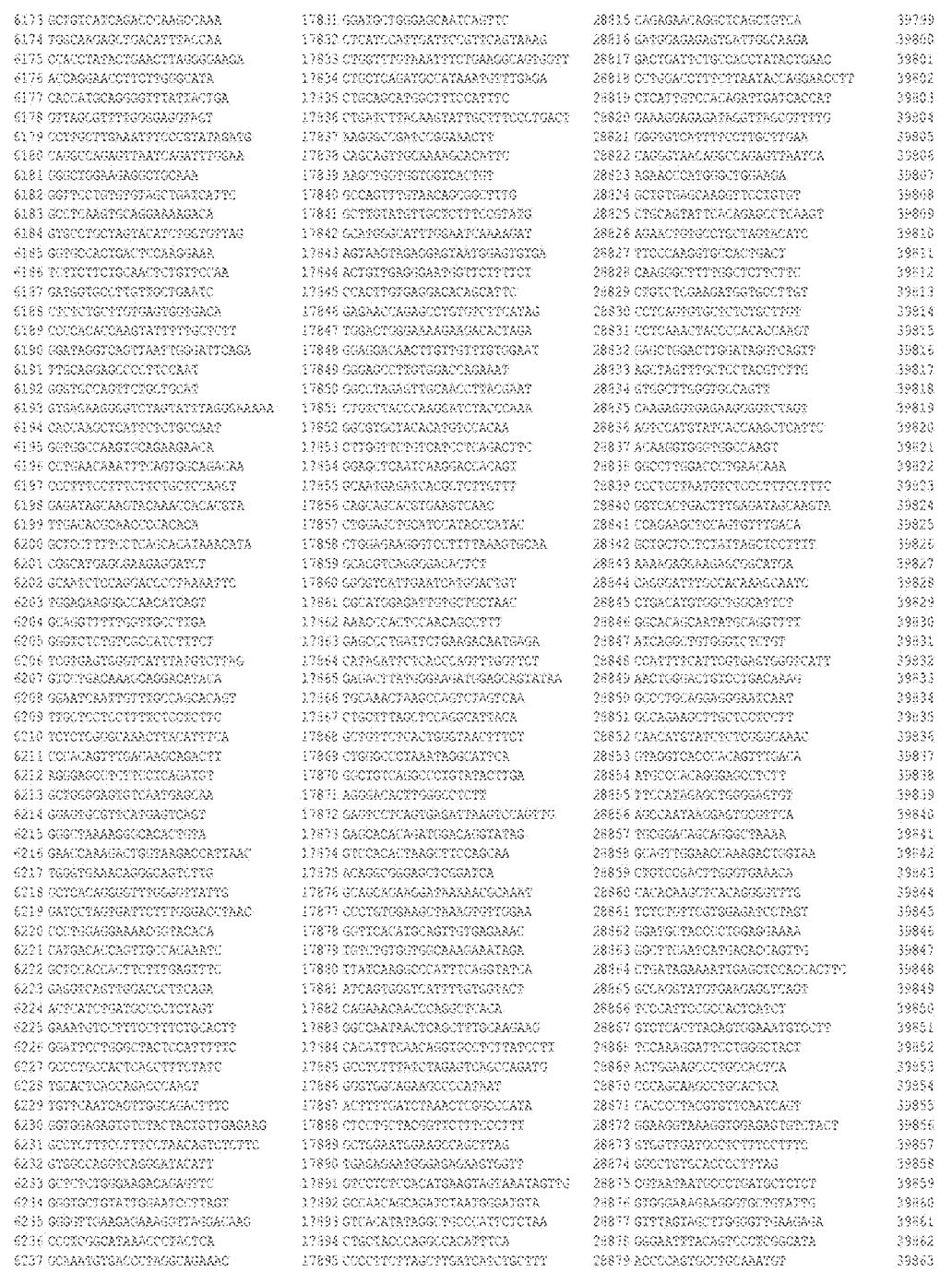
Figure 36J7:
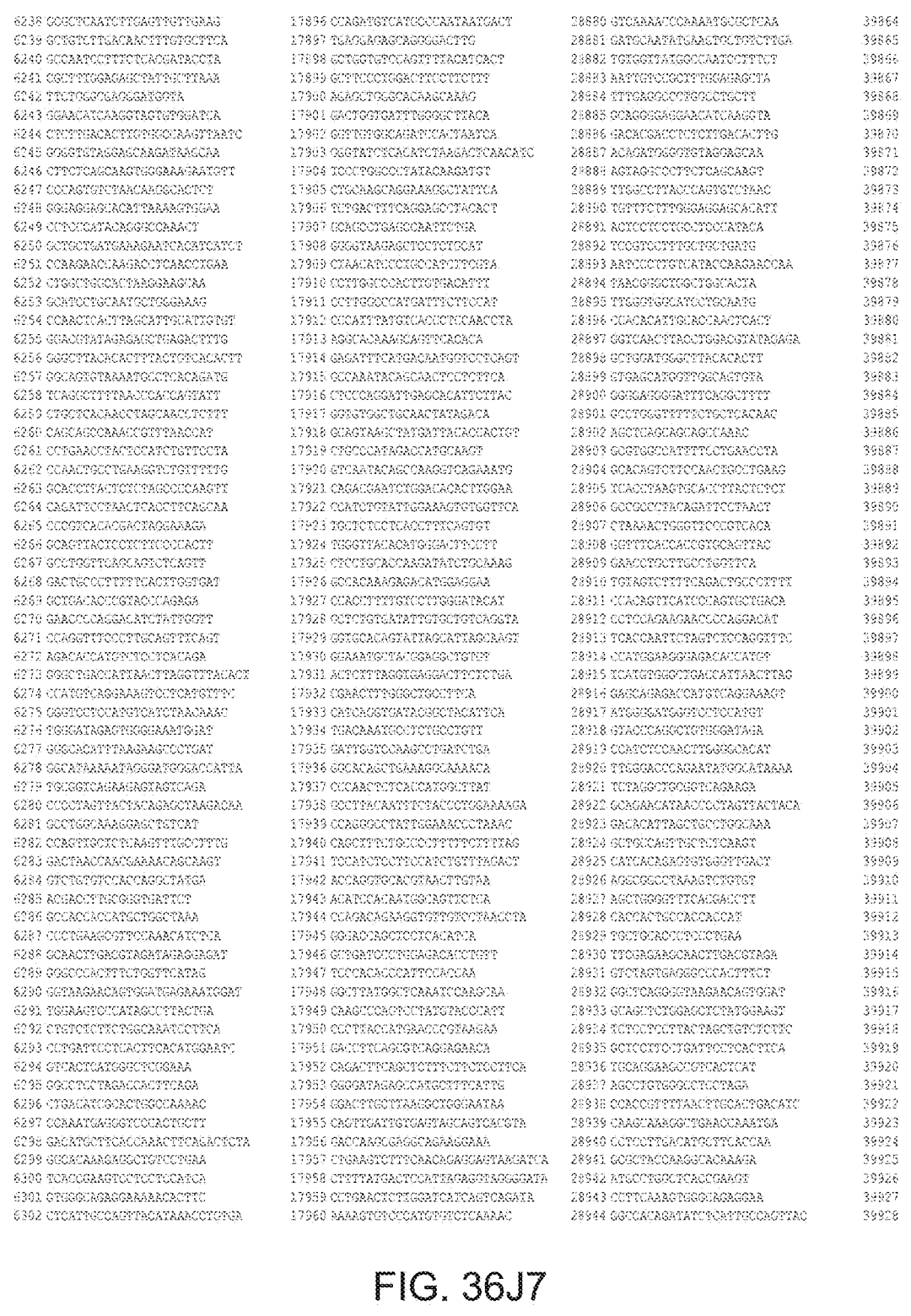
Figure 36J8:
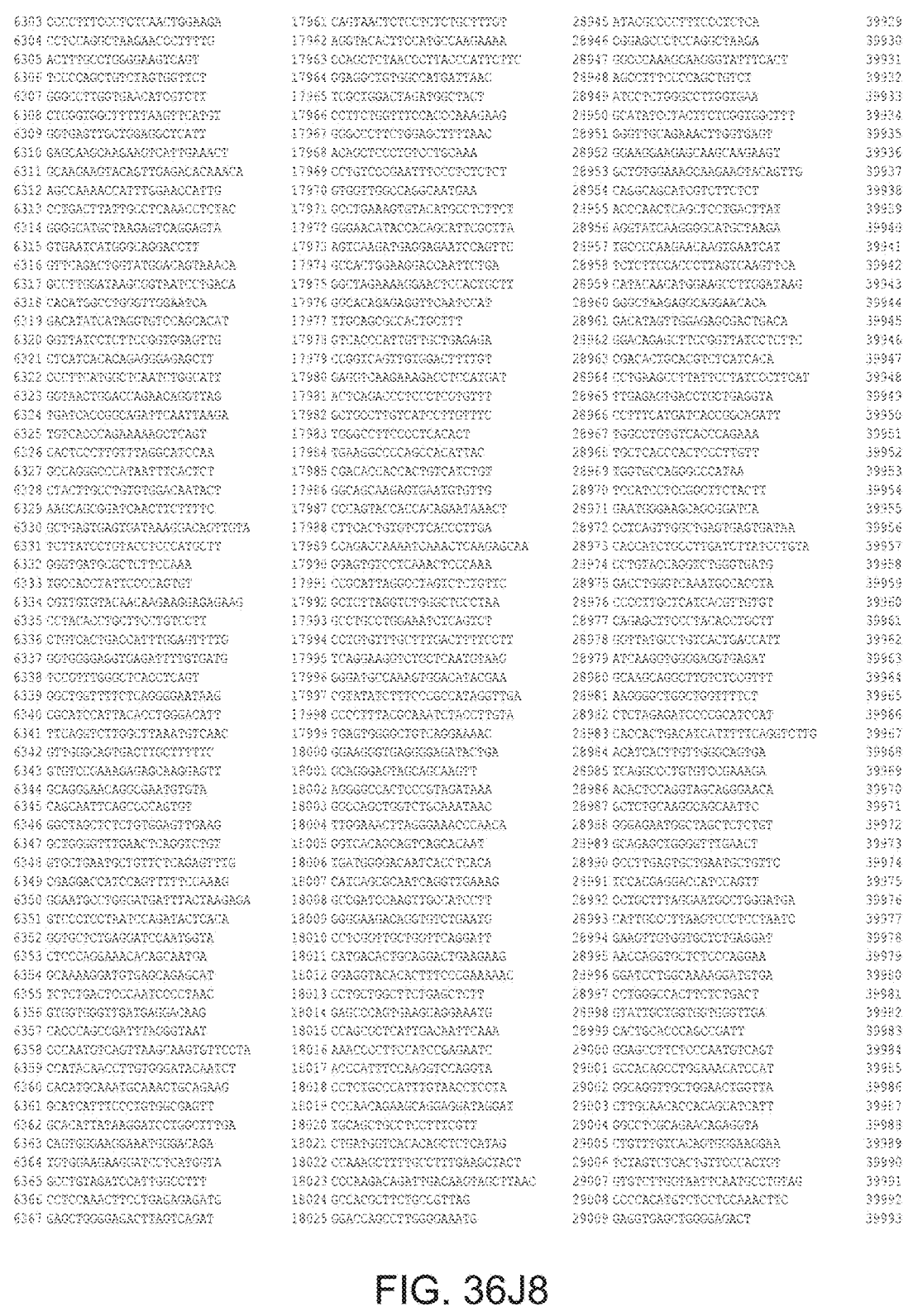
Figure 36J9:
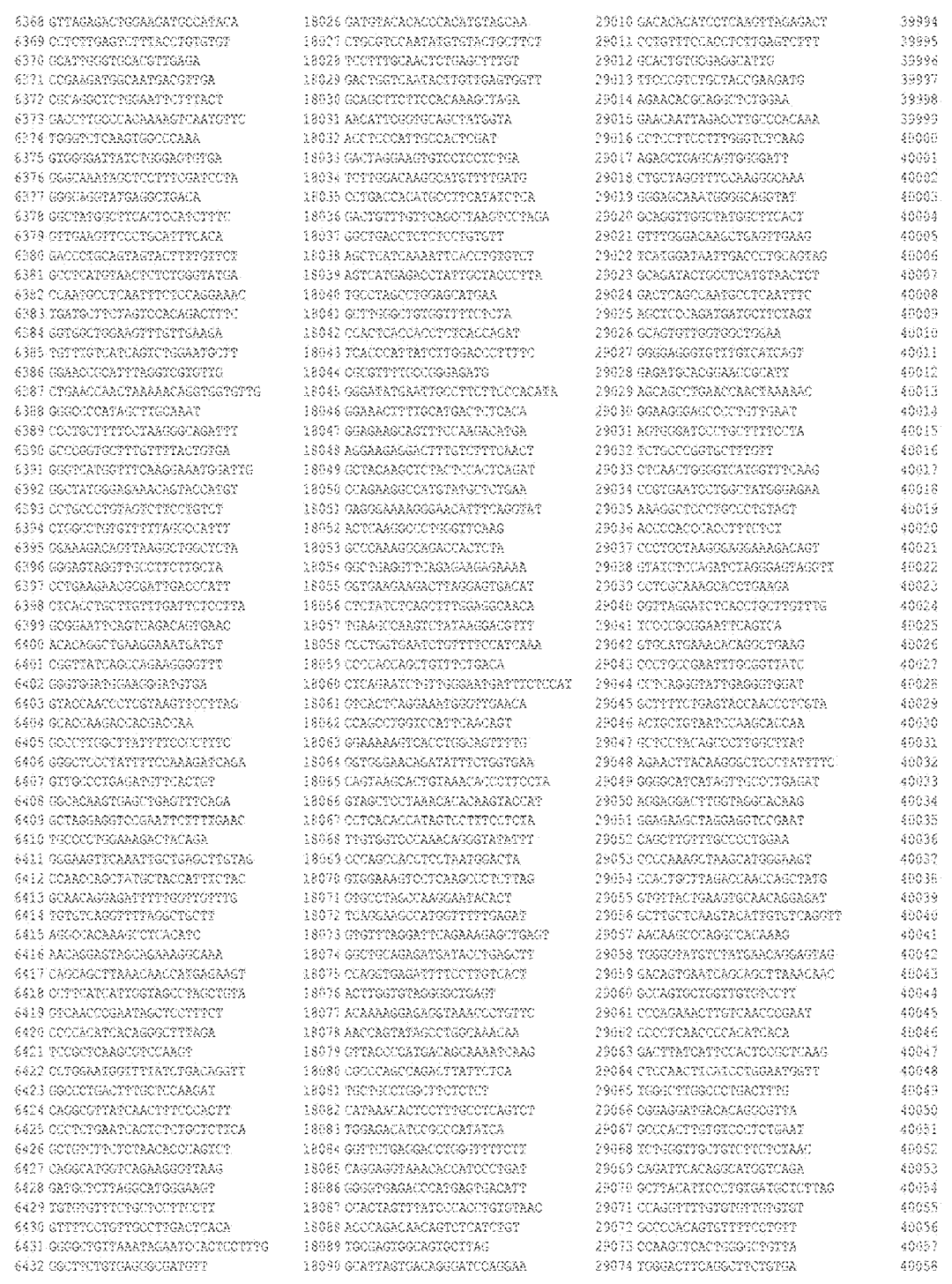
Figure 36J10:
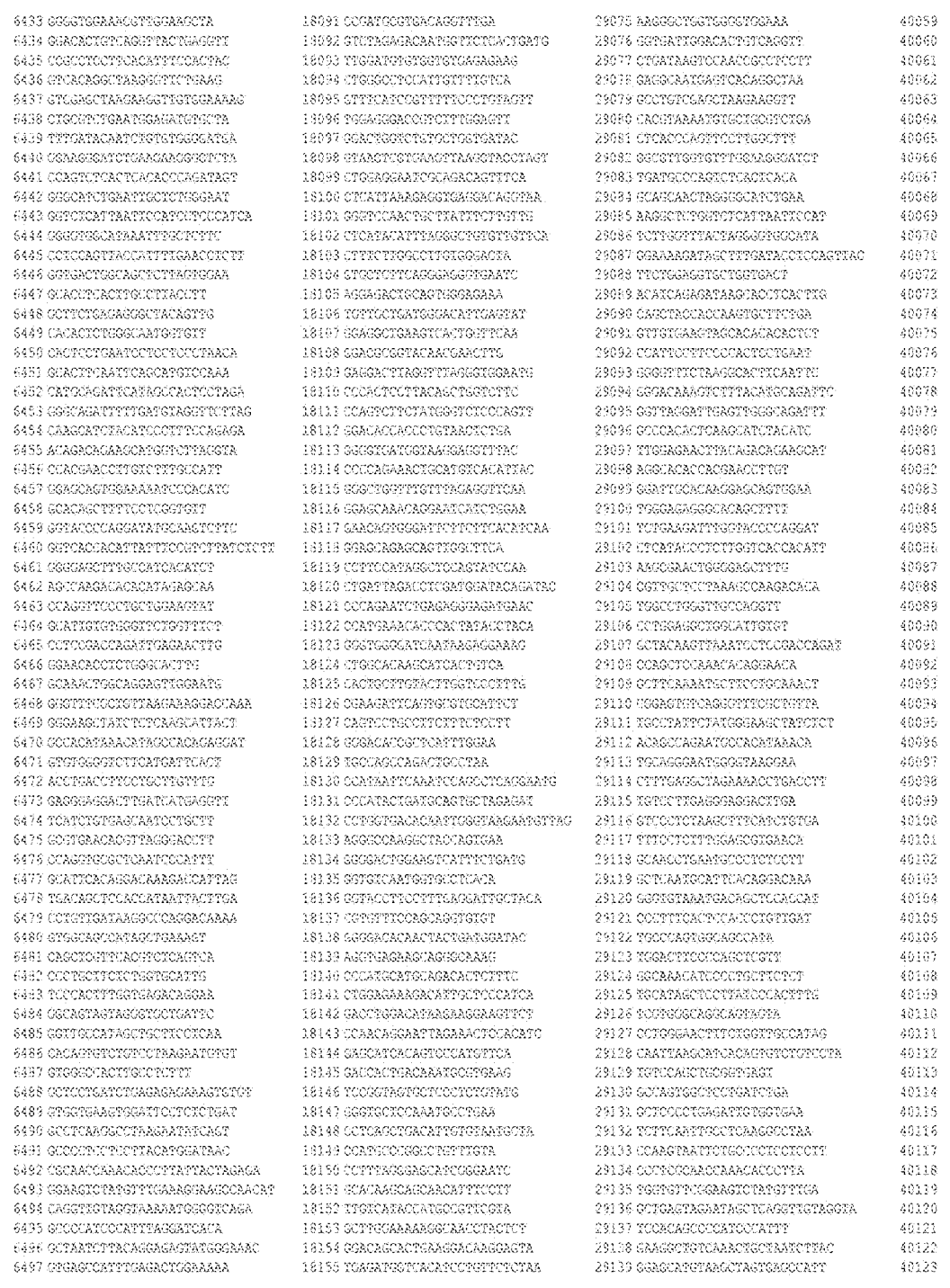
Figure 36K1:
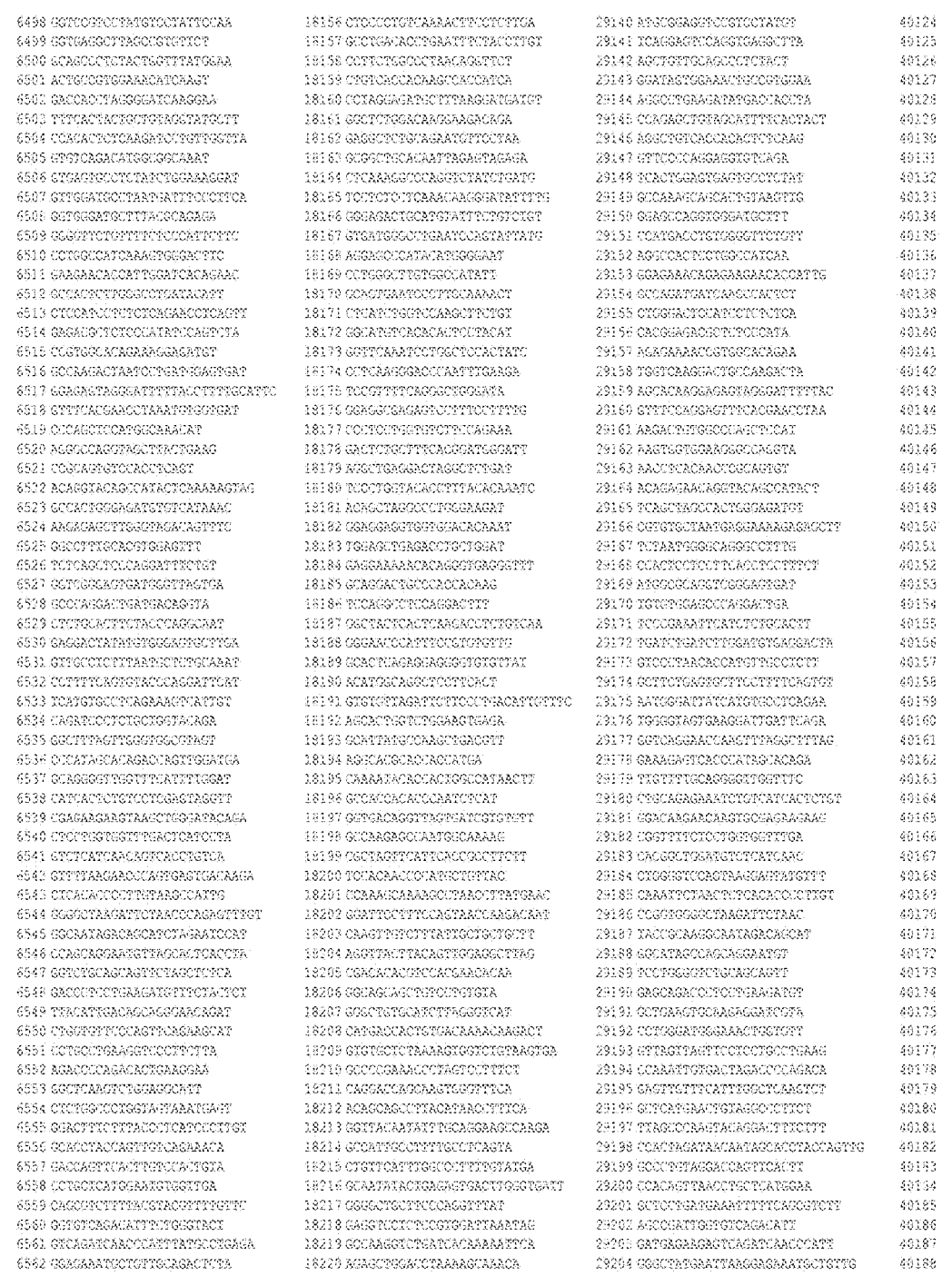
Figure 36K2:
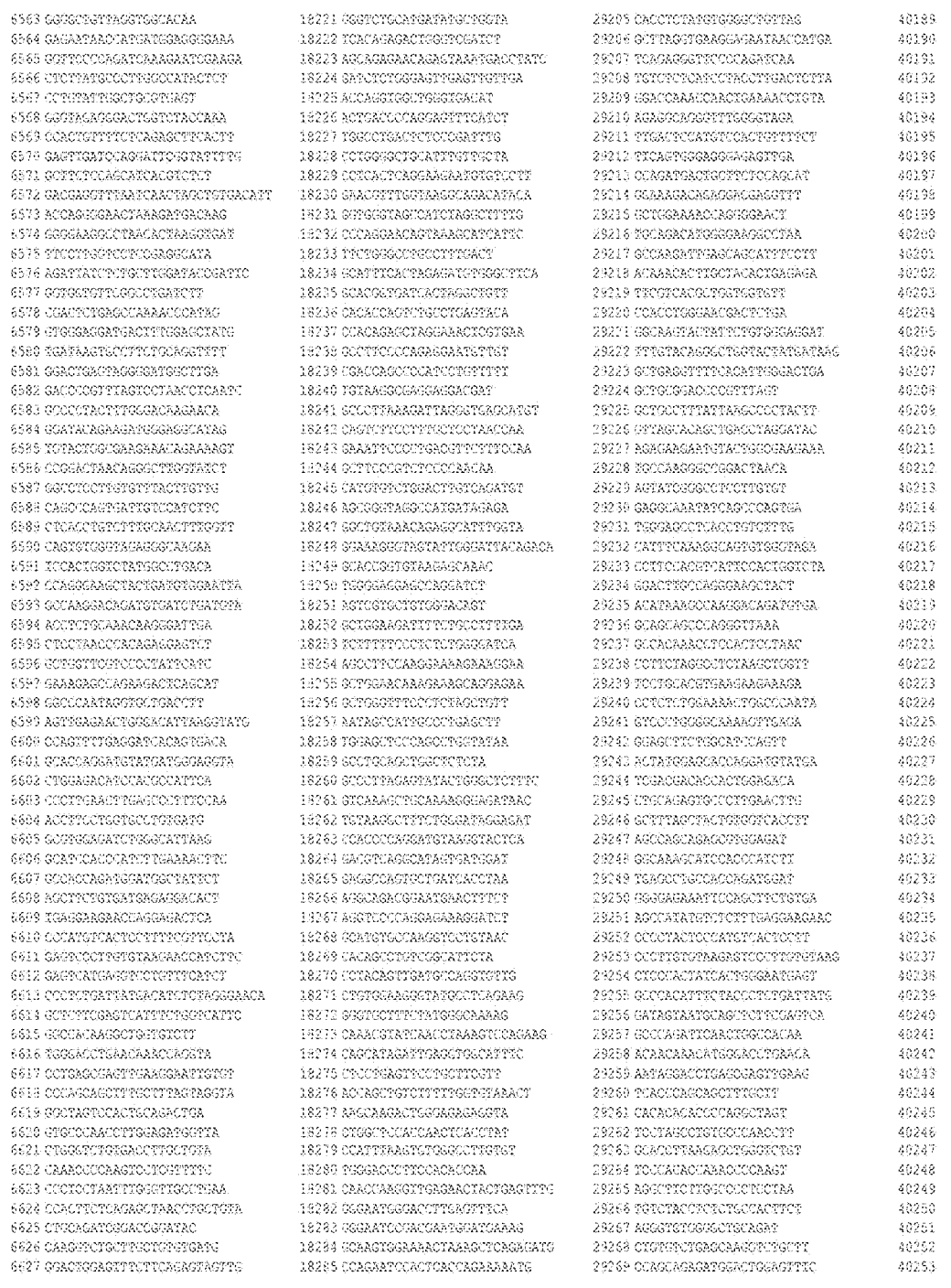
Figure 36K3:
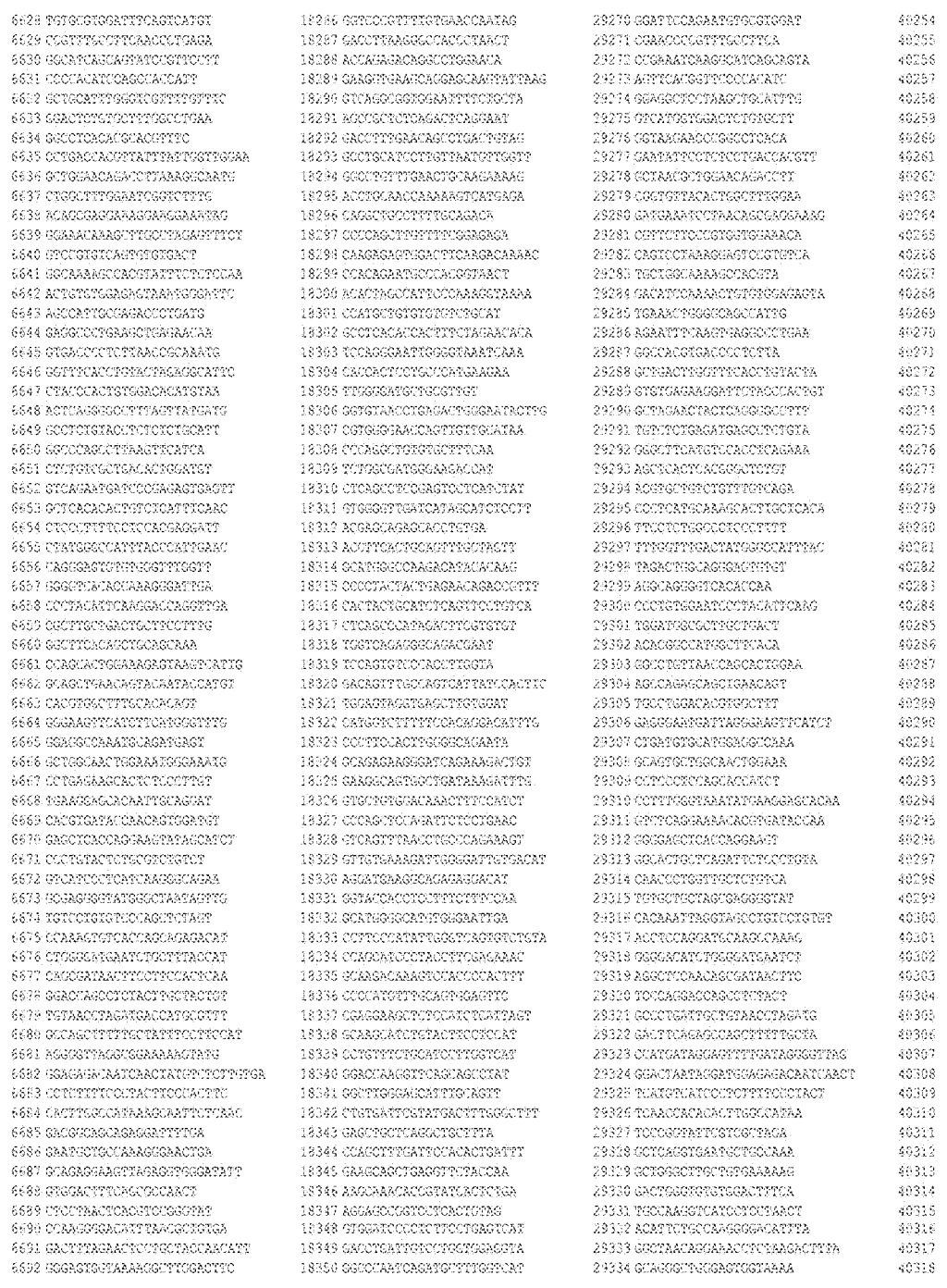
Figure 36K4:
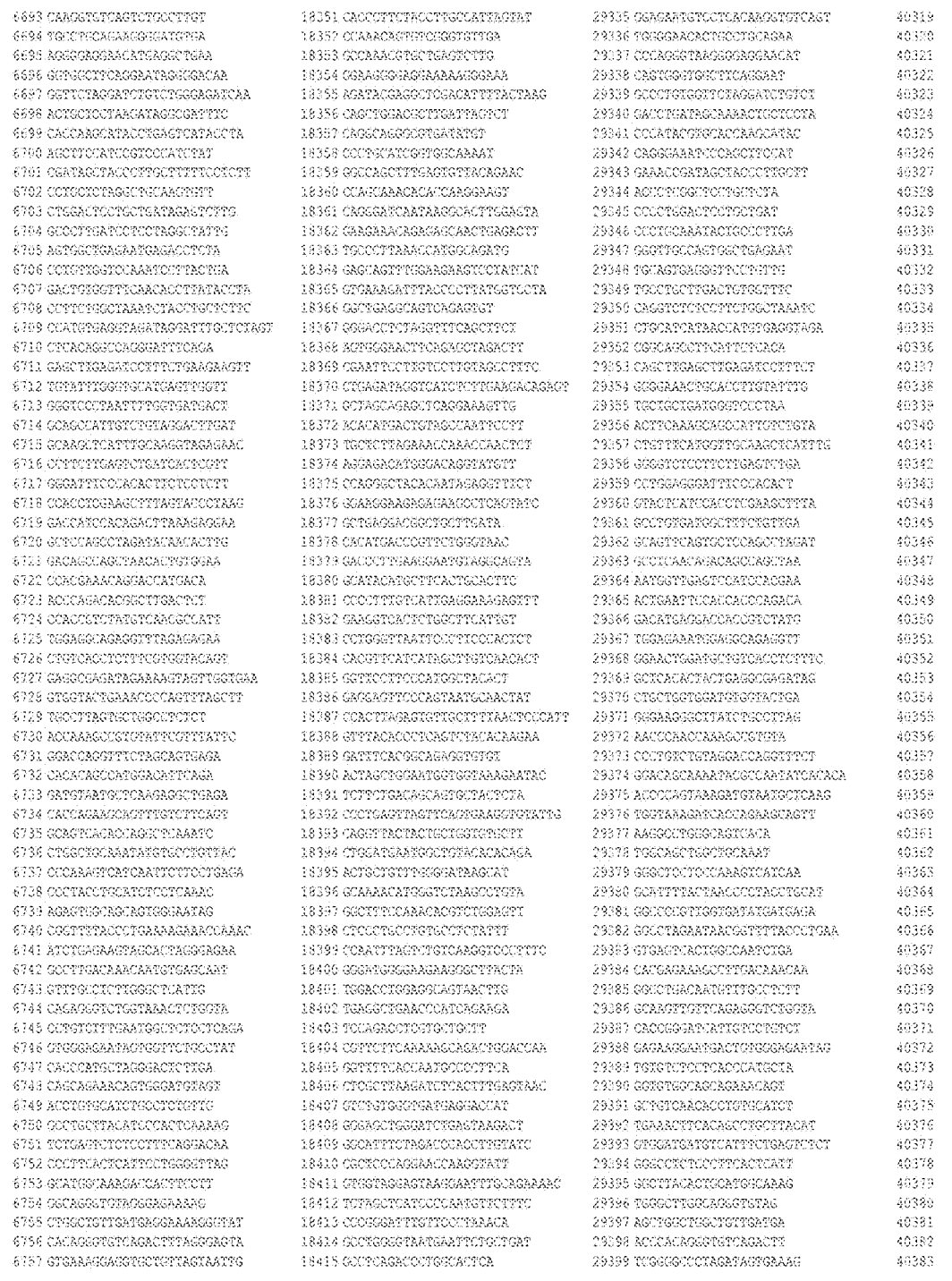
Figure 36K5:
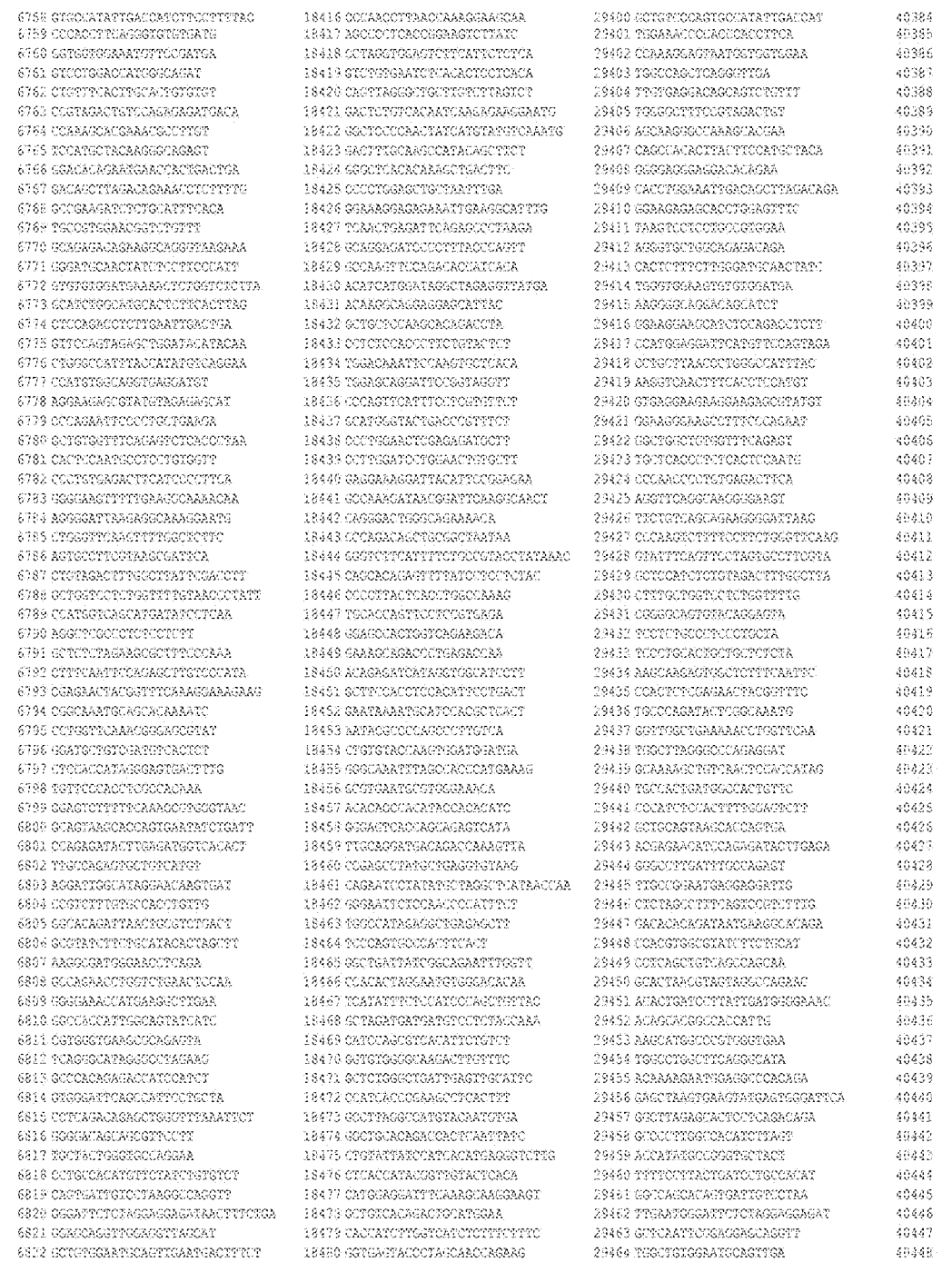
Figure 36K7:
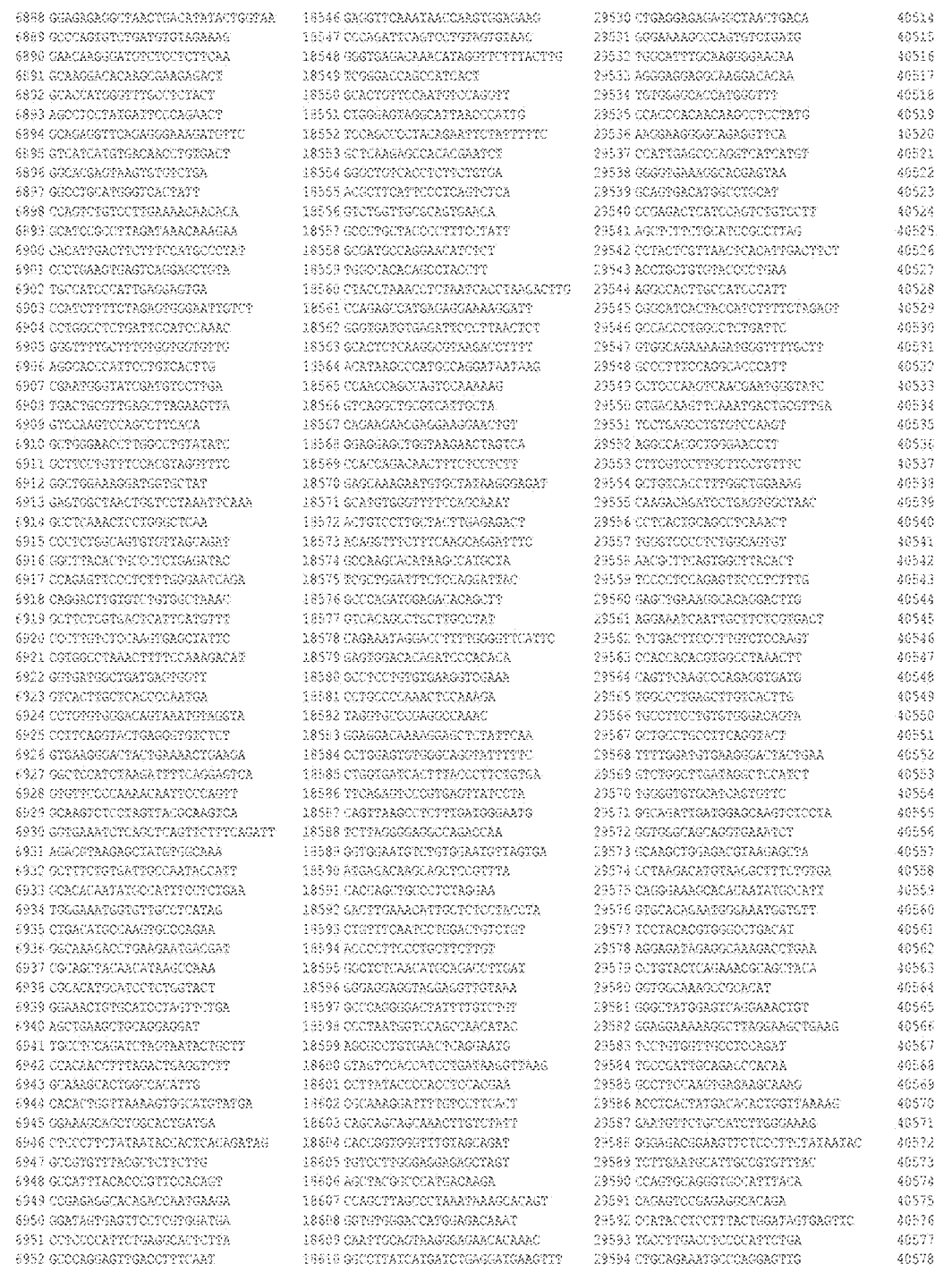
Figure 36K10:
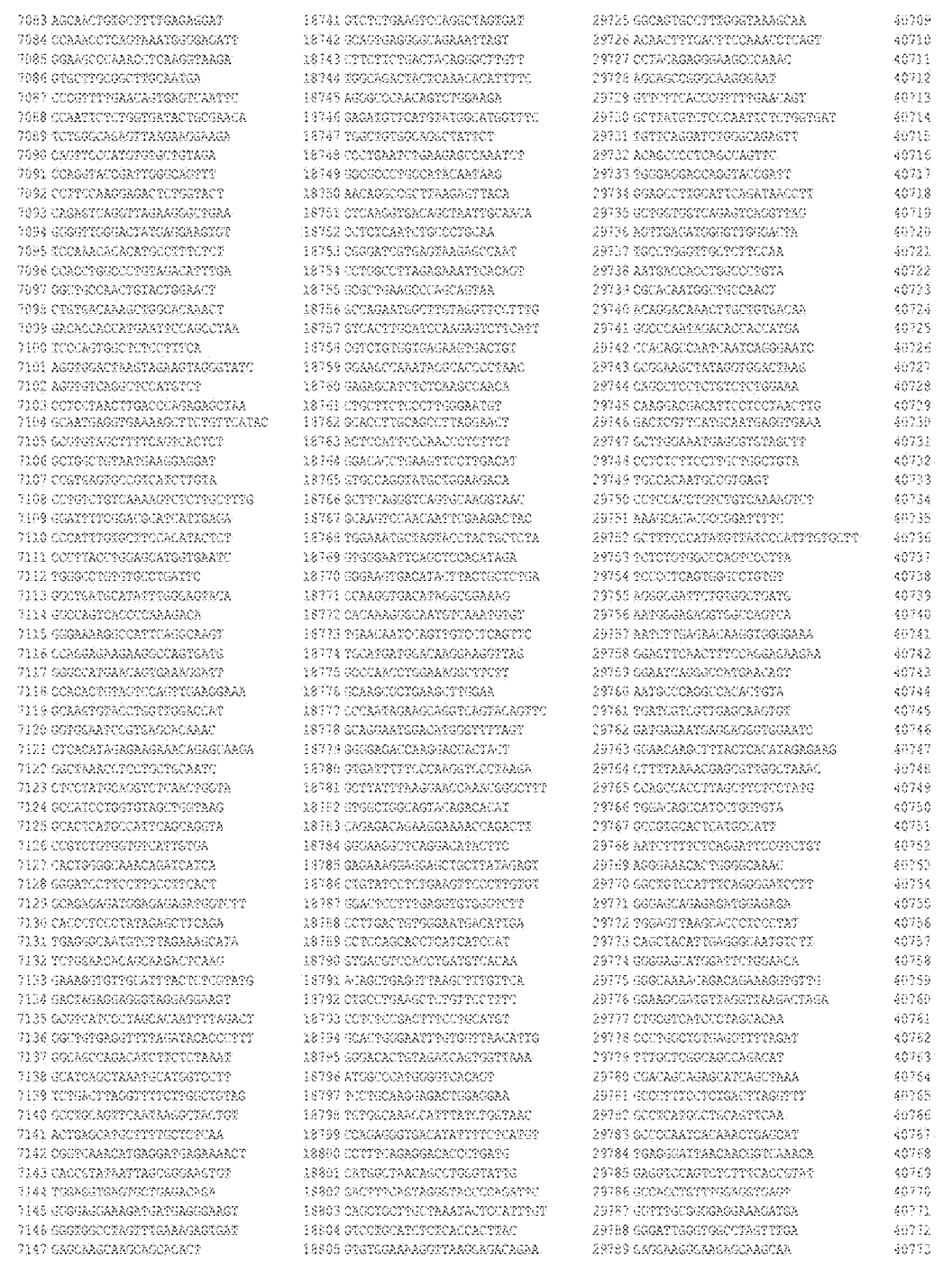
Figure 36L2:
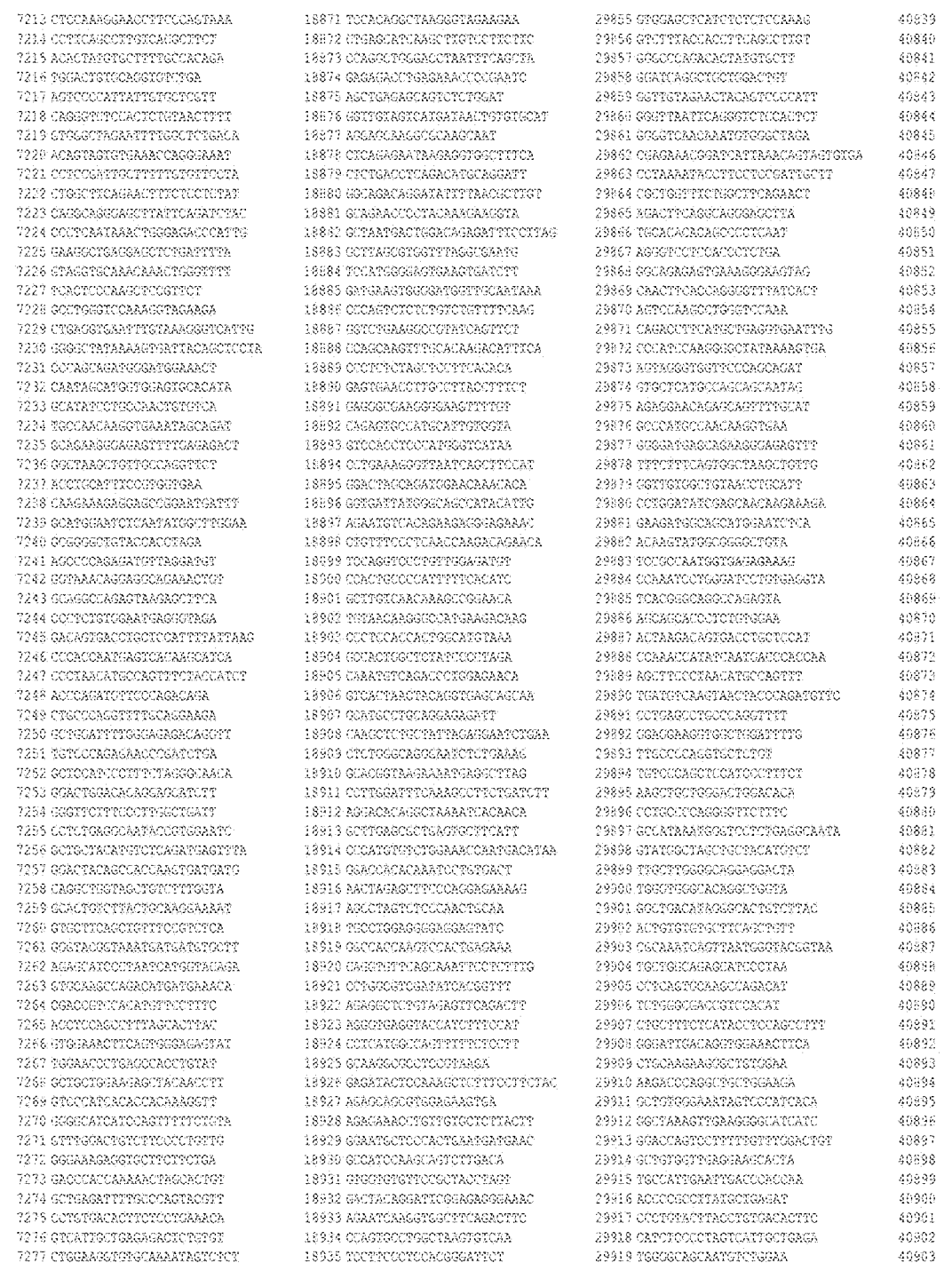
Figure 36L3:
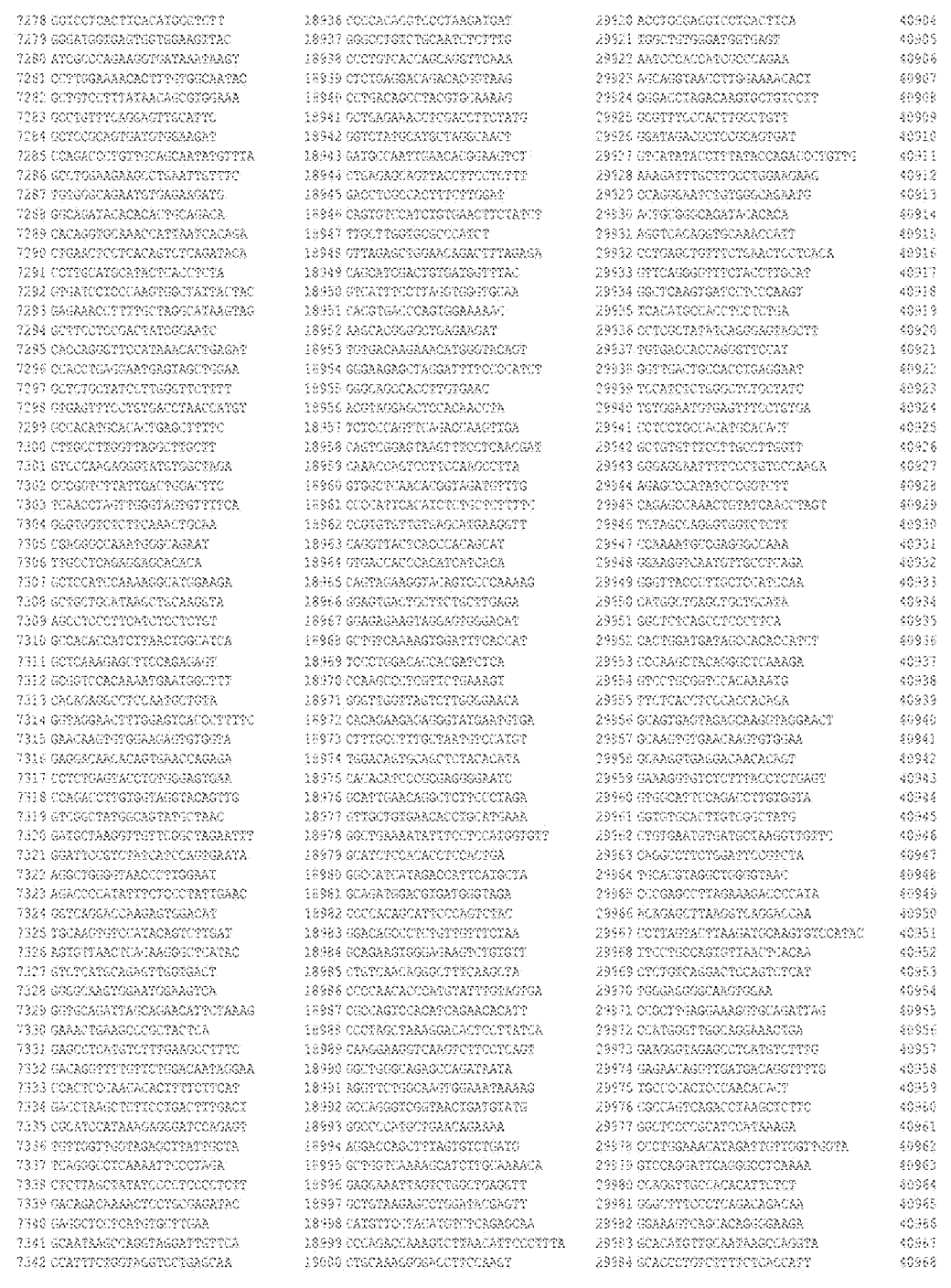
Figure 36L4:
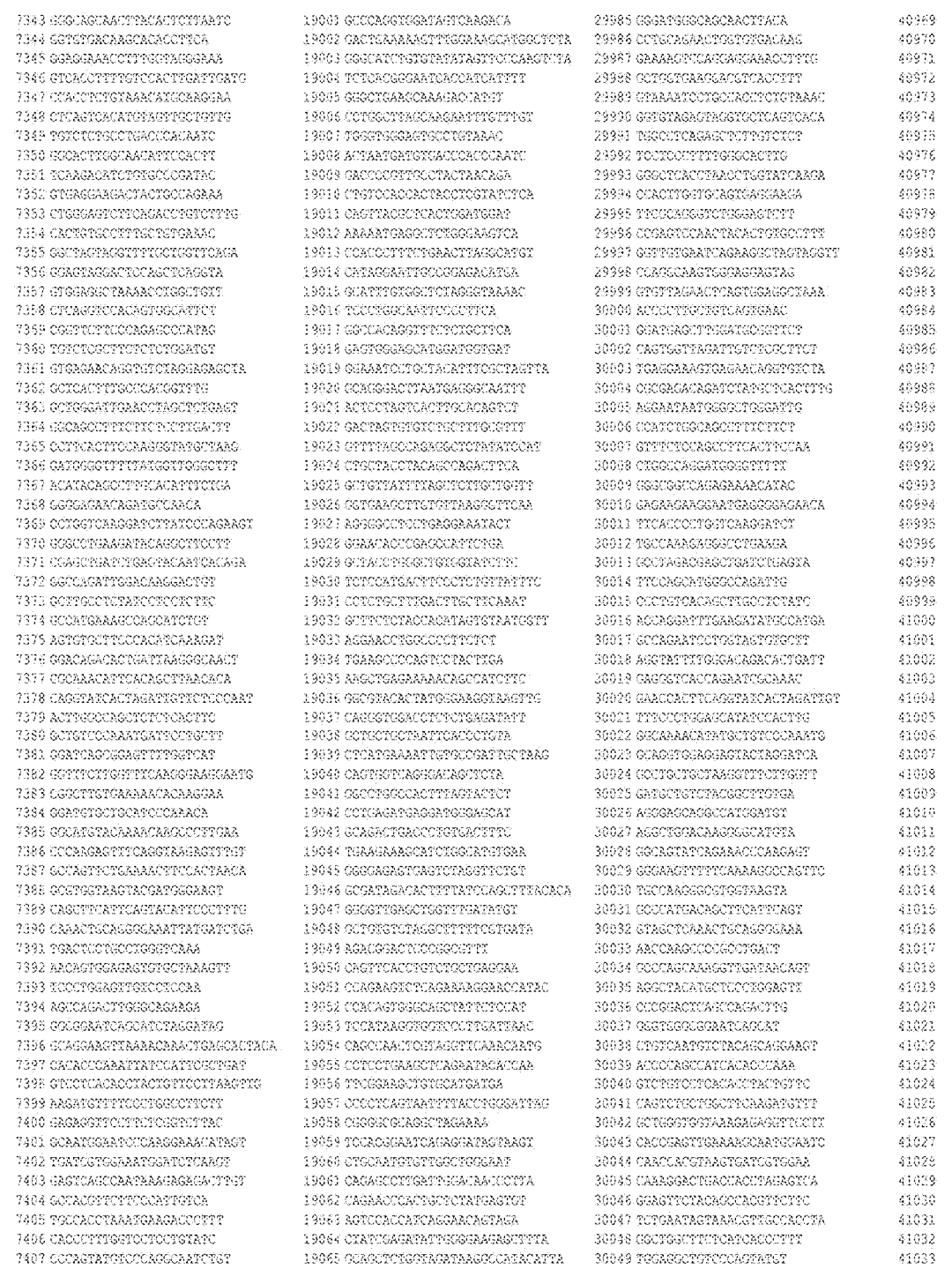
Figure 36L5:
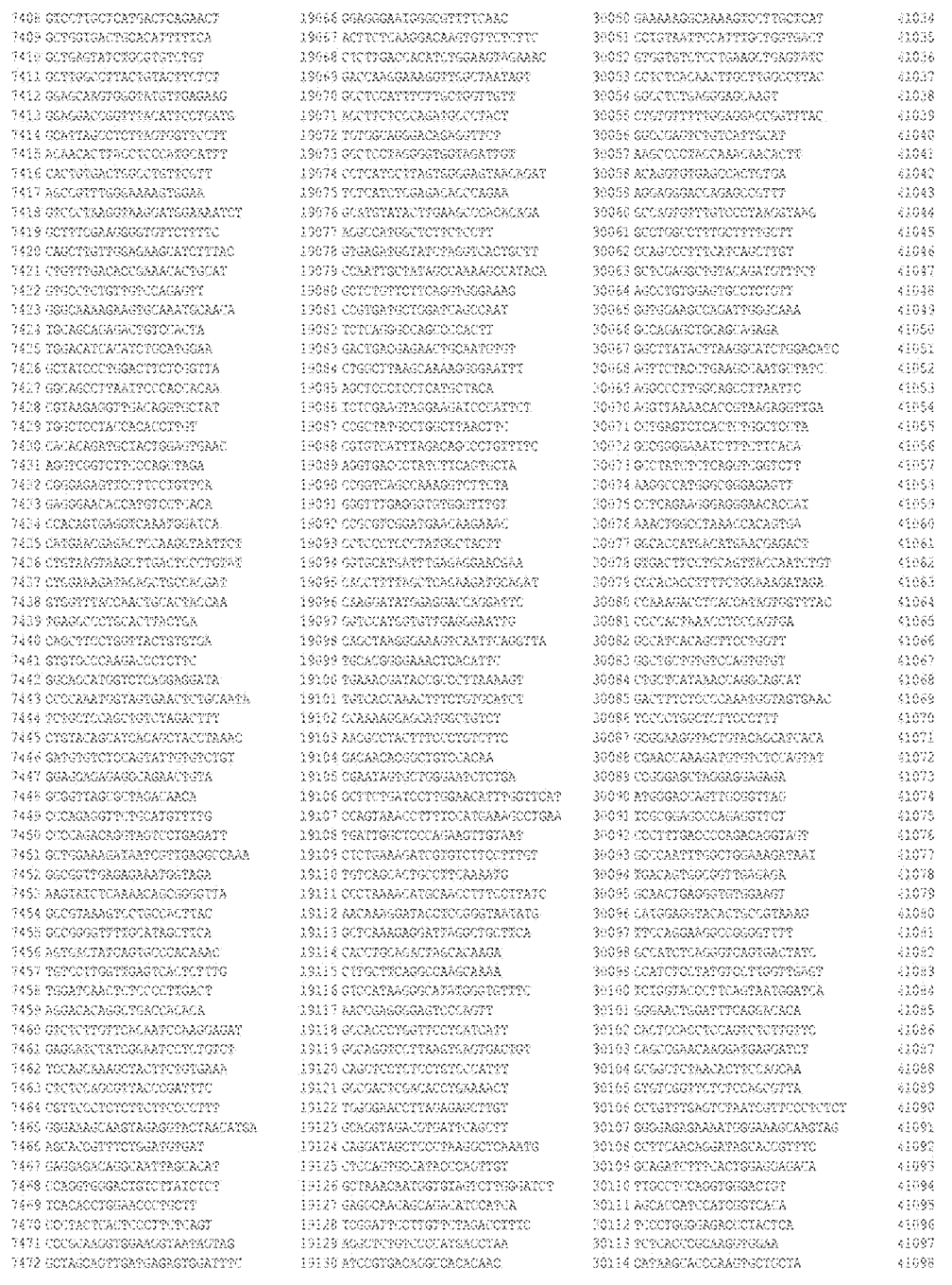
Figure 36L6:
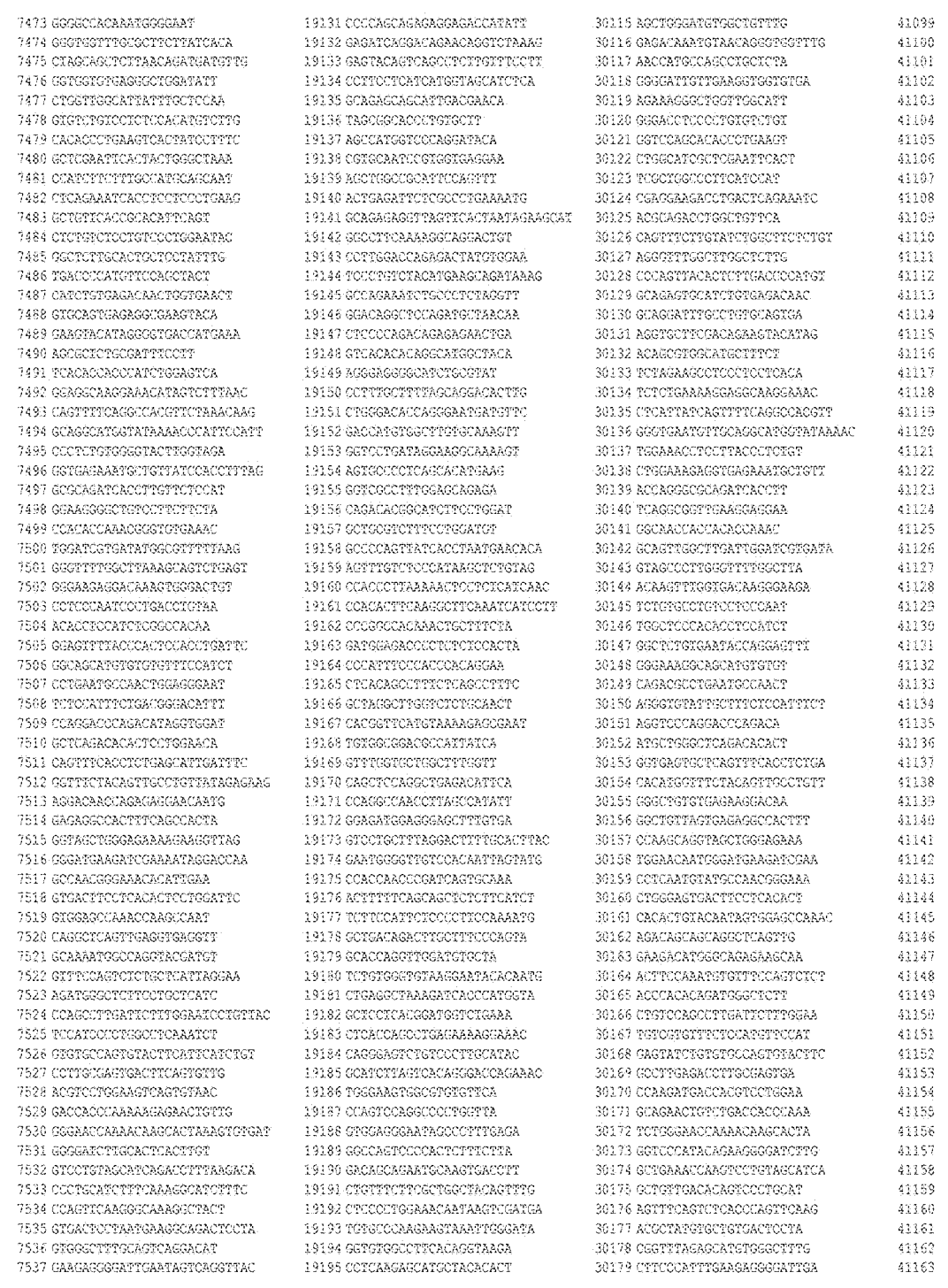
Figure 36L9:
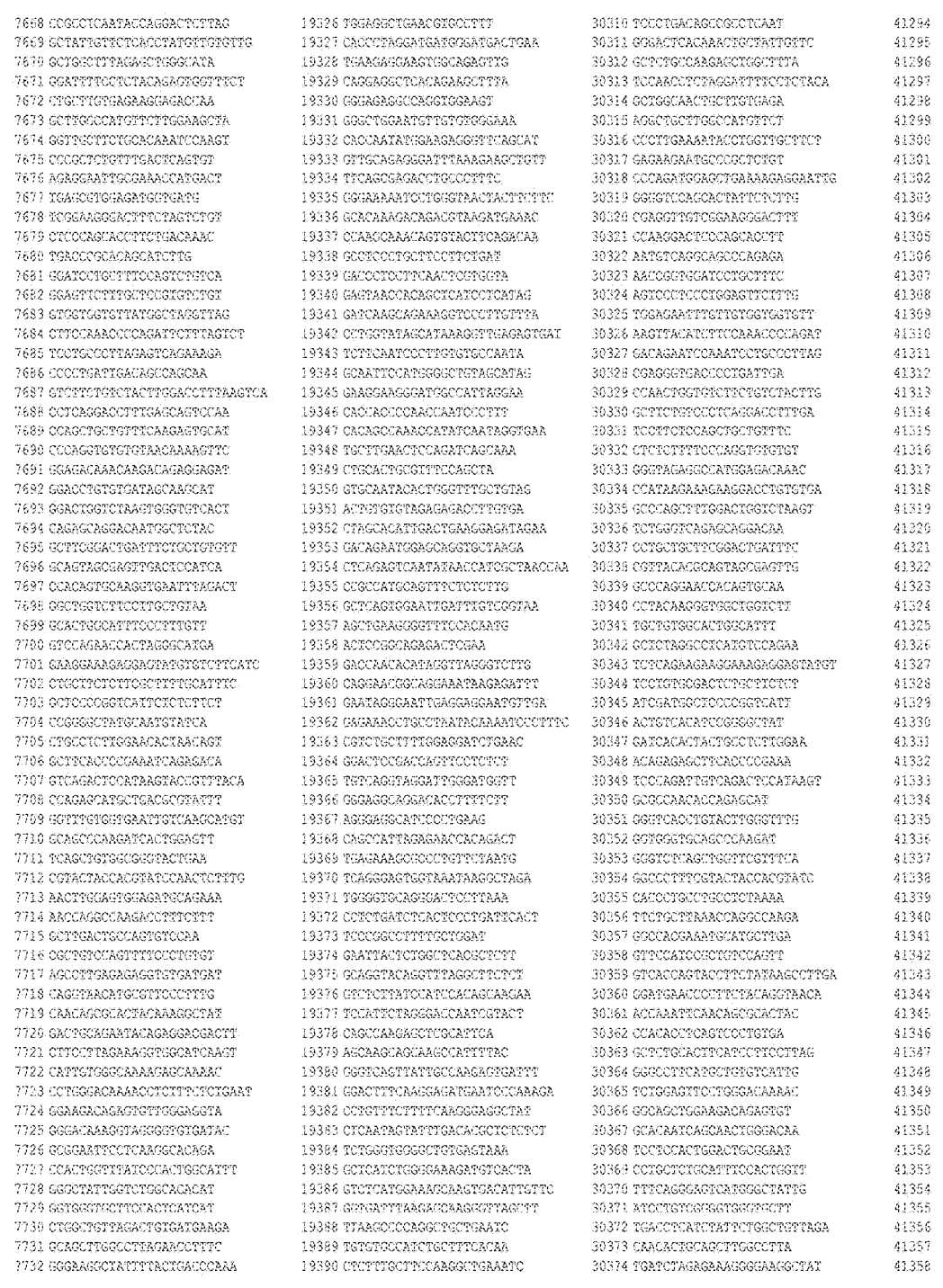
Figure 36L10:
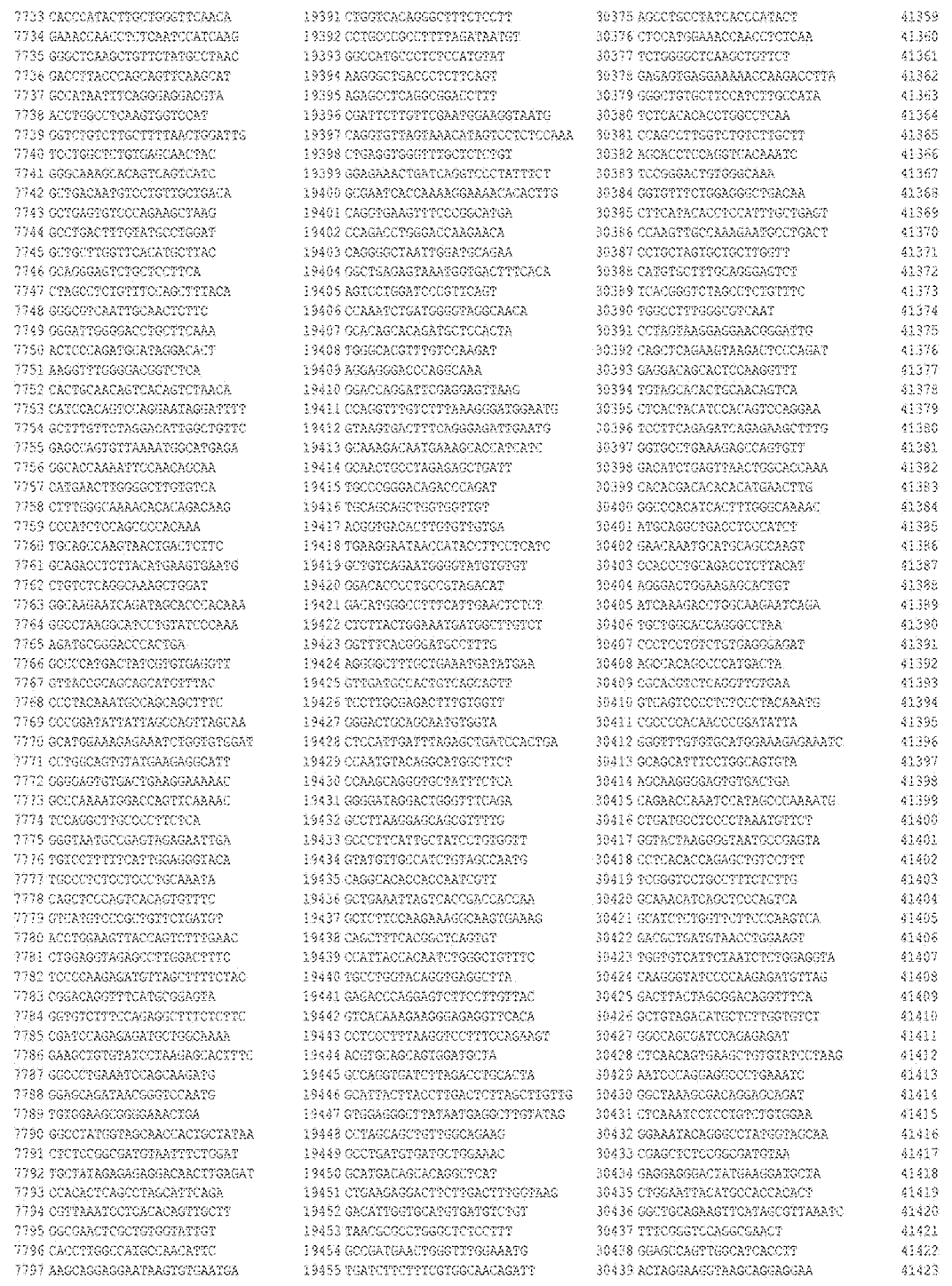
Figure 36M3:
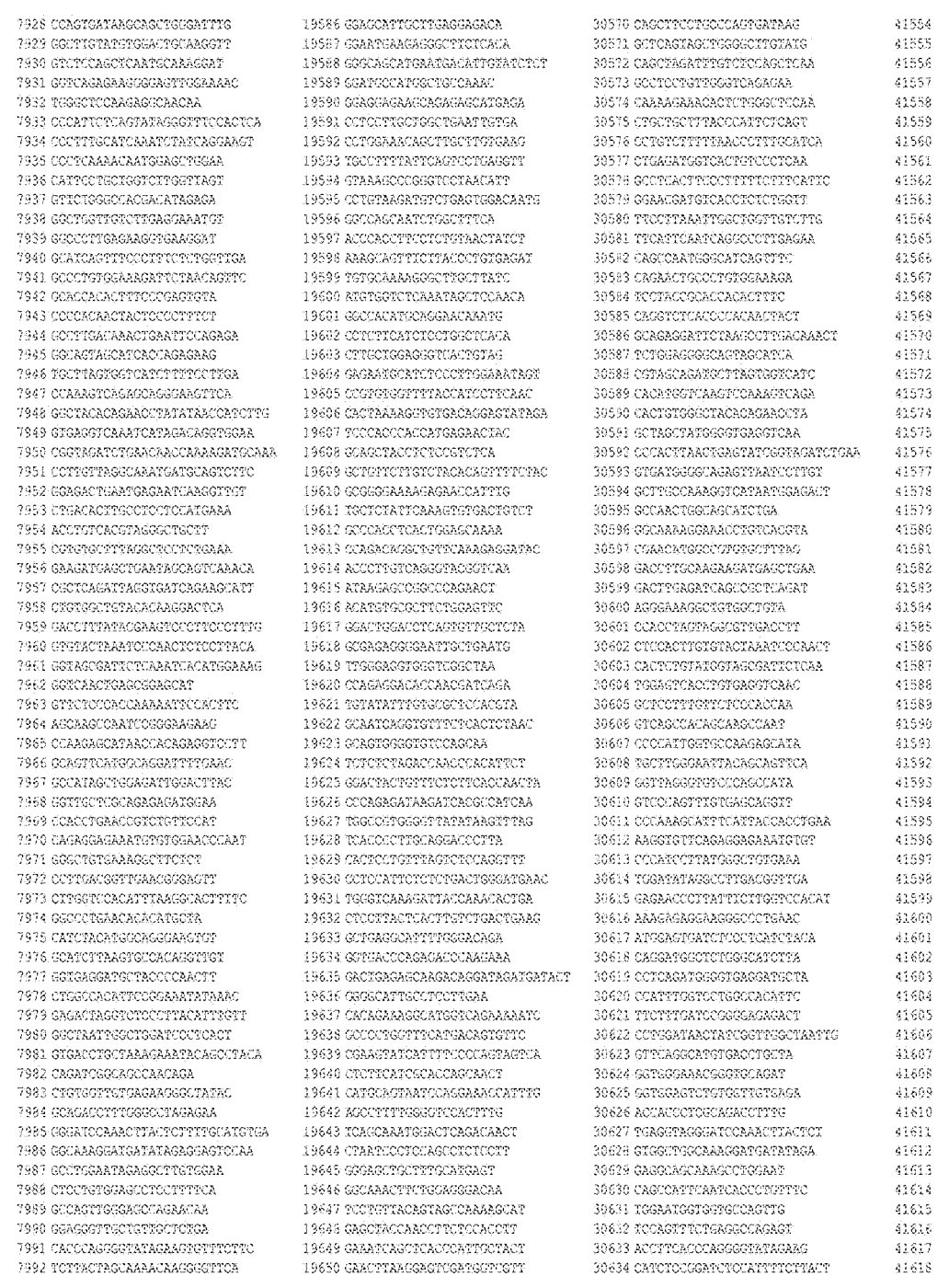
Figure 36M4:
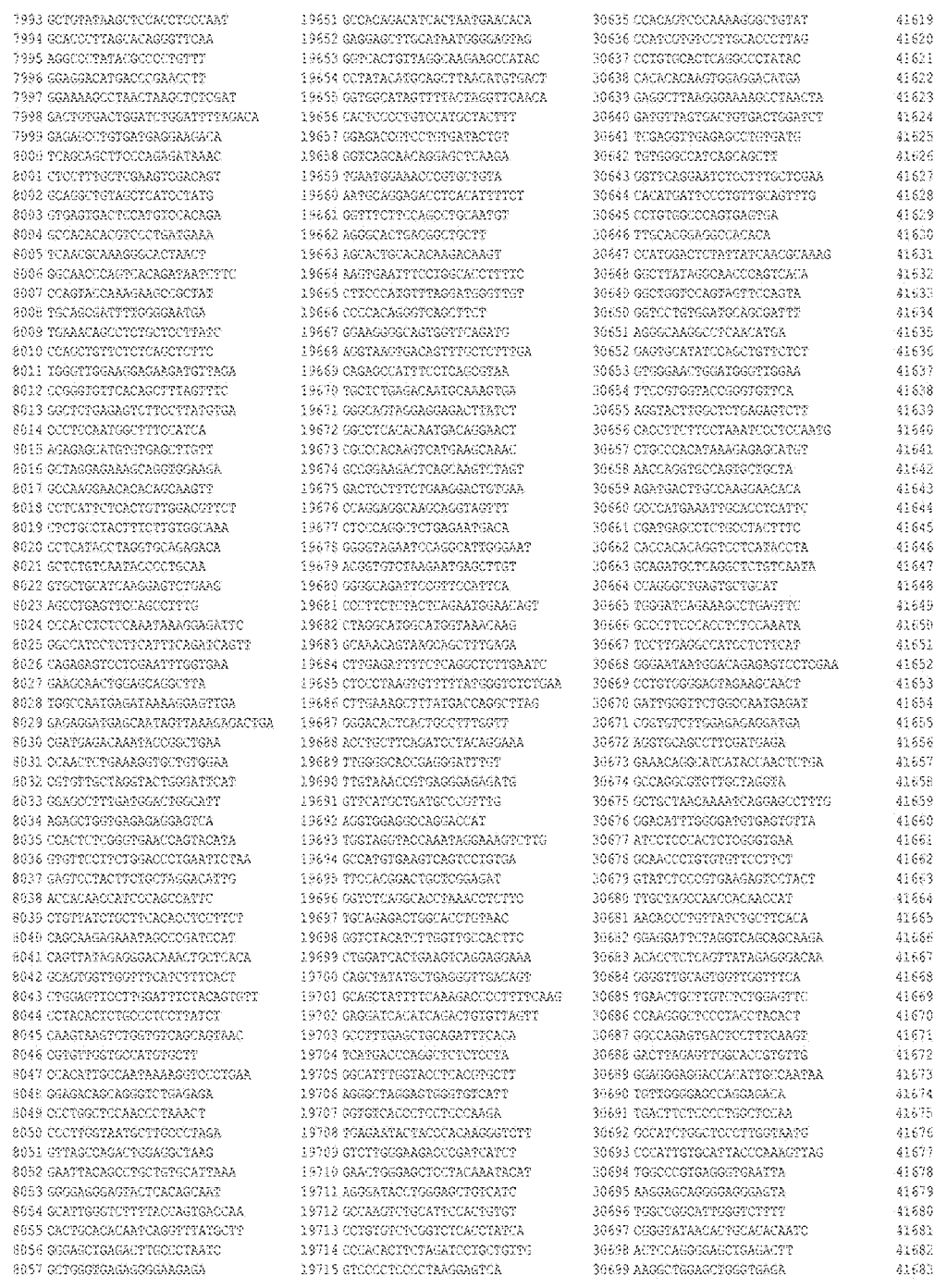
Figure 36M5:
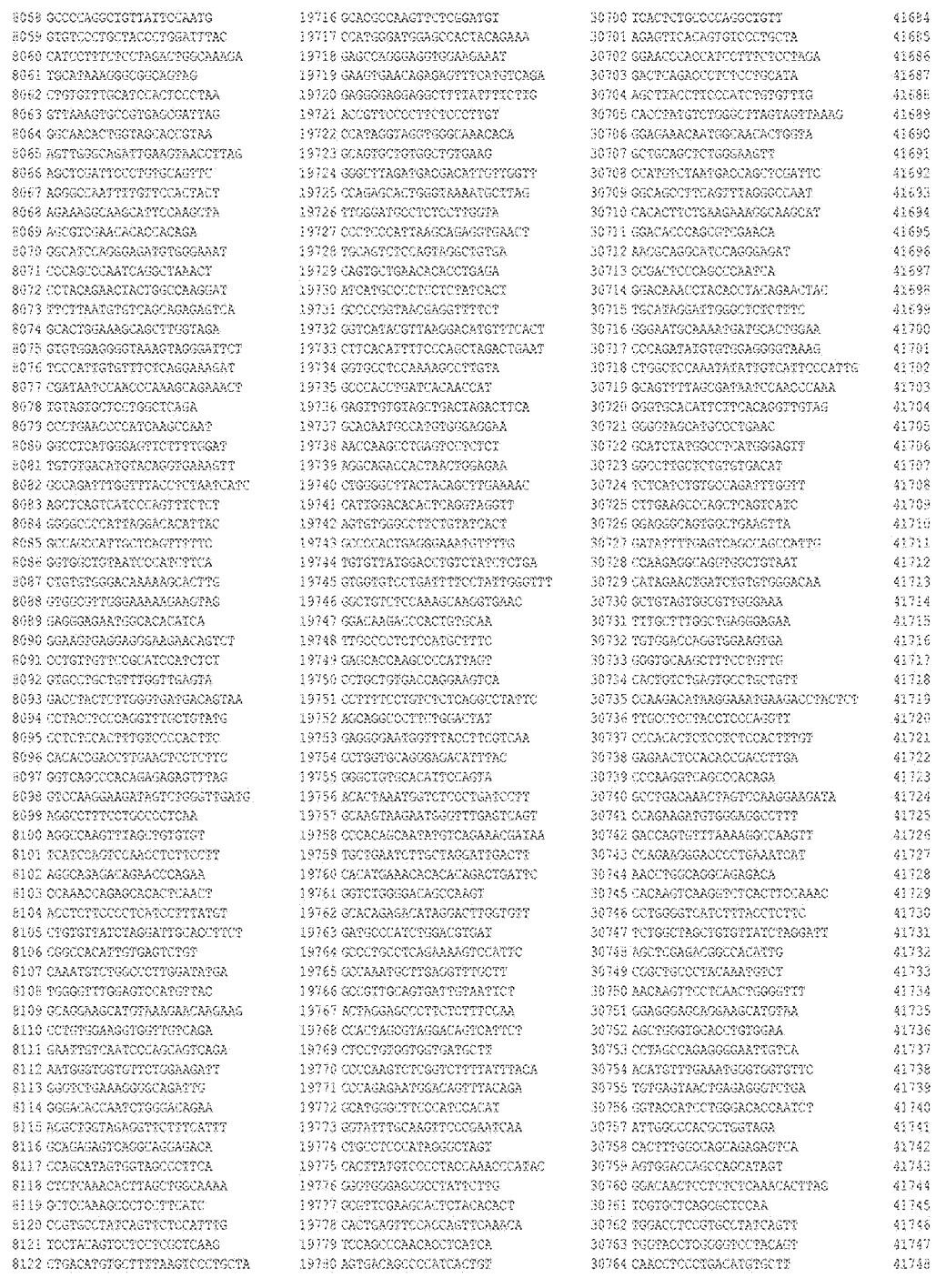
Figure 36M9:
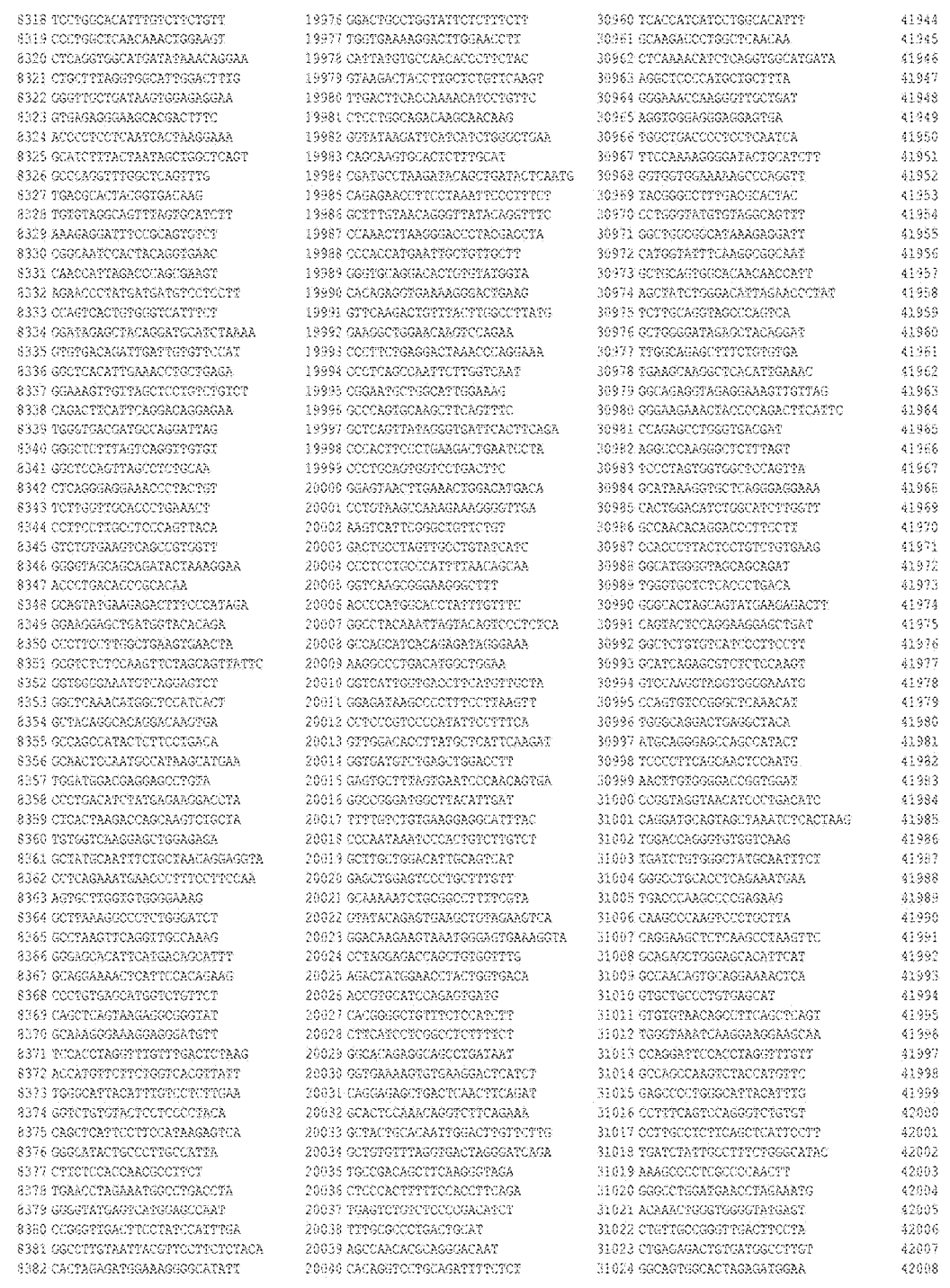
Figure 36M10:
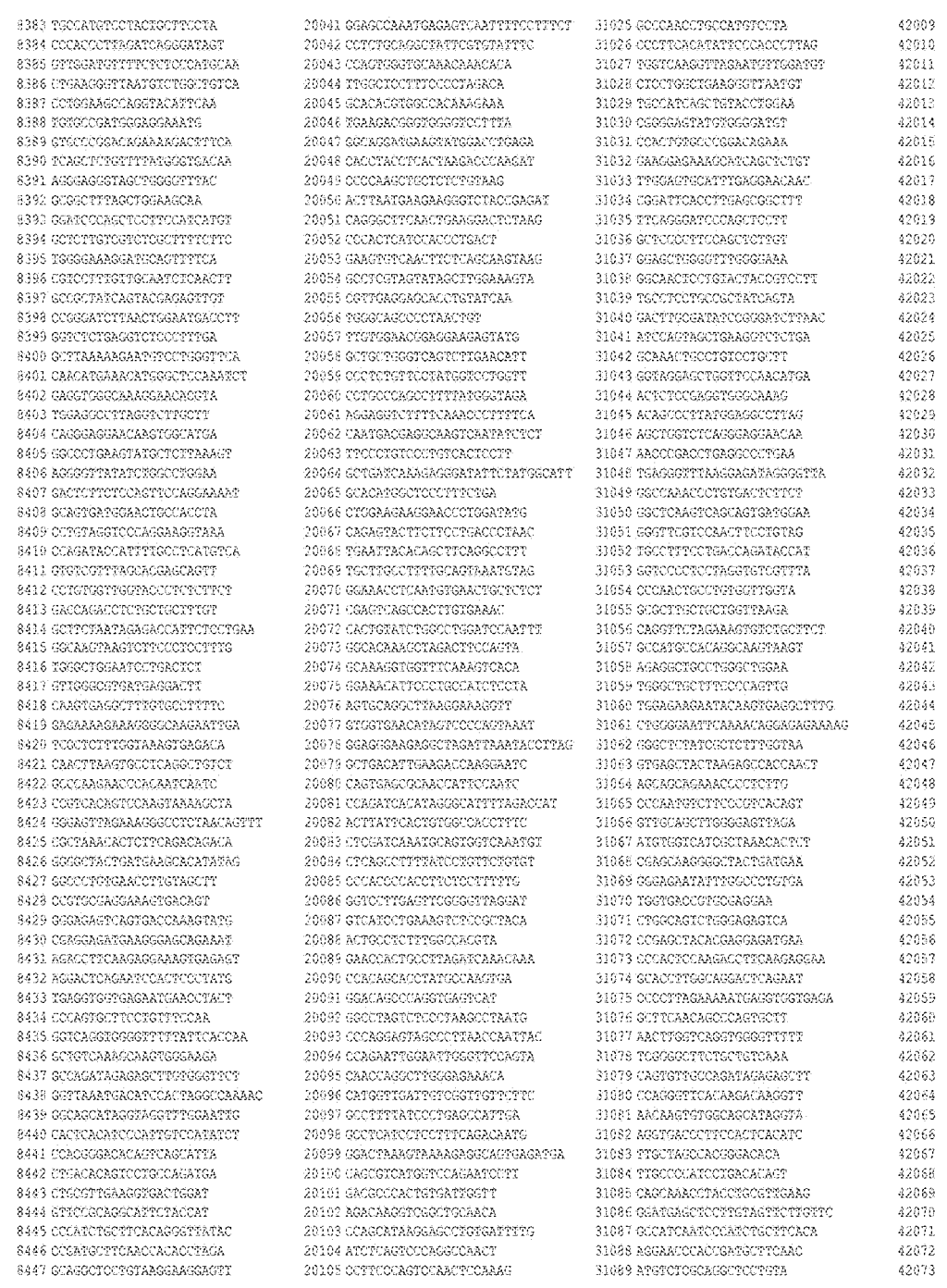
Figure 36N6:
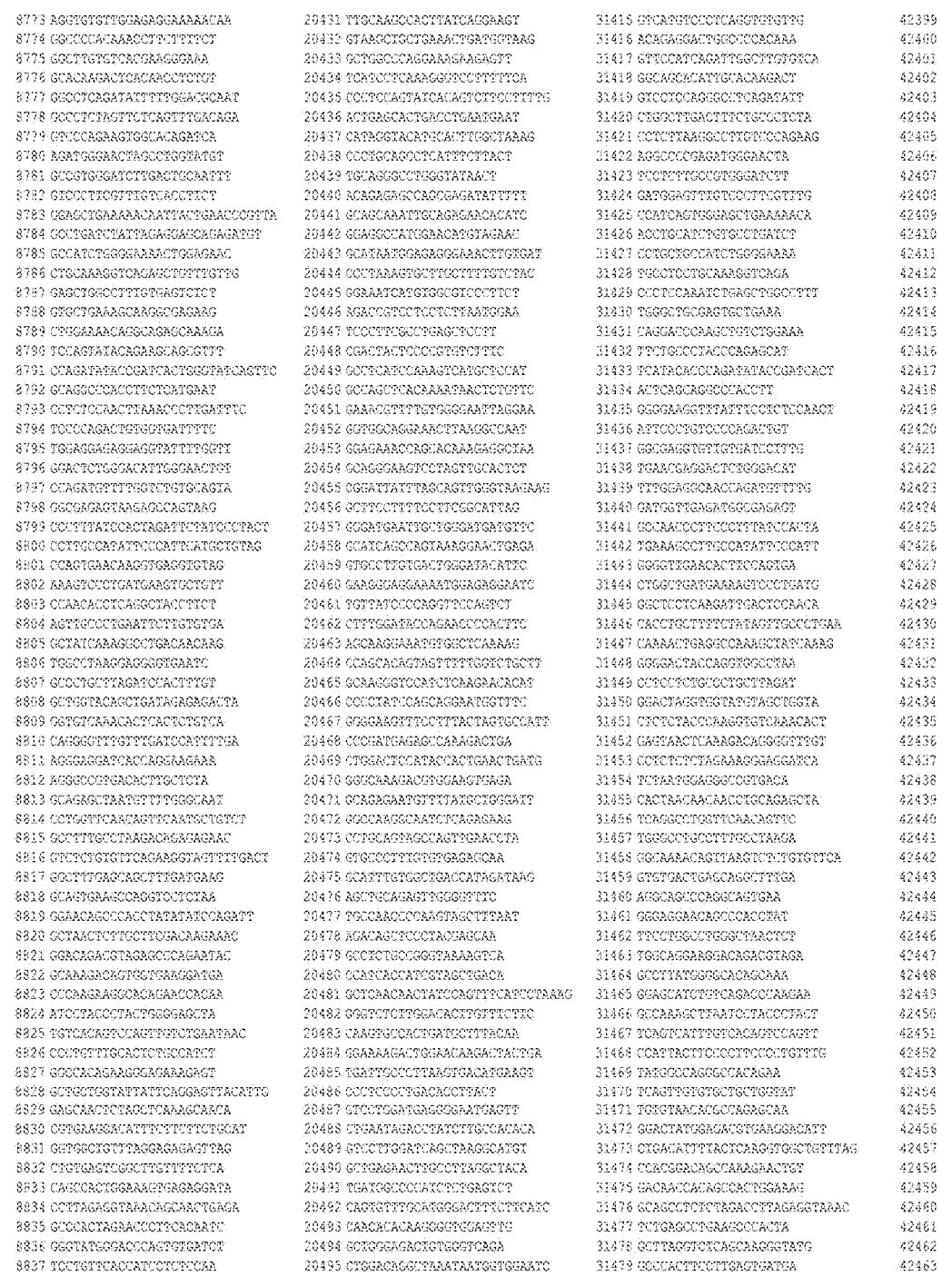
Figure 36N7:
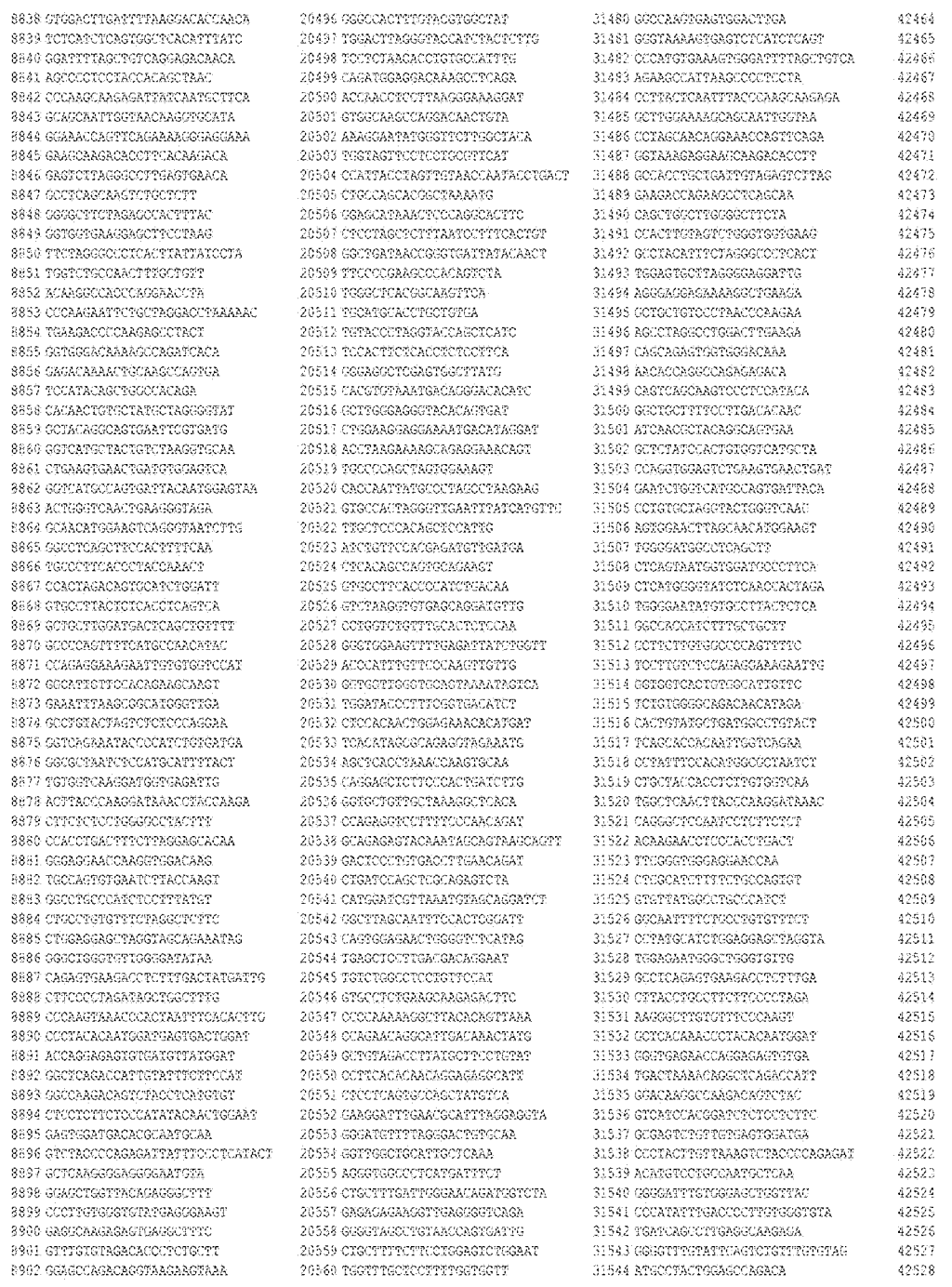
Figure 36N8:
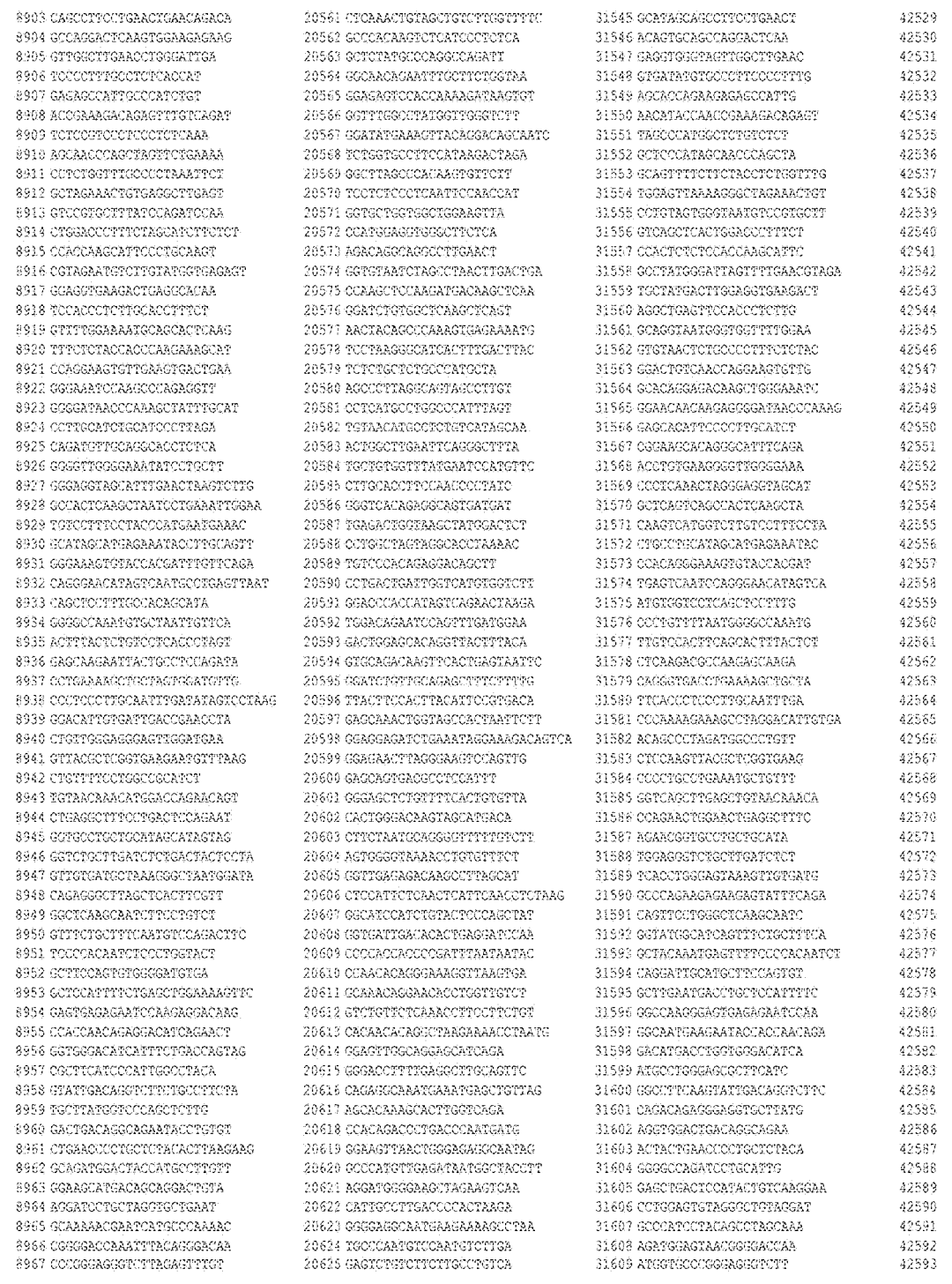
Figure 36N10:
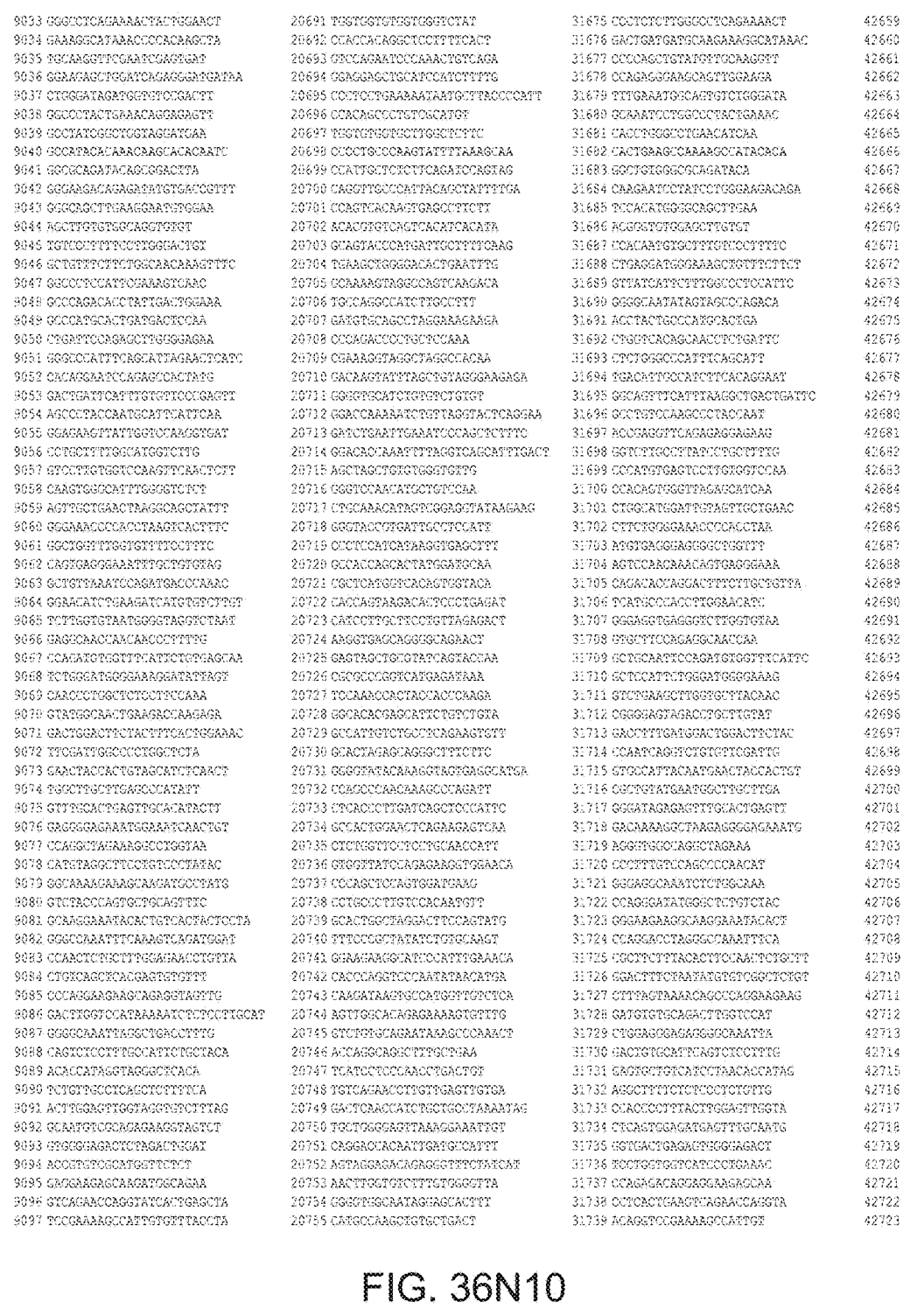
Figure 36O1:
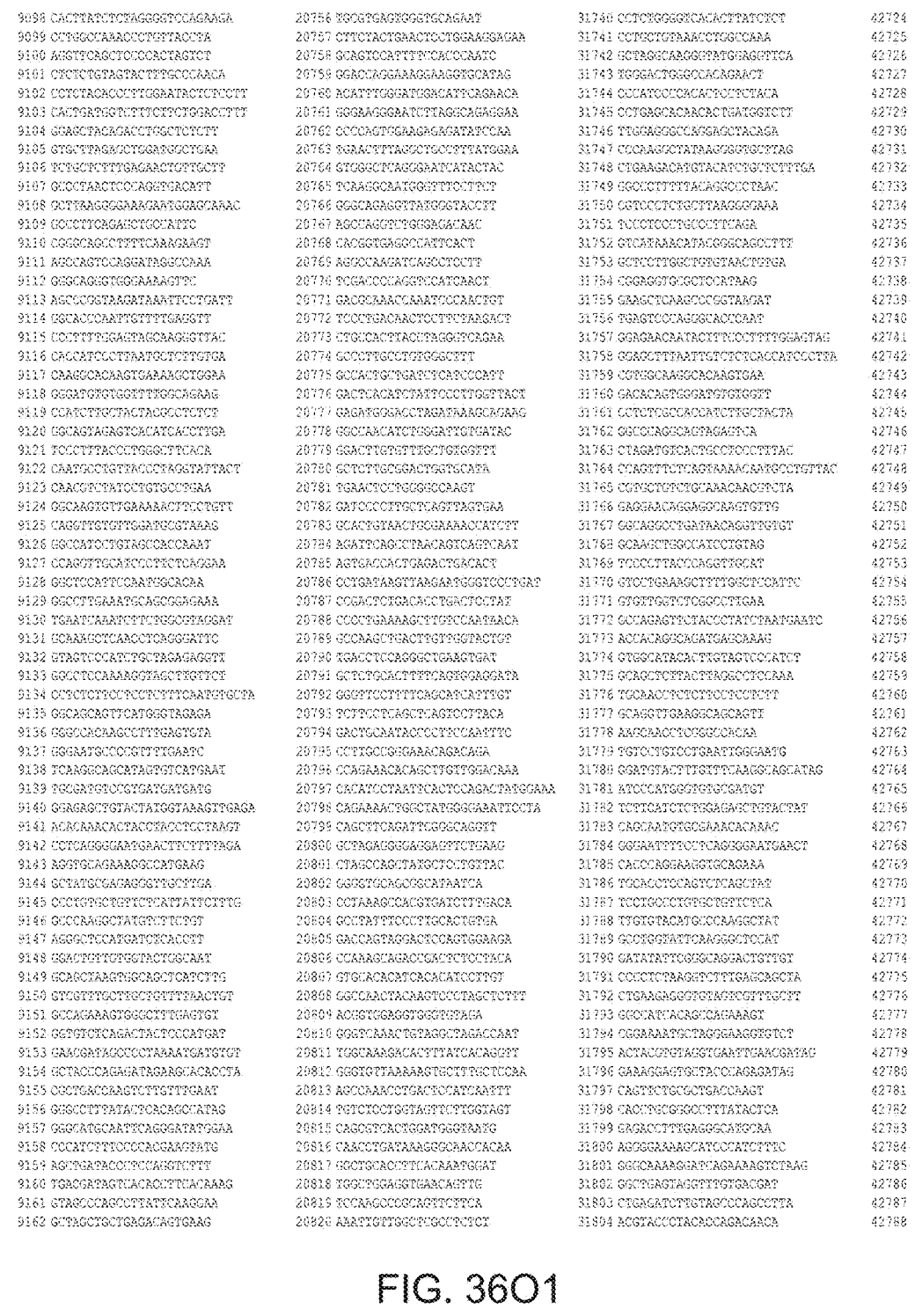
Figure 36O3:
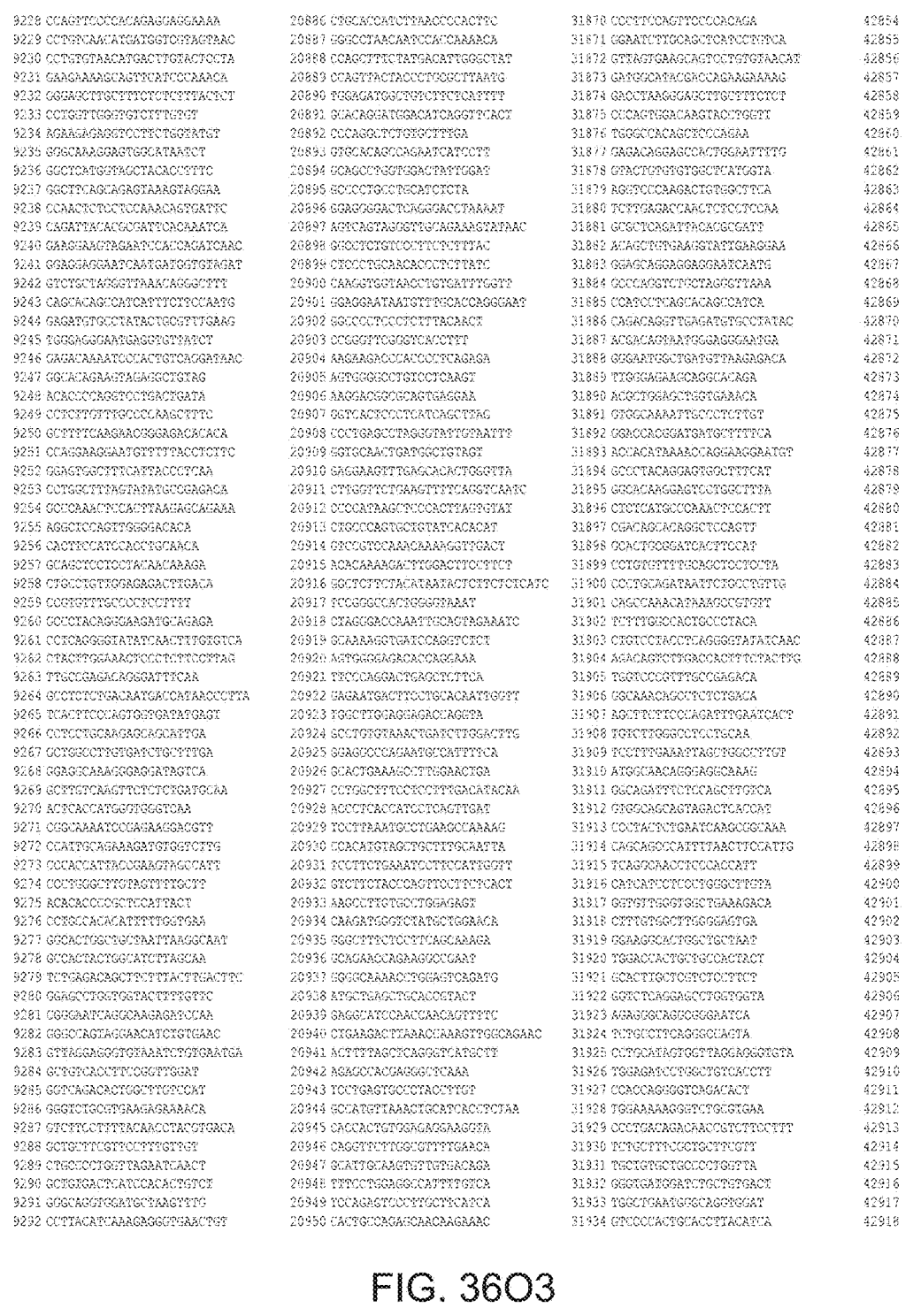
Figure 36O7:
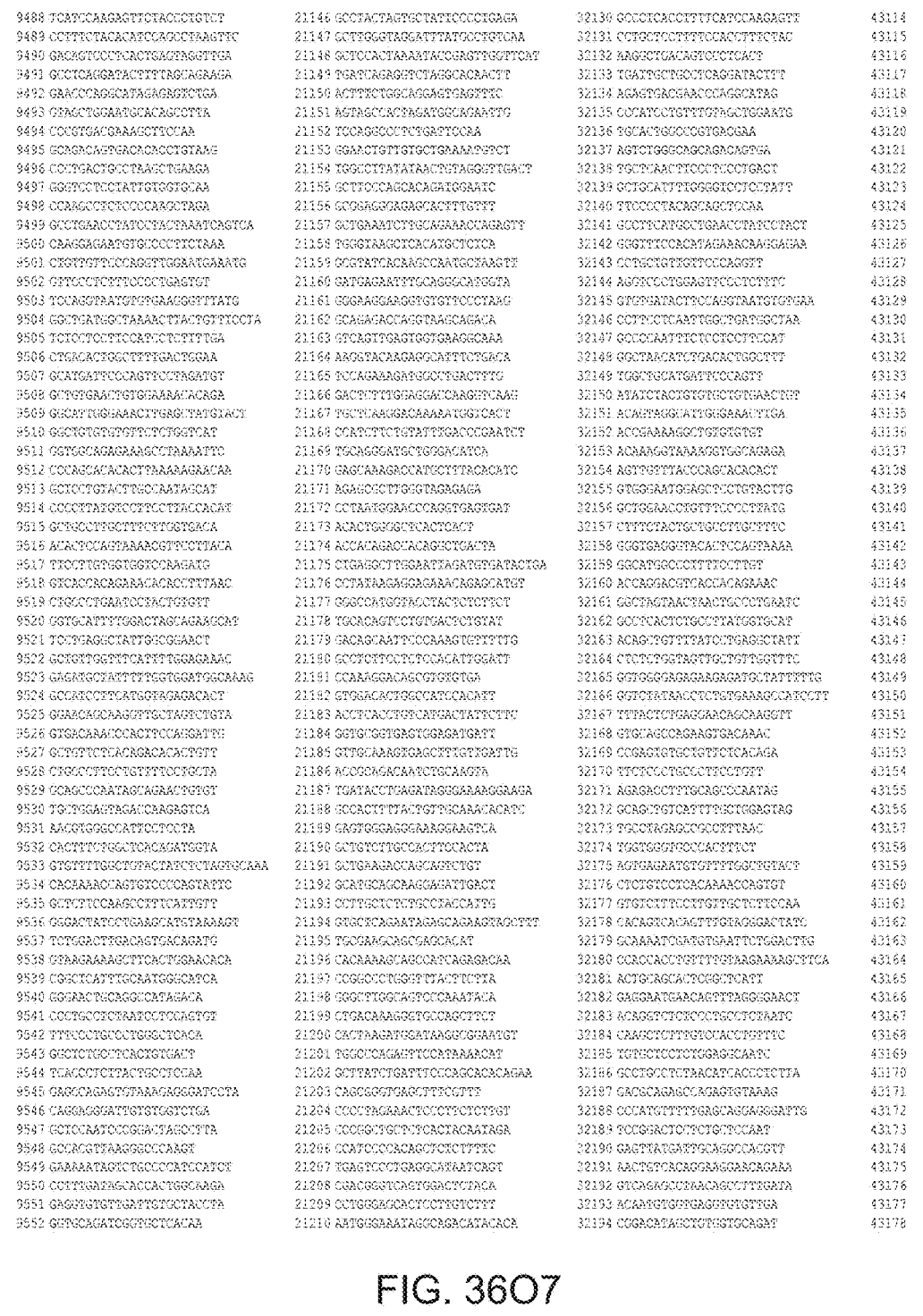
Figure 36O10:
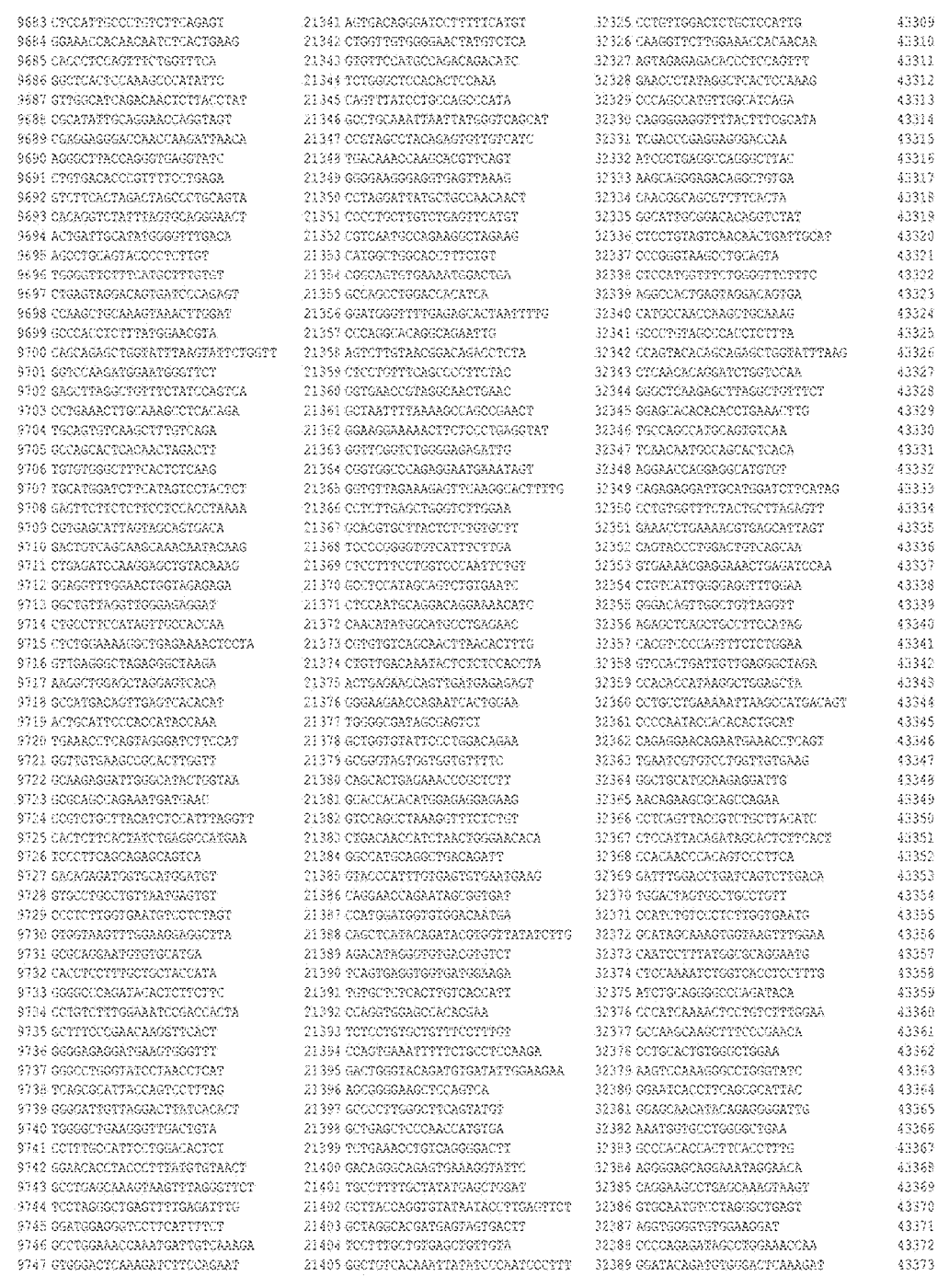
Figure 36P3:
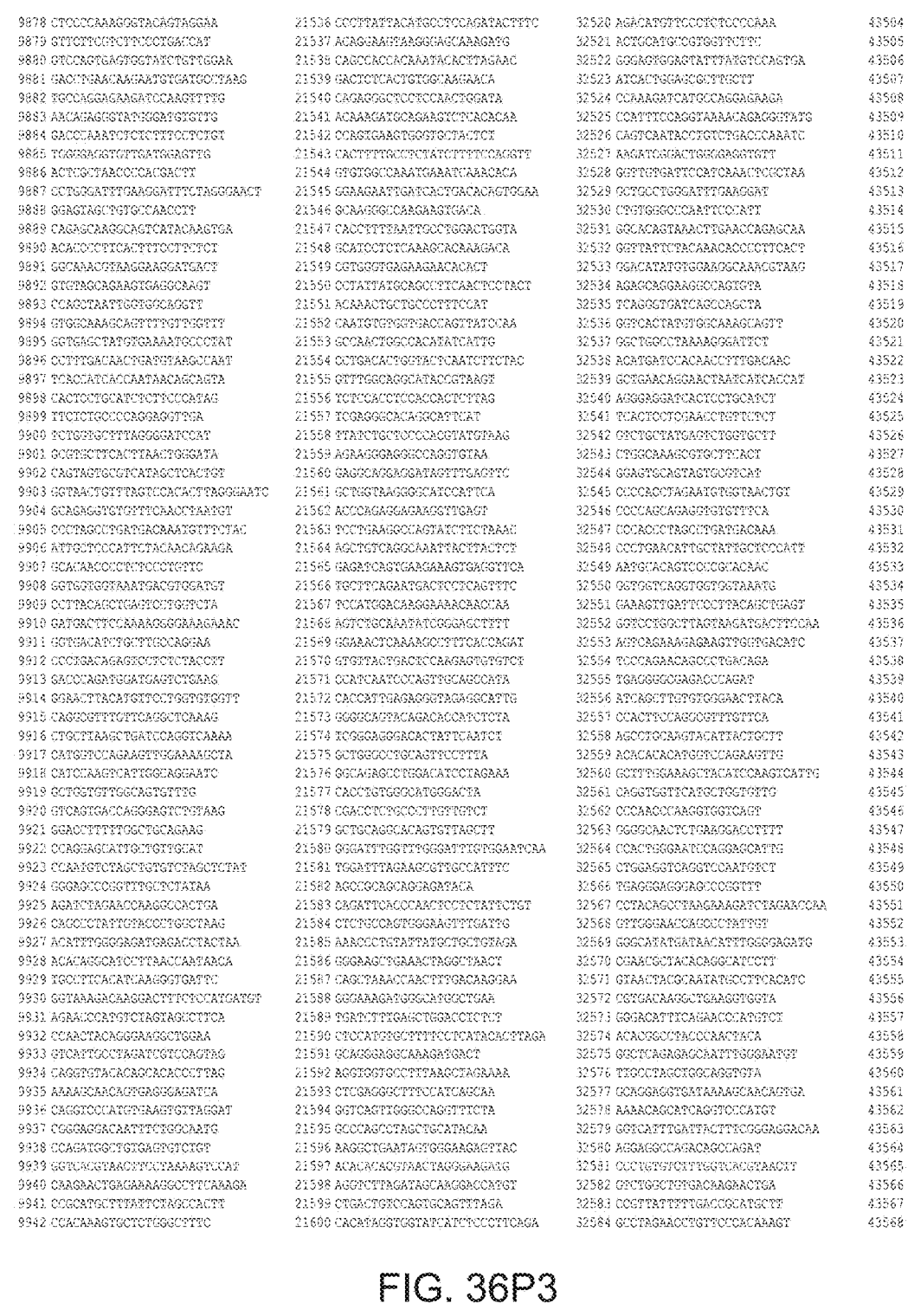
Figure 36P6:
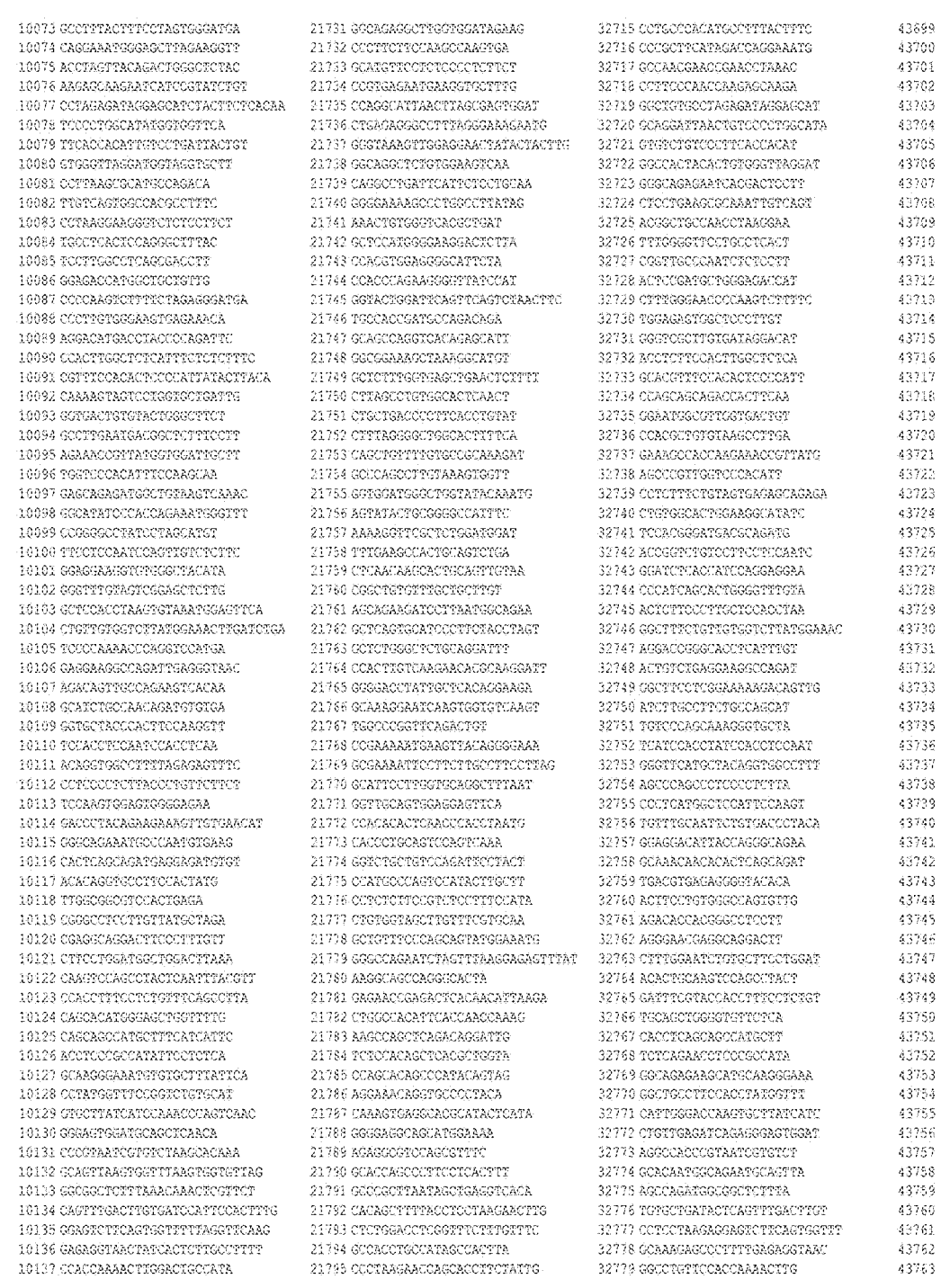
Figure 36P8:
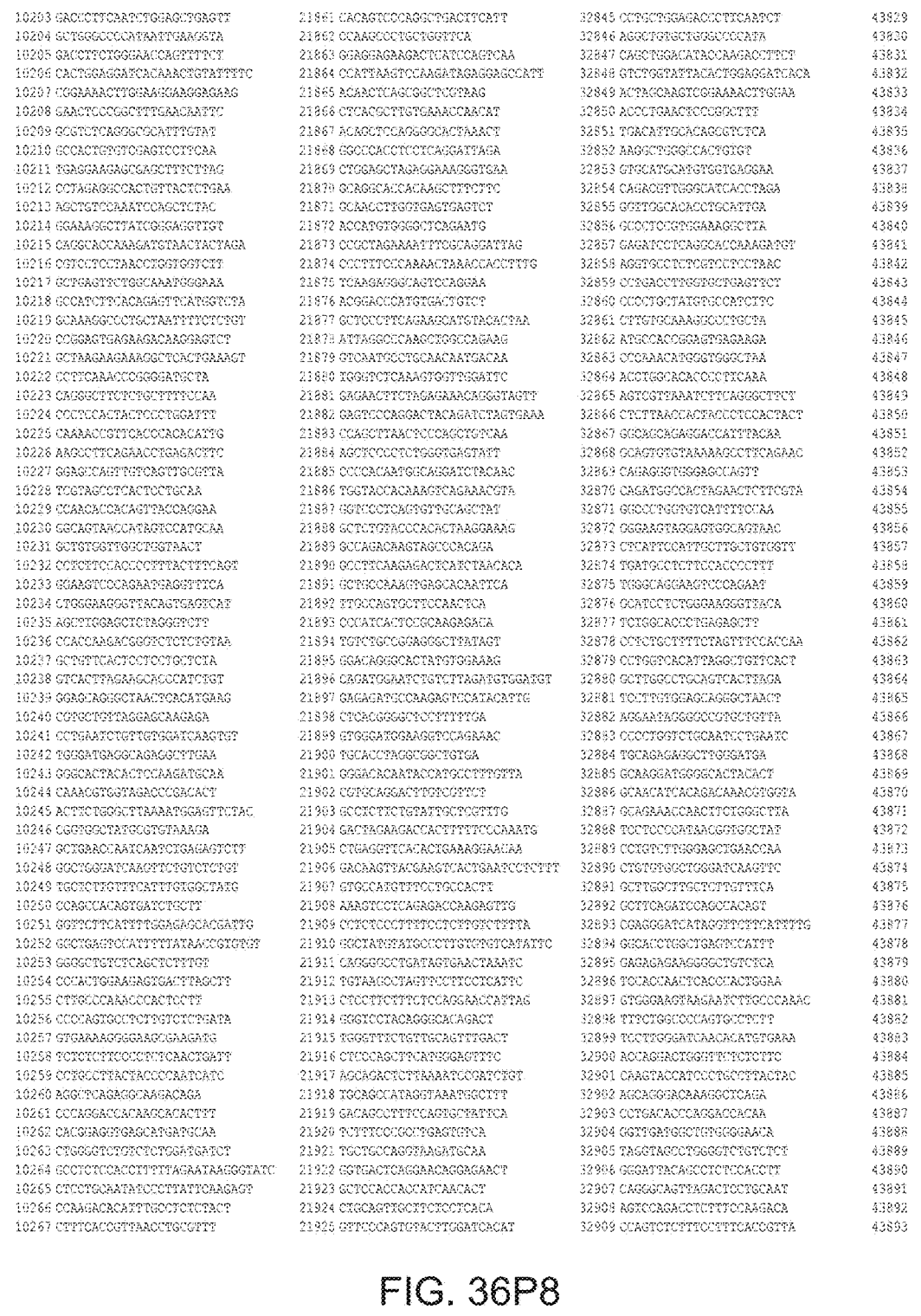
Figure 36P9:
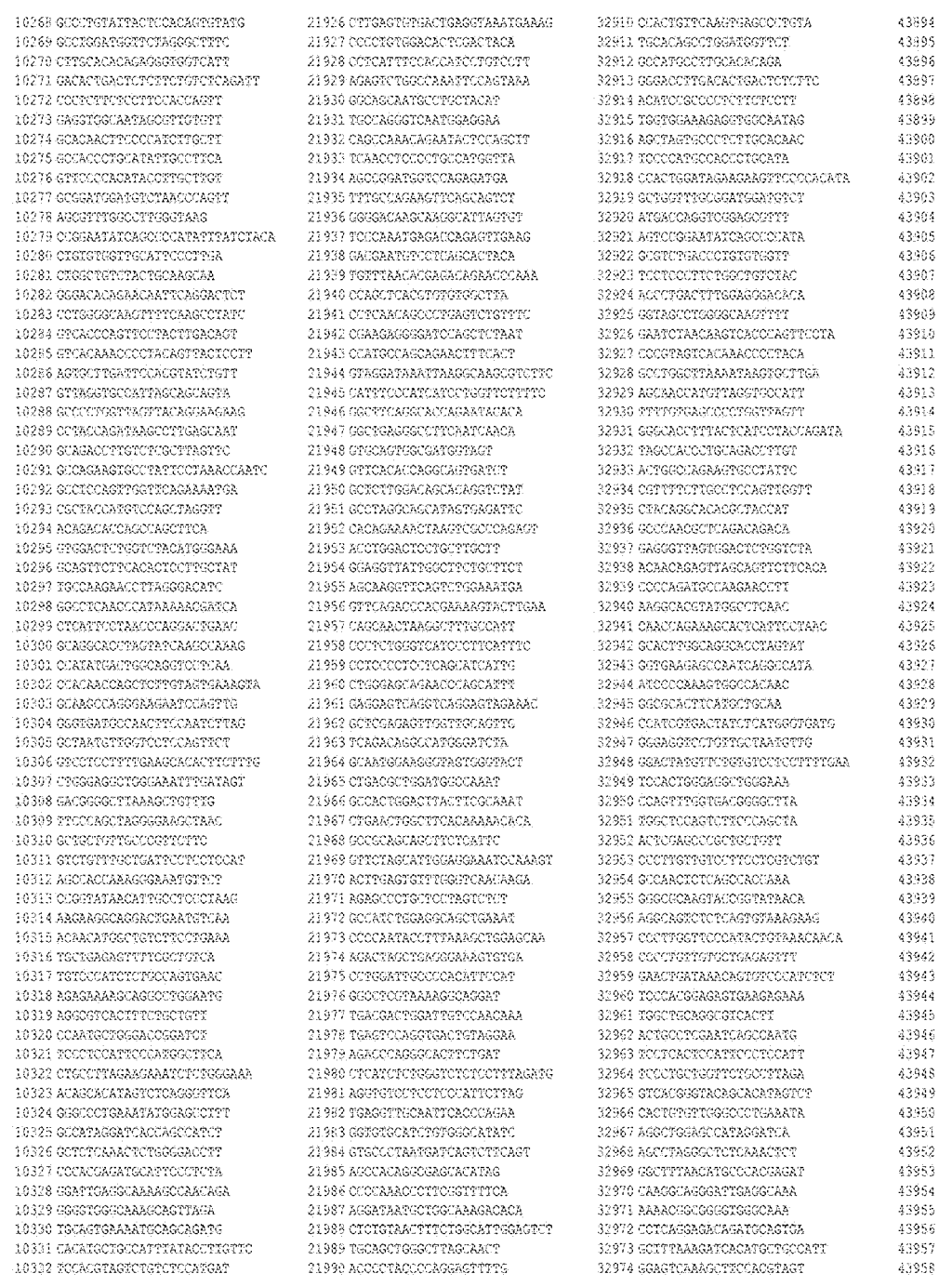
Figure 36P10:
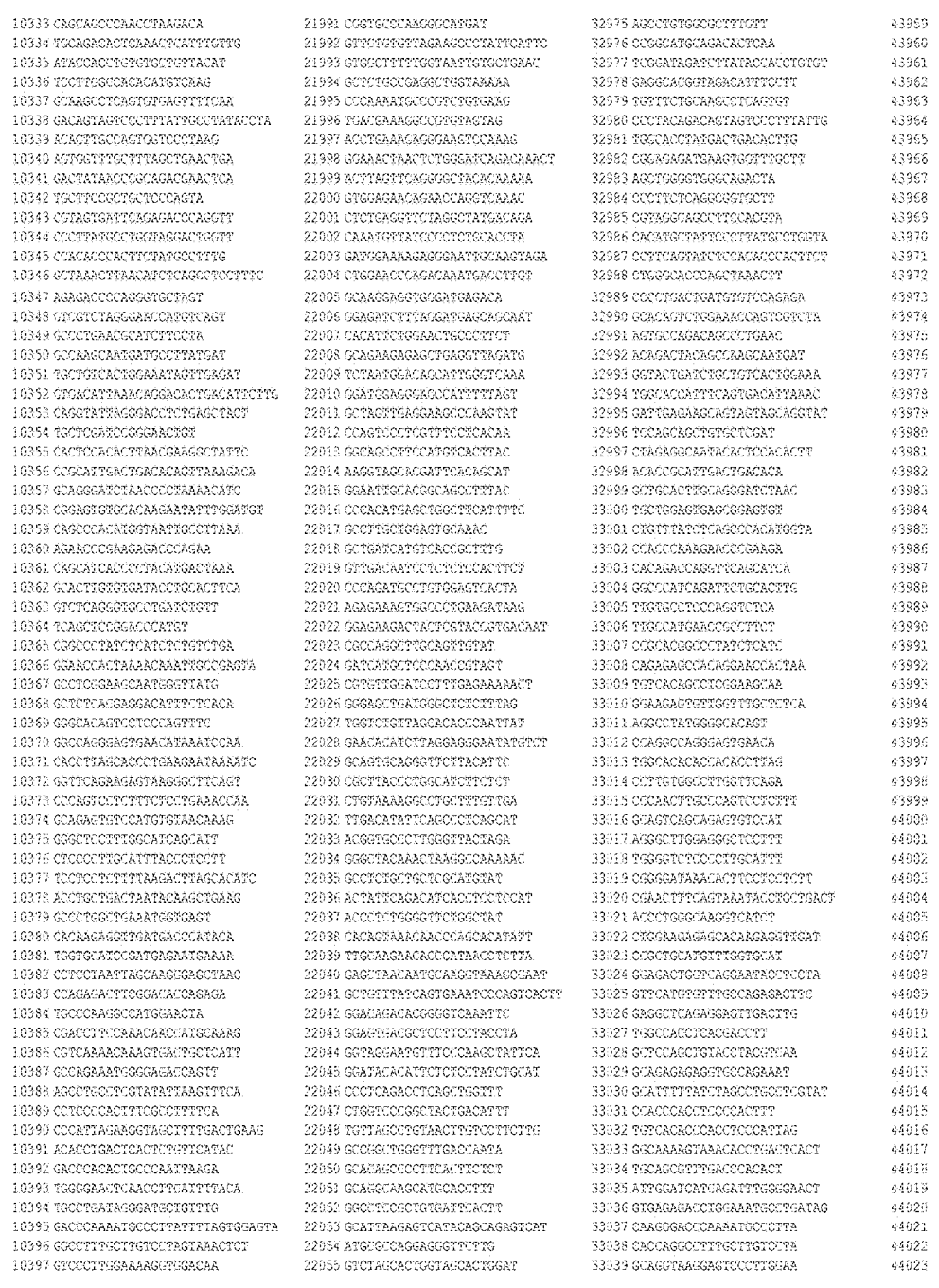
Figure 36Q1:
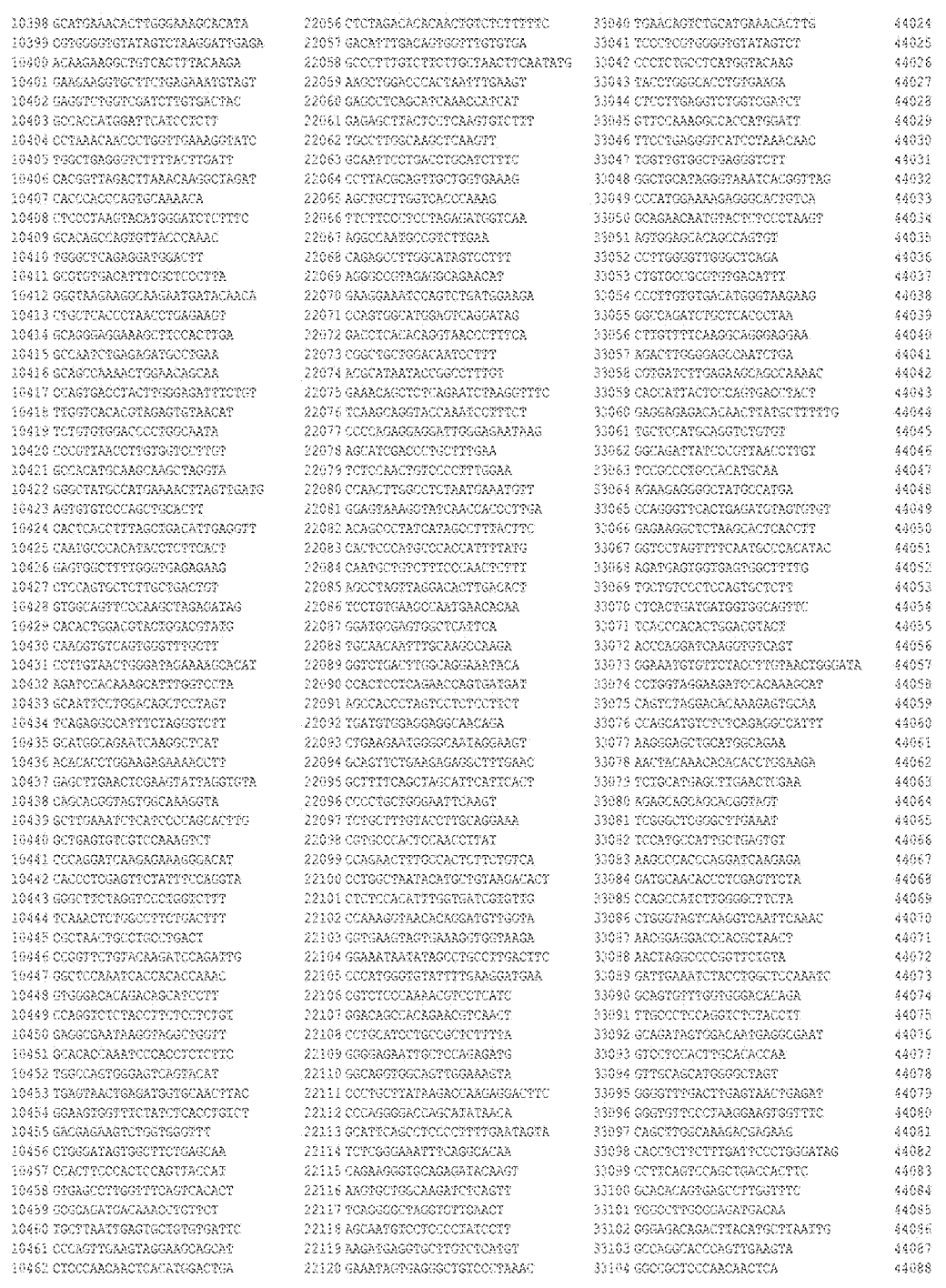
Figure 36Q3:
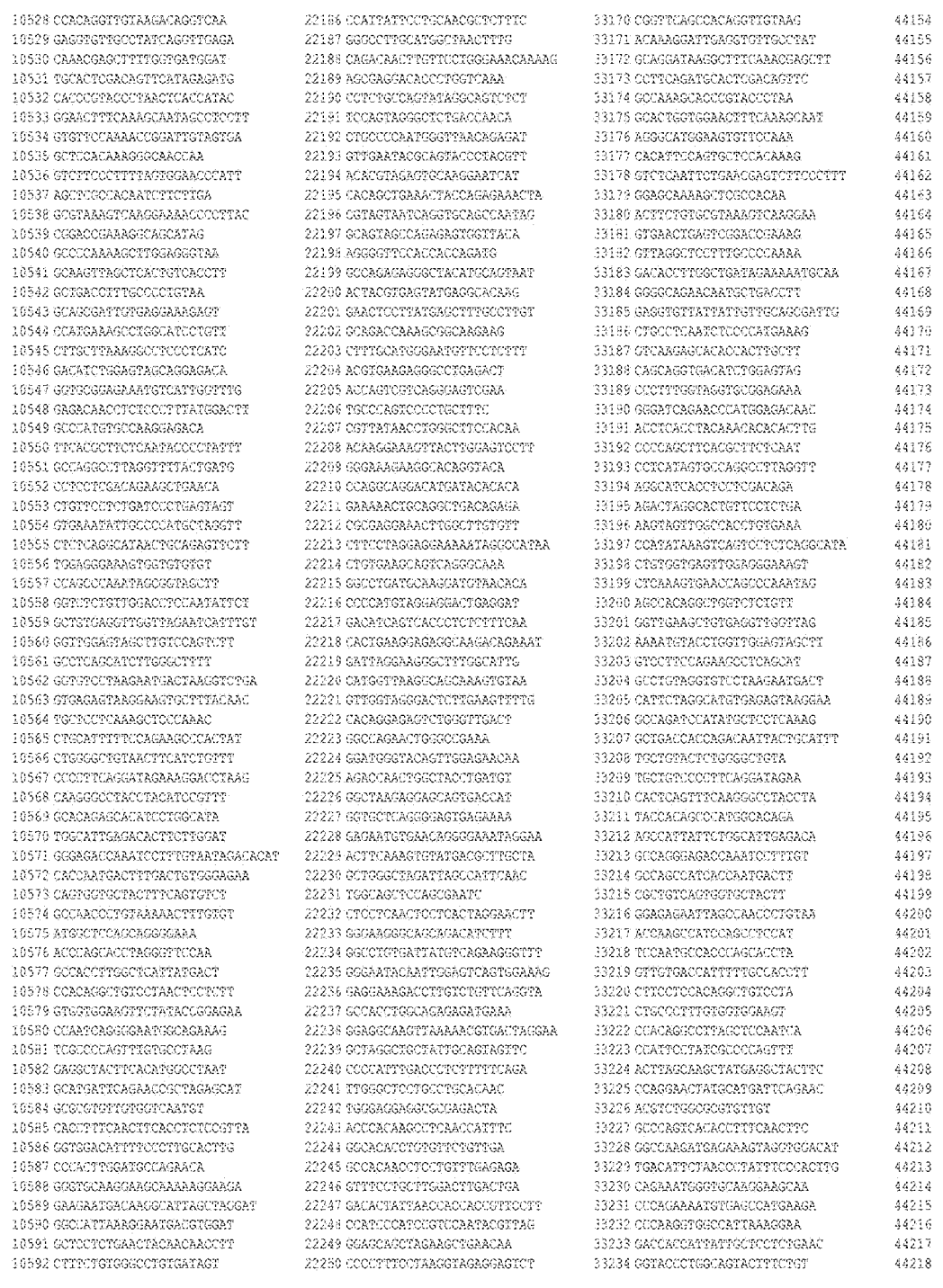
Figure 36Q7:
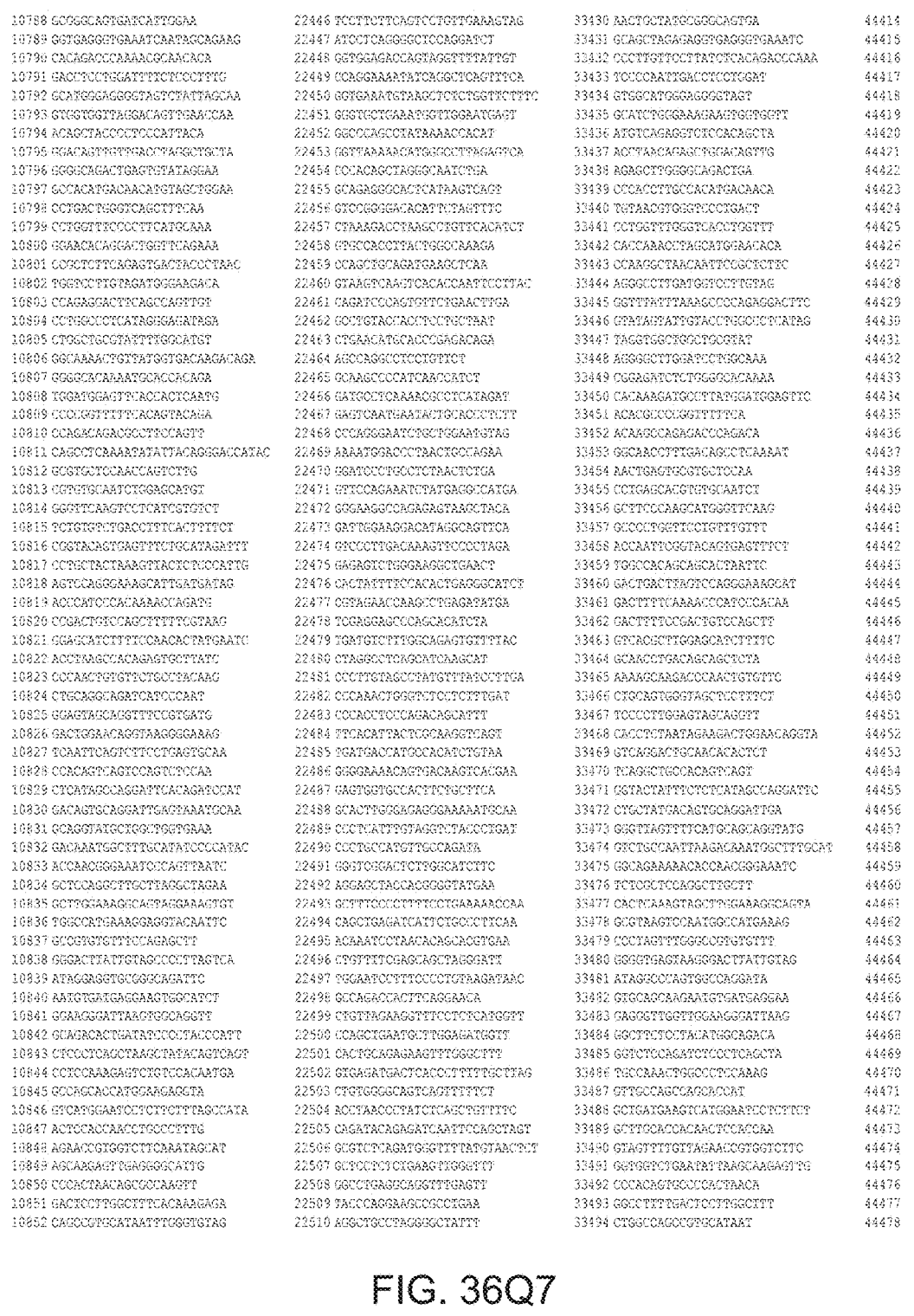

FIG. 36A1-Q7: Sequences of an exemplary 10,984-plex primer library (SEQ ID NOs 11,659-44,610). The three primers (one from pool A, one from pool B, and one from pool C) in each row all hybridize to the same target locus.

FIG. 37: Table of the percentage of reads that map to target loci for genomic DNA samples and for samples of a single cell from a cell line for both mother and child samples.

FIG. 39: Table of the percentage of reads that map to target loci for blastoceol fluid and for a single blastocyst cell.

FIG. 46 is a table comparing error call metrics for genomic DNA and DNA from a single cell.

FIG. 47 is a graph of error rates for transition mutations and transversion mutations.

FIG. 48 is a table of data (such as percent mapped reads and error rate) from multiplex PCR with various buffers. "1×MM" denotes 1× QIAGEN Master Mix (the recommended concentration) discussed above, and "2×MM" denotes 2× QIAGEN Master Mix (twice the recommended concentration).

Figure 1:
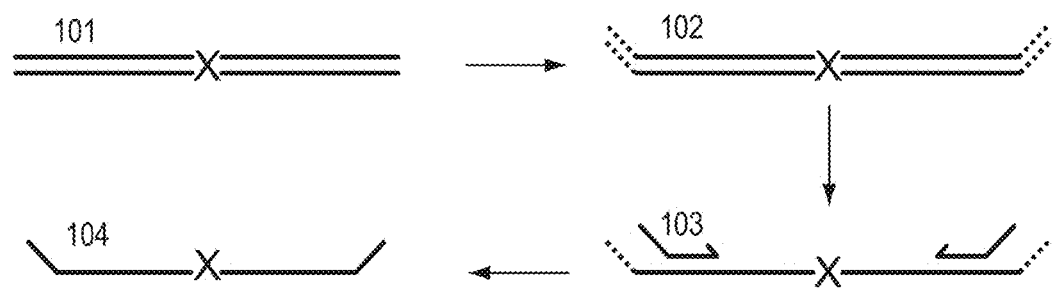
FIG. 1: Graphical representation of direct multiplexed mini-PCR method. Specific target amplification (STA) of a plurality of target sequences with tagged primers is shown. 101 denotes double stranded DNA with a polymorphic locus of interest at X. 102 denotes the double stranded DNA with ligation adaptors added for universal amplification. 103 denotes the single stranded DNA that has been universally amplified with PCR primers hybridized. 104 denotes the final PCR product.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The present invention is based in part on the surprising discovery that often only a relatively small number of primers in a library of primers are responsible for a substantial amount of the amplified primer dimers that form during multiplex PCR reactions. Methods have been developed to select the most undesirable primers for removal from a library of candidate primers. By reducing the amount of primer dimers to a negligible amount (~0.1% of the PCR products), these methods allow the resulting primer libraries to simultaneously amplify a large number of target loci in a single multiplex PCR reaction. Because the primers hybridize to the target loci and amplify them rather than hybridizing to other primers and forming amplified primer dimers, the number of different target loci that can be amplified is increased. It was also discovered that using lower primer concentrations and much longer annealing times than normal increases the likelihood that the primers hybridize to the target loci instead of hybridizing to each other and forming primer dimers (see, e.g., U.S. Ser. No. 13/683,604, filed Nov. 21, 2012, which is hereby incorporated by reference in its entirety). The methods can also be used to amplify a large number of target loci even if the primers have a relatively large range of melting temperatures (in contrast to other methods that require primers to have very similar melting temperatures to successfully amplify multiple loci simultaneously due to the need for the primers to be functional under the same reaction conditions). Additionally, it was discovered that the annealing temperature can optionally be higher than the melting temperatures of the primers (in contrast to other methods that use an annealing temperature below the melting temperatures of the primers). A higher annealing temperature improves the specificity of the PCR amplification and reduces or prevents amplification of non-target loci.

During the PCR amplification and sequencing of 19,488 target loci in a genomic sample, 99.4-99.7% of the sequencing reads mapped to the genome, of those, 99.99% of the mapped to target loci. For plasma samples with 10 million sequencing reads, typically at least 19,350 of the 19,488 target loci (99.3%) were amplified and sequenced. This primer library has even been used to amplify the nucleic acids in a single cell (FIGS. 37-40).

During the PCR amplification and sequencing of ~28,000 target loci in a genomic sample, 99% of the sequencing reads mapped to target loci. This primer library has also been used to amplify nucleic acids in a single cell.

Being able to simultaneously amplify such a large number of target loci at once greatly decreases the amount of time and the amount of DNA required to analyze thousands of target loci. For example, DNA from a single cell is sufficient to simultaneously analyze thousands of target loci, which is important for applications in which the amount of DNA is low, such as genetic testing of a single cell from an embryo prior to in vitro fertilization or genetic testing of a forensic sample with little DNA. In addition, being able to analyze the target loci in one reaction volume (such as in one chamber, well, or vessel) rather than splitting the sample into multiple different reactions reduces variability that can occur between reactions. In addition, methods have been developed to use reference standards to correct for amplification bias that may occur between different target loci. For example, differences in amplification efficiency between target loci due to factors such as GC content may cause differing amounts of PCR products to be produced for target loci that are actually present in the same amount. The use of reference standards similar to the target loci allows the detection of such amplification bias so that it can be corrected for during the quantitation of the target loci.

During sequencing of PCR products, artifacts such as primer dimers are detected and thus inhibit the detection of target amplicons. Because of this limitation, microarrays with hybridization probes are often used for detection since microarrays are less sensitive to interference from primer dimers (for example, microarrays can be used as a target specific detection that uses probes to hybridize to target amplicons but does not have probes to hybridize to undesired primer dimers). The high level of multiplexing with minimal non-target amplicons that has now been achieved allows PCR followed by sequencing to be used as an alternative to microarrays. For example, the present multiplex PCR methods can be used with a non-target specific method of detection, such as sequencing that detects all amplified products (including both target amplicons and primer dimers, if any). The small amount of primer dimers that are produced allows detection of target amplicons by methods that detect all amplicons. Thus, in some embodiments, the method includes multiplex PCR followed by sequencing without use of an array. In other embodiments, the method includes multiplex PCR followed by an array for detection of the amplified products.

The multiplex-PCR methods of the invention can be in a variety of applications, such as genotyping, detection of chromosomal abnormalities (such as a fetal chromosome aneuploidy), gene mutation and polymorphism (such as single nucleotide polymorphisms, SNPs) analysis, gene deletion analysis, determination of paternity, analysis of genetic differences among populations, forensic analysis, measuring predisposition to disease, quantitative analysis of mRNA, and detection and identification of infectious agents (such as bacteria, parasite, and viruses). The multiplex PCR methods can also be used for non-invasive prenatal testing, such as paternity testing or the detection of fetal chromosome abnormalities.

Exemplary Primer Design Methods

Highly multiplexed PCR can often result in the production of a very high proportion of product DNA that results from unproductive side reactions such as primer dimer formation. In an embodiment, the particular primers that are most likely to cause unproductive side reactions may be removed from the primer library to give a primer library that will result in a greater proportion of amplified DNA that maps to the genome. The step of removing problematic primers, that is, those primers that are particularly likely to firm dimers has unexpectedly enabled extremely high PCR multiplexing levels for subsequent analysis by sequencing. In systems such as sequencing, where performance significantly degrades by primer dimers and/or other mischief products, greater than 10, greater than 50, and greater than 100 times higher multiplexing than other described multiplexing has been achieved. Note this is opposed to probe based detection methods, e.g. microarrays, TAQMAN, PCR etc. where an excess of primer dimers will not affect the outcome appreciably. Also note that the general belief in the art is that multiplexing PCR for sequencing is limited to about 100 assays in the same well. Fluidigm and Rain Dance offer platforms to perform 48 or 1000s of PCR assays in parallel reactions for one sample.

There are a number of ways to choose primers for a library where the amount of non-mapping primer dimer or other primer mischief products are minimized. Empirical data indicate that a small number of 'bad' primers are responsible for a large amount of non-mapping primer dimer side reactions. Removing these 'bad' primers can increase the percent of sequence reads that map to targeted loci. One way to identify the 'bad' primers is to look at the sequencing data of DNA that was amplified by targeted amplification; those primer dimers that are seen with greatest frequency can be removed to give a primer library that is significantly less likely to result in side product DNA that does not map to the genome. There are also publicly available programs that can calculate the binding energy of various primer combinations, and removing those with the highest binding energy will also give a primer library that is significantly less likely to result in side product DNA that does not map to the genome.

In some embodiments for selecting primers, an initial library of candidate primers is created by designing one or more primers or primer pairs to candidate target loci. A set of candidate target loci (such as SNPs) can selected based on publically available information about desired parameters for the target loci, such as frequency of the SNPs within a target population or the heterozygosity rate of the SNPs. In one embodiment, the PCR primers may be designed using the Primer3 program (the worldwide web at primer3.sourceforge.net; libprimer3 release 2.2.3, which is hereby incorporated by reference in its entirety). If desired, the primers can be designed to anneal within a particular annealing temperature range, have a particular range of GC contents, have a particular size range, produce target amplicons in a particular size range, and/or have other parameter characteristics. Starting with multiple primers or primer pairs per candidate target locus increases the likelihood that a primer or prime pair will remain in the library for most or all of the target loci. In one embodiment, the selection criteria may require that at least one primer pair per target locus remains in the library. That way, most or all of the target loci will be amplified when using the final primer library. This is desirable for applications such as screening for deletions or duplications at a large number of locations in the genome or screening for a large number of sequences (such as polymorphisms or other mutations) associated with a disease or an increased risk for a disease. If a primer pair from the library would produces a target amplicon that overlaps with a target amplicon produced by another primer pair, one of the primer pairs may be removed from the library to prevent interference.

In some embodiments, a score such as an "undesirability score" (higher score representing least desirability) is calculated (such as calculation on a computer) for most or all of the possible combinations of two primers from a library of candidate primers. In various embodiments, a score (such as an undesirability score) is calculated for at least 80, 90, 95, 98, 99, or 99.5% of the possible combinations of candidate primers in the library. Each score (such as an undesirability score) is based at least in part on the likelihood of dimer formation between the two candidate primers. If desired, the score (such as the undesirability score) may also be based on one or more other parameters selected from the group consisting of heterozygosity rate of the target locus, disease prevalence associated with a sequence (e.g., a polymorphism) at the target locus, disease penetrance associated with a sequence (e.g., a polymorphism) at the target locus, specificity of the candidate primer for the target locus, size of the candidate primer, melting temperature of the candidate primer, melting temperature of the target amplicon, GC content of the target amplicon, GC content of the 3' end of the candidate primer, homopolymer length in the candidate primer, amplification efficiency of the target amplicon, size of the target amplicon. number of SNPs within the candidate primer, location of SNPs within the candidate primer, distance from an end of the amplicon to the target bases within the amplicon, and the number of target loci in an amplicon. In some embodiments, the lower the number of SNPs with the candidate primer (such as 2, 1 or 0 SNPs) the better. In some embodiments, there are no SNPs in the candidate primer. In some embodiments, SNPs (if any) are preferably not in the last 5 nucleotides in the 3' end of the candidate primer. In some embodiments, the target bases (the bases of interest in a target locus) are preferably near an end (the 3' or 5' end) of the amplicon; this may improve the quality of sequencing data (since bases near the end of an amplicon are sequenced more accurately), and/or allow shorter sequencing reads to be performed. In some embodiments, a single amplicon includes 2 or more target loci (such as 2 or more nearby SNPs or variants). In some embodiments, the specificity of the candidate primer for the target locus includes the likelihood that the candidate primer will mis-prime by binding and amplifying a locus other than the target locus it was designed to amplify. In some embodiments, one or more or all the candidate primers that mis-prime are removed from the library. In some embodiments to increase the number of candidate primers to choose from, candidate primers that may mis-prime are not removed from the library. In some embodiments, the optimal melting temperature for selection of the candidate primer is 57° C. In some embodiments, the optimal size for selection of the candidate primers is a length of 24 nucleotides. In some embodiments, the optimal GC content for selection of the candidate primers is 50%. If multiple factors are considered, the score (such as the undesirability score) may be calculated based on a weighted average of the various parameters. The parameters may be assigned different weights based on their importance for the particular application that the primers will be used for. An exemplary score (such as an undesirability score) for a primer is shown below in which the parameters are weighted by various factors.

score=(1)(total number of targets−number of targets covered)+(100)(number of SNPs in GC clamp)+(10)(number of SNPs in primer binding site)+(10)(number of similar primer pair designs)+(0.1)(distance of target base from amplicon end)+(0.1)(amplicon length)+(100)(interaction score)

where interaction score=max (−1*ΔG value) as described herein

Another exemplary score for a primer is shown below.

score=(100)(number of SNPs in GC clamp)+(10)(number of SNPs in primer binding site)+(0.1)(distance of target base from amplicon end)+(0.1)(amplicon length)+(100)(interaction score)

where interaction score=max (−1*ΔG value) as described herein

In some embodiments, the score for a primer pair is the worse score out of the scores for the two primers in the pair. An exemplary score (such as an undesirability score or the score in Experiment 20) for a pairs of designs (in which each design is one primer pair so that a pair of designs includes two primer pairs with a total of 4 primers) is shown below.

score=(10000000)(amplicon overlap)+(100)(distance between designs)+(1)(total number of targets−number of targets covered)+(100)(number of SNPs in GC clamp)+(10)(number of SNPs in primer binding site)+(10)(number of similar primer pair designs)+(0.1)(distance of target base from amplicon end)+(0.1)(amplicon length)+(100)(interaction score)

where interaction score=max (−1*ΔG value) as described herein;

where amplicon overlap=overlap between the two amplicons formed by a pair of designs In some embodiments, the score for a pair of designs is the worse score out of the scores for the four primers in the pair of designs.

In some embodiments, the primer with the highest score (such as the undesirability score) or any score representing least desirability is removed from the library. If the removed primer is a member of a primer pair that hybridizes to one target locus, then the other member of the primer pair may be removed from the library. The process of removing primers may be repeated as desired. In some embodiments, the selection method is performed until the score (such as the undesirability score) for the candidate primer combinations remaining in the library are all equal to or below a minimum threshold (such as any threshold for which the primers remaining in the library all have at least that level of desirability). In some embodiments, the selection method is performed until the number of candidate primers remaining in the library is reduced to a desired number.

In various embodiments, after the score (such as the undesirability score) are calculated, the candidate primer that is part of the greatest number of combinations of two candidate primers with a score (such as an undesirability score) above a first minimum threshold (such as any threshold for which the primers remaining in the library all have at least that level of desirability) is removed from the library. This step ignores interactions equal to or below the first minimum threshold since these interactions are less significant. If the removed primer is a member of a primer pair that hybridizes to one target locus, then the other member of the primer pair may be removed from the library. The process of removing primers may be repeated as desired. In some embodiments, the selection method is performed until the score (such as the undesirability score) for the candidate primer combinations remaining in the library are all equal to or below the first minimum threshold. If the number of candidate primers remaining in the library is higher than desired, the number of primers may be reduced by decreasing the first minimum threshold to a lower second minimum threshold (such as any threshold with a stricter cutoff than the first minimum threshold so that some of the least desirable primers are removed from the library) and repeating the process of removing primers. If the number of candidate primers remaining in the library is lower than desired, the method can be continued by increasing the first minimum threshold to a higher second minimum threshold (such as any threshold with a less strict cutoff than the first minimum threshold) and repeating the process of removing primers using the original candidate primer library, thereby allowing more of the candidate primers to remain in the library. In some embodiments, the selection method is performed until the score (such as the undesirability score) for the candidate primer combinations remaining in the library are all equal to or below the second minimum threshold, or until the number of candidate primers remaining in the library is reduced to a desired number.

If desired, primer pairs that produce a target amplicon that overlaps with a target amplicon produced by another primer pair can be divided into separate amplification reactions. Multiple PCR amplification reactions may be desirable for applications in which it is desirable to analyze all of the candidate target loci (instead of omitting candidate target loci from the analysis due to overlapping target amplicons).

In various embodiments of any of the aspects of the invention, the selection method selects candidate primers and divides them into different pools (e.g., 2, 3, 4, 5, 6, or more different pools). Each pool can be used to simultaneously amplify a large number of target loci (or a subset of target loci) in a single reaction volume. In some embodiments, a graph coloring algorithm is used to divide candidate primers into different pools. If desired, this method can be used to minimize the number of different pools needed to amplify most or all of the target loci.

In some embodiments, most or all of the target loci (such as at least 70, 80, 90, 92, 94, 96, 98, 99, or 100% of the target loci) are amplified by at least 2, 3, 4, 5, 6, or more different pools. In some embodiments, most or all of the bases in the target loci (such as at least 70, 80, 90, 92, 94, 96, 98, 99, or 100% of the bases in the target loci) are amplified by at least 2, 3, 4, 5, 6, or more different pools. In some embodiments, most or all of the bases in the target loci (such as at least 70, 80, 90, 92, 94, 96, 98, 99, or 100% of the bases in the target loci) are amplified by at least 2, 3, 4, 5, 6, or more different primers or primer pairs in different pools. For example, a particular base in a target locus may be amplified by at least 2, 3, 4, 5, 6, or more different primers or primer pairs; wherein each different primer or primer pair is in a different pool. Using different primers or primer pairs to amplify each base allows multiple independent measurements of the base to be made, thereby increasing the accuracy of the method. Dividing the different primers or primer pairs that amplify the same base into different pools prevents interference due to overlapping amplicons being formed by different primers or primer pairs.

In one aspect, the invention features methods of selecting test primers from a library of candidate primers to form 2 or more different primer pools. In various embodiments, the selection involves (i) calculating on a computer a score (such as an undesirability score) for most or all of the possible combinations of two candidate primers from the library, wherein each score (such as an undesirability score) is based at least in part on the likelihood of dimer formation between the two candidate primers; (ii) removing the candidate primer with the highest or worst score (such as an undesirability score) from the library of candidate primers; and (iii) if the candidate primer removed in step (ii) is a member of a primer pair, then removing the other member of the primer pair from the library of candidate primers; and (iv) optionally repeating steps (ii) and (iii), thereby selecting a first pool. In some embodiments, the selection method is performed until the score (such as the undesirability score) for the candidate primer combinations remaining in the library are all equal to or below a minimum threshold for the first pool. In some embodiments, the selection method is performed until the number of candidate primers remaining in the library is reduced to a desired number for the first pool. In some embodiments, after the first pool is selected those primers are removed from further consideration and steps of the method (such as steps (ii) and (iii)) are repeated with the remaining primers to select a second pool. If desired, this method may be repeated to select the desired number of primer pools. In some embodiments, the score is based at least in part on the current coverage of the bases in the target locus (such as the number of other primer pools that have a primer or primer pair that amplifies a particular base in the target locus).

In one aspect, the invention features methods of selecting test primers from a library of candidate primers to form 2 or more different primer pools. In various embodiments, the selection of test primers are selected from a library of candidate primers involves (i) calculating on a computer a score (such as an undesirability score) for most or all of the possible combinations of two candidate primers from the library, wherein each score (such as an undesirability score) is based at least in part on the likelihood of dimer formation between the two candidate primers; (ii) removing from the library of candidate primers the candidate primer that is part of the greatest number of combinations of two candidate primers with a score (such as an undesirability score) above a first minimum threshold; (iii) if the candidate primer removed in step (ii) is a member of a primer pair, then removing the other member of the primer pair from the library of candidate primers; and (iv) optionally repeating steps (ii) and (iii), thereby selecting a first pool. In some embodiments, the selection method is performed until the score (such as the undesirability score) for the candidate primer combinations remaining in the library are all equal to or below the first minimum threshold for the first pool. In some embodiments, the selection method is performed until the number of candidate primers remaining in the library is reduced to a desired number for the first pool. In various embodiments, the selection method involves further reducing the number of candidate primers remaining in the library by decreasing the first minimum threshold used in step (ii) to a lower second minimum threshold and optionally repeating steps (ii) and (iii). In some embodiments, the selection method involves increasing the first minimum threshold used in step (ii) to a higher second minimum threshold and optionally repeating steps (ii) and (iii). In some embodiments, the selection method is performed until the score (such as the undesirability score) for the candidate primer combinations remaining in the library are all equal to or below the second minimum threshold, or until the number of candidate primers remaining in the library is reduced to a desired number for the first pool. In some embodiments, after the first pool is selected those primers are removed from further consideration and steps of the method (such as steps (ii) and (iii)) are repeated with the remaining primers to select a second pool. If desired, this method may be repeated to select the desired number of primer pools. In some embodiments, the score is based at least in part on the current coverage of the bases in the target locus (such as the number of other primer pools that have a primer or primer pair that amplifies a particular base in the target locus).

As discussed above, in some embodiments, a library is formed by starting with a library of candidate primers and removing primers until the primers remaining in the library have the desired characteristics for use as a final primer library.

In other embodiments, candidate primers are added to a library (such as a library starting with no primers) to form a library with the desired characteristics. In some embodiments, the candidate primer or primer pair with the most desirable score (such as the lowest undesirability score) is added to a library (such as a library starting with no primers). The process of adding candidate primers may be repeated as desired. In some embodiments, the selection method is performed until the score (such as the undesirability score) for the candidate primers that have not been added to the library are all above a minimum threshold (such that all the candidate primers that have not been chosen for the library all have worse scores than the threshold). In some embodiments, the selection method is performed until the number of candidate primers that have been added to the library reaches a desired number. The library of selected primers can then be used in any of the methods of the invention.

In some embodiments, most (such as at least 50, 60, 70, 80, 90, 95, 96, 97, 98, 99, or 99.5%) or all of the possible sets of two primer pairs (two primer pairs with a total of 4 primers) are considered for inclusion in a library. In some embodiments, the set of two different candidate primer pair with the most desirable score (such as the lowest undesirability score) is added to a first pool (such as a first pool starting with no primers). In some embodiments, the set of two different candidate primer pairs with the next most desirable score is added to the first pool if it is connected to at most two sets of two different candidate primer pairs in the first pool. By "connected" for purposes of this step is meant that a single candidate primer pair in one set of two different candidate primer pairs is the same as a single candidate primer pair in another set of two different candidate primer pairs. If the set of two different candidate primer pairs is connected to more than two sets, it may be added to a different pool than the first pool. The process of set of two different candidate primer pair to pool(s) may be repeated as desired for the next set of two different candidate primer pairs with the next most desirable score. In some embodiments, the selection method is performed until the score (such as the undesirability score) for the candidate primers that have not been added to the pool(s) are all above a minimum threshold (such that all the candidate primers that have not been chosen for the pool(s) all have worse scores than the threshold). In some embodiments, the selection method is performed until the number of candidate primers that have been added to the pool(s) reaches a desired number. In some embodiments, the method involves storing designs in N number of doubly linked list data structures with the design pairs. N represents the current number of different primer pools. Initially, N=1, since there is only one primer pool. In some embodiments, a second pool is only created if necessary to include the desired target loci or the desired level of coverage of target loci. The library of selected primers can then be used in any of the methods of the invention.

In some embodiments, the minimum threshold, the first minimum threshold, or the second minimum threshold is an interaction score equal to or about 20, 18, 16, 14, 12, 10, 9, 8, 7, 6, 5, 4, 3, 2, or 1 kcal/mol. In some embodiments, the interaction score is calculated as followed as described further herein:

Interaction score=max(−1*ΔG value); or interaction_score=max(−deltaG_2,0.8*(−deltaG_1))

where
deltaG_2=Gibbs energy (energy required to break the dimer) for a dimer that is extensible by PCR on both ends, i.e., the 3' end of each primer anneals to the other primer; and
deltaG_1=Gibbs energy for a dimer that is extensible by PCR on at least one end.

These selection methods minimize the number of candidate primers that have to be removed from the library to achieve the desired reduction in primer dimers. By removing a smaller number of candidate primers from the library, more (or all) of the target loci can be amplified using the resulting primer library.

Multiplexing large numbers of primers imposes considerable constraint on the assays that can be included. Assays that unintentionally interact result in spurious amplification products. The size constraints of miniPCR may result in further constraints. In an embodiment, it is possible to begin with a very large number of potential SNP targets (between about 500 to greater than 1 million) and attempt to design primers to amplify each SNP. Where primers can be designed it is possible to attempt to identify primer pairs likely to form spurious products by evaluating the likelihood of spurious primer duplex formation between all possible pairs of primers using published thermodynamic parameters for DNA duplex formation. Primer interactions may be ranked by a scoring function related to the interaction and primers with the worst interaction scores are eliminated until the number of primers desired is met. In cases where SNPs likely to be heterozygous are most useful, it is possible to also rank the list of assays and select the most heterozygous compatible assays. Experiments have validated that primers with high interaction scores are most likely to form primer dimers. At high multiplexing it is not possible to eliminate all spurious interactions, but it is essential to remove the primers or pairs of primers with the highest interaction scores in silky as they can dominate an entire reaction, greatly limiting amplification from intended targets. We have performed this procedure to create multiplex primer sets of up to and in some cases more than 10,000 primers. The improvement due to this procedure is substantial, enabling amplification of more than 80%, more than 90%, more than 95%, more than 98%, and even more than 99% on target products as determined by sequencing of all PCR products, as compared to 10% from a reaction in which the worst primers were not removed. When combined with a partial semi-nested approach as previously described, more than 90%, and even more than 95% of amplicons may map to the targeted sequences.

Note that there are other methods for determining which PCR probes are likely to form dimers. In an embodiment, analysis of a pool of DNA that has been amplified using a non-optimized set of primers may be sufficient to determine problematic primers. For example, analysis may be done using sequencing, and those dimers which are present in the greatest number are determined to be those most likely to form dimers, and may be removed.

This method has a number of potential application, for example to SNP genotyping, heterozygosity rate determination, copy number measurement, and other targeted sequencing applications. In an embodiment, the method of primer design may be used in combination with the mini-PCR method described elsewhere in this document. In some embodiments, the primer design method may be used as part of a massive multiplexed PCR method.

The use of tags on the primers may reduce amplification and sequencing of primer dimer products. In some embodiments, the primer contains an internal region that forms a loop structure with a tag. In particular embodiments, the primers include a 5' region that is specific for a target locus, an internal region that is not specific for the target locus and forms a loop structure, and a 3' region that is specific for the target locus. In some embodiments, the loop region may lie between two binding regions where the two binding regions are designed to bind to contiguous or neighboring regions of template DNA. In various embodiments, the length of the 3' region is at least 7 nucleotides. In some embodiments, the length of the 3' region is between 7 and 20 nucleotides, such as between 7 to 15 nucleotides, or 7 to 10 nucleotides, inclusive. In various embodiments, the primers include a 5' region that is not specific for a target locus (such as a tag or a universal primer binding site) followed by a region that is specific for a target locus, an internal region that is not specific for the target locus and forms a loop structure, and a 3' region that is specific for the target locus. Tag-primers can be used to shorten necessary target-specific sequences to below 20, below 15, below 12, and even below 10 base pairs. This can be serendipitous with standard primer design when the target sequence is fragmented within the primer binding site or, or it can be designed into the primer design. Advantages of this method include: it increases the number of assays that can be designed for a certain maximal amplicon length, and it shortens the "non-informative" sequencing of primer sequence. It may also be used in combination with internal tagging (see elsewhere in this document).

In an embodiment, the relative amount of nonproductive products in the multiplexed targeted PCR amplification can be reduced by raising the annealing temperature. In cases where one is amplifying libraries with the same tag as the target specific primers, the annealing temperature can be increased in comparison to the genomic DNA as the tags will contribute to the primer binding. In some embodiments we are using considerably lower primer concentrations than previously reported along with using longer annealing times than reported elsewhere. In some embodiments the annealing times may be longer than 3 minutes, longer than 5 minutes, longer than 8 minutes, longer than 10 minutes, longer than 15 minutes, longer than 20 minutes, longer than 30 minutes, longer than 60 minutes, longer than 120 minutes, longer than 240 minutes, longer than 480 minutes, and even longer than 960 minutes. In an embodiment, longer annealing times are used than in previous reports, allowing lower primer concentrations. In various embodiments, longer than normal extension times are used, such as greater than 3, 5, 8, 10, or 15 minutes. In some embodiments, the primer concentrations are as low as 50 nM, 20 nM, 10 nM, 5 nM, 1 nM, and lower than 1 uM. This surprisingly results in robust performance for highly multiplexed reactions, for example 1,000-plex reactions, 2,000-plex reactions, 5,000-plex reactions, 10,000-plex reactions, 20,000-plex reactions, 50,000-plex reactions, and even 100,000-plex reactions. In an embodiment, the amplification uses one, two, three, four or five cycles run with long annealing times, followed by PCR cycles with more usual annealing times with tagged primers.

To select target locations, one may start with a pool of candidate primer pair designs and create a thermodynamic model of potentially adverse interactions between primer pairs, and then use the model to eliminate designs that are incompatible with other the designs in the pool.

In an embodiment, the invention features a method of decreasing the number of target loci (such as loci that may contain a polymorphism or mutation associated with a disease or disorder or an increased risk for a disease or disorder such as cancer) that need to be detected for a diagnosis and/or increasing the disease load that is detected (e.g., increasing the number of polymorphisms or mutations that are detected). In some embodiments, the method includes ranking (such as ranking from highest to lowest) loci by frequency or reoccurrence of a polymorphism or mutation (such as a single nucleotide variation, insertion, or deletion, or any of the other variations described herein) in each locus among subjects with the disease or disorder such as cancer. In some embodiments, PCR primers are designed to some or all of the loci. During selection of PCR primers for a library of primers, primers to loci that have a higher frequency or reoccurrence (higher ranking loci) are favored over those with a lower frequency or reoccurrence (lower ranking loci). In some embodiments, this parameter is included as one of the parameters in the calculation of the scores (such as the undesirability scores) described herein. If desired, primers (such as primers to high ranking loci) that are incompatible with other designs in the library can be included in a different PCR library/pool. In some embodiments, multiple libraries/pools (such as 2, 3, 4, 5 or more) are used in separate PCR reactions to enable amplification of all (or a majority) of the loci represented by all the libraries/pools. In some embodiment, this method is continued until sufficient primers are included in one or more libraries/pools such that the primers, in aggregate, enable the desired disease load to be captured for the disease or disorder (e.g., such as by detection of at least 80, 85, 90, 95, or 99% of the disease load).

In some embodiments, the library of candidate primers includes at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different primers or different primer pairs. In some embodiments, only a relatively small number of candidate primers need to be removed from the library to achieve the desired reduction in primer dimers. In some embodiments, less than 30, 20, 15, 10, 5, or 2% of the candidate primers are removed from the library prior to use of the resulting library for multiplex PCR amplification of target loci. In some embodiments, a relatively large number of candidate primers are removed from the library to achieve the desired characteristics for the resulting library. In some embodiments, at least 20, 30, 40, 50, 60, 70, 80, or 90% of the candidate primers are removed from the library prior to use of the resulting library for multiplex PCR amplification of target loci. In some embodiments, at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different primers or different primer pairs remain in the library (after removal of some candidate primers from the library).

After the selection process, the primers remaining in the library may be used in any of the methods of the invention.

Exemplary Methods for Determining Interaction Scores

Exemplary methods of determining a ΔG value (such as the change in Gibbs free energy for primer dimer formation) or an interaction score that indicates the likelihood of dimer formation between candidate primers are described below. In some embodiments, a thermodynamic Nearest-Neighbors approach is used to calculate the likelihood of dimer formation between any two primers (see, e.g., Rahmann and Grafe (2004), "Mean and variance of the Gibbs free energy of oligonucleotides in the nearest neighbor model under varying conditions" Bioinformatics 20, 2928-2933; Allawi, H. T. & SantaLucia, J., Jr. (1998), "Thermodynamics of Internal C-T Mismatches in DNA", *Nucleic Acids Res.* 26, 2694-2701; Peyret, N., Seneviratne, P. A., Allawi, H. T. & SantaLucia, J., Jr. (1999), "Nearest-Neighbor Thermodynamics and NMR of DNA Sequences with Internal A-A, C-C, G-G, and T-T Mismatches", *Biochemistry* 38, 3468-3477; Allawi, H. T. & SantaLucia, J., Jr. (1998), "Nearest-Neighbor Thermodynamics of Internal A-C Mismatches in DNA: Sequence Dependence and pH Effects", *Biochemistry* 37, 9435-9444; Allawi, H. T. & SantaLucia, J., Jr. (1998), "Nearest Neighbor Thermodynamic Parameters for Internal G-A Mismatches in DNA", *Biochemistry* 37, 2170-2179; and Allawi, H. T. & SantaLucia, J., Jr. (1997), "Thermodynamics and NMR of Internal G-T Mismatches in DNA", *Biochemistry* 36, 10581-10594; MultiPLX 2.1 (Kaplinski L, Andreson R, Puurand T, Remm M. MultiPLX: automatic grouping and evaluation of PCR primers. Bioinformatics. 2005 Apr. 15; 21(8):1701-2, which are each hereby incorporated by reference in its entirety).

In some embodiments, the following steps are performed.

Step 1

Figure 33A:
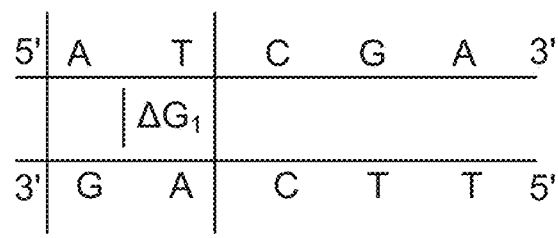
FIGS. 33A-33F: Illustrations of the calculation of an interaction score between primers in a primer library.

For each primer in a set of candidate primers, compare to every other candidate primer in the following way. Implement an ungapped thermodynamic alignment between the two primers, matching the 5' end of the first primer to the 3' end of the second primer. Taking the first two bases (dinucleotide) that align to the other primer and vice versa, determine the ΔH and ΔS values for the dinucleotide in one primer hybridizing to the dinucleotide in the other primer (see the "AT" hybridizing to "GA" in FIG. 33A). ΔH and ΔS values for various combinations of dinucleotides are known and can be determined, for example, using a thermodynamic look up table (such as the Unified NN model parameters according to Allawi and SantaLucia (1997) "Thermodynamics and NMR of internal G-T mismatches in DNA". *Biochemistry*, 36: 10581-10594, which is hereby incorporated by reference in its entirety). Use the ΔH and ΔS values to calculate ΔG for that interaction as follows or as described in any known equation for this.

$$\Delta G = (1000.0 * \Delta H - (\text{temperature} * (\Delta S + 0.368 * (\text{numPhosphates}/2) * \log(\text{saltConcentration}))))/1000.0$$

Figure 33B:
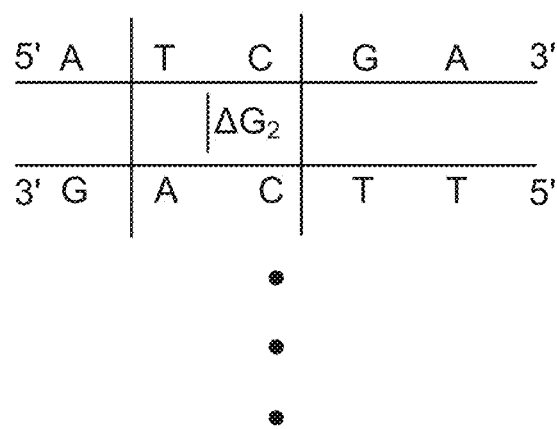

In some embodiments, one or more of the following conditions are assumed for this calculation: temperature: of 60.0° C., primer concentration of 100 nM, or salt concentration of 100 mM. In some embodiments, other conditions are assumed for this calculation, such as the conditions that will be used for multiplex PCR with the pool. Iterate over the remainder of the primer that aligns with the other primer by sliding the bases being observing one base to the right. Continue until ΔG has been calculated for all dinucleotides that align (FIG. 33B). The ΔG for that alignment of the primer pair is the sum of the ΔG values for the various dinucleotides.

Step 2

Figure 33C:
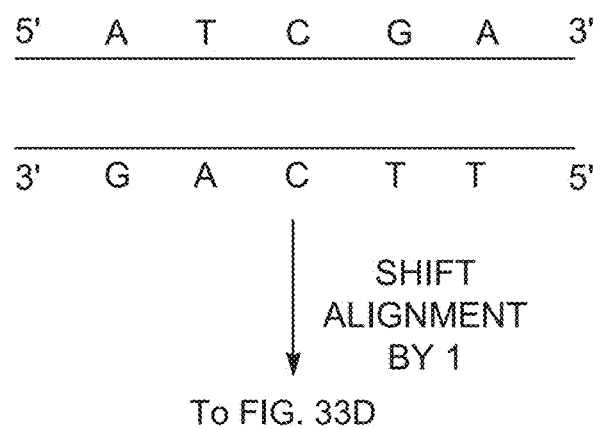
Figure 33D:
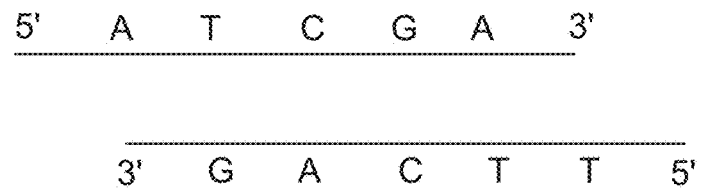

Shift the alignment of the two primers (FIGS. 33C and 33D).

Step 3

Figure 33E:
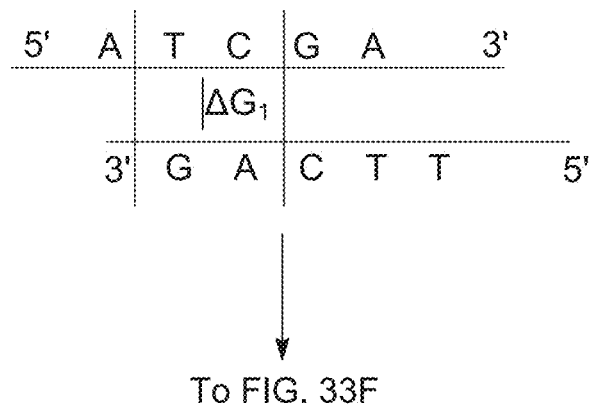
Figure 33F:
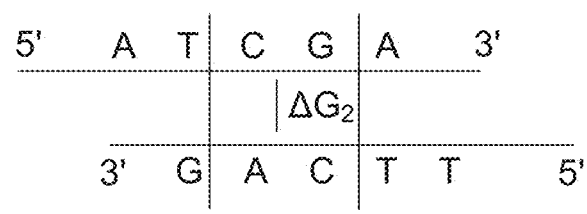

Repeat step 1 again for the new alignment (FIGS. 33E and 33F).

Step 4

After aligning all possible alignments between the two primers, determine the final ΔG value and the interaction score.

In some embodiments, the ΔG value for a combination of primers is the lowest ΔG value (the lowest numerical value, which is indicative of the greatest likelihood of primer dimer formation) out of the ΔG values for all possible alignments between the two primers. For example, if one alignment has a ΔG value of −12 kcal/mol and another alignment has a ΔG value of −2 kcal/mol then −12 kcal/mol (worse value) is used as the ΔG value for that combination of primers.

For algorithms such as the one in Experiment 16 in which it is easiest to rank primers based on assigning the worse combination of primers (those with the greatest likelihood of dimer formation) the highest interaction score, then the interaction score can be calculated as follows.

$$\text{Interaction score} = \max(-1 * \Delta G \text{ value})$$

For example, if one alignment has a ΔG value of −12 kcal/mol and another alignment has a ΔG value of −2 kcal/mol, then 12 kcal/mol is used as the interaction score. In this case, the interaction score with the largest numerical positive number indicates the least desirable combination of primers due to the greatest likelihood of primer dimer formation.

In some embodiments, the interaction score is calculated as follows (this score weights the ΔG values depending on the number of ends that a dimer can be extended by PCR).

$$\text{interaction\_score} = \max(-\text{delta}G\_2, 0.8 * (-\text{delta}G\_1))$$

where deltaG_2=Gibbs energy (energy required to break the dimer) for a dimer that is extensible by PCR on both ends, i.e., the 3' end of each primer anneals to the other primer; and deltaG_1=Gibbs energy for a dimer that is extensible by PCR on at least one end.

In some embodiments, deltaG_2 is determined by performing steps 1-4 above for all the alignments in which a dimer is extensible by PCR on both ends. The deltaG_2 value is the lowest ΔG value (the lowest numerical value, which is indicative of the greatest likelihood of primer dimer formation) for all the alignments in which a dimer is extensible by PCR on both ends.

In some embodiments, deltaG_1 is determined by performing steps 1-4 above for all the alignments in which a dimer is extensible by PCR on at least one end (such as by PCR on one end or by PCR on both ends). The deltaG_1 value is the lowest ΔG value (the lowest numerical value, which is indicative of the greatest likelihood of primer dimer formation) for all the alignments in which a dimer is extensible by PCR on at least one end.

In some embodiments, possible loop structures or gaps in alignment between primers are also considered.

In some embodiments, ΔG values from step 4 for each possible combination of two primers (each possible primer dimer) in a library are all equal to or greater than −20, −18, −16, −14, −12, −10, −9, −8, −7, −6, −5, −4, −3, −2, or −1 kcal/mol. In some embodiments, ΔG values from step 4 for at least 80, 85, 90, 92, 94, 96, 98, 99, or 100% of the primers in the library for possible combinations of that primer with other primers in the library are all equal to or greater than −20, −18, −16, −14, −12, −10, −9, −8, −7, −6, −5, −4, −3, −2, or −1 kcal/mol. In some embodiments, possible combinations of two primers in a library that have positive ΔG values are ignored since these values are indicative of no likelihood to for primer dimers. In some embodiments for the possible combination of two primers in a library that have negative ΔG values, the ΔG values are between −20 and 0 kcal/mol, such as between −15 and 0 kcal/mol, −10 and 0 kcal/mol, −8 and 0 kcal/mol, −7 and 0 kcal/mol, −6 and 0 kcal/mol, −5.5 and 0 kcal/mol, −5 and 0 kcal/mol, −4.5 and 0 kcal/mol, −4 and 0 kcal/mol, −3.5 and 0 kcal/mol, −3 and 0 kcal/mol, −2.5 and 0 kcal/mol, −2 and 0 kcal/mol, or −1.5 and 0 kcal/mol, inclusive.

In some embodiments, the interaction scores from step 4 for each possible combination of two primers in a library are all equal to or less than 20, 18, 16, 14, 12, 10, 9, 8, 7, 6, 5, 4, 3, 2, or 1 kcal/mol. In some embodiments, the interaction scores from step 4 for at least 80, 85, 90, 92, 94, 96, 98, 99, or 100% of the primers in the library for possible combinations of that primer with other primers in the library are all equal to or less than 20, 18, 16, 14, 12, 10, 9, 8, 7, 6, 5, 4, 3, 2, or 1 kcal/mol. In some embodiments, possible combination of two primers in a library that have negative interaction scores are ignored since these values are indicative of no likelihood to for primer dimers. In some embodiments for the possible combination of two primers in a library that have positive interaction scores, the interaction scores are between 20 and 0 kcal/mol, such as between 15 and 0 kcal/mol, 10 and 0 kcal/mol, 8 and 0 kcal/mol, 7 and 0 kcal/mol, 6 and 0 kcal/mol, 5.5 and 0 kcal/mol, 5 and 0 kcal/mol, 4.5 and 0 kcal/mol, 4 and 0 kcal/mol, 3.5 and 0 kcal/mol, 3 and 0 kcal/mol, 2.5 and 0 kcal/mol, 2 and 0 kcal/mol, or 1.5 and 0 kcal/mol, inclusive.

In some embodiments, the score (such as the undesirability score) for candidate primers is based at least in part on the ΔG value or the interaction score that indicates the likelihood of dimer formation between candidate primers as calculated using any of these methods.

Exemplary Primer Libraries

In one aspect, the invention features libraries of primers, such as primers selected from a library of candidate primers using any of the methods of the invention. In some embodiments, the library includes primers that simultaneously hybridize (or are capable of simultaneously hybridizing) to or that simultaneously amplify (or are capable of simultaneously amplifying) at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci in one reaction volume. In various embodiments, the library includes primers that simultaneously amplify (or are capable of simultaneously amplifying) between 1,000 to 2,000; 2,000 to 5,000; 5,000 to 7,500; 7,500 to 10,000; 10,000 to 20,000; 20,000 to 25,000; 25,000 to 30,000; 30,000 to 40,000; 40,000 to 50,000; 50,000 to 75,000; or 75,000 to 100,000 different target loci in one reaction volume, inclusive. In various embodiments, the library includes primers that simultaneously amplify (or are capable of simultaneously amplifying) between 1,000 to 100,000 different target loci in one reaction volume, such as between 1,000 to 50,000; 1,000 to 30,000; 1,000 to 20,000; 1,000 to 10,000; 2,000 to 30,000; 2,000 to 20,000; 2,000 to 10,000; 5,000 to 30,000; 5,000 to 20,000; or 5,000 to 10,000 different target loci, inclusive. In some embodiments, the library includes primers that simultaneously amplify (or are capable of simultaneously amplifying) the target loci in one reaction volume such that less than 60, 40, 30, 20, 10, 5, 4, 3, 2, 1, 0.5, 0.25, 0.1, or 0.5% of the amplified products are primer dimers. The various embodiments, the amount of amplified products that are primer dimers is between 0.5 to 60%, such as between 0.1 to 40%, 0.1 to 20%, 0.25 to 20%, 0.25 to 10%, 0.5 to 20%, 0.5 to 10%, 1 to 20%, or 1 to 10%, inclusive. In some embodiments, the primers simultaneously amplify (or are capable of simultaneously amplifying) the target loci in one reaction volume such that at least 50, 60, 70, 80, 90, 95, 96, 97, 98, 99, or 99.5% of the amplified products are target amplicons. In various embodiments, the amount of amplified products that are target amplicons is between 50 to 99.5%, such as between 60 to 99%, 70 to 98%, 80 to 98%, 90 to 99.5%, or 95 to 99.5%, inclusive. In some embodiments, the primers simultaneously amplify (or are capable of simultaneously amplifying) the target loci in one reaction volume such that at least 50, 60, 70, 80, 90, 95, 96, 97, 98, 99, or 99.5% of the target loci are amplified. In various embodiments, the amount target loci that are amplified is between 50 to 99.5%, such as between 60 to 99%, 70 to 98%, 80 to 99%, 90 to 99.5%, 95 to 99.9%, or 98 to 99.99% inclusive. In some embodiments, at least 50, 60, 70, 80, 90, 95, 96, 97, 98, 99, or 99.5% of the target loci are amplified at least 5, 10, 20, 40, 50, 60, 80, 100, 120, 150, 200, 300, or 400-fold. In some embodiments, the library of primers includes at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 primer pairs, wherein each pair of primers includes a forward test primer and a reverse test primer where each pair of test primers hybridize to a target locus. In some embodiments, the library of primers includes at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 individual primers that each hybridize to a different target locus, wherein the individual primers are not part of primer pairs.

In some embodiments, the library includes primers (such as at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different primers or different primer pairs) that simultaneously amplify (or are capable of simultaneously amplifying) the target loci (such as at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci) in one reaction volume such that one or more of the following: (i) less than 60, 40, 30, 20, 10, 5, 4, 3, 2, 1, 0.5, 0.25, 0.1, or 0.5% of the amplified products are primer dimers, (ii) at least 50, 60, 70, 80, 90, 95, 96, 97, 98, 99, or 99.5% of the amplified products are target amplicons, (iii) at least 50, 60, 70, 80, 90, 95, 96, 97, 98, 99, or 99.5% of the target loci are amplified, (iv) at least 50, 60, 70, 80, 90, 95, 96, 97, 98, 99, or 99.5% of the target loci are amplified at least 5, 10, 20, 40, 50, 60, 80, 100, 120, 150, 200, 300, or 400-fold, (v) at least 60, 70, 80, 90, 95, 96, 97, 98, 99, 99.5, or 100% of the amplified products map to the human genome, or (vi) any combination thereof.

In some embodiments, the library includes at least 1,000 different primers or different primer pairs (such as at least 2,000; 5,000; 7,500; 10,000; 15,000; 19,000; 20,000; 25,000; 27,000; 28,000; 30,000; 40,000; 50,000; 75,000; or 100,000 different primers or different primer pairs) that simultaneously amplify (or are capable of simultaneously amplifying) at least 1,000 different target loci (such as at least 2,000; 5,000; 7,500; 10,000; 15,000; 19,000; 20,000; 25,000; 27,000; 28,000; 30,000; 40,000; 50,000; 75,000; or 100,000 different target loci) in one reaction volume such that one or more of the following: (i) less than 60% of the amplified products are primer dimers and at least 40% of the amplified products are target amplicons, (ii) less than 40% of the amplified products are primer dimers and at least 60% of the amplified products are target amplicons, (iii) less than 20% of the amplified products are primer dimers and at least 80% of the amplified products are target amplicons, (iv) less than 10% of the amplified products are primer dimers and at least 90% of the amplified products are target amplicons, or (v) less than 5% of the amplified products are primer dimers and at least 95% of the amplified products are target amplicons. In some embodiments for the amplification of nucleic acids (such as DNA or RNA) from a single cell (such as a fetal or embryonic cell), the library includes at least 1,000 different primers or different primer pairs (such as at least 2,000; 5,000; 7,500; 10,000; 15,000; 19,000; 20,000; 25,000; 27,000; 28,000; 30,000; 40,000; 50,000; 75,000; or 100,000 different primers or different primer pairs) that simultaneously amplify (or are capable of simultaneously amplifying) at least 1,000 different target loci (such as at least 2,000; 5,000; 7,500; 10,000; 15,000; 19,000; 20,000; 25,000; 27,000; 28,000; 30,000; 40,000; 50,000; 75,000; or 100,000 different target loci) in one reaction volume such that one or more of the following: (i) less than 60% of the amplified products are primer dimers and at least 10% of the amplified products are target amplicons, (ii) less than 40% of the amplified products are primer dimers and at least 10% of the amplified products are target amplicons, (iii) less than 20% of the amplified products are primer dimers and at least 10% of the amplified products are target amplicons, (iv) less than 10% of the amplified products are primer dimers and at least 10% of the amplified products are target amplicons, (v) less than 5% of the amplified products are primer dimers and at least 15% of the amplified products are target amplicons; (vi) less than 60% of the amplified products are primer dimers and at least 20% of the amplified products are target amplicons, (vii) less than 40% of the amplified products are primer dimers and at least 20% of the amplified products are target amplicons, (viii) less than 20% of the amplified products are primer dimers and at least 20% of the amplified products are target amplicons, (ix) less than 10% of the amplified products are primer dimers and at least 20% of the amplified products are target amplicons, (x) less than 5% of the amplified products are primer dimers and at least 20% of the amplified products are target amplicons; (xi) less than 60% of the amplified products are primer dimers and at least 40% of the amplified products are target amplicons, (xii) less than 40% of the amplified products are primer dimers and at least 40% of the amplified products are target amplicons, (xiii) less than 20% of the amplified products are primer dimers and at least 40% of the amplified products are target amplicons, (xiv) less than 10% of the amplified products are primer dimers and at least 40% of the amplified products are target amplicons, (xv) less than 5% of the amplified products are primer dimers and at least 45% of the amplified products are target amplicons; (xvi) less than 40% of the amplified products are primer dimers and at least 60% of the amplified products are target amplicons, (xvii) less than 20% of the amplified products are primer dimers and at least 80% of the amplified products are target amplicons, (xviii) less than 10% of the amplified products are primer dimers and at least 90% of the amplified products are target amplicons, or (xviiii) less than 5% of the amplified products are primer dimers and at least 95% of the amplified products are target amplicons. In some embodiments, at least 50, 60, 70, 80, 90, 95, 96, 97, 98, 99, or 99.5% of the target loci are amplified at least 5, 10, 20, 40, 50, 60, 80, 100, 120, 150, 200, 300, or 400-fold. In some embodiments, one or more of these embodiments (e.g., percent of primer dimers, target amplicons, or amplified target loci) is achieved after greater than or equal to 5, 10, 20, 30, 40, 50, or 60 cycles of PCR are performed. In some embodiments for a library that amplifies human target loci, at least 60, 70, 80, 90, 95, 96, 97, 98, 99, 99.5, or 100% of the amplified products map to the human genome.

In various embodiments, the concentration of each primer is less than 100, 75, 50, 25, 20, 10, 5, 2, 1, 0.5, 0.1, or 0.05 nM, or less than 500, 100, 10, or 1 uM. In various embodiments, the concentration of each primer is between 1 uM to 100 nM, such as between 1 uM to 1 nM, 1 to 75 nM, 1 to 20 nM, 1 to 10 nM, 2 to 50 nM or 5 to 50 nM, inclusive. In some embodiments, the concentration of one or more universal primers is between 0.2 to 3 µM, such as between 0.5 and 2.5 µM, 0.5 to 1 µM, or 1 to 2.5 µM per primer, inclusive, and the concentration of each primer except the universal primer(s) is between 1 uM to 100 nM, such as between 1 uM to 1 nM, 1 to 75 nM, 1 to 20 nM, 1 to 10 nM, 2 to 50 nM or 5 to 50 nM, inclusive. In various embodiments, the GC content of the primers is between 30 to 80%, such as between 20 to 70%, 40 to 70%, or 50 to 60%, inclusive. In some embodiments, the range of GC content of the primers is less than 30, 20, 10, or 5%. In some embodiments, the range of GC content of the primers is between 5 to 30%, such as 5 to 20% or 5 to 10%, inclusive. In some embodiments, there is a high GC content in the 3' end of the primers. In some embodiments, there are at least 2 (such as 3, 4, or 5) guanines or cytosines in the last t bases at the 3' end of the primers. In some embodiments, there are at least 1 (such as 2 or 3) guanines or cytosines in the last 3 bases at the 3' end of the primers. In some embodiments, a maximum of 2 (such as 2, 1, or 0) bases in the last 5 bases at the 3' end of the primers are guanines or cytosines. In some embodiments, a maximum of 1 (such as 1 or 0) base in the last 5 bases at the 3' end of the primers is a guanine or cytosine. In some embodiments, the maximum length of a homopolymer (the same base in a row) in the primers is 12, 10, 8, 6, 5, 4, 3, or 2 consecutive nucleotides. In some embodiments, the melting temperature ($T_m$) of the test primers is between 40 to 80° C., such as 50 to 70° C., 55 to 65° C., 54 to 60.5° C., or 57 to 60.5° C., inclusive. In some embodiments, the $T_m$ is calculated using the Primer3 program (libprimer3 release 2.2.3) using the built-in SantaLucia parameters (the world wide web at primer3.sourceforge.net). In some embodiments, the range of melting temperature of the primers is less than 15, 10, 5, 3, or 1° C. In some embodiments, the range of melting temperature of the primers is between 1 to 15° C., such as between 1 to 10° C., 1 to 5° C., or 1 to 3° C., inclusive. In some embodiments, the range of melting temperatures of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the primers is between 1 to 25° C., such as between 1 to 10° C., 1 to 5° C., 1 to 3° C., 2 to 5° C., 3 to 10° C., or 3 to 5° C., inclusive. In some embodiments, the length of the primers is between 15 to 100 nucleotides, such as between 15 to 75 nucleotides, 15 to 40 nucleotides, 17 to 35 nucleotides, 18 to 30 nucleotides, 20 to 65 nucleotides, inclusive. In some embodiments, the range of the length of the primers is less than 50, 40, 30, 20, 10, or 5 nucleotides. In some embodiments, the range of the length of the primers is between 5 to 50 nucleotides, such as 5 to 40 nucleotides, 5 to 20 nucleotides, or 5 to 10 nucleotides, inclusive. In some embodiments, the length of the target amplicons is between 50 and 100 nucleotides, such as between 60 and 80 nucleotides, or 60 to 75 nucleotides, inclusive. In some embodiments, the length of the target amplicons is between 30 and 400 nucleotides, such as between 30 and 200 nucleotides, or 100 and 400 nucleotides, inclusive. In some embodiments, the length of the target amplicons is at least 100; 200; 300; 400; 500; 600; 700; 800; 900; 1,000; 1,200; 1,500; 2,000; or 3,000 nucleotides. In some embodiments, the length of the target amplicons is between 100 and 1,500 nucleotides, such as between 100 to 1,000; 100 to 500, 500 to 750, or 750 to 1,000 nucleotides, inclusive. Longer amplicons may be desirable, e.g., for applications in which is it desirable to screen for multiple potential mutations in one amplicon, such as carrier screening. In some embodiments, one round of PCR is performed to produce relatively long amplicons (such as at least 250 or 500 nucleotides in length) and then a second round of PCR is performed to produce shorter amplicons (to amplify regions within the amplicons amplified in the first round of PCR, such as regions of less than 200 or 100 nucleotides in length). In some embodiments, the range of the length of the target amplicons is less than 50, 25, 15, 10, or 5 nucleotides. In some embodiments, the range of the length of the target amplicons is between 5 to 50 nucleotides, such as 5 to 25 nucleotides, 5 to 15 nucleotides, or 5 to 10 nucleotides, inclusive. In some embodiments, at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 or all of the target amplicons have a length that falls within the range of the average length of the amplicons ±5% of the average length, average length ±20%, average length ±20%, or average length ±30%, or average length ±50%. In some embodiments, library includes at least at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different primers that each includes a target specific sequence, such as a sequence that binds a target locus but does not substantially bind to other nucleic acids (such as non-target loci) in a sample, e.g., a biological sample, which naturally includes other nucleic acids. In some embodiments, each primer binds and amplifies a target locus by at least 2, 4, 6, 8, 10, 20, 50-fold or more than one or more (or all) other nucleic acids (such as non-target loci) in a sample. In some embodiments, the library includes at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target specific primers (e.g., primers that are specific for a target locus). In some embodiments, part or all of the polynucleotide sequence is a non-random sequence for at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different primers in the library. In some embodiments, library also includes a universal primer, a random primer, a primer with a non-naturally occurring polynucleotide sequence, or a primer with a polynucleotide sequence not naturally found in a human In some embodiments, the universal or random primer has a non-naturally occurring polynucleotide sequence or a polynucleotide sequence not naturally found in a human.

In some embodiments, the composition includes at least one primer (e.g., at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical primers) with a polynucleotide sequence of a human nucleic acid and at least one primer (e.g., at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical primers) with a polynucleotide sequence that is not found in a human (such as a universal primer, a primer that comprises a region or consists entirely of random nucleotides, or a primer with a region such as a tag or barcode of one or more nucleotides that are not found in a human or are not found in nature as part of the polynucleotide sequence of the primer). In some embodiments, at least one primer (e.g., at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical primers) includes a region of one or more nucleotides that is not naturally part of the primer sequence (such as a region added to the 5' end of the target specific sequence in the primer or an internal region added between the 5' and 3' ends of the primer). In some embodiments, the primer is free of the nucleic acids (such as genes) which, in the naturally-occurring genome of the organism from which the nucleic acid of the invention is derived, flank the gene. In some embodiments, the primer has been separated from one or more components that naturally accompany the corresponding sequence in nature (such as in the genome of a human). Typically, each primer is at least 90, 95, 98, 99, 99.9, or 100%, by weight, free from the molecules (such as proteins, nucleic acids, and naturally-occurring organic molecules) that naturally accompany the corresponding sequence in nature (such as in the genome of a human). Purity can be assayed by any appropriate method, e.g., by electrophoresis or HPLC analysis.

In some embodiments, the primers in the library are not immobilized (such as not immobilized to a solid support) or not part of a microarray. In some embodiments, the primers are dissolved in solution (such as dissolved in the liquid phase). In some embodiments, the library comprises a microarray. In some embodiments, the amplified products are detected using an array, such as an array with probes to one or more chromosomes of interest (e.g., chromosome 13, 18, 21, X, Y, or any combination thereof).

In some embodiments, at least one of the primers (such as at least 20, 40, 80, 90, 95, 98, 99, 99.5, or 100% of the primers) in a library are nucleic acid analogs that have a lower likelihood of primer dimerization compared to the naturally-occurring nucleic acids (see, e.g., U.S. Pat. Nos. 7,414,118 and 6,001,611; which are each hereby incorporated by reference in its entirety). Exemplary nucleic acid analogs have a modified pyrimidine nucleobase, or a purine or pyrimidine base that contains an exocyclic amine.

In some embodiments, the primer library includes a small number of primers (such as less than 5, 2, 1, or 0.5% of the primers in the library) that do not have one or more of the properties described herein. In various embodiments, at least 80, 90, 95, 96, 97, 98, 99, 99.5, or 100% of the primers in the library have one or more of the following properties: (i) ΔG values for possible combinations of that primer with other primers in the library are all equal to or greater than −20, −18, −16, −14, −12, −10, −9, −8, −7, −6, −5, −4, −3, −2, or −1 kcal/mol; (ii) ΔG values for the possible combination of that primer with other primers in the library that have negative ΔG are between −20 and 0 kcal/mol, such as between −15 and 0 kcal/mol, −10 and 0 kcal/mol, −8 and 0 kcal/mol, −7 and 0 kcal/mol, −6 and 0 kcal/mol, −5.5 and 0 kcal/mol, −5 and 0 kcal/mol, −4.5 and 0 kcal/mol, −4 and 0 kcal/mol, −3.5 and 0 kcal/mol, −3 and 0 kcal/mol, −2.5 and 0 kcal/mol, −2 and 0 kcal/mol, or −1.5 and 0 kcal/mol, inclusive; (iii) the GC content is between 30 to 80%, such as between 20 to 70%, 40 to 70%, or 50 to 60%, inclusive; (iv) the range of GC content is less than 30, 20, 10, or 5% or the range of GC content of the primers is between 5 to 30%, such as 5 to 20%, or 5 to 10%, inclusive; (v) a maximum of 2 (such as 2, 1, or 0) bases in the last 5 bases at the 3' end of the primers are guanines or cytosines; (vi) the melting temperature ($T_m$) of the primers is between 40 to 80° C., such as 50 to 70° C., 55 to 65° C., 54 to 60.5° C., or 57 to 60.5° C., inclusive; (vii) the range of melting temperature of the primers is less than 15, 10, 5, 3, or 1° C.; (viii) the range of melting temperature of the primers is between 1 to 15° C., such as between 1 to 10° C., 1 to 5° C., 1 to 3° C., 2 to 5° C., 3 to 10° C., or 3 to 5° C., inclusive; (ix) the length of the primers is between 15 to 100 nucleotides, such as between 15 to 75 nucleotides, 15 to 40 nucleotides, 17 to 35 nucleotides, 18 to 30 nucleotides, or 20 to 65 nucleotides, inclusive; (x) the range of the length of the primers is less than 50, 40, 30, 20, 10, or 5 nucleotides; (xi) the range of the length of the primers is between 5 to 50 nucleotides, such as 5 to 40 nucleotides, 5 to 20 nucleotides, or 5 to 10 nucleotides, (xii) the length of the target amplicons is between 50 and 100 nucleotides, such as between 60 and 80 nucleotides, or 60 to 75 nucleotides; (xiii) the length of the target amplicons is between 30 and 400 nucleotides, such as between 30 and 200 nucleotides, or 100 and 400 nucleotides; (xiv) the range of the length of the target amplicons is less than 50, 25, 15, 10, or 5 nucleotides; (xv) the range of the length of the target amplicons is between 5 to 50 nucleotides, such as 5 to 25 nucleotides, 5 to 15 nucleotides, or 5 to 10 nucleotides; (xvi) the maximum length of a homopolymer in the primers is 12, 10, 8, 6, 5, 4, 3, or 2 consecutive nucleotides; (xvii) the concentration of each primer is less than 100, 75, 50, 25, 20, 10, 5, 2, 1, 0.5, 0.1, or 0.05 nM, or less than 500, 100, 10, or 1 uM; (xviii) the concentration of each primer is between 1 uM to 100 nM, such as between 1 uM to 1 nM, 1 to 75 nM, 1 to 20 nM, 1 to 10 nM, 2 to 50 nM, or 5 to 50 nM, inclusive; (xix) at least 80, 90, 92, 94, 96, 98, 99, or 100% of the molecules of that primer are extended to form amplified products; (xx) SNPs (if any) are not in the last 5 nucleotides in the 3' end of the candidate primer; (xxi) the target bases (the bases of interest in a target locus) are near an end (the 3' or 5' end) of the amplicon; (xxii) the region of hybridization is separated from the polymorphic site by a small number of bases, where the small number is selected from the group consisting of 1, 2, 3, 4, 5, 6 to 10, 11 to 15, 16 to 20, 21 to 25, 26 to 30, and 31 to 60; (xxiii) the length of the annealing step is greater than 1, 3, 5, 8, 10, 15, 20, 30, 45, 60, 75, 90, 120, 150, or 180 minutes, (xxiv) the length of the annealing step (per PCR cycle) is between 5 and 180 minutes, such as 5 to 60, 10 to 60, 5 to 30, or 10 to 30 minutes, inclusive, (xxv) the length of the annealing step is greater than 5 minutes (such greater than 10, or 15 minutes), and the concentration of each primer is less than 20 nM, (xxvi) the length of the annealing step is greater than 5 minutes (such greater than 10, or 15 minutes), and the concentration of each primer is between 1 to 20 nM, or 1 to 10 nM, inclusive; (xxvii) the length of the annealing step is greater than 20 minutes (such as greater than 30, 45, 60, or 90 minutes), and the concentration of each primer is less than 1 nM; (xxviii) the annealing temperature is at least 1, 2, 3, 4, 5, 6, 7, 8, 9, 10, 11, 12, 13, or 15° C. greater than the melting temperature (such as the empirically measured or calculated $T_m$) of the primers; (xxix) the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the melting temperature (such as the empirically measured or calculated $T_m$) of the primers; (xxx) the annealing temperature is at least 1, 2, 3, 4, 5, 6, 7, 8, 9, 10, 11, 12, 13, or 15° C. greater than the highest melting temperature of the primers; (xxxi) the annealing temperature is at least 1, 2, 3, 4, 5, 6, 7, 8, 9, 10, 11, 12, 13, or 15° C. greater than the average melting temperature of the primers, (xxxii) the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the average melting temperature of the primers; and (xxviii) any combination thereof. In various embodiments, at least 80, 90, 95, 96, 97, 98, 99, 99.5, or 100% of the primers in the library have one or more of the following properties: (i) ΔG value s for possible combinations of that primer with other primers in the library are all equal to or greater than −20, −18, −16, −14, −12, −10, −9, −8, −7, −6, −5, −4, −3, −2, or −1 kcal/mol; (ii) ΔG values for the possible combination of that primer with other primers in the library that have negative ΔG are between −20 and 0 kcal/mol, such as between −15 and 0 kcal/mol, −10 and 0 kcal/mol, −8 and 0 kcal/mol, −7 and 0 kcal/mol, −6 and 0 kcal/mol, −5.5 and 0 kcal/mol, −5 and 0 kcal/mol, −4.5 and 0 kcal/mol, −4 and 0 kcal/mol, −3.5 and 0 kcal/mol, −3 and 0 kcal/mol, −2.5 and 0 kcal/mol, −2 and 0 kcal/mol, or −1.5 and 0 kcal/mol, inclusive; (iii) the melting temperature ($T_m$) of the primers is between 40 to 80° C., such as 50 to 70° C., 55 to 65° C., 54 to 60.5° C., or 57 to 60.5° C., inclusive; (iv) the range of melting temperature of the primers is less than 15, 10, 5, 3, or 1° C.; (v) the range of melting temperature of the primers is between 1 to 15° C., such as between 1 to 10° C., 1 to 5° C., 1 to 3° C., 2 to 5° C., 3 to 10° C., or 3 to 5° C., inclusive; (vi) the length of the target amplicons is between 50 and 100 nucleotides, such as between 60 and 80 nucleotides, or 60 to 75 nucleotides; (vii) the length of the target amplicons is between 30 and 400 nucleotides, such as between 30 and 200 nucleotides, or 100 and 400 nucleotides; (viii) the range of the length of the target amplicons is less than 50, 25, 15, 10, or 5 nucleotides; (ix) the range of the length of the target amplicons is between 5 to 50 nucleotides, such as 5 to 25 nucleotides, 5 to 15 nucleotides, or 5 to 10 nucleotides; (x) the concentration of each primer is less than 100, 75, 50, 25, 20, 10, 5, 2, 1, 0.5, 0.1, or 0.05 nM, or less than 500, 100, 10, or 1 uM; (xi) the concentration of each primer is between 1 uM to 100 nM, such as between 1 uM to 1 nM, 1 to 75 nM, 1 to 20 nM, 1 to 10 nM, 2 to 50 nM, or 5 to 50 nM, inclusive; (xii) the annealing temperature is at least 1, 2, 3, 4, 5, 6, 7, 8, 9, 10, 11, 12, 13, or 15° C. greater than the melting temperature (such as the empirically measured or calculated Tm) of the primers; (xiii) the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the melting temperature (such as the empirically measured or calculated $T_m$) of the primers; (xiv) the annealing temperature is at least 1, 2, 3, 4, 5, 6, 7, 8, 9, 10, 11, 12, 13, or 15° C. greater than the highest melting temperature of the primers; (xv) the annealing temperature is at least 1, 2, 3, 4, 5, 6, 7, 8, 9, 10, 11, 12, 13, or 15° C. greater than the average melting temperature of the primers, (xvi) the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the average melting temperature of the primers; and (xvii) any combination thereof.

In various embodiments, at least 80, 90, 95, 96, 97, 98, 99, 99.5, or 100% of the primers in the library have one or more of the following properties: (i) ΔG values for possible combinations of that primer with other primers in the library are all equal to or greater than −10 kcal/mol, (ii) the range of melting temperature of the primers is between 1 to 15° C., (iii) the length of the target amplicons is between 50 and 100 nucleotides, (iv) the concentration of each primer is less than 20 nM, (v) the length of the annealing step is greater than 5 minutes (such as greater than 10 minutes), (vi) the length of the annealing step is greater than 5 minutes (such greater than 10 minutes), and the concentration of each primer is less than 20 nM, and (vii) any combination thereof. In various embodiments, at least 80, 90, 95, 96, 97, 98, 99, 99.5, or 100% of the primers in the library have the following properties: (i) ΔG values for possible combinations of that primer with other primers in the library are all equal to or greater than −10 kcal/mol and (ii) the range of melting temperature of the primers is between 1 to 15° C. In various embodiments, at least 80, 90, 95, 96, 97, 98, 99, 99.5, or 100% of the primers in the library have the following properties: (i) the length of the target amplicons is between 50 and 100 nucleotides, and (ii) the concentration of each primer is less than 20 nM. In various embodiments, at least 80, 90, 95, 96, 97, 98, 99, 99.5, or 100% of the primers in the library have the following properties: (i) the length of the target amplicons is between 50 and 100 nucleotides and (ii) the length of the annealing step is greater than 5 minutes (such as greater than 10 minutes). In various embodiments, at least 80, 90, 95, 96, 97, 98, 99, 99.5, or 100% of the primers in the library have the following properties: (i) the length of the target amplicons is between 50 and 100 nucleotides, (ii) the length of the annealing step is greater than 5 minutes (such greater than 10 minutes), and (iii) the concentration of each primer is less than 20 nM, and (vii) any combination thereof.

In various embodiments, at least 80, 90, 95, 96, 97, 98, 99, 99.5, or 100% of the primers in the library have one or more of the following properties: (i) the annealing temperature is at least 5° C. (such as at least 6, 8, or 10° C.) greater than the melting temperature (such as the empirically measured or calculated Tm) of the primers; (ii) the annealing temperature is between 5 and 15° C., inclusive greater than the melting temperature of the primers; (iii) the annealing temperature is at least 5° C. (such as at least 6, 8, or 10° C.) greater than the highest melting temperature of the primers; (iv) the annealing temperature is at least 5° C. (such as at least 6, 8, or 10° C.) greater than the average melting temperature of the primers, (v) the annealing temperature is between 4 and 15° C. inclusive greater than the average melting temperature of the primers; and (vi) any combination thereof. In various embodiments, at least 80, 90, 95, 96, 97, 98, 99, 99.5, or 100% of the primers in the library have one or more of the following properties: (i) the annealing temperature is at least 5° C. (such as at least 6, 8, or 10° C.) greater than the melting temperature (such as the empirically measured or calculated Tm) of the primers and the length of the annealing step is greater than 5 minutes (such greater than 10 minutes); (ii) the annealing temperature is between 5 and 15° C., inclusive greater than the melting temperature of the primers and the length of the annealing 15 step is greater than 5 minutes (such greater than 10 minutes); (iii) the annealing temperature is at least 5° C. (such as at least 6, 8, or 10° C.) greater than the highest melting temperature of the primers and the length of the annealing step is greater than 5 minutes (such greater than 10 minutes); (iv) the annealing temperature is at least 5° C. (such as at least 6, 8, or 10° C.) greater than the average melting temperature of the primers and the length of the annealing step is greater than 5 minutes (such greater than 10 minutes), (v) the annealing temperature is between and 15° C. inclusive greater than the average melting temperature of the primers and the length of the annealing step is greater than 5 minutes (such greater than 10 minutes); and (vii) any combination thereof. In some embodiments, the guanine-cytosine (GC) content of the primers is between 30% and 80%, inclusive; the range of melting temperatures of the primers is less than 5° C.; and the length of the primers is between 15 to 75 nucleotides, inclusive;

In some embodiments, some (such as at least 80, 90, or 95%) or all of the adaptors or primers include one or more linkages between adjacent nucleotides other than a naturally-occurring phosphodiester linkage. Examples of such linkages include phosphoramide, phosphorothioate, and phosphorodithioate linkages. In some embodiments, some (such as at least 80, 90, or 95%) or all of the adaptors or primers include a thiophosphate (such as a monothiophosphate) between the last 3' nucleotide and the second to last 3' nucleotide. In some embodiments, some (such as at least 80, 90, or 95%) or all of the adaptors or primers include a thiophosphate (such as a monothiophosphate) between the last 2, 3, 4, or 5 nucleotides at the 3' end. In some embodiments, some (such as at least 80, 90, or 95%) or all of the adaptors or primers include a thiophosphate (such as a monothiophosphate) between at least 1, 2, 3, 4, or 5 nucleotides out of the last 10 nucleotides at the 3' end. In some embodiments, such primers are less likely to be cleaved or degraded, such primers may be desirable if a polymerase with proof-reading ability is used (to reduce or prevent the polymerase from removing nucleotides from the primers). In some embodiments, any of the embodiments involving primers with at least one linkage other than a naturally-occurring phosphodiester linkage are used with a polymerase having proof-reader activity. In some embodiments, the primers do not contain an enzyme cleavage site (such as a protease cleavage site). In some embodiments, equal to or greater than 1, 10, 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 primers in the library are non-naturally occurring nucleic acids (such nucleic acids with one or more linkages between adjacent nucleotides other than a naturally-occurring phosphodiester linkage).

In some embodiments, the primers have any combination of two or more of the aspects or embodiments disclosed herein.

These primer libraries can be used in any of the methods of the invention.

Exemplary Primers

The primer design methods of the invention have been used to generate several exemplary primer libraries to human target loci. For example, the primer design methods of the invention were used to generate the primer libraries shown in FIG. 34 (SEQ ID NOs. 1-3,600), FIG. 35 (SEQ ID NOs. 3,601-11,658), and FIG. 36 (SEQ ID NOs 11,659-44, 610). Each of these libraries is composed of three primers (one each from pool A, pool B, and pool C in the same row of each figure) per target locus for 1,200; 2,686; or 10,984 different target loci, respectively. The methods of the invention can also be used to generate libraries to non-human target loci.

For an experiment using the 2,686-plex library FIG. 35 (SEQ ID NOs. 3,601-11,658) for multiplex PCR followed by sequencing, the percent of the amplified products that were primer dimers was 11.13%, the median depth of read per target that was amplified was 799.5× coverage, the percent of amplified products that were target amplicons out of the amplified products that were not primer dimers was 93.15% (this is the percent of on target reads when reads for amplified primer dimers are ignored); the number of target loci that were not amplified (failed assay count) was 246; the percent of target loci that were not amplified (failed assay percentage) was 9.16%; the percent of target loci that were amplified was 90.84%; and the total number of reads was 2,522,742. For this primer library, the ΔG values for each possible combination of two primers (each possible primer dimer) in the library are all equal to or greater than −3.86 kcal/mol. This −3.86 kcal/mol value was used as a threshold value to select candidate primer that all had a value equal to or greater than (more desirable than) this value from an initial library of candidate primers.

For an experiment using the 10,984-plex library FIG. 36 (SEQ ID NOs 11,659-44,610). for multiplex PCR followed by sequencing, the percent of the amplified products that were primer dimers was 5.50%, the median depth of read per target that was amplified was 1,286.5× coverage, the percent of amplified products that were target amplicons out of the amplified products that were not primer dimers was 60.16% (this is the percent of on target reads when reads for amplified primer dimers were ignored); the number of target loci that were not amplified (failed assay count) was 3,712; the percent of target loci that were not amplified (failed assay percentage) was 33.79%; the percent of target loci that were amplified was 66.21%; and the total number of reads was 25,372,858.

For an experiment using the 1,200-plex library FIG. 34 (SEQ ID NOs. 1-3,600), for multiplex PCR of a sample of only a single cell followed by sequencing, the percent of the amplified products that were primer dimers was 24.13%. This library has primers to human target loci on chromosome 1, chromosome 21, and the X chromosome. For chromosomes 1 and 21, the median depth of read per target that was amplified was 436× coverage; the percent of target loci that were not amplified (failed assay percentage) was 32.69%; and the percent of target loci that were amplified was 67.31%. The total number of reads was 808,106.

The primer design methods of the invention were also used to generate a library for ~11,000 different target loci (such as amplifying 10,732 different target human loci using 10,732 different primer pairs). For an experiment using this library for multiplex PCR followed by sequencing, the percent of the amplified products that were primer dimers was 14.75%, the median depth of read per target that was amplified was 72.27× coverage, the percent of the amplified products that were target amplicons was 84.32%; the number of target loci that were not amplified (failed assay count) was 118; the percent of target loci that were not amplified (failed assay percentage) was 1.10%; the percent of target loci that were amplified was 98.9%; and the total number of reads was 6,345,782. For this primer library, the ΔG values for each possible combination of two primers (each possible primer dimer) in the library are all equal to or greater than −4.28 kcal/mol. This −4.28 kcal/mol value was used as a threshold value to select candidate primer that all had a value equal to or greater than (more desirable than) this value from an initial library of candidate primers. For the initial candidate primers that were used to select primers for this library, the following interaction cost histogram shows the number of candidate primers for each of the following ranges of ΔG values. This illustrates how the values for the candidate primers compares to the −4.28 kcal/mol threshold value for the final library.

0 to −0.497 kcal/mol: 88357
−0.497 to −0.993 kcal/mol: 30529
−0.993 to −1.49 kcal/mol: 7862
−1.49 to −1.99 kcal/mol: 2639
−1.99 to −2.48 kcal/mol: 1086
−2.48 to −2.98 kcal/mol: 393
−2.98 to −3.48 kcal/mol: 148
−3.48 to −3.97 kcal/mol: 58
−3.97 to −4.47 kcal/mol: 18
−4.47 to −4.97 kcal/mol: 4
−4.97 to −5.46 kcal/mol: 3
−5.46 to −5.96 kcal/mol: 0
−5.96 to −6.46 kcal/mol: 2
−6.46 to −6.95 kcal/mol: 3

The primer design methods of the invention were also used to generate a library for ~14,000 different target loci (such as amplify 13,392 different target human loci with 13,392 different primer pairs). For an experiment using this library for multiplex PCR followed by sequencing, the percent of the amplified products that were primer dimers was 0.56%, the median depth of read per target that was amplified was 69.09× coverage, the percent of the amplified products that were target amplicons was 99.42%; the number of target loci that were not amplified (failed assay count) was 44; the percent of target loci that were not amplified (failed assay percentage) was 0.33%; the percent of target loci that were amplified was 99.67%; and the total number of reads was 7,772,454.

Figure 38:
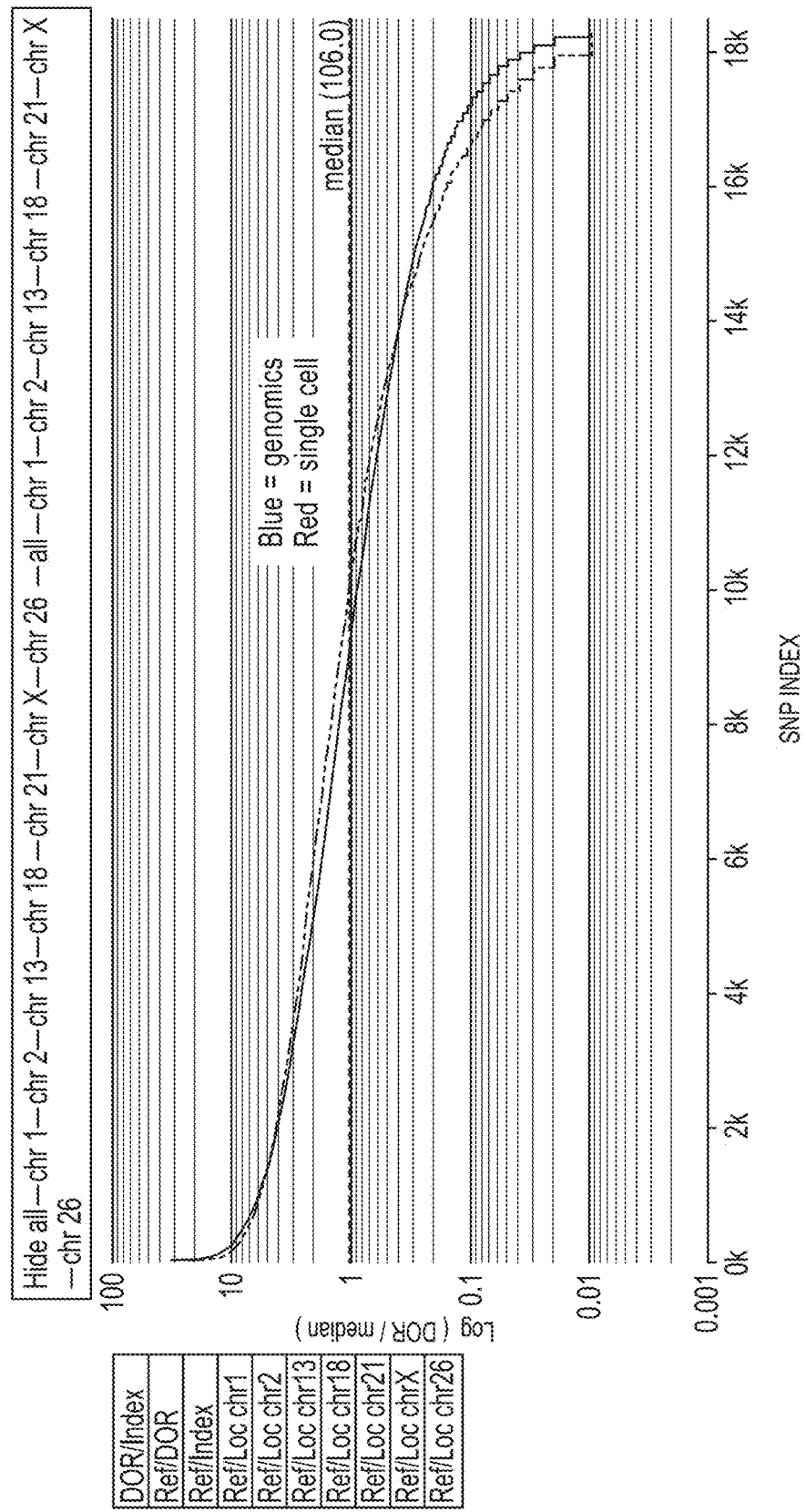
FIG. 38: Overlay of depth of read for a genomic (blue) and a single cell (red) sample for different SNPs.
Figure 40:
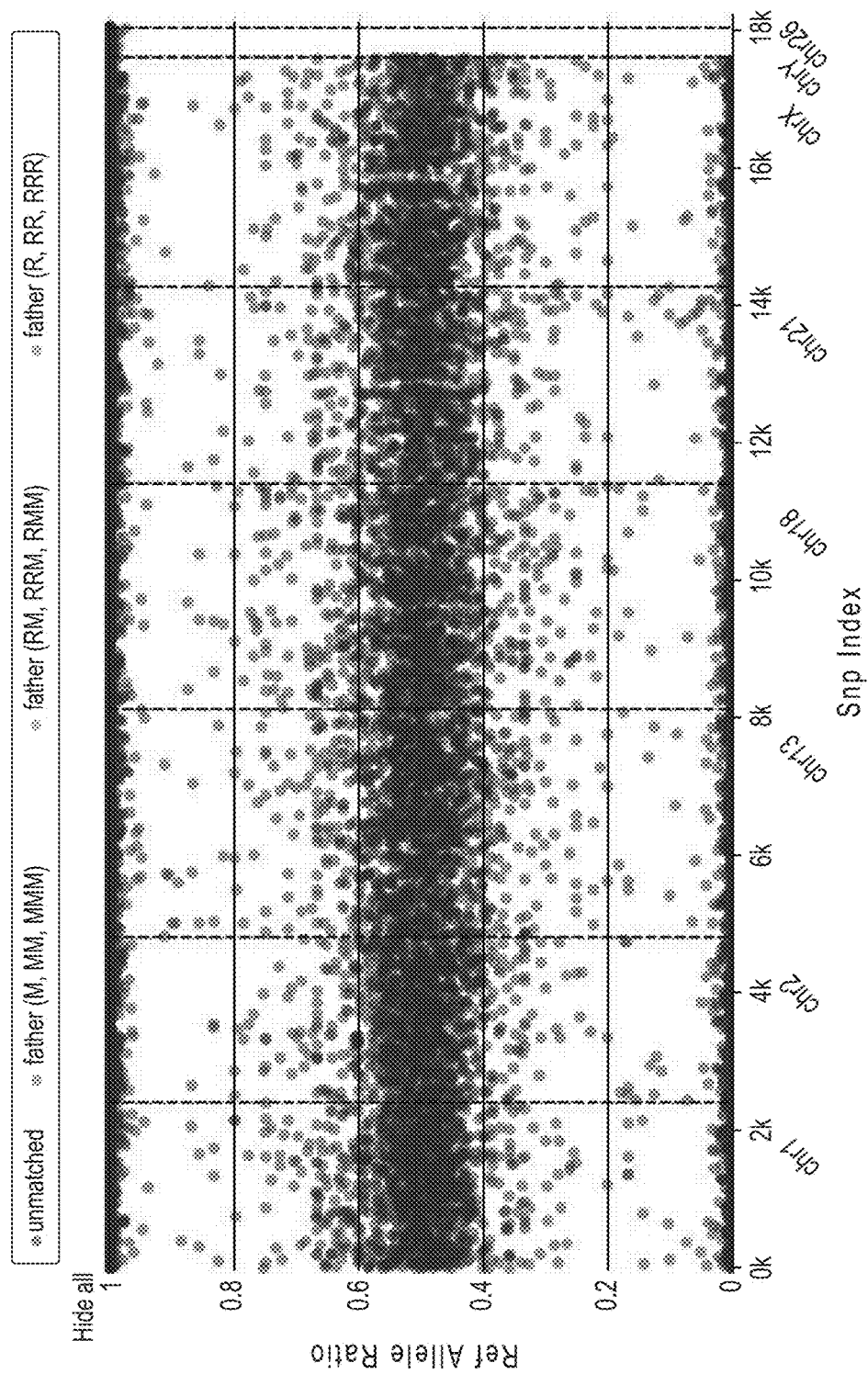
FIG. 40. Graph of reference counts (counts of one allele, such as the "A" allele) divided by total counts for that locus for a single blastocyst cell.

The primer design methods of the invention were also used to generate a library composed of three primers per target locus for 19,488 different target loci. Experiments 15, 18, and 19 describe the use of this library. During the PCR amplification and sequencing of a genomic sample, 99.4-99.7% of the sequencing reads mapped to the genome, of those, 99.99% of the mapped to target loci. For plasma samples with million sequencing reads, typically at least 19,350 of the 19,488 target loci (99.3%) were amplified and sequenced. For another experiment, the percent of the amplified products that were primer dimers was 1.62%, the median depth of read per target that was amplified was 30× coverage; the percent of the amplified products that were target amplicons was 98.15%; the number of target loci that were not amplified (failed assay count) was 736; the percent of target loci that were not amplified (failed assay percentage) was 0.56%; the percent of target loci that were amplified was 99.44%; and the total number of reads was 6,476,975. For this 19,488-plex library, FIG. 37 is a table of the percentage of reads that map to target loci for genomic DNA samples and for samples of a single cell from a cell line for both mother and child samples using this primer library. There was variability in the single cell data which may have resulted from some dead cells being selected, which may have had most of the DNA leaked out. FIG. 38 is an overlay of depth of read for genomic (blue) and a single cell (red) sample for different SNPs. FIG. 39 is a table of the percentage of reads that map to target loci for blastoceol fluid and for a single blastocyst cell. The blastoceol fluid produced no mapped reads, possibly due to no DNA being detected. For a single blastocyst, 50-80% of the reads mapped to target loci. FIG. 40 is a graph of reference counts (counts of one allele, such as the "A" allele) divided by total counts for that locus for a single blastocyst cell. For this primer library, the ΔG values for each possible combination of two primers (each possible primer dimer) in the library are all equal to or greater than −3.86 kcal/mol. This −3.86 kcal/mol value was used as a threshold value to select candidate primer that all had a value equal to or greater than (more desirable than) this value from an initial library of candidate primers.

The primer design methods of the invention were used to generate a library for ~28,000 different target loci (such as amplifying 27,744 different loci with 27,744 different primer pairs). For multiplex PCR and sequencing of genomic DNA samples, 99% of the sequencing reads mapped to target loci. The number of different target human loci that were amplified was 23,776.

For an experiment using this library, the percent of the amplified products that were primer dimers was 0.63%, the median depth of read per target that was amplified was 20× coverage, the percent of the amplified products that were target amplicons was 99.33%; the number of target loci that were not amplified (failed assay count) was 3,968; the percent of target loci that were not amplified (failed assay percentage) was 14.29%; the percent of target loci that were amplified was 85.71%; and the total number of reads was 4,456,636. For a single cell from a cell line, between 2 and 8% of the reads mapped to target loci.

The primer design methods of the invention were used to generate a library for ~9,600 different target loci. As described in Experiment 10, 7.6 million (97%) of reads mapped to the genome, and 6.3 million (80%) of the reads mapped to the targeted SNPs. The average depth of read was 751, and the median depth of read was 396. As described in Experiment 9, another experiment produced 3.7 million reads mapping to the genome (94%), and of those, 2.9 million reads (74%) mapped to targeted SNPs with an average depth of read of 344 and a median depth of read of 255.

The primer design methods of the invention were used to generate a library for ~2,400 different target loci. As described in Experiment 12, when four portions were each amplified with ~2,400 primers, 4.5 million reads mapped to targeted SNPs, the average depth of read was 535 and the median depth of read was 412.

If desired, any of the results may be improved by increasing the number of cells or the amount of nucleic acid template used for the analysis or by optimizing the conditions. For example, if results from single cell samples are not as good as desired for a particular application, a sample with more cells or more nucleic acids may be used instead (such as to decrease the percentage of primer dimers, increase the percentage of target amplicons, or increase the percentage of target loci that are amplified). Samples with more nucleic acids have more template molecules for the primers to bind (instead of primers binding each other and forming primer dimers).

These primer libraries can be used in any of the PCR methods of the invention. In some embodiments, primers from one of the primer pools in FIG. 34, 35, or 36 (either pool A, pool B, or pool C) are used in combination with a universal primer to amplify the target loci. In some embodiments, multiple rounds of PCR are performed in which each round of PCR uses primers from one of the primer pools of FIG. 34, 35, or 36 and a universal primer. In some embodiments, primer from two of the primer pools (such as primers from pools C and B or primers from pools A and C) are used to amplify the target loci. In some embodiments, multiple rounds of PCR are performed. In some embodiments, primers from pools C and B are used for the first round of PCR and then primers from pools A and C are used for the second of PCR. In some embodiments, primers from pools C and B are used for the first round of PCR and then primers from pools A and B are used for the second of PCR. In some embodiments, at least 60, 70, 80, 90, 95, or 100% of the primers from one or more of the primer pools in FIG. 34, 35, or 36 (e.g., pool A, pool B, and/or pool C) are used for the PCR 5 amplification. In some embodiments, primers from FIG. 34, 35, or 36 are combined with other primers that are not included in FIG. 34, 35, or 36.

In one aspect, the invention features one or more primers (e.g., at least 10; 20; 50; 75; 100; 300; 500; 750; 1,000; 2,000; 5,000; 7,500; 10,000; 15,000; 20,000; 25,000; 30,000; 40,000; or 50,000 different primers) with at least 60, 70, 80, 90, 95, 96, 97, 98, 99, 99.5, or 100% identity to the corresponding region (e.g., a region of at least 10, 20, 30, 40, 50 or more contiguous nucleotides) of a primer in pool A, pool B, and/or pool C in FIG. 34, 35, or 36 (SEQ ID NOs 1-44,610). In one aspect, the invention features one or more primers (e.g., at least 10; 20; 50; 75; 100; 300; 500; 750; 1,000; 2,000; 5,000; 7,500; 10,000; 15,000; 20,000; 25,000; 30,000; 40,000; or 50,000 different primers) with at least 60, 70, 80, 90, 95, 96, 97, 98, 99, 99.5, or 100% identity over the entire length of a primer in pool A, pool B, and/or pool C in FIG. 34, 35, or 36. If desired, the primers in FIG. 34, 35, or 36 can be modified by the insertion, deletion, or substitution of one or more nucleotides (e.g., at least 1, 2, 3, 4, 5, 6, 8, 20, or more nucleotides). In some embodiments, a region that is not specific for a target locus (such as a tag, bar code, or universal binding site) is added to one or more primers in FIG. 34, 35, or 36. In various embodiments, the nonspecific region is added to the 5' end of the primer, to the 3' end of the primer, or to an internal region of the primer. In some embodiments, the primers are fragments (such as fragments of at least 10, 20, 30, 40, 50 or more contiguous nucleotides that are less than full-length) of primers in FIG. 34, 35, or 36.

In some embodiments, the invention provides a library of primers that includes at least 10; 20; 50; 75; 100; 300; 500; 750; 1,000; 2,000; 5,000; 7,500; 10,000; 15,000; 20,000; 25,000; 30,000; 40,000; or 50,000 different primers that comprise the polynucleotide sequence of a primer in pool A, pool B, and/or pool C in FIG. 34, 35, or 36. In some embodiments, the invention provides a library of primers that includes at least 10; 20; 50; 75; 100; 300; 500; 750; 1,000; 2,000; 5,000; 7,500; 10,000; 15,000; 20,000; 25,000; 30,000; 40,000; or 50,000 different primers or all of the primer from pool A, pool B, and/or pool C in one of FIG. 34, 35, or 36. In some embodiment, some or all of the primers in two or three of the primer libraries of FIG. 34, 35, or 36 are combined.

Percent identity in reference to nucleic acid sequences refers to the degree of sequence identity between nucleic acid sequences. Percent identity can be determined in various ways that are within the skill in the art, for instance, using publicly available computer software with the default parameters such as Smith Waterman Alignment (Smith and Waterman J. Mol. Biol. 147:195-7, 1981); "BestFit" (Smith and Waterman, Advances in Applied Mathematics, 482-489, 1981); Basic Local Alignment Search Tool (BLAST, Altschul, S. F., W. Gish, et al., J. Mol. Biol. 215: 403-410, 1990; available through the U.S. government's National Center for Biotechnology Information web site at the world wide web at ncbi.nlm.nih.gov), BLAST-2, BLAST-N, WU-BLAST, WU-BLAST-2, ENTREZ (available through the National Center for Biotechnology Information), CLUSTALW, CLUSTAL Omega, or Megalign (DNASTAR, Inc. Madison, Wis.) software. In addition, those skilled in the art can determine appropriate parameters for measuring alignment, including any algorithms needed to achieve maximal alignment over the length of the sequences being compared. In general, the length of comparison will generally be at least 20, 30, 40, 45, 50, or more nucleotides.

In some embodiments, percent identity is calculated by determining the number of matched positions in aligned nucleic acid sequences, dividing the number of matched positions by the total number of aligned nucleotides, and multiplying by 100. A matched position refers to a position in which identical nucleotides occur at the same position in aligned nucleic acid sequences. The percent identity over a particular length is determined by counting the number of matched positions over that length and dividing that number by the length followed by multiplying the resulting value by 100. For example, if (i) a 500-nucleotide nucleic acid target sequence is compared to a subject nucleic acid sequence, (ii) an alignment program presents 200 nucleotides from the target sequence aligned with a region of the subject sequence where the first and last nucleotides of that 200-nucleotide region are matches, and (iii) the number of matches over those 200 aligned nucleotides is 180, then the 500-nucleotide nucleic acid target sequence contains a length of 200 and a sequence identity over that length of 90% (i.e., 180, 200×100=90).

In one aspect, the invention features one or more primers (e.g., at least 10; 20; 50; 75; 100; 300; 500; 750; 1,000; 2,000; 5,000; 7,500; 10,000; 15,000; 20,000; 25,000; 30,000; 40,000; or 50,000 different primers) that comprise a polynucleotide sequence that hybridizes to the complement of a primer in pool A, pool B, and/or pool C in FIG. 34, 35, or 36 under very high stringency hybridization conditions, high stringency hybridization conditions, or low stringency hybridization conditions. In some embodiments, one or more primers (e.g., at least 10; 20; 50; 75; 100; 300; 500; 750; 1,000; 2,000; 5,000; 7,500; 10,000; 15,000; 20,000; 25,000; 30,000; 40,000; or 50,000 different primers) hybridize to the complement of a primer in pool A, pool B, and/or pool C in FIG. 34, 35, or 36 under very high stringency hybridization conditions, high stringency hybridization conditions, or low stringency hybridization conditions. Hybridization conditions resulting in a particular degree of stringency will vary depending upon the nature of the hybridization method and the composition and length of the hybridizing nucleic acid sequences. Generally, the temperature of hybridization and the ionic strength (such as the Na$^+$ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11); Nucleic Acid Hybridization, A Practical Approach, Ed. Hames, B. D. and Higgins, S. J., IRL Press, 1985; Ausubel et al. Current Protocols in Molecular Biology, Wiley, New York 1994; and U.S. Pat. No. 8,357,488, filed May 16, 2008. In some embodiments, very high stringency hybridization conditions includes an overnight incubation at 42° C. in a solution comprising 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C. The following is an exemplary set of hybridization conditions and is not limiting:

Very High Stringency (Detects Sequences that Share at Least 90% Identity)
  a) Hybridization: 5×SSC at 65° C. for 16 hours
  b) Wash twice: 2×SSC at room temperature for 15 minutes each
  c) Wash twice: 0.5×SSC at 65° C. for 20 minutes each High Stringency (Detects Sequences that Share at Least 80% Identity)
  a) Hybridization: 5×-6×SSC at 65° C.-70° C. for 16-20 hours
  b) Wash twice: 2×SSC at room temperature for 5-20 minutes each
  c) Wash twice: 1×SSC at 55° C.-70° C. for 30 minutes each Low Stringency (Detects Sequences that Share at Least 50% Identity)
  a) Hybridization: 6×SSC at room temperature to 55° C. for 16-20 hours
  b) Wash at least twice: 2×-3×SSC at room temperature to 55° C. for 20-30 minutes each These primers can be used in any of the primer libraries or methods of the invention. In some embodiments, the library of primers consists essentially of, or consists of primers from any one of FIGS. 34-36.

Exemplary Primer Libraries for Detection of Recombination

In some embodiments, primers in the primer library are designed to determine whether or not recombination occurred at one or more known recombination hotspots (such as crossovers between homologous human chromosomes). Knowing what crossovers occurred between chromosomes allows more accurate phased genetic data to be determined for an individual. Recombination hotspots are local regions of chromosomes in which recombination events tend to be concentrated. Often they are flanked by "coldspots," regions of lower than average frequency of recombination. Recombination hotspots tend to share a similar morphology and are approximately 1 to 2 kb in length. The hotspot distribution is positively correlated with GC content and repetitive element distribution. A partially degenerated 13-mer motif CCNCCNTNNCCNC plays a role in some hotspot activity. It has been shown that the zinc finger protein called PRDM9 binds to this motif and initiates recombination at its location. The average distance between the centers of recombination hot spots is reported to be ~80 kb. In some embodiments, the distance between the centers of recombination hot spots ranges between ~3 kb to ~100 kb. Public databases include a large number of known human recombination hotspots, such as the HUMHOT and International HapMap Project databases (see, for example, Nishant et al., "HUMHOT: a database of human meiotic recombination hot spots," Nucleic Acids Research, 34: D25-D28, 2006, Database issue; Mackiewicz et al., "Distribution of Recombination Hotspots in the Human Genome—A Comparison of Computer Simulations with Real Data" PLoS ONE 8(6): e65272, doi:10.1371/journal.pone. 0065272; and the world wide web at hapmap.ncbi.nlm.nih.gov/downloads/index.html.en, which are each hereby incorporated by reference in its entirety).

In some embodiments, primers in the primer library are clustered at or near recombination hotspots (such as known human recombination hotspots). In some embodiments, the corresponding amplicons are used to determine the sequence within or near a recombination hotspot to determine whether or not recombination occurred at that particular hotspot (such as whether the sequence of the amplicon is the sequence expected if a recombination had occurred or the sequence expected if a recombination had not occurred). In some embodiments, primers are designed to amplify part or all of a recombination hotspot (and optionally sequence flanking a recombination hotspot). In some embodiments, long read sequencing (such as sequencing using the Molecular Technology developed by Illumina to sequence up to ~10 kb) or paired end sequencing is used to sequence part or all of a recombination hotspot. Knowledge of whether or not a recombination event occurred can be used to determine which haplotype blocks flank the hotspot. If desired, the presence of particular haplotype blocks can be confirmed using primers specific to regions within the haplotype blocks. In some embodiments, it is assumed there are no crossovers between known recombination hotspots. In some embodiments, primers in the primer library are clustered at or near the ends of chromosomes. For example, such primers can be used to determine whether or not a particular arm or section at the end of a chromosome is present. In some embodiments, primers in the primer library are clustered at or near recombination hotspots and at or near the ends of chromosomes.

In some embodiments, the primer library includes one or more primers (such as at least 5; 10; 50; 100; 200; 500; 750; 1,000; 2,000; 5,000; 7,500; 10,000; 20,000; 25,000; 30,000; 40,000; or 50,000 different primers or different primer pairs) that are specific for a recombination hotspot (such as a known human recombination hotspot) and/or are specific for a region near a recombination hotspot (such as within 10, 8, 5, 3, 2, 1, or 0.5 kb of the 5' or 3' end of a recombination hotspot). In some embodiments, at least 1, 5, 10, 20, 40, 60, 80, 100, or 150 different primer (or primer pairs) are specific for the same recombination hotspot, or are specific for the same recombination hotspot or a region near the recombination hotspot. In some embodiments, at least 1, 5, 10, 20, 40, 60, 80, 100, or 150 different primer (or primer pairs) are specific for a region between recombination hotspots (such as a region unlikely to have undergone recombination); these primers can be used to confirm the presence of haplotype blocks (such as those that would be expected depending on whether or not recombination has occurred). In some embodiments, at least 10, 20, 30, 40, 50, 60, 70, 80, or 90% of the primers in the primer library are specific for a recombination hotspot and/or are specific for a region near a recombination hotspot (such as within 10, 8, 5, 3, 2, 1, or 0.5 kb of the 5' or 3' end of the recombination hotspot). In some embodiments, the primer library is used to determine whether or not recombination has occurred at greater than or equal to 5; 10; 50; 100; 200; 500; 750; 1,000; 2,000; 5,000; 7,500; 10,000; 20,000; 25,000; 30,000; 40,000; or 50,000 different recombination hotspots (such as known human recombination hotspots). In some embodiments, the regions targeted by primers to a recombination hotspot or nearby region are approximately evenly spread out along that portion of the genome. In some embodiments, at least 1, 5, 10, 20, 40, 60, 80, 100, or 150 different primer (or primer pairs) are specific for the a region at or near the end of a chromosome (such as a region within 20, 10, 5, 1, 0.5, 0.1, 0.01, or 0.001 mb from the end of a chromosome). In some embodiments, at least 10, 20, 30, 40, 50, 60, 70, 80, or 90% of the primers in the primer library are specific for the a region at or near the end of a chromosome (such as a region within 20, 10, 5, 1, 0.5, 0.1, 0.01, or 0.001 mb from the end of a chromosome). In some embodiments, at least 1, 5, 10, 20, 40, 60, 80, 100, or 150 different primer (or primer pairs) are specific for a region within a potential microdeletion in a chromosome. In some embodiments, at least 10, 20, 30, 40, 50, 60, 70, 80, or 90% of the primers in the primer library are specific for a region within a potential microdeletion in a chromosome. In some embodiments, at least 10, 20, 30, 40, 50, 60, 70, 80, or 90% of the primers in the primer library are specific for a recombination hotspot, a region near a recombination hotspot, a region at or near the end of a chromosome, or a region within a potential microdeletion in a chromosome. In some embodiments, the primers have one or more of the properties described herein. Other embodiments are disclosed in U.S. Ser. No. 61/987,407, filed May 1, 2014 and 62/066,514, filed Oct. 21, 2014.

Exemplary Primer Kits

In one aspect, the invention features a kit (such as kits for amplifying target loci in a nucleic acid sample) the includes any of the primer libraries of the invention. In some embodiments, a kit may be formulated that comprises a plurality of primers designed to achieve the methods described in this disclosure. The primers may be outer forward and reverse primers, inner forward and reverse primers as disclosed herein, they could be primers that have been designed to have low binding affinity to other primers in the kit as disclosed in the section on primer design, they could be hybrid capture probes or pre-circularized probes as described in the relevant sections, or some combination thereof. In an embodiment, a kit may be formulated for determining a ploidy status of a target chromosome in a gestating fetus designed to be used with the methods disclosed herein, the kit comprising a plurality of inner forward primers and optionally the plurality of inner reverse primers, and optionally outer forward primers and outer reverse primers, where each of the primers is designed to hybridize to the region of DNA immediately upstream and/or downstream from one of the target sites (e.g., polymorphic sites) on the target chromosome, and optionally additional chromosomes. In an embodiment, the primer kit may be used in combination with the diagnostic box described elsewhere in this document. In some embodiments, the kit includes instructions for using the library to amplify the target loci. In some embodiments, the kit consists essentially of, or consists of primers (or of primers and instructions for using the primers).

Exemplary Amplicons

In one aspect, the invention provides a composition comprising at least 100 different amplicons (e.g., at least 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical amplicons) in solution in one reaction volume. In some embodiments, the amplicons are produced from the simultaneous PCR amplification of at least 100 different target loci (e.g., at least 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical target loci) using at least 100 different primers or primer pairs (e.g., at least 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical primers or primer pairs) in one reaction volume. In some embodiments, (i) less than 60% of the amplified products are primer dimers and at least 40% of the amplified products are target amplicons, (ii) less than 40% of the amplified products are primer dimers and at least 60% of the amplified products are target amplicons, (iii) less than 20% of the amplified products are primer dimers and at least 80% of the amplified products are target amplicons, (iv) less than 10% of the amplified products are primer dimers and at least 90% of the amplified products are target amplicons, or (v) less than 5% of the amplified products are primer dimers and at least 95% of the amplified products are target amplicons. In some embodiments, the length of the target amplicons is between 50 and 100 nucleotides, such as between 60 and 80 nucleotides, or 60 to 75 nucleotides, inclusive. In some embodiments, the range of the length of the target amplicons is less than 50, 25, 15, 10, or 5 nucleotides. In some embodiments, the range of the length of the target amplicons is between 5 to 50 nucleotides, such as 5 to 25 nucleotides, 5 to 15 nucleotides, or 5 to 10 nucleotides, inclusive. In some embodiments, the composition includes at least 1,000 different amplicons in solution in one reaction volume; wherein the amplicons are produced from the simultaneous PCR amplification of at least 1,000 different target human loci using at least 1,000 different primers in one reaction volume; wherein (i) less than 20% of the amplicons are primer dimers, and (ii) at least 80% of the amplicons comprise one of the target human loci and are between 50 and 100 nucleotides in length, inclusive. In some embodiments, the composition consists essentially of, or consists of one or more of the following: amplicons, primers (such as any of the primers disclosed herein), free nucleotide(s), non-human or non-naturally occurring enzyme(s), buffer(s), or any combination thereof.

In some embodiments, a large percentage or substantially all of the primers used for the multiplex PCR method are consumed during the PCR reaction or are removed from the reaction volume after the PCR amplification. In some embodiments, at least 80, 90, 92, 94, 96, 98, 99, or 100% of the primer molecules are extended to form amplified products. In some embodiments, for at least 80, 90, 92, 94, 96, 98, 99, or 100% of target loci, at least 80, 90, 92, 94, 96, 98, 99, or 100% of the primer molecules to that target loci are extended to form amplified products. In some embodiments, multiple cycles are performed until all or substantially all of the primers are consumed. If desired, a higher percentage of the primers can be consumed by decreasing the initial primer concentration and/or increasing the number of PCR cycles that are performed. In some embodiments, at least 80, 90, 95, 96, 97, 98, 99, or 100% of the nucleic acids in the composition are amplicons (instead of unextended dimers).

In one aspect, the invention provides a composition comprising at least 100 different primers or primer pairs (e.g., at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical primers or primer pairs) and at least 100 different amplicons (e.g., at least 300, 500, 750; 1,000; 2,000; 5,000; 7,500; 10,000; 15,000; 19,000; 20,000; 25,000; 27,000; 28,000; 30,000; 40,000; 50,000; 75,000; or 100,000 non-identical amplicons) in solution in one reaction volume. In some embodiments, the amplicons are produced from the simultaneous PCR amplification of at least 100 different target loci (e.g., at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical target loci) using the primers or primer pairs in one reaction volume. In some embodiments, (i) less than 60% of the amplified products are primer dimers and at least 40% of the amplified products are target amplicons, (ii) less than 40% of the amplified products are primer dimers and at least 60% of the amplified products are target amplicons, (iii) less than 20% of the amplified products are primer dimers and at least 80% of the amplified products are target amplicons, (iv) less than 10% of the amplified products are primer dimers and at least 90% of the amplified products are target amplicons, or (v) less than 5% of the amplified products are primer dimers and at least 95% of the amplified products are target amplicons. In some embodiments, the length of the target amplicons is between 50 and 100 nucleotides, such as between 60 and 80 nucleotides, or 60 to 75 nucleotides, inclusive. In some embodiments, the range of the length of the target amplicons is less than 50, 25, 15, 10, or 5 nucleotides. In some embodiments, the range of the length of the target amplicons is between 5 to 50 nucleotides, such as 5 to 25 nucleotides, 5 to 15 nucleotides, or 5 to 10 nucleotides, inclusive. In some embodiments, the composition comprising at least 1,000 different primers and at least 1,000 different amplicons in solution in one reaction volume; wherein the amplicons are produced from the simultaneous PCR amplification of at least 1,000 different target human loci with the primers in one reaction volume; wherein (i) less than 20% of the amplicons are primer dimers, and (ii) at least 80% of the amplicons comprise one of the target loci and are between 50 and 100 nucleotides in length, inclusive. In some embodiments, the composition consists essentially of, or consists of one or more of the following: amplicons, primers (such as any of the primers disclosed herein), free nucleotide(s), non-human or non-naturally occurring enzyme(s), buffer(s), or any combination thereof.

In some embodiments, the amplification of different target loci is substantially uniform. In some embodiments, target loci (such as nonpolymorphic target loci or polymorphic target loci that are amplified regardless of what allele is present at the polymorphic site) that were present in the same amount (or substantially the same amount) in the initial unamplified sample are also present in substantially the same amount in the PCR-amplified products. In some embodiments, for at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different targets, the target loci that is amplified the most out of these targets (which can be all of the targets or a subset of the targets for a library) is amplified less than 2,000; 1,500; 1,000; 500, 400, 300, 200, 100%, 50, 20, 10, 5, or 2% more than the target loci that is amplified the least out of these targets. In some embodiments, for at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target amplicons, the target amplicon in greatest abundance out of these target amplicons (which can be all of the target amplicons or a subset of the target amplicons produced by a library) is present in an amount that is less than 2,000; 1,500; 1,000; 500, 400, 300, 200, 100%, 50, 20, 10, 5, or 2% more than the target amplicon in least abundance out of these target amplicons. In some embodiments, at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target amplicons are present in an amount that is at least 5, 10, 15, 20, 40, 50, 60, 70, 80, or 90% of the amount of the target amplicon in greatest abundance. In some embodiments, for at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different amplicons that are produced by multiplex PCR and then sequenced, at least 80, 90, 95, 96, 97, 98, 99, or 99.5% of the target amplicons produce a number of sequencing reads within 20, 30, 50, or 80% above or below the mean number of sequences for target amplicons. If desired, the uniformity can be increased by using primers with more similar primer lengths, target amplicon lengths, GC contents, melting temperatures, or any combination thereof. In some embodiments, the uniformity can be increased by using TMAC in the reaction volume during amplification. In some embodiments, having most or all the primers consumed in the PCR reaction increases the uniformity of amplification.

If desired, the uniformity in DOR can be measured using standard methods such as depth of read slope (DOR slope), normalized median depth of read (nmDOR), or breadth of read (BOR). DOR slope represents the slope of the line in the linear portion of a list of loci sorted in descending DOR order. Closer to zero is better, as it represents a flat line. In some embodiments, the uniformity in DOR can be measured using the Percent of reads in the $90^{th}$-$95^{th}$ Percentile. For this measurement, the loci are sorted in descending DOR order. In the ideal DOR distribution, the $90^{th}$-$95^{th}$ percentile should contain 5% of reads. The reads of all loci between the $90^{th}$ Percentile and $95^{th}$ percentile are counted and divided by the total reads for all loci. In one experiment, the DOR slope versus percent of reads in the $90^{th}$-$95^{th}$ percentile for all samples had an $R^2$=0.81.

In some embodiments, the magnitude of the DOR slope is less than 0.005, 0.001, 0.0005, 0.0001, 0.00005, 0.00001, 0.000005, or 0.000001. In some embodiments, the magnitude of the DOR slope is between 0 and 0.005, such as 0.000001 to 0.005, such as between 0.000005 to 0.00001, 0.00001 to 0.00005, 0.00005 to 0.0001, 0.0001 to 0.0005, 0.0005 to 0.001, or 0.001 to 0.005, inclusive. In some embodiments, the percent of reads in the $90^{th}$-$95^{th}$ percentile is between 0.2 and 9%, such as between 1 to 8%, 2 to 7%, 0.2 to 1.0%, 1 to 2%, 2 to 3%, 2 to 4%, 3 to 4%, 4 to 5%, 5 to 6%, or 6 to 8%, or 7 to 9& inclusive. In some embodiments, the invention features a composition comprising at least 100 different amplicons (e.g., at least 300, 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical amplicons) with the magnitude of the DOR slope in any of these ranges or with a percent of reads in the $90^{th}$-$95^{th}$ percentile in any of these ranges. In some embodiments, the amplification method produces at least 100 different amplicons (e.g., at least 300, 500; 750; 1,000; 2,000; 5,000; 7,500; 10,000; 15,000; 19,000; 20,000; 25,000; 27,000; 28,000; 30,000; 40,000; 50,000; 75,000; or 100,000 non-identical amplicons) with the magnitude of the DOR slope in any of these ranges or with a percent of reads in the $90^{th}$-$95^{th}$ percentile in any of these ranges.

Exemplary Multiplex PCR Methods

In one aspect, the invention features methods of amplifying target loci in a nucleic acid sample that involve (i) contacting the nucleic acid sample with a library of primers that simultaneously hybridize to least 1,000; 2,000; 5,000; 7,500; 10,000; 15,000; 19,000; 20,000; 25,000; 27,000; 28,000; 30,000; 40,000; 50,000; 75,000; or 100,000 different target loci to produce a reaction mixture; and (ii) subjecting the reaction mixture to primer extension reaction conditions (such as PCR conditions) to produce amplified products that include target amplicons. In some embodiments, the method also includes determining the presence or absence of at least one target amplicon (such as at least 50, 60, 70, 80, 90, 95, 96, 97, 98, 99, or 99.5% of the target amplicons). In some embodiments, the method also includes determining the sequence of at least one target amplicon (such as at least 50, 60, 70, 80, 90, 95, 96, 97, 98, 99, or 99.5% of the target amplicons). In some embodiments, at least 50, 60, 70, 80, 90, 95, 96, 97, 98, 99, or 99.5% of the target loci are amplified. In some embodiments, at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci are amplified at least 5, 10, 20, 40, 50, 60, 80, 100, 120, 150, 200, 300, or 400-fold. In some embodiments, at least 50, 60, 70, 80, 90, 95, 96, 97, 98, 99, 99.5, or 100% of the target loci are amplified at least 5, 10, 20, 40, 50, 60, 80, 100, 120, 150, 200, 300, or 400-fold. In various embodiments, less than 60, 50, 40, 30, 20, 10, 5, 4, 3, 2, 1, 0.5, 0.25, 0.1, or 0.05% of the amplified products are primer dimers. In some embodiments, the method involves multiplex PCR and sequencing (such as high throughput sequencing).

In various embodiments, long annealing times and/or low primer concentrations are used. In various embodiments, the length of the annealing step is greater than 3, 5, 8, 10, 15, 20, 30, 45, 60, 75, 90, 120, 150, or 180 minutes. In various embodiments, the length of the annealing step (per PCR cycle) is between 5 and 180 minutes, such as 5 to 60, 10 to 60, 5 to 30, or 10 to 30 minutes, inclusive. In various embodiments, the length of the annealing step is greater than 5 minutes (such greater than 10, or 15 minutes), and the concentration of each primer is less than 20 nM. In various embodiments, the length of the annealing step is greater than 5 minutes (such greater than 10, or 15 minutes), and the concentration of each primer is between 1 to 20 nM, or 1 to 10 nM, inclusive. In various embodiments, the length of the annealing step is greater than 20 minutes (such as greater than 30, 45, 60, or 90 minutes), and the concentration of each primer is less than 1 nM.

At high level of multiplexing, the solution may become viscous due to the large amount of primers in solution. If the solution is too viscous, one can reduce the primer concentration to an amount that is still sufficient for the primers to bind the template DNA. In various embodiments, less than 60,000 different primers are used and the concentration of each primer is less than 20 nM, such as less than 10 nM or between 1 and 10 nM, inclusive. In various embodiments, more than 60,000 different primers (such as between 60,000 and 120,000 different primers) are used and the concentration of each primer is less than 10 nM, such as less than 5 nM or between 1 and 10 nM, inclusive.

It was discovered that the annealing temperature can optionally be higher than the melting temperatures of some or all of the primers (in contrast to other methods that use an annealing temperature below the melting temperatures of the primers) (Experiment 25). The melting temperature ($T_m$) is the temperature at which one-half (50%) of a DNA duplex of an oligonucleotide (such as a primer) and its perfect complement dissociates and becomes single strand DNA. The annealing temperature ($T_A$) is the temperature one runs the PCR protocol at. For prior methods, it is usually 5 C below the lowest $T_m$ of the primers used, thus close to all possible duplexes are formed (such that essentially all the primer molecules bind the template nucleic acid). While this is highly efficient, at lower temperatures there are more unspecific reactions bound to occur. One consequence of having too low a $T_A$ is that primers may anneal to sequences other than the true target, as internal single-base mismatches or partial annealing may be tolerated. In some embodiments of the present inventions, the $T_A$ is higher than ($T_m$), where at a given moment only a small fraction of the targets have a primer annealed (such as only ~1-5%). If these get extended, they are removed from the equilibrium of annealing and dissociating primers and target (as extension increases Tm quickly to above 70 C), and a new ~1-5% of targets has primers. Thus, by giving the reaction long time for annealing, one can get ~100% of the targets copied per cycle. Thus, the most stable molecule pairs (those with perfect DNA pairing between the primer and the template DNA) are preferentially extended to produce the correct target amplicons. For example, the same experiment was performed with 57° C. as the annealing temperature and with 63° C. as the annealing temperature with primers that had a melting temperature below 63° C. When the annealing temperature was 57° C., the percent of mapped reads for the amplified PCR products was as low as 50% (with ~50% of the amplified products being primer-dimer). When the annealing temperature was 63° C., the percentage of amplified products that were primer dimer dropped to ~2%.

In various embodiments, the annealing temperature is at least 1, 2, 3, 4, 5, 6, 7, 8, 9, 10, 11, 12, 13, or 15° C. greater than the melting temperature (such as the empirically measured or calculated $T_m$) of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers. In some embodiments, the annealing temperature is at least 1, 2, 3, 4, 5, 6, 7, 8, 9, 10, 11, 12, 13, or 15° C. greater than the melting temperature (such as the empirically measured or calculated $T_m$) of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers, and the length of the annealing step (per PCR cycle) is greater than 1, 3, 5, 8, 10, 15, 20, 30, 45, 60, 75, 90, 120, 150, or 180 minutes.

In various embodiments, the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the melting temperature (such as the empirically measured or calculated $T_m$) of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers. In various embodiments, the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the melting temperature (such as the empirically measured or calculated $T_m$) of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers, and the length of the annealing step (per PCR cycle) is between 5 and 180 minutes, such as 5 to 60, 10 to 60, 5 to 30, or 10 to 30 minutes, inclusive.

In some embodiments, the annealing temperature is at least 1, 2, 3, 4, 5, 6, 7, 8, 9, 10, 11, 12, 13, or 15° C. greater than the highest melting temperature (such as the empirically measured or calculated $T_m$) of the primers. In some embodiments, the annealing temperature is at least 1, 2, 3, 4, 5, 6, 7, 8, 9, 10, 11, 12, 13, or 15° C. greater than the highest melting temperature (such as the empirically measured or calculated $T_m$) of the primers, and the length of the annealing step (per PCR cycle) is greater than 1, 3, 5, 8, 10, 15, 20, 30, 45, 60, 75, 90, 120, 150, or 180 minutes In some embodiments, the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the highest melting temperature (such as the empirically measured or calculated $T_m$) of the primers. In some embodiments, the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the highest melting temperature (such as the empirically measured or calculated $T_m$) of the primers, and the length of the annealing step (per PCR cycle) is between 5 and 180 minutes, such as 5 to 60, 10 to 60, 5 to 30, or 10 to 30 minutes, inclusive.

In some embodiments, the annealing temperature is at least 1, 2, 3, 4, 5, 6, 7, 8, 9, 10, 11, 12, 13, or 15° C. greater than the average melting temperature (such as the empirically measured or calculated $T_m$) of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers.

In some embodiments, the annealing temperature is at least 1, 2, 3, 4, 5, 6, 7, 8, 9, 10, 11, 12, 13, or 15° C. greater than the average melting temperature (such as the empirically measured or calculated $T_m$) of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers, and the length of the annealing step (per PCR cycle) is greater than 1, 3, 5, 8, 10, 15, 20, 30, 45, 60, 75, 90, 120, 150, or 180 minutes.

In some embodiments, the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the average melting temperature (such as the empirically measured or calculated $T_m$) of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers. In some embodiments, the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the average melting temperature (such as the empirically measured or calculated $T_m$) of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers, and the length of the annealing step (per PCR cycle) is between 5 and 180 minutes, such as 5 to 60, 10 to 60, 5 to 30, or 10 to 30 minutes, inclusive.

In some embodiments, the annealing temperature is between 50 to 70° C., such as between 55 to 60, 60 to 65, or 65 to 70° C., inclusive. In some embodiments, the annealing temperature is between 50 to 70° C., such as between 55 to 60, 60 to 65, or 65 to 70° C., inclusive, and either (i) the length of the annealing step (per PCR cycle) is greater than 3, 5, 8, 10, 15, 20, 30, 45, 60, 75, 90, 120, 150, or 180 minutes or (ii) the length of the annealing step (per PCR cycle) is between 5 and 180 minutes, such as 5 to 60, 10 to 60, 5 to 30, or 10 to 30 minutes, inclusive.

In some embodiments, one or more of the following conditions are used for empirical measurement of $T_m$ or are assumed for calculation of $T_m$: temperature: of 60.0° C., primer concentration of 100 nM, and/or salt concentration of 100 mM. In some embodiments, other conditions are used, such as the conditions that will be used for multiplex PCR with the library. In some embodiments, 100 mM KCl, 50 mM $(NH_4)_2SO_4$, 3 mM $MgCl_2$, 7.5 nM of each primer, and 50 mM TMAC, at pH 8.1 is used. In some embodiments, the $T_m$ is calculated using the Primer3 program (libprimer3 release 2.2.3) using the built-in SantaLucia parameters (the world wide web at primer3.sourceforge.net, which is hereby incorporated by reference in its entirety). For example, the $T_m$ values may be calculated using the method in Experiment 25. In some embodiments, the calculated melting temperature for a primer is the temperature at which half of the primers molecules are expected to be annealed. As discussed above, even at a temperature higher than the calculated melting temperature, a percentage of primers will be annealed, and therefore PCR extension is possible. In some embodiments, the empirically measured Tm (the actual Tm) is determined by using a thermostatted cell in a UV spectrophotometer. In some embodiments, temperature is plotted vs. absorbance, generating an S-shaped curve with two plateaus. The absorbance reading halfway between the plateaus corresponds to Tm.

In some embodiments, the absorbance at 260 nm is measured as a function of temperature on an ultrospec 2100 pr UV/visible spectrophotometer (Amershambiosciences) (see, e.g., Takiya et al., "An empirical approach for thermal stability (Tm) prediction of PNA/DNA duplexes," Nucleic Acids Symp Ser (Oxf); (48): 131-2, 2004, which is hereby incorporated by reference in its entirety). In some embodiments, absorbance at 260 nm is measured by decreasing the temperature in steps of 2° C. per minute from 95 to 20° C. In some embodiments, a primer and its perfect complement (such as 2 uM of each paired oligomer) are mixed and then annealing is performed by heating the sample to 95° C., keeping it there for 5 minutes, followed by cooling to room temperature during 30 minutes, and keeping the samples at 95° C. for at least 60 minutes. In some embodiments, melting temperature is determined by analyzing the data using SWIFT Tm software. In some embodiments of any of the methods of the invention, the method includes empirically measuring or calculating (such as calculating with a computer) the melting temperature for at least 50, 80, 90, 92, 94, 96, 98, 99, or 100% of the primers in the library either before or after the primers are used for PCR amplification of target loci.

In some embodiments, the library comprises a microarray. In some embodiments, the library does not comprise a microarray.

In some embodiments, most or all of the primers are extended to form amplified products. Having all the primers consumed in the PCR reaction increases the uniformity of amplification of the different target loci since the same or similar number of primer molecules are converted to target amplicons for each target loci. In some embodiment, at least 80, 90, 92, 94, 96, 98, 99, or 100% of the primer molecules are extended to form amplified products. In some embodiments, for at least 80, 90, 92, 94, 96, 98, 99, or 100% of target loci, at least 80, 90, 92, 94, 96, 98, 99, or 100% of the primer molecules to that target loci are extended to form amplified products. In some embodiments, multiple cycles are performed until this percentage of the primers are consumed. In some embodiments, multiple cycles are performed until all or substantially all of the primers are consumed. If desired, a higher percentage of the primers can be consumed by decreasing the initial primer concentration and/or increasing the number of PCR cycles that are performed.

In some embodiments, the PCR methods may be performed with microliter reaction volumes, for which it can be harder to achieve specific PCR amplification (due to the lower local concentration of the template nucleic acids) compared to nanoliter or picoliter reaction volumes used in microfluidics applications. In some embodiments, the reaction volume is between 1 and 60 uL, such as between 5 and 50 uL, 10 and 50 uL, 10 and 20 uL, 20 and 30 uL, 30 and 40 uL, or 40 to 50 uL, inclusive.

In an embodiment, a method disclosed herein uses highly efficient highly multiplexed targeted PCR to amplify DNA followed by high throughput sequencing to determine the allele frequencies at each target locus. The ability to multiplex more than about 50 or 100 PCR primers in one reaction volume in a way that most of the resulting sequence reads map to targeted loci is novel and non-obvious. One technique that allows highly multiplexed targeted PCR to perform in a highly efficient manner involves designing primers that are unlikely to hybridize with one another. The PCR probes, typically referred to as primers, are selected by creating a thermodynamic model of potentially adverse interactions between at least 300; at least 500; at least 750; at least 1,000; at least 2,000; at least 5,000; at least 7,500; at least 10,000; at least 20,000; at least 25,000; at least 30,000; at least 40,000; at least 50,000; at least 75,000; or at least 100,000 potential primer pairs, or unintended interactions between primers and sample DNA, and then using the model to eliminate designs that are incompatible with other the designs in the pool. Another technique that allows highly multiplexed targeted PCR to perform in a highly efficient manner is using a partial or full nesting approach to the targeted PCR. Using one or a combination of these approaches allows multiplexing of at least 300, at least 800, at least 1,200, at least 4,000 or at least 10,000 primers in a single pool with the resulting amplified DNA comprising a majority of DNA molecules that, when sequenced, will map to targeted loci. Using one or a combination of these approaches allows multiplexing of a large number of primers in a single pool with the resulting amplified DNA comprising greater than 50%, greater than 60%, greater than 67%, greater than 80%, greater than 90%, greater than 95%, greater than 96%, greater than 97%, greater than 98%, greater than 99%, or greater than 99.5% DNA molecules that map to targeted loci.

In some embodiments the detection of the target genetic material may be done in a multiplexed fashion. The number of genetic target sequences that may be run in parallel can range from one to ten, ten to one hundred, one hundred to one thousand, one thousand to ten thousand, ten thousand to one hundred thousand, one hundred thousand to one million, or one 5 million to ten million. Prior attempts to multiplex more than 100 primers per pool have resulted in significant problems with unwanted side reactions such as primer-dimer formation.

Targeted PCR

In some embodiments, PCR can be used to target specific locations of the genome. In plasma samples, the original DNA is highly fragmented (typically less than 500 bp, with an average length less than 200 bp). In PCR, both forward and reverse primers anneal to the same fragment to enable amplification. Therefore, if the fragments are short, the PCR assays must amplify relatively short regions as well. Like MIPS, if the polymorphic positions are too close the polymerase binding site, it could result in biases in the amplification from different alleles. Currently, PCR primers that target polymorphic regions, such as those containing SNPs, are typically designed such that the 3' end of the primer will hybridize to the base immediately adjacent to the polymorphic base or bases. In an embodiment of the present disclosure, the 3' ends of both the forward and reverse PCR primers are designed to hybridize to bases that are one or a few positions away from the variant positions (polymorphic sites) of the targeted allele. The number of bases between the polymorphic site (SNP or otherwise) and the base to which the 3' end of the primer is designed to hybridize may be one base, it may be two bases, it may be three bases, it may be four bases, it may be five bases, it may be six bases, it may be seven to ten bases, it may be eleven to fifteen bases, or it may be sixteen to twenty bases. The forward and reverse primers may be designed to hybridize a different number of bases away from the polymorphic site.

PCR assay can be generated in large numbers, however, the interactions between different PCR assays makes it difficult to multiplex them beyond about one hundred assays. Various complex molecular approaches can be used to increase the level of multiplexing, but it may still be limited to fewer than 100, perhaps 200, or possibly 500 assays per reaction. Samples with large quantities of DNA can be split among multiple sub-reactions and then recombined before sequencing. For samples where either the overall sample or some subpopulation of DNA molecules is limited, splitting the sample would introduce statistical noise. In an embodiment, a small or limited quantity of DNA may refer to an amount below 10 pg, between 10 and 100 pg, between 100 pg and 1 ng, between 1 and 10 ng, or between 10 and 100 ng. Note that while this method is particularly useful on small amounts of DNA where other methods that involve splitting into multiple pools can cause significant problems related to introduced stochastic noise, this method still provides the benefit of minimizing bias when it is run on samples of any quantity of DNA. In these situations a universal pre-amplification step may be used to increase the overall sample quantity. Ideally, this pre-amplification step should not appreciably alter the allelic distributions.

In an embodiment, a method of the present disclosure can generate PCR products that are specific to a large number of targeted loci, specifically 1,000 to 5,000 loci, 5,000 to 10,000 loci or more than 10,000 loci, for genotyping by sequencing or some other genotyping method, from limited samples such as single cells or DNA from body fluids. Currently, performing multiplex PCR reactions of more than 5 to 10 targets presents a major challenge and is often hindered by primer side products, such as primer dimers, and other artifacts. When detecting target sequences using microarrays with hybridization probes, primer dimers and other artifacts may be ignored, as these are not detected. However, when using sequencing as a method of detection, the vast majority of the sequencing reads would sequence such artifacts and not the desired target sequences in a sample. Methods described in the prior art used to multiplex more than 50 or 100 reactions in one reaction volume followed by sequencing will typically result in more than 20%, and often more than 50%, in many cases more than 80% and in some cases more than 90% off-target sequence reads.

In general, to perform targeted sequencing of multiple (n) targets of a sample (greater than 50, greater than 100, greater than 500, or greater than 1,000), one can split the sample into a number of parallel reactions that amplify one individual target. This has been performed in PCR multiwell plates or can be done in commercial platforms such as the FLUIDIGM ACCESS ARRAY (48 reactions per sample in microfluidic chips) or DROPLET PCR by RAIN DANCE TECHNOLOGY (100s to a few thousands of targets). Unfortunately, these split-and-pool methods are problematic for samples with a limited amount of DNA, as there is often not enough copies of the genome to ensure that there is one copy of each region of the genome in each well. This is an especially severe problem when polymorphic loci are targeted, and the relative proportions of the alleles at the polymorphic loci are needed, as the stochastic noise introduced by the splitting and pooling will cause very poorly accurate measurements of the proportions of the alleles that were present in the original sample of DNA. Described here is a method to effectively and efficiently amplify many PCR reactions that is applicable to cases where only a limited amount of DNA is available. In an embodiment, the method may be applied for analysis of single cells, body fluids, mixtures of DNA such as the free floating DNA found in maternal plasma, biopsies, environmental and/or forensic samples.

In an embodiment, the targeted sequencing may involve one, a plurality, or all of the following steps. a) Generate and amplify a library with adaptor sequences on both ends of DNA fragments. b) Divide into multiple reactions after library amplification. c) Generate and optionally amplify a library with adaptor sequences on both ends of DNA fragments. d) Perform 1000- to 10,000-plex amplification of selected targets using one target specific "Forward" primer per target and one tag specific primer. e) Perform a second amplification from this product using "Reverse" target specific primers and one (or more) primer specific to a universal tag that was introduced as part of the target specific forward primers in the first round. f) Perform a 1000-plex preamplification of selected target for a limited number of cycles. g) Divide the product into multiple aliquots and amplify subpools of targets in individual reactions (for example, 50 to 500-plex, though this can be used all the way down to singleplex. h) Pool products of parallel subpools reactions. i) During these amplifications primers may carry sequencing compatible tags (partial or full length) such that the products can be sequenced.

Highly Multiplexed PCR

Disclosed herein are methods that permit the targeted amplification of over a hundred to tens of thousands of target sequences (e.g., SNP loci) from a nucleic acid sample such as genomic DNA obtained from plasma. The amplified sample may be relatively free of primer dimer products and have low allelic bias at target loci. If during or after amplification the products are appended with sequencing compatible adaptors, analysis of these products can be performed by sequencing.

Performing a highly multiplexed PCR amplification using methods known in the art results in the generation of primer dimer products that are in excess of the desired amplification products and not suitable for sequencing. These can be reduced empirically by eliminating primers that form these products, or by performing in silico selection of primers. However, the larger the number of assays, the more difficult this problem becomes.

One solution is to split the 5000-plex reaction into several lower-plexed amplifications, e.g. one hundred 50-plex or fifty 100-plex reactions, or to use microfluidics or even to split the sample into individual PCR reactions. However, if the sample DNA is limited, such as in non-invasive prenatal diagnostics from pregnancy plasma, dividing the sample between multiple reactions should be avoided as this will result in bottlenecking.

Described herein are methods to first globally amplify the plasma DNA of a sample and then divide the sample up into multiple multiplexed target enrichment reactions with more moderate numbers of target sequences per reaction. In an embodiment, a method of the present disclosure can be used for preferentially enriching a DNA mixture at a plurality of loci, the method comprising one or more of the following steps: generating and amplifying a library from a mixture of DNA where the molecules in the library have adaptor sequences ligated on both ends of the DNA fragments, dividing the amplified library into multiple reactions, performing a first round of multiplex amplification of selected targets using one target specific "forward" primer per target and one or a plurality of adaptor specific universal "reverse" primers. In an embodiment, a method of the present disclosure further includes performing a second amplification using "reverse" target specific primers and one or a plurality of primers specific to a universal tag that was introduced as part of the target specific forward primers in the first round. In an embodiment, the method may involve a fully nested, hemi-nested, semi-nested, one sided fully nested, one sided hemi-nested, or one sided semi-nested PCR approach. In an embodiment, a method of the present disclosure is used for preferentially enriching a DNA mixture at a plurality of loci, the method comprising performing a multiplex preamplification of selected targets for a limited number of cycles, dividing the product into multiple aliquots and amplifying subpools of targets in individual reactions, and pooling products of parallel subpools reactions. Note that this approach could be used to perform targeted amplification in a manner that would result in low levels of allelic bias for 50-500 loci, for 500 to 5,000 loci, for 5,000 to 50,000 loci, or even for 50,000 to 500,000 loci. In an embodiment, the primers carry partial or full length sequencing compatible tags.

The workflow may entail (1) extracting DNA such as plasma DNA, (2) preparing fragment library with universal adaptors on both ends of fragments, (3) amplifying the library using universal primers specific to the adaptors, (4) dividing the amplified sample "library" into multiple aliquots, (5) performing multiplex (e.g. about 100-plex, 1,000, or 10,000-plex with one target specific primer per target and a tag-specific primer) amplifications on aliquots, (6) pooling aliquots of one sample, (7) barcoding the sample, (8) mixing the samples and adjusting the concentration, (9) sequencing the sample. The workflow may comprise multiple sub-steps that contain one of the listed steps (e.g. step (2) of preparing the library step could entail three enzymatic steps (blunt ending, dA tailing and adaptor ligation) and three purification steps). Steps of the workflow may be combined, divided up or performed in different order (e.g. bar coding and pooling of samples).

It is important to note that the amplification of a library can be performed in such a way that it is biased to amplify short fragments more efficiently. In this manner it is possible to preferentially amplify shorter sequences, e.g. mononucleosomal DNA fragments as the cell free fetal DNA (of placental origin) found in the circulation of pregnant women. Note that PCR assays can have the tags, for example sequencing tags, (usually a truncated form of 15-25 bases). After multiplexing, PCR multiplexes of a sample are pooled and then the tags are completed (including bar coding) by a tag-specific PCR (could also be done by ligation). Also, the full sequencing tags can be added in the same reaction as the multiplexing. In the first cycles targets may be amplified with the target specific primers, subsequently the tag-specific primers take over to complete the SQ-adaptor sequence. The PCR primers may carry no tags. The sequencing tags may be appended to the amplification products by ligation.

In an embodiment, highly multiplex PCR followed by evaluation of amplified material by clonal sequencing may be used for various applications such as the detection of fetal aneuploidy. Whereas traditional multiplex PCRs evaluate up to fifty loci simultaneously, the approach described herein may be used to enable simultaneous evaluation of more than 50 loci simultaneously, more than 100 loci simultaneously, more than 500 loci simultaneously, more than 1,000 loci simultaneously, more than 5,000 loci simultaneously, more than 10,000 loci simultaneously, more than 50,000 loci simultaneously, and more than 100,000 loci simultaneously. Experiments have shown that up to, including and more than 10,000 distinct loci can be evaluated simultaneously, in a single reaction, with sufficiently good efficiency and specificity to make non-invasive prenatal aneuploidy diagnoses and/or copy number calls with high accuracy. Assays may be combined in a single reaction with the entirety of a sample such as a cfDNA sample isolated from maternal plasma, a fraction thereof, or a further processed derivative of the cfDNA sample. The sample (e.g., cfDNA or derivative) may also be split into multiple parallel multiplex reactions. The optimum sample splitting and multiplex is determined by trading off various performance specifications. Due to the limited amount of material, splitting the sample into multiple fractions can introduce sampling noise, handling time, and increase the possibility of error. Conversely, higher multiplexing can result in greater amounts of spurious amplification and greater inequalities in amplification both of which can reduce test performance.

Two crucial related considerations in the application of the methods described herein are the limited amount of original sample (e.g., plasma) and the number of original molecules in that material from which allele frequency or other measurements are obtained. If the number of original molecules falls below a certain level, random sampling noise becomes significant, and can affect the accuracy of the test. Typically, data of sufficient quality for making non-invasive prenatal aneuploidy diagnoses can be obtained if measurements are made on a sample comprising the equivalent of 500-1000 original molecules per target locus. There are a number of ways of increasing the number of distinct measurements, for example increasing the sample volume. Each manipulation applied to the sample also potentially results in losses of material. It is essential to characterize losses incurred by various manipulations and avoid, or as necessary improve yield of certain manipulations to avoid losses that could degrade performance of the test.

In an embodiment, it is possible to mitigate potential losses in subsequent steps by amplifying all or a fraction of the original sample (e.g., cfDNA sample). Various methods are available to amplify all of the genetic material in a sample, increasing the amount available for downstream procedures. In an embodiment, ligation mediated PCR (LM-PCR) DNA fragments are amplified by PCR after ligation of either one distinct adaptors, two distinct adapters, or many distinct adaptors. In an embodiment, multiple displacement amplification (MDA) phi-29 polymerase is used to amplify all DNA isothermally. In DOP-PCR and variations, random priming is used to amplify the original material DNA. Each method has certain characteristics such as uniformity of amplification across all represented regions of the genome, efficiency of capture and amplification of original DNA, and amplification performance as a function of the length of the fragment.

In an embodiment LM-PCR may be used with a single heteroduplexed adaptor having a 3-prime tyrosine. The heteroduplexed adaptor enables the use of a single adaptor molecule that may be converted to two distinct sequences on 5-prime and 3-prime ends of the original DNA fragment during the first round of PCR. In an embodiment, it is possible to fractionate the amplified library by size separations, or products such as AMPURE, TASS or other similar methods. Prior to ligation, sample DNA may be blunt ended, and then a single adenosine base is added to the 3-prime end. Prior to ligation the DNA may be cleaved using a restriction enzyme or some other cleavage method. During ligation the 3-prime adenosine of the sample fragments and the complementary 3-prime tyrosine overhang of adaptor can enhance ligation efficiency. The extension step of the PCR amplification may be limited from a time standpoint to reduce amplification from fragments longer than about 200 bp, about 300 bp, about 400 bp, about 500 bp or about 1,000 bp. Since longer DNA found in the maternal plasma is nearly exclusively maternal, this may result in the enrichment of fetal DNA by 10-50% and improvement of test performance. A number of reactions were run using conditions as specified by commercially available kits; the resulted in successful ligation of fewer than 10% of sample DNA molecules. A series of optimizations of the reaction conditions for this improved ligation to approximately 70%.

Mini-PCR

The following Mini-PCR method is desirable for samples containing short nucleic acids, digested nucleic acids, or fragmented nucleic acids, such as cfDNA. Traditional PCR assay design results in significant losses of distinct fetal molecules, but losses can be greatly reduced by designing very short PCR assays, termed mini-PCR assays. Fetal cfDNA in maternal serum is highly fragmented and the fragment sizes are distributed in approximately a Gaussian fashion with a mean of 160 bp, a standard deviation of 15 bp, a minimum size of about 100 bp, and a maximum size of about 220 bp. The distribution of fragment start and end positions with respect to the targeted polymorphisms, while not necessarily random, vary widely among individual targets and among all targets collectively and the polymorphic site of one particular target locus may occupy any position from the start to the end among the various fragments originating from that locus. Note that the term mini-PCR may equally well refer to normal PCR with no additional restrictions or limitations.

During PCR, amplification will only occur from template DNA fragments comprising both forward and reverse primer sites. Because fetal cfDNA fragments are short, the likelihood of both primer sites being present the likelihood of a fetal fragment of length L comprising both the forward and reverse primers sites is ratio of the length of the amplicon to the length of the fragment. Under ideal conditions, assays in which the amplicon is 45, 50, 55, 60, 65, or 70 bp will successfully amplify from 72%, 69%, 66%, 63%, 59%, or 56%, respectively, of available template fragment molecules. The amplicon length is the distance between the 5-prime ends of the forward and reverse priming sites. Amplicon length that is shorter than typically used by those known in the art may result in more efficient measurements of the desired polymorphic loci by only requiring short sequence reads. In an embodiment, a substantial fraction of the amplicons should be less than 100 bp, less than 90 bp, less than 80 bp, less than 70 bp, less than 65 bp, less than 60 bp, less than 55 bp, less than 50 bp, or less than 45 bp.

Note that in methods known in the prior art, short assays such as those described herein are usually avoided because they are not required and they impose considerable constraint on primer design by limiting primer length, annealing characteristics, and the distance between the forward and reverse primer.

Also note that there is the potential for biased amplification if the 3-prime end of the either primer is within roughly 1-6 bases of the polymorphic site. This single base difference at the site of initial polymerase binding can result in preferential amplification of one allele, which can alter observed allele frequencies and degrade performance. All of these constraints make it very challenging to identify primers that will amplify a particular locus successfully and furthermore, to design large sets of primers that are compatible in the same multiplex reaction. In an embodiment, the 3' end of the inner forward and reverse primers are designed to hybridize to a region of DNA upstream from the polymorphic site, and separated from the polymorphic site by a small number of bases. Ideally, the number of bases may be between 6 and 10 bases, but may equally well be between 4 and 15 bases, between three and 20 bases, between two and 30 bases, or between 1 and 60 bases, and achieve substantially the same end.

Multiplex PCR may involve a single round of PCR in which all targets are amplified or it may involve one round of PCR followed by one or more rounds of nested PCR or some variant of nested PCR. Nested PCR consists of a subsequent round or rounds of PCR amplification using one or more new primers that bind internally, by at least one base pair, to the primers used in a previous round. Nested PCR reduces the number of spurious amplification targets by amplifying, in subsequent reactions, only those amplification products from the previous one that have the correct internal sequence. Reducing spurious amplification targets improves the number of useful measurements that can be obtained, especially in sequencing. Nested PCR typically entails designing primers completely internal to the previous primer binding sites, necessarily increasing the minimum DNA segment size required for amplification. For samples such as maternal plasma cfDNA, in which the DNA is highly fragmented, the larger assay size reduces the number of distinct cfDNA molecules from which a measurement can be obtained. In an embodiment, to offset this effect, one may use a partial nesting approach where one or both of the second round primers overlap the first binding sites extending internally some number of bases to achieve additional specificity while minimally increasing in the total assay size.

In an embodiment, a multiplex pool of PCR assays are designed to amplify potentially heterozygous SNP or other polymorphic or non-polymorphic loci on one or more chromosomes and these assays are used in a single reaction to amplify DNA. The number of PCR assays may be between 50 and 200 PCR assays, between 200 and 1,000 PCR assays, between 1,000 and 5,000 PCR assays, or between 5,000 and 20,000 PCR assays (50 to 200-plex, 200 to 1,000-plex, 1,000 to 5,000-plex, 5,000 to 20,000-plex, more than 20,000-plex respectively). In an embodiment, a multiplex pool of about 10,000 PCR assays (10,000-plex) are designed to amplify potentially heterozygous SNP loci on chromosomes X, Y, 13, 18, and 21 and 1 or 2 and these assays are used in a single reaction to amplify cfDNA obtained from a material plasma sample, chorion villus samples, amniocentesis samples, single or a small number of cells, other bodily fluids or tissues, cancers, or other genetic matter. The SNP frequencies of each locus may be determined by clonal or some other method of sequencing of the amplicons. Statistical analysis of the allele frequency distributions or ratios of all assays may be used to determine if the sample contains a trisomy of one or more of the chromosomes included in the test. In another embodiment the original cfDNA samples is split into two samples and parallel 5,000-plex assays are performed. In another embodiment the original cfDNA samples is split into n samples and parallel (~10,000/n)-plex assays are performed where n is between 2 and 12, or between 12 and 24, or between 24 and 48, or between 48 and 96. Data is collected and analyzed in a similar manner to that already described. Note that this method is equally well applicable to detecting translocations, deletions, duplications, and other chromosomal abnormalities.

In an embodiment, tails with no homology to the target genome may also be added to the 3-prime or 5-prime end of any of the primers. These tails facilitate subsequent manipulations, procedures, or measurements. In an embodiment, the tail sequence can be the same for the forward and reverse target specific primers. In an embodiment, different tails may be used for the forward and reverse target specific primers. In an embodiment, a plurality of different tails may be used for different loci or sets of loci. Certain tails may be shared among all loci or among subsets of loci. For example, using forward and reverse tails corresponding to forward and reverse sequences required by any of the current sequencing platforms can enable direct sequencing following amplification. In an embodiment, the tails can be used as common priming sites among all amplified targets that can be used to add other useful sequences. In some embodiments, the inner primers may contain a region that is designed to hybridize either upstream or downstream of the targeted locus (e.g, a polymorphic locus). In some embodiments, the primers may contain a molecular barcode. In some embodiments, the primer may contain a universal priming sequence designed to allow PCR amplification.

In an embodiment, a 10,000-plex PCR assay pool is created such that forward and reverse primers have tails corresponding to the required forward and reverse sequences required by a high throughput sequencing instrument such as the HISEQ, GAIIX, or MYSEQ available from ILLUMINA. In addition, included 5-prime to the sequencing tails is an additional sequence that can be used as a priming site in a subsequent PCR to add nucleotide barcode sequences to the amplicons, enabling multiplex sequencing of multiple samples in a single lane of the high throughput sequencing instrument.

In an embodiment, a 10,000-plex PCR assay pool is created such that reverse primers have tails corresponding to the required reverse sequences required by a high throughput sequencing instrument. After amplification with the first 10,000-plex assay, a subsequent PCR amplification may be performed using a another 10,000-plex pool having partly nested forward primers (e.g. 6-bases nested) for all targets and a reverse primer corresponding to the reverse sequencing tail included in the first round. This subsequent round of partly nested amplification with just one target specific primer and a universal primer limits the required size of the assay, reducing sampling noise, but greatly reduces the number of spurious amplicons. The sequencing tags can be added to appended ligation adaptors and/or as part of PCR probes, such that the tag is part of the final amplicon.

Fetal fraction affects performance of the test. There are a number of ways to enrich the fetal fraction of the DNA found in maternal plasma. Fetal fraction can be increased by the previously described LM-PCR method already discussed as well as by a targeted removal of long maternal fragments. In an embodiment, prior to multiplex PCR amplification of the target loci, an additional multiplex PCR reaction may be carried out to selectively remove long and largely maternal fragments corresponding to the loci targeted in the subsequent multiplex PCR. Additional primers are designed to anneal a site a greater distance from the polymorphism than is expected to be present among cell free fetal DNA fragments. These primers may be used in a one cycle multiplex PCR reaction prior to multiplex PCR of the target polymorphic loci. These distal primers are tagged with a molecule or moiety that can allow selective recognition of the tagged pieces of DNA. In an embodiment, these molecules of DNA may be covalently modified with a biotin molecule that allows removal of newly formed double stranded DNA comprising these primers after one cycle of PCR. Double stranded DNA formed during that first round is likely maternal in origin. Removal of the hybrid material may be accomplish by the used of magnetic streptavidin beads. There are other methods of tagging that may work equally well. In an embodiment, size selection methods may be used to enrich the sample for shorter strands of DNA; for example those less than about 800 bp, less than about 500 bp, or less than about 300 bp. Amplification of short fragments can then proceed as usual.

The mini-PCR method described in this disclosure enables highly multiplexed amplification and analysis of hundreds to thousands or even millions of loci in a single reaction, from a single sample. At the same, the detection of the amplified DNA can be multiplexed; tens to hundreds of samples can be multiplexed in one sequencing lane by using barcoding PCR. This multiplexed detection has been successfully tested up to 49-plex, and a much higher degree of multiplexing is possible. In effect, this allows hundreds of samples to be genotyped at thousands of SNPs in a single sequencing run. For these samples, the method allows determination of genotype and heterozygosity rate and simultaneously determination of copy number, both of which may be used for the purpose of aneuploidy detection. This method is particularly useful in detecting aneuploidy of a gestating fetus from the free floating DNA found in maternal plasma. This method may be used as part of a method for sexing a fetus, and/or predicting the paternity of the fetus. It may be used as part of a method for mutation dosage. This method may be used for any amount of DNA or RNA, and the targeted regions may be SNPs, other polymorphic regions, non-polymorphic regions, and combinations thereof.

In some embodiments, ligation mediated universal-PCR amplification of fragmented DNA may be used. The ligation mediated universal-PCR amplification can be used to amplify plasma DNA, which can then be divided into multiple parallel reactions. It may also be used to preferentially amplify short fragments, thereby enriching fetal fraction. In some embodiments the addition of tags to the fragments by ligation can enable detection of shorter fragments, use of shorter target sequence specific portions of the primers and/or annealing at higher temperatures which reduces unspecific reactions.

The methods described herein may be used for a number of purposes where there is a target set of DNA that is mixed with an amount of contaminating DNA. In some embodiments, the target DNA and the contaminating DNA may be from individuals who are genetically related. For example, genetic abnormalities in a fetus (target) may be detected from maternal plasma which contains fetal (target) DNA and also maternal (contaminating) DNA; the abnormalities include whole chromosome abnormalities (e.g. aneuploidy) partial chromosome abnormalities (e.g. deletions, duplications, inversions, translocations), polynucleotide polymorphisms (e.g. STRs), single nucleotide polymorphisms, and/or other genetic abnormalities or differences. In some embodiments, the target and contaminating DNA may be from the same individual, but where the target and contaminating DNA are different by one or more mutations, for example in the case of cancer. (see e.g. H. Mamon et al. *Preferential Amplification of Apoptotic DNA from Plasma: Potential for Enhancing Detection of Minor DNA Alterations in Circulating DNA*. Clinical Chemistry 54:9 (2008). In some embodiments, the DNA may be found in cell culture (apoptotic) supernatant. In some embodiments, it is possible to induce apoptosis in biological samples (e.g., blood) for subsequent library preparation, amplification and/or sequencing. A number of enabling workflows and protocols to achieve this end are presented elsewhere in this disclosure.

In some embodiments, the target DNA may originate from single cells, from samples of DNA consisting of less than one copy of the target genome, from low amounts of DNA, from DNA from mixed origin (e.g. pregnancy plasma: placental and maternal DNA; cancer patient plasma and tumors: mix between healthy and cancer DNA, transplantation etc), from other body fluids, from cell cultures, from culture supernatants, from forensic samples of DNA, from ancient samples of DNA (e.g. insects trapped in amber), from other samples of DNA, and combinations thereof.

In some embodiments, a short amplicon size may be used. Short amplicon sizes are especially suited for fragmented DNA (see e.g. A. Sikora, et sl. Detection of increased amounts of cell-free fetal DNA with short PCR amplicons. Clin Chem. 2010 January; 56(1):136-8.) The use of short amplicon sizes may result in some significant benefits.

Short amplicon sizes may result in optimized amplification efficiency. Short amplicon sizes typically produce shorter products, therefore there is less chance for nonspecific priming. Shorter products can be clustered more densely on sequencing flow cell, as the clusters will be smaller. Note that the methods described herein may work equally well for longer PCR amplicons. Amplicon length may be increased if necessary, for example, when sequencing larger sequence stretches. Experiments with 146-plex targeted amplification with assays of 100 bp to 200 bp length as first step in a nested-PCR protocol were run on single cells and on genomic DNA with positive results.

In some embodiments, the methods described herein may be used to amplify and/or detect SNPs, copy number, nucleotide methylation, mRNA levels, other types of RNA expression levels, other genetic and/or epigenetic features. The mini-PCR methods described herein may be used along with next-generation sequencing; it may be used with other downstream methods such as microarrays, counting by digital PCR, real-time PCR, Mass-spectrometry analysis etc.

In some embodiment, the mini-PCR amplification methods described herein may be used as part of a method for accurate quantification of minority populations. It may be used for absolute quantification using spike calibrators. It may be used for mutation/minor allele quantification through very deep sequencing, and may be run in a highly multiplexed fashion. It may be used for standard paternity and identity testing of relatives or ancestors, in human, animals, plants or other creatures. It may be used for forensic testing. It may be used for rapid genotyping and copy number analysis (CN), on any kind of material, e.g. amniotic fluid and CVS, sperm, product of conception (POC). It may be used for single cell analysis, such as genotyping on samples biopsied from embryos. It may be used for rapid embryo analysis (within less than one, one, or two days of biopsy) by targeted sequencing using min-PCR.

In some embodiments, it may be used for tumor analysis: tumor biopsies are often a mixture of health and tumor cells. Targeted PCR allows deep sequencing of SNPs and loci with close to no background sequences. It may be used for copy number and loss of heterozygosity analysis on tumor DNA. Said tumor DNA may be present in many different body fluids or tissues of tumor patients. It may be used for detection of tumor recurrence, and/or tumor screening. It may be used for quality control testing of seeds. It may be used for breeding, or fishing purposes. Note that any of these methods could equally well be used targeting non-polymorphic loci for the purpose of ploidy calling.

Some literature describing some of the fundamental methods that underlie the methods disclosed herein include: (1) Wang H Y, Luo M, Tereshchenko I V, Frikker D M, Cui X, Li J Y, Hu G, Chu Y, Azaro M A, Lin Y, Shen L, Yang Q, Kambouris M E, Gao R, Shih W, Li H. Genome Res. 2005 February; 15(2):276-83. Department of Molecular Genetics, Microbiology and Immunology/The Cancer Institute of New Jersey, Robert Wood Johnson Medical School, New Brunswick, N.J. 08903, USA. (2) High-throughput genotyping of single nucleotide polymorphisms with high sensitivity. Li H, Wang H Y, Cui X, Luo M, Hu G, Greenawalt D M, Tereshchenko I V, Li J Y, Chu Y, Gao R. Methods Mol Biol. 2007; 396-PubMed PMID: 18025699. (3) A method comprising multiplexing of an average of 9 assays for sequencing is described in: Nested Patch PCR enables highly multiplexed mutation discovery in candidate genes. Varley K E, Mitra R D. Genome Res. 2008 November; 18(11): 1844-50. Epub 2008 Oct. 10. Note that the methods disclosed herein allow multiplexing of orders of magnitude more than in the above references.

Targeted PCR Variants—Nesting

There are many workflows that are possible when conducting PCR; some workflows typical to the methods disclosed herein are described. The steps outlined herein are not meant to exclude other possible steps nor does it imply that any of the steps described herein are required for the method to work properly. A large number of parameter variations or other modifications are known in the literature, and may be made without affecting the essence of the invention. One particular generalized workflow is given below followed by a number of possible variants. The variants typically refer to possible secondary PCR reactions, for example different types of nesting that may be done (step 3). It is important to note that variants may be done at different times, or in different orders than explicitly described herein. Examples that use polymorphic loci for illustration can be readily adapted for the amplification of nonpolymorphic loci if desired.

1. The DNA in the sample may have ligation adapters, often referred to as library tags or ligation adaptor tags (LTs), appended, where the ligation adapters contain a universal priming sequence, followed by a universal amplification. In an embodiment, this may be done using a standard protocol designed to create sequencing libraries after fragmentation. In an embodiment, the DNA sample can be blunt ended, and then an A can be added at the 3' end. A Y-adaptor with a T-overhang can be added and ligated. In some embodiments, other sticky ends can be used other than an A or T overhang. In some embodiments, other adaptors can be added, for example looped ligation adaptors. In some embodiments, the adaptors may have tag designed for PCR amplification.

2. Specific Target Amplification (STA): Pre-amplification of hundreds to thousands to tens of thousands and even hundreds of thousands of targets may be multiplexed in one reaction volume. STA is typically run from 10 to 30 cycles, though it may be run from 5 to 40 cycles, from 2 to 50 cycles, and even from 1 to 100 cycles. Primers may be tailed, for example for a simpler workflow or to avoid sequencing of a large proportion of dimers. Note that typically, dimers of both primers carrying the same tag will not be amplified or sequenced efficiently. In some embodiments, between 1 and 10 cycles of PCR may be carried out; in some embodiments between 10 and 20 cycles of PCR may be carried out; in some embodiments between 20 and 30 cycles of PCR may be carried out; in some embodiments between 30 and 40 cycles of PCR may be carried out; in some embodiments more than 40 cycles of PCR may be carried out. The amplification may be a linear amplification. The number of PCR cycles may be optimized to result in an optimal depth of read (DOR) profile. Different DOR profiles may be desirable for different purposes. In some embodiments, a more even distribution of reads between all assays is desirable; if the DOR is too small for some assays, the stochastic noise can be too high for the data to be too useful, while if the depth of read is too high, the marginal usefulness of each additional read is relatively small.

Primer tails may improve the detection of fragmented DNA from universally tagged libraries. If the library tag and the primer-tails contain a homologous sequence, hybridization can be improved (for example, melting temperature ($T_M$) is lowered) and primers can be extended if only a portion of the primer target sequence is in the sample DNA fragment. In some embodiments, 13 or more target specific base pairs may be used. In some embodiments, 10 to 12 target specific base pairs may be used. In some embodiments, 8 to 9 target specific base pairs may be used. In some embodiments, 6 to 7 target specific base pairs may be used. In some embodiments, STA may be performed on pre-amplified DNA, e.g. MDA, RCA, other whole genome amplifications, or adaptor-mediated universal PCR. In some embodiments, STA may be performed on samples that are enriched or depleted of certain sequences and populations, e.g. by size selection, target capture, directed degradation.

3. In some embodiments, it is possible to perform secondary multiplex PCRs or primer extension reactions to increase specificity and reduce undesirable products. For example, full nesting, semi-nesting, hemi-nesting, and/or subdividing into parallel reactions of smaller assay pools are all techniques that may be used to increase specificity. Experiments have shown that splitting a sample into three 400-plex reactions resulted in product DNA with greater specificity than one 1,200-plex reaction with exactly the same primers. Similarly, experiments have shown that splitting a sample into four 2,400-plex reactions resulted in product DNA with greater specificity than one 9,600-plex reaction with exactly the same primers. In an embodiment, it is possible to use target-specific and tag specific primers of the same and opposing directionality.

4. In some embodiments, it is possible to amplify a DNA sample (dilution, purified or otherwise) produced by an STA reaction using tag-specific primers and "universal amplification", i.e. to amplify many or all pre-amplified and tagged targets. Primers may contain additional functional sequences, e.g. barcodes, or a full adaptor sequence necessary for sequencing on a high throughput sequencing platform.

These methods may be used for analysis of any sample of DNA, and are especially useful when the sample of DNA is particularly small, or when it is a sample of DNA where the DNA originates from more than one individual, such as in the case of maternal plasma. These methods may be used on DNA samples such as a single or small number of cells, genomic DNA, plasma DNA, amplified plasma libraries, amplified apoptotic supernatant libraries, or other samples of mixed DNA. In an embodiment, these methods may be used in the case where cells of different genetic constitution may be present in a single individual, such as with cancer or transplants. In an embodiment, some of the DNA is from the recipient of a transplant (such as recipient cell-free or cellular DNA) and some of the DNA is from the donor of the transplant (such as cell-free or cellular DNA from the transplant). In an embodiment, the method is used to amplify one or more loci that differ between the recipient and the donor (such as loci for which a different combination of alleles are present in the recipient compared to the donor). In some embodiments, the recipient is homozygous for a first allele (such as AA) and the donor is homozygous for a second allele (such as BB) or is heterozygous with the first allele and a second allele (such as AB) at one or more loci. In some embodiments, the method is used to measure the absolute or relative amount of DNA from the donor of the transplant (such as cell-free or cellular DNA from the transplant). In some embodiments, this method is used to prognose, diagnose, detect, or monitor a transplant status or outcome, such as transplant rejection, tolerance, non-rejection based allograft injury, transplant function, transplant survival, chronic transplant injury, or tittering of pharmacological immuno suppression.

Protocol Variants (Variants and/or Additions to the Workflow Above)

Direct Multiplexed Mini-PCR:

Specific target amplification (STA) of a plurality of target sequences with tagged primers is shown in FIG. 1. 101 denotes double stranded DNA with a polymorphic locus of interest at X. 102 denotes the double stranded DNA with ligation adaptors added for universal amplification. 103 denotes the single stranded DNA that has been universally amplified with PCR primers hybridized. 104 denotes the final PCR product. In some embodiments, STA may be done on more than 100, more than 200, more than 500, more than 1,000, more than 2,000, more than 5,000, more than 10,000, more than 20,000, more than 50,000, more than 100,000 or more than 200,000 targets. In a subsequent reaction, tag-specific primers amplify all target sequences and lengthen the tags to include all necessary sequences for sequencing, including sample indexes. In an embodiment, primers may not be tagged or only certain primers may be tagged. Sequencing adaptors may be added by conventional adaptor ligation. In an embodiment, the initial primers may carry the tags.

In an embodiment, primers are designed so that the length of DNA amplified is unexpectedly short. Prior art demonstrates that ordinary people skilled in the art typically design 100+bp amplicons. In an embodiment, the amplicons may be designed to be less than 80 bp. In an embodiment, the amplicons may be designed to be less than 70 bp. In an embodiment, the amplicons may be designed to be less than 60 bp. In an embodiment, the amplicons may be designed to be less than 50 bp. In an embodiment, the amplicons may be designed to be less than 45 bp. In an embodiment, the amplicons may be designed to be less than 40 bp. In an embodiment, the amplicons may be designed to be less than 35 bp. In an embodiment, the amplicons may be designed to be between 40 and 65 bp.

An experiment was performed using this protocol using 1200-plex amplification. Both genomic DNA and pregnancy plasma were used; about 70% of sequence reads mapped to targeted sequences. Details are given elsewhere in this document. Sequencing of a 1042-plex without design and selection of assays resulted in >99% of sequences being primer dimer products.

Sequential PCR:

After STA1 multiple aliquots of the product may be amplified in parallel with pools of reduced complexity with the same primers. The first amplification can give enough material to split. This method is especially good for small samples, for example those that are about 6-100 pg, about 100 pg to 1 ng, about 1 ng to 10 ng, or about 10 ng to 100 ng. The protocol was performed with 1200-plex into three 400-plexes. Mapping of sequencing reads increased from around 60 to 70% in the 1200-plex alone to over 95%.

Figure 2:
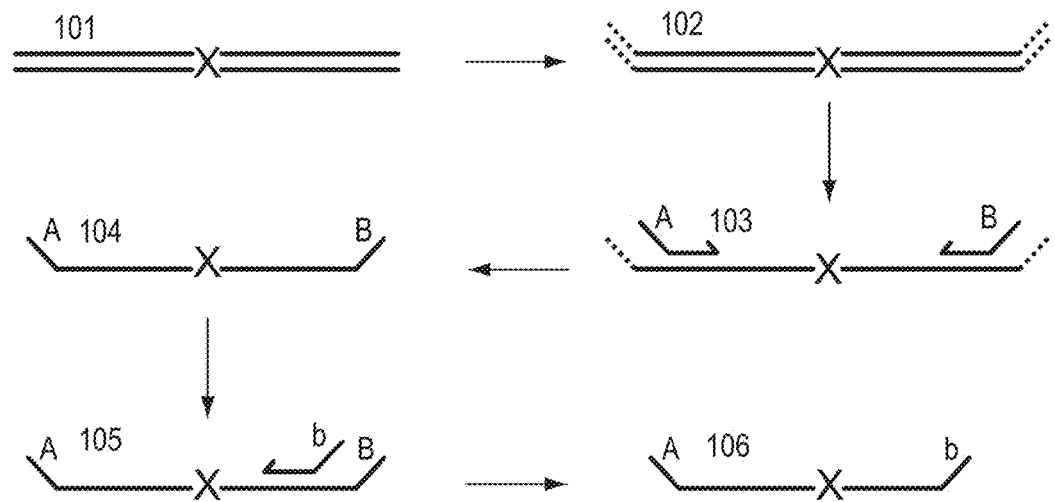
FIG. 2: Graphical representation of semi-nested mini-PCR method. After STA 1 a second STA is performed comprising a multiplex set of internal nested Forward primers (103 B, 105 b) and one (or few) tag-specific Reverse primers (103 A). 101 denotes double stranded DNA with a polymorphic locus of interest at X. 102 denotes the double stranded DNA with ligation adaptors added for universal amplification. 103 denotes the single stranded DNA that has been universally amplified with Forward primer B and Reverse Primer A hybridized. 104 denotes the PCR product from 103. 105 denotes the product from 104 with nested Forward primer b hybridized, and Reverse tag A already part of the molecule from the PCR that occurred between 103 and 104. 106 denotes the final PCR product.

Semi-Nested Mini-PCR:

(see FIG. 2) After STA 1 a second STA is performed comprising a multiplex set of internal nested Forward primers (103 B, 105 b) and one (or few) tag-specific Reverse primers (103 A). 101 denotes double stranded DNA with a polymorphic locus of interest at X. 102 denotes the double stranded DNA with ligation adaptors added for universal amplification. 103 denotes the single stranded DNA that has been universally amplified with Forward primer B and Reverse Primer A hybridized. 104 denotes the PCR product from 103. 105 denotes the product from 104 with nested Forward primer b hybridized, and Reverse tag A already part of the molecule from the PCR that occurred between 103 and 104. 106 denotes the final PCR product. With this workflow usually greater than 95% of sequences map to the intended targets. The nested primer may overlap with the outer Forward primer sequence but introduces additional 3'-end bases. In some embodiments it is possible to use between one and 20 extra 3' bases. Experiments have shown that using 9 or more extra 3' bases in a 1200-plex designs works well. As readily apparent, the primers for the second STA can alternatively be considered a multiplex set of internal nested Reverse primers and one (or a few) tag-specific Forward primers.

Figure 3:
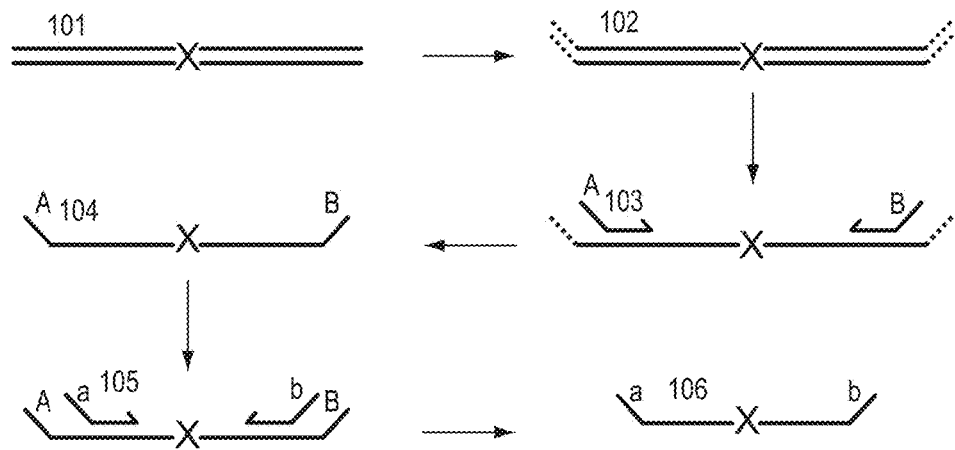
FIG. 3: Graphical representation of fully nested mini-PCR method. After STA step 1, it is possible to perform a second multiplex PCR (or parallel m.p. PCRs of reduced complexity) with two nested primers carrying tags (A, a, B, b). 101 denotes double stranded DNA with a polymorphic locus of interest at X. 102 denotes the double stranded DNA with ligation adaptors added for universal amplification. 103 denotes the single stranded DNA that has been universally amplified with Forward primer B and Reverse Primer A hybridized. 104 denotes the PCR product from 103. 105 denotes the product from 104 with nested Forward primer b and nested Reverse primer a hybridized. 106 denotes the final PCR product.

Fully Nested Mini-PCR:

(see FIG. 3) After STA step 1, it is possible to perform a second multiplex PCR (or parallel m.p. PCRs of reduced complexity) with two nested primers carrying tags (A, a, B, b). 101 denotes double stranded DNA with a polymorphic locus of interest at X. 102 denotes the double stranded DNA with ligation adaptors added for universal amplification. 103 denotes the single stranded DNA that has been universally amplified with Forward primer B and Reverse Primer A hybridized. 104 denotes the PCR product from 103. 105 denotes the product from 104 with nested Forward primer b and nested Reverse primer a hybridized. 106 denotes the final PCR product. In some embodiments, it is possible to use two full sets of primers. Experiments using a fully nested mini-PCR protocol were used to perform 146-plex amplification on single and three cells without step 102 of appending universal ligation adaptors and amplifying.

Figure 4:
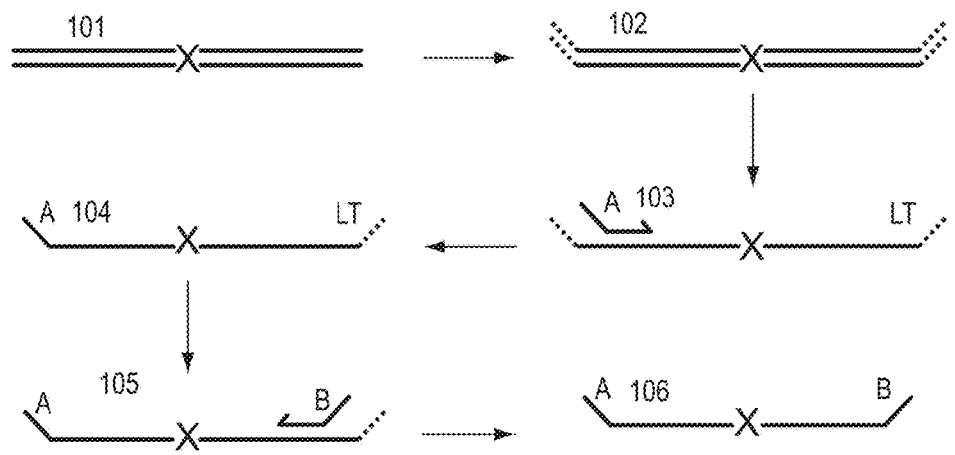
FIG. 4: Graphical representation of hemi-nested mini-PCR method. STA is performed comprising a multiplex set of Forward primers (B) and one (or few) tag-specific Reverse primers (A). A second STA can be performed using a universal tag-specific Forward primer and target specific Reverse primer. Forward primer and target specific Reverse primer. 101 denotes double stranded DNA with a polymorphic locus of interest at X. 102 denotes the double stranded DNA with ligation adaptors added for universal amplification. 103 denotes the single stranded DNA that has been universally amplified with Reverse Primer A hybridized. 104 denotes the PCR product from 103 that was amplified using Reverse primer A and ligation adaptor tag primer LT. 105 denotes the product from 104 with Forward primer B hybridized. 106 denotes the final PCR product.

Hemi-Nested Mini-PCR:

(see FIG. 4) It is possible to use target DNA that has and adaptors at the fragment ends. STA is performed comprising a multiplex set of Forward primers (B) and one (or few) tag-specific Reverse primers (A). A second STA can be performed using a universal tag-specific Forward primer and target specific Reverse primer. 101 denotes double stranded DNA with a polymorphic locus of interest at X. 102 denotes the double stranded DNA with ligation adaptors added for universal amplification. 103 denotes the single stranded DNA that has been universally amplified with Reverse Primer A hybridized. 104 denotes the PCR product from 103 that was amplified using Reverse primer A and ligation adaptor tag primer LT. 105 denotes the product from 104 with Forward primer B hybridized. 106 denotes the final PCR product. In this workflow, target specific Forward and Reverse primers are used in separate reactions, thereby reducing the complexity of the reaction and preventing dimer formation of forward and reverse primers. Note that in this example, primers A and B may be considered to be first primers, and primers 'a' and 'b' may be considered to be inner primers. This method is a big improvement on direct PCR as it is as good as direct PCR, but it avoids primer dimers. After first round of hemi nested protocol one typically sees ~99% non-targeted DNA, however, after second round there is typically a big improvement. As readily apparent, the primers for the first STA can be considered a multiplex set of Reverse primers and one (or few) tag-specific Forward primers, and the primers for the second STA can be considered a universal tag-specific Reverse primer and target specific Forward primer(s).

Figure 5:
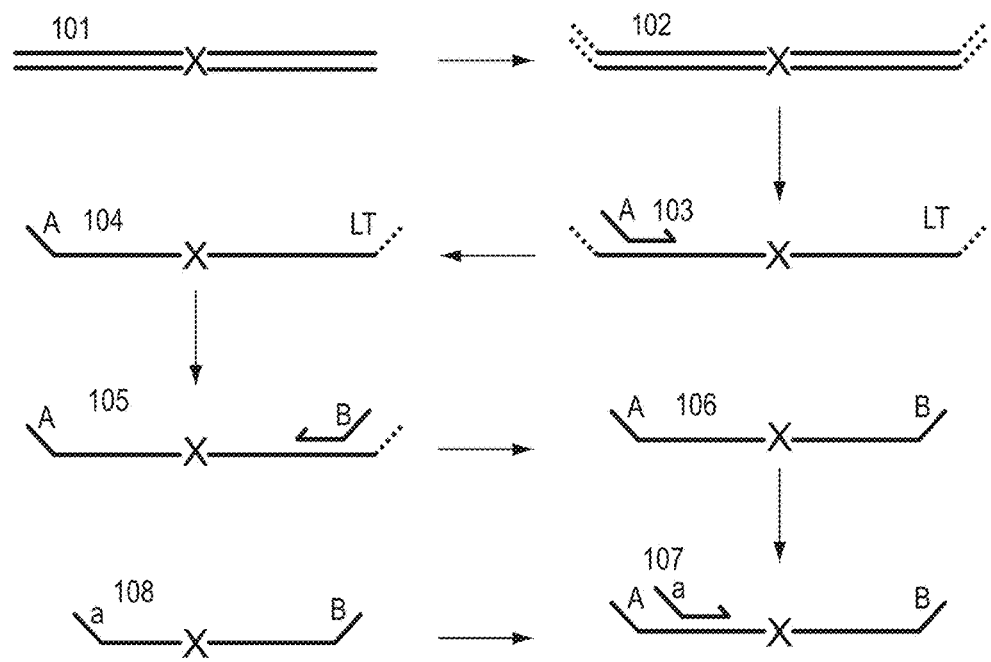
FIG. 5: Graphical representation of triply hemi-nested mini-PCR method. STA is performed comprising a multiplex set of Forward primers (B) and one (or few) tag-specific Reverse primers (A) and (a). A second STA can be performed using a universal tag-specific Forward primer and target specific Reverse primer. 101 denotes double stranded DNA with a polymorphic locus of interest at X. 102 denotes the double stranded DNA with ligation adaptors added for universal amplification. 103 denotes the single stranded DNA that has been universally amplified with Reverse Primer A hybridized. 104 denotes the PCR product from 103 that was amplified using Reverse primer A and ligation adaptor tag primer LT. 105 denotes the product from 104 with Forward primer B hybridized. 106 denotes the PCR product from 105 that was amplified using Reverse primer A and Forward primer B. 107 denotes the product from 106 with Reverse primer 'a' hybridized. 108 denotes the final PCR product.

Triply Hemi-Nested Mini-PCR:

(see FIG. 5) It is possible to use target DNA that has and adaptor at the fragment ends. STA is performed comprising a multiplex set of Forward primers (B) and one (or few) tag-specific Reverse primers (A) and (a). A second STA can be performed using a universal tag-specific Forward primer and target specific Reverse primer. 101 denotes double stranded DNA with a polymorphic locus of interest at X. 102 denotes the double stranded DNA with ligation adaptors added for universal amplification. 103 denotes the single stranded DNA that has been universally amplified with Reverse Primer A hybridized. 104 denotes the PCR product from 103 that was amplified using Reverse primer A and ligation adaptor tag primer LT. 105 denotes the product from 104 with Forward primer B hybridized. 106 denotes the PCR product from 105 that was amplified using Reverse primer A and Forward primer B. 107 denotes the product from 106 with Reverse primer 'a' hybridized. 108 denotes the final PCR product. Note that in this example, primers 'a' and B may be considered to be inner primers, and A may be considered to be a first primer. Optionally, both A and B may be considered to be first primers, and 'a' may be considered to be an inner primer. The designation of reverse and forward primers may be switched. In this workflow, target specific Forward and Reverse primers are used in separate reactions, thereby reducing the complexity of the reaction and preventing dimer formation of forward and reverse primers. This method is a big improvement on direct PCR as it is as good as direct PCR, but it avoids primer dimers. After first round of hemi nested protocol one typically sees ~99% non-targeted DNA, however, after second round there is typically a big improvement.

Figure 6:
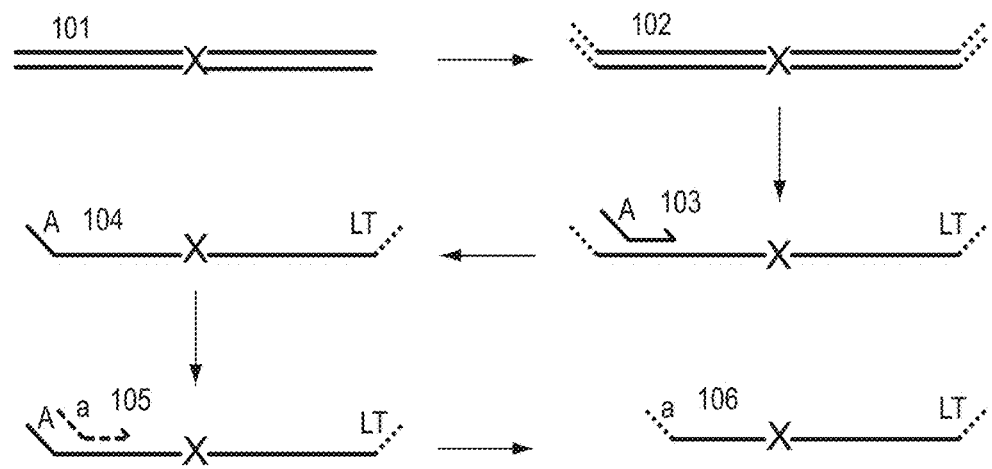
FIG. 6: Graphical representation of one-sided nested mini-PCR method. It is possible to use target DNA that has an adaptor at the fragment ends. STA may also be performed with a multiplex set of nested Forward primers and using the ligation adapter tag as the Reverse primer. A second STA may then be performed using a set of nested Forward primers and a universal Reverse primer. 101 denotes double stranded DNA with a polymorphic locus of interest at X. 102 denotes the double stranded DNA with ligation adaptors added for universal amplification. 103 denotes the single stranded DNA that has been universally amplified with Forward Primer A hybridized. 104 denotes the PCR product from 103 that was amplified using Forward primer A and ligation adaptor tag Reverse primer LT. 105 denotes the product from 104 with nested Forward primer a hybridized. 106 denotes the final PCR product.
Figure 7:
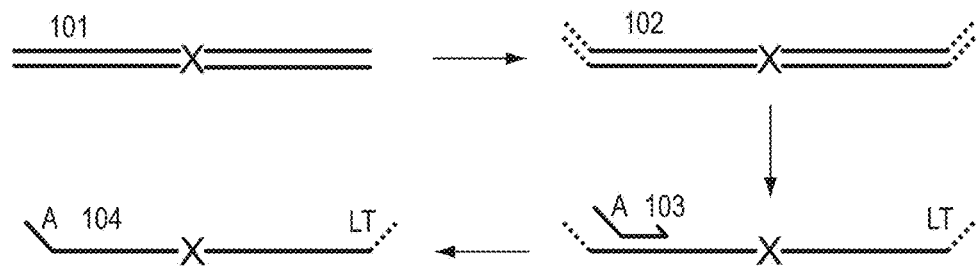
FIG. 7: Graphical representation of one-sided mini-PCR method. STA may be performed with a multiplex set of Forward primers and one (or few) tag-specific Reverse primer. 101 denotes double stranded DNA with a polymorphic locus of interest at X. 102 denotes the double stranded DNA with ligation adaptors added for universal amplification. 103 denotes the single stranded DNA with Forward Primer A hybridized. 104 denotes the PCR product from 103 that was amplified using Forward primer A and ligation adaptor tag Reverse primer LT, and which is the final PCR product.
Figure 8:
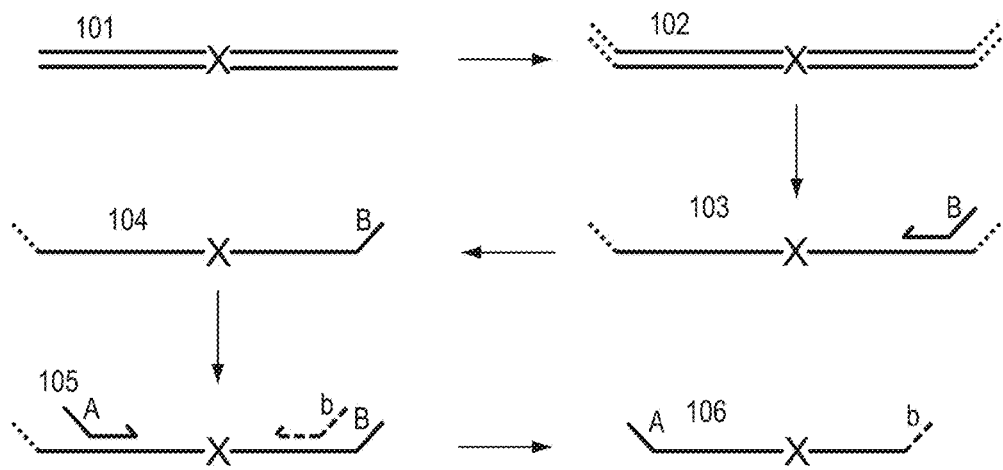
FIG. 8: Graphical representation of reverse semi-nested mini-PCR method. STA may be performed with a multiplex set of Forward primers and one (or few) tag-specific Reverse primer. 101 denotes double stranded DNA with a polymorphic locus of interest at X. 102 denotes the double stranded DNA with ligation adaptors added for universal amplification. 103 denotes the single stranded DNA with Reverse Primer B hybridized. 104 denotes the PCR product from 103 that was amplified using Reverse primer B and ligation adaptor tag Forward primer LT. 105 denotes the PCR product 104 with hybridized Forward Primer A, and inner Reverse primer 'b'. 106 denotes the PCR product that has been amplified from 105 using Forward primer A and Reverse primer 'b', and which is the final PCR product.

One-Sided Nested Mini-PCR:

(see FIG. 6) It is possible to use target DNA that has an adaptor at the fragment ends. STA may also be performed with a multiplex set of nested Forward primers and using the ligation adapter tag as the Reverse primer. A second STA may then be performed using a set of nested Forward primers and a universal Reverse primer. 101 denotes double stranded DNA with a polymorphic locus of interest at X. 102 denotes the double stranded DNA with ligation adaptors added for universal amplification. 103 denotes the single stranded DNA that has been universally amplified with Forward Primer A hybridized. 104 denotes the PCR product from 103 that was amplified using Forward primer A and ligation adaptor tag Reverse primer LT. 105 denotes the product from 104 with nested Forward primer a hybridized. 106 denotes the final PCR product. This method can detect shorter target sequences than standard PCR by using overlapping primers in the first and second STAs. The method is typically performed off a sample of DNA that has already undergone STA step 1 above—appending of universal tags and amplification; the two nested primers are only on one side, other side uses the library tag. The method was performed on libraries of apoptotic supernatants and pregnancy plasma. With this workflow around 60% of sequences mapped to the intended targets. Note that reads that contained the reverse adaptor sequence were not mapped, so this number is expected to be higher if those reads that contain the reverse adaptor sequence are mapped One-Sided Mini-PCR:

It is possible to use target DNA that has an adaptor at the fragment ends (see FIG. 7). STA may be performed with a multiplex set of Forward primers and one (or few) tag-specific Reverse primer. 101 denotes double stranded DNA with a polymorphic locus of interest at X. 102 denotes the double stranded DNA with ligation adaptors added for universal amplification. 103 denotes the single stranded DNA with Forward Primer A hybridized. 104 denotes the PCR product from 103 that was amplified using Forward primer A and ligation adaptor tag Reverse primer LT, and which is the final PCR product. This method can detect shorter target sequences than standard PCR. However it may be relatively unspecific, as only one target specific primer is used. This protocol is effectively half of the one sided nested mini PCR Reverse Semi-Nested Mini-PCR:

It is possible to use target DNA that has an adaptor at the fragment ends (see FIG. 8). STA may be performed with a multiplex set of Forward primers and one (or few) tag-specific Reverse primer. 101 denotes double stranded DNA with a polymorphic locus of interest at X. 102 denotes the double stranded DNA with ligation adaptors added for universal amplification. 103 denotes the single stranded DNA with Reverse Primer B hybridized. 104 denotes the PCR product from 103 that was amplified using Reverse primer B and ligation adaptor tag Forward primer LT. 105 denotes the PCR product 104 with hybridized Forward Primer A, and inner Reverse primer 'b'. 106 denotes the PCR product that has been amplified from 105 using Forward primer A and Reverse primer 'b', and which is the final PCR product. This method can detect shorter target sequences than standard PCR.

There also may be more variants that are simply iterations or combinations of the above methods such as doubly nested PCR, where three sets of primers are used. Another variant is one-and-a-half sided nested mini-PCR, where STA may also be performed with a multiplex set of nested Forward primers and one (or few) tag-specific Reverse primer.

Note that in all of these variants, the identity of the Forward primer and the Reverse primer may be interchanged. Note that in some embodiments, the nested variant can equally well be run without the initial library preparation that comprises appending the adapter tags, and a universal amplification step. Note that in some embodiments, additional rounds of PCR may be included, with additional Forward and/or Reverse primers and amplification steps; these additional steps may be particularly useful if it is desirable to further increase the percent of DNA molecules that correspond to the targeted loci.

Nesting Workflows

Figure 9:
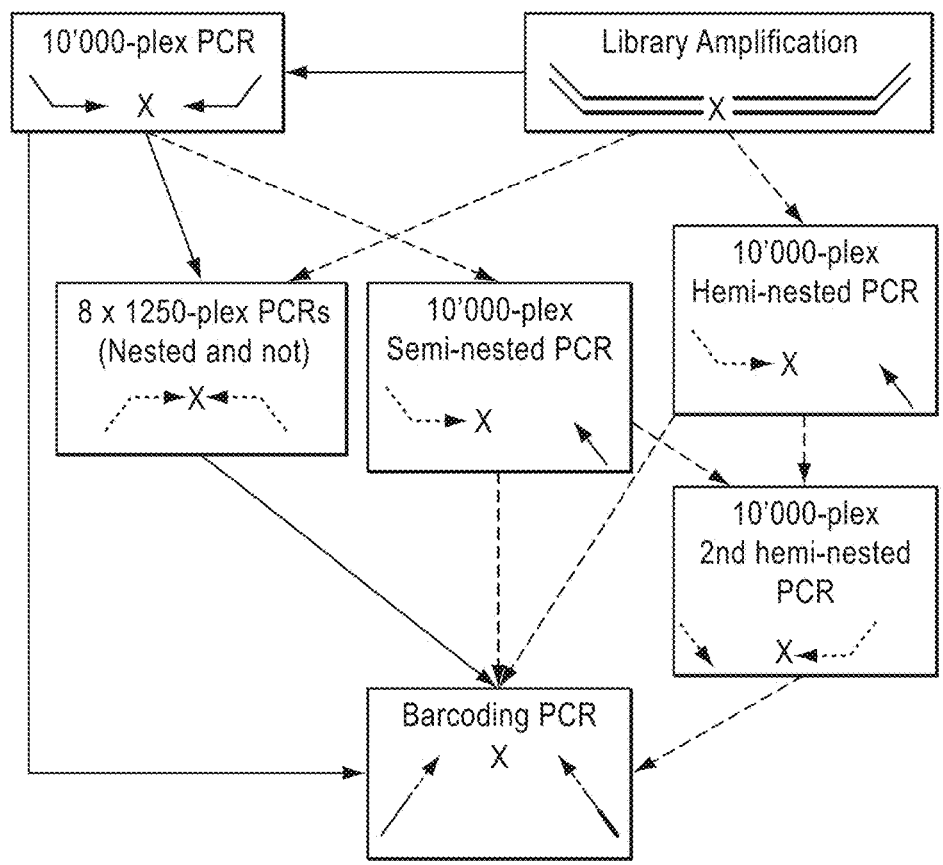
FIG. 9: Some possible workflows for semi-nested methods.

There are many ways to perform the amplification, with different degrees of nesting, and with different degrees of multiplexing. In FIG. 9, a flow chart is given with some of the possible workflows. Note that the use of 10,000-plex PCR is only meant to be an example; these flow charts would work equally well for other degrees of multiplexing.

Looped Ligation Adaptors

When adding universal tagged adaptors for example for the purpose of making a library for sequencing, there are a number of ways to ligate adaptors. One way is to blunt end the sample DNA, perform A-tailing, and ligate with adaptors that have a T-overhang. There are a number of other ways to ligate adaptors. There are also a number of adaptors that can be ligated. For example, a Y-adaptor can be used where the adaptor consists of two strands of DNA where one strand has a double strand region, and a region specified by a forward primer region, and where the other strand specified by a double strand region that is complementary to the double strand region on the first strand, and a region with a reverse primer. The double stranded region, when annealed, may contain a T-overhang for the purpose of ligating to double stranded DNA with an A overhang.

In an embodiment, the adaptor can be a loop of DNA where the terminal regions are complementary, and where the loop region contains a forward primer tagged region (LFT), a reverse primer tagged region (LRT), and a cleavage site between the two (See FIG. 10). 101 refers to the double stranded, blunt ended target DNA. 102 refers to the A-tailed target DNA. 103 refers to the looped ligation adaptor with T overhang 'T' and the cleavage site 'Z'. 104 refers to the target DNA with appended looped ligation adaptors. 105 refers to the target DNA with the ligation adaptors appended cleaved at the cleavage site. LFT refers to the ligation adaptor Forward tag, and the LRT refers to the ligation adaptor Reverse tag. The complementary region may end on a T overhang, or other feature that may be used for ligation to the target DNA. The cleavage site may be a series of uracils for cleavage by UNG, or a sequence that may be recognized and cleaved by a restriction enzyme or other method of cleavage or just a basic amplification. These adaptors can be uses for any library preparation, for example, for sequencing. These adaptors can be used in combination with any of the other methods described herein, for example the mini-PCR amplification methods.

Internally Tagged Primers

Figure 11:
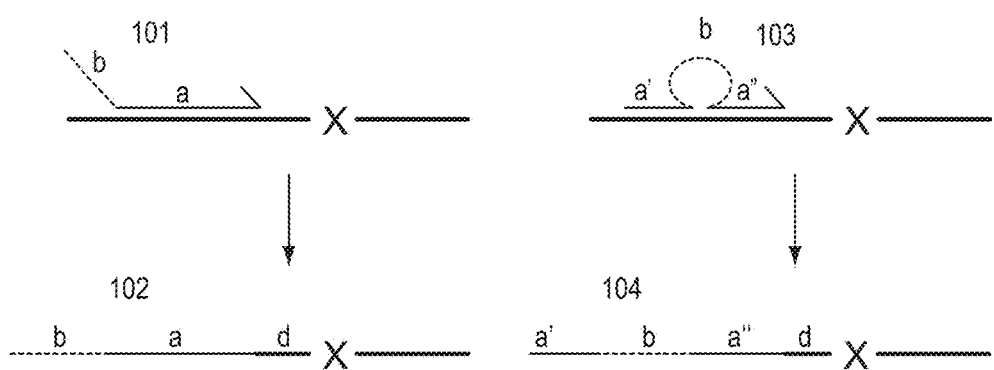
FIG. 11: Graphical representation of internally tagged primers. 101 refers to the single stranded target DNA with polymorphic locus of interest 'X', and primer 'a' with appended tag 'b'. Distance 'd' is distance between 'a' and 'X'. The primer binding site (a) is split in to a plurality of segments (a', a", a'" . . . ), and the sequence tag (b) is on a segment of DNA that is in the middle of two of the primer binding sites, see 103.

When using sequencing to determine the allele present at a given polymorphic locus, the sequence read typically begins upstream of the primer binding site (a), and then to the polymorphic site (X). Tags are typically configured as shown in FIG. 11, left. 101 refers to the single stranded target DNA with polymorphic locus of interest 'X', and primer 'a' with appended tag 'b'. In order to avoid nonspecific hybridization, the primer binding site (region of target DNA complementary to 'a') is typically 18 to 30 bp in length. Sequence tag 'b' is typically about 20 bp; in theory these can be any length longer than about 15 bp, though many people use the primer sequences that are sold by the sequencing platform company. The distance 'd' between 'a' and 'X' may be at least 2 bp so as to avoid allele bias. When performing multiplexed PCR amplification using the methods disclosed herein or other methods, where careful primer design is necessary to avoid excessive primer primer interaction, the window of allowable distance 'd' between 'a' and 'X' may vary quite a bit: from 2 bp to 10 bp, from 2 bp to 20 bp, from 2 bp to 30 bp, or even from 2 bp to more than 30 bp. Therefore, when using the primer configuration shown in FIG. 11, left, sequence reads must be a minimum of 40 bp to obtain reads long enough to measure the polymorphic locus, and depending on the lengths of 'a' and 'd' the sequence reads may need to be up to 60 or 75 bp. Usually, the longer the sequence reads, the higher the cost and time of sequencing a given number of reads, therefore, minimizing the necessary read length can save both time and money. In addition, since, on average, bases read earlier on the read are read more accurately than those read later on the read, decreasing the necessary sequence read length can also increase the accuracy of the measurements of the polymorphic region.

In an embodiment, termed internally tagged primers, the primer binding site (a) is split in to a plurality of segments (a', a", a'" . . . ), and the sequence tag (b) is on a segment of DNA that is in the middle of two of the primer binding sites, as shown in FIG. 11, 103. This configuration allows the sequencer to make shorter sequence reads. In an embodiment, a'+a" should be at least about 18 bp, and can be as long as 30, 40, 50, 60, 80, 100 or more than 100 bp. In an embodiment, a" should be at least about 6 bp, and in an embodiment is between about 8 and 16 bp. All other factors being equal, using the internally tagged primers can cut the length of the sequence reads needed by at least 6 bp, as much as 8 bp, 10 bp, 12 bp, 15 bp, and even by as many as 20 or 30 bp. This can result in a significant money, time and accuracy advantage. An example of internally tagged primers is given in FIG. 12.

Primers with Ligation Adaptor Binding Region

Figure 10:
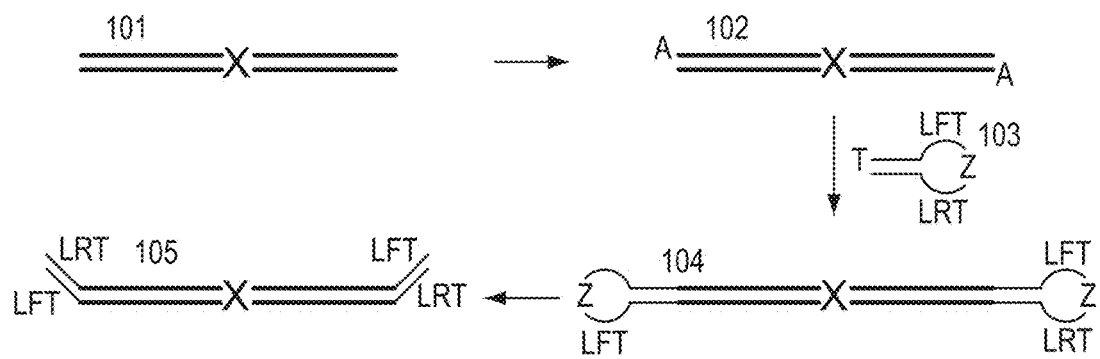
FIG. 10: Graphical representation of looped ligation adaptors. The adaptor can be a loop of DNA where the terminal regions are complementary, and where the loop region contains a forward primer tagged region (LFT), a reverse primer tagged region (LRT), and a cleavage site between the two. 101 refers to the double stranded, blunt ended target DNA. 102 refers to the A-tailed target DNA. 103 refers to the looped ligation adaptor with T overhang 'T' and the cleavage site 'Z'. 104 refers to the target DNA with appended looped ligation adaptors. 105 refers to the target DNA with the ligation adaptors appended cleaved at the cleavage site. LFT refers to the ligation adaptor Forward tag, and the LRT refers to the ligation adaptor Reverse tag.
Figure 13:
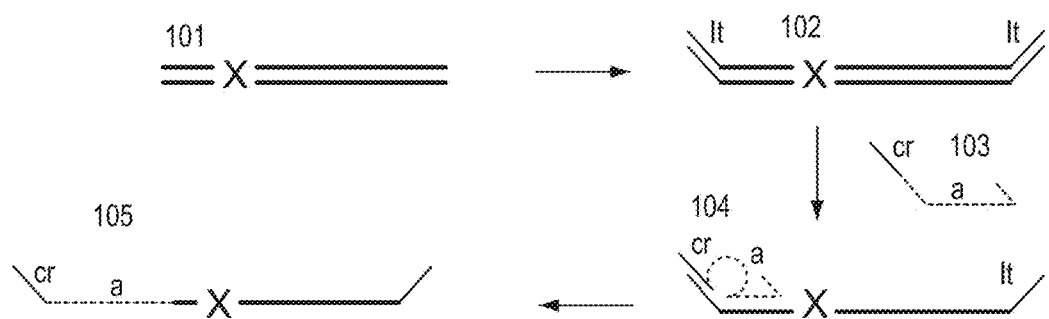
FIG. 13: Graphical representation of a method using primers with a ligation adaptor binding region. Target DNA 101 can have ligation adaptors appended 102, and the target primer 103 can have a region (cr) that is complementary to the ligation adaptor tag (lt) appended upstream of the designed binding region (a).

One issue with fragmented DNA is that since it is short in length, the chance that a polymorphism is close to the end of a DNA strand is higher than for a long strand (e.g. 101, FIG. 10). Since PCR capture of a polymorphism requires a primer binding site of suitable length on both sides of the polymorphism, a significant number of strands of DNA with the targeted polymorphism will be missed due to insufficient overlap between the primer and the targeted binding site. In an embodiment, the target DNA 101 can have ligation adaptors appended 102, and the target primer 103 can have a region (cr) that is complementary to the ligation adaptor tag (lt) appended upstream of the designed binding region (a) (see FIG. 13); thus in cases where the binding region (region of 101 that is complementary to a) is shorter than the 18 bp typically required for hybridization, the region (cr) on the primer than is complementary to the library tag is able to increase the binding energy to a point where the PCR can proceed. Note that any specificity that is lost due to a shorter binding region can be made up for by other PCR primers with suitably long target binding regions. Note that this embodiment can be used in combination with direct PCR, or any of the other methods described herein, such as nested PCR, semi nested PCR, hemi nested PCR, one sided nested or semi or hemi nested PCR, or other PCR protocols.

When using the sequencing data to determine ploidy in combination with an analytical method that involves comparing the observed allele data to the expected allele distributions for various hypotheses, each additional read from alleles with a low depth of read will yield more information than a read from an allele with a high depth of read. Therefore, ideally, one would wish to see uniform depth of read (DOR) where each locus will have a similar number of representative sequence reads. Therefore, it is desirable to minimize the DOR variance. In an embodiment, it is possible to decrease the coefficient of variance of the DOR (this may be defined as the standard deviation of the DOR/the average DOR) by increasing the annealing times. In some embodiments the annealing temperatures may be longer than 2 minutes, longer than 4 minutes, longer than ten minutes, longer than 30 minutes, and longer than one hour, or even longer. Since annealing is an equilibrium process, there is no limit to the improvement of DOR variance with increasing annealing times. In an embodiment, increasing the primer concentration may decrease the DOR variance.

Exemplary Amplification Methods

Improved PCR amplification methods have also been developed that minimize or prevent interference due to the amplification of nearby or adjacent target loci in the same reaction volume (such as part of the sample multiplex PCR reaction that simultaneously amplifies all the target loci) (see, U.S. Ser. No. 61/982,245, filed Apr. 21, 2014; U.S. Ser. No. 61/987,407, filed May 1, 2014, and U.S. Ser. No. 62/066,514, filed Oct. 21, 2014, which are each hereby incorporated by reference in its entirety). These methods can be used to simultaneously amplify nearby or adjacent target loci, which is faster and cheaper than having to separate nearby target loci into different reaction volumes so that they can be amplified separately to avoid interference. In particular embodiments, these methods are used to tile a region such that the amplicons include all the nucleotides in the region (such as an exon or all the exons of a gene such as cystic fibrosis).

In some embodiments, the amplification of target loci is performed using a polymerase (e.g., a DNA polymerase, RNA polymerase, or reverse transcriptase) with low 5'→3' exonuclease and/or low strand displacement activity. In some embodiments, the low level of 5'→3' exonuclease reduces or prevents the degradation of a nearby primer (e.g., an unextended primer or a primer that has had one or more nucleotides added to during primer extension). In some embodiments, the low level of strand displacement activity reduces or prevents the displacement of a nearby primer (e.g., an unextended primer or a primer that has had one or more nucleotides added to it during primer extension). In some embodiments, target loci that are adjacent to each other (e.g., no bases between the target loci) or nearby (e.g., loci are within 50, 40, 30, 20, 15, 10, 9, 8, 7, 6, 5, 4, 3, 2, or 1 base) are amplified. In some embodiments, the 3' end of one locus is within 50, 40, 30, 20, 15, 10, 9, 8, 7, 6, 5, 4, 3, 2, or 1 base of the 5' end of next downstream locus.

In some embodiments, at least 100, 200, 500, 750, 1,000; 2,000; 5,000; 7,500; 10,000; 15,000; 19,000; 20,000; 25,000; 27,000; 28,000; 30,000; 40,000; 50,000; 75,000; or 100,000 different target loci are amplified, such as by the simultaneous amplification in one reaction volume In some embodiments, at least 50, 60, 70, 80, 90, 95, 96, 97, 98, 99, or 99.5% of the amplified products are target amplicons. In various embodiments, the amount of amplified products that are target amplicons is between 50 to 99.5%, such as between 60 to 99%, 70 to 98%, 80 to 98%, 90 to 99.5%, or 95 to 99.5%, inclusive. In some embodiments, at least 50, 60, 70, 80, 90, 95, 96, 97, 98, 99, or 99.5% of the target loci are amplified (e.g, amplified at least 5, 10, 20, 30, 50, or 100-fold compared to the amount prior to amplification), such as by the simultaneous amplification in one reaction volume. In various embodiments, the amount target loci that are amplified (e.g, amplified at least 5, 10, 20, 30, 50, or 100-fold compared to the amount prior to amplification) is between 50 to 99.5%, such as between 60 to 99%, 70 to 98%, 80 to 99%, 90 to 99.5%, 95 to 99.9%, or 98 to 99.99% inclusive. In some embodiments, fewer non-target amplicons are produced, such as fewer amplicons formed from a forward primer from a first primer pair and a reverse primer from a second primer pair. Such undesired non-target amplicons can be produced using prior amplification methods if, e.g., the reverse primer from the first primer pair and/or the forward primer from the second primer pair are degraded and/or displaced.

In some embodiments, these methods allows longer extension times to be used since the polymerase bound to a primer being extended is less likely to degrade and/or displace a nearby primer (such as the next downstream primer) given the low 5'→3' exonuclease and/or low strand displacement activity of the polymerase. In various embodiments, reaction conditions (such as the extension time and temperature) are used such that the extension rate of the polymerase allows the number of nucleotides that are added to a primer being extended to be equal to or greater than 80, 90, 95, 100, 110, 120, 130, 140, 150, 175, or 200% of the number of nucleotides between the 3' end of the primer binding site and the 5'end of the next downstream primer binding site on the same strand.

In some embodiments, a DNA polymerase is used produce DNA amplicons using DNA as a template. In some embodiments, a RNA polymerase is used produce RNA amplicons using DNA as a template. In some embodiments, a reverse transcriptase is used produce cDNA amplicons using RNA as a template.

In some embodiments, the low level of 5'→3' exonuclease of the polymerase is less than 80, 70, 60, 50, 40, 30, 20, 10, 5, 1, or 0.1% of the activity of the same amount of *Thermus aquaticus* polymerase ("Taq" polymerase, which is a commonly used DNA polymerase from a thermophilic bacterium, PDB 1BGX, EC 2.7.7.7, Murali et al., "Crystal structure of Taq DNA polymerase in complex with an inhibitory Fab: the Fab is directed against an intermediate in the helix-coil dynamics of the enzyme," Proc. Natl. Acad. Sci. USA 95:12562-12567, 1998, which is hereby incorporated by reference in its entirety) under the same conditions. In some embodiments, the low level of strand displacement activity of the polymerase is less than 80, 70, 60, 50, 40, 30, 20, 10, 5, 1, or 0.1% of the activity of the same amount of Taq polymerase under the same conditions.

In some embodiments, the polymerase is a PUSHION DNA polymerase, such as PHUSION High Fidelity DNA polymerase (M0530S, New England BioLabs, Inc.) or PHUSION Hot Start Flex DNA polymerase (M0535S, New England BioLabs, Inc.; Frey and Suppman *BioChemica.* 2:34-35, 1995; Chester and Marshak *Analytical Biochemistry.* 209:284-290, 1993, which are each hereby incorporated by reference in its entirety). The PHUSION DNA polymerase is a *Pyrococcus*-like enzyme fused with a processivity-enhancing domain. PHUSION DNA polymerase possesses 5'→3' polymerase activity and 3'→5' exonuclease activity, and generates blunt-ended products. PHUSION DNA polymerase lacks 5'→3' exonuclease activity and strand displacement activity.

In some embodiments, the polymerase is a Q5® DNA Polymerase, such as Q5® High-Fidelity DNA Polymerase (M0491S, New England BioLabs, Inc.) or Q5® Hot Start High-Fidelity DNA Polymerase (M0493S, New England BioLabs, Inc.). Q5® High-Fidelity DNA polymerase is a high-fidelity, thermostable, DNA polymerase with 3'→5' exonuclease activity, fused to a processivity-enhancing Sso7d domain. Q5® High-Fidelity DNA polymerase lacks 5'→3' exonuclease activity and strand displacement activity.

In some embodiments, the polymerase is a T4 DNA polymerase (M0203S, New England BioLabs, Inc.; Tabor and Struh. (1989). "DNA-Dependent DNA Polymerases," In Ausebel et al. (Ed.), *Current Protocols in Molecular Biology.* 3.5.10-3.5.12. New York: John Wiley & Sons, Inc., 1989; Sambrook et al. *Molecular Cloning: A Laboratory Manual.* (2nd ed.), 5.44-5.47. Cold Spring Harbor: Cold Spring Harbor Laboratory Press, 1989, which are each hereby incorporated by reference in its entirety). T4 DNA Polymerase catalyzes the synthesis of DNA in the 5'→3' direction and requires the presence of template and primer. This enzyme has a 3'→5' exonuclease activity which is much more active than that found in DNA Polymerase I. T4 DNA polymerase lacks 5'→3' exonuclease activity and strand displacement activity.

In some embodiments, the polymerase is a *Sulfolobus* DNA Polymerase IV (M0327S, New England BioLabs, Inc.; (Boudsocq., et al. (2001). *Nucleic Acids Res.,* 29:4607-4616, 2001; McDonald, et al. (2006). *Nucleic Acids Res.,* 34:1102-1111, 2006, which are each hereby incorporated by reference in its entirety). *Sulfolobus* DNA Polymerase IV is a thermostable Y-family lesion-bypass DNA Polymerase that efficiently synthesizes DNA across a variety of DNA template lesions McDonald, J. P. et al. (2006). *Nucleic Acids Res.,* 34, 1102-1111, which is hereby incorporated by reference in its entirety). *Sulfolobus* DNA Polymerase IV lacks 5'→3' exonuclease activity and strand displacement activity.

In some embodiments, if a primer binds a region with a SNP, the primer may bind and amplify the different alleles with different efficiencies or may only bind and amplify one allele. For subjects who are heterozygous, one of the alleles may not be amplified by the primer. In some embodiments, a primer is designed for each allele. For example, if there are two alleles (e.g., a biallelic SNP), then two primers can be used to bind the same location of a target locus (e.g., a forward primer to bind the "A" allele and a forward primer to bind the "B" allele). Standard methods, such as the dbSNP database, can be used to determine the location of known SNPs, such as SNP hot spots that have a high heterozygosity rate.

In some embodiments, the amplicons are similar in size. In some embodiments, the range of the length of the target amplicons is less than 100, 75, 50, 25, 15, 10, or 5 nucleotides. In some embodiments (such as the amplification of target loci in fragmented DNA or RNA), the length of the target amplicons is between 50 and 100 nucleotides, such as between 60 and 80 nucleotides, or 60 and 75 nucleotides, inclusive. In some embodiments (such as the amplification of multiple target loci throughout an exon or gene), the length of the target amplicons is between 100 and 500 nucleotides, such as between 150 and 450 nucleotides, 200 and 400 nucleotides, 200 and 300 nucleotides, or 300 and 400 nucleotides, inclusive.

In some embodiments, multiple target loci are simultaneously amplified using a primer pair that includes a forward and reverse primer for each target locus to be amplified in that reaction volume. In some embodiments, one round of PCR is performed with a single primer per target locus, and then a second round of PCR is performed with a primer pair per target locus. For example, the first round of PCR may be performed with a single primer per target locus such that all the primers bind the same strand (such as using a forward primer for each target locus). This allows the PCR to amplify in a linear manner and reduces or eliminates amplification bias between amplicons due to sequence or length differences. In some embodiments, the amplicons are then amplified using a forward and reverse primer for each target locus.

Exemplary Whole Genome Amplification Methods

In some embodiments, a method of the present disclosure may involve amplifying DNA, such as the use of whole genome application to amplify a nucleic acid sample before amplifying just the target loci. Amplification of the DNA, a process which transforms a small amount of genetic material to a larger amount of genetic material that comprises a similar set of genetic data, can be done by a wide variety of methods, including, but not limited to polymerase chain reaction (PCR). One method of amplifying DNA is whole genome amplification (WGA). There are a number of methods available for WGA: ligation-mediated PCR (LM-PCR), degenerate oligonucleotide primer PCR (DOP-PCR), and multiple displacement amplification (MDA). In LM-PCR, short DNA sequences called adapters are ligated to blunt ends of DNA. These adapters contain universal amplification sequences, which are used to amplify the DNA by PCR. In DOP-PCR, random primers that also contain universal amplification sequences are used in a first round of annealing and PCR. Then, a second round of PCR is used to amplify the sequences further with the universal primer sequences. MDA uses the phi-29 polymerase, which is a highly processive and non-specific enzyme that replicates DNA and has been used for single-cell analysis. The major limitations to amplification of material from a single cell are (1) necessity of using extremely dilute DNA concentrations or extremely small volume of reaction mixture, and (2) difficulty of reliably dissociating DNA from proteins across the whole genome. Regardless, single-cell whole genome amplification has been used successfully for a variety of applications for a number of years. There are other methods of amplifying DNA from a sample of DNA. The DNA amplification transforms the initial sample of DNA into a sample of DNA that is similar in the set of sequences, but of much greater quantity. In some cases, amplification may not be required.

In some embodiments, DNA may be amplified using a universal amplification, such as WGA or MDA. In some embodiments, DNA may be amplified by targeted amplification, for example using targeted PCR, or circularizing probes. In some embodiments, the DNA may be preferentially enriched using a targeted amplification method, or a method that results in the full or partial separation of desired from undesired DNA, such as capture by hybridization approaches. In some embodiments, DNA may be amplified by using a combination of a universal amplification method and a preferential enrichment method. A fuller description of some of these methods can be found elsewhere in this document.

Exemplary Enrichment and Sequencing Methods

In an embodiment, a method disclosed herein uses selective enrichment techniques that preserve the relative allele frequencies that are present in the original sample of DNA at each target loci (e.g., each polymorphic locus) from a set of target loci (e.g., polymorphic loci). While enrichment is particularly advantageous for methods for analyzing polymorphic loci, these enrichment methods can be readily adapted for nonpolymorphic loci if desired. In some embodiments the amplification and/or selective enrichment technique may involve PCR such as ligation mediated PCR, fragment capture by hybridization, Molecular Inversion Probes, or other circularizing probes. In some embodiments, methods for amplification or selective enrichment may involve using probes where, upon correct hybridization to the target sequence, the 3-prime end or 5-prime end of a nucleotide probe is separated from the polymorphic site of the allele by a small number of nucleotides. This separation reduces preferential amplification of one allele, termed allele bias. This is an improvement over methods that involve using probes where the 3-prime end or 5-prime end of a correctly hybridized probe are directly adjacent to or very near to the polymorphic site of an allele. In an embodiment, probes in which the hybridizing region may or certainly contains a polymorphic site are excluded. Polymorphic sites at the site of hybridization can cause unequal hybridization or inhibit hybridization altogether in some alleles, resulting in preferential amplification of certain alleles. These embodiments are improvements over other methods that involve targeted amplification and/or selective enrichment in that they better preserve the original allele frequencies of the sample at each polymorphic locus, whether the sample is pure genomic sample from a single individual or mixture of individuals.

The use of a technique to enrich a sample of DNA at a set of target loci followed by sequencing as part of a method for non-invasive prenatal allele calling or ploidy calling may confer a number of unexpected advantages. In some embodiments of the present disclosure, the method involves measuring genetic data for use with an informatics based method, such as PARENTAL SUPPORT™ (PS). The ultimate outcome of some of the embodiments is the actionable genetic data of an embryo or a fetus. There are many methods that may be used to measure the genetic data of the individual and/or the related individuals as part of embodied methods. In an embodiment, a method for enriching the concentration of a set of targeted alleles is disclosed herein, the method comprising one or more of the following steps: targeted amplification of genetic material, addition of loci specific oligonucleotide probes, ligation of specified DNA strands, isolation of sets of desired DNA, removal of unwanted components of a reaction, detection of certain sequences of DNA by hybridization, and detection of the sequence of one or a plurality of strands of DNA by DNA sequencing methods. In some cases the DNA strands may refer to target genetic material, in some cases they may refer to primers, in some cases they may refer to synthesized sequences, or combinations thereof. These steps may be carried out in a number of different orders.

For example, a universal amplification step of the DNA prior to targeted amplification may confer several advantages, such as removing the risk of bottlenecking and reducing allelic bias. The DNA may be mixed an oligonucleotide probe that can hybridize with two neighboring regions of the target sequence, one on either side. After hybridization, the ends of the probe may be connected by adding a polymerase, a means for ligation, and any necessary reagents to allow the circularization of the probe. After circularization, an exonuclease may be added to digest to non-circularized genetic material, followed by detection of the circularized probe. The DNA may be mixed with PCR primers that can hybridize with two neighboring regions of the target sequence, one on either side. After hybridization, the ends of the probe may be connected by adding a polymerase, a means for ligation, and any necessary reagents to complete PCR amplification. Amplified or unamplified DNA may be targeted by hybrid capture probes that target a set of loci; after hybridization, the probe may be localized and separated from the mixture to provide a mixture of DNA that is enriched in target sequences.

The use of a method to target certain loci followed by sequencing as part of a method for allele calling or ploidy calling may confer a number of unexpected advantages. Some methods by which DNA may be targeted, or preferentially enriched, include using circularizing probes, linked inverted probes (LIPs, MIPs), capture by hybridization methods such as SURESELECT, and targeted PCR or ligation-mediated PCR amplification strategies.

In some embodiments, a method of the present disclosure involves measuring genetic data for use with an informatics based method, such as PARENTAL SUPPORT™ (PS), which is described further herein. PARENTAL SUPPORT™ is an informatics based approach to manipulating genetic data, aspects of which are described herein. The ultimate outcome of some of the embodiments is the actionable genetic data of an embryo or a fetus followed by a clinical decision based on the actionable data. The algorithms behind the PS method take the measured genetic data of the target individual, often an embryo or fetus, and the measured genetic data from related individuals, and are able to increase the accuracy with which the genetic state of the target individual is known. In an embodiment, the measured genetic data is used in the context of making ploidy determinations during prenatal genetic diagnosis. In an embodiment, the measured genetic data is used in the context of making ploidy determinations or allele calls on embryos during in vitro fertilization. There are many methods that may be used to measure the genetic data of the individual and/or the related individuals in the aforementioned contexts. The different methods comprise a number of steps, those steps often involving amplification of genetic material, addition of oligonucleotide probes, ligation of specified DNA strands, isolation of sets of desired DNA, removal of unwanted components of a reaction, detection of certain sequences of DNA by hybridization, detection of the sequence of one or a plurality of strands of DNA by DNA sequencing methods. In some cases the DNA strands may refer to target genetic material, in some cases they may refer to primers, in some cases they may refer to synthesized sequences, or combinations thereof. These steps may be carried out in a number of different orders.

Note that in theory it is possible to target any number loci in the genome, anywhere from one loci to well over one million loci. If a sample of DNA is subjected to targeting, and then sequenced, the percentage of the alleles that are read by the sequencer will be enriched with respect to their natural abundance in the sample. The degree of enrichment can be anywhere from one percent (or even less) to ten-fold, a hundred-fold, a thousand-fold or even many million-fold. In the human genome there are roughly 3 billion base pairs, and nucleotides, comprising approximately 75 million polymorphic loci. The more loci that are targeted, the smaller the degree of enrichment is possible. The fewer the number of loci that are targeted, the greater degree of enrichment is possible, and the greater depth of read may be achieved at those loci for a given number of sequence reads.

In an embodiment of the present disclosure, the targeting or preferential may focus entirely on SNPs. In an embodiment, the targeting or preferential may focus on any polymorphic site. A number of commercial targeting products are available to enrich exons. Surprisingly, targeting exclusively SNPs, or exclusively polymorphic loci, is particularly advantageous when using a method for NPD that relies on allele distributions. There are also published methods for NPD using sequencing, for example U.S. Pat. No. 7,888,017, involving a read count analysis where the read counting focuses on counting the number of reads that map to a given chromosome, where the analyzed sequence reads do not focused on regions of the genome that are polymorphic. Those types of methodology that do not focus on polymorphic alleles would not benefit as much from targeting or preferential enrichment of a set of alleles.

In an embodiment of the present disclosure, it is possible to use a targeting method that focuses on SNPs to enrich a genetic sample in polymorphic regions of the genome. In an embodiment, it is possible to focus on a small number of SNPs, for example between 1 and 100 SNPs, or a larger number, for example, between 100 and 1,000, between 1,000 and 10,000, between 10,000 and 100,000 or more than 100,000 SNPs. In an embodiment, it is possible to focus on one or a small number of chromosomes that are correlated with live trisomic births, for example chromosomes 13, 18, 21, X and Y, or some combination thereof. In an embodiment, it is possible to enrich the targeted SNPs by a small factor, for example between 1.01 fold and 100 fold, or by a larger factor, for example between 100 fold and 1,000,000 fold, or even by more than 1,000,000 fold. In an embodiment of the present disclosure, it is possible to use a targeting method to create a sample of DNA that is preferentially enriched in polymorphic regions of the genome. In an embodiment, it is possible to use this method to create a mixture of DNA with any of these characteristics where the mixture of DNA contains maternal DNA and also free floating fetal DNA. In an embodiment, it is possible to use this method to create a mixture of DNA that has any combination of these factors. For example, the method described herein may be used to produce a mixture of DNA that comprises maternal DNA and fetal DNA, and that is preferentially enriched in DNA that corresponds to 200 SNPs, all of which are located on either chromosome 18 or 21, and which are enriched an average of 1000 fold. In another example, it is possible to use the method to create a mixture of DNA that is preferentially enriched in 10,000 SNPs that are all or mostly located on chromosomes 13, 18, 21, X and Y, and the average enrichment per loci is greater than 500 fold. Any of the targeting methods described herein can be used to create mixtures of DNA that are preferentially enriched in certain loci.

In some embodiments, a method of the present disclosure further includes measuring the DNA in the mixed fraction using a high throughput DNA sequencer, where the DNA in the mixed fraction contains a disproportionate number of sequences from one or more chromosomes, wherein the one or more chromosomes are taken from the group comprising chromosome 13, chromosome 18, chromosome 21, chromosome X, chromosome Y and combinations thereof.

Described herein are three methods: multiplex PCR, targeted capture by hybridization, and linked inverted probes (LIPs), which may be used to obtain and analyze measurements from a sufficient number of polymorphic loci from a maternal plasma sample in order to detect fetal aneuploidy; this is not meant to exclude other methods of selective enrichment of targeted loci. Other methods may equally well be used without changing the essence of the method. In each case the polymorphism assayed may include single nucleotide polymorphisms (SNPs), small indels, or STRs. A preferred method involves the use of SNPs. Each approach produces allele frequency data; allele frequency data for each targeted locus and/or the joint allele frequency distributions from these loci may be analyzed to determine the ploidy of the fetus. Each approach has its own considerations due to the limited source material and the fact that maternal plasma consists of mixture of maternal and fetal DNA. This method may be combined with other approaches to provide a more accurate determination. In an embodiment, this method may be combined with a sequence counting approach such as that described in U.S. Pat. No. 7,888,017. The approaches described could also be used to detect fetal paternity noninvasively from maternal plasma samples. In addition each approach may be applied to other mixtures of DNA or pure DNA samples to detect the presence or absence of aneuploid chromosomes, to genotype a large number of SNP from degraded DNA samples, to detect segmental copy number variations (CNVs), to detect other genotypic states of interest, or some combination thereof.

Accurately Measuring the Allelic Distributions in a Sample

Current sequencing approaches can be used to estimate the distribution of alleles in a sample. One such method involves randomly sampling sequences from a pool DNA, termed shotgun sequencing. The proportion of a particular allele in the sequencing data is typically very low and can be determined by simple statistics. The human genome contains approximately 3 billion base pairs. So, if the sequencing method used make 100 bp reads, a particular allele will be measured about once in every 30 million sequence reads.

In an embodiment, a method of the present disclosure is used to determine the presence or absence of two or more different haplotypes that contain the same set of loci in a sample of DNA from the measured allele distributions of loci from that chromosome. The different haplotypes could represent two different homologous chromosomes from one individual, three different homologous chromosomes from a trisomic individual, three different homologous haplotypes from a mother and a fetus where one of the haplotypes is shared between the mother and the fetus, three or four haplotypes from a mother and fetus where one or two of the haplotypes are shared between the mother and the fetus, or other combinations. Alleles that are polymorphic between the haplotypes tend to be more informative, however any alleles where the mother and father are not both homozygous for the same allele will yield useful information through measured allele distributions beyond the information that is available from simple read count analysis.

Shotgun sequencing of such a sample, however, is extremely inefficient as it results in many sequences for regions that are not polymorphic between the different haplotypes in the sample, or are for chromosomes that are not of interest, and therefore reveal no information about the proportion of the target haplotypes. Described herein are methods that specifically target and/or preferentially enrich segments of DNA in the sample that are more likely to be polymorphic in the genome to increase the yield of allelic information obtained by sequencing. Note that for the measured allele distributions in an enriched sample to be truly representative of the actual amounts present in the target individual, it is critical that there is little or no preferential enrichment of one allele as compared to the other allele at a given loci in the targeted segments. Current methods known in the art to target polymorphic alleles are designed to ensure that at least some of any alleles present are detected. However, these methods were not designed for the purpose of measuring the unbiased allelic distributions of polymorphic alleles present in the original mixture. It is non-obvious that any particular method of target enrichment would be able to produce an enriched sample wherein the measured allele distributions would accurately represent the allele distributions present in the original unamplified sample better than any other method. While many enrichment methods may be expected, in theory, to accomplish such an aim, an ordinary person skilled in the art is well aware that there is a great deal of stochastic or deterministic bias in current amplification, targeting and other preferential enrichment methods. One embodiment of a method described herein allows a plurality of alleles found in a mixture of DNA that correspond to a given locus in the genome to be amplified, or preferentially enriched in a way that the degree of enrichment of each of the alleles is nearly the same. Another way to say this is that the method allows the relative quantity of the alleles present in the mixture as a whole to be increased, while the ratio between the alleles that correspond to each locus remains essentially the same as they were in the original mixture of DNA. For some reported methods, preferential enrichment of loci can result in allelic biases of more than 1%, more than 2%, more than 5% and even more than 10%. This preferential enrichment may be due to capture bias when using a capture by hybridization approach, or amplification bias which may be small for each cycle, but can become large when compounded over 20, 30 or 40 cycles. For the purposes of this disclosure, for the ratio to remain essentially the same means that the ratio of the alleles in the original mixture divided by the ratio of the alleles in the resulting mixture is between 0.95 and 1.05, between 0.98 and 1.02, between 0.99 and 1.01, between 0.995 and 1.005, between 0.998 and 1.002, between 0.999 and 1.001, or between 0.9999 and 1.0001. Note that the calculation of the allele ratios presented here may not be used in the determination of the ploidy state of the target individual, and may only a metric to be used to measure allelic bias.

In an embodiment, once a mixture has been preferentially enriched at the set of target loci, it may be sequenced using any one of the previous, current, or next generation of sequencing instruments that sequences a clonal sample (a sample generated from a single molecule; examples include ILLUMINA GAIIx, ILLUMINA HiSEQ, LIFE TECHNOLOGIES SOLiD, 5500XL). The ratios can be evaluated by sequencing through the specific alleles within the targeted region. These sequencing reads can be analyzed and counted according the allele type and the rations of different alleles determined accordingly. For variations that are one to a few bases in length, detection of the alleles will be performed by sequencing and it is essential that the sequencing read span the allele in question in order to evaluate the allelic composition of that captured molecule. The total number of captured molecules assayed for the genotype can be increased by increasing the length of the sequencing read. Full sequencing of all molecules would guarantee collection of the maximum amount of data available in the enriched pool. However, sequencing is currently expensive, and a method that can measure allele distributions using a lower number of sequence reads will have great value. In addition, there are technical limitations to the maximum possible length of read as well as accuracy limitations as read lengths increase. The alleles of greatest utility will be of one to a few bases in length, but theoretically any allele shorter than the length of the sequencing read can be used. While allele variations come in all types, the examples provided herein focus on SNPs or variants contained of just a few neighboring base pairs. Larger variants such as segmental copy number variants can be detected by aggregations of these smaller variations in many cases as whole collections of SNP internal to the segment are duplicated. Variants larger than a few bases, such as STRs require special consideration and some targeting approaches work while others will not.

There are multiple targeting approaches that can be used to specifically isolate and enrich a one or a plurality of variant positions in the genome. Typically, these rely on taking advantage of the invariant sequence flanking the variant sequence. There are reports by others related to targeting in the context of sequencing where the substrate is maternal plasma (see, e.g., Liao et al., Clin. Chem. 2011; 57(1): pp. 92-101). However, these approaches use targeting probes that target exons, and do not focus on targeting polymorphic regions of the genome. In an embodiment, a method of the present disclosure involves using targeting probes that focus exclusively or almost exclusively on polymorphic regions. In an embodiment, a method of the present disclosure involves using targeting probes that focus exclusively or almost exclusively on SNPs. In some embodiments of the present disclosure, the targeted polymorphic sites consist of at least 10% SNPs, at least 20% SNPs, at least 30% SNPs, at least 40% SNPs, at least 50% SNPs, at least 60% SNPs, at least 70% SNPs, at least 80% SNPs, at least 90% SNPs, at least 95% SNPs, at least 98% SNPs, at least 99% SNPs, at least 99.9% SNPs, or exclusively SNPs.

In an embodiment, a method of the present disclosure can be used to determine genotypes (base composition of the DNA at specific loci) and relative proportions of those genotypes from a mixture of DNA molecules, where those DNA molecules may have originated from one or a number of genetically distinct individuals. In an embodiment, a method of the present disclosure can be used to determine the genotypes at a set of polymorphic loci, and the relative ratios of the amount of different alleles present at those loci. In an embodiment the polymorphic loci may consist entirely of SNPs. In an embodiment, the polymorphic loci can comprise SNPs, single tandem repeats, and other polymorphisms. In an embodiment, a method of the present disclosure can be used to determine the relative distributions of alleles at a set of polymorphic loci in a mixture of DNA, where the mixture of DNA comprises DNA that originates from a mother, and DNA that originates from a fetus. In an embodiment, the joint allele distributions can be determined on a mixture of DNA isolated from blood from a pregnant woman. In an embodiment, the allele distributions at a set of loci can be used to determine the ploidy state of one or more chromosomes on a gestating fetus.

In an embodiment, the mixture of DNA molecules could be derived from DNA extracted from multiple cells of one individual. In an embodiment, the original collection of cells from which the DNA is derived may comprise a mixture of diploid or haploid cells of the same or of different genotypes, if that individual is mosaic (germline or somatic). In an embodiment, the mixture of DNA molecules could also be derived from DNA extracted from single cells. In an embodiment, the mixture of DNA molecules could also be derived from DNA extracted from mixture of two or more cells of the same individual, or of different individuals. In an embodiment, the mixture of DNA molecules could be derived from DNA isolated from biological material that has already liberated from cells such as blood plasma, which is known to contain cell free DNA. In an embodiment, the this biological material may be a mixture of DNA from one or more individuals, as is the case during pregnancy where it has been shown that fetal DNA is present in the mixture. In an embodiment, the biological material could be from a mixture of cells that were found in maternal blood, where some of the cells are fetal in origin. In an embodiment, the biological material could be cells from the blood of a pregnant which have been enriched in fetal cells.

Circularizing Probes

Some embodiments of the present disclosure involve the use of "Linked Inverted Probes" (LIPs), which have been previously described in the literature, to amplify the target loci before or after amplification using primers that are not LIPs in the multiplex PCR methods of the invention. LIPs is a generic term meant to encompass technologies that involve the creation of a circular molecule of DNA, where the probes are designed to hybridize to targeted region of DNA on either side of a targeted allele, such that addition of appropriate polymerases and/or ligases, and the appropriate conditions, buffers and other reagents, will complete the complementary, inverted region of DNA across the targeted allele to create a circular loop of DNA that captures the information found in the targeted allele. LIPs may also be called pre-circularized probes, pre-circularizing probes, or circularizing probes. The LIPs probe may be a linear DNA molecule between 50 and 500 nucleotides in length, and in an embodiment between 70 and 100 nucleotides in length; in some embodiments, it may be longer or shorter than described herein. Others embodiments of the present disclosure involve different incarnations, of the LIPs technology, such as Padlock Probes and Molecular Inversion Probes (MIPs).

One method to target specific locations for sequencing is to synthesize probes in which the 3' and 5' ends of the probes anneal to target DNA at locations adjacent to and on either side of the targeted region, in an inverted manner, such that the addition of DNA polymerase and DNA ligase results in extension from the 3' end, adding bases to single stranded probe that are complementary to the target molecule (gap-fill), followed by ligation of the new 3' end to the 5' end of the original probe resulting in a circular DNA molecule that can be subsequently isolated from background DNA. The probe ends are designed to flank the targeted region of interest. One aspect of this approach is commonly called MIPS and has been used in conjunction with array technologies to determine the nature of the sequence filled in. One drawback to the use of MIPs in the context of measuring allele ratios is that the hybridization, circularization and amplification steps do not happed at equal rates for different alleles at the same loci. This results in measured allele ratios that are not representative of the actual allele ratios present in the original mixture.

In an embodiment, the circularizing probes are constructed such that the region of the probe that is designed to hybridize upstream of the targeted polymorphic locus and the region of the probe that is designed to hybridize downstream of the targeted polymorphic locus are covalently connected through a non-nucleic acid backbone. This backbone can be any biocompatible molecule or combination of biocompatible molecules. Some examples of possible biocompatible molecules are poly(ethylene glycol), polycarbonates, polyurethanes, polyethylenes, polypropylenes, sulfone polymers, silicone, cellulose, fluoropolymers, acrylic compounds, styrene block copolymers, and other block copolymers.

In an embodiment of the present disclosure, this approach has been modified to be easily amenable to sequencing as a means of interrogating the filled in sequence. In order to retain the original allelic proportions of the original sample at least one key consideration must be taken into account. The variable positions among different alleles in the gap-fill region must not be too close to the probe binding sites as there can be initiation bias by the DNA polymerase resulting in differential of the variants. Another consideration is that additional variations may be present in the probe binding sites that are correlated to the variants in the gap-fill region which can result unequal amplification from different alleles. In an embodiment of the present disclosure, the 3' ends and 5' ends of the pre-circularized probe are designed to hybridize to bases that are one or a few positions away from the variant positions (polymorphic sites) of the targeted allele. The number of bases between the polymorphic site (SNP or otherwise) and the base to which the 3' end and/or 5' of the pre-circularized probe is designed to hybridize may be one base, it may be two bases, it may be three bases, it may be four bases, it may be five bases, it may be six bases, it may be seven to ten bases, it may be eleven to fifteen bases, or it may be sixteen to twenty bases, twenty to thirty bases, or thirty to sixty bases. The forward and reverse primers may be designed to hybridize a different number of bases away from the polymorphic site. Circularizing probes can be generated in large numbers with current DNA synthesis technology allowing very large numbers of probes to be generated and potentially pooled, enabling interrogation of many loci simultaneously. It has been reported to work with more than 300,000 probes. Two papers that discuss a method involving circularizing probes that can be used to measure the genomic data of the target individual include: Porreca et al., Nature Methods, 2007 4(11), pp. 931-936; and also Turner et al., Nature Methods, 2009, 6(5), pp. 315-316. The methods described in these papers may be used in combination with other methods described herein. Certain steps of the method from these two papers may be used in combination with other steps from other methods described herein.

In some embodiments of the methods disclosed herein, the genetic material of the target individual is optionally amplified, followed by hybridization of the pre-circularized probes, performing a gap fill to fill in the bases between the two ends of the hybridized probes, ligating the two ends to form a circularized probe, and amplifying the circularized probe, using, for example, rolling circle amplification. Once the desired target allelic genetic information is captured by circularizing appropriately designed oligonucleotide probes, such as in the LIPs system, the genetic sequence of the circularized probes may be being measured to give the desired sequence data. In an embodiment, the appropriately designed oligonucleotides probes may be circularized directly on unamplified genetic material of the target individual, and amplified afterwards. Note that a number of amplification procedures may be used to amplify the original genetic material, or the circularized LIPs, including rolling circle amplification, MDA, or other amplification protocols. Different methods may be used to measure the genetic information on the target genome, for example using high throughput sequencing, Sanger sequencing, other sequencing methods, capture-by-hybridization, capture-by-circularization, multiplex PCR, other hybridization methods, and combinations thereof.

Once the genetic material of the individual has been measured using one or a combination of the above methods, an informatics based method, such as the PARENTAL SUPPORT™ method, along with the appropriate genetic measurements, can then be used to determination the ploidy state of one or more chromosomes on the individual, and/or the genetic state of one or a set of alleles, specifically those alleles that are correlated with a disease or genetic state of interest. Note that the use of LIPs has been reported for multiplexed capture of genetic sequences, followed by genotyping with sequencing. However, the use of sequencing data resulting from a LIPs-based strategy for the amplification of the genetic material found in a single cell, a small number of cells, or extracellular DNA, has not been used for the purpose of determining the ploidy state of a target individual.

Applying an informatics based method to determine the ploidy state of an individual from genetic data as measured by hybridization arrays, such as the ILLUMINA INFINIUM array, or the AFFYMETRIX gene chip has been described in documents references elsewhere in this document. However, the method described herein shows improvements over methods described previously in the literature. For example, the LIPs based approach followed by high throughput sequencing unexpectedly provides better genotypic data due to the approach having better capacity for multiplexing, better capture specificity, better uniformity, and low allelic bias. Greater multiplexing allows more alleles to be targeted, giving more accurate results. Better uniformity results in more of the targeted alleles being measured, giving more accurate results. Lower rates of allelic bias result in lower rates of miscalls, giving more accurate results. More accurate results result in an improvement in clinical outcomes, and better medical care.

It is important to note that LIPs may be used as a method for targeting specific loci in a sample of DNA for genotyping by methods other than sequencing. For example, LIPs may be used to target DNA for genotyping using SNP arrays or other DNA or RNA based microarrays.

Ligation-Mediated PCR

Ligation-mediated PCR may be used to amplify the target loci before or after PCR amplification using primers that are not ligated. Ligation-mediated PCR is a method of PCR used to preferentially enrich a sample of DNA by amplifying one or a plurality of loci in a mixture of DNA, the method comprising: obtaining a set of primer pairs, where each primer in the pair contains a target specific sequence and a non-target sequence, where the target specific sequence is preferably designed to anneal to a target region, one upstream and one downstream from the polymorphic site, and which can be separated from the polymorphic site by 0, 1, 2, 3, 4, 5, 6, 7, 8, 9, 10, 11-20, 21-30, 31-40, 41-50, 51-100, or more than 100; polymerization of the DNA from the 3-prime end of upstream primer to the fill the single strand region between it and the 5-prime end of the downstream primer with nucleotides complementary to the target molecule; ligation of the last polymerized base of the upstream primer to the adjacent 5-prime base of the downstream primer; and amplification of only polymerized and ligated molecules using the non-target sequences contained at the 5-prime end of the upstream primer and the 3-prime end of the downstream primer. Pairs of primers to distinct targets may be mixed in the same reaction. The non-target sequences serve as universal sequences such that of all pairs of primers that have been successfully polymerized and ligated may be amplified with a single pair of amplification primers.

Capture by Hybridization

In some embodiments, a method of the present disclosure may involve using any of the following capture by hybridization methods in addition to using multiplex PCR to amplify the target loci. Preferential enrichment of a specific set of sequences in a target genome can be accomplished in a number of ways. Elsewhere in this document is a description of how LIPs can be used to target a specific set of sequences, but in all of those applications, other targeting and/or preferential enrichment methods can be used equally well for the same ends. One example of another targeting method is the capture by hybridization approach. Some examples of commercial capture by hybridization technologies include AGILENT's SURE SELECT and ILLUMINA's TRUSEQ. In capture by hybridization, a set of oligonucleotides that is complimentary or mostly complimentary to the desired targeted sequences is allowed to hybridize to a mixture of DNA, and then physically separated from the mixture. Once the desired sequences have hybridized to the targeting oligonucleotides, the effect of physically removing the targeting oligonucleotides is to also remove the targeted sequences. Once the hybridized oligos are removed, they can be heated to above their melting temperature and they can be amplified. Some ways to physically remove the targeting oligonucleotides is by covalently bonding the targeting oligos to a solid support, for example a magnetic bead, or a chip. Another way to physically remove the targeting oligonucleotides is by covalently bonding them to a molecular moiety with a strong affinity for another molecular moiety. An example of such a molecular pair is biotin and streptavidin, such as is used in SURE SELECT. Thus that targeted sequences could be covalently attached to a biotin molecule, and after hybridization, a solid support with streptavidin affixed can be used to pull down the biotinylated oligonucleotides, to which are hybridized to the targeted sequences.

Hybrid capture involves hybridizing probes that are complementary to the targets of interest to the target molecules. Hybrid capture probes were originally developed to target and enrich large fractions of the genome with relative uniformity between targets. In that application, it was important that all targets be amplified with enough uniformity that all regions could be detected by sequencing, however, no regard was paid to retaining the proportion of alleles in original sample. Following capture, the alleles present in the sample can be determined by direct sequencing of the captured molecules. These sequencing reads can be analyzed and counted according the allele type. However, using the current technology, the measured allele distributions the captured sequences are typically not representative of the original allele distributions.

In an embodiment, detection of the alleles is performed by sequencing. In order to capture the allele identity at the polymorphic site, it is essential that the sequencing read span the allele in question in order to evaluate the allelic composition of that captured molecule. Since the capture molecules are often of variable lengths upon sequencing cannot be guaranteed to overlap the variant positions unless the entire molecule is sequenced. However, cost considerations as well as technical limitations as to the maximum possible length and accuracy of sequencing reads make sequencing the entire molecule unfeasible. In an embodiment, the read length can be increased from about 30 to about 50 or about 70 bases can greatly increase the number of reads that overlap the variant positions within the targeted sequences.

Another way to increase the number of reads that interrogate the position of interest is to decrease the length of the probe, as long as it does not result in bias in the underlying enriched alleles. The length of the synthesized probe should be long enough such that two probes designed to hybridize to two different alleles found at one locus will hybridize with near equal affinity to the various alleles in the original sample. Currently, methods known in the art describe probes that are typically longer than 120 bases. In a current embodiment, if the allele is one or a few bases then the capture probes may be less than about 110 bases, less than about 100 bases, less than about 90 bases, less than about 80 bases, less than about 70 bases, less than about 60 bases, less than about 50 bases, less than about 40 bases, less than about 30 bases, and less than about 25 bases, and this is sufficient to ensure equal enrichment from all alleles. When the mixture of DNA that is to be enriched using the hybrid capture technology is a mixture comprising free floating DNA isolated from blood, for example maternal blood, the average length of DNA is quite short, typically less than 200 bases. The use of shorter probes results in a greater chance that the hybrid capture probes will capture desired DNA fragments. Larger variations may require longer probes. In an embodiment, the variations of interest are one (a SNP) to a few bases in length. In an embodiment, targeted regions in the genome can be preferentially enriched using hybrid capture probes wherein the hybrid capture probes are of a length below 90 bases, and can be less than 80 bases, less than 70 bases, less than 60 bases, less than 50 bases, less than 40 bases, less than 30 bases, or less than 25 bases. In an embodiment, to increase the chance that the desired allele is sequenced, the length of the probe that is designed to hybridize to the regions flanking the polymorphic allele location can be decreased from above 90 bases, to about 80 bases, or to about 70 bases, or to about 60 bases, or to about 50 bases, or to about 40 bases, or to about 30 bases, or to about 25 bases.

There is a minimum overlap between the synthesized probe and the target molecule in order to enable capture. This synthesized probe can be made as short as possible while still being larger than this minimum required overlap. The effect of using a shorter probe length to target a polymorphic region is that there will be more molecules that overlap the target allele region. The state of fragmentation of the original DNA molecules also affects the number of reads that will overlap the targeted alleles. Some DNA samples such as plasma samples are already fragmented due to biological processes that take place in vivo. However, samples with longer fragments by benefit from fragmentation prior to sequencing library preparation and enrichment. When both probes and fragments are short (~60-80 bp) maximum specificity may be achieved relatively few sequence reads failing to overlap the critical region of interest.

In an embodiment, the hybridization conditions can be adjusted to maximize uniformity in the capture of different alleles present in the original sample. In an embodiment, hybridization temperatures are decreased to minimize differences in hybridization bias between alleles. Methods known in the art avoid using lower temperatures for hybridization because lowering the temperature has the effect of increasing hybridization of probes to unintended targets. However, when the goal is to preserve allele ratios with maximum fidelity, the approach of using lower hybridization temperatures provides optimally accurate allele ratios, despite the fact that the current art teaches away from this approach. Hybridization temperature can also be increased to require greater overlap between the target and the synthesized probe so that only targets with substantial overlap of the targeted region are captured. In some embodiments of the present disclosure, the hybridization temperature is lowered from the normal hybridization temperature to about 40° C., to about 45° C., to about 50° C., to about 55° C., to about 60° C., to about 65, or to about 70° C.

In an embodiment, the hybrid capture probes can be designed such that the region of the capture probe with DNA that is complementary to the DNA found in regions flanking the polymorphic allele is not immediately adjacent to the polymorphic site. Instead, the capture probe can be designed such that the region of the capture probe that is designed to hybridize to the DNA flanking the polymorphic site of the target is separated from the portion of the capture probe that will be in van der Waals contact with the polymorphic site by a small distance that is equivalent in length to one or a small number of bases. In an embodiment, the hybrid capture probe is designed to hybridize to a region that is flanking the polymorphic allele but does not cross it; this may be termed a flanking capture probe. The length of the flanking capture probe may be less than about 120 bases, less than about 110 bases, less than about 100 bases, less than about 90 bases, and can be less than about 80 bases, less than about 70 bases, less than about 60 bases, less than about 50 bases, less than about 40 bases, less than about 5 bases, or less than about 25 bases. The region of the genome that is targeted by the flanking capture probe may be separated by the polymorphic locus by 1, 2, 3, 4, 5, 6, 7, 8, 9, 10, 11-20, or more than 20 base pairs.

Description of a targeted capture based disease screening test using targeted sequence capture. Custom targeted sequence capture, like those currently offered by AGILENT (SURE SELECT), ROCHE-NIMBLEGEN, or ILLUMINA. Capture probes could be custom designed to ensure capture of various types of mutations. For point mutations, one or more probes that overlap the point mutation should be sufficient to capture and sequence the mutation.

For small insertions or deletions, one or more probes that overlap the mutation may be sufficient to capture and sequence fragments comprising the mutation. Hybridization may be less efficient between the probe-limiting capture efficiency, typically designed to the reference genome sequence. To ensure capture of fragments comprising the mutation one could design two probes, one matching the normal allele and one matching the mutant allele. A longer probe may enhance hybridization. Multiple overlapping probes may enhance capture. Finally, placing a probe immediately adjacent to, but not overlapping, the mutation may permit relatively similar capture efficiency of the normal and mutant alleles.

For Simple Tandem Repeats (STRs), a probe overlapping these highly variable sites is unlikely to capture the fragment well. To enhance capture a probe could be placed adjacent to, but not overlapping the variable site. The fragment could then be sequenced as normal to reveal the length and composition of the STR.

For large deletions, a series of overlapping probes, a common approach currently used in exon capture systems may work. However, with this approach it may be difficult to determine whether or not an individual is heterozygous. Targeting and evaluating SNPs within the captured region could potentially reveal loss of heterozygosity across the region indicating that an individual is a carrier. In an embodiment, it is possible to place non-overlapping or singleton probes across the potentially deleted region and use the number of fragments captured as a measure of heterozygosity. In the case where an individual caries a large deletion, one-half the number of fragments are expected to be available for capture relative to a non-deleted (diploid) reference locus. Consequently, the number of reads obtained from the deleted regions should be roughly half that obtained from a normal diploid locus. Aggregating and averaging the sequencing read depth from multiple singleton probes across the potentially deleted region may enhance the signal and improve confidence of the diagnosis. The two approaches, targeting SNPs to identify loss of heterozygosity and using multiple singleton probes to obtain a quantitative measure of the quantity of underlying fragments from that locus can also be combined. Either or both of these strategies may be combined with other strategies to better obtain the same end.

If during testing cfDNA detection of a male fetus, as indicated by the presence of the Y-chromosome fragments, captured and sequenced in the same test, and either an X-linked dominant mutation where mother and father are unaffected, or a dominant mutation where mother is not affected would indicated heighted risk to the fetus. Detection of two mutant recessive alleles within the same gene in an unaffected mother would imply the fetus had inherited a mutant allele from father and potentially a second mutant allele from mother. In all cases, follow-up testing by amniocentesis or chorionic villus sampling may be indicated.

A targeted capture based disease screening test could be combined with a targeted capture based non-invasive prenatal diagnostic test for aneuploidy.

There are a number of ways to decrease depth of read (DOR) variability: for example, one could increase primer concentrations, one could use longer targeted amplification probes, or one could run more STA cycles (such as more than 25, more than 30, more than 35, or even more than 40) Exemplary Methods of Determining the Number of DNA Molecules in a Sample.

A method is described herein to determine the number of DNA molecules in a sample by generating a uniquely identified molecule for each original DNA molecules in the sample during the first round of DNA amplification. Described here is a procedure to accomplish the above end followed by a single molecule or clonal sequencing method.

The approach entails targeting one or more specific loci and generating a tagged copy of the original molecules such manner that most or all of the tagged molecules from each targeted locus will have a unique tag and can be distinguished from one another upon sequencing of this barcode using clonal or single molecule sequencing. Each unique sequenced barcode represents a unique molecule in the original sample. Simultaneously, sequencing data is used to ascertain the locus from which the molecule originates. Using this information one can determine the number of unique molecules in the original sample for each locus.

This method can be used for any application in which quantitative evaluation of the number of molecules in an original sample is required. Furthermore, the number of unique molecules of one or more targets can be related to the number of unique molecules to one or more other targets to determine the relative copy number, allele distribution, or allele ratio. Alternatively, the number of copies detected from various targets can be modeled by a distribution in order to identify the mostly likely number of copies of the original targets. Applications include but are not limited to detection of insertions and deletions such as those found in carriers of Duchenne Muscular Dystrophy; quantitation of deletions or duplications segments of chromosomes such as those observed in copy number variants; chromosome copy number of samples from born individuals; chromosome copy number of samples from unborn individuals such as embryos or fetuses.

The method can be combined with simultaneous evaluation of variations contained in the targeted by sequence. This can be used to determine the number of molecules representing each allele in the original sample. This copy number method can be combined with the evaluation of SNPs or other sequence variations to determine the chromosome copy number of born and unborn individuals; the discrimination and quantification of copies from loci which have short sequence variations, but in which PCR may amplifies from multiple target regions such as in carrier detection of Spinal Muscle Atrophy; determination of copy number of different sources of molecules from samples consisting of mixtures of different individual such as in detection of fetal aneuploidy from free floating DNA obtained from maternal plasma.

In an embodiment, the method as it pertains to a single target locus may comprise one or more of the following steps: (1) Designing a standard pair of oligomers for PCR amplification of a specific locus. (2) Adding, during synthesis, a sequence of specified bases with no or minimal complimentarity to the target locus or genome to the 5' end of the one of the target specific oligomer. This sequence, termed the tail, is a known sequence, to be used for subsequent amplification, followed by a sequence of random nucleotides. These random nucleotides comprise the random region. The random region comprises a randomly generated sequence of nucleic acids that probabilistically differ between each probe molecule. Consequently, following synthesis, the tailed oligomer pool will consists of a collection of oligomers beginning with a known sequence followed by unknown sequence that differs between molecules, followed by the target specific sequence. (3) Performing one round of amplification (denaturation, annealing, extension) using only the tailed oligomer. (4) adding exonuclease to the reaction, effectively stopping the PCR reaction, and incubating the reaction at the appropriate temperature to remove forward single stranded oligos that did not anneal to temple and extend to form a double stranded product. (5) Incubating the reaction at a high temperature to denature the exonuclease and eliminate its activity. (6) Adding to the reaction a new oligonucleotide that is complementary to tail of the oligomer used in the first reaction along with the other target specific oligomer to enable PCR amplification of the product generated in the first round of PCR. (7) Continuing amplification to generate enough product for downstream clonal sequencing. (8) Measuring the amplified PCR product by a multitude of methods, for example, clonal sequencing, to a sufficient number of bases to span the sequence.

In an embodiment, a method of the present disclosure involves targeting multiple loci in parallel or otherwise.

Primers to different target loci can be generated independently and mixed to create multiplex PCR pools. In an embodiment, original samples can be divided into sub-pools and different loci can be targeted in each sub-pool before being recombined and sequenced. In an embodiment, the tagging step and a number of amplification cycles may be performed before the pool is subdivided to ensure efficient targeting of all targets before splitting, and improving subsequent amplification by continuing amplification using smaller sets of primers in subdivided pools.

One example of an application where this technology would be particularly useful is non-invasive prenatal aneuploidy diagnosis where the ratio of alleles at a given locus or a distribution of alleles at a number of loci can be used to help determine the number of copies of a chromosome present in a fetus. In this context, it is desirable to amplify the DNA present in the initial sample while maintaining the relative amounts of the various alleles. In some circumstances, especially in cases where there is a very small amount of DNA, for example, fewer than 5,000 copies of the genome, fewer than 1,000 copies of the genome, fewer than 500 copies of the genome, and fewer than 100 copies of the genome, one can encounter a phenomenon called bottlenecking. This is where there are a small number of copies of any given allele in the initial sample, and amplification biases can result in the amplified pool of DNA having significantly different ratios of those alleles than are in the initial mixture of DNA. By applying a unique or nearly unique set of barcodes to each strand of DNA before standard PCR amplification, it is possible to exclude n−1 copies of DNA from a set of n identical molecules of sequenced DNA that originated from the same original molecule.

For example, imagine a heterozygous SNP in the genome of an individual, and a mixture of DNA from the individual where ten molecules of each allele are present in the original sample of DNA. After amplification there may be 100,000 molecules of DNA corresponding to that locus. Due to stochastic processes, the ratio of DNA could be anywhere from 1:2 to 2:1, however, since each of the original molecules was tagged with a unique tag, it would be possible to determine that the DNA in the amplified pool originated from exactly 10 molecules of DNA from each allele. This method would therefore give a more accurate measure of the relative amounts of each allele than a method not using this approach. For methods where it is desirable for the relative amount of allele bias to be minimized, this method will provide more accurate data.

Association of the sequenced fragment to the target locus can be achieved in a number of ways. In an embodiment, a sequence of sufficient length is obtained from the targeted fragment to span the molecule barcode as well a sufficient number of unique bases corresponding to the target sequence to allow unambiguous identification of the target locus. In another embodiment, the molecular bar-coding primer that contains the randomly generated molecular barcode can also contain a locus specific barcode (locus barcode) that identifies the target to which it is to be associated. This locus barcode would be identical among all molecular bar-coding primers for each individual target and hence all resulting amplicons, but different from all other targets. In an embodiment, the tagging method described herein may be combined with a one-sided nesting protocol.

In an embodiment, the design and generation of molecular barcoding primers may be reduced to practice as follows: the molecular barcoding primers may consist of a sequence that is not complementary to the target sequence followed by random molecular barcode region followed by a target specific sequence. The sequence 5' of molecular barcode may be used for subsequence PCR amplification and may comprise sequences useful in the conversion of the amplicon to a library for sequencing. The random molecular barcode sequence could be generated in a multitude of ways. The preferred method synthesize the molecule tagging primer in such a way as to include all four bases to the reaction during synthesis of the barcode region. All or various combinations of bases may be specified using the IUPAC DNA ambiguity codes. In this manner the synthesized collection of molecules will contain a random mixture of sequences in the molecular barcode region. The length of the barcode region will determine how many primers will contain unique barcodes. The number of unique sequences is related to the length of the barcode region as $N^L$ where N is the number of bases, typically 4, and L is the length of the barcode. A barcode of five bases can yield up to 1024 unique sequences; a barcode of eight bases can yield 65536 unique barcodes. In an embodiment, the DNA can be measured by a sequencing method, where the sequence data represents the sequence of a single molecule. This can include methods in which single molecules are sequenced directly or methods in which single molecules are amplified to form clones detectable by the sequence instrument, but that still represent single molecules, herein called clonal sequencing.

Exemplary Methods and Reagents for Quantification of Amplification Products

Quantitation of specific nucleic acid sequences of interest is typically done by quantitative real-time PCR techniques such as TAQMAN (LIFE TECHNOLOGIES), INVADER probes (THIRD WAVE TECHNOLOGIES), and the like. Such techniques suffer from numerous shortcomings such as limited ability to achieve the simultaneous analysis of multiple sequences in parallel (multiplexation) and the ability to provide accurate quantitative data for only a narrow range of possible amplification cycles (e.g., when the logarithm of PCR amplification production quantity versus the number of cycles is in the linear range). DNA sequencing techniques, particularly high throughput next-generation sequencing techniques (often referred to as massively parallel sequencing techniques) such as those employed in MYSEQ (ILLUMINA), HISEQ (ILLUMINA), ION TORRENT (LIFE TECHNOLOGIES), GENOME ANALYZER ILX (ILLUMINA), GS FLEX+ (ROCHE 454) etc., can be used for by quantitative measurements of the number of copies of sequence of interest present in sample, thereby providing quantitative information about the starting materials, e.g., copy number or transcription levels. High throughput genetic sequencers are amenable to the use of bar coding (i.e., sample tagging with distinctive nucleic acid sequences) so as to identify specific samples from individuals thereby permitting the simultaneous analysis of multiple samples in a single run of the DNA sequencer. The number of times a given region of the genome in a library preparation (or other nucleic preparation of interest) is sequenced (number of reads) will be proportional to the number of copies of that sequence in the genome of interest (or expression level in the case of cDNA containing preparations). However, the preparation and sequencing of genetic libraries (and similar genome derived preparations) can introduce numerous biases that interfere with obtaining an accurate quantitative reading for the nucleic acid sequence of interest. For example, different nucleic acid sequences can amplify with different efficiencies during nucleic amplification steps that take place during the genetic library preparation or sample preparation.

The problem with differential amplification efficiencies can be mitigated by using certain embodiments of the subject invention. The subject invention includes various methods and compositions that relate to the use of standards for inclusion in amplification processes that can be used to improve the accuracy of quantitation. The invention is of use in, among other areas, the detection of aneuploidy in a fetus by analyzing free floating fetal DNA in maternal blood, as described herein and as described, among other places, U.S. Pat. No. 8,008,018; U.S. Pat. No. 7,332,277; PCT Published Application WO 2012/078792A2; and PCT Published Application WO 2011/146632 A1, which are each herein incorporated by reference in its entirety Embodiments of the invention are also of use in the detection of aneuploidy in an in vitro generated embryos. Commercially significant aneuploidies that may be detected include aneuploidy of the human chromosomes 13, 18, 21, X and Y.

Embodiments of the invention may be used with either human or non-human nucleic acids, and may be applied to both animal and plant derived nucleic acids. Embodiments of the invention may also be used to detect and/or quantitate alleles for other genetic disorders characterized by deletions or insertions. The deletion containing alleles can be detected in suspected carriers of the allele of interest.

One embodiment of the subject invention includes standards that are present in a known quantity (relative or absolute). For example, consider a genetic library made from a genetic source that is diploid for chromosome 8 (containing locus A) and triploid for chromosome 21 (containing locus B). A genetic library can be produced from this sample that will contain sequences in quantities that are a function of the number of chromosomes present in the sample, e.g., 200 copies of locus A and 300 copies of locus B. However, if locus A amplifies much more efficiently than locus B, after PCR there may be 60,000 copies of the A amplicon and 30,000 copies of the B amplicon, thus obscuring the true chromosomal copy number of the initial genomic sample when analysis by high throughput DNA sequencing (or other quantitative nucleic acid detection techniques). To mitigate this problem a standard sequence for locus A is employed, wherein the standard sequence amplifies with essentially the same efficiency as locus A. Similarly, a standard sequence for locus B is created, wherein the standard sequence amplifies with the essentially the same efficiency as locus B. A standard sequence of locus A and a standard sequence for locus B are added to the mixture prior to PCR (or other amplification techniques). These standard sequences are present in known quantities, either relative quantities or absolute quantities. Thus if a 1:1 mixture of standard sequence A and standard sequence B were added (prior to amplification) to the mixture in the previous example, 3000 copies of the standard A amplicon would be produced and 1000 copies of the standard B amplicon would be produced, showing that locus A is amplified 3 times more efficiently than locus B, under the same set of conditions.

In various embodiments one or more selected regions of a genome containing a SNP (or other polymorphism) of interest can be specifically amplified and subsequently sequenced. This target specific amplification can take place during the formation of a genetic library for sequencing. The library can contain numerous targeted regions for amplification. In some embodiments at least 10; 100, 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 regions of interest. Examples of such libraries are described herein and can be found in U.S. Patent Application No. 2012/0270212, filed Nov. 18, 2011, which is herein incorporated by reference in its entirety.

Many high throughput DNA sequencing techniques require the modification of the genetic starting material, e.g., the litigation of universal priming sites and/or barcodes, so as to form libraries to facilitate the clonal amplification of small nucleic acid fragments prior to performing subsequent sequencing reactions. In some embodiments, one or more standard sequences are added during genetic library formation or added to a precursor component of a genetic library prior to amplification of the library. The standard sequences can be selected so as to mimic (yet be distinguishable based on nucleotide base sequence) target genomic fragments to be prepared for sequencing by a high throughput genetic sequencing technique. In one embodiment, the standard sequence can be identical to the target genomic fragment excepting one, two, three, four to ten, or eleven to twenty nucleotides. In some embodiments, when the target genetic sequence contains a SNP, the standard sequence can be identical to the SNP excepting the nucleotide at the polymorphic base, which may be chosen to be one of the four nucleotides that is not observed at that location in nature. The standard sequences can be used in a highly multiplexed analysis of multiple target loci (such as polymorphic loci). Standard sequences can be added during the process of library formation (prior to amplification) in known quantities (relative or absolute) so as to provide a standard metric for greater accuracy in determining the amount of target sequence of interest in the sample of analysis. The combination of knowledge of the known quantities of the standard sequences used in conjunction with the knowledge of the ploidy level formation of library for sequencing formed from a genome of previously characterized ploidy level, e.g., known to be diploid for all autosomal chromosomes, can be used to calibrate the amplification properties of each standard sequence with respect to its corresponding target sequence and account for variations between batches of mixtures comprising multiple standard sequences. Given that it is often necessary to simultaneously analyze a large number of loci, it is useful to produce a mixture comprising a large set standard sequences. Embodiments of the invention include mixtures comprising multiple standard sequences. Ideally the amount of each standard sequence in the mixture is known with high precision. However, it is extremely difficult to achieve this ideal because as a practical matter there is a significant amount of variation in the quantity of each standard sequence in the mixture, particularly for mixtures comprising a large number of different synthetic oligonucleotides. This variation has numerous sources, e.g., variations in in vitro oligonucleotide synthesis reaction efficiencies between batch, inaccuracies in volume measurement, variations in pipetting, Furthermore, this variation can occur between different batches of that theoretically contain the exact same set of standard sequences in the exact same amounts. Accordingly, it is of interest to calibrate each batch of standard sequences independently. Batches of standard sequences can be calibrated against reference genomes of known chromosomal composition. Batched of standard sequences can be calibrated by sequencing the batch of standard sequences with minimal or no amplifications steps included in the sequencing protocol. Embodiments of the invention include calibrated mixtures of different standard sequences. Other embodiments of the invention include methods of calibrating mixtures of different standard sequences and calibrated mixtures of different standard sequences made by the subject methods.

Various embodiments of the subject mixtures of standard sequences and methods for using them can comprise at least 10; 100, 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 or more standards sequences, as well as various intermediate amounts. The number of the standard sequences can be the same as the number of target sequences selected for analysis during the generation of a targeted library for DNA sequencing. However, in some embodiments, it may be advantageous to use a lower number of standard sequences than the number of targeted regions in the library being constructed. It may be advantageous to use the lower number so as avoid coming up against the limits of the sequencing capacity of the high throughput DNA sequencer being employed. The number of standard sequences can be 50% or less than the number of targeted regions, 40% or less than the number of targeted regions, be 30% or less than the number of targeted regions, 20% or less than the number of targeted regions, be 10% or less than the number of targeted regions, 5% or less than the number of targeted regions, 1% or less than the number of targeted regions, as well as various intermediate values. For example, if a genetic library is created using 15,000 pairs of primers targeted to specific SNP containing loci, a suitable mixture containing 1500 standard sequences corresponding to 1500 of the 15,000 targeted loci can be added prior to the amplification step of library constructions.

The amount of standard sequences added during library construction can vary considerably among different embodiments. In some embodiments, the amount of each standard sequence can be approximately the same as the predicted amount of the target sequence present in the genomic material sample used for library preparation. In other embodiments, the amount of each standard sequence can be greater or less than the predicted amount of the target sequence present in the genomic material sample used for library preparation. While the initial relative amounts of the target sequence and the standard sequence are not critical for the function of the invention, it is preferable that the amount be within the range 100 times greater to 100 times less than the amount of the target sequence present in the genomic material sample used for library preparation. Excessive amounts of standard may use too much sequencing capacity of the DNA sequencer in a given run of the instrument. Using too low an amount of standard sequences will produce insufficient data to aid in the analysis of variation in amplification efficiency.

The standard sequences may be selected to be very similar in nucleotide base sequence to the amplified regions of interest; preferably the standard sequence has the exact same primer-binding sites as the analyzed genomic region, i.e., the "target sequence." The standard sequence must be distinguishable from the corresponding target sequence at a given locus. For the sake of convenience, this distinguishable region of the standard sequence will be referred to as a "marker sequence." In some embodiments, the marker sequence region of the target sequences contains the polymorphic region, e.g., a SNP, and can be flanked on both sides by primer binding regions. The standard sequence may be selected to closely match the GC content of the corresponding target sequence. In some embodiments, the primer binding regions of the standard sequence are flanked by universal priming sites. These universal priming sites are selected to match universal priming sites used in a genomic library for analysis. In other embodiments, the standard sequences do not have universal priming sites and the universal priming sites are added during the creation of a library. Standard sequences are typically provided in single stranded form. A standard sequence is defined with respect to a corresponding target sequence and the sequence specific reagents used to amplify the target sequence. In some embodiments, the target sequence contains the polymorphism of interest, e.g., a SNP, a deletion, or insertion, present in the nucleic acid sample for analysis. The standard sequence is a synthetic polynucleotide that is similar in nucleotide base sequence to the target sequence, but is nonetheless distinguishable from the target sequence by virtue of at least one nucleotide base difference, thereby providing a mechanism for distinguishing amplicon sequences derived from the standard sequence form amplicon sequences derived from the target sequence. Standard sequences are selected so as to have essentially the same amplification properties as the corresponding target sequence when amplified with the same set of amplification reagents, e.g., PCR primers. In some embodiments, the standard sequences can have the same primer sequence binding sites than the corresponding target sequences. In other embodiments, the standard sequences can have a different primer sequence binding sites than the corresponding target sequences. In some embodiments, the standard sequences can be selected to produce amplicons that have the same length as the length of amplicons produced from the corresponding target sequences. In other embodiments, the standard sequences can be selected to produce amplicons that have the slightly different lengths than the length of amplicons produced from the corresponding target sequences.

After the amplification reactions have been completed, the library is sequenced on a high throughput DNA sequencer where individual molecule are clonally amplified and sequenced. The number of sequence reads for each allele of the target sequence is counted, also counted are the number of sequence reads for the standard sequence corresponding to the target sequence. The process is also carried out for at least one other pair of target sequences and corresponding standard sequences. Consider for example, locus A, $X_{A1}$ reads for allele 1 of locus A are produced; $X_{A2}$ reads for allele 2 of locus A are produced, and $X_{AC}$ reads for standard sequence A are produced. The ratio of (XA1 plus $X_{A2}$) to $X_{AC}$ is determined for each locus of interest. As discussed earlier, the process can be performed on a reference genome, e.g., a genome that is known to be diploid for all chromosomes. The process can be repeated many times in order to provide a large number of read values so as to determine a mean number of reads and the standard deviation in the number of reads. The process is performed with a mixture comprising a large number of different standard sequences corresponding to different loci. By assuming that (1) $X_{A1}$ plus $X_{A2}$ corresponds to the known number of chromosome, e.g., 2 for the normal human female genome and (2) the standard sequences have similar amplification (and detectability) properties as their corresponding natural loci, the relative amounts of the different standard sequences in the multiplex standard mixture can be determined. The calibrated multiplex standard sequence mixture can then be used to adjust for the variability in amplification efficiency between the different loci in a multiplex amplification reaction.

Other embodiments of the invention include methods and compositions for measuring the copy number of specific genes of interest, including duplications and mutant genes characterized by large deletions that would interfere with quantitation by sequencing. Sequencing would have problems detecting alleles having such deletions. Standard sequences included the amplification process can be used to reduce this problem.

In one embodiment of the invention the target sequence for analysis is a gene having a wild type (i.e. functional) form and a mutant form characterized by a deletion. Exemplary of such genes is SMN1, an allele having deletion being responsible for the genetic disease spinal muscular atrophy (SMA). It is of interest to detect an individual carrying the mutant form of the gene by means of high throughput genetic sequencing techniques. The application of such techniques to the detection of deletion mutations can be problematic because, among other reasons, the lack of sequences observed in sequencing (as opposed to detecting a simple point mutation or SNP). Such embodiments employ (1) a pair of amplification primers specific for the gene of interest, where in the amplification primers will amplify the gene of interest (or a portion thereof) and will not significantly amplify the mutant allele, (2) a standard sequence corresponding to the wild type allele of the gene of interest (i.e., a target sequence), but differing by at least one detectable nucleotide base, (3) a pair of amplification primers specific for a second target sequence that serves as a reference sequence, and (4) a standard sequence corresponding to the reference sequence.

In one embodiment of the invention is provided a method for measuring the number of copies of the gene of interest, where in the gene of interest has one meaning allele that comprises a deletion. The method can employ amplification reagent specific for the gene of interest, e.g., PCR primers, that are specific for the gene of interest by amplifying at least a portion of the gene of interest, or the entire gene of interest, or a region adjacent to the gene of interest, while not amplifying the deletion comprising allele of the gene of interest. Additionally the subject method employs a standard sequence corresponding to the gene of interest, wherein the standard sequence differs by at least one nucleotide base from the gene of interest (so that the sequence of the standard sequence can be readily distinguished from the naturally occurring gene of interest). Typically, the standard sequence will contain the same primer binding sites as the gene of interest so as to minimize any amplification discrimination between the gene of interest and the standard sequence corresponding to the gene of interest. The reaction will also comprises amplification reagents specific for a reference sequence. The reference sequence is a sequence of known (or at least assumed to be known) copy number in the genome to be analyzed. The reaction further comprises a standard sequence corresponding to the reference sequence. Typically, the standard sequence corresponding to the reference sequence will contain the same primer binding sites as the reference sequence so as to minimize any amplification discrimination between the reference sequence and the standard sequence corresponding to the reference sequence.

Exemplary PCR Conditions

If desired, any of the PCR conditions disclosed herein or any standard PCR conditions can be used to test a primer library to determine, e.g., the percent of primer dimers, percent of target amplicons, and percent of target loci that are amplified. If desired, standard methods can be used to optimize the reaction conditions to improve the performance of a primer library. Any of these PCR conditions may also be used in any of the methods of the invention to amplify target loci. It was determined that high ionic strength solutions can surprisingly be used for multiplex PCR. In some embodiments, monovalent cations are used to increase the ionic strength to, e.g., help the primers bind the template.

In some embodiments, the reaction volume includes ethylenediaminetetraacetic acid (EDTA), magnesium, tetramethyl ammonium chloride (TMAC), or any combination thereof. In some embodiments, the concentration of TMAC is between 20 and 80 mM, such as between 25 and 70 mM, 30 and 60 mM, 30 and 40 mM, 40 and 50 mM, 50 and 60 mM, or 60 and 70 mM, inclusive. While not meant to be bound to any particular theory, it is believed that TMAC binds to DNA, stabilizes duplexes, increases primer specificity, and/or equalizes the melting temperatures of different primers. In some embodiments, TMAC increases the uniformity in the amount of amplified products for the different targets. In some embodiments, the concentration of magnesium (such as magnesium from magnesium chloride) is between 1 and 10 mM, such as between 1 and 8 mM, 1 and 5 mM, 1 and 3 mM, 3 and 5 mM, 3 and 6 mM, or 5 and 8 mM, inclusive.

In some embodiments, the concentration of available magnesium (the concentration of magnesium that is assumed to be available for binding the polymerase and not bound to molecules other than the polymerase), such as the magnesium that is not bound by phosphate groups on dNTPs, primers, or nucleic acid templates, or carboxylic acid groups on magnetic or other beads, if present) is between 0.5 to 10 mM, such as between 1 and 8 mM, 1 and 5 mM, 1 and 3 mM, 3 and 5 mM, 3 and 6 mM, 4 and 6 mM, or 5 and 8 mM, inclusive. The large number of primers used for multiplex PCR of a large number of targets may chelate a lot of the magnesium (2 phosphates in the primers chelate 1 magnesium). For example, if enough primers are used such that the concentration of phosphate from the primers is ~9 mM, then the primers may reduce the effective magnesium concentration by ~4.5 mM. In some embodiments, EDTA is used to decrease the amount of magnesium available as a cofactor for the polymerase since high concentrations of magnesium can result in PCR errors, such as amplification of non-target loci. In some embodiments, the concentration of EDTA reduces the amount of available magnesium to between 1 and 5 mM (such as between 3 and 5 mM).

In some embodiments, the pH is between 7.5 and 8.5, such as between 7.5 and 8, 8 and 8.3, or 8.3 and 8.5, inclusive. In some embodiments, Tris is used at, for example, a concentration of between 10 and 100 mM, such as between 10 and 25 mM, 25 and 50 mM, 50 and 75 mM, or 25 and 75 mM, inclusive. In some embodiments, any of these concentrations of Tris are used at a pH between 7.5 and 8.5. In some embodiments, a combination of KCl and $(NH_4)_2SO_4$ is used, such as between 50 and 150 mM KCl and between 10 and 90 mM $(NH_4)_2SO_4$, inclusive. In some embodiments, the concentration of KCl is between 0 and 30 mM, between 50 and 100 mM, or between 100 and 150 mM, inclusive. In some embodiments, the concentration of $(NH_4)_2SO_4$ is between 10 and 50 mM, 50 and 90 mM, 10 and 20 mM, 20 and 40 mM, 40 mM and 60, or 60 mM and 80 mM $(NH_4)_2SO_4$, inclusive. In some embodiments, the ammonium $[NH_4^+]$ concentration is between 0 and 160 mM, such as between 0 to 50, 50 to 100, or 100 to 160 mM, inclusive. In some embodiments, the sum of the potassium and ammonium concentration ($[K^+]+[NH_4^+]$) is between 0 and 160 mM, such as between 0 to 25, 25 to 50, 50 to 150, 50 to 75, 75 to 100, 100 to 125, or 125 to 160 mM, inclusive. An exemplary buffer with $[K^+]+[NH_4^+]=120$ mM is 20 mM KCl and 50 mM $(NH_4)_2SO_4$. In some embodiments, the buffer includes 25 to 75 mM Tris, pH 7.2 to 8, 0 to 50 mM KCL, 10 to 80 mM ammonium sulfate, and 3 to 6 mM magnesium, inclusive. In some embodiments, the buffer includes 25 to 75 mM Tris pH 7 to 8.5, 3 to 6 mM MgCl$_2$, 10 to 50 mM KCl, and 20 to 80 mM (NH$_4$)$_2$SO$_4$, inclusive. In some embodiments, 100 to 200 Units/mL of polymerase are used. In some embodiments, 100 mM KCl, 50 mM (NH$_4$)$_2$SO$_4$, 3 mM MgCl$_2$, 7.5 nM of each primer in the library, 50 mM TMAC, and 7 ul DNA template in a 20 ul final volume at pH 8.1 is used.

In some embodiments, a crowding agent is used, such as polyethylene glycol (PEG, such as PEG 8,000) or glycerol. In some embodiments, the amount of PEG (such as PEG 8,000) is between 0.1 to 20%, such as between 0.5 to 15%, 1 to 10%, 2 to 8%, or 4 to 8%, inclusive. In some embodiments, the amount of glycerol is between 0.1 to 20%, such as between 0.5 to 15%, 1 to 10%, 2 to 8%, or 4 to 8%, inclusive. In some embodiments, a crowding agent allows either a low polymerase concentration and/or a shorter annealing time to be used. In some embodiments, a crowding agent improves the uniformity of the DOR and/or reduces dropouts (undetected alleles). For example, at 8% PEG, and 50 U/mL polymerase, the uniformity was as good as 150 U/mL polymerase and no PEG. If the error rate increases when PEG is included, a higher magnesium chloride concentration (such greater than or about 4, 5, 6, 7, 8, 9, or 10 MgCl$_2$) can be used to reduce or prevent the increase in error rate. Inclusion of 8% PEG 8,000 allowed successful multiplexing with an annealing time of only 1 minute at an annealing temperature of 63° C.

In some embodiments, a polymerase with proof-reading activity, a polymerase without (or with negligible) proof-reading activity, or a mixture of a polymerase with proof-reading activity and a polymerase without (or with negligible) proof-reading activity is used. In some embodiments, a hot start polymerase, a non-hot start polymerase, or a mixture of a hot start polymerase and a non-hot start polymerase is used. In some embodiments, a HotStarTaq DNA polymerase is used (see, for example, QIAGEN catalog No. 203203, see, e.g., information available at the world wide web at qiagen. com/us/products/catalog/assay-technologies/end-point-pcr-and-rt-pcr-reagents/hotstartaq-dna-polymerase/, which is hereby incorporated by reference in its entirety). In some embodiments, AmpliTaq Gold® DNA Polymerase is used; it is a chemically modified form of AmpliTaq® DNA Polymerase requiring thermal activation (see, for example, Applied Biosystems catalog No. N8080241 see, e.g., information available at the world wide web at lifetechnologies.com/order/catalog/product/ N8080241, which is hereby incorporated by reference in its entirety). In some embodiments, KAPA Taq DNA Polymerase or KAPA Taq HotStart DNA Polymerase is used; they are based on the single-subunit, wild-type Taq DNA polymerase of the thermophilic bacterium *Thermus aquaticus*. KAPA Taq and KAPA Taq HotStart DNA Polymerase have 5'-3' polymerase and 5'-3' exonuclease activities, but no 3' to 5' exonuclease (proofreading) activity (see, for example, KAPA BIOSYSTEMS catalog No. BK1000 see, e.g., information available at the world wide web at kapabiosystems.com/product-applications/products/pcr-2/kapa-taq-pcr-kits/, which is hereby incorporated by reference in its entirety). In some embodiments, Pfu DNA polymerase is used; it is a highly thermostable DNA polymerase from the hyperthermophilic archaeum *Pyrococcus furiosus*. The enzyme catalyzes the template-dependent polymerization of nucleotides into duplex DNA in the 5'→3' direction. Pfu DNA Polymerase also exhibits 3'→5' exonuclease (proofreading) activity that enables the polymerase to correct nucleotide incorporation errors. It has no 5'→3' exonuclease activity (see, for example, Thermo Scientific catalog No. EP0501 see, e.g., information available at the world wide web at thermoscientificbio.com/per-enzymes-master-mixes-and-reagents/pfu-dna-polymerase/, which is hereby incorporated by reference in its entirety). In some embodiments Klentaq1 is used; it is a Klenow-fragment analog of Taq DNA polymerase, it has no exonuclease or endonuclease activity (see, for example, DNA POLYMERASE TECHNOLOGY, Inc, St. Louis, Mo., catalog No. 100 see, e.g., information available at the world wide web at klentaq.com/ products/klentaq, which is hereby incorporated by reference in its entirety). In some embodiments, the polymerase is a PUSHION DNA polymerase, such as PHUSION High Fidelity DNA polymerase (M0530S, New England BioLabs, Inc.) or PHUSION Hot Start Flex DNA polymerase (M0535S, New England BioLabs, Inc.; Frey and Suppman *BioChemica*. 2:34-35, 1995; Chester and Marshak *Analytical Biochemistry*. 209:284-290, 1993, which are each hereby incorporated by reference in its entirety). In some embodiments, the polymerase is a Q5® DNA Polymerase, such as Q5® High-Fidelity DNA Polymerase (M0491S, New England BioLabs, Inc.) or Q5® Hot Start High-Fidelity DNA Polymerase (M04935, New England BioLabs, Inc.). In some embodiments, the polymerase is a T4 DNA polymerase (M0203S, New England BioLabs, Inc.; Tabor and Struh. (1989). "DNA-Dependent DNA Polymerases," In Ausebel et al. (Ed.), *Current Protocols in Molecular Biology*. 3.5.10-3.5.12. New York: John Wiley & Sons, Inc., 1989; Sambrook et al. *Molecular Cloning: A Laboratory Manual*. (2nd ed.), 5.44-5.47. Cold Spring Harbor: Cold Spring Harbor Laboratory Press, 1989, which are each hereby incorporated by reference in its entirety).

In some embodiment, between 5 and 600 Units/mL (Units per 1 mL of reaction volume) of polymerase is used, such as between 5 to 100, 100 to 200, 200 to 300, 300 to 400, 400 to 500, or 500 to 600 Units/mL, inclusive. One unit is commonly defined as the amount of enzyme that will incorporate 15 nmol of dNTP into acid-insoluble material in 30 minutes at 75° C. Exemplary assay conditions for measuring unit activity include 1× THERMOPOL Reaction Buffer, 200 µM dNTPs including [$^3$H]-dTTP and 200 µg/ml activated Calf Thymus DNA (see, e.g., information available at the world wide web at neb.com/products/m0267-taq-dna-polymerase-with-thermopol-buffer, which is hereby incorporated by reference in its entirety). 1×THERMOPOL® Reaction Buffer contains 20 mM Tris-HCl, 10 mM (NH$_4$)$_2$SO$_4$, 10 mM KCl, 2 mM MgSO$_4$, and 0.1% TRITON® X-100, pH 8.8.

In some embodiments, hot-start PCR is used to reduce or prevent polymerization prior to PCR thermocycling. Exemplary hot-start PCR methods include initial inhibition of the DNA polymerase, or physical separation of reaction components reaction until the reaction mixture reaches the higher temperatures. In some embodiments, the enzyme is spatially separated from the reaction mixture by wax that melts when the reaction reaches high temperature. In some embodiments, slow release of magnesium is used. DNA polymerase requires magnesium ions for activity, so the magnesium is chemically separated from the reaction by binding to a chemical compound, and is released into the solution only at high temperature. In some embodiments, non-covalent binding of an inhibitor is used. In this method a peptide, antibody, or aptamer are non-covalently bound to the enzyme at low temperature and inhibit its activity. After incubation at elevated temperature, the inhibitor is released and the reaction starts. In some embodiments, a cold-sensitive Taq polymerase is used, such as a modified DNA polymerase with almost no activity at low temperature. In some embodiments, chemical modification is used. In this method, a molecule is covalently bound to the side chain of an amino acid in the active site of the DNA polymerase. The molecule is released from the enzyme by incubation of the reaction mixture at elevated temperature. Once the molecule is released, the enzyme is activated.

In some embodiments, the amount to template nucleic acids (such as an RNA or DNA sample) is between 20 and 5,000 ng, such as between 20 to 200, 200 to 400, 400 to 600, 600 to 1,000; 1,000 to 1,500; or 2,000 to 3,000 ng, inclusive.

In some embodiments QIAGEN Multiplex PCR Kit is used (QIAGEN catalog No. 206143; see, e.g., information available at the world wide web at qiagen.com/products/catalog/assay-technologies/end-point-pcr-and-rt-pcr-reagents/qiagen-multiplex-pcr-kit, which is hereby incorporated by reference in its entirety). For 100×50 µl 10 multiplex PCR reactions, the kit includes 2× QIAGEN Multiplex PCR Master Mix (providing a final concentration of 3 mM $MgCl_2$, 3×0.85 ml), 5× Q-Solution (1×2.0 ml), and RNase-Free Water (2×1.7 ml). The QIAGEN Multiplex PCR Master Mix (MM) contains a combination of KCl and $(NH4)_2SO_4$ as well as the PCR additive, Factor MP, which increases the local concentration of primers at the template. Factor MP stabilizes specifically bound primers, allowing efficient primer extension by HotStarTaq DNA Polymerase. HotStarTaq DNA Polymerase is a modified form of Taq DNA polymerase and has no polymerase activity at ambient temperatures. In some embodiments, HotStarTaq DNA Polymerase is activated by a 15-minute incubation at 95° C. which can be incorporated into any existing thermal-cycler program.

In some embodiments, 1× QIAGEN MM final concentration (the recommended concentration), 7.5 nM of each primer in the library, 50 mM TMAC, and 7 ul DNA template in a 20 ul final volume is used. In some embodiments, the PCR thermocycling conditions include 95° C. for 10 minutes (hot start); 20 cycles of 96° C. for 30 seconds; 65° C. for 15 minutes; and 72° C. for 30 seconds; followed by 72° C. for 2 minutes (final extension); and then a 4° C. hold.

In some embodiments, 2× QIAGEN MM final concentration (twice the recommended concentration), 2 nM of each primer in the library, 70 mM TMAC, and 7 ul DNA template in a 20 ul total volume is used. In some embodiments, up to 4 mM EDTA is also included. In some embodiments, the PCR thermocycling conditions include 95° C. for 10 minutes (hot start); 25 cycles of 96° C. for 30 seconds; 65° C. for 20 minutes; and 72° C. for 30 seconds); followed by 72° C. for 2 minutes (final extension); and then a 4° C. hold.

Another exemplary set of PCR thermocyling conditions includes 95° C. for 10 minutes, 15 cycles of 95° C. for 30 seconds, 65° C. for 1 minute, 60° C. for 5 minutes, 65° C. for 5 minutes and 72° C. for 30 seconds; and then 72° C. for 2 minutes. In some embodiments, this set of PCR thermocyling conditions is used with the following reaction conditions: 100 mM KCl, 50 mM $(NH_4)_2SO_4$, 3 mM $MgCl_2$, 7.5 nM of each primer in the library, 50 mM TMAC, and 7 ul DNA template in a 20 ul final volume at pH 8.1.

Another exemplary set of conditions includes a semi-nested PCR approach. The first PCR reaction uses 20 ul a reaction volume with 2× QIAGEN MM final concentration, 1.875 nM of each primer in the library (outer forward and reverse primers), and DNA template. Thermocycling parameters include 95° C. for 10 minutes; 25 cycles of 96° C. for 30 seconds, 65° C. for 1 minute, 58° C. for 6 minutes, 60° C. for 8 minutes, 65° C. for 4 minutes, and 72° C. for 30 seconds; and then 72° C. for 2 minutes, and then a 4° C. hold. Next, 2 ul of the resulting product, diluted 1:200, is as input in a second PCR reaction. This reaction uses a 10 ul reaction volume with 1× QIAGEN MM final concentration, 20 nM of each inner forward primer, and 1 uM of reverse primer tag. Thermocycling parameters include 95° C. for 10 minutes; 15 cycles of 9°5 C for 30 seconds, 65° C. for 1 minute, 60° C. for 5 minutes, 65° C. for 5 minutes, and 72° C. for 30 seconds; and then 72° C. for 2 minutes, and then a 4° C. hold.

Any of the methods disclosed herein or any standard methods can be used to test a primer library to determine, e.g., the percent of primer dimers, percent of target amplicons, and percent of target loci that are amplified. In some embodiments, the PCR products are sequenced as described in Experiment 15 or using standard sequencing methods. In some embodiments, the percentage of primer dimers can be determined by measuring the number of sequencing reads from primer dimers, the percentage of amplified products that are target amplicons can be determined by measuring the number of sequencing reads that map to target loci; the percent of target loci that are amplified can be determined by measuring the number of target loci for which there are sequencing reads that map to the target loci; the number of copies of a particular amplified target loci can be determined based on the number of sequencing reads that map to that target loci (such as by comparing the number of sequencing reads compared to the sequences reads from a standard of known concentration or amount).

Figure 49:
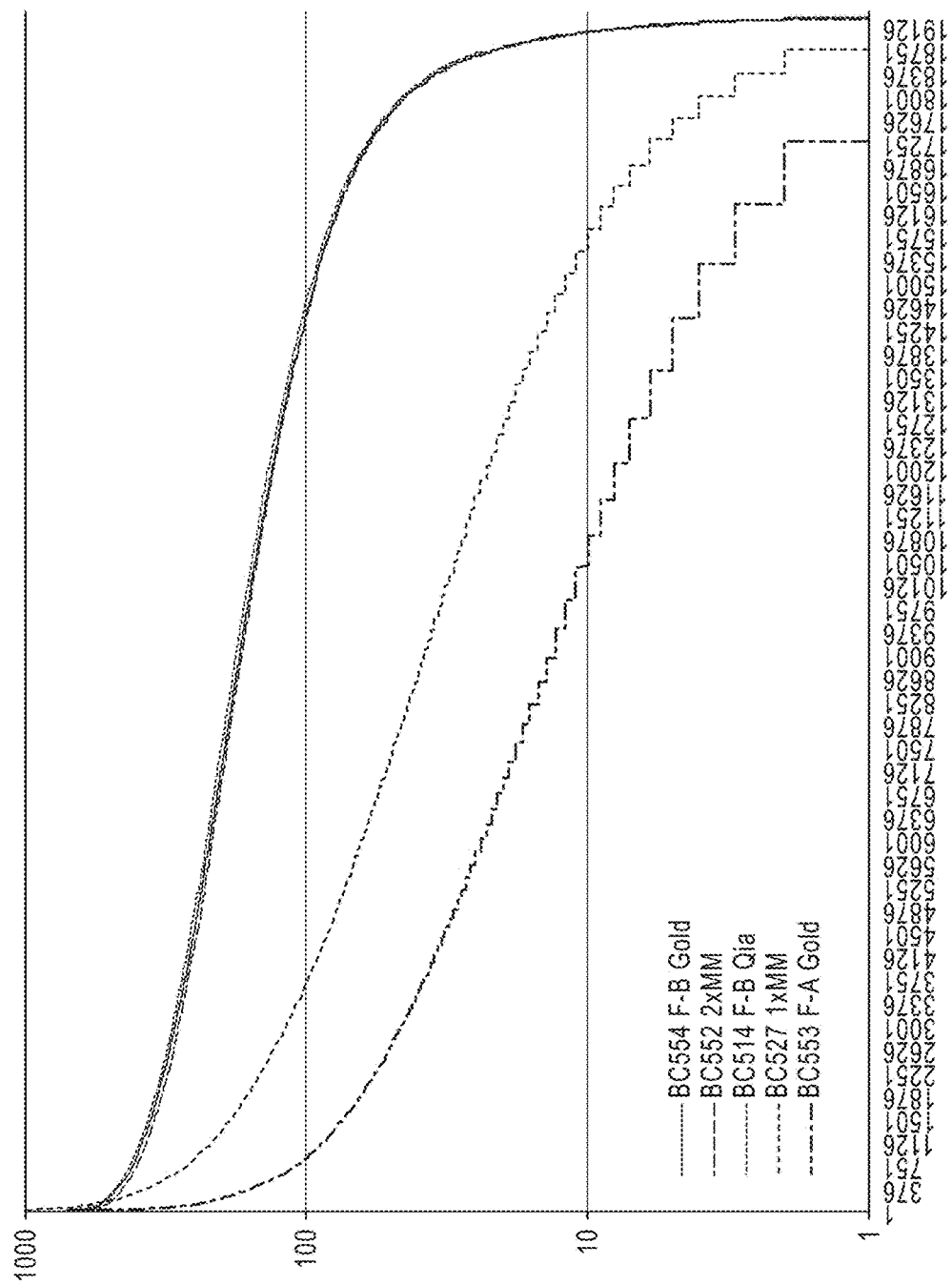
FIG. 49 is a graph illustrating the uniformity in DOR for multiplex PCR with buffers from FIG. 48.
Figure 50:
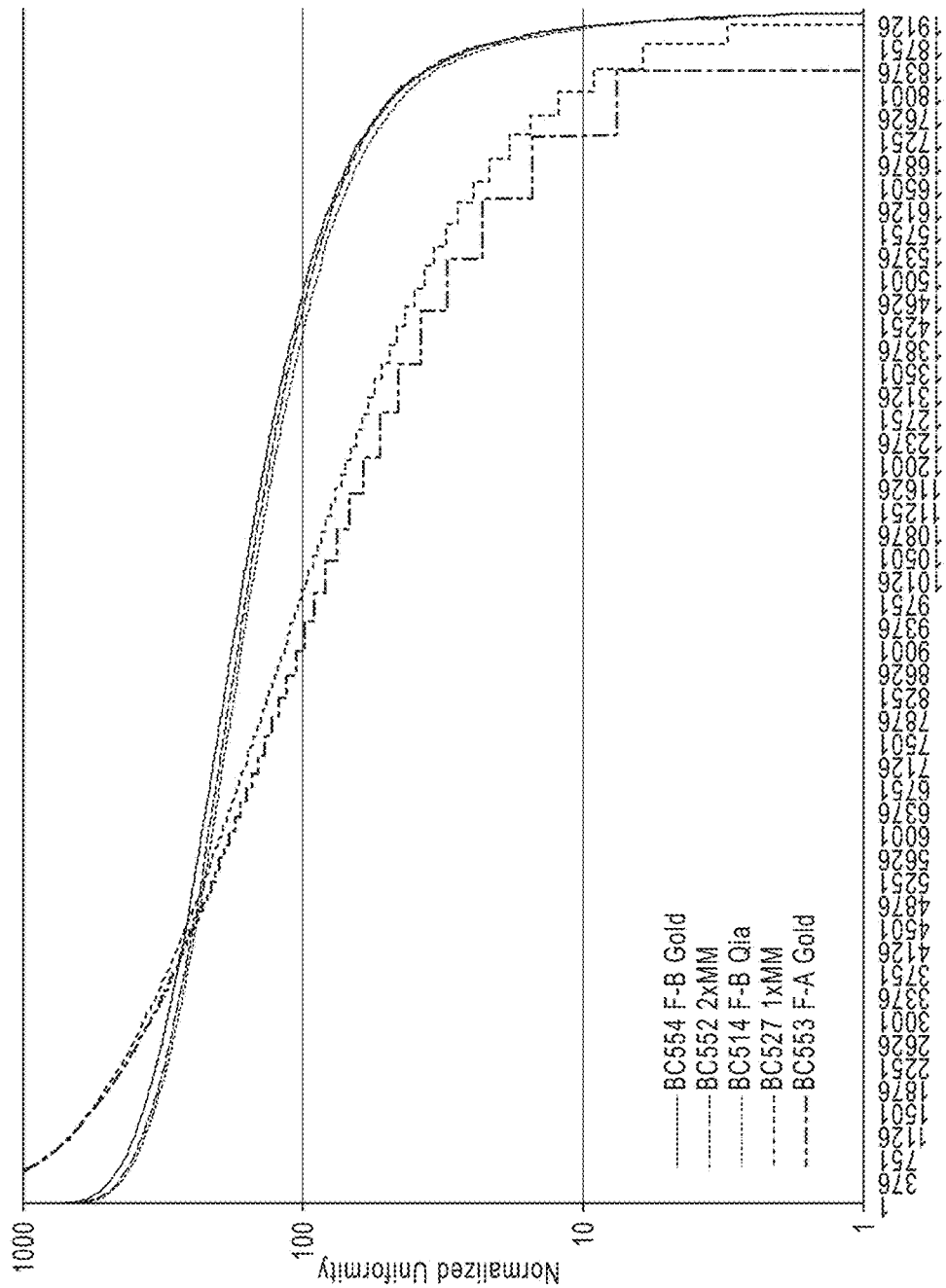
FIG. 50 is a graph illustrating the normalized depth of read (DOR) for multiplex PCR with buffers from FIG. 48 with the DOR normalized to that of buffer 2×MM.

FIG. 48 contains data (such as percent mapped reads and error rate) from multiplex PCR with various buffers. In this figure, "1×MM" denotes 1× QIAGEN Master Mix (the recommended concentration) discussed above, and "2×MM" denotes 2× QIAGEN Master Mix (twice the recommended concentration). FIG. 48 also lists the components of buffer F-A (also called F-A Gold), F-B (also called F-B Gold), F-D, and F-J (also called F-B Qiagen or F-B Qia) as well as the amount and type of polymerase used to generate the data. FIG. 49 is a graph illustrating the uniformity in DOR for multiplex PCR with buffers from FIG. 48. FIG. 50 is a graph illustrating the normalized depth of read (DOR) for multiplex PCR with buffers from FIG. 48 with the DOR normalized to that of buffer 2×MM.

Limit of Detection

In some embodiments, a limit of detection of a mutation (such as an SNV or CNV) of a method of the invention is less than or equal to 10, 5, 2, 1, 0.5, 0.1, 0.05, 0.01, or 0.005%. In some embodiments, a limit of detection of a mutation (such as an SNV or CNV) of a method of the invention is between 15 to 0.005%, such as between 10 to 0.005%, 10 to 0.01%, 10 to 0.1%, 5 to 0.005%, 5 to 0.01%, 5 to 0.1%, 1 to 0.005%, 1 to 0.01%, 1 to 0.1%, 0.5 to 0.005%, 0.5 to 0.01%, 0.5 to 0.1%, or 0.1 to 0.01%, inclusive.

In some embodiments, a limit of detection is such that a mutation (such as an SNV or CNV) that is present in less than or equal to 10, 5, 2, 1, 0.5, 0.1, 0.05, 0.01, or 0.005% of the DNA or RNA molecules with that locus in a sample (such as a sample that has undergone PCR amplification with any of the methods of the invention, such as a sample of PCR-amplified cfDNA or cfRNA) is detected (or is capable of being detected). For example, the mutation can be detected even if less than or equal to 10, 5, 2, 1, 0.5, 0.1, 0.05, 0.01, or 0.005% of the DNA or RNA molecules that have that locus have that mutation in the locus (instead of, for example, a wild-type or non-mutated version of the locus or a different mutation at that locus). In some embodiments, a limit of detection is such that a mutation (such as an SNV or CNV) that is present in less than or equal to 10, 5, 2, 1, 0.5, 0.1, 0.05, 0.01, or 0.005% of the DNA or RNA molecules in a sample (such as a sample that has undergone PCR amplification with any of the methods of the invention, such as a sample of PCR-amplified cfDNA or cfRNA) is detected (or is capable of being detected). In some embodiments in which the CNV is a deletion, the deletion can be detected even if it is only present in less than or equal to 10, 5, 2, 1, 0.5, 0.1, 05, 0.01, or 0.005% of the DNA or RNA molecules that have a region of interest that may or may not contain the deletion in a sample. In some embodiments in which the CNV is a deletion, the deletion can be detected even if it is only present in less than or equal to 10, 5, 2, 1, 0.5, 0.1, 0.05, 0.01, or 0.005% of the DNA or RNA molecules in a sample. In some embodiments in which the CNV is a duplication, the duplication can be detected even if the extra duplicated DNA or RNA that is present is less than or equal to 10, 5, 2, 1, 0.5, 0.1, 0.05, 0.01, or 0.005% of the DNA or RNA molecules that have a region of interest that may or may not be duplicated in a sample (such as a sample that has undergone PCR amplification, such as a sample of PCR-amplified cfDNA or cfRNA from, e.g., a blood sample). In some embodiments in which the CNV is a duplication, the duplication can be detected even if the extra duplicated DNA or RNA that is present is less than or equal to 10, 5, 2, 1, 0.5, 0.1, 0.05, 0.01, or 0.005% of the DNA or RNA molecules in a sample (such as a sample that has undergone PCR amplification, such as a sample of PCR-amplified cfDNA or cfRNA from, e.g., a blood sample) is detected (or is capable of being detected). In some embodiments, a mutation (such as an SNV or CNV) that is present in less than 1,000, 500, 100, 50, 20, 10, 5, 4, 3, or 2 DNA or RNA molecules after PCR amplification with any of the methods of the invention in a sample (such as a sample that has undergone PCR amplification, such as a sample of PCR-amplified cfDNA or cfRNA from, e.g., a blood sample) is detected (or is capable of being detected). In some embodiments, a mutation (such as an SNV or CNV) that is present in less than 1,000, 500, 100, 50, 20, 10, 5, 4, 3, or 2 original DNA or RNA molecules (before amplification) in a sample (such as a sample of cfDNA or cfRNA from, e.g., a blood sample) is detected (or is capable of being detected). In some embodiments, a mutation (such as an SNV or CNV) that is present in only 1 original DNA or RNA molecule (before amplification) in a sample (such as a sample of cfDNA or cfRNA from, e.g., a blood sample) is detected (or is capable of being detected). Experiment 23 provides exemplary methods for calculating the limit of detection. In some embodiments, the "LOD-zs5.0-mr5" method of Experiment 23 is used.

Exemplary Nucleic Acid Samples

In some embodiments, the genetic sample may be prepared and/or purified. There are a number of standard procedures known in the art to accomplish such an end. In some embodiments, the sample may be centrifuged to separate various layers. In some embodiments, the DNA may be isolated using filtration. In some embodiments, the preparation of the DNA may involve amplification, separation, purification by chromatography, liquid separation, isolation, preferential enrichment, preferential amplification, targeted amplification, or any of a number of other techniques either known in the art or described herein.

In some embodiments, a method disclosed herein could be used in situations where there is a very small amount of DNA present, such as in in vitro fertilization, or in forensic situations, where one or a few cells are available (typically less than ten cells, less than twenty cells or less than 40 cells.) In these embodiments, a method disclosed herein serves to make ploidy calls from a small amount of DNA that is not contaminated by other DNA, but where the ploidy calling very difficult the small amount of DNA. In some embodiments, a method disclosed herein could be used in situations where the target DNA is contaminated with DNA of another individual, for example in maternal blood in the context of prenatal diagnosis, paternity testing, or products of conception testing. Some other situations where these methods would be particularly advantageous would be in the case of cancer testing where only one or a small number of cells were present among a larger amount of normal cells. The genetic measurements used as part of these methods could be made on any sample comprising DNA or RNA, for example but not limited to: blood, plasma, body fluids, urine, hair, tears, saliva, tissue, skin, fingernails, blastomeres, embryos, fetal cells, amniotic fluid, chorionic villus samples, feces, bile, lymph, cervical mucus, semen, or other cells or materials comprising nucleic acids. In an embodiment, a method disclosed herein could be run with nucleic acid detection methods such as sequencing, microarrays, qPCR, digital PCR, or other methods used to measure nucleic acids. If for some reason it were found to be desirable, the ratios of the allele count probabilities at a locus could be calculated, and the allele ratios could be used to determine ploidy state in combination with some of the methods described herein, provided the methods are compatible. In some embodiments, a method disclosed herein involves calculating, on a computer, allele ratios at the plurality of polymorphic loci from the DNA measurements made on the processed samples. In some embodiments, a method disclosed herein involves calculating, on a computer, allele ratios at the plurality of polymorphic loci from the DNA measurements made on the processed samples along with any combination of other improvements described in this disclosure. Exemplary methods for isolating fetal cells, such as a single fetal cell are disclosed in U.S. Ser. No. 61/978,648, filed Apr. 11, 2014 and U.S. Ser. No. 61/984,546, filed Apr. 25, 2014. Fetal cells or fetal nucleic acids can be isolated from a pregnant mother using invasive (such as CVS or amniocentesis) or noninvasive methods (such as from a maternal blood sample).

In some embodiments, this method may be used to genotype a single cell, a small number of cells, two to five cells, six to ten cells, ten to twenty cells, twenty to fifty cells, fifty to one hundred cells, one hundred to one thousand cells, or a small amount of extracellular DNA, for example from one to ten picograms, from ten to one hundred pictograms, from one hundred pictograms to one nanogram, from one to ten nanograms, from ten to one hundred nanograms, from 30 to 500 nanograms, or from one hundred nanograms to one microgram. In some embodiments, nucleic acids (such as DNA and/or RNA) from less than 100, 75, 50, 40, 30, 20, 10, 8, 6, 4, 2, or 1 cell is amplified with any of the methods of the invention. In some embodiments, the nucleic acid sample includes less than 80, 60, 40, 20, or 10% of the nucleic acids (such as DNA and/or RNA) from a single cell. In some embodiments, in which a small number of cells (such as one cell) or a small amount of nucleic acids is used, nested PCR such as hemi-nested or semi-nested PCR is used and/or the number of PCR cycles is increased compare to that used for samples with a larger amount of cells or nucleic acids. In some embodiments, a large amount of cells or nucleic acids are used (such as in cases in which a larger amount is desired to improve performance of any of the methods of the invention. In some embodiments, a sample with at least 2, 5, 10, 15, 20, 30, 50, 100, or more cells (or DNA or RNA from such cells) is used in any of the methods of the invention. In some embodiments, at least 0.5, 1, 10, 25, 50, 100, 500, 1,000; or 5,000 ng of DNA or RNA is used.

In some embodiments, the cells in the sample are lysed prior to PCR. In some embodiments, the: Arcturus PicoPure DNA extraction kit from Applied Biosystems is used. (Applied Biosystems cat. No. KIT0103, see, e.g., information available at the world wide web at lifetechnologies.com/order/catalog/product/KIT0103?ICID=search-product, which is hereby incorporated by reference in its entirety). This kit contains Arcturus reconstitution buffer and Protease K. In some embodiments, the following cell lysis thermocycling protocol is used: 56° C. for 1 hour, 95° C. for 10 minutes, 25° C. for 15 minutes, and then a 4° C. hold.

In some embodiments, the nucleic acids are processed using the consecutive steps of end-repairing, dA-tailing, and adaptor ligating the nucleic acids. The consecutive steps exclude purifying the end-repaired products prior to the dA-tailing step and exclude purifying the dA-tailing products prior to the adaptor ligating step. The resulting products are amplified in any of the multiplex PCR methods of the invention. In some embodiments, the amplified products are then sequenced.

Exemplary Nucleic Acid Studies

The multiplex PCR methods of the invention can be used to increase the number of target loci that can be evaluated to measure the amount of one or more specific nucleic acid molecules of interest or of one or more types of nucleic acids. In some embodiments, there is a change in the total amount or concentration of one or more types of DNA (such as cfDNA cf mDNA, cf nDNA, cellular DNA, or mitochondrial DNA) or RNA (cfRNA, cellular RNA, cytoplasmic RNA, coding cytoplasmic RNA, non-coding cytoplasmic RNA, mRNA, miRNA, mitochondrial RNA, rRNA, or tRNA). In some embodiments, there is a change in the amount or concentration of one or more specific DNA (such as cfDNA cf mDNA, cf nDNA, cellular DNA, or mitochondrial DNA) or RNA (cfRNA, cellular RNA, cytoplasmic RNA, coding cytoplasmic RNA, non-coding cytoplasmic RNA, mRNA, miRNA, mitochondrial RNA, rRNA, or tRNA) molecules. In some embodiments, one allele is expressed more than another allele of a locus of interest. Exemplary miRNAs are short 20-22 nucleotide RNA molecules that regulate the expression of a gene. In some embodiments, there is a change in the transcriptome, such as a change in the identity or amount of one or more RNA molecules.

In some embodiments, an increase in the total amount or concentration of cfDNA or cfRNA is associated with a disease such as cancer, or an increased risk for a disease such as cancer. In some embodiments, the total concentration of a type of DNA (such as cfDNA cf mDNA, cf nDNA, cellular DNA, or mitochondrial DNA) or RNA (cfRNA, cellular RNA, cytoplasmic RNA, coding cytoplasmic RNA, non-coding cytoplasmic RNA, mRNA, miRNA, mitochondrial RNA, rRNA, or tRNA) increases by at least 2, 3, 4, 5, 6, 7, 8, 9, 10-fold, or more compared to the total concentration of that type of DNA or RNA in healthy (such as non-cancerous) subjects. In some embodiments, a total concentration of cfDNA between 75 to 100 ng/mL, 100 to 150 ng/mL, 150 to 200 ng/mL, 200 to 300 ng/mL, 300 to 400 ng/mgL, 400 to 600 ng/mL, 600 to 800 ng/mL, 800 to 1,000 ng/mL, inclusive, or a total concentration of cfDNA of more than 100 ng, mL, such as more than 200, 300, 400, 500, 600, 700, 800, 900, or 1,000 ng/mL is indicative of cancer, an increased risk for cancer, an increased risk of a tumor being malignant rather than benign, a decreased probably of the cancer going into remission, or a worse prognosis for the cancer. In some embodiments, the amount of a type of DNA (such as cfDNA cf mDNA, cf nDNA, cellular DNA, or mitochondrial DNA) or RNA (cfRNA, cellular RNA, cytoplasmic RNA, coding cytoplasmic RNA, non-coding cytoplasmic RNA, mRNA, miRNA, mitochondrial RNA, rRNA, or tRNA) having one or more polymorphisms/mutations (such as deletions or duplications) associated with a disease such as cancer or an increased risk for a disease such as cancer is at least 2, 3, 4, 5, 6, 7, 8, 9, 10, 11, 12, 14, 16, 18, 20, or 25% of the total amount of that type of DNA or RNA. In some embodiments, at least 2, 3, 4, 5, 6, 7, 8, 9, 10, 11, 12, 14, 16, 18, 20, or 25% of the total amount of a type of DNA (such as cfDNA cf mDNA, cf nDNA, cellular DNA, or mitochondrial DNA) or RNA (cfRNA, cellular RNA, cytoplasmic RNA, coding cytoplasmic RNA, non-coding cytoplasmic RNA, mRNA, miRNA, mitochondrial RNA, rRNA, or tRNA) has a particular polymorphism or mutation (such as a deletion or duplication) associated with a disease such as cancer or an increased risk for a disease such as cancer.

Exemplary RNA Expression Studies

The multiplex PCR methods of the invention can be used to increase the number of target loci that can be evaluated during gene expression profiling experiments. For example, the expression levels of thousands of genes can be simultaneously monitored to determine whether a person has a sequence (such as a polymorphism or other mutation) associated with a disease (such as cancer) or an increased risk of a disease. These methods can be used to identify sequences (such as polymorphisms or other mutations) associated with an increased or decreased risk for a disease such as cancer by comparing gene expression (such as the expression of particular mRNA alleles) in samples from patients with and without the disease. Additionally, the effect of particular treatments, diseases, or developmental stages on gene expression can be determined. Similarly, these methods can be used to identify genes whose expression is changed in response to pathogens or other organisms by comparing gene expression in infected and uninfected cells or tissues. In these methods the number of sequencing reads can be adjusted based on the frequency of the polymorphisms that are being analyzed such that sufficient reads are performed for the polymorphisms to be detected if they are present. In some embodiments, the polymorphisms or mutation is present at a higher frequency in subjects with a disease or disorder (such as cancer) than subjects without the disease or disorder (such as cancer). In some embodiments, the polymorphisms or mutation is indicative of cancer, such as a causative mutation.

In some embodiments, a sample containing RNA (such as mRNA) is amplified using a reverse transcriptase (RT) and the resulting DNA (such as cDNA) is then amplified using a DNA polymerase (PCR). The RT and PCR steps may be carried out sequentially in the same reaction volume or separately. Any of the primer libraries of the invention can be used in this reverse transcription polymerase chain reaction (RT-PCR) method. In various embodiments, the reverse transcription is performed using oligo-dT, random primers, a mixture of oligo-dT and random primers, or primers specific to the target loci. To avoid amplification of contaminating genomic DNA, primers for RT-PCR can be designed so that part of one primer hybridizes to the 3' end of one exon and the other part of the primer hybridizes to the 5' end of the adjacent exon. Such primers anneal to cDNA synthesized from spliced mRNAs, but not to genomic DNA. To detect amplification of contaminating DNA, RT-PCR primer pairs may be designed to flank a region that contains at least one intron. Products amplified from cDNA (no introns) are smaller than those amplified from genomic DNA (containing introns). Size difference in products is used to detect the presence of contaminating DNA. In some embodiments when only the mRNA sequence is known, primer annealing sites are chosen that are at least 300-400 base pairs apart since it is likely that fragments of this size from eukaryotic DNA contain splice junctions. Alternatively, the sample can be treated with DNase to degrade contaminating DNA.

Exemplary Methods for Paternity Testing

The multiplex PCR methods of the invention can be used to improve the accuracy of paternity testing since so many target loci can be analyzed at once (see, e.g, U.S. Publication No. 2012/0122701, filed Dec. 22, 2011, is which is hereby incorporated by reference in its entirety). For example, the multiplex PCR method can allow thousands of polymorphic loci (such as SNPs) to be analyzed for use in the PARENTAL SUPPORT algorithm described herein to determine whether an alleged father in is the biological father of a fetus. In some embodiments the method involves (i) simultaneously amplifying a plurality of polymorphic loci that includes at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different polymorphic loci on genetic material from the alleged father to produce a first set of amplified products; (ii) simultaneously amplifying the corresponding plurality of polymorphic loci on a mixed sample of DNA originating from a blood sample from the pregnant mother to produce a second set of amplified products; wherein the mixed sample of DNA comprises fetal DNA and maternal DNA; (iii) determining on a computer the probability that the alleged father is the biological father of the fetus using genotypic measurements based on the first and second sets of amplified products; and (iv) establishing whether the alleged father is the biological father of the fetus using the determined probability that the alleged father is the biological father of the fetus. In various embodiments, the method further includes simultaneously amplifying the corresponding plurality of polymorphic loci on genetic material from the mother to produce a third set of amplified products; wherein the probability that the alleged father is the biological father of the fetus is determined using genotypic measurements based on the first, second, and third sets of amplified products.

Exemplary Methods for Embryo Characterization and Selection

The multiplex PCR methods of the invention can be used to improve the selection of embryos for in vitro fertilization by allowing thousands of target loci to be analyzed at once (see, e.g, U.S. Pub. No. 2011/0092763, filed May 27, 2008, filed Dec. 22, 2011, is which is hereby incorporated by reference in its entirety). For example, the multiplex PCR method can allow thousands of polymorphic loci (such as SNPs) to be analyzed for use in the PARENTAL SUPPORT algorithm described herein to select an embryo out of a set of embryos for in vitro fertilization In some embodiments, the invention provides methods of estimating relative likelihoods that each embryo from a set of embryos will develop as desired. In some embodiments, the method involves contacting a sample from each embryo with a library of primers that simultaneously hybridize to at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci to produce a reaction mixture for each embryo, wherein the samples are each derived from one or more cells from an embryo. In some embodiments, each reaction mixture is subjected to primer extension reaction conditions to produce amplified products. In some embodiments, the method includes determining on a computer one or more characteristics of at least one cell from each embryo based on the amplified products; and estimating on a computer the relative likelihoods that each embryo will develop as desired, based on the one or more characteristics of the at least one cell for each embryo. In some embodiments, the method includes using an informatics based method to determine the at least one characteristic, such as the PARENTAL SUPPORT algorithm described herein. In some embodiments, the characteristic includes a ploidy state. In some embodiments, the characteristic is selected from the group consisting of aneuploid, euploid, mosaic, nullsomy, monosomy, uniparental disomy, trisomy, tetrasomy, a type of aneuploidy, unmatched copy error trisomy, matched copy error trisomy, maternal origin of aneuploidy, paternal origin of aneuploidy, a presence or absence of a disease-linked gene, a chromosomal identity of any aneuploid chromosome, an abnormal genetic condition, a deletion or duplication, a likelihood of a characteristic, and combinations thereof. The characteristic may be associated with a chromosome taken from the group consisting of chromosome one, chromosome two, chromosome three, chromosome four, chromosome five, chromosome six, chromosome seven, chromosome eight, chromosome nine, chromosome ten, chromosome eleven, chromosome twelve, chromosome thirteen, chromosome fourteen, chromosome fifteen, chromosome sixteen, chromosome seventeen, chromosome eighteen, chromosome nineteen, chromosome twenty, chromosome twenty-one, chromosome twenty-two, X chromosome or Y chromosome, and combinations thereof.

Exemplary Prenatal Diagnostic Methods

The multiplex PCR methods of the present invention can be used to improve prenatal diagnostic methods, such as the determination of the ploidy status of fetal chromosomes. Given that the large number of target loci that can be simultaneously amplified, more accurate determinations can be made.

In an embodiment, the present disclosure provides ex vivo methods for determining the ploidy status of a chromosome in a gestating fetus from genotypic data measured from a mixed sample of DNA (i.e., DNA from the mother of the fetus, and DNA from the fetus) and optionally from genotypic data measured from a sample of genetic material from the mother and possibly also from the father, wherein the determining is done by using a joint distribution model to create a set of expected allele distributions for different possible fetal ploidy states given the parental genotypic data, and comparing the expected allelic distributions to the actual allelic distributions measured in the mixed sample, and choosing the ploidy state whose expected allelic distribution pattern most closely matches the observed allelic distribution pattern. In an embodiment, the mixed sample is derived from maternal blood, or maternal serum or plasma. In an embodiment, the mixed sample of DNA may be preferentially enriched at a target loci (e.g., plurality of polymorphic loci). In an embodiment, the preferential enrichment is done in a way that minimizes the allelic bias. In an embodiment, the present disclosure relates to a composition of DNA that has been preferentially enriched at a plurality of loci such that the allelic bias is low. In an embodiment, the allelic distribution(s) are measured by sequencing the DNA from the mixed sample. In an embodiment, the joint distribution model assumes that the alleles will be distributed in a binomial fashion. In an embodiment, the set of expected joint allele distributions are created for genetically linked loci while considering the extant recombination frequencies from various sources, for example, using data from the International HapMap Consortium.

In an embodiment, the present disclosure provides methods for non-invasive prenatal diagnosis (NPD), specifically, determining the aneuploidy status of a fetus by observing allele measurements at a plurality of polymorphic loci in genotypic data measured on DNA mixtures, where certain allele measurements are indicative of an aneuploid fetus, while other allele measurements are indicative of a euploid fetus. In an embodiment, the genotypic data is measured by sequencing DNA mixtures that were derived from maternal plasma. In an embodiment, the DNA sample may be preferentially enriched in molecules of DNA that correspond to the plurality of loci whose allele distributions are being calculated. In an embodiment a sample of DNA comprising only or almost only genetic material from the mother and possibly also a sample of DNA comprising only or almost only genetic material from the father are measured. In an embodiment, the genetic measurements of one or both parents along with the estimated fetal fraction are used to create a plurality of expected allele distributions corresponding to different possible underlying genetic states of the fetus; the expected allele distributions may be termed hypotheses. In an embodiment, the maternal genetic data is not determined by measuring genetic material that is exclusively or almost exclusively maternal in nature, rather, it is estimated from the genetic measurements made on maternal plasma that comprises a mixture of maternal and fetal DNA. In some embodiments the hypotheses may comprise the ploidy of the fetus at one or more chromosomes, which segments of which chromosomes in the fetus were inherited from which parents, and combinations thereof. In some embodiments, the ploidy state of the fetus is determined by comparing the observed allele measurements to the different hypotheses where at least some of the hypotheses correspond to different ploidy states, and selecting the ploidy state that corresponds to the hypothesis that is most likely to be true given the observed allele measurements. In an embodiment, this method involves using allele measurement data from some or all measured SNPs, regardless of whether the loci are homozygous or heterozygous, and therefore does not involve using alleles at loci that are only heterozygous. This method may not be appropriate for situations where the genetic data pertains to only one polymorphic locus. This method is particularly advantageous when the genetic data comprises data for more than ten polymorphic loci for a target chromosome or more than twenty polymorphic loci. This method is especially advantageous when the genetic data comprises data for more than 50 polymorphic loci for a target chromosome, more than 100 polymorphic loci or more than 200 polymorphic loci for a target chromosome. In some embodiments, the genetic data may comprise data for more than 500 polymorphic loci for a target chromosome, more than 1,000 polymorphic loci, more than 2,000 polymorphic loci, or more than 5,000 polymorphic loci for a target chromosome.

In an embodiment, a method disclosed herein yields a quantitative measure of the number of independent observations of each allele at a polymorphic locus. This is unlike most methods such as microarrays or qualitative PCR which provide information about the ratio of two alleles but do not quantify the number of independent observations of either allele. With methods that provide quantitative information regarding the number of independent observations, only the ratio is utilized in ploidy calculations, while the quantitative information by itself is not useful. To illustrate the importance of retaining information about the number of independent observations consider the sample locus with two alleles, A and B. In a first experiment twenty A alleles and twenty B alleles are observed, in a second experiment 200 A alleles and 200 B alleles are observed. In both experiments the ratio (A/(A+B)) is equal to 0.5, however the second experiment conveys more information than the first about the certainty of the frequency of the A or B allele. Some methods by others involve averaging or summing allele ratios (channel ratios) (i.e. $x_i/y_i$) from individual allele and analyzes this ratio, either comparing it to a reference chromosome or using a rule pertaining to how this ratio is expected to behave in particular situations. No allele weighting is implied in such methods, where it is assumed that one can ensure about the same amount of PCR product for each allele and that all the alleles should behave the same way. Such a method has a number of disadvantages, and more importantly, precludes the use a number of improvements that are described elsewhere in this disclosure.

In an embodiment, a method disclosed herein explicitly models the allele frequency distributions expected in disomy as well as a plurality of allele frequency distributions that may be expected in cases of trisomy resulting from nondisjunction during meiosis I, nondisjunction during meiosis II, and/or nondisjunction during mitosis early in fetal development. To illustrate why this is important, imagine a case where there were no crossovers: nondisjunction during meiosis I would result a trisomy in which two different homologs were inherited from one parent; in contrast, nondisjunction during meiosis II or during mitosis early in fetal development would result in two copies of the same homolog from one parent. Each scenario would result in different expected allele frequencies at each polymorphic locus and also at all loci considered jointly, due to genetic linkage. Crossovers, which result in the exchange of genetic material between homologs, make the inheritance pattern more complex; in an embodiment, the instant method accommodates for this by using recombination rate information in addition to the physical distance between loci. In an embodiment, to enable improved distinction between meiosis I nondisjunction and meiosis II or mitotic nondisjunction the instant method incorporate into the model an increasing probability of crossover as the distance from the centromere increases. Meiosis II and mitotic nondisjunction can distinguished by the fact that mitotic nondisjunction typically results in identical or nearly identical copies of one homolog while the two homologs present following a meiosis II nondisjunction event often differ due to one or more crossovers during gametogenesis.

In some embodiments, a method disclosed herein involves comparing the observed allele measurements to theoretical hypotheses corresponding to possible fetal genetic aneuploidy, and does not involve a step of quantitating a ratio of alleles at a heterozygous locus. Where the number of loci is lower than about 20, the ploidy determination made using a method comprising quantitating a ratio of alleles at a heterozygous locus and a ploidy determination made using a method comprising comparing the observed allele measurements to theoretical allele distribution hypotheses corresponding to possible fetal genetic states may give a similar result. However, where the number of loci is above 50 these two methods is likely to give significantly different results; where the number of loci is above 400, above, 1,000 or above 2,000 these two methods are very likely to give results that are increasingly significantly different. These differences are due to the fact that a method that comprises quantitating a ratio of alleles at a heterozygous locus without measuring the magnitude of each allele independently and aggregating or averaging the ratios precludes the use of techniques including using a joint distribution model, performing a linkage analysis, using a binomial distribution model, and/or other advanced statistical techniques, whereas using a method comprising comparing the observed allele measurements to theoretical allele distribution hypotheses corresponding to possible fetal genetic states may use these techniques which can substantially increase the accuracy of the determination.

In an embodiment, a method disclosed herein involves determining whether the distribution of observed allele measurements is indicative of a euploid or an aneuploid fetus using a joint distribution model. The use of a joint distribution model is a different from and a significant improvement over methods that determine heterozygosity rates by treating polymorphic loci independently in that the resultant determinations are of significantly higher accuracy. Without being bound by any particular theory, it is believed that one reason they are of higher accuracy is that the joint distribution model takes into account the linkage between SNPs, and likelihood of crossovers having occurred during the meiosis that gave rise to the gametes that formed the embryo that grew into the fetus. The purpose of using the concept of linkage when creating the expected distribution of allele measurements for one or more hypotheses is that it allows the creation of expected allele measurements distributions that correspond to reality considerably better than when linkage is not used. For example, imagine that there are two SNPs, 1 and 2 located nearby one another, and the mother is A at SNP 1 and A at SNP 2 on one homolog, and B at SNP 1 and B at SNP 2 on homolog two. If the father is A for both SNPs on both homologs, and a B is measured for the fetus SNP 1, this indicates that homolog two has been inherited by the fetus, and therefore that there is a much higher likelihood of a B being present on the fetus at SNP 2. A model that takes into account linkage would predict this, while a model that does not take linkage into account would not. Alternately, if a mother was AB at SNP 1 and AB at nearby SNP 2, then two hypotheses corresponding to maternal trisomy at that location could be used—one involving a matching copy error (nondisjunction in meiosis II or mitosis in early fetal development), and one involving an unmatching copy error (nondisjunction in meiosis I). In the case of a matching copy error trisomy, if the fetus inherited an AA from the mother at SNP 1, then the fetus is much more likely to inherit either an AA or BB from the mother at SNP 2, but not AB. In the case of an unmatching copy error, the fetus would inherit an AB from the mother at both SNPs. The allele distribution hypotheses made by a ploidy calling method that takes into account linkage would make these predictions, and therefore correspond to the actual allele measurements to a considerably greater extent than a ploidy calling method that did not take into account linkage. Note that a linkage approach is not possible when using a method that relies on calculating allele ratios and aggregating those allele ratios.

One reason that it is believed that ploidy determinations that use a method that comprises comparing the observed allele measurements to theoretical hypotheses corresponding to possible fetal genetic states are of higher accuracy is that when sequencing is used to measure the alleles, this method can glean more information from data from alleles where the total number of reads is low than other methods; for example, a method that relies on calculating and aggregating allele ratios would produce disproportionately weighted stochastic noise. For example, imagine a case that involved measuring the alleles using sequencing, and where there was a set of loci where only five sequence reads were detected for each locus. In an embodiment, for each of the alleles, the data may be compared to the hypothesized allele distribution, and weighted according to the number of sequence reads; therefore the data from these measurements would be appropriately weighted and incorporated into the overall determination. This is in contrast to a method that involved quantitating a ratio of alleles at a heterozygous locus, as this method could only calculate ratios of 0%, 20%, 40%, 60%, 80% or 100% as the possible allele ratios; none of these may be close to expected allele ratios. In this latter case, the calculated allele rations would either have to be discarded due to insufficient reads or else would have disproportionate weighting and introduce stochastic noise into the determination, thereby decreasing the accuracy of the determination. In an embodiment, the individual allele measurements may be treated as independent measurements, where the relationship between measurements made on alleles at the same locus is no different from the relationship between measurements made on alleles at different loci.

In an embodiment, a method disclosed herein involves determining whether the distribution of observed allele measurements is indicative of a euploid or an aneuploid fetus without comparing any metrics to observed allele measurements on a reference chromosome that is expected to be disomic (termed the RC method). This is a significant improvement over methods, such as methods using shotgun sequencing which detect aneuploidy by evaluating the proportion of randomly sequenced fragments from a suspect chromosomes relative to one or more presumed disomic reference chromosome. This RC method yields incorrect results if the presumed disomic reference chromosome is not actually disomic. This can occur in cases where aneuploidy is more substantial than trisomy of a single chromosome or where the fetus is triploid and all autosomes are trisomic. In the case of a female triploid (69, XXX) fetus there are in fact no disomic chromosomes at all. The method described herein does not require a reference chromosome and would be able to correctly identify trisomic chromosomes in a female triploid fetus. For each chromosome, hypothesis, child fraction and noise level, a joint distribution model may be fit, without any of: reference chromosome data, an overall child fraction estimate, or a fixed reference hypothesis.

In an embodiment, a method disclosed herein demonstrates how observing allele distributions at polymorphic loci can be used to determine the ploidy state of a fetus with greater accuracy than methods in the prior art. In an embodiment, the method uses the targeted sequencing to obtain mixed maternal-fetal genotypes and optionally mother and/ or father genotypes at a plurality of SNPs to first establish the various expected allele frequency distributions under the different hypotheses, and then observing the quantitative allele information obtained on the maternal-fetal mixture and evaluating which hypothesis fits the data best, where the genetic state corresponding to the hypothesis with the best fit to the data is called as the correct genetic state. In an embodiment, a method disclosed herein also uses the degree of fit to generate a confidence that the called genetic state is the correct genetic state. In an embodiment, a method disclosed herein involves using algorithms that analyze the distribution of alleles found for loci that have different parental contexts, and comparing the observed allele distributions to the expected allele distributions for different ploidy states for the different parental contexts (different parental genotypic patterns). This is different from and an improvement over methods that do not use methods that enable the estimation of the number of independent instances of each allele at each locus in a mixed maternal-fetal sample. In an embodiment, a method disclosed herein involves determining whether the distribution of observed allele measurements is indicative of a euploid or an aneuploid fetus using observed allelic distributions measured at loci where the mother is heterozygous. This is different from and an improvement over methods that do not use observed allelic distributions at loci where the mother is heterozygous because, in cases where the DNA is not preferentially enriched or is preferentially enriched for loci that are not known to be highly informative for that particular target individual, it allows the use of about twice as much genetic measurement data from a set of sequence data in the ploidy determination, resulting in a more accurate determination.

In an embodiment, a method disclosed herein uses a joint distribution model that assumes that the allele frequencies at each locus are multinomial (and thus binomial when SNPs are biallelic) in nature. In some embodiments the joint distribution model uses beta-binomial distributions. When using a measuring technique, such as sequencing, provides a quantitative measure for each allele present at each locus, binomial model can be applied to each locus and the degree underlying allele frequencies and the confidence in that frequency can be ascertained. With methods known in the art that generate ploidy calls from allele ratios, or methods in which quantitative allele information is discarded, the certainty in the observed ratio cannot be ascertained. The instant method is different from and an improvement over methods that calculate allele ratios and aggregate those ratios to make a ploidy call, since any method that involves calculating an allele ratio at a particular locus, and then aggregating those ratios, necessarily assumes that the measured intensities or counts that are indicative of the amount of DNA from any given allele or locus will be distributed in a Gaussian fashion. The method disclosed herein does not involve calculating allele ratios. In some embodiments, a method disclosed herein may involve incorporating the number of observations of each allele at a plurality of loci into a model. In some embodiments, a method disclosed herein may involve calculating the expected distributions themselves, allowing the use of a joint binomial distribution model which may be more accurate than any model that assumes a Gaussian distribution of allele measurements. The likelihood that the binomial distribution model is significantly more accurate than the Gaussian distribution increases as the number of loci increases. For example, when fewer than 20 loci are interrogated, the likelihood that the binomial distribution model is significantly better is low. However, when more than 100, or especially more than 400, or especially more than 1,000, or especially more than 2,000 loci are used, the binomial distribution model will have a very high likelihood of being significantly more accurate than the Gaussian distribution model, thereby resulting in a more accurate ploidy determination. The likelihood that the binomial distribution model is significantly more accurate than the Gaussian distribution also increases as the number of observations at each locus increases. For example, when fewer than 10 distinct sequences are observed at each locus are observed, the likelihood that the binomial distribution model is significantly better is low. However, when more than 50 sequence reads, or especially more than 100 sequence reads, or especially more than 200 sequence reads, or especially more than 300 sequence reads are used for each locus, the binomial distribution model will have a very high likelihood of being significantly more accurate than the Gaussian distribution model, thereby resulting in a more accurate ploidy determination.

In an embodiment, a method disclosed herein uses sequencing to measure the number of instances of each allele at each locus in a DNA sample. Each sequencing read may be mapped to a specific locus and treated as a binary sequence read; alternately, the probability of the identity of the read and/or the mapping may be incorporated as part of the sequence read, resulting in a probabilistic sequence read, that is, the probable whole or fractional number of sequence reads that map to a given loci. Using the binary counts or probability of counts it is possible to use a binomial distribution for each set of measurements, allowing a confidence interval to be calculated around the number of counts. This ability to use the binomial distribution allows for more accurate ploidy estimations and more precise confidence intervals to be calculated. This is different from and an improvement over methods that use intensities to measure the amount of an allele present, for example methods that use microarrays, or methods that make measurements using fluorescence readers to measure the intensity of fluorescently tagged DNA in electrophoretic bands.

In an embodiment, a method disclosed herein uses aspects of the present set of data to determine parameters for the estimated allele frequency distribution for that set of data. This is an improvement over methods that utilize training set of data or prior sets of data to set parameters for the present expected allele frequency distributions, or possibly expected allele ratios. This is because there are different sets of conditions involved in the collection and measurement of every genetic sample, and thus a method that uses data from the instant set of data to determine the parameters for the joint distribution model that is to be used in the ploidy determination for that sample will tend to be more accurate.

In an embodiment, a method disclosed herein involves determining whether the distribution of observed allele measurements is indicative of a euploid or an aneuploid fetus using a maximum likelihood technique. The use of a maximum likelihood technique is different from and a significant improvement over methods that use single hypothesis rejection technique in that the resultant determinations will be made with significantly higher accuracy. One reason is that single hypothesis rejection techniques set cut off thresholds based on only one measurement distribution rather than two, meaning that the thresholds are usually not optimal. Another reason is that the maximum likelihood technique allows the optimization of the cut off threshold for each individual sample instead of determining a cut off threshold to be used for all samples regardless of the particular characteristics of each individual sample. Another reason is that the use of a maximum likelihood technique allows the calculation of a confidence for each ploidy call. The ability to make a confidence calculation for each call allows a practitioner to know which calls are accurate, and which are more likely to be wrong. In some embodiments, a wide variety of methods may be combined with a maximum likelihood estimation technique to enhance the accuracy of the ploidy calls. In an embodiment, the maximum likelihood technique may be used in combination with the method described in U.S. Pat. No. 7,888,017. In an embodiment, the maximum likelihood technique may be used in combination with the method of using targeted PCR amplification to amplify the DNA in the mixed sample followed by sequencing and analysis using a read counting method such as used by TANDEM DIAGNOSTICS, as presented at the International Congress of Human Genetics 2011, in Montreal in October 2011. In an embodiment, a method disclosed herein involves estimating the fetal fraction of DNA in the mixed sample and using that estimation to calculate both the ploidy call and the confidence of the ploidy call. Note that this is both different and distinct from methods that use estimated fetal fraction as a screen for sufficient fetal fraction, followed by a ploidy call made using a single hypothesis rejection technique that does not take into account the fetal fraction nor does it produce a confidence calculation for the call.

In an embodiment, a method disclosed herein takes into account the tendency for the data to be noisy and contain errors by attaching a probability to each measurement. The use of maximum likelihood techniques to choose the correct hypothesis from the set of hypotheses that were made using the measurement data with attached probabilistic estimates makes it more likely that the incorrect measurements will be discounted, and the correct measurements will be used in the calculations that lead to the ploidy call. To be more precise, this method systematically reduces the influence of data that is incorrectly measured on the ploidy determination. This is an improvement over methods where all data is assumed to be equally correct or methods where outlying data is arbitrarily excluded from calculations leading to a ploidy call. Existing methods using channel ratio measurements claim to extend the method to multiple SNPs by averaging individual SNP channel ratios. Not weighting individual SNPs by expected measurement variance based on the SNP quality and observed depth of read reduces the accuracy of the resulting statistic, resulting in a reduction of the accuracy of the ploidy call significantly, especially in borderline cases.

In an embodiment, a method disclosed herein does not presuppose the knowledge of which SNPs or other polymorphic loci are heterozygous on the fetus. This method allows a ploidy call to be made in cases where paternal genotypic information is not available. This is an improvement over methods where the knowledge of which SNPs are heterozygous must be known ahead of time in order to appropriately select loci to target, or to interpret the genetic measurements made on the mixed fetal/maternal DNA sample.

The methods described herein are particularly advantageous when used on samples where a small amount of DNA is available, or where the percent of fetal DNA is low. This is due to the correspondingly higher allele dropout rate that occurs when only a small amount of DNA is available and/or the correspondingly higher fetal allele dropout rate when the percent of fetal DNA is low in a mixed sample of fetal and maternal DNA. A high allele dropout rate, meaning that a large percentage of the alleles were not measured for the target individual, results in poorly accurate fetal fractions calculations, and poorly accurate ploidy determinations. Since methods disclosed herein may use a joint distribution model that takes into account the linkage in inheritance patterns between SNPs, significantly more accurate ploidy determinations may be made. The methods described herein allow for an accurate ploidy determination to be made when the percent of molecules of DNA that are fetal in the mixture is less than 40%, less than 30%, less than 20%, less than 10%, less than 8%, and even less than 6%.

In an embodiment, it is possible to determine the ploidy state of an individual based on measurements when that individual's DNA is mixed with DNA of a related individual. In an embodiment, the mixture of DNA is the free floating DNA found in maternal plasma, which may include DNA from the mother, with known karyotype and known genotype, and which may be mixed with DNA of the fetus, with unknown karyotype and unknown genotype. It is possible to use the known genotypic information from one or both parents to predict a plurality of potential genetic states of the DNA in the mixed sample for different ploidy states, different chromosome contributions from each parent to the fetus, and optionally, different fetal DNA fractions in the mixture. Each potential composition may be referred to as a hypothesis. The ploidy state of the fetus can then be determined by looking at the actual measurements, and determining which potential compositions are most likely given the observed data.

Further discussion of the points above may be found elsewhere in this document.

Non-Invasive Prenatal Diagnosis (NPD)

The process of non-invasive prenatal diagnosis involves a number of steps. Some of the steps may include: (1) obtaining the genetic material from the fetus; (2) enriching the genetic material of the fetus that may be in a mixed sample, ex vivo; (3) amplifying the genetic material, ex vivo; (4) preferentially enriching specific loci in the genetic material, ex vivo; (5) measuring the genetic material, ex vivo; and (6) analyzing the genotypic data, on a computer, and ex vivo. Methods to reduce to practice these six and other relevant steps are described herein. At least some of the method steps are not directly applied on the body. In an embodiment, the present disclosure relates to methods of treatment and diagnosis applied to tissue and other biological materials isolated and separated from the body. At least some of the method steps are executed on a computer.

Some embodiments of the present disclosure allow a clinician to determine the genetic state of a fetus that is gestating in a mother in a non-invasive manner such that the health of the baby is not put at risk by the collection of the genetic material of the fetus, and that the mother is not required to undergo an invasive procedure. Moreover, in certain aspects, the present disclosure allows the fetal genetic state to be determined with high accuracy, significantly greater accuracy than, for example, the non-invasive maternal serum analyte based screens, such as the triple test, that are in wide use in prenatal care.

The high accuracy of the methods disclosed herein is a result of an informatics approach to analysis of the genotype data, as described herein. Modern technological advances have resulted in the ability to measure large amounts of genetic information from a genetic sample using such methods as high throughput sequencing and genotyping arrays. The methods disclosed herein allow a clinician to take greater advantage of the large amounts of data available, and make a more accurate diagnosis of the fetal genetic state. The details of a number of embodiments are given below. Different embodiments may involve different combinations of the aforementioned steps. Various combinations of the different embodiments of the different steps may be used interchangeably.

In an embodiment, a blood sample is taken from a pregnant mother, and the free floating DNA in the plasma of the mother's blood, which contains a mixture of both DNA of maternal origin, and DNA of fetal origin, is isolated and used to determine the ploidy status of the fetus. In an embodiment, a method disclosed herein involves preferential enrichment of those DNA sequences in a mixture of DNA that correspond to polymorphic alleles in a way that the allele ratios and/or allele distributions remain mostly consistent upon enrichment. In an embodiment, a method disclosed herein involves the highly efficient targeted PCR based amplification such that a very high percentage of the resulting molecules correspond to targeted loci. In an embodiment, a method disclosed herein involves sequencing a mixture of DNA that contains both DNA of maternal origin, and DNA of fetal origin. In an embodiment, a method disclosed herein involves using measured allele distributions to determine the ploidy state of a fetus that is gestating in a mother. In an embodiment, a method disclosed herein involves reporting the determined ploidy state to a clinician. In an embodiment, a method disclosed herein involves taking a clinical action, for example, performing follow up invasive testing such as chorionic villus sampling or amniocentesis, preparing for the birth of a trisomic individual or an elective termination of a trisomic fetus.

This application makes reference to U.S. Utility application Ser. No. 11/603,406, filed Nov. 28, 2006 (US Publication No.: 20070184467); U.S. Utility application Ser. No. 12/076,348, filed Mar. 17, 2008 (US Publication No.: 20080243398); PCT Application Serial No. PCT/US09/52730, filed Aug. 4, 2009 (PCT Publication No.: W0/2010/017214); 10 PCT Application Serial No. PCT/US10/050824, filed Sep. 30, 2010 (PCT Publication No.: W0/2011/041485), U.S. Utility application Ser. No. 13/110,685, filed May 18, 2011, and PCT Application Serial No. PCT/12/58578, filed Oct. 3, 2012, which are each herein incorporated by reference in its entirety. Some of the vocabulary used in this filing may have its antecedents in these references. Some of the concepts described herein may be better understood in light of the concepts found in these references.

Screening Maternal Blood Comprising Free Floating Fetal DNA

The methods described herein may be used to help determine the genotype of a child, fetus, or other target individual where the genetic material of the target is found in the presence of a quantity of other genetic material. In some embodiments the genotype may refer to the ploidy state of one or a plurality of chromosomes, it may refer to one or a plurality of disease linked alleles, or some combination thereof. In this disclosure, the discussion focuses on determining the genetic state of a fetus where the fetal DNA is found in maternal blood, but this example is not meant to limit to possible contexts that this method may be applied to. In addition, the method may be applicable in cases where the amount of target DNA is in any proportion with the non-target DNA; for example, the target DNA could make up anywhere between 0.000001 and 99.999999% of the DNA present. In addition, the non-target DNA does not necessarily need to be from one individual, or even from a related individual, as long as genetic data from some or all of the relevant non-target individual(s) is known. In an embodiment, a method disclosed herein can be used to determine genotypic data of a fetus from maternal blood that contains fetal DNA. It may also be used in a case where there are multiple fetuses in the uterus of a pregnant woman, or where other contaminating DNA may be present in the sample, for example from other already born siblings.

This technique may make use of the phenomenon of fetal blood cells gaining access to maternal circulation through the placental villi. Ordinarily, only a very small number of fetal cells enter the maternal circulation in this fashion (not enough to produce a positive Kleihauer-Betke test for fetal-maternal hemorrhage). The fetal cells can be sorted out and analyzed by a variety of techniques to look for particular DNA sequences, but without the risks that invasive procedures inherently have. This technique may also make use of the phenomenon of free floating fetal DNA gaining access to maternal circulation by DNA release following apoptosis of placental tissue where the placental tissue in question contains DNA of the same genotype as the fetus. The free floating DNA found in maternal plasma has been shown to contain fetal DNA in proportions as high as 30-40% fetal DNA.

In an embodiment, blood may be drawn from a pregnant woman. Research has shown that maternal blood may contain a small amount of free floating DNA from the fetus, in addition to free floating DNA of maternal origin. In addition, there also may be enucleated fetal blood cells comprising DNA of fetal origin, in addition to many blood cells of maternal origin, which typically do not contain nuclear DNA. There are many methods know in the art to isolate fetal DNA, or create fractions enriched in fetal DNA. For example, chromatography has been show to create certain fractions that are enriched in fetal DNA.

Once the sample of maternal blood, plasma, or other fluid, drawn in a relatively non-invasive manner, and that contains an amount of fetal DNA, either cellular or free floating, either enriched in its proportion to the maternal DNA, or in its original ratio, is in hand, one may genotype the DNA found in said sample. In some embodiments, the blood may be drawn using a needle to withdraw blood from a vein, for example, the basilica vein. The method described herein can be used to determine genotypic data of the fetus. For example, it can be used to determine the ploidy state at one or more chromosomes, it can be used to determine the identity of one or a set of SNPs, including insertions, deletions, and translocations. It can be used to determine one or more haplotypes, including the parent of origin of one or more genotypic features.

Note that this method will work with any nucleic acids that can be used for any genotyping and/or sequencing methods, such as the ILLUMINA INFINIUM ARRAY platform, AFFYMETRIX GENECHIP, ILLUMINA GENOME ANALYZER, or LIFE TECHNOLGIES' SOLID SYSTEM. This includes extracted free-floating DNA from plasma or amplifications (e.g. whole genome amplification, PCR) of the same; genomic DNA from other cell types (e.g. human lymphocytes from whole blood) or amplifications of the same. For preparation of the DNA, any extraction or purification method that generates genomic DNA suitable for the one of these platforms will work as well. This method could work equally well with samples of RNA. In an embodiment, storage of the samples may be done in a way that will minimize degradation (e.g. below freezing, at about −20 C, or at a lower temperature).

Parental Support

Some embodiments may be used in combination with the PARENTAL SUPPORT™ (PS) method, embodiments of which are described in U.S. application Ser. No. 11/603,406 (US Publication No.: 20070184467), U.S. application Ser. No. 12/076,348 (US Publication No.: 20080243398), U.S. application Ser. No. 13/110,685, PCT Application PCT/US09/52730 (PCT Publication No.: WO/2010/017214), and PCT Application No. PCT/US10/050824 (PCT Publication No.: WO/2011/041485) which are incorporated herein by reference in their entirety. PARENTAL SUPPORT™ is an informatics based approach that can be used to analyze genetic data. In some embodiments, the methods disclosed herein may be considered as part of the PARENTAL SUPPORT™ method. In some embodiments, The PARENTAL SUPPORT™ method is a collection of methods that may be used to determine the genetic data of a target individual, with high accuracy, of one or a small number of cells from that individual, or of a mixture of DNA consisting of DNA from the target individual and DNA from one or a plurality of other individuals, specifically to determine disease-related alleles, other alleles of interest, and/or the ploidy state of one or a plurality of chromosomes in the target individual. PARENTAL SUPPORT™ may refer to any of these methods. PARENTAL SUPPORT™ is an example of an informatics based method. Exemplary embodiments of the PARENTAL SUPPORT™ method are illustrated in FIGS. 29-31G and described in Experiment 19.

The PARENTAL SUPPORT™ method makes use of known parental genetic data, i.e. haplotypic and/or diploid genetic data of the mother and/or the father, together with the knowledge of the mechanism of meiosis and the imperfect measurement of the target DNA, and possibly of one or more related individuals, along with population based crossover frequencies, in order to reconstruct, in silico, the genotype at a plurality of alleles, and/or the ploidy state of an embryo or of any target cell(s), and the target DNA at the location of key loci with a high degree of confidence. The PARENTAL SUPPORT™ method can reconstruct not only single nucleotide polymorphisms (SNPs) that were measured poorly, but also insertions and deletions, and SNPs or whole regions of DNA that were not measured at all. Furthermore, the PARENTAL SUPPORT™ method can both measure multiple disease-linked loci as well as screen for aneuploidy, from a single cell. In some embodiments, the PARENTAL SUPPORT™ method may be used to characterize one or more cells from embryos biopsied during an IVF cycle to determine the genetic condition of the one or more cells.

The PARENTAL SUPPORT™ method allows the cleaning of noisy genetic data. This may be done by inferring the correct genetic alleles in the target genome (embryo) using the genotype of related individuals (parents) as a reference. PARENTAL SUPPORT™ may be particularly relevant where only a small quantity of genetic material is available (e.g. PGD) and where direct measurements of the genotypes are inherently noisy due to the limited amounts of genetic material. PARENTAL SUPPORT™ may be particularly relevant where only a small fraction of the genetic material available is from the target individual (e.g. NPD) and where direct measurements of the genotypes are inherently noisy due to the contaminating DNA signal from another individual. The PARENTAL SUPPORT™ method is able to reconstruct highly accurate ordered diploid allele sequences on the embryo, together with copy number of chromosomes segments, even though the conventional, unordered diploid measurements may be characterized by high rates of allele dropouts, drop-ins, variable amplification biases and other errors. The method may employ both an underlying genetic model and an underlying model of measurement error. The genetic model may determine both allele probabilities at each SNP and crossover probabilities between SNPs. Allele probabilities may be modeled at each SNP based on data obtained from the parents and model crossover probabilities between SNPs based on data obtained from the HapMap database, as developed by the International HapMap Project. Given the proper underlying genetic model and measurement error model, maximum a posteriori (MAP) estimation may be used, with modifications for computationally efficiency, to estimate the correct, ordered allele values at each SNP in the embryo.

The techniques outlined above, in some cases, are able to determine the genotype of an individual given a very small amount of DNA originating from that individual. This could be the DNA from one or a small number of cells, or it could be from the small amount of fetal DNA found in maternal blood.

Hypotheses

In the context of this disclosure, a hypothesis refers to a possible genetic state. It may refer to a possible ploidy state. It may refer to a possible allelic state. A set of hypotheses may refer to a set of possible genetic states, a set of possible allelic states, a set of possible ploidy states, or combinations thereof. In some embodiments, a set of hypotheses may be designed such that one hypothesis from the set will correspond to the actual genetic state of any given individual. In some embodiments, a set of hypotheses may be designed such that every possible genetic state may be described by at least one hypothesis from the set. In some embodiments of the present disclosure, one aspect of a method is to determine which hypothesis corresponds to the actual genetic state of the individual in question.

In another embodiment of the present disclosure, one step involves creating a hypothesis. In some embodiments it may be a copy number hypothesis. In some embodiments it may involve a hypothesis concerning which segments of a chromosome from each of the related individuals correspond genetically to which segments, if any, of the other related individuals. Creating a hypothesis may refer to the act of setting the limits of the variables such that the entire set of possible genetic states that are under consideration are encompassed by those variables.

A "copy number hypothesis," also called a "ploidy hypothesis," or a "ploidy state hypothesis," may refer to a hypothesis concerning a possible ploidy state for a given chromosome copy, chromosome type, or section of a chromosome, in the target individual. It may also refer to the ploidy state at more than one of the chromosome types in the individual. A set of copy number hypotheses may refer to a set of hypotheses where each hypothesis corresponds to a different possible ploidy state in an individual. A set of hypotheses may concern a set of possible ploidy states, a set of possible parental haplotypes contributions, a set of possible fetal DNA percentages in the mixed sample, or combinations thereof. In some embodiments, the copy number hypotheses include all fetuses in a multiple pregnancy being euploid, all fetuses in a multiple pregnancy being aneuploid (such as any of the aneuploidies disclosed herein), and/or one or more fetuses in a multiple pregnancy being euploid and one or more fetuses in a multiple pregnancy being aneuploidy. In some embodiments, the copy number hypotheses include identical twins (also referred to as monozygotic twins) or fraternal twins (also referred to as dizygotic twins). In some embodiments, the copy number hypotheses include a molar pregnancy, such as a complete or partial molar pregnancy.

A normal individual contains one of each chromosome type from each parent. However, due to errors in meiosis and mitosis, it is possible for an individual to have 0, 1, 2, or more of a given chromosome type from each parent. In practice, it is rare to see more that two of a given chromosomes from a parent. In this disclosure, some embodiments only consider the possible hypotheses where 0, 1, or 2 copies of a given chromosome come from a parent; it is a trivial extension to consider more or less possible copies originating from a parent. In some embodiments, for a given chromosome, there are nine possible hypotheses: the three possible hypothesis concerning 0, 1, or 2 chromosomes of maternal origin, multiplied by the three possible hypotheses concerning 0, 1, or 2 chromosomes of paternal origin. Let (m,f) refer to the hypothesis where m is the number of a given chromosome inherited from the mother, and f is the number of a given chromosome inherited from the father. Therefore, the nine hypotheses are (0,0), (0,1), (0,2), (1,0), (1,1), (1,2), (2,0), (2,1), and (2,2). These may also be written as $H_{00}$, $H_{01}$, $H_{02}$, $H_{10}$, $H_{12}$, $H_{20}$, $H_{21}$, and $H_{22}$. The different hypotheses correspond to different ploidy states. For example, (1,1) refers to a normal disomic chromosome; (2,1) refers to a maternal trisomy, and (0,1) refers to a paternal monosomy. In some embodiments, the case where two chromosomes are inherited from one parent and one chromosome is inherited from the other parent may be further differentiated into two cases: one where the two chromosomes are identical (matched copy error), and one where the two chromosomes are homologous but not identical (unmatched copy error). In these embodiments, there are sixteen possible hypotheses. It should be understood that it is possible to use other sets of hypotheses, and a different number of hypotheses.

In some embodiments of the present disclosure, the ploidy hypothesis refers to a hypothesis concerning which chromosome from other related individuals correspond to a chromosome found in the target individual's genome. In some embodiments, a key to the method is the fact that related individuals can be expected to share haplotype blocks, and using measured genetic data from related individuals, along with a knowledge of which haplotype blocks match between the target individual and the related individual, it is possible to infer the correct genetic data for a target individual with higher confidence than using the target individual's genetic measurements alone. As such, in some embodiments, the ploidy hypothesis may concern not only the number of chromosomes, but also which chromosomes in related individuals are identical, or nearly identical, with one or more chromosomes in the target individual.

Once the set of hypotheses have been defined, when the algorithms operate on the input genetic data, they may output a determined statistical probability for each of the hypotheses under consideration. The probabilities of the various hypotheses may be determined by mathematically calculating, for each of the various hypotheses, the value that the probability equals, as stated by one or more of the expert techniques, algorithms, and/or methods described elsewhere in this disclosure, using the relevant genetic data as input.

Once the probabilities of the different hypotheses are estimated, as determined by a plurality of techniques, they may be combined. This may entail, for each hypothesis, multiplying the probabilities as determined by each technique. The product of the probabilities of the hypotheses may be normalized. Note that one ploidy hypothesis refers to one possible ploidy state for a chromosome.

The process of "combining probabilities," also called "combining hypotheses," or combining the results of expert techniques, is a concept that should be familiar to one skilled in the art of linear algebra. One possible way to combine probabilities is as follows: When an expert technique is used to evaluate a set of hypotheses given a set of genetic data, the output of the method is a set of probabilities that are associated, in a one-to-one fashion, with each hypothesis in the set of hypotheses. When a set of probabilities that were determined by a first expert technique, each of which are associated with one of the hypotheses in the set, are combined with a set of probabilities that were determined by a second expert technique, each of which are associated with the same set of hypotheses, then the two sets of probabilities are multiplied. This means that, for each hypothesis in the set, the two probabilities that are associated with that hypothesis, as determined by the two expert methods, are multiplied together, and the corresponding product is the output probability. This process may be expanded to any number of expert techniques. If only one expert technique is used, then the output probabilities are the same as the input probabilities. If more than two expert techniques are used, then the relevant probabilities may be multiplied at the same time. The products may be normalized so that the probabilities of the hypotheses in the set of hypotheses sum to 100%.

In some embodiments, if the combined probabilities for a given hypothesis are greater than the combined probabilities for any of the other hypotheses, then it may be considered that that hypothesis is determined to be the most likely. In some embodiments, a hypothesis may be determined to be the most likely, and the ploidy state, or other genetic state, may be called if the normalized probability is greater than a threshold. In an embodiment, this may mean that the number and identity of the chromosomes that are associated with that hypothesis may be called as the ploidy state. In an embodiment, this may mean that the identity of the alleles that are associated with that hypothesis may be called as the allelic state. In some embodiments, the threshold may be between about 50% and about 80%. In some embodiments the threshold may be between about 80% and about 90%. In some embodiments the threshold may be between about 90% and about 95%. In some embodiments the threshold may be between about 95% and about 99%. In some embodiments the threshold may be between about 99% and about 99.9%. In some embodiments the threshold may be above about 99.9%.

Parental Contexts

The parental context refers to the genetic state of a given allele, on each of the two relevant chromosomes for one or both of the two parents of the target. Note that in an embodiment, the parental context does not refer to the allelic state of the target, rather, it refers to the allelic state of the parents. The parental context for a given SNP may consist of four base pairs, two paternal and two maternal; they may be the same or different from one another. It is typically written as "$m_1m_2|f_1f_2$," where $m_1$ and $m_2$ are the genetic state of the given SNP on the two maternal chromosomes, and $f_1$ and $f_2$ are the genetic state of the given SNP on the two paternal chromosomes. In some embodiments, the parental context may be written as "$f_1f_2|m_1m_2$." Note that subscripts "1" and "2" refer to the genotype, at the given allele, of the first and second chromosome; also note that the choice of which chromosome is labeled "1" and which is labeled "2" is arbitrary.

Note that in this disclosure, A and B are often used to generically represent base pair identities; A or B could equally well represent C (cytosine), G (guanine), A (adenine) or T (thymine). For example, if, at a given SNP based allele, the mother's genotype was T at that SNP on one chromosome, and G at that SNP on the homologous chromosome, and the father's genotype at that allele is G at that SNP on both of the homologous chromosomes, one may say that the target individual's allele has the parental context of AB|BB; it could also be said that the allele has the parental context of AB|AA. Note that, in theory, any of the four possible nucleotides could occur at a given allele, and thus it is possible, for example, for the mother to have a genotype of AT, and the father to have a genotype of GC at a given allele. However, empirical data indicate that in most cases only two of the four possible base pairs are observed at a given allele. It is possible, for example when using single tandem repeats, to have more than two parental, more than four and even more than ten contexts. In this disclosure the discussion assumes that only two possible base pairs will be observed at a given allele, although the embodiments disclosed herein could be modified to take into account the cases where this assumption does not hold.

A "parental context" may refer to a set or subset of target SNPs that have the same parental context. For example, if one were to measure 1000 alleles on a given chromosome on a target individual, then the context AA|BB could refer to the set of all alleles in the group of 1,000 alleles where the genotype of the mother of the target was homozygous, and the genotype of the father of the target is homozygous, but where the maternal genotype and the paternal genotype are dissimilar at that locus. If the parental data is not phased, and thus AB=BA, then there are nine possible parental contexts: AA|AA, AA|AB, AA|BB, AB|AA, AB|AB, AB|BB, BB|AA, BB|AB, and BB|BB. If the parental data is phased, and thus AB # BA, then there are sixteen different possible parental contexts: AA|AA, AA|AB, AA|BA, AA|BB, AB|AA, AB|AB, AB|BA, AB|BB, BA|AA, BA|AB, BA|BA, BA|BB, BB|AA, BB|AB, BB|BA, and BB|BB. Every SNP allele on a chromosome, excluding some SNPs on the sex chromosomes, has one of these parental contexts. The set of SNPs wherein the parental context for one parent is heterozygous may be referred to as the heterozygous context.

Use of Parental Contexts in NPD

Non-invasive prenatal diagnosis is an important technique that can be used to determine the genetic state of a fetus from genetic material that is obtained in a non-invasive manner, for example from a blood draw on the pregnant mother. The blood could be separated and the plasma isolated, followed by isolation of the plasma DNA. Size selection could be used to isolate the DNA of the appropriate length. The DNA may be preferentially enriched at a set of loci. This DNA can then be measured by a number of means, such as by hybridizing to a genotyping array and measuring the fluorescence, or by sequencing on a high throughput sequencer.

When sequencing is used for ploidy calling of a fetus in the context of non-invasive prenatal diagnosis, there are a number of ways to use the sequence data. The most common way one could use the sequence data is to simply count the number of reads that map to a given chromosome. For example, imagine if you are trying to determine the ploidy state of chromosome 21 on the fetus. Further imagine that the DNA in the sample is comprised of 10% DNA of fetal origin, and 90% DNA of maternal origin. In this case, you could look at the average number of reads on a chromosome which can be expected to be disomic, for example chromosome 3, and compare that to the number of read on chromosome 21, where the reads are adjusted for the number of base pairs on that chromosome that are part of a unique sequence. If the fetus were euploid, one would expect the amount of DNA per unit of genome to be about equal at all locations (subject to stochastic variations). On the other hand, if the fetus were trisomic at chromosome 21, then one would expect there to be more slightly more DNA per genetic unit from chromosome 21 than the other locations on the genome. Specifically one would expect there to be about 5% more DNA from chromosome 21 in the mixture. When sequencing is used to measure the DNA, one would expect about 5% more uniquely mappable reads from chromosome 21 per unique segment than from the other chromosomes. One could use the observation of an amount of DNA from a particular chromosome that is higher than a certain threshold, when adjusted for the number of sequences that are uniquely mappable to that chromosome, as the basis for an aneuploidy diagnosis. Another method that may be used to detect aneuploidy is similar to that above, except that parental contexts could be taken into account.

When considering which alleles to target, one may consider the likelihood that some parental contexts are likely to be more informative than others. For example, AA|BB and the symmetric context BB|AA are the most informative contexts, because the fetus is known to carry an allele that is different from the mother. For reasons of symmetry, both AA|BB and BB|AA contexts may be referred to as AA|BB. Another set of informative parental contexts are AA|AB and BB|AB, because in these cases the fetus has a 50% chance of carrying an allele that the mother does not have. For reasons of symmetry, both AA|AB and BB|AB contexts may be referred to as AA|AB. A third set of informative parental contexts are AB|AA and AB|BB, because in these cases the fetus is carrying a known paternal allele, and that allele is also present in the maternal genome. For reasons of symmetry, both AB|AA and AB|BB contexts may be referred to as AB|AA. A fourth parental context is AB|AB where the fetus has an unknown allelic state, and whatever the allelic state, it is one in which the mother has the same alleles. The fifth parental context is AA|AA, where the mother and father are heterozygous.

Different Implementations of the Presently Disclosed Embodiments

Methods are disclosed herein for determining the ploidy state of a target individual. The target individual may be a blastomere, an embryo, or a fetus. In some embodiments of the present disclosure, a method for determining the ploidy state of one or more chromosome in a target individual may include any of the steps described in this document, and combinations thereof:

In some embodiments the source of the genetic material to be used in determining the genetic state of the fetus may be fetal cells, such as nucleated fetal red blood cells, isolated from the maternal blood. The method may involve obtaining a blood sample from the pregnant mother. The method may involve isolating a fetal red blood cell using visual techniques, based on the idea that a certain combination of colors are uniquely associated with nucleated red blood cell, and a similar combination of colors is not associated with any other present cell in the maternal blood. The combination of colors associated with the nucleated red blood cells may include the red color of the hemoglobin around the nucleus, which color may be made more distinct by staining, and the color of the nuclear material which can be stained, for example, blue. By isolating the cells from maternal blood and spreading them over a slide, and then identifying those points at which one sees both red (from the Hemoglobin) and blue (from the nuclear material) one may be able to identify the location of nucleated red blood cells. One may then extract those nucleated red blood cells using a micromanipulator, use genotyping and/or sequencing techniques to measure aspects of the genotype of the genetic material in those cells.

In an embodiment, one may stain the nucleated red blood cell with a die that only fluoresces in the presence of fetal hemoglobin and not maternal hemoglobin, and so remove the ambiguity between whether a nucleated red blood cell is derived from the mother or the fetus. Some embodiments of the present disclosure may involve staining or otherwise marking nuclear material. Some embodiments of the present disclosure may involve specifically marking fetal nuclear material using fetal cell specific antibodies.

There are many other ways to isolate fetal cells from maternal blood, or fetal DNA from maternal blood, or to enrich samples of fetal genetic material in the presence of maternal genetic material. Some of these methods are listed here, but this is not intended to be an exhaustive list. Some appropriate techniques are listed here for convenience: using fluorescently or otherwise tagged antibodies, size exclusion chromatography, magnetically or otherwise labeled affinity tags, epigenetic differences, such as differential methylation between the maternal and fetal cells at specific alleles, density gradient centrifugation succeeded by CD45/14 depletion and CD71-positive selection from CD45/14 negative-cells, single or double Percoll gradients with different osmolalities, or galactose specific lectin method.

In an embodiment of the present disclosure, the target individual is a fetus, and the different genotype measurements are made on a plurality of DNA samples from the fetus. In some embodiments of the present disclosure, the fetal DNA samples are from isolated fetal cells where the fetal cells may be mixed with maternal cells. In some embodiments of the present disclosure, the fetal DNA samples are from free floating fetal DNA, where the fetal DNA may be mixed with free floating maternal DNA. In some embodiments, the fetal DNA samples may be derived from maternal plasma or maternal blood that contains a mixture of maternal DNA and fetal DNA. In some embodiments, the fetal DNA may be mixed with maternal DNA in maternal:fetal ratios ranging from 99.9:0.1% to 99:1%; 99:1% to 90:10%; 90:10% to 80:20%; 80:20% to 70:30%; 70:30% to 50:50%; 50:50% to 10:90%; or 10:90% to 1:99%; 1:99% to 0.1:99.9%.

The genetic data of the target individual and/or of the related individual can be transformed from a molecular state to an electronic state by measuring the appropriate genetic material using tools and or techniques taken from a group including, but not limited to: genotyping microarrays, and high throughput sequencing. Some high throughput sequencing methods include Sanger DNA sequencing, pyrosequencing, the ILLUMINA SOLEXA platform, ILLUMINA's GENOME ANALYZER, or APPLIED BIOSYSTEM's 454 sequencing platform, HELICOS's TRUE SINGLE MOLECULE SEQUENCING platform, HALCYON MOLECULAR's electron microscope sequencing method, or any other sequencing method. All of these methods physically transform the genetic data stored in a sample of DNA into a set of genetic data that is typically stored in a memory device in route to being processed.

A relevant individual's genetic data may be measured by analyzing substances taken from a group including, but not limited to: the individual's bulk diploid tissue, one or more diploid cells from the individual, one or more haploid cells from the individual, one or more blastomeres from the target individual, extra-cellular genetic material found on the individual, extra-cellular genetic material from the individual found in maternal blood, cells from the individual found in maternal blood, one or more embryos created from (a) gamete(s) from the related individual, one or more blastomeres taken from such an embryo, extra-cellular genetic material found on the related individual, genetic material known to have originated from the related individual, and combinations thereof.

In some embodiments, a set of at least one ploidy state hypothesis may be created for each of the chromosomes types of interest of the target individual. Each of the ploidy state hypotheses may refer to one possible ploidy state of the chromosome or chromosome segment of the target individual. The set of hypotheses may include some or all of the possible ploidy states that the chromosome of the target individual may be expected to have. Some of the possible ploidy states may include nullsomy, monosomy, disomy, uniparental disomy, euploidy, trisomy, matching trisomy, unmatching trisomy, maternal trisomy, paternal trisomy, tetrasomy, balanced (2:2) tetrasomy, unbalanced (3:1) tetrasomy, pentasomy, hexasomy, other aneuploidy, and combinations thereof. Any of these aneuploidy states may be mixed or partial aneuploidy such as unbalanced translocations, balanced translocations, Robertsonian translocations, recombinations, deletions, insertions, crossovers, and combinations thereof.

In some embodiments, the knowledge of the determined ploidy state may be used to make a clinical decision. This knowledge, typically stored as a physical arrangement of matter in a memory device, may then be transformed into a report. The report may then be acted upon. For example, the clinical decision may be to terminate the pregnancy; alternately, the clinical decision may be to continue the pregnancy. In some embodiments the clinical decision may involve an intervention designed to decrease the severity of the phenotypic presentation of a genetic disorder, or a decision to take relevant steps to prepare for a special needs child.

In an embodiment of the present disclosure, any of the methods described herein may be modified to allow for multiple targets to come from same target individual, for example, multiple blood draws from the same pregnant mother. This may improve the accuracy of the model, as multiple genetic measurements may provide more data with which the target genotype may be determined. In an embodiment, one set of target genetic data served as the primary data which was reported, and the other served as data to double-check the primary target genetic data. In an embodiment, a plurality of sets of genetic data, each measured from genetic material taken from the target individual, are considered in parallel, and thus both sets of target genetic data serve to help determine which sections of parental genetic data, measured with high accuracy, composes the fetal genome.

In an embodiment, the method may be used for the purpose of paternity testing. For example, given the SNP-based genotypic information from the mother, and from a man who may or may not be the genetic father, and the measured genotypic information from the mixed sample, it is possible to determine if the genotypic information of the male indeed represents that actual genetic father of the gestating fetus. A simple way to do this is to simply look at the contexts where the mother is AA, and the possible father is AB or BB. In these cases, one may expect to see the father contribution half (AA|AB) or all (AA|BB) of the time, respectively. Taking into account the expected ADO, it is straightforward to determine whether or not the fetal SNPs that are observed are correlated with those of the possible father.

One embodiment of the present disclosure could be as follows: a pregnant woman wants to know if her fetus is afflicted with Down Syndrome, and/or if it will suffer from Cystic Fibrosis, and she does not wish to bear a child that is afflicted with either of these conditions. A doctor takes her blood, and stains the hemoglobin with one marker so that it appears clearly red, and stains nuclear material with another marker so that it appears clearly blue. Knowing that maternal red blood cells are typically anuclear, while a high proportion of fetal cells contain a nucleus, the doctor is able to visually isolate a number of nucleated red blood cells by identifying those cells that show both a red and blue color. The doctor picks up these cells off the slide with a micromanipulator and sends them to a lab which amplifies and genotypes ten individual cells. By using the genetic measurements, the PARENTAL SUPPORT™ method is able to determine that six of the ten cells are maternal blood cells, and four of the ten cells are fetal cells. If a child has already been born to a pregnant mother, PARENTAL SUPPORT™ can also be used to determine that the fetal cells are distinct from the cells of the born child by making reliable allele calls on the fetal cells and showing that they are dissimilar to those of the born child. Note that this method is similar in concept to the paternal testing embodiment of the present disclosure. The genetic data measured from the fetal cells may be of very poor quality, comprising many allele drop outs, due to the difficulty of genotyping single cells. The clinician is able to use the measured fetal DNA along with the reliable DNA measurements of the parents to infer aspects of the genome of the fetus with high accuracy using PARENTAL SUPPORT™, thereby transforming the genetic data contained on genetic material from the fetus into the predicted genetic state of the fetus, stored on a computer. The clinician is able to determine both the ploidy state of the fetus, and the presence or absence of a plurality of disease-linked genes of interest. It turns out that the fetus is euploid, and is not a carrier for cystic fibrosis, and the mother decides to continue the pregnancy.

In an embodiment of the present disclosure, a pregnant mother would like to determine if her fetus is afflicted with any whole chromosomal abnormalities. She goes to her doctor, and gives a sample of her blood, and she and her husband gives samples of their own DNA from cheek swabs. A laboratory researcher genotypes the parental DNA using the MDA protocol to amplify the parental DNA, and ILLUMINA INFINIUM arrays to measure the genetic data of the parents at a large number of SNPs. The researcher then spins down the blood, takes the plasma, and isolates a sample of free-floating DNA using size exclusion chromatography. Alternately, the researcher uses one or more fluorescent antibodies, such as one that is specific to fetal hemoglobin to isolate a nucleated fetal red blood cell. The researcher then takes the isolated or enriched fetal genetic material and amplifies it using a library of 70-mer oligonucleotides appropriately designed such that two ends of each oligonucleotide corresponded to the flanking sequences on either side of a target allele. Upon addition of a polymerase, ligase, and the appropriate reagents, the oligonucleotides underwent gap-filling circularization, capturing the desired allele. An exonuclease was added, heat-inactivated, and the products were used directly as a template for PCR amplification. The PCR products were sequenced on an ILLUMINA GENOME ANALYZER. The sequence reads were used as input for the PARENTAL SUPPORT™ method, which then predicted the ploidy state of the fetus.

In another embodiment, a couple—where the mother, who is pregnant, and is of advanced maternal age—wants to know whether the gestating fetus has Down syndrome, Turner Syndrome, Prader Willi syndrome, or some other whole chromosomal abnormality. The obstetrician takes a blood draw from the mother and father. The blood is sent to a laboratory, where a technician centrifuges the maternal sample to isolate the plasma and the buffy coat. The DNA in the buffy coat and the paternal blood sample are transformed through amplification and the genetic data encoded in the amplified genetic material is further transformed from molecularly stored genetic data into electronically stored genetic data by running the genetic material on a high throughput sequencer to measure the parental genotypes. The plasma sample is preferentially enriched at a set of loci using a 5,000-plex hemi-nested targeted PCR method. The mixture of DNA fragments is prepared into a DNA library suitable for sequencing. The DNA is then sequenced using a high throughput sequencing method, for example, the ILLUMINA GAIIx GENOME ANALYZER. The sequencing transforms the information that is encoded molecularly in the DNA into information that is encoded electronically in computer hardware. An informatics based technique that includes the presently disclosed embodiments, such as PARENTAL SUPPORT™, may be used to determine the ploidy state of the fetus. This may involve calculating, on a computer, allele count probabilities at the plurality of polymorphic loci from the DNA measurements made on the prepared sample; creating, on a computer, a plurality of ploidy hypotheses each pertaining to a different possible ploidy state of the chromosome; building, on a computer, a joint distribution model for the expected allele counts at the plurality of polymorphic loci on the chromosome for each ploidy hypothesis; determining, on a computer, a relative probability of each of the ploidy hypotheses using the joint distribution model and the allele counts measured on the prepared sample; and calling the ploidy state of the fetus by selecting the ploidy state corresponding to the hypothesis with the greatest probability. It is determined that the fetus has Down syndrome. A report is printed out, or sent electronically to the pregnant woman's obstetrician, who transmits the diagnosis to the woman. The woman, her husband, and the doctor sit down and discuss their options. The couple decides to terminate the pregnancy based on the knowledge that the fetus is afflicted with a trisomic condition.

In an embodiment, a company may decide to offer a diagnostic technology designed to detect aneuploidy in a gestating fetus from a maternal blood draw. Their product may involve a mother presenting to her obstetrician, who may draw her blood. The obstetrician may also collect a genetic sample from the father of the fetus. A clinician may isolate the plasma from the maternal blood, and purify the DNA from the plasma. A clinician may also isolate the buffy coat layer from the maternal blood, and prepare the DNA from the buffy coat. A clinician may also prepare the DNA from the paternal genetic sample. The clinician may use molecular biology techniques described in this disclosure to append universal amplification tags to the DNA in the DNA derived from the plasma sample. The clinician may amplify the universally tagged DNA. The clinician may preferentially enrich the DNA by a number of techniques including capture by hybridization and targeted PCR. The targeted PCR may involve nesting, hemi-nesting or semi-nesting, or any other approach to result in efficient enrichment of the plasma derived DNA. The targeted PCR may be massively multiplexed, for example with 10,000 primers in one reaction volume, where the primers target SNPs on chromosomes 13, 18, 21, X and those loci that are common to both X and Y, and optionally other chromosomes as well. The selective enrichment and/or amplification may involve tagging each individual molecule with different tags, molecular barcodes, tags for amplification, and/or tags for sequencing. The clinician may then sequence the plasma sample, and also possibly also the prepared maternal and/or paternal DNA. The molecular biology steps may be executed either wholly or partly by a diagnostic box. The sequence data may be fed into a single computer, or to another type of computing platform such as may be found in 'the cloud'. The computing platform may calculate allele counts at the targeted polymorphic loci from the measurements made by the sequencer. The computing platform may create a plurality of ploidy hypotheses pertaining to nullsomy, monosomy, disomy, matched trisomy, and unmatched trisomy for each of chromosomes 13, 18, 21, X and Y. The computing platform may build a joint distribution model for the expected allele counts at the targeted loci on the chromosome for each ploidy hypothesis for each of the five chromosomes being interrogated. The computing platform may determine a probability that each of the ploidy hypotheses is true using the joint distribution model and the allele counts measured on the preferentially enriched DNA derived from the plasma sample. The computing platform may call the ploidy state of the fetus, for each of chromosome 13, 18, 21, X and Y by selecting the ploidy state corresponding to the germane hypothesis with the greatest probability. A report may be generated comprising the called ploidy states, and it may be sent to the obstetrician electronically, displayed on an output device, or a printed hard copy of the report may be delivered to the obstetrician. The obstetrician may inform the patient and optionally the father of the fetus, and they may decide which clinical options are open to them, and which is most desirable.

In another embodiment, a pregnant woman, hereafter referred to as "the mother" may decide that she wants to know whether or not her fetus(es) are carrying any genetic abnormalities or other conditions. She may want to ensure that there are not any gross abnormalities before she is confident to continue the pregnancy. She may go to her obstetrician, who may take a sample of her blood. He may also take a genetic sample, such as a buccal swab, from her cheek. He may also take a genetic sample from the father of the fetus, such as a buccal swab, a sperm sample, or a blood sample. He may send the samples to a clinician. The clinician may enrich the fraction of free floating fetal DNA in the maternal blood sample. The clinician may enrich the fraction of enucleated fetal blood cells in the maternal blood sample. The clinician may use various aspects of the methods described herein to determine genetic data of the fetus. That genetic data may include the ploidy state of the fetus, and/or the identity of one or a number of disease linked alleles in the fetus. A report may be generated summarizing the results of the prenatal diagnosis. The report may be transmitted or mailed to the doctor, who may tell the mother the genetic state of the fetus. The mother may decide to discontinue the pregnancy based on the fact that the fetus has one or more chromosomal, or genetic abnormalities, or undesirable conditions. She may also decide to continue the pregnancy based on the fact that the fetus does not have any gross chromosomal or genetic abnormalities, or any genetic conditions of interest.

Another example may involve a pregnant woman who has been artificially inseminated by a sperm donor, and is pregnant. She wants to minimize the risk that the fetus she is carrying has a genetic disease. She has blood drawn at a phlebotomist, and techniques described in this disclosure are used to isolate three nucleated fetal red blood cells, and a tissue sample is also collected from the mother and genetic father. The genetic material from the fetus and from the mother and father are amplified as appropriate and genotyped using the ILLUMINA INFINIUM BEADARRAY, and the methods described herein clean and phase the parental and fetal genotype with high accuracy, as well as to make ploidy calls for the fetus. The fetus is found to be euploid, and phenotypic susceptibilities are predicted from the reconstructed fetal genotype, and a report is generated and sent to the mother's physician so that they can decide what clinical decisions may be best.

In an embodiment, the raw genetic material of the mother and the father is transformed by way of amplification to an amount of DNA that is similar in sequence, but larger in quantity. Then, by way of a genotyping method, the genotypic data that is encoded by nucleic acids is transformed into genetic measurements that may be stored physically and/or electronically on a memory device, such as those described above. The relevant algorithms that makeup the PARENTAL SUPPORT™ algorithm, relevant parts of which are discussed in detail herein, are translated into a computer program, using a programming language. Then, through the execution of the computer program on the computer hardware, instead of being physically encoded bits and bytes, arranged in a pattern that represents raw measurement data, they become transformed into a pattern that represents a high confidence determination of the ploidy state of the fetus. The details of this transformation will rely on the data itself and the computer language and hardware system used to execute the method described herein. Then, the data that is physically configured to represent a high quality ploidy determination of the fetus is transformed into a report which may be sent to a health care practitioner. This transformation may be carried out using a printer or a computer display. The report may be a printed copy, on paper or other suitable medium, or else it may be electronic. In the case of an electronic report, it may be transmitted, it may be physically stored on a memory device at a location on the computer accessible by the health care practitioner; it also may be displayed on a screen so that it may be read. In the case of a screen display, the data may be transformed to a readable format by causing the physical transformation of pixels on the display device. The transformation may be accomplished by way of physically firing electrons at a phosphorescent screen, by way of altering an electric charge that physically changes the transparency of a specific set of pixels on a screen that may lie in front of a substrate that emits or absorbs photons. This transformation may be accomplished by way of changing the nanoscale orientation of the molecules in a liquid crystal, for example, from nematic to cholesteric or smectic phase, at a specific set of pixels. This transformation may be accomplished by way of an electric current causing photons to be emitted from a specific set of pixels made from a plurality of light emitting diodes arranged in a meaningful pattern. This transformation may be accomplished by any other way used to display information, such as a computer screen, or some other output device or way of transmitting information. The health care practitioner may then act on the report, such that the data in the report is transformed into an action. The action may be to continue or discontinue the pregnancy, in which case a gestating fetus with a genetic abnormality is transformed into non-living fetus. The transformations listed herein may be aggregated, such that, for example, one may transform the genetic material of a pregnant mother and the father, through a number of steps outlined in this disclosure, into a medical decision consisting of aborting a fetus with genetic abnormalities, or consisting of continuing the pregnancy. Alternately, one may transform a set of genotypic measurements into a report that helps a physician treat his pregnant patient.

In an embodiment of the present disclosure, the method described herein can be used to determine the ploidy state of a fetus even when the host mother, i.e. the woman who is pregnant, is not the biological mother of the fetus she is carrying. In an embodiment of the present disclosure, the method described herein can be used to determine the ploidy state of a fetus using only the maternal blood sample, and without the need for a paternal genetic sample.

Some of the math in the presently disclosed embodiments makes hypotheses concerning a limited number of states of aneuploidy. In some cases, for example, only zero, one or two chromosomes are expected to originate from each parent. In some embodiments of the present disclosure, the mathematical derivations can be expanded to take into account other forms of aneuploidy, such as quadrosomy, where three chromosomes originate from one parent, pentasomy, hexasomy etc., without changing the fundamental concepts of the present disclosure. At the same time, it is possible to focus on a smaller number of ploidy states, for example, only trisomy and disomy. Note that ploidy determinations that indicate a non-whole number of chromosomes may indicate mosaicism in a sample of genetic material.

In some embodiments, the genetic abnormality is a type of aneuploidy, such as Down syndrome (or trisomy 21), Edwards syndrome (trisomy 18), Patau syndrome (trisomy 13), Turner Syndrome (45x), Klinefelter's syndrome (a male with 2x chromosomes), Prader-Willi syndrome, and DiGeorge syndrome (UPD 15). Congenital disorders, such as those listed in the prior sentence, are commonly undesirable, and the knowledge that a fetus is afflicted with one or more phenotypic abnormalities may provide the basis for a decision to terminate the pregnancy, to take necessary precautions to prepare for the birth of a special needs child, or to take some therapeutic approach meant to lessen the severity of a chromosomal abnormality.

In some embodiments, the methods described herein can be used at a very early gestational age, for example as early as four week, as early as five weeks, as early as six weeks, as early as seven weeks, as early as eight weeks, as early as nine weeks, as early as ten weeks, as early as eleven weeks, and as early as twelve weeks.

In some embodiments, a method disclosed herein is used in the context of pre-implantation genetic diagnosis (PGD) for embryo selection during in vitro fertilization, where the target individual is an embryo, and the parental genotypic data can be used to make ploidy determinations about the embryo from sequencing data from a single or two cell biopsy from a day 3 embryo or a trophectoderm biopsy from a day 5 or day 6 embryo. In a PGD setting, only the child DNA is measured, and only a small number of cells are tested, generally one to five but as many as ten, twenty or fifty. The total number of starting copies of the A and B alleles (at a SNP) are then trivially determined by the child genotype and the number of cells. In NPD, the number of starting copies is very high and so the allele ratio after PCR is expected to accurately reflect the starting ratio. However, the small number of starting copies in PGD means that contamination and imperfect PCR efficiency have a non-trivial effect on the allele ratio following PCR. This effect may be more important than depth of read in predicting the variance in the allele ratio measured after sequencing. The distribution of measured allele ratio given a known child genotype may be created by Monte Carlo simulation of the PCR process based on the PCR probe efficiency and probability of contamination. Given an allele ratio distribution for each possible child genotype, the likelihoods of various hypotheses can be calculated as described for NIPD.

Maximum Likelihood Estimates

Most methods known in the art for detecting the presence or absence of biological phenomenon or medical condition involve the use of a single hypothesis rejection test, where a metric that is correlated with the condition is measured, and if the metric is on one side of a given threshold, the condition is present, while of the metric falls on the other side of the threshold, the condition is absent. A single-hypothesis rejection test only looks at the null distribution when deciding between the null and alternate hypotheses. Without taking into account the alternate distribution, one cannot estimate the likelihood of each hypothesis given the observed data and therefore cannot calculate a confidence on the call. Hence with a single-hypothesis rejection test, one gets a yes or no answer without a feeling for the confidence associated with the specific case.

In some embodiments, the method disclosed herein is able to detect the presence or absence of biological phenomenon or medical condition using a maximum likelihood method. This is a substantial improvement over a method using a single hypothesis rejection technique as the threshold for calling absence or presence of the condition can be adjusted as appropriate for each case. This is particularly relevant for diagnostic techniques that aim to determine the presence or absence of aneuploidy in a gestating fetus from genetic data available from the mixture of fetal and maternal DNA present in the free floating DNA found in maternal plasma. This is because as the fraction of fetal DNA in the plasma derived fraction changes, the optimal threshold for calling aneuploidy vs. euploidy changes. As the fetal fraction drops, the distribution of data that is associated with an aneuploidy becomes increasingly similar to the distribution of data that is associated with a euploidy.

The maximum likelihood estimation method uses the distributions associated with each hypothesis to estimate the likelihood of the data conditioned on each hypothesis. These conditional probabilities can then be converted to a hypothesis call and confidence. Similarly, maximum a posteriori estimation method uses the same conditional probabilities as the maximum likelihood estimate, but also incorporates population priors when choosing the best hypothesis and determining confidence.

Therefore, the use of a maximum likelihood estimate (MLE) technique, or the closely related maximum a posteriori (MAP) technique give two advantages, first it increases the chance of a correct call, and it also allows a confidence to be calculated for each call. In an embodiment, selecting the ploidy state corresponding to the hypothesis with the greatest probability is carried out using maximum likelihood estimates or maximum a posteriori estimates. In an embodiment, a method is disclosed for determining the ploidy state of a gestating fetus that involves taking any method currently known in the art that uses a single hypothesis rejection technique and reformulating it such that it uses a MLE or MAP technique. Some examples of methods that can be significantly improved by applying these techniques can be found in U.S. Pat. No. 8,008,018, U.S. Pat. No. 7,888,017, or U.S. Pat. No. 7,332,277.

In an embodiment, a method is described for determining presence or absence of fetal aneuploidy in a maternal plasma sample comprising fetal and maternal genomic DNA, the method comprising: obtaining a maternal plasma sample; measuring the DNA fragments found in the plasma sample with a high throughput sequencer; mapping the sequences to the chromosome and determining the number of sequence reads that map to each chromosome; calculating the fraction of fetal DNA in the plasma sample; calculating an expected distribution of the amount of a target chromosome that would be expected to be present if that if the second target chromosome were euploid and one or a plurality of expected distributions that would be expected if that chromosome were aneuploid, using the fetal fraction and the number of sequence reads that map to one or a plurality of reference chromosomes expected to be euploid; and using a MLE or MAP determine which of the distributions is most likely to be correct, thereby indicating the presence or absence of a fetal aneuploidy. In an embodiment, the measuring the DNA from the plasma may involve conducting massively parallel shotgun sequencing. In an embodiment, the measuring the DNA from the plasma sample may involve sequencing DNA that has been preferentially enriched, for example through targeted amplification, at a plurality of polymorphic or non-polymorphic loci. The plurality of loci may be designed to target one or a small number of suspected aneuploid chromosomes and one or a small number of reference chromosomes. The purpose of the preferential enrichment is to increase the number of sequence reads that are informative for the ploidy determination.

Ploidy Calling Informatics Methods

Described herein is a method for determining the ploidy state of a fetus given sequence data. In some embodiments, this sequence data may be measured on a high throughput sequencer. In some embodiments, the sequence data may be measured on DNA that originated from free floating DNA isolated from maternal blood, wherein the free floating DNA comprises some DNA of maternal origin, and some DNA of fetal/placental origin. This section will describe one embodiment of the present disclosure in which the ploidy state of the fetus is determined assuming that fraction of fetal DNA in the mixture that has been analyzed is not known and will be estimated from the data. It will also describe an embodiment in which the fraction of fetal DNA ("fetal fraction") or the percentage of fetal DNA in the mixture can be measured by another method, and is assumed to be known in determining the ploidy state of the fetus. In some embodiments the fetal fraction can be calculated using only the genotyping measurements made on the maternal blood sample itself, which is a mixture of fetal and maternal DNA. In some embodiments the fraction may be calculated also using the measured or otherwise known genotype of the mother and/or the measured or otherwise known genotype of the father. In another embodiment ploidy state of the fetus can be determined solely based on the calculated fraction of fetal DNA for the chromosome in question compared to the calculated fraction of fetal DNA for the reference chromosome assumed disomic.

In the preferred embodiment, suppose that, for a particular chromosome, we observe and analyze N SNPs, for which we have:

Set of NR free floating DNA sequence measurements $S=(s_1, \ldots, s_{NR})$. Since this method utilizes the SNP measurements, all sequence data that corresponds to non-polymorphic loci can be disregarded. In a simplified version, where we have (A,B) counts on each SNP, where A and B correspond to the two alleles present at a given locus, S can be written as $S=((a_1,b_1), \ldots, (a_N, b_N))$, where $a_i$ is the A count on SNP i, $b_i$ is the B count on SNP i, and $\Sigma_{i=1:N}(a_i+b_i)=NR$ Parent data consisting of genotypes from a SNP microarray or other intensity based genotyping platform: mother $M=(m_1, \ldots, m_N)$, father $F=(f_1, \ldots, f_N)$, where $m_i, f_i \in (AA, AB, BB)$.

AND/OR sequence data measurements: NRM mother measurements $SM=(sm_1, \ldots, sm_{nrm})$, NRF father measurements $SF=(sf_1, \ldots, sf_{nrf})$. Similar to the above simplification, if we have (A,B) counts on each SNP $SM=((am_1,bm_1), \ldots, (am_N, bm_N))$, $SF=((af_1,bf_1), \ldots, (af_N, bf_N))$ Collectively, the mother, father child data are denoted as D=(M,F,SM,SF,S). Note that the parent data is desired and increases the accuracy of the algorithm, but is NOT necessary, especially the father data. This means that even in the absence of mother and/or father data, it is possible to get very accurate copy number results.

It is possible to derive the best copy number estimate (H*) by maximizing the data log likelihood LIK(D|H) over all hypotheses (H) considered. In particular it is possible to determine the relative probability of each of the ploidy hypotheses using the joint distribution model and the allele counts measured on the prepared sample, and using those relative probabilities to determine the hypothesis most likely to be correct as follows:

$$H^* = \underset{H}{\mathrm{argmax}}\, LIK(D\mid H)$$

Similarly the a posteriori hypothesis likelihood given the data may be written as:

$$H^* = \underset{H}{\mathrm{argmax}}\, LIK(D\mid H) * priorprob(H)$$

Where priorprob(H) is the prior probability assigned to each hypothesis H, based on model design and prior knowledge. It is also possible to use priors to find the maximum a posteriori estimate:

$$H_{MA} = \underset{H}{\mathrm{argmax}}\, LIK(D\mid H)$$

In an embodiment, the copy number hypotheses that may be considered are:

Monosomy:
  maternal H10 (one copy from mother)
  paternal H01 (one copy from father)
Disomy: H11 (one copy each mother and father)
Simple trisomy, no crossovers considered:
  Maternal: H21_matched (two identical copies from mother, one copy from father), H21_unmatched (BOTH copies from mother, one copy from father)
  Paternal: H12_matched (one copy from mother, two identical copies from father), H12_unmatched (one copy from mother, both copies from father)
Composite trisomy, allowing for crossovers (using a joint distribution model):
  maternal H21 (two copies from mother, one from father),
  paternal H12 (one copy from mother, two copies from father)

In other embodiments, other ploidy states, such as nullsomy (H00), uniparental disomy (H20 and H02), and tetrasomy (H04, H13, H22, H31 and H40), may be considered.

If there are no crossovers, each trisomy, whether the origin was mitosis, meiosis I, or meiosis II, would be one of the matched or unmatched trisomies. Due to crossovers, true trisomy is usually a combination of the two. First, a method to derive hypothesis likelihoods for simple hypotheses is described. Then a method to derive hypothesis likelihoods for composite hypotheses is described, combining individual SNP likelihood with crossovers.

LIK(D|H) for a Simple Hypothesis

In an embodiment, LIK(D|H) may be determined for simple hypotheses, as follows. For simple hypotheses H, LIK(H), the log likelihood of hypothesis H on a whole chromosome, may be calculated as the sum of log likelihoods of individual SNPs, assuming known or derived child fraction cf. In an embodiment it is possible to derive cf from the data.

$$LIK(D \mid H) = \sum_i LIK(D \mid H, cf, i)$$

This hypothesis does not assume any linkage between SNPs, and therefore does not utilize a joint distribution model.

In some embodiments, the Log Likelihood may be determined on a per SNP basis. On a particular SNP i, assuming fetal ploidy hypothesis H and percent fetal DNA cf, log likelihood of observed data D is defined as:

$$LIK(D \mid H, i) = \log P(D \mid H, cf, i) =$$

$$\log\left(\sum_{m,f,c} P(D \mid m, f, c, H, cf, i) P(c \mid m, f, H) P(m \mid i) P(f \mid i)\right)$$

where m are possible true mother genotypes, f are possible true father genotypes, where m, f ∈ {AA,AB,BB}, and c are possible child genotypes given the hypothesis H. In particular, for monosomy c ∈ {A,B}, for disomy c ∈ {AA, AB, BB}, for trisomy c ∈ {AAA, AAB, ABB, BBB}.

Genotype prior frequency: p(m|i) is the general prior probability of mother genotype m on SNP i, based on the known population frequency at SNP I, denoted $pA_i$. In particular $p(AA|pA_i) = (pA_i)^2, p(AB|pA_i) = 2(pA_i) \ast (1-pA_i), p(BB|pA_i) = (1-pA_i)^2$ Father genotype probability, p(f|i), may be determined in an analogous fashion.

True child probability: p(c|m, f H) is the probability of getting true child genotype=c, given parents m, f, and assuming hypothesis H, which can be easily calculated. For example, for H11, H21 matched and H21 unmatched, p(c|m, f,H) is given below.

father genotype f, true child genotype c, hypothesis H and child fraction cf. It can be broken down into the probability of mother, father and child data as follows:

$P(D|m,f,c,H,cf,i) = P(SM|m,i)P(M|m,i)P(SF|f,i)P(F|f,i)$
$P(S|m,c,H,cf,i)$

Mother SNP array data likelihood: Probability of mother SNP array genotype data $m_i$ at SNP i compared to true genotype m, assuming SNP array genotypes are correct, is simply $$P(M \mid m, i) = \begin{cases} 1 & m_i = m \\ 0 & m_i \neq m \end{cases}$$

Mother sequence data likelihood: the probability of the mother sequence data at SNP i, in the case of counts $S_i = (am_i, bm_i)$, with no extra noise or bias involved, is the binomial probability defined as $P(SM|m,i) = P_{X|m}(am_i)$ where $X|m \sim \text{Binom}(p_m(A), am_i+bm_i)$ with $p_m(A)$ defined as

| m | AA | AB | BB | A | B | nocall |
|---|----|----|----|----|----|--------|
| p(A) | 1 | 0.5 | 0 | 1 | 0 | 0.5 |

Father data likelihood: a similar equation applies for father data likelihood.

Note that it is possible to determine the child genotype without the parent data, especially father data. For example if no father genotype data F is available, one may just use P(F|f, i)=1. If no father sequence data SF is available, one may just use P(SF|f,i)=1.

In some embodiments, the method involves building a joint distribution model for the expected allele counts at a plurality of polymorphic loci on the chromosome for each ploidy hypothesis; one method to accomplish such an end is described here. Free fetal DNA data likelihood: P(S|m, c, H, cf, i) is the probability of free fetal DNA sequence data on SNP i, given true mother genotype m, true child genotype c, child copy number hypothesis H, and assuming child fraction cf. It is in fact the probability of sequence data S on SNP I, given the true probability of A content on SNP i μ(m, c, cf, H)

$P(S|m,c,H,cf,i) = P(S|\mu(m,c,cf,H),i)$

For counts, where $S_i = (a_i, b_i)$, with no extra noise or bias in data involved, $P(S|\mu(m,c,cf,H),i) = P_x(a_i)$

| | | p(c \| m, f, H) | | | | | | | | | |
|---|---|---|---|---|---|---|---|---|---|---|---|
| | | H11 | | | H21 matched | | | | H21 unmatched | | | |
| m | f | AA | AB | BB | AAA | AAB | ABB | BBB | AAA | AAB | ABB | BBB |
| AA | AA | 1 | 0 | 0 | 1 | 0 | 0 | 0 | 1 | 0 | 0 | 0 |
| AB | AA | 0.5 | 0.5 | 0 | 0.5 | 0 | 0.5 | 0 | 0 | 1 | 0 | 0 |
| BB | AA | 0 | 1 | 0 | 0 | 0 | 1 | 0 | 0 | 0 | 1 | 0 |
| AA | AB | 0.5 | 0.5 | 0 | 0.5 | 0.5 | 0 | 0 | 0.5 | 0.5 | 0 | 0 |
| AB | AB | 0.25 | 0.5 | 0.25 | 0.25 | 0.25 | 0.25 | 0.25 | 0 | 0.5 | 0.5 | 0 |
| BB | AB | 0 | 0.5 | 0.5 | 0 | 0 | 0.5 | 0.5 | 0 | 0 | 0.5 | 0.5 |
| AA | BB | 0 | 1 | 0 | 0 | 1 | 0 | 0 | 0 | 1 | 0 | 0 |
| AB | BB | 0 | 0.5 | 0.5 | 0 | 0.5 | 0 | 0.5 | 0 | 0 | 1 | 0 |
| BB | BB | 0 | 0 | 1 | 0 | 0 | 0 | 1 | 0 | 0 | 0 | 1 |

Data likelihood: P(D|m, f, c, H, i, cf) is the probability of given data D on SNP i, given true mother genotype m, true where $X \sim \text{Binom}(p(A), a_i+b_i)$ with $p(A) = \mu(m, c, cf, H)$. In a more complex case where the exact alignment and (A,B)

counts per SNP are not known, P(S|µ(m, c, cf, H), i) is a combination of integrated binomials.

True A content probability: µ(m, c, cf, H), the true probability of A content on SNP i in this mother/child mixture, assuming that true mother genotype=m, true child genotype=c, and overall child fraction=cf, is defined as $$\mu(m, c, cf, H) = \frac{\#A(m)*(1-cf) + \#A(c)*cf}{n_m*(1-cf) + n_c*cf}$$

where #A(g)=number of A's in genotype g, $n_m$=2 is somy of mother and $n_c$ is ploidy of the child under hypothesis H (1 for monosomy, 2 for disomy, 3 for trisomy).

Using a Joint Distribution Model: LIK(D|H) for a Composite Hypothesis

In some embodiments, the method involves building a joint distribution model for the expected allele counts at the plurality of polymorphic loci on the chromosome for each ploidy hypothesis; one method to accomplish such an end is described here. In many cases, trisomy is usually not purely matched or unmatched, due to crossovers, so in this section results for composite hypotheses H21 (maternal trisomy) and H12 (paternal trisomy) are derived, which combine matched and unmatched trisomy, accounting for possible crossovers.

In the case of trisomy, if there were no crossovers, trisomy would be simply matched or unmatched trisomy. Matched trisomy is where child inherits two copies of the identical chromosome segment from one parent. Unmatched trisomy is where child inherits one copy of each homologous chromosome segment from the parent. Due to crossovers, some segments of a chromosome may have matched trisomy, and other parts may have unmatched trisomy. Described in this section is how to build a joint distribution model for the heterozygosity rates for a set of alleles; that is, for the expected allele counts at a number of loci for one or more hypotheses.

Suppose that on SNP i, LIK(D|Hm, i) is the fit for matched hypothesis $H_m$, and LIK(D|Hu, i) is the fit for unmatched hypothesis $H_u$, and pc(i)=probability of crossover between SNPs i-1 and i. One may then calculate the full likelihood as:

LIK(D|H)=$\Sigma_E$LIK(D|E,1:N)

where LIK(D|E, 1:N) is the likelihood of ending in hypothesis E, for SNPs 1:N. E=hypothesis of the last SNP, E∈(Hm, Hu). Recursively, one may calculate:

$$LIK(D|E, 1:i) = LIK(D|E, i) + \log(\exp(LIK(D|E, 1:i-1))*(1-pc(i)) + \exp(LIK(D|\sim E, 1:i-1))*pc(i))$$

where ~E is the hypothesis other than E (not E), where hypotheses considered are $H_m$ and $H_u$. In particular, one may calculate the likelihood of 1:i SNPs, based on likelihood of 1 to (i-1) SNPs with either the same hypothesis and no crossover, or the opposite hypothesis and a crossover, multiplied by the likelihood of the SNP i For SNP 1, i=1, LIK(D|E, 1:1)=LIK(D|E, 1).
For SNP 2, i=2, LIK(D|E, 1:2)=LIK(D|E, 2)+log (exp(LIK (D|E, 1))*(1-pc(2))+exp (LIK(D|~E, 1))*pc(2)),
and so on for i=3:N.

In some embodiments, the child fraction may be determined. The child fraction may refer to the proportion of sequences in a mixture of DNA that originate from the child. In the context of non-invasive prenatal diagnosis, the child fraction may refer to the proportion of sequences in the maternal plasma that originate from the fetus or the portion of the placenta with fetal genotype. It may refer to the child fraction in a sample of DNA that has been prepared from the maternal plasma, and may be enriched in fetal DNA. One purpose of determining the child fraction in a sample of DNA is for use in an algorithm that can make ploidy calls on the fetus, therefore, the child fraction could refer to whatever sample of DNA was analyzed by sequencing for the purpose of non-invasive prenatal diagnosis.

Some of the algorithms presented in this disclosure that are part of a method of non-invasive prenatal aneuploidy diagnosis assume a known child fraction, which may not always be the case. In an embodiment, it is possible to find the most likely child fraction by maximizing the likelihood for disomy on selected chromosomes, with or without the presence of the parental data In particular, suppose that LIK(D|H11, cf, chr)=log likelihood as described above, for the disomy hypothesis, and for child fraction cf on chromosome chr. For selected chromosomes in Cset (usually 1:16), assumed to be euploid, the full likelihood is:

LIK(cf)=$\Sigma_{chr\in Cset}$Lik(D|H11,cf,chr)

The most likely child fraction (cf*) is derived as cf*=argmax$_{cf}$LIK(cf).

It is possible to use any set of chromosomes. It is also possible to derive child fraction without assuming euploidy on the reference chromosomes. Using this method it is possible to determine the child fraction for any of the following situations: (1) one has array data on the parents and shotgun sequencing data on the maternal plasma; (2) one has array data on the parents and targeted sequencing data on the maternal plasma; (3) one has targeted sequencing data on both the parents and maternal plasma; (4) one has targeted sequencing data on both the mother and the maternal plasma fraction; (5) one has targeted sequencing data on the maternal plasma fraction; (6) other combinations of parental and child fraction measurements.

In some embodiments the informatics method may incorporate data dropouts; this may result in ploidy determinations of higher accuracy. Elsewhere in this disclosure it has been assumed that the probability of getting an A is a direct function of the true mother genotype, the true child genotype, the fraction of the child in the mixture, and the child copy number. It is also possible that mother or child alleles can drop out, for example instead of measuring true child AB in the mixture, it may be the case that only sequences mapping to allele A are measured. One may denote the parent dropout rate for genomic illumina data $d_{pg}$, parent dropout rate for sequence data $d_{ps}$ and child dropout rate for sequence data $d_{cs}$. In some embodiments, the mother dropout rate may be assumed to be zero, and child dropout rates are relatively low; in this case, the results are not severely affected by dropouts. In some embodiments the possibility of allele dropouts may be sufficiently large that they result in a significant effect of the predicted ploidy call. For such a case, allele dropouts have been incorporated into the algorithm here:

Parent SNP array data dropouts: For mother genomic data M, suppose that the genotype after the dropout is $m_d$, then $$P(M \mid m, i) = \sum_{m_d} P(M \mid m_d, i) P(m_d \mid m)$$

where $$P(M \mid m_d, i) = \begin{cases} 1 & m_i = m_d \\ 0 & m_i \neq m_d \end{cases}$$

as before, and $P(m_d|m)$ is the likelihood of genotype $m_d$ after the possible dropout given the true genotype m, defined as below, for dropout rate d

| | | | md | | | |
|---|---|---|---|---|---|---|
| m | AA | AB | BB | A | B | nocall |
| AA | $(1-d)^2$ | 0 | 0 | $2d(1-d)$ | 0 | $d^2$ |
| AB | 0 | $(1-d)^2$ | 0 | $d(1-d)$ | $d(1-d)$ | $d^2$ |
| BB | 0 | 0 | $(1-d)^2$ | 0 | $2d(1-d)$ | $d^2$ |

A similar equation applies for father SNP array data.

Parent sequence data dropouts: For mother sequence data SM $$P(SM \mid m, i) = \sum_{m_d} P_{X|m_d}(am_i) P(m_d \mid m)$$

where $P(m_d|m)$ is defined as in previous section and $P_{X|m_d}(am_i)$ probability from a binomial distribution is defined as before in the parent data likelihood section. A similar equation applies to the paternal sequence data.

Free floating DNA sequence data dropout:

$$P(S \mid m, c, H, cf, i) = \sum_{m_d, c_d} P(S \mid \mu(m_d, c_d, cf, H), i) P(m_d \mid m) P(c_d \mid c)$$

where $P(S|\mu(m_d,c_d,cf,H),i)$ is as defined in the section on free floating data likelihood.

In an embodiment, $p(m_d|m)$ is the probability of observed mother genotype $m_d$, given true mother genotype m, assuming dropout rate $d_{ps}$, and $p(c_d|c)$ is the probability of observed child genotype $c_d$, given true child genotype c, assuming dropout rate $d_{ds}$. If $nA_T$=number of A alleles in true genotype c, $nA_D$=number of A alleles in observed genotype $c_d$, where $nA_T > nA_D$, and similarly $nB_T$=number of B alleles in true genotype c, $nB_D$=number of B alleles in observed genotype $c_d$, where $nB_T > nB_D$ and d=dropout rate, then $$p(c_d \mid c) = \binom{nA_T}{nA_D} * d^{nA_T - nA_D} * (1-d)^{nA_D} * \binom{nB_T}{nB_D} * d^{nB_T - nB_D} * (1-d)^{nB_D}$$

In an embodiment, the informatics method may incorporate random and consistent bias. In an ideal word there is no per SNP consistent sampling bias or random noise (in addition to the binomial distribution variation) in the number of sequence counts. In particular, on SNP i, for mother genotype m, true child genotype c and child fraction cf, and X=the number of A's in the set of (A+B) reads on SNP i, X acts like a X~Binomial(p, A+B), where p=μ(m, c, cf, H)=true probability of A content.

In an embodiment, the informatics method may incorporate random bias. As is often the case, suppose that there is a bias in the measurements, so that the probability of getting an A on this SNP is equal to q, which is a bit different than p as defined above. How much different p is from q depends on the accuracy of the measurement process and number of other factors and can be quantified by standard deviations of q away from p. In an embodiment, it is possible to model q as having a beta distribution, with parameters α; β depending on the mean of that distribution being centered at p, and some specified standard deviation s. In particular, this gives X\q~Bin(q,$D_i$), where q~Beta(α, β). If we let E(q)=p, V(q)=$s^2$, and parameters α, β can be derived as α=pN, β=(1−p)N, where $$N = \frac{p(1-p)}{s^2} - 1.$$

This is the definition of a beta-binomial distribution, where one is sampling from a binomial distribution with variable parameter q, where q follows a beta distribution with mean p. So, in a setup with no bias, on SNP i, the parent sequence data (SM) probability assuming true mother genotype (m), given mother sequence A count on SNP i ($am_i$) and mother sequence B count on SNP i ($bm_i$) may be calculated as:

$P(SM|m,i) = P_{X|m}(am_i)$ where $X|m$~Binom($p_m(A), am_i + bm_i$)

Now, including random bias with standard deviation s, this becomes:

$X|m$~BetaBinom($p_m(A), am_i + bm_i, s$)

In the case with no bias, the maternal plasma DNA sequence data (S) probability assuming true mother genotype (m), true child genotype (c), child fraction (cf), assuming child hypothesis H, given free floating DNA sequence A count on SNP i ($a_i$) and free floating sequence B count on SNP i ($b_i$) may be calculated as $P(S|m,c,cf,H,i) = P_x(a_i)$ where X~Binom(p(A), $a_i + b_i$) with p(A)=μ(m, c, cf, H).

In an embodiment, including random bias with standard deviation s, this becomes X~BetaBinom(p(A),$a_i+b_i$,s), where the amount of extra variation is specified by the deviation parameter s, or equivalently N. The smaller the value of s (or the larger the value of N) the closer this distribution is to the regular binomial distribution. It is possible to estimate the amount of bias, i.e. estimate N above, from unambiguous contexts AA|AA, BB|BB, AA|BB, BB|AA and use estimated N̂ in the above probability. Depending on the behavior of the data, N may be made to be a constant irrespective of the depth of read $a_i+b_i$ or a function of $a_i+b_i$ making bias smaller for larger depths of read.

In an embodiment, the informatics method may incorporate consistent per-SNP bias. Due to artifacts of the sequencing process, some SNPs may have consistently lower or higher counts irrespective of the true amount of A content. Suppose that SNP i consistently adds a bias of $w_i$ percent to the number of A counts. In some embodiments, this bias can be estimated from the set of training data derived under same conditions, and added back in to the parent sequence data estimate as:

$$P(SM|m,i)=P_{X|m}(am_i) \text{ where } X|m \sim \text{BetaBinom}(p_m(A)+w_i,am_i+bm_i,s)$$

and with the free floating DNA sequence data probability estimate as:

$$P(S|m,c,cf,H,i)=P_X(a_i) \text{ where } X \sim \text{BetaBinom}(p(A)+w_i,a_i+b_i,s),$$

In some embodiments, the method may be written to specifically take into account additional noise, differential sample quality, differential SNP quality, and random sampling bias. An example of this is given here. This method has been shown to be particularly useful in the context of data generated using the massively multiplexed mini-PCR protocol, and was used in Experiments 7 through 13. The method involves several steps that each introduce different kind of noise and/or bias to the final model:

(1) Suppose the first sample that comprises a mixture of maternal and fetal DNA contains an original amount of DNA of size=$N_0$ molecules, usually in the range 1,000-40,000, where p=true % refs (2) In the amplification using the universal ligation adaptors, assume that $N_1$ molecules are sampled; usually $N_1 \sim N_0/2$ molecules and random sampling bias is introduced due to sampling. The amplified sample may contain a number of molecules $N_2$ where $N_2 \gg N_1$. Let $X_1$ represent the amount of reference loci (on per SNP basis) out of $N_1$ sampled molecules, with a variation in $p_1=X_1/N_1$ that introduces random sampling bias throughout the rest of protocol. This sampling bias is included in the model by using a Beta-Binomial (BB) distribution instead of using a simple Binomial distribution model. Parameter N of the Beta-Binomial distribution may be estimated later on per sample basis from training data after adjusting for leakage and amplification bias, on SNPs with 0<p<1. Leakage is the tendency for a SNP to be read incorrectly.

(3) The amplification step will amplify any allelic bias, thus amplification bias introduced due to possible uneven amplification. Suppose that one allele at a locus is amplified f times another allele at that locus is amplified g times, where $f=ge^b$, where b=0 indicates no bias. The bias parameter, b, is centered at 0, and indicates how much more or less the A allele get amplified as opposed to the B allele on a particular SNP. The parameter b may differ from SNP to SNP. Bias parameter b may be estimated on per SNP basis, for example from training data.

(4) The sequencing step involves sequencing a sample of amplified molecules. In this step there may be leakage, where leakage is the situation where a SNP is read incorrectly. Leakage may result from any number of problems, and may result in a SNP being read not as the correct allele A, but as another allele B found at that locus or as an allele C or D not typically found at that locus. Suppose the sequencing measures the sequence data of a number of DNA molecules from an amplified sample of size $N_3$, where $N_3 < N_2$. In some embodiments, $N_3$ may be in the range of 20,000 to 100,000; 100,000 to 500,000; 500,000 to 4,000,000; 4,000,000 to 20,000,000; or 20,000,000 to 100,000,000. Each molecule sampled has a probability $p_g$ of being read correctly, in which case it will show up correctly as allele A. The sample will be incorrectly read as an allele unrelated to the original molecule with probability 1-$p_g$, and will look like allele A with probability $p_r$, allele B with probability pm or allele C or allele D with probability $p_o$, where $p_r+p_m+p_o=1$. Parameters $p_g$, $p_r$, $p_m$, $p_o$ are estimated on per SNP basis from the training data.

Different protocols may involve similar steps with variations in the molecular biology steps resulting in different amounts of random sampling, different levels of amplification and different leakage bias. The following model may be equally well applied to each of these cases. The model for the amount of DNA sampled, on per SNP basis, is given by:

$$X_3 \sim \text{BetaBinomial}(L(F(p,b),p_r,p_g),N*H(p,b))$$

where p=the true amount of reference DNA, b=per SNP bias, and as described above, $p_g$ is the probability of a correct read, $p_r$ is the probability of read being read incorrectly but serendipitously looking like the correct allele, in case of a bad read, as described above, and:

$$F(p,b)=pe^b/(pe^b+(1-p)), H(p,b)=(e^b p+(1-p))^2/e^b, L(p,p_r,p_g)=p*p \ g+p_r*(1-p_g).$$

In some embodiments, the method uses a Beta-Binomial distribution instead of a simple binomial distribution; this takes care of the random sampling bias. Parameter N of the Beta-Binomial distribution is estimated on per sample basis on an as needed basis. Using bias correction F(p,b), H(p,b), instead of just p, takes care of the amplification bias. Parameter b of the bias is estimated on per SNP basis from training data ahead of time.

In some embodiments the method uses leakage correction $L(p,p_r,p_g)$, instead of just p; this takes care of the leakage bias, i.e. varying SNP and sample quality. In some embodiments, parameters $p_g$, $p_r$, $p_o$ are estimated on per SNP basis from the training data ahead of time. In some embodiments, the parameters $p_g$, $p_r$, $p_o$ may be updated with the current sample on the go, to account for varying sample quality.

The model described herein is quite general and can account for both differential sample quality and differential SNP quality. Different samples and SNPs are treated differently, as exemplified by the fact that some embodiments use Beta-Binomial distributions whose mean and variance are a function of the original amount of DNA, as well as sample and SNP quality.

Platform Modeling

Consider a single SNP where the expected allele ratio present in the plasma is r (based on the maternal and fetal genotypes). The expected allele ratio is defined as the expected fraction of A alleles in the combined maternal and fetal DNA. For maternal genotype gm and child genotype $g_c$, the expected allele ratio is given by equation 1, assuming that the genotypes are represented as allele ratios as well.

$$r=fg_c+(1-f)g_m \quad (1)$$

The observation at the SNP consists of the number of mapped reads with each allele present, $n_a$ and $n_b$, which sum to the depth of read d. Assume that thresholds have already been applied to the mapping probabilities and phred scores such that the mappings and allele observations can be considered correct. A phred score is a numerical measure that relates to the probability that a particular measurement at a particular base is wrong. In an embodiment, where the base has been measured by sequencing, the phred score may be calculated from the ratio of the dye intensity corresponding to the called base to the dye intensity of the other bases. The simplest model for the observation likelihood is a binomial distribution which assumes that each of the d reads is drawn independently from a large pool that has allele ratio r. Equation 2 describes this model.

$$P(n_a, n_b \mid r) = p_{bino}(n_a; n_a + n_b, r) = \binom{n_a + n_b}{n_a} r^{n_a}(1-r)^{n_b} \quad (2)$$

The binomial model can be extended in a number of ways. When the maternal and fetal genotypes are either all A or all B, the expected allele ratio in plasma will be 0 or 1, and the binomial probability will not be well-defined. In practice, unexpected alleles are sometimes observed in practice. In an embodiment, it is possible to use a corrected allele ratio $\hat{r}=1/(n_a+n_b)$ to allow a small number of the unexpected allele. In an embodiment, it is possible to use training data to model the rate of the unexpected allele appearing on each SNP, and use this model to correct the expected allele ratio. When the expected allele ratio is not 0 or 1, the observed allele ratio may not converge with a sufficiently high depth of read to the expected allele ratio due to amplification bias or other phenomena. The allele ratio can then be modeled as a beta distribution centered at the expected allele ratio, leading to a beta-binomial distribution for $P(n_a, n_b \mid r)$ which has higher variance than the binomial.

The platform model for the response at a single SNP will be defined as $F(a, b, g_c, g_m, f)$ (3), or the probability of observing $n_a=a$ and $n_b=b$ given the maternal and fetal genotypes, which also depends on the fetal fraction through equation 1. The functional form of F may be a binomial distribution, beta-binomial distribution, or similar functions as discussed above.

$$F(a,b,g_c,g_m,f)=P(n_a=a,n_b=b \mid g_c,g_m,f)=P(n_a=a,n_b=b \mid r(g_c,g_m,f)) \quad (3)$$

In an embodiment, the child fraction may be determined as follows. A maximum likelihood estimate of the fetal fraction f for a prenatal test may be derived without the use of paternal information. This may be relevant where the paternal genetic data is not available, for example where the father of record is not actually the genetic father of the fetus. The fetal fraction is estimated from the set of SNPs where the maternal genotype is 0 or 1, resulting in a set of only two possible fetal genotypes. Define $S_0$ as the set of SNPs with maternal genotype 0 and $S_1$ as the set of SNPs with maternal genotype 1. The possible fetal genotypes on $S_0$ are 0 and 0.5, resulting in a set of possible allele ratios $R_0(f)=\{0, f/2\}$. Similarly, $R_1(f)=\{1-f/2, 1\}$. This method can be trivially extended to include SNPs where maternal genotype is 0.5, but these SNPs will be less informative due to the larger set of possible allele ratios.

Define $N_{a0}$ and $N_{b0}$ as the vectors formed by $n_{as}$ and $n_{bs}$ for SNPs s in $S_0$, and $N_{a1}$ and $N_{b1}$ similarly for $S_1$. The maximum likelihood estimate $\hat{f}$ is defined by equation 4.

$$\hat{f}=\mathrm{argmax}_f P(N_{a0},N_{b0} \mid f)P(N_{a1},N_{b1} \mid f) \quad (4)$$

Assuming that the allele counts at each SNP are independent conditioned on the SNP's plasma allele ratio, the probabilities can be expressed as products over the SNPs in each set (5)

$$P(N_{a0},N_{b0} \mid f)=\Pi_{s \in S_0} P(n_{as},n_{bs} \mid f)$$

$$P(N_{a1},N_{b1} \mid f)=\Pi_{s \in S_1} P(n_{as},n_{bs} \mid f) \quad (5)$$

The dependence on f is through the sets of possible allele ratios $R_0(f)$ and $R_1(f)$. The SNP probability $P(n_{as}, n_{bs} \mid f)$ can be approximated by assuming the maximum likelihood genotype conditioned on f. At reasonably high fetal fraction and depth of read, the selection of the maximum likelihood genotype will be high confidence. For example, at fetal fraction of 10 percent and depth of read of 1000, consider a SNP where the mother has genotype zero. The expected allele ratios are 0 and 5 percent, which will be easily distinguishable at sufficiently high depth of read. Substitution of the estimated child genotype into equation 5 results in the complete equation (6) for the fetal fraction estimate.

$$\hat{f}=\mathrm{argmax}_f$$

$$[\Pi_{s \in S_0}(\max_{r_s \in R_0(f)} P(n_{as},n_{bs} \mid r_s)) \Pi_{s \in S_1}(\max_{r_s \in R_1(f)} P(n_{as}, n_{bs} \mid r_s))] \quad (6)$$

The fetal fraction must be in the range [0, 1] and so the optimization can be easily implemented by a constrained one-dimensional search.

In the presence of low depth of read or high noise level, it may be preferable not to assume the maximum likelihood genotype, which may result in artificially high confidences. Another method would be to sum over the possible genotypes at each SNP, resulting in the following expression (7) for $P(n_a, n_b \mid f)$ for a SNP in $S_0$. The prior probability $P(r)$ could be assumed uniform over $R_0(f)$, or could be based on population frequencies. The extension to group $S_1$ is trivial.

$$P(n_a,n_b \mid f)=\Sigma_{r \in R_0(f)} P(n_a,n_a \mid r)P(r) \quad (7)$$

In some embodiments the probabilities may be derived as follows. A confidence can be calculated from the data likelihoods of the two hypotheses $H_t$ and $H_f$. The likelihood of each hypothesis is derived based on the response model, the estimated fetal fraction, the mother genotypes, allele population frequencies, and the plasma allele counts.

Define the following notation:

$G_m$, $G_c$ true maternal and child genotypes $G_{af}$, $G_{tf}$ true genotypes of alleged father and of true father $G(g_c, g_m, g_{tf})=P(G_c=g_c \mid G_m=g_m, G_{tf}=g_{tf})$ inheritance probabilities $P(g)=P(G_{tf}=g)$ population frequency of genotype g at particular SNP Assuming that the observation at each SNP is independent conditioned on the plasma allele ratio, the likelihood of a paternity hypothesis is the product of the likelihoods on the SNPs. The following equations derive the likelihood for a single SNP. Equation 8 is a general expression for the likelihood of any hypothesis h, which will then be broken down into the specific cases of $H_t$ and $H_f$.

$$P(n_a, n_b \mid h, G_m, G_{tf}, f) = \sum_{g_c \in \{0,0.5,1\}} P(n_a, n_b \mid G_c = g_c, G_m, G_{tf}, h, f) P(G_c = g_c, G_m, G_{tf}, h, f) \quad (8)$$

$$= \sum_{g_c \in \{0,0.5,1\}} P(n_a, n_b \mid G_c = g_c, G_m, f) P(G_c = g_c \mid G_m, G_{tf}, h)$$

$$= \sum_{g_c \in \{0,0.5,1\}} F(n_a, n_b, g_c, g_m, f) P(G_c = g_c \mid G_m, G_{tf}, h)$$

In the case of $H_t$, the alleged father is the true father and the fetal genotypes are inherited from the maternal genotypes and alleged father genotypes according to equation 9.

$$P(n_a, n_b \mid H_t, G_m, G_{tf}, f) = \sum_{g_c \in \{0,0.5,1\}} F(n_a, n_b, g_c, g_m, f) P(G_c = g_c \mid G_m, G_{tf}, H_t) \quad (9)$$

$$= \sum_{g_c \in \{0,0.5,1\}} F(n_a, n_b, g_c, g_m, f) G(g_c, G_m, G_{tf})$$

In the case of $H_f$ the alleged father is not the true father. The best estimate of the true father genotypes are given by the population frequencies at each SNP. Thus, the probabilities of child genotypes are determined by the known mother genotypes and the population frequencies, as in equation 10.

$$P(n_a, n_b \mid H_t, G_m, G_{tf}, f) = \sum\nolimits_{g_c \in (0,0.5,1)} F(n_a, n_b, n_c, g_m, f)$$
$$P(G_c = g_c \mid G_m, G_{tf}, H_f)$$
$$= \sum\nolimits_{g_c \in (0,0.5,1)} F(n_a, n_b, g_c, g_m, f)$$
$$P(G_c = g_c \mid G_m)$$
$$= \sum\nolimits_{g_c \in (0,0.5,1)} \sum\nolimits_{g_{tf} \in (0,0.5,1)} F(n_a, n_b, g_c, g_m, f)$$
$$P(G_c = g_c \mid G_m, G_{tf} = g_{tf}) P(G_{tf} = g_{tf})$$
$$= \sum\nolimits_{g_c \in (0,0.5,1)} \sum\nolimits_{g_{tf} \in (0,0.5,1)} F(n_a, n_b, g_c, g_m, f)$$
$$G(g_c, G_m, g_{tf}) P(g_{tf})$$

The confidence $C_p$ on correct paternity is calculated from the product over SNPs of the two likelihoods using Bayes rule (11).

$$Cp = \frac{\prod_s P(n_{as}, n_{bs} \mid H_t, G_{ms}, G_{tf}, f)}{\prod_s P(n_{as}, n_{bs} \mid H_t, G_{ms}, G_{tf}, f) + \prod_s P(n_{as}, n_{bs} \mid H_f, G_{ms}, G_{tf}, f)} \quad (11)$$

Exemplary Methods for Identifying and Analyzing Multiple Pregnancies

In some embodiments, any of the methods of the present invention are used to detect the presence of a multiple pregnancy, such as a twin pregnancy, where at least one of the fetuses is genetically different from at least one other fetus. In some embodiments, fraternal twins are identified based on the presence of two fetus with different allele, different allele ratios, or different allele distributions at some (or all) of the tested loci. In some embodiments, fraternal twins are identified by determining the expected allele ratio at each locus (such as SNP loci) for two fetuses that may have the same or different fetal fractions in the sample (such as a plasma sample). In some embodiments, the likelihood of a particular pair of fetal fractions (where f1 is the fetal fraction for fetus 1, and f2 is the fetal fraction for fetus 2) is calculated by considering some or all of the possible genotypes of the two fetuses, conditioned on the mother's genotype and genotype population frequencies. The mixture of two fetal and one maternal genotype, combined with the fetal fractions, determine the expected allele ratio at a SNP. For example, if the mother is AA, fetus 1 is AA, and fetus 2 is AB, the overall fraction of B allele at the SNP is one-half of f2. The likelihood calculation asks how well all of the SNPs together match the expected allele ratios based on all of the possible combinations of fetal genotypes. The fetal fraction pair (f1, f2) that best matches the data is selected. It is not necessary to calculated specific genotypes of the fetuses; instead, one can, for example, considered all of the possible genotypes in a statistical combination. In some embodiments, if the method does not distinguish between singleton and identical twins, an ultrasound can be performed to determine whether there is a singleton or identical twin pregnancy. If the ultrasound detects a twin pregnancy it can be assumed that the pregnancy is an identical twin pregnancy because a fraternal twin pregnancy would have been detected based on the SNP analysis discussed above.

In some embodiments, a pregnant mother is known to have a multiple pregnancy (such as a twin pregnancy) based on prior testing, such as an ultrasound. Any of the methods of the present invention can be used to determine whether the multiple pregnancy includes identical or fraternal twins. For example, the measured allele ratios can be compared to what would be expected for identical twins (the same allele ratios as a singleton pregnancy) or for fraternal twins (such as the calculation of allele ratios as described above). Some identical twins are monochorionic twins, which have a risk of twin-to-twin transfusion syndrome. Thus, twins determined to be identical twins using a method of the invention are desirably tested (such as by ultrasound) to determine if they are monochorionic twins, and if so, these twins can be monitored (such as bi-weekly ultrasounds from 16 weeks) for signs of win-to-twin transfusion syndrome.

In some embodiments, any of the methods of the present invention are used to determine whether any of the fetuses in a multiple pregnancy, such as a twin pregnancy, are aneuploid. Aneuploidy testing for twins begins with the fetal fraction estimate. In some embodiments, the fetal fraction pair (f1, f2) that best matches the data is selected as described above. In some embodiments, a maximum likelihood estimate is performed for the parameter pair (f1, f2) over the range of possible fetal fractions. In some embodiments, the range of f2 is from 0 to f1 because 12 is defined as the smaller fetal fraction. Given a pair (f1, f2), data likelihood is calculated from the allele ratios observed at a set of loci such as SNP loci. In some embodiments, the data likelihood reflects the genotypes of the mother, the father if available, population frequencies, and the resulting probabilities of fetal genotypes. In some embodiments, SNPs are assumed independent. The estimated fetal fraction pair is the one that produces the highest data likelihood. If f2 is 0 then the data is best explained by only one set of fetal genotypes, indicating identical twins, where f1 is the combined fetal fraction. Otherwise f1 and f2 are the estimates of the individual twin fetal fractions. Having established the best estimate of (f1, f2), one can predict the overall fraction of B allele in the plasma for any combination of maternal and fetal genotypes, if desired. It is not necessary to assign individual sequence reads to the individual fetuses. Ploidy testing is performed using another maximum likelihood estimate which compares the data likelihood of two hypotheses. In some embodiments for identical twins, one consider the hypotheses (i) both twins are euploid, and (ii) both twins are trisomic. In some embodiments for fraternal twins, one considers the hypotheses (i) both twins are euploid and (ii) at least one twin is trisomic. The trisomy hypotheses for fraternal twins are based on the lower fetal fraction, since a trisomy in the twin with a higher fetal fraction would also be detected. Ploidy likelihoods are calculated using a method which predicts the expected number of reads at each targeted genome locus conditioned on either the disomy or trisomy hypothesis. There is no requirement for a disomy reference chromosome. The variance model for the expected number of reads takes into account the performance of individual target loci as well as the correlation between loci (see, for example, U.S. Ser. No. 62/008,235, filed Jun. 5, 2014, and U.S. Ser. No. 62/032,785, filed Aug. 4, 2014, which are each hereby incorporated by reference in its entirety). If the smaller twin has fetal fraction f1, our ability to detect a trisomy in that twin is equivalent to our ability to detect a trisomy in a singleton pregnancy at the same fetal fraction. This is because the part of the method that detects the trisomy in some embodiments does not depend on genotypes and does not distinguish between multiple or singleton pregnancy. It simply looks for an increased number of reads in accordance with the determined fetal fraction.

In some embodiments, the method includes detecting the presence of twins based on SNP loci (such as described above). If twins are detected, SPNs are used to determine the fetal fraction of each fetus (f1, f2) such as described above. In some embodiments, samples that have high confidence disomy calls are used to determine the amplification bias on a per-SNP basis. In some embodiments, these samples with high confidence disomy calls are analyzed in the same run as one or more samples of interest. In some embodiments, the amplification bias on a per-SNP basis is used to model the distribution of reads for one or more chromosomes or chromosome segments of interest such as chromosome 21 that are expected or the disomy hypothesis and the trisomy hypothesis given the lower of the two twin fetal fraction. The likelihood or probability of disomy or trisomy is calculated given the two models and the measured quantity of the chromosome or chromosome segment of interest.

In some embodiments, the threshold for a positive aneuploidy call (such as a trisomy call) is set based on the twin with the lower fetal fraction. This way, if the other twin is positive, or if both are positive, the total chromosome representation is definitely above the threshold.

Maximum Likelihood Model Using Percent Fetal Fraction

Determining the ploidy status of a fetus by measuring the free floating DNA contained in maternal serum, or by measuring the genotypic material in any mixed sample, is a non-trivial exercise. There are a number of methods, for example, performing a read count analysis where the presumption is that if the fetus is trisomic at a particular chromosome, then the overall amount of DNA from that chromosome found in the maternal blood will be elevated with respect to a reference chromosome. One way to detect trisomy in such fetuses is to normalize the amount of DNA expected for each chromosome, for example, according to the number of SNPs in the analysis set that correspond to a given chromosome, or according to the number of uniquely mappable portions of the chromosome. Once the measurements have been normalized, any chromosomes for which the amount of DNA measured exceeds a certain threshold are determined to be trisomic. This approach is described in Fan, et al. PNAS, 2008; 105(42); pp. 16266-16271, and also in Chiu et al. BMJ 2011; 342:c7401. In the Chiu et al. paper, the normalization was accomplished by calculating a Z score as follows:

Z score for percentage chromosome 21 in test case= ((percentage chromosome 21 in test case)−(mean percentage chromosome 21 in reference controls))/(standard deviation of percentage chromosome 21 in reference controls).

These methods determine the ploidy status of the fetus using a single hypothesis rejection method. However, they suffer from some significant shortcomings. Since these methods for determining ploidy in the fetus are invariant according to the percentage of fetal DNA in the sample, they use one cut off value; the result of this is that the accuracies of the determinations are not optimal, and those cases where the percentage of fetal DNA in the mixture are relatively low will suffer the worst accuracies.

In an embodiment, a method of the present disclosure is used to determine the ploidy state of the fetus involves taking into account the fraction of fetal DNA in the sample. In another embodiment of the present disclosure, the method involves the use of maximum likelihood estimations. In an embodiment, a method of the present disclosure involves calculating the percent of DNA in a sample that is fetal or placental in origin. In an embodiment, the threshold for calling aneuploidy is adaptively adjusted based on the calculated percent fetal DNA. In some embodiments, the method for estimating the percentage of DNA that is of fetal origin in a mixture of DNA, comprises obtaining a mixed sample that comprises genetic material from the mother, and genetic material from the fetus, obtaining a genetic sample from the father of the fetus, measuring the DNA in the mixed sample, measuring the DNA in the father sample, and calculating the percentage of DNA that is of fetal origin in the mixed sample using the DNA measurements of the mixed sample, and of the father sample.

In an embodiment of the present disclosure, the fraction of fetal DNA, or the percentage of fetal DNA in the mixture can be measured. In some embodiments the fraction can be calculated using only the genotyping measurements made on the maternal plasma sample itself, which is a mixture of fetal and maternal DNA. In some embodiments the fraction may be calculated also using the measured or otherwise known genotype of the mother and/or the measured or otherwise known genotype of the father. In some embodiments the percent fetal DNA may be calculated using the measurements made on the mixture of maternal and fetal DNA along with the knowledge of the parental contexts. In an embodiment, the fraction of fetal DNA may be calculated using population frequencies to adjust the model on the probability on particular allele measurements.

In an embodiment of the present disclosure, a confidence may be calculated on the accuracy of the determination of the ploidy state of the fetus. In an embodiment, the confidence of the hypothesis of greatest likelihood ($H_{major}$) may be calculated as $(1-H_{major})/\Sigma(\text{all } H)$. It is possible to determine the confidence of a hypothesis if the distributions of all of the hypotheses are known. It is possible to determine the distribution of all of the hypotheses if the parental genotype information is known. It is possible to calculate a confidence of the ploidy determination if the knowledge of the expected distribution of data for the euploid fetus and the expected distribution of data for the aneuploid fetus are known. It is possible to calculate these expected distributions if the parental genotype data are known. In an embodiment one may use the knowledge of the distribution of a test statistic around a normal hypothesis and around an abnormal hypothesis to determine both the reliability of the call as well as refine the threshold to make a more reliable call. This is particularly useful when the amount and/or percent of fetal DNA in the mixture is low. It will help to avoid the situation where a fetus that is actually aneuploid is found to be euploid because a test statistic, such as the Z statistic does not exceed a threshold that is made based on a threshold that is optimized for the case where there is a higher percent fetal DNA.

In an embodiment, a method disclosed herein can be used to determine a fetal aneuploidy by determining the number of copies of maternal and fetal target chromosomes in a mixture of maternal and fetal genetic material. This method may entail obtaining maternal tissue comprising both maternal and fetal genetic material; in some embodiments this maternal tissue may be maternal plasma or a tissue isolated from maternal blood. This method may also entail obtaining a mixture of maternal and fetal genetic material from said maternal tissue by processing the aforementioned maternal tissue. This method may entail distributing the genetic material obtained into a plurality of reaction samples, to randomly provide individual reaction samples that comprise a target sequence from a target chromosome and individual reaction samples that do not comprise a target sequence from a target chromosome, for example, performing high throughput sequencing on the sample. This method may entail analyzing the target sequences of genetic material present or absent in said individual reaction samples to provide a first number of binary results representing presence or absence of a presumably euploid fetal chromosome in the reaction samples and a second number of binary results representing presence or absence of a possibly aneuploid fetal chromosome in the reaction samples. Either of the number of binary results may be calculated, for example, by way of an informatics technique that counts sequence reads that map to a particular chromosome, to a particular region of a chromosome, to a particular locus or set of loci. This method may involve normalizing the number of binary events based on the chromosome length, the length of the region of the chromosome, or the number of loci in the set. This method may entail calculating an expected distribution of the number of binary results for a presumably euploid fetal chromosome in the reaction samples using the first number. This method may entail calculating an expected distribution of the number of binary results for a presumably aneuploid fetal chromosome in the reaction samples using the first number and an estimated fraction of fetal DNA found in the mixture, for example, by multiplying the expected read count distribution of the number of binary results for a presumably euploid fetal chromosome by (1+n/2) where n is the estimated fetal fraction. In some embodiments, the sequence reads may be treated at probabilistic mappings rather than binary results; this method would yield higher accuracies, but require more computing power. The fetal fraction may be estimated by a plurality of methods, some of which are described elsewhere in this disclosure. This method may involve using a maximum likelihood approach to determine whether the second number corresponds to the possibly aneuploid fetal chromosome being euploid or being aneuploid. This method may involve calling the ploidy status of the fetus to be the ploidy state that corresponds to the hypothesis with the maximum likelihood of being correct given the measured data.

Note that the use of a maximum likelihood model may be used to increase the accuracy of any method that determines the ploidy state of a fetus. Similarly, a confidence may be calculated for any method that determines the ploidy state of the fetus. The use of a maximum likelihood model would result in an improvement of the accuracy of any method where the ploidy determination is made using a single hypothesis rejection technique. A maximum likelihood model may be used for any method where a likelihood distribution can be calculated for both the normal and abnormal cases. The use of a maximum likelihood model implies the ability to calculate a confidence for a ploidy call.

Further Discussion of the Method

In an embodiment, a method disclosed herein utilizes a quantitative measure of the number of independent observations of each allele at a polymorphic locus, where this does not involve calculating the ratio of the alleles. This is different from methods, such as some microarray based methods, which provide information about the ratio of two alleles at a locus but do not quantify the number of independent observations of either allele. Some methods known in the art can provide quantitative information regarding the number of independent observations, but the calculations leading to the ploidy determination utilize only the allele ratios, and do not utilize the quantitative information. To illustrate the importance of retaining information about the number of independent observations consider the sample locus with two alleles, A and B. In a first experiment twenty A alleles and twenty B alleles are observed, in a second experiment 200 A alleles and 200 B alleles are observed. In both experiments the ratio (A/(A+B)) is equal to 0.5, however the second experiment conveys more information than the first about the certainty of the frequency of the A or B allele. The instant method, rather than utilizing the allele ratios, uses the quantitative data to more accurately model the most likely allele frequencies at each polymorphic locus.

In an embodiment, the instant methods build a genetic model for aggregating the measurements from multiple polymorphic loci to better distinguish trisomy from disomy and also to determine the type of trisomy. Additionally, the instant method incorporates genetic linkage information to enhance the accuracy of the method. This is in contrast to some methods known in the art where allele ratios are averaged across all polymorphic loci on a chromosome. The method disclosed herein explicitly models the allele frequency distributions expected in disomy as well as and trisomy resulting from nondisjunction during meiosis I, nondisjunction during meiosis II, and nondisjunction during mitosis early in fetal development. To illustrate why this is important, if there were no crossovers nondisjunction during meiosis I would result a trisomy in which two different homologs were inherited from one parent; nondisjunction during meiosis II or during mitosis early in fetal development would result in two copies of the same homolog from one parent. Each scenario results in different expected allele frequencies at each polymorphic locus and also at all physically linked loci (i.e. loci on the same chromosome) considered jointly. Crossovers, which result in the exchange of genetic material between homologs, make the inheritance pattern more complex, but the instant method accommodates for this by using genetic linkage information, i.e. recombination rate information and the physical distance between loci. To better distinguish between meiosis I nondisjunction and meiosis II or mitotic nondisjunction the instant method incorporates into the model an increasing probability of crossover as the distance from the centromere increases. Meiosis II and mitotic nondisjunction can distinguished by the fact that mitotic nondisjunction typically results in identical or nearly identical copies of one homolog while the two homologs present following a meiosis II nondisjunction event often differ due to one or more crossovers during gametogenesis.

In an embodiment, a method of the present disclosure may not determine the haplotypes of the parents if disomy is assumed. In an embodiment, in case of trisomy, the instant method can make a determination about the haplotypes of one or both parents by using the fact that plasma takes two copies from one parent, and parent phase information can be determined by noting which two copies have been inherited from the parent in question. In particular, a child can inherit either two of the same copies of the parent (matched trisomy) or both copies of the parent (unmatched trisomy). At each SNP one can calculate the likelihood of the matched trisomy and of the unmatched trisomy. A ploidy calling method that does not use the linkage model accounting for crossovers would calculate the overall likelihood of the trisomy as a simple weighted average of the matched and unmatched trisomies over all chromosomes. However, due to the biological mechanisms that result in disjunction error and crossing over, trisomy can change from matched to unmatched (and vice versa) on a chromosome only if a crossover occurs. The instant method probabilistically takes into account the likelihood of crossover, resulting in ploidy calls that are of greater accuracy than those methods that do not.

In an embodiment, a reference chromosome is used to determine the child fraction and noise level amount or probability distribution. In an embodiment, the child fraction, noise level, and/or probability distribution is determined using only the genetic information available from the chromosome whose ploidy state is being determined. The instant method works without the reference chromosome, as well as without fixing the particular child fraction or noise level. This is a significant improvement and point of differentiation from methods known in the art where genetic data from a reference chromosome is necessary to calibrate the child fraction and chromosome behavior.

In an embodiment where a reference chromosome is not needed to determine the fetal fraction, determining the hypothesis is done as follows:

$$H^* = \underset{H}{\operatorname{argmax}} LIK(D|H) * priorprob(H)$$

With the algorithm with reference chromosome, one typically assumes that the reference chromosome is a disomy, and then one may either (a) fix the most likely child fraction and random noise level N based on this assumption and reference chromosome data:

$$[cfr^*, N^*] = \underset{cfr,N}{\operatorname{argmax}} LIK(D(ref.chrom)|H11, cfr, N)$$

And then reduce $$LIK(D|H) = LIK(D|H, cfr^*, N^*)$$

or (b) estimate the child fraction and noise level distribution based on this assumption and reference chromosome data. In particular, one would not fix just one value for cfr and N, but assign probability p(cfr, N) for the wider range of possible cfr, N values:

$$p(cfr,N) \sim LIK(D(ref.chrom)|H11,cfr,N) * priorprob(cfr, N)$$

where priorprob(cfr, N) is the prior probability of particular child fraction and noise level, determined by prior knowledge and experiments. If desired, just uniform over the range of cfr, N. One may then write:

$$LIK(D|H) = \sum_{cfr,N} LIK(D|H, cfr, N) * p(cfr, N)$$

Both methods above give good results.

Note that in some instances using a reference chromosome is not desirable, possible or feasible. In such a case, it is possible to derive the best ploidy call for each chromosome separately. In particular:

$$LIK(D|H) = \sum_{cfr,N} LIK(D|H, cfr, N) * p(cfr, N|H)$$

p(cfr, N|H) may be determined as above, for each chromosome separately, assuming hypothesis H, not just for the reference chromosome assuming disomy. It is possible, using this method, to keep both noise and child fraction parameters fixed, fix either of the parameters, or keep both parameters in probabilistic form for each chromosome and each hypothesis.

Measurements of DNA are noisy and/or error prone, especially measurements where the amount of DNA is small, or where the DNA is mixed with contaminating DNA. This noise results in less accurate genotypic data, and less accurate ploidy calls. In some embodiments, platform modeling or some other method of noise modeling may be used to counter the deleterious effects of noise on the ploidy determination. The instant method uses a joint model of both channels, which accounts for the random noise due to the amount of input DNA, DNA quality, and/or protocol quality.

This is in contrast to some methods known in the art where the ploidy determinations are made using the ratio of allele intensities at a locus. This method precludes accurate SNP noise modeling. In particular, errors in the measurements typically do not specifically depend on the measured channel intensity ratio, which reduces the model to using one-dimensional information. Accurate modeling of noise, channel quality and channel interaction requires a two-dimensional joint model, which can not be modeled using allele ratios.

In particular, projecting two channel information to the ratio r where f(x,y) is r=x/y, does not lend itself to accurate channel noise and bias modeling. Noise on a particular SNP is not a function of the ratio, i.e. noise(x,y)≠f(x,y) but is in fact a joint function of both channels. For example, in the binomial model, noise of the measured ratio has a variance of r(1−r)/(x+y) which is not a function purely of r. In such a model, where any channel bias or noise is included, suppose that on SNP i, the observed channel X value is x=$a_i$X+$b_i$, where X is the true channel value, $b_i$ is the extra channel bias and random noise. Similarly, suppose that y=$c_i$Y+$d_i$. The observed ratio r=x/y can not accurately predict the true ratio X/Y or model the leftover noise, since (aiX+bi)/(ciY+di) is not a function of X/Y.

The method disclosed herein describes an effective way to model noise and bias using joint binomial distributions of all of the measurement channels individually. Relevant equations may be found elsewhere in the document in sections which speaks of per SNP consistent bias, P(good) and P(ref|bad), P(mut|bad) which effectively adjust SNP behavior. In an embodiment, a method of the present disclosure uses a BetaBinomial distribution, which avoids the limiting practice of relying on the allele ratios only, but instead models the behavior based on both channel counts.

In an embodiment, a method disclosed herein can call the ploidy of a gestating fetus from genetic data found in maternal plasma by using all available measurements. In an embodiment, a method disclosed herein can call the ploidy of a gestating fetus from genetic data found in maternal plasma by using the measurements from only a subset of parental contexts. Some methods known in the art only use measured genetic data where the parental context is from the AA|BB context, that is, where the parents are both homozygous at a given locus, but for a different allele. One problem with this method is that a small proportion of polymorphic loci are from the AA|BB context, typically less than 10%. In an embodiment of a method disclosed herein, the method does not use genetic measurements of the maternal plasma made at loci where the parental context is AA|BB. In an embodiment, the instant method uses plasma measurements for only those polymorphic loci with the AA|AB, AB|AA, and AB|AB parental context.

Some methods known in the art involve averaging allele ratios from SNPs in the AA|BB context, where both parent genotypes are present, and claim to determine the ploidy calls from the average allele ratio on these SNPs. This method suffers from significant inaccuracy due differential SNP behavior. Note that this method assumes that have both parent genotypes are known. In contrast, in some embodiments, the instant method uses a joint channel distribution model that does not assume the presence of either of the parents, and does not assume the uniform SNP behavior. In some embodiments, the instant method accounts for the different SNP behavior/weighing. In some embodiments, the instant method does not require the knowledge of one or both parental genotypes. An example of how the instant method may accomplish this follows:

In some embodiments, the log likelihood of a hypothesis may be determined on a per SNP basis. On a particular SNP i, assuming fetal ploidy hypothesis H and percent fetal DNA cf, the log likelihood of observed data D is defined as:

$$LIK(D \mid H, i) = \log P(D \mid H, cf, i)$$

$$= \log\left(\sum_{m,f,c} P(D \mid m, f, c, H, cf, i) \right.$$

$$\left. P(c \mid m, f, H) P(m \mid i) P(f \mid i)\right)$$

where m are possible true mother genotypes, f are possible true father genotypes, where m,f∈{AA,AB,BB}, and where c are possible child genotypes given the hypothesis H. In particular, for monosomy c{A,B}, for disomy c∈{AA,AB, BB}, for trisomy c∈[AAA, AAB, ABB, BBB]. Note that including parental genotypic data typically results in more accurate ploidy determinations, however, parental genotypic data is not necessary for the instant method to work well.

Some methods known in the art involve averaging allele ratios from SNPs where the mother is homozygous but a different allele is measured in the plasma (either AA|AB or AA|BB contexts), and claim to determine the ploidy calls from the average allele ratio on these SNPs. This method is intended for cases where the paternal genotype is not available. Note that it is questionable how accurately one can claim that plasma is heterozygous on a particular SNP without the presence of homozygous and opposite father BB: for cases with low child fraction, what looks like presence of B allele could be just presence of noise; additionally, what looks like no B present could be simple allele drop out of the fetal measurements. Even in a case where one can actually determine heterozygosity of the plasma, this method will not be able to distinguish paternal trisomies. In particular, for SNPs where mother is AA, and where some B is measured in the plasma, if the father is GG, the resulting child genotype is AGG, resulting in an average ratio of 33% A (for child fraction=100%). But in the case where the father is AG, the resulting child genotype could be AGG for matched trisomy, contributing to the 33% A ratio, or AAG for unmatched trisomy, drawing the average ratio more toward 66% A. Given that many trisomies are on chromosomes with crossovers, the overall chromosome can have anywhere between no unmatched trisomy and all unmatched trisomy, this ratio can vary anywhere between 33-66%. For a plain disomy, the ratio should be around 50%. Without the use of a linkage model or an accurate error model of the average, this method would miss many cases of paternal trisomy. In contrast, the method disclosed herein assigns parental genotype probabilities for each parental genotypic candidate, based on available genotypic information and population frequency, and does not explicitly require parental genotypes. Additionally, the method disclosed herein is able to detect trisomy even in the absence or presence of parent genotypic data, and can compensate by identifying the points of possible crossovers from matched to unmatched trisomy using a linkage model.

Some methods known in the art claim a method for averaging allele ratios from SNPs where neither the maternal or paternal genotype is known, and for determining the ploidy calls from average ratio on these SNPs. However, a method to accomplish these ends is not disclosed. The method disclosed herein is able to make accurate ploidy calls in such a situation, and the reduction to practice is disclosed elsewhere in this document, using a joint probability maximum likelihood method and optionally utilizes SNP noise and bias models, as well as a linkage model.

Some methods known in the art involve averaging allele ratios and claim to determine the ploidy calls from the average allele ratio at one or a few SNPs. However, such methods do not utilize the concept of linkage. The methods disclosed herein do not suffer from these drawbacks.

Using Sequence Length as a Prior to Determine the Origin of DNA

It has been reported that the distribution of length of sequences differ for maternal and fetal DNA, with fetal generally being shorter. In an embodiment of the present disclosure, it is possible to use previous knowledge in the form of empirical data, and construct prior distribution for expected length of both mother(P(X|maternal)) and fetal DNA (P(X|fetal)). Given new unidentified DNA sequence of length x, it is possible to assign a probability that a given sequence of DNA is either maternal or fetal DNA, based on prior likelihood of x given either maternal or fetal. In particular if P(x|maternal)>P(x|fetal), then the DNA sequence can be classified as maternal, with P(x|maternal)= P(x|maternal)/[(P(x|maternal)+P(x|fetal)], and if p(x|maternal)<p(x|fetal), then the DNA sequence can be classified as fetal, P(x|fetal)=P(x|fetal)/[(P(x|maternal)+P(x|fetal)]. In an embodiment of the present disclosure, a distributions of maternal and fetal sequence lengths can be determined that is specific for that sample by considering the sequences that can be assigned as maternal or fetal with high probability, and then that sample specific distribution can be used as the expected size distribution for that sample.

Variable Read Depth to Minimize Sequencing Cost

In many clinical trials concerning a diagnostic, for example, in Chiu et al. BMJ 2011; 342:c7401, a protocol with a number of parameters is set, and then the same protocol is executed with the same parameters for each of the patients in the trial. In the case of determining the ploidy status of a fetus gestating in a mother using sequencing as a method to measure genetic material one pertinent parameter is the number of reads. The number of reads may refer to the number of actual reads, the number of intended reads, fractional lanes, full lanes, or full flow cells on a sequencer. In these studies, the number of reads is typically set at a level that will ensure that all or nearly all of the samples achieve the desired level of accuracy. Sequencing is currently an expensive technology, a cost of roughly $200 per 5 mappable million reads, and while the price is dropping, any method which allows a sequencing based diagnostic to operate at a similar level of accuracy but with fewer reads will necessarily save a considerable amount of money.

The accuracy of a ploidy determination is typically dependent on a number of factors, including the number of reads and the fraction of fetal DNA in the mixture. The accuracy is typically higher when the fraction of fetal DNA in the mixture is higher. At the same time, the accuracy is typically higher if the number of reads is greater. It is possible to have a situation with two cases where the ploidy state is determined with comparable accuracies wherein the first case has a lower fraction of fetal DNA in the mixture than the second, and more reads were sequenced in the first case than the second. It is possible to use the estimated fraction of fetal DNA in the mixture as a guide in determining the number of reads necessary to achieve a given level of accuracy.

In an embodiment of the present disclosure, a set of samples can be run where different samples in the set are sequenced to different reads depths, wherein the number of reads run on each of the samples is chosen to achieve a given level of accuracy given the calculated fraction of fetal DNA in each mixture. In an embodiment of the present disclosure, this may entail making a measurement of the mixed sample to determine the fraction of fetal DNA in the mixture; this estimation of the fetal fraction may be done with sequencing, it may be done with TAQMAN, it may be done with qPCR, it may be done with SNP arrays, it may be done with any method that can distinguish different alleles at a given loci. The need for a fetal fraction estimate may be eliminated by including hypotheses that cover all or a selected set of fetal fractions in the set of hypotheses that are considered when comparing to the actual measured data. After the fraction fetal DNA in the mixture has been determined, the number of sequences to be read for each sample may be determined.

In an embodiment of the present disclosure, 100 pregnant women visit their respective OB's, and their blood is drawn into blood tubes with an anti-lysant and/or something to inactivate DNAase. They each take home a kit for the father of their gestating fetus who gives a saliva sample. Both sets of genetic materials for all 100 couples are sent back to the laboratory, where the mother blood is spun down and the buffy coat is isolated, as well as the plasma. The plasma comprises a mixture of maternal DNA as well as placentally derived DNA. The maternal buffy coat and the paternal blood is genotyped using a SNP array, and the DNA in the maternal plasma samples are targeted with SURESELECT hybridization probes. The DNA that was pulled down with the probes is used to generate 100 tagged libraries, one for each of the maternal samples, where each sample is tagged with a different tag. A fraction from each library is withdrawn, each of those fractions are mixed together and added to two lanes of a ILLUMINA HISEQ DNA sequencer in a multiplexed fashion, wherein each lane resulted in approximately 50 million mappable reads, resulting in approximately 100 million mappable reads on the 100 multiplexed mixtures, or approximately 1 million reads per sample. The sequence reads were used to determine the fraction of fetal DNA in each mixture. 50 of the samples had more than 15% fetal DNA in the mixture, and the 1 million reads were sufficient to determine the ploidy status of the fetuses with a 99.9% confidence.

Of the remaining mixtures, 25 had between 10 and 15% fetal DNA; a fraction of each of the relevant libraries prepped from these mixtures were multiplexed and run down one lane of the HISEQ generating an additional 2 million reads for each sample. The two sets of sequence data for each of the mixture with between 10 and 15% fetal DNA were added together, and the resulting 3 million reads per sample which were sufficient to determine the ploidy state of those fetuses with 99.9% confidence.

Of the remaining mixtures, 13 had between 6 and 10% fetal DNA; a fraction of each of the relevant libraries prepped from these mixtures were multiplexed and run down one lane of the HISEQ generating an additional 4 million reads for each sample. The two sets of sequence data for each of the mixture with between 6 and 10% fetal DNA were added together, and the resulting 5 million total reads per mixture which were sufficient to determine the ploidy state of those fetuses with 99.9% confidence.

Of the remaining mixtures, 8 had between 4 and 6% fetal DNA; a fraction of each of the relevant libraries prepped from these mixtures were multiplexed and run down one lane of the HISEQ generating an additional 6 million reads for each sample. The two sets of sequence data for each of the mixture with between 4 and 6% fetal DNA were added together, and the resulting 7 million total reads per mixture which were sufficient to determine the ploidy state of those fetuses with 99.9% confidence.

Of the remaining four mixtures, all of them had between 2 and 4% fetal DNA; a fraction of each of the relevant libraries prepped from these mixtures were multiplexed and run down one lane of the HISEQ generating an additional 12 million reads for each sample. The two sets of sequence data for each of the mixture with between 2 and 4% fetal DNA were added together, and the resulting 13 million total reads per mixture which were sufficient to determine the ploidy state of those fetuses with 99.9% confidence.

This method required six lanes of sequencing on a HISEQ machine to achieve 99.9% accuracy over 100 samples. If the same number of runs had been required for every sample, to ensure that every ploidy determination was made with a 99.9% accuracy, it would have taken 25 lanes of sequencing, and if a no-call rate or error rate of 4% was tolerated, it could have been achieved with 14 lanes of sequencing.

Using Raw Genotyping Data

There are a number of methods that can accomplish NPD using fetal genetic information measured on fetal DNA found in maternal blood. Some of these methods involve making measurements of the fetal DNA using SNP arrays, some methods involve untargeted sequencing, and some methods involve targeted sequencing. The targeted sequencing may target SNPs, it may target STRs, it may target other polymorphic loci, it may target non-polymorphic loci, or some combination thereof. Some of these methods may involve using a commercial or proprietary allele caller that calls the identity of the alleles from the intensity data that comes from the sensors in the machine doing the measuring. For example, the ILLUMINA INFINIUM system or the AFFYMETRIX GENECHIP microarray system involves beads or microchips with attached DNA sequences that can hybridize to complementary segments of DNA; upon hybridization, there is a change in the fluorescent properties of the sensor molecule that can be detected. There are also sequencing methods, for example the ILLUMINA SOLEXA GENOME SEQUENCER or the ABI SOLID GENOME SEQUENCER, wherein the genetic sequence of fragments of DNA are sequenced; upon extension of the strand of DNA complementary to the strand being sequenced, the identity of the extended nucleotide is typically detected via a fluorescent or radio tag appended to the complementary nucleotide. In all of these methods the genotypic or sequencing data is typically determined on the basis of fluorescent or other signals, or the lack thereof. These systems are typically combined with low level software packages that make specific allele calls (secondary genetic data) from the analog output of the fluorescent or other detection device (primary genetic data). For example, in the case of a given allele on a SNP array, the software will make a call, for example, that a certain SNP is present or not present if the fluorescent intensity is measure above or below a certain threshold. Similarly, the output of a sequencer is a chromatogram that indicates the level of fluorescence detected for each of the dyes, and the software will make a call that a certain base pair is A or T or C or G. High throughput sequencers typically make a series of such measurements, called a read, that represents the most likely structure of the DNA sequence that was sequenced. The direct analog output of the chromatogram is defined here to be the primary genetic data, and the base pair/SNP calls made by the software are considered here to be the secondary genetic data. In an embodiment, primary data refers to the raw intensity data that is the unprocessed output of a genotyping platform, where the genotyping platform may refer to a SNP array, or to a sequencing platform. The secondary genetic data refers to the processed genetic data, where an allele call has been made, or the sequence data has been assigned base pairs, and/or the sequence reads have been mapped to the genome.

Many higher level applications take advantage of these allele calls, SNP calls and sequence reads, that is, the secondary genetic data, that the genotyping software produces. For example, DNA NEXUS, ELAND or MAQ will take the sequencing reads and map them to the genome. For example, in the context of non-invasive prenatal diagnosis, complex informatics, such as PARENTAL SUPPORT™, may leverage a large number of SNP calls to determine the genotype of an individual. Also, in the context of preimplantation genetic diagnosis, it is possible to take a set of sequence reads that are mapped to the genome, and by taking a normalized count of the reads that are mapped to each chromosome, or section of a chromosome, it may be possible to determine the ploidy state of an individual. In the context of non-invasive prenatal diagnosis it may be possible to take a set of sequence reads that have been measured on DNA present in maternal plasma, and map them to the genome. One may then take a normalized count of the reads that are mapped to each chromosome, or section of a chromosome, and use that data to determine the ploidy state of an individual. For example, it may be possible to conclude that those chromosomes that have a disproportionately large number of reads are trisomic in the fetus that is gestating in the mother from which the blood was drawn.

However, in reality, the initial output of the measuring instruments is an analog signal. When a certain base pair is called by the software that is associated with the sequencing software, for example the software may call the base pair a T, in reality the call is the call that the software believes to be most likely. In some cases, however, the call may be of low confidence, for example, the analog signal may indicate that the particular base pair is only 90% likely to be a T, and 10% likely to be an A. In another example, the genotype calling software that is associated with a SNP array reader may call a certain allele to be G. However, in reality, the underlying analog signal may indicate that it is only 70% likely that the allele is G, and 30% likely that the allele is T. In these cases, when the higher level applications use the genotype calls and sequence calls made by the lower level software, they are losing some information. That is, the primary genetic data, as measured directly by the genotyping platform, may be messier than the secondary genetic data that is determined by the attached software packages, but it contains more information. In mapping the secondary genetic data sequences to the genome, many reads are thrown out because some bases are not read with enough clarity and or mapping is not clear. When the primary genetic data sequence reads are used, all or many of those reads that may have been thrown out when first converted to secondary genetic data sequence read can be used by treating the reads in a probabilistic manner.

In an embodiment of the present disclosure, the higher level software does not rely on the allele calls, SNP calls, or sequence reads that are determined by the lower level software. Instead, the higher level software bases its calculations on the analog signals directly measured from the genotyping platform. In an embodiment of the present disclosure, an informatics based method such as PARENTAL SUPPORT™ is modified so that its ability to reconstruct the genetic data of the embryo/fetus/child is engineered to directly use the primary genetic data as measured by the genotyping platform. In an embodiment of the present disclosure, an informatics based method such as PARENTAL SUPPORT™ is able to make allele calls, and/or chromosome copy number calls using primary genetic data, and not using the secondary genetic data. In an embodiment of the present disclosure, all genetic calls, SNPs calls, sequence reads, sequence mapping is treated in a probabilistic manner by using the raw intensity data as measured directly by the genotyping platform, rather than converting the primary genetic data to secondary genetic calls. In an embodiment, the DNA measurements from the prepared sample used in calculating allele count probabilities and determining the relative probability of each hypothesis comprise primary genetic data.

In some embodiments, the method can increase the accuracy of genetic data of a target individual which incorporates genetic data of at least one related individual, the method comprising obtaining primary genetic data specific to a target individual's genome and genetic data specific to the genome(s) of the related individual(s), creating a set of one or more hypotheses concerning possibly which segments of which chromosomes from the related individual(s) correspond to those segments in the target individual's genome, determining the probability of each of the hypotheses given the target individual's primary genetic data and the related individual(s)'s genetic data, and using the probabilities associated with each hypothesis to determine the most likely state of the actual genetic material of the target individual. In some embodiments, the method can determining the number of copies of a segment of a chromosome in the genome of a target individual, the method comprising creating a set of copy number hypotheses about how many copies of the chromosome segment are present in the genome of a target individual, incorporating primary genetic data from the target individual and genetic information from one or more related individuals into a data set, estimating the characteristics of the platform response associated with the data set, where the platform response may vary from one experiment to another, computing the conditional probabilities of each copy number hypothesis, given the data set and the platform response characteristics, and determining the copy number of the chromosome segment based on the most probable copy number hypothesis. In an embodiment, a method of the present disclosure can determine a ploidy state of at least one chromosome in a target individual, the method comprising obtaining primary genetic data from the target individual and from one or more related individuals, creating a set of at least one ploidy state hypothesis for each of the chromosomes of the target individual, using one or more expert techniques to determine a statistical probability for each ploidy state hypothesis in the set, for each expert technique used, given the obtained genetic data, combining, for each ploidy state hypothesis, the statistical probabilities as determined by the one or more expert techniques, and determining the ploidy state for each of the chromosomes in the target individual based on the combined statistical probabilities of each of the ploidy state hypotheses. In an embodiment, a method of the present disclosure can determine an allelic state in a set of alleles, in a target individual, and from one or both parents of the target individual, and optionally from one or more related individuals, the method comprising obtaining primary genetic data from the target individual, and from the one or both parents, and from any related individuals, creating a set of at least one allelic hypothesis for the target individual, and for the one or both parents, and optionally for the one or more related individuals, where the hypotheses describe possible allelic states in the set of alleles, determining a statistical probability for each allelic hypothesis in the set of hypotheses given the obtained genetic data, and determining the allelic state for each of the alleles in the set of alleles for the target individual, and for the one or both parents, and optionally for the one or more related individuals, based on the statistical probabilities of each of the allelic hypotheses.

In some embodiments, the genetic data of the mixed sample may comprise sequence data wherein the sequence data may not uniquely map to the human genome. In some embodiments, the genetic data of the mixed sample may comprise sequence data wherein the sequence data maps to a plurality of locations in the genome, wherein each possible mapping is associated with a probability that the given mapping is correct. In some embodiments, the sequence reads are not assumed to be associated with a particular position in the genome. In some embodiments, the sequence reads are associated with a plurality of positions in the genome, and an associated probability belonging to that position.

Counting Method to Determine Chromosome Copy Number

In one aspect, the invention features methods of testing for an abnormal distribution of a fetal chromosome by comparing the number of sequence tags that align to different chromosomes (see, e.g., U.S. Pat. No. 8,296,076, filed Apr. 20, 2012, which is hereby incorporated by reference in its entirety). As is known in the art, the term "sequence tag" refers to a relatively short (e.g., 15-100) nucleic acid sequence that can be used to identify a certain larger sequence, e.g., be mapped to a chromosome or genomic region or gene. In some embodiments, the method involves (i) contacting a sample that includes a mixture of maternal and fetal DNA with a library of primers that simultaneously hybridize to at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different target loci to produce a reaction mixture; wherein the target loci are from a plurality of different chromosomes; and wherein the plurality of different chromosomes comprise at least one first chromosome suspected of having an abnormal distribution in the sample and at least one second chromosome presumed to be normally distributed in the sample; (ii) subjecting the reaction mixture to primer extension reaction conditions to produce amplified products; (iii) sequencing the amplified products to obtain a plurality of sequence tags aligning to the target loci; wherein the sequence tags are of sufficient length to be assigned to a specific target locus; (iv) assigning on a computer the plurality of sequence tags to their corresponding target loci; (v) determining on a computer a number of sequence tags aligning to the target loci of the first chromosome and a number of sequence tags aligning to the target loci of the second chromosome; and (vi) comparing the numbers from step (v) to determine the presence or absence of an abnormal distribution of the first chromosome.

In one aspect, the invention provides methods for detecting the presence or absence of a fetal aneuploidy by comparing the relative frequency of target amplicons between chromosomes (see, e.g., PCT Publ. No. WO 2012/103031, filed Jan. 23, 2012, which is hereby incorporated by reference in its entirety). In some embodiments, the method involves (i) contacting a sample that includes a mixture of maternal and fetal DNA with a library of primers that simultaneously hybridize to at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different non-polymorphic target loci to produce a reaction mixture; wherein the target loci are from a plurality of different chromosomes; (ii) subjecting the reaction mixture to primer extension reaction conditions to produce amplified products that includes target amplicons; (iii) quantifying on a computer a relative frequency of the target amplicons from the first and second chromosomes of interest; (iv) comparing on a computer the relative frequency of the target amplicons from the first and second chromosomes of interest; and (v) identifying the presence or absence of an aneuploidy based on the compared relative frequencies of the first and second chromosome of interest. In some embodiments, the first chromosome is a chromosome suspected of being euploid. In some embodiments, the second chromosome is a chromosome suspected of being aneuploidy Combining Methods of Prenatal Diagnosis There are many methods that may be used for prenatal diagnosis or prenatal screening of aneuploidy or other genetic defects. Described elsewhere in this document, and in U.S. Utility application Ser. No. 11/603,406, filed Nov. 28, 2006; U.S. Utility application Ser. No. 12/076,348, filed Mar. 17, 2008, and PCT Application Serial No. PCT/S09/52730 is one such method that uses the genetic data of related individuals to increase the accuracy with which genetic data of a target individual, such as a fetus, is known, or estimated. Other methods used for prenatal diagnosis involve measuring the levels of certain hormones in maternal blood, where those hormones are correlated with various genetic abnormalities. An example of this is called the triple test, a test wherein the levels of several (commonly two, three, four or five) different hormones are measured in maternal blood. In a case where multiple methods are used to determine the likelihood of a given outcome, where none of the methods are definitive in and of themselves, it is possible to combine the information given by those methods to make a prediction that is more accurate than any of the individual methods. In the triple test, combining the information given by the three different hormones can result in a prediction of genetic abnormalities that is more accurate than the individual hormone levels may predict.

Disclosed herein is a method for making more accurate predictions about the genetic state of a fetus, specifically the possibility of genetic abnormalities in a fetus that comprises combining predictions of genetic abnormalities in a fetus where those predictions were made using a variety of methods. A "more accurate" method may refer to a method for diagnosing an abnormality that has a lower false negative rate at a given false positive rate. In a favored embodiment of the present disclosure, one or more of the predictions are made based on the genetic data known about the fetus, where the genetic knowledge was determined using the PARENTAL SUPPORT™ method, that is, using genetic data of individual related to the fetus to determine the genetic data of the fetus with greater accuracy. In some embodiments the genetic data may include ploidy states of the fetus. In some embodiments, the genetic data may refer to a set of allele calls on the genome of the fetus. In some embodiments some of the predictions may have been made using the triple test. In some embodiments, some of the predictions may have been made using measurements of other hormone levels in maternal blood. In some embodiments, predictions made by methods considered diagnoses may be combined with predictions made by methods considered screening. In some embodiments, the method involves measuring maternal blood levels of alpha-fetoprotein (AFP). In some embodiments, the method involves measuring maternal blood levels of unconjugated estriol ($UE_3$). In some embodiments, the method involves measuring maternal blood levels of beta human chorionic gonadotropin (beta-hCG). In some embodiments, the method involves measuring maternal blood levels of invasive trophoblast antigen (ITA). In some embodiments, the method involves measuring maternal blood levels of inhibin. In some embodiments, the method involves measuring maternal blood levels of pregnancy-associated plasma protein A (PAPP-A). In some embodiments, the method involves measuring maternal blood levels of other hormones or maternal serum markers. In some embodiments, some of the predictions may have been made using other methods. In some embodiments, some of the predictions may have been made using a fully integrated test such as one that combines ultrasound and blood test at around 12 weeks of pregnancy and a second blood test at around 16 weeks. In some embodiments, the method involves measuring the fetal nuchal translucency (NT). In some embodiments, the method involves using the measured levels of the aforementioned hormones for making predictions. In some embodiments the method involves a combination of the aforementioned methods.

There are many ways to combine the predictions, for example, one could convert the hormone measurements into a multiple of the median (MoM) and then into likelihood ratios (LR). Similarly, other measurements could be transformed into LRs using the mixture model of NT distributions. The LRs for NT and the biochemical markers could be multiplied by the age and gestation-related risk to derive the risk for various conditions, such as trisomy 21. Detection rates (DRs) and false-positive rates (FPRs) could be calculated by taking the proportions with risks above a given risk threshold.

In an embodiment, a method to call the ploidy state involves combining the relative probabilities of each of the ploidy hypotheses determined using the joint distribution model and the allele count probabilities with relative probabilities of each of the ploidy hypotheses that are calculated using statistical techniques taken from other methods that determine a risk score for a fetus being trisomic, including but not limited to: a read count analysis, comparing heterozygosity rates, a statistic that is only available when parental genetic information is used, the probability of normalized genotype signals for certain parent contexts, a statistic that is calculated using an estimated fetal fraction of the first sample or the prepared sample, and combinations thereof.

Another method could involve a situation with four measured hormone levels, where the probability distribution around those hormones is known: $p(x_1, x_2, x_3, x_4|e)$ for the euploid case and $p(x_1, x_2, x_3, x_4|a)$ for the aneuploid case. Then one could measure the probability distribution for the DNA measurements, $g(y|e)$ and $g(y|a)$ for the euploid and aneuploid cases respectively. Assuming they are independent given the assumption of euploid/aneuploid, one could combine as $p(x_1, x_2, x_3, x_4|a)g(y|a)$ and $p(x_1, x_2, x_3, x_4|e)g(y|e)$ and then multiply each by the prior $p(a)$ and $p(e)$ given the maternal age. One could then choose the one that is highest.

In an embodiment, it is possible to evoke central limit theorem to assume distribution on $g(y|a$ or $e)$ is Gaussian, and measure mean and standard deviation by looking at multiple samples. In another embodiment, one could assume they are not independent given the outcome and collect enough samples to estimate the joint distribution $p(x_1, x_2, x_3, x_4|a$ or $e)$.

In an embodiment, the ploidy state for the target individual is determined to be the ploidy state that is associated with the hypothesis whose probability is the greatest. In some cases, one hypothesis will have a normalized, combined probability greater than 90%. Each hypothesis is associated with one, or a set of, ploidy states, and the ploidy state associated with the hypothesis whose normalized, combined probability is greater than 90%, or some other threshold value, such as 50%, 80%, 95%, 98%, 99%, or 99.9%, may be chosen as the threshold required for a hypothesis to be called as the determined ploidy state.

DNA from Children from Previous Pregnancies in Maternal Blood

One difficulty to non-invasive prenatal diagnosis is differentiating fetal cells from the current pregnancy from fetal cells from previous pregnancies. Some believe that genetic matter from prior pregnancies will go away after some time, but conclusive evidence has not been shown. In an embodiment of the present disclosure, it is possible to determine fetal DNA present in the maternal blood of paternal origin (that is, DNA that the fetus inherited from the father) using the PARENTAL SUPPORT™ (PS) method, and the knowledge of the paternal genome. This method may utilize phased parental genetic information. It is possible to phase the parental genotype from unphased genotypic information using grandparental genetic data (such as measured genetic data from a sperm from the grandfather), or genetic data from other born children, or a sample of a miscarriage. One could also phase unphased genetic information by way of a HapMap-based phasing, or a haplotyping of paternal cells. Successful haplotyping has been demonstrated by arresting cells at phase of mitosis when chromosomes are tight bundles and using microfluidics to put separate chromosomes in separate wells. In another embodiment it is possible to use the phased parental haplotypic data to detect the presence of more than one homolog from the father, implying that the genetic material from more than one child is present in the blood. By focusing on chromosomes that are expected to be euploid in a fetus, one could rule out the possibility that the fetus was afflicted with a trisomy. Also, it is possible to determine if the fetal DNA is not from the current father, in which case one could use other methods such as the triple test to predict genetic abnormalities.

There may be other sources of fetal genetic material available via methods other than a blood draw. In the case of the fetal genetic material available in maternal blood, there are two main categories: (1) whole fetal cells, for example, nucleated fetal red blood cells or erythroblats, and (2) free floating fetal DNA. In the case of whole fetal cells, there is some evidence that fetal cells can persist in maternal blood for an extended period of time such that it is possible to isolate a cell from a pregnant woman that contains the DNA from a child or fetus from a prior pregnancy. There is also evidence that the free floating fetal DNA is cleared from the system in a matter of weeks. One challenge is how to determine the identity of the individual whose genetic material is contained in the cell, namely to ensure that the measured genetic material is not from a fetus from a prior pregnancy. In an embodiment of the present disclosure, the knowledge of the maternal genetic material can be used to ensure that the genetic material in question is not maternal genetic material. There are a number of methods to accomplish this end, including informatics based methods such as PARENTAL SUPPORT™, as described in this document or any of the patents referenced in this document.

In an embodiment of the present disclosure, the blood drawn from the pregnant mother may be separated into a fraction comprising free floating fetal DNA, and a fraction comprising nucleated red blood cells. The free floating DNA may optionally be enriched, and the genotypic information of the DNA may be measured. From the measured genotypic information from the free floating DNA, the knowledge of the maternal genotype may be used to determine aspects of the fetal genotype. These aspects may refer to ploidy state, and/or a set of allele identities. Then, individual nucleated red blood cells may be genotyped using methods described elsewhere in this document, and other referent patents, especially those mentioned in the first section of this document. The knowledge of the maternal genome would allow one to determine whether or not any given single blood cell is genetically maternal. And the aspects of the fetal genotype that were determined as described above would allow one to determine if the single blood cell is genetically derived from the fetus that is currently gestating. In essence, this aspect of the present disclosure allows one to use the genetic knowledge of the mother, and possibly the genetic information from other related individuals, such as the father, along with the measured genetic information from the free floating DNA found in maternal blood to determine whether an isolated nucleated cell found in maternal blood is either (a) genetically maternal, (b) genetically from the fetus currently gestating, or (c) genetically from a fetus from a prior pregnancy.

Prenatal Sex Chromosome Aneuploidy Determination

In methods known in the art, people attempting to determine the sex of a gestating fetus from the blood of the mother have used the fact that fetal free floating DNA (fffDNA) is present in the plasma of the mother. If one is able to detect Y-specific loci in the maternal plasma, this implies that the gestating fetus is a male. However, the lack of detection of Y-specific loci in the plasma does not always guarantee that the gestating fetus is a female when using methods known in the art, as in some cases the amount of fffDNA is too low to ensure that the Y-specific loci would be detected in the case of a male fetus.

Presented here is a novel method that does not require the measurement of Y-specific nucleic acids, that is, DNA that is from loci that are exclusively paternally derived. The Parental Support method, disclosed previously, uses crossover frequency data, parental genotypic data, and informatics techniques, to determine the ploidy state of a gestating fetus. The sex of a fetus is simply the ploidy state of the fetus at the sex chromosomes. A child that is XX is female, and XY is male. The method described herein is also able to determine the ploidy state of the fetus. Note that sexing is effectively synonymous with ploidy determination of the sex chromosomes; in the case of sexing, an assumption is often made that the child is euploid, therefore there are fewer possible hypotheses.

The method disclosed herein involves looking at loci that are common to both the X and Y chromosome to create a baseline in terms of expected amount of fetal DNA present for a fetus. Then, those regions that are specific only to the X chromosome can be interrogated to determine if the fetus is female or male. In the case of a male, we expect to see less fetal DNA from loci that are specific to the X chromosome than from loci that are specific to both the X and the Y. In contrast, in female fetuses, we expect the amount of DNA for each of these groups to be the same. The DNA in question can be measured by any technique that can quantitate the amount of DNA present on a sample, for example, qPCR, SNP arrays, genotyping arrays, or sequencing. For DNA that is exclusively from an individual we would expect to see the following:

|  | DNA specific to X | DNA specific to X and Y | DNA specific to Y |
|---|---|---|---|
| Male (XY) | A | 2A | A |
| Female (XX) | 2A | 2A | 0 |

In the case of DNA from a fetus that is mixed with DNA from the mother, and where the fraction of fetal DNA in the mixture is F, and where the fraction of maternal DNA in the mixture is M, such that F+M=100%, we would expect to see the following:

|  | DNA specific to X | DNA specific to X and Y | DNA specific to Y |
|---|---|---|---|
| Male fetus (XY) | M + ½ F | M + F | ½ F |
| Female fetus (XX) | M + F | M + F | 0 |

In the case where F and M are known, the expected ratios can be computed, and the observed data can be compared to the expected data. In the case where M and F are not known, a threshold can be selected based on historical data. In both cases, the measured amount of DNA at loci specific to both X and Y can be used as a baseline, and the test for the sex of the fetus can be based on the amount of DNA observed on loci specific to only the X chromosome. If that amount is lower than the baseline by an amount roughly equal to ½ F, or by an amount that causes it to fall below a predefined threshold, the fetus is determined to be male, and if that amount is about equal to the baseline, or if is not lower by an amount that causes it to fall below a predefined threshold, the fetus is determined to be female.

In another embodiment, one can look only at those loci that are common to both the X and the Y chromosomes, often termed the Z chromosome. A subset of the loci on the Z chromosome are typically always A on the X chromosome, and B on the Y chromosome. If SNPs from the Z chromosome are found to have the B genotype, then the fetus is called a male; if the SNPs from the Z chromosome are found to only have A genotype, then the fetus is called a female. In another embodiment, one can look at the loci that are found only on the X chromosome. Contexts such as AA|B are particularly informative as the presence of a B indicates that the fetus has an X chromosome from the father. Contexts such as AB|B are also informative, as we expect to see B present only half as often in the case of a female fetus as compared to a male fetus. In another embodiment, one can look at the SNPs on the Z chromosome where both A and B alleles are present on both the X and the Y chromosome, and where the it is known which SNPs are from the paternal Y chromosome, and which are from the paternal X chromosome.

In an embodiment, it is possible to amplify single nucleotide positions known to varying between the homologous non-recombining (HNR) region shared by chromosome Y and chromosome X. The sequence within this HNR region is largely identical between the X and Y chromosomes. Within this identical region are single nucleotide positions that, while invariant among X chromosomes and among Y chromosomes in the population, are different between the X and Y chromosomes. Each PCR assay could amplify a sequence from loci that are present on both the X and Y chromosomes. Within each amplified sequence would be a single base that can be detected using sequencing or some other method (see, for example, U.S. Publication No. 2011/0178719, filed Feb. 3, 2011, which is hereby incorporated by reference in its entirety).

In an embodiment, the sex of the fetus could be determined from the fetal free floating DNA found in maternal plasma, the method comprising some or all of the following steps: 1) Design PCR (either regular or mini-PCR, plus multiplexing if desired) primers amplify X/Y variant single nucleotide positions within HNR region, 2) obtain maternal plasma, 3) PCR Amplify targets from maternal plasma using HNR X/Y PCR assays, 4) sequence the amplicons, 5) Examine sequence data for presence of Y-allele within one or more of the amplified sequences. The presence of one or more would indicate a male fetus. Absence of all Y-alleles from all amplicons indicates a female fetus.

In an embodiment, one could use targeted sequencing to measure the DNA in the maternal plasma and/or the parental genotypes. In an embodiment, one could ignore all sequences that clearly originate from paternally sourced DNA. For example, in the context AA|AB, one could count the number of A sequences and ignore all the B sequences. In order to determine a heterozygosity rate for the above algorithm, one could compare the number of observed A sequences to the expected number of total sequences for the given probe. There are many ways one could calculate an expected number of sequences for each probe on a per sample basis. In an embodiment, it is possible to use historical data to determine what fraction of all sequence reads belongs to each specific probe and then use this empirical fraction, combined with the total number of sequence reads, to estimate the number of sequences at each probe. Another approach could be to target some known homozygous alleles and then use historical data to relate the number of reads at each probe with the number of reads at the known homozygous alleles. For each sample, one could then measure the number of reads at the homozygous alleles and then use this measurement, along with the empirically derived relationships, to estimate the number of sequence reads at each probe.

In some embodiments, it is possible to determine the sex of the fetus by combining the predictions made by a plurality of methods. In some embodiments the plurality of methods are taken from methods described in this disclosure. In some embodiments, at least one of the plurality of methods are taken from methods described in this disclosure.

In some embodiments the method described herein can be used to determine the ploidy state of the gestating fetus. In an embodiment, the ploidy calling method uses loci that are specific to the X chromosome, or common to both the X and Y chromosome, but does not make use of any Y-specific loci. In an embodiment, the ploidy calling method uses one or more of the following: loci that are specific to the X chromosome, loci that are common to both the X and Y chromosome, and loci that are specific to the Y chromosome. In an embodiment, where the ratios of sex chromosomes are similar, for example 45,X (Turner Syndrome), 46,XX (normal female) and 47,XXX (trisomy X), the differentiation can be accomplished by comparing the allele distributions to expected allele distributions according to the various hypotheses. In another embodiment, this can be accomplished by comparing the relative number of sequence reads for the sex chromosomes to one or a plurality of reference chromosomes that are assumed to be euploid. Also note that these methods can be expanded to include aneuploid cases.

Single Gene Disease Screening

In an embodiment, a method for determining the ploidy state of the fetus may be extended to enable simultaneous testing for single gene disorders. Single-gene disease diagnosis leverages the same targeted approach used for aneuploidy testing, and requires additional specific targets. In an embodiment, the single gene NPD diagnosis is through linkage analysis. In many cases, direct testing of the cfDNA sample is not reliable, as the presence of maternal DNA makes it virtually impossible to determine if the fetus has inherited the mother's mutation. Detection of a unique paternally-derived allele is less challenging, but is only fully informative if the disease is dominant and carried by the father, limiting the utility of the approach. In an embodiment, the method involves PCR or related amplification approaches.

In some embodiments, the method involves phasing the abnormal allele with surrounding very tightly linked SNPs in the parents using information from first-degree relatives. Then Parental Support may be run on the targeted sequencing data obtained from these SNPs to determine which homologs, normal or abnormal, were inherited by the fetus from both parents. As long as the SNPs are sufficiently linked, the inheritance of the genotype of the fetus can be determined very reliably. In some embodiments, the method comprises (a) adding a set of SNP loci to densely flank a specified set of common diseases to our multiplex pool for aneuploidy testing; (b) reliably phasing the alleles from these added SNPs with the normal and abnormal alleles based on genetic data from various relatives; and (c) reconstructing the fetal haplotype, or set of phased SNP alleles on the inherited maternal and paternal homologs in the region surrounding the disease locus to determine fetal genotype. In some embodiments additional probes that are closely linked to a disease linked locus are added to the set of polymorphic locus being used for aneuploidy testing.

Reconstructing fetal diplotype is challenging because the sample is a mixture of maternal and fetal DNA. In some embodiments, the method incorporates relative information to phase the SNPs and disease alleles, then take into account physical distance of the SNPs and recombination data from location specific recombination likelihoods and the data observed from the genetic measurements of the maternal plasma to obtain the most likely genotype of the fetus.

In an embodiment, a number of additional probes per disease linked locus are included in the set of targeted polymorphic loci; the number of additional probes per disease linked locus may be between 4 and 10, between 11 and 20, between 21 and 40, between 41 and 60, between 61 and 80, or combinations thereof.

Phasing the diploid data from the parents can be challenging, and there are a number of ways this can be accomplished. Some are discussed in this disclosure, others are described in greater detail in other disclosures (see, e.g., PCT Publ. No. WO2009105531, filed Feb. 9, 2009, and PCT Publ. No. WO2010017214, filed Aug. 4, 2009, which are each hereby incorporated by reference in its entirety). In one embodiment, a parent can be phased by inference by measuring tissue from the parent that is haploid, for example by measuring one or more sperm or eggs. In one embodiment the parent can be phased by inference using the measured genotypic data of a first degree relative such as the parent's parent(s) or siblings. In one embodiment, the parent can be phased by dilution where the DNA is diluted, in one or a plurality of wells, to the point where there is expected to be no more than approximately one copy of each haplotype in each well, and then measuring the DNA in the one or more wells. In one embodiment, the parent genotype can be phased by using computer programs that use population based haplotype frequencies to infer the most likely phase. In one embodiment, the parent can be phased if the phased haplotypic data is known for the other parent, along with the unphased genetic data of one or more genetic offspring of the parents. In some embodiments, the genetic offspring of the parents may be one or more embryos, fetuses, and/or born children. Some of these methods and other methods for phasing one or both parents are disclosed in greater detail in, e.g., U.S. Publ. No. 2011/0033862, filed Aug. 19, 2010; U.S. Publ. No. 2011/0178719, filed Feb. 3, 2011; U.S. Publ. No. 2007/0184467, filed Nov. 22, 2006; U.S. Publ. No. 2008/0243398, filed Mar. 17, 2008, which are each hereby incorporated by reference in its entirety.

Fetal Genome Reconstruction

In one aspect, the invention features methods for determining a haplotype of a fetus. In various embodiments, this method allows one to determine which polymorphic loci (such as SNPs) were inherited by the fetus and to reconstruct which homologs (including recombination events) are present in the fetus (and thereby interpolate the sequence between the polymorphic loci). If desired, essentially the entire genome of the fetus can be reconstructed. If there is some remaining ambiguity in the genome of the fetus (such as in intervals with a crossover), this ambiguity can be minimized if desired by analyzing additional polymorphic loci. In various embodiments, the polymorphic loci are chosen to cover one or more of the chromosomes at a density to reduce any ambiguity to a desired level. This method has important applications for the detection of polymorphisms or other mutations of interest in a fetus since it enables their detection based on linkage (such as the presence of linked polymorphic loci in the fetal genome) rather than by directing detecting the polymorphism or other mutation of interest in the fetal genome. For example, if a parent is a carrier for a mutation associated with cystic fibrosis (CF), a nucleic acid sample that includes maternal DNA from the mother of the fetus and fetal DNA from the fetus can be analyzed to determine whether the fetal DNA include the haplotype containing the CF mutation. In particular, polymorphic loci can be analyzed to determine whether the fetal DNA includes the haplotype containing the CF mutation without having to detect the CF mutation itself in the fetal DNA.

This is useful in screening for one or more mutations, such as disease-linked mutations, without having to directly detect the mutations.

In some embodiments, the method involves determining a parental haplotype (e.g., a haplotype of the mother or father of the fetus). In some embodiments, this determination is made without using data from a relative of the mother or father. In some embodiments, a parental haplotype is determined using a dilution approach followed by SNP genotyping or sequencing as described herein and elsewhere (see, e.g., U.S. Publ. No. 2011/0033862, filed Aug. 19, 2010, which is hereby incorporated by reference in its entirety). Because the DNA is diluted, it is unlikely that more than one haplotype is in the same fraction (or tube). Thus, there may be effectively a single molecule of DNA in the tube, which allows the haplotype on a single DNA molecule to be determined. In some embodiments, the method includes dividing a DNA sample into a plurality of fractions such that at least one of the fractions includes one chromosome or one chromosome segment from a pair of chromosomes, and genotyping (e.g., determining the presence of two or more polymorphic loci) the DNA sample in at least one of the fractions, thereby determining a parental haplotype. In some embodiments, the genotyping involves sequencing (such as shotgun sequencing). In some embodiments, the genotyping involves use of a SNP array to detect polymorphic loci, such as at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different polymorphic loci. In some embodiments, the genotyping involves the use of multiplex PCR. In some embodiments, the method involves contacting the sample in a fraction with a library of primers that simultaneously hybridize to at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different polymorphic loci (such as SNPs) to produce a reaction mixture; and subjecting the reaction mixture to primer extension reaction conditions to produce amplified products that are measured with a high throughput sequencer to produce sequencing data.

In some embodiments, a haplotype of the mother is determined by any of the methods described herein using data from a relative of the mother. In some embodiments, a haplotype of the father is determined by any of the methods described herein using data from a relative of the father. In some embodiments, a haplotype is determined for both the father and the mother. In some embodiments, a SNP array is used to determine the presence of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different polymorphic loci in a DNA sample from the mother (or father) and a relative of the mother (or father). In some embodiments, the method involves contacting a DNA sample from the mother (or father) and/or a relative of the mother (or father) with a library of primers that simultaneously hybridize to at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different polymorphic loci (such as SNPs) to produce a reaction mixture; and subjecting the reaction mixture to primer extension reaction conditions to produce amplified products that are measured with a high throughput sequencer to produce sequencing data. The parental haplotype may be determined based on the SNP array or sequencing data. In some embodiments, parental data may be phased by methods described or referred to elsewhere in this document.

This parental haplotype data can be used to determine if the fetus inherited the parental haplotype. In some embodiments, a nucleic acid sample that includes maternal DNA from the mother of the fetus and fetal DNA from the fetus is analyzed using a SNP array to detect at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different polymorphic loci. In some embodiments, a nucleic acid sample that includes maternal DNA from the mother of the fetus and fetal DNA from the fetus is analyzed by contacting the sample with a library of primers that simultaneously hybridize to at least 25; 50; 75; 100; 300; 500; 750; 1,000; 2,000;

5,000; 7,500; 10,000; 15,000; 19,000; 20,000; 25,000; 27,000; 28,000; 30,000; 40,000; 50,000; 75,000; or 100,000 different polymorphic loci (such as SNPs) to produce a reaction mixture. In some embodiments, the reaction mixture is subjected to primer extension reaction conditions to produce amplified products. In some embodiments, the amplified products are measured with a high throughput sequencer to produce sequencing data. In various embodiments, the SNP array or sequencing data is used to determine a parental haplotype by using data about the probability of chromosomes crossing over at different locations in a chromosome (such as by using recombination data such as may be found in the HapMap database to create a recombination risk score for any interval) to model dependence between polymorphic alleles on the chromosome. In some embodiments, allele counts at the polymorphic loci are calculated on a computer based on the sequencing data. In some embodiments, a plurality of ploidy hypotheses each pertaining to a different possible ploidy state of the chromosome are created on a computer; a model (such as a joint distribution model) for the expected allele counts at the polymorphic loci on the chromosome is built on a computer for each ploidy hypothesis; a relative probability of each of the ploidy hypotheses is determined on a computer using the joint distribution model and the allele counts; and the ploidy state of the fetus is called by selecting the ploidy state corresponding to the hypothesis with the greatest probability. In some embodiments, building a joint distribution model for allele counts and the step of determining the relative probability of each hypothesis are done using a method that does not require the use of a reference chromosome.

In some embodiments, a fetal haplotype is determined for one or more chromosomes taken from the group consisting of chromosomes 13, 18, 21, X, and Y. In some embodiments, a fetal haplotype is determined for all of the fetal chromosomes. In various embodiments, the method determines essentially the entire genome of the fetus. In some embodiments, the haplotype is determined for at least 30, 40, 50, 60, 70, 80, 90, or 95% of the genome of the fetus. In some embodiments, the haplotype determination of the fetus includes information about which allele is present for at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; or 100,000 different polymorphic loci.

Compositions of DNA

When performing an informatics analysis on sequencing data measured on a mixture of fetal and maternal blood to determine genomic information pertaining to the fetus, for example the ploidy state of the fetus, it may be advantageous to measure the allele distributions at a set of alleles. Unfortunately, in many cases, such as when attempting to determine the ploidy state of a fetus from the DNA mixture found in the plasma of a maternal blood sample, the amount of DNA available is not sufficient to directly measure the allele distributions with good fidelity in the mixture. In these cases, amplification of the DNA mixture will provide sufficient numbers of DNA molecules that the desired allele distributions may be measured with good fidelity. However, current methods of amplification typically used in the amplification of DNA for sequencing are often very biased, meaning that they do not amplify both alleles at a polymorphic locus by the same amount. A biased amplification can result in allele distributions that are quite different from the allele distributions in the original mixture. For most purposes, highly accurate measurements of the relative amounts of alleles present at polymorphic loci are not needed. In contrast, in an embodiment of the present disclosure, amplification or enrichment methods that specifically enrich polymorphic alleles and preserve allelic ratios is advantageous.

A number of methods are described herein that may be used to preferentially enrich a sample of DNA at a plurality of loci in a way that minimizes allelic bias. Some examples are using circularizing probes to target a plurality of loci where the 3' ends and 5' ends of the pre-circularized probe are designed to hybridize to bases that are one or a few positions away from the polymorphic sites of the targeted allele. Another is to use PCR probes where the 3' end PCR probe is designed to hybridize to bases that are one or a few positions away from the polymorphic sites of the targeted allele. Another is to use a split and pool approach to create mixtures of DNA where the preferentially enriched loci are enriched with low allelic bias without the drawbacks of direct multiplexing. Another is to use a hybrid capture approach where the capture probes are designed such that the region of the capture probe that is designed to hybridize to the DNA flanking the polymorphic site of the target is separated from the polymorphic site by one or a small number of bases.

In the case where measured allele distributions at a set of polymorphic loci are used to determine the ploidy state of an individual, it is desirable to preserve the relative amounts of alleles in a sample of DNA as it is prepared for genetic measurements. This preparation may involve WGA amplification, targeted amplification, selective enrichment techniques, hybrid capture techniques, circularizing probes or other methods meant to amplify the amount of DNA and/or selectively enhance the presence of molecules of DNA that correspond to certain alleles.

In some embodiments of the present disclosure, there is a set of DNA probes designed to target loci where the loci have maximal minor allele frequencies. In some embodiments of the present disclosure, there is a set of probes that are designed to target where the loci have the maximum likelihood of the fetus having a highly informative SNP at those loci. In some embodiments of the present disclosure, there is a set of probes that are designed to target loci where the probes are optimized for a given population subgroup. In some embodiments of the present disclosure, there is a set of probes that are designed to target loci where the probes are optimized for a given mix of population subgroups. In some embodiments of the present disclosure, there is a set of probes that are designed to target loci where the probes are optimized for a given pair of parents which are from different population subgroups that have different minor allele frequency profiles. In some embodiments of the present disclosure, there is a circularized strand of DNA that comprises at least one base pair that annealed to a piece of DNA that is of fetal origin. In some embodiments of the present disclosure, there is a circularized strand of DNA that comprises at least one base pair that annealed to a piece of DNA that is of placental origin. In some embodiments of the present disclosure, there is a circularized strand of DNA that circularized while at least some of the nucleotides were annealed to DNA that was of fetal origin. In some embodiments of the present disclosure, there is a circularized strand of DNA that circularized while at least some of the nucleotides were annealed to DNA that was of placental origin. In some embodiments of the present disclosure, there is a set of probes wherein some of the probes target single tandem repeats, and some of the probes target single nucleotide polymorphisms. In some embodiments, the loci are selected for the purpose of non-invasive prenatal diagnosis. In some embodiments, the probes are used for the purpose of noninvasive prenatal diagnosis. In some embodiments, the loci are targeted using a method that could include circularizing probes, MIPs, capture by hybridization probes, probes on a SNP array, or combinations thereof. In some embodiments, the probes are used as circularizing probes, MIPs, capture by hybridization probes, probes on a SNP array, or combinations thereof. In some embodiments, the loci are sequenced for the purpose of non-invasive prenatal diagnosis.

In the case where the relative informativeness of a sequence is greater when combined with relevant parent contexts, it follows that maximizing the number of sequence reads that contain a SNP for which the parental context is known may maximize the informativeness of the set of sequencing reads on the mixed sample. In an embodiment, the number of sequence reads that contain a SNP for which the parent contexts are known may be enhanced by using qPCR to preferentially amplify specific sequences. In an embodiment, the number of sequence reads that contain a SNP for which the parent contexts are known may be enhanced by using circularizing probes (for example, MIPs) to preferentially amplify specific sequences. In an embodiment, the number of sequence reads that contain a SNP for which the parent contexts are known may be enhanced by using a capture by hybridization method (for example SURESELECT) to preferentially amplify specific sequences. Different methods may be used to enhance the number of sequence reads that contain a SNP for which the parent contexts are known. In an embodiment, the targeting may be accomplished by extension ligation, ligation without extension, capture by hybridization, or PCR.

In a sample of fragmented genomic DNA, a fraction of the DNA sequences map uniquely to individual chromosomes; other DNA sequences may be found on different chromosomes. Note that DNA found in plasma, whether maternal or fetal in origin is typically fragmented, often at lengths under 500 bp. In a typical genomic sample, roughly 3.3% of the mappable sequences will map to chromosome 13; 2.2% of the mappable sequences will map to chromosome 18; 1.35% of the mappable sequences will map to chromosome 21; 4.5% of the mappable sequences will map to chromosome X in a female; 2.25% of the mappable sequences will map to chromosome X (in a male); and 0.73% of the mappable sequences will map to chromosome Y (in a male). These are the chromosomes that are most likely to be aneuploid in a fetus. Also, among short sequences, approximately 1 in 20 sequences will contain a SNP, using the SNPs contained on dbSNP. The proportion may well be higher given that there may be many SNPs that have not been discovered.

In an embodiment of the present disclosure, targeting methods may be used to enhance the fraction of DNA in a sample of DNA that map to a given chromosome such that the fraction significantly exceeds the percentages listed above that are typical for genomic samples. In an embodiment of the present disclosure, targeting methods may be used to enhance the fraction of DNA in a sample of DNA such that the percentage of sequences that contain a SNP are significantly greater than what may be found in typical for genomic samples. In an embodiment of the present disclosure, targeting methods may be used to target DNA from a chromosome or from a set of SNPs in a mixture of maternal and fetal DNA for the purposes of prenatal diagnosis.

Note that a method has been reported (U.S. Pat. No. 7,888,017) for determining fetal aneuploidy by counting the number of reads that map to a suspect chromosome and comparing it to the number of reads that map to a reference chromosome, and using the assumption that an overabundance of reads on the suspect chromosome corresponds to a triploidy in the fetus at that chromosome. Those methods for prenatal diagnosis would not make use of targeting of any sort, nor do they describe the use of targeting for prenatal diagnosis.

By making use of targeting approaches in sequencing the mixed sample, it may be possible to achieve a certain level of accuracy with fewer sequence reads. The accuracy may refer to sensitivity, it may refer to specificity, or it may refer to some combination thereof. The desired level of accuracy may be between 90% and 95%; it may be between 95% and 98%; it may be between 98% and 99%; it may be between 99% and 99.5%; it may be between 99.5% and 99.9%; it may be between 99.9% and 99.99%; it may be between 99.99% and 99.999%, it may be between 99.999% and 100%. Levels of accuracy above 95% may be referred to as high accuracy.

There are a number of published methods in the prior art that demonstrate how one may determine the ploidy state of a fetus from a mixed sample of maternal and fetal DNA, for example: G. J. W. Liao et al. Clinical Chemistry 2011; 57(1) pp. 92-101. These methods focus on thousands of locations along each chromosome. The number of locations along a chromosome that may be targeted while still resulting in a high accuracy ploidy determination on a fetus, for a given number of sequence reads, from a mixed sample of DNA is unexpectedly low. In an embodiment of the present disclosure, an accurate ploidy determination may be made by using targeted sequencing, using any method of targeting, for example qPCR, ligand mediated PCR, other PCR methods, capture by hybridization, or circularizing probes, wherein the number of loci along a chromosome that need to be targeted may be between 5,000 and 2,000 loci; it may be between 2,000 and 1,000 loci; it may be between 1,000 and 500 loci; it may be between 500 and 300 loci; it may be between 300 and 200 loci; it may be between 200 and 150 loci; it may be between 150 and 100 loci; it may be between 100 and 50 loci; it may be between 50 and 20 loci; it may be between 20 and 10 loci. Optimally, it may be between 100 and 500 loci. The high level of accuracy may be achieved by targeting a small number of loci and executing an unexpectedly small number of sequence reads. The number of reads may be between 100 million and 50 million reads; the number of reads may be between 50 million and 20 million reads; the number of reads may be between 20 million and 10 million reads; the number of reads may be between 10 million and 5 million reads; the number of reads may be between 5 million and 2 million reads; the number of reads may be between 2 million and 1 million; the number of reads may be between 1 million and 500,000; the number of reads may be between 500,000 and 200,000; the number of reads may be between 200,000 and 100,000; the number of reads may be between 100,000 and 50,000; the number of reads may be between 50,000 and 20,000; the number of reads may be between 20,000 and 10,000; the number of reads may be below 10,000. Fewer number of read are necessary for larger amounts of input DNA.

In some embodiments, there is a composition comprising a mixture of DNA of fetal origin, and DNA of maternal origin, wherein the percent of sequences that uniquely map to chromosome 13 is greater than 4%, greater than 5%, greater than 6%, greater than 7%, greater than 8%, greater than 9%, greater than 10%, greater than 12%, greater than 15%, greater than 20%, greater than 25%, or greater than 30%. In some embodiments of the present disclosure, there is a composition comprising a mixture of DNA of fetal origin, and DNA of maternal origin, wherein the percent of sequences that uniquely map to chromosome 18 is greater than 3%, greater than 4%, greater than 5%, greater than 6%, greater than 7%, greater than 8%, greater than 9%, greater than 10%, greater than 12%, greater than 15%, greater than 20%, greater than 25%, or greater than 30%. In some embodiments of the present disclosure, there is a composition comprising a mixture of DNA of fetal origin, and DNA of maternal origin, wherein the percent of sequences that uniquely map to chromosome 21 is greater than 2%, greater than 3%, greater than 4%, greater than 5%, greater than 6%, greater than 7%, greater than 8%, greater than 9%, greater than 10%, greater than 12%, greater than 15%, greater than 20%, greater than 25%, or greater than 30%. In some embodiments of the present disclosure, there is a composition comprising a mixture of DNA of fetal origin, and DNA of maternal origin, wherein the percent of sequences that uniquely map to chromosome X is greater than 6%, greater than 7%, greater than 8%, greater than 9%, greater than 10%, greater than 12%, greater than 15%, greater than 20%, greater than 25%, or greater than 30%. In some embodiments of the present disclosure, there is a composition comprising a mixture of DNA of fetal origin, and DNA of maternal origin, wherein the percent of sequences that uniquely map to chromosome Y is greater than 1%, greater than 2%, greater than 3%, greater than 4%, greater than 5%, greater than 6%, greater than 7%, greater than 8%, greater than 9%, greater than 10%, greater than 12%, greater than 15%, greater than 20%, greater than 25%, or greater than 30%.

In some embodiments, a composition is described comprising a mixture of DNA of fetal origin, and DNA of maternal origin, wherein the percent of sequences that uniquely map to a chromosome, and that contains at least one single nucleotide polymorphism is greater than 0.2%, greater than 0.3%, greater than 0.4%, greater than 0.5%, greater than 0.6%, greater than 0.7%, greater than 0.8%, greater than 0.9%, greater than 1%, greater than 1.2%, greater than 1.4%, greater than 1.6%, greater than 1.8%, greater than 2%, greater than 2.5%, greater than 3%, greater than 4%, greater than 5%, greater than 6%, greater than 7%, greater than 8%, greater than 9%, greater than 10%, greater than 12%, greater than 15%, or greater than 20%, and where the chromosome is taken from the group 13, 18, 21, X, or Y. In some embodiments of the present disclosure, there is a composition comprising a mixture of DNA of fetal origin, and DNA of maternal origin, wherein the percent of sequences that uniquely map to a chromosome and that contain at least one single nucleotide polymorphism from a set of single nucleotide polymorphisms is greater than 0.15%, greater than 0.2%, greater than 0.3%, greater than 0.4%, greater than 0.5%, greater than 0.6%, greater than 0.7%, greater than 0.8%, greater than 0.9%, greater than 1%, greater than 1.2%, greater than 1.4%, greater than 1.6%, greater than 1.8%, greater than 2%, greater than 2.5%, greater than 3%, greater than 4%, greater than 5%, greater than 6%, greater than 7%, greater than 8%, greater than 9%, greater than 10%, greater than 12%, greater than 15%, or greater than 20%, where the chromosome is taken from the set of chromosome 13, 18, 21, X and Y, and where the number of single nucleotide polymorphisms in the set of single nucleotide polymorphisms is between 1 and 10, between 10 and 20, between 20 and 50, between 50 and 100, between 100 and 200, between 200 and 500, between 500 and 1,000, between 1,000 and 2,000, between 2,000 and 5,000, between 5,000 and 10,000, between 10,000 and 20,000, between 20,000 and 50,000, and between 50,000 and 100,000.

In theory, each cycle in the amplification doubles the amount of DNA present; however, in reality, the degree of amplification is slightly lower than two. In theory, amplification, including targeted amplification, will result in bias free amplification of a DNA mixture; in reality, however, different alleles tend to be amplified to a different extent than other alleles. When DNA is amplified, the degree of allelic bias typically increases with the number of amplification steps. In some embodiments, the methods described herein involve amplifying DNA with a low level of allelic bias. Since the allelic bias compounds with each additional cycle, one can determine the per cycle allelic bias by calculating the nth root of the overall bias where n is the base 2 logarithm of degree of enrichment. In some embodiments, there is a composition comprising a second mixture of DNA, where the second mixture of DNA has been preferentially enriched at a plurality of polymorphic loci from a first mixture of DNA where the degree of enrichment is at least 10, at least 100, at least 1,000, at least 10,000, at least 100,000 or at least 1,000,000, and where the ratio of the alleles in the second mixture of DNA at each locus differs from the ratio of the alleles at that locus in the first mixture of DNA by a factor that is, on average, less than 1,000%, 500%, 200%, 100%, 50%, 20%, 10%, 5%, 2%, 1%, 0.5%, 0.2%, 0.1%, 0.05%, 0.02%, or 0.01%. In some embodiments, there is a composition comprising a second mixture of DNA, where the second mixture of DNA has been preferentially enriched at a plurality of polymorphic loci from a first mixture of DNA where the per cycle allelic bias for the plurality of polymorphic loci is, on average, less than 10%, 5%, 2%, 1%, 0.5%, 0.2%, 0.1%, 0.05%, or 0.02%. In some embodiments, the plurality of polymorphic loci comprises at least 10 loci, at least 20 loci, at least 50 loci, at least 100 loci, at least 200 loci, at least 500 loci, at least 1,000 loci, at least 2,000 loci, at least 5,000 loci, at least 10,000 loci, at least 20,000 loci, or at least 50,000 loci.

Some Embodiments

In some embodiments, a method is disclosed herein for generating a report disclosing the determined ploidy status of a chromosome in a gestating fetus, the method comprising: obtaining a first sample that contains DNA from the mother of the fetus and DNA from the fetus; obtaining genotypic data from one or both parents of the fetus; preparing the first sample by isolating the DNA so as to obtain a prepared sample; measuring the DNA in the prepared sample at a plurality of polymorphic loci; calculating, on a computer, allele counts or allele count probabilities at the plurality of polymorphic loci from the DNA measurements made on the prepared sample; creating, on a computer, a plurality of ploidy hypotheses concerning expected allele count probabilities at the plurality of polymorphic loci on the chromosome for different possible ploidy states of the chromosome; building, on a computer, a joint distribution model for allele count probability of each polymorphic locus on the chromosome for each ploidy hypothesis using genotypic data from the one or both parents of the fetus; determining, on a computer, a relative probability of each of the ploidy hypotheses using the joint distribution model and the allele count probabilities calculated for the prepared sample; calling the ploidy state of the fetus by selecting the ploidy state corresponding to the hypothesis with the greatest probability; and generating a report disclosing the determined ploidy status.

In some embodiments, the method is used to determine the ploidy state of a plurality of gestating fetuses in a plurality of respective mothers, the method further comprising: determining the percent of DNA that is of fetal origin in each of the prepared samples; and wherein the step of measuring the DNA in the prepared sample is done by sequencing a number of DNA molecules in each of the prepared samples, where more molecules of DNA are sequenced from those prepared samples that have a smaller fraction of fetal DNA than those prepared samples that have a larger fraction of fetal DNA.

In some embodiments, the method is used to determine the ploidy state of a plurality of gestating fetuses in a plurality of respective mothers, and where the measuring the DNA in the prepared sample is done, for each of the fetuses, by sequencing a first fraction of the prepared sample of DNA to give a first set of measurements, the method further comprising: making a first relative probability determination for each of the ploidy hypotheses for each of the fetuses, given the first set of DNA measurements; resequencing a second fraction of the prepared sample from those fetuses where the first relative probability determination for each of the ploidy hypotheses indicates that a ploidy hypothesis corresponding to an aneuploid fetus has a significant but not conclusive probability, to give a second set of measurements; making a second relative probability determination for ploidy hypotheses for the fetuses using the second set of measurements and optionally also the first set of measurements; and calling the ploidy states of the fetuses whose second sample was resequenced by selecting the ploidy state corresponding to the hypothesis with the greatest probability as determined by the second relative probability determination.

In some embodiments, a composition of matter is disclosed, the composition of matter comprising: a sample of preferentially enriched DNA, wherein the sample of preferentially enriched DNA has been preferentially enriched at a plurality of polymorphic loci from a first sample of DNA, wherein the first sample of DNA consisted of a mixture of maternal DNA and fetal DNA derived from maternal plasma, where the degree of enrichment is at least a factor of 2, and wherein the allelic bias between the first sample and the preferentially enriched sample is, on average, selected from the group consisting of less than 2%, less than 1%, less than 0.5%, less than 0.2%, less than 0.1%, less than 0.05%, less than 0.02%, and less than 0.01%. In some embodiments, a method is disclosed to create a sample of such preferentially enriched DNA.

In some embodiment, a method is disclosed for determining the presence or absence of a fetal aneuploidy in a maternal tissue sample comprising fetal and maternal genomic DNA, wherein the method comprises: (a) obtaining a mixture of fetal and maternal genomic DNA from said maternal tissue sample; (b) selectively enriching the mixture of fetal and maternal DNA at a plurality of polymorphic alleles; (c) distributing selectively enriched fragments from the mixture of fetal and maternal genomic DNA of step a to provide reaction samples comprising a single genomic DNA molecule or amplification products of a single genomic DNA molecule; (d) conducting massively parallel DNA sequencing of the selectively enriched fragments of genomic DNA in the reaction samples of step c) to determine the sequence of said selectively enriched fragments; (e) identifying the chromosomes to which the sequences obtained in step d) belong; (f) analyzing the data of step d) to determine i) the number of fragments of genomic DNA from step d) that belong to at least one first target chromosome that is presumed to be diploid in both the mother and the fetus, and ii) the number of fragments of genomic DNA from step d) that belong to a second target chromosome, wherein said second chromosome is suspected to be aneuploid in the fetus; (g) calculating an expected distribution of the number of fragments of genomic DNA from step d) for the second target chromosome if the second target chromosome is euploid, using the number determined in step f) part i); (h) calculating an expected distribution of the number of fragments of genomic DNA from step d) for the second target chromosome if the second target chromosome is aneuploid, using the first number is step f) part i) and an estimated fraction of fetal DNA found in the mixture of step b); and (i) using a maximum likelihood or maximum a posteriori approach to determine whether the number of fragments of genomic DNA determined in step f) part ii) is more likely to be part of the distribution calculated in step g) or the distribution calculated in step h); thereby indicating the presence or absence of a fetal aneuploidy.

Exemplary Cancer Diagnostic Methods

Note that it has been demonstrated that DNA that originated from cancer that is living in a host can be found in the blood of the host. In the same way that genetic diagnoses can be made from the measurement of mixed DNA found in maternal blood, genetic diagnoses can equally well be made from the measurement of mixed DNA found in host blood. The genetic diagnoses may include aneuploidy states, or gene mutations. Any claim in the instant disclosure that reads on determining the ploidy state or genetic state of a fetus from the measurements made on maternal blood can equally well read on determining the ploidy state or genetic state of a cancer from the measurements on host blood.

In some embodiments, a method of the present disclosure allows one to determine the ploidy status of a cancer, the method including obtaining a mixed sample that contains genetic material from the host, and genetic material from the cancer; measuring the DNA in the mixed sample; calculating the fraction of DNA that is of cancer origin in the mixed sample; and determining the ploidy status of the cancer using the measurements made on the mixed sample and the calculated fraction. In some embodiments, the method may further include administering a cancer therapeutic based on the determination of the ploidy state of the cancer. In some embodiments, the method may further include administering a cancer therapeutic based on the determination of the ploidy state of the cancer, wherein the cancer therapeutic is taken from the group comprising a pharmaceutical, a biologic therapeutic, and antibody based therapy and combination thereof.

Exemplary Clinical Actions

In some embodiments, any of the methods include taking a clinical action based on a result of a method of the invention (such as the determination of the presence or absence of a polymorphism or mutation, ploidy state, or paternity). In some embodiments in which an embryo or fetus has one or more one or more polymorphisms or mutations of interest (such as a CNV) based on a result of a method of the invention, the clinical action includes performing additional testing (such as testing to confirm the presence of the polymorphism or mutation), not implanting the embryo for IVF, implanting a different embryo for IVF, terminating a pregnancy, preparing for a special needs child, or undergoing an intervention designed to decrease the severity of the phenotypic presentation of a genetic disorder. In some embodiments, the clinical action is selected from the group consisting of performing an ultrasound, amniocentesis on the fetus, amniocentesis on a subsequent fetus that inherits genetic material from the mother and/or father, chorion villus biopsy on the fetus, chorion villus biopsy on a subsequent fetus that inherits genetic material from the mother and/or father, in vitro fertilization, preimplantation genetic diagnosis on one or more embryos that inherited genetic material from the mother and/or father, karyotyping on the mother, karyotyping on the father, fetal echocardiogram (such as an echocardiogram of a fetus with trisomy 21, 18, or 13, monosomy X, or a microdeletion), and combinations thereof. In some embodiments, the clinical action is selected from the group consisting of administering growth hormone to a born child with monosomy X (such as administration starting at ~9 months), administering calcium to a born child with a 22q deletion (such as DiGeorge syndrome), administering an androgen such as testosterone to a born child with 47,XXY (such as one injection per month for 3 months of 25 mg testosterone enanthate to an infant or toddler), performing a test for cancer on a woman with a complete or partial molar pregnancy (such as a triploid fetus), administering a therapy for cancer such as a chemotherapeutic agent to a woman with a complete or partial molar pregnancy (such as a triploid fetus), screening a fetus determined to be male (such as a fetus determined to be male using a method of the invention) for one or more X-linked genetic disorders such as Duchenne muscular dystrophy (DMD), adrenoleukodystrophy, or hemophilia, performing amniocentesis on a male fetus at risk for an X-linked disorder, administering dexamethasone to a women with a female fetus at risk male (such as a fetus determined to be female using a method of the invention) for congenital adrenal hyperplasia, performing amniocentesis on a female fetus at risk for congenital adrenal hyperplasia, administering killed vaccines (instead of live vaccines) or not administering certain vaccines to a born child who is (or is suspected of being) immune deficient from a 22q11.2 deletion, performing occupational and/or physical therapy, performing early intervention in education, delivering the baby at a tertiary care center with a NICU and/or having pediatric specialists available at delivery, behavioral intervention for born child (such as a child with XXX, XXY, or XYY), and combinations thereof.

In some embodiments, ultrasound or another screening test is performed on a women determined to have multiple pregnancies (such as twins) to determine whether or not two or more of the fetus are monochorionic. Monozygotic twins result from ovulation and fertilization of a single oocyte, with subsequent division of the zygote; placentation may be dichorionic or monochorionic. Dizygotic twins occur from ovulation and fertilization of two oocytes, which usually results in dichorionic placentation. Monochorionic twins have a risk of twin-to-twin transfusion syndrome, which may cause unequal distribution of blood between fetuses that results in differences in their growth and development, sometimes resulting in stillbirth. Thus, twins determined to be monozygotic twins using a method of the invention are desirably tested (such as by ultrasound) to determine if they are monochorionic twins, and if so, these twins can be monitored (such as bi-weekly ultrasounds from 16 weeks) for signs of win-to-twin transfusion syndrome.

In some embodiments in which an embryo or fetus does not have one or more one or more polymorphisms or mutations of interest (such as a CNV) based on a result of a method of the invention, the clinical action includes implanting the embryo for IVF or continuing a pregnancy. In some embodiments, the clinical action is additional testing to confirm the absence of the polymorphism or mutation selected from the group consisting of performing an ultrasound, amniocentesis, chorion villus biopsy, and combinations thereof.

In some embodiments in which an individual has one or more polymorphisms or mutations (such as a polymorphism or mutation associated with a disease or disorder such as cancer or an increased risk for a disease or disorder such as cancer) based on a result of a method of the invention, the clinical action includes performing additional testing or administering one or more therapies for a disease or disorder (such as a therapy for cancer, a therapy for the specific type of cancer or type of mutation the individual is diagnosed with, or any of the therapies disclosed herein). In some embodiments, the clinical action is additional testing to confirm the presence or absence of a polymorphism or mutation selected from the group consisting of biopsy, surgery, medical imaging (such as a mammogram or an ultrasound), and combinations thereof.

In some embodiments, the additional testing includes performing the same or a different method (such as any of the methods described herein) to confirm the presence or absence of the polymorphism or mutation (such as a CNV), such as testing either a second fraction of the same sample that was tested or a different sample from the same individual (such as the same pregnant mother, fetus, embryo, or individual at increased risk for cancer). In some embodiments, the additional testing is performed for an individual for whom the probability of a polymorphism or mutation (such as a CNV) is above a threshold value. In some embodiments, the additional testing is performed for an individual for whom the confidence or z-score for the determination of a polymorphism or mutation (such as a CNV) is above a threshold value (such as additional testing to confirm the presence of a likely polymorphism or mutation). In some embodiments, the additional testing is performed for an individual for whom the confidence or z-score for the determination of a polymorphism or mutation (such as a CNV) is between minimum and maximum threshold values (such as additional testing to increase the confidence that the initial result is correct). In some embodiments, the additional testing is performed for an individual for whom the confidence for the determination of the presence or absence of a polymorphism or mutation (such as a CNV) is below a threshold value (such as a "no call" result due to not being able to determine the presence or absence of the CNV with sufficient confidence). An exemplary Z core is calculated in Chiu et al. BMJ 2011; 342:c7401 (which is hereby incorporated by reference in its entirety) in which chromosome 21 is used as an example and can be replaced with any other chromosome or chromosome segment in the test sample.

Z score for percentage chromosome 21 in test case= ((percentage chromosome 21 in test case)−(mean percentage chromosome 21 in reference controls))/(standard deviation of percentage chromosome 21 in reference controls). In some embodiments, the additional testing is performed for an individual for whom the initial sample did not meet quality control guidelines or had a fetal fraction or a tumor fraction below a threshold value. In some embodiments, the method includes selecting an individual for additional testing based on the result of a method of the invention, the probability of the result, the confidence of the result, or the z-score; and performing the additional testing on the individual (such as on the same or a different sample). In some embodiments, a subject diagnosed with a disease or disorder (such as cancer) undergoes repeat testing using a method of the invention or known testing for the disease or disorder at multiple time points to monitor the progression of the disease or disorder or the remission or reoccurrence of the disease or disorder.

Exemplary Implementation Methods

Any of the embodiments disclosed herein may be implemented in digital electronic circuitry, integrated circuitry, specially designed ASICs (application-specific integrated circuits), computer hardware, firmware, software, or in combinations thereof. Apparatus of the presently disclosed embodiments can be implemented in a computer program product tangibly embodied in a machine-readable storage device for execution by a programmable processor; and method steps of the presently disclosed embodiments can be performed by a programmable processor executing a program of instructions to perform functions of the presently disclosed embodiments by operating on input data and generating output. The presently disclosed embodiments can be implemented advantageously in one or more computer programs that are executable and/or interpretable on a programmable system including at least one programmable processor, which may be special or general purpose, coupled to receive data and instructions from, and to transmit data and instructions to, a storage system, at least one input device, and at least one output device. Each computer program can be implemented in a high-level procedural or object-oriented programming language or in assembly or machine language if desired; and in any case, the language can be a compiled or interpreted language. A computer program may be deployed in any form, including as a stand-alone program, or as a module, component, subroutine, or other unit suitable for use in a computing environment. A computer program may be deployed to be executed or interpreted on one computer or on multiple computers at one site, or distributed across multiple sites and interconnected by a communication network.

Computer readable storage media, as used herein, refers to physical or tangible storage (as opposed to signals) and includes without limitation volatile and non-volatile, removable and non-removable media implemented in any method or technology for the tangible storage of information such as computer-readable instructions, data structures, program modules or other data. Computer readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other physical or material medium which can be used to tangibly store the desired information or data or instructions and which can be accessed by a computer or processor.

In some embodiments, the invention features a computer configured to accomplish one or more of the in vitro methods described herein. In some embodiments, the data is analyzed by the computer system as described herein. In some embodiments, genetic data (such as sequencing or microarray data) from at least 100; 200; 500; 750; 1,000; 2,000; 5,000; 7,500; 10,000; 20,000; 25,000; 30,000; 40,000; 50,000; 75,000; or 100,000 different loci is analyzed by the computer is less than 200, 100, 60, 30, 20, 10, 5, or 1 minute, or in less than 30 or 10 seconds to detect the present or absence of a mutation (such as a CNV or SNV) at the loci.

Any of the methods described herein may include the output of data in a physical format, such as on a computer screen, or on a paper printout. In explanations of any embodiments elsewhere in this document, it should be understood that the described methods may be combined with the output of the actionable data in a format that can be acted upon by a physician. In addition, the described methods may be combined with the actual execution of a clinical decision that results in a clinical treatment, or the execution of a clinical decision to make no action. Some of the embodiments described in the document for determining genetic data pertaining to a target individual may be combined with the decision to select one or more embryos for transfer in the context of IVF, optionally combined with the process of transferring the embryo to the womb of the prospective mother. Some of the embodiments described in the document for determining genetic data pertaining to a target individual may be combined with the notification of a potential chromosomal abnormality, or lack thereof, with a medical professional, optionally combined with the decision to abort, or to not abort, a fetus in the context of prenatal diagnosis. Some of the embodiments described herein may be combined with the output of the actionable data, and the execution of a clinical decision that results in a clinical treatment, or the execution of a clinical decision to make no action.

Exemplary Diagnostic Boxes

In an embodiment, the present disclosure comprises a diagnostic box that is capable of partly or completely carrying out any of the methods described in this disclosure. In an embodiment, the diagnostic box may be located at a physician's office, a hospital laboratory, or any suitable location reasonably proximal to the point of patient care. The box may be able to run the entire method in a wholly automated fashion, or the box may require one or a number of steps to be completed manually by a technician. In an embodiment, the box may be able to analyze at least the genotypic data measured on the maternal plasma. In an embodiment, the box may be linked to means to transmit the genotypic data measured on the diagnostic box to an external computation facility which may then analyze the genotypic data, and possibly also generate a report. The diagnostic box may include a robotic unit that is capable of transferring aqueous or liquid samples from one container to another. It may comprise a number of reagents, both solid and liquid. It may comprise a high throughput sequencer. It may comprise a computer.

Experimental Section

The presently disclosed embodiments are described in the following Examples, which are set forth to aid in the understanding of the disclosure, and should not be construed to limit in any way the scope of the disclosure as defined in the claims which follow thereafter. The following examples are put forth so as to provide those of ordinary skill in the art with a complete disclosure and description of how to use the described embodiments, and are not intended to limit the scope of the disclosure nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by volume, and temperature is in degrees Centigrade. It should be understood that variations in the methods as described may be made without changing the fundamental aspects that the experiments are meant to illustrate.

Experiment 1

The objective was to show that a Bayesian maximum likelihood estimation (MLE) algorithm that uses parent genotypes to calculate fetal fraction improves accuracy of non-invasive prenatal trisomy diagnosis compared to published methods.

Figure 14:
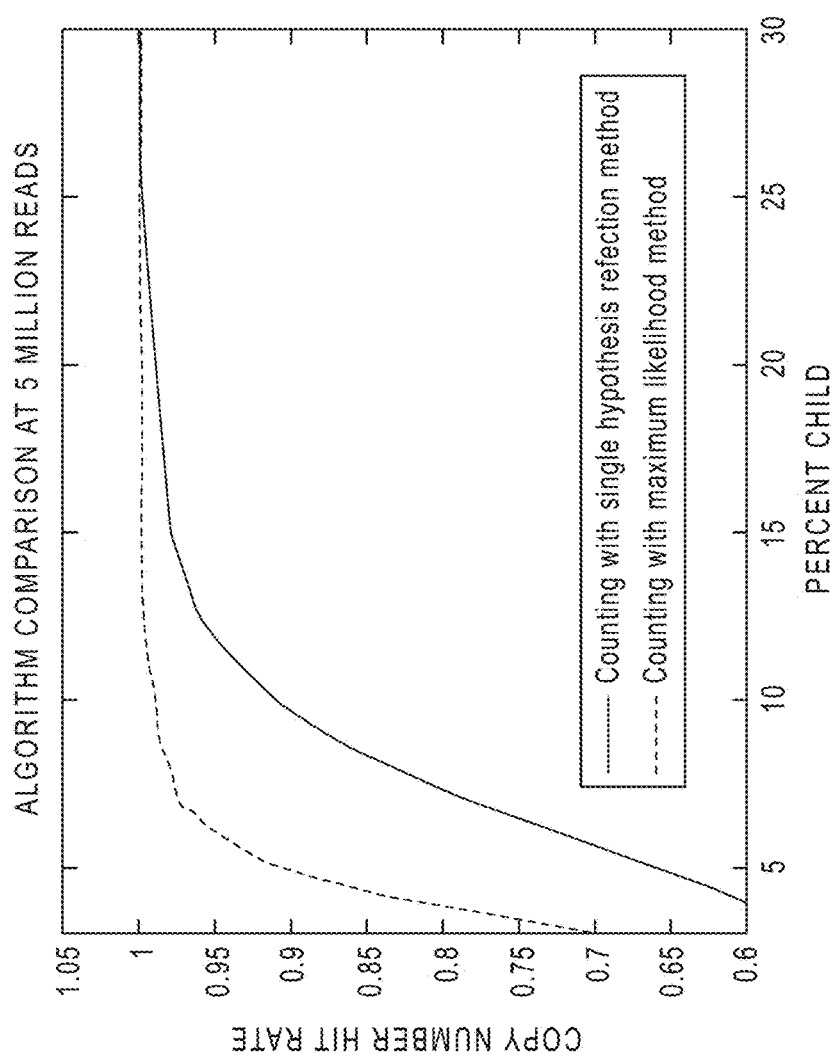
FIG. 14: Simulated ploidy call accuracies for counting method with two different analysis techniques.

Simulated sequencing data for maternal cfDNA was created by sampling reads obtained on trisomy-21 and respective mother cell lines. The rate of correct disomy and trisomy calls were determined from 500 simulations at various fetal fractions for a published method (Chiu et al. BMJ 2011; 342:c7401) and our MLE-based algorithm. We validated the simulations by obtaining 5 million shotgun reads from four pregnant mothers and respective fathers collected under an IRB-approved protocol. Parental genotypes were obtained on a 290K SNP array. (See FIG. 14)

In simulations, the MLE-based approach achieved 99.0% accuracy for fetal fractions as low as 9% and reported confidences that corresponded well to overall accuracy. We validated these results using four real samples wherein we obtained all correct calls with a computed confidence exceeding 99%. In contrast, our implementation of the published algorithm for Chiu et al. required 18% fetal fraction to achieve 99.0% accuracy, and achieved only 87.8% accuracy at 9% fetal DNA.

Fetal fraction determination from parental genotypes in conjunction with a MLE-based approach achieves greater accuracy than published algorithms at the fetal fractions expected during the 1st and early 2nd trimester. Furthermore, the method disclosed herein produces a confidence metric that is crucial in determining the reliability of the result, especially at low fetal fractions where ploidy detection is more difficult. Published methods use a less accurate threshold method for calling ploidy based on large sets of disomy training data, an approach that predefines a false positive rate. In addition, without a confidence metric, published methods are at risk of reporting false negative results when there is insufficient fetal cfDNA to make a call. In some embodiments, a confidence estimate is calculated for the called ploidy state.

Experiment 2

The objective was to improve non-invasive detection of fetal trisomy 18, 21, and X particularly in samples consisting of low fetal fraction by using a targeted sequencing approach combined with parent genotypes and Hapmap data in a Bayesian Maximum Likelihood Estimation (MLE) algorithm.

Maternal samples from four euploid and two trisomy-positive pregnancies and respective paternal samples were obtained under an IRB-approved protocol from patients where fetal karyotype was known. Maternal cfDNA was extracted from plasma and roughly 10 million sequence reads were obtained following preferential enrichment that targeted specific SNPs. Parent samples were similarly sequenced to obtain genotypes.

The described algorithm correctly called chromosome 18 and 21 disomy for all euploid samples and normal chromosomes of aneuploid samples. Trisomy 18 and 21 calls were correct, as were chromosome X copy numbers in male and female fetuses. The confidence produced by the algorithm was in excess of 98% in all cases.

The method described accurately reported the ploidy of all tested chromosomes from six samples, including samples comprised of less than 12% fetal DNA, which account for roughly 30% of $1^{st}$ and early $2^{nd}$-trimester samples. The crucial difference between the instant MLE algorithm and published methods is that it leverages parent genotypes and Hapmap data to improve accuracy and generate a confidence metric. At low fetal fractions, all methods become less accurate; it is important to correctly identify samples without sufficient fetal cfDNA to make a reliable call. Others have used chromosome Y specific probes to estimate fetal fraction of male fetuses, but concurrent parental genotyping enables estimation of fetal fraction for both sexes. Another inherent limitation of published methods using untargeted shotgun sequencing is that accuracy of ploidy calling varies among chromosomes due to differences in factors such as GC richness. The instant targeted sequencing approach is largely independent of such chromosome-scale variations and yields more consistent performance between chromosomes.

Experiment 3

The objective was to determine if trisomy is detectable with high confidence on a triploid fetus, using novel informatics to analyze SNP loci of free floating fetal DNA in maternal plasma.

20 mL of blood was drawn from a pregnant patient following abnormal ultrasound. After centrifugation, maternal DNA was extracted from the buffy coat (DNEASY, QIAGEN); cell-free DNA was extracted from plasma (QIAAMP QIAGEN). Targeted sequencing was applied to SNP loci on chromosomes 2, 21, and X in both DNA samples. Maximum—Likelihood Bayesian estimation selected the most likely hypothesis from the set of all possible ploidy states. The method determines fetal DNA fraction, ploidy state and explicit confidences in the ploidy determination. No assumptions are made about the ploidy of a reference chromosome. The diagnostic uses a test statistic that is independent of sequence read counts, which is the recent state of the art.

The instant method accurately diagnosed trisomy of chromosomes 2 and 21. Child fraction was estimated at 11.9% [CI 11.7-12.1]. The fetus was found to have one maternal and two paternal copies of chromosomes 2 and 21 with confidence of effectively 1 (error probability<$10^{-30}$). This was achieved with 92,600 and 258,100 reads on chromosomes 2 and 21 respectively.

This is the first demonstration of non-invasive prenatal diagnosis of trisomic chromosomes from maternal blood where the fetus was triploid, as confirmed by metaphase karyotype. Extant methods of non-invasive diagnosis would not detect aneuploidy in this sample. Current methods rely on a surplus of sequence reads on a trisomic chromosome relative to disomic reference chromosomes; but a triploid fetus has no disomic reference.

Furthermore, extant methods would not achieve similarly high-confidence ploidy determination with this fraction of fetal DNA and number of sequence reads. It is straightforward to extend the approach to all 24 chromosomes.

Experiment 4

Figure 15:
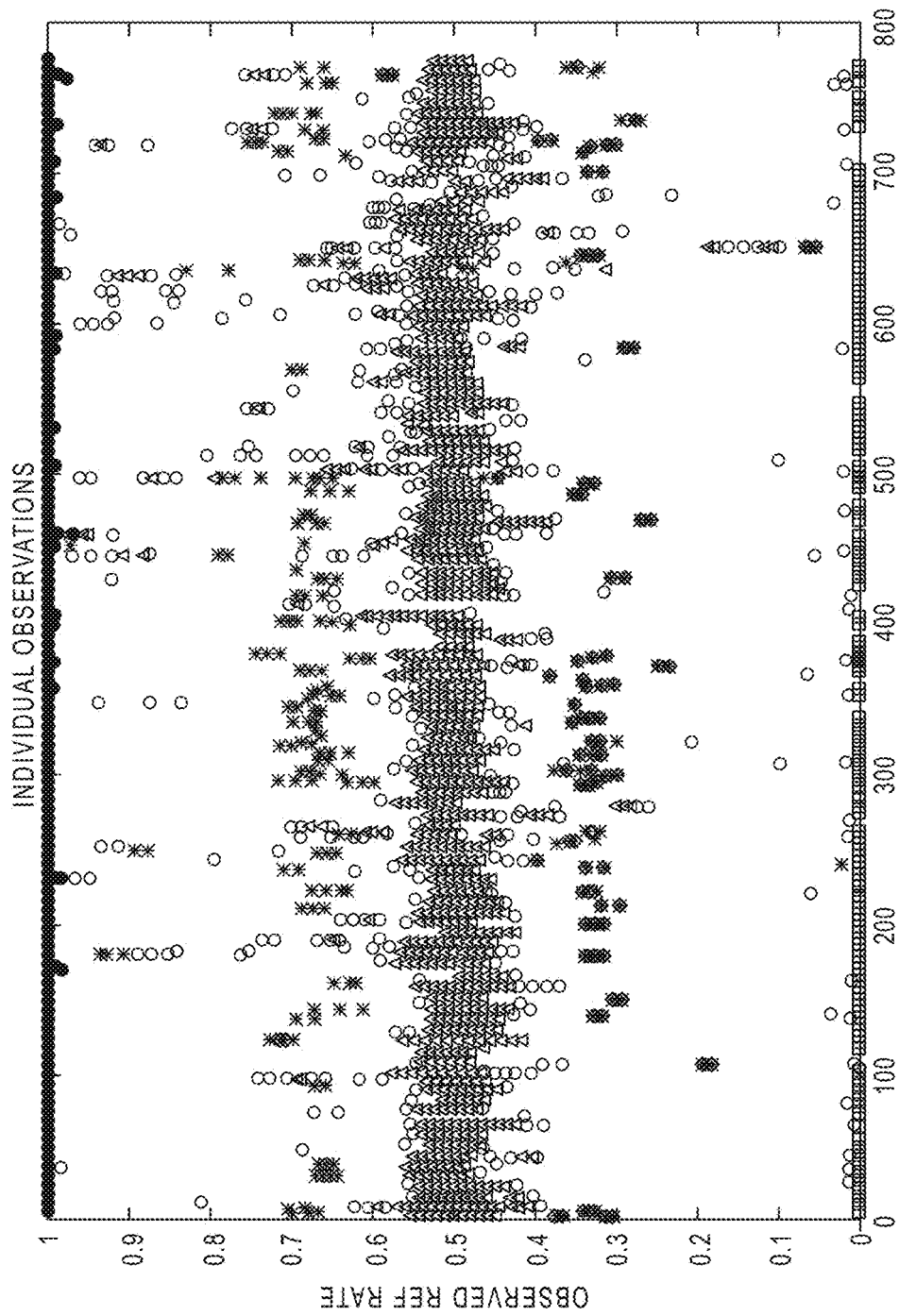
FIG. 15: Ratio of two alleles for a plurality of SNPs in a cell line in Experiment 4. The circles represent SNPs on disomic chromosomes, while the stars represent SNPs on a trisomic chromosome.
Figure 16:
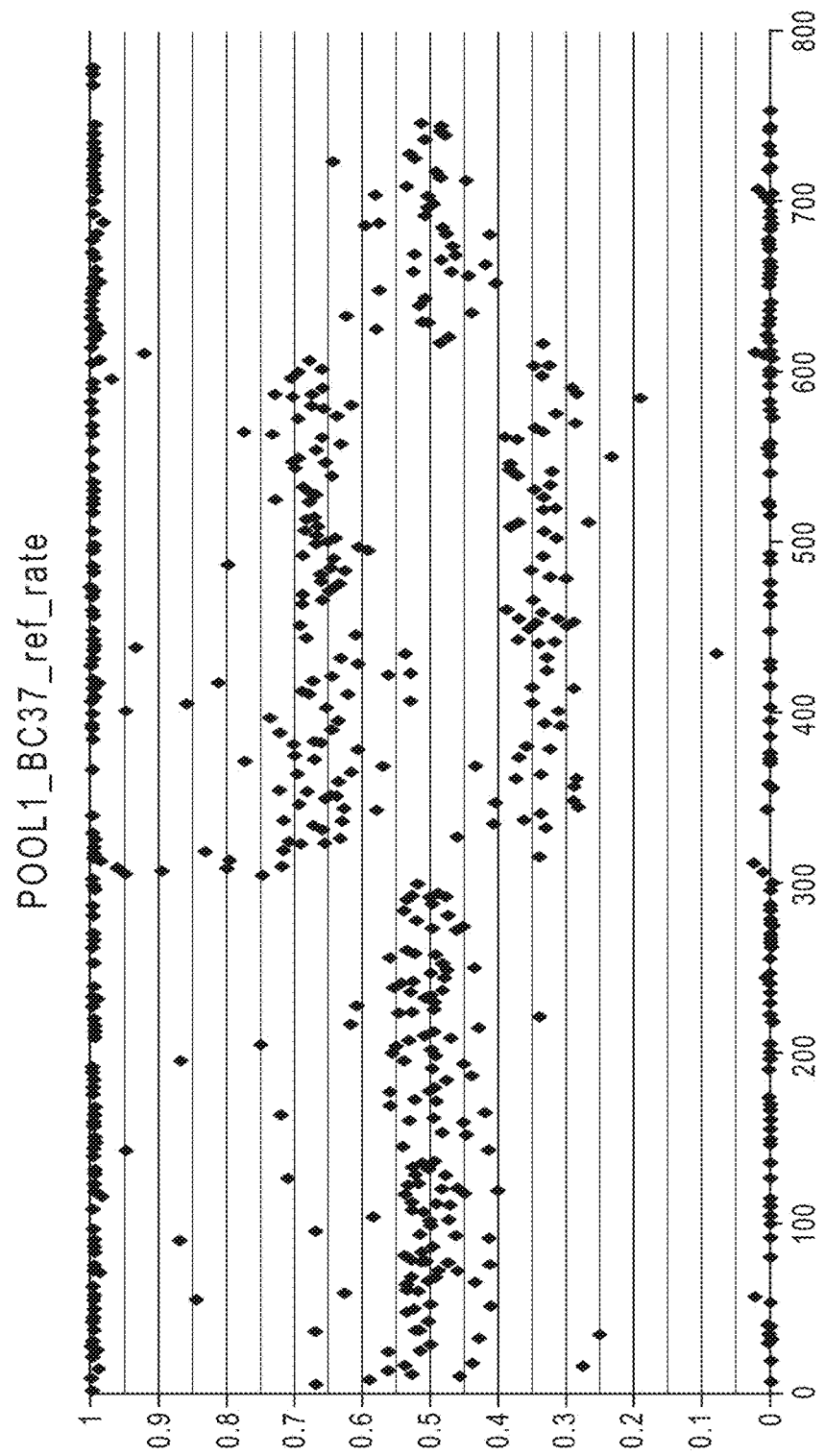
FIG. 16: Ratio of two alleles for a plurality of SNPs in a cell line in Experiment 4 sorted by chromosome. SNP 1 to 312 are found on chromosome 2, SNP 313 to 605 are found on chromosome 21 which is trisomic, and SNP 606 to 800 are on chromosome X. The data from chromosomes 2 and X show a disomic chromosome, as the relative sequence counts lie in three clusters: AA at the top of the graph, BB at the bottom of the graph, and AB in the middle of the graph. The data from chromosome 21, which is trisomic, shows four clusters: AAA at the top of the graph, AAB around the 0.65 line (⅔), ABB around the 0.35 line (⅓), and BBB at the bottom of the graph.
Figure 17A:
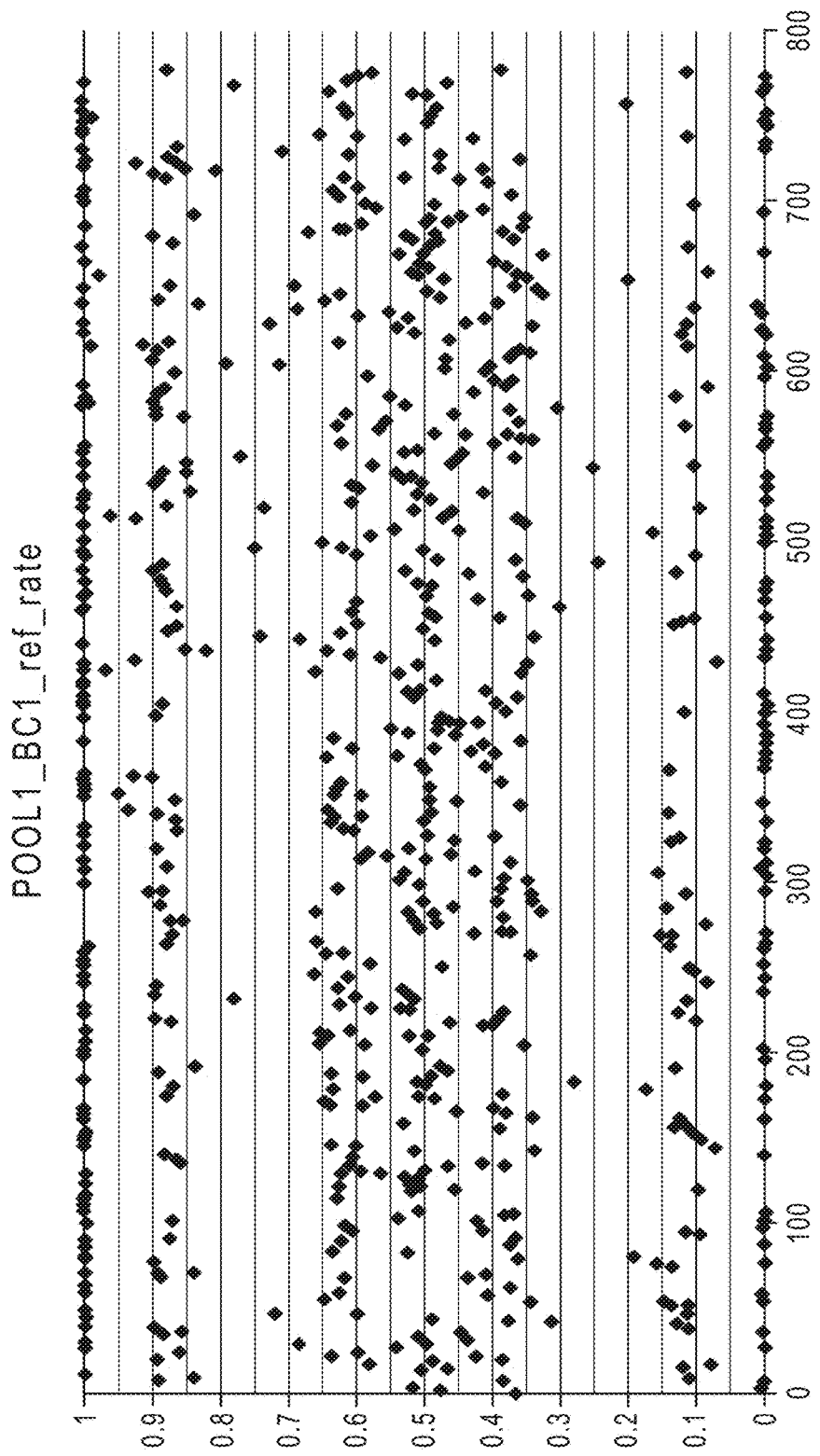
FIGS. 17A-17D: Ratio of two alleles for a plurality of SNPs in four pregnant women plasma samples, sorted by chromosome.
Figure 17B:
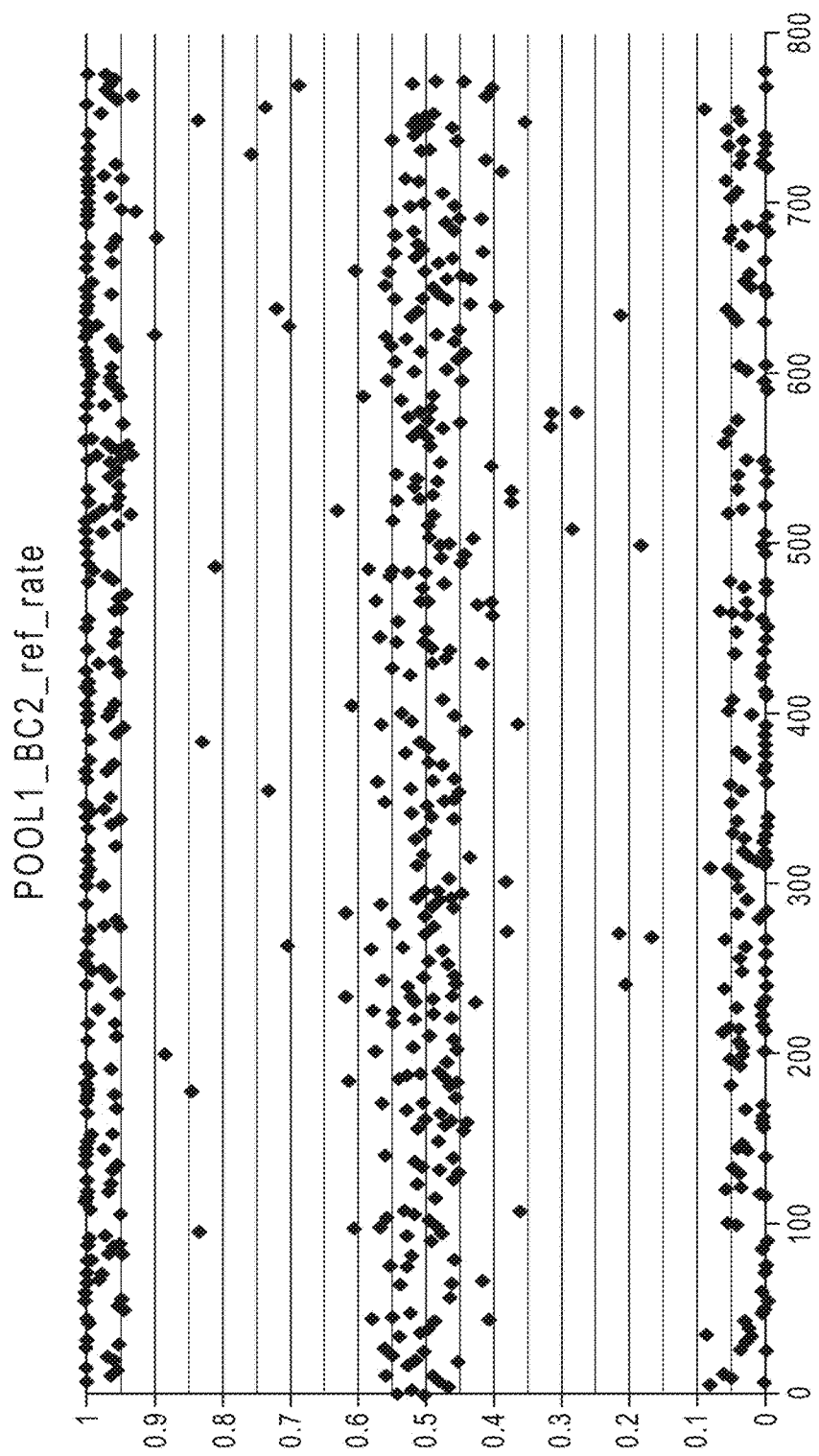
Figure 17C:
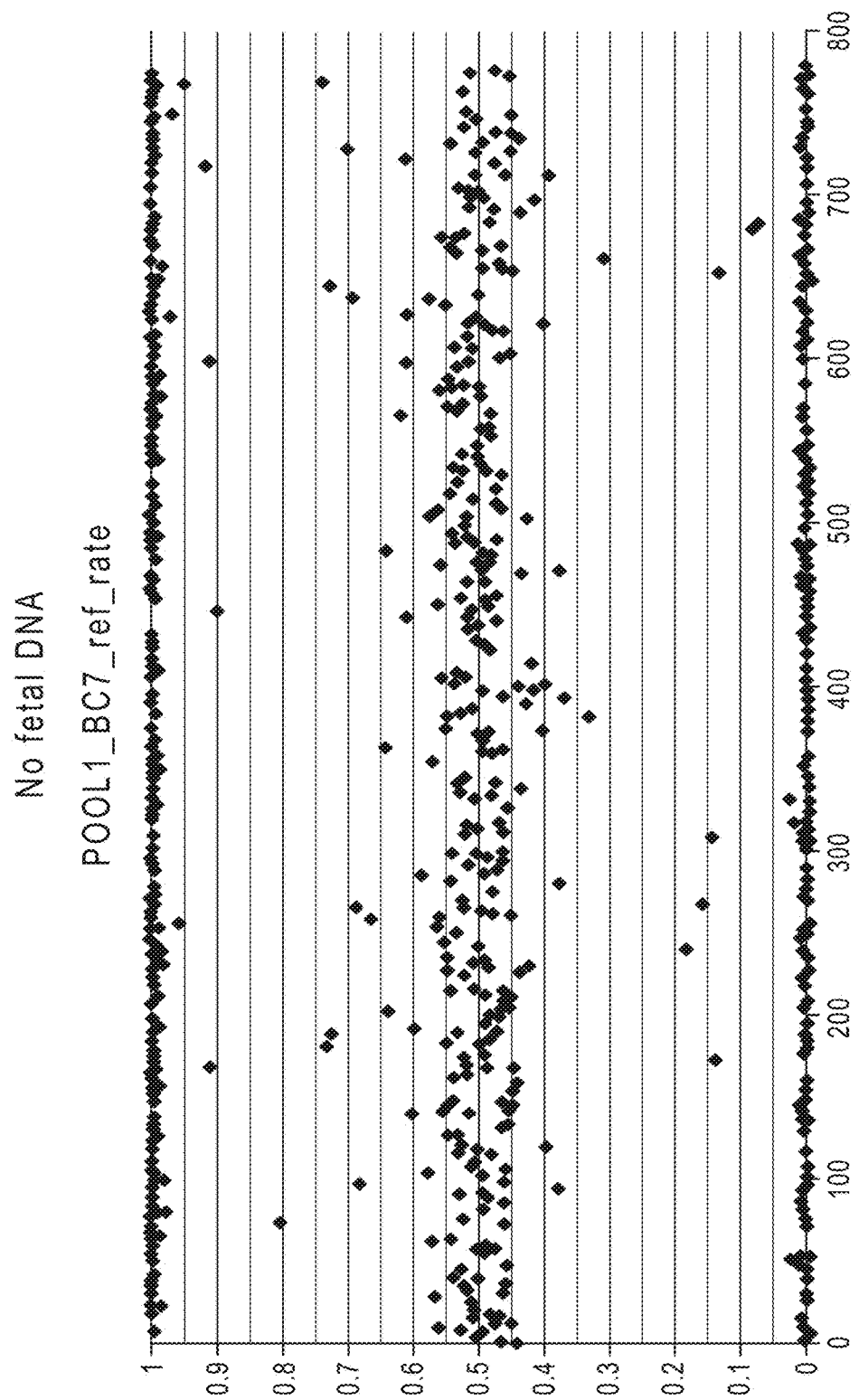
Figure 17D:
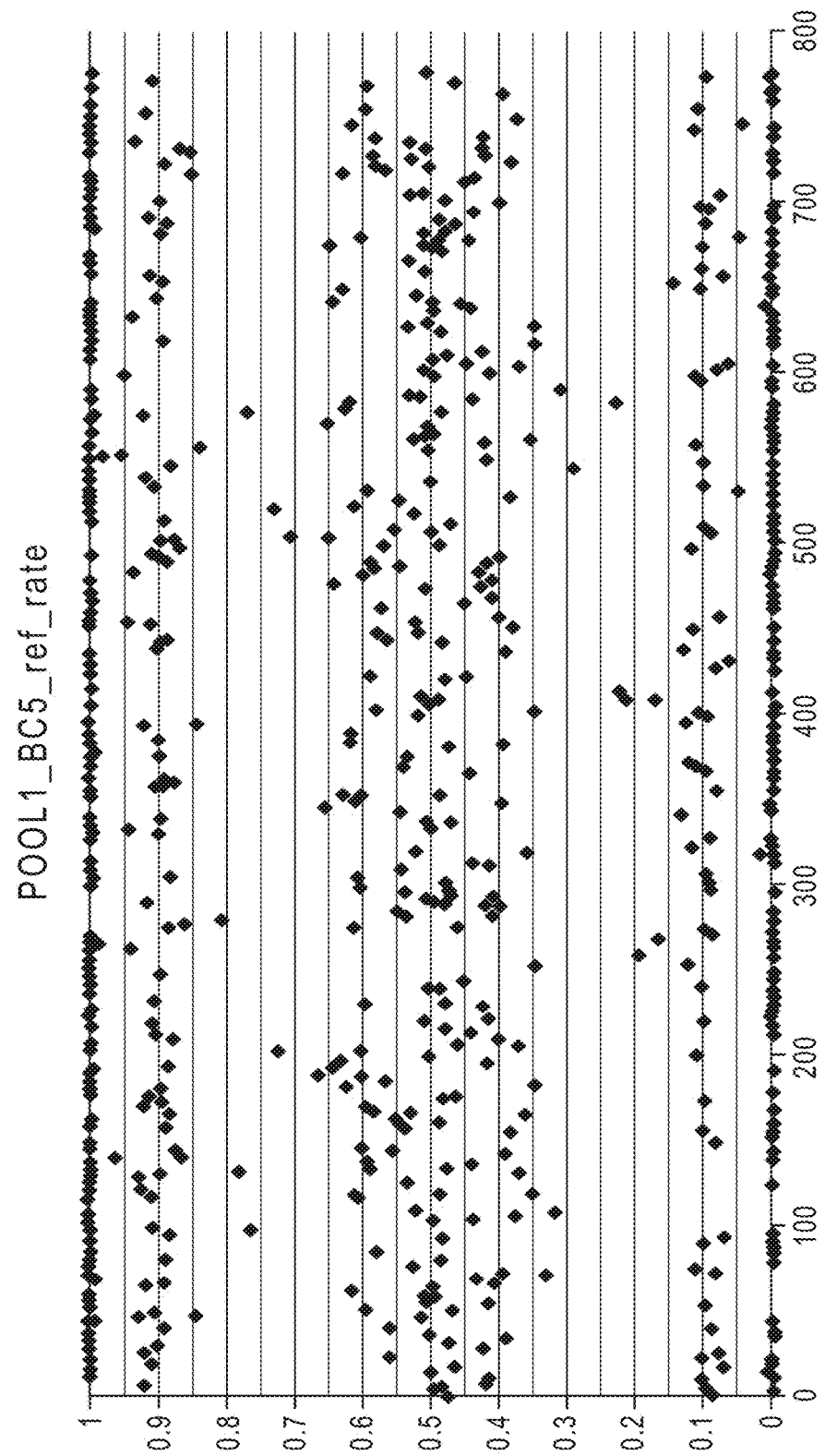

The following protocol was used for 800-plex amplification of DNA isolated from maternal plasma from a euploid pregnancy and also genomic DNA from a triploidy 21 cell line using standard PCR (meaning no nesting was used). Library preparation and amplification involved single tube blunt ending followed by A-tailing. Adaptor ligation was run using the ligation kit found in the AGILENT SURESELECT kit, and PCR was run for 7 cycles. Then, 15 cycles of STA (95° C. for 30 s; 72° C. for 1 min; 60° C. for 4 min; 65° C. for 1 min; 72° C. for 30 s) using 800 different primer pairs targeting SNPs on chromosomes 2, 21 and X. The reaction was run with 12.5 nM primer concentration. The DNA was then sequenced with an ILLUMINA IIGAX sequencer. The sequencer output 1.9 million reads, of which 92% mapped to the genome; of those reads that mapped to the genome, more than 99% mapped to one of the regions targeted by the targeted primers. The numbers were essentially the same for both the plasma DNA and the genomic DNA. FIG. 15 shows the ratio of the two alleles for the ~780 SNPs that were detected by the sequencer in the genomic DNA that was taken from a cell line with known trisomy at chromosome 21. Note that the allele ratios are plotted here for ease of visualization, because the allele distributions are not straightforward to read visually. The circles represent SNPs on disomic chromosomes, while the stars represent SNPs on a trisomic chromosome. FIG. 16 is another representation of the same data as in FIG. X, where the Y-axis is the relative number of A and B measured for each SNP, and where the X-axis is the SNP number where the SNPs are separated by chromosome. In FIG. 16, SNP 1 to 312 are found on chromosome 2, from SNP 313 to 605 are found on chromosome 21 which is trisomic, and from SNP 606 to 800 are on chromosome X. The data from chromosomes 2 and X show a disomic chromosome, as the relative sequence counts lie in three clusters: AA at the top of the graph, BB at the bottom of the graph, and AB in the middle of the graph. The data from chromosome 21, which is trisomic, shows four clusters: AAA at the top of the graph, AAB around the 0.65 line (⅔), ABB around the 0.35 line (⅓), and BBB at the bottom of the graph.

FIGS. 17A-D show data for the same 800-plex protocol, but measured on DNA that was amplified from four plasma samples from pregnant women. For these four samples, we expect to see seven clusters of dots: (1) along the top of the graph are those loci where both the mother and the fetus are AA, (2) slightly below the top of the graph are those loci where the mother is AA and the fetus is AB, (3) slightly above the 0.5 line are those loci where the mother is AB and the fetus is AA, (4) along the 0.5 line are those loci where the mother and the fetus are both AB, (5) slightly below the 0.5 line are those loci where the mother is AB and the fetus is BB, (6) slightly above the bottom of the graph are those loci where the mother is BB and the fetus is AB, (1) along the bottom of the graph are those loci where both the mother and the fetus are BB. The smaller the fetal fraction, the less the separation between clusters (1) and (2), between clusters (3), (4) and (5), and between clusters (6) and (7). The separation is expected to be half of the fraction of DNA that is of fetal origin. For example if the DNA is 20% fetal, and 80% maternal, we expect (1) through (7) to be centered at 1.0, 0.9, 0.6, 0.5, 0.4, 0.1 and 0.0 respectively; see for example FIG. 17D, POOL1_BC5_ref_rate. If, instead the DNA is 8% fetal, and 92% maternal, we expect (1) through (7) to be centered at 1.00, 0.96, 0.54, 0.50, 0.46, 0.04 and 0.00 respectively; see for example FIG. 17B, POOL1_BC2_ref_rate. If there is not fetal DNA detected, we do not expect to see (2), (3), (5), or (6); alternately we could say that the separation is zero, and therefore (1) and (2) are on top of each other, as are (3), (4) and (5), and also (6) and (7); see e.g., FIG. 17C, POOL1_BC7_ref_rate. Note that the fetal fraction for FIG. 17A, POOL1 BC1_ref_rate is about 25%.

Experiment 5

Figure 18:
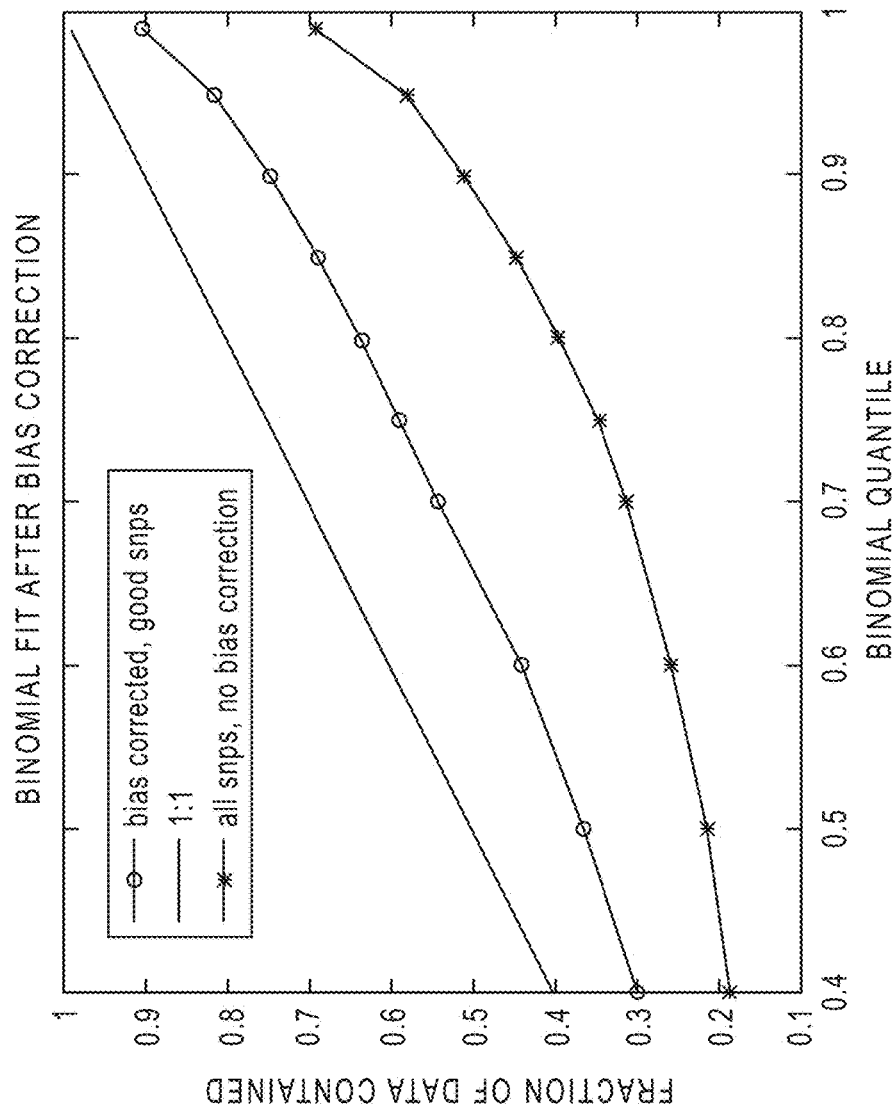
FIG. 18: Fraction of data that can be explained by binomial variance before and after data correction. The stars represent the observed allele bias on raw sequence data for the 800-plex experiment; the circles represent the allele bias after correction. Note that if there were no allele bias at all, we would expect the data to fall along the x=y line.

Most methods of DNA amplification and measurement will produce some allele bias, wherein the two alleles that are typically found at a locus are detected with intensities or counts that are not representative of the actual amounts of alleles in the sample of DNA. For example, for a single individual, at a heterozygous locus we expect to see a 1:1 ratio of the two alleles, which is the theoretical ratio expected for a heterozygous locus; however due to allele bias, we may see 55:45, or even 60:40. Also note that in the context of sequencing, if the depth of read is low, then simple stochastic noise could result in significant allele bias. In an embodiment, it is possible to model the behavior of each SNP such that if a consistent bias is observed for particular alleles, this bias can be corrected for. FIG. 18 shows the fraction of data that can be explained by binomial variance, before and after bias correction. In FIG. 18, the stars represent the observed allele bias on raw sequence data for the 800-plex experiment; the circles represent the allele bias after correction. Note that if there were no allele bias at all, we would expect the data to fall along the x=y line. A similar set of data that was produced by amplifying DNA using a 150-plex targeted amplification produced data that fell very closely on the 1:1 line after bias correction.

Experiment 6

Figure 19:
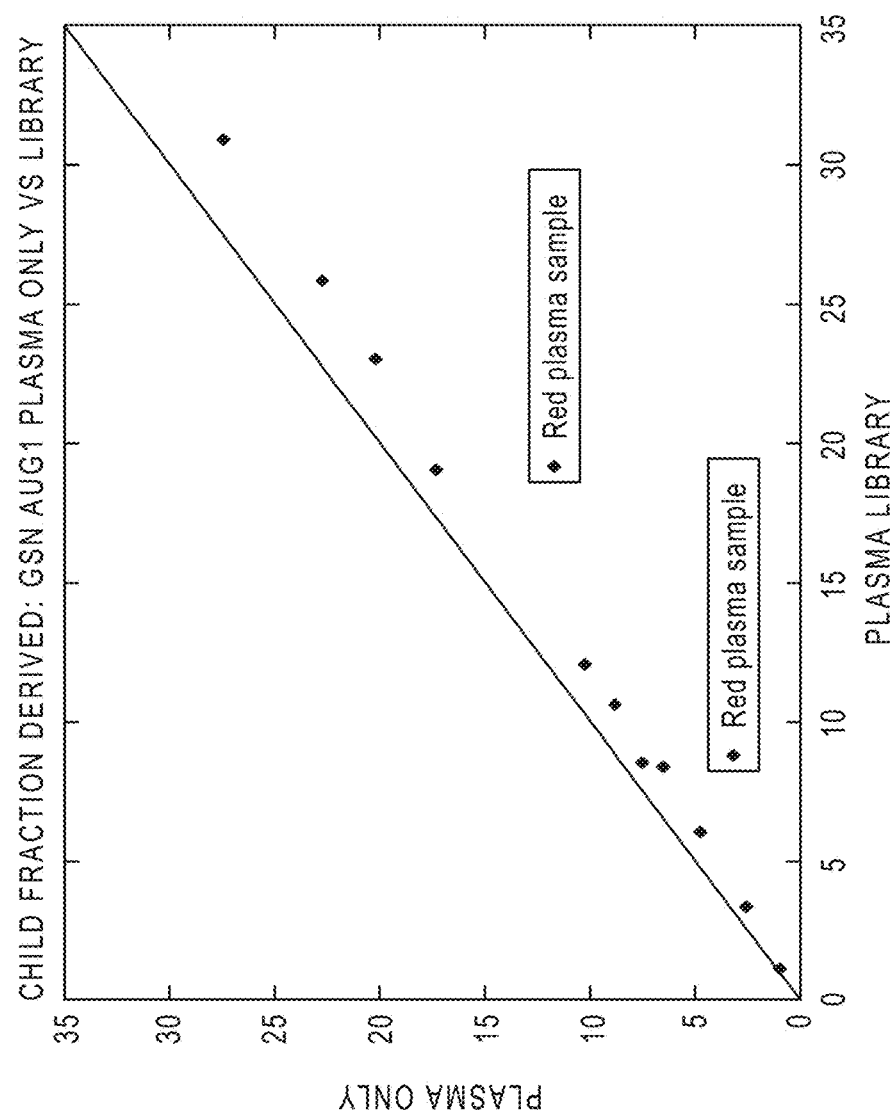
FIG. 19: Graph showing relative enrichment of fetal DNA in samples following a short library preparation protocol. The measured fetal percent when the input is plasma DNA (vertical axis) vs. the measured fetal percent when the input DNA is plasma DNA that has had a library prepared using the ILLUMINA GAIIx library preparation protocol is shown. All the dots fall below the line, indicating that the library preparation step enriches the fraction of DNA that is of fetal origin. Two samples of plasma that were red, indicating hemolysis and therefore that there would be an increased amount of long maternal DNA present from cell lysis, show a particularly significant enrichment of fetal fraction when the library preparation is performed prior to targeted amplification.

Universal amplification of DNA using ligated adaptors with primers specific to the adaptor tags, where the primer annealing and extension times are limited to a few minutes has the effect of enriching the proportion of shorter DNA strands. Most library protocols designed for creating DNA libraries suitable for sequencing contain such a step, and example protocols are published and well known to those in the art. In some embodiments of the invention, adaptors with a universal tag are ligated to the plasma DNA, and amplified using primers specific to the adaptor tag. In some embodiments, the universal tag can be the same tag as used for sequencing, it can be a universal tag only for PCR amplification, or it can be a set of tags. Since the fetal DNA is typically short in nature, while the maternal DNA can be both short and long in nature, this method has the effect of enriching the proportion of fetal DNA in the mixture. The free floating DNA, thought to be DNA from apoptotic cells, and which contains both fetal and maternal DNA, is short— mostly under 200 bp. Cellular DNA released by cell lysis, a common phenomenon after phlebotomy, is typically almost exclusively maternal, and is also quite long—mostly above 500 bp. Therefore, blood samples that have sat around for more than a few minutes will contain a mixture of short (fetal+maternal) and longer (maternal) DNA. Performing a universal amplification with relatively short extension times on maternal plasma followed by targeted amplification will tend to increase the relative proportion of fetal DNA when compared to the plasma that has been amplified using targeted amplification alone. This can be seen in FIG. 19 which shows the measured fetal percent when the input is plasma DNA (vertical axis) vs. the measured fetal percent when the input DNA is plasma DNA that has had a library prepared using the ILLUMINA GAIIx library preparation protocol. All the dots fall below the line, indicating that the library preparation step enriches the fraction of DNA that is of fetal origin. Two samples of plasma that were red, indicating hemolysis and therefore that there would be an increased amount of long maternal DNA present from cell lysis, show a particularly significant enrichment of fetal fraction when the library preparation is performed prior to targeted amplification. The method disclosed herein is particularly useful in cases where there is hemolysis or some other situation has occurred where cells comprising relatively long strands of contaminating DNA have lysed, contaminating the mixed sample of short DNA with the long DNA. Typically the relatively short annealing and extension times are between 30 seconds and 2 minutes, though they could be as short as 5 or 10 seconds or less, or as long as 5 or 10 minutes.

Experiment 7

The following protocol was used for 1,200-plex amplification of DNA isolated from maternal plasma from a euploid pregnancy and also genomic DNA from a triploidy 21 cell line using a direct PCR protocol, and also a semi-nested approach. Library preparation and amplification involved single tube blunt ending followed by A-tailing. Adaptor ligation was run using a modification of the ligation kit found in the AGILENT SURESELECT kit, and PCR was run for 7 cycles. In the targeted primer pool, there were 550 assays for SNPs from chromosome 21, and 325 assays for SNPs from each of chromosomes 1 and X. Both protocols involved 15 cycles of STA (95° C. for 30 s; 72° C. for 1 min; 60° C. for 4 min; 65° C. for 30 s; 72° C. for 30 s) using 16 nM primer concentration. The semi-nested PCR protocol involved a second amplification of 15 cycles of STA (95° C. for 30 s; 72° C. for 1 min; 60° C. for 4 min; 65° C. for 30 s; 72° C. for 30 s) using an inner forward tag concentration of 29 nM, and a reverse tag concentration of 1 uM or 0.1 uM. The DNA was then sequenced with an ILLUMINA IIGAX sequencer. For the direct PCR protocol, 73% of the reads map to the genome; for the semi-nested protocol, 97.2% of the sequence reads map to the genome. Therefore, the semi-nested protocol result in approximately 30% more information, presumably mostly due to the elimination of primers that are most likely to cause primer dimers.

Figure 20:
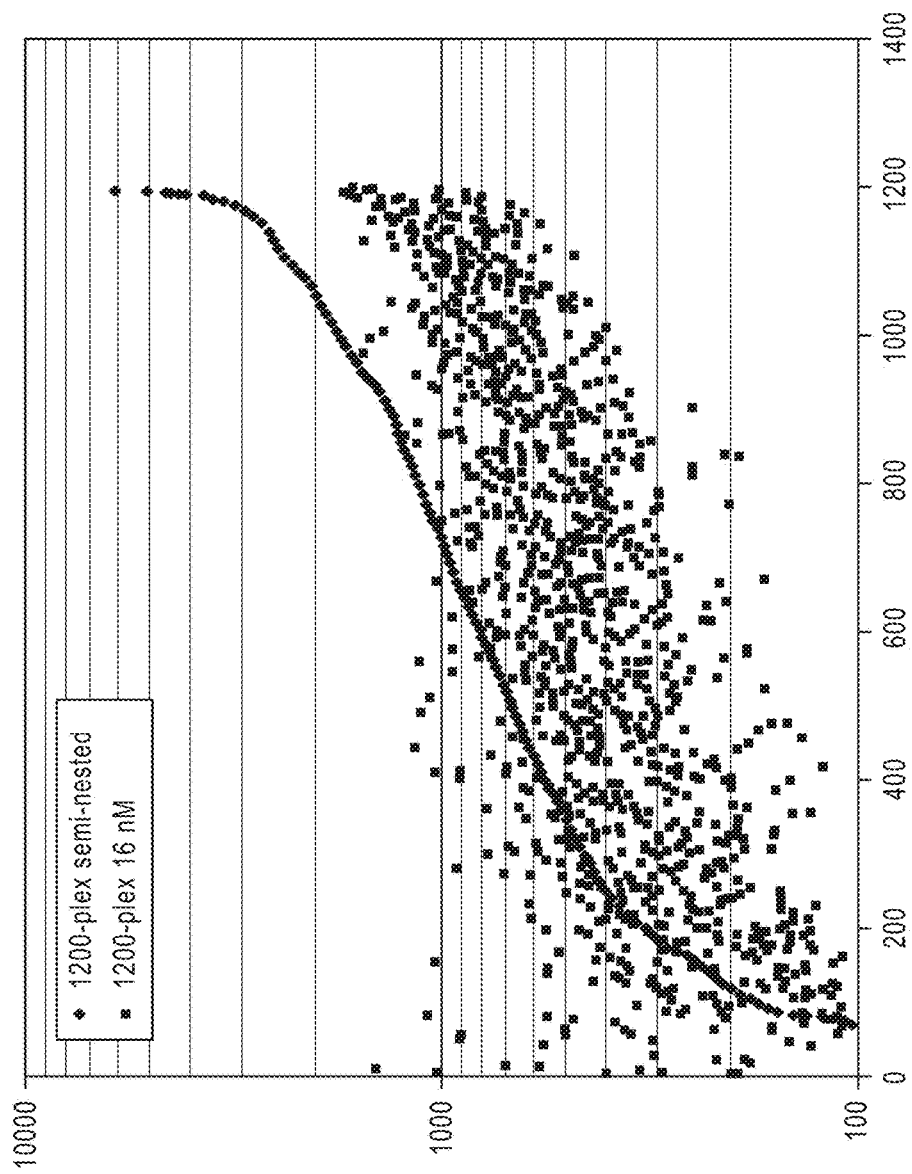
FIG. 20: Depth of read graph comparing direct PCR and semi-nested methods. The diamonds refer to the depth of read for loci run with the semi-nested protocol, and the squares refer to the depth of read for loci run with no nesting. The SNPs are arranged by depth of read for the diamonds, so the diamonds all fall on a curved line, while the squares appear to be loosely correlated; the arrangements of the SNPs is arbitrary, and it is the height of the dot that denotes depth of read rather than its location left to right.

The depth of read variability tends to be higher when using the semi-nested protocol than when the direct PCR protocol is used (see FIG. 20) where the diamonds refer to the depth of read for loci run with the semi-nested protocol, and the squares refer to the depth of read for loci run with no nesting. The SNPs are arranged by depth of read for the diamonds, so the diamonds all fall on a curved line, while the squares appear to be loosely correlated; the arrangements of the SNPs is arbitrary, and it is the height of the dot that denotes depth of read rather than its location left to right.

Figure 21:
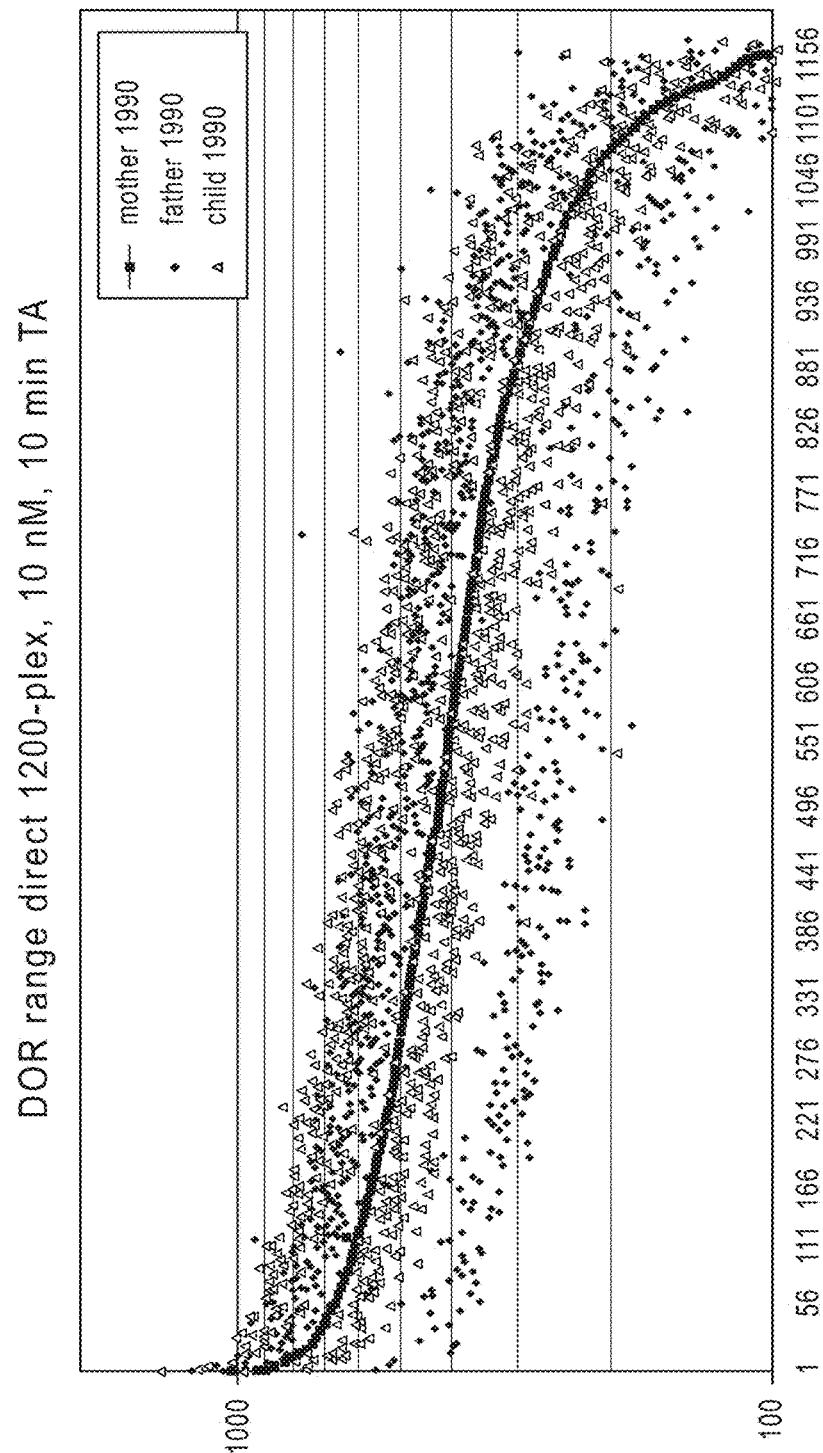
FIG. 21: Comparison of depth of read for direct PCR of three genomic samples. A 1,200-plex direct PCR amplification of genomic DNA was used, of the 1,200 assays: 1186 assays had a DOR greater than 10; the average depth of read was 400; 1063 assays (88.6%) had a depth of read of between 200 and 800, and ideal window where the number of reads for each allele is high enough to give meaningful data, while the number of reads for each allele is not so high that the marginal use of those reads was particularly small. The standard deviation of the DOR was 290, the average DOR was 453, the coefficient of variance of the DOR was 64%, there were 950,000 total reads, and 63.1% of the reads mapped to the genome.
Figure 22:
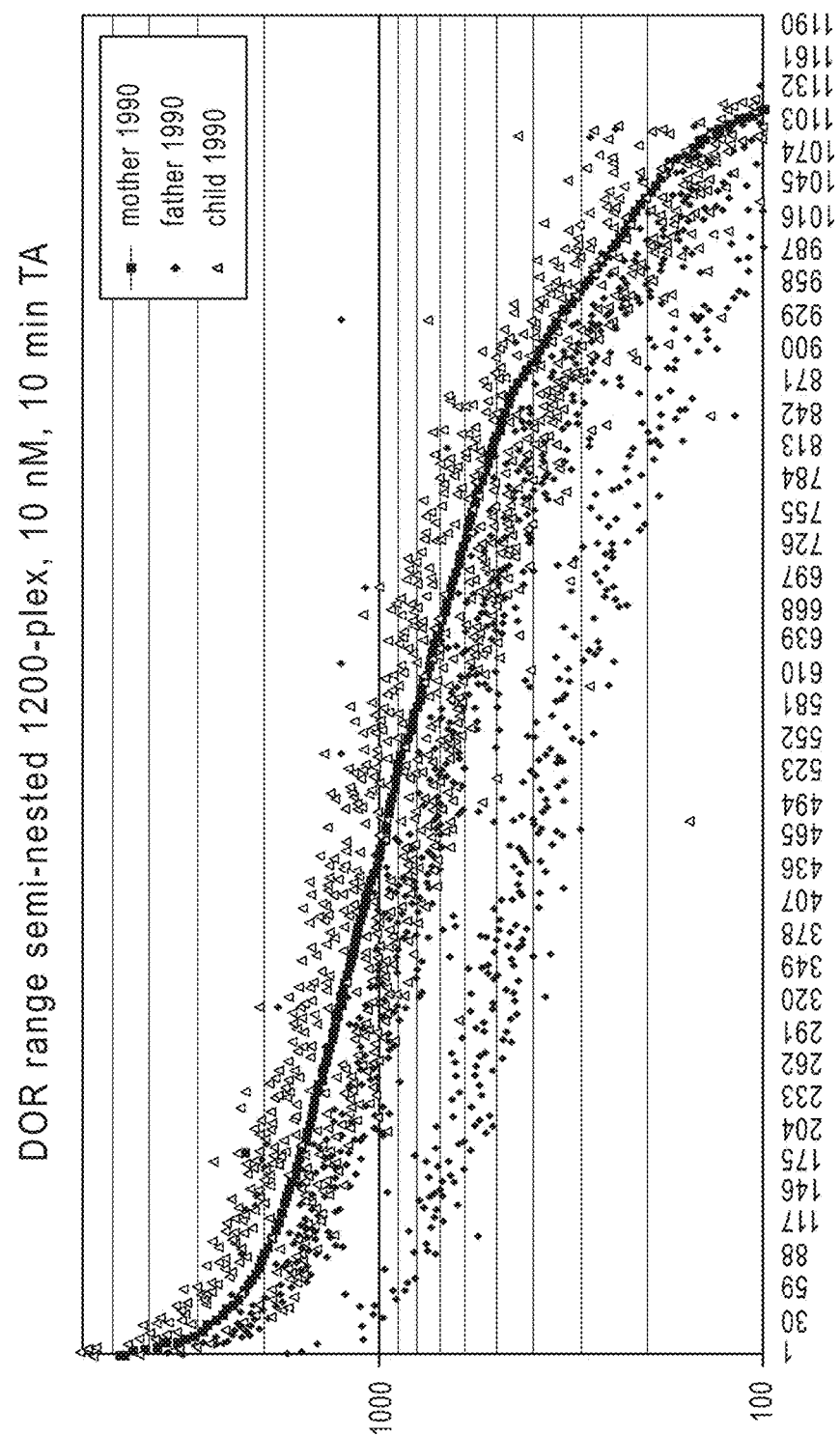
FIG. 22: Comparison of depth of read for semi-nested mini-PCR of three samples. Using a 1,200-plex semi-nested protocol, the DOR was higher. The standard deviation of the DOR was 583, the average DOR was 630, the coefficient of variance of the DOR was 93%, there were 870,000 total reads, and 96.3% of the reads mapped to the genome.

In some embodiments, the methods described herein can achieve excellent depth of read (DOR) variances. For example, in one version of this experiment (FIG. 21) using a 1,200-plex direct PCR amplification of genomic DNA, of the 1,200 assays: 1186 assays had a DOR greater than 10; the average depth of read was 400; 1063 assays (88.6%) had a depth of read of between 200 and 800, and ideal window where the number of reads for each allele is high enough to give meaningful data, while the number of reads for each allele is not so high that the marginal use of those reads was particularly small. Only 12 alleles had higher depth of read with the highest at 1035 reads. The standard deviation of the DOR was 290, the average DOR was 453, the coefficient of variance of the DOR was 64%, there were 950,000 total reads, and 63.1% of the reads mapped to the genome. In another experiment (FIG. 22) using a 1,200-plex semi-nested protocol, the DOR was higher. The standard deviation of the DOR was 583, the average DOR was 630, the coefficient of variance of the DOR was 93%, there were 870,000 total reads, and 96.3% of the reads mapped to the genome. Note, in both these cases, the SNPs are arranged by the depth of read for the mother, so the curved line represents the maternal depth of read. The differentiation between child and father is not significant; it is only the trend that is significant for the purpose of this explanation.

Experiment 8

In an experiment, the semi-nested 1,200-plex PCR protocol was used to amplify DNA from one cell and from three cells. This experiment is relevant to prenatal aneuploidy testing using fetal cells isolated from maternal blood, or for preimplantation genetic diagnosis using biopsied blastomeres or trophectoderm samples. There were 3 replicates of 1 and 3 cells from 2 individuals (46 XY and 47 XX+21) per condition. Assays targeted chromosomes 1, 21 and X. Three different lysis methods were used: ARCTURUS, MPERv2 and Alkaline lysis. Sequencing was run multiplexing 48 samples in one sequencing lane. The algorithm returned correct ploidy calls for each of the three chromosomes, and for each of the replicates.

Experiment 9

In one experiment, four maternal plasma samples were prepared and amplified using a hemi-nested 9,600-plex protocol. The samples were prepared in the following way: Up to 40 mL of maternal blood were centrifuged to isolate the buffy coat and the plasma. The genomic DNA in the maternal sample was prepared from the buffy coat and paternal DNA was prepared from a blood sample or saliva sample. Cell-free DNA in the maternal plasma was isolated using the QIAGEN CIRCULATING NUCLEIC ACID kit and eluted in 45 uL TE buffer according to manufacturer's instructions. Universal ligation adapters were appended to the end of each molecule of 35 uL of purified plasma DNA and libraries were amplified for 7 cycles using adaptor specific primers. Libraries were purified with AGENCOURT AMPURE beads and eluted in 50 ul water.

3 ul of the DNA was amplified with 15 cycles of STA (95° C. for 10 min for initial polymerase activation, then 15 cycles of 95° C. for 30 s; 72° C. for 10 s; 65° C. for 1 min; 60° C. for 8 min; 65° C. for 3 min and 72° C. for 30 s; and a final extension at 72° C. for 2 min) using 14.5 nM primer concentration of 9600 target-specific tagged reverse primers and one library adaptor specific forward primer at 500 nM.

The hemi-nested PCR protocol involved a second amplification of a dilution of the first STAs product for 15 cycles of STA (95° C. for 10 min for initial polymerase activation, then 15 cycles of 95° C. for 30 s; 65° C. for 1 min; 60° C. for 5 min; 65° C. for 5 min and 72° C. for 30 s; and a final extension at 72° C. for 2 min) using reverse tag concentration of 1000 nM, and a concentration of 16.6 u nM for each of 9600 target-specific forward primers.

An aliquot of the STA products was then amplified by standard PCR for 10 cycles with 1 uM of tag-specific forward and barcoded reverse primers to generate barcoded sequencing libraries. An aliquot of each library was mixed with libraries of different barcodes and purified using a spin column.

In this way, 9,600 primers were used in the single-well reactions; the primers were designed to target SNPs found on chromosomes 1, 2, 13, 18, 21, X and Y. The amplicons were then sequenced using an ILLUMINA GAIIX sequencer. Per sample, approximately 3.9 million reads were generated by the sequencer, with 3.7 million reads mapping to the genome (94%), and of those, 2.9 million reads (74%) mapped to targeted SNPs with an average depth of read of 344 and a median depth of read of 255. The fetal fraction for the four samples was found to be 9.9%, 18.9%, 16.3%, and 21.2%

Relevant maternal and paternal genomic DNA samples amplified using a semi-nested 9600-plex protocol and sequenced. The semi-nested protocol is different in that it applies 9,600 outer forward primers and tagged reverse primers at 7.3 nM in the first STA. Thermocycling conditions and composition of the second STA, and the barcoding PCR were the same as for the hemi-nested protocol.

The sequencing data was analyzed using informatics methods disclosed herein and the ploidy state was called at six chromosomes for the fetuses whose DNA was present in the 4 maternal plasma samples. The ploidy calls for all 28 chromosomes in the set were called correctly with confidences above 99.2% except for one chromosome that was called correctly, but with a confidence of 83%.

Figure 23:
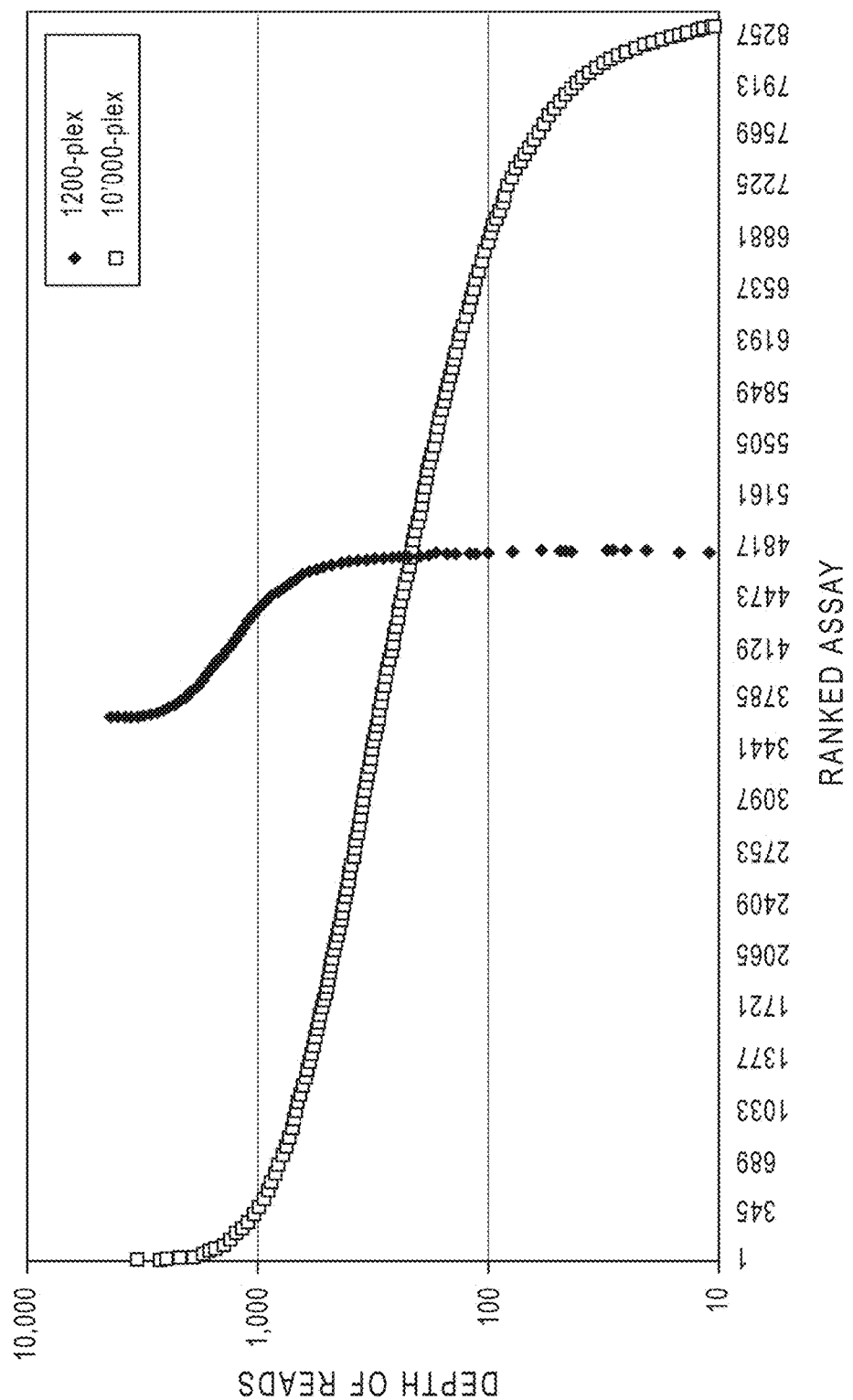
FIG. 23: Comparison of depth of read for 1,200-plex and 9,600-plex reactions.

FIG. 23 shows the depth of read of the 9,600-plex hemi-nesting approach along with the depth of read of the 1,200-plex semi-nested approach described in Experiment 7, though the number of SNPs with a depth of read greater than 100, greater than 200 and greater than 400 was significantly higher than in the 1,200-plex protocol. The number of reads at the $90^{th}$ percentile can be divided by the number of reads at the $10^{th}$ percentile to give a dimensionless metric that is indicative of the uniformity of the depth of read; the smaller the number, the more uniform (narrow) the depth of read. The average $90^{th}$ percentile/$10^{th}$ percentile ratio is 11.5 for the method run in Experiment 9, while it is 5.6 for the method run in Experiment 7. A narrower depth of read for a given protocol plexity is better for sequencing efficiency, as fewer sequence reads are necessary to ensure that a certain percentage of reads are above a read number threshold.

Experiment 10

In one experiment, four maternal plasma samples were prepared and amplified using a semi-nested 9,600-plex protocol. Details of Experiment 10 were very similar to Experiment 9, the exception being the nesting protocol, and including the identity of the four samples. The ploidy calls for all 28 chromosomes in the set were called correctly with confidences above 99.7%. 7.6 million (97%) of reads mapped to the genome, and 6.3 million (80%) of the reads mapped to the targeted SNPs. The average depth of read was 751, and the median depth of read was 396.

Experiment 11

In one experiment, three maternal plasma samples were split into five equal portions, and each portion was amplified using either 2,400 multiplexed primers (four portions) or 1,200 multiplexed primers (one portion) and amplified using a semi-nested protocol, for a total of 10,800 primers. After amplification, the portions were pooled together for sequencing. Details of Experiment 11 were very similar to Experiment 9, the exception being the nesting protocol, and the split and pool approach. The ploidy calls for all 21 chromosomes in the set were called correctly with confidences above 99.7%, except for one missed call where the confidence was 83%. 3.4 million reads mapped to targeted SNPs, the average depth of read was 404 and the median depth of read was 258.

Experiment 12

In one experiment, four maternal plasma samples were split into four equal portions, and each portion was amplified using 2,400 multiplexed primers and amplified using a semi-nested protocol, for a total of 9,600 primers. After amplification, the portions were pooled together for sequencing. Details of Experiment 12 were very similar to Experiment 9, the exception being the nesting protocol, and the split and pool approach. The ploidy calls for all 28 chromosomes in the set were called correctly with confidences above 97%, except for one missed call where the confidence was 78%. 4.5 million reads mapped to targeted SNPs, the average depth of read was 535 and the median depth of read was 412.

Experiment 13

In one experiment, four maternal plasma samples were prepared and amplified using a 9,600-plex triply hemi-nested protocol, for a total of 9,600 primers. Details of Experiment 12 were very similar to Experiment 9, the exception being the nesting protocol which involved three rounds of amplification; the three rounds involved 15, 10 and 15 STA cycles respectively. The ploidy calls for 27 of 28 chromosomes in the set were called correctly with confidences above 99.9%, except for one that was called correctly with 94.6%, and one missed call with a confidence of 80.8%. 3.5 million reads mapped to targeted SNPs, the average depth of read was 414 and the median depth of read was 249.

Experiment 14

In one experiment 45 sets of cells were amplified using a 1,200-plex semi-nested protocol, sequenced, and ploidy determinations were made at three chromosomes. Note that this experiment is meant to simulate the conditions of performing pre-implantation genetic diagnosis on single-cell biopsies from day 3 embryos, or trophectoderm biopsies from day 5 embryos. 15 individual single cells and 30 sets of three cells were placed in 45 individual reaction tubes for a total of 45 reactions where each reaction contained cells from only one cell line, but the different reactions contained cells from different cell lines. The cells were prepared into 5 ul washing buffer and lysed the by adding 5 ul ARCTURUS PICOPURE lysis buffer (APPLIED BIOSYSTEMS) and incubating at 56° C. for 20 min, 95° C. for 10 min.

The DNA of the single/three cells was amplified with 25 cycles of STA (95° C. for 10 min for initial polymerase activation, then 25 cycles of 95° C. for 30 s; 72° C. for 10 s; 65° C. for 1 min; 60° C. for 8 min; 65° C. for 3 min and 72° C. for 30 s; and a final extension at 72° C. for 2 min) using 50 nM primer concentration of 1200 target-specific forward and tagged reverse primers.

The semi-nested PCR protocol involved three parallel second amplification of a dilution of the first STAs product for 20 cycles of STA (95° C. for 10 min for initial polymerase activation, then 15 cycles of 95° C. for 30 s; 65° C. for 1 min; 60° C. for 5 min; 65° C. for 5 min and 72° C. for 30 s; and a final extension at 72° C. for 2 min) using reverse tag specific primer concentration of 1000 nM, and a concentration of 60 nM for each of 400 target-specific nested forward primers. In the three parallel 400-plex reactions the total of 1200 targets amplified in the first STA were thus amplified.

An aliquot of the STA products was then amplified by standard PCR for 15 cycles with 1 uM of tag-specific forward and barcoded reverse primers to generate barcoded sequencing libraries. An aliquot of each library was mixed with libraries of different barcodes and purified using a spin column.

In this way, 1,200 primers were used in the single cell reactions; the primers were designed to target SNPs found on chromosomes 1, 21 and X. The amplicons were then sequenced using an ILLUMINA GAIIX sequencer. Per sample, approximately 3.9 million 10 reads were generated by the sequencer, with 500,000 to 800,000 million reads mapping to the genome (74% to 94% of all reads per sample).

Relevant maternal and paternal genomic DNA samples from cell lines were analyzed using the same semi-nested 1200-plex assay pool with a similar protocol with fewer cycles and 1200-plex second STA, and sequenced.

The sequencing data was analyzed using informatics methods disclosed herein and the ploidy state was called at the three chromosomes for the samples.

Figure 24:
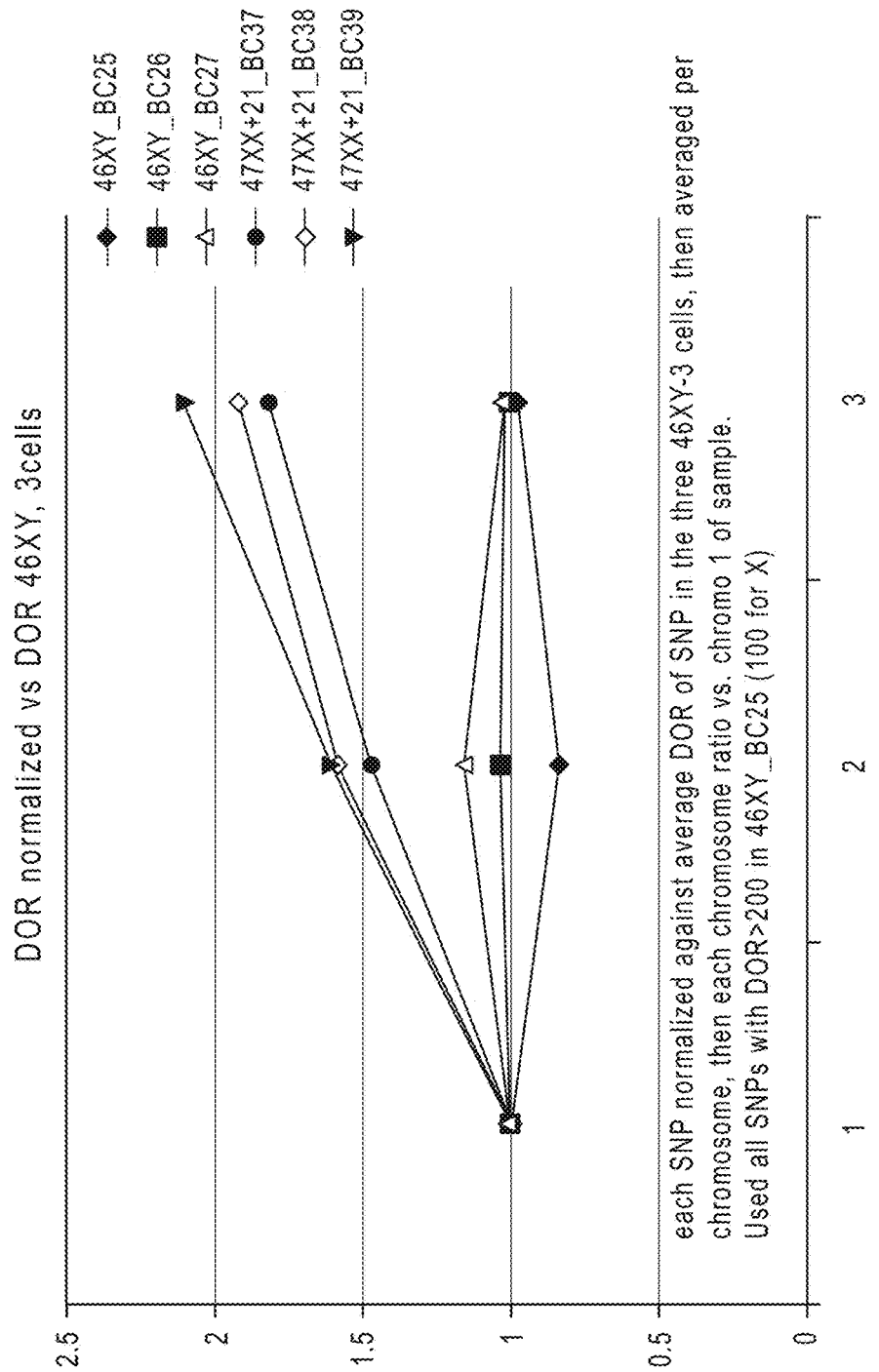
FIG. 24: Read count ratios for six cells at three chromosomes.

FIG. 24 shows normalized depth of read ratios (vertical axis) for six samples at three chromosomes (1=chrom 1; 2=chrom 21; 3=chrom X). The ratios were set to be equal to the number of reads mapping to that chromosome, normalized, and divided by the number of reads mapping to that chromosome averaged over three wells each comprising three 46XY cells. The three sets of data points corresponding to the 46XY reactions are expected to have ratios of 1:1. The three sets of data points corresponding to the 47XX+21 cells are expected to have ratios of 1:1 for chromosome 1, 1.5:1 for chromosome 21, and 2:1 for chromosome X.

Figure 25A:
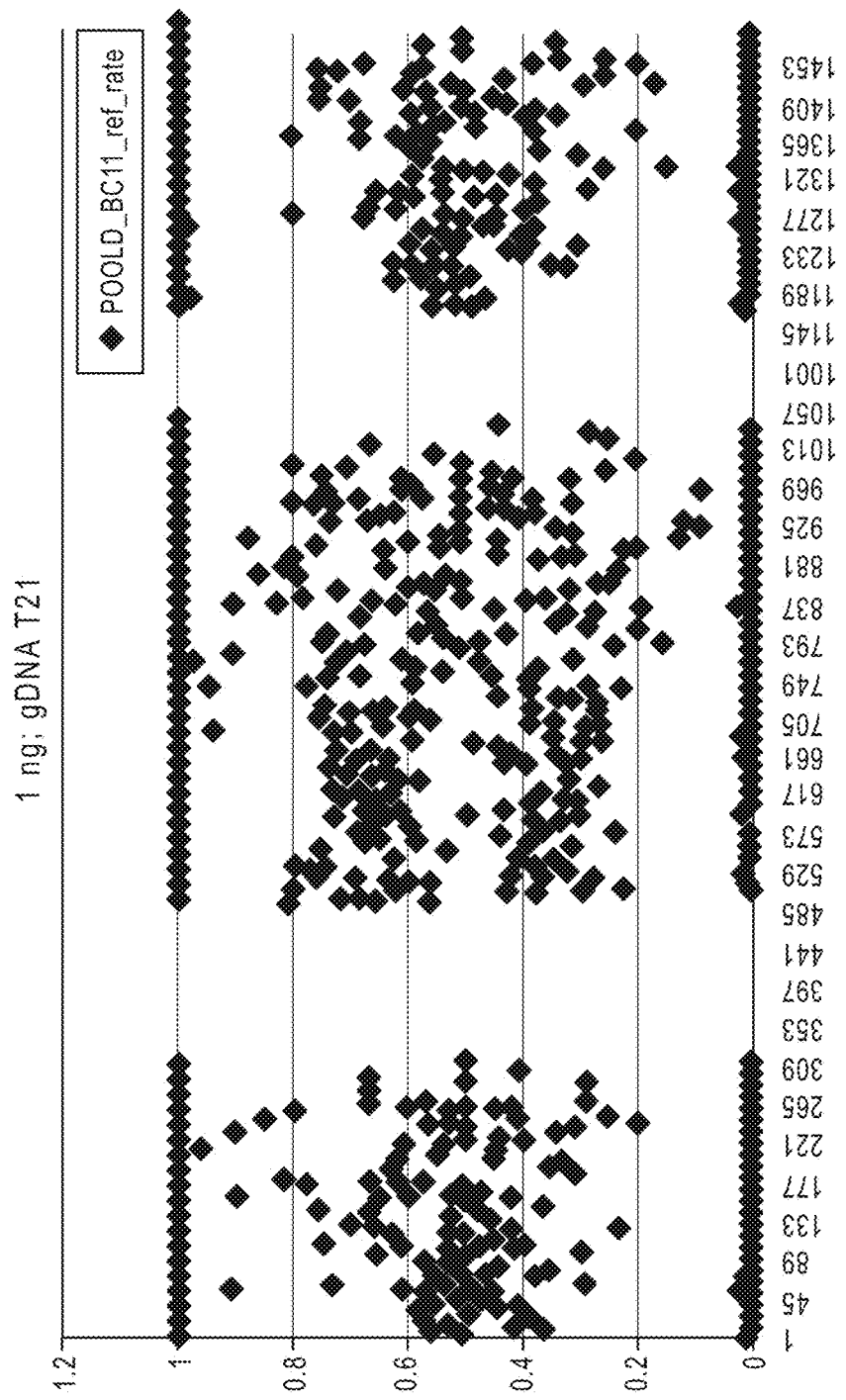
FIGS. 25A-25C: Allele ratios for two three-cell reactions (FIGS. 25B and 25C) and a third reaction run on 1 ng of genomic DNA at three chromosomes (FIG. 25A).
Figure 25B:
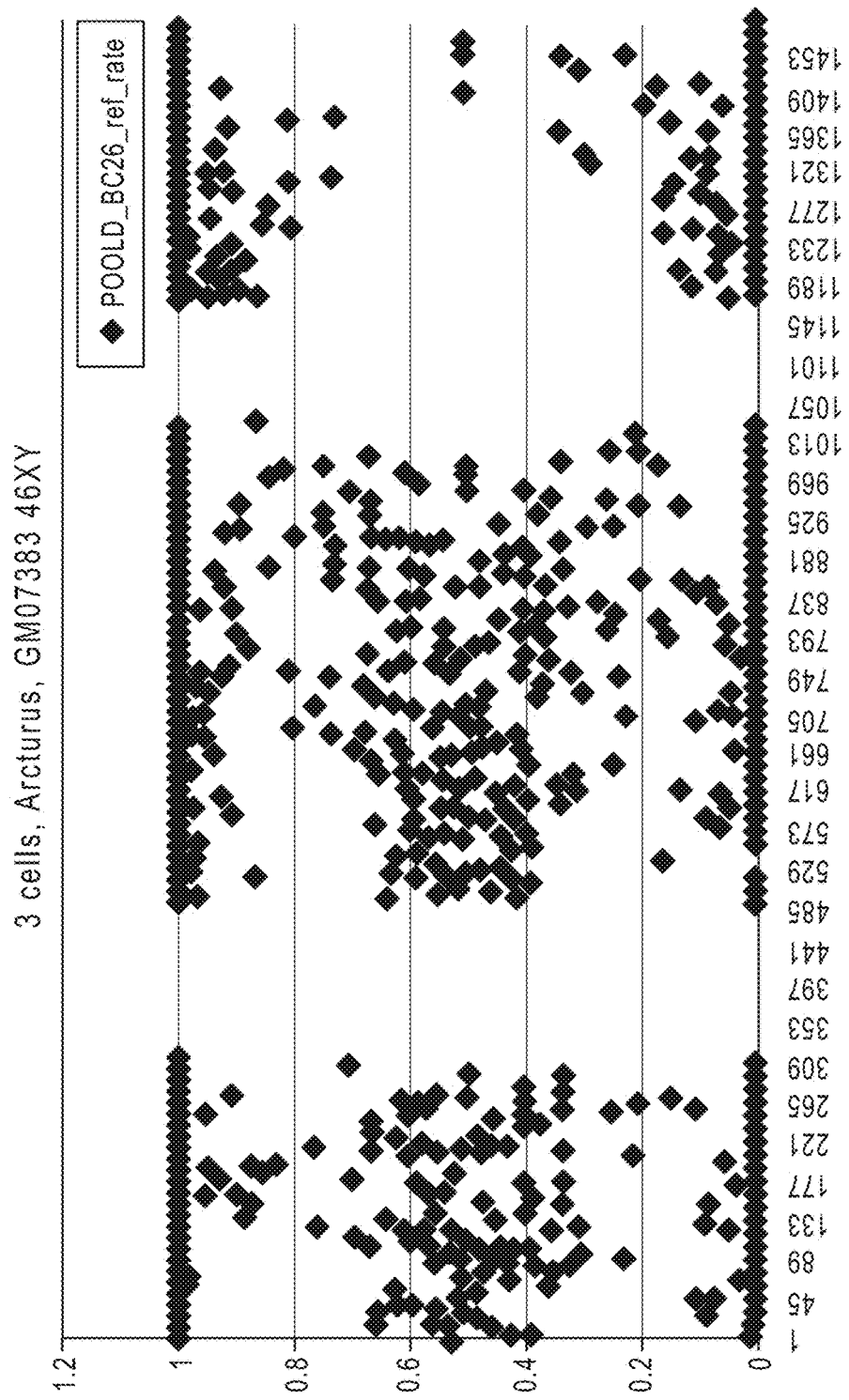
Figure 25C:
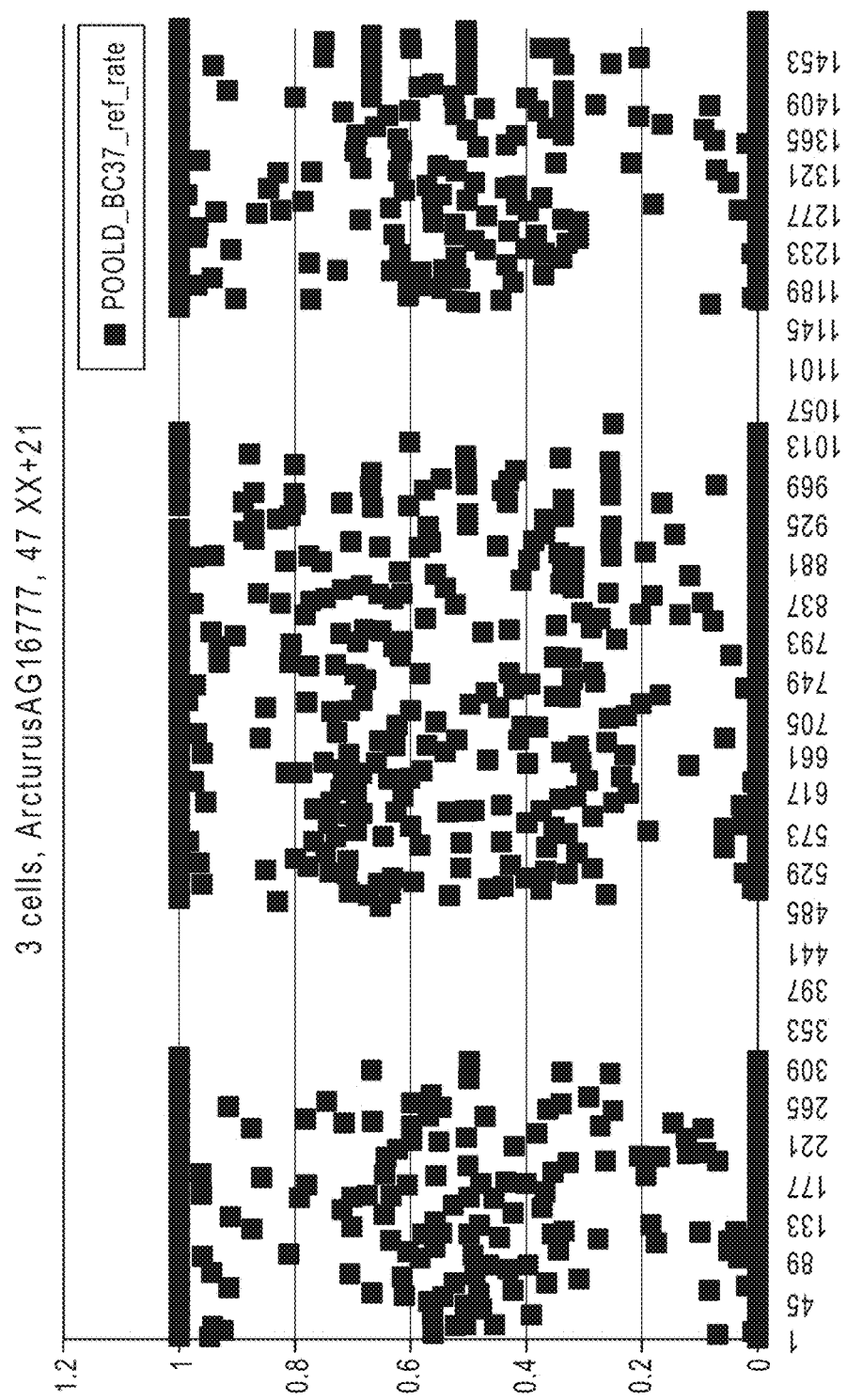
Figure 26A:
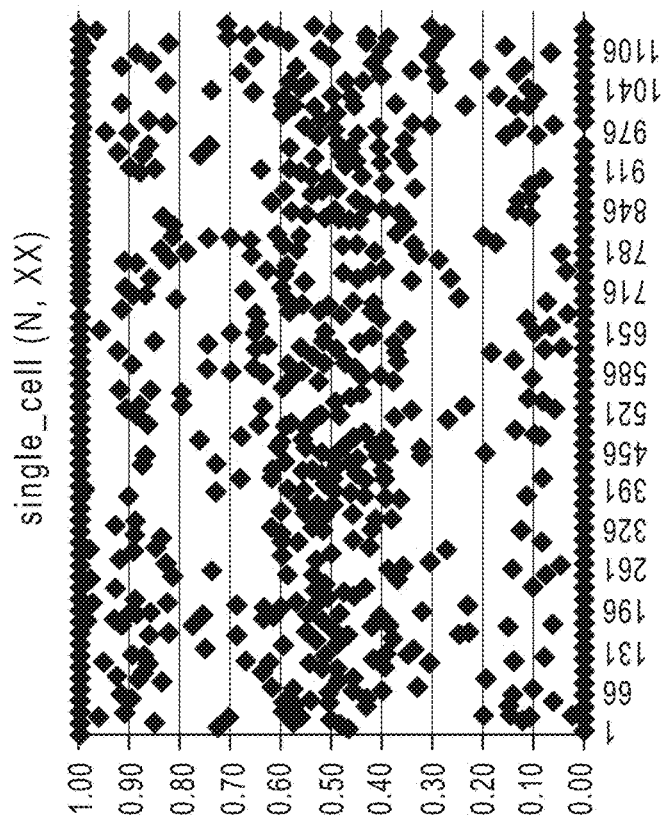
FIGS. 26A and 26B shows the same graphs as in FIG. 25A-25C, but for reactions performed on only one cell.
Figure 26B:
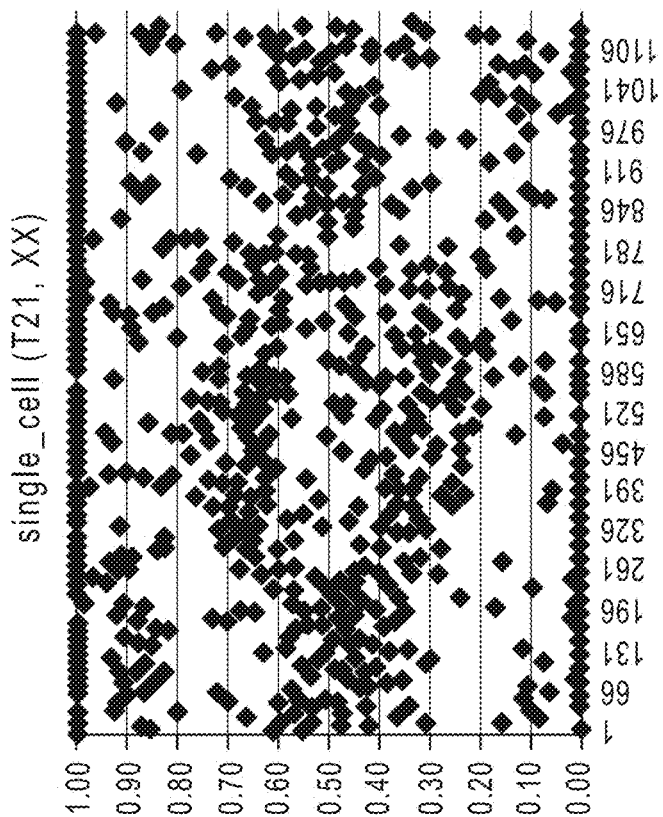

FIG. 25A-25C show allele ratios plotted for three chromosomes (1, 21, X) for three reaction. The reaction in the lower left shows a reaction on three 46XY cells (FIG. 25B). The left region are the allele ratios for chromosome 1, the middle region are the allele ratios for chromosome 21, and the right region are the allele ratios for chromosome X. For the 46XY cells, for chromosome 1 we expect to see ratios of 1, 0.5 and 0, corresponding to AA, AB and BB SNP genotypes. For the 46XY cells, for chromosome 21 we expect to see ratios of 1, 0.5 and 0, corresponding to AA, AB and BB SNP genotypes. For the 46XY cells, for chromosome X we expect to see ratios of 1 and 0, corresponding to A, and B SNP genotypes. The reaction in the lower right shows a reaction on three 47XX+21 cells (FIG. 25C). The allele ratios are segregated by chromosome as in the lower left graph. For the 47XX+21 cells, for chromosome 1 we expect to see ratios of 1, 0.5 and 0, corresponding to AA, AB and BB SNP genotypes. For the 47XX+21 cells, for chromosome 21 we expect to see ratios of 1, 0.67, 0.33 and 0, corresponding to AAA, AAB, ABB and BBB SNP genotypes. For the 47XX+21 cells, for chromosome X we expect to see ratios of 1, 0.5 and 0, corresponding to AA, AB, and BB SNP genotypes. The plot in the upper right was made on a reaction comprising 1 ng of genomic DNA from the 47XX+21 cell line (FIG. 25A). FIGS. and 26B shows the same graphs as in FIG. 25A-25C, but for reactions performed on only one cell. The left graph was a reaction that contained a 47XX+21 cell (FIG. 26A), and the right graph was for a reaction that contained a 46XX cell (FIG. 26B).

From the graphs shown in FIGS. 25A-25C and FIGS. 26A and 26B, it is visually apparent that there are two clusters of dots for chromosomes where we expect to see ratios of 1 and 0; three clusters of dots for chromosomes where we expect to see ratios of 1, 0.5, and 0, and four clusters of dots for chromosomes where we expect to see ratios of 1, 0.67, 0.33 and 0. The parental support algorithm was able to make correct calls on all of the three chromosomes for all of the 45 reactions.

Experiment 15

In one experiment, maternal plasma samples were prepared and amplified using a hemi-nested 19,488-plex protocol. The samples were prepared in the following way: up to 20 mL of maternal blood were centrifuged to isolate the buffy coat and the plasma. The genomic DNA in the maternal sample was prepared from the buffy coat and paternal DNA was prepared from a blood sample or saliva sample. Cell-free DNA in the maternal plasma was isolated using the QIAGEN CIRCULATING NUCLEIC ACID kit and eluted in 50 uL TE buffer according to manufacturer's instructions. Universal ligation adapters were appended to the end of each molecule of 40 uL of purified plasma DNA and libraries were amplified for 9 cycles using adaptor specific primers. Libraries were purified with AGENCOURT AMPURE beads and eluted in 50 ul DNA suspension buffer.

6 ul of the DNA was amplified with 15 cycles of STAR 1 (95° C. for 10 min for initial polymerase activation, then 15 cycles of 96° C. for 30 s; 65° C. for 1 min; 58° C. for 6 min; 60° C. for 8 min; 65° C. for 4 min and 72° C. for 30 s; and a final extension at 72° C. for 2 min) using 7.5 nM primer concentration of 19,488 target-specific tagged reverse primers and one library adaptor specific forward primer at 500 nM.

The hemi-nested PCR protocol involved a second amplification of a dilution of the STAR 1 product for 15 cycles (STAR 2) (95° C. for 10 min for initial polymerase activation, then 15 cycles of 95° C. for 30 s; 65° C. for 1 min; 60° C. for 5 min; 65° C. for 5 min and 72° C. for 30 s; and a final extension at 72° C. for 2 min) using reverse tag concentration of 1000 nM, and a concentration of 20 nM for each of 19,488 target-specific forward primers.

An aliquot of the STAR 2 products was then amplified by standard PCR for 12 cycles with 1 uM of tag-specific forward and barcoded reverse primers to generate barcoded sequencing libraries. An aliquot of each library was mixed with libraries of different barcodes and purified using a spin column.

In this way, 19,488 primers were used in the single-well reactions; the primers were designed to target SNPs found on chromosomes 1, 2, 13, 18, 21, X and Y. The amplicons were then sequenced using an ILLUMINA GAIIX sequencer. For plasma samples, approximately 10 million reads were generated by the sequencer, with 9.4-9.6 million reads mapping to the genome (94-96%), and of those, 99.95% mapped to targeted SNPs with a mean depth of read of 460 and a median depth of read of 350. For comparison, a perfectly even distribution would be: 10M reads/19,488 targets=513 reads/target. For primer-dimers, 30,000 reads were from sequenced primer-dimers (0.3% of the reads generated by the sequencer). For genomic samples, 99.4-99.7% of the reads mapped to the genome, of those, 99.99% of the mapped to targeted SNPs, and 0.1% of the reads generated by the sequencer were primer-dimers.

For plasma samples with 10 million sequencing reads, typically at least 19,350 of the 19,488 targeted SNPs (99.3%) are amplified and sequenced. For DNA samples with 2M sequencing reads, typically at least 19,000 targeted SNPs (97.5%) are amplified and sequenced. The lower number may be due to sampling noise since the number of reads is lower and the sequencer misses some of the amplified products. If desired, the number of sequencing reads can be increased to increase the number of targeted SNPs that are amplified and sequenced.

Relevant maternal and paternal genomic DNA samples amplified using a semi-nested 19,488 outer forward primers and tagged reverse primers at 7.5 nM in the STAR 1. Thermocycling conditions and composition of STAR 2, and the barcoding PCR were the same as for the hemi-nested protocol.

The average fetal fraction for 407 samples was found to be 14.8%. The sequencing data was analyzed using informatics methods disclosed herein and the ploidy state was called at four chromosomes (13, 18, 21, Y) for the fetuses whose DNA was present in 378 of the 407 maternal plasma samples, and at chromosome X in 375 of the 407 maternal plasma samples.

The ploidy calls for all 1,887 chromosomes in the set were called correctly with confidences above 90%. 1882 of the 1887 calls were above 95%; and 1,862 of the 1,887 calls were called with confidences above 99%.

A similar control experiment was performed using water instead of DNA extracted from plasma in the plasma PCR protocol. Based on six such trials of an experiment, 5-6% of the sequenced reads were primer-dimers. Other sequenced reads were due to background noise. This experiment demonstrates that even in the absence of a nucleic acid sample with target loci for the primers to hybridize to (rather than hybridizing to other primers and forming amplified primer dimers) few primer dimers are formed.

Experiment 16

The following experiment illustrates an exemplary method for designing and selecting a library of primers that can be used in any of the multiplexed PCR methods of the invention. The goal is to select primers from an initial library of candidate primers that can be used to simultaneously amplify a large number of target loci (or a subset of target loci) in a single reaction. For an initial set of candidate target loci, primers did not have to be designed or selected for each target locus. Preferably, primers are designed and selected for a large portion of the most desirable target loci.

Step 1

A set of candidate target loci (such as SNPs) were selected based on publically available information about desired parameters for the target loci, such as frequency of the SNPs within a target population or heterozygosity rate of the SNPs (worldwide web at ncbi.nlm.nih.gov/projects/SNP/; Sherry S T, Ward M H, Kholodov M, et al. dbSNP: the NCBI database of genetic variation. Nucleic Acids Res. 2001 Jan. 1; 29(1):308-11, which are each incorporated by reference in its entirety). For each candidate locus, one or more PCR primer pairs were designed using the Primer3 program (the worldwide web at primer3.sourceforge.net; libprimer3 release 2.2.3, which is hereby incorporated by reference in its entirety). If there were no feasible designs for PCR primers for a particular target locus, then that target locus was eliminated from further consideration. If desired, a "target locus score" (higher score representing higher desirability) can be calculated for most or all of the target loci, such as a target locus score calculated based on a weighted average of various desired parameters for the target loci. The parameters may be assigned different weights based on their importance for the particular application that the primers will be used for. Exemplary parameters include the heterozygosity rate of the target locus, the disease prevalence associated with a sequence (e.g., a polymorphism) at the target locus, the disease penetrance associated with a sequence (e.g., a polymorphism) at the target locus, the specificity of the candidate primer(s) used to amplify the target locus, the size of the candidate primer(s) used to amply the target locus, and the size of the target amplicon. In some embodiments, the specificity of the candidate primer for the target locus includes the likelihood that the candidate primer will mis-prime by binding and amplifying a locus other than the target locus it was designed to amplify. In some embodiments, one or more or all the candidate primers that misprime are removed from the library.

Step 2

A thermodynamic interaction score was calculated between each primer and all primers for all other target loci from Step 1 (see, e.g., Allawi, H. T. & SantaLucia, J., Jr. (1998), "Thermodynamics of Internal C-T Mismatches in DNA", *Nucleic Acids Res.* 26, 2694-2701; Peyret, N., Seneviratne, P. A., Allawi, H. T. & SantaLucia, J., Jr. (1999), "Nearest-Neighbor Thermodynamics and NMR of DNA Sequences with Internal A-A, C-C, G-G, and T-T Mismatches", *Biochemistry* 38, 3468-3477; Allawi, H. T. & SantaLucia, J., Jr. (1998), "Nearest-Neighbor Thermodynamics of Internal A-C Mismatches in DNA: Sequence Dependence and pH Effects", *Biochemistry* 37, 9435-9444; Allawi, H. T. & SantaLucia, J., Jr. (1998), "Nearest Neighbor Thermodynamic Parameters for Internal G-A Mismatches in DNA", *Biochemistry* 37, 2170-2179; and Allawi, H. T. & SantaLucia, J., Jr. (1997), "Thermodynamics and NMR of Internal G-T Mismatches in DNA", *Biochemistry* 36, 10581-10594; MultiPLX 2.1 (Kaplinski L, Andreson R, Puurand T, Remm M. MultiPLX: automatic grouping and evaluation of PCR primers. Bioinformatics. 2005 Apr. 15; 21(8):1701-2, which are each hereby incorporated by reference in its entirety). This step resulted in a 2D matrix of interaction scores. The interaction score predicted the likelihood of primer-dimers involving the two interacting primers. The score was calculated as follows:

$$\text{interaction\_score} = \max(-\text{delta}G\_2, 0.8 \cdot (-\text{delta}G\_1))$$

where deltaG_2=Gibbs energy (energy required to break the dimer) for a dimer that is extensible by PCR on both ends, i.e., the 3' end of each primer anneals to the other primer; and deltaG_1=Gibbs energy for a dimer that is extensible by PCR on at least one end.

Step 3:

For each target locus, if there was more than one primer-pair design, then one design was selected using the following method:

1 For each primer-pair design for the locus, find the worst-case (highest) interaction score for the two primers in that design and all primers from all designs for all other target loci.

2 Pick the design with the best (lowest) worst-case interaction score.

Step 4

A graph was built such that each node represented one locus and its associated primer-pair design (e.g., a Maximal Clique problem). One edge was created between every pair of nodes. A weight was assigned to each edge equal to the worst-case (highest) interaction score between the primers associated with the two nodes connected by the edge.

Step 5

If desired, for every pair of designs for two different target loci where one of the primers from one design and one of the primers from the other design would anneal to overlapping target regions, an additional edge was added between the nodes for the two design. The weight of these edges was set equal to the highest weight assigned in Step 4. Thus, Step 5 prevents the library from having primers that would anneal to overlapping target regions, and thus interfere with each other during a multiplex PCR reaction.

Step 6

An initial interaction score threshold was calculated as follows:

weight_threshold=max(edge_weight)−0.05*(max (edge_weight)−min(edge_weight))

where max(edge_weight) is the maximum edge weight in the graph; and min(edge_weight) is the minimum edge weight in the graph.

The initial bounds for the threshold were set as follows:

max_weight_threshold=max(edge_weight)
min_weight_threshold=min(edge_weight)

Step 7

A new graph was constructed consisting of the same set of nodes as the graph from Step 5, only including edges with weights that exceed weight_threshold. Thus, step ignores interactions with scores equal to or below weight_threshold.

Step 8

Nodes (and all of the edges connected to the removed nodes) were removed from the graph of Step 7 until there were no edges left. Nodes were removed by applying the following procedure repeatedly:

1 Find the node with the highest degree (highest number of edges). If there is more than one then pick one arbitrarily.
2 Define the set of nodes consisting of the node picked above and all of the nodes connected to it, but excluding any nodes that have degree less than the node picked above.
3 Choose the node from the set that has the lowest target locus score (lower score representing lower desirability) from Step 1. Remove that node from the graph.

Step 9

If the number of nodes remaining in the graph satisfies the required number of target loci for the multiplexed PCR pool (within an acceptable tolerance), then the method was continued at Step 10.

If there were too many or too few nodes remaining in the graph, then a binary search was performed to determine what threshold values would result in the desired number of nodes remaining in the graphs. If there were too many nodes in the graph then, the weight threshold bounds were adjusted as follows:

max_weight_threshold=weight_threshold

Otherwise (if there are two few nodes in the graph), then the weight threshold bounds were adjusted as follows:

min_weight_threshold=weight_threshold

Then, the weight threshold was adjusted follows:

weight_threshold=(max_weight_threshold+min_weight_threshold)/2

Steps 7-9 were repeated.

Step 10

The primer-pair designs associated with the nodes remaining in the graph were selected for the library of primers. This primer library can be used in any of the methods of the invention.

If desired, this method of designing and selecting primers can be performed for primer libraries in which only one primer (instead of a primer pair) is used for amplification of a target locus. In this case, a node presents one primer per target locus (rather than a primer pair).

Experiment 17

Figure 27:
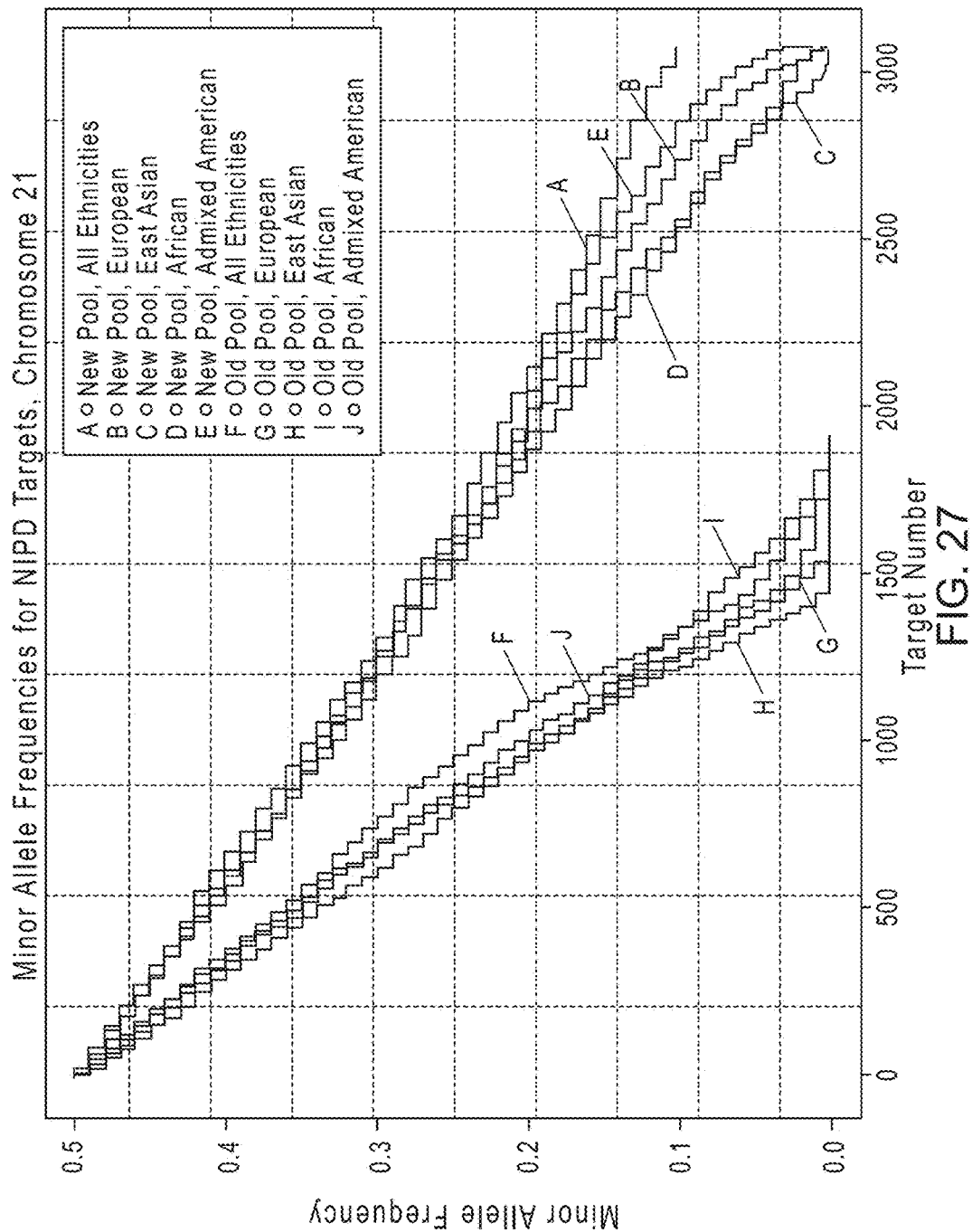
FIG. 27: Comparison of two primer libraries showing the number of loci with a particular minor allele frequency that are targeted by each primer library. This graph shows the number of loci with a particular minor allele frequency that are targeted by each primer library. During the selection of the "new pool" library, more primers were retained. This library enables the amplification of more target loci, especially target loci with relatively large minor allele frequencies (which are the more informative alleles for some method of the invention, such as for detecting fetal chromosomal abnormalities).
Figure 28C:
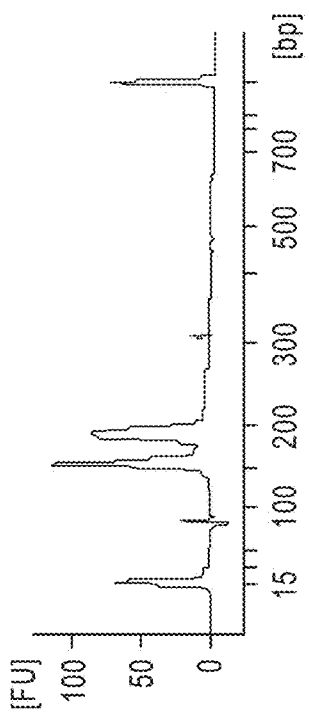
Figure 28B:
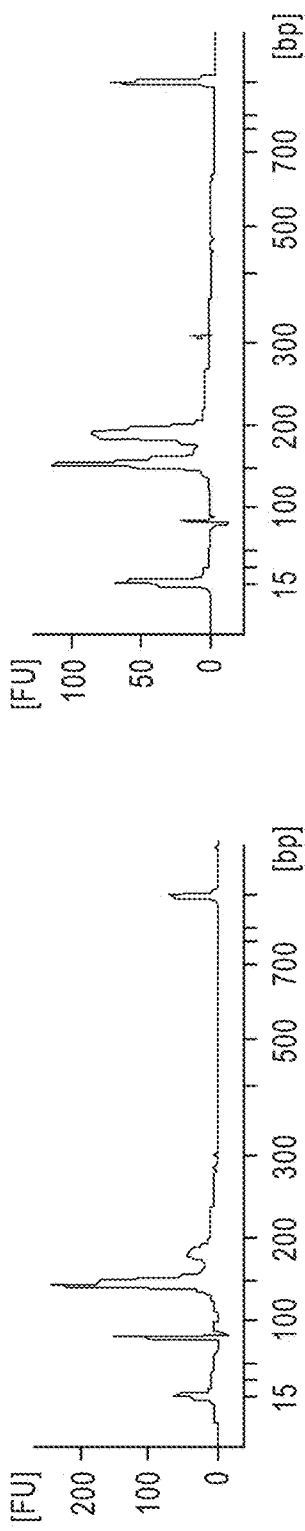
Figure 28E:
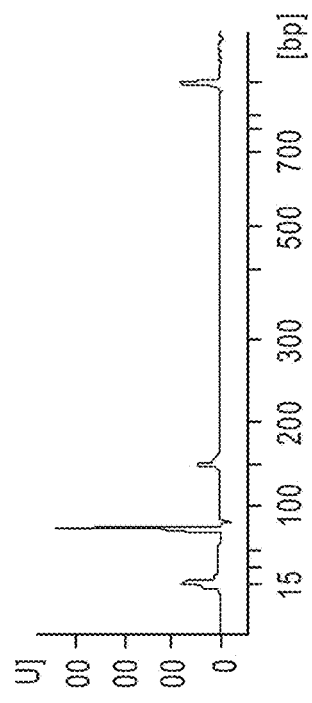
Figure 28D:
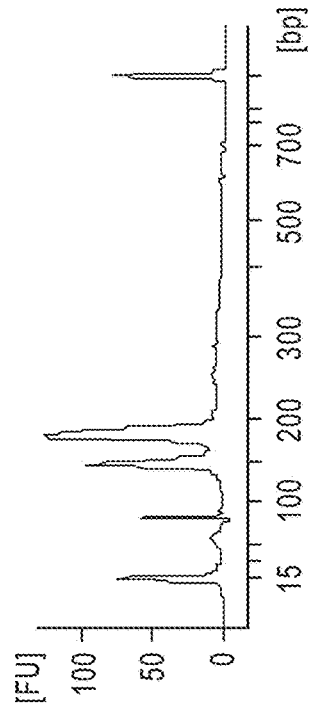
Figure 28J:
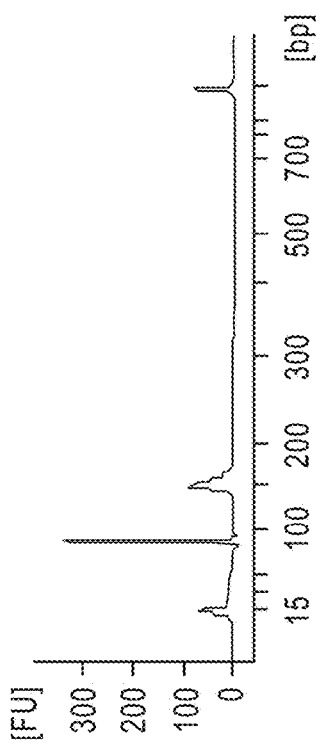
Figure 28K:
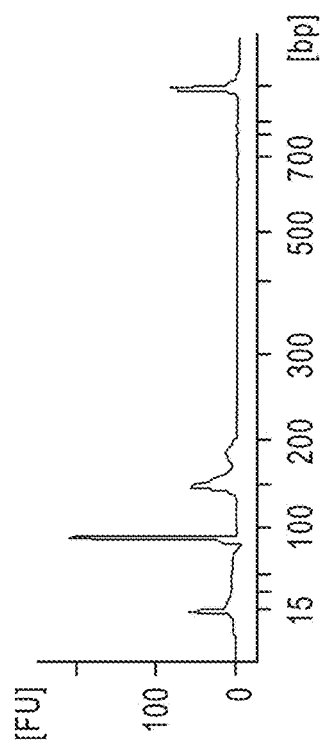
Figure 28L:
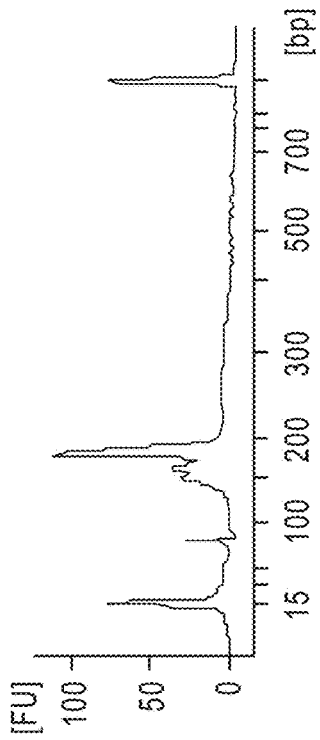
Figure 28M:
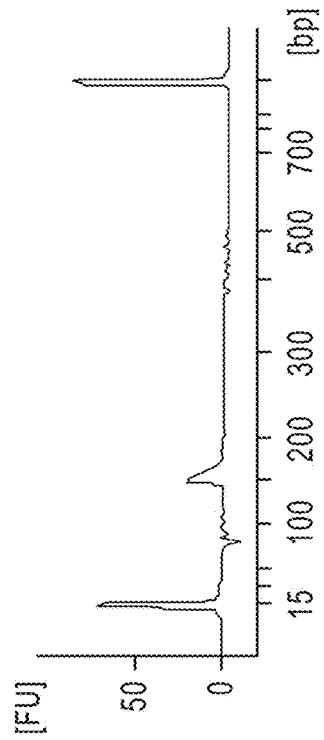

FIG. 27 is a graph comparing two primer libraries designed using the methods of the invention. This graph shows the number of loci with a particular minor allele frequency that are targeted by each primer library. During the selection of the "new pool" library, more primers were retained. This library enables the amplification of more target loci, especially target loci with relatively large minor allele frequencies (which are the more informative alleles for some method of the invention, such as for detecting fetal chromosomal abnormalities).

These primer libraries were used in the following multiplex PCR method. Blood (20-40 mL) was collected from each subject into two to four CELL-FREE™ DNA tubes (Streck). Plasma (a minimum of 7 mL) was isolated from each sample via a double centrifugation protocol of 2,000 g for 20 min, followed by 3,220 g for 30 min, with supernatant transfer following the first spin. cfDNA was isolated from 7-20 mL plasma using the QIAGEN QIAamp Circulating Nucleic Acid kit and eluted in 45 uL TE buffer. Pure maternal genomic DNA was isolated from the buffy coat obtained following the first centrifugation, and pure paternal genomic DNA was prepared similarly from a blood, saliva or buccal sample.

Maternal cfDNA, maternal genomic DNA, and paternal genomic DNA samples were pre-amplified for 15 cycles using 11,000 target-specific assays and an aliquot was transferred to a second PCR reaction of 15 cycles using nested primers. Finally, samples were prepared for sequencing by adding barcoded tags in a third 12-cycle round of PCR. Thus, 11,000 targets were amplified in a single reaction; the targets included SNPs found on chromosomes 13, 18, 21, X, and Y. The amplicons were then sequenced using an ILLUMINA GAIIx or HISEQ sequencer. Parental genotypes were sequenced at a lower read depth (~20% of cfDNA read depth) than the fetal genotypes.

Experiment 18

If desired, the size and quantity of the PCR products can be analyzed using standard methods, such as the use of the Agilent Technologies 2100 Bioanalyzer (FIG. 28A-M). For example, direct PCR methods described herein without nesting were used in 2,400-plex (FIGS. 28B-28G) and 19,488-plex experiments (FIGS. 28H to 28M). The amount of primer was 10 nM for FIGS. 28B-28D and 28H to 28J. The amount of primer was 1 nM for FIGS. 28E-28G and 28K to 28M. The amount of input DNA was 24 ng for FIGS. 28B, 28E, 28H, and 28K; 80 ng for FIGS. 28C, 28F, 28I, and 28L; and 250 ng for FIGS. 28D, 28G, 28J, and 28M. More input DNA resulted in a greater proportion of the desired 180 base pair product. The peak at 140 base pairs is a primer dimer product.

Experiment 19

A proof-of-principle study demonstrated the detection of T13, T18, T21, 45,X, and 47,XXY with equally high accuracies across all chromosomes.

Patients

Pregnant couples were enrolled at specific prenatal care centers under protocols approved by an Institutional Review Board pursuant to local laws. Inclusion criteria were at least 18 years of age, gestational age of at least nine weeks, singleton pregnancies, and signed informed consent. Blood samples were drawn from pregnant mothers, and a blood or buccal sample was collected from the father. Samples from 2 pregnancies with T13 (Patau Syndrome), 2 with T18 (Edwards Syndrome), 2 with T21 (Down's Syndrome), 2 with 45,X, 2 with 47,XXY, and 90 normal pregnancies were selected prior to testing from a cohort of ~500 women to test which chromosomal abnormalities the method detects. Normal fetal karyotype was confirmed by molecular karyotyping for the samples where post-birth child tissue was available. Euploid sample were drawn prior to invasive testing from low-risk women. Aneuploid samples were drawn at least 7 days after invasive testing and aneuploidy was confirmed via cytogenetic karyotyping or fluorescence in situ hybridization at independent laboratories.

Sample Preparation and Multiplex PCR

For the data in FIGS. 30A-E, 30G, 30H, and 31A-31G, sample preparation and 19,488-plex-PCR were performed as described in Experiment 15. For the data in FIG. 30F, sample preparation and 11,000-plex-PCR were performed as described in Experiment 17.

Methodology and Data Analysis

Figures 29A, 29B, 29C, 29D, 29E:
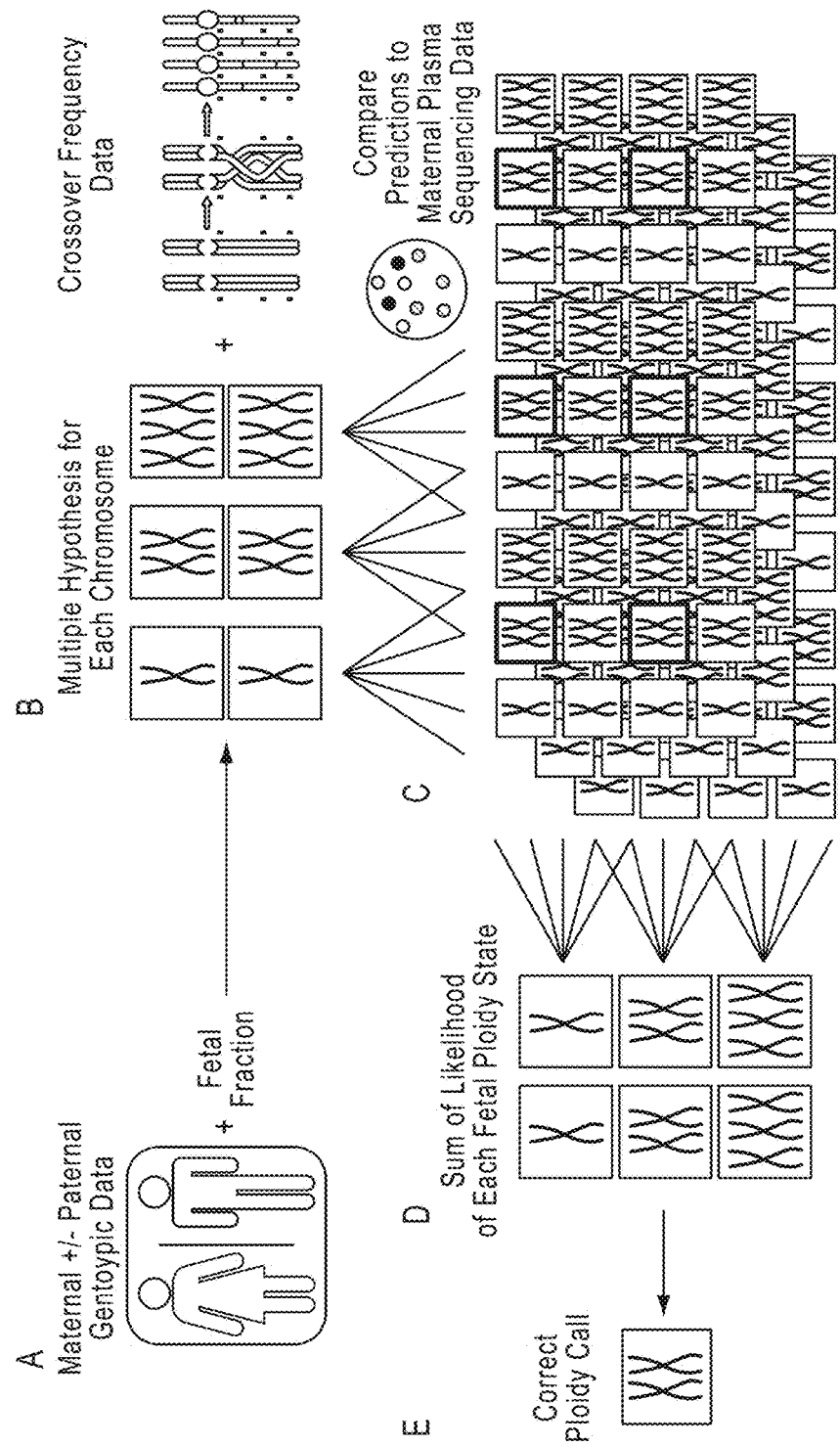
FIGS. 29A-29E: Cartoon depiction of a method of the invention for the determination of a fetal aneuploidy (FIG. 29A). Maternal and paternal genotype data (from blood or buccal swabs) and crossover frequency data from the HapMap database are utilized to generate (FIG. 29B) multiple independent hypotheses for each potential fetal ploidy state in silico (FIG. 29C). Each of these hypotheses is expanded to include sub-hypotheses with take into consideration the different possible crossover points. The data model predicts what the sequencing data would look like (the expected allele distributions) given each hypothetical fetal genotype and at different fetal cfDNA fractions, and is compared to the actual sequencing data; the likelihood for each hypothesis is determined using Bayesian statistics. In this hypothetical example, the hypotheses with the highest likelihoods (euploidy) are determined (FIG. 29D and FIG. 29E). The individual likelihoods from FIG. 29C are summed for each copy number hypothesis family (monosomy, disomy, or triploidy). The hypothesis with the maximum likelihood is called as the ploidy state, reveals the fetal fraction, and represents the sample-specific calculated accuracy.

The algorithm considers parental genotypes and crossover frequency data (such as data from the HapMap database) to calculate expected allele distributions for 19,488 polymorphic loci for a very large number possible fetal ploidy states, and at various fetal cfDNA fractions. (FIGS. 29A-29C). Unlike allele ratio based-methods, it also takes into account linkage disequilibrium, and uses non-Gaussian data models to describe the expected distribution of allele measurements at a SNP given observed platform characteristics and amplification biases. It then compares the various predicted allele distributions to the actual allelic distributions as measured in the cfDNA sample (FIG. 29C), and calculates the likelihood of each hypothesis (monosomy, disomy, or trisomy, for which there are numerous hypotheses based on the various potential crossovers) based on the sequencing data. The algorithm sums the likelihoods of each individual monosomy, disomy, or trisomy hypotheses (FIG. 29D), and calls the ploidy state with the maximum overall likelihood as the copy number and fetal fraction (FIG. 29E). Although laboratory researchers were not blinded to sample karyotype, the algorithm called the ploidy states without human intervention and was blind to the truth.

Data Interpretation

Graphical Representations of the Generated Data

To determine the ploidy state of a chromosome of interest, the algorithm considers the distribution of sequence counts from each of two possible alleles at 3,000 to 4,000 SNPs per chromosome. It is important to note that the algorithm makes ploidy calls using an approach that does not lend itself to visualization. Thus, for the purposes of illustration, the data is displayed here in a simplified fashion as ratios of the two most likely alleles, labeled as A and B, so that the relevant trends can be more readily visualized. This simplified illustration does not take into account some of the features of the algorithm. For example, two important aspects of the algorithm that are not possible to illustrate with a method of visualization that displays allele ratios are: 1) the ability to leverage linkage disequilibrium, i.e. the influence that a measurement at one SNP has on the likely identity of a neighboring SNP, and 2) the use of non-Gaussian data models that describe the expected distribution of allele measurements at a SNP given platform characteristics and amplification biases. Also note that the algorithm only considers the two most common alleles at each SNP, ignoring other possible alleles.

The graphical representations in FIG. 30A-30H include samples for which two, one, or three fetal chromosomes are present. Generally, these indicate euploidy (FIGS. 30A-30C) monosomy (FIG. 30D), and trisomy (FIGS. 30E-30H), respectively. In all plots, each spot represents a single SNP, where the targeted SNPs are plotted sequentially from left to right for one chromosome along the horizontal axes. The vertical axes indicate the number of reads for the A allele as a fraction of the total number of reads for both the A and B alleles for that SNP. Note that the measurements are made on total cfDNA isolated from maternal blood, and the cfDNA includes both maternal and fetal cfDNA; thus, each spot represents the combination of the fetal and maternal DNA contribution for that SNP. Therefore, increasing the proportion of maternal cfDNA from 0% to 100% will gradually shift some spots up or down within the plots, depending on the maternal and fetal genotype. This is described in more detail below with the corresponding plots.

If desired to facilitate visualization, the spots may be color-coded according to maternal genotype, as maternal genotype contributes more to the localization of each spot and the majority of trisomies are maternally-inherited; this assists in visualizing ploidy states. Specifically, SNPs for which the maternal genotype is AA may be indicated in red, those for which the maternal genotype is AB may be indicated in green, and those for which the maternal genotype is BB may be indicated in blue.

In all cases, SNPs that are homozygous for the A allele (AA) in both the mother and the fetus are found tightly associated with the upper limit of the plots, as the fraction of A allele reads is high because there should be no B alleles present. Conversely, SNPs that are homozygous for the B allele in both the mother and the fetus are found tightly associated with the lower limit of the plots, as the fraction of A allele reads is low because there should be only B alleles. The spots that are not tightly associated with the upper and lower limits of the plots represent SNPs for which the mother, the fetus, or both are heterozygous; these spots are useful for identifying fetal ploidy, but can also be informative for determining paternal versus maternal inheritance. These spots segregate based on both maternal and fetal genotypes and fetal fraction, and as such the precise position of each individual spot along the y-axis depends on both stoichiometry and fetal fraction. For example, loci where the mother is AA and the fetus is AB are expected to have a different fraction of A allele reads, and thus different positioning along the y-axis, depending on the fetal fraction.

Two Chromosomes Present

Figures 30A, 30B, 30C:
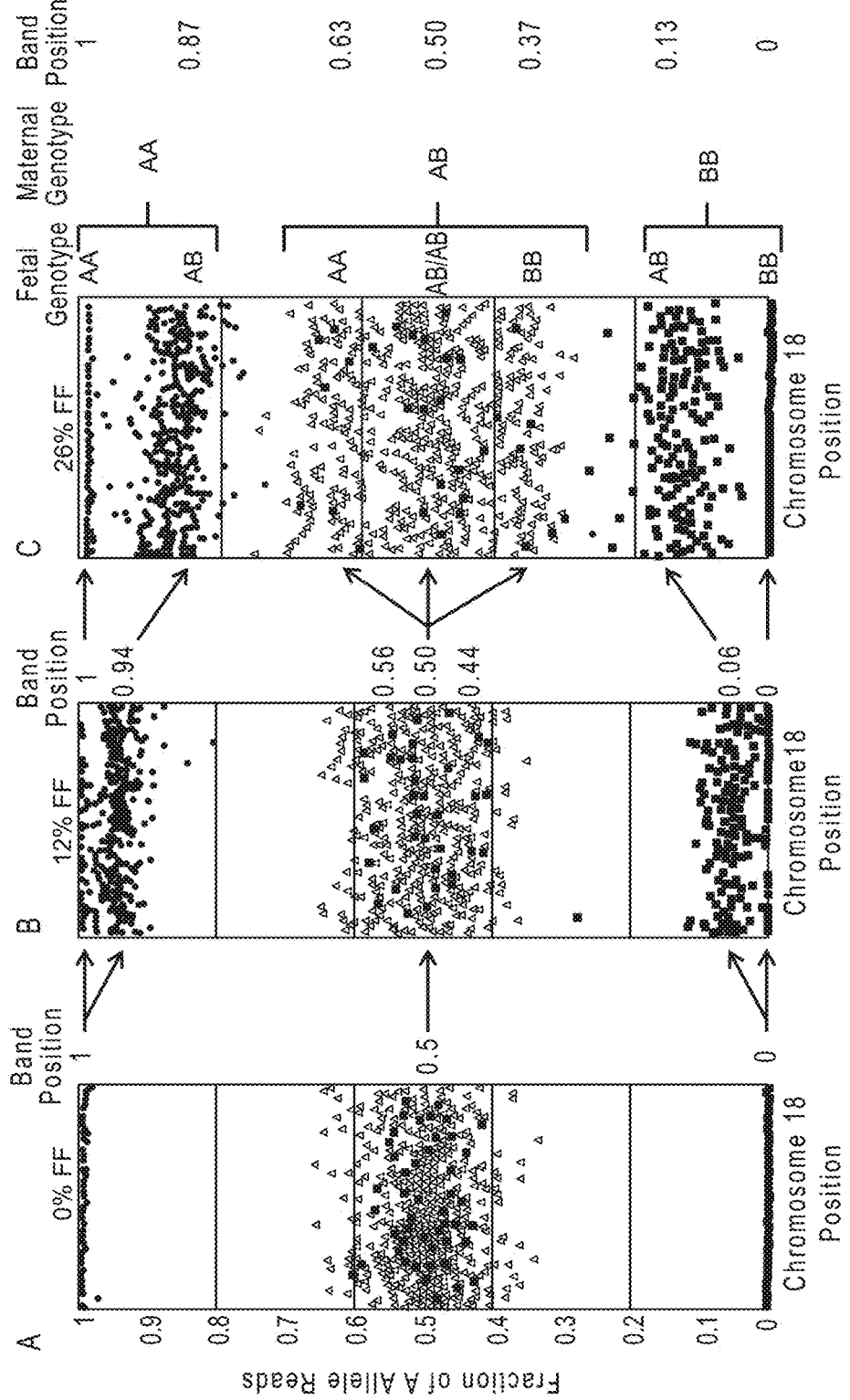

FIGS. 30A-30C depict data that indicate the presence of two chromosomes when the sample is entirely maternal (no fetal cfDNA present, FIG. 30A), contains a moderate fetal cfDNA fraction (FIG. 30B), or contains a high fetal cfDNA fraction (FIG. 30C).

FIG. 30A shows data obtained from cfDNA isolated from the blood of a non-pregnant woman. When there is no fetal cfDNA present and the sample contains only maternal cfDNA, the plots represent purely the euploid maternal genotype; the hallmark pattern includes "clusters" of spots: a red cluster tightly associated with the top of the plot (SNPs where the maternal genotype is AA), a blue cluster tightly associated with the bottom of the plot (SNPs where the maternal genotype is BB), and a single, centered green cluster (SNPs where the maternal genotype is AB).

When fetal cfDNA is present, the location of the spots shifts such that the clusters segregate into discrete "bands". Note that for samples with a fetal fraction of 0%, the groupings of spots are referred to as "clusters" (as in FIG. 30A), and for all samples with a fetal fraction of >0%, the groupings of spots are referred to as "bands" (as in FIGS.

30B-30J). If the fetal fraction is high enough, these discrete bands will be readily visible. Specifically, FIGS. 30B and 30C demonstrate the characteristic pattern associated with two fetal chromosomes present at moderate and high fetal fractions, respectively. This pattern includes three central green bands that correspond to SNPs that are heterozygous in the mother, and two "peripheral" bands each at both the top (red) and bottom (blue) of the plots that correspond to SNPs that are homozygous in the mother.

FIG. 30B shows data obtained from cfDNA isolated from a plasma sample from a woman carrying a euploid fetus and with a 12% fetal cfDNA fraction. Here, the clusters of spots tightly associated with the top and bottom of the plot segregate into two discrete bands each: one red and one blue external peripheral band that remains tightly associated with the upper or lower limit of the plots, and one red and one blue internal peripheral band that has separated from the limits of the plots. These internal peripheral bands, centered around 0.92 and 0.08, represent SNPs for which the maternal genotype is AA and the fetal genotype is AB (indicated in red), and SNPs for which the maternal genotype is BB and the fetal genotype is AB (indicated in blue), respectively. The center cluster of green spots broadens, but at this fetal fraction the segregation into distinct bands is not readily visible.

At a high fetal cfDNA fraction, the typical pattern that indicates the presence of two chromosomes (a trio of green bands as well as two red and two blue peripheral bands) is readily apparent. FIG. 30C displays data obtained from a plasma sample from a woman carrying a euploid fetus at a fetal cfDNA fraction of 26%. Here, the peripheral bands have separated such that the internal band has shifted towards the center of the plot due to the altered levels of B alleles from the increased fetal cfDNA fraction. Significantly, at higher fetal fractions, the separation of the center green cluster into three distinct bands is now readily apparent. This central trio of bands, in this case clustering around 0.37, 0.50 and 0.63, corresponds to those SNPs where the maternal genotype is AB, and the fetal genotype is AA (top), AB (middle) and BB (bottom).

These hallmark patterns, namely three green bands and four peripheral bands (two red and two blue), indicate the presence of two chromosomes, as in autosomal euploidy or for the X chromosome in a female (XX) fetus.

One Chromosome Present

Figures 30D, 30E:
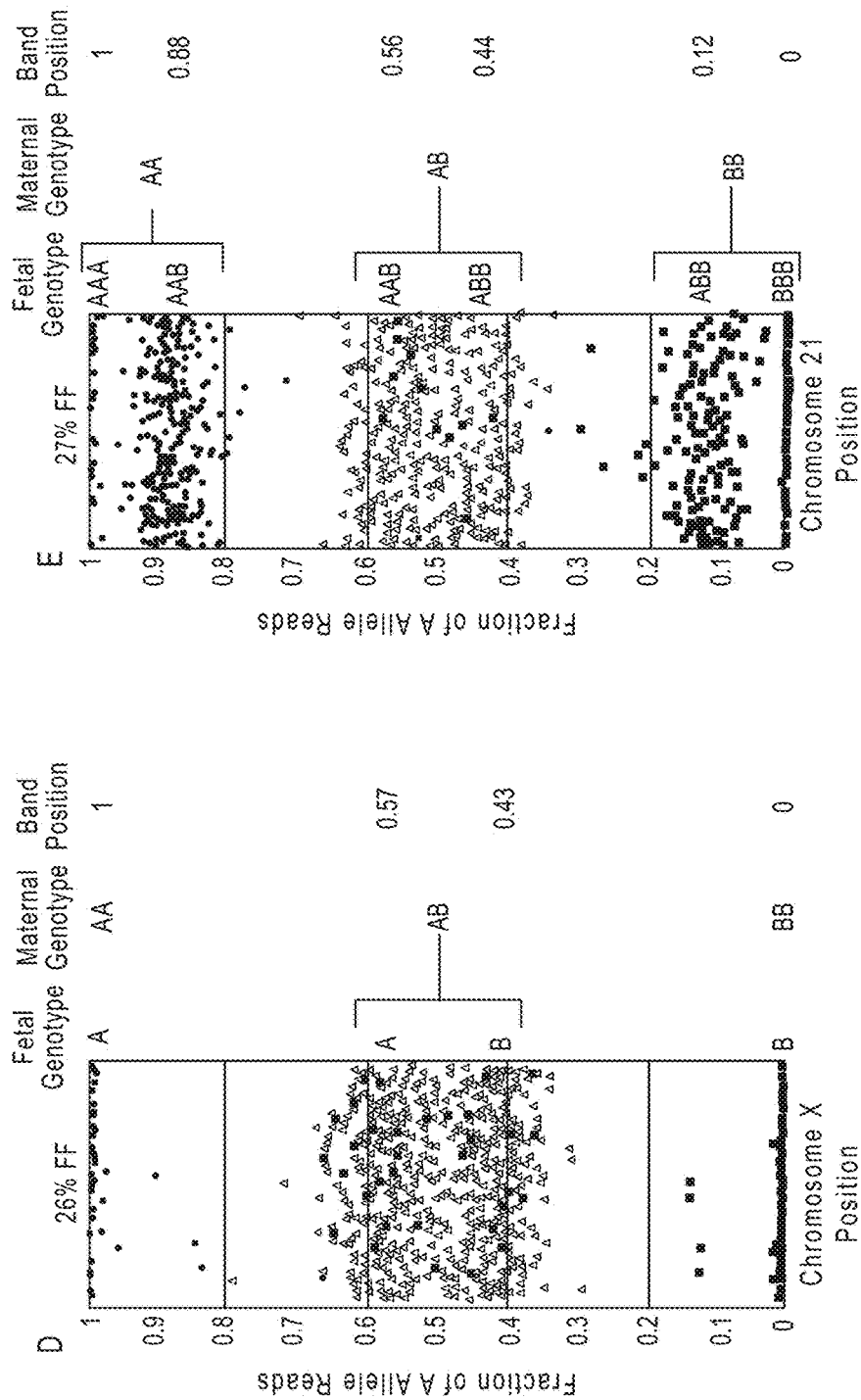
Figure 30H:
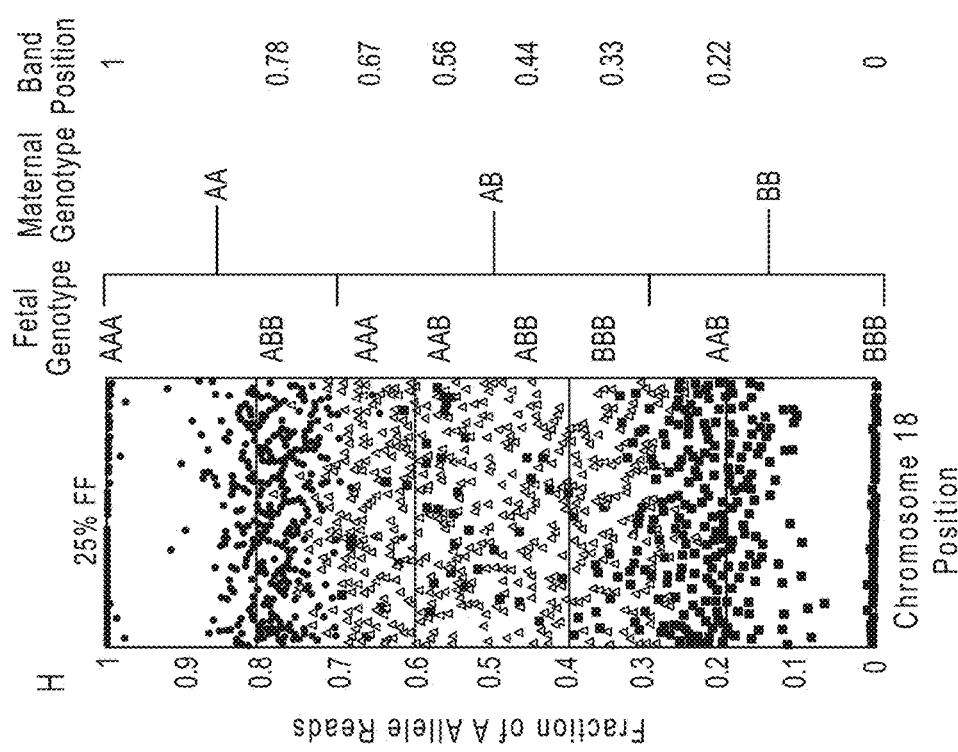

When the fetus only inherits a single chromosome, and thus only inherits a single allele, heterozygosity of the fetus is not possible. As such, the only possible fetal SNP identities are A or B. Thus, maternally-inherited monosomic chromosomes have a characteristic pattern of two central green bands that represent SNPs for which the mother is heterozygous, and only have single peripheral red and blue bands that represent SNPs for which the mother is homozygous, and which remain tightly associated with the upper and lower limits of the plots (1 and 0), respectively (FIG. 30D). Note the absence of internal peripheral bands. This pattern indicates the presence of one chromosome, as in maternally-inherited autosomal monosomy, or for the X chromosome in a male (XY) fetus.

Three Chromosomes Present

Trisomic chromosomes have three characteristic patterns. The first pattern indicates maternally-inherited meiotic trisomy, a meiotic error where the fetus inherited two homologous, non-identical chromosomes from the mother (FIG. 30E); this pattern includes two central green bands with two each of the peripheral red and blue bands. The second pattern indicates paternally-inherited meiotic trisomy, where the fetus inherited two homologous, non-identical chromosomes from the father (FIG. 30F); this pattern includes four central green bands and three each of the peripheral red and blue bands. The third pattern indicates either maternally- (FIG. 30G) or paternally-inherited (FIG. 30H) mitotic trisomy, a mitotic error where the fetus inherited two identical chromosomes from either the mother or the father; this pattern includes four central green bands with two each of the peripheral red and blue bands. Maternally- and paternally-inherited mitotic trisomies can be distinguished by the placement of the flanking red and blue bands, such that the red and blue internal peripheral bands (those not associated with the limits of the plots) are closer to the center in paternally-inherited mitotic trisomy. This is due to the paternal contribution of identical chromosomes. Note that our previous results indicate that at the blastomere stage, 66.7% of maternally-inherited trisomies are meiotic, and that only 10.2% of trisomies are paternally-inherited.

For the Y chromosome, the PS method considers a different set of hypotheses: zero, one, or two chromosomes present. As there is no maternal contribution to the sequence reads at each locus and because heterozygous loci are not possible (cases of two Y chromosomes necessarily involve two identical chromosomes), the bands remain tightly associated with the top (A alleles) or the bottom (B alleles) of the plot (data not shown), and analysis is greatly simplified, relying on quantitative allele count data. Note that since the method interrogates SNPs, it uses homologous non-recombinant SNPs from the Y chromosome, thus obtaining data on both X and Y for one probe pair.

Identifying Aneuploidies

Identification of autosomal aneuploidies using this plot-based visualization method is straightforward given a sufficient fetal fraction, and requires only identifying plots for which there are an abnormal number of chromosomes present, as described above. Combining the knowledge of copy number of the X and Y chromosomes identifies whether sex chromosome aneuploidies are present. Specifically, plots representing a fetus with a 47,XXX genotype will have a typical "three-chromosome" pattern, and plots representing a fetus with a 47,XXY genotype will have the typical "two-chromosome" pattern for the X chromosome, but will also have allele reads indicating the presence of one Y chromosome. The method is similarly able to call 47,XYY, where a "one chromosome" pattern indicates the presence of a single X chromosome, and allele reads indicate the presence of two Y chromosomes. A fetus with a 45,X genotype will have the typical "one-chromosome" pattern for the X chromosome, and data indicating zero Y chromosomes.

Effects of Fetal Fraction

As discussed above, the number of sequence reads from the fetus contributes to the precise location of each spot along the y-axis in the plots. As fetal fraction will affect the proportion of reads that originate from the fetus and the mother, it will also affect the positioning of each spot. At a high fraction of fetal cfDNA (generally above ~20%), as in FIGS. 30C-30E and FIGS. 30G and 30H, it is readily apparent that although the spots cluster based mainly on maternal genotype, the presence of fetal DNA from alleles whose genotype is distinct from the maternal genotype shift the clusters into multiple, distinct bands. However, as the fetal fraction decreases (as in FIGS. 30B and 30F), the spots regress towards the poles and center of the plot, resulting in tighter clusters. Specifically, the set of peripheral red bands, where the maternal genotype is AA, regress towards the top of the plot; the set of peripheral blue bands, where the maternal genotype is BB, regress towards the bottom; the set of central green bands, where the mother is heterozygous, condense into a single cluster at the center of the plot (compare FIGS. 30B and 30C). Although aneuploidy is not readily apparent by eye using this visualization technique for low fetal fraction cases, the algorithm is able to identify ploidy states with a very low fetal fraction, such as 3% fetal fraction. It is able to do this because the statistical technique compares the observed data to very precise data models that predict the allele distributions for a given sample parameter set (including copy number, parental genotypes, and fetal fraction, for example). Data model precision is critical in low fetal fraction cases, as the differences between the allele distributions for different ploidy states are proportional to the fetal fraction. In addition, the algorithm is able to determine when a data set does not contain enough data to make a confident fetal ploidy determination.

Results

Figure 31G:
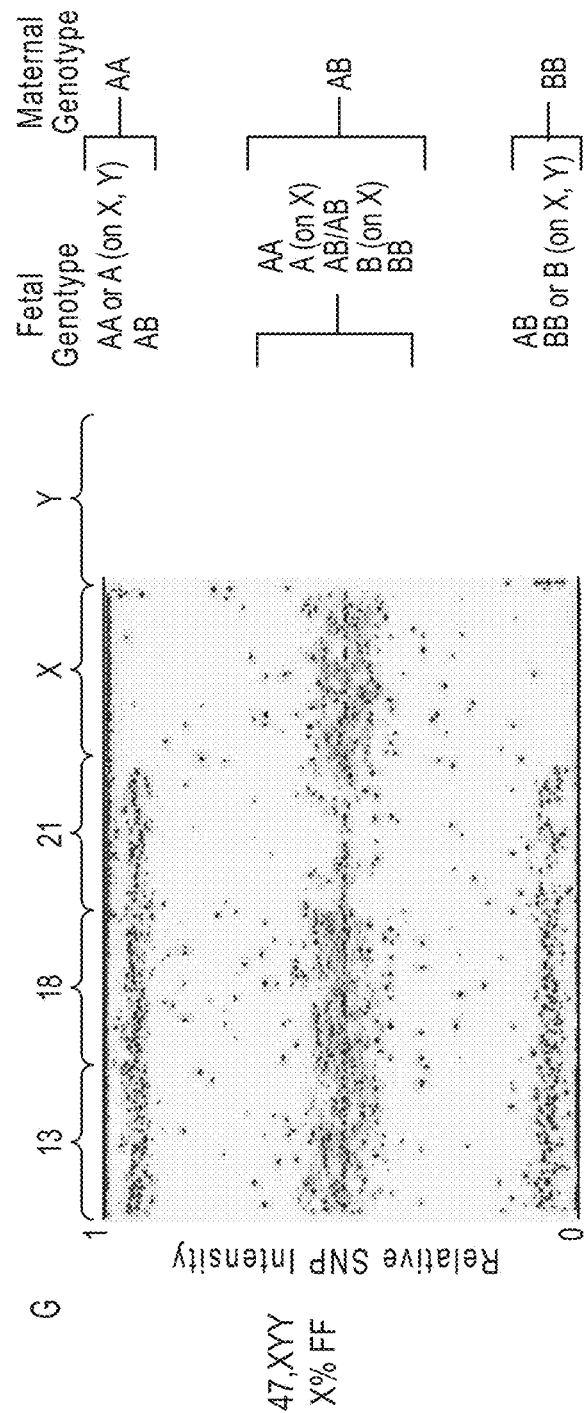
FIG. 31: Graphical representations of (FIG. 31A) euploid, (FIG. 31B) T13, (FIG. 31C) T18, (FIG. 31D) T21, (FIG. 31E) 45,X, (FIG. 31F) 47,XXY, and (FIG. 31G) 47,XYY test samples as indicated. Each chromosome is indicated at the top of the plot, fetal and maternal genotypes are indicated to the right of the plots, the x-axis represents the linear position of the SNPs along each chromosome, and the y-axis indicates the number of A allele reads as a fraction of the total reads. Note the altered cluster positioning based on fetal fraction, as described herein. Each spot represents a single SNP locus. Fetal and maternal genotypes are indicated to the right of the plot, and chromosome identities are indicated at the top of the plots.

Sequencing reads that mapped to targeted SNPs were deemed to be informative and were used by the algorithm. More than 95% of targeted loci were observed in the sequencing results. The plots for visualizing key ploidy calls are depicted in FIG. 31A-31G. FIG. 31A indicates a euploid sample. Here, chromosomes 13, 18, and 21 have the typical "two chromosome" pattern (as described herein). This includes a trio of center green bands, and two red and two blue peripheral bands. This, together with the two center green bands for the X chromosome and the presence of Y chromosome bands along the plots' peripheries, indicate a euploid XY genotype.

The most prevalent autosomal trisomies, T13, T18, and T21, are indicated by the plots in FIGS. 31B, 31C, and 31D, respectively. Specifically, FIG. 31B depicts a T13 sample. Here, chromosomes 18 and 21 display the typical "two chromosome" pattern, chromosome X displays the typical "one chromosome" pattern, and there are reads from the Y chromosome. Together, this indicates disomy at chromosomes 18 and 21, and identifies a fetal XY genotype. However, chromosome 13 depicts a typical "three chromosome" pattern—specifically. Similarly, FIG. 31C depicts a T18 sample, and FIG. 31D depicts a T21 sample.

The method is also able to detect sex chromosome aneuploidies, including 45,X (FIG. 31E), 47,XXY (FIG. 31F), and 47,XYY (FIG. 31G). Note that the method is calling copy number at chromosomes 13, 18, 21, X, and Y; the overall chromosome number is reported assuming disomy at the remaining chromosomes. The X chromosome regions of the plot depicting a 45,X sample reveals the presence of a single chromosome. However, the lack of reads from the Y chromosome, coupled with the "two chromosome" pattern for chromosomes 13, 18, and 21, indicate a 45,X genotype. Conversely, the 47,XXY samples generate a plot revealing the presence of two X chromosomes. The data also revealed reads for alleles from the Y chromosome. Together with the presence of two copies of chromosomes 13, 18, and 21, this indicates a 47,XXY genotype. A 47,XYY genotype is indicated by the presence of a "one chromosome" pattern for the X chromosome, and reads indicating the presence of two Y chromosomes.

Discussion

This method detected T13, T18, T21, 45,X, 47,XXY, and 47,XYY non-invasively from maternal blood. This method interrogates cfDNA from maternal plasma by targeted multiplex PCR amplification and high-throughput sequencing of 19,488 SNPs. This, coupled with the method's sophisticated informatics analyses that take into account parental genotypic information and numerous sample parameters, including fetal fraction and DNA quality, more robustly detects the fetal signal and makes highly accurate ploidy calls at all of the five chromosomes implicated in the seven most common types of at-birth aneuploidy (T13, T18, T21, 45,X, 47,XXX, 47,XXY, and 47,XYY). This method offers a number of clinical advantages over previous methods, including and most significantly greater clinical coverage and sample-specific calculated accuracies (analogous to a personalized risk score).

Increased Clinical Coverage

This method offers approximately a two-fold increase in aneuploidy coverage compared to clinically available NIPT methodologies, given its ability to accurately detect autosomal trisomies and sex chromosome aneuploidies. The method presented here is the only noninvasive test that calls ploidy at the sex chromosomes with high accuracy. Prior DNA mixing experiments and separate plasma samples analyzed in our experimental assays suggest that this method will detect a larger cohort of sex chromosome anomalies, including 47,XXX. The method presented here also detects aneuploidies at chromosomes 13, 18, and 21 with high sensitivities and specificities, and with appropriate primer design is expected to be able to detect copy number at the remaining chromosomes as well.

Sample-Specific Calculated Accuracies

Significantly, this method calculates a sample-specific accuracy for ploidy calls on each chromosome in each sample. Accuracies calculated by this method are expected to significantly lower the rate of incorrect calls by identifying and flagging individual samples that have poor quality DNA or low fetal fractions that are likely to result in a poor accuracy test result. By contrast, massively parallel shotgun sequencing (MPSS)-based methods produce a positive or negative call using a single-hypothesis rejection test, and their accuracy estimate is based on a published study cohort rather than on the characteristics of the individual sample, which are assumed to have the same accuracy as the cohort. However, individual accuracies for samples with parameters in the tail of the cohort distribution may differ significantly. This is exacerbated at low fetal fractions, as in early gestational age, or for samples with low DNA quality. These samples are generally not identified and flagged for follow-up, which can result in missed calls. The present method, however, takes into account many parameters, including fetal fraction and a number of DNA quality metrics, to make each chromosome copy number call, calculating a sample-specific accuracy for that call. This allows the method to identify individual samples with low accuracy and flag them for follow-up. This is expected to nearly eliminate missed calls, especially at the early stages of pregnancy when fetal fractions are typically low. The presumption is that a no call is much preferred to a missed call, since a no call simply requires a redraw and reanalysis.

Converting Calculated Accuracies to Traditional Risk Scores

This method can offer an adjusted risk of aneuploidy for high-risk pregnant women, where the adjusted risk takes into account an a priori risk (Benn P, Cuckle H, Pergament E. Non-invasive prenatal diagnosis for Down syndrome: the paradigm will shift, but slowly. Ultrasound Obstet Gynecol 2012; 39:127-130, which is hereby incorporated by reference in its entirety). Although the present method offers each patient a customized calculated accuracy, for clinical use these accuracies can be converted to traditional risk scores, which also denote the risk of an aneuploid pregnancy but are expressed as fractions. Traditional risk scores take into account various parameters, including maternal age-related risk and serum levels of biochemical markers, to offer a risk score above which a mother is considered high-risk and for whom follow-up invasive diagnostic procedures are recommended. This method significantly refines this risk score, thus reducing both the false positive and false negative rates, and offering a more accurate assessment of individual maternal risk. A calculated accuracy as used here is the likelihood that the ploidy call is correct, and is expressed as a percentage, but the calculated accuracies used in Experiment 19 do not include an age-related risk. Because calculation of a risk score typically includes an age-related risk, the calculated accuracies and traditional risk scores are not interchangeable; they must be combined to convert into a traditional risk score. The formula to combine the age-related risk with the calculated accuracy is:

$$\frac{R_1 R_2}{R_1 R_2 + [1 - R_1][1 - R_2]}$$

where $R_1$ is the risk score as calculated by the present method and $R_2$ is the risk score as calculated by first trimester screening.

SNP-Based Methods Negate Issues with Amplification Variation

An inherent drawback to the counting methods used by some other methods is that they determine fetal ploidy state by measuring the ratio of the number of reads mapping to the chromosome of interest (e.g., chromosome 21) to those mapping to a reference chromosome. Chromosomes with high or low GC content, including chromosomes 13, X, and Y, amplify with high variability. This can result in signal variation that is comparable in magnitude to the fetal cfDNA signal, which can confound copy number calls by altering the ratio of allele reads from the chromosome-of-interest to those from the reference chromosome. This can result in low accuracy for chromosomes 13, X, and Y. Significantly, this problem is exacerbated at low fetal cfDNA fractions, as tends to be the case at early gestational ages.

In contrast, SNP-based methods do not rely on consistent amplification levels between chromosomes, and are thus expected to provide results that are equally accurate across all chromosomes. Because the present method looks, in part, at relative counts of different alleles at polymorphic loci, which by definition differ only by a single nucleotide, it does not require the use of reference chromosomes, and this obviates the problems with chromosome-to-chromosome amplification variation that are inherent to methods that rely on quantitating read counts. Unlike quantitative methods that require reference chromosomes that are euploid, the present method is expected to be able to detect triploidy as well as copy-number neutral anomalies like uniparental disomy.

The Importance of Early Detection

Figure 32:
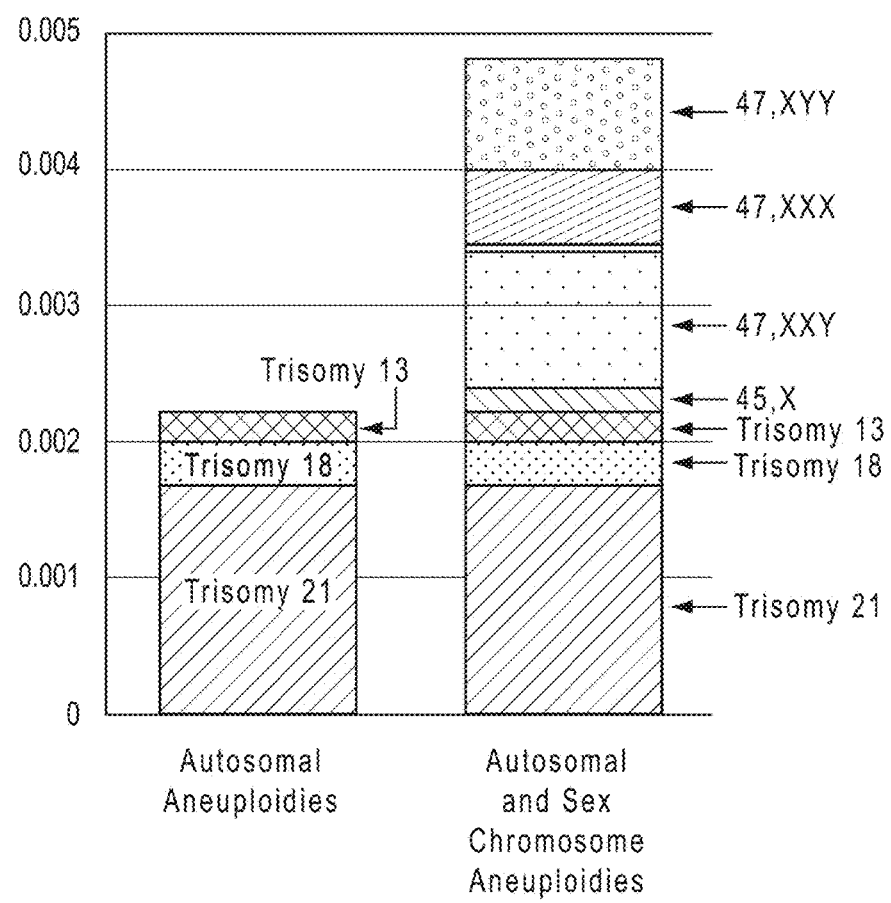
FIG. 32: The combined at-birth prevalence of sex chromosome aneuploidies is greater than that of autosomal aneuploidies.

Significantly, the combined at-birth prevalence of sex chromosome aneuploidies is higher than that of the most common autosomal aneuploidies (FIG. 32). However, there are currently no routine non-invasive screening methods that reliably detect sex chromosome abnormalities. Thus, sex chromosome anomalies are generally detected prenatally as a side-effect of routine testing for Down syndrome or other autosomal aneuploidies; a large proportion of cases are missed entirely. Early and accurate detection is crucial for many of these disorders where early therapeutic intervention improves clinical outcomes. For example, Turner syndrome is often not diagnosed until adolescence, although its overall at-birth prevalence is 1 in 2,500 females. Growth hormone therapy is known to prevent short stature that results from the disorder, but treatments are significantly more effective when initiated prior to the age of 4. Additionally, estrogen replacement therapy can stimulate secondary sexual characteristics in patients with Turner syndrome, but again therapy must be initiated in the pre-teen years, before the syndrome is usually detected. Together, this underscores the importance of early, routine, and safe detection of sex chromosome aneuploidies. This method offers the first approach with the potential to serve as a routine screen for sex chromosome anomalies.

Experiment 20

The following experiment illustrates an exemplary method for designing and selecting primers that can be used in any of the multiplexed PCR methods of the invention. In some embodiments, primers from an initial library of candidate primers are selected so that they can be used to simultaneously amplify a large number of target loci (or a subset of target loci) in a single reaction. In some embodiments, primers from an initial library of candidate primers are selected to form multiple primer pools such that each pool can be used to simultaneously amplify a subset of target loci in a single reaction. Preferably, primers are designed and selected for a large portion or all of the most desirable target loci. Preferably, the minimum number of pools needed to amplify the target loci are created.

Step 1

Calculate a first score for each primer pair design using one or more of the following parameters: number of SNPs within the primers, location of SNPs within the primers, distance from an end of the amplicon to the target bases within the amplicon, number of target loci in an amplicon, heterozygosity rate of the target locus, disease prevalence associated with a sequence (e.g., a polymorphism) at the target locus, disease penetrance associated with a sequence (e.g., a polymorphism) at the target locus, specificity of the candidate primer for the target locus, size of the candidate primer, melting temperature of the candidate primer, melting temperature of the target amplicon, GC content of the target amplicon, GC content of the 3' end of the candidate primer, homopolymer length in the candidate primer, amplification efficiency of the target amplicon, and size of the target amplicon.

Step 2

Compare each primer pair to every other primer pair, and calculate a second score for the pair using one or more of the following parameters: likelihood of dimer formation, amplicon overlap, number of primer designs for a particular target locus, and distance between amplicons. In some embodiments, the score is infinite if amplicons overlap so that two different primer pairs that generate overlapping amplicons are not included in the same primer pool.

Step 3

Aggregate the first score and the second score together (such as by using a weighted average of the scores).

Step 4

If desired, order all target loci into one contiguous list based upon their genomic location in ascending order.

Step 5

Build a minimum priority queue data structure that prioritizes the pairs of designs (in which each design is one primer pair so that a pair of designs includes two primer pairs with a total of 4 primers) based on their score (such as the aggregate score from step 3). In some embodiments, the score for a pair of designs is the worse score (such as the worse aggregate score from step 3) out of the scores for all 4 primers in the pair of designs. The pair of designs with the best (most desirable) score is first in the queue, and the pair of designs with the worst (least desirable) score is last in the queue. If desired, pairs of designs with a score above a threshold (least desirable) are removed from the library of candidate primers such that they are not included in the final pool(s) (for example, these primers may be omitted from the queue). In some embodiments, pairs of design with an interaction score above (worse than) 20, 18, 16, 14, 12, 10, 9, 8, 7, 6, 5, 4, 3, 2, or 1 kcal/mol are removed from the library of candidate primers. In some embodiments, pairs of design with a ΔG value below (worse than) −20, −18, −16, −14, −12, −10, −9, −8, −7, −6, −5, −4, −3, −2, or −1 kcal/mol are removed from the library of candidate primers.

Each design pair can be stored as a node of a doubly linked list with initial "next" and "previous" pointers set to NULL.

Step 6

Begin forming all pools simultaneously by doing the following steps. Take the design pair with the best (most desirable) score from the priority queue and add it to "the potential pools." Begin storing designs in N number of doubly linked list data structures with the design pairs. N represents the current number of different primer pools. Initially, N=1, since there is only one primer pool. In some embodiments, a second pool is only created if necessary to include the desired target loci or the desired level of coverage of target loci. Check to see if the design pair removed from the queue is "connected" to any other existing design pair. By "connected" for purposes of this step is meant that a single design in one pair is the same as a single design in another pair. If two pairs are connected, then assign the appropriate next and previous pointers to one another. If two pairs are not connected, then add them to the "potential pools" In some embodiments, a design pair is only placed in a particular pool if it would be connected to at most two other design pairs in that pool (otherwise it can be assigned to a different pool).

Check to see if (i) any linked list spans from the first target to the last target (such that all the desired target loci are included) or (ii) if a pool meets the cutoff for the desired minimum pool level. If it does, that list now forms a pool and can be added to the "final pools" list.

Step 7

If desired, check to see if the desired level of coverage (such as all the bases in the target loci being included in amplicons from 4 different primer pairs) that is desired for each location. Repeat step 6 until achieving the desired level of coverage.

The resulting primer pool(s) can be used in any of the methods of the invention.

Experiment 21

The following experiment illustrates an exemplary method for designing and selecting primers that can be used in any of the multiplexed PCR methods of the invention. In some embodiments, the primers are divided into different pools (e.g., 2, 3, 4, 5, 6, or more different pools) such that each pool is used to amplify target loci in a different reaction volume. Each pool is used to simultaneously amplify a large number of target loci (or a subset of target loci) in a single reaction volume. Preferably, primers are designed and selected for a large portion of the most desirable target loci or for all of the target loci. A set of candidate target loci can be selected as described in Experiments 16 or 20 based on the particular polymorphisms or mutations of interest. In some embodiments, one or more of the following type of target loci are included: SNPs, short indels, long indels, exons, and combinations thereof. In some embodiments for target loci that are short indels, the PCR primer or primer pair targets a sequence of adjacent base pairs; and the indel is completely covered by one sequencing read. In some embodiments for target loci that are large indels, two primer pairs are used to target a pair of breakpoints at the boundaries of the indel. In this case, the two primer pairs are designed such that when the deletion is present there is a PCR product and the two primer pairs are selected together for inclusion in the same pool (the four primers are treated by the algorithm as a single assay rather than two assays). In some embodiments for target loci that are exons, a set of primers pairs are designed to tile the full exon.

For each candidate locus, one or more PCR primer pairs are designed using the Primer3 program (available at the worldwide web at primer3.sourceforge.net; libprimer3 release 2.2.3, which is hereby incorporated by reference in its entirety). If there are no feasible designs for PCR primers for a particular target locus, then that target locus is eliminated from further consideration. In some embodiments, each target base is covered by at least two independent PCR assays (such as two independent primer pairs that will amplify the target base) and preferably by four assays, although not all of the available assays for a target must be used. In some embodiments, no targets are omitted. Desirably, the algorithm produces as few pools as possible but may produce more than one pool. In some embodiments, two different primer pairs that are in close proximity in the genome (such as within 2 kbases or 1 kbase) and whose forward primers are on the same strand are not be assigned to the same pool. This constraint avoids primer interference in the extension-and-ligation amplification method In some embodiments in which the PCR will be performed using a polymerase with low 5'→3' exonuclease and/or low strand displacement activity, different primer pairs that are in close proximity in the genome and whose forward primers are on the same strand can be assigned to the same pool since the with low 5'→3' exonuclease and/or low strand displacement activity of the polymerase will reduce or prevent primer interference and allow nearby or adjacent amplicons to be produced.

Step 1

Build an interaction graph. Each node represents one assay (such as one primer pair). Each edge represents a conflict between two assays. There are three types. Interaction edges represent a potential primer dimer and have a score indicating the interaction strength. Proximity edges represent physical proximity of the primer binding sites which may result in interference. Target edges represent redundant designs associated with the same target (a special case of a proximity edge).

Step 2

Select an initial value for the maximum interaction score (e.g., 95% of the maximum score).

Step 3

Compute a score such as a utility score for each assay as follows using steps 3A and 3B.

Step 3A

Calculate a score for each assay based on one or more of its intrinsic characteristics.

For example, favor assays with amplicons close to the optimal length (such as 300 bp); favor assays with a shorter distance from the beginning of the amplicon to the target;

and/or penalize assays with primers overlapping known SNPs. Any other parameter, such as the parameters disclosed herein can also be included.

Step 3B

Multiply the score for each assay by a factor that varies from 0 to 1 according to the current coverage of the assay's target bases. This factor gives lower weight to targets that are already covered by assays. At the beginning of the algorithm this factor is 1 for all assays because none have been covered. Calculate the factor as follows. For each base in the target, compute a coverage score as $1/(2^c)$ where c is the number of previously-selected assays (in other pools) that cover that base. For instance, if three assays cover the base then the coverage score is $1/(2^3)=0.125$. The factor for the target is the maximum value of the coverage score for all bases in the target. For instance, if the target contains 10 bases, 3 bases are covered by 1 target, and 7 bases are covered by 3 targets, then the factor is $MAX(1/(2^1), 1/(2^3))=0.5$.

The score in step 3A is then multiplied by this factor.

Step 4

Use a single iteration of the algorithm in Experiment 16 to design a pool given the current maximum interaction score: Construct a new graph with the assays that have not been assigned to a pool yet and with the edges that have weights exceeding the maximum interaction score. Remove nodes (assays) according to the algorithm in Experiment 16 until there are no edges left. The assay utility scores come from step 3 in this experiment rather than the calculation used for Experiment 16

Step 5

Save the assays selected in step 4 as a new pool and remove them from consideration. Then repeat steps 3 and 4 with the remaining assays, and iterate until all targets have sufficient coverage.

Step 6

If desired, evaluate the result. If the total number of pools meets the design goal then reduce the maximum interaction score; otherwise increase the maximum interaction score. Then go back to step 3. Iterate, using a binary search strategy to find the lowest maximum interaction score that produces the desired number of pools.

Step 7

Output the pools from the final iteration. After the selection process, the primers remaining in the pools may be used in any of the methods of the invention.

Experiment 22

The following experiment illustrates an exemplary method for designing and selecting primers that can be used in any of the multiplexed PCR methods of the invention. In some embodiments, the primers are divided into different pools (e.g., 2, 3, 4, 5, 6, or more different pools) such that each pool is used to amplify target loci in a different reaction volume. Any of the embodiments listed in Experiment 21 can be used for this experiment as well.

This method uses a graph coloring algorithm.

Step 1

Select 2, 3 or 4 of the best assays (such as primer pairs) for each target locus from all of the available assays.

Step 2

Select an initial maximum interaction score.

Step 3

Build an interaction graph containing only edges that exceed the maximum interaction score.

Step 4

Color the graph such that no adjacent nodes have the same color (this is a standard problem with many heuristic solutions). Each color represents a different pool.

Step 5

Go back to step 3 and iterate, refining the maximum interaction score until the desired number of pools is achieved. In some embodiments, after the primers are selected in step 1, the algorithm assumes all assays must be included in a pool.

After the primers are divided into different pools, the pools may be used in any of the methods of the invention.

Experiment 23

This example illustrates there exemplary methods for calculating the limit of detection for any of the methods of the invention. These methods were used to calculate the limit of detection for single nucleotide variants (SNVs) in a tumor biopsy (FIG. 41) and a plasma sample (FIG. 42).

The first method (denoted "LOD-mr5" in FIGS. 41 and 42) calculates the limit of detection based on a minimum of 5 reads being chosen as the minimum number of times a SNV is observed in the sequencing data to have sufficient confidence the SNV is actually present. The limit of detection is based on whether the observed the depth of read (DOR) is above this minimum of 5. The gray lines in FIGS. 41 and 42 indicate SNVs for which the limit of detection is limited by the DOR. In these cases, not enough reads were measured to reach the error limit of the assay. If desired, the limit of detection can be improved (resulting in a lower numerical value) for these SNVs by increasing the DOR.

The second method (denoted "LOD-zs5.0" in FIGS. 41 and 42) calculates the limit of detection based on the z-score. The Z-score is the number of standard deviations an observed error percentage is away from the background mean error. If desired, outliers can be removed and the z-score can be recalculated and this process can be repeated. The final weighted mean and the standard deviation of the error rate are used to calculate the z-score. The mean is weighted by the DOR since the accuracy is higher when the DOR is higher.

For the exemplary z-score calculation used for this example, the background mean error and standard deviation were calculated from all the other samples of the same sequencing run weighted by their depth of read, for each genomic loci and substitution type. Samples were not considered in the background distribution if they were 5 standard deviations away from the background mean. The orange lines in FIGS. 41 and 42 indicate SNVs for which the limit of detection is limited by the error rate. For these SNV's enough reads were taken to reach the 5 read minimum, and the limit of detection was limited by the error rate. If desired, the limit of detection can be improved by optimizing the assay to reduce the error rate.

The third method (denoted "LOD-zs5.0-mr5" in FIGS. 41 and 42) calculates the limit of detection based on the maximum value of the above two metrics.

Figure 41:
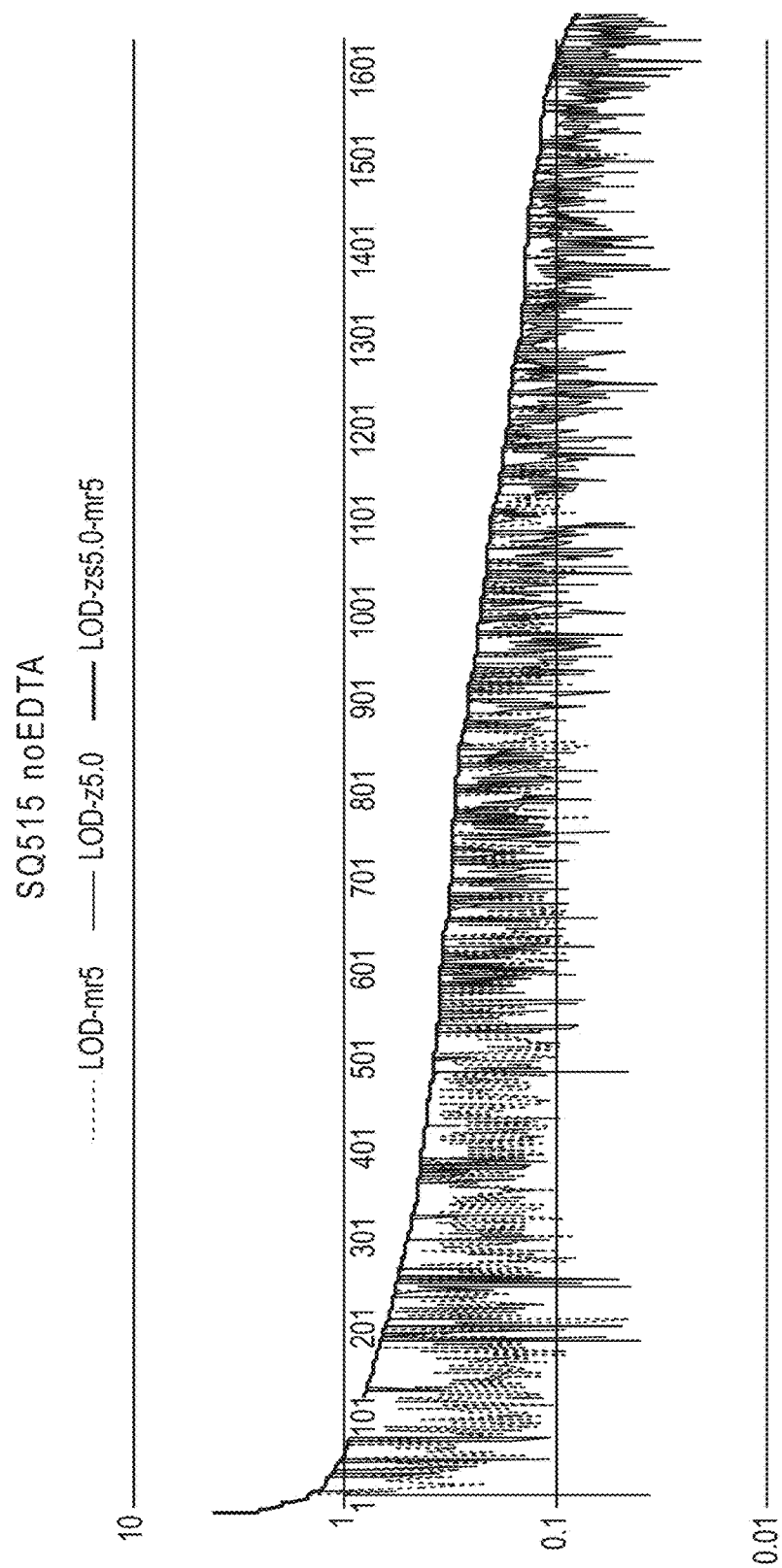
FIG. 41 is a graph showing the limit of detection for single nucleotide variants in a tumor biopsy using three different methods described in Experiment 23. The mean limit of detection was 0.36%, and the median limit of detection was 0.28%. The number of DOR limited (gray lines) SNVs was 934. The number of error rate limited (orange lines) SNVs was 738.
Figure 42:
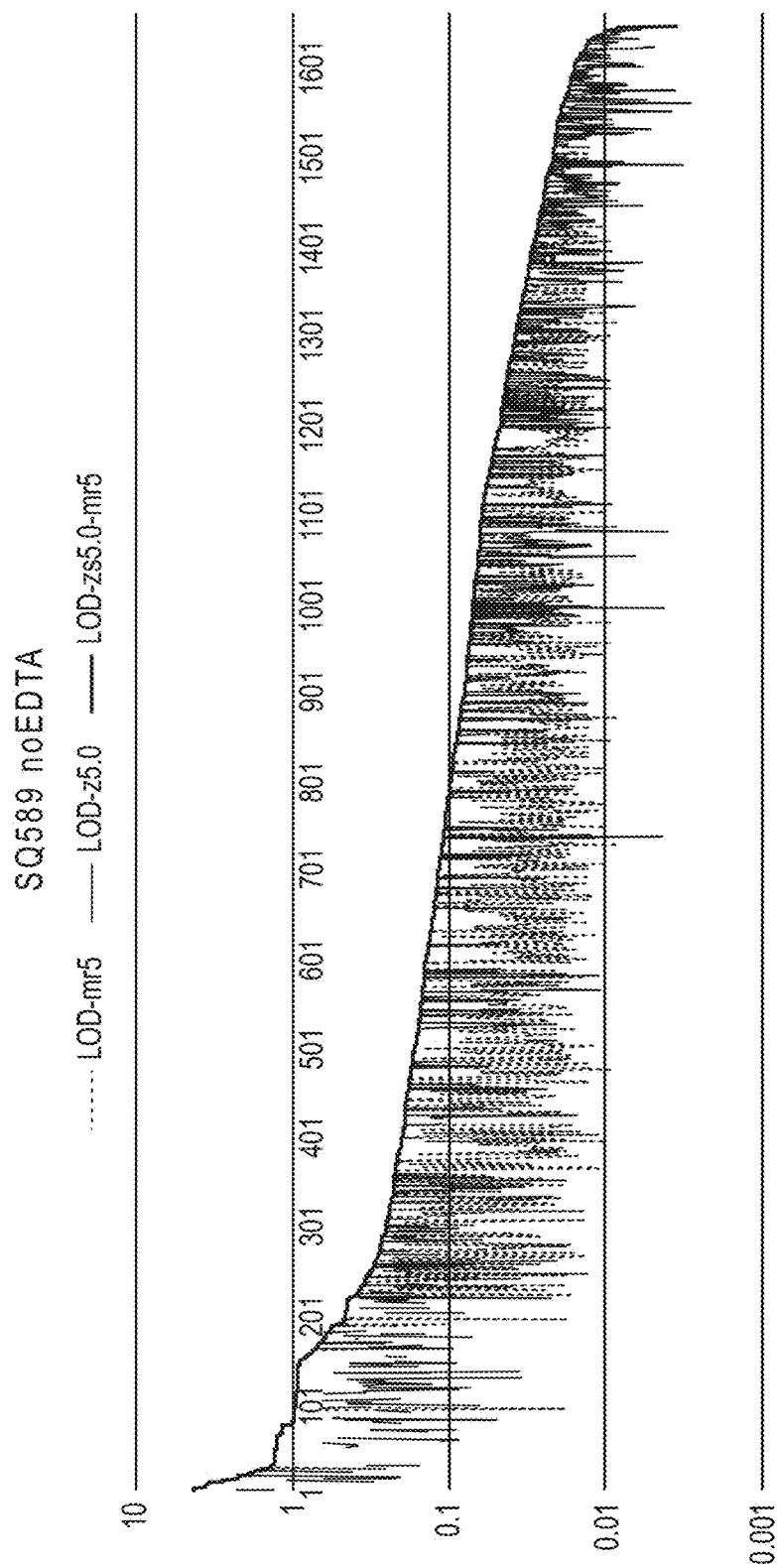
FIG. 42 is a graph showing the limit of detection for single nucleotide variants in a plasma sample using three different methods described in Experiment 23. The mean limit of detection was 0.24%, and the median limit of detection was 0.09%. The number of DOR limited (gray lines) SNVs was 732. The number of error rate limited (orange lines) SNVs was 921.

For the analysis of a tumor sample shown in FIG. 41, the mean limit of detection was 36%, and the median limit of detection was 0.28%. The number of DOR limited (gray lines) SNVs was 934. The number of error rate limited (orange lines) SNVs was 738.

For the analysis of cDNA in a plasma sample shown in FIG. 42, the mean limit of detection was 0.24%, and the median limit of detection was 0.09%. The number of DOR limited (gray lines) SNVs was 732. The number of error rate limited (orange lines) SNVs was 921.

Experiment 24

This example illustrates the detection of CNVs and SNVs from the same single cell. The following primer libraries were used a library of ~28,000 primers for detecting CNVs, a library of ~3,000 primers for detecting CNVs, and library of primers for detecting SNVs. For analysis of a single cell, cells were serial diluted until there were 3 or 4 cells per droplet. An individual cell was pipetted and placed into a PCR tube. The cell was lysed using Protease K, salt, and DTT using the following thermocycling conditions: 56° C. for 20 minutes, 95° C. for 10 minutes, and then a 4° C. hold. For analysis of genomic DNA, DNA from the same cell line as the analyzed single cell was either purchased or obtained by growing the cells and extracting the DNA.

For amplification with the library of ~28,000 primers, the following PCR conditions were used a 40 uL reaction volume, 7.5 nM of each primer, and 2× master mix (MM). In some embodiments QIAGEN Multiplex PCR Kit is used for the master mix (QIAGEN catalog No. 206143; see, e.g., information available at the world wide web at qiagen.com/products/catalog/assay-technologies/end-point-pcr-and-rt-pcr-reagents/qiagen-multiplex-pcr-kit, is which is hereby incorporated by reference in its entirety). The kit includes 2× QIAGEN Multiplex PCR Master Mix (providing a final concentration of 3 mM $MgCl_2$, 3×0.85 ml), 5× Q-Solution (1×2.0 ml), and RNase-Free Water (2×1.7 ml). The QIAGEN Multiplex PCR Master Mix (MM) contains a combination of KCl and $(NH_4)_2SO_4$ as well as the PCR additive, Factor MP, which increases the local concentration of primers at the template. Factor MP stabilizes specifically bound primers, allowing efficient primer extension by, e.g., HotStarTaq DNA Polymerase. HotStarTaq DNA Polymerase is a modified form of Taq DNA polymerase and has no polymerase activity at ambient temperatures. The following thermocycling conditions were used for the first round of PCR: 95° C. for 10 minutes; 25 cycles of 96° C. for 30 seconds, 65° C. for 29 minutes, and 72° C. for 30 seconds; and then 72° C. for 2 minutes, and a 4° C. hold. For the second round of PCR a 10 ul reaction volume, 1×MM, and 5 nM of each primer was used. The following thermocycling conditions were used: 95° C. for 15 minutes; 25 cycles of 94° C. for 30 seconds, 65° C. for 1 minute, 60° C. for 5 minutes, 65° C. for 5 minutes, and 72° C. for 30 seconds; and then 72° C. for 2 minutes, and a 4° C. 5 hold.

For the library of ~3,000 primers, exemplary reaction conditions include a 10 ul reaction volume, 2× MM, 70 mM TMAC, and 2 nM primer of each primer. For the library of primers for detecting SNVs, exemplary reaction conditions include a 10 ul reaction volume, 2× MM, 4 mM EDTA, and 7.5 nM primer of each primer. Exemplary thermocycling conditions include 95° C. for 15 minutes, 20 cycles of 94° C. for 30 seconds, 65° C. for 15 minutes, and 72° C. for 30 seconds; and then 72° C. for 2 minutes, and a 4° C. hold.

The amplified products were barcoded. One run of sequencing was performed with an approximately equal number of reads per sample.

Figure 43A:
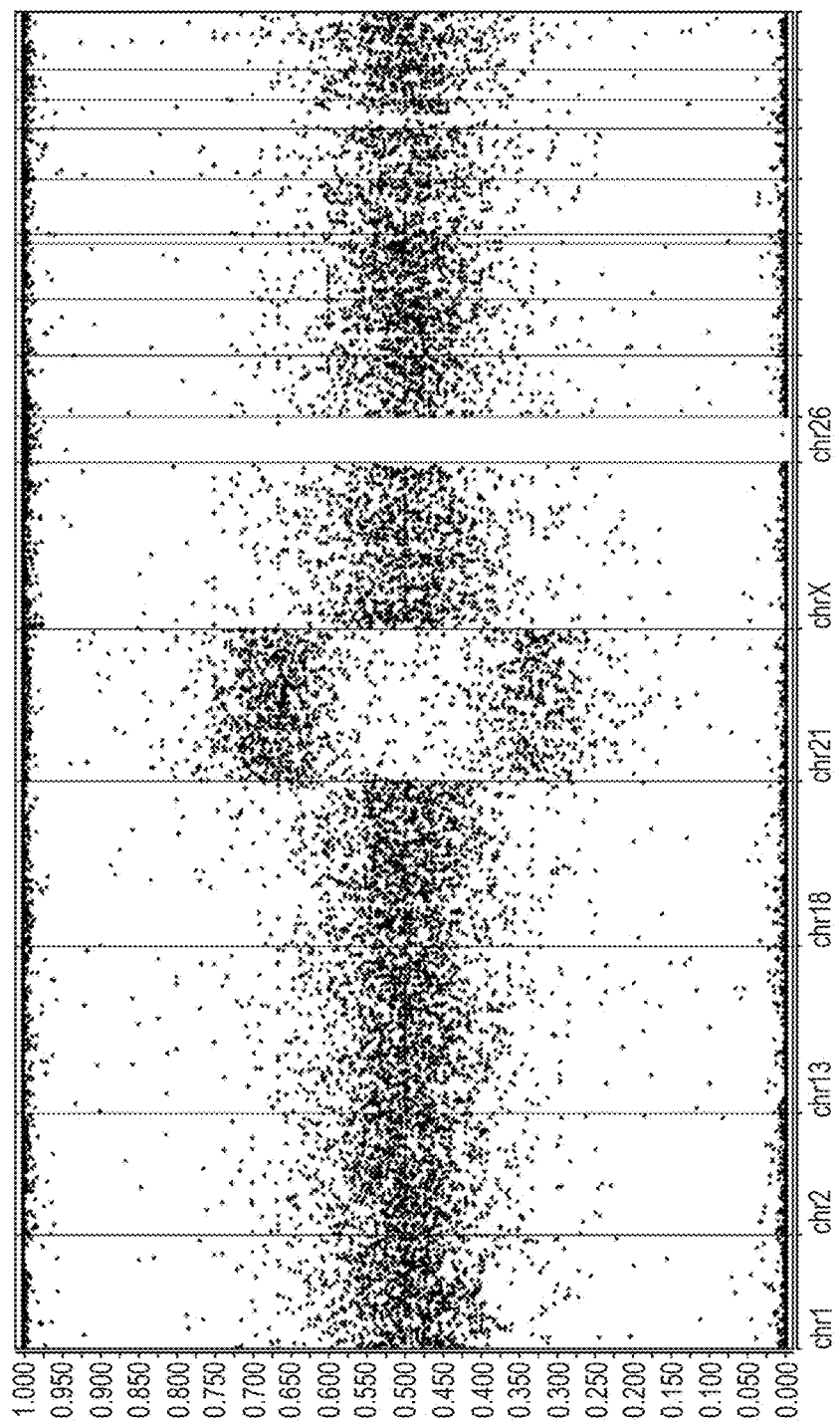
FIGS. 43A and 43B are graphs of the analysis of genomic DNA (FIG. 43A) or DNA from a single cell (FIG. 43B) using a library of approximately 28,000 primers designed to detect CNVs. The presence of two central bands instead of one central band indicates the presence of a CNV. The x-axis represents the linear position of the SNPs, and the y-axis indicates the fraction of A allele reads out of the total reads.
Figure 43B:
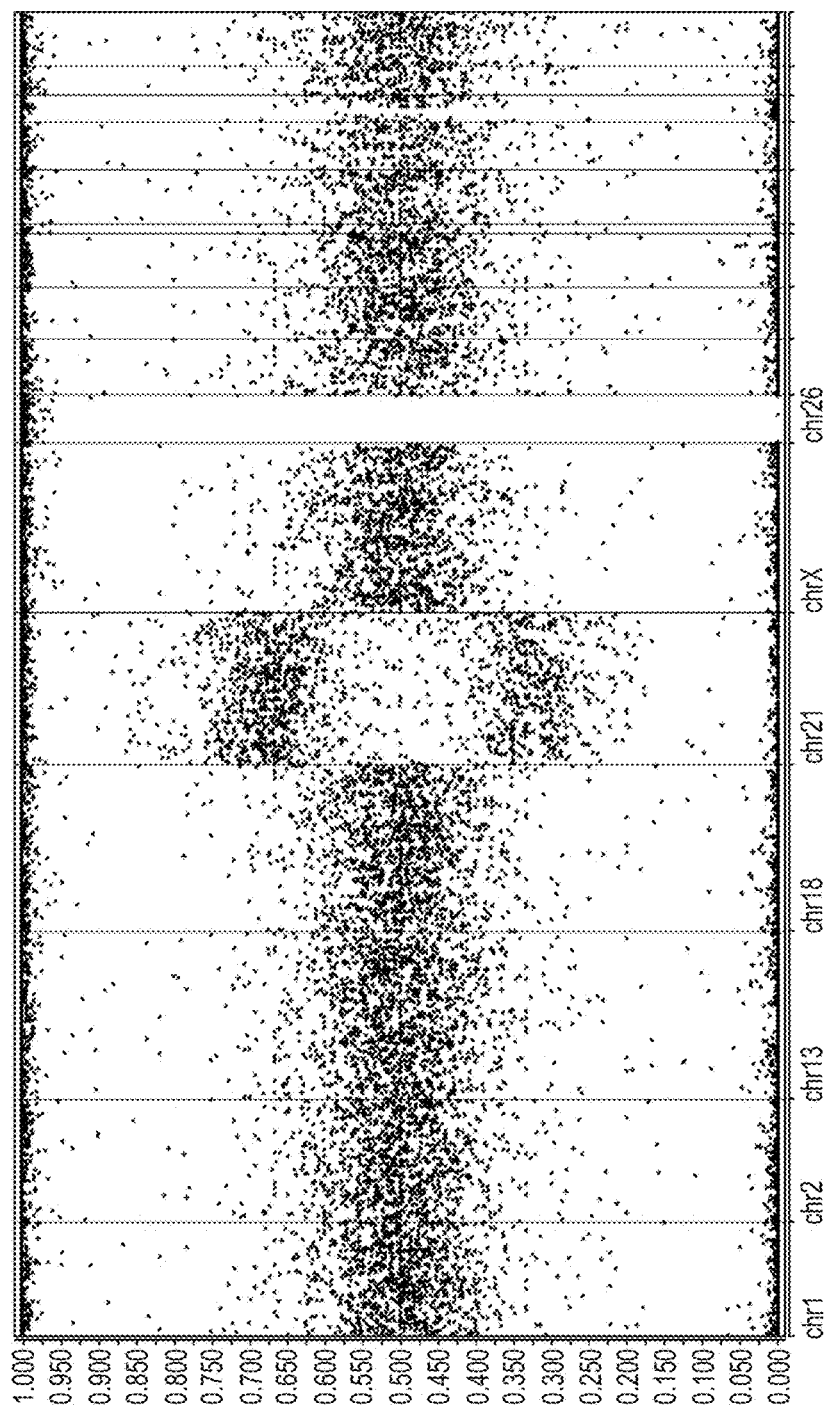

FIGS. 43A and 43B show results from analysis of genomic DNA (FIG. 43A) or DNA from a single cell (FIG. 43B) using a library of approximately 28,000 primers designed to detect CNVs. Approximately 4 million reads were measured per sample. The presence of two central bands instead of one central band indicates the presence of a CNV. For three samples of DNA from a single cell, the percent of mapped reads was 89.9%, 94.0%, and 93.4%, respectively. For two samples of genomic DNA the percent of mapped reads was 99.1% for each sample.

Figure 44A:
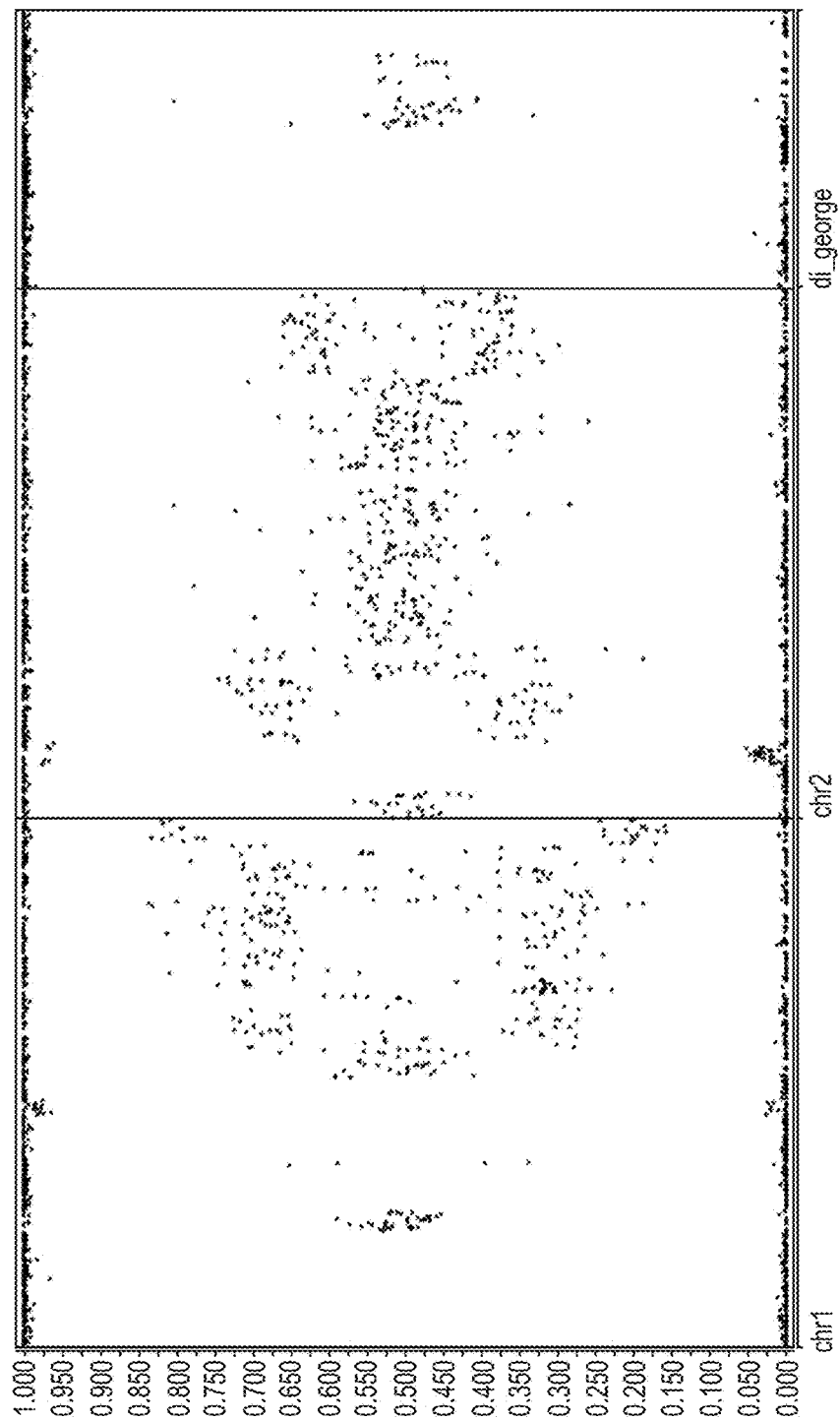
FIGS. 44A and 44B are graphs of the analysis of genomic DNA (FIG. 44A) or DNA from a single cell (FIG. 44B) using a library of approximately 3,000 primers designed to detect CNVs. The presence of two central bands instead of one central band indicates the presence of a CNV. The x-axis represents the linear position of the SNPs, and the y-axis indicates the fraction of A allele reads out of the total reads.
Figure 44B:
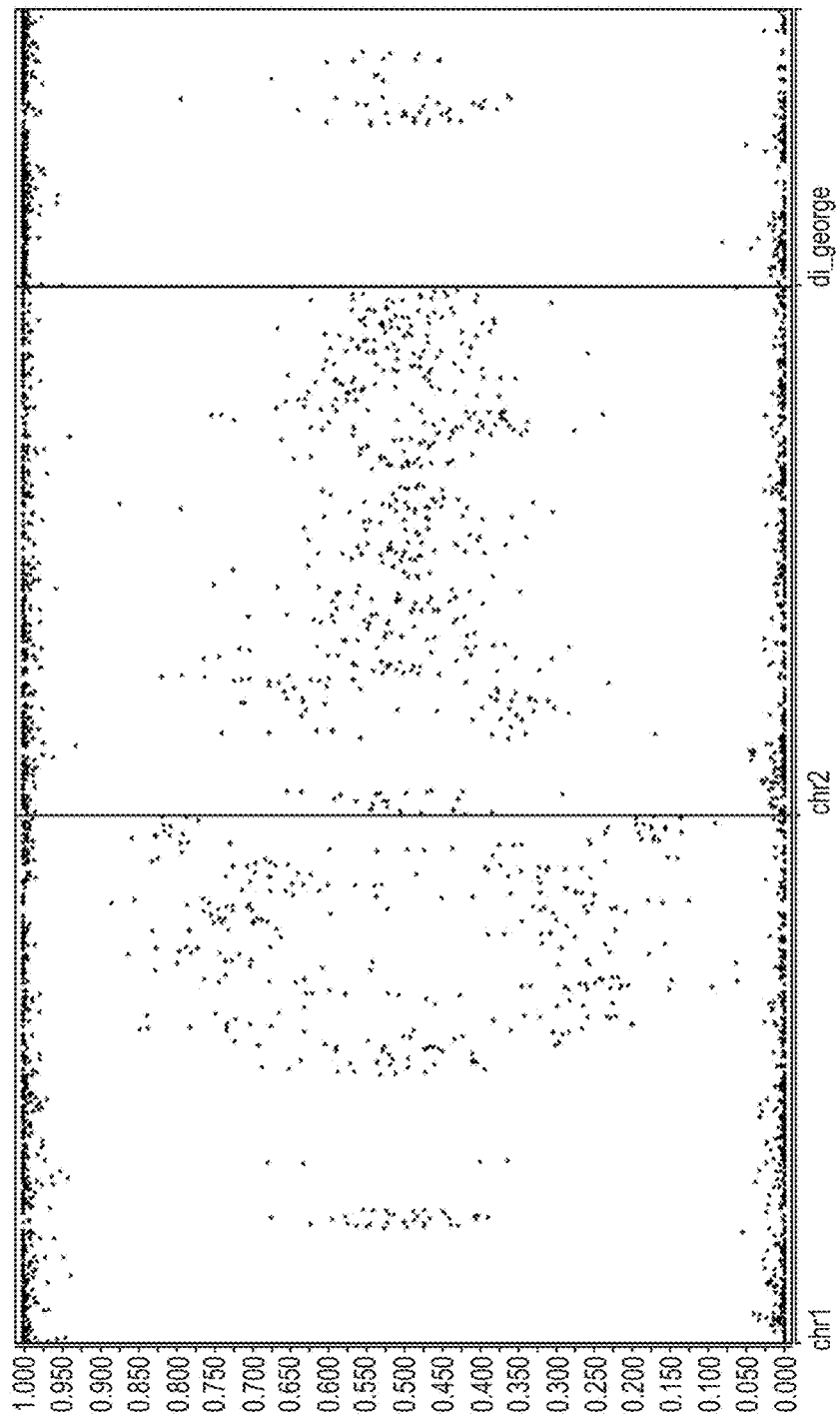
Figure 45:
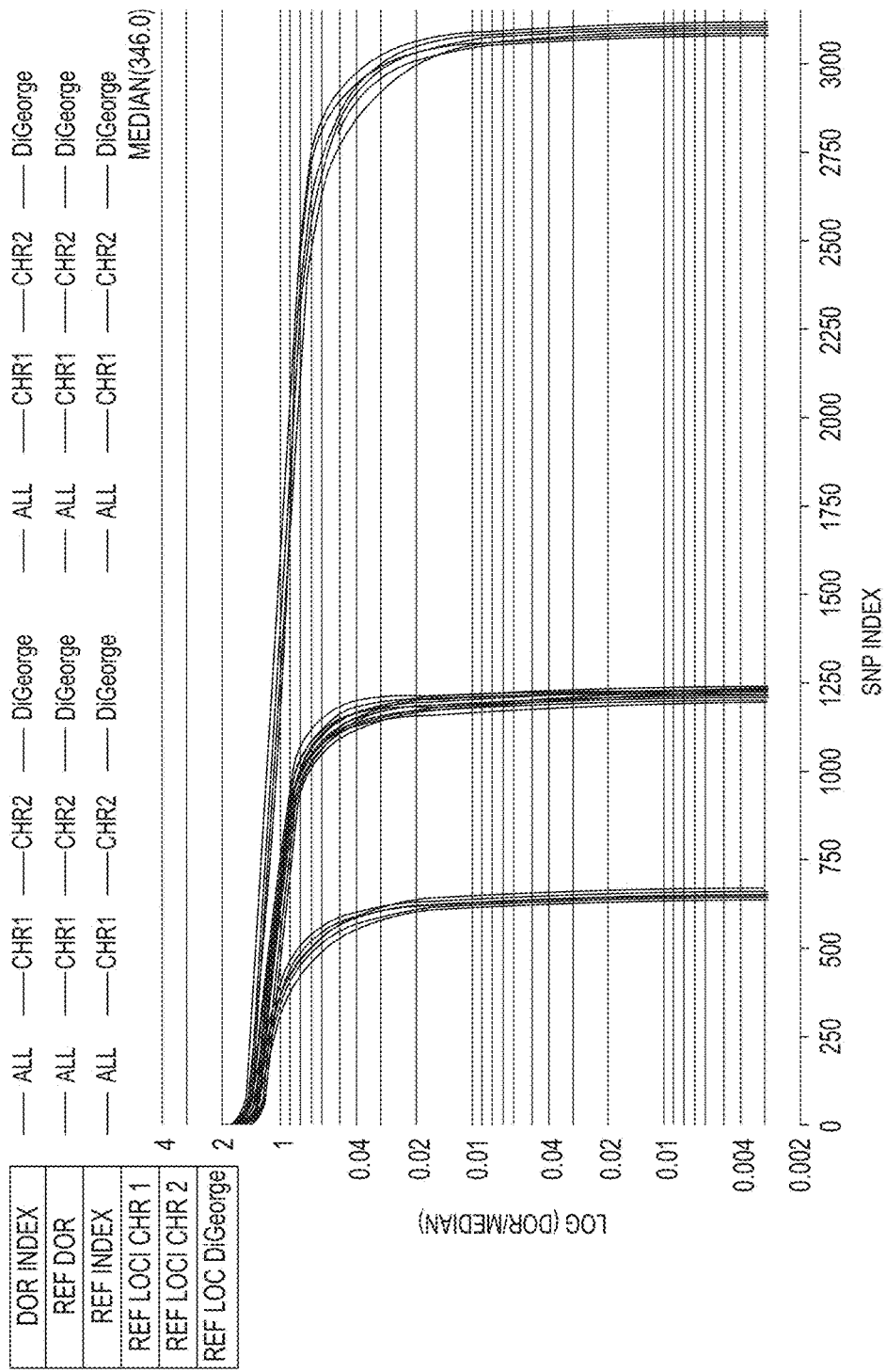
FIG. 45 is a graph illustrating the uniformity in depth of read (DOR) for these ~3,000 loci.

FIGS. 44A and 44B show results from analysis of genomic DNA (FIG. 44A) or DNA from a single cell (FIG. 44B) using a library of approximately 3,000 primers designed to detect CNVs. Approximately 1.2 million reads were measured per sample. The presence of two central bands instead of one central band indicates the presence of a CNV. For three samples of DNA from a single cell, the percent of mapped reads was 98.2%, 98.2%, and 97.9%, respectively. For two samples of genomic DNA the percent of mapped reads was 98.8% for each sample. FIG. 45 illustrates the uniformity in DOR for these ~3,000 loci.

For calling SNVs, the call percent for true positive mutations was similar for DNA from a single cell and genomic DNA. A graph of call percent for true positive mutations for single cells on the y-axis versus that for genomic DNA on the x-axis yielded a curve fit of $y=1.0076x-0.3088$ with $R^2=0.9834$. FIG. 46 shows similar error call metrics for genomic DNA and DNA from a single cell. FIG. 47 shows that the error rate for detecting transition mutations was greater than for detecting transversion mutations, indicating it may be desirable to select transversion mutations for detection rather than transition mutations when possible. In some embodiments, at least 50, 60, 70, 80, 90, 95, 96, 98, 99, or 100% of the SNVs tested for are transversion mutations rather than transition mutations.

Experiment 25

The following is an example of multiplex PCR conditions in which the annealing temperature is significantly higher than the average or maximum melting ($T_m$) of the primers in the library. A 3,168-plex reaction was performed with 3,168 primer pairs to 3,168 different target loci. For the PCR amplification a 20 ul total volume was used with 2 nM of each primer (3,168 pairs of forward and reverse primers), 70 mM TMAC (tetra-methyl ammonium chloride), and 7 ul library DNA or genomic DNA. The following thermocycling conditions were used: 95° C. for 10 minutes and then 25 cycles of 96° C. for 30 seconds, 65° C. for 20 minutes (this annealing temperature is higher than the $T_m$ of the primers, listed above), and 72° C. for 30 seconds. Then, 72° C. for 2 minutes and a 4° C. hold were used.

The minimum $T_m$ (the lowest numerical value for the $T_m$ for any of the primers) for this primer library is 54.0° C. The maximum $T_m$ (the highest numerical value for the $T_m$ for any of the primers) for this primer library is 60.36° C. The average $T_m$ (average value of the $T_m$ values of the primers) for this primer library is 55.25° C. These $T_m$ values were calculated using the following exemplary method for calculating $T_m$ values. This method is used by the Primer3 program (the worldwide web at primer3.sourceforge.net, which is hereby incorporated by reference in its entirety) to calculate $T_m$ values. In some embodiments, one or more of the following conditions are assumed for this calculation: temperature: of 60.0° C., primer concentration of 100 nM, and/or salt concentration of 100 mM. In some embodiments, other conditions are assumed for this calculation, such as the conditions that will be used for multiplex PCR with the library.

$$Tm=deltaH/(deltaS+R*\ln(C/4))$$

Below is documentation from the Primer3 program for its Tm calculations; PRIMER_TM_FORMULA (int; default 0) specifies details of melting temperature calculation. This is new in version 1.1.0, and added by Maido Remm and Triinu Koressaar (the world wide web at primer3.ut.ee/primer3web_help.htm#PRIMER_TM_FORMULA, which is hereby incorporated by reference in its entirety). A value of 0 directs primer3 to a backward compatible calculation (in other words, the only calculation available in previous version of primer3). This backward compatible calculation uses the table of thermodynamic parameters in the paper (Breslauer K J et al. (1986) "Predicting DNA duplex stability from the base sequence" Proc Natl Acad Sci 83:4746-50, dx.doi.org/10.1073/pnas.83.11.3746, which is hereby incorporated by reference in its entirety), and the method in the paper (Rychlik W, Spencer W J and Rhoads R E (1990) "Optimization of the annealing temperature for DNA amplification in vitro", Nucleic Acids Res 18:6409-12, dx.doi.org/10.1093/nar/18.21.6409, which is hereby incorporated by reference in its entirety).

A value of 1 (which is recommended) directs primer3 to use the table of thermodynamic values and the method for melting temperature calculation suggested in the following paper (SantaLucia J R (1998) "A unified view of polymer, dumbbell and oligonucleotide DNA nearest-neighbor thermodynamics", Proc Natl Acad Sci 95:1460-65, dx.doi.org/10.1073/pnas.95.4.1460, which is hereby incorporated by reference in its entirety). The tag PRIMER_SALT_CORRECTIONS can be used to specify the salt correction method for melting temperature calculation.

The following is an example of calculating the melting temperature of an oligo with PRIMER_TM_FORMULA=1 and PRIMER_SALT_CORRECTION S=1 recommended values for primer=CGTGACGTGACGGACT.

Using default salt and DNA concentrations gives $Tm = \text{delta}H/(\text{delta}S + R^*\ln(C/4))$ where R is the gas constant (1.987 cal/K mol) and C is the DNA concentration.

$\text{delta}H(\text{predicted}) = dH(CG) + dH(GT) + dH(TG) + \ldots + dH(CT) + dH(\text{init.w.term.}GC) + 25dH(\text{init.w.term.}AT)$ $= -10.6 + (-8.4) + (-8.5) + \ldots + (-7.8) + 0.1 + 2.3$ $= -128.8 \text{ kcal/mol}$ where 'init.w.term GC' and 'init.w.term AT' are two initiation parameters for duplex formation: 'initiation with terminal GC' and 'initiation with terminal AT.'

$\text{delta}S(\text{predicted}) = dS(CG) + dS(GT) + dS(TG) + \ldots + dS(CT) + dS(\text{init.w.term.}GC) + dS(\text{init.w.term.}AT)$ $= -27.2 + (-22.4) + (-22.7) + \ldots + (-21.0) + (-2.8) + 4.1$ $= -345.2 \text{ cal/k*mol}$ $\text{delta}S(\text{salt corrected}) = \text{delta}S(\text{predicted}) + 0.368*15 \text{ } (NN \text{ pairs})*\ln(0.05M \text{ monovalent cations})$ $= -361.736$ $Tm = -128.800/(-361.736 + 1.987*\ln((5*10^{\wedge}(-8))/4)) = 323.704 \text{ K}$ $Tm(C) = 323.704 - 273.15 = 50.554 \text{ C}$ Additional Applications Because this method utilizes targeted amplification, it is uniquely poised to detect sub-microscopic anomalies, such as microdeletions and microduplications. Although non-targeted methods like MPSS have been shown to detect the DiGeorge microdeletion syndrome, this required a sufficiently high level of genomic coverage so as to make the approach unfeasible. This is because non-targeted amplification will be several orders of magnitude less efficient on submicroscopic regions, as very small fraction of the sequencing reads will be informative. Additionally, the fact that the currently available methods have trouble accurately identifying ploidy state for the sex chromosomes suggests that they will also encounter variable amplification problems on smaller chromosomal segments.

Similarly, SNP based methods can detect UPD disorders, which are copy number-neutral anomalies that will not be detected by either the current noninvasive methods that rely on counting or the traditional invasive methods like amniocentesis and CVS that rely on cytogenetic karyotyping and/or fluorescence in situ hybridization. This is because SNP-based methods are uniquely able to distinguish individual haplotypes, whereas the clinically available MPSS-based and targeted methods amplify non-polymorphic loci and are thus unable to determine, for example, whether the chromosomes-of-interest originate from the same parent. This means that these microdeletion/microduplication and UPD syndromes, including Prader-Willi, Angelman, and Beckwith-Wiedemann syndromes, are generally not diagnosed prenatally, and are often initially misdiagnosed post-natally. This significantly delays therapeutic intervention. Additionally, because this method targets SNPs, this method will also facilitate parental haplotype reconstruction, allowing for detection of fetal inheritance of individual disease-linked loci (Kitzman J O, Snyder M W, Ventura M, et al. Noninvasive whole-genome sequencing of a human fetus. Sci Transl Med 2012; 4:137ra76, which is hereby incorporated by reference in its entirety).

The results presented here confirm the expanded scope of this method for identifying prenatal aneuploidy. Specifically, by amplifying and sequencing 19,488 SNPs, this method is able to determine copy number at chromosomes 13, 18, 21, X, and Y, and is uniquely expected to detect other chromosomal abnormalities, such as triploidy and UPD, that are not detected by any other clinically available non-invasive method. The increased clinical coverage and powerful sample-specific calculated accuracies suggest that this method may offer a viable adjunct to invasive testing for detecting fetal chromosomal aneuploidies.

All patents, patent applications, and published references cited herein are hereby incorporated by reference in their entirety. While the methods of the present disclosure have been described in connection with the specific embodiments thereof, it will be understood that it is capable of further modification. Furthermore, this application is intended to cover any variations, uses, or adaptations of the methods of the present disclosure, including such departures from the present disclosure as come within known or customary practice in the art to which the methods of the present disclosure pertain, and as fall within the scope of the appended claims. For example, any of the methods disclosed herein for DNA can be readily adapted for RNA by including a reverse transcription step to convert the RNA into DNA. Examples that use polymorphic loci for illustration can be readily adapted for the amplification of nonpolymorphic loci if desired. Any of the methods disclosed herein can be used with a low level of multiplexing if desired (such as with less than 1,000, 750, 500, 250, 100, 75, 50, 25, or 10 different primers or different primer pairs to different target loci).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09677118B2). An electronic copy of the "Sequence Listing" will also be available from the USPTO upon request and payment of the fee set forth in 37 CFR 1.19(b)(3).

What is claimed is:

1. A method of amplifying target loci in a nucleic acid sample, the method comprising:
   (a) contacting a sample comprising target human loci with a library of at least 50 non-immobilized, non-identical primers that simultaneously hybridize to at least 50 non-identical target human loci to produce a reaction mixture; wherein the primers do not include molecular inversion probes (MIPs);
   (b) subjecting the reaction mixture to primer extension reaction conditions to produce amplified products comprising target amplicons; wherein the annealing temperature for the reaction conditions is greater than a melting temperature of the at least 50 non-identical primers; wherein the length of the annealing step of the reaction conditions is greater than 5 minutes; and wherein at least 50 non-identical target human loci are simultaneously amplified; and
   (c) sequencing the amplified products.

2. The method of claim 1, wherein the annealing temperature is at least 3° C. greater than the melting temperature of the at least 50 non-identical primers.

3. The method of claim 1, wherein the annealing temperature is at least 3° C. greater than the highest melting temperature of the at least 50 non-identical primers.

4. The method of claim 3, wherein the annealing temperature is at least 8° C. greater than the highest melting temperature of the at least 50 non-identical primers.

5. The method of claim 1, wherein the annealing temperature is at least 3° C. greater than the average melting temperature of the at least 50 non-identical primers.

6. The method of claim 5, wherein the annealing temperature is at least 8° C. greater than the average melting temperature of the at least 50 non-identical primers.

7. The method of claim 1, wherein the range of melting temperature of the at least 50 non-identical primers is between 1 to 5° C., inclusive.

8. The method of claim 1, wherein the range of melting temperatures of the at least 50 non-identical primers is less than 5° C.

9. The method of claim 1, wherein the ΔG values for each possible combination of two primers in the library are all equal to or greater than −5 kcal/mol.

10. The method of claim 1, further comprising performing universal amplification on nucleic acids in the sample prior to step (a).

11. The method of claim 1, wherein at least 50 of the primers have at least 90% identity to the corresponding region of SEQ ID Nos. 1-44,610.

12. The method of claim 1, wherein the library comprises at least 500 non-immobilized, non-identical primers that simultaneously hybridize to the at least 500 non-identical target human loci, wherein the annealing temperature for the reaction conditions is greater than a melting temperature of the at least 500 non-identical primers, and wherein at least 500 non-identical target human loci are simultaneously amplified.

13. The method of claim 1, wherein at least 90% of the amplified products are target amplicons.

14. The method of claim 1, wherein at least 90% of the target human loci are amplified.

15. The method of claim 1, wherein less than 20% of the amplified products are primer dimers.

16. The method of claim 1, wherein the concentration of each primer in the library is less than 20 nM.

17. The method of claim 1, wherein the at least 50 non-identical primers have 2, 1, or 0 guanines or cytosines in the last 5 bases at the 3' end of the primers.

18. The method of claim 1, wherein the at least 50 non-identical primers comprise a 5' region that is not specific for a target human locus followed by a region that is specific for a target human locus, an internal region that is not specific for the target human locus and forms a loop structure, and a 3' region that is specific for the target human locus.

19. The method of claim 1, wherein the sample comprises maternal DNA from the pregnant mother of a fetus and fetal DNA, and wherein the method further comprises determining the presence or absence of a fetal chromosome abnormality from the sequencing data.

20. The method of claim 1, wherein the sample comprises DNA from a single cell.

21. The method of claim 1, wherein the annealing temperature is 1 to 15° C. greater than the highest melting temperature of the at least 50 non-identical primers.

22. The method of claim 1, wherein the annealing temperature is 1 to 10° C. greater than the highest melting temperature of the at least 50 non-identical primers.

23. The method of claim 1, wherein the library comprises at least 1000 non-immobilized, non-identical primer pairs that simultaneously hybridize to at least 1000 non-identical target human loci, wherein the annealing temperature for the reaction conditions is greater than a melting temperature of the at least 1000 non-identical primers, and wherein the at least 1000 non-identical target human loci are simultaneously amplified.

24. The method of claim 1, wherein the length of the annealing step of the reaction conditions is between 5 and 60 minutes.

* * * * *